(12) United States Patent
Schnell et al.

(10) Patent No.: US 11,478,543 B1
(45) Date of Patent: Oct. 25, 2022

(54) CORONAVIRUS DISEASE (COVID-19) VACCINE

(71) Applicant: THOMAS JEFFERSON UNIVERSITY, Philadelphia, PA (US)

(72) Inventors: Matthias J. Schnell, Harleysville, PA (US); Christoph Wirblich, Wernau (DE); Drishya Kurup, Philadelphia, PA (US)

(73) Assignee: Thomas Jefferson University, Philadelphia, PA (US)

(*) Notice: Subject to any disclaimer, the term of this patent is extended or adjusted under 35 U.S.C. 154(b) by 0 days.

(21) Appl. No.: 17/193,890

(22) Filed: Mar. 5, 2021

Related U.S. Application Data

(60) Provisional application No. 63/017,241, filed on Apr. 29, 2020, provisional application No. 62/986,396, filed on Mar. 6, 2020.

(51) Int. Cl.
*A61K 39/00* (2006.01)
*A61P 31/14* (2006.01)
*C07K 16/10* (2006.01)
*A61K 39/215* (2006.01)
*C12N 7/00* (2006.01)

(52) U.S. Cl.
CPC .......... *A61K 39/215* (2013.01); *C12N 7/00* (2013.01); *A61K 2039/5252* (2013.01); *A61K 2039/55572* (2013.01); *C12N 2760/20042* (2013.01); *C12N 2770/20034* (2013.01)

(58) Field of Classification Search
CPC .......... A61P 31/14; A61K 2300/00; C12N 2770/20034; G01N 2333/165; G01N 33/56983
See application file for complete search history.

(56) References Cited

U.S. PATENT DOCUMENTS

2019/0062785 A1* 2/2019 Johnson ............... C12N 15/86

OTHER PUBLICATIONS

Sun et al., "SARS-CoV-2 and SARS-CoV Spike-RBD Structure and Receptor Binding Comparison and Potential Implications on Neutralizing Antibody and Vaccine Development", bioRxiv, 2020:1-18.*
International Search Report and Written Opinion dated Aug. 5, 2021 for International Appln. No. PCT/US21/21200.
Bhandari, et al., "A dose-escalation safety and immunogenicity study of live attenuated oral rotavirus vaccine 116E in infants: a randomized, double-blind, placebo-controlled trial", J Infect Dis., 200(3), Epub Jun. 24, 2009. doi 10.1086/600104. PubMed PMID: 19545211, 2009, 421-9.
Bhandari, et al., "Efficacy of a monovalent human-bovine (116E) rotavirus vaccine in Indian children in the second year of life". Vaccine, 32 Suppl 1, doi: 10.1016/j.vaccine.2014.04.079. PubMed PMID: 25091663; PMCID: 25091663, 2014, A110-6.
Bhandari, et al., "Efficacy of a monovalent human-bovine (116E) rotavirus vaccine in Indian infants: a randomised, double-blind, placebo-controlled trial", Lancet, 383(9935), Epub Mar. 19, 2014. doi: 10.1016/s0140-6736(13)62630-6. PubMed PMID: 24629994; PMCID: PMC4532697, 2014, 2136-43.
Blaney, et al., "Antibody quality and protection from lethal Ebola virus challenge in nonhuman primates immunized with rabies virus based bivalent vaccine", PLoS pathogens, 9(5):e1003389. doi: 10.1371/journal.ppat.1003389. PubMed PMID: 23737747; PMCID: 3667758., 2013.
Blaney, et al., "Inactivated or live-attenuated bivalent vaccines that confer protection against rabies and Ebola viruses", J Virol., 85(20), Epub Aug. 19, 2011. doi: 10.1128/JVI.00558-11. PubMed PMID: 21849459; PMCID: 3187516., 2011, 10605-16.
Burkard, et al., "Coronavirus cell entry occurs through the endo-/lysosomal pathway in a proteolysis-dependent manner", PLoS pathogens, 10(11):e1004502. doi: 10.1371/journal.ppat.1004502. PubMed PMID: 25375324; PMCID PMC422306, 2014.
Hudacek, et al., "Recombinant rabies virus particles presenting botulinum neurotoxin antigens elicit a protective humoral response in vivo", Molecular therapy Methods & clinical development. 2014;1:14046. doi: 10.1038/mtm.2014.46. PubMed PMID: 26015984; PMCID: 4362357, 2014.
Huttner, "The effect of dose on the safety and immunogenicity of the VSV Ebola candidate vaccine: a randomised double-blind, placebo-controlled phase 1/2 trial", Lancet Infect Dis., 15(10):. doi: 10.1016/S1473-3099(15)00154-1. PubMed PMID: 26248510, 2015, 1156-66.
Jin, et al., "Efficacy and immunogenicity of a Vi-tetanus toxoid conjugate vaccine in the prevention of typhoid fever using a controlled human infection model of *Salmonella typhi*: a randomised controlled, phase 2b trial", The Lancet, 390(10111), doi: doi.org/10.1016/S0140-6736(17)32149-9, 2017, 2472-80.
Johnson, et al., "An Inactivated Rabies Virus-Based Ebola Vaccine, FILORAB1, Adjuvanted With Glucopyranosyl Lipid A in Stable Emulsion Confers Complete Protection in Nonhuman Primate Challenge Models", The Journal of infectious diseases, 214(suppl 3):S342-S54. doi: 10.1093/infdis/jiw231. PubMed PMID: 27456709; PMCID: PMC5050469, 2016.
Kurup, et al., "Rhabdoviral-Based Vaccine Platforms against Henipaviruses", J Virol., doi: 10.1128/JVI. PubMed PMID: 25320306, 2014, 02308-14.
Ma, et al., "Searching for an ideal vaccine candidate among different MERS coronavirus receptor-binding fragments—the importance of immunofocusing in subunit vaccine design", Vaccine. 2014;32(46), doi: 10.1016/j.vaccine.2014.08.086, doi: 10.1016/j.vaccine.2014.08.086. PubMed PMID: 25240756; PMCID: PMC4194190, 2014, 6170-6.
McGettigan, et al., "Functional human immunodeficiency virus type 1 (HIV-1) Gag-Pol or HIV-1 Gag-Pol and env expressed from a single rhabdovirus-based vaccine vector genome", J Virol., 77(20), Epub Sep. 27, 2003. PubMed PMID: 14512539; PMCID: 224996, 2003, 10889-99.

(Continued)

*Primary Examiner* — Barry A Chestnut
(74) *Attorney, Agent, or Firm* — Saul Ewing Arnstein & Lehr LLP; Kathryn Doyle; Alireza Behrooz

(57) ABSTRACT

The present invention includes a vaccine comprising a SARS-CoV-2 spike protein (S) or portion thereof, and methods of use thereof.

12 Claims, 173 Drawing Sheets

Specification includes a Sequence Listing.

(56) References Cited

OTHER PUBLICATIONS

McGettigan, et al., "Second-generation rabies virus-based vaccine vectors expressing human immunodeficiency virus type 1 gag have greatly reduced pathogenicity but are highly immunogenic", J Virol.,77(1), Epub Dec. 13, 2002. PubMed PMID: 12477829; PMCID: 140592, 2003, 237-44.

Mohan, et al., "Safety and immunogenicity of a Vi polysaccharide-tetanus toxoid conjugate vaccine (Typbar-TCV) in healthy infants, children, and adults in typhoid endemic areas: a multicenter, 2-cohort, open-label, double-blind, randomized controlled phase 3 study", Clinical infectious diseases: an official publication of the Infectious Diseases Society of America, 61(3), Epub Apr. 15, 2015. doi: 10.1093/cid/civ295. PubMed PMID: 25870324, 2015, 393-402.

Muthumani, et al., "A synthetic consensus anti-spike protein DNA vaccine induces protective immunity against Middle East respiratory syndrome coronavirus in nonhuman primates", Sci Transl Med., 7(301):301ra132. doi 10.1126/scitranslmed.aac7462. PubMed PMID: 26290414; PMCID: PMC4573558, 2015.

Pfaller, et al., "Reverse genetics of Mononegavirales: How they work, new vaccines, and new cancer therapeutics", Virology, 479-480, doi: 10.1016/j.virol.2015.01.029 PubMed PMID: 25702088; PMCID: 4557643, 331-44.

Raj, et al., "Dipeptidyl peptidase 4 is a functional receptor for the emerging human coronavirus-EMC", Nature, 495 (7440), doi: 10.1038/nature12005. PubMed PMID: 23486063, 2013, 251-4.

Shakya et al., "Phase 3 Efficacy Analysis of a Typhoid Conjugate Vaccine Trial in Nepal", New England Journal of Medicine, 381(23), doi: 10.1056/NEJMoa1905047, 2019, 2209-18.

Shi, et al., "Susceptibility of ferrets, cats, dogs, and other domesticated animals to SARS-coronavirus 2", Science, vol. 368, Issue 6494, May 29, 2020, 1016-1020.

Singh, et al., "A Japanese Encephalitis Vaccine From India Induces Durable and Cross-protective Immunity Against Temporally and Spatially Wide-ranging Global Field Strains", The Journal of Infectious Diseases, 212(5),. doi: 10.1093/infdis/jiv023, 2015, 715-25.

Sun, et al., "SARS-CoV-2 and SARS-CoV Spike-RBD Structure and Receptor Binding Comparison and Potential Implications on Neutralizing Antibody and Vaccine Development", bioRxiv. Feb. 20, 2020 [online]. [Retrieved on Jun. 28, 2021]. Retrieved from the internet: <URL: https://www .biorxiv.org/contenUbiorxiv/early/2020/02/20/2020.02.16.951723. full.pdf>.

Vadrevu, et al., "Persistence of Immune Responses With an Inactivated Japanese Encephalitis Single-Dose Vaccine, JENVAC and Interchangeability With a Live-Attenuated Vaccine", The Journal of Infectious Diseases, doi: 10.1093/infdis/jiz672, 2019.

Volz, et al., "Protective Efficacy of Recombinant Modified Vaccinia Virus Ankara Delivering Middle East Respiratory Syndrome Coronavirus Spike Glycoprotein", J Virol., 89(16). doi: 10.1128/JVI.00614-15. PubMed PMID: 26018172; PMCID: PMC4524222, 2015, 8651-6.

Voysey, et al., "Seroefficacy of Vi Polysaccharide-Tetanus Toxoid Typhoid Conjugate Vaccine (Typbar TCV)", Clinical Infectious Diseases, 67(1), doi: 10.1093/cid/cix1145, 2018, 18-24.

Willet, et al., "Preclinical Development of Inactivated Rabies Virus-Based Polyvalent Vaccine Against Rabies and Filoviruses", J Infect Dis., 212 Suppl 2:. doi: 10.1093/infdis/jiv251. PubMed PMID: 26063224; PMCID: 4564550, 2015, S414-24.

Wirblich, et al., "One-Health: a Safe, Efficient, Dual-Use Vaccine for Humans and Animals against Middle East Respiratory Syndrome Coronavirus and Rabies Virus", Journal of virology, 91(2). Epub Nov. 4, 2016. doi: 10.1128/JVI.02040-16. PubMed PMID: 27807241; PMCID: PMC5215356, 2017.

Zhao, et al., "Rapid generation of a mouse model for Middle East respiratory syndrome", Proc Natl Acad Sci U S A., 111(13), Epub Mar. 7, 2014. doi: 10.1073/pnas.1323279111. PubMed PMID: 24599590; PMCID: 3977243, 2014, 4970-5.

Bhandari, et al., "Safety and immunogenicity of two live attenuated human rotavirus vaccine candidates, 116E and I321, in infants: results of a randomised controlled trial", Vaccine., 24(31-32), Epub Jun. 1, 2006. doi: 10.1016/j.vaccine.2006.05.01. PubMed PMID: 16735085, 2006, 5817-23.

Conzelmann, et al., "Molecular cloning and complete nucleotide sequence of the attenuated rabies virus SAD B19", Virology, 175(2), PubMed PMID: 2139267, 1990, 485-99.

Papaneri, et al., "Alanine scanning of the rabies virus glycoprotein antigenic site III using recombinant rabies virus: implication for post-exposure treatment", Vaccine, 31(49), Epub Oct. 15, 2013. doi: 10.1016/j.vaccine.2013.09.038. PubMed PMID: 24120673, 2013, 5897-902.

Servat, et al., "A quantitative indirect ELISA to monitor the effectiveness of rabies vaccination in domestic and wild carnivores", J Immunol Methods., 318(1-2), doi: 10 1016/j.jim.2006.07.026. PubMed PMID: 17166510, 2007, 1-10.

Wasniewski, et al., "Evaluation of an ELISA to detect rabies antibodies in orally vaccinated foxes and raccoon dogs sampled in the field", J Virol Methods, 187(2):264-70. doi: 10.1016/j.jviromet. 2012.11.022. PubMed PMID: 23201293, 2013, 264-70.

Wasniewski, et al., "Evaluation of ELISA for detection of rabies antibodies in domestic carnivores", J Virol Methods., 179(1), doi: 10.1016/j.jviromet.2011.10.019. PubMed PMID: 22080853, 2012, 166-75.

\* cited by examiner

| Show | Type | Name | Range | Strand | Length | Description |
|---|---|---|---|---|---|---|
| ✓ | misc_feature | Ampicillin | complement(16304..17081) | ▼ | 858 | Ampicillin |
| ✓ | misc_feature | CMV promoter | 626..1206 | ▲ | 581 | CMV promoter |
| ✓ | misc_feature | CP1685M | 8023..8041 | ▲ | 19 | CP1685M |
| ✓ | misc_feature | HH ribozyme | 1276..1323 | ▲ | 48 | HH ribozyme |
| ✓ | misc_feature | HdR | 14799..14894 | ▲ | 96 | HdR |
| ✓ | misc_feature | Leader | 1324..1386 | ▲ | 63 | Leader |
| ✓ | insert | PCR 676B-677 | | | 2074 | |
| ✓ | insert | PCW489-1 | 8048..8257 | ▲ | 210 | |
| ✓ | misc_feature | RP659M | 1324..3397 | ▼ | 20 | RP659M |
| ✓ | misc_feature | RP660 | 5051.5070 | ▲ | 20 | RP660 |
| ✓ | misc_feature | RP77 | complement(3496..3518) | ▼ | 21 | RP77 |
| ✓ | misc_feature | Signal Peptide | 5996..6040 | ▲ | 45 | Signal Peptide |
| ✓ | misc_feature | Stop | 2700..2706 | ▲ | 7 | Stop |
| ✓ | misc_feature | Stop | 8351..8357 | ▲ | 7 | Stop |
| ✓ | misc_feature | T7 | 1238..1258 | ▲ | 21 | T7 |
| ✓ | misc_feature | T7Term | 14965..15012 | ▲ | 48 | T7Term |
| ✓ | misc_feature | TM | 8125..8193 | ▲ | 69 | TM |
| ✓ | misc_feature | Trailer | 14700..14798 | ▲ | 99 | Trailer |
| ✓ | misc_feature | VP1F | 1710..1729 | ▲ | 20 | VP1F |
| ✓ | misc_feature | VP2F | 2196..2215 | ▲ | 20 | VP2F |
| ✓ | mis

FIG. 8

| Show | Type | Name | Range | Strand | Length | Description |
|---|---|---|---|---|---|---|
| ✓ | misc_feature | | 4555..4560 | ▲ | 6 | |
| ✓ | misc_feature | | 4546..4551 | ▲ | 6 | |
| ✓ | misc_feature | Ampicillin | complement(21955..22815) | ▼ | 861 | Ampicillin |
| ✓ | misc_feature | CP1685M | complement(4530..4561) | ▼ | 32 | CP1685M |
| ✓ | misc_feature | F | 10095..11756 | ▲ | 1662 | F |
| ✓ | misc_feature | H | 11917..13770 | ▲ | 1854 | H |
| ✓ | misc_feature | HH Ribozyme | 667..716 | ▲ | 50 | HH Ribozyme |
| ✓ | misc_feature | L | 13880..20431 | ▲ | 6552 | L |
| ✓ | misc_feature | M | 8084..9091 | ▲ | 1008 | M |
| ✓ | insert | MV-GFP corrected | 824..2471 | ▲ | 1648 | |
| ✓ | insert | MV-GFP corrected | 6336..6689 | ▲ | 354 | |
|

| Show | Type | Name | Range | Strand | Length | Description |
|---|---|---|---|---|---|---|
| ✓ | misc_feature | | 3870..3889 | ▶ | 20 | |
| ✓ | misc_feature | Ampicillin | complement (21925..22785) | ◀ | 861 | Ampicillin |
| ✓ | misc_feature | F | 10065..11726 | ▶ | 1662 | F |
| ✓ | misc_feature | GE | 2450..2460 | ▶ | 11 | GE |
| ✓ | misc_feature | GE | 758..768 | ▶ | 11 | GE |
| ✓ | misc_feature | GE | 9477..9487 | ▶ | 11 | GE |
| ✓ | misc_feature | GE | 4097..4107 | ▶ | 11 | GE |
| ✓ | misc_feature | GE | 11853..11858 | ▶ | 6 | GE |
| ✓ | misc_feature | GE | 8008..8018 | ▶ | 11 | GE |
| ✓ | misc_feature | GE | 20460..20470 | ▶ | 11 | GE |
| ✓ | misc_feature | GS | 2464..2480 | ▶ | 17 | GS |
| ✓ | misc_feature | GS | 772..788 | ▶ | 17 | GS |
| ✓ | misc_feature | GS | 9491..9507 | ▶ | 17 | GS |
| ✓ | misc_feature | GS | 20474..20490 | ▶ | 17 | GS |
| ✓ | misc_feature | GS | 8022..8038 | ▶ | 17 | GS |
| ✓ | misc_feature | GS | 4111..4127 | ▶ | 17 | GS |
| ✓ | misc_feature | H | 11987..13740 | ▶ | 1854 | H |
| ✓ | misc_feature | HH Ribozyme | 667..716 | ▶ | 50 | HH Ribozyme |
| ✓ | misc_feature | L | 13850..20401 | ▶ | 6552 | L |
| ✓ | misc_feature | M | 8054..9061 | ▶ | 1008 | M |
| ✓ | insert | MV-GFP corrected | 2523..2759 | ▶ | 237 | |
| ✓ | insert | MV-GFP corrected | 824..2401 | ▶ | 1578 | |
| ✓ | misc_feature | MV33F | 19956..19975 | ▶ | 20 | MV33F |
| ✓ | misc_feature | MV4F | 2158..2177 | ▶ | 20 | MV4F |
| ✓ | misc_feature | MV5F | 2643..2661 | ▶ | 19 | MV5F |
| ✓ | misc_feature | MV6F | 3147..3166 | ▶ | 20 | MV6F |
| ✓ | misc_feature | MV7F | 3639..3658 | ▶ | 20 | MV7F |
| ✓ | misc_feature | MV8F | 8030..8049 | ▶ | 20 | MV8F |
| ✓ | misc_feature | MVPos3 Rev | complement (8093..8111) | ◀ | 19 | MVPos3 Rev |
| ✓ | misc_feature | N | 824..2398 | ▶ | 1575 | N |
| ✓ | misc_feature | P | 2523..4046 | ▶ | 1524 | P |
| ✓ | insert | PCR 240-1 | 713..820 | ▶ | 108 | |
| ✓ | insert | PCR 240-2 | 713..823 | ▶ | 111 | |
| ✓ | insert | PCR 245-3 | 713..2401 | ▶ | 1689 | |
| ✓ | insert | PCR 254 | 2523..2759 | ▶ | 237 | |
| ✓ | insert | PCR238-1 | 20740..20743 | ▶ | 4 | |
| ✓ | misc_feature | RP602 | complement (20699..20716) | ◀ | 18 | RP602 |
| ✓ | misc_feature | Spike Protein | 4150..7968 | ▶ | 3819 | Spike Protein |
| ✓ | misc_feature | T7 TERM | 20658..20733 | ▶ | 76 | T7 TERM |
| ✓ | misc_feature | T7 promoter | 829..845 | ▶ | 17 | T7 promoter |
| ✓ | misc_feature | UTR | 717..820 | ▶ | 104 | UTR |
| ✓ | misc_feature | UTR | 20402..20510 | ▶ | 109 | UTR |
| ✓ | insert | coWuhan-Virus Spike protein Gene | 4137

| | | | | | | |
|---|---|---|---|---|---|---|
| ✓ | | misc_feature | Ampicillin | complement(21925..22776) | ◀ 851 | Ampicillin |
| ✓ | | misc_feature | F | 6166..7826 | ▶ 1662 | F |
| ✓ | | PCR_primer | GCAGAGACGCGTCTCACTTGGTTCCTAAGTTTTTATAACAATG | complement(9900..9943) | ◀ 44 | RP1418MvMV IGR PCR |
| ✓ | | PCR_primer | GCTATAACGCGTATCACTTGGTTCCTAAGTTTTTATAACAATG | complement(9900..9943) | ◀ 44 | RP1424 MV full length |
| ✓ | | misc_feature | GE | 758..768 | ▶ 11 | GE |
| ✓ | | misc_feature | GE | 2450..2460 | ▶ 11 | GE |
| ✓ | | misc_feature | GE | 4108..4118 | ▶ 11 | GE |
| ✓ | | misc_feature | GE | 5577..5587 | ▶ 11 | GE |
| ✓ | | misc_feature | GE | 7953..7958 | ▶ 6 | GE |
| ✓ | | misc_feature | GE | 20460..20470 | ▶ 11 | GE |
| ✓ | | misc_feature | GS | 5591..5607 | ▶ 17 | GS |
| ✓ | | misc_feature | GS | 4122..4138 | ▶ 17 | GS |
| ✓ | | misc_feature | GS | 20474..20490 | ▶ 17 | GS |
| ✓ | | misc_feature | GS | 2464..2480 | ▶ 17 | GS |
| ✓ | | misc_feature | GS | 772..788 | ▶ 17 | GS |
| ✓ | | misc_feature | H | 7987..9837 | ▶ 1851 | H |
| ✓ | | insert | H-MCS-L | 9813..9943, 13788..13791 | ▶ 135 | |
| ✓ | | misc_feature | HH Ribozyme | 667..716 | ▶ 50 | HH Ribozyme |
| ✓ | | misc_feature | L | 13850..20401 | ▶ 6552 | L |
| ✓ | | misc_feature | M | 4154..5161 | ▶ 1008 | M |
| ✓ | | insert | MV Wu S in position 3 | 9944..13787 | ▶ 3844 | |
| | | insert | MV-GFP corrected | 2523..2759 | ▶ 237 | |
| | | insert | MV-GFP corrected | 824..2401 | ▶ 1578 | |
| ✓ | | misc_feature | MV33F | 19956..19975 | ▶ 20 | MV33F |
| ✓ | | misc_feature | MV4F | 2158..2177 | ▶ 20 | MV4F |
| ✓ | | misc_feature | MV5F | 2643..2661 | ▶ 19 | MV5F |
| ✓ | | misc_feature | N | 824..2398 | ▶ 1575 | N |
| ✓ | | misc_feature | P | 2523..4046 | ▶ 1524 | P |
| ✓ | | insert | PCR 240-1 | 713..820 | ▶ 108 | |
| ✓ | | insert | PCR 240-2 | 713..823 | ▶ 111 | |
| | | insert | PCR 245-3 | 713..2401 | ▶ 1689 | |
| ✓ | | insert | PCR 254 | 2523..2759 | ▶ 237 | |
| ✓ | | insert | PCR238-1 | 20740..20743 | ▶ 4 | |
| ✓ | | misc_feature | RP602 | complement(20699..20716) | ◀ 18 | RP602 |
| ✓ | | misc_feature | T7 TERM | 20658..20733 | ▶ 76 | T7 TERM |
| ✓ | | misc_feature | T7 promoter | 629..645 | ▶ 17 | T7 promoter |
| ✓ | | PCR_primer | TATCACTCTGTGTGGACCTGGTTCCTAAGTTTTTATAACAATG | complement(9900..9943) | ◀ 44 | RP1433 MV PCR |
| ✓ | | misc_feature | UTR | 717..820 | ▶ 104 | UTR |
| ✓ | | misc_feature | UTR | 20402..20510 | ▶ 109 | UTR |
| ✓ | | misc_feature | co Spike Protein Gene | 9957..13775 | ▶ 3819 | co Spike Protein Gene |
| | | insert | coWuhan-Virus Spike protein Gene | 9944..13787 | ▶ 3844 | |
| ✓ | | misc_feature | hHdVRzym | 20511..20596 | ▶ 86 | hHdVRzym |
| ✓ | | insert | pCW64001 | 2402..2522 | ▶ 121 | |
| | | insert | pCW661 | 7959..9943, 13788..13791 | ▶ 1989 | |

BBV151 Vaccine Presentations

FIG. 19, continued

FIG. 20, continued

CORONAVIRUS DISEASE (COVID-19) VACCINE

CROSS-REFERENCE TO RELATED APPLICATIONS

This application claims priority to U.S. Provisional Application No. 62/986,396 filed Mar. 6, 2020 and to U.S. Provisional Application No. 63/017,241 filed Apr. 29, 2020, each of which is herein incorporated by reference in its entirety.

STATEMENT REGARDING FEDERALLY SPONSORED RESEARCH OR DEVELOPMENT

This invention was made with government support under grant no. 1R21AI158044-01 awarded by the National Institute of Health. The government has certain rights in the invention.

REFERENCE TO SEQUENCE LISTING

The Sequence Listing concurrently submitted herewith as a text file named "205961_7055US1_Sequence_Listing.txt," created on Mar. 4, 2021 and having a size of 577,339 bytes is herein incorporated by reference pursuant to 37 C.F.R. § 1.52(e)(5).

BACKGROUND OF THE INVENTION

The recently emerged coronavirus, currently called 2019-nCoV or SARS-CoV-2 virus, is rapidly spreading in China and Asia with over 42,000 cases, 500 deaths and cases in 18 countries as of Feb. 10, 2020. This novel coronavirus is thought to have emerged from a live animal market in Wuhan, China, and has quickly spread in the community with large clusters of human to human transmission. The sequence of several isolates have been determined, and the closest strains are SARS-like bat coronavirus lineages. Little is known about this virus including its susceptibility to anti-viral compounds, ability to replicate in cell lines or host factors regulating replication. Importantly there are no therapeutics available to treat the virus, although investigational studies are underway. Modeling of the current outbreak suggests that the virus could infect >1 billion people and become a yearly epidemic.

A need exists for novel methods for generating vaccines to treat Coronaviruses, in particular, COVID-19. The present invention addresses and satisfies this need.

SUMMARY OF THE INVENTION

In some aspects, the present disclosure provides an isolated nucleic acid encoding a recombinant virus comprising a SARS-CoV-2 spike protein (S) or a portion thereof.

In other aspects, the present disclosure provides a recombinant virus comprising a SARS-CoV-2 spike protein (S) or a portion thereof.

In one aspect, the present disclosure provides a recombinant virus encoded by a nucleic acid described herein. In some embodiments, the nucleic acid encodes a recombinant virus comprising a SARS-CoV-2 spike protein (S) or a portion thereof.

In another aspect, the present disclosure provides a recombinant fusion protein comprising (a) a glycoprotein (G) of a virus or a portion thereof, and (b) a SARS-CoV-2 spike protein (S) or a portion thereof In some aspects, the present disclosure provides a vector comprising a nucleic acid described herein. In one embodiment, the nucleic acid encodes a recombinant virus comprising a SARS-CoV-2 spike protein (S) or a portion thereof.

In other aspects, the present disclosure provides a vaccine comprising a recombinant virus comprising a SARS-CoV-2 spike protein (S) or a portion thereof, and a pharmaceutically acceptable carrier.

In one aspect, the present disclosure provides a method of generating an immune response against a SARS-CoV-2 virus in a subject in need thereof, the method comprising administering to the subject an effective amount of a vaccine described herein. In some embodiments, the vaccine comprises a recombinant virus comprising a SARS-CoV-2 spike protein (S) or a portion thereof, and a pharmaceutically acceptable carrier.

In another aspect, the present disclosure provides a method of vaccinating a subject against a SARS-CoV-2 virus, the method comprising administering to the subject an effective amount of the vaccine described herein. In some embodiments, the vaccine comprises a recombinant virus comprising a SARS-CoV-2 spike protein (S) or a portion thereof, and a pharmaceutically acceptable carrier.

In other aspects, the present disclosure provides a method of providing immunity against a SARS-CoV-2 virus in a subject, the method comprising administering to the subject an effective amount of the vaccine described herein. In some embodiments, the vaccine comprises a recombinant virus comprising a SARS-CoV-2 spike protein (S) or a portion thereof, and a pharmaceutically acceptable carrier.

In some aspects, the present disclosure provides a method of treating and/or preventing a disease or disorder associated with a SARS-CoV-2 virus in a subject in need thereof, the method comprising administering to the subject an effective amount of the vaccine described herein. In some embodiments, the vaccine comprises a recombinant virus comprising a SARS-CoV-2 spike protein (S) or a portion thereof, and a pharmaceutically acceptable carrier.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 7 shows the features of the map shown in FIG. 1.
FIG. 8 shows the features of the map shown in FIG. 2.
FIG. 9 shows the features of the map shown in FIG. 3.
FIG. 10 shows the features of the map shown in FIG. 4.
FIG. 11 shows the features of the map shown in FIG. 5.

Figure 12:
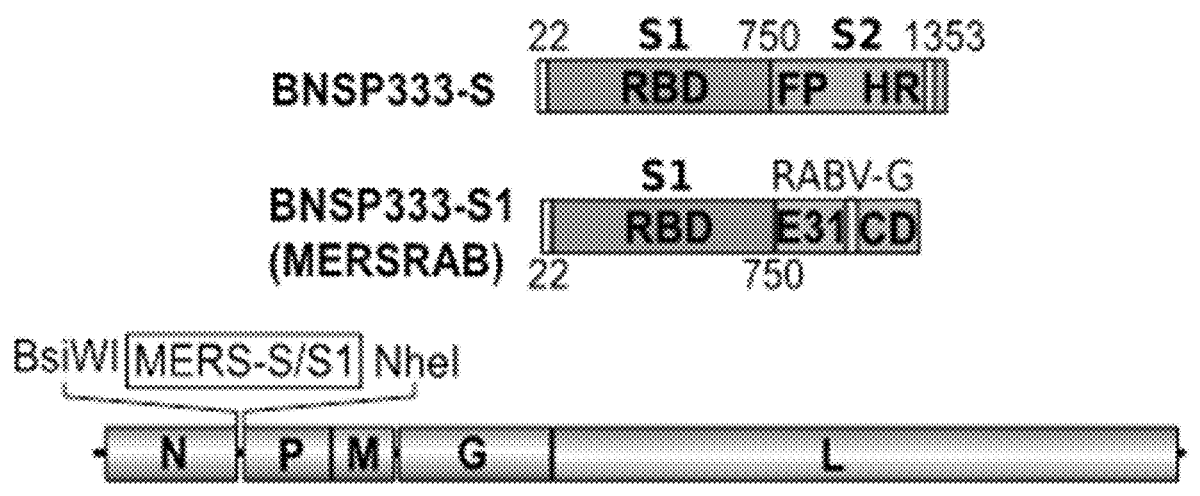

FIG. 12: Schematic illustration of the 2019-nCoV vaccine constructs used in this study. Spike protein cDNA is inserted between the N and P genes of the SAD-B19-derived RABV virus vaccine vector BNSP333. The BNSP333-S1-G construct expresses a chimeric protein that contains the entire S1 domain fused to the C-terminal part of the RABV G glycoprotein (amino acids 428-524), which encompasses the entire cytoplasmic domain (CD), the transmembrane domain (TM), plus 31 amino acids of the ectodomain (E31) of RABV G. Different structural elements of the spike protein are indicated in the full length construct: signal peptide (SP), receptor-binding domain (RBD), fusion peptide (FP), heptad repeat regions 1 and 2 (HR1 and HR2), transmembrane domain (TM), and cytoplasmic domain (CD).

Figures 16A, 16B:
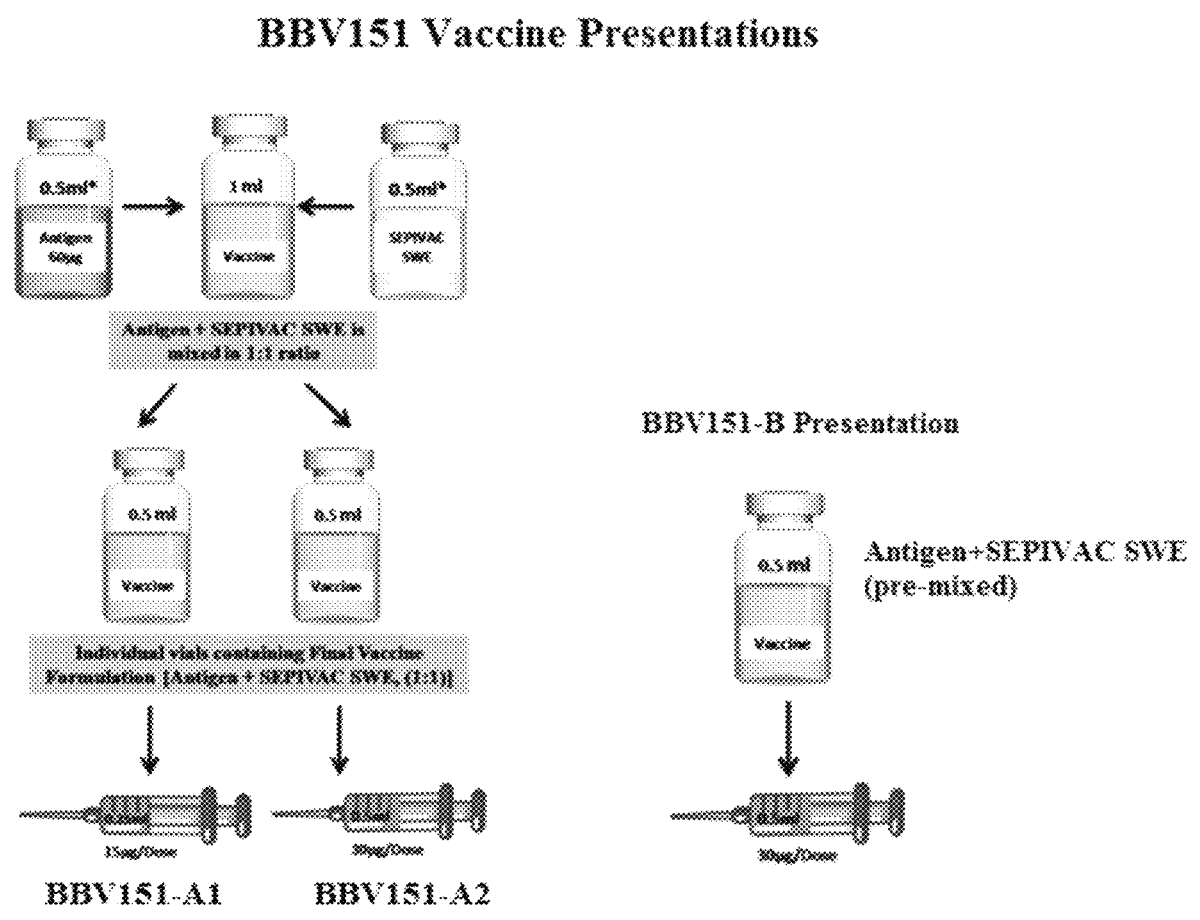

FIGS. 16A-16B: FIG. 16A is a presentation showing formulation of BBV151-A vaccine (BBV151-A1 & BBV151-A2) and FIG. 16B is a presentation showing formulation of BBV-151-B vaccine.

Figure 17:
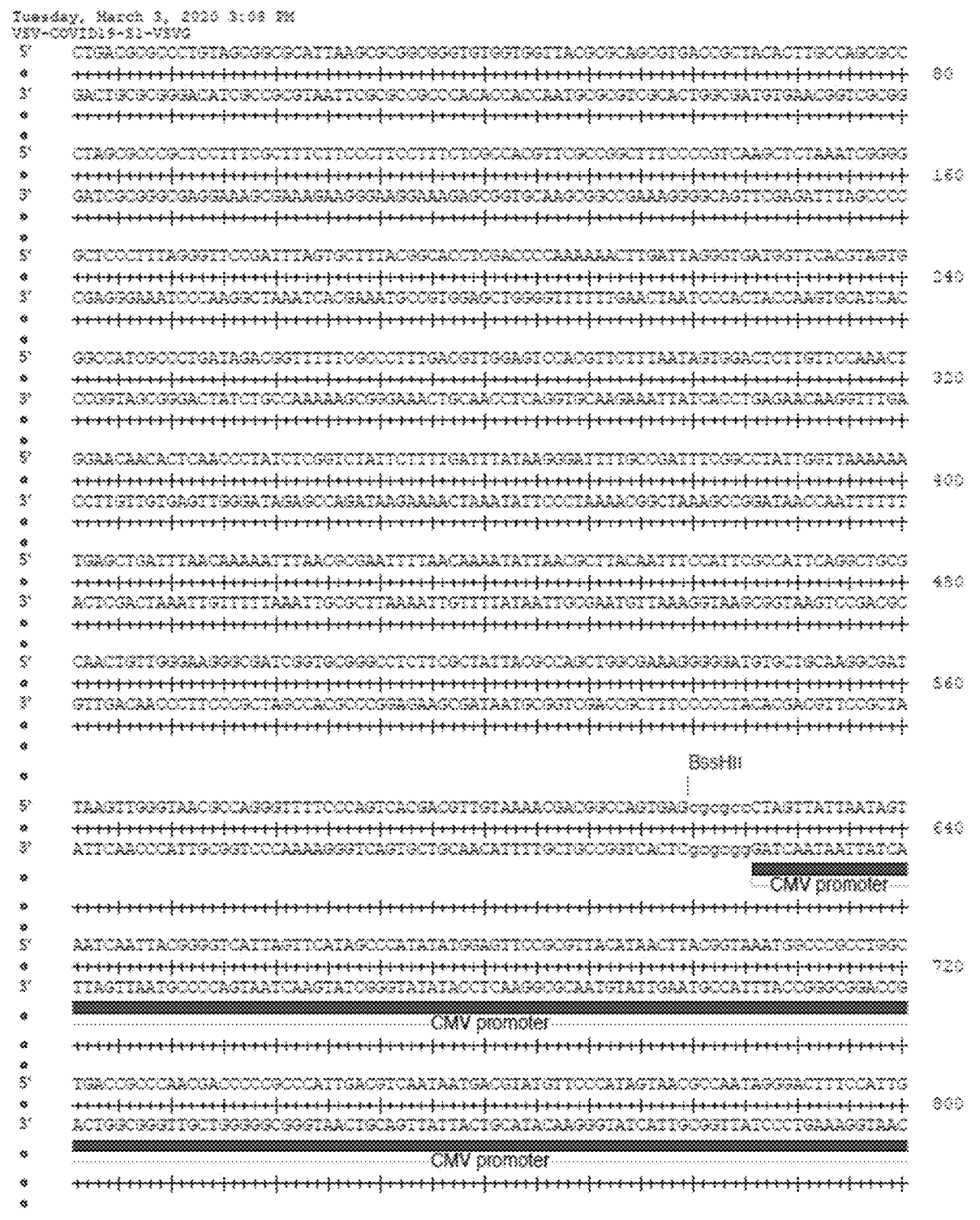
Figure 17:
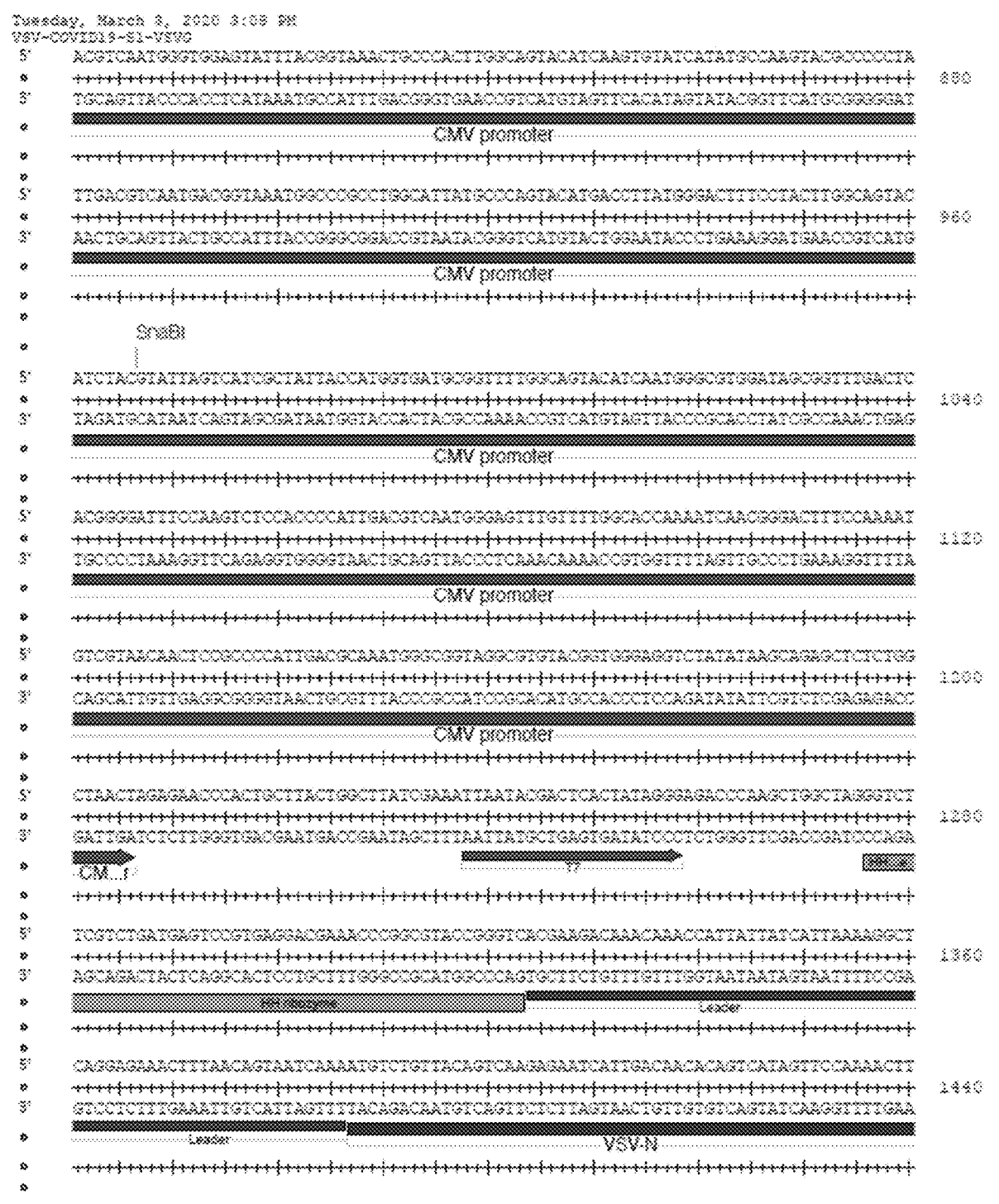
Figure 17:
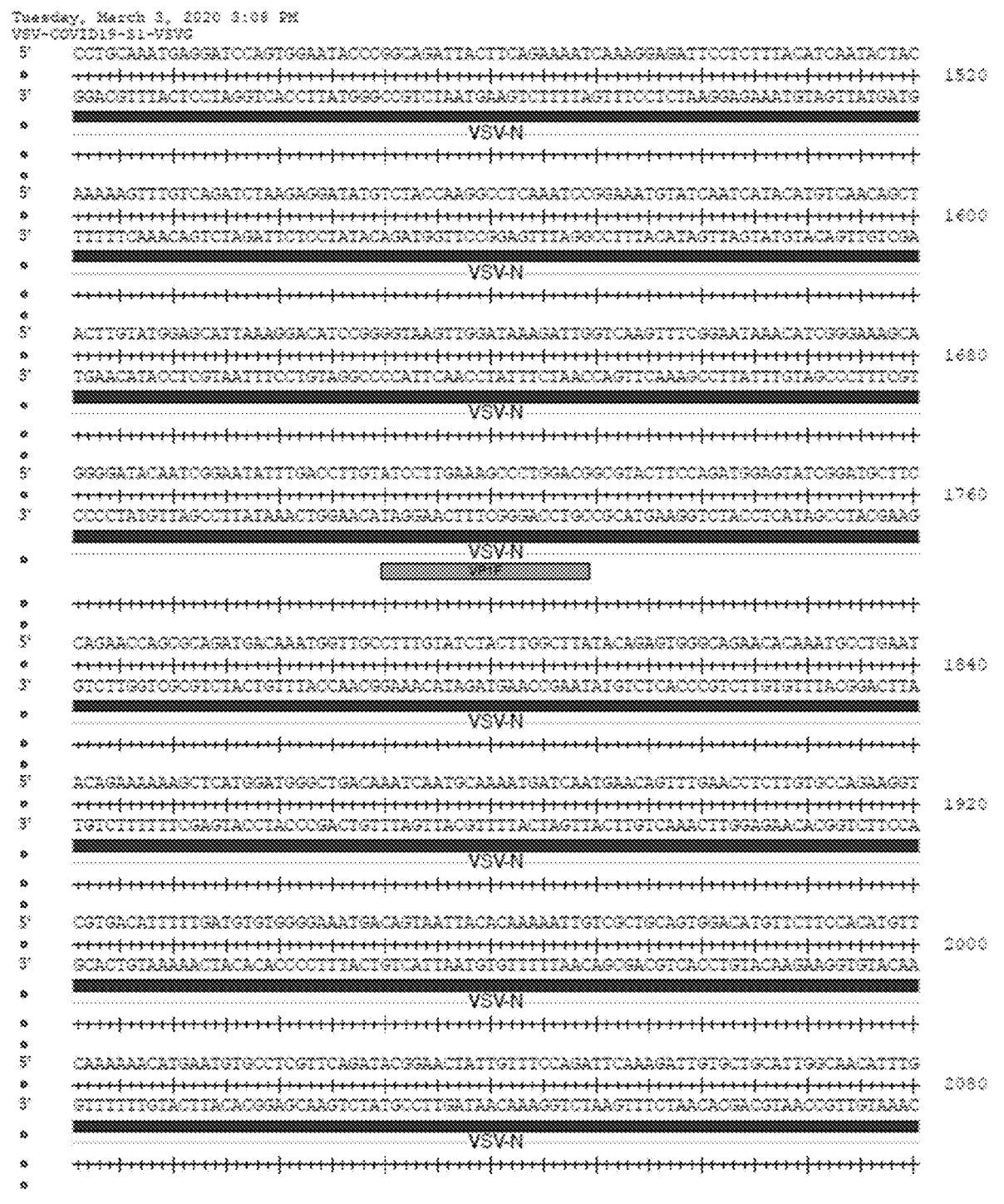
Figure 17:
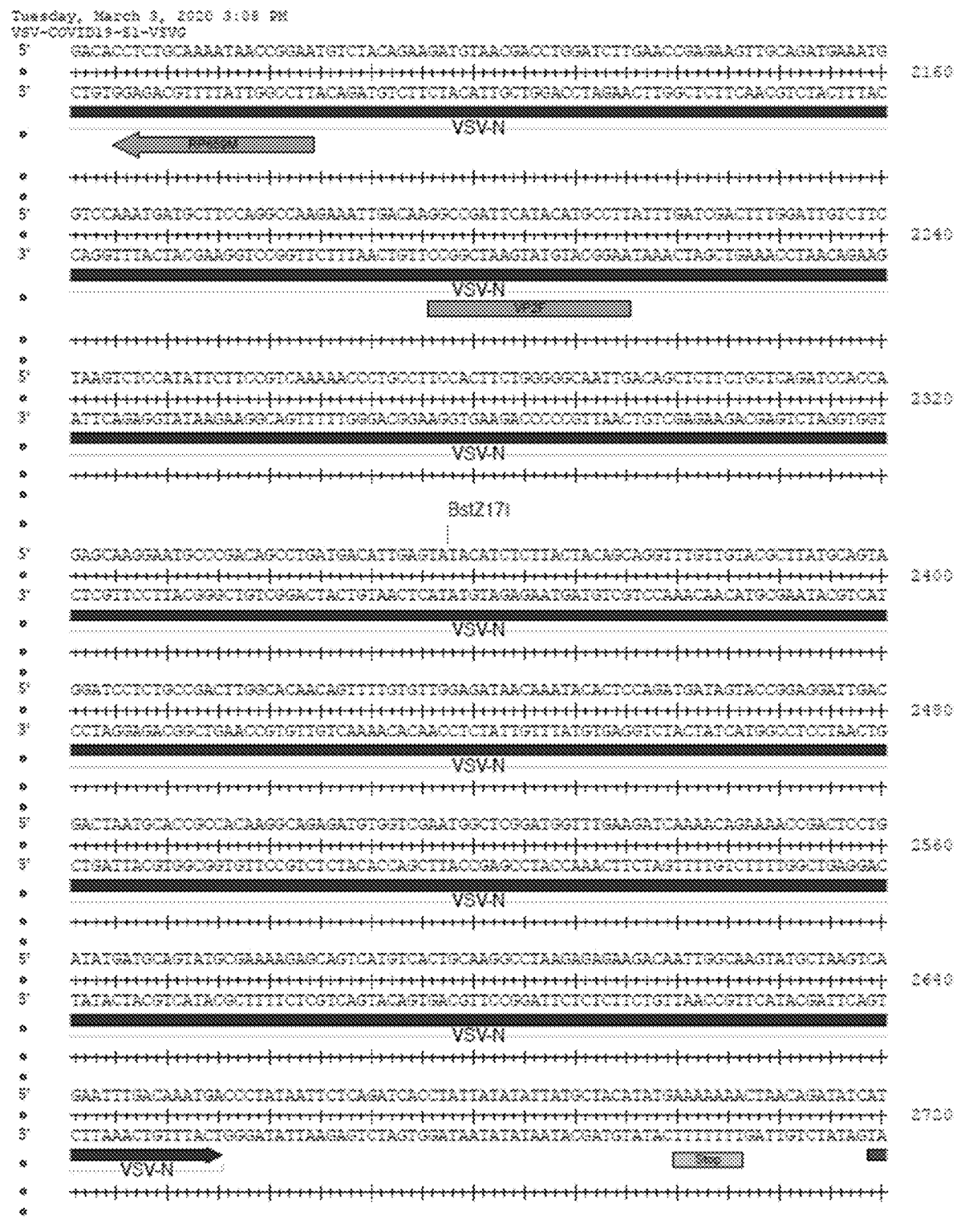
Figure 17:
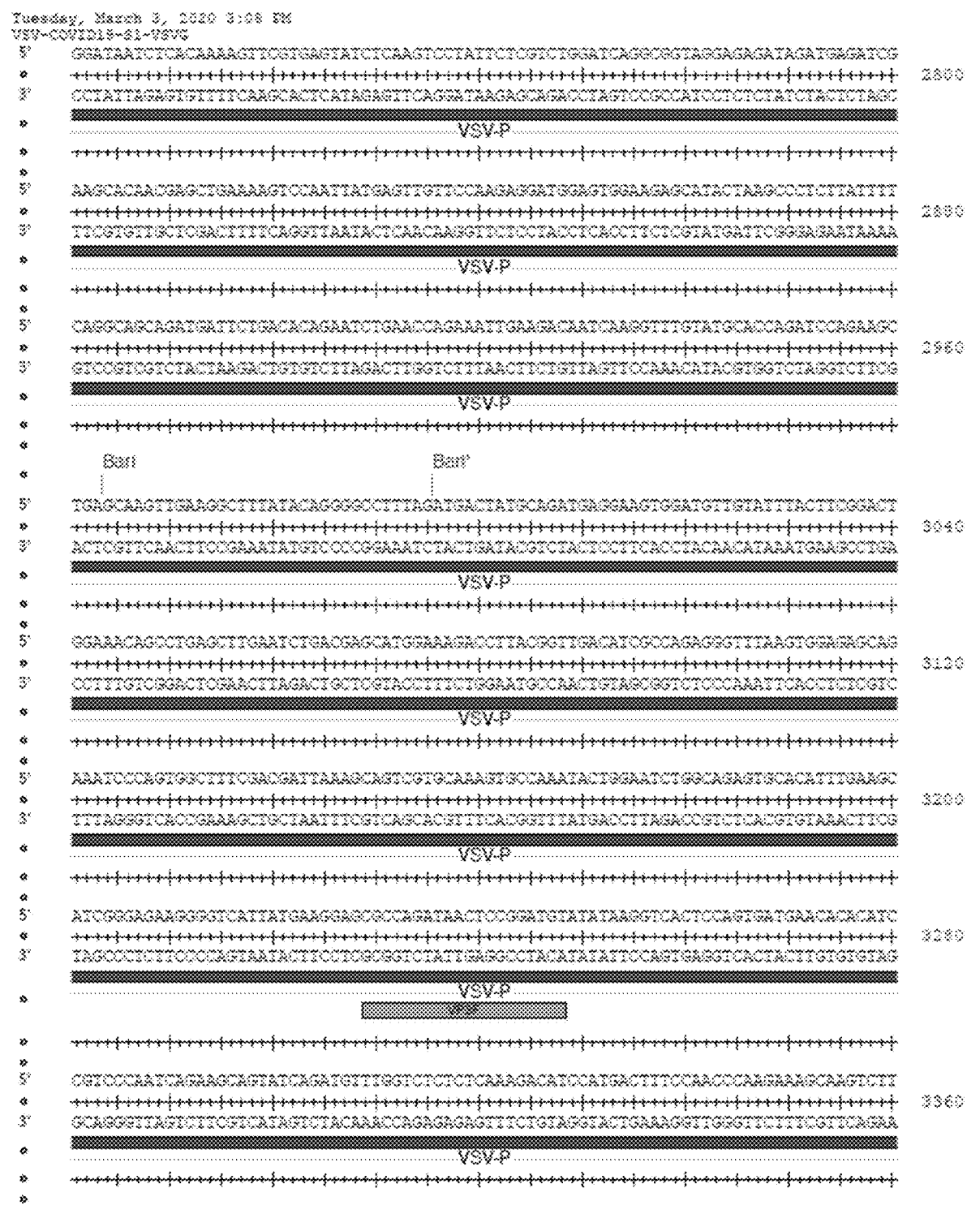
Figure 17:
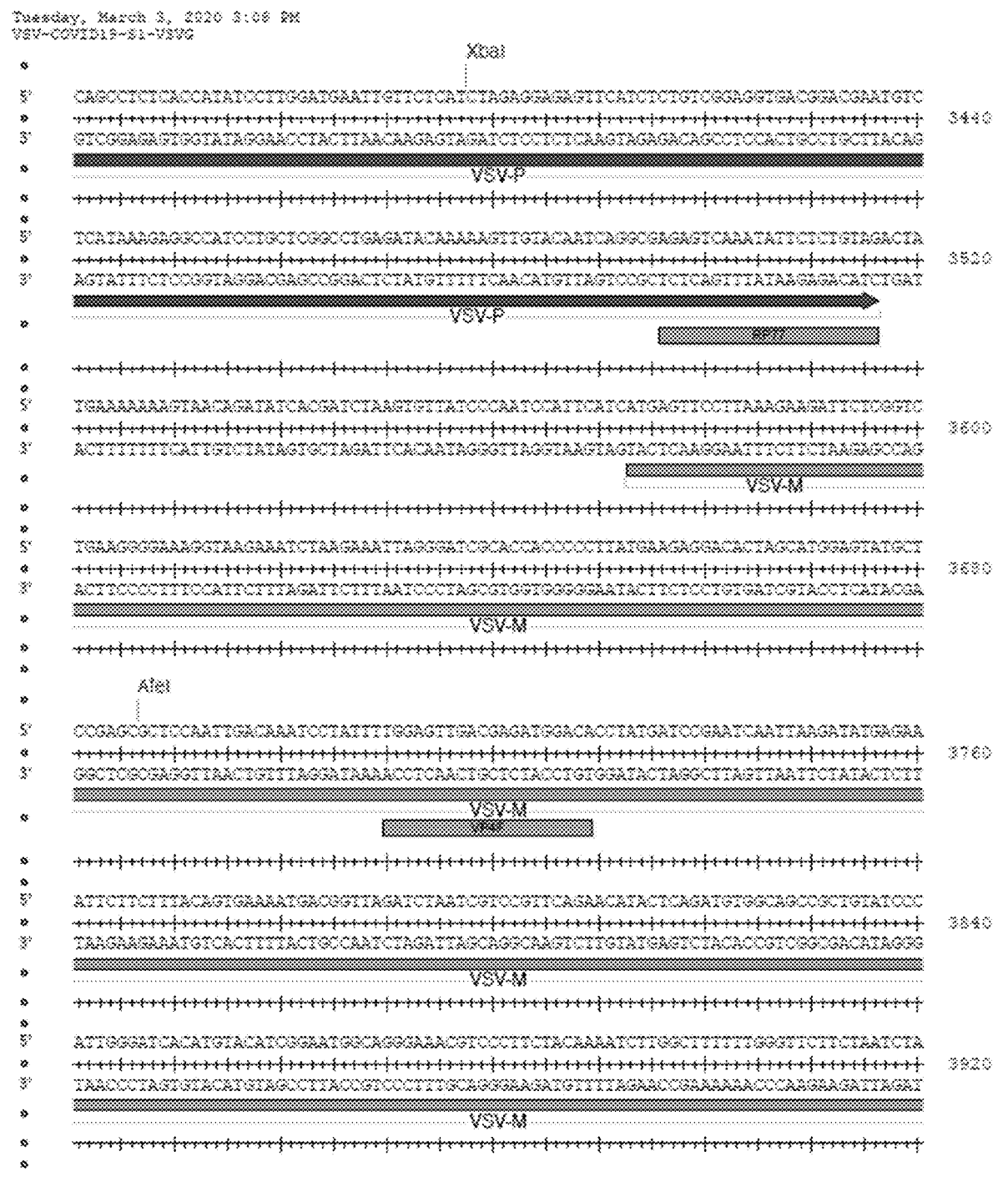
Figure 17:
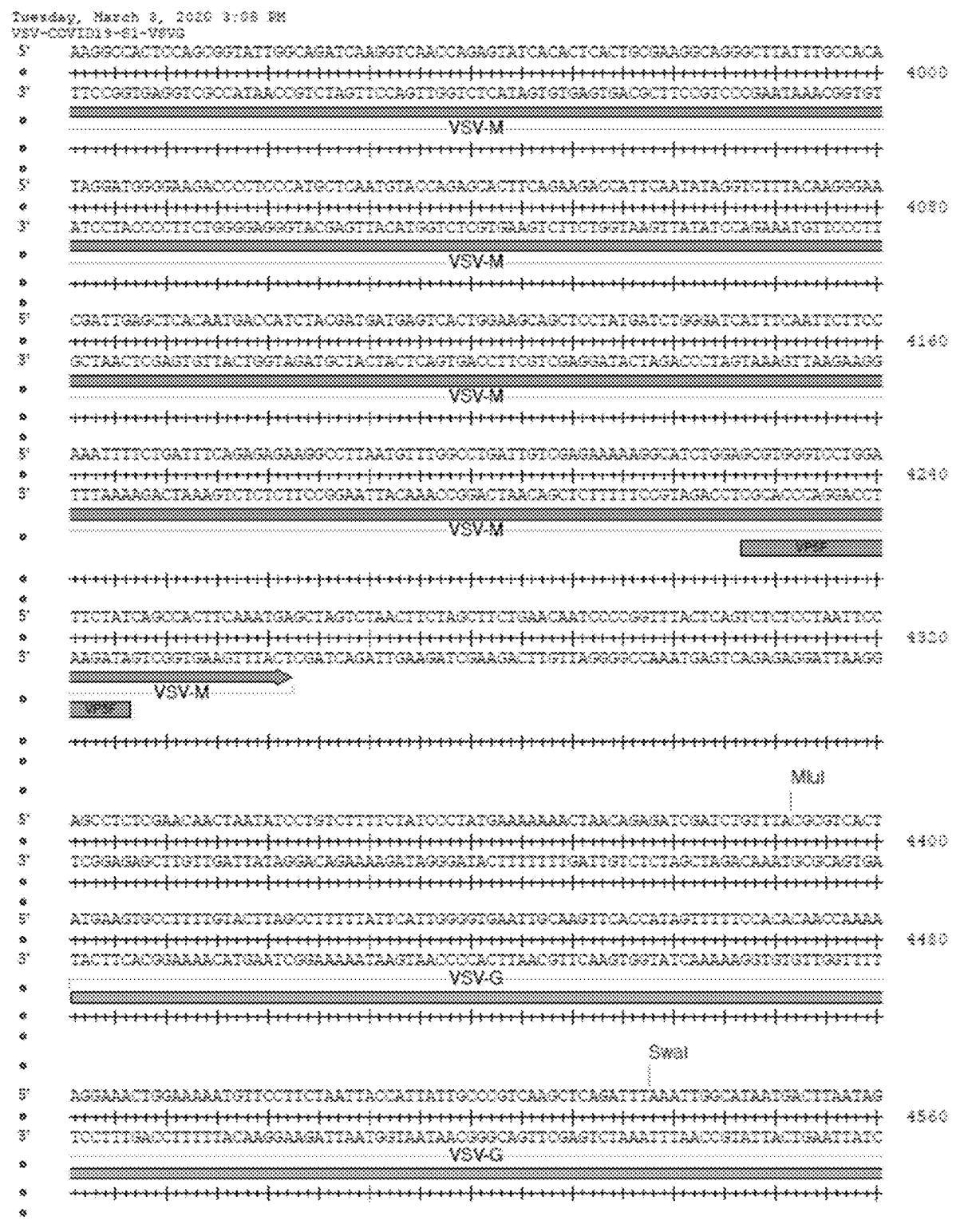
Figure 17:
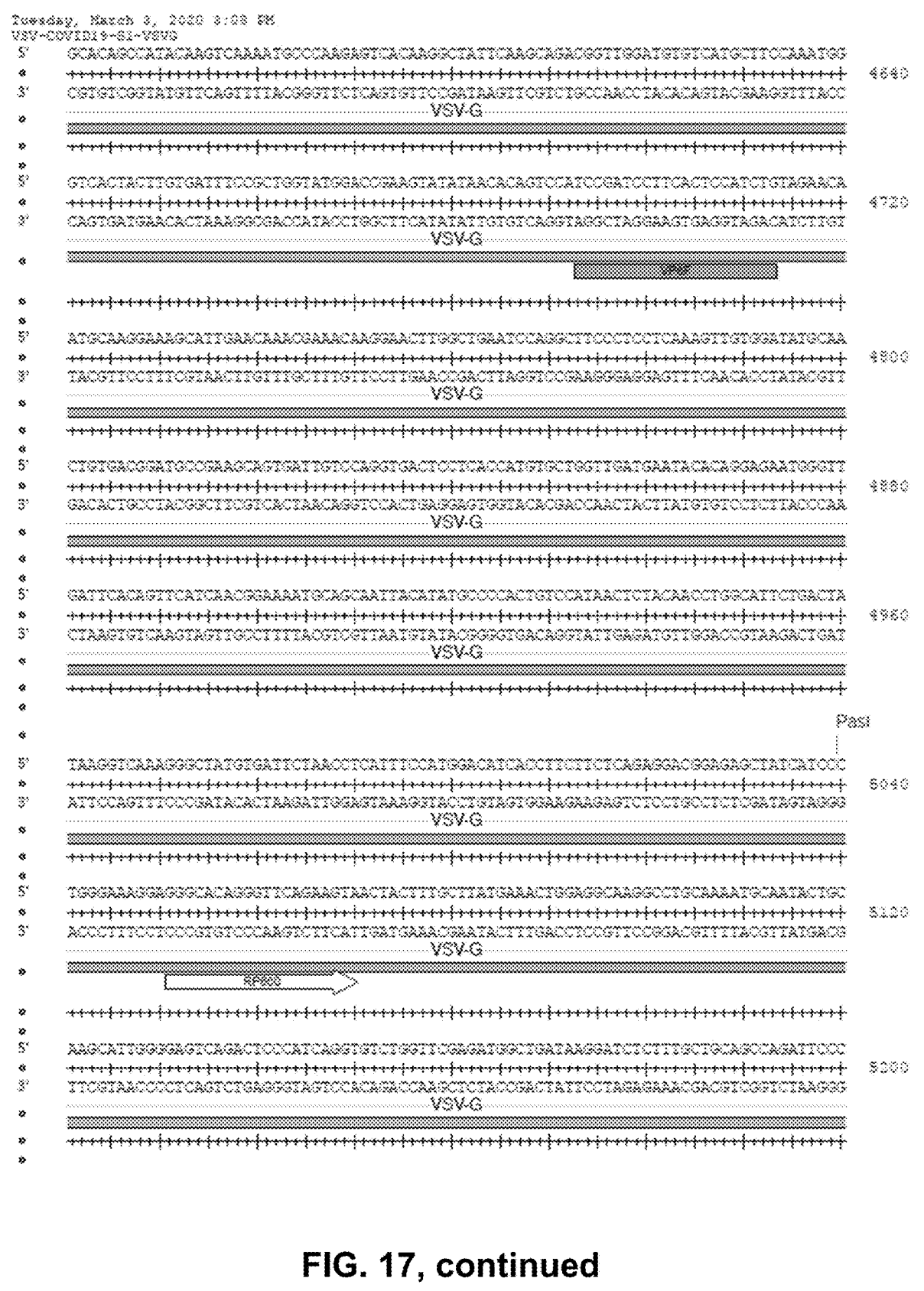
Figure 17:
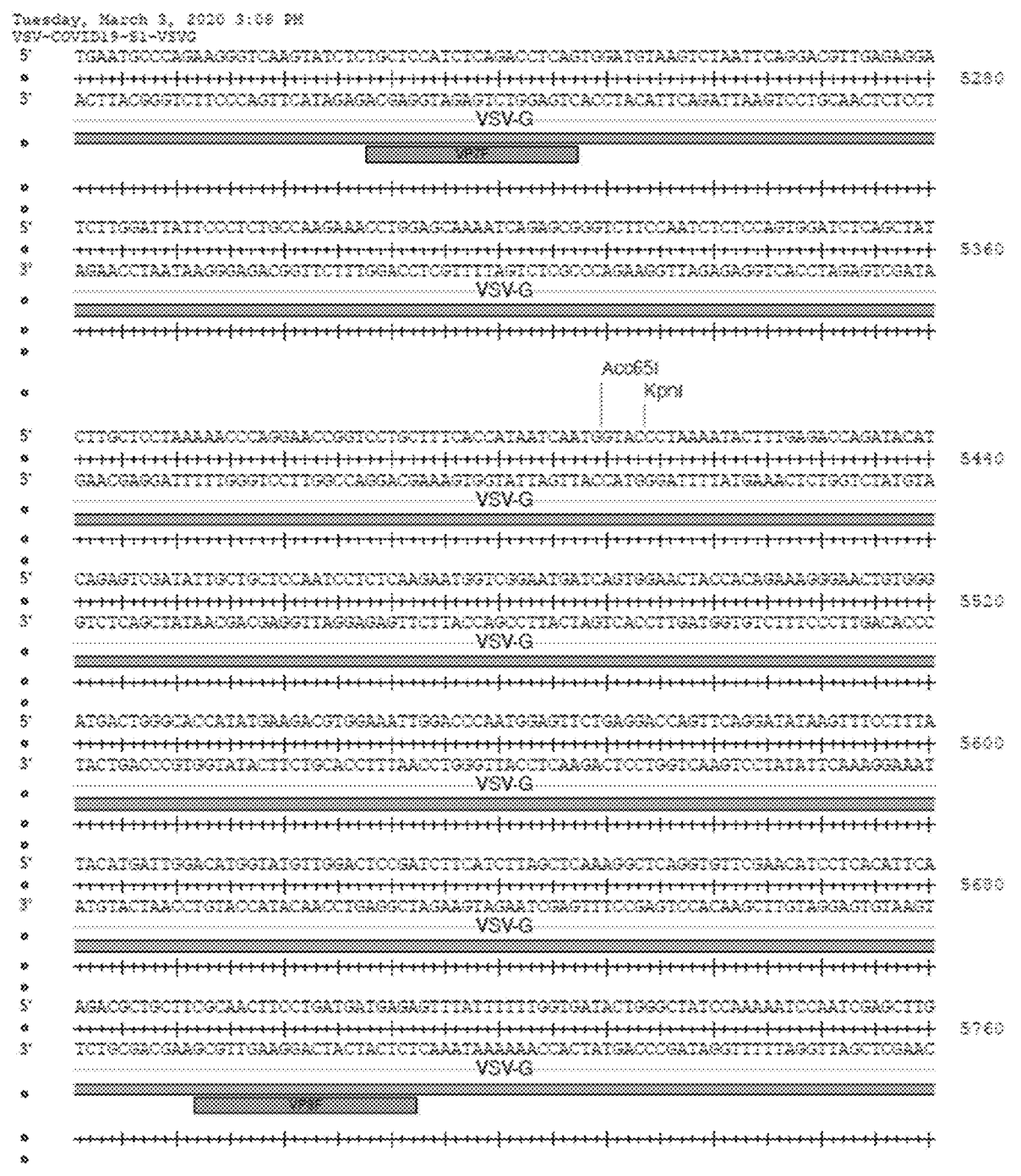
Figure 17:
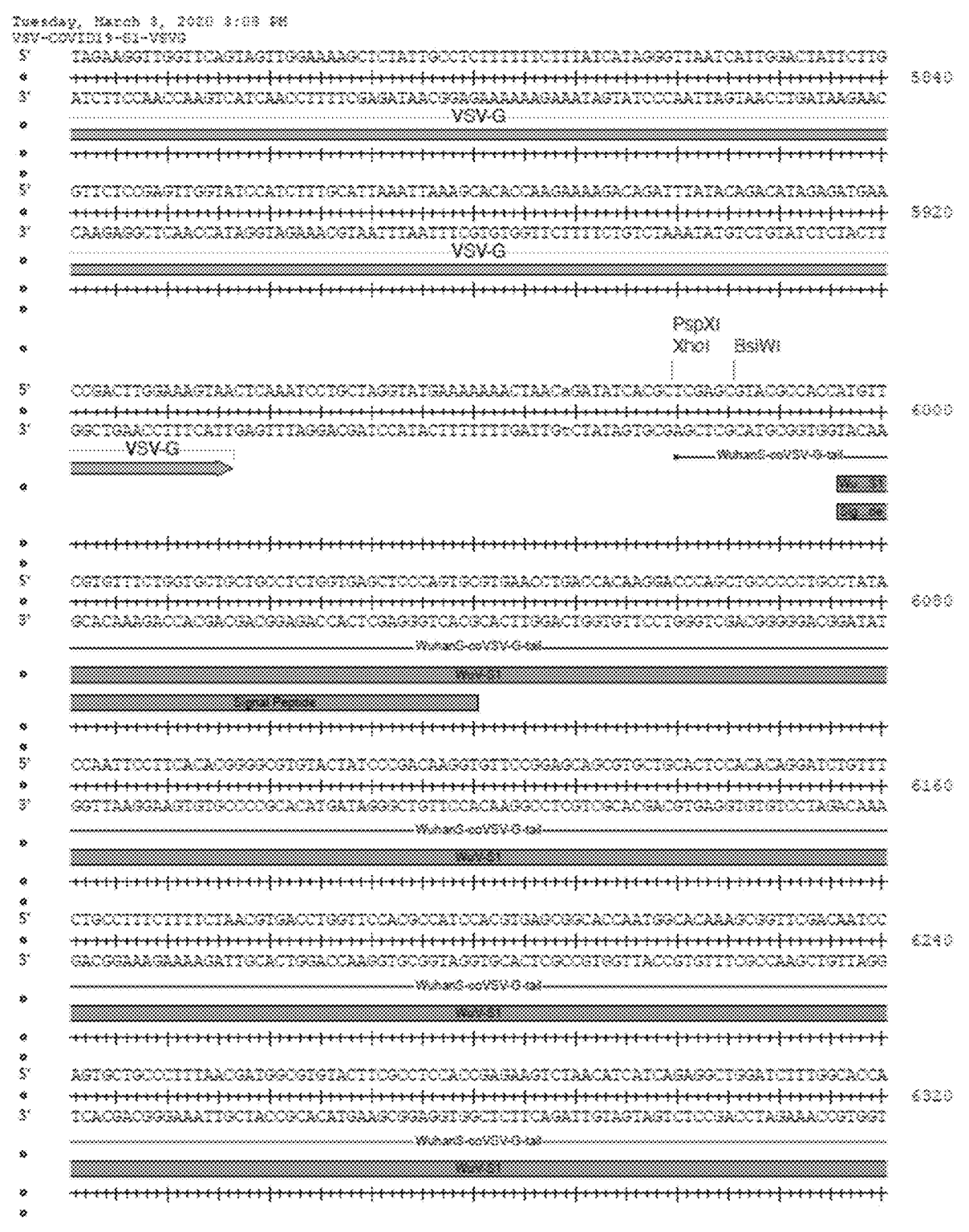
Figure 17:
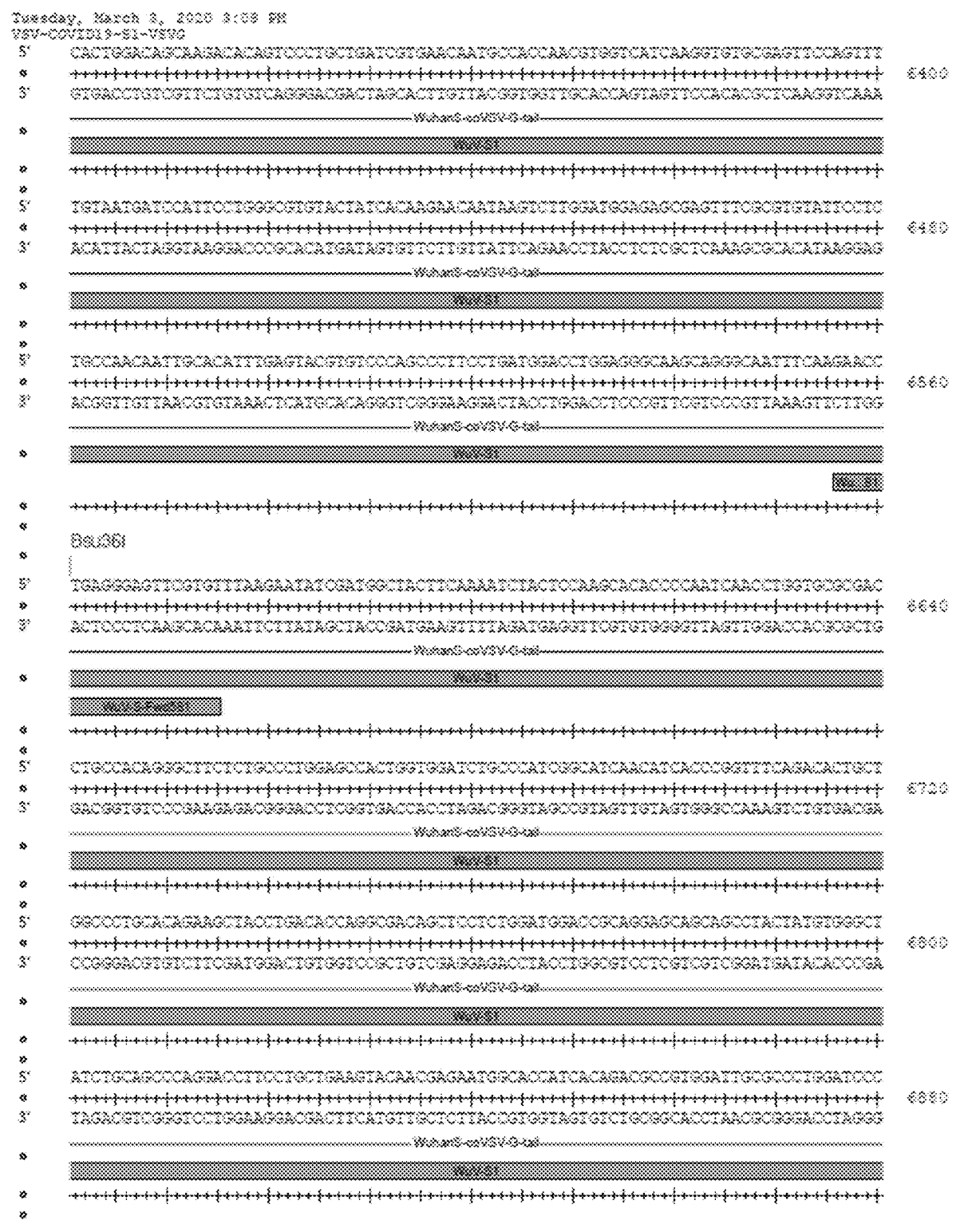
Figure 17:
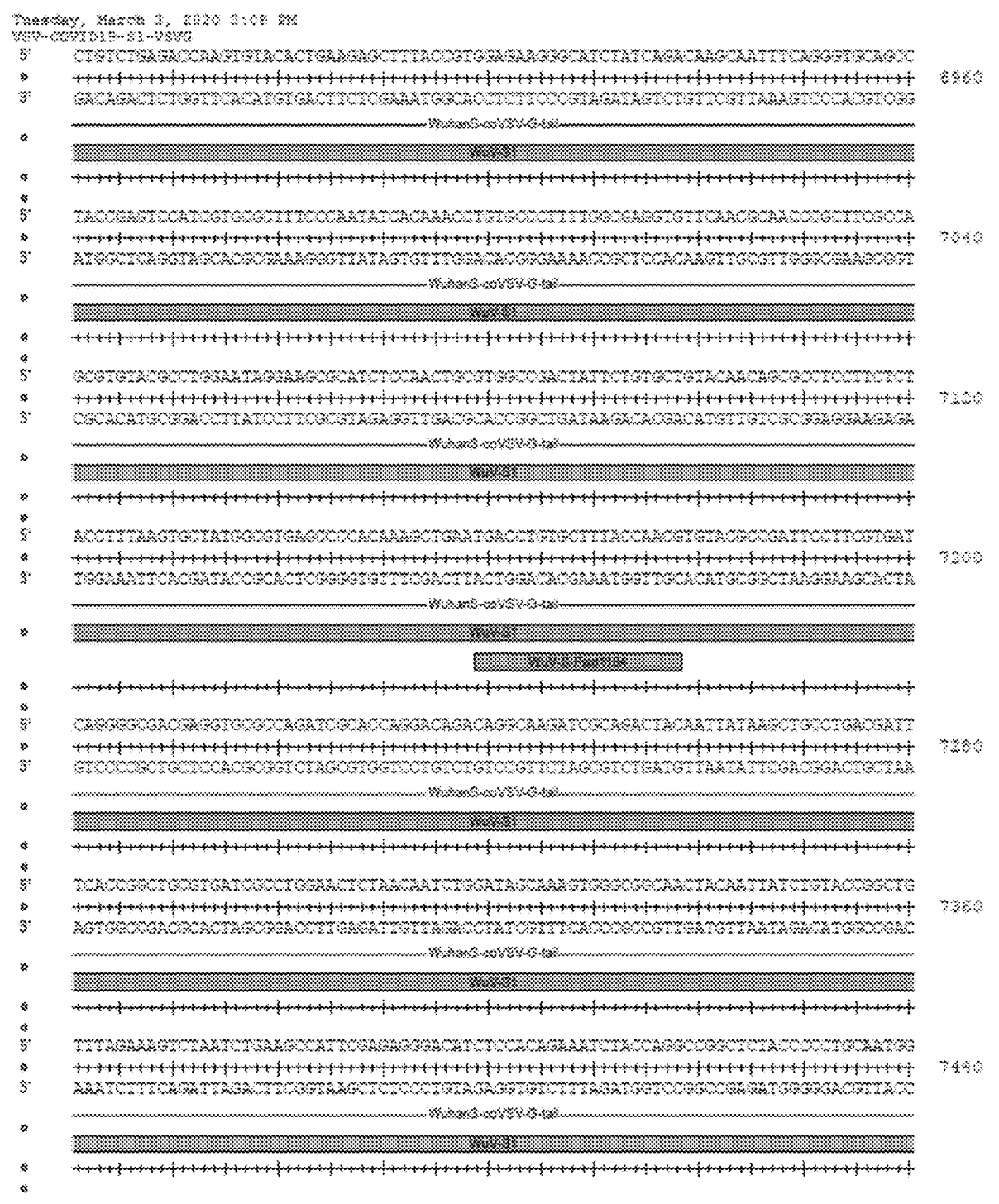
Figure 17:
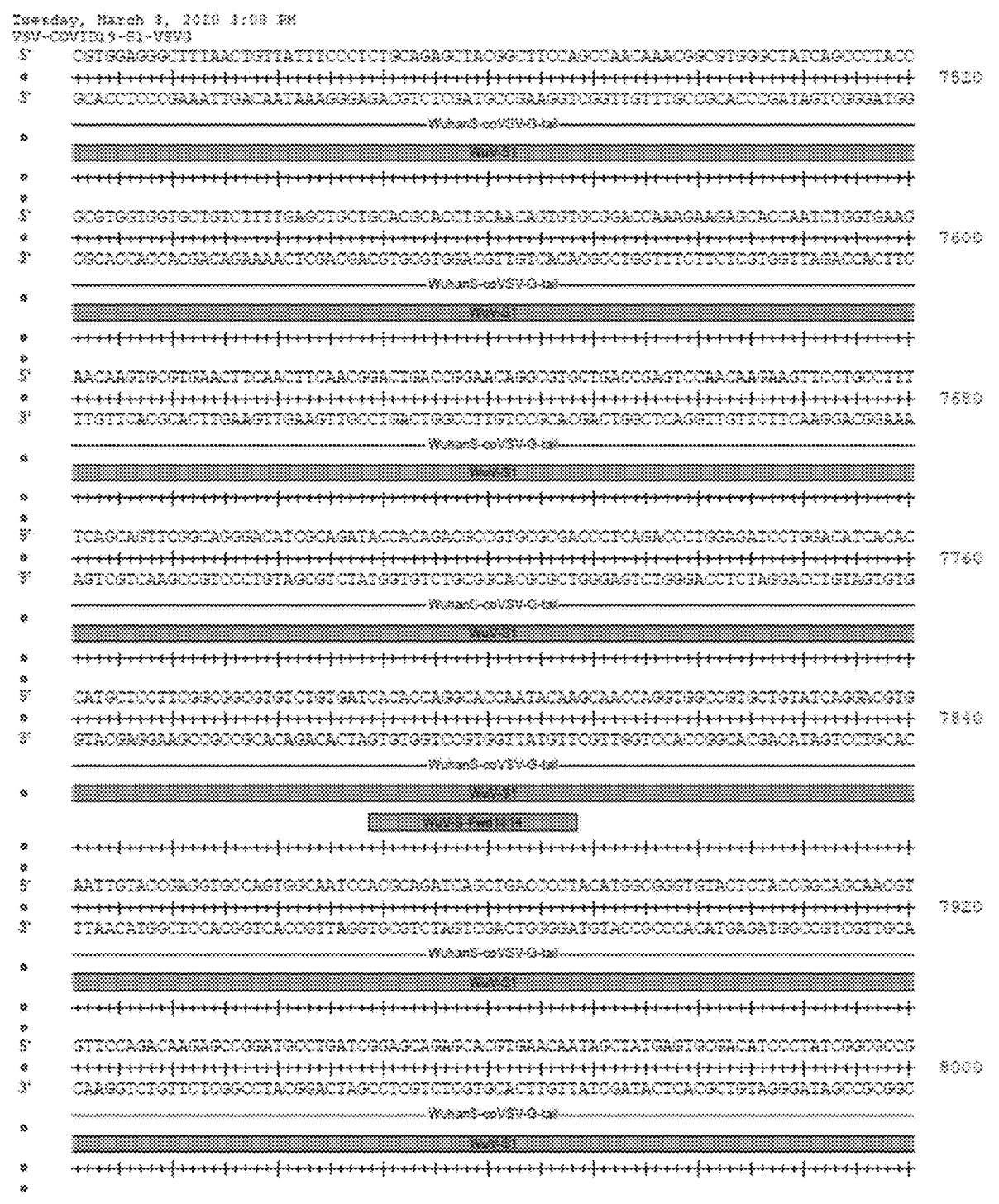
Figure 17:
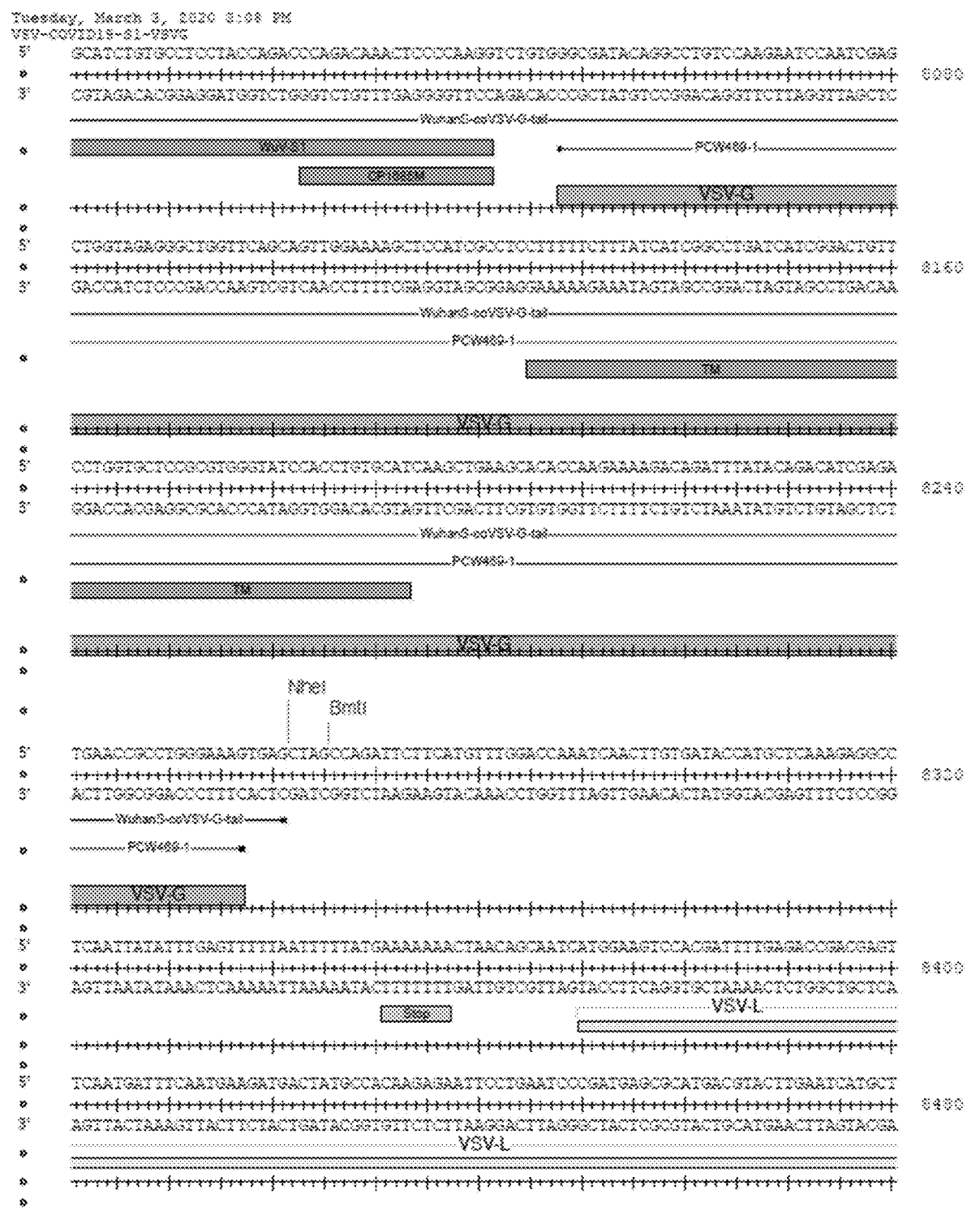
Figure 17:
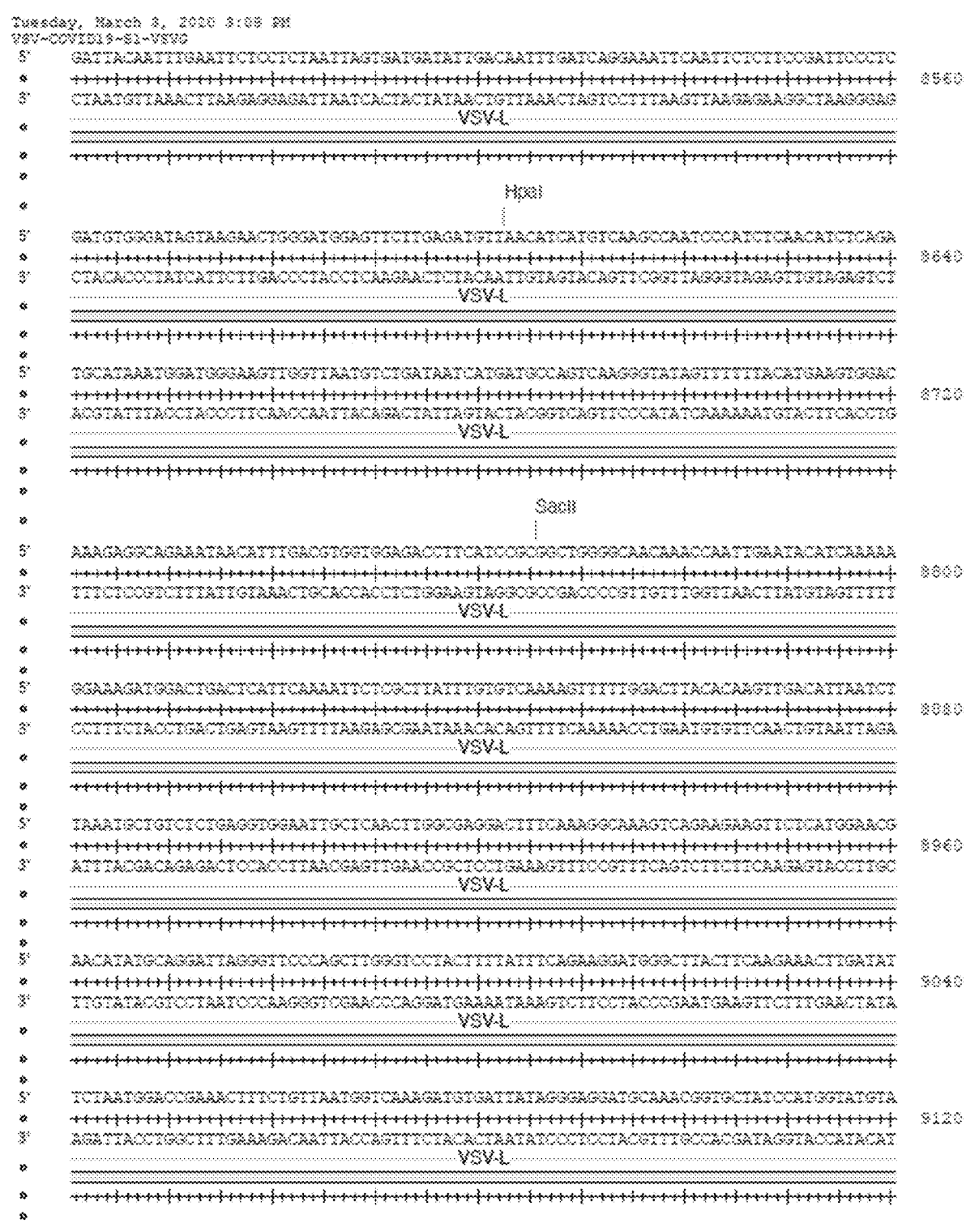
Figure 17:
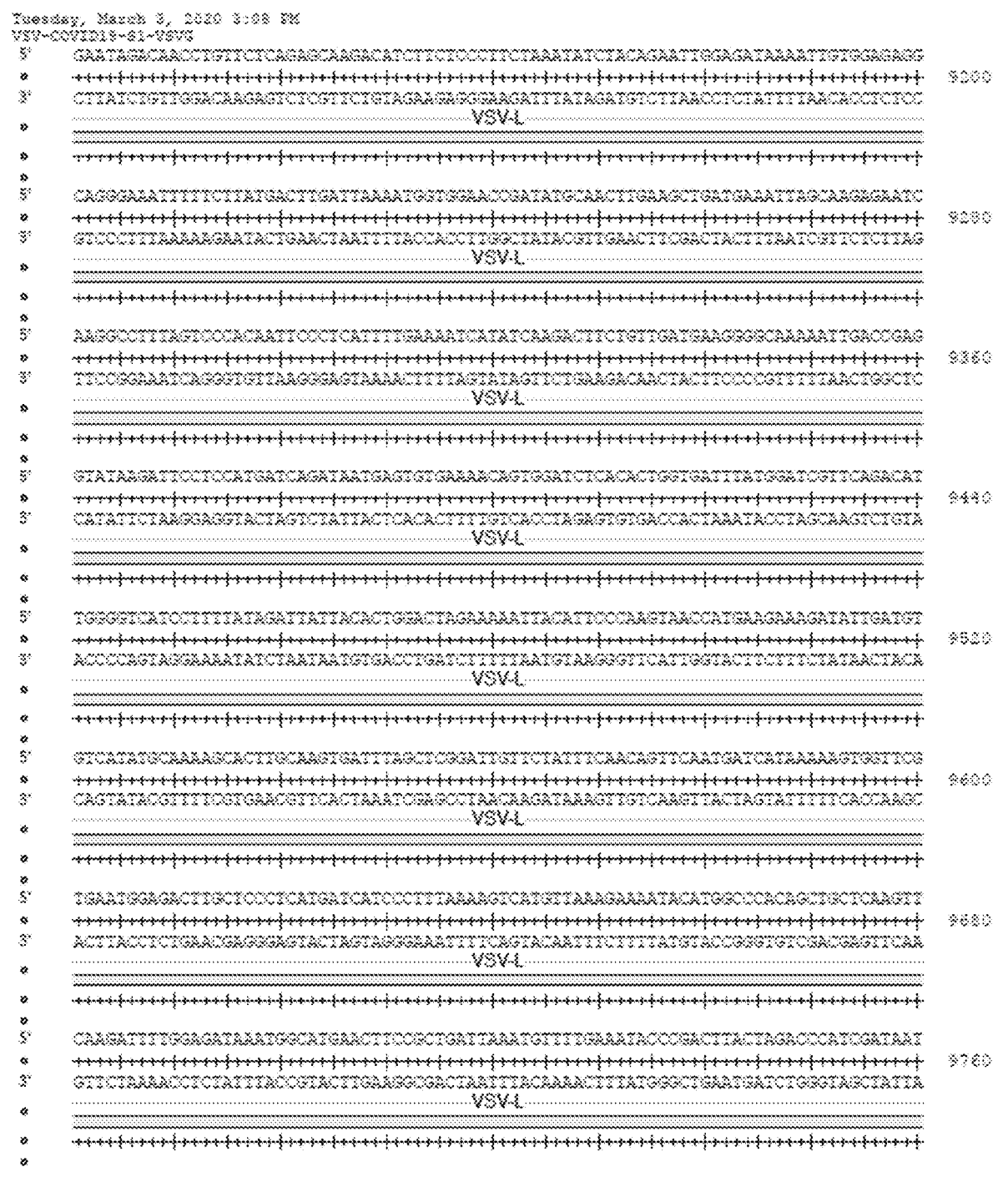
Figure 17:
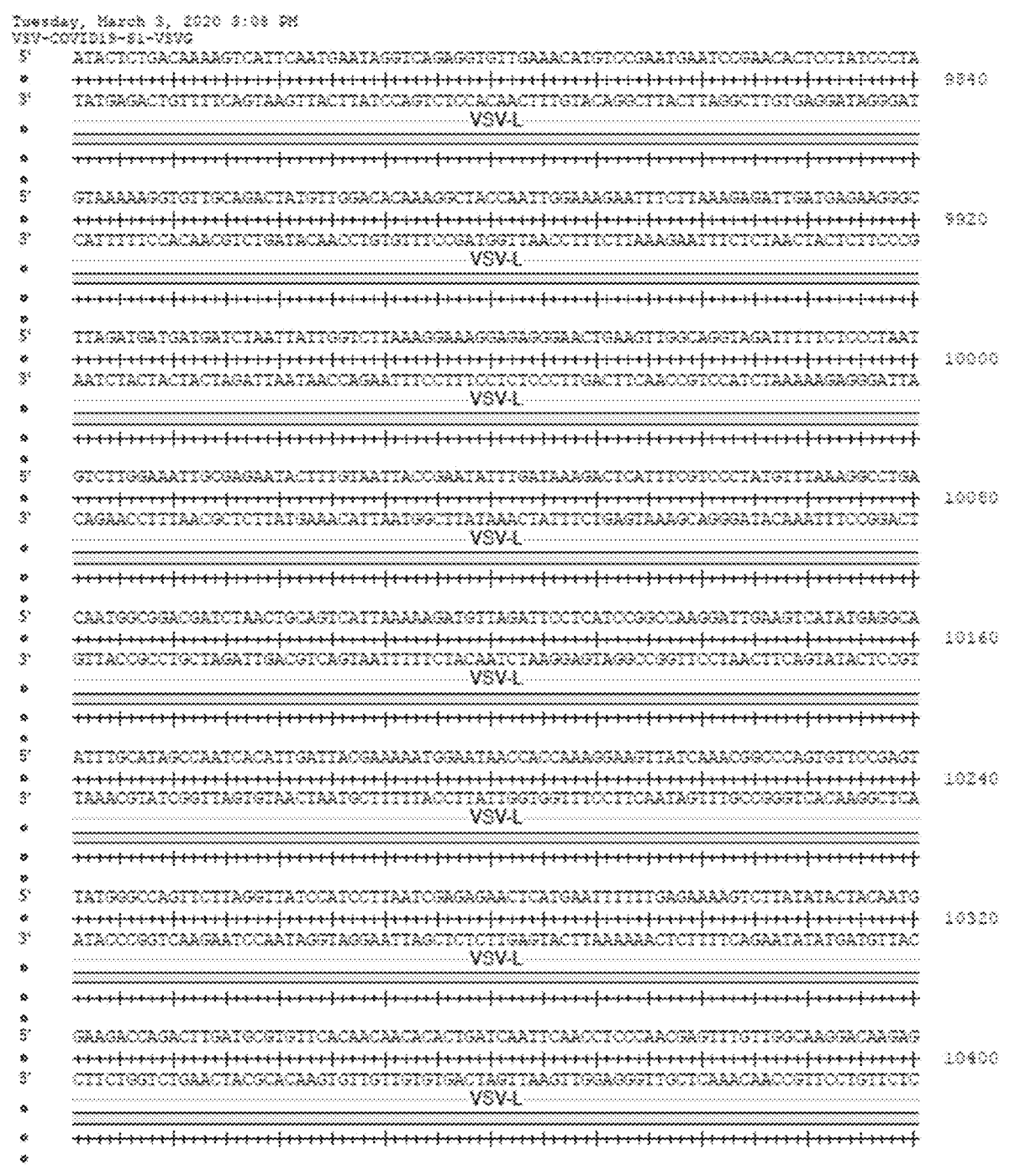
Figure 17:
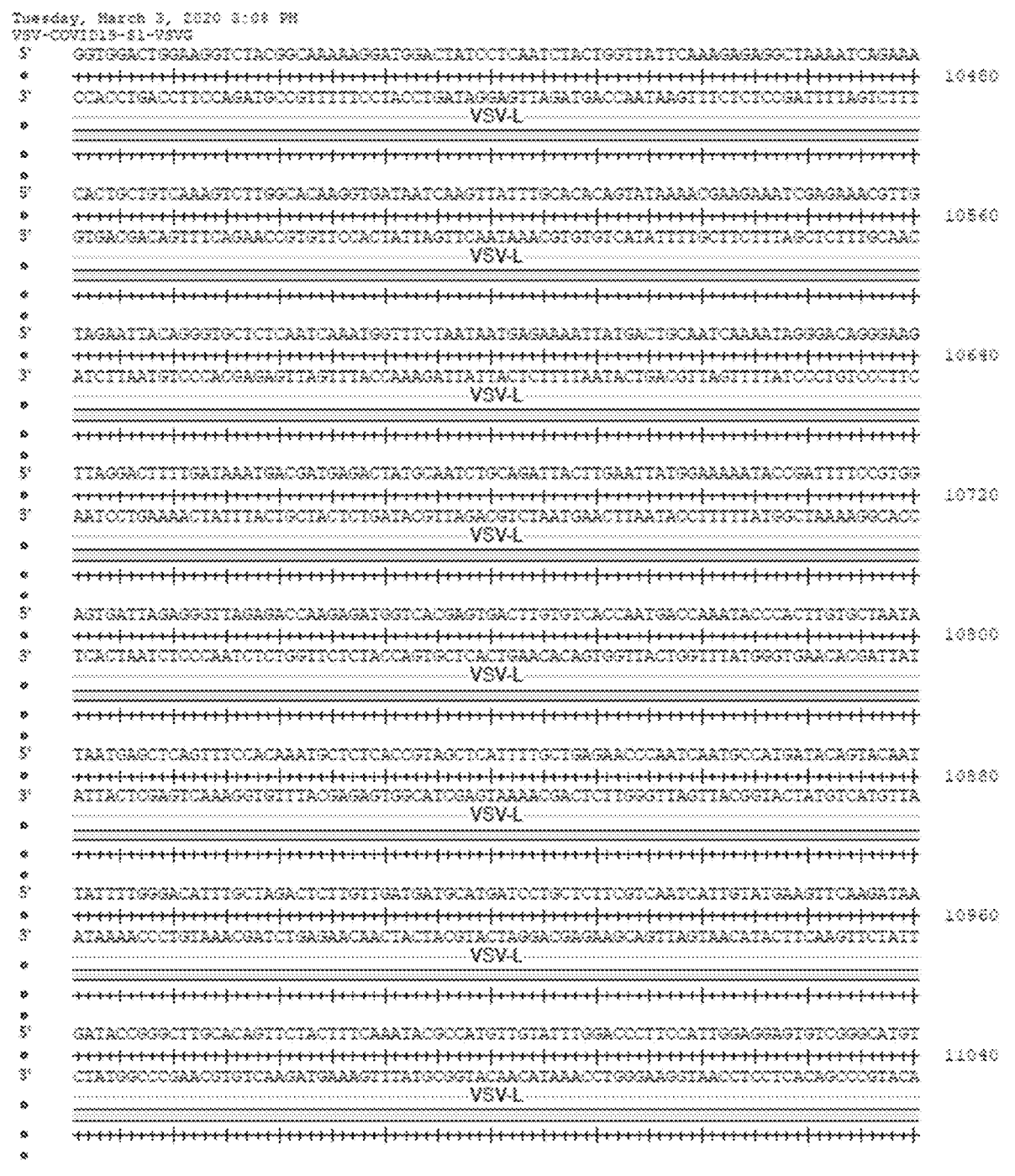
Figure 17:
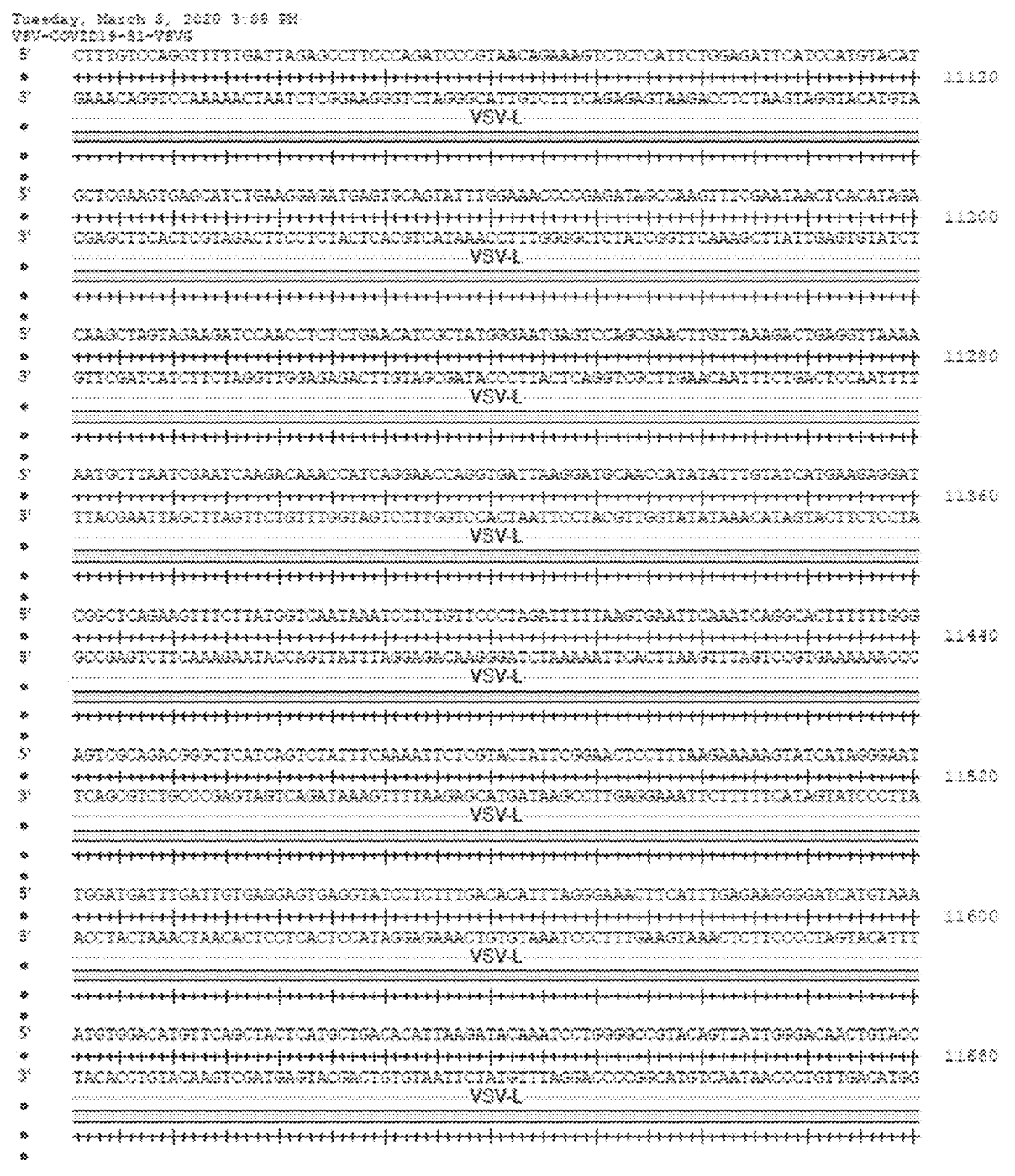
Figure 17:
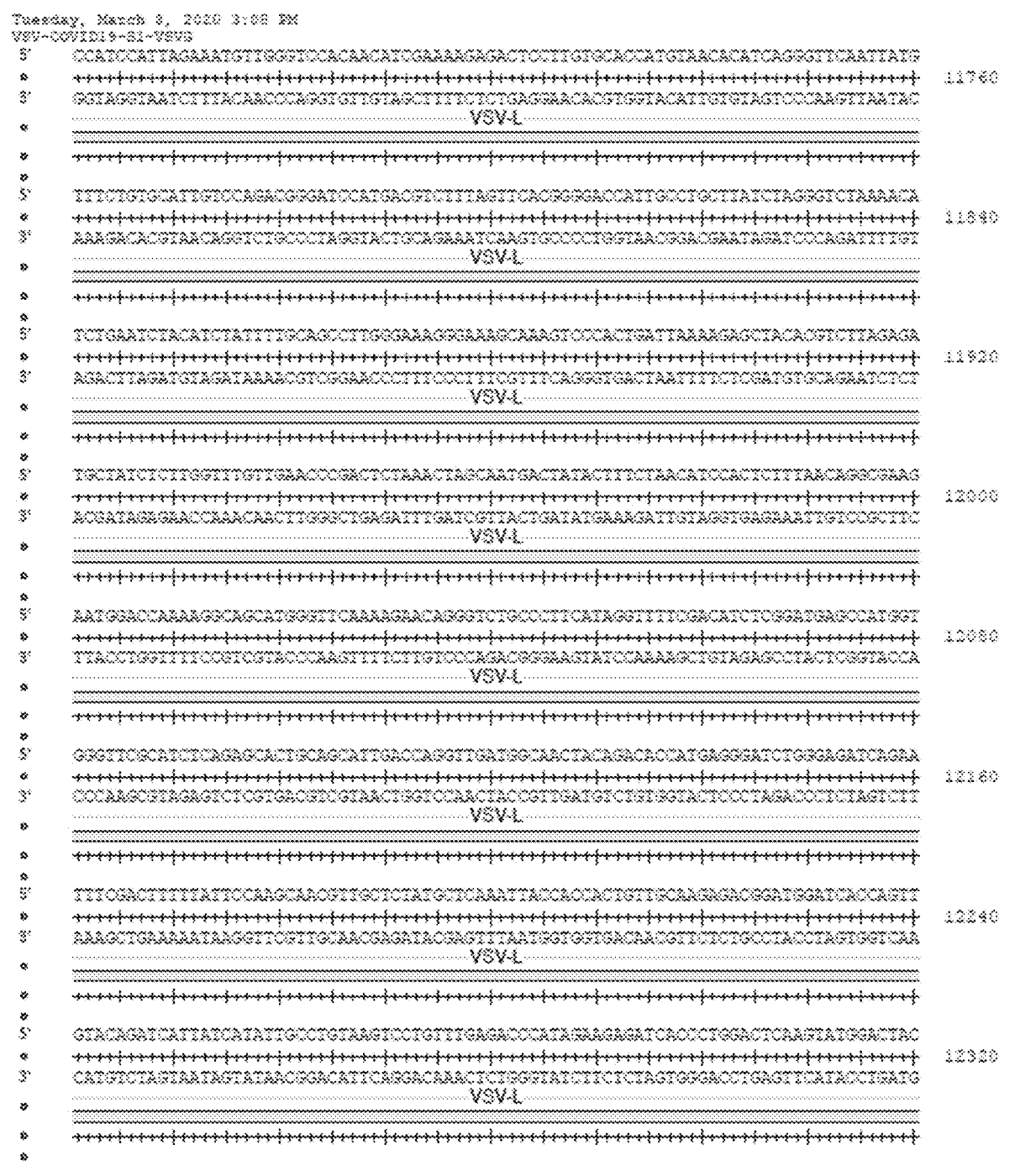
Figure 17:
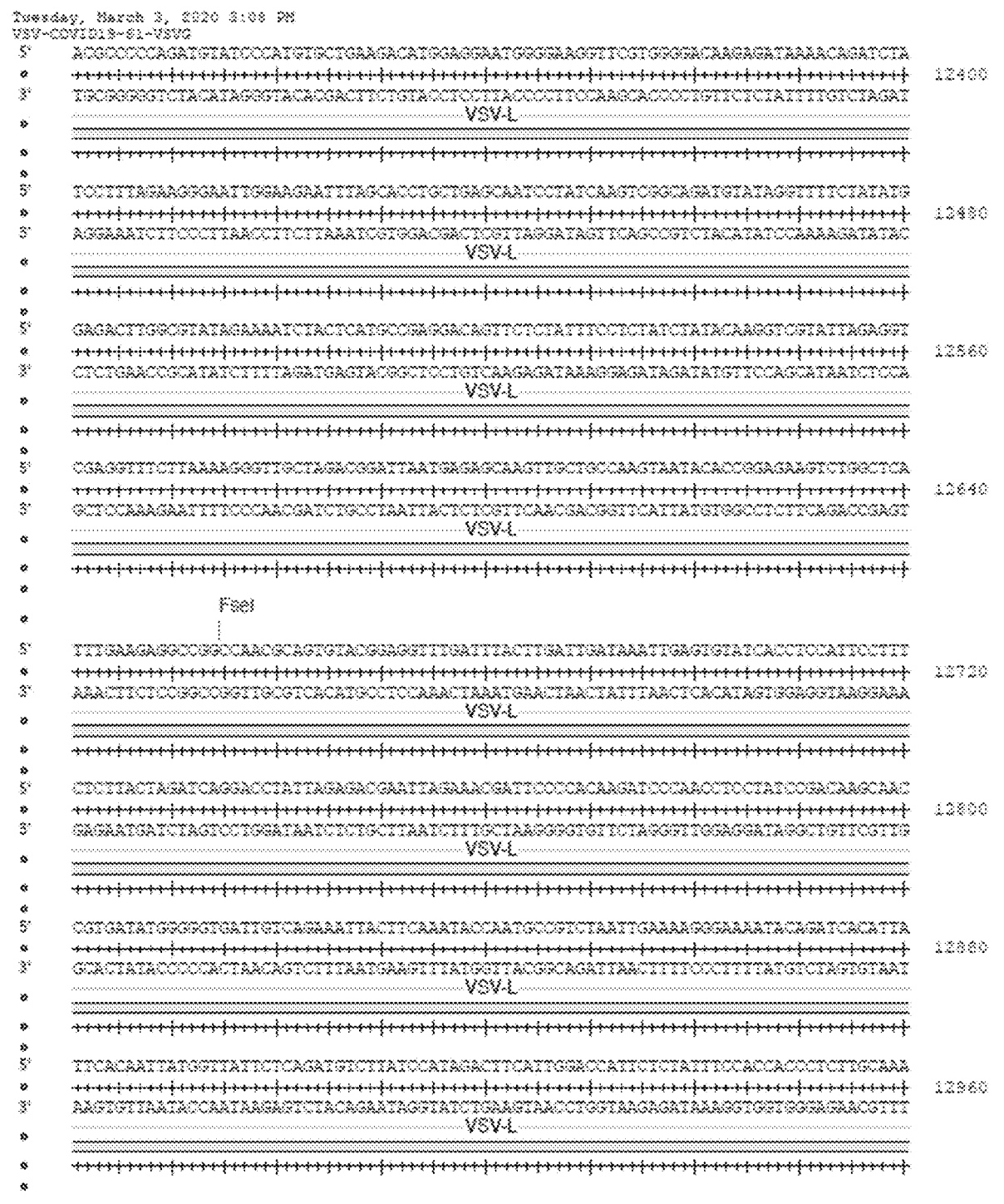
Figure 17:
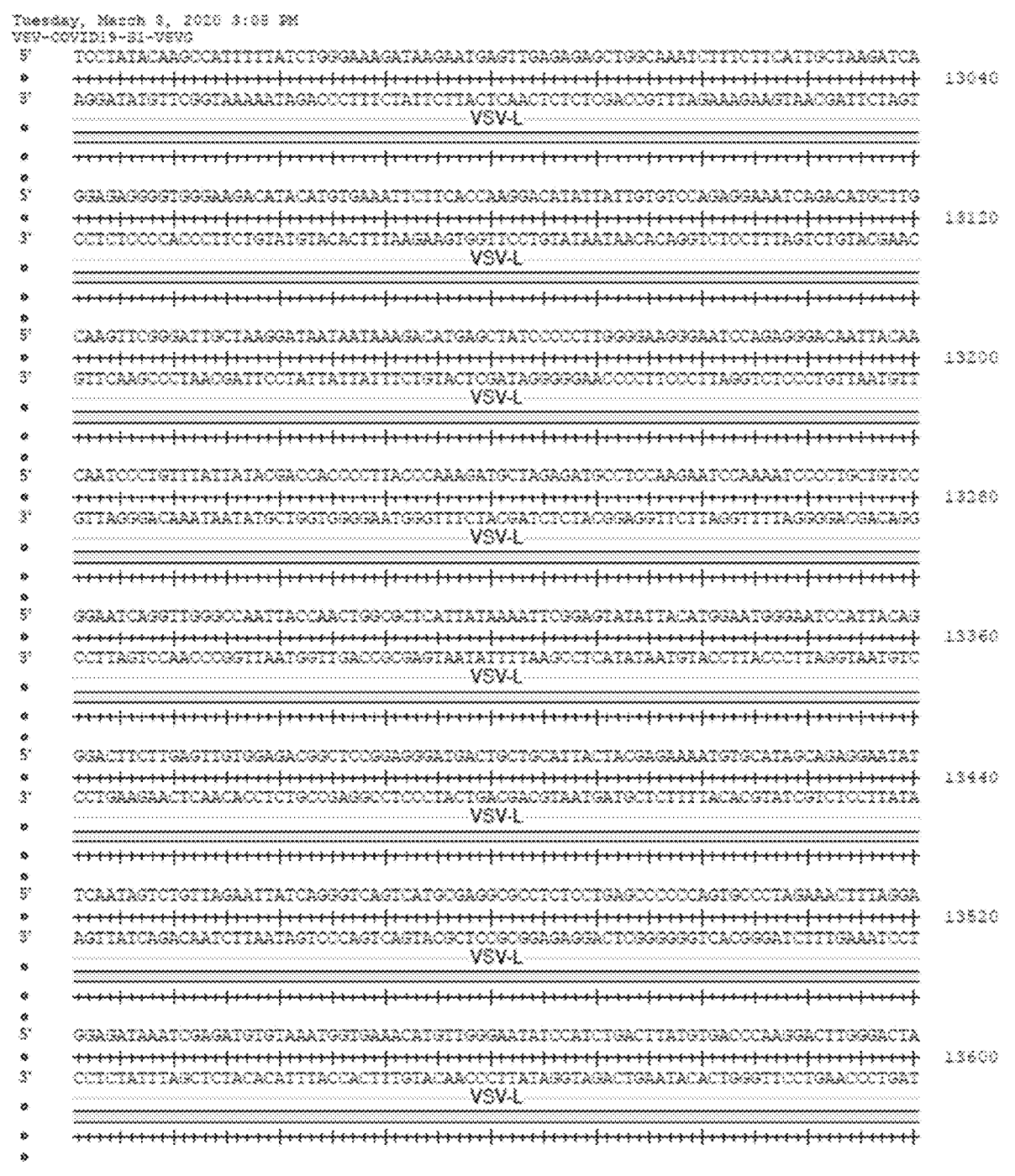
Figure 17:
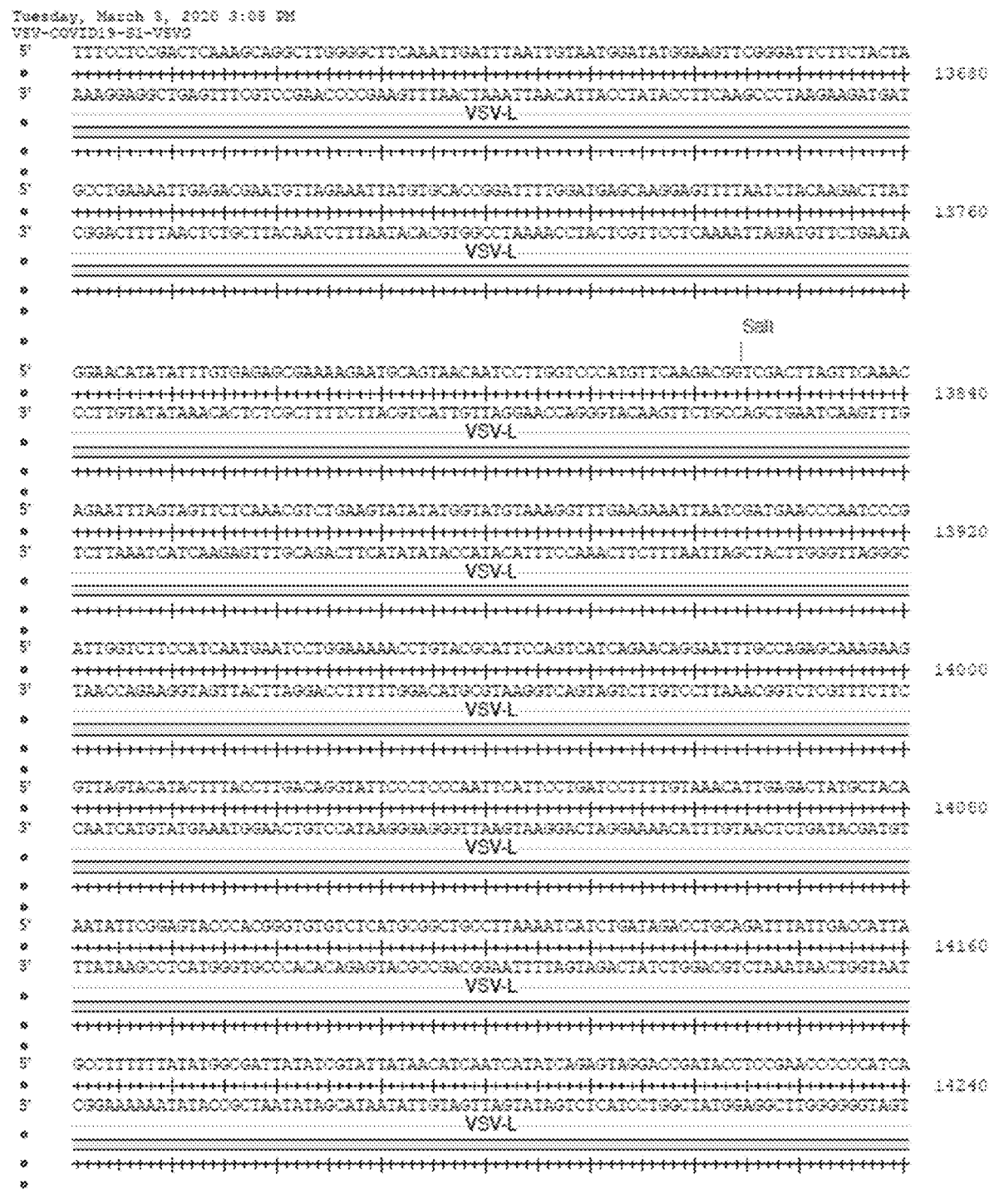
Figure 17:
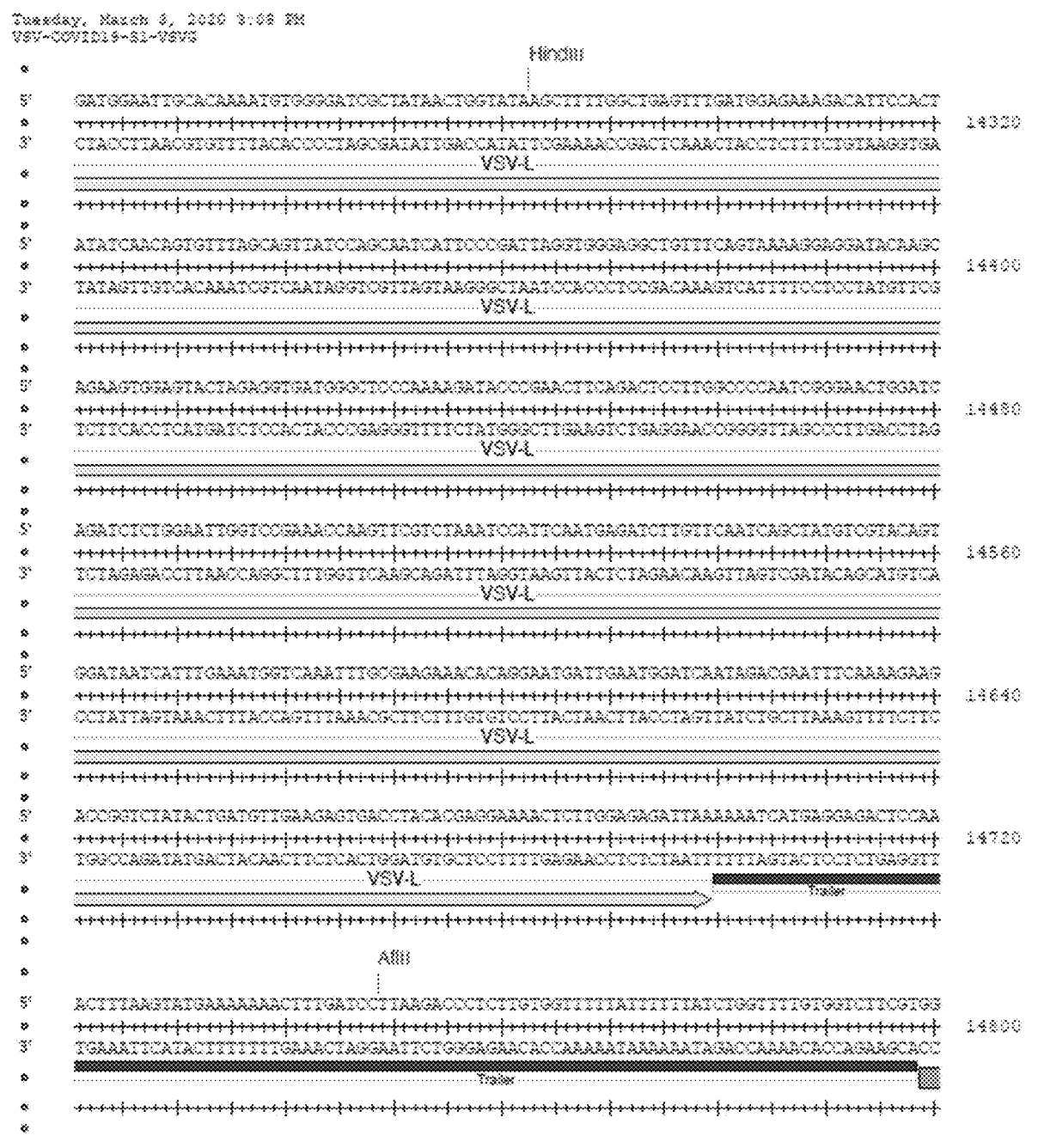
Figure 17:
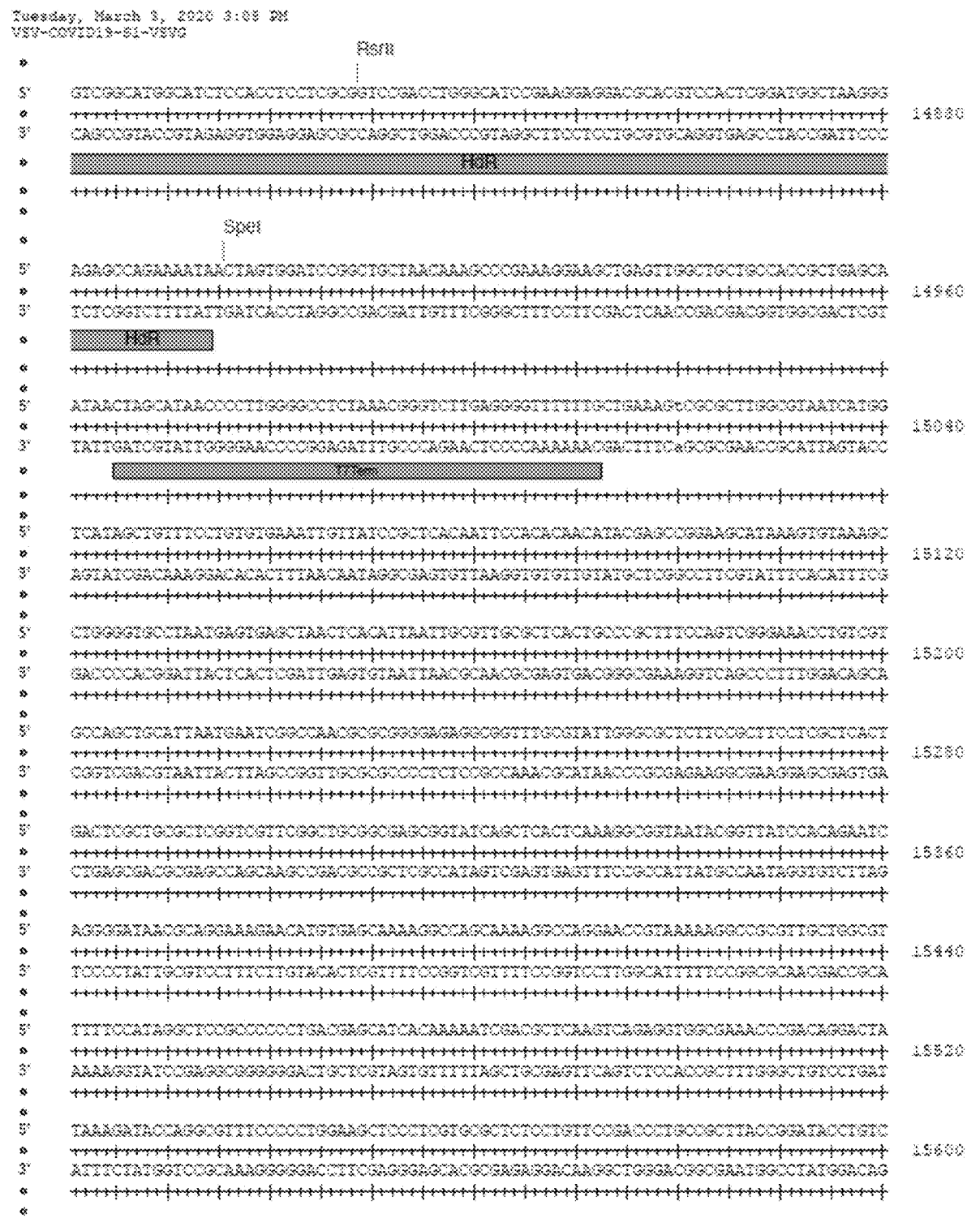
Figure 17:
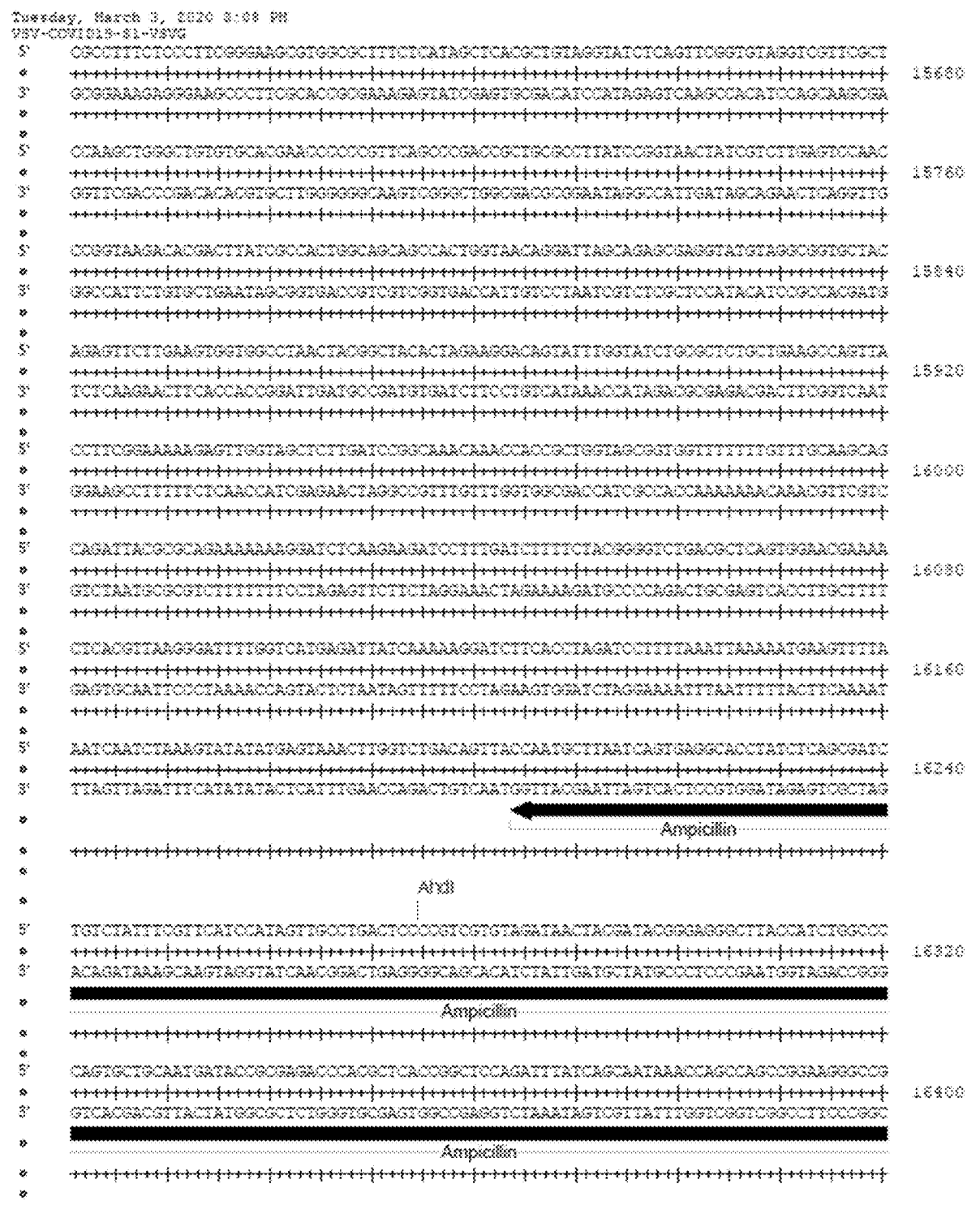
Figure 17:
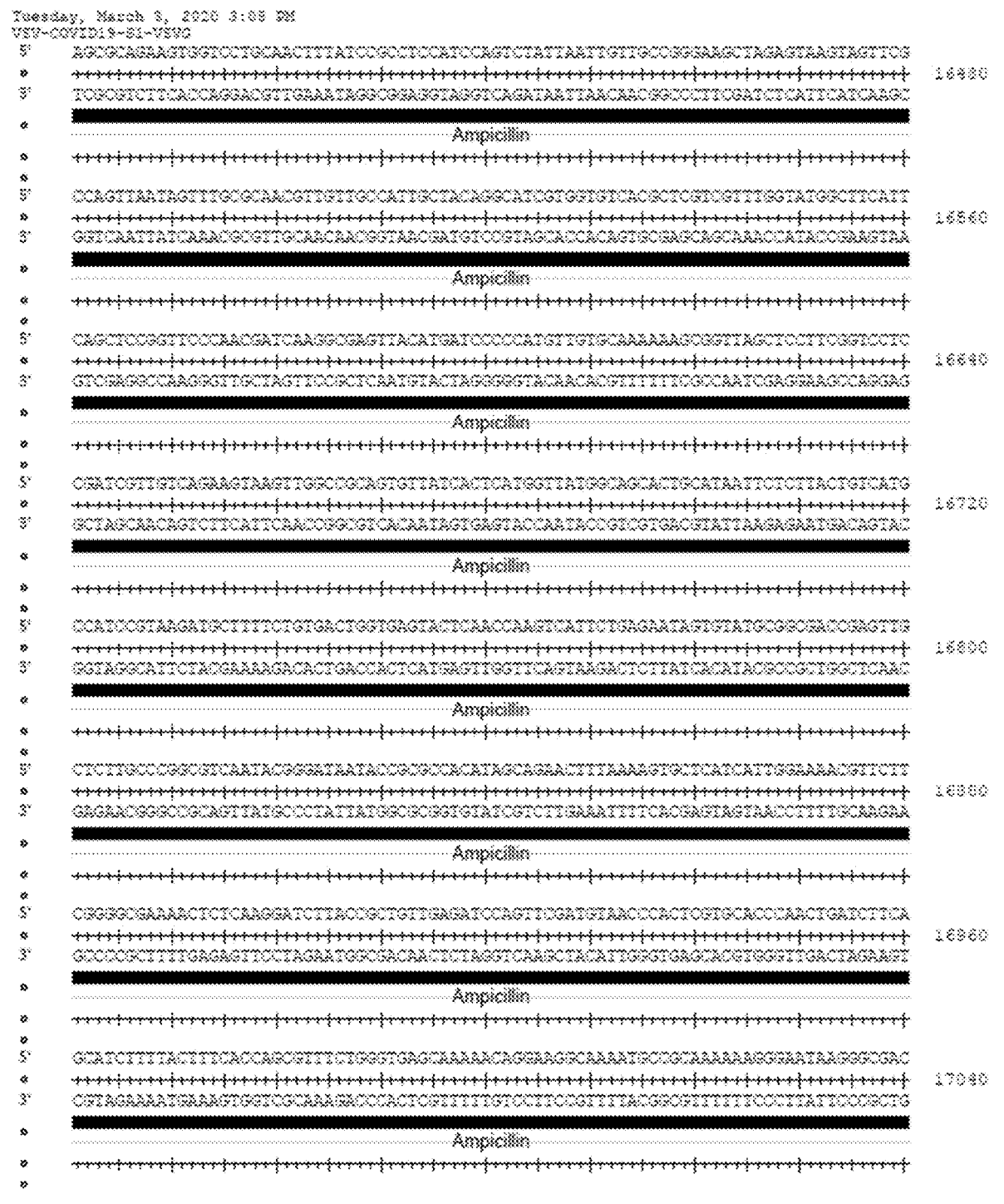
Figure 17:
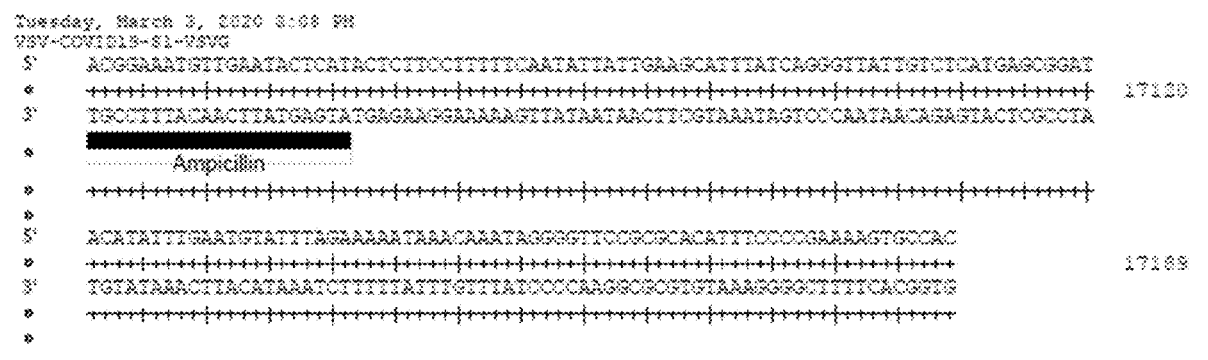

FIG. 17 shows the sequence (SEQ ID NO: 1) and features of "VSV-COVID19-S1-VSVG.

Figure 18:
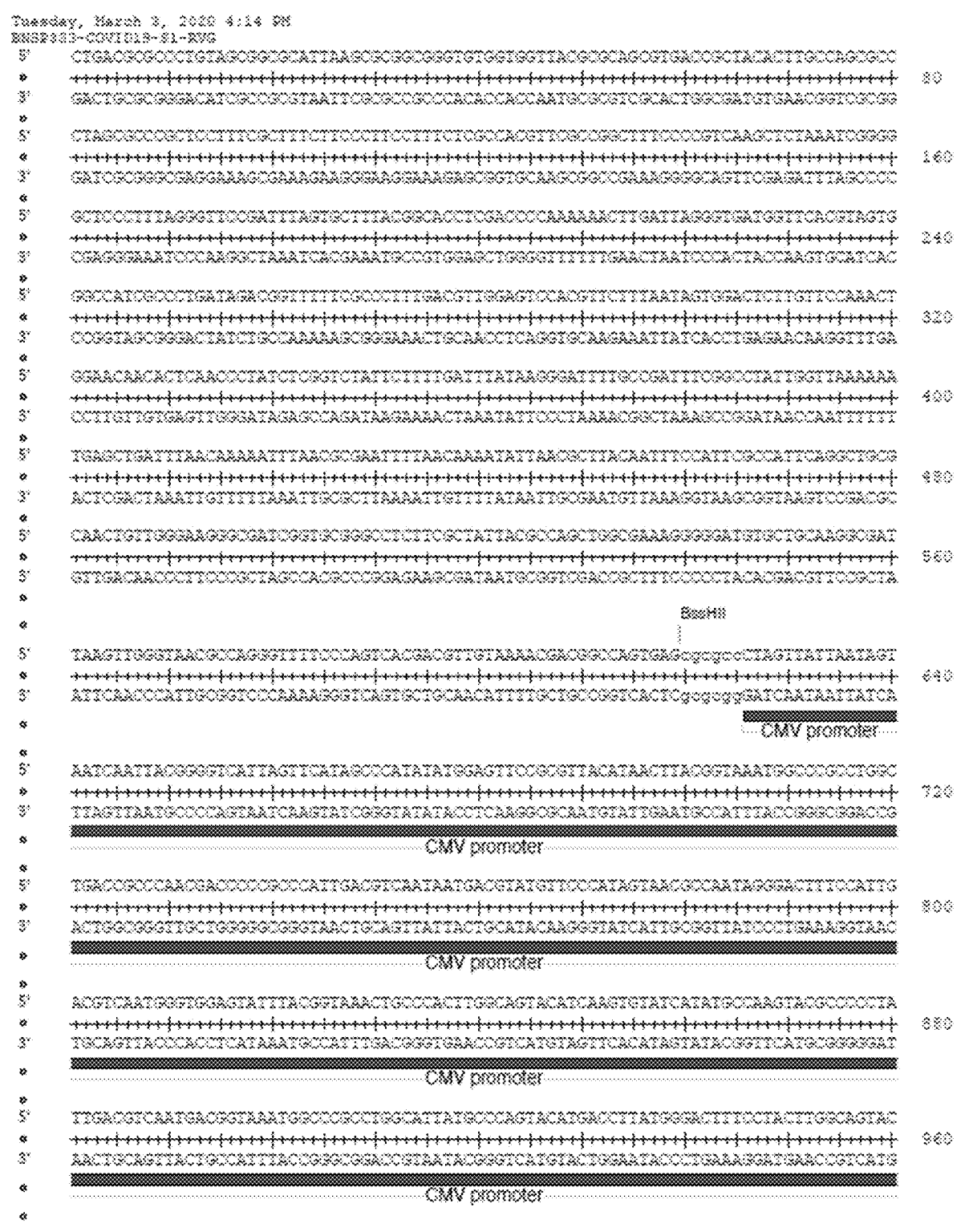
Figure 18:
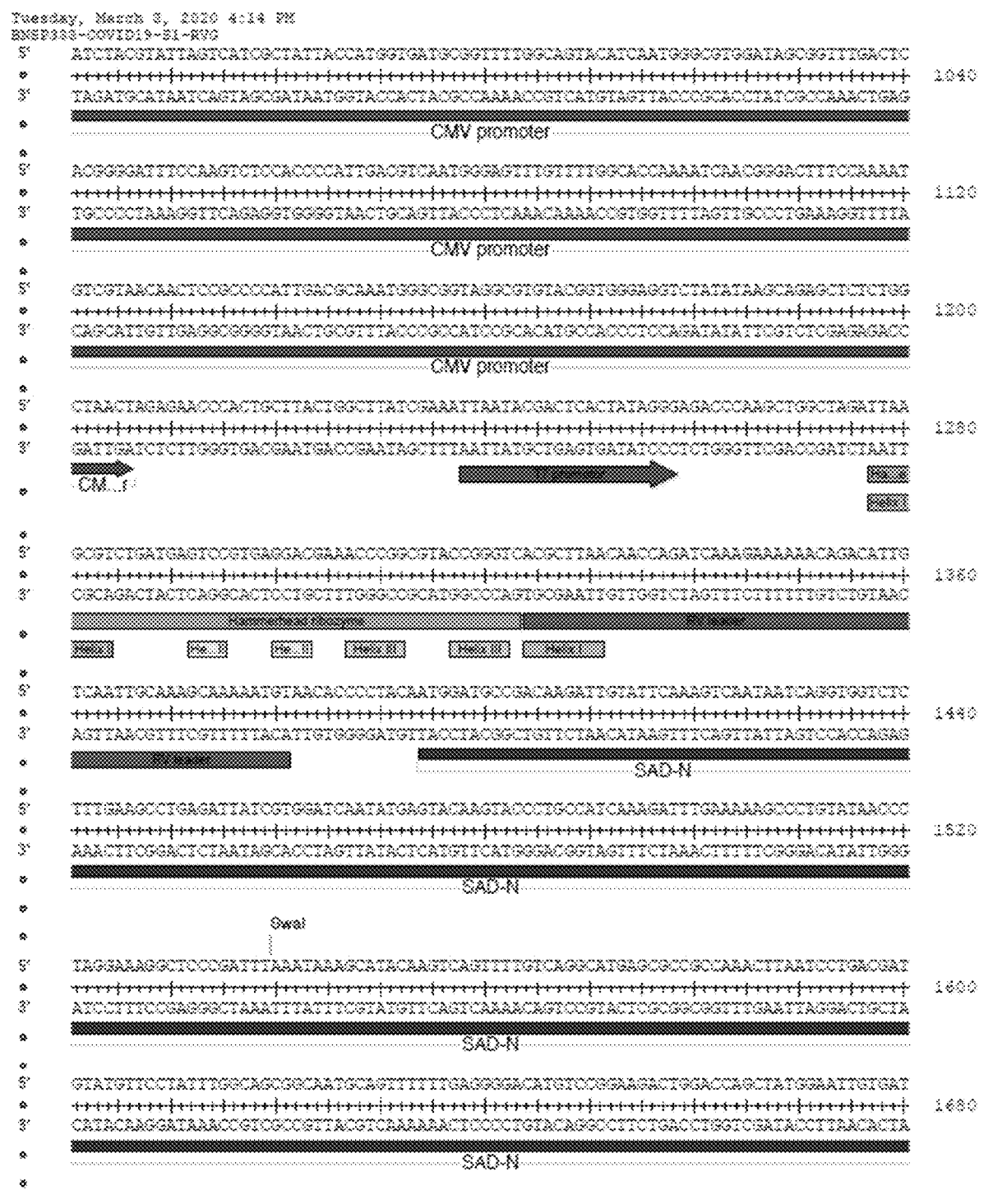
Figure 18:
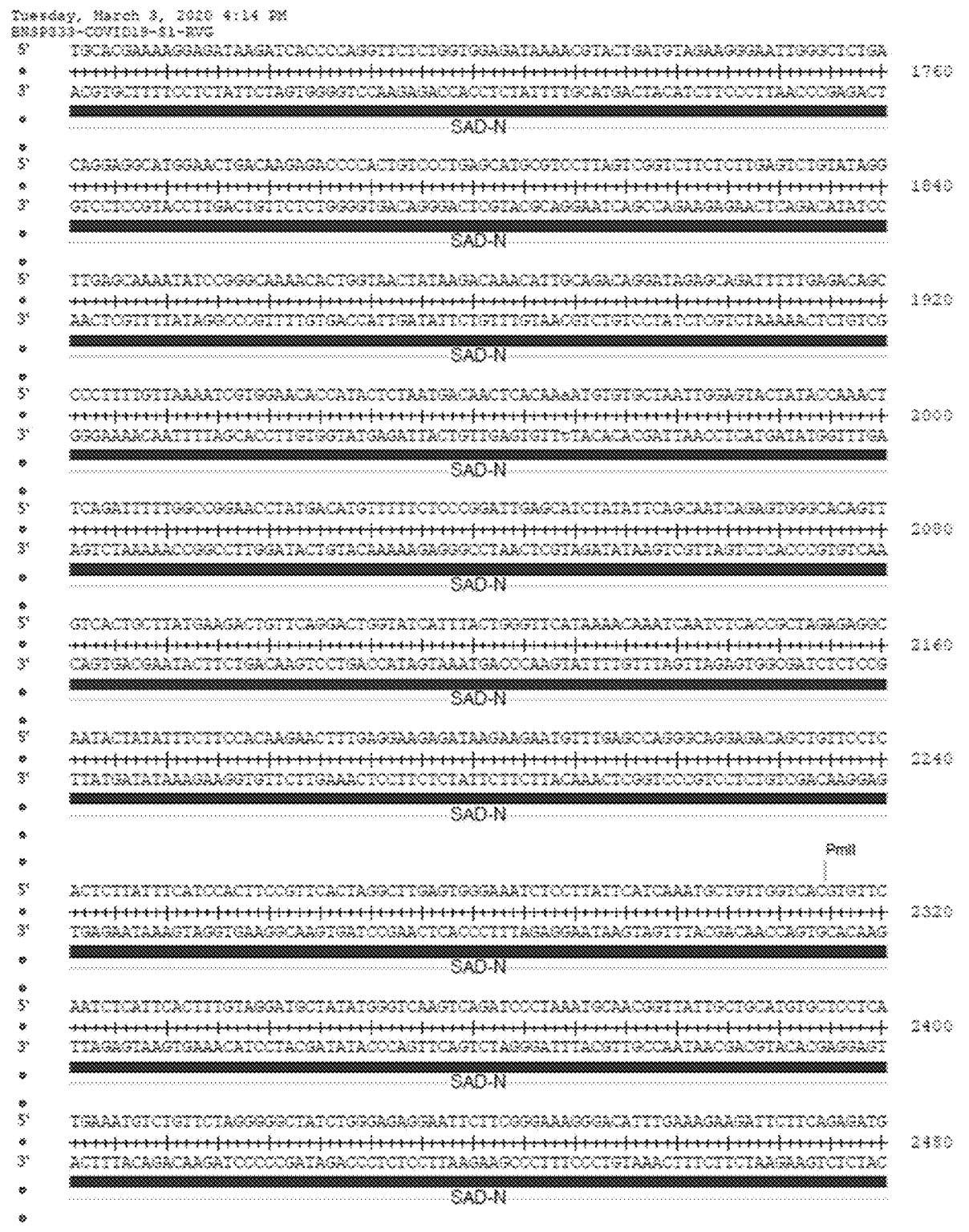
Figure 18:
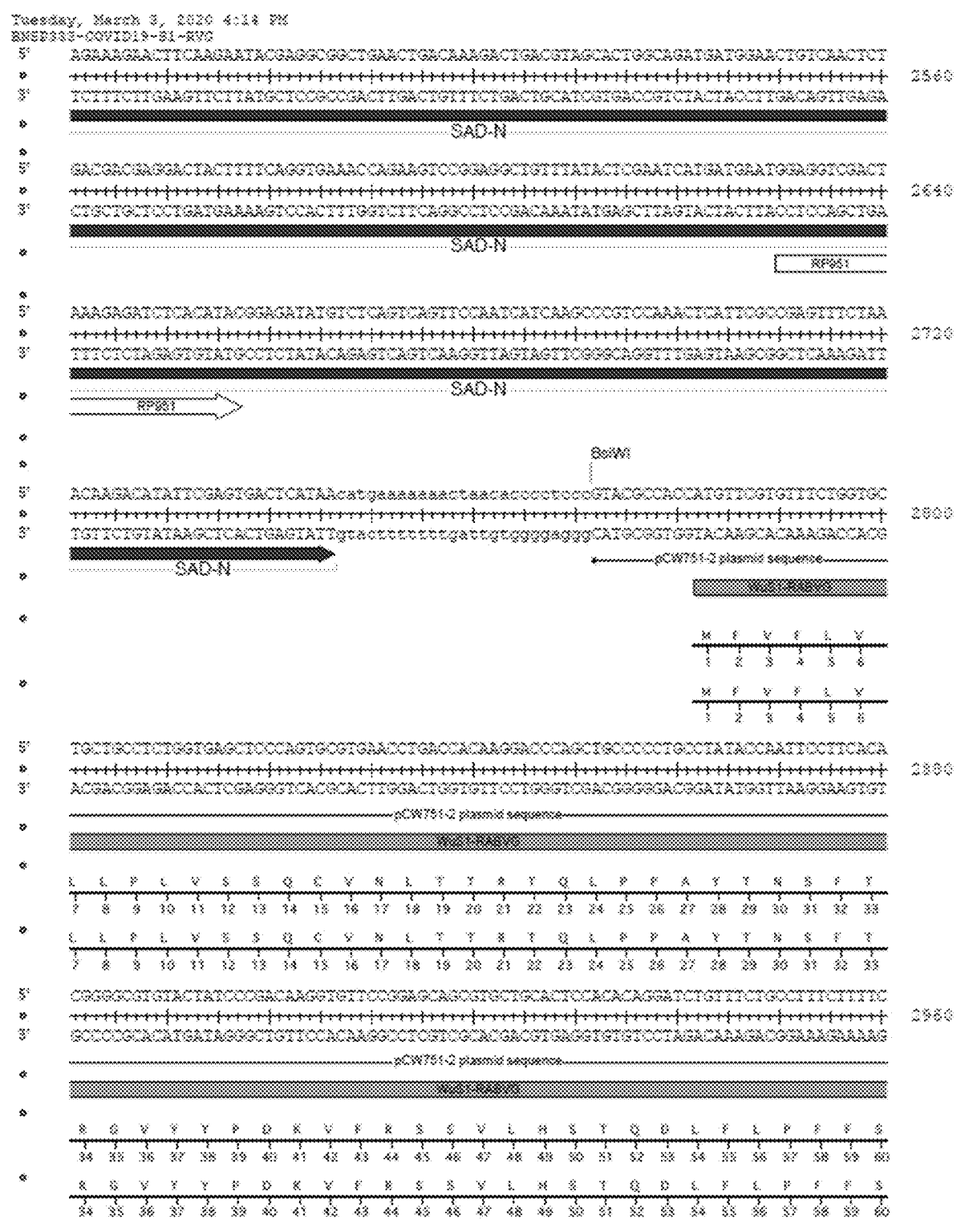
Figure 18:
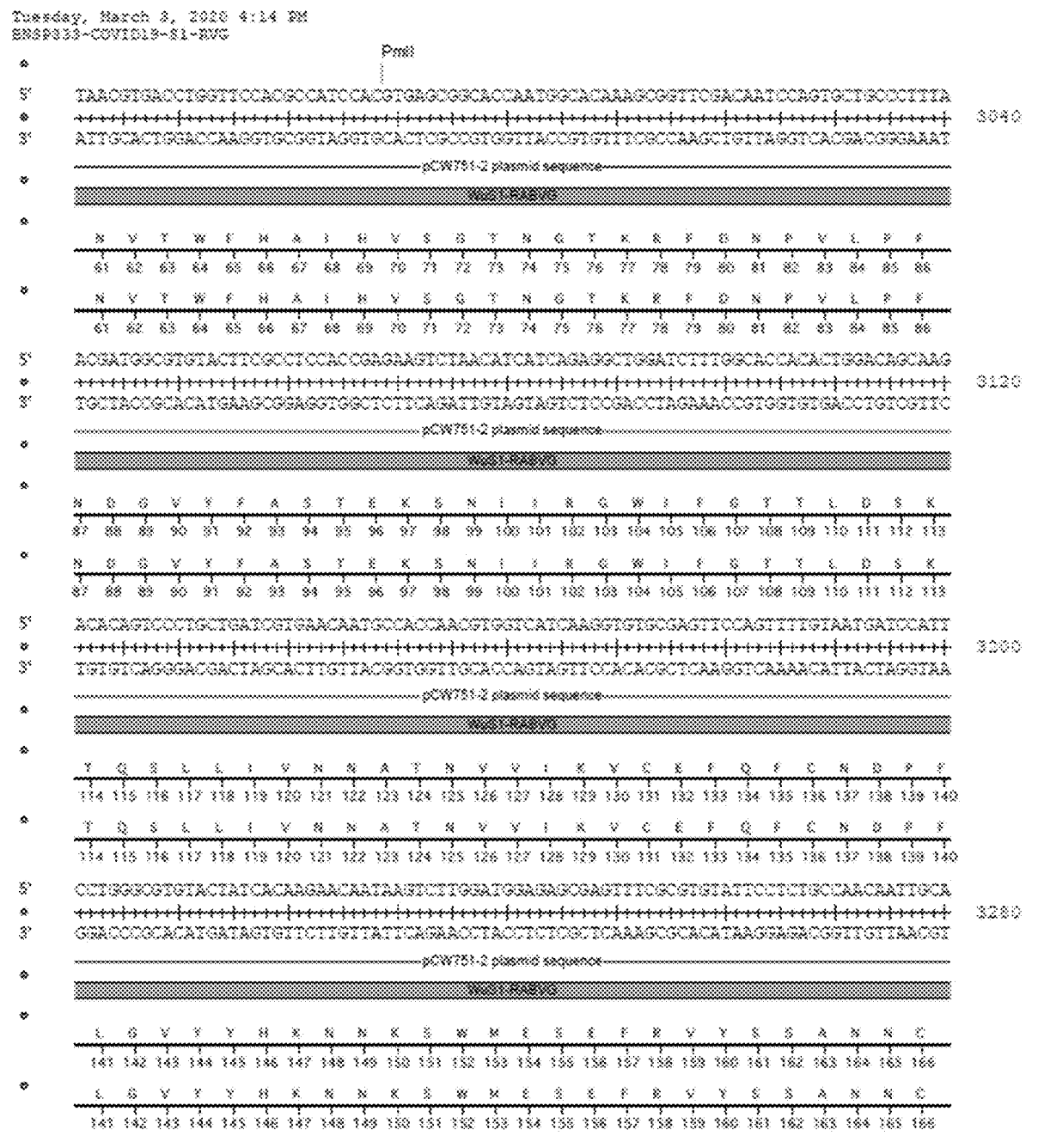
Figure 18:
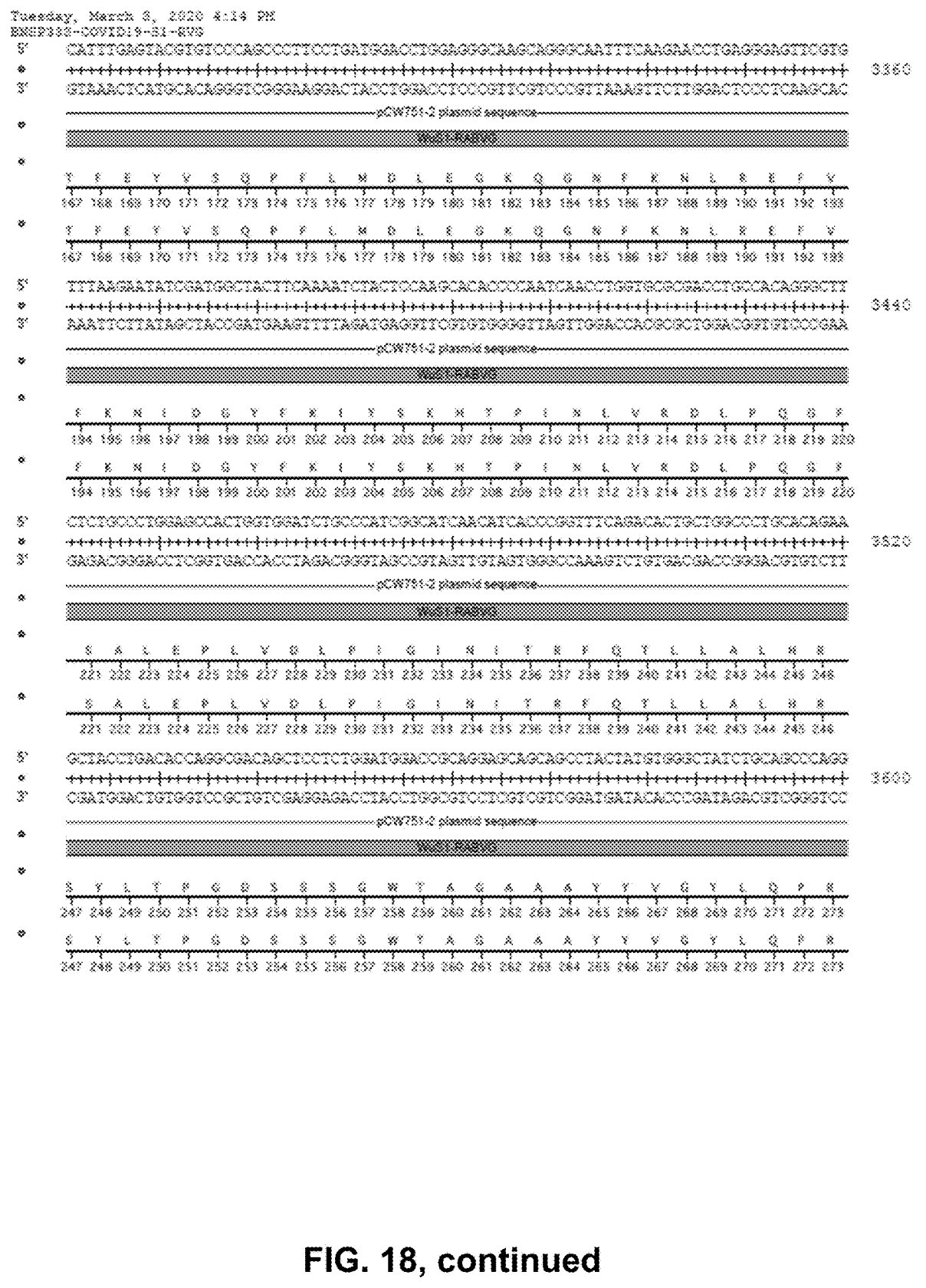
Figure 18:
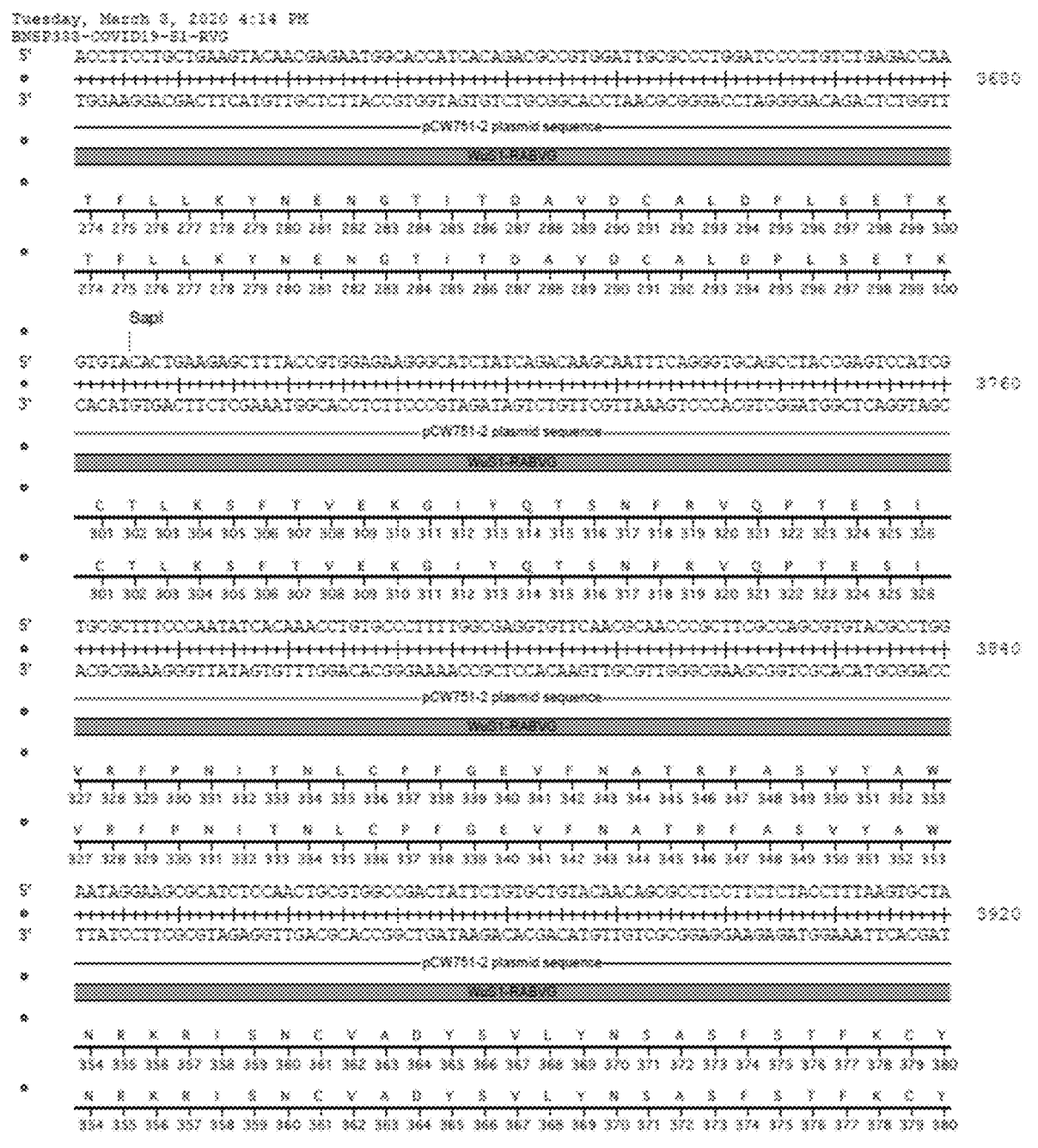
Figure 18:
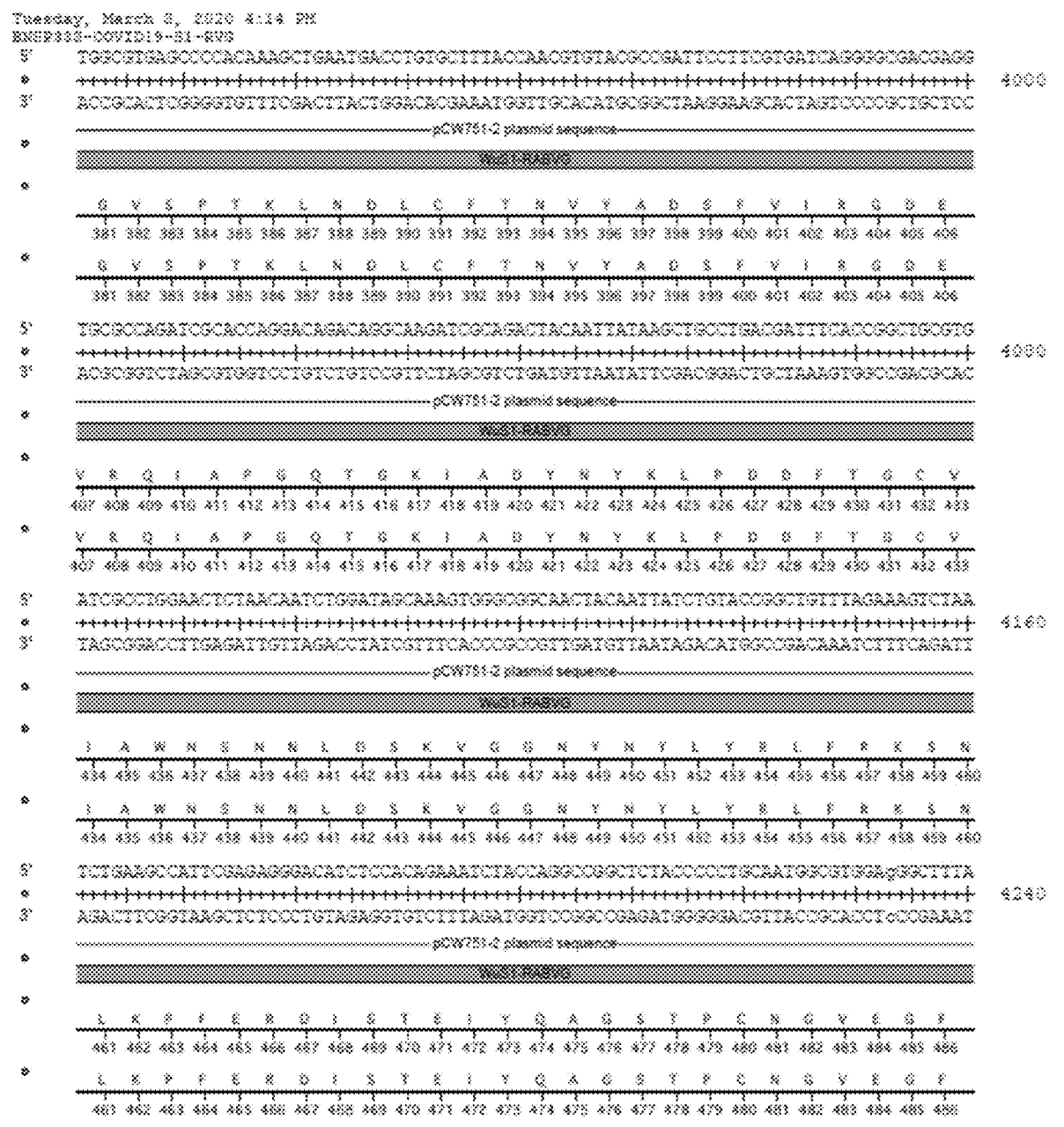
Figure 18:
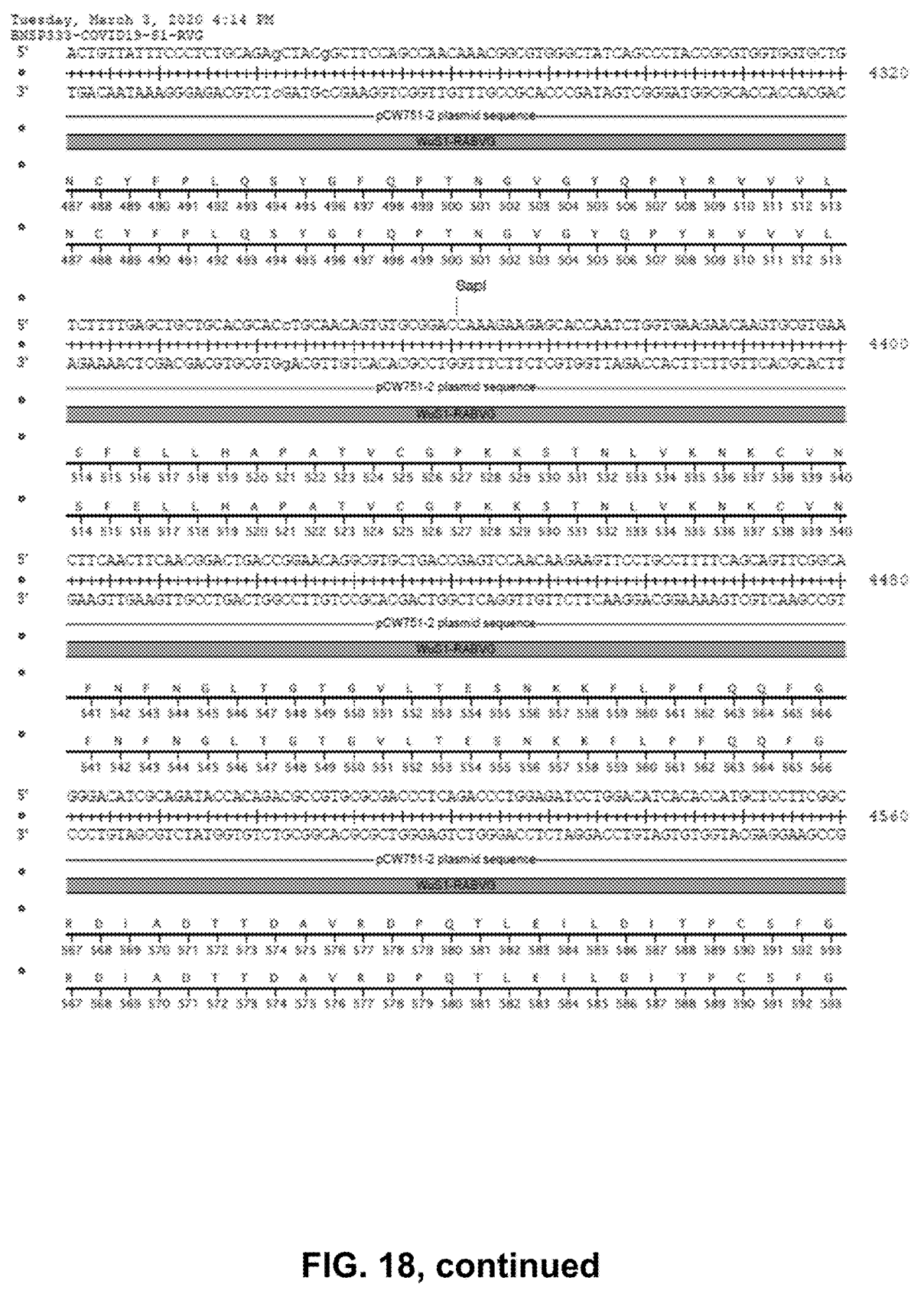
Figure 18:
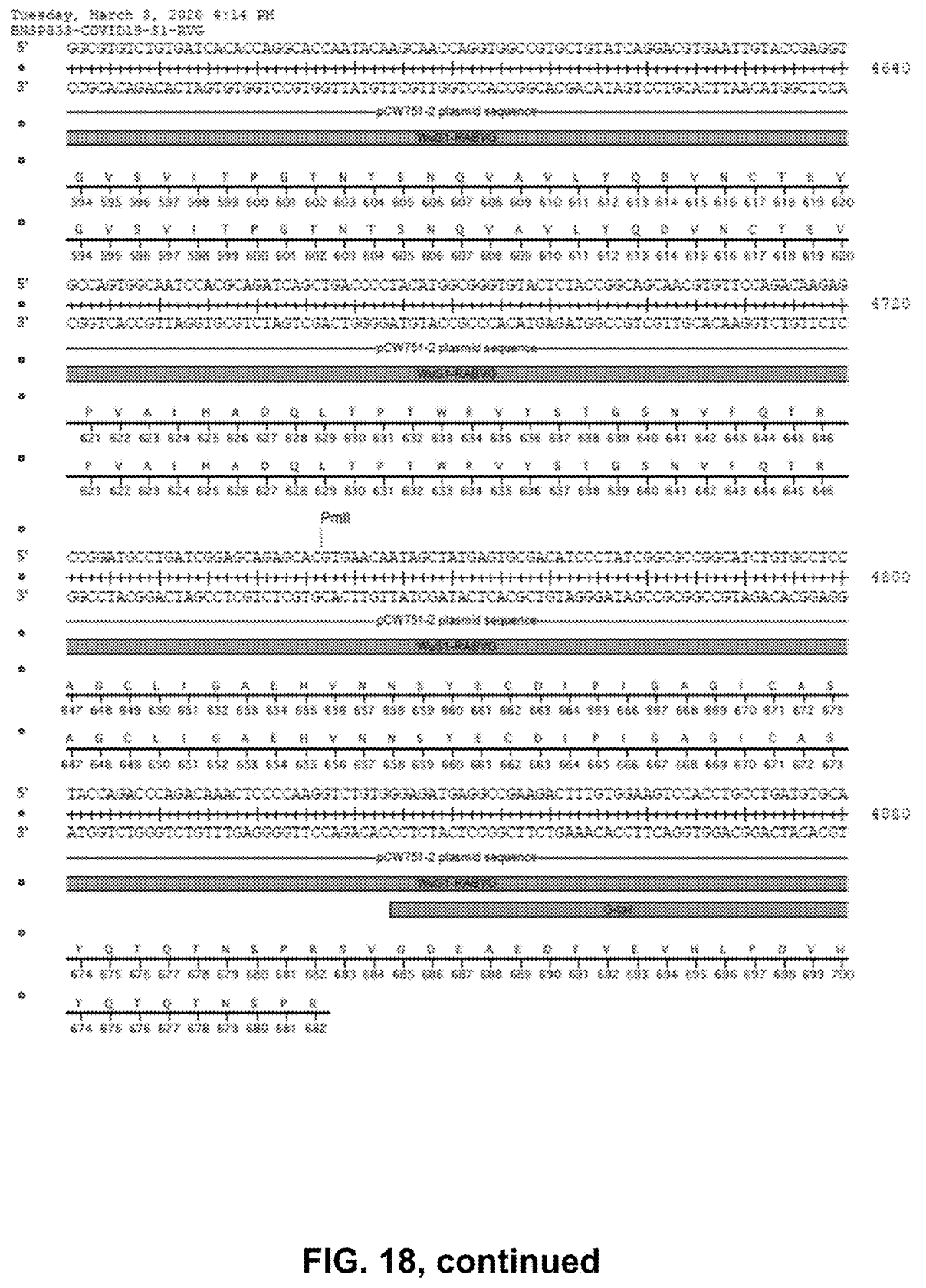
Figure 18:
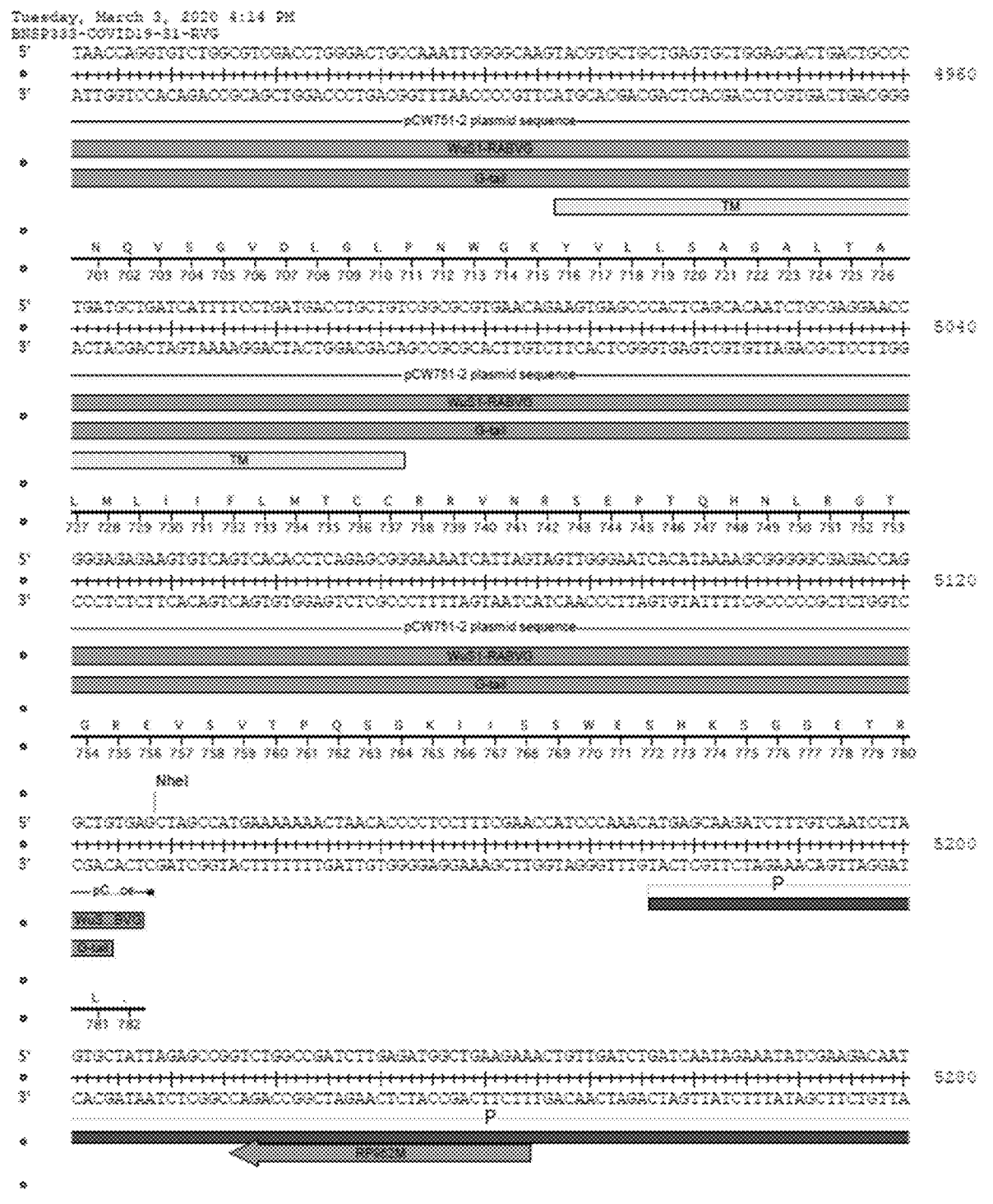
Figure 18:
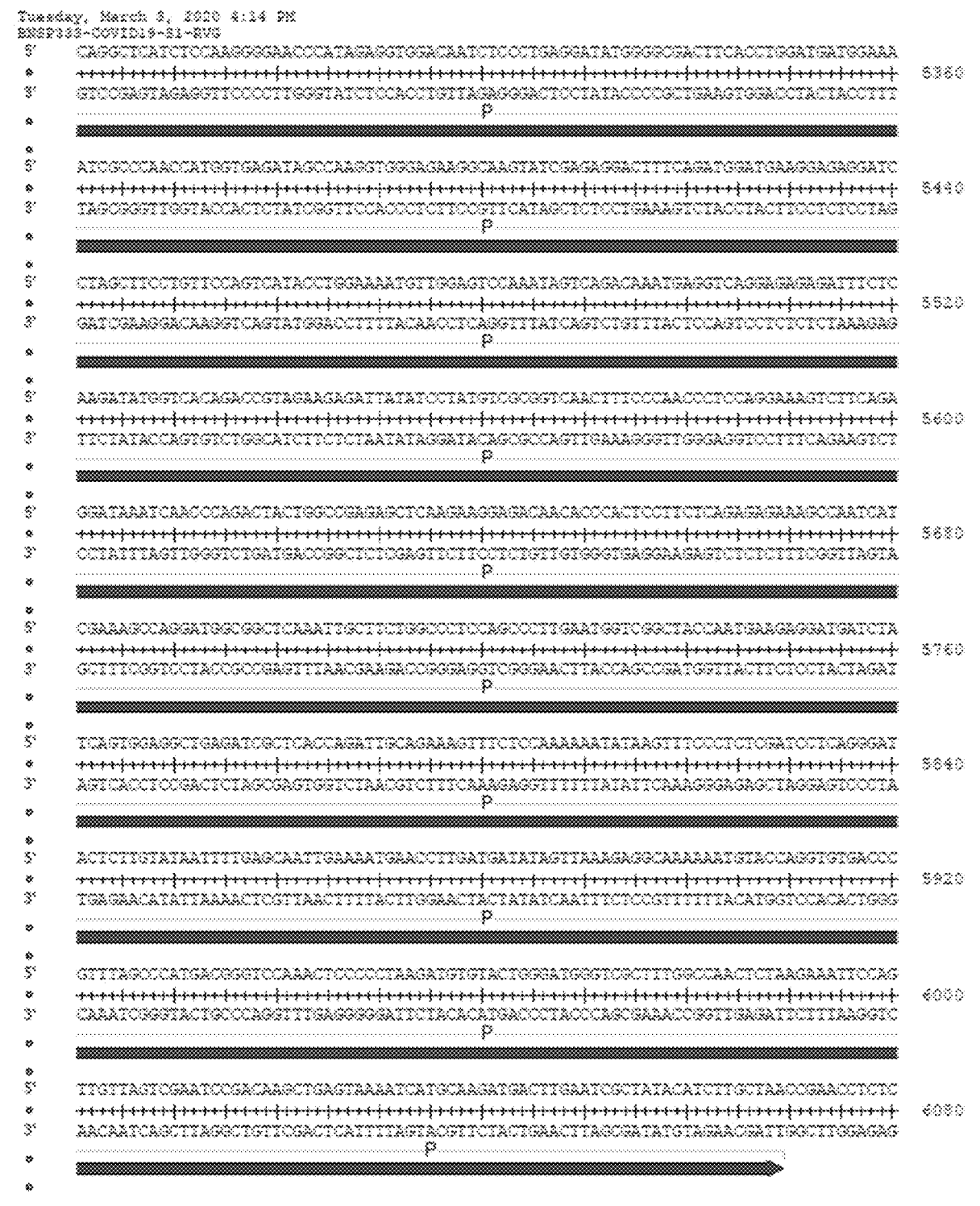
Figure 18:
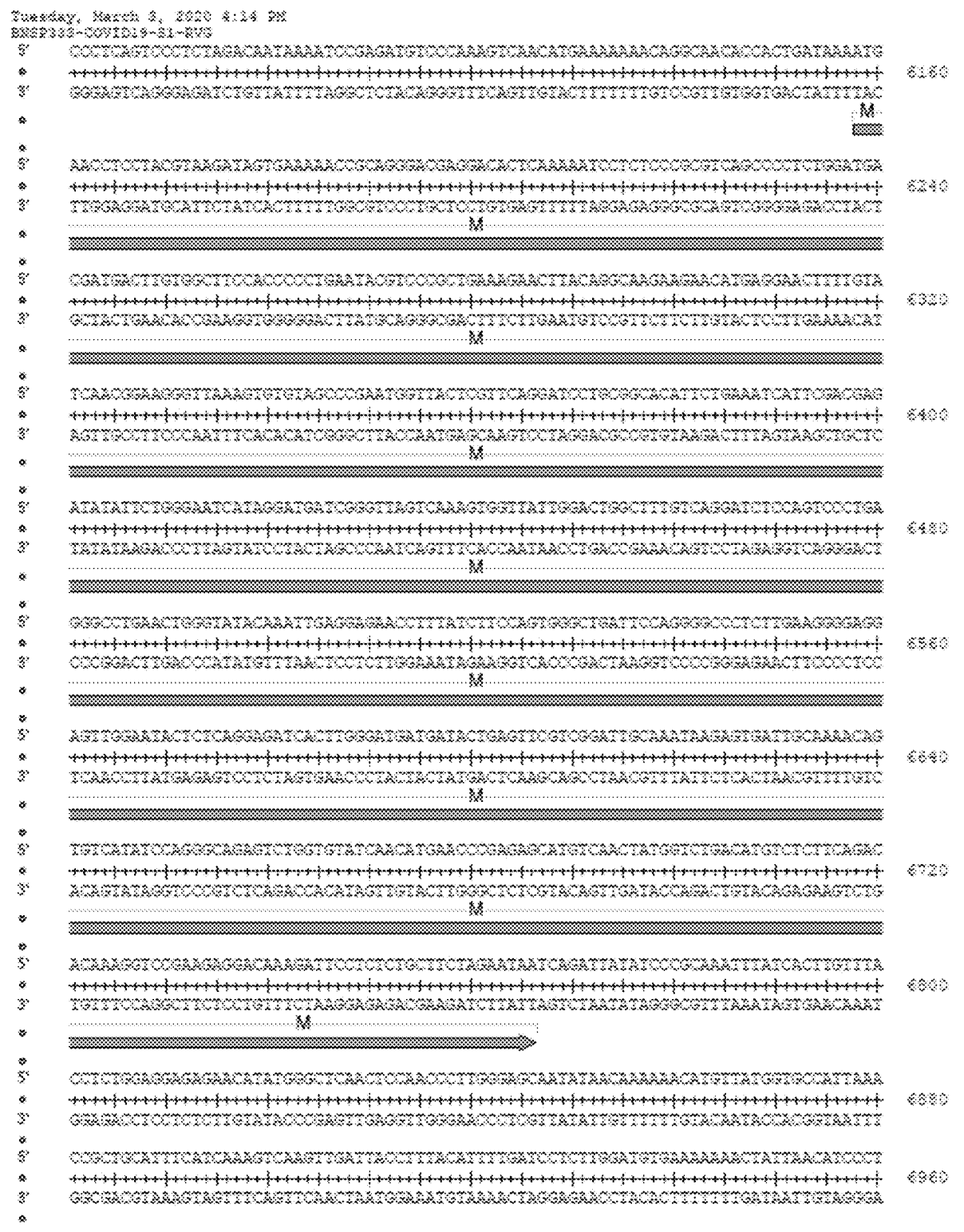
Figure 18:
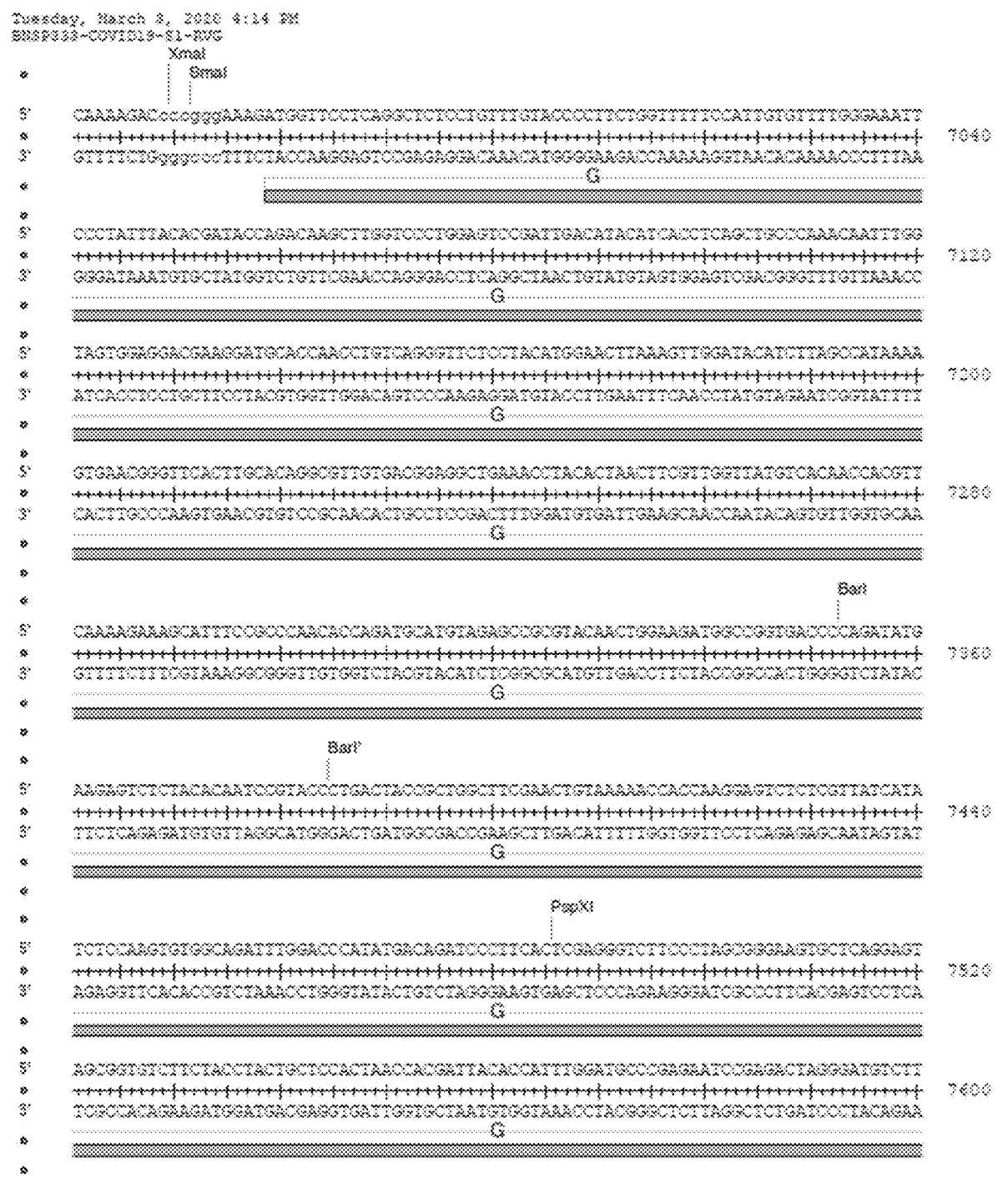
Figure 18:
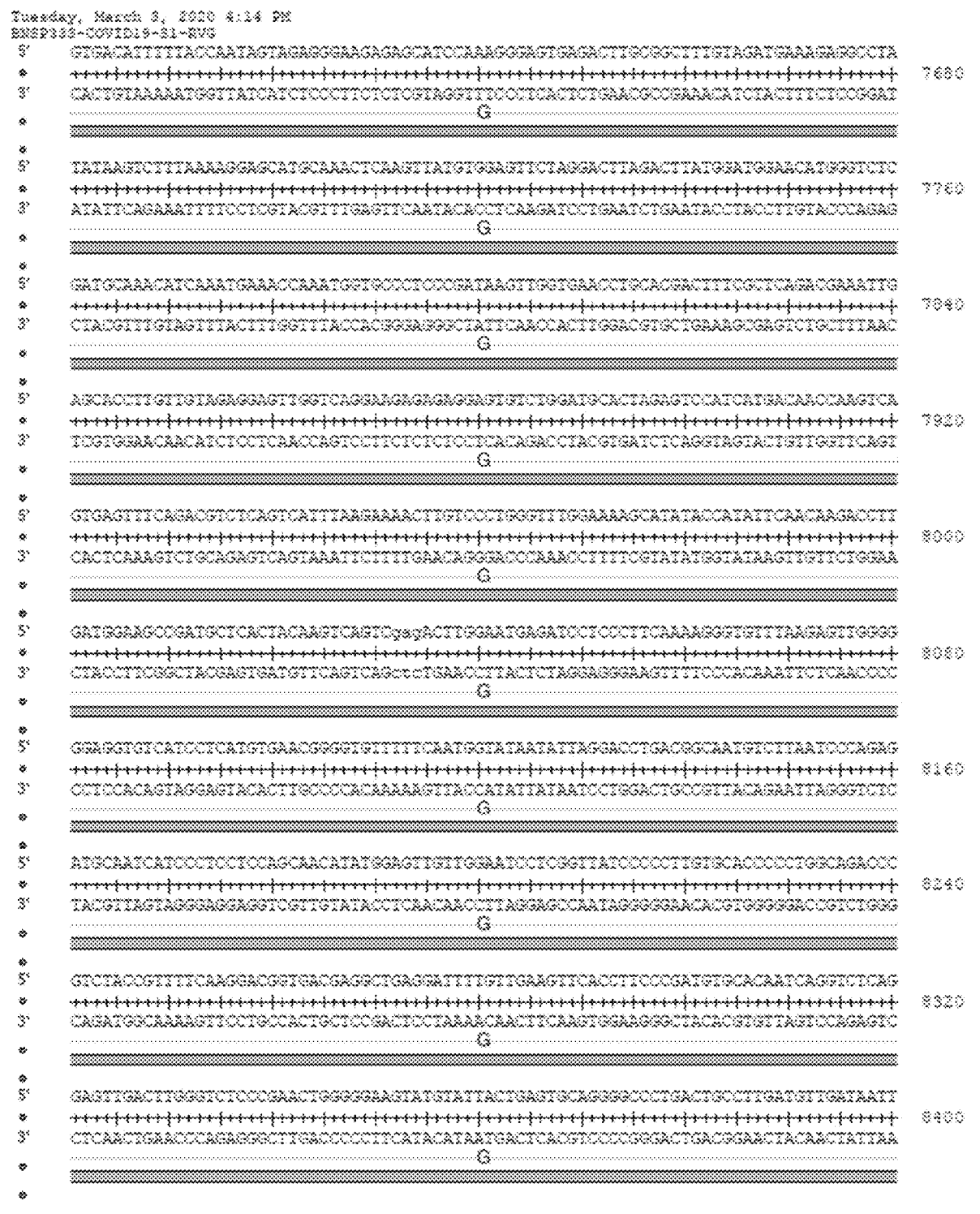
Figure 18:
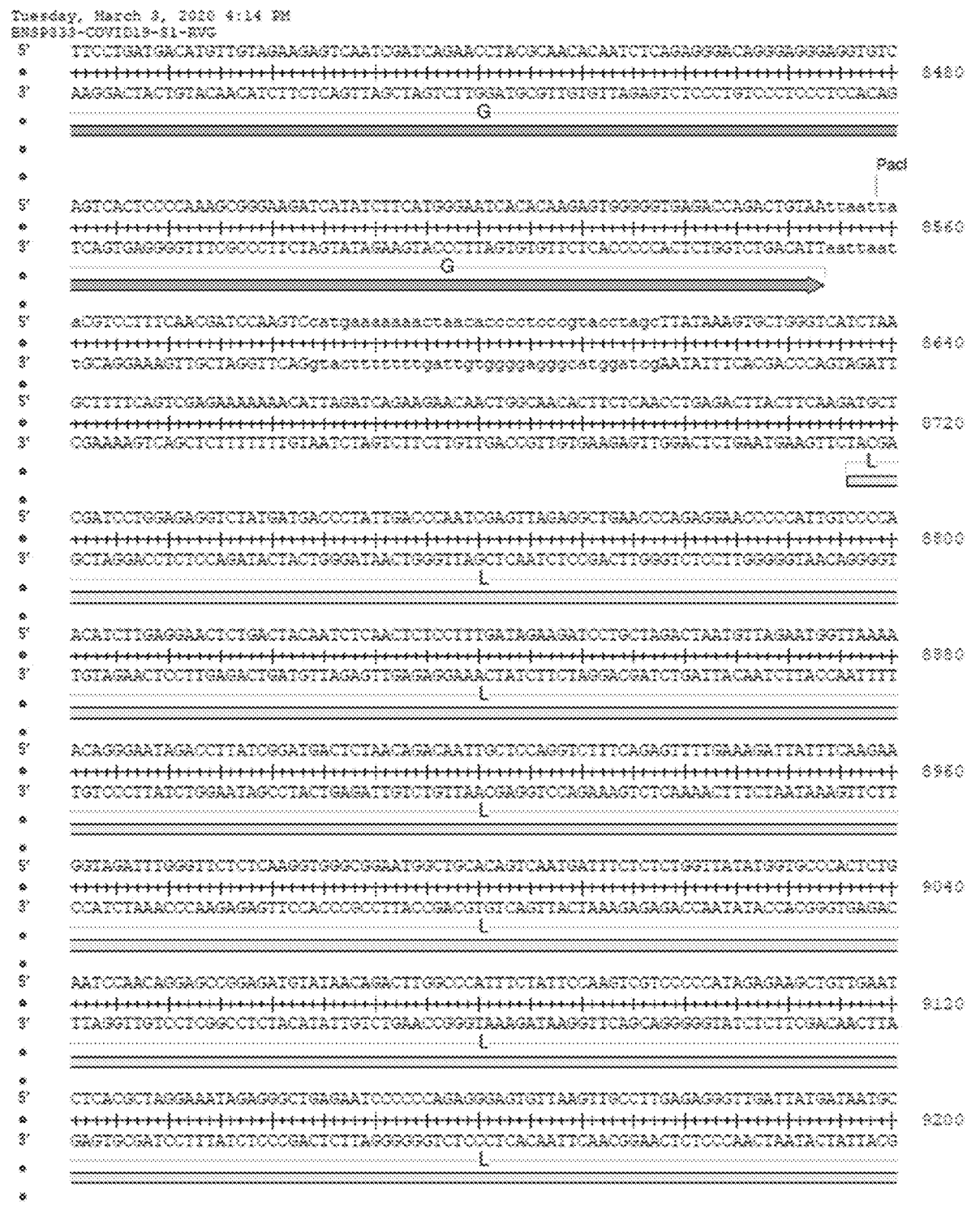
Figure 18:
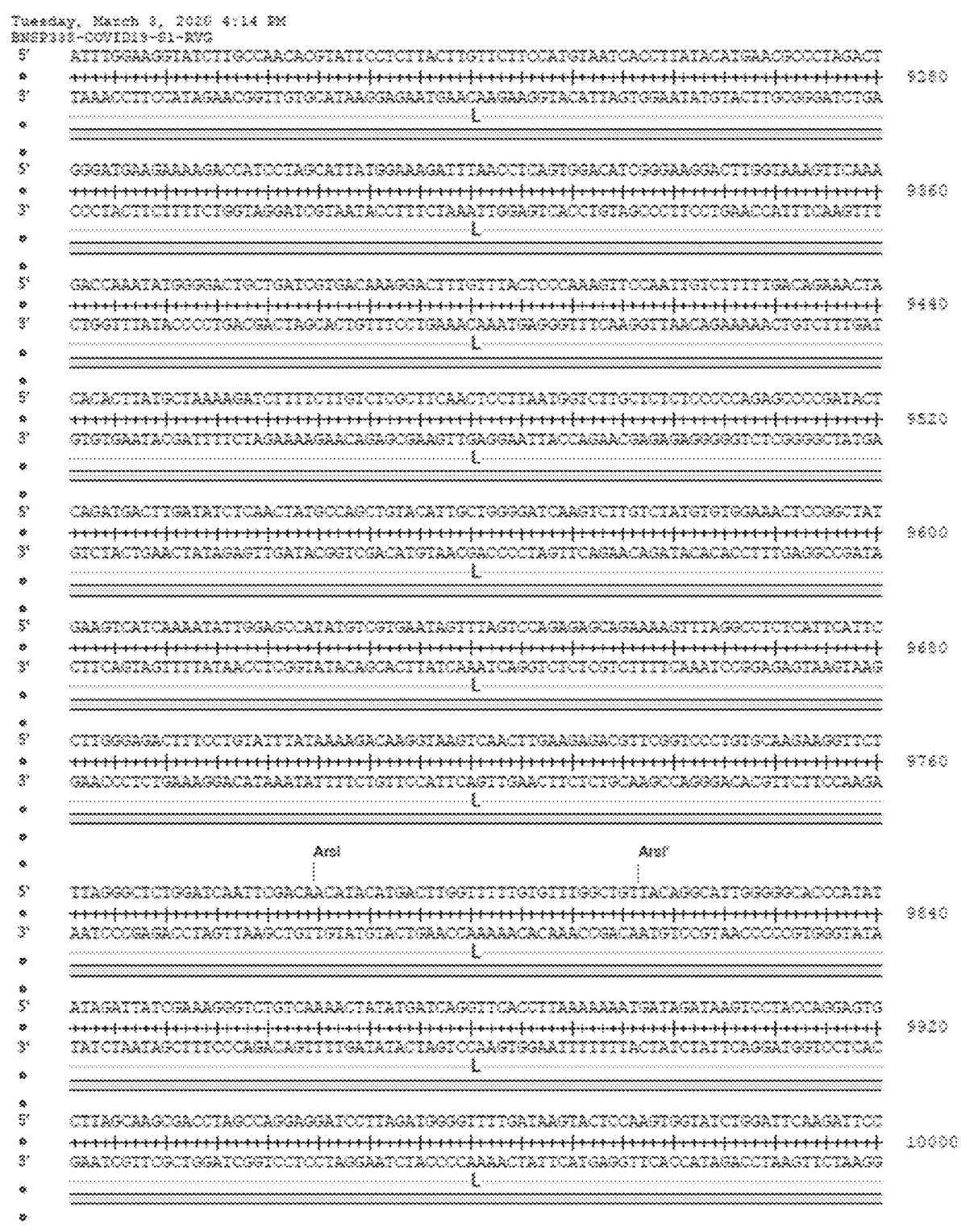
Figure 18:
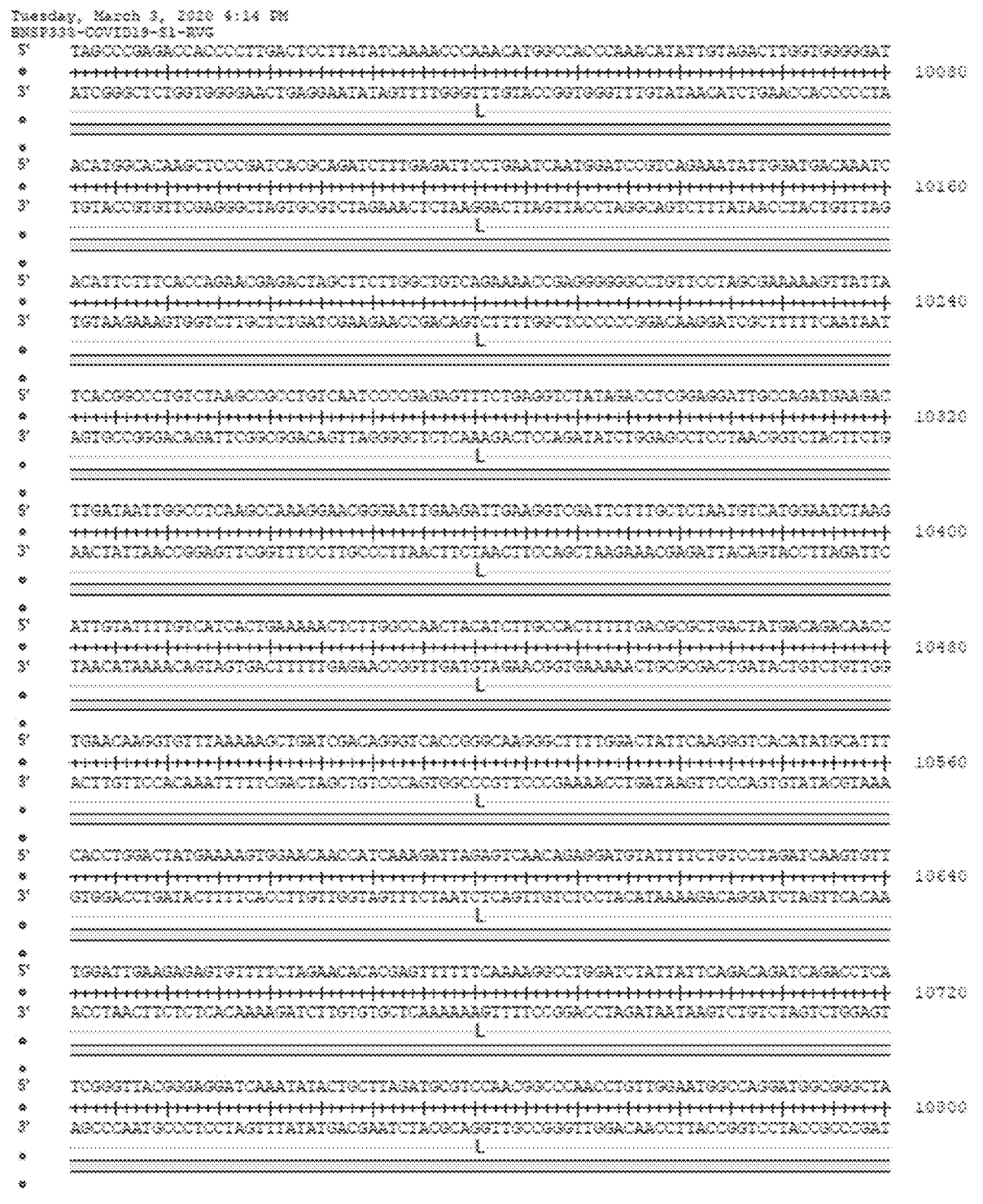
Figure 18:
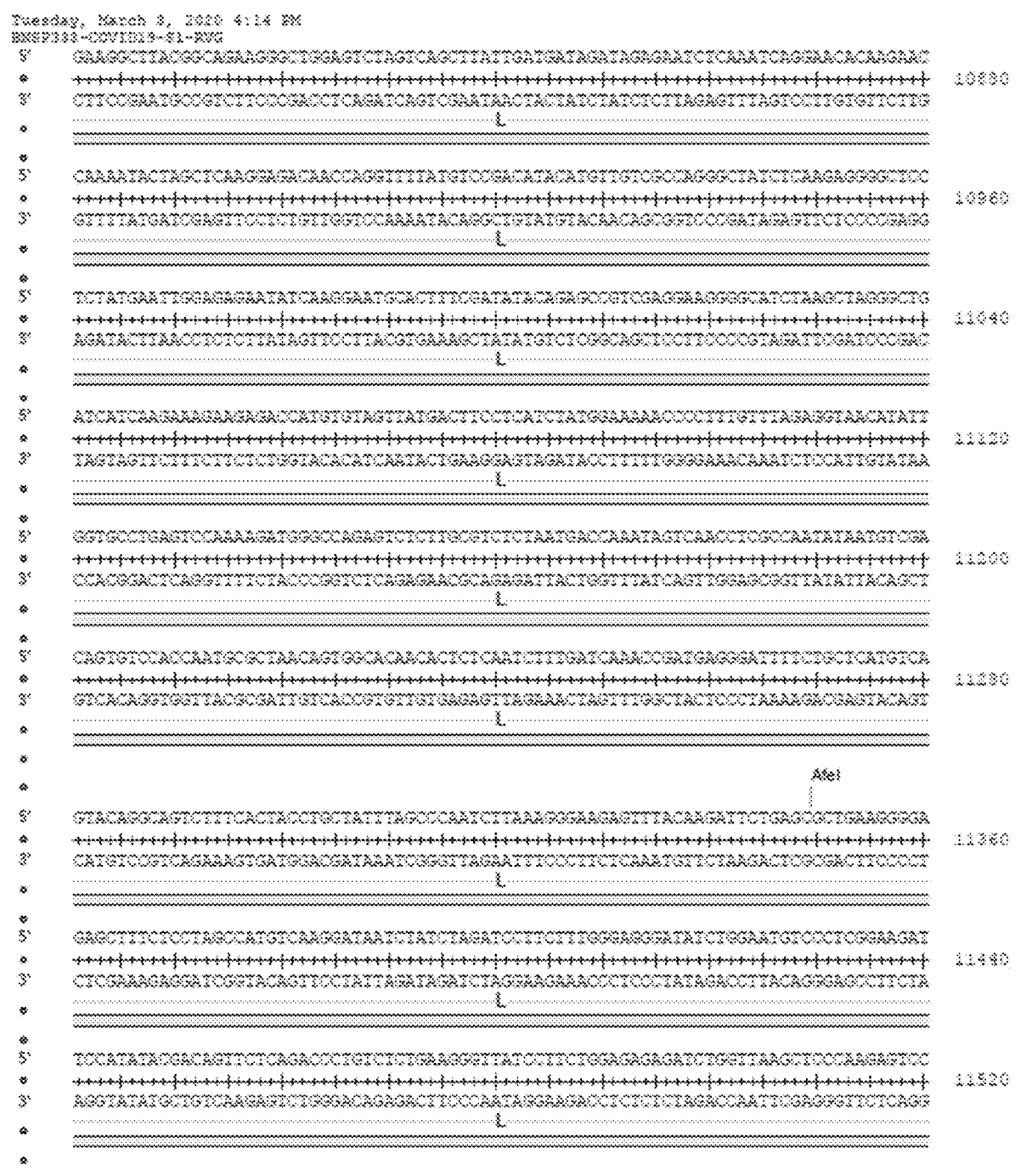
Figure 18:
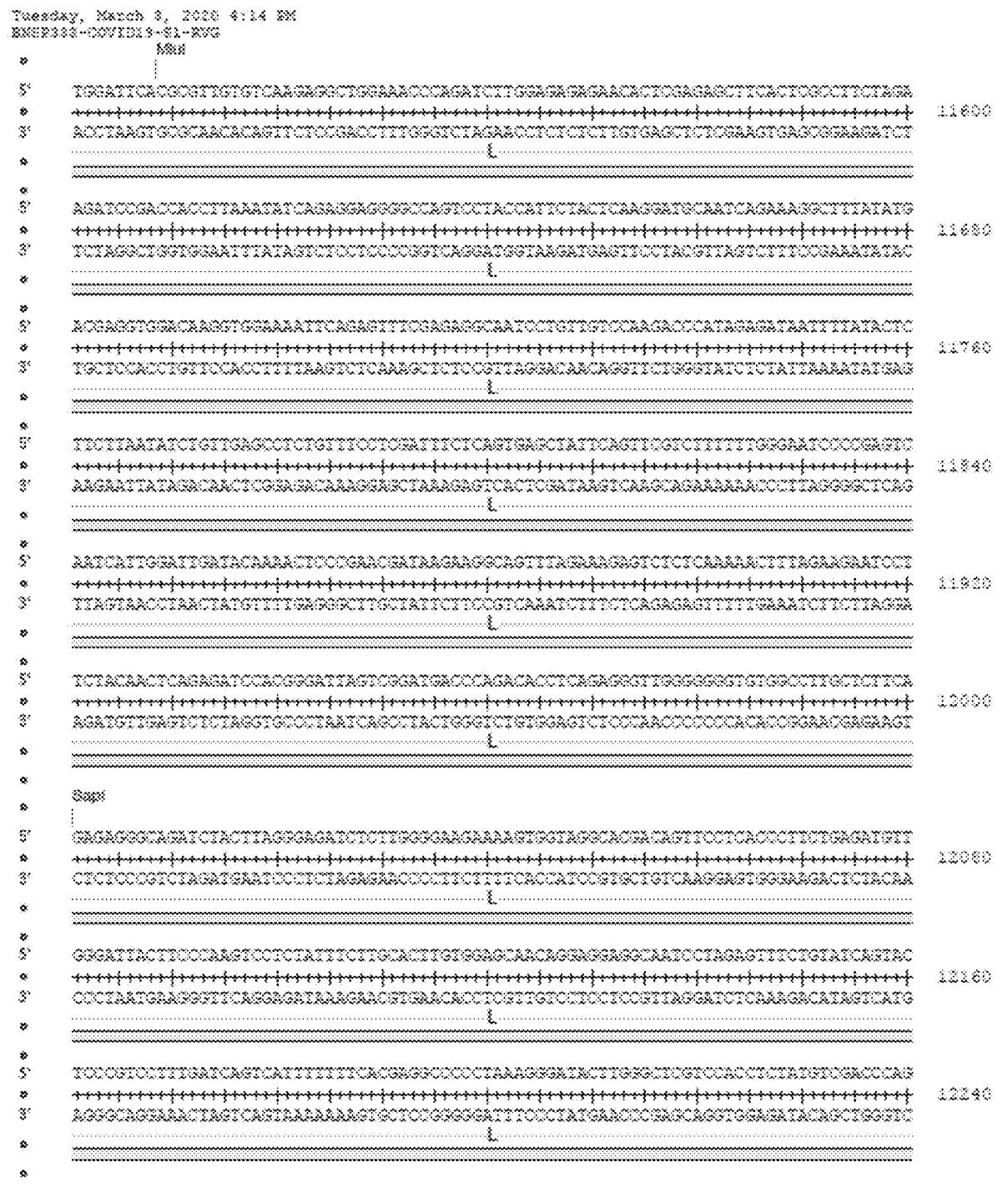
Figure 18:
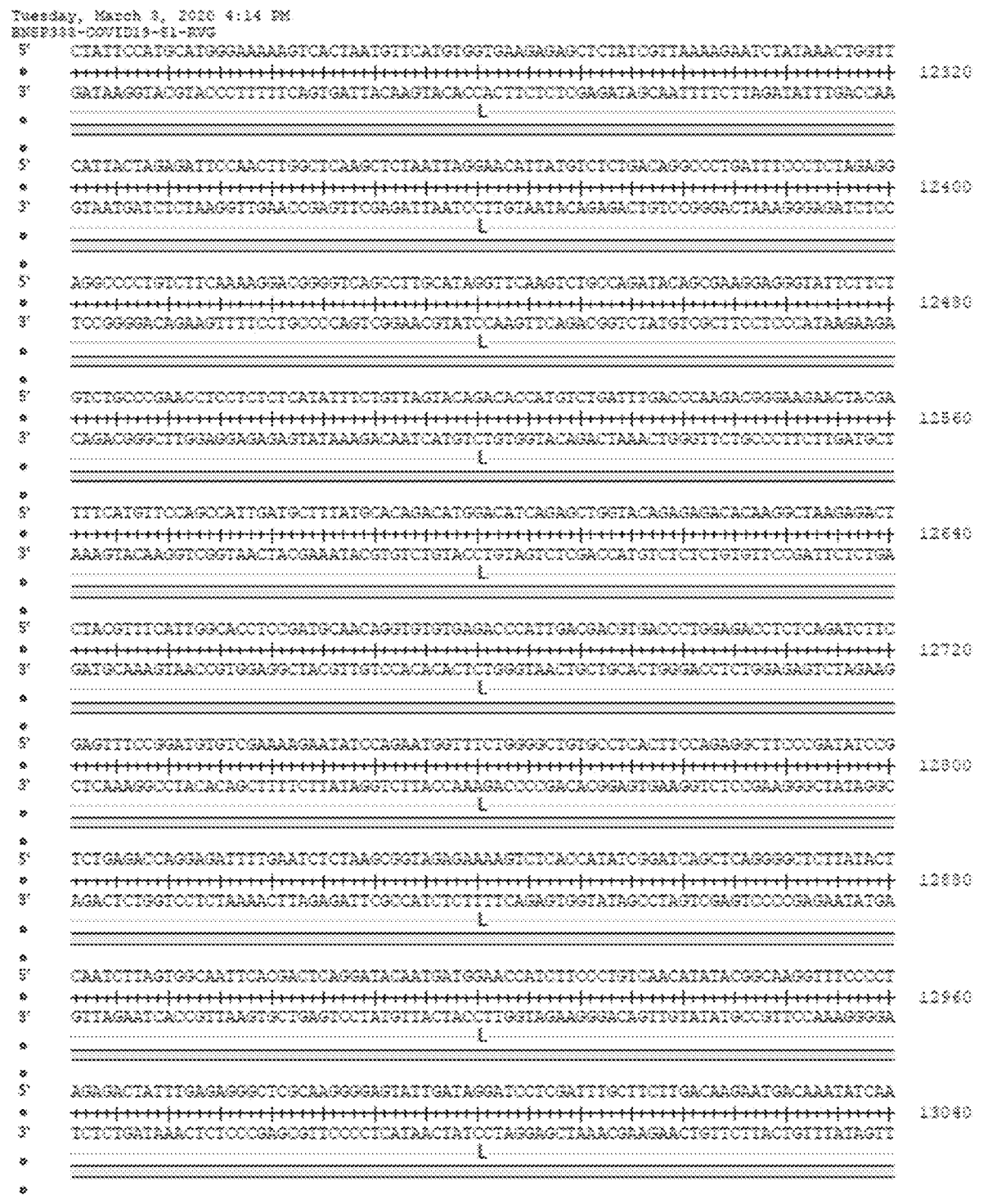
Figure 18:
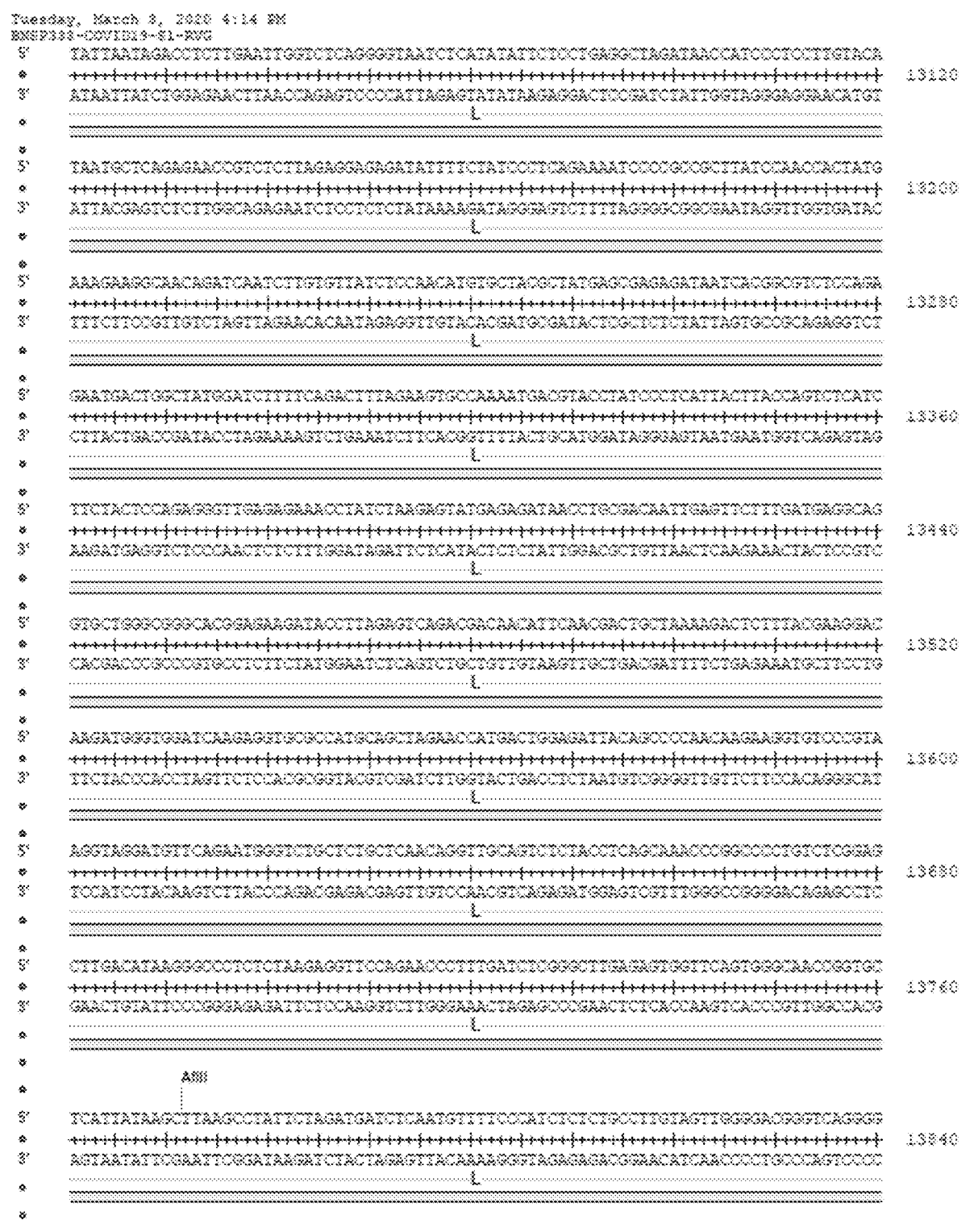
Figure 18:
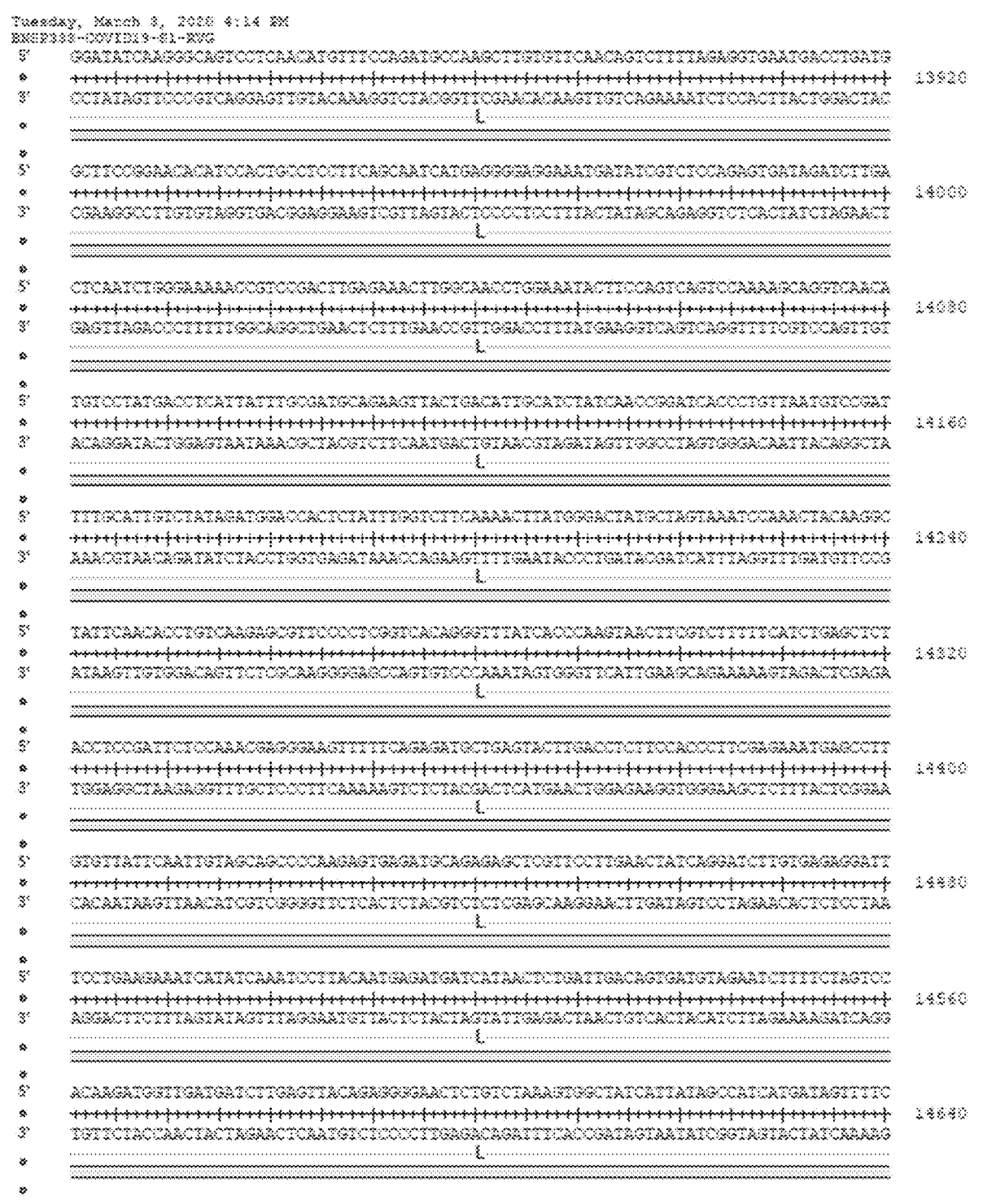
Figure 18:
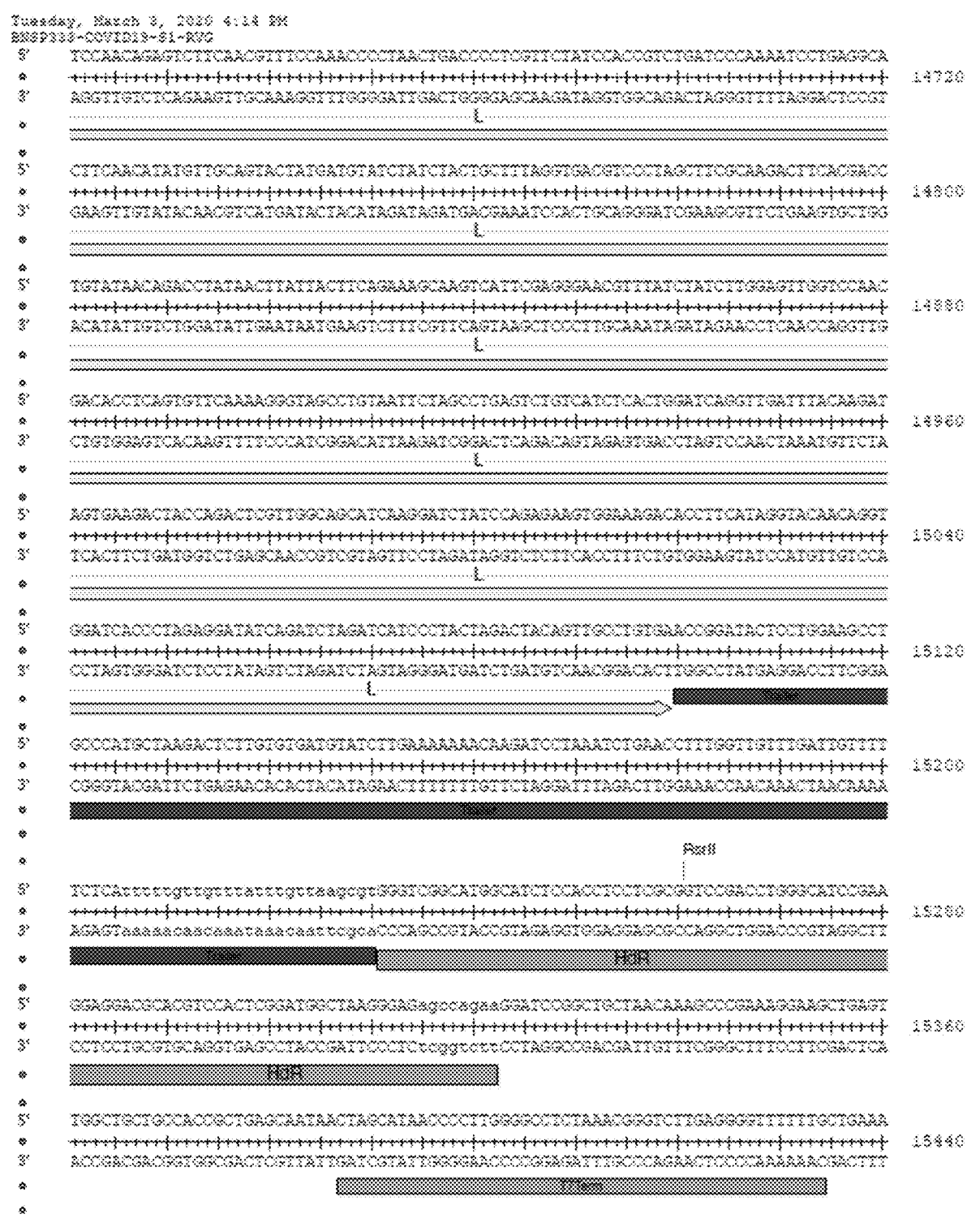
Figure 18:
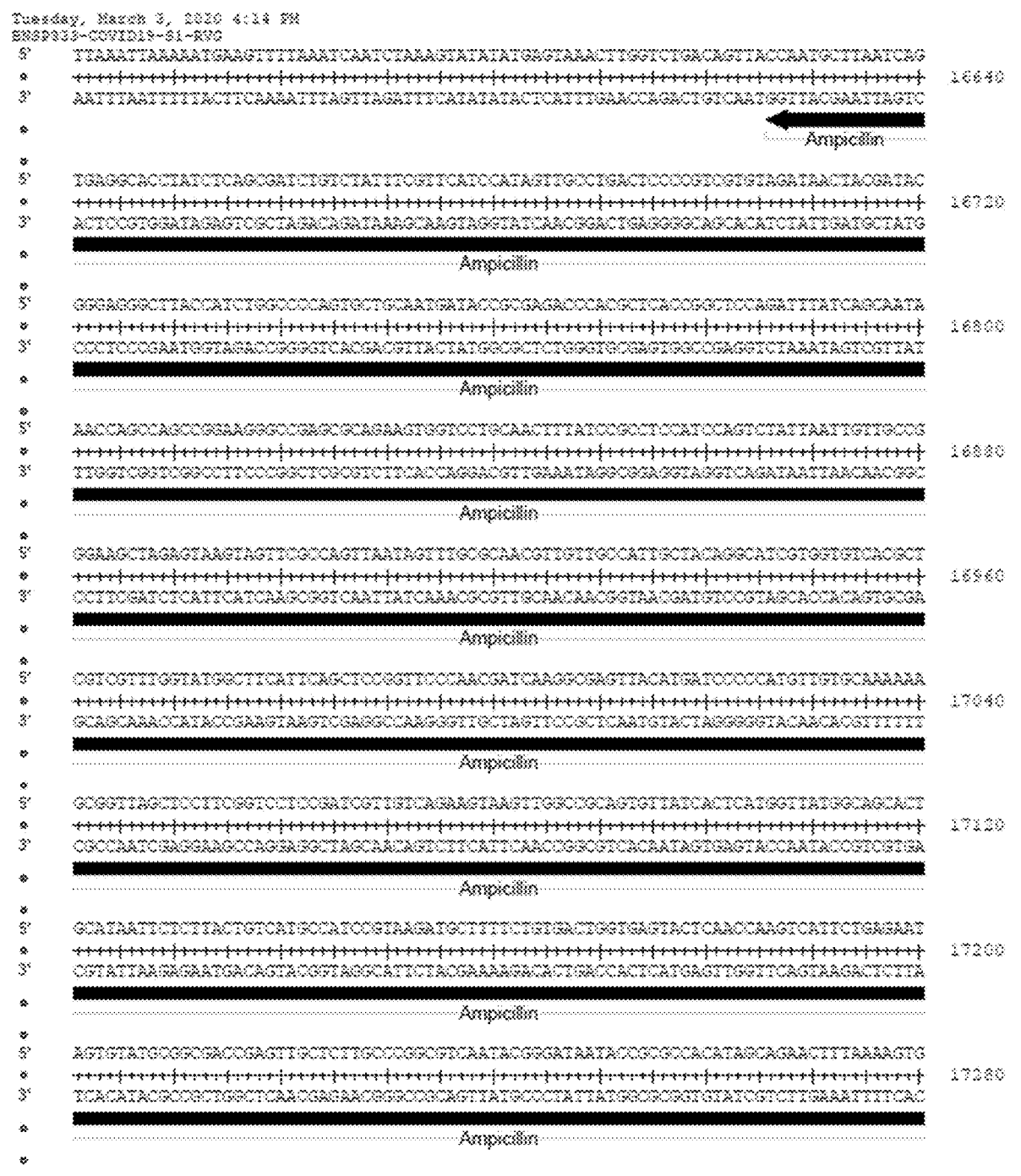
Figure 18:
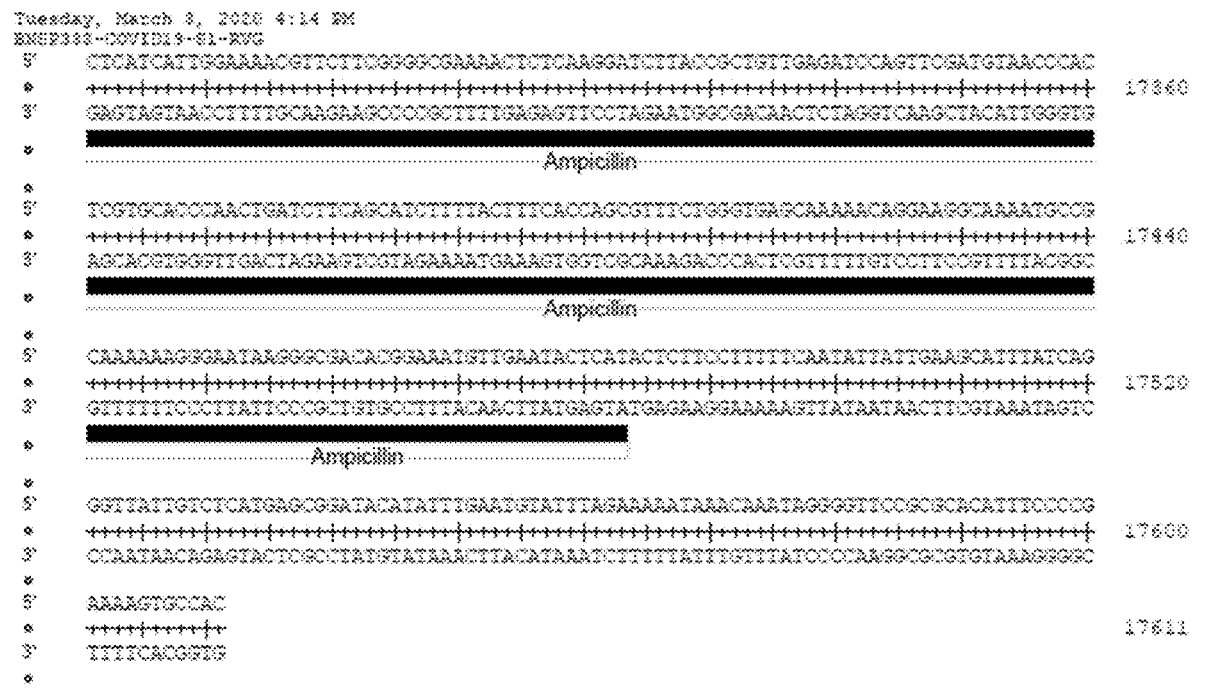

FIG. 18 shows the sequence (SEQ ID NO: 2) and features of "BNSP333-COVID19-S1-RVG".

Figure 19:
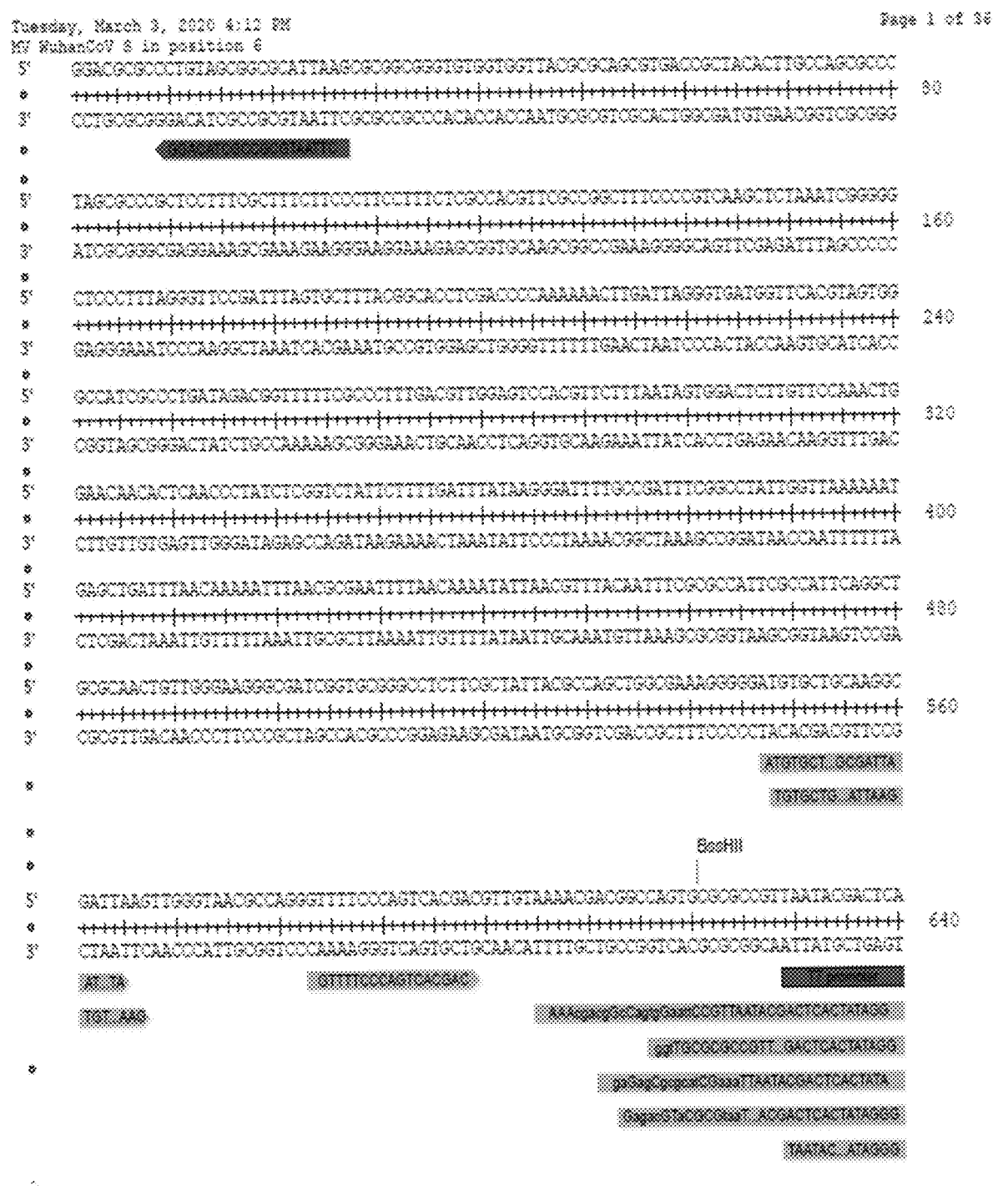
Figure 19:
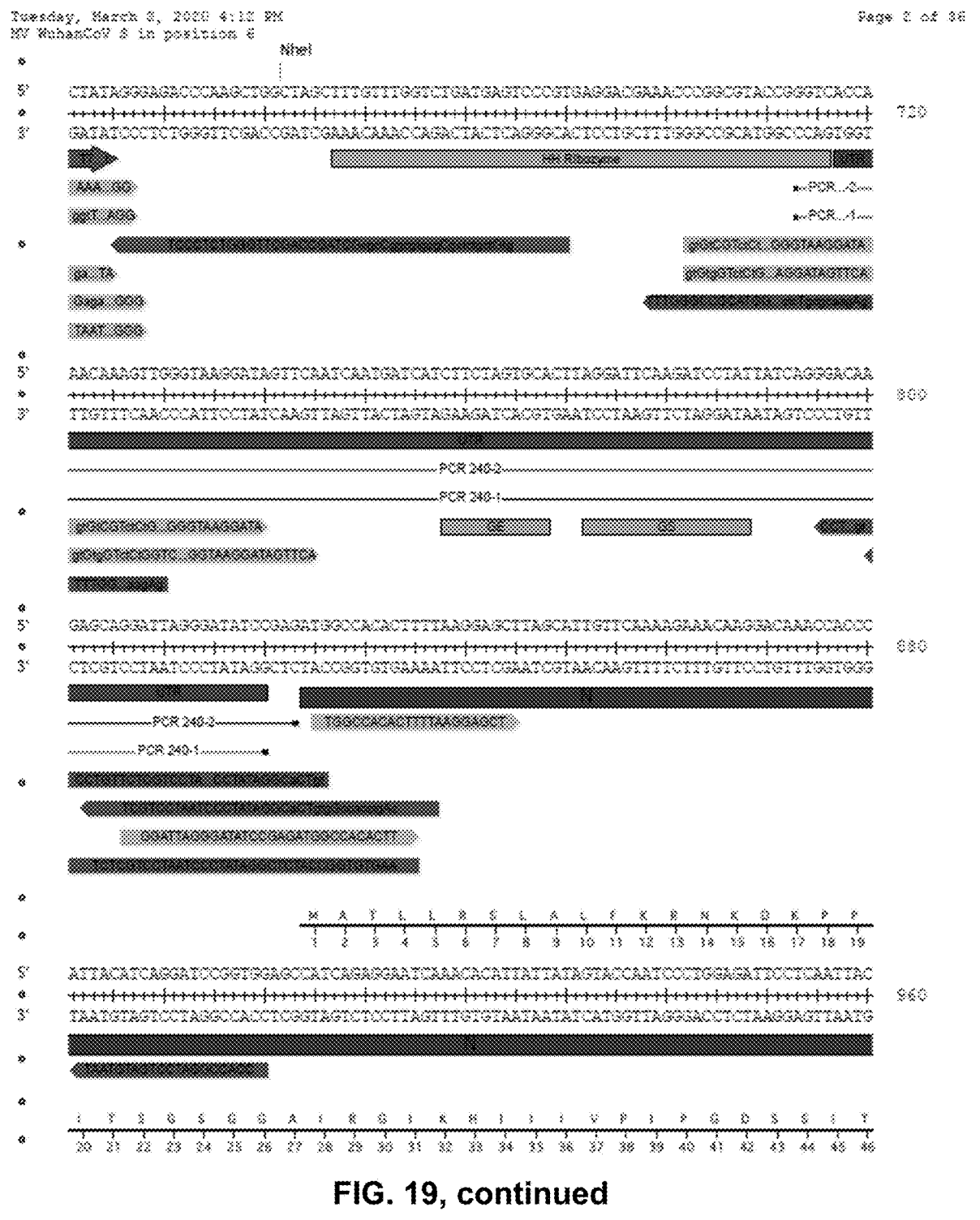
Figure 19:
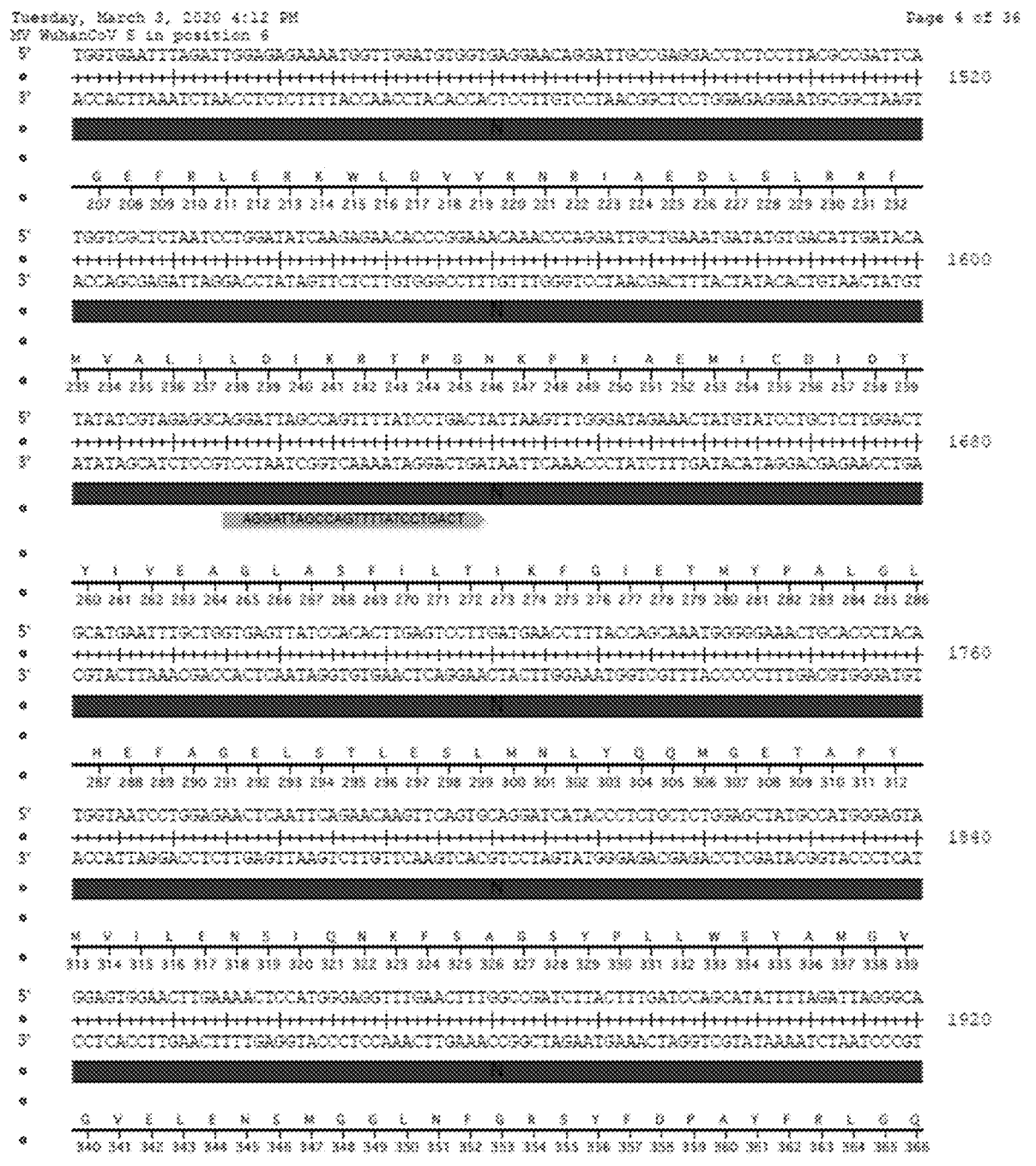
Figure 19:
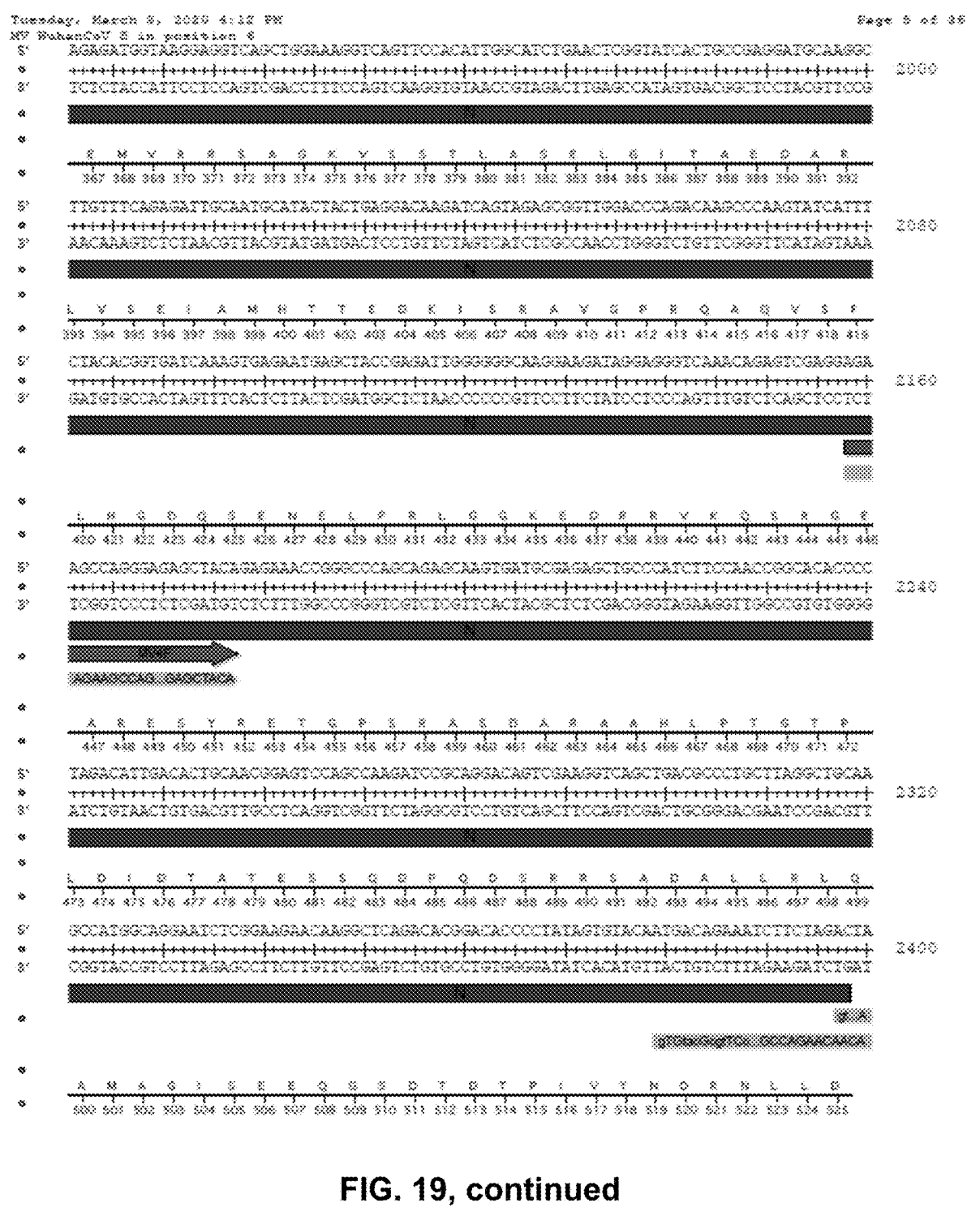
Figure 19:
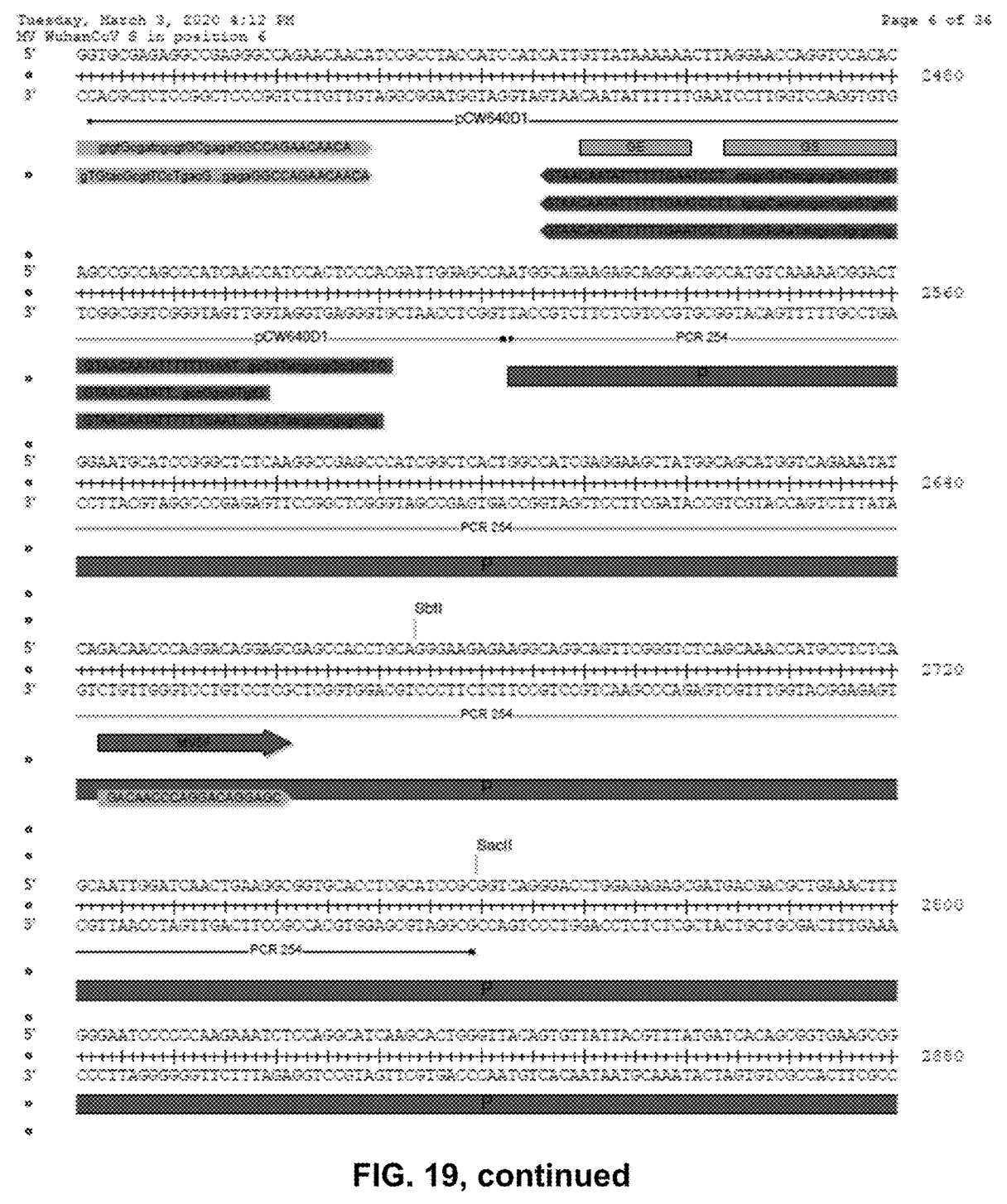
Figure 19:
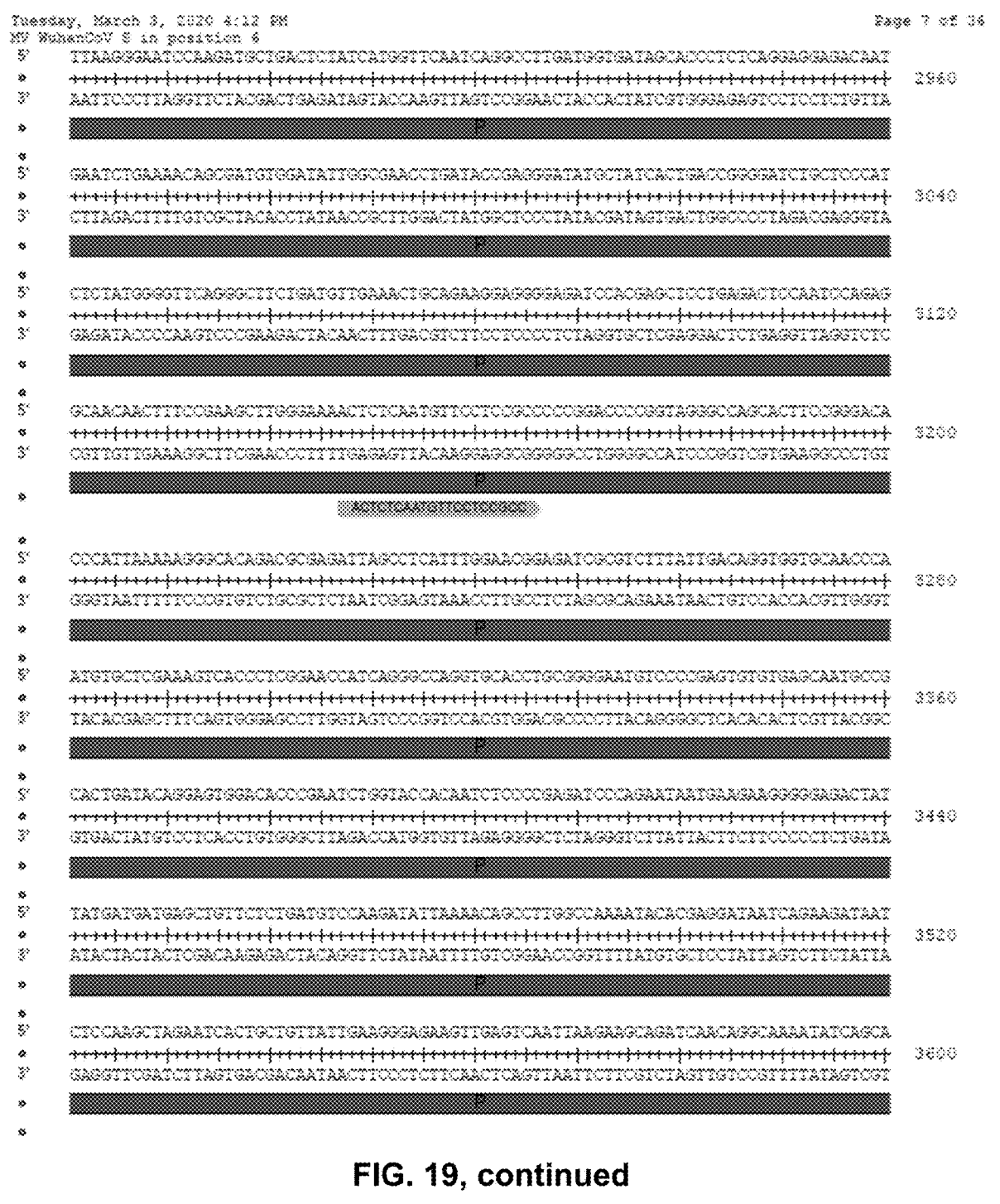
Figure 19:
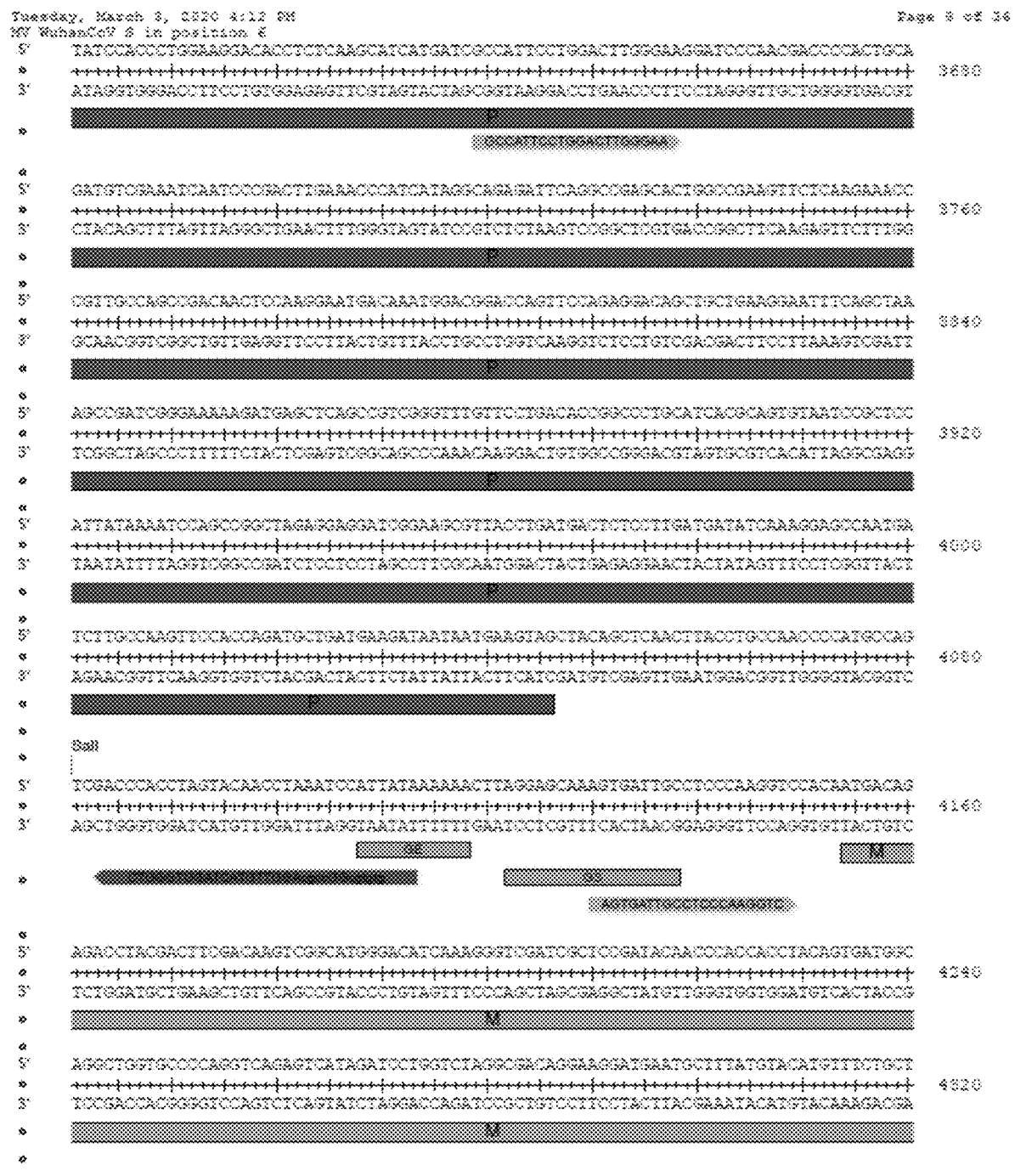
Figure 19:
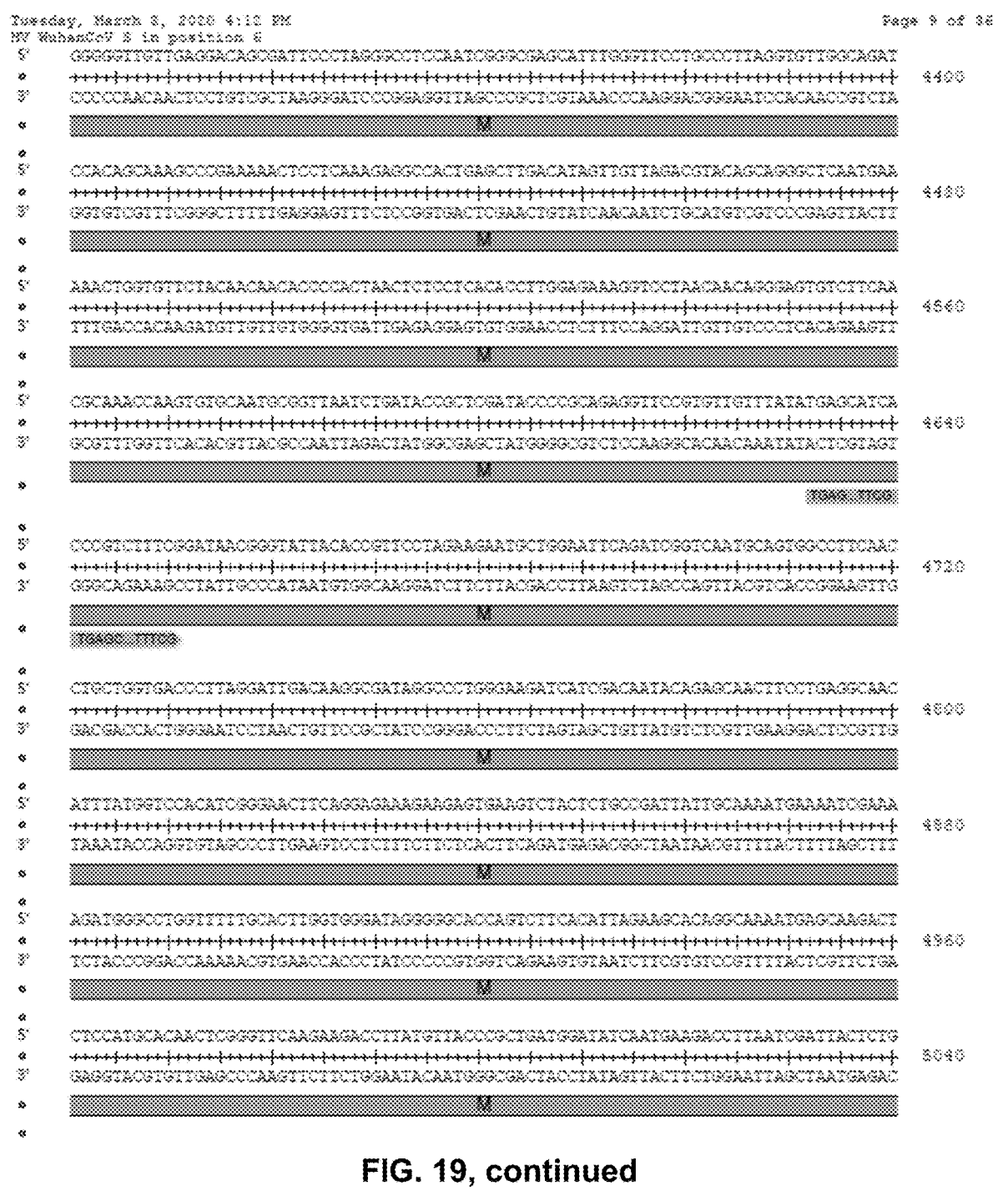
Figure 19:
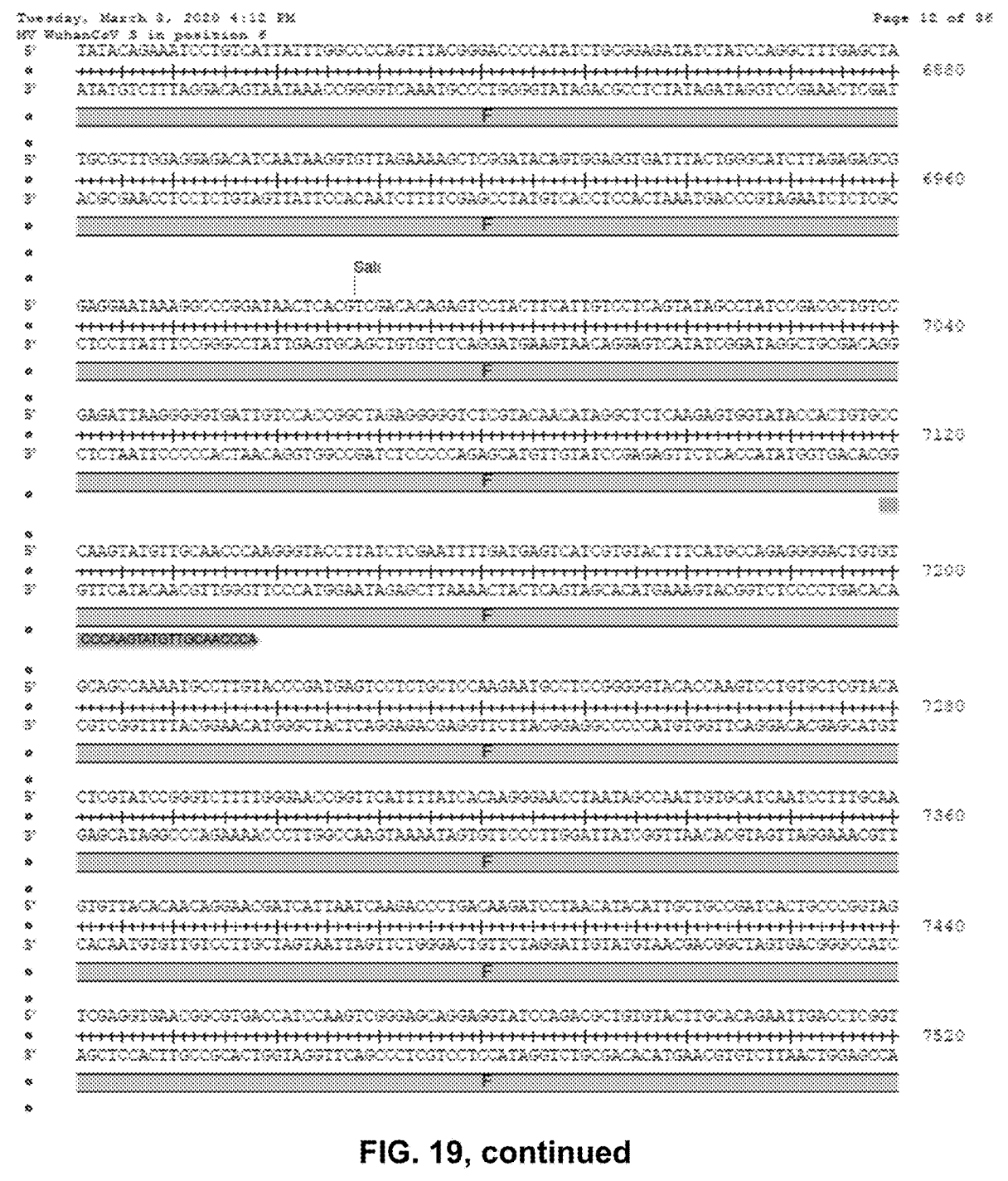
Figure 19:
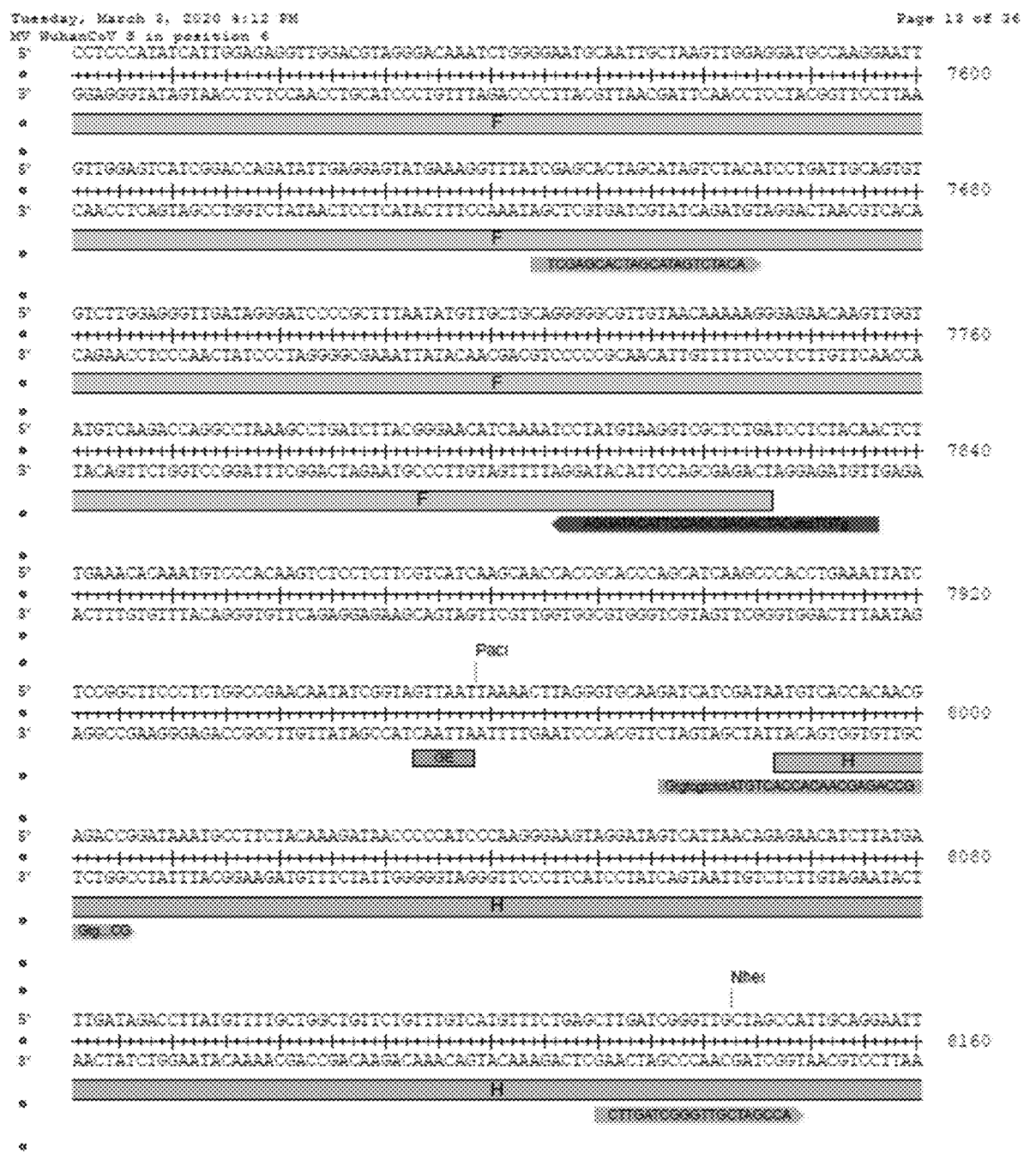
Figure 19:
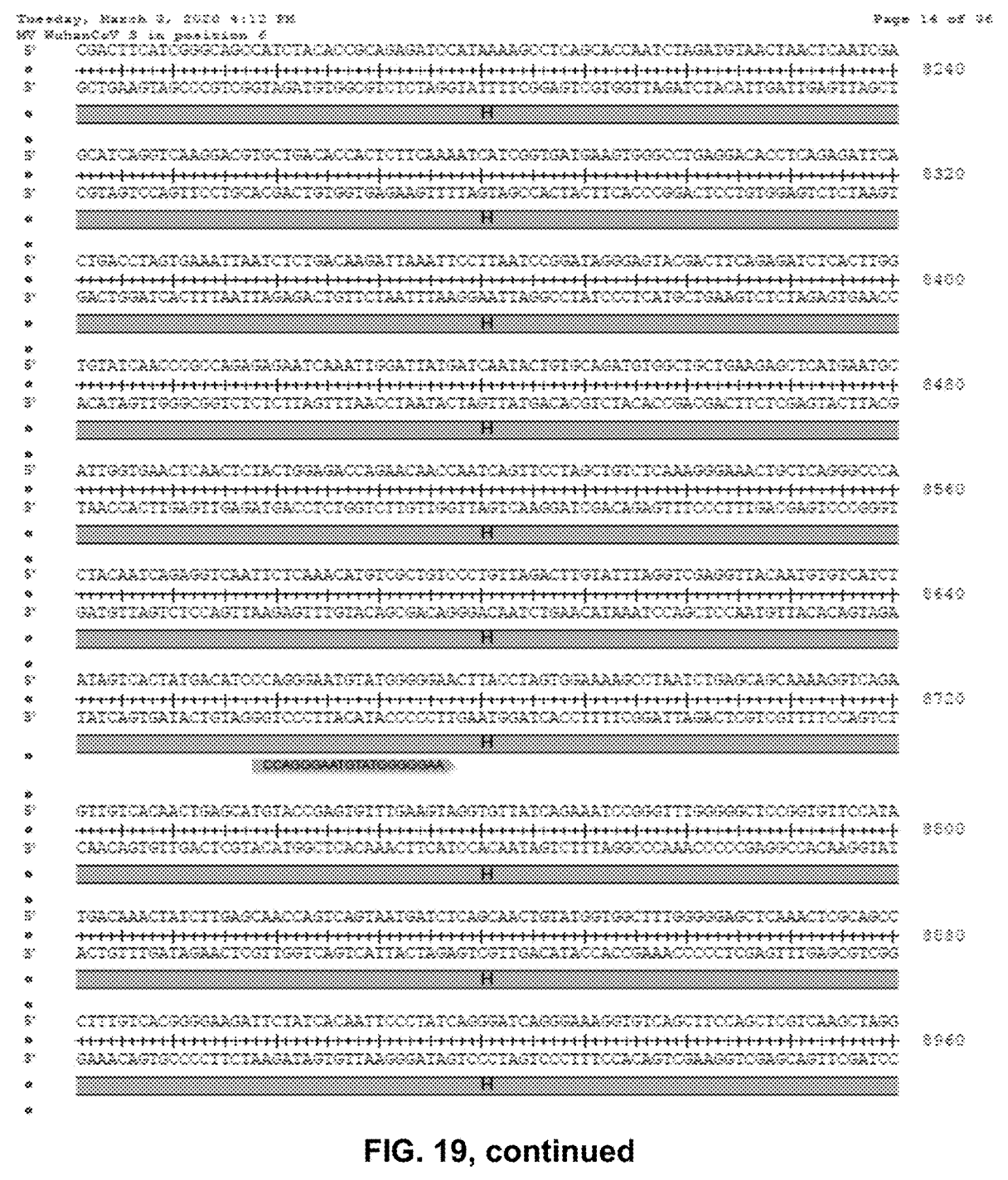
Figure 19:
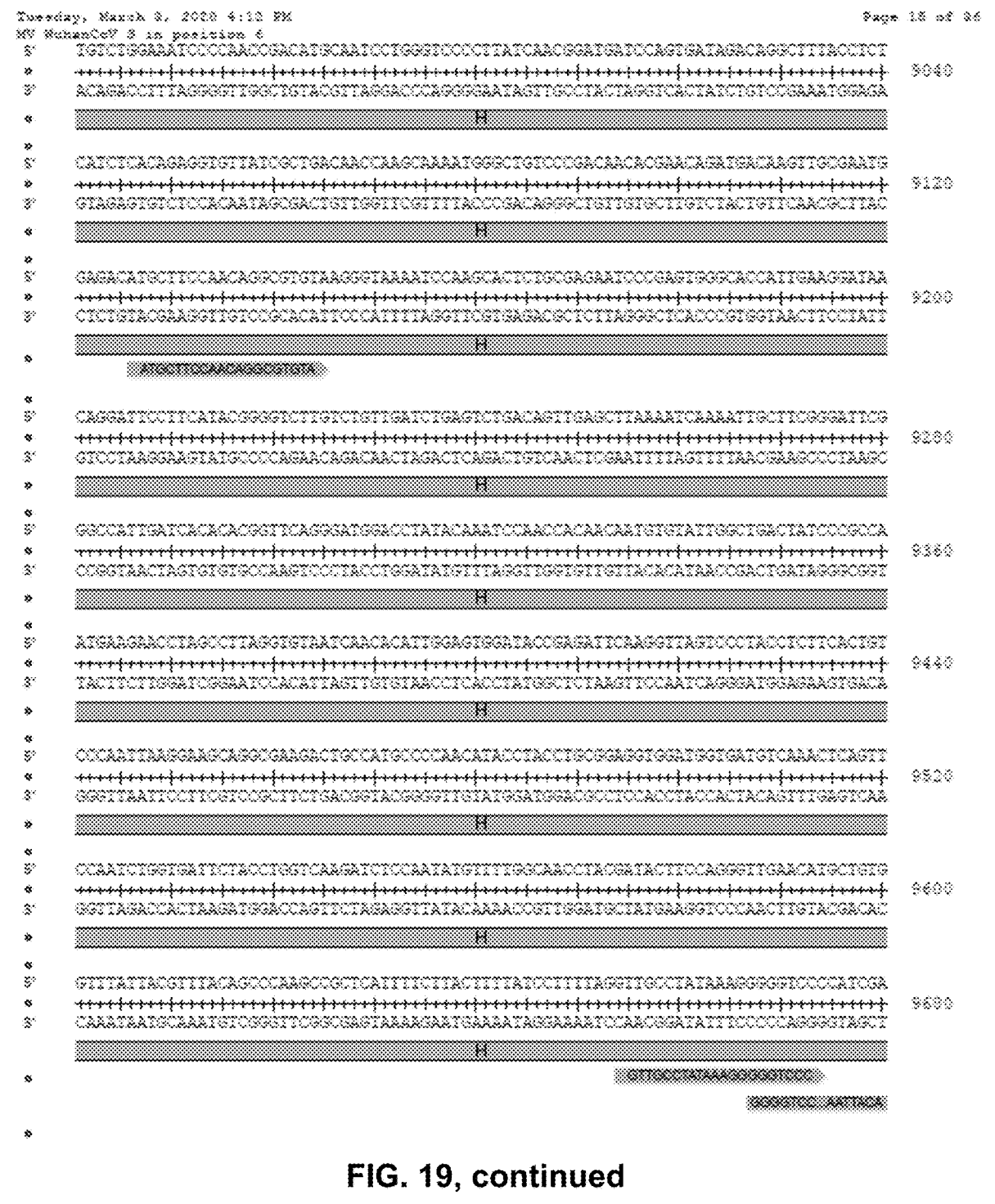
Figure 19:
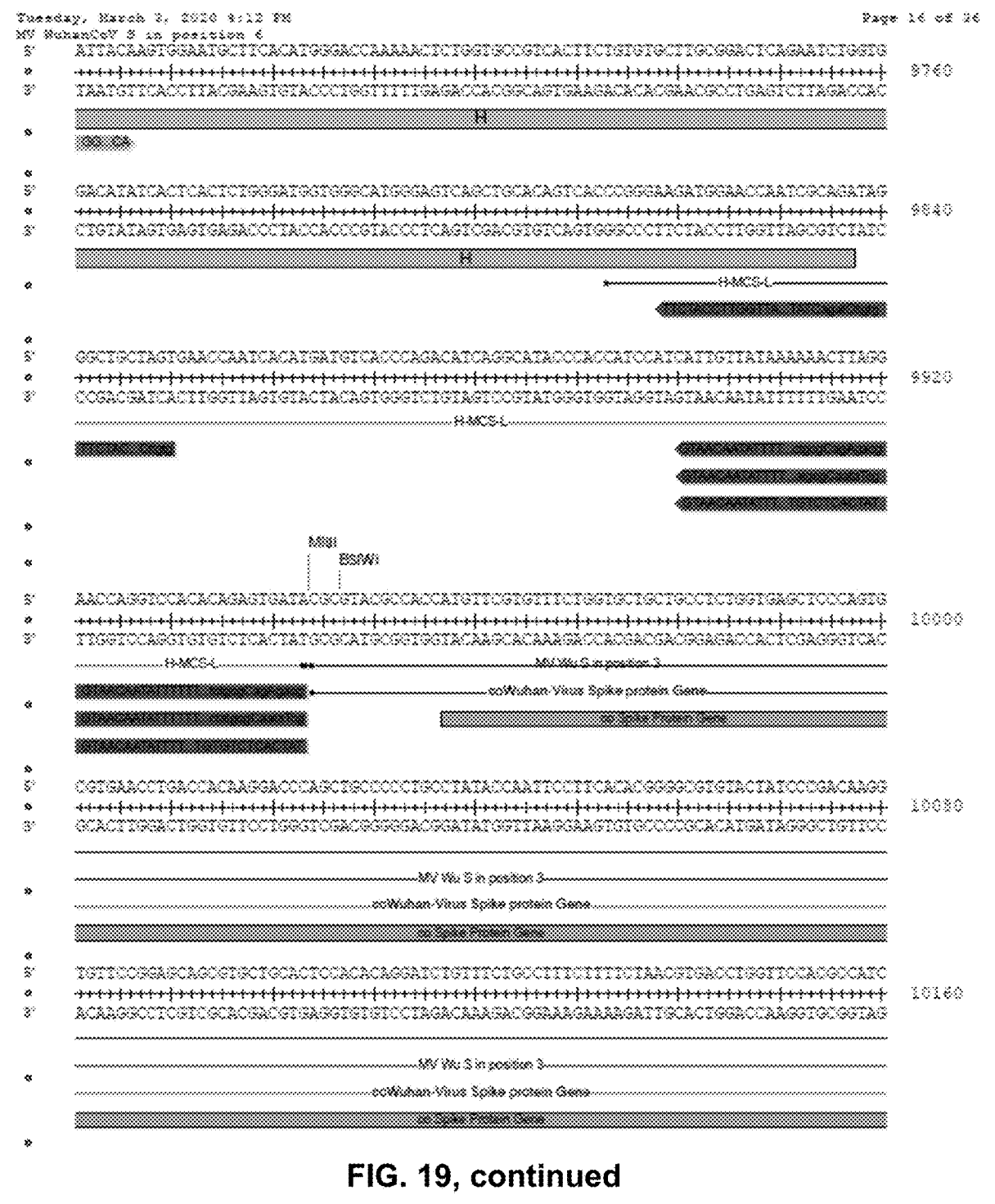
Figure 19:
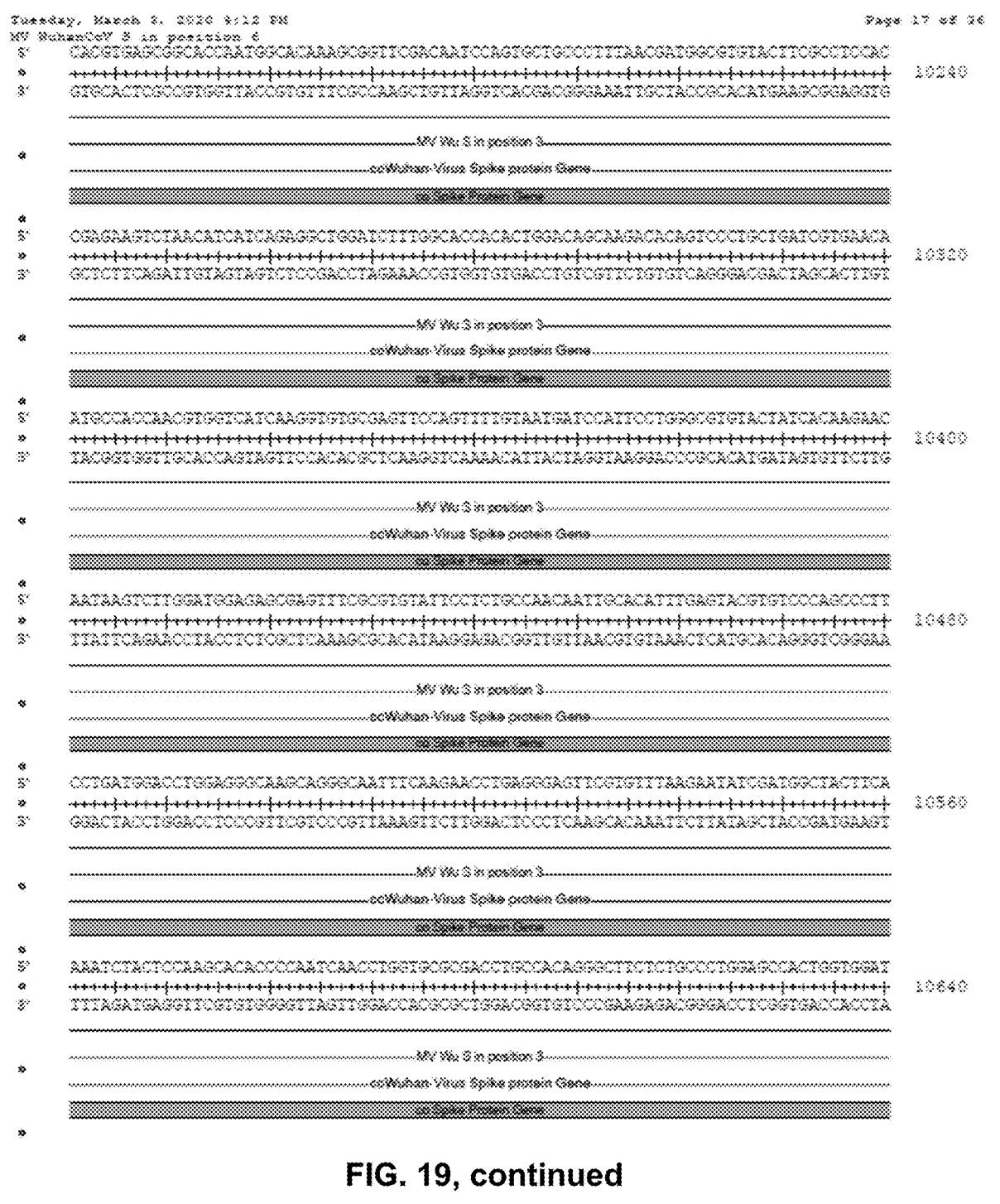
Figure 19:
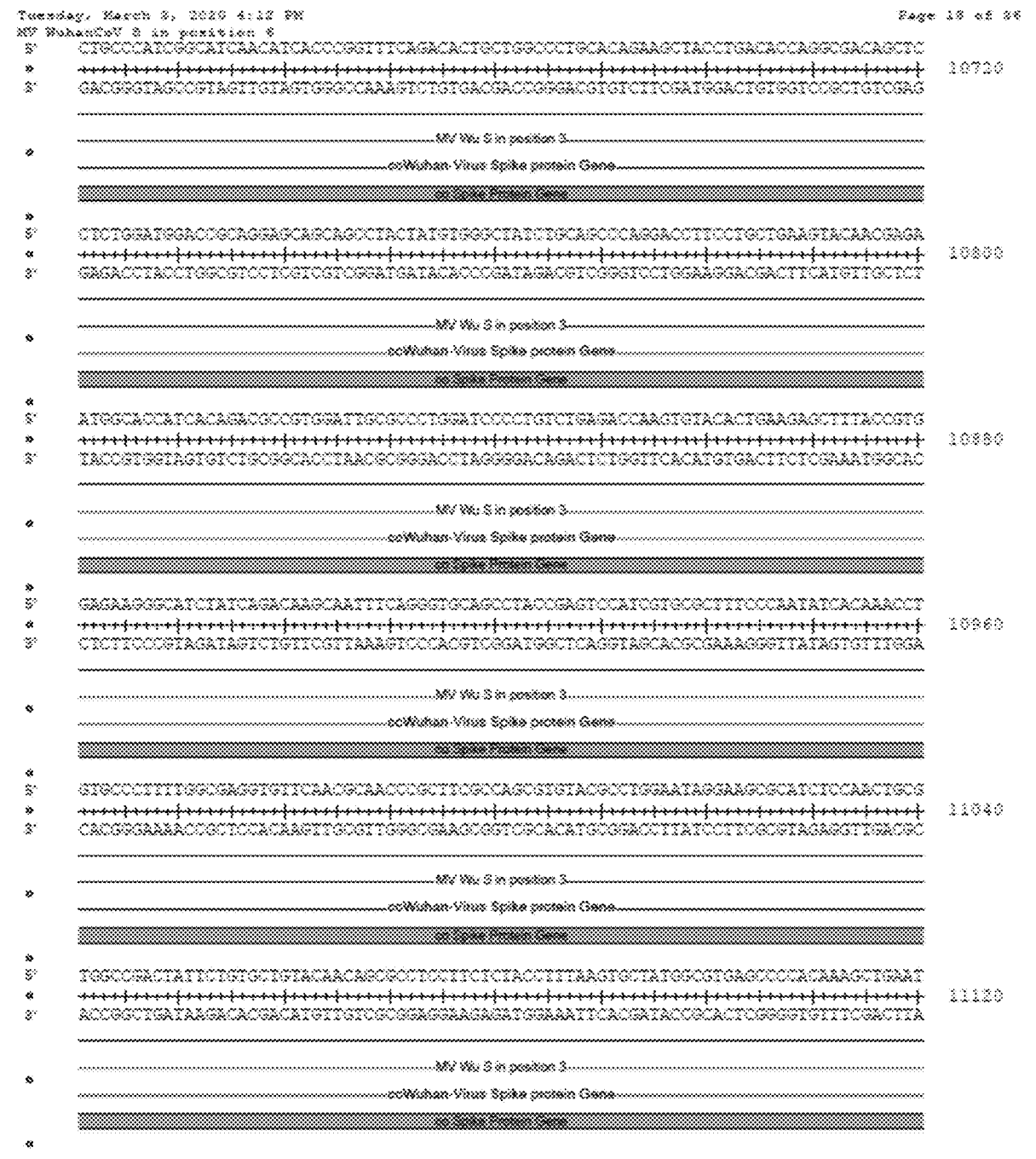
Figure 19:
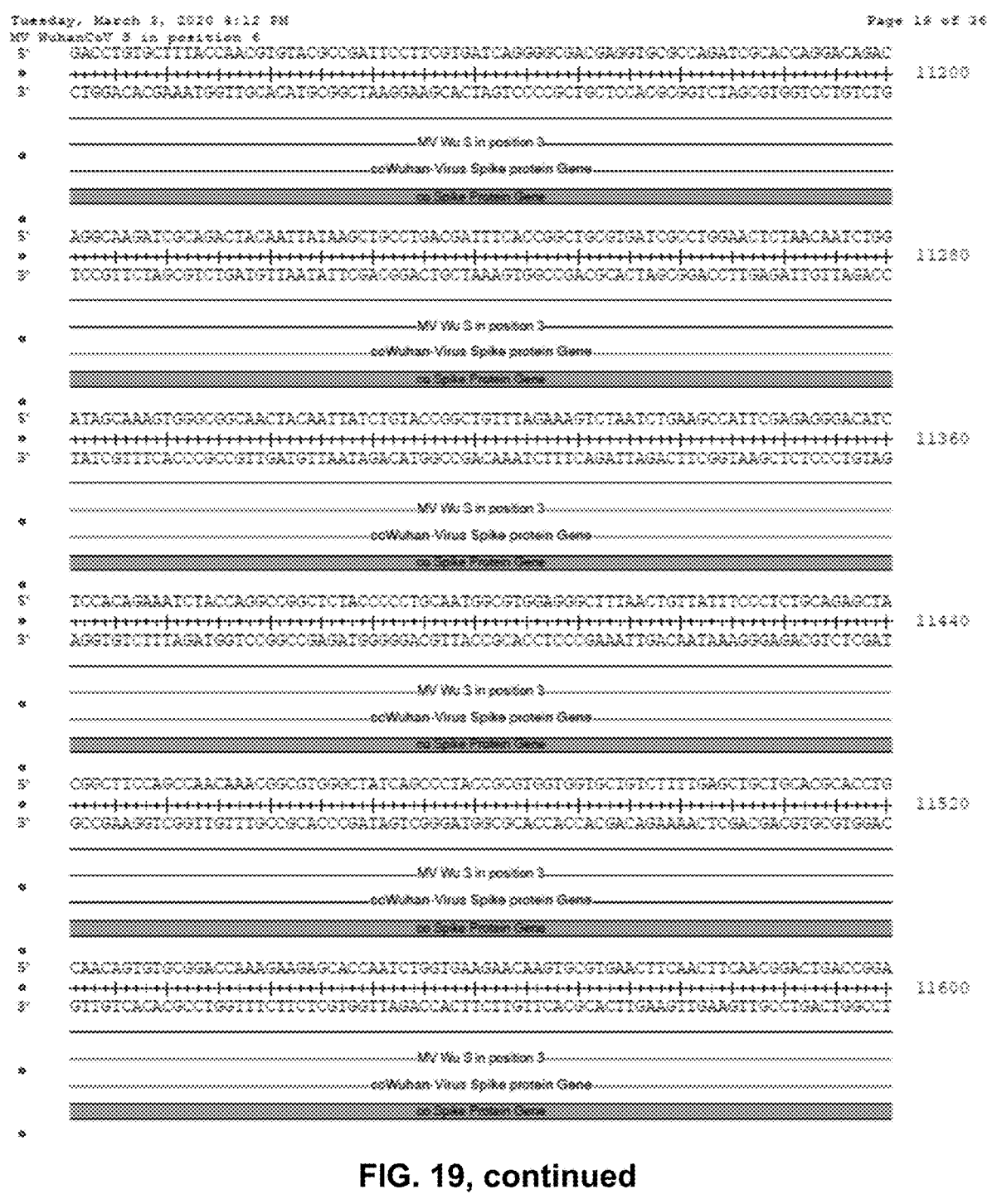
Figure 19:
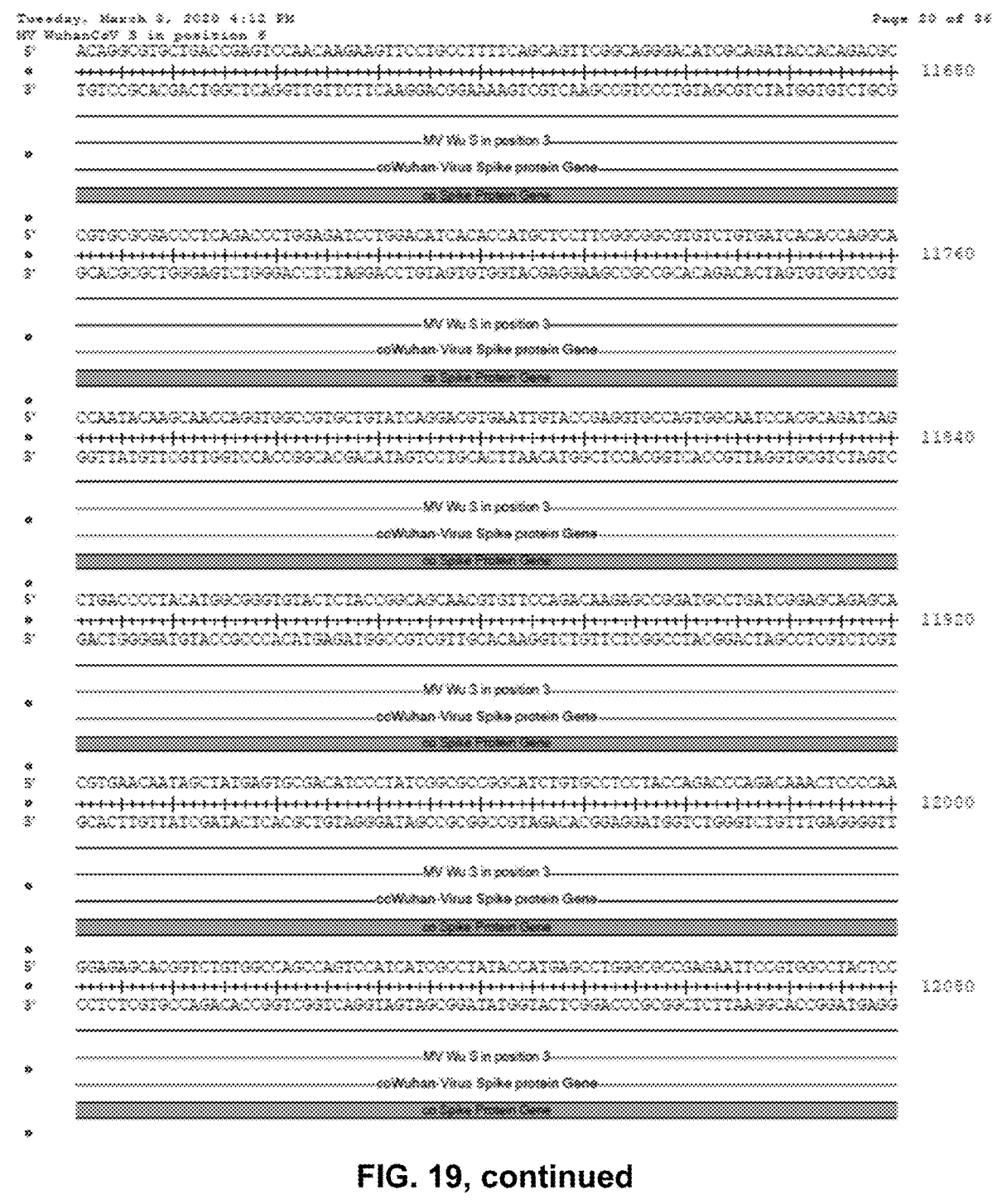
Figure 19:
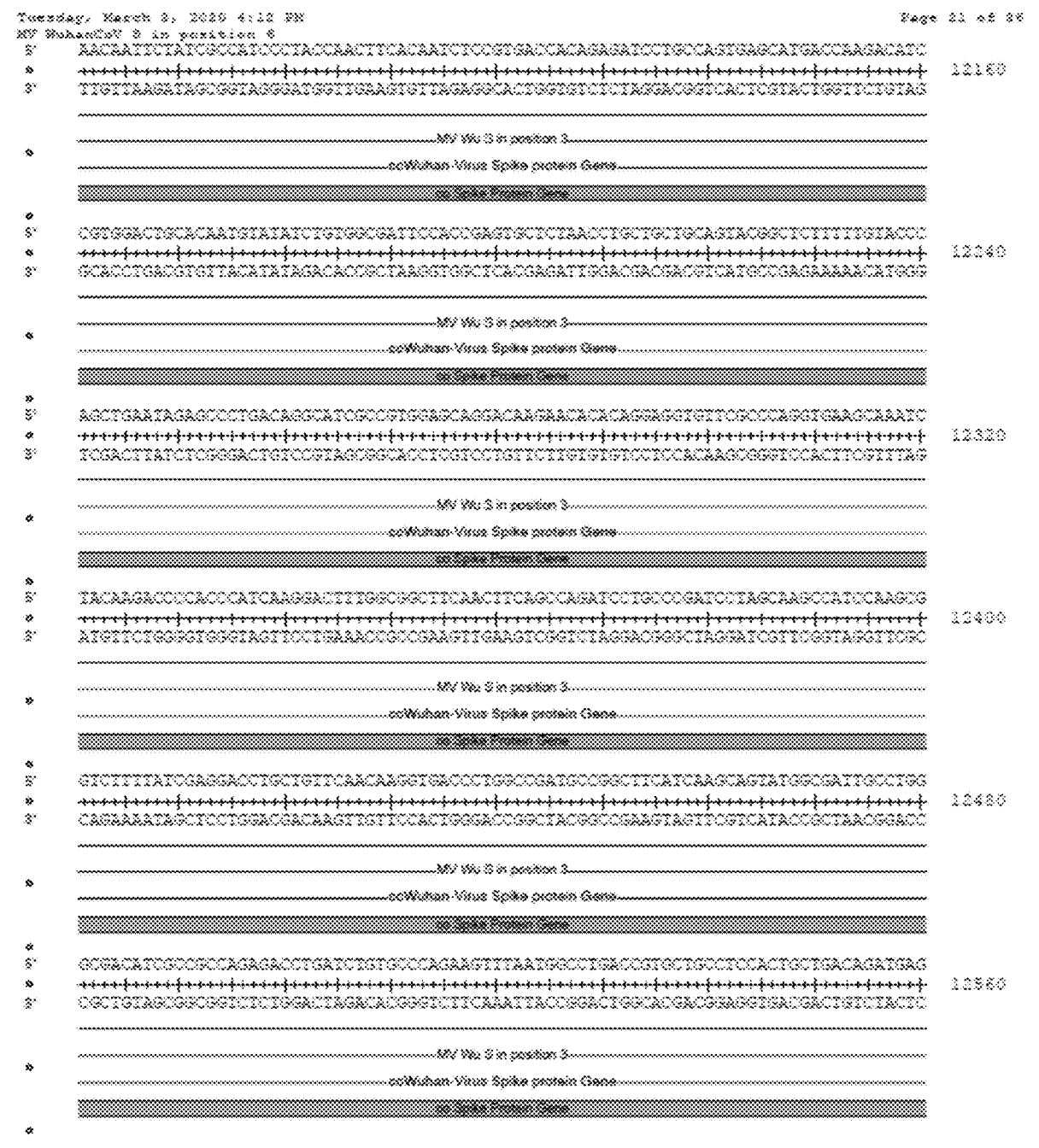
Figure 19:
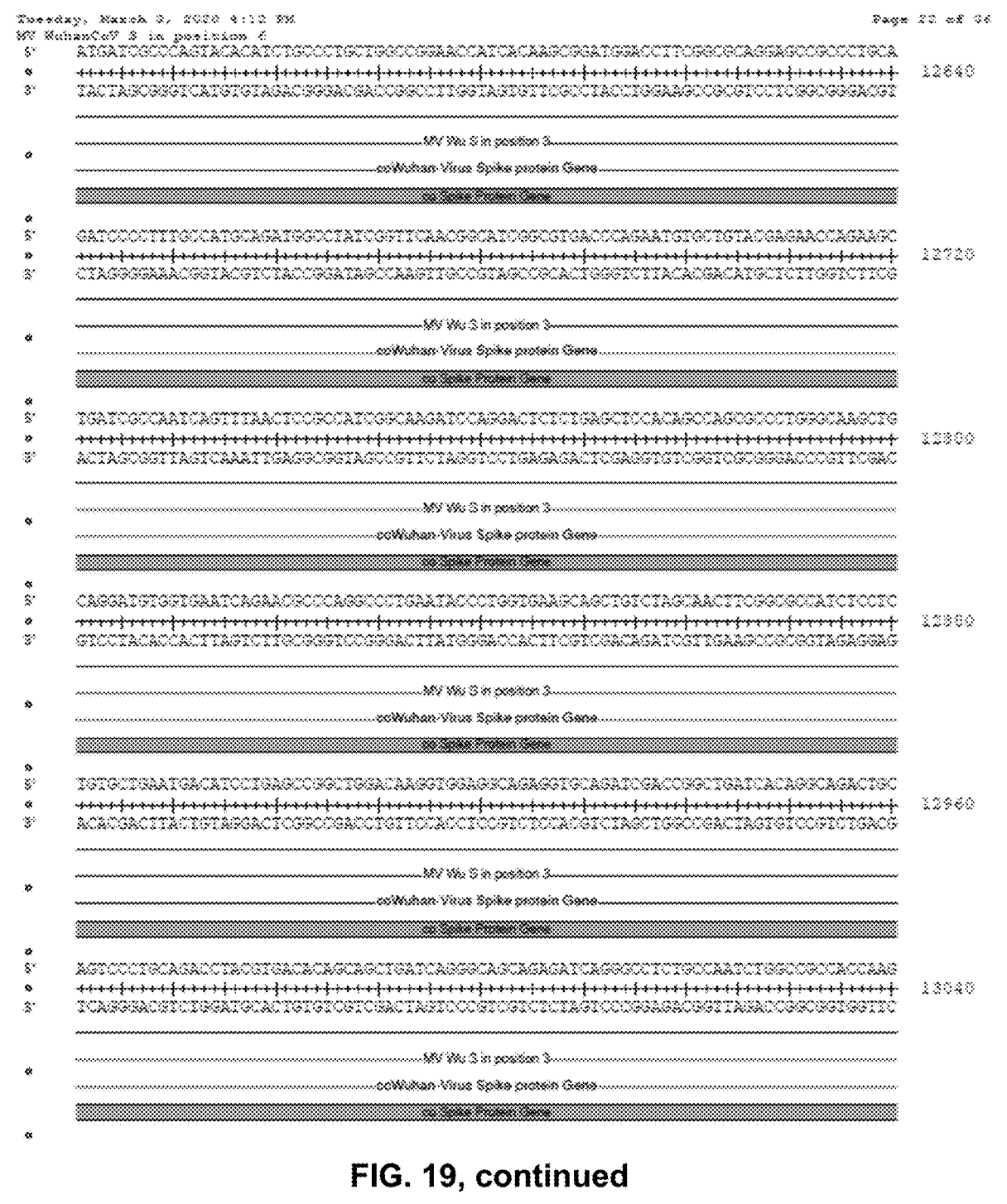
Figure 19:
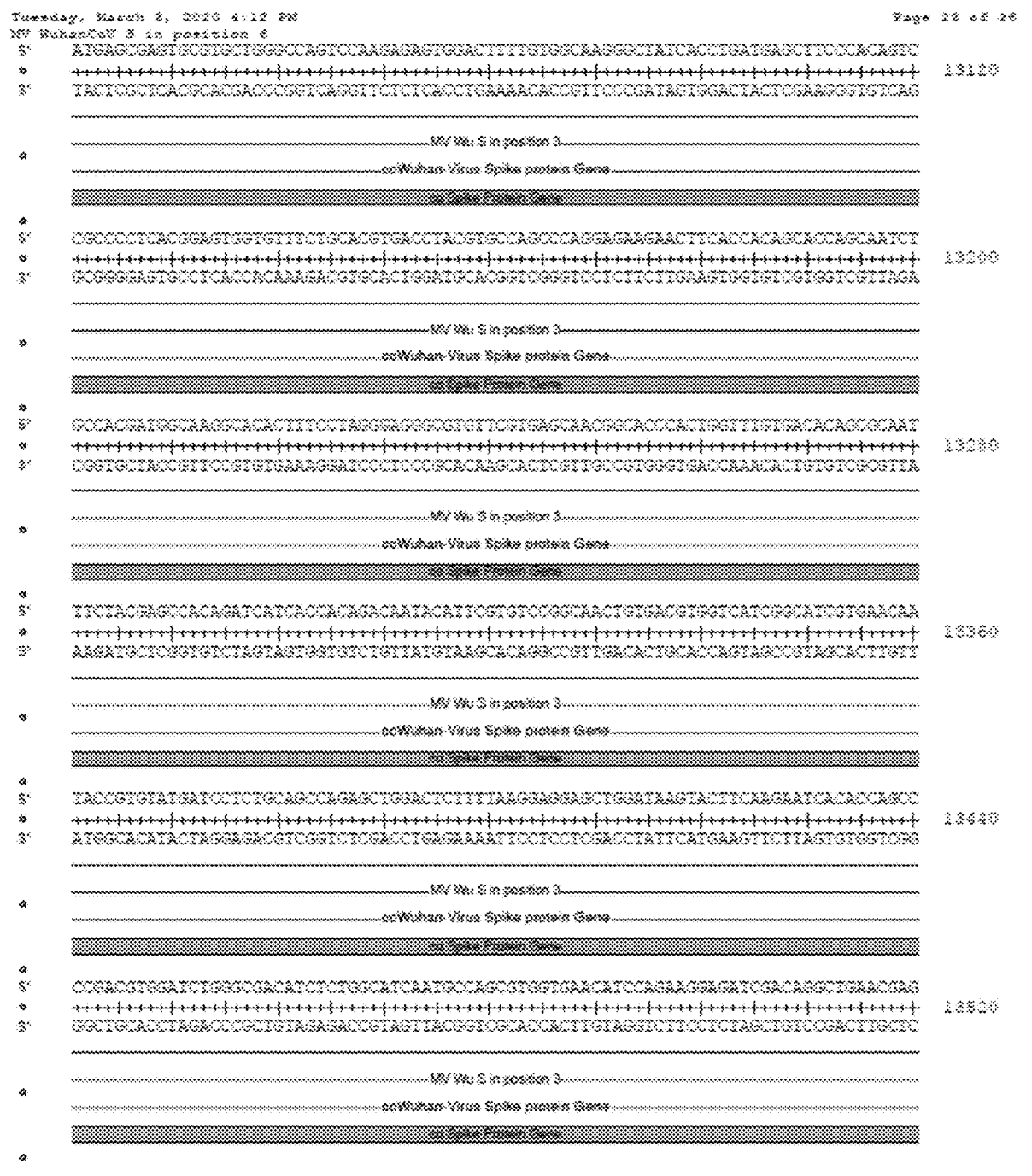
Figure 19:
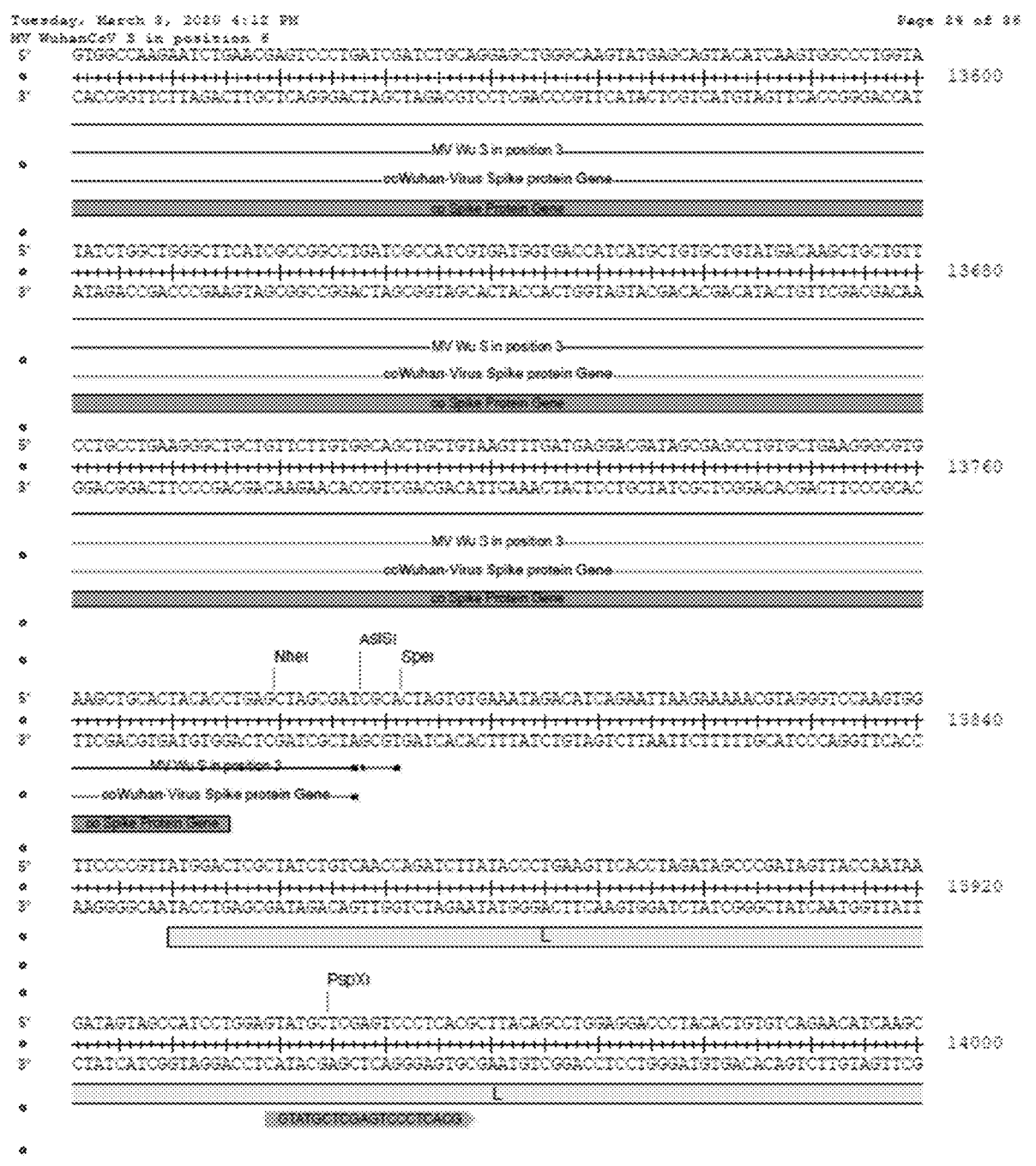
Figure 19:
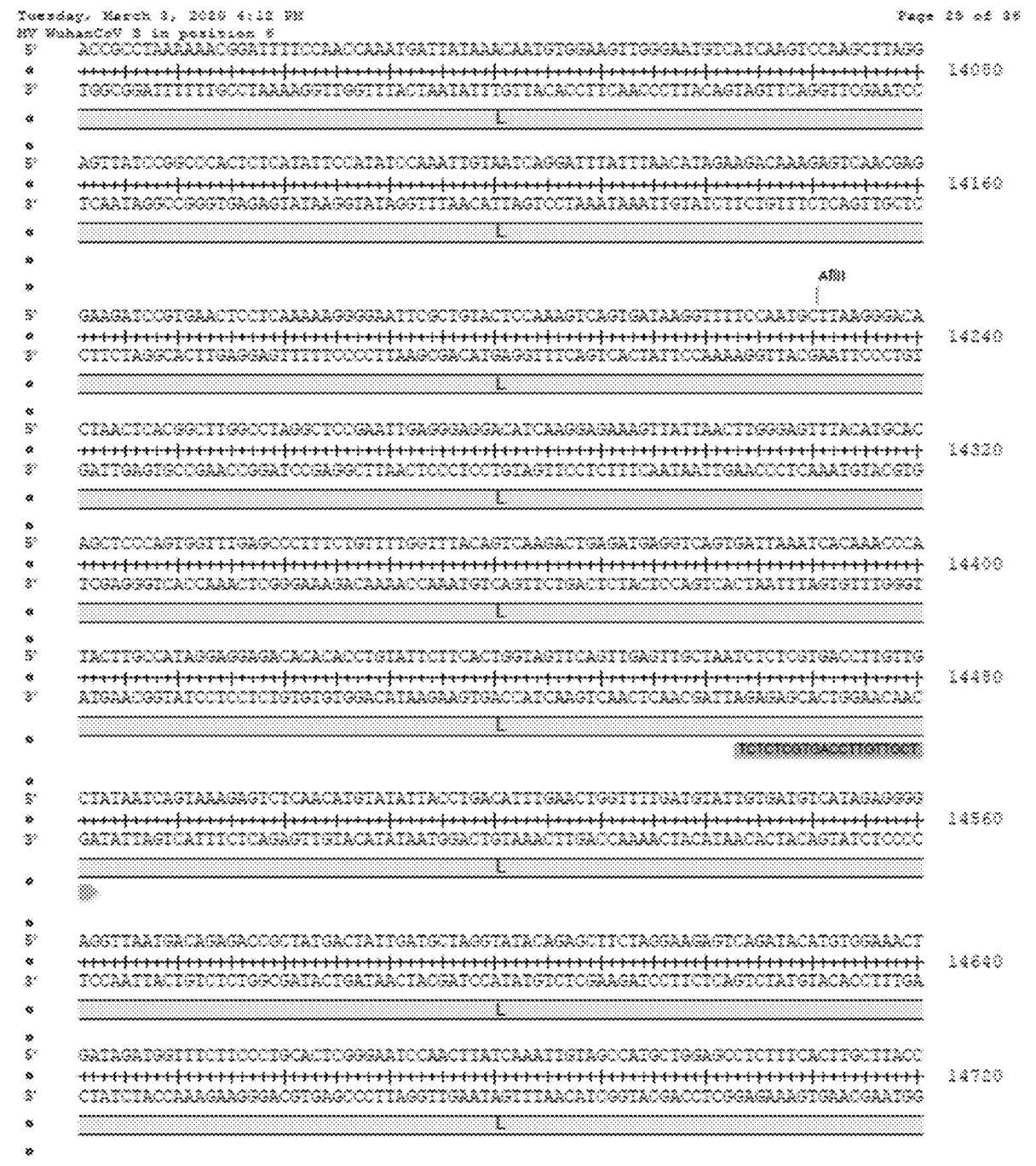
Figure 19:
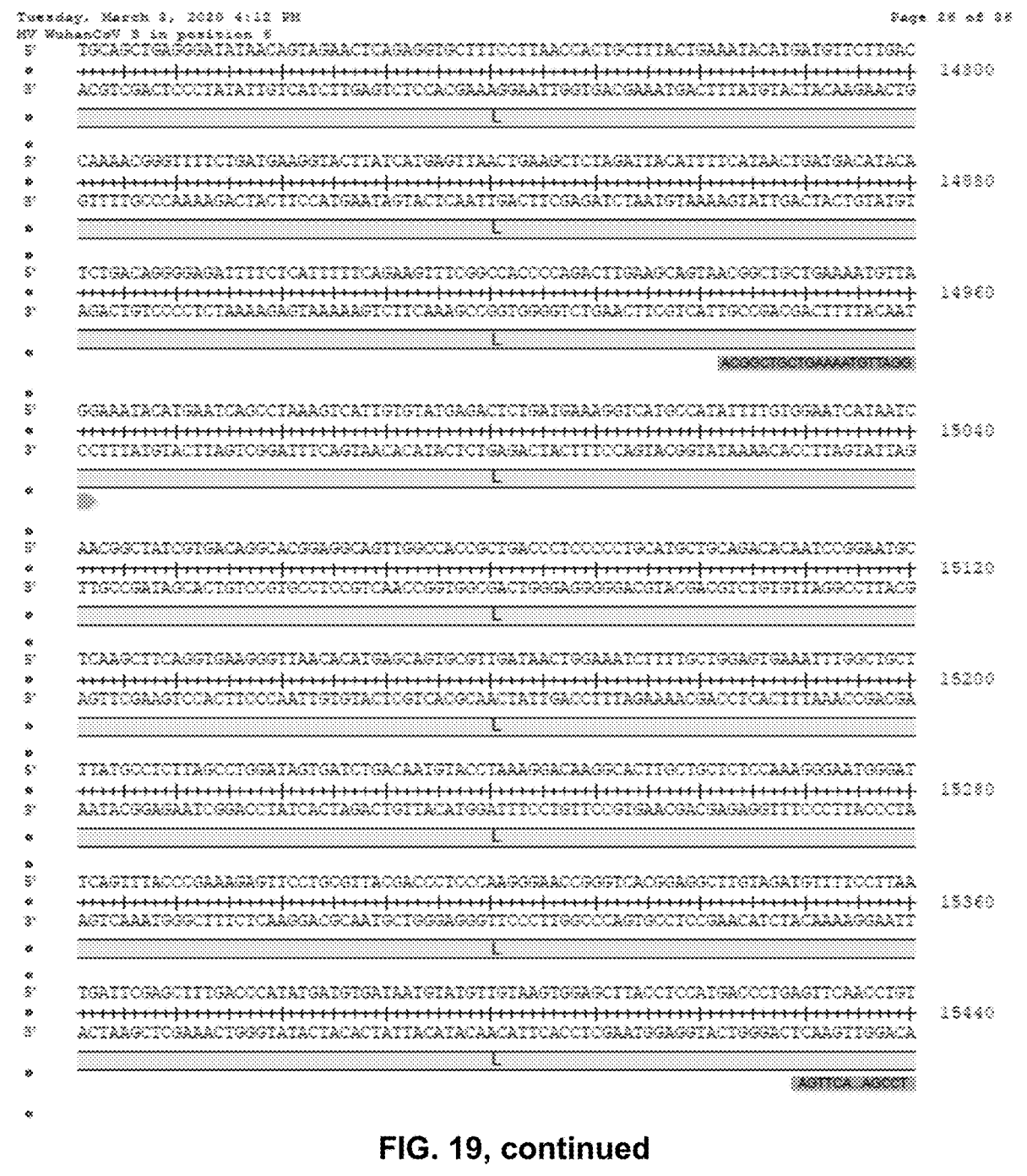
Figure 19:
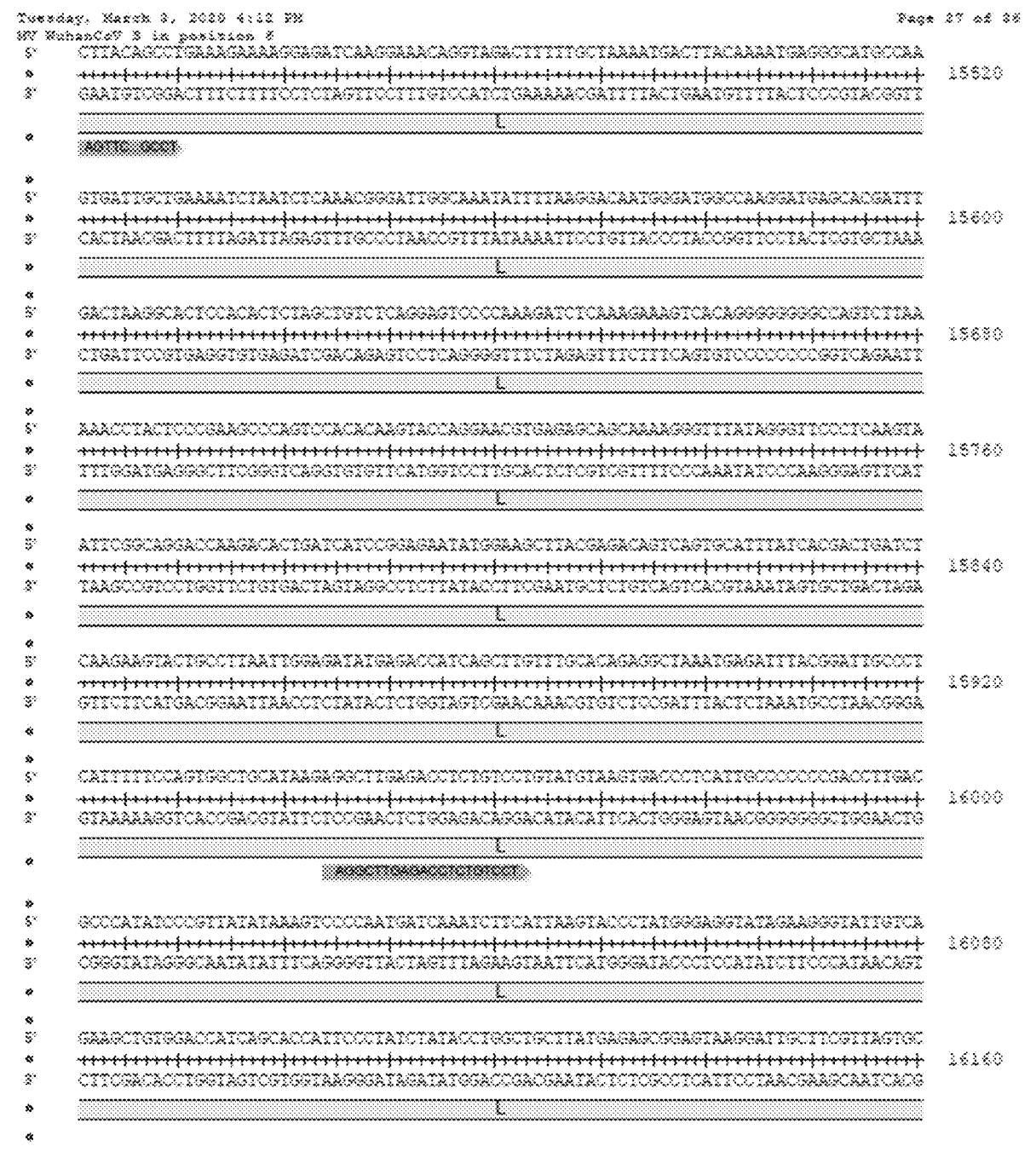
Figure 19:
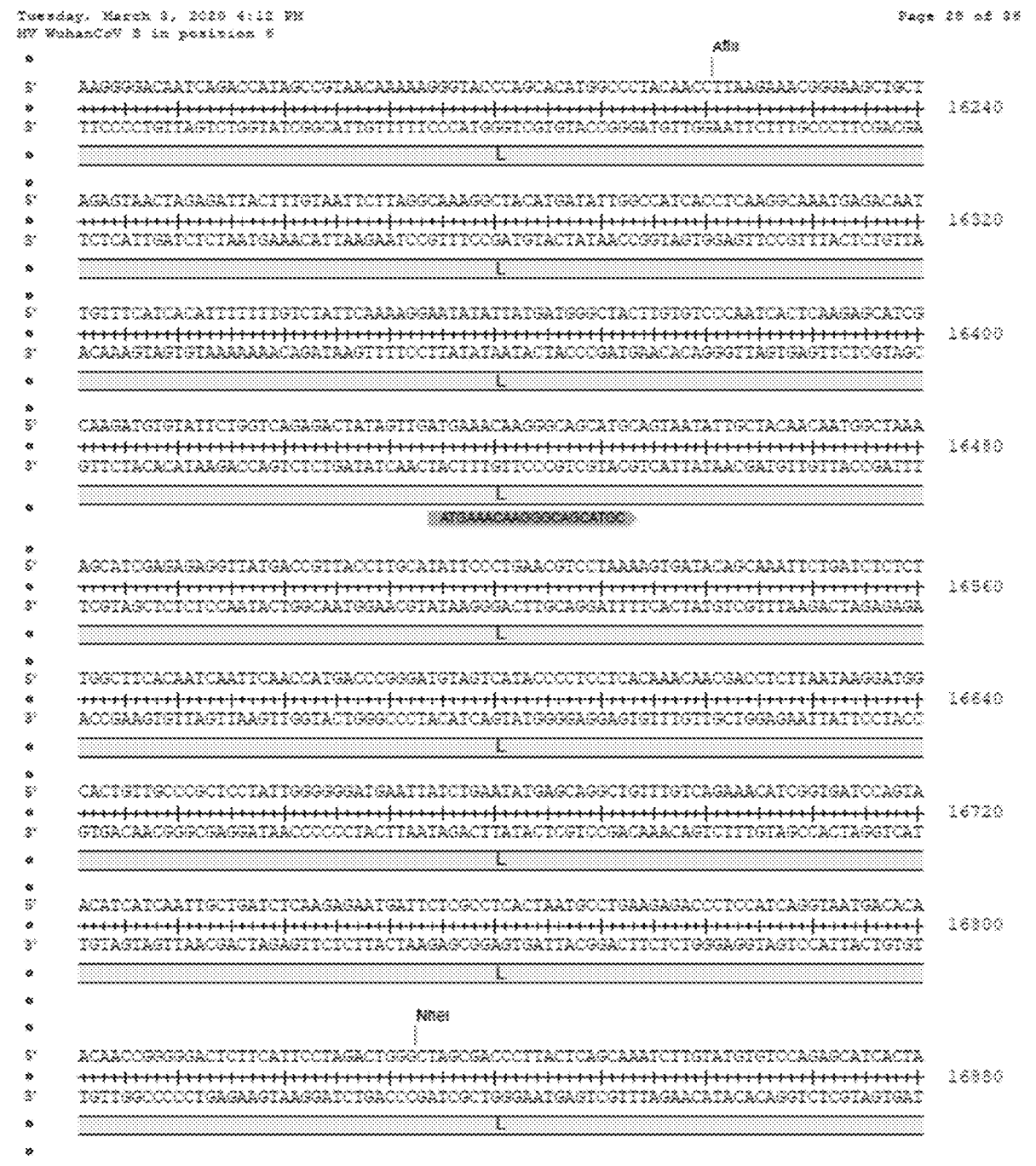
Figure 19:
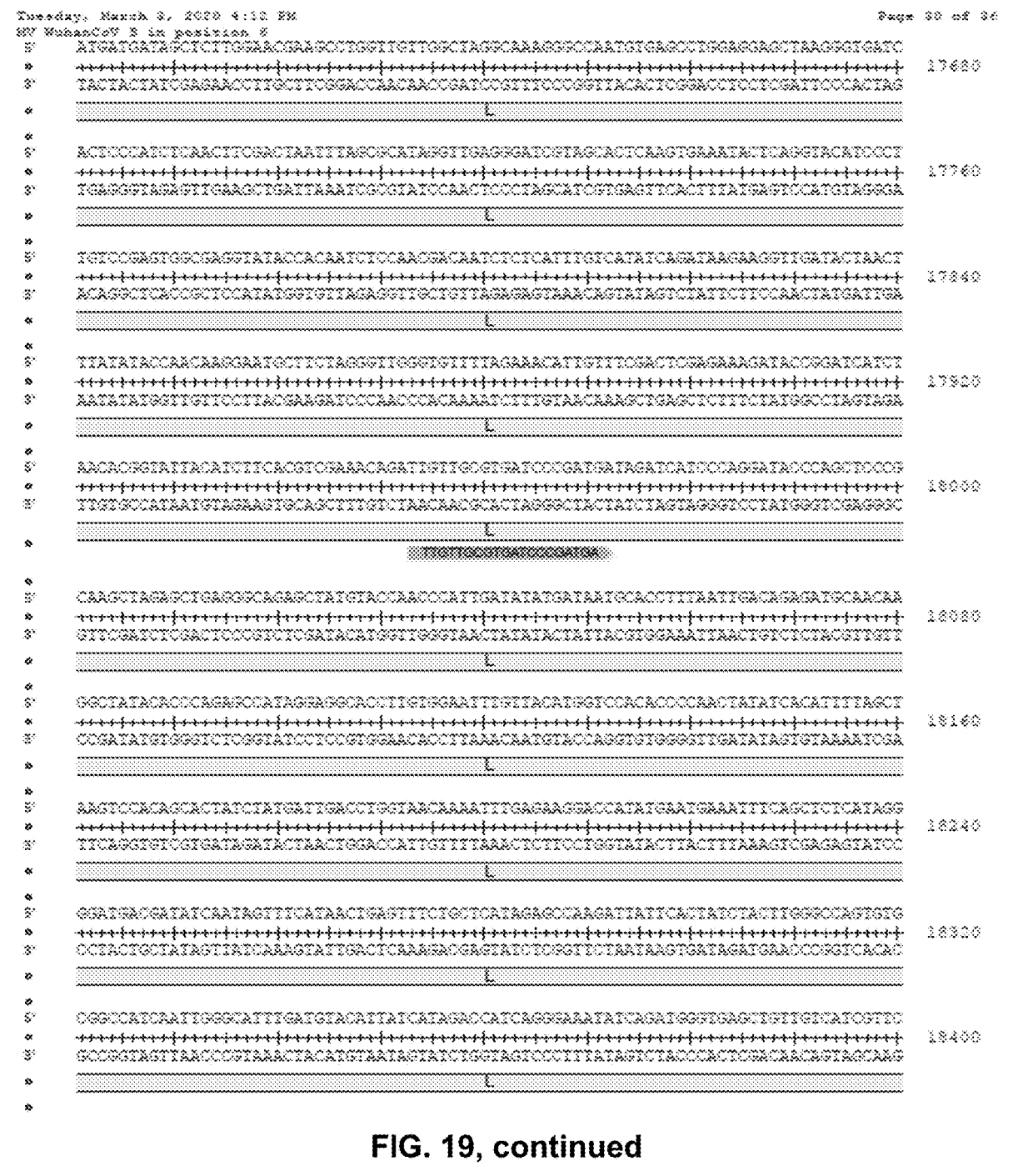
Figure 19:
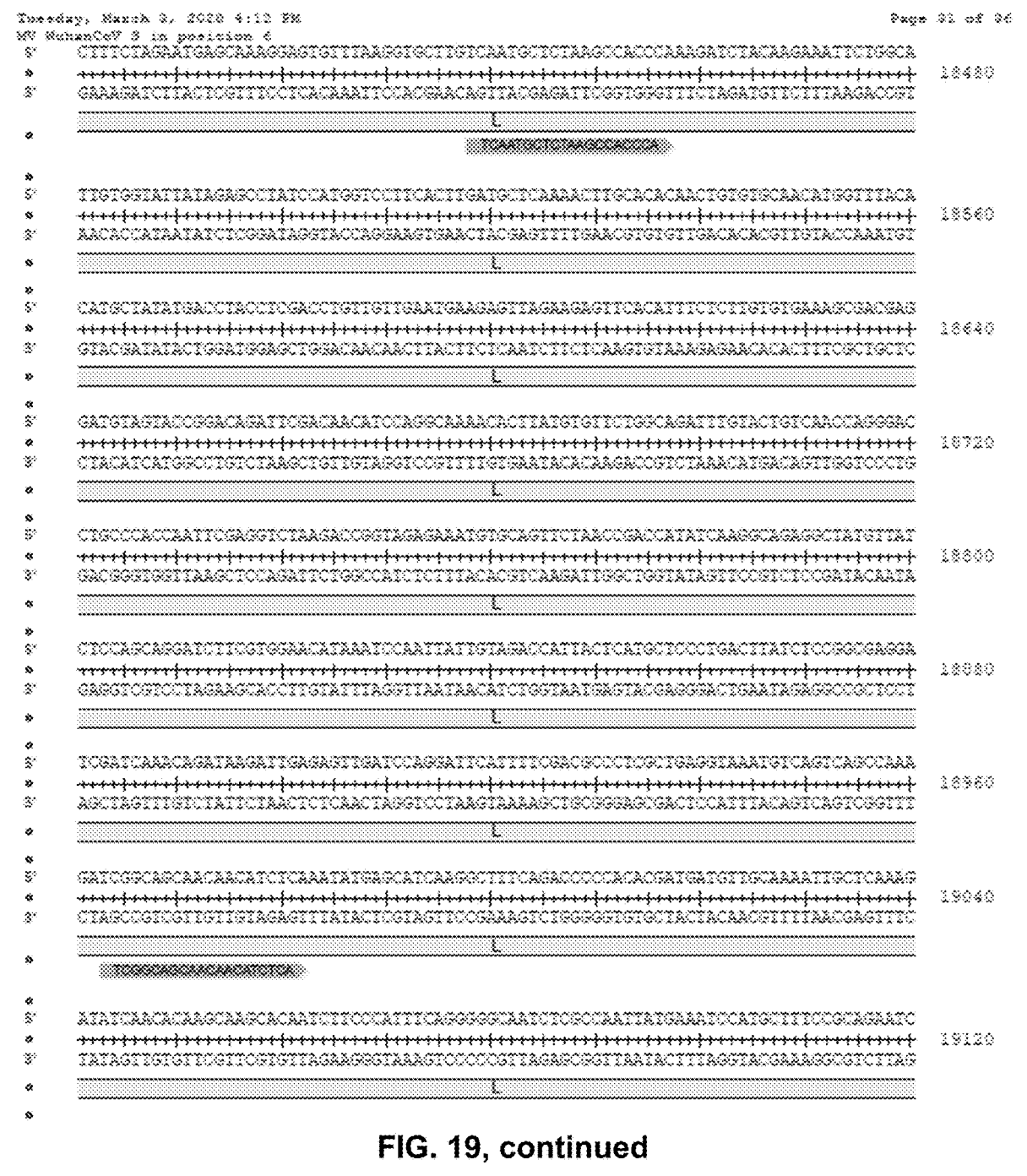
Figure 19:
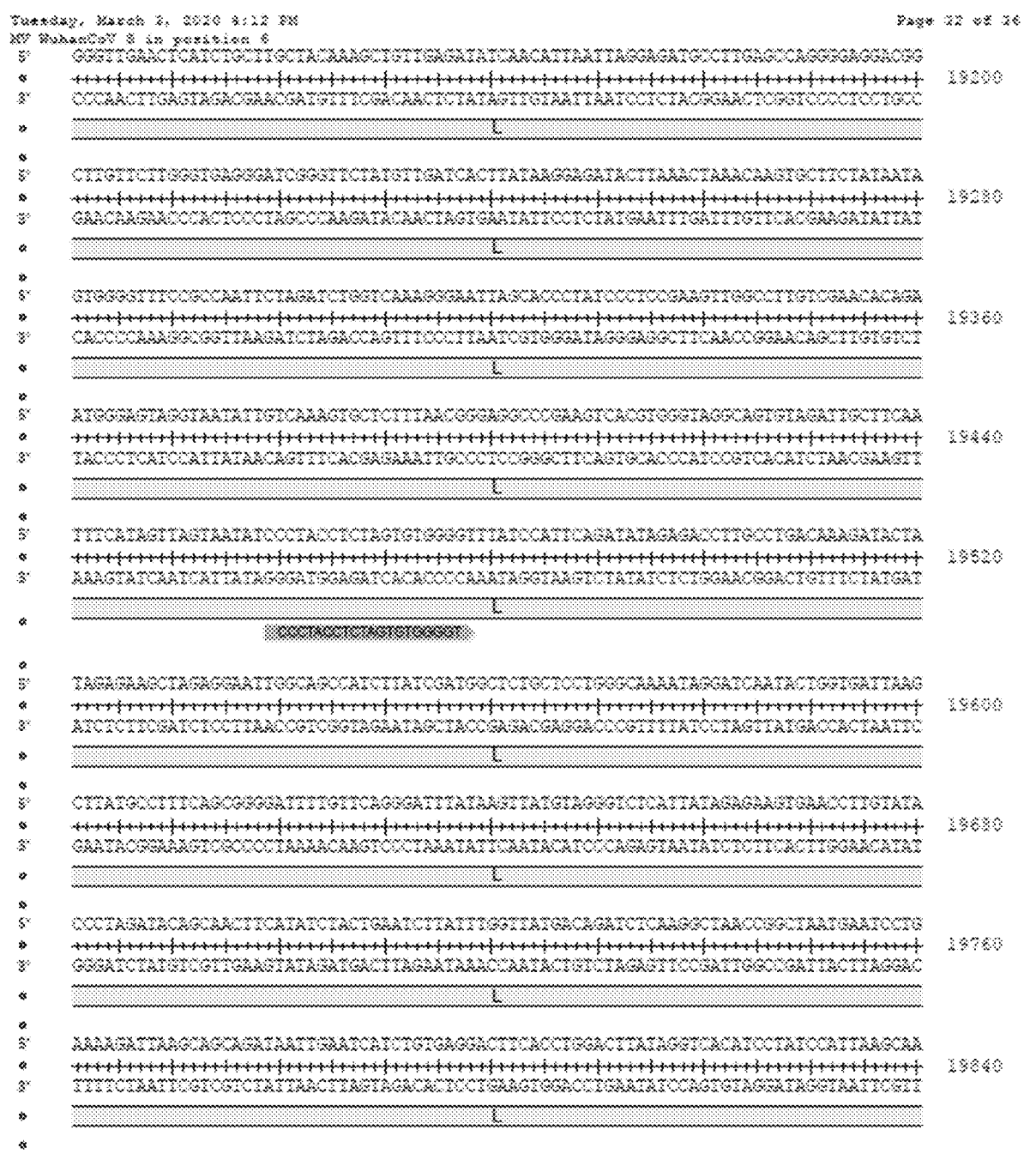
Figure 19:
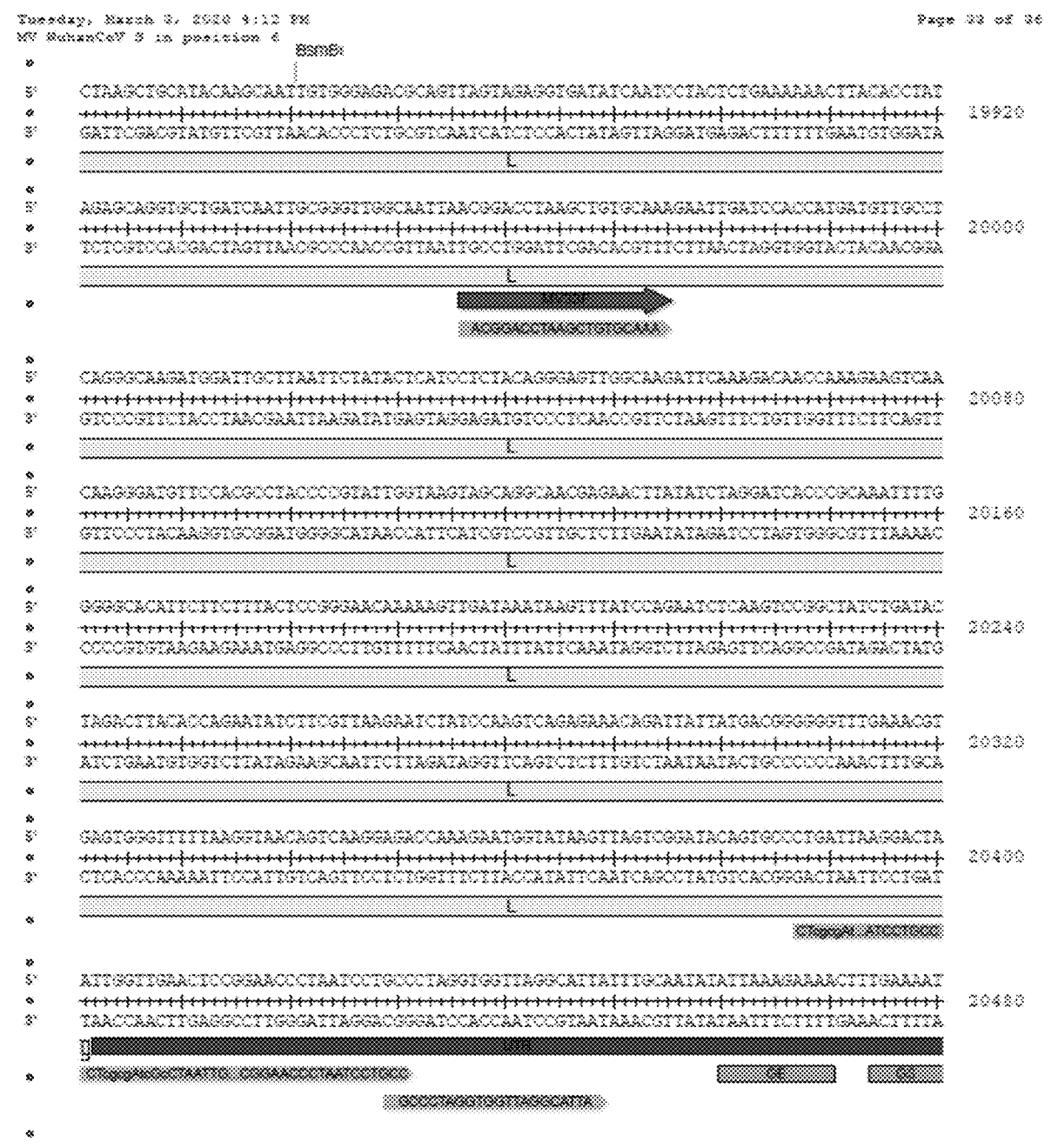
Figure 19:
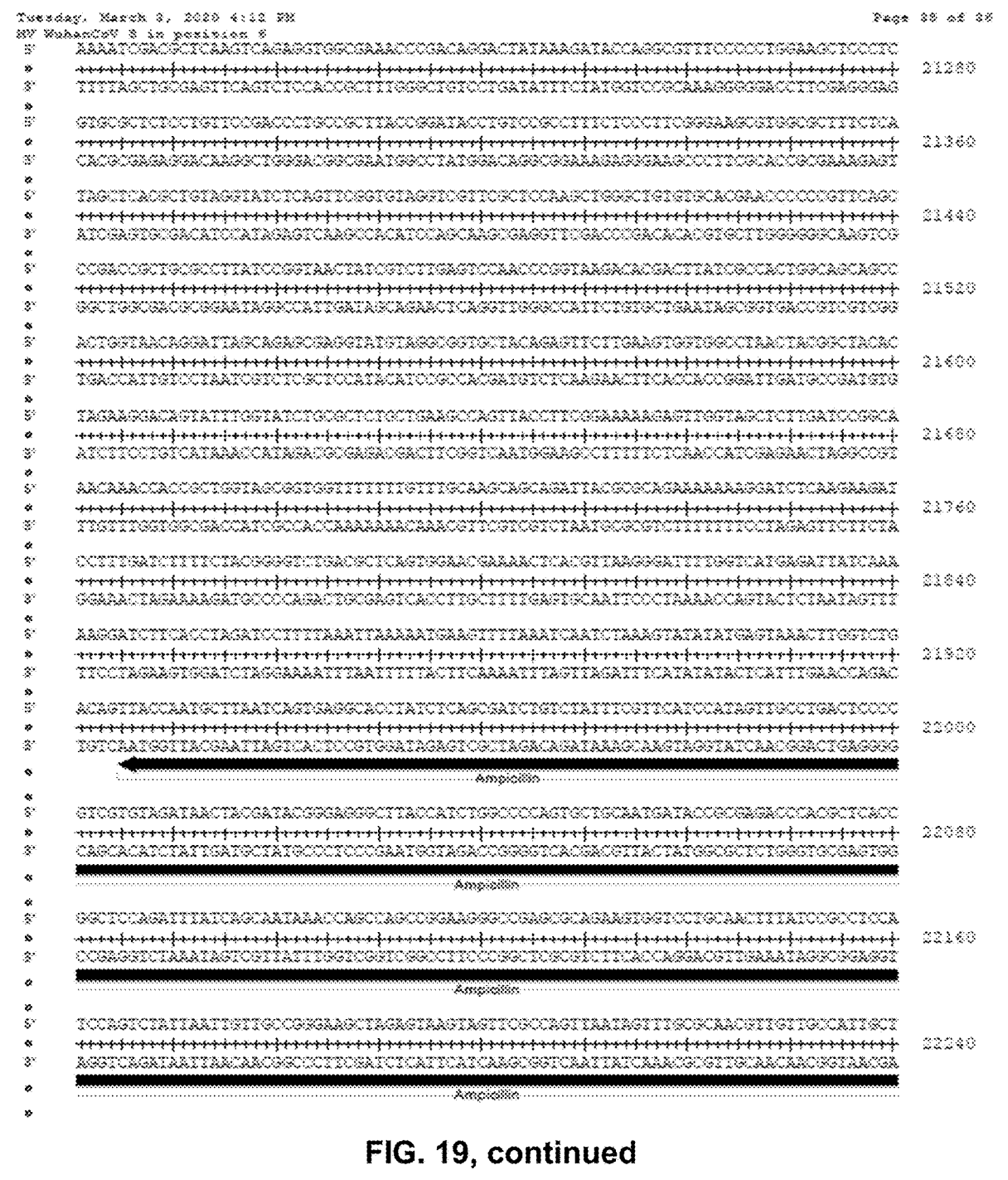
Figure 19:
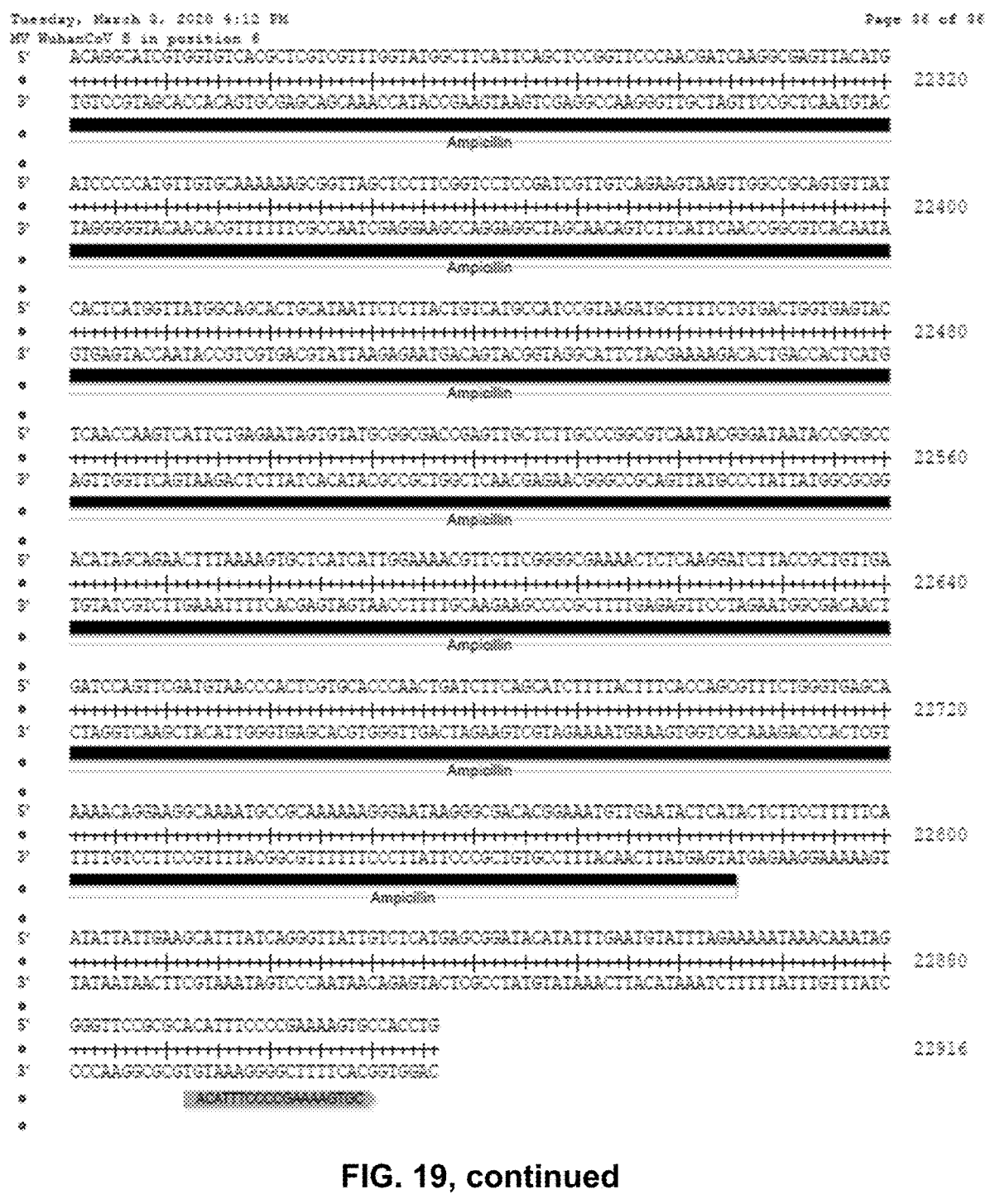

FIG. 19 shows the sequence (SEQ ID NO: 5) and features of "MV WuhanCoV S in position 6". FIG. 19 additionally shows the sequences of SEQ ID NOs: 33-106.

Figure 20:
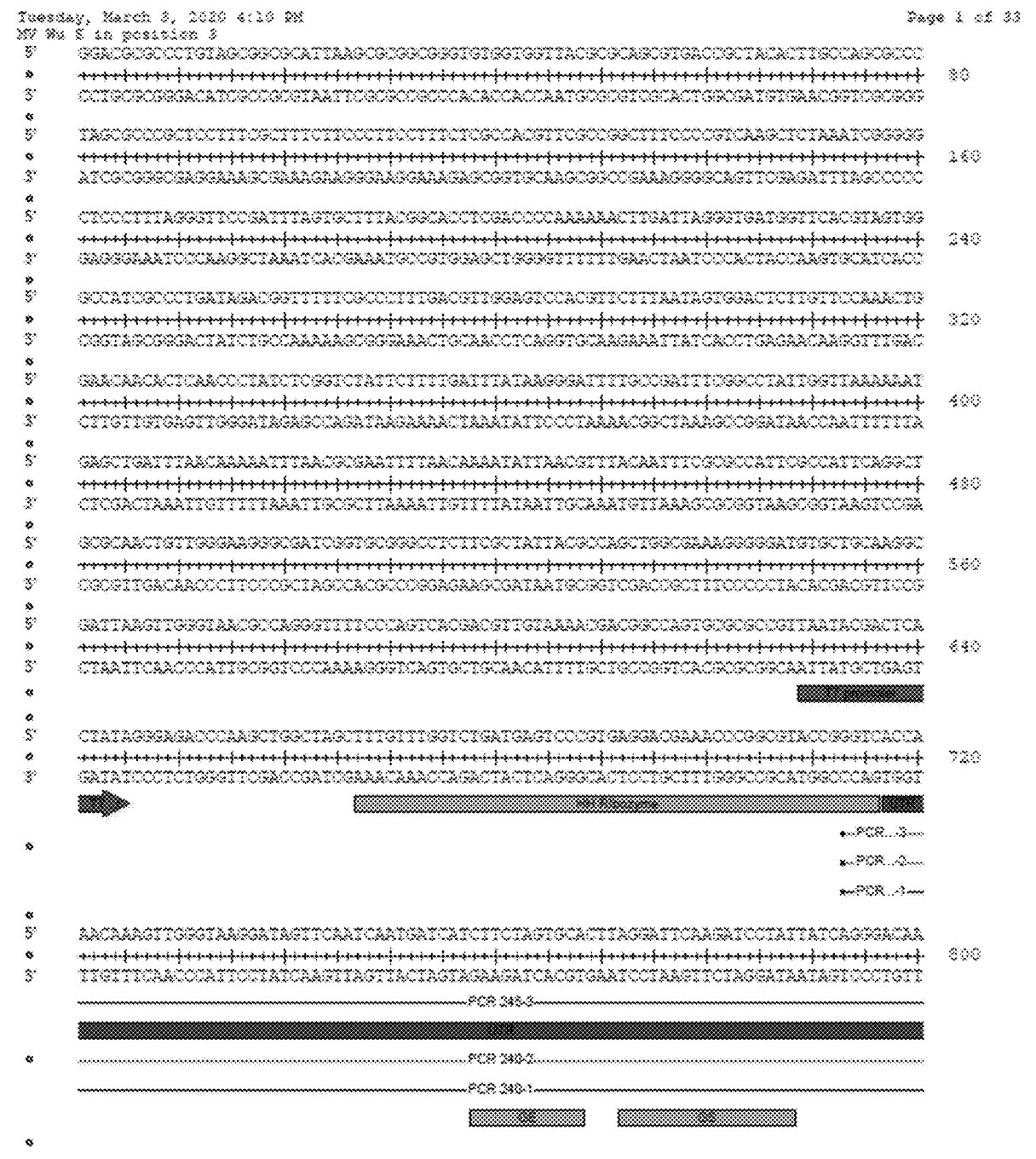
Figure 20:
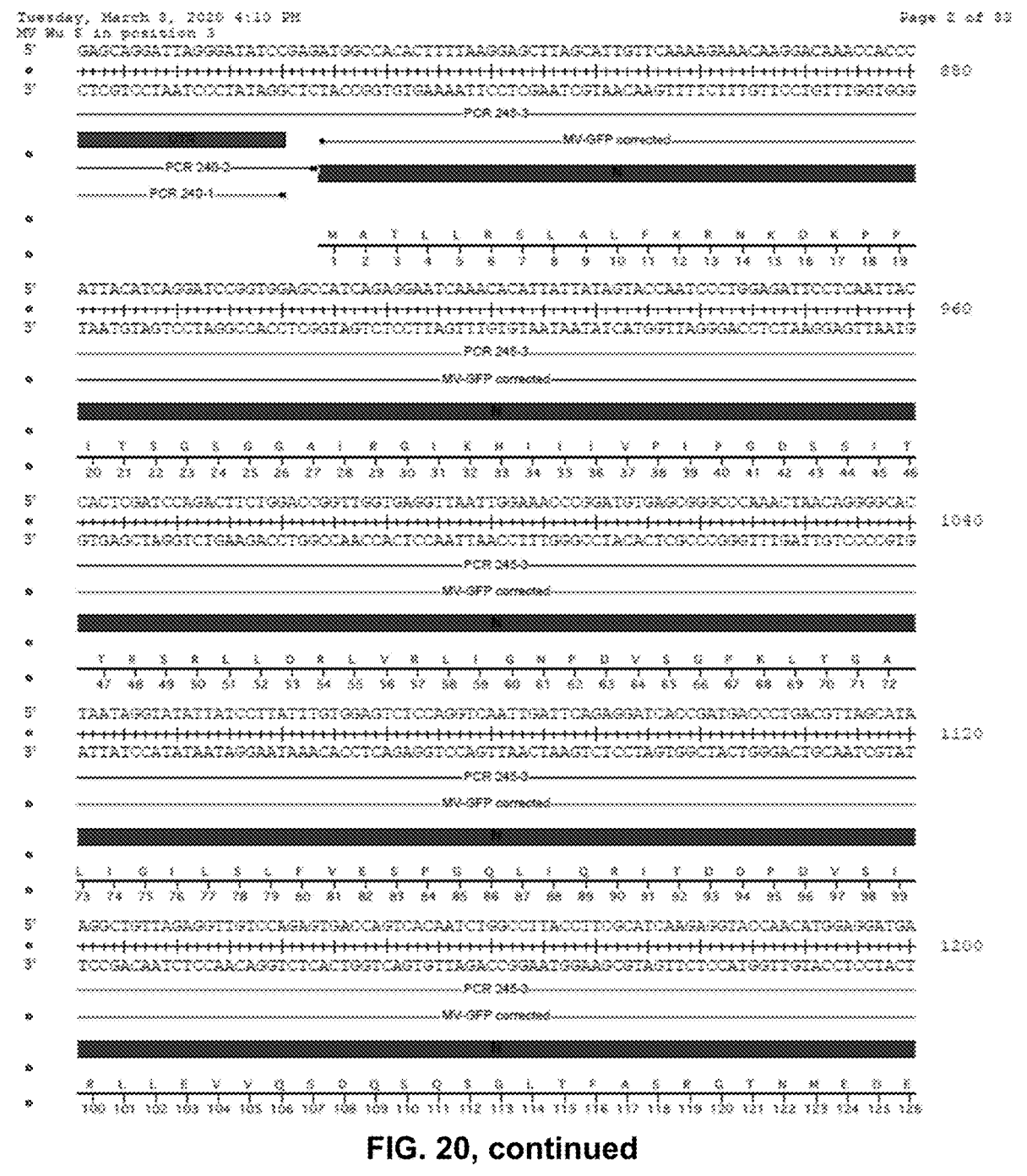
Figure 20:
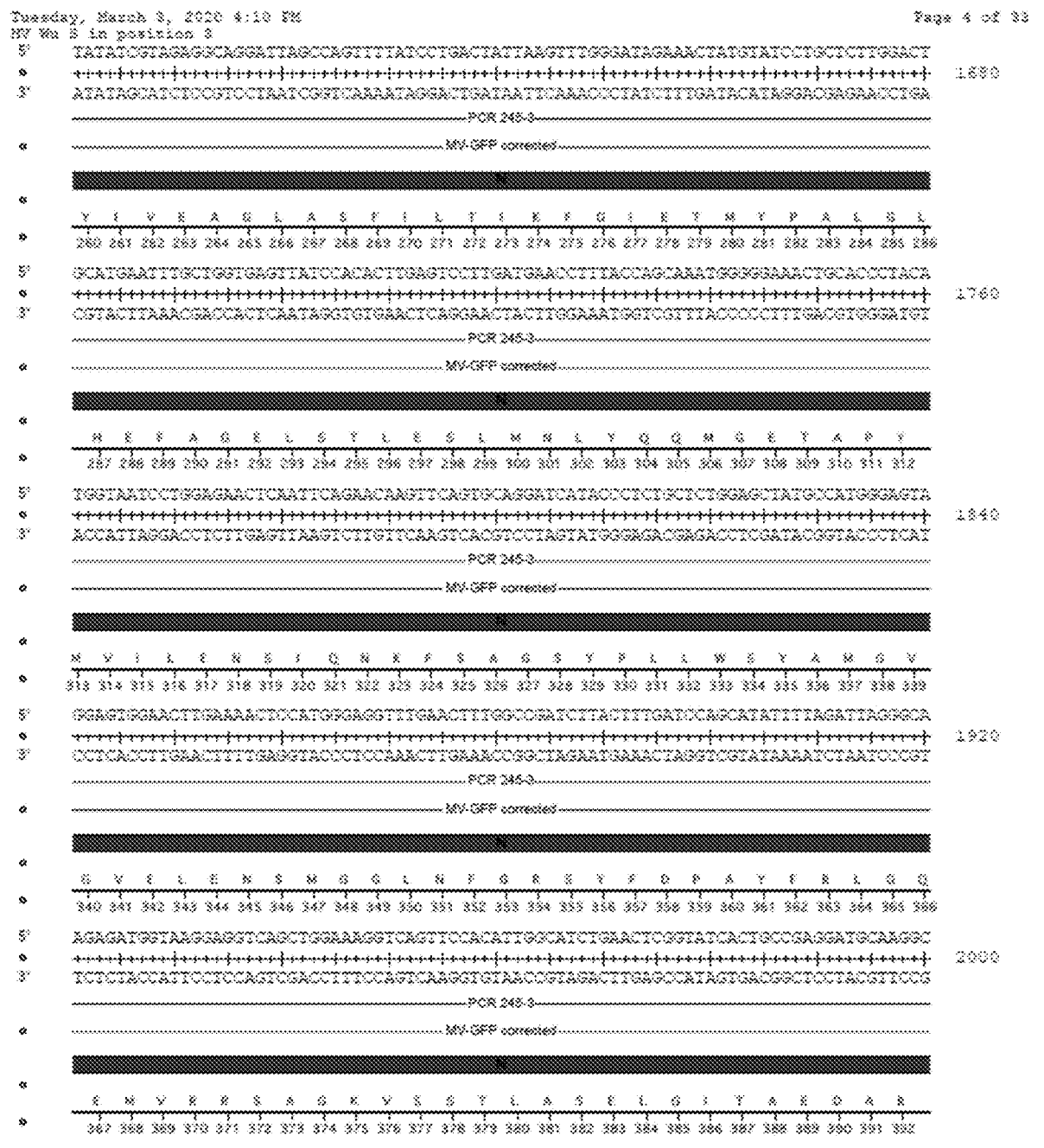
Figure 20:
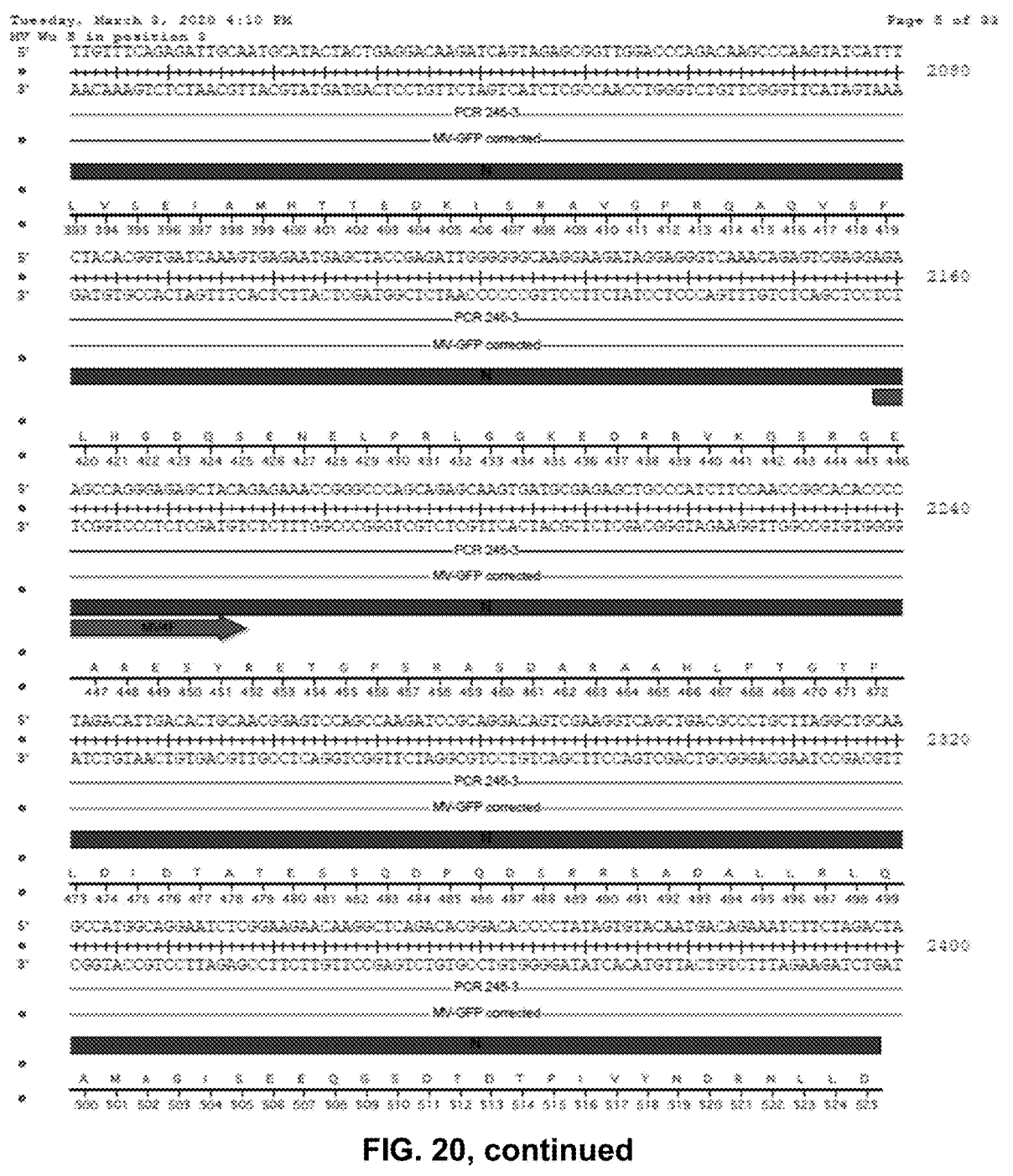
Figure 20:
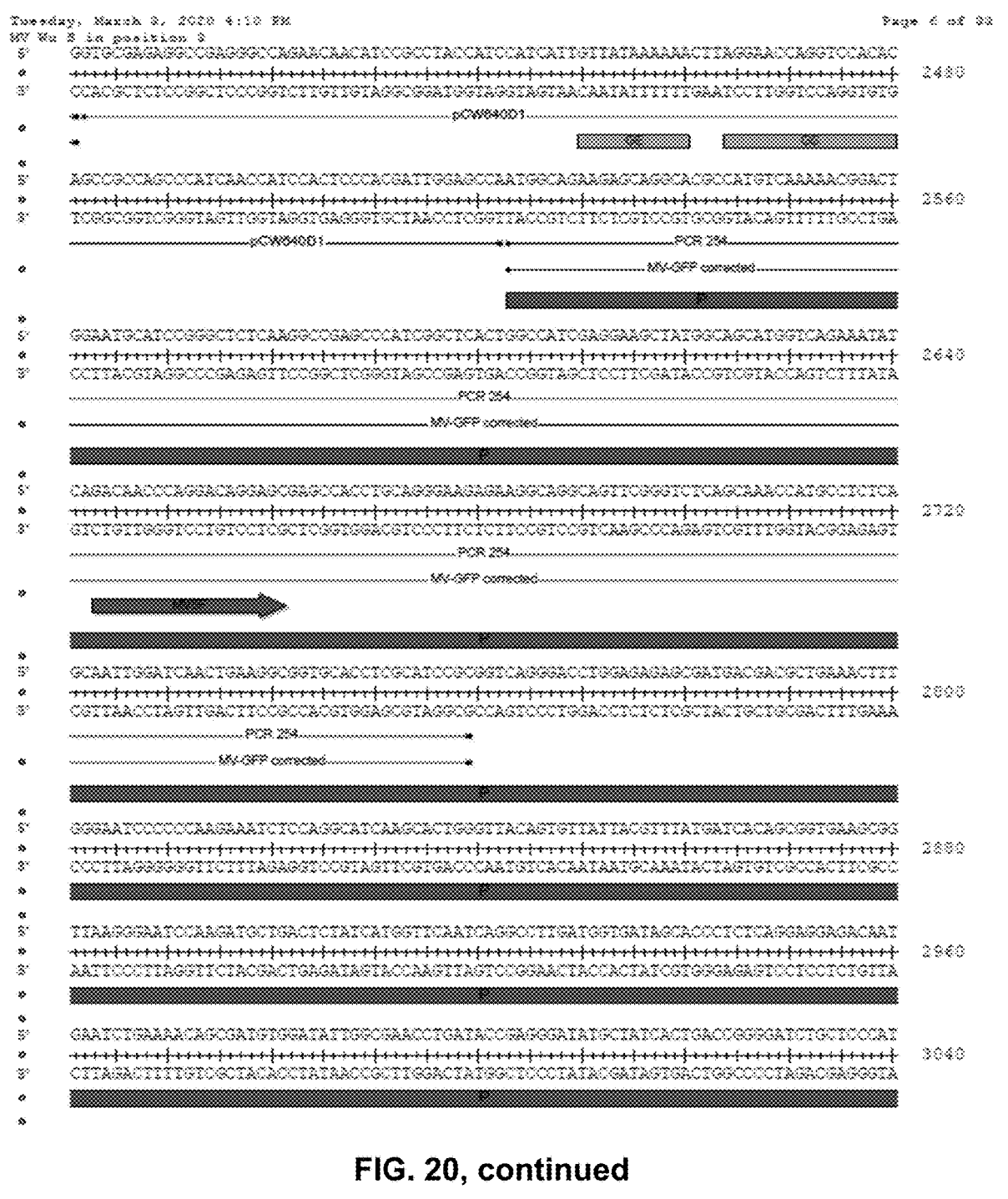
Figure 20:
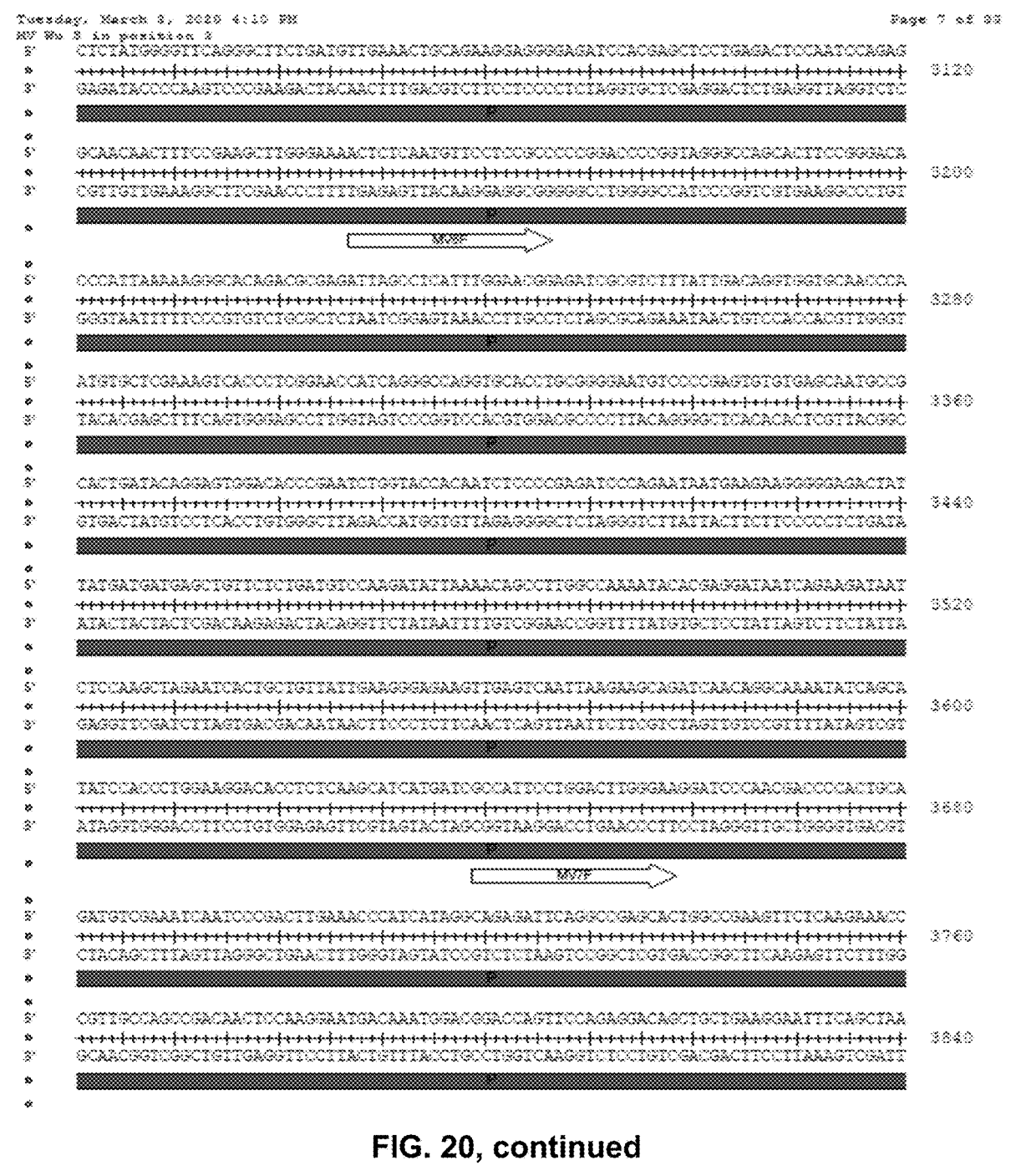
Figure 20:
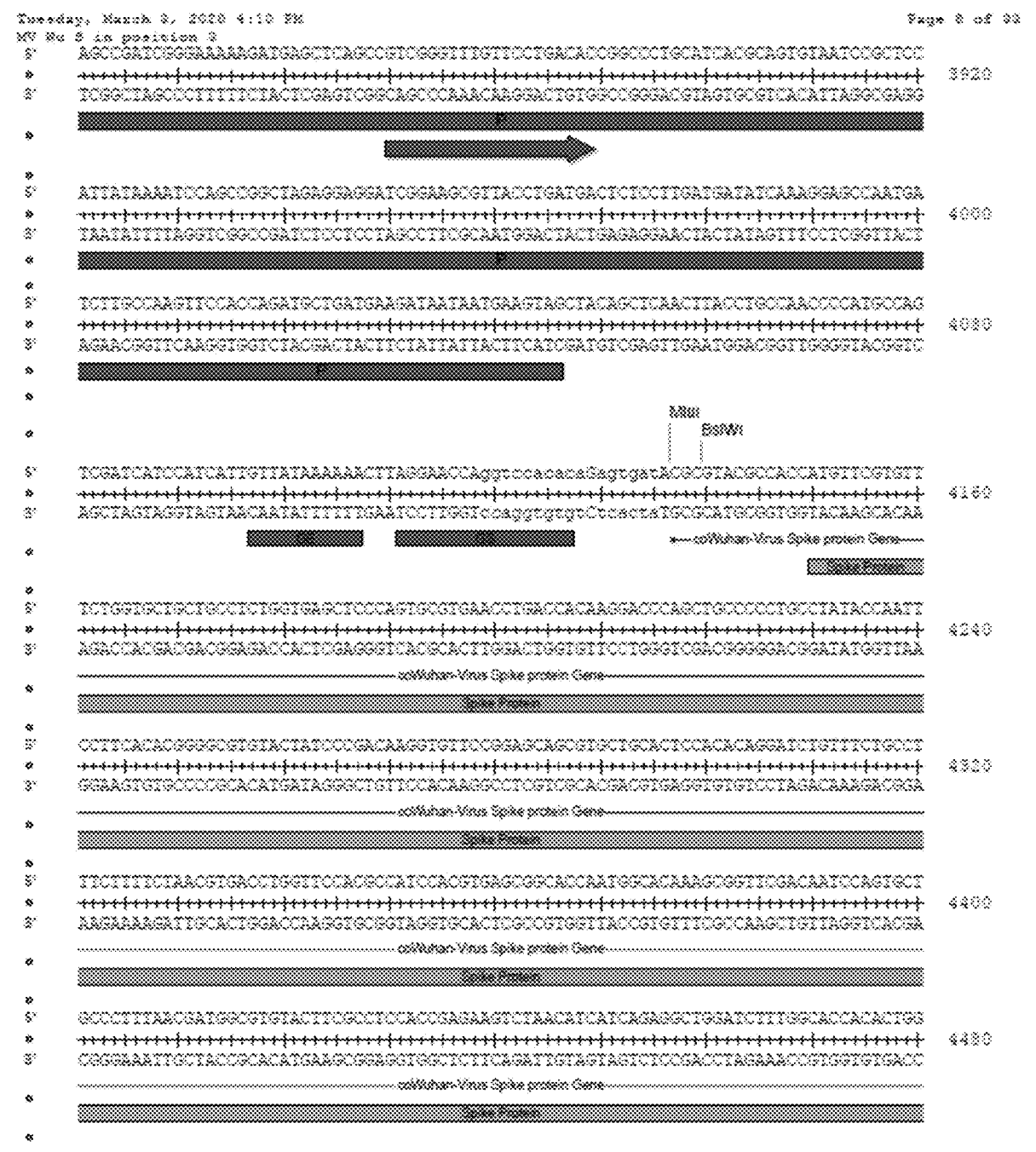
Figure 20:
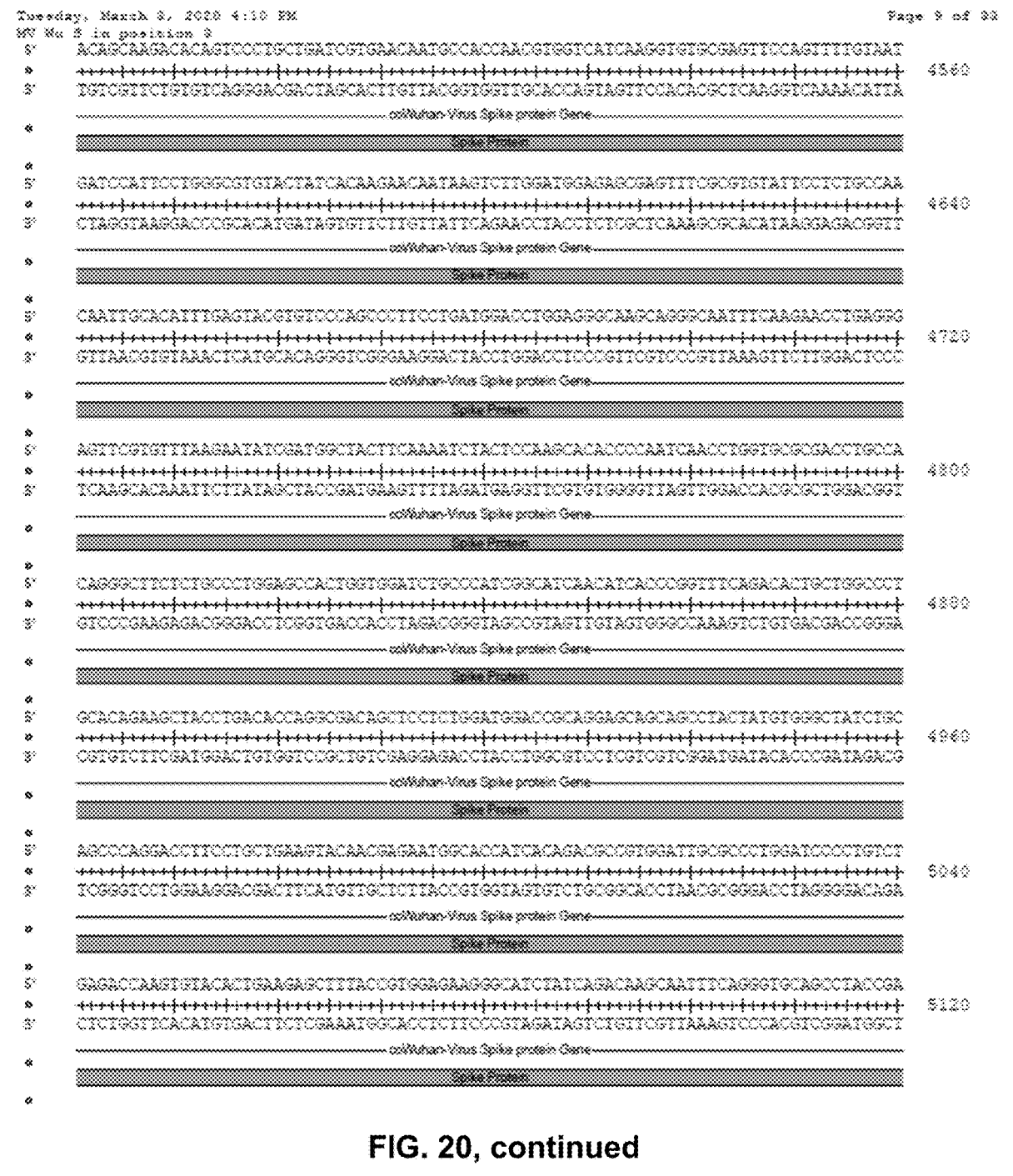
Figure 20:
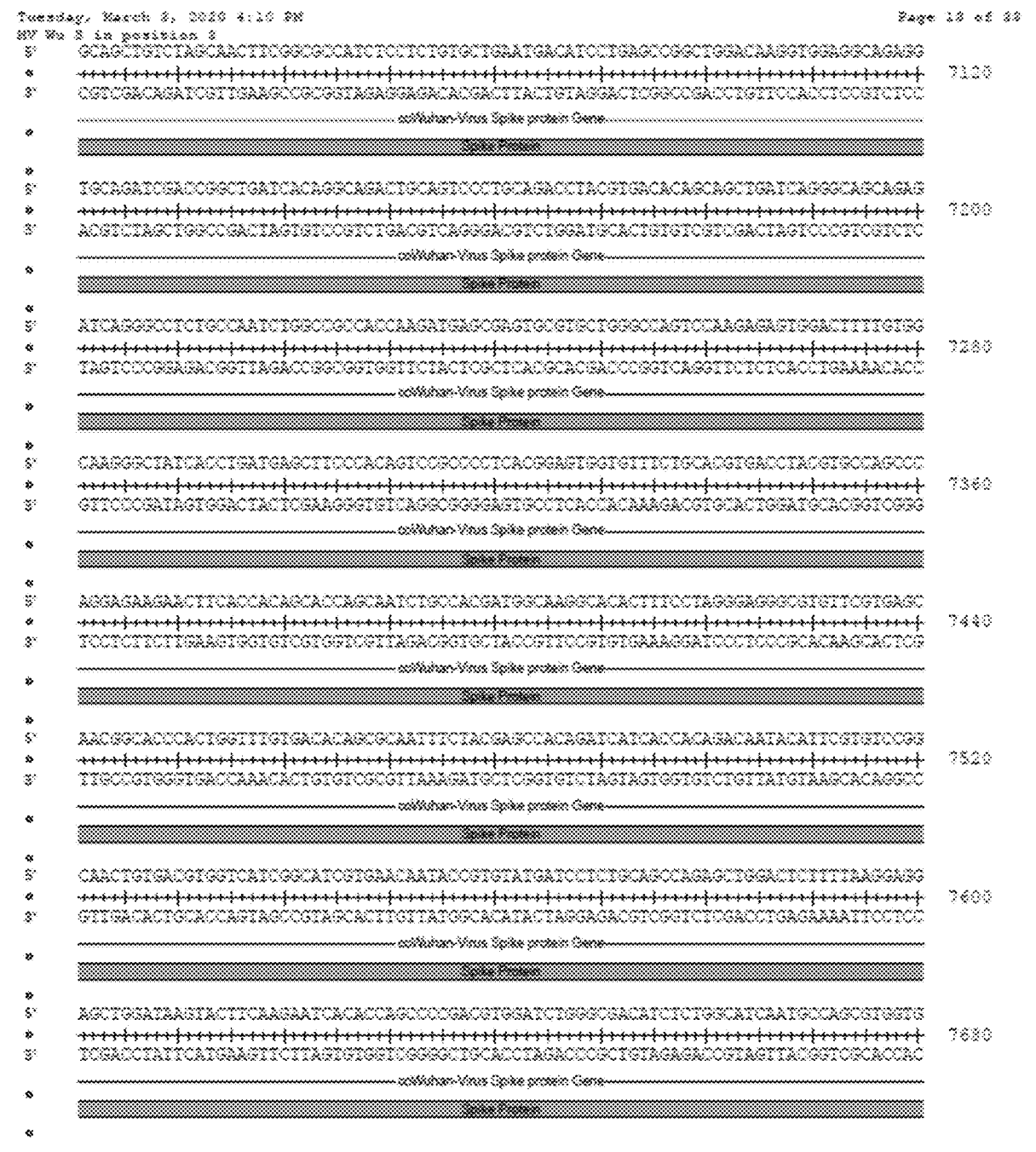
Figure 20:
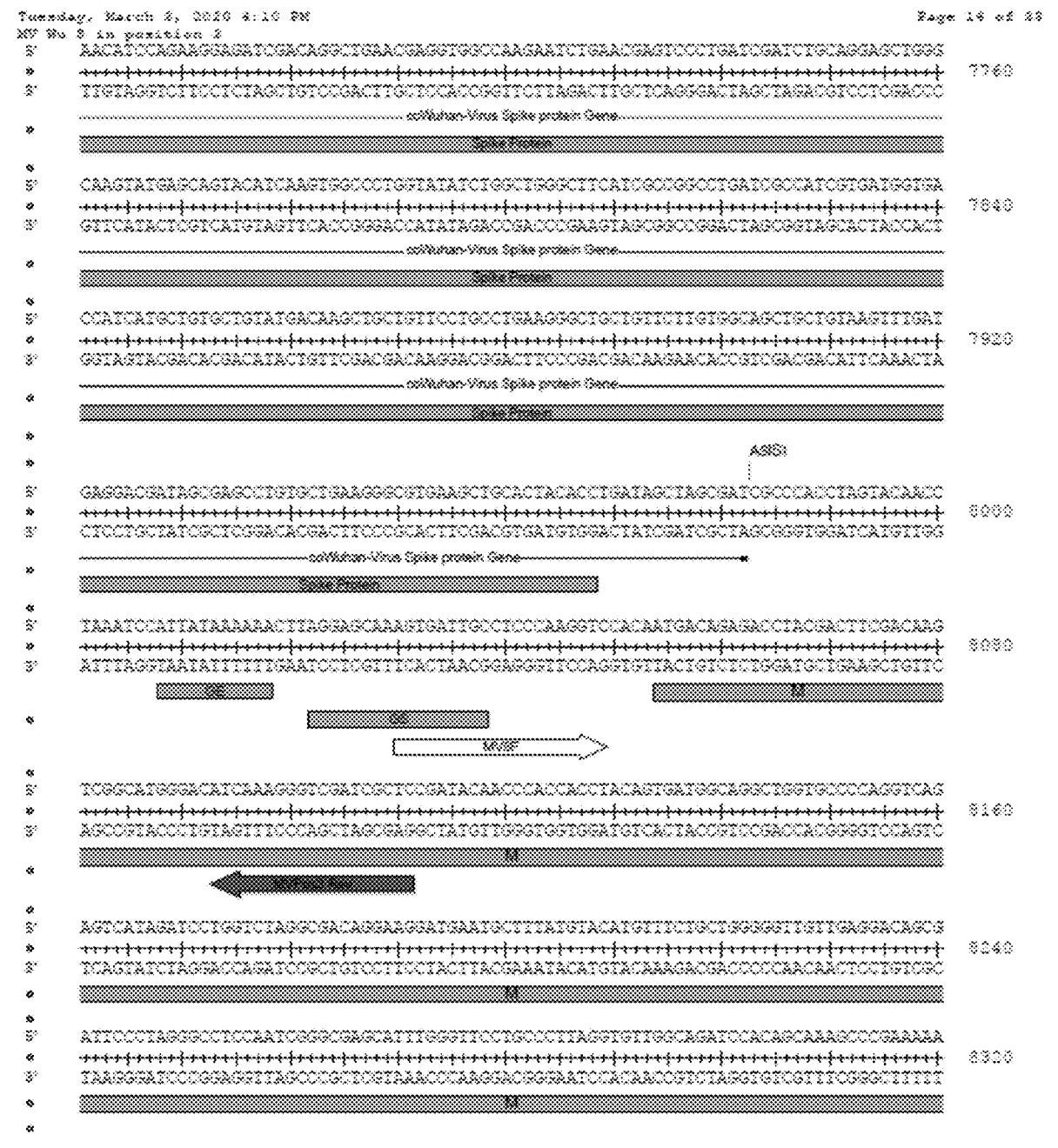
Figure 20:
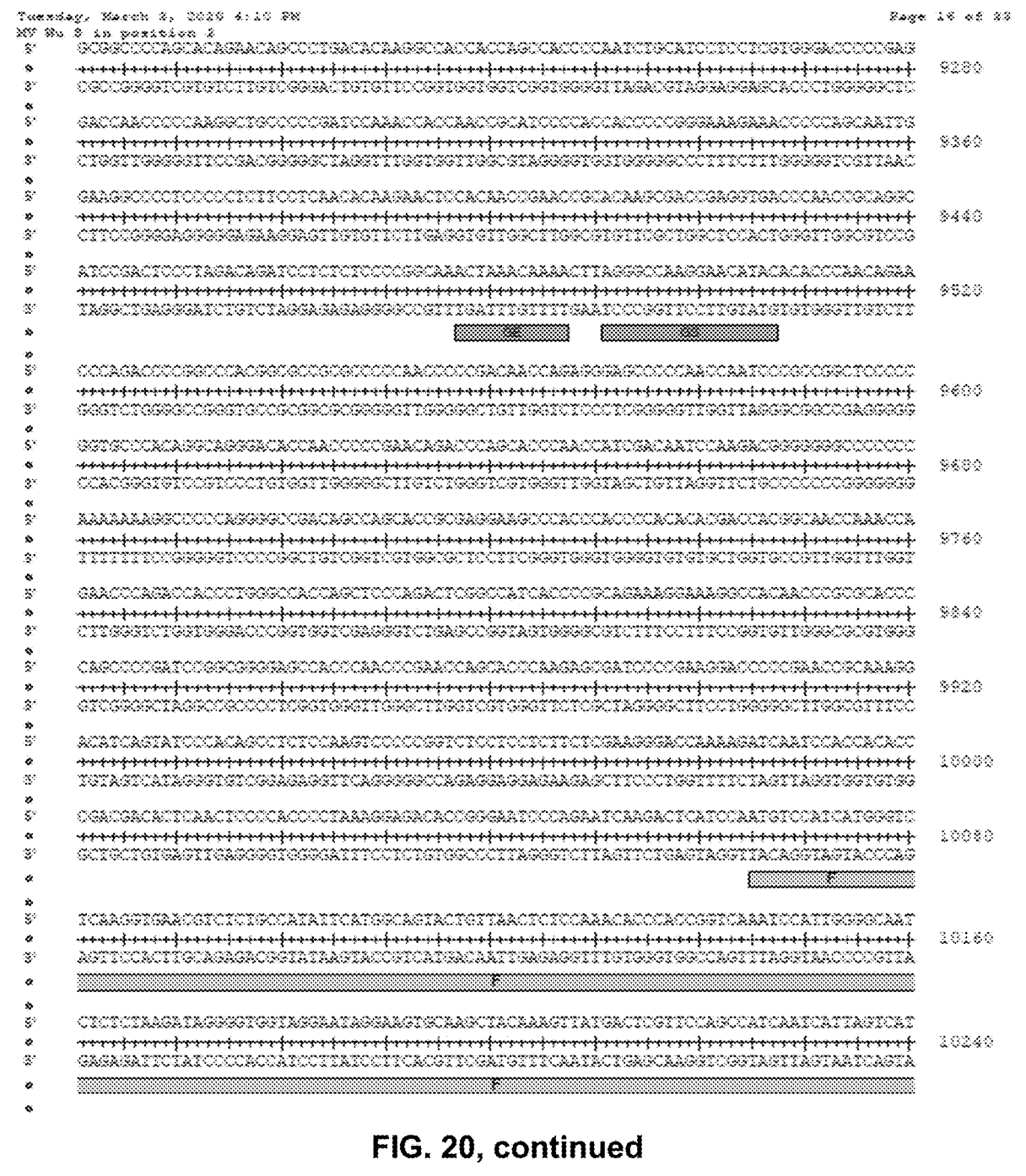
Figure 20:
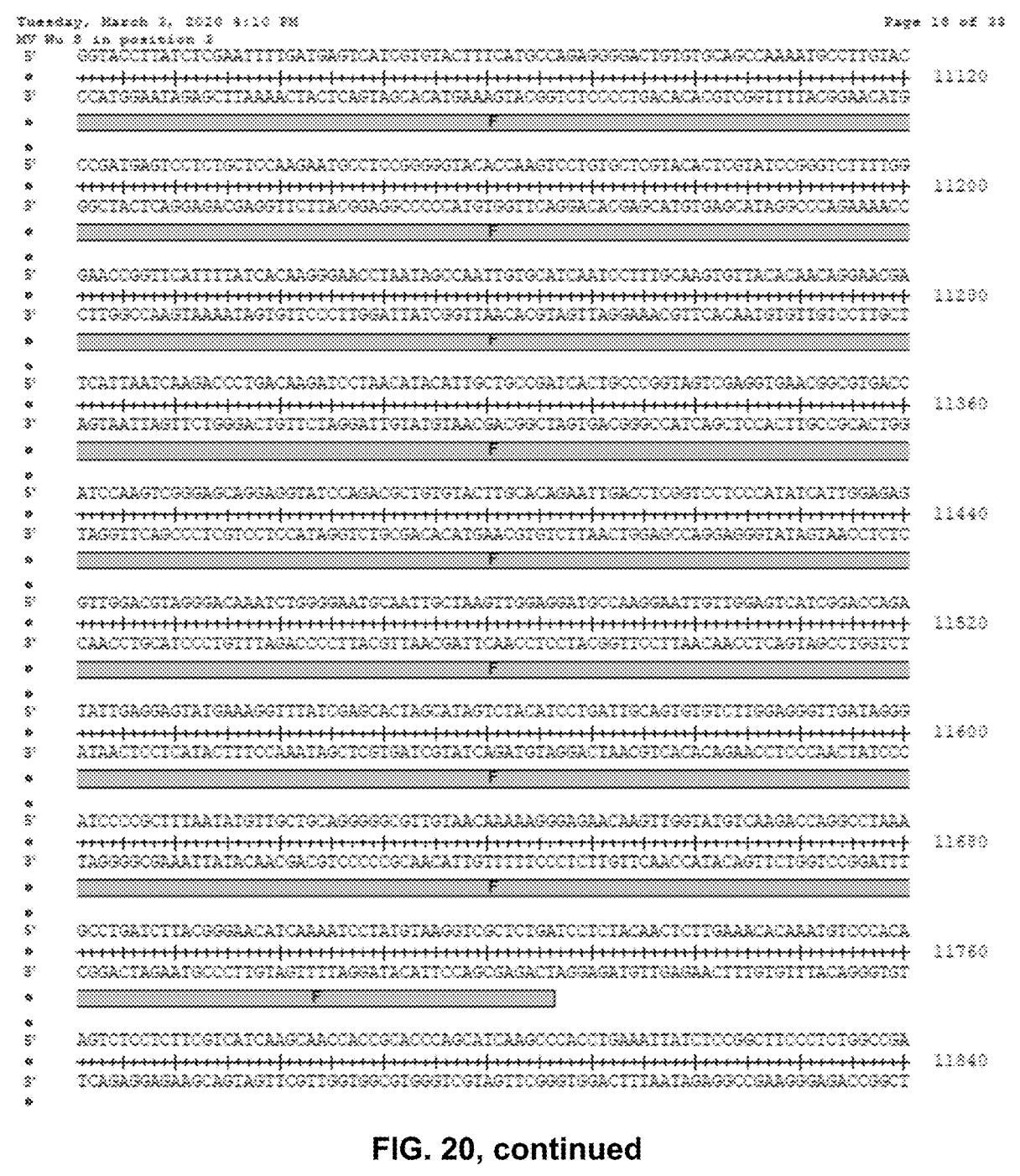
Figure 20:
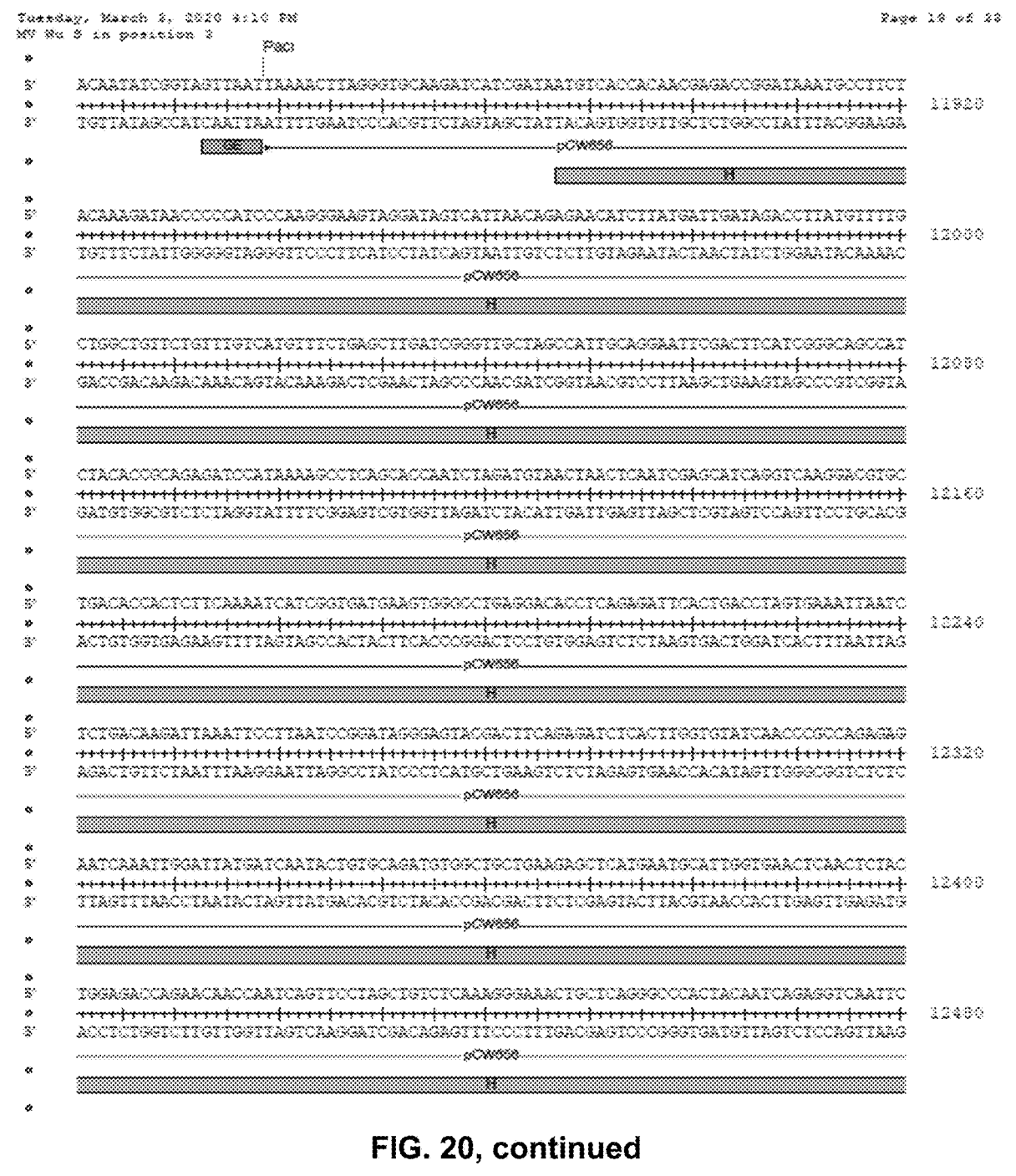
Figure 20:
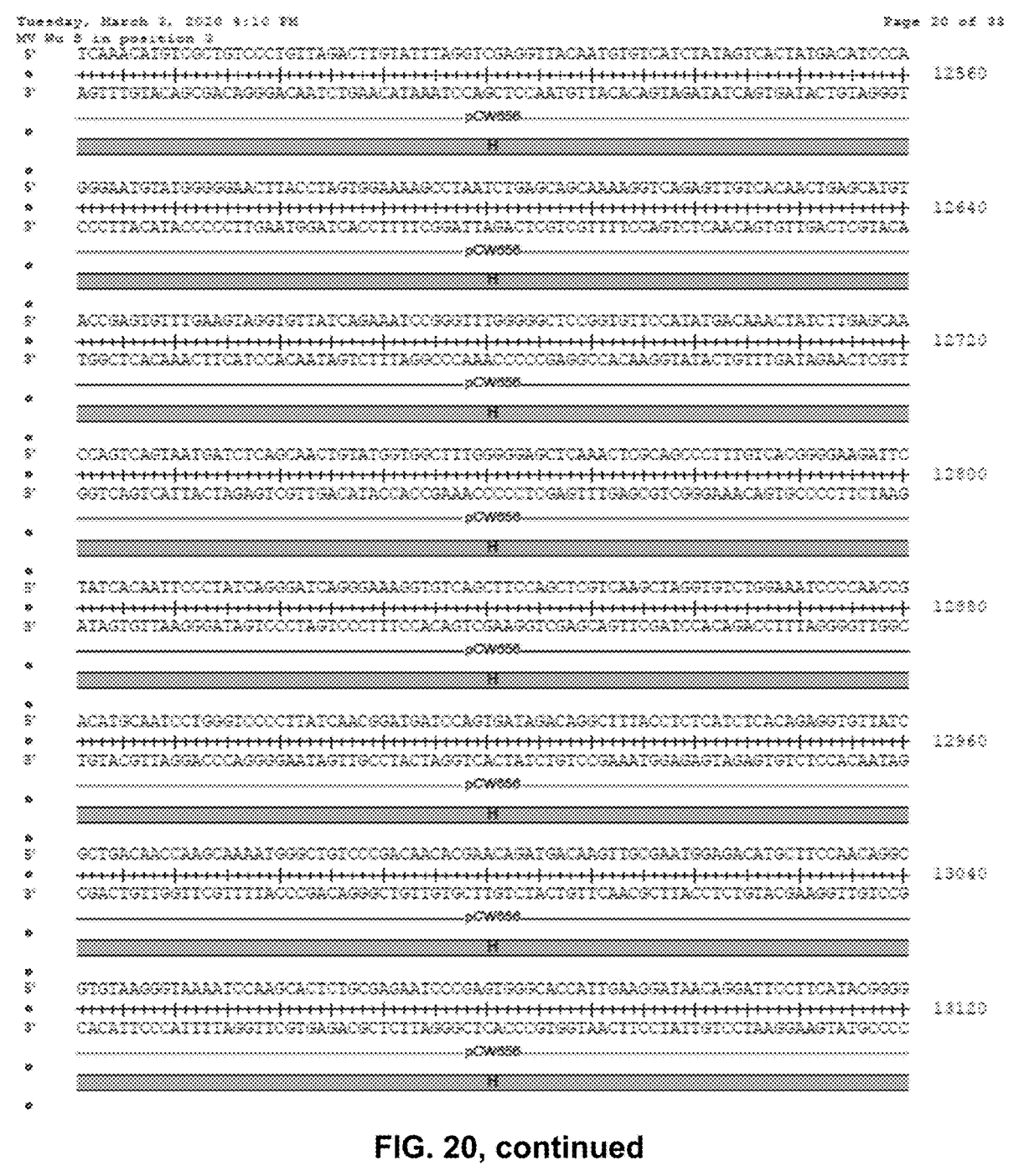
Figure 20:
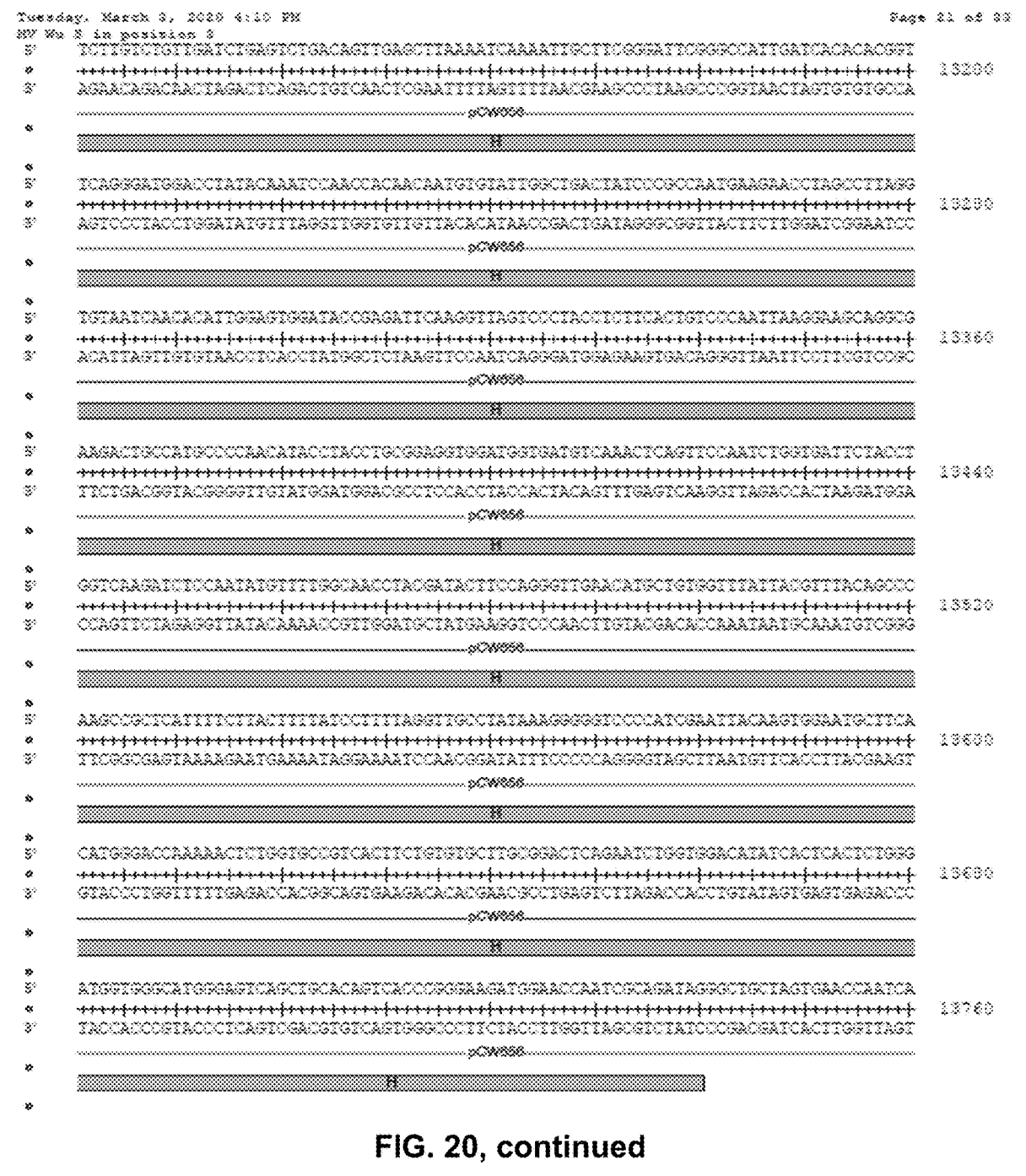
Figure 20:
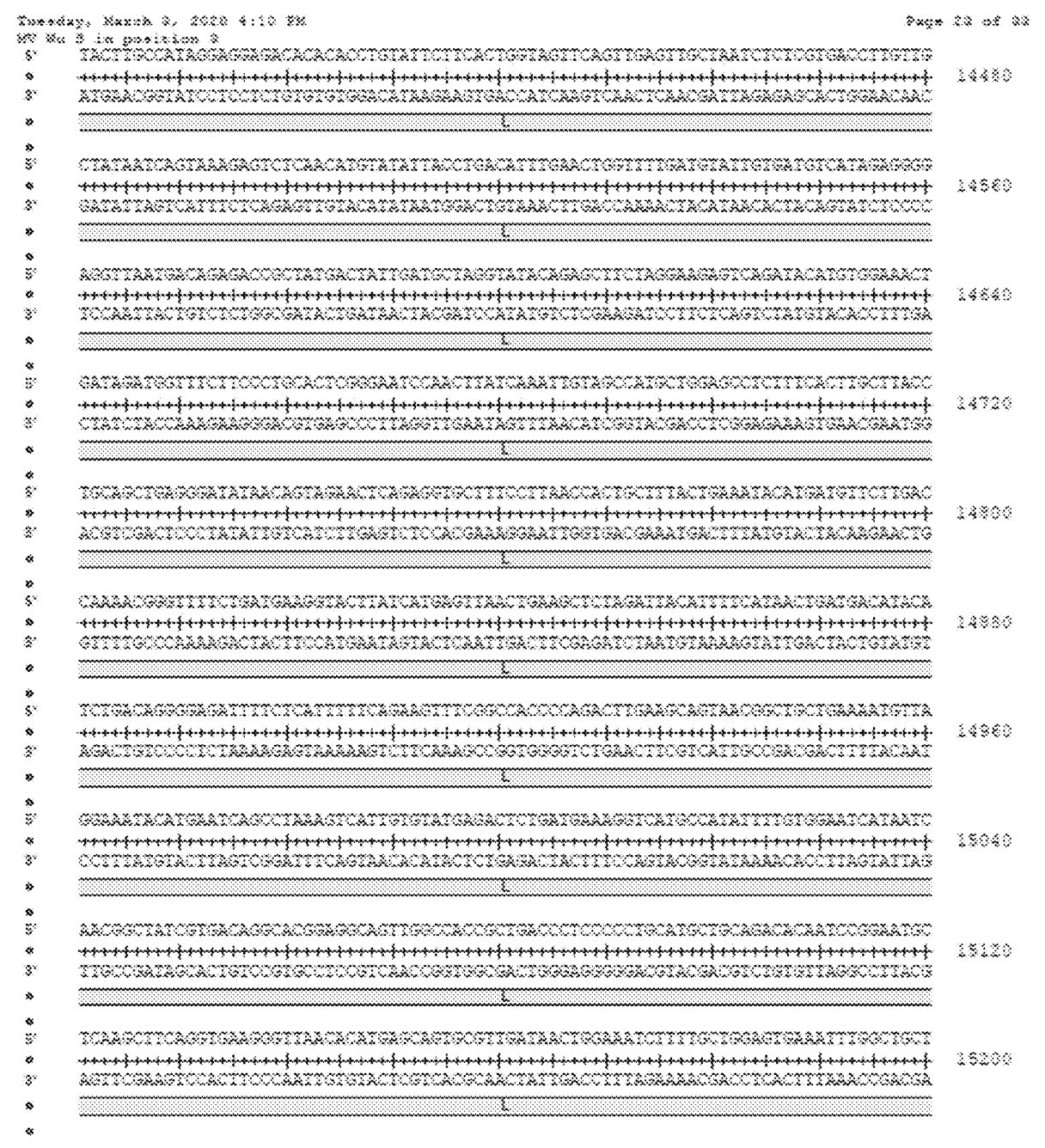
Figure 20:
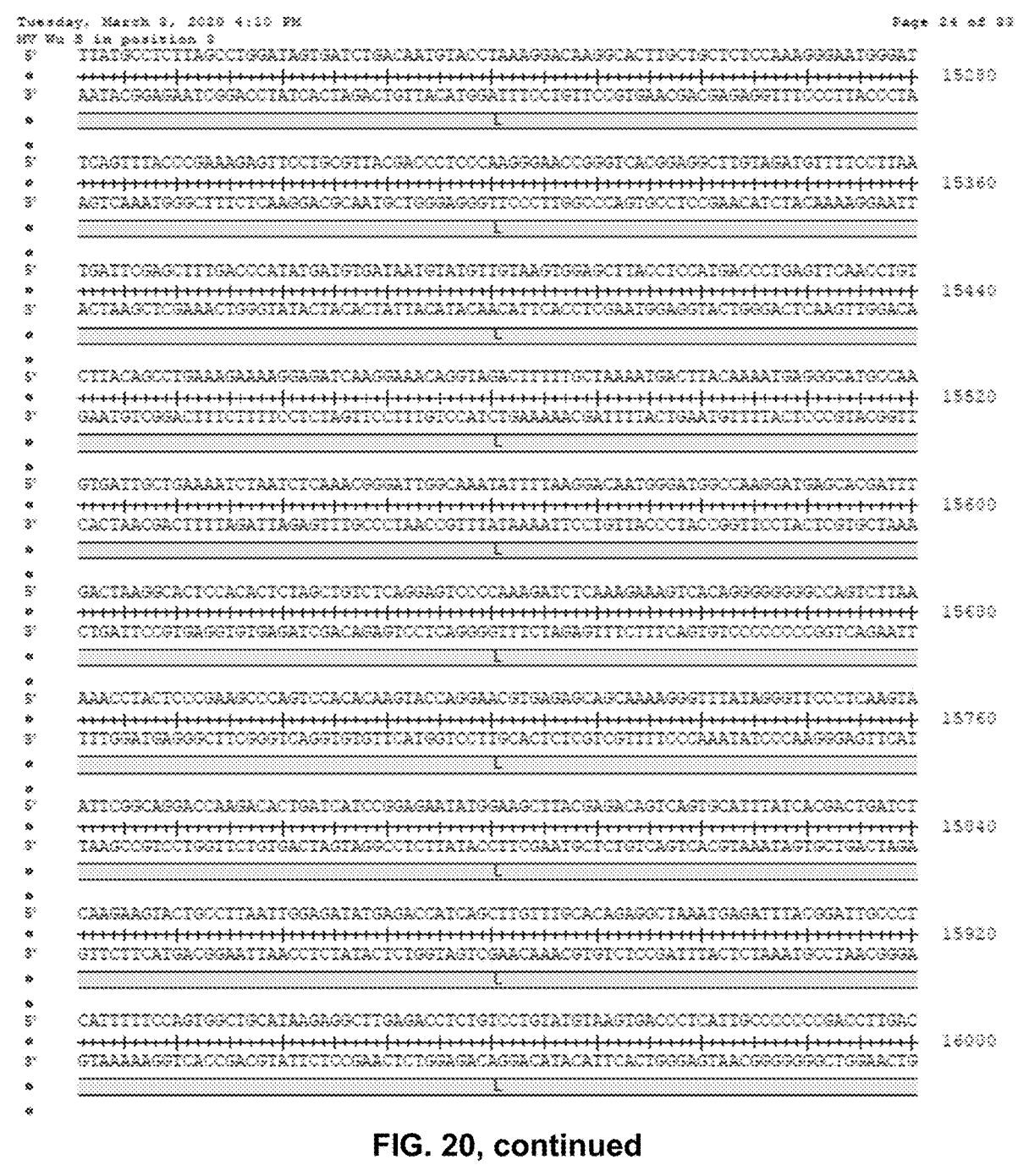
Figure 20:
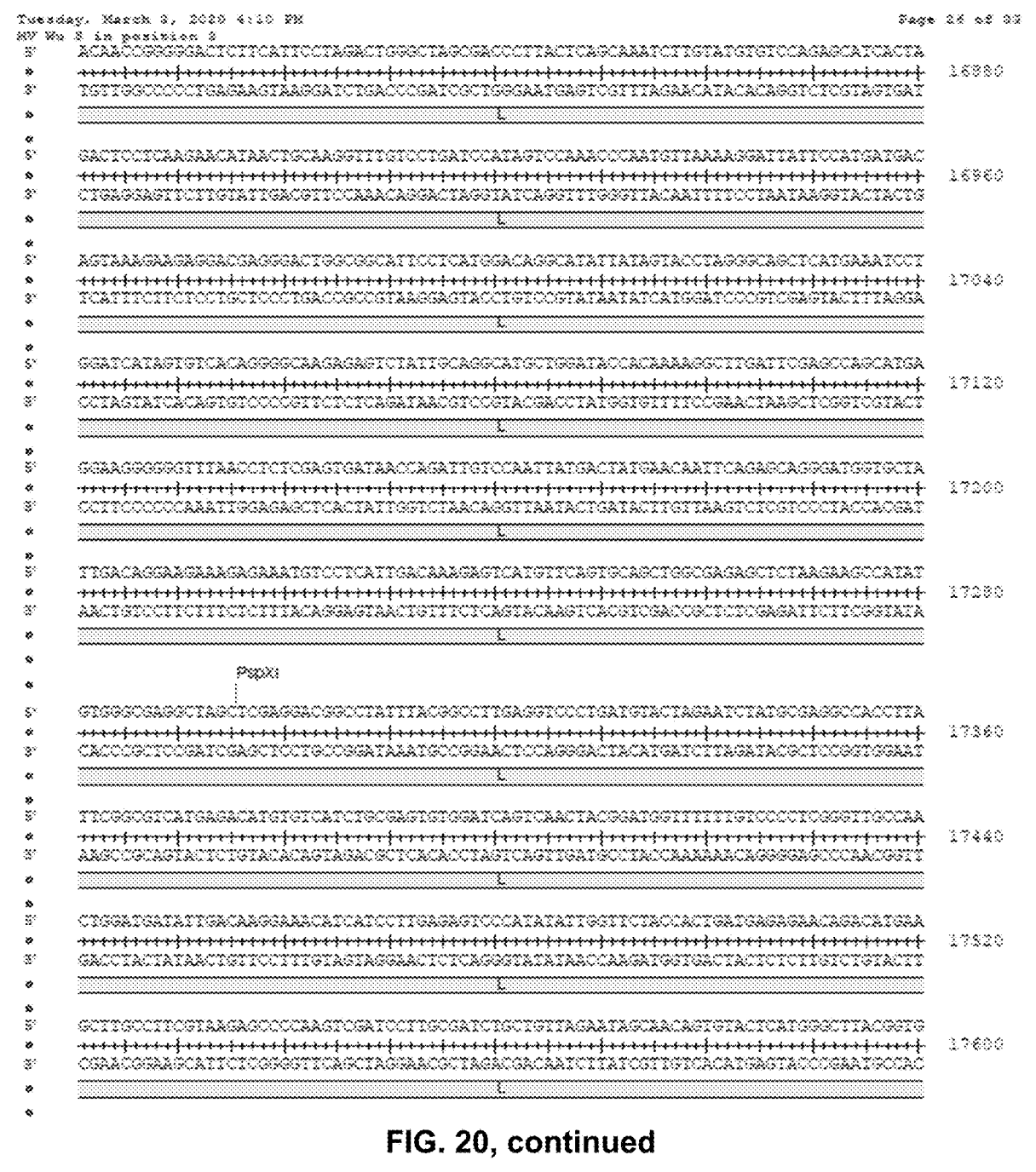
Figure 20:
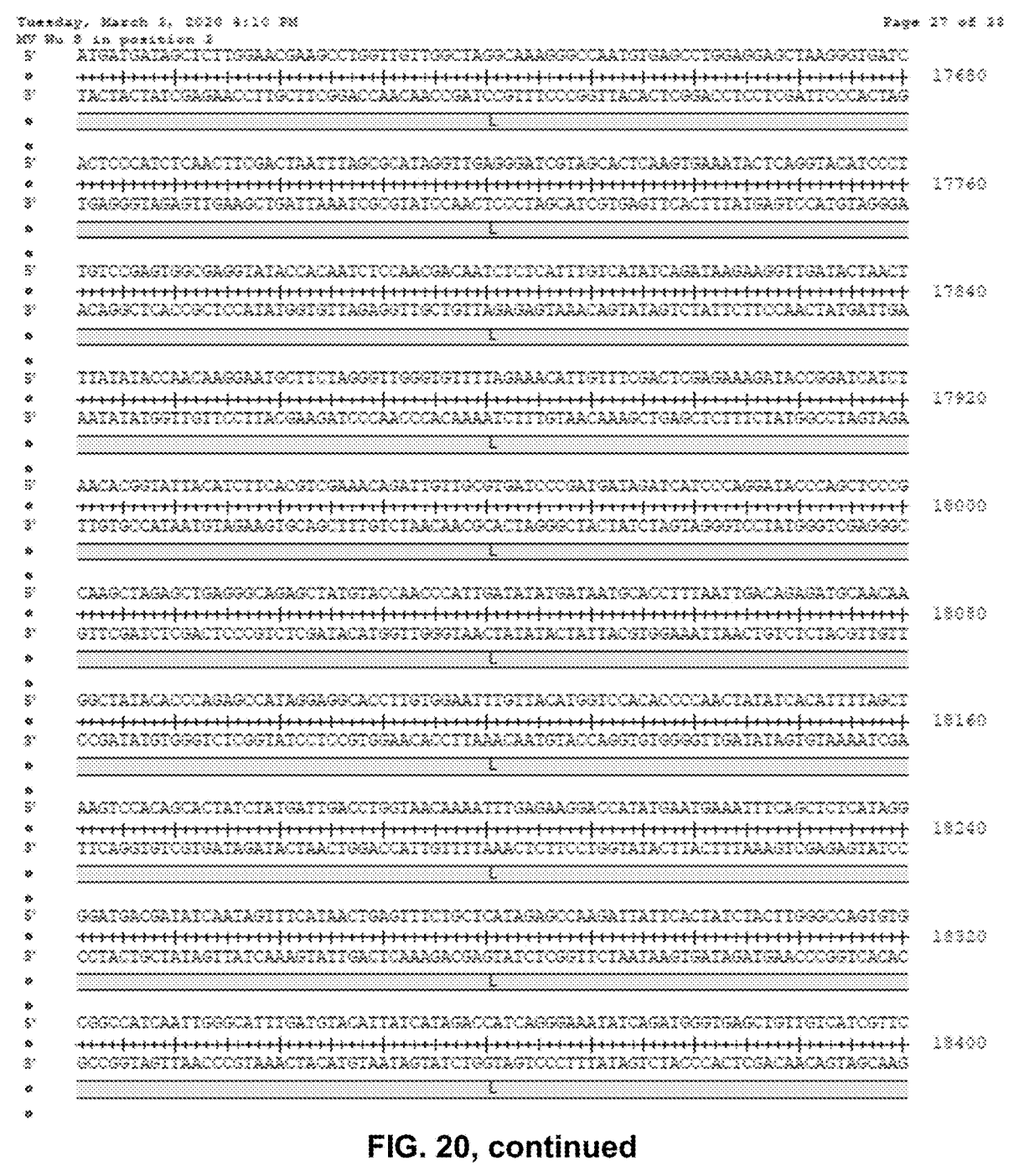
Figure 20:
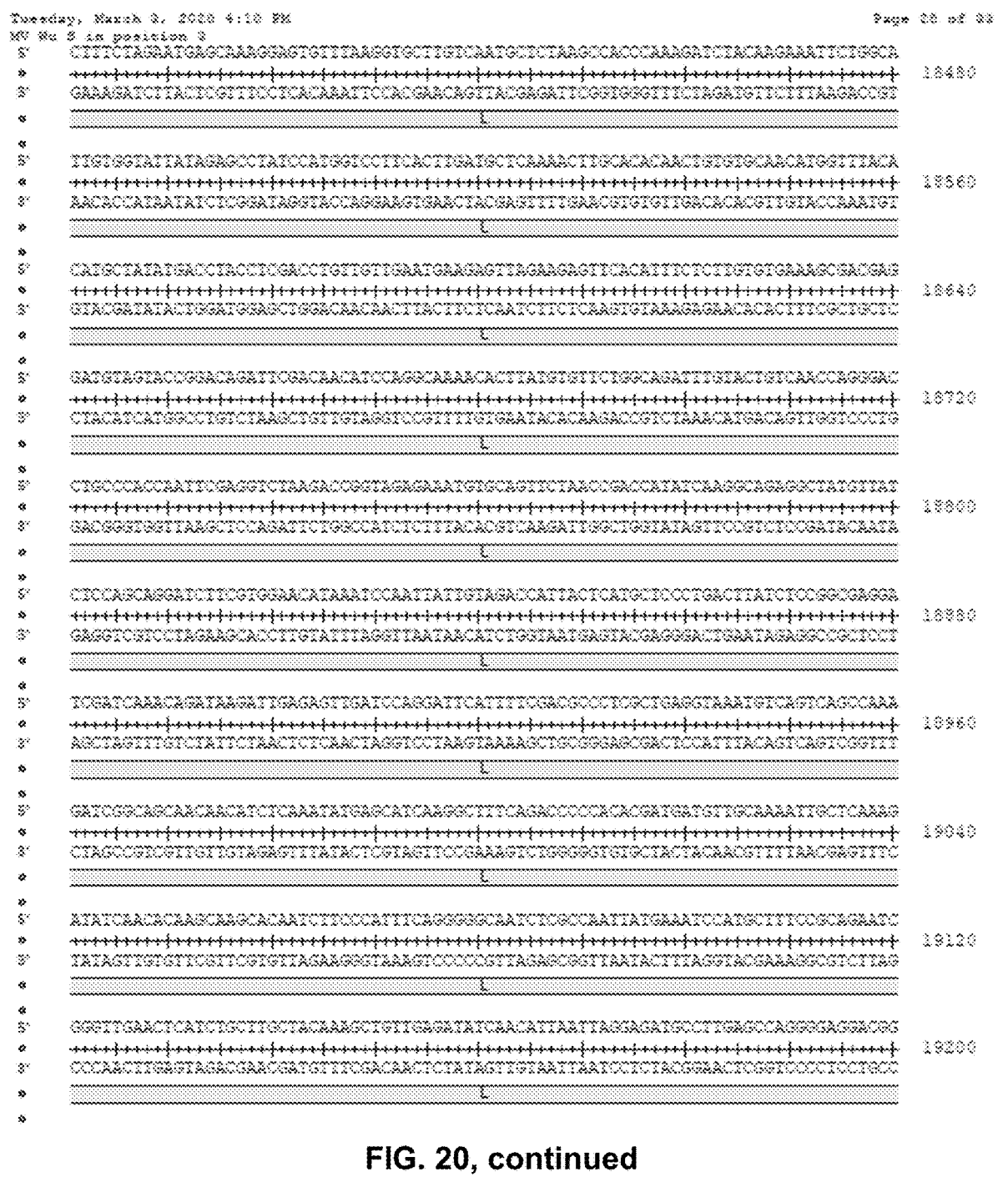
Figure 20:
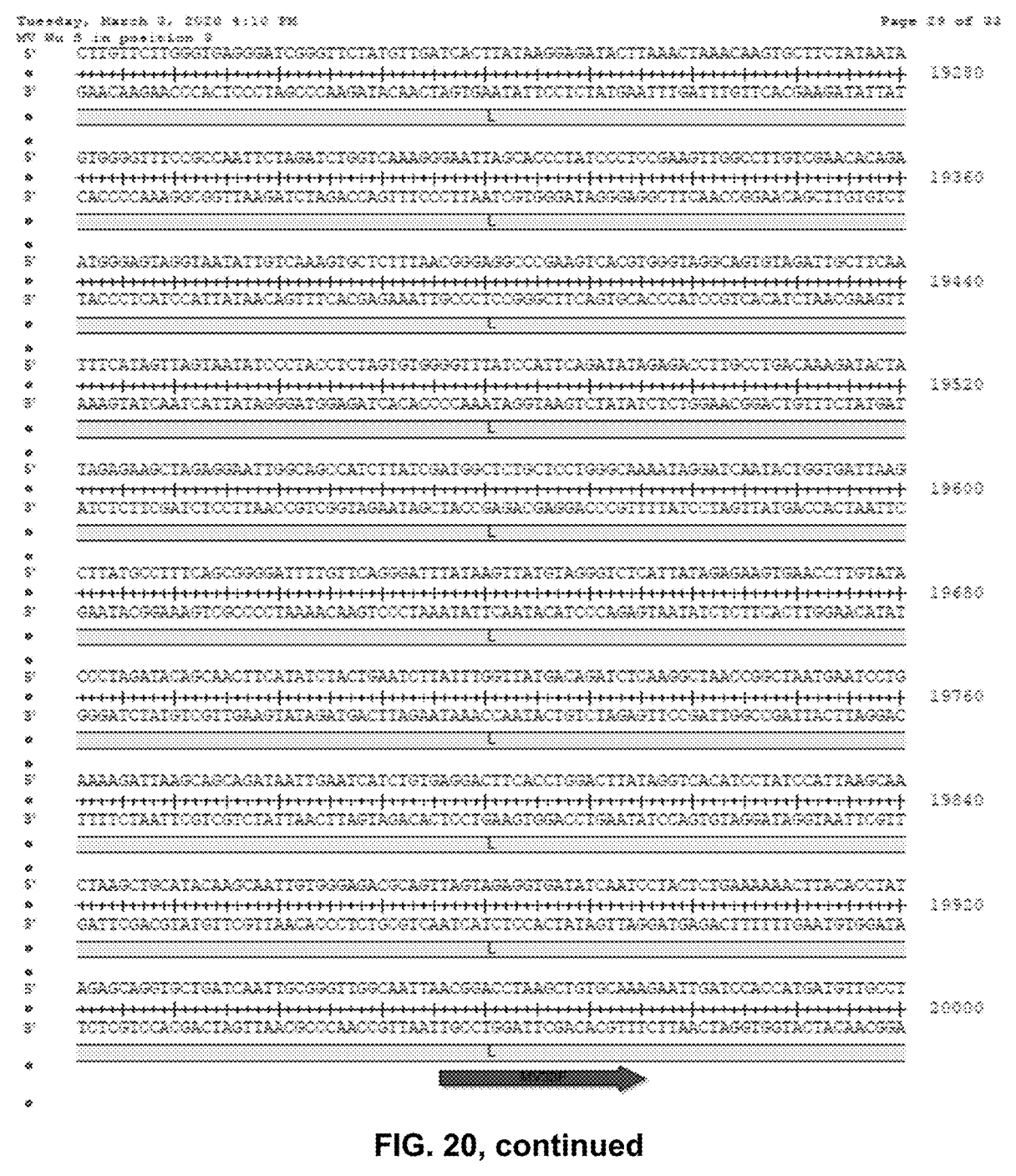
Figure 20:
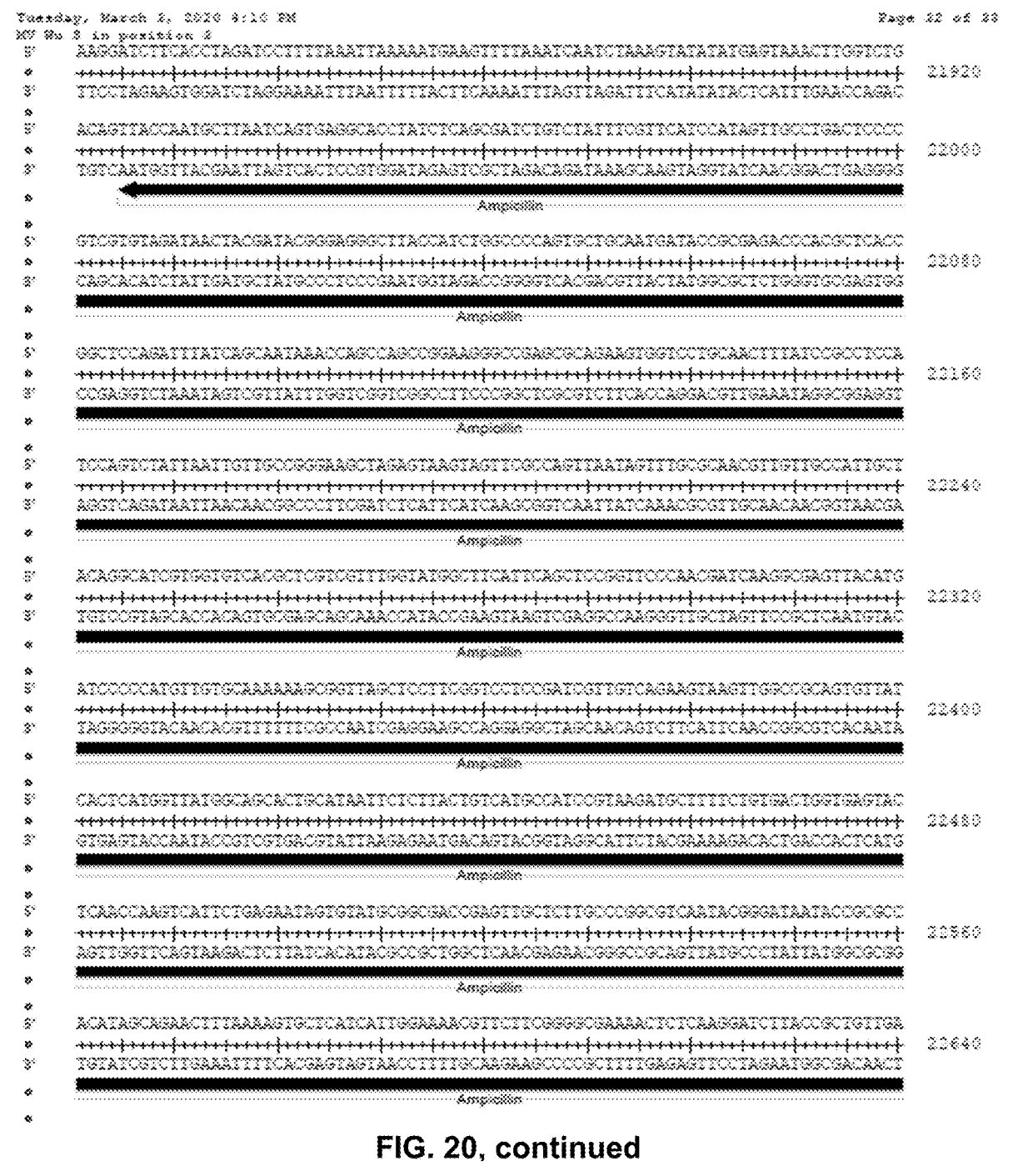
Figure 20:
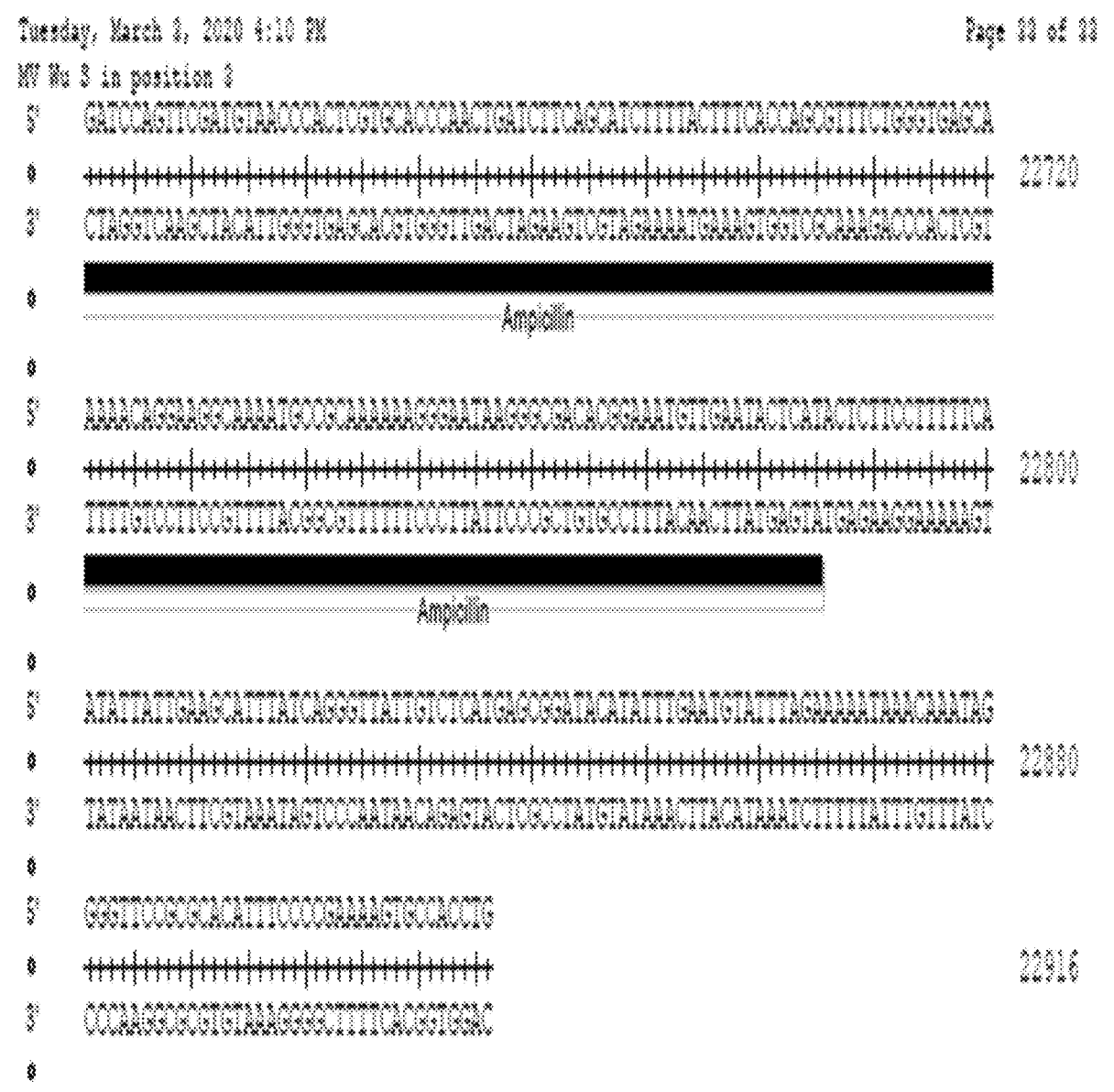

FIG. 20 shows the sequence (SEQ ID NO: 4) and features of "MV Wu S in position 3".

Figure 21:
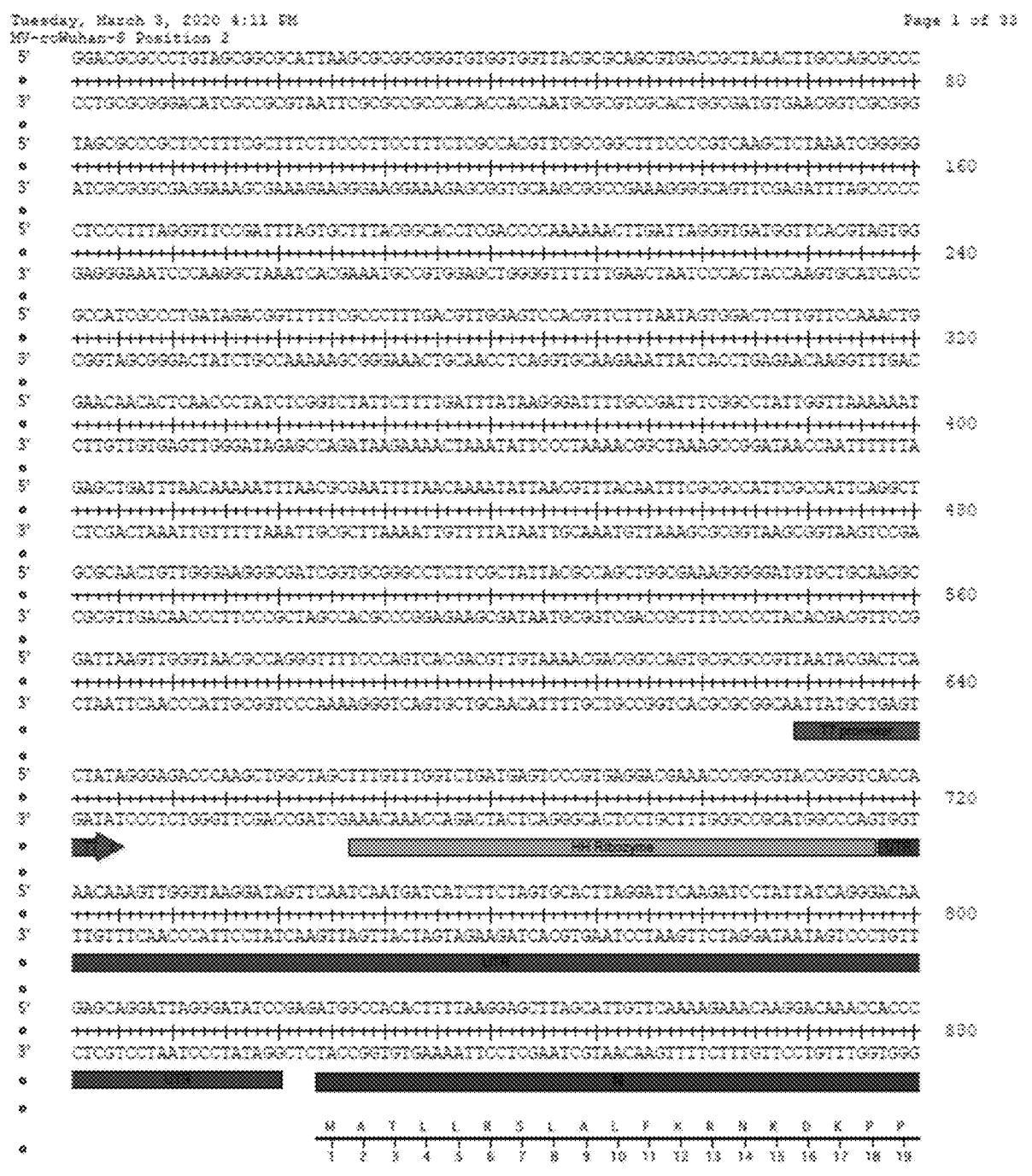
Figure 21:
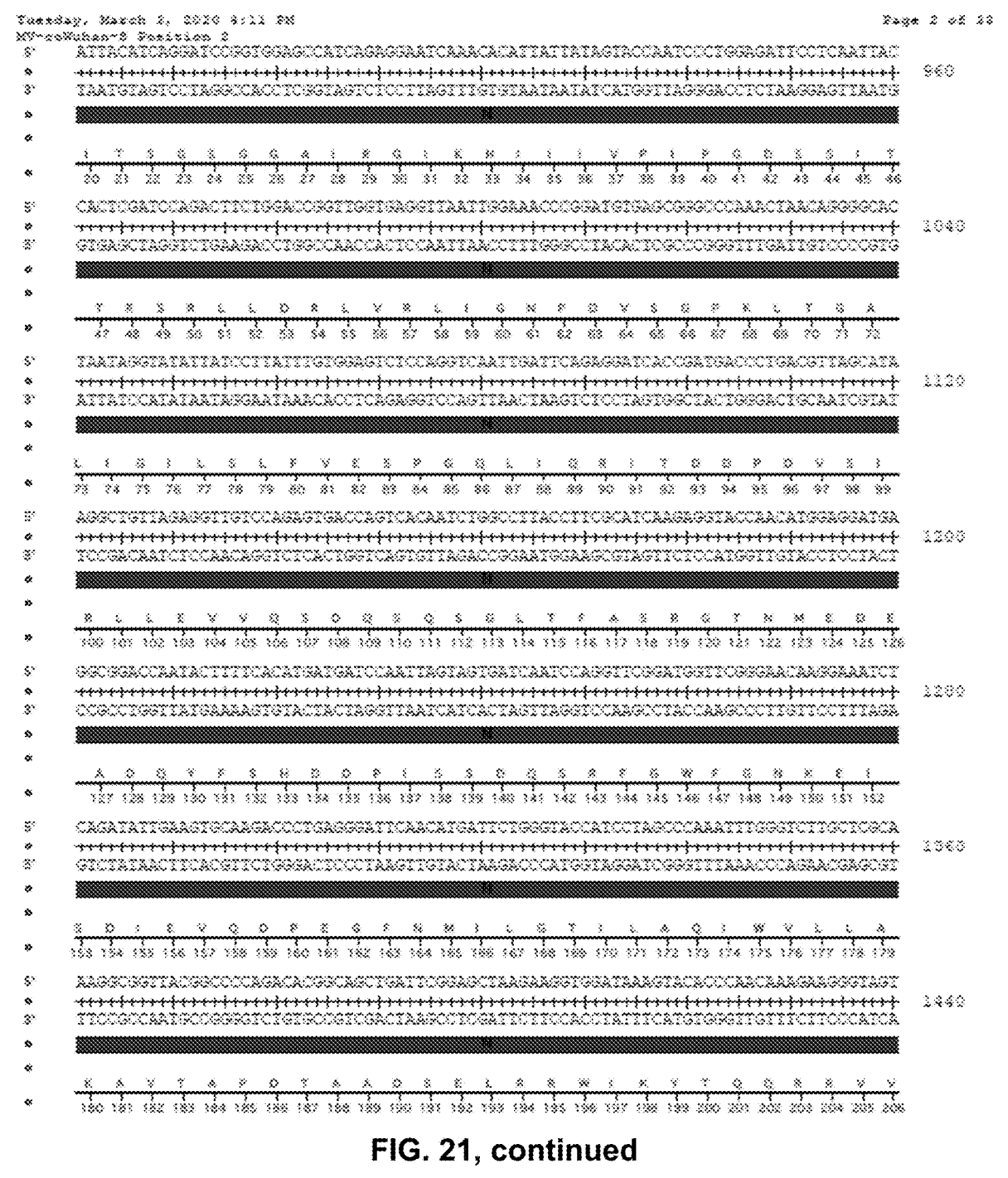
Figure 21:
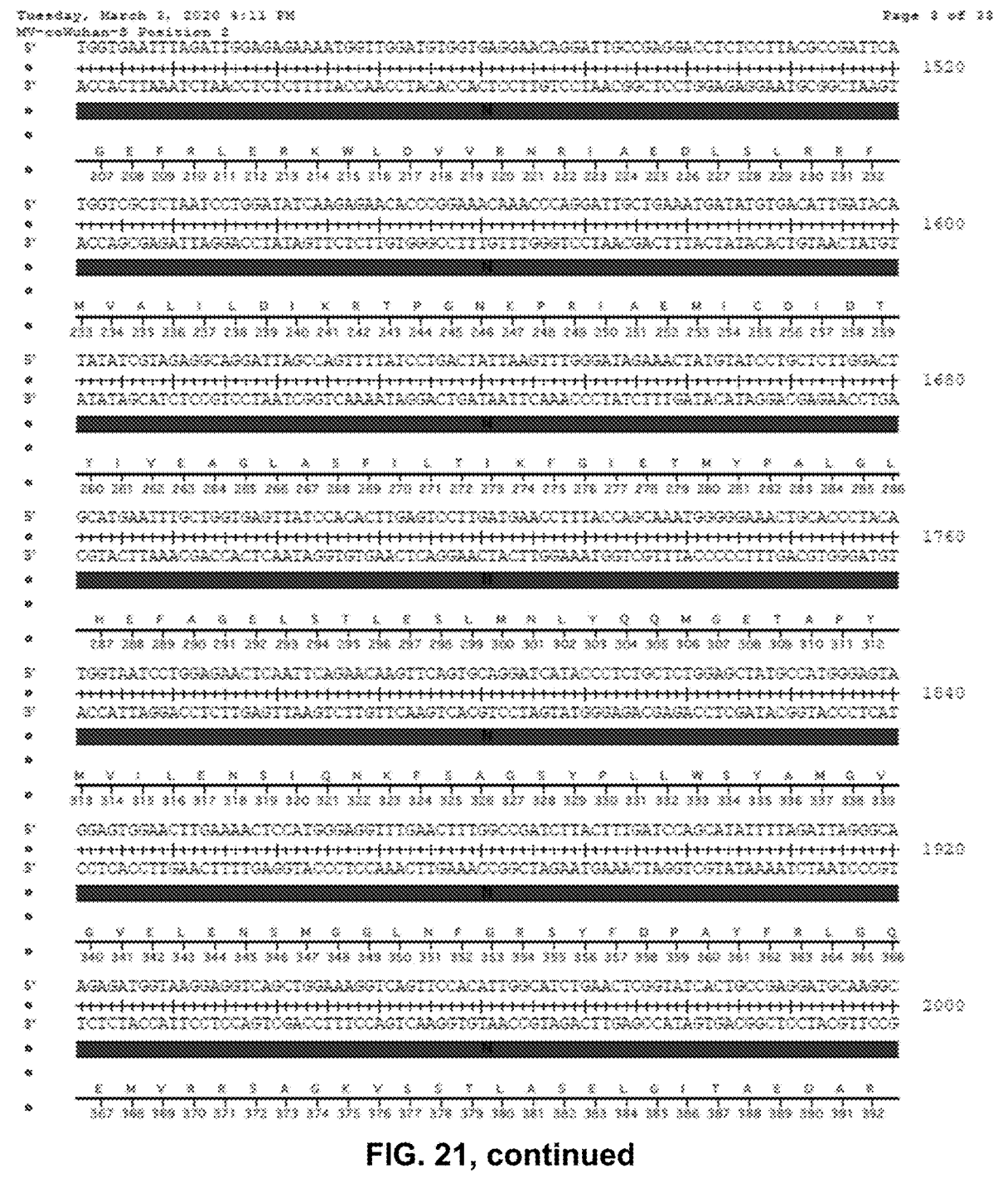
Figure 21:
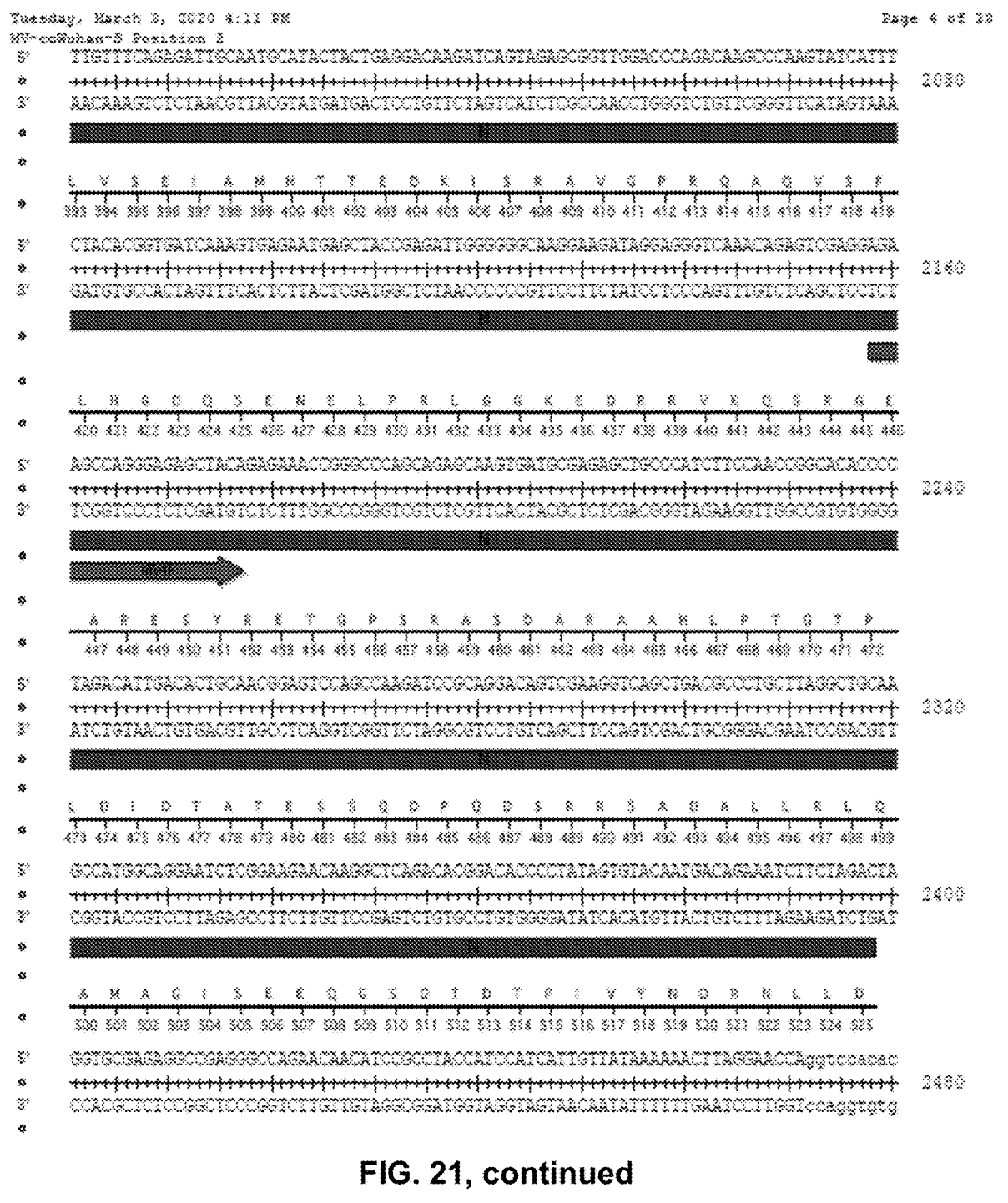
Figure 21:
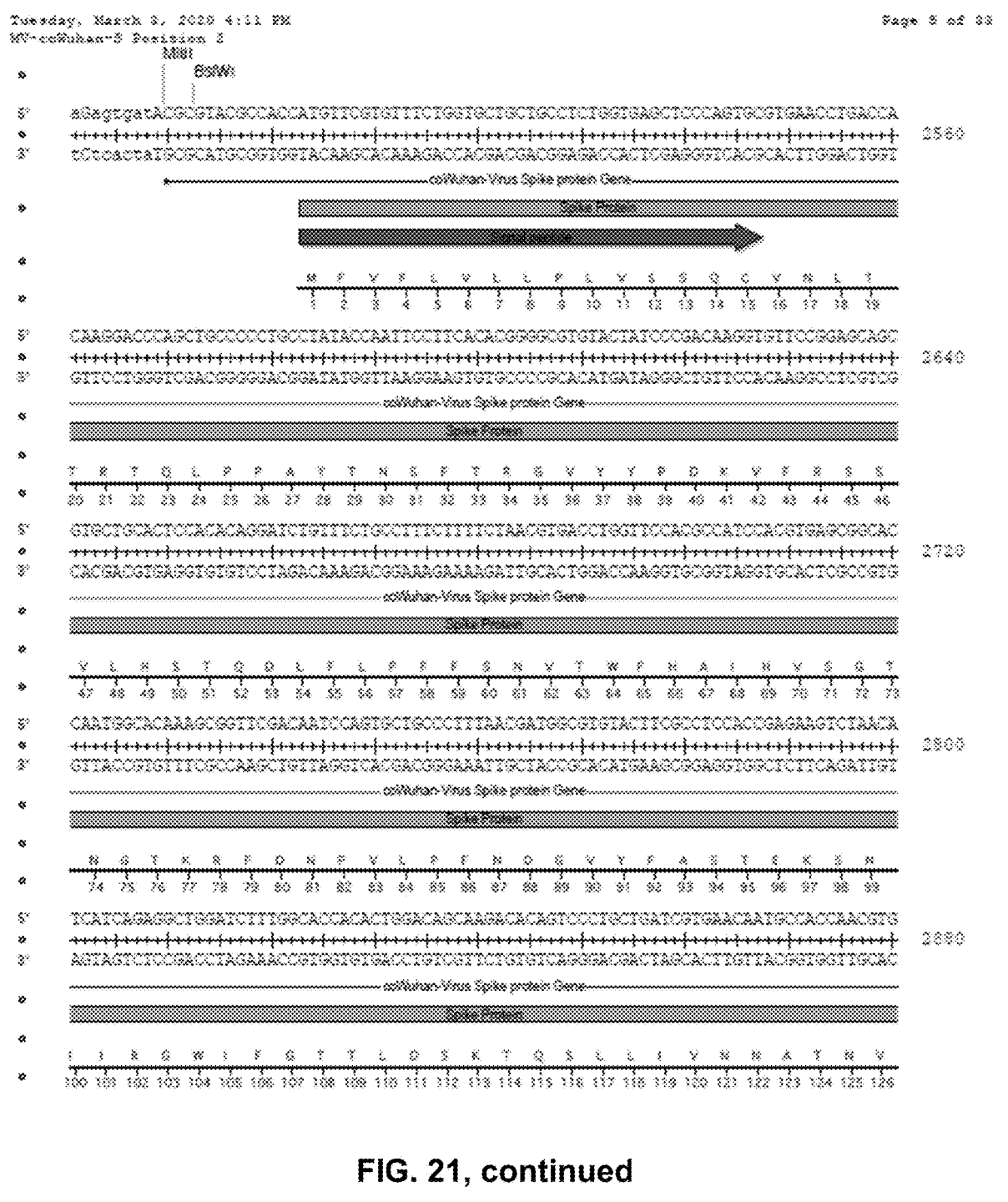
Figure 21:
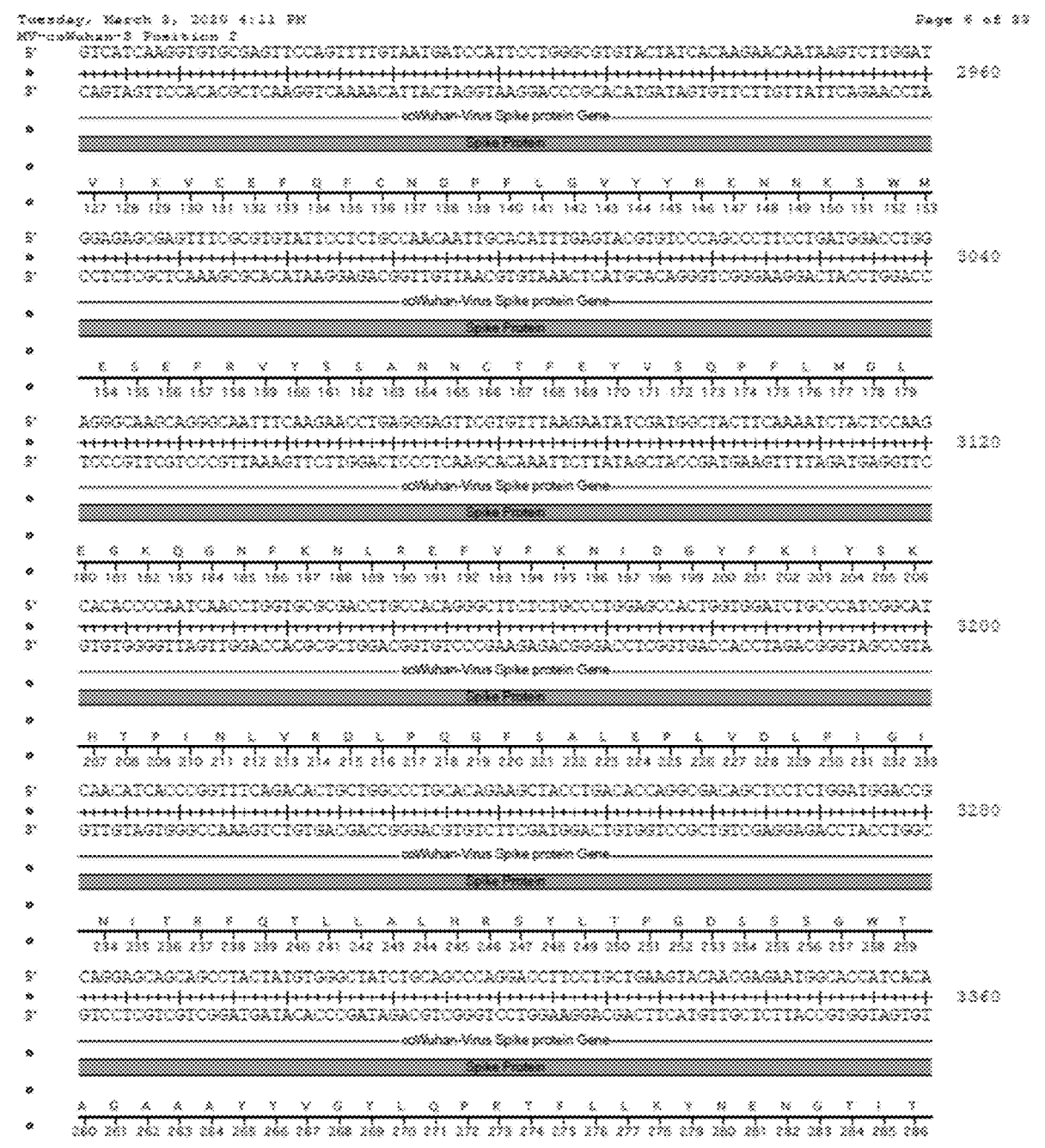
Figure 21:
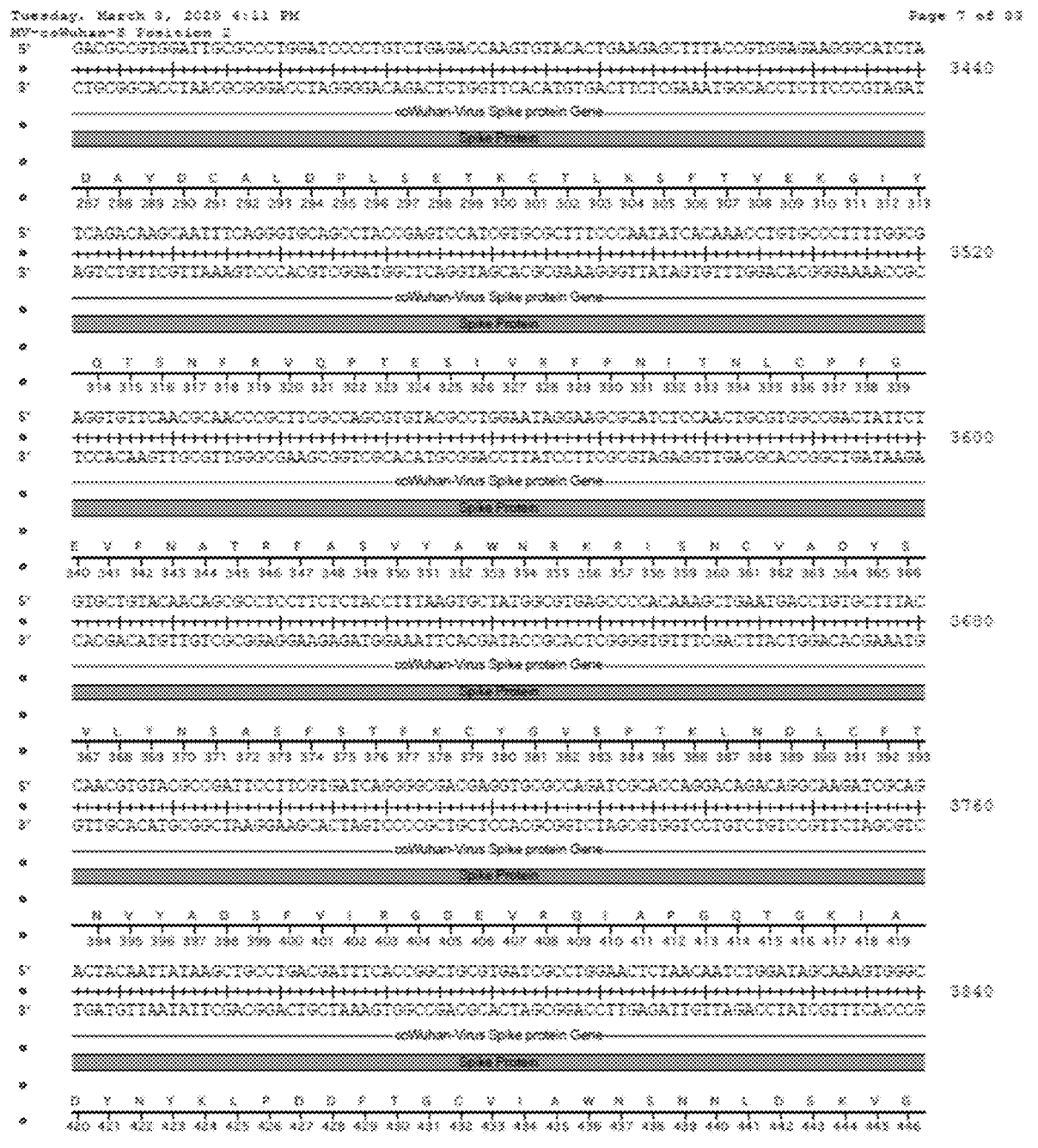
Figure 21:
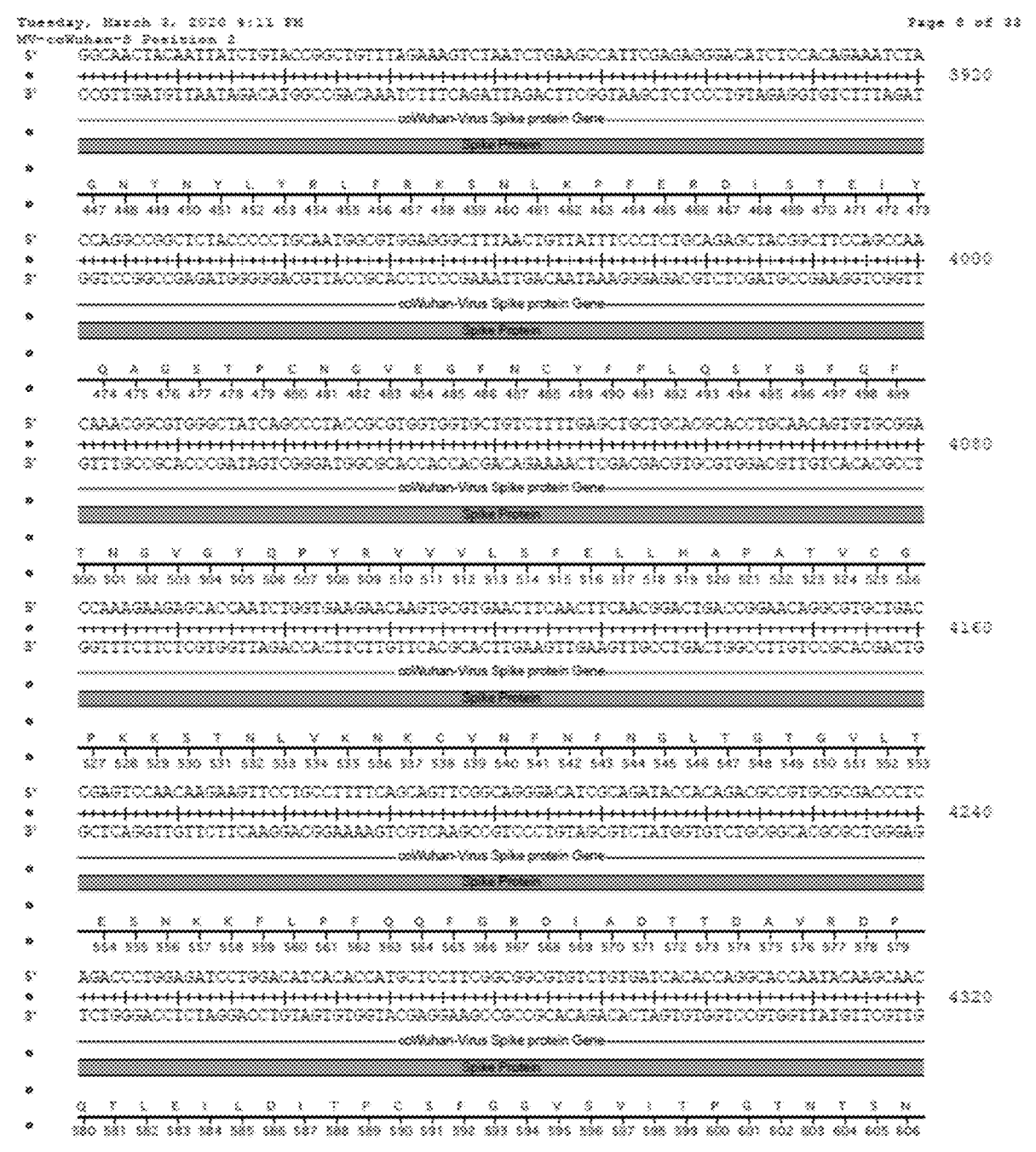
Figure 21:
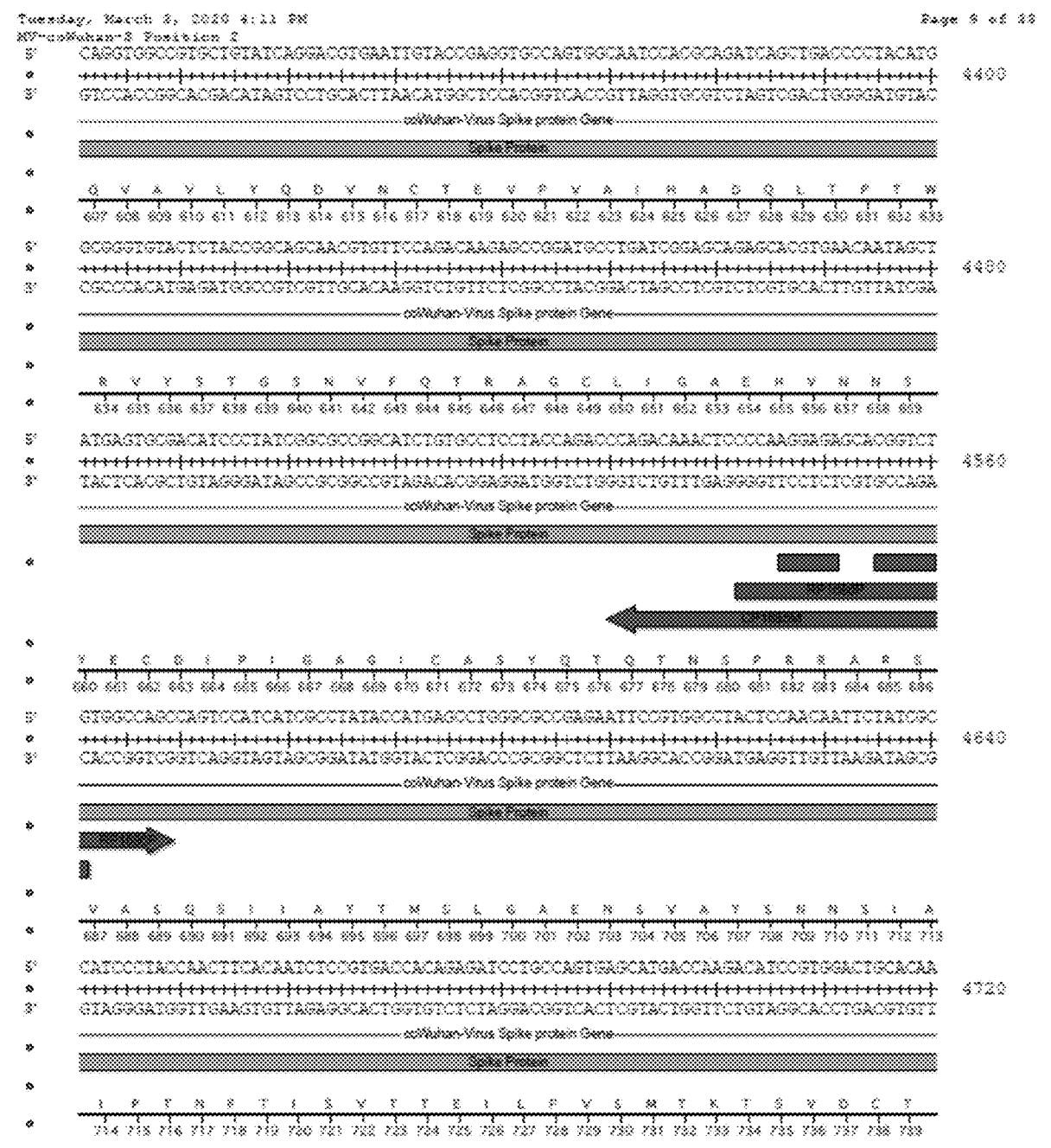
Figure 21:
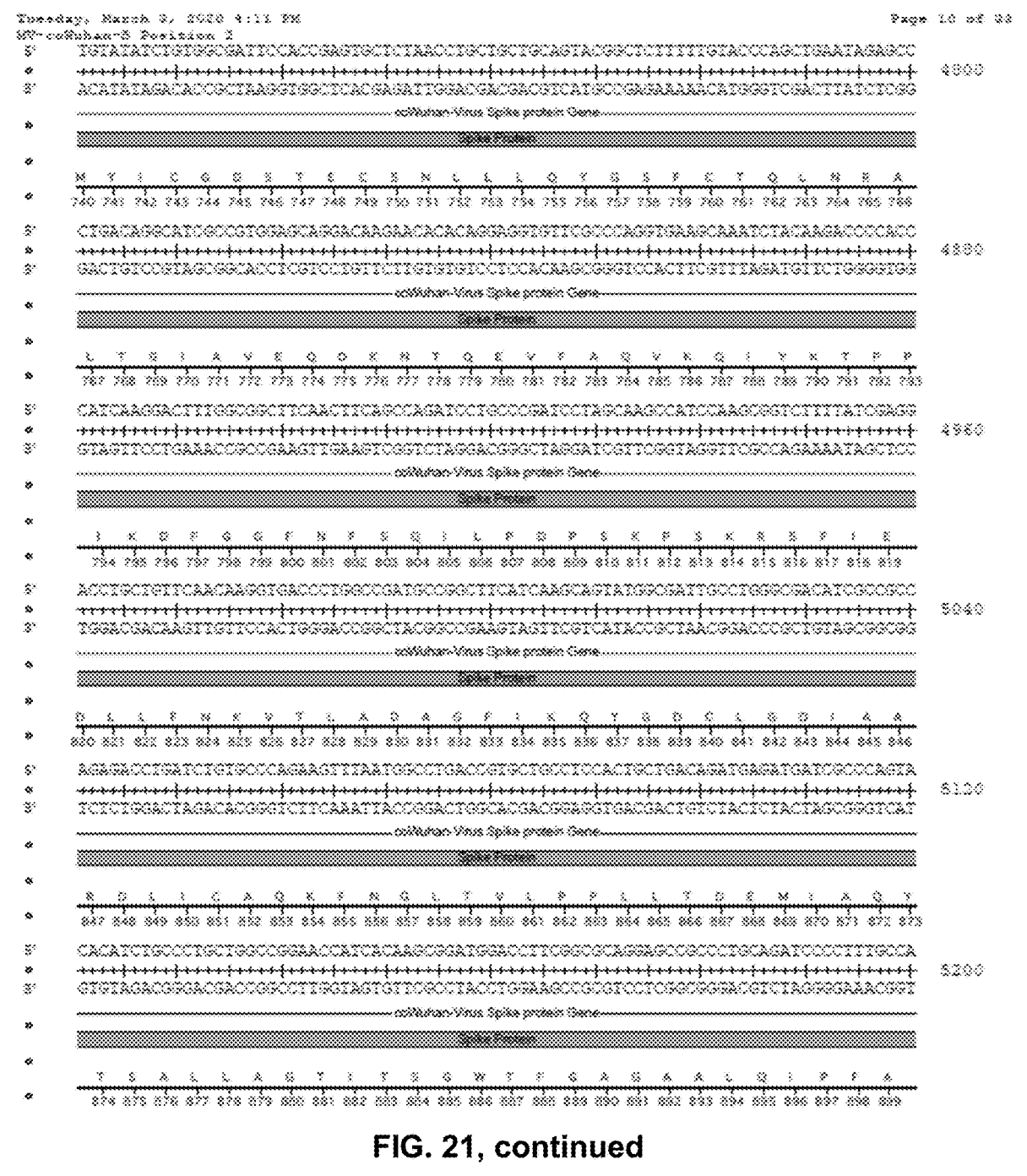
Figure 21:
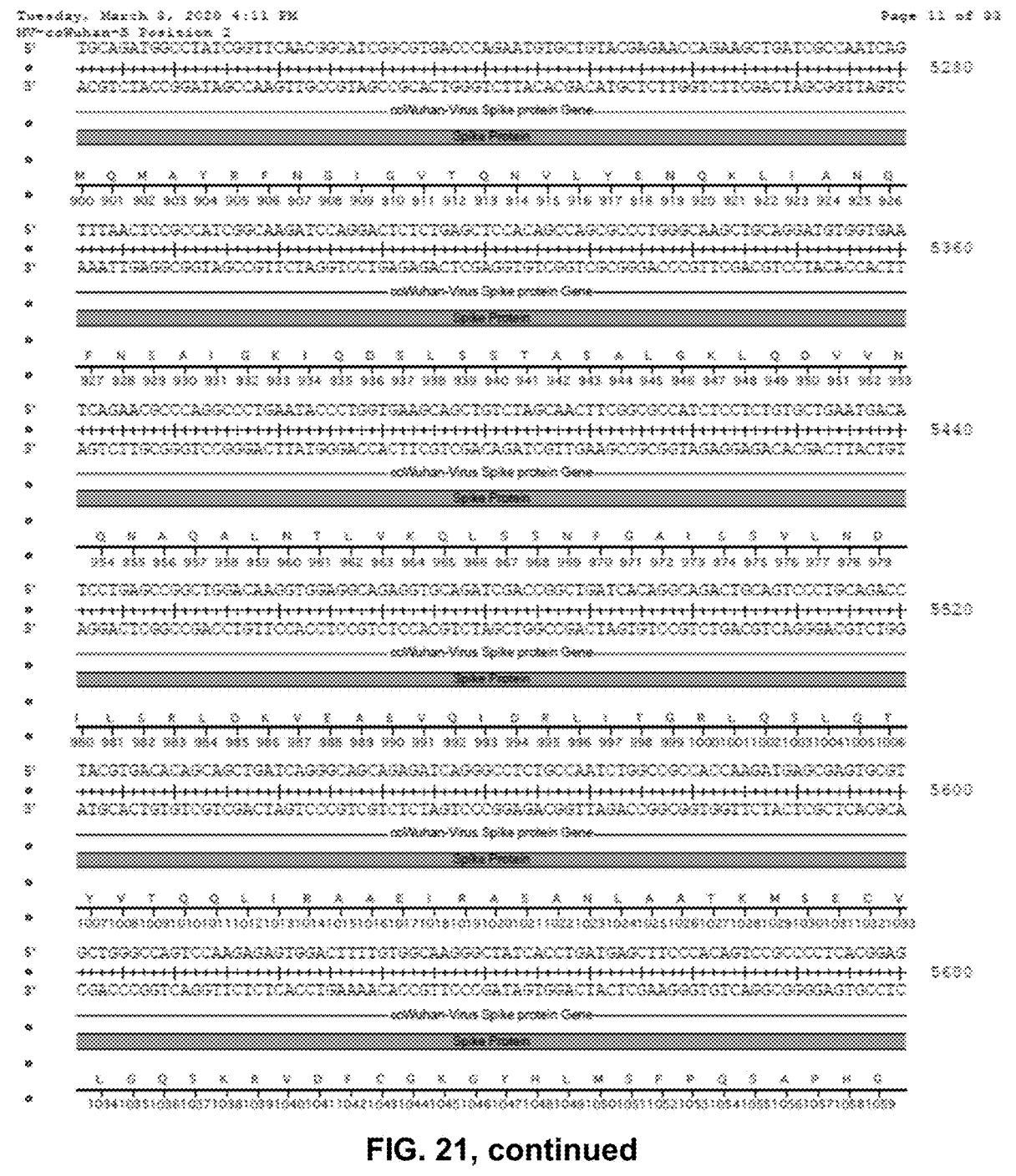
Figure 21:
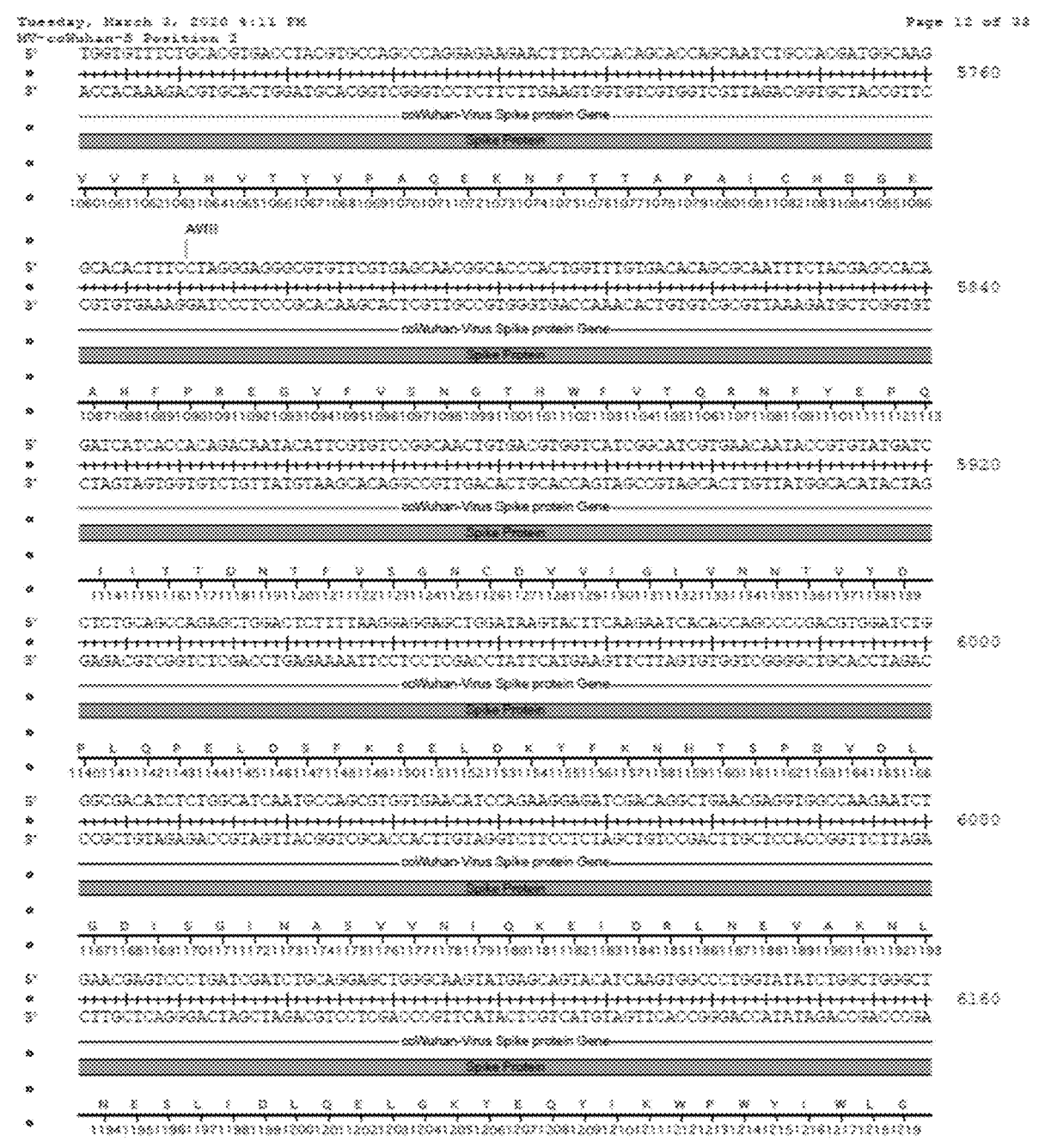
Figure 21:
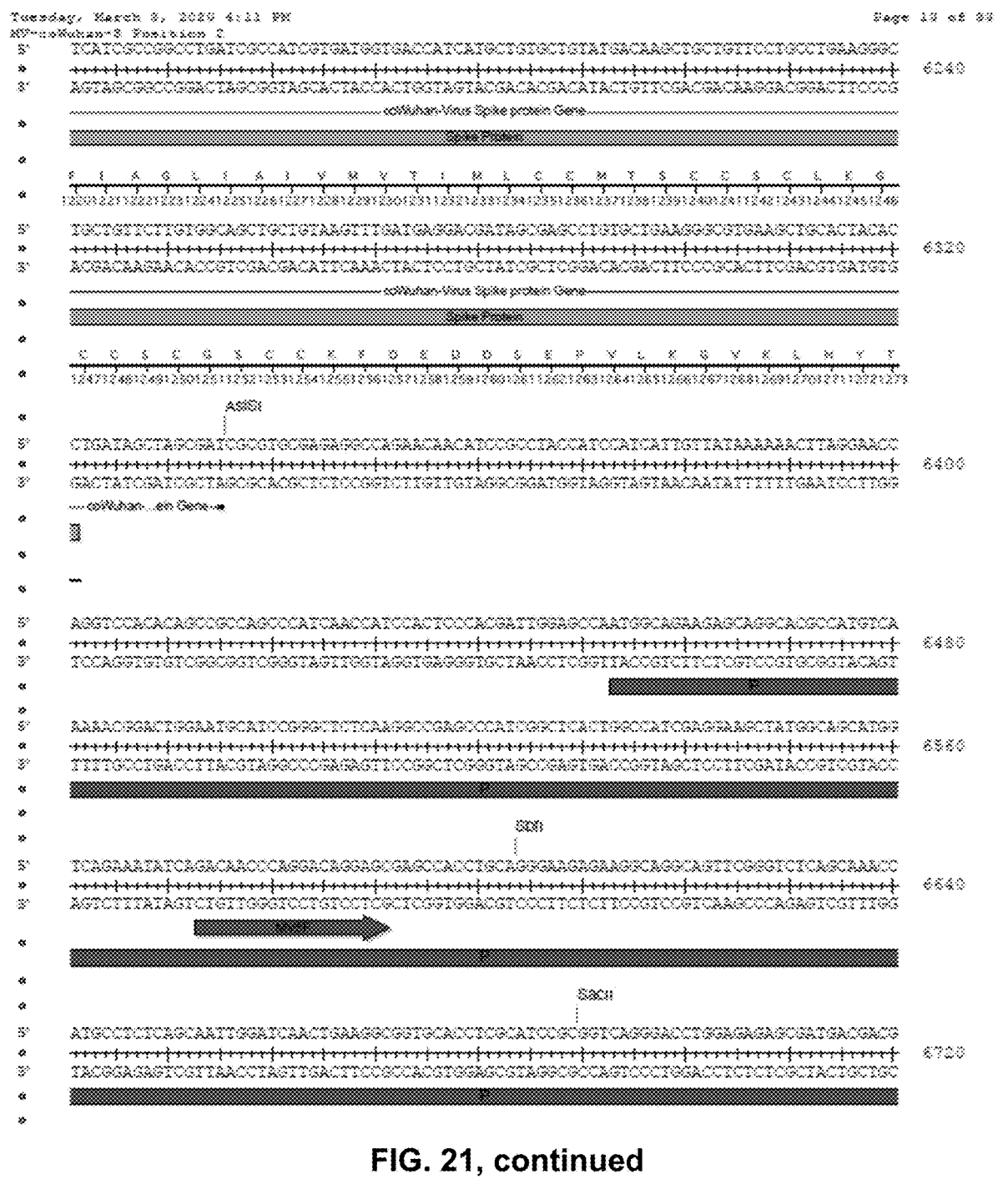
Figure 21:
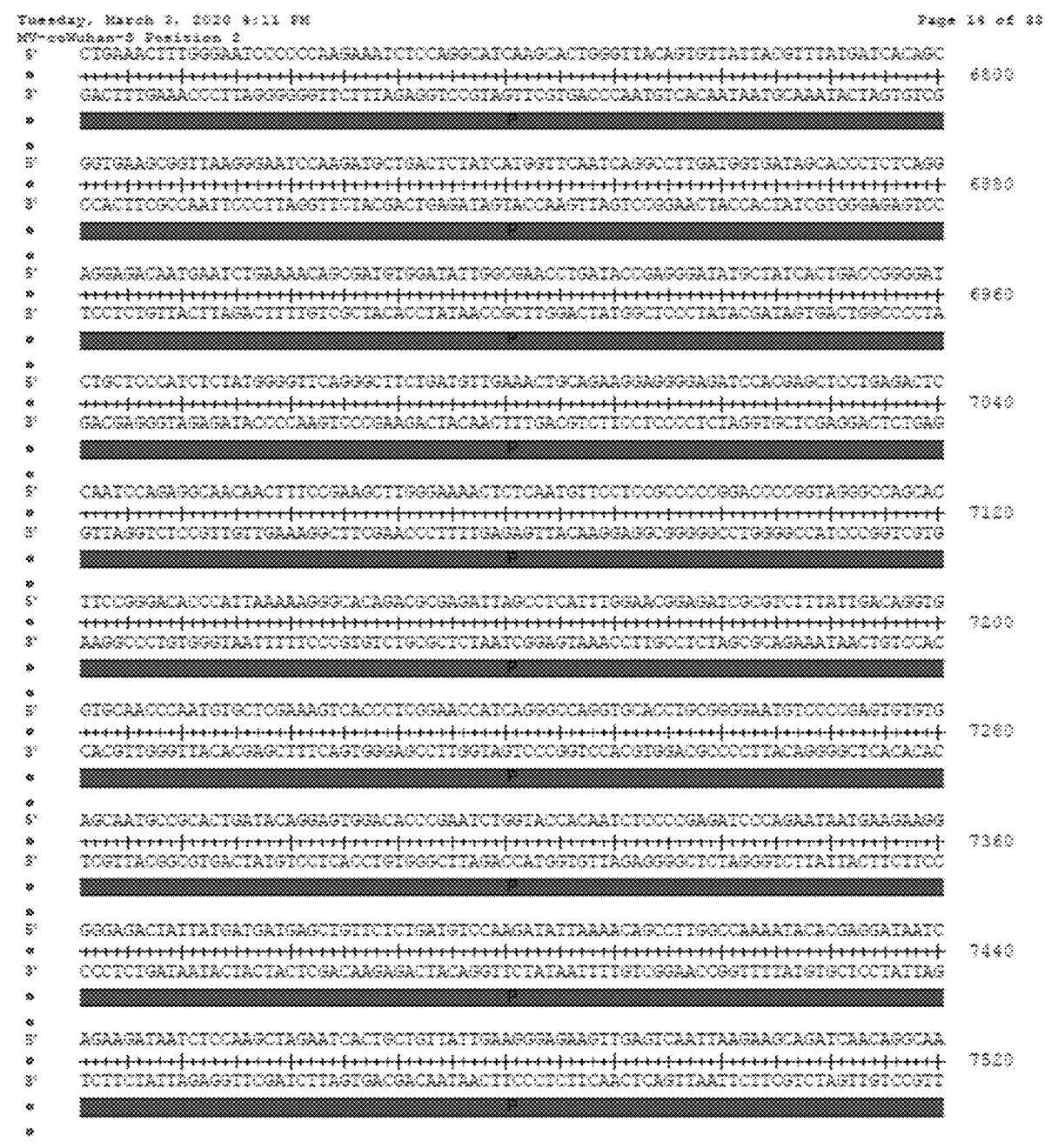
Figure 21:
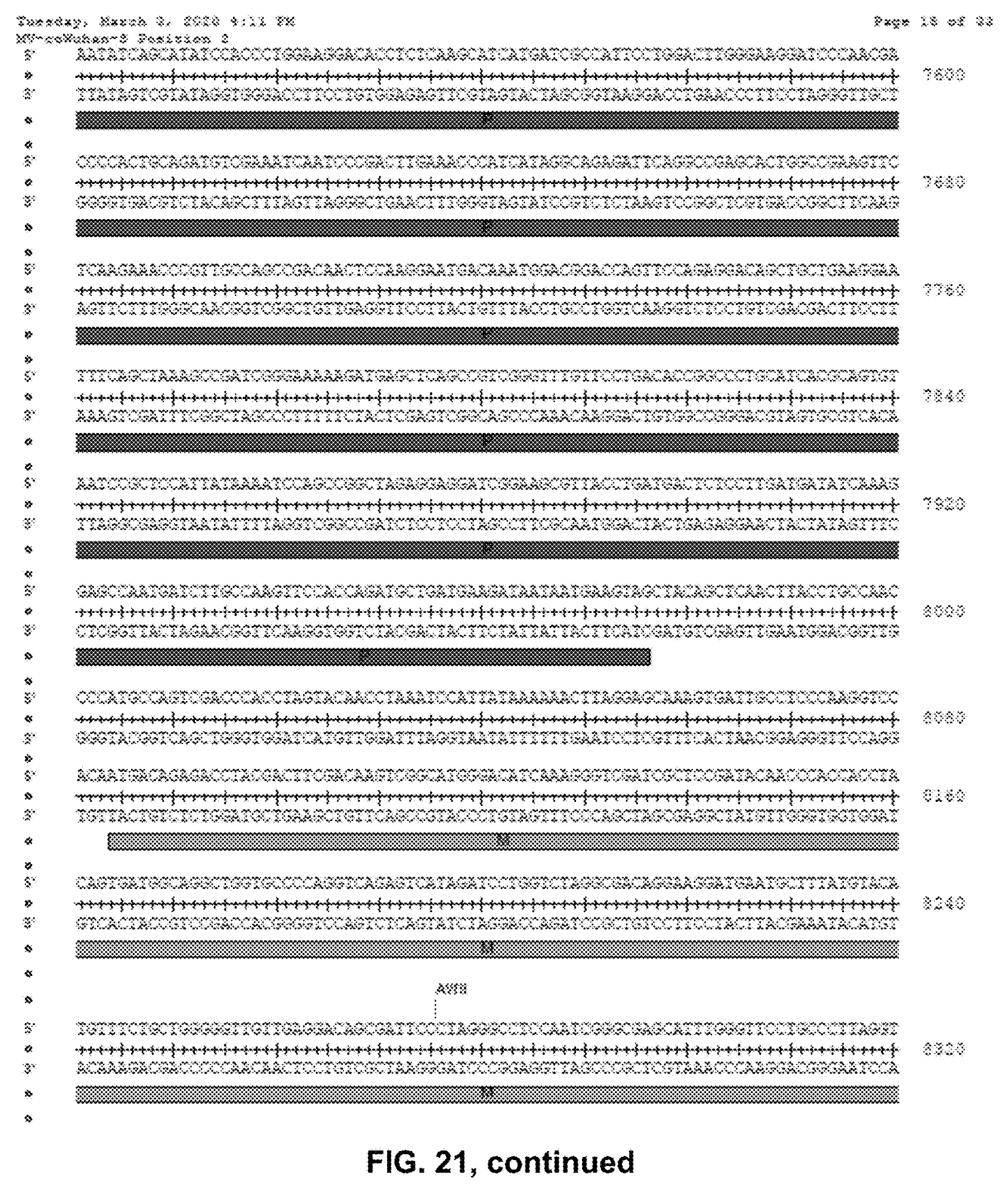
Figure 21:
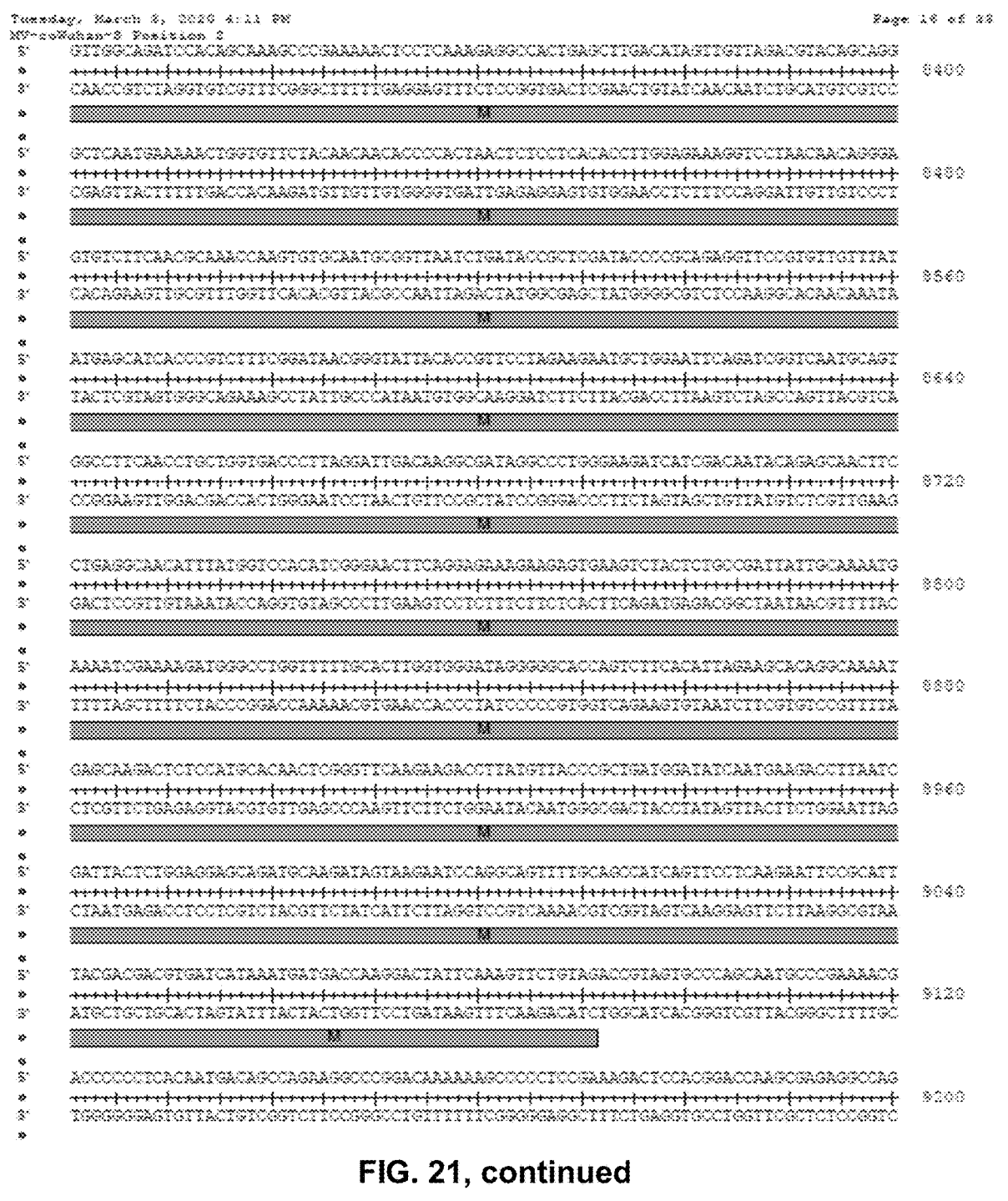
Figure 21:
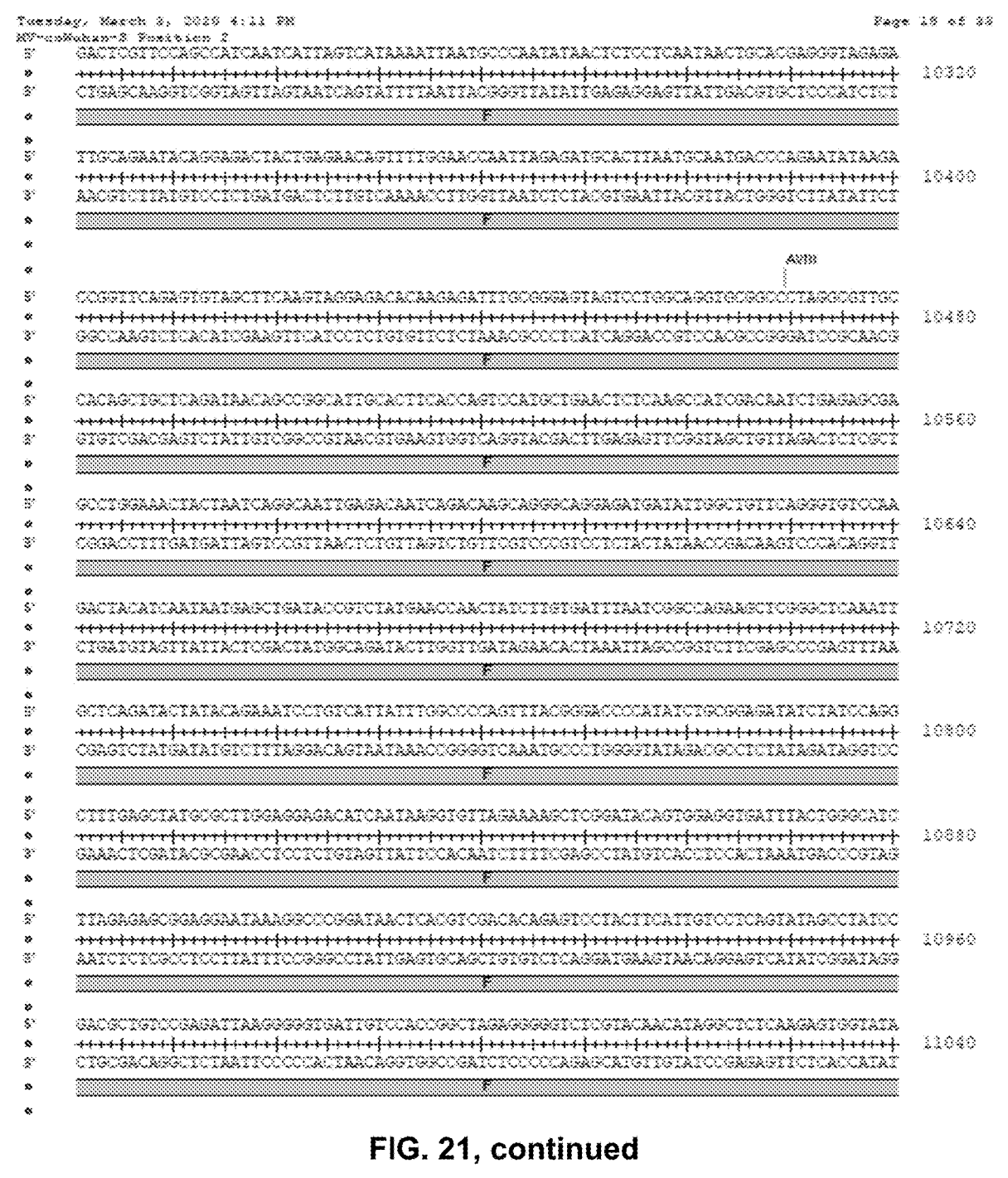
Figure 21:
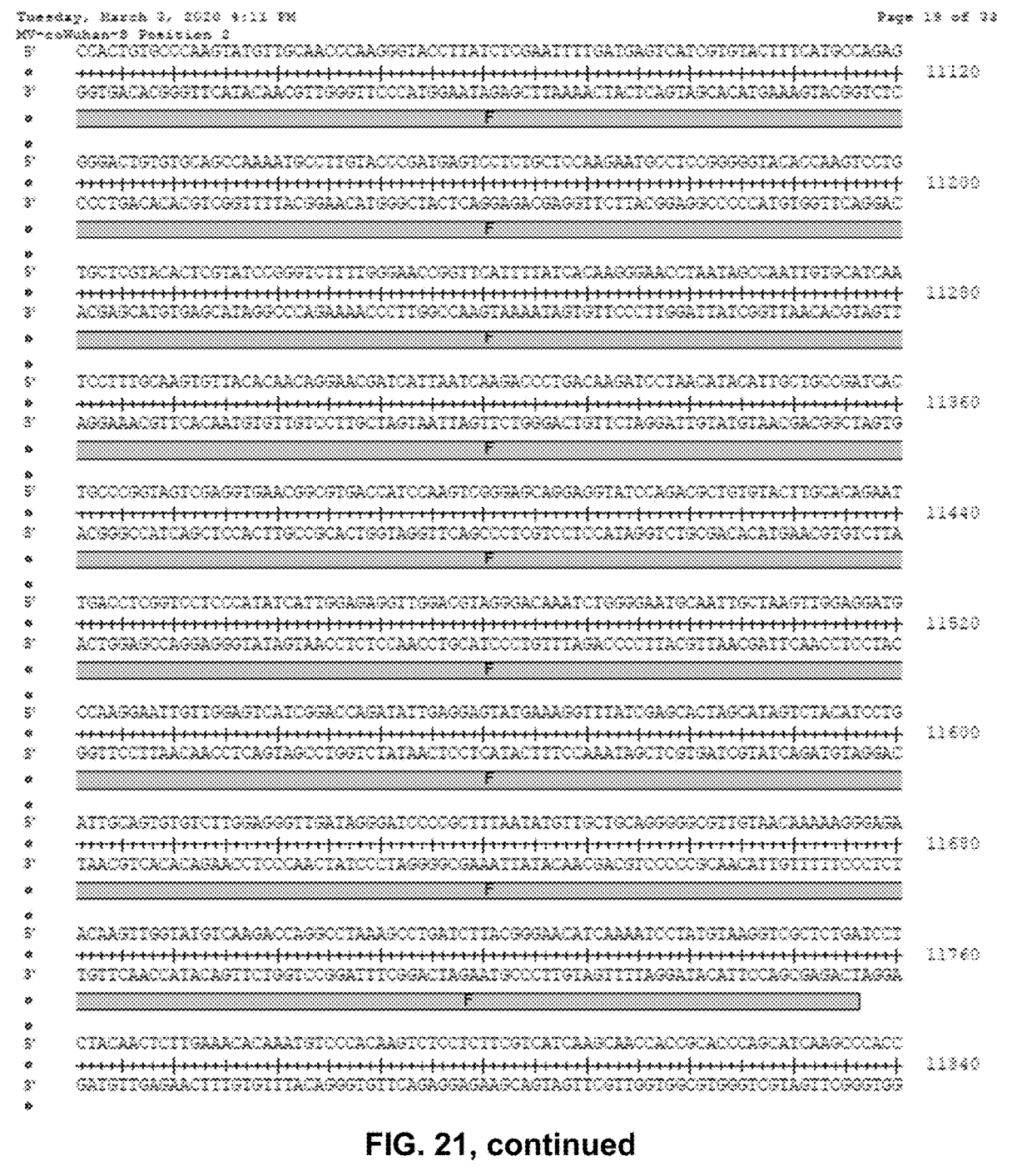
Figure 21:
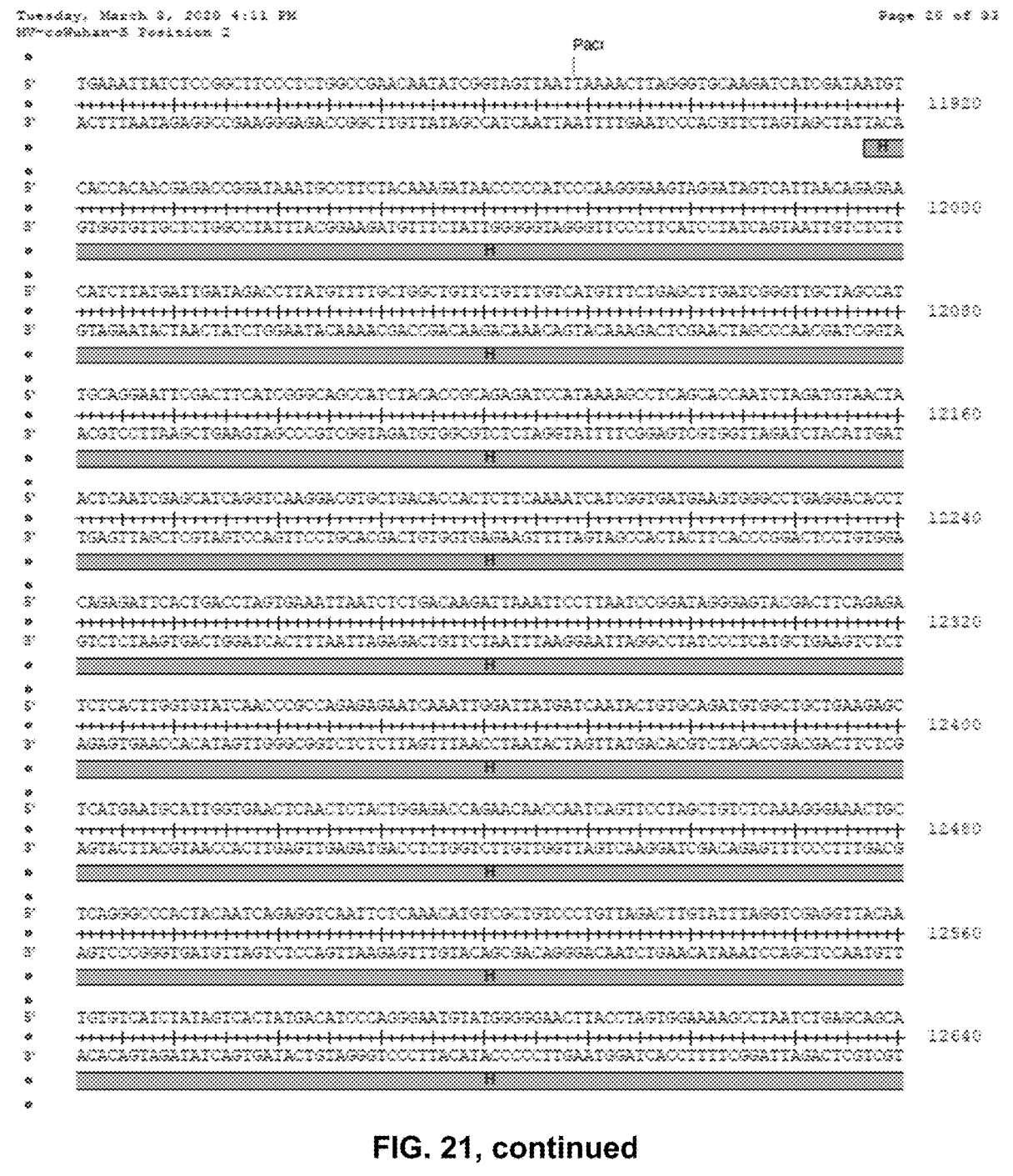
Figure 21:
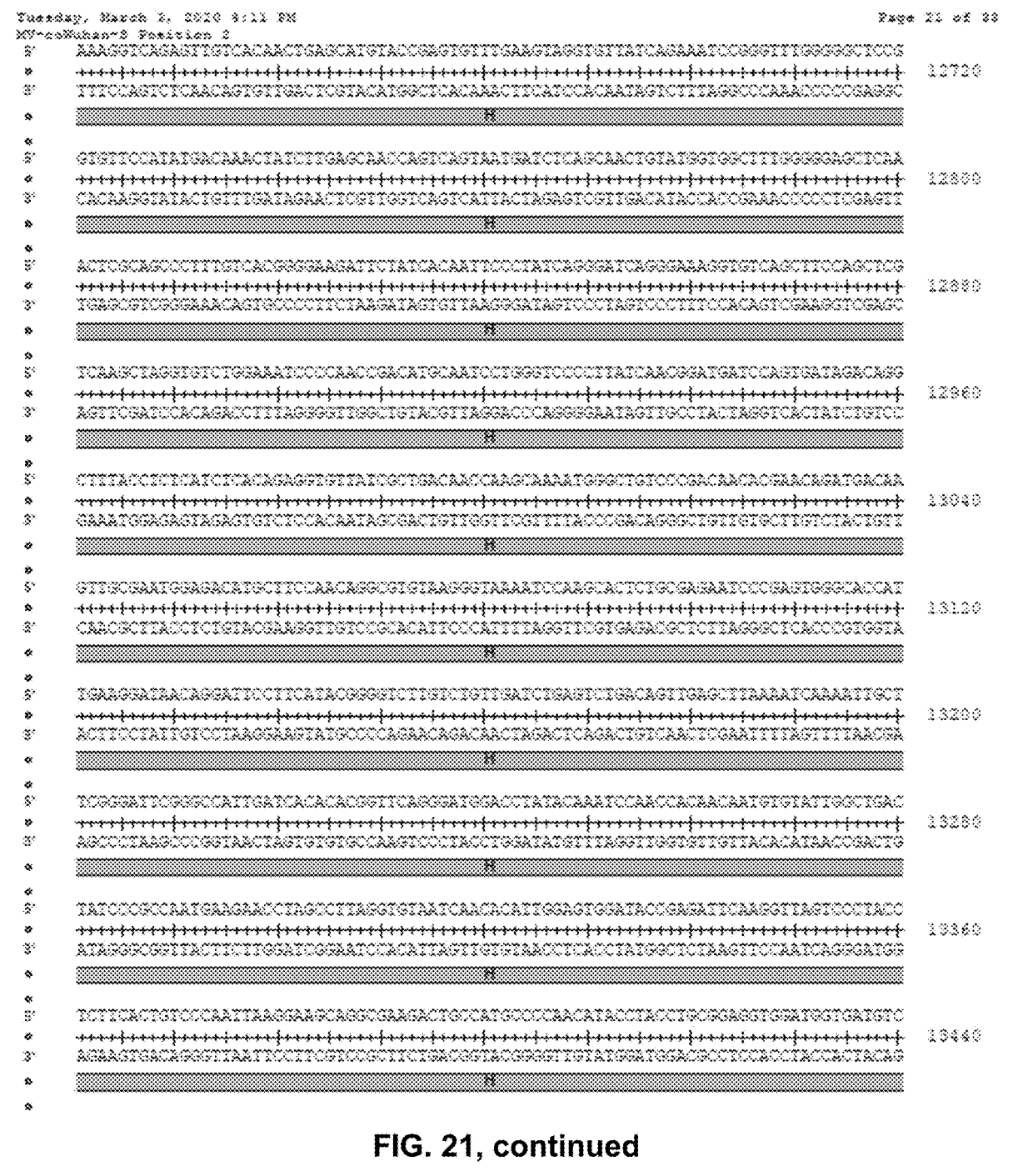
Figure 21:
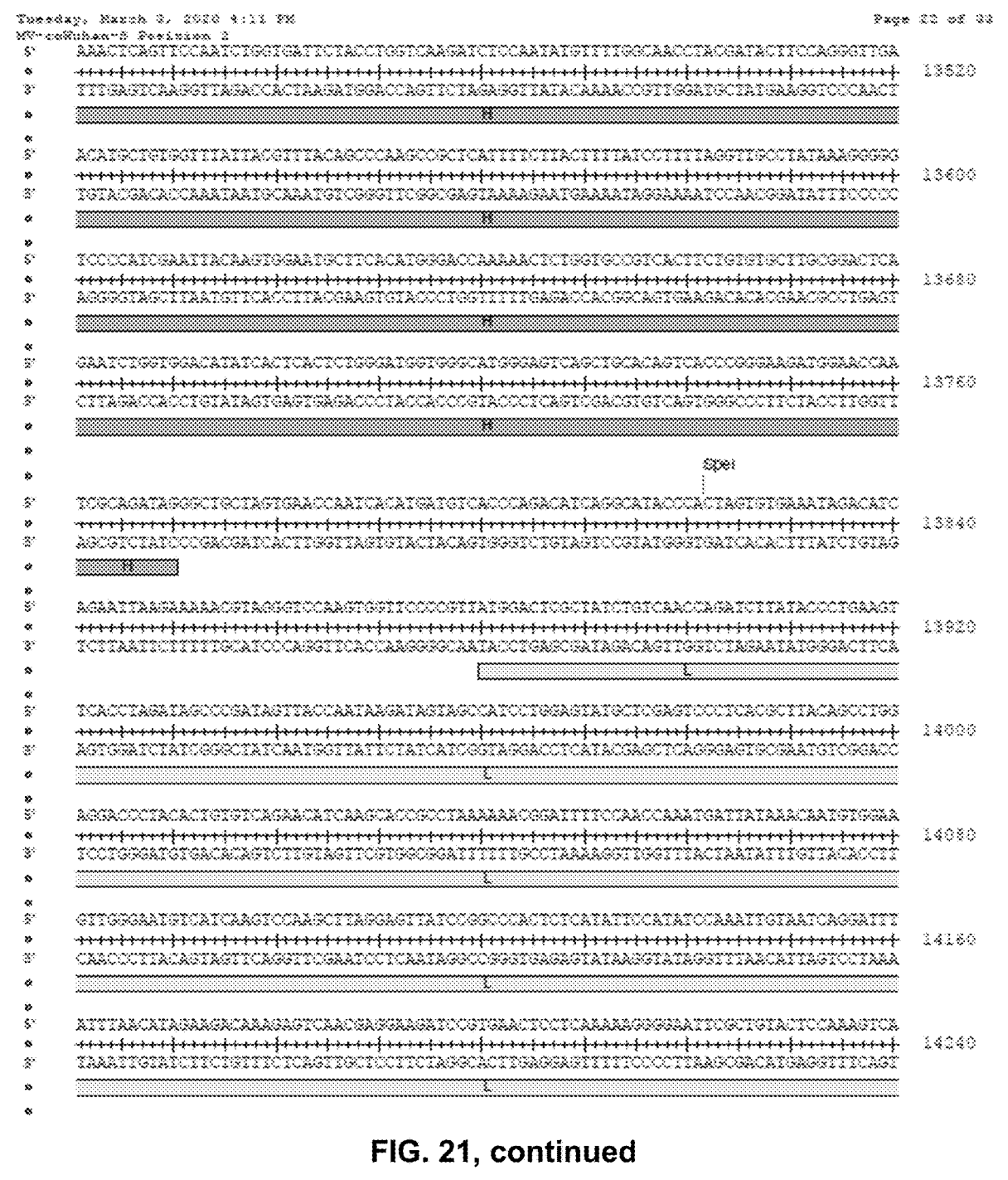
Figure 21:
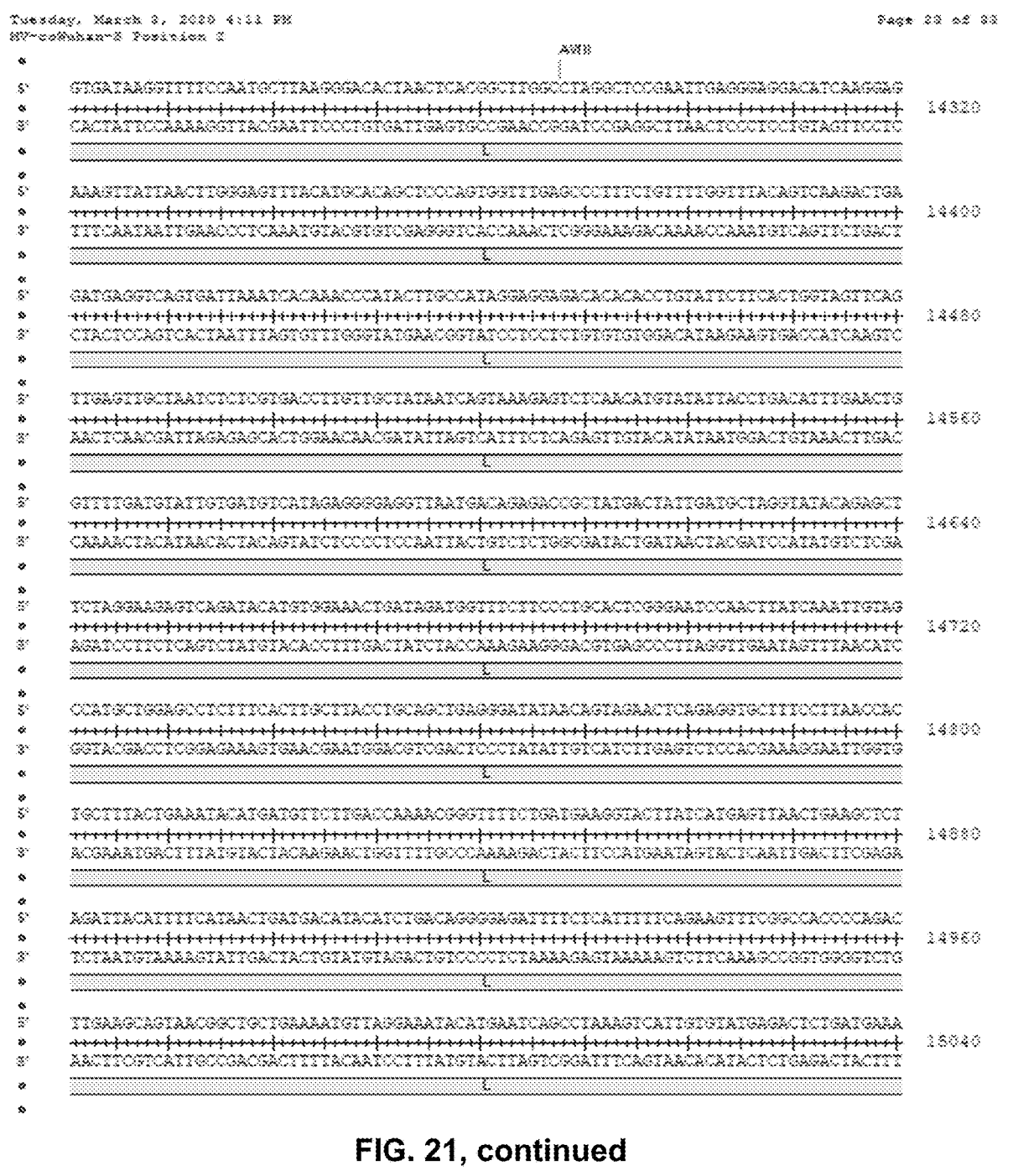
Figure 21:
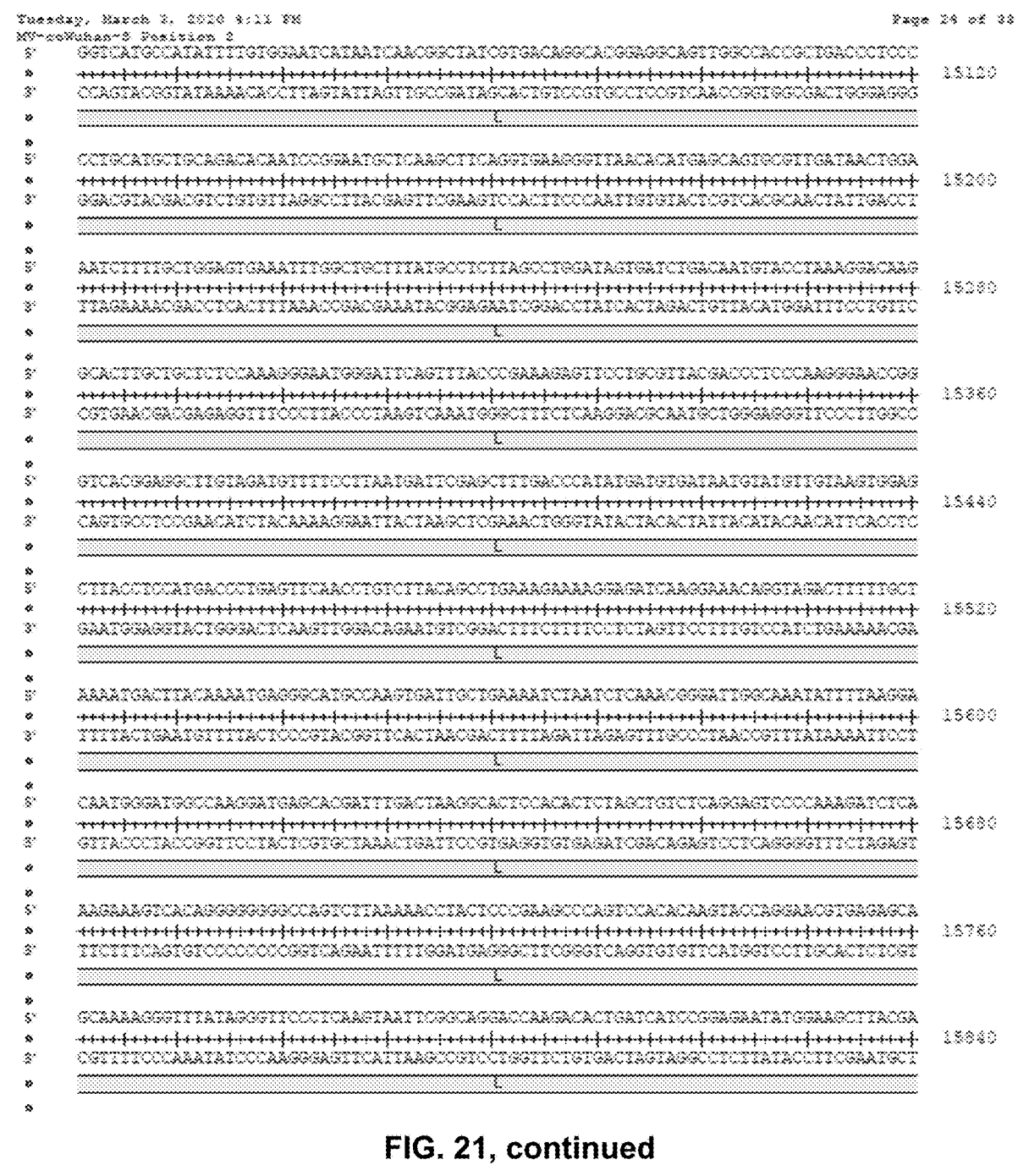
Figure 21:
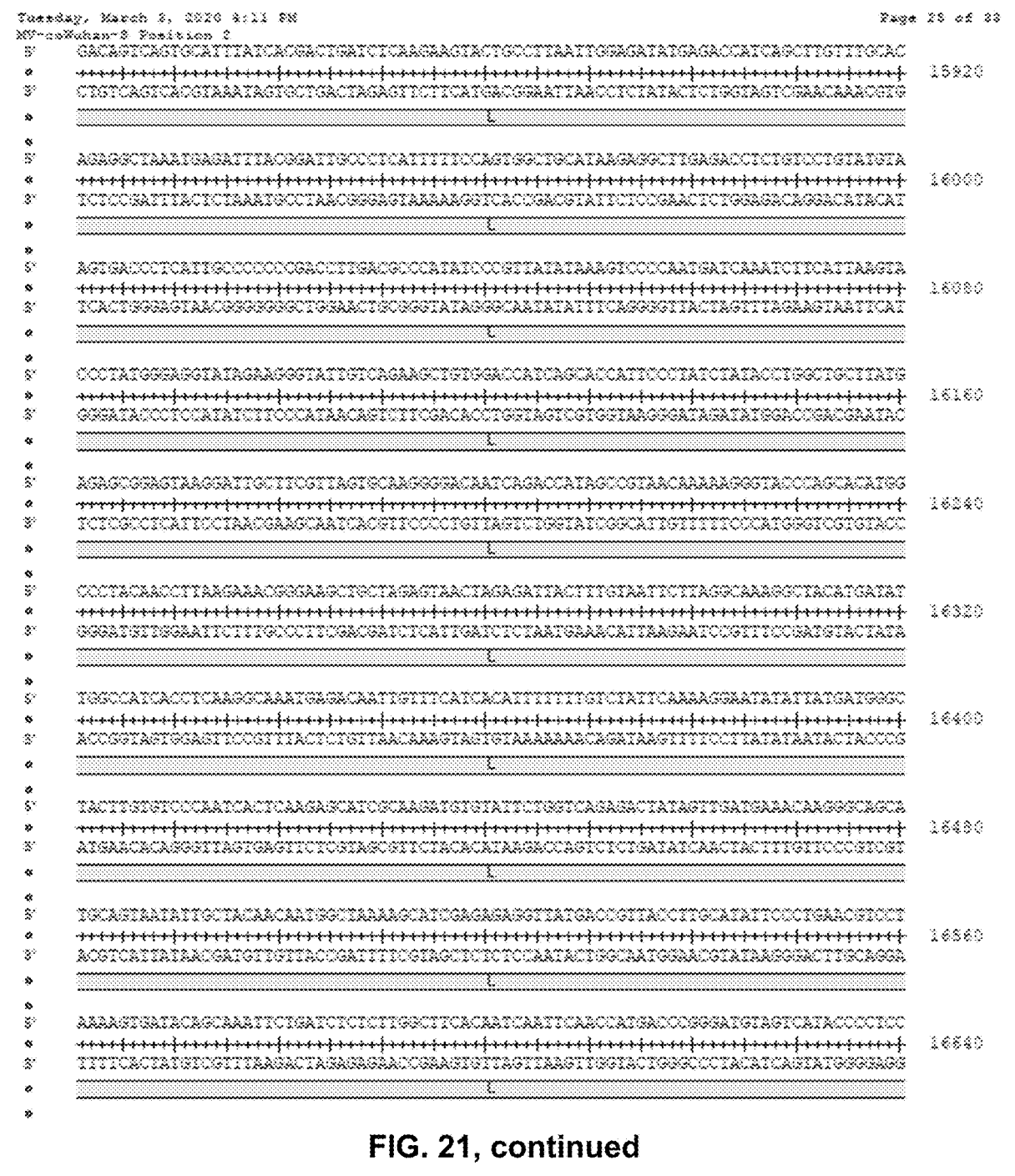
Figure 21:
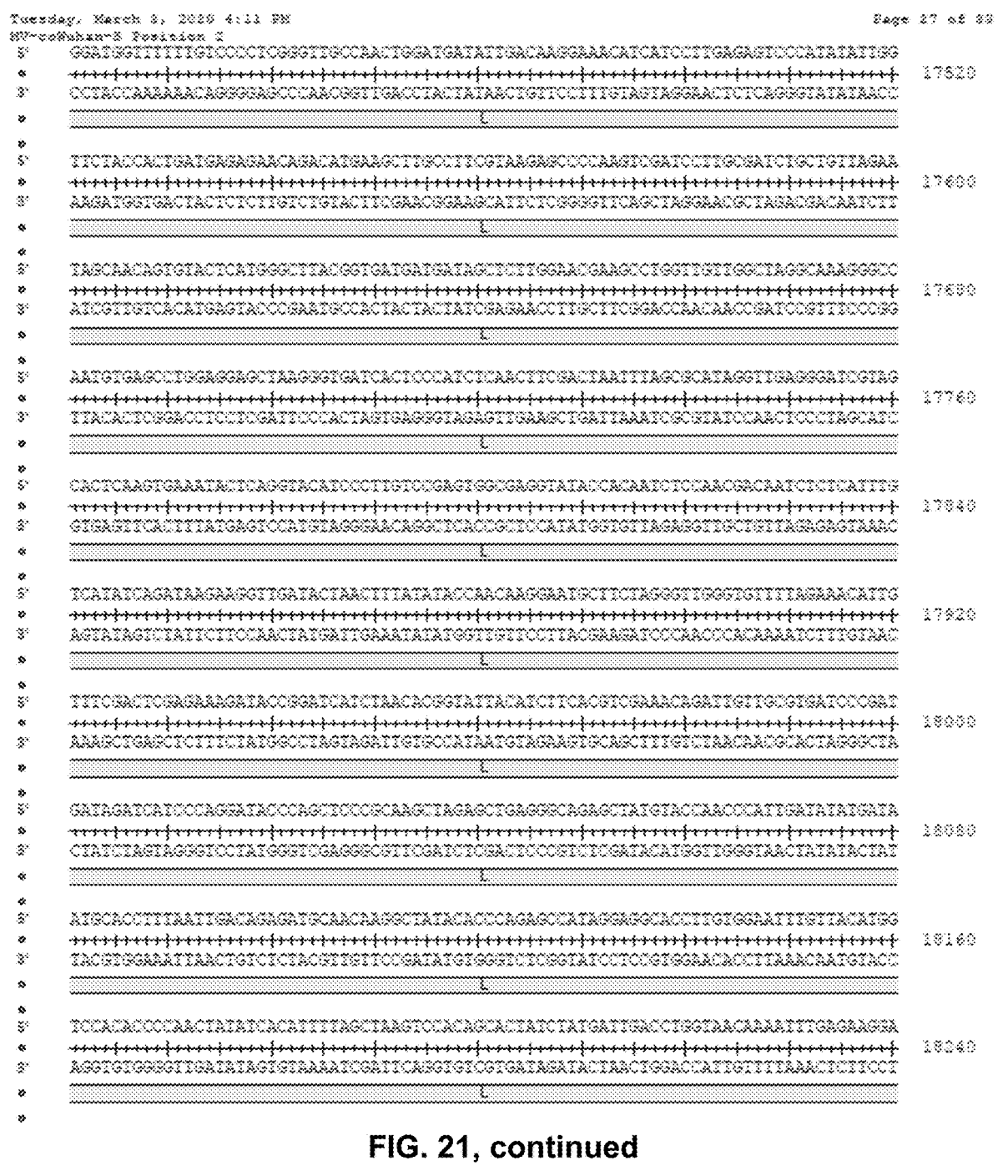
Figure 21:
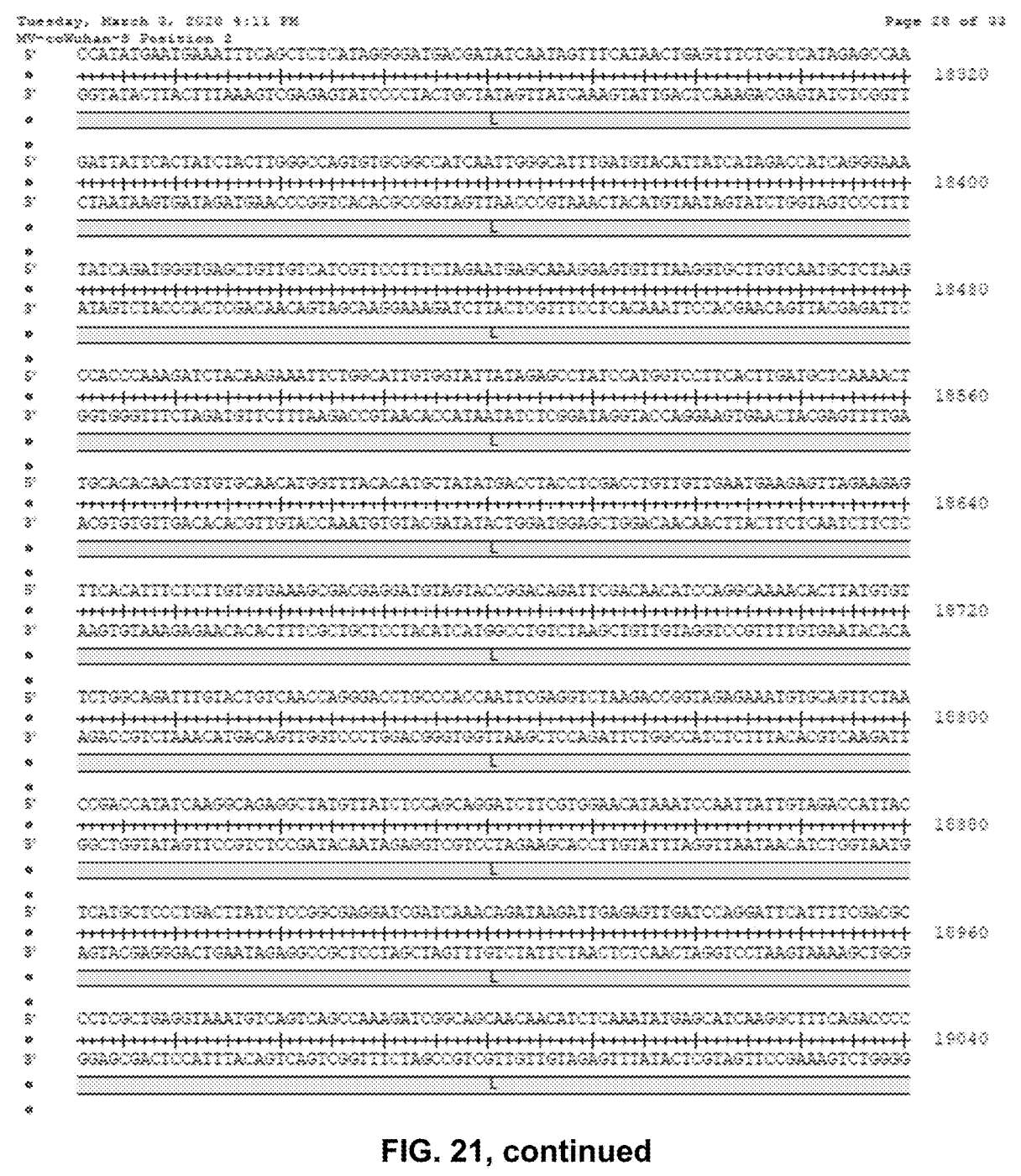
Figure 21:
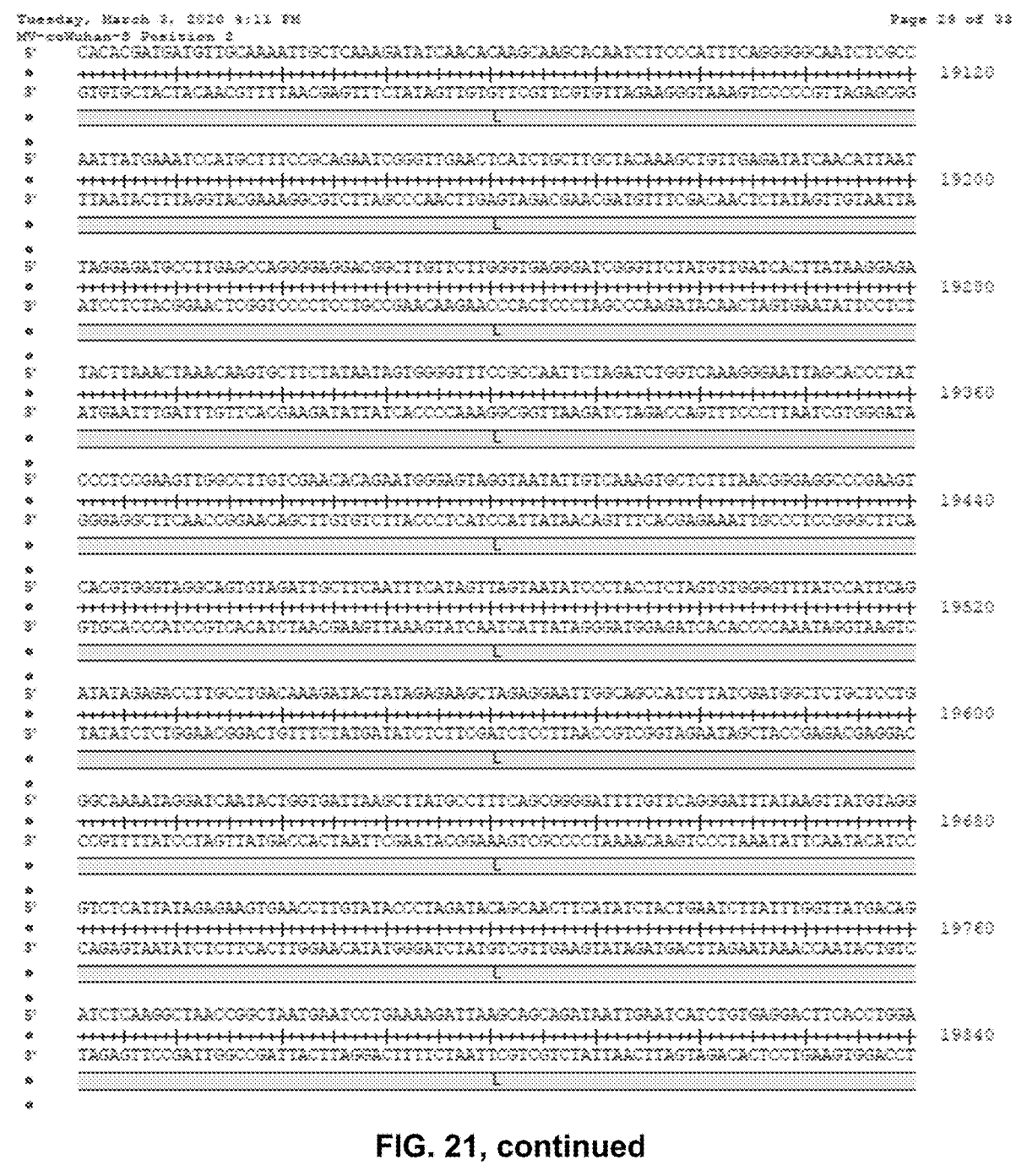
Figure 21:
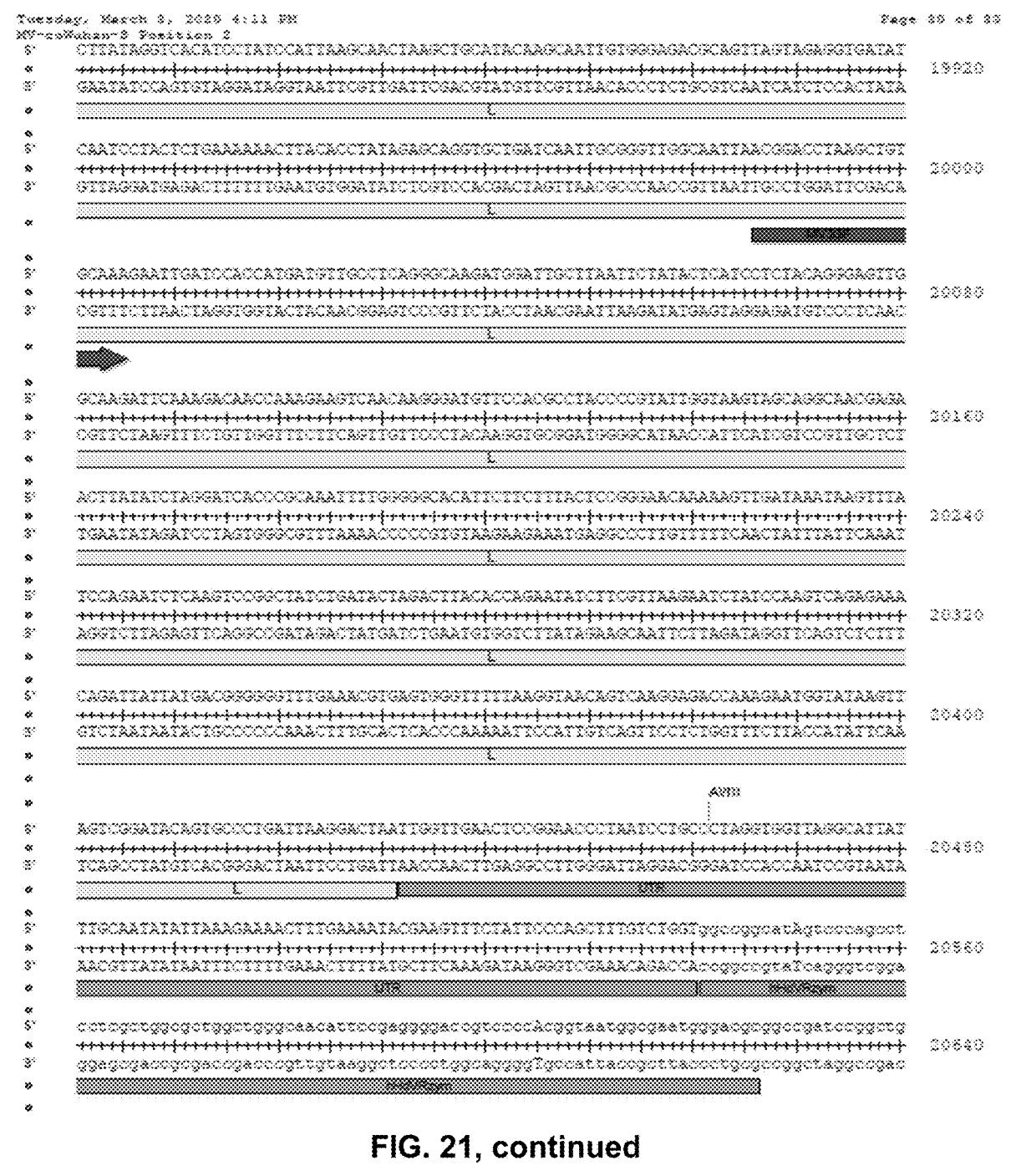
Figure 21:
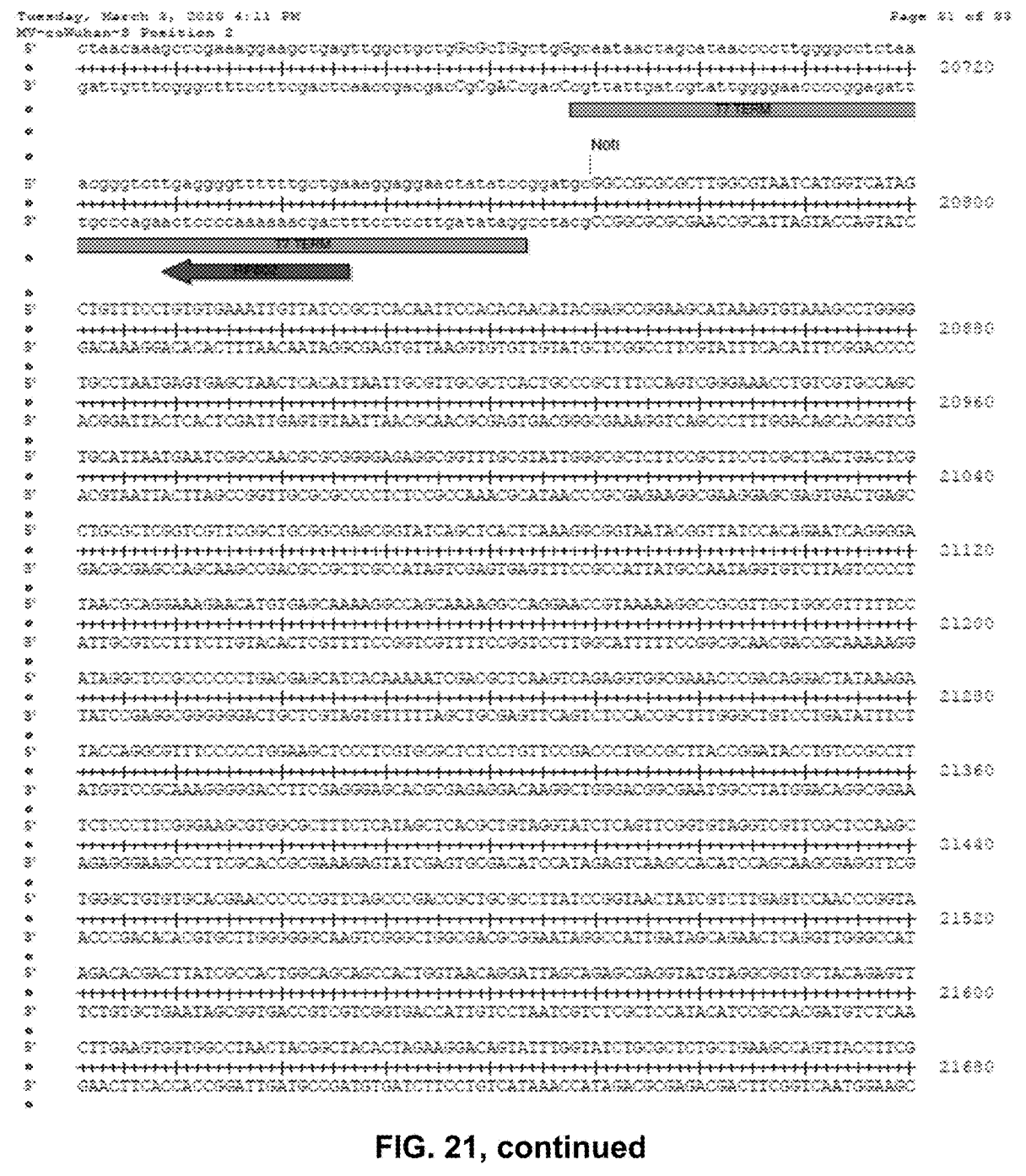
Figure 21:
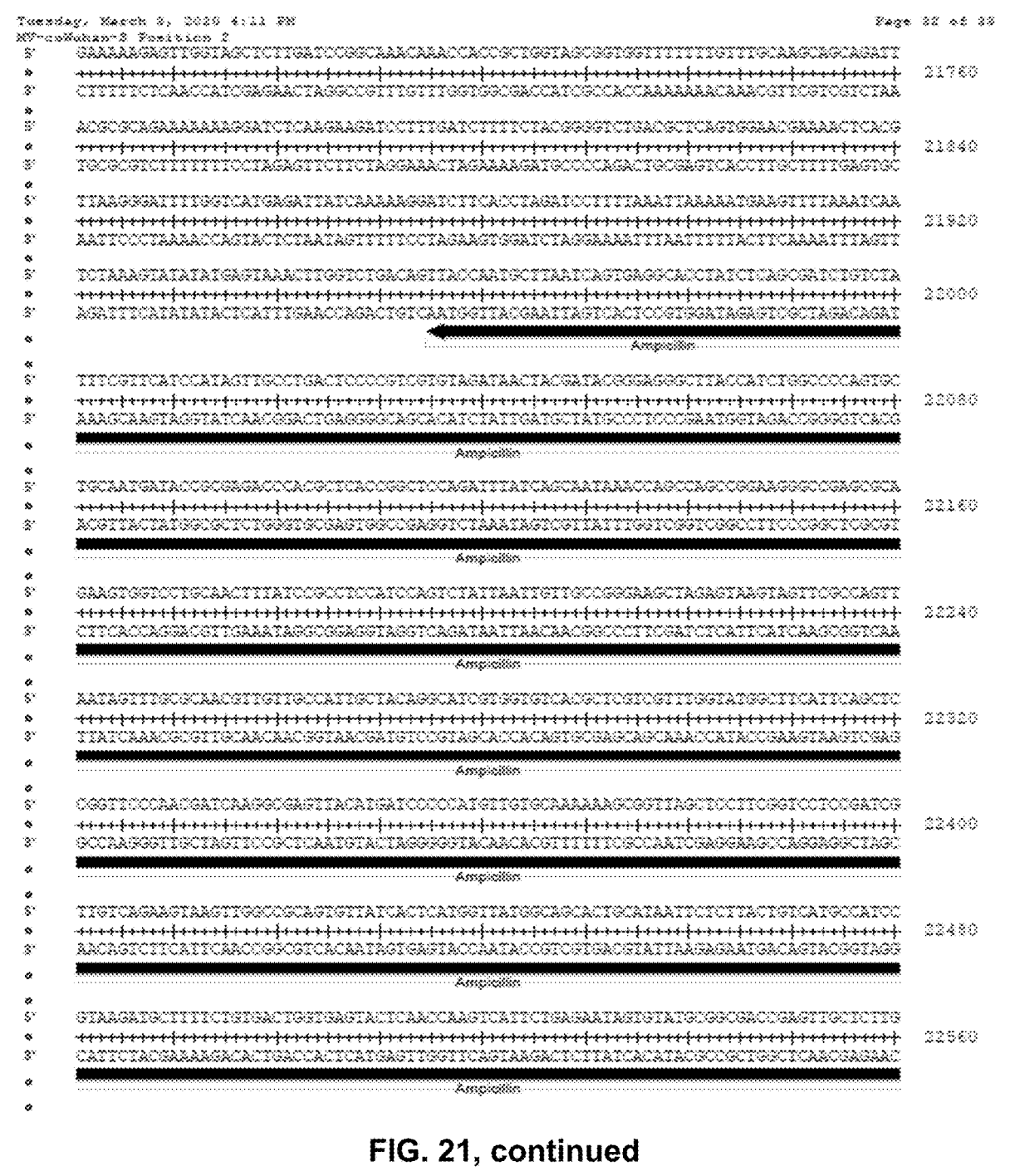

FIG. 21 shows the sequence (SEQ ID NO: 3) and features of "MV-coWuhan-S Position 2".

DETAILED DESCRIPTION

Definitions

Figure 1:
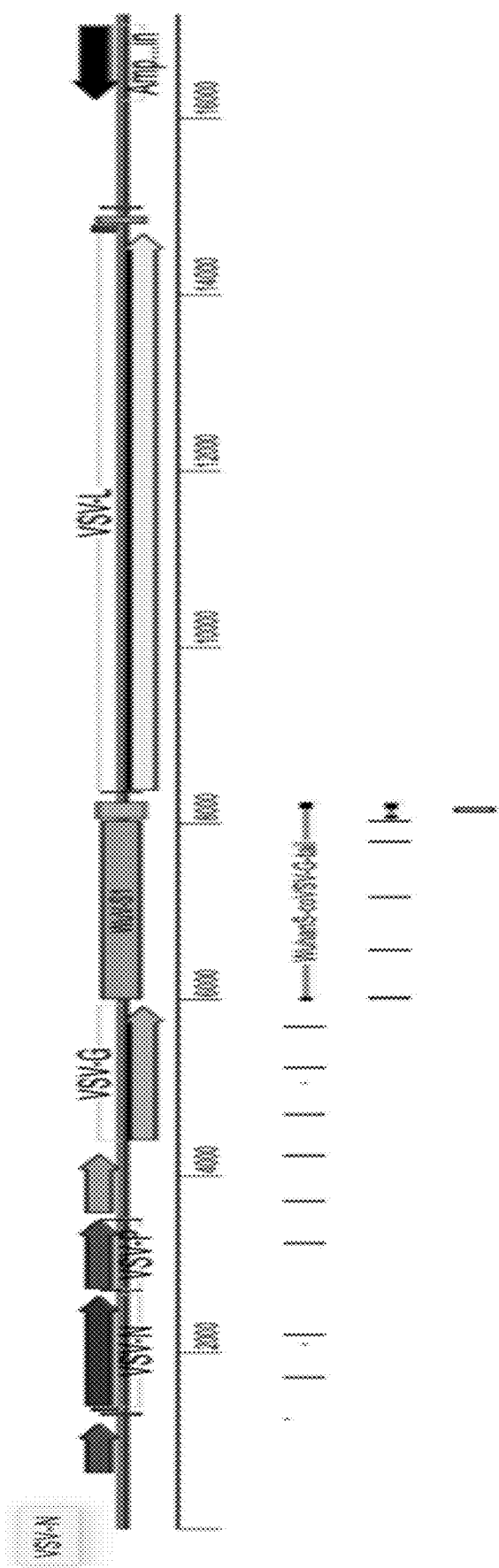
FIG. 1: VSV expressing codon-optimized Covid-S1. The map shows the viral sequence including the plasmids utilized to create the recombinant virus. The sequence is shown in SEQ ID NO: 1 and features are shown in FIG. 7. The sequence and features are also shown in FIG. 17 ("VSV-COVID19-S1-VSVG").
Figure 2:
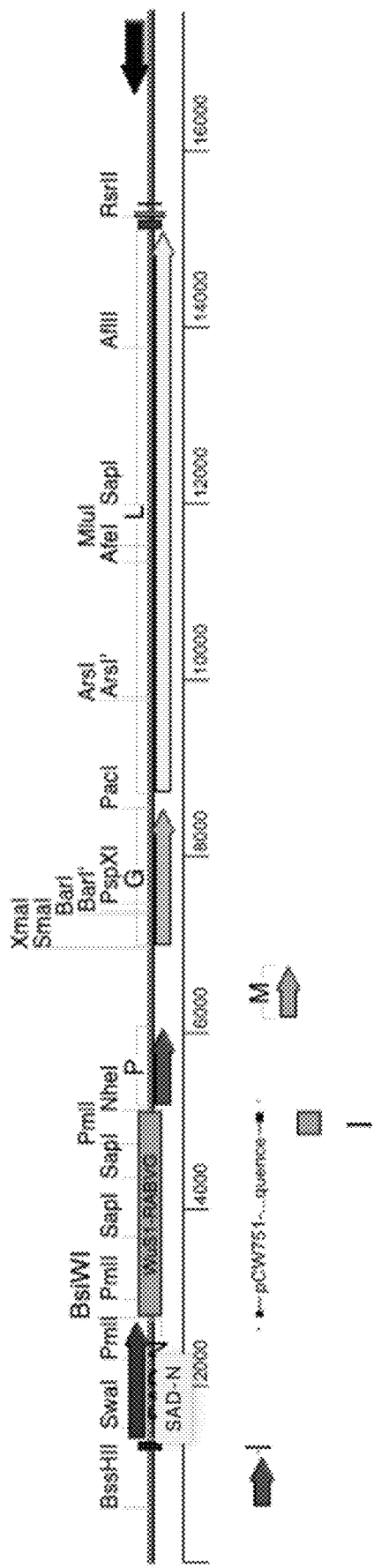
FIG. 2: RABV expressing codon-optimized Covid-S1. The map shows the viral sequence, including the plasmids utilized to create the recombinant virus. The sequence is shown in SEQ ID NO: 2 and features are shown in FIG. 8. The sequence and features are also shown in FIG. 18 ("BNSP333-COVID19-S1-RVG").
Figure 3:
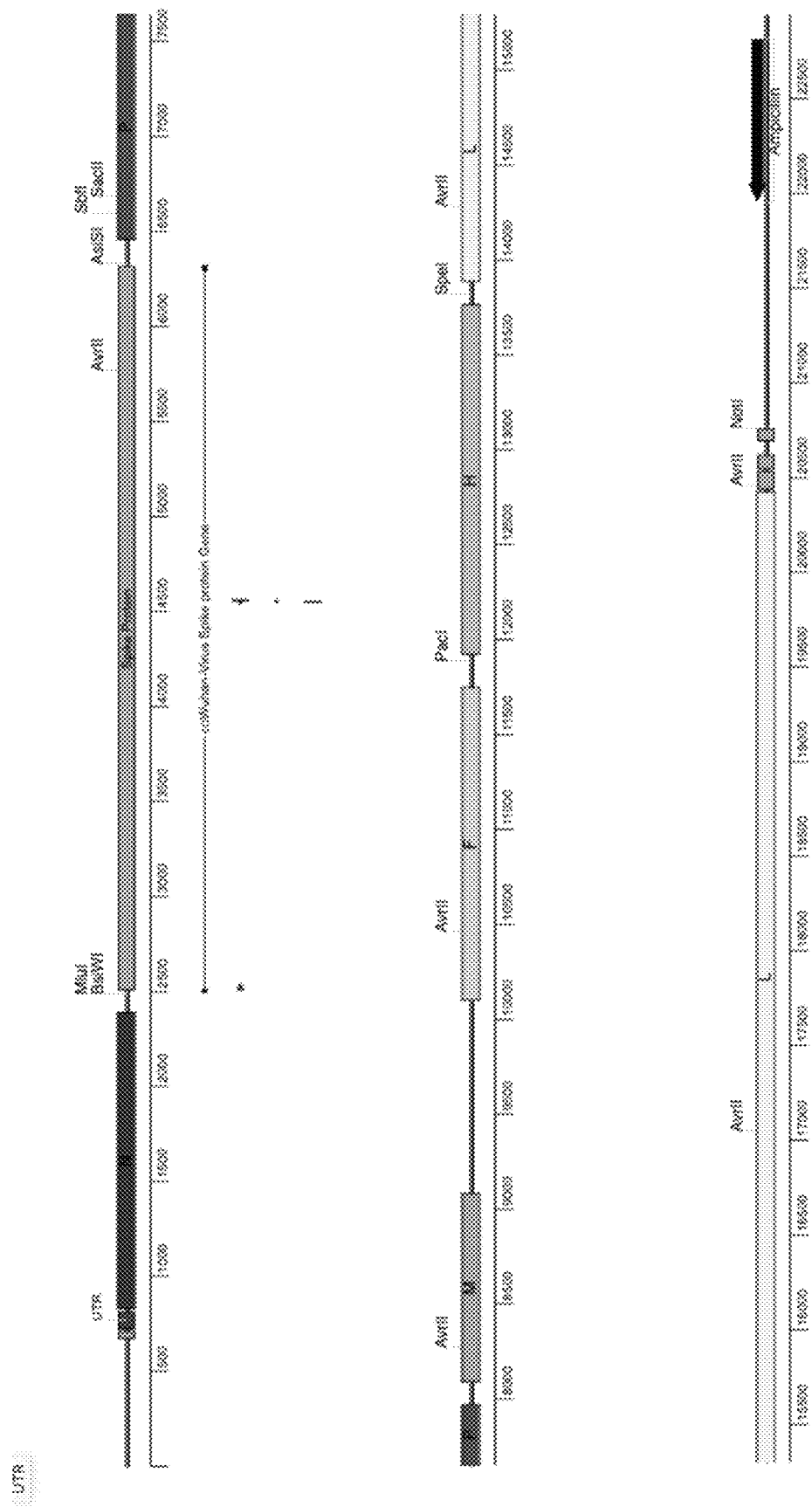
FIG. 3: MV expressing codon-optimized Covid-S from position 2 of the genome. The map shows the viral sequence, including the plasmids utilized to create the recombinant virus. The sequences is shown in SEQ ID NO: 3 and features are shown in FIG. 9. The sequence and features are also shown in FIG. 21 ("MV-coWuhan-S Position 2").
Figure 4:
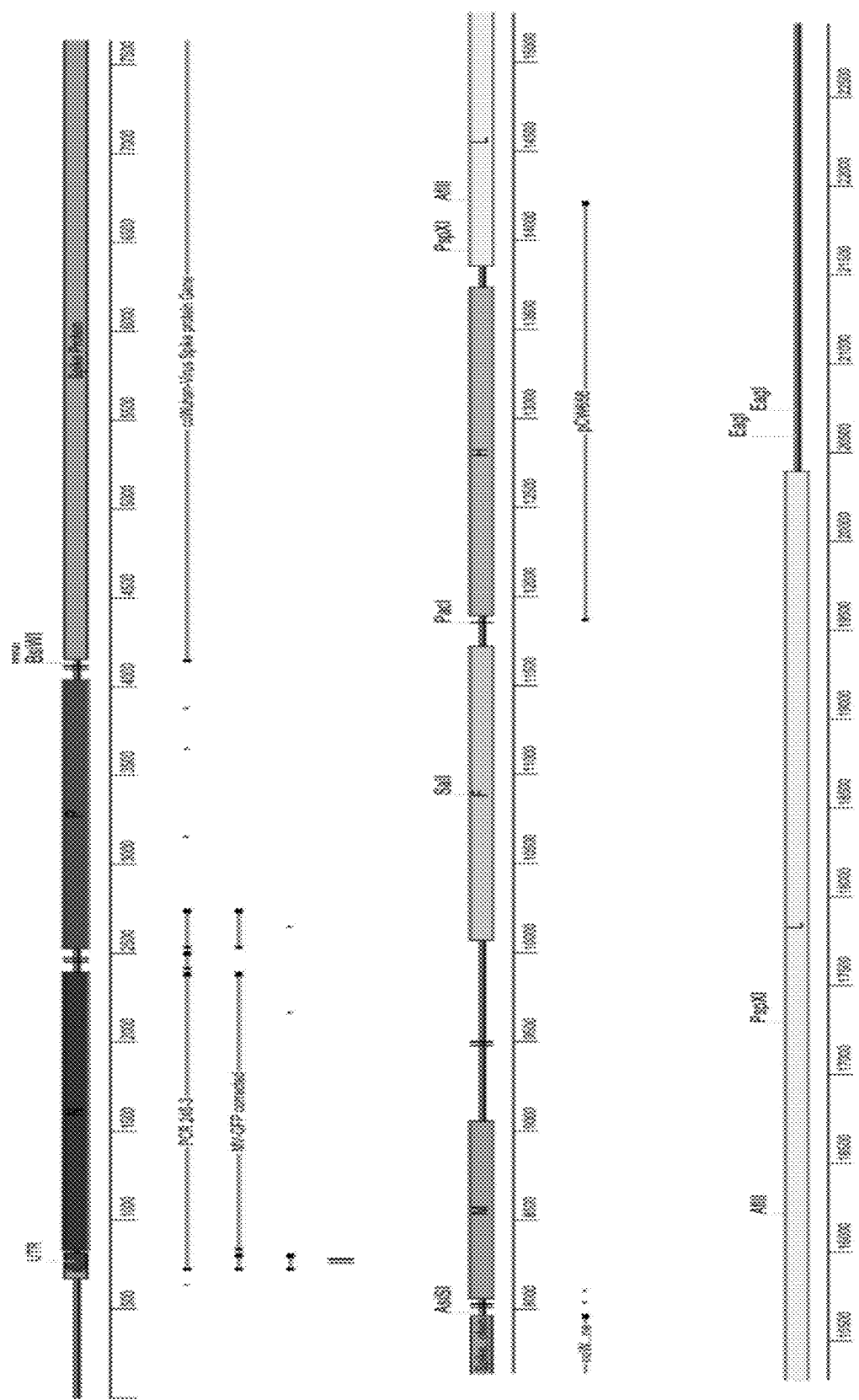
FIG. 4: MV expressing codon-optimized Covid-S from position 3 of the genome. The map shows the viral sequence, including the plasmids utilized to create the recombinant virus. The sequence is shown in SEQ ID NO: 4 and features are shown in FIG. 10. The sequence and features are also depicted in FIG. 20 ("MV Wu S in position 3").
Figure 5:
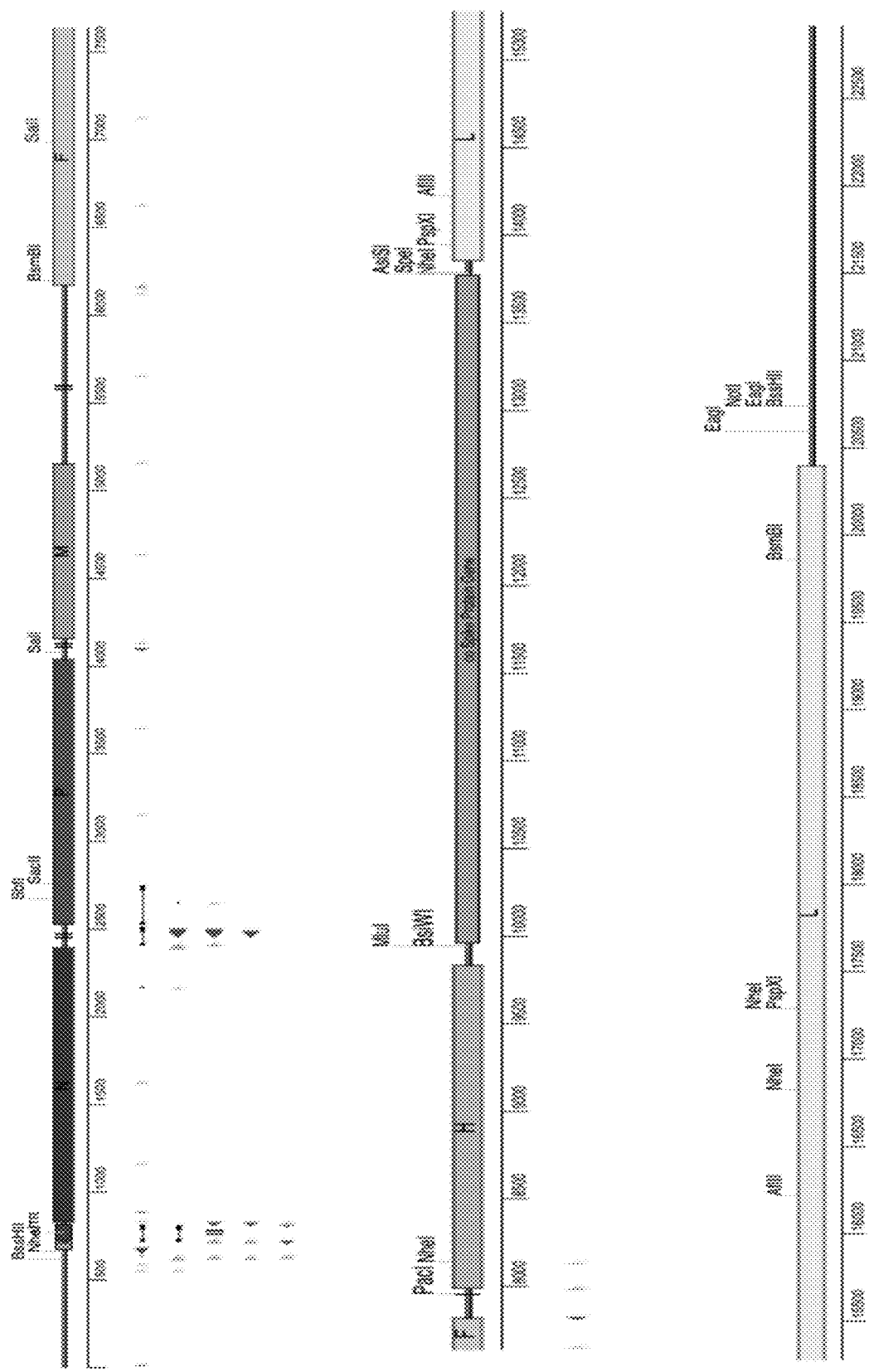
FIG. 5: MV expressing codon-optimized Covid-S from position 6 of the genome. The map shows the viral sequence, including the plasmids utilized to create the recombinant virus. The sequence is shown in SEQ ID NO: 5 and features are shown in FIG. 11. The sequence and features are also depicted in FIG. 19 ("MV WuhanCoV S in position 6").

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

The term "antibody" or "Ab" as used herein, refers to a protein, or polypeptide sequence derived from an immunoglobulin molecule, which specifically binds to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv) and humanized antibodies (Harlow et al., 1998, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426). An antibody may be derived from natural sources or from recombinant sources. Antibodies are typically tetramers of immunoglobulin molecules.

The term "ameliorating" or "treating" means that the clinical signs and/or the symptoms associated with a disease are lessened as a result of the actions performed. The signs or symptoms to be monitored will be well known to the skilled clinician.

As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

The term "biological" or "biological sample" refers to a sample obtained from an organism or from components (e.g., cells) of an organism. The sample may be of any biological tissue or fluid. Frequently the sample will be a "clinical sample" which is a sample derived from a patient. Such samples include, but are not limited to, bone marrow, cardiac tissue, sputum, blood, lymphatic fluid, blood cells (e.g., white cells), tissue or fine needle biopsy samples, urine, peritoneal fluid, and pleural fluid, or cells therefrom.

Biological samples may also include sections of tissues such as frozen sections taken for histological purposes.

As used herein, the terms "control," or "reference" are used interchangeably and refer to a value that is used as a standard of comparison.

The term "immunogenicity" as used herein, refers to the innate ability of an antigen or organism to elicit an immune response in an animal when the antigen or organism is administered to the animal. Thus, "enhancing the immunogenicity" refers to increasing the ability of an antigen or organism to elicit an immune response in an animal when the antigen or organism is administered to an animal. The increased ability of an antigen or organism to elicit an immune response can be measured by, among other things, a greater number of antibodies that bind to an antigen or organism, a greater diversity of antibodies to an antigen or organism, a greater number of T-cells specific for an antigen or organism, a greater cytotoxic or helper T-cell response to an antigen or organism, a greater expression of cytokines in response to an antigen, and the like.

As used herein, the terms "eliciting an immune response" or "immunizing" refer to the process of generating a B cell and/or a T cell response against a heterologous protein.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"Heterologous antigens" used herein to refer to an antigen that is not endogenous to the organism comprising or expressing an antigen. As an example, a virus vaccine vector comprising or expressing a viral or tumor antigen comprises a heterologous antigen. The term "Heterologous protein" as used herein refers to a protein that elicits a beneficial immune response in a subject (i.e. mammal), irrespective of its source.

The term "specifically binds", "selectively binds" or "binding specificity" refers to the ability of the humanized antibodies or binding compounds of the invention to bind to a target epitope with a greater affinity than that which results when bound to a non-target epitope. In certain embodiments, specific binding refers to binding to a target with an affinity that is at least 10, 50, 100, 250, 500, or 1000 times greater than the affinity for a non-target epitope.

As used herein, by "combination therapy" is meant that a first agent is administered in conjunction with another agent. "In combination with" or "In conjunction with" refers to administration of one treatment modality in addition to another treatment modality. As such, "in combination with" refers to administration of one treatment modality before, during, or after delivery of the other treatment modality to the individual. Such combinations are considered to be part of a single treatment regimen or regime.

"Humoral immunity" or "humoral immune response" both refer to B-cell mediated immunity and are mediated by highly specific antibodies, produced and secreted by B-lymphocytes (B-cells).

"Prevention" refers to the use of a pharmaceutical compositions for the vaccination against a disorder.

"Adjuvant" refers to a substance that is capable of potentiating the immunogenicity of an antigen. Adjuvants can be one substance or a mixture of substances and function by acting directly on the immune system or by providing a slow release of an antigen. Examples of adjuvants include, but are not limited to, emulsions (e.g., oil in water (o/w) emulsions), aluminium salts, polyanions, bacterial glycopeptides and slow release agents such as Freund's incomplete.

"Delivery vehicle" refers to a composition that helps to target the antigen to specific cells and to facilitate the effective recognition of an antigen by the immune system. The best-known delivery vehicles are liposomes, virosomes, microparticles including microspheres and nanospheres, polymers, bacterial ghosts, bacterial polysaccharides, attenuated bacteria, virus like particles, attenuated viruses and ISCOMS.

The term "expression" as used herein is defined as the transcription and/or translation of a particular nucleotide sequence driven by its promoter.

As used herein, the term "expression cassette" means a nucleic acid sequence capable of directing the transcription and/or translation of a heterologous coding sequence. In some embodiments, the expression cassette comprises a promoter sequence operably linked to a sequence encoding a heterologous protein. In some embodiments, the expression cassette further comprises at least one regulatory sequence operably linked to the sequence encoding the heterologous protein.

"Incorporated into" or "encapsulated in" refers to an antigenic peptide and/or nucleic acid molecule that is/are within a delivery vehicle, such as microparticles, bacterial ghosts, attenuated bacteria, virus like particles, attenuated viruses, ISCOMs, liposomes and preferably virosomes.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that may comprise a protein or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "fusion protein" as used herein refers to a protein wherein the protein comprises two or more proteins linked together by peptide bonds or other chemical bonds. The proteins can be linked together directly by a peptide or other chemical bond, or with one or more amino acids between the two or more proteins, referred to herein as a spacer.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "RNA" as used herein is defined as ribonucleic acid.

"Transform", "transforming", and "transformation" is used herein to refer to a process of introducing an isolated nucleic acid into the interior of an organism.

The term "treatment" as used within the context of the present invention is meant to include therapeutic treatment as well as prophylactic, or suppressive measures for the disease or disorder. As used herein, the term "treatment" and associated terms such as "treat" and "treating" means the reduction of the progression, severity and/or duration of a disease condition or at least one symptom thereof. The term 'treatment' therefore refers to any regimen that can benefit a subject. The treatment may be in respect of an existing condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease.

The term "equivalent," when used in reference to nucleotide sequences, is understood to refer to nucleotide sequences encoding functionally equivalent polypeptides. Equivalent nucleotide sequences will include sequences that differ by one or more nucleotide substitutions, additions- or deletions, such as allelic variants; and will, therefore, include sequences that differ from the nucleotide sequence of the nucleic acids described herein due to the degeneracy of the genetic code.

The term "isolated" as used herein with respect to nucleic acids, such as DNA or RNA, refers to molecules separated from other DNAs or RNAs, respectively that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments, which are not naturally occurring as fragments and would not be found in the natural state. The term "isolated" is also used herein to refer to polypeptides, which are isolated from other cellular proteins and is meant to encompass both purified and recombinant polypeptides. An "isolated cell" or "isolated population of cells" is a cell or population of cells that is not present in its natural environment.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

A "mutation" as used therein is a change in a DNA sequence resulting in an alteration from its natural state. The mutation can comprise a deletion and/or insertion and/or duplication and/or substitution of at least one deoxyribonucleic acid base such as a purine (adenine and/or thymine) and/or a pyrimidine (guanine and/or cytosine).

Mutations may or may not produce discernible changes in the observable characteristics (phenotype) of an organism.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids. As used herein, nucleic acids include but are not limited to, all nucleic acid sequences which are obtained by any means available in the art, including, without limitation, recombinant means, i.e., the cloning of nucleic acid sequences from a recombinant library or a viral genome, using ordinary cloning technology and PCR™, and the like, and by synthetic means.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. There are numerous expression control sequences, including promoters which are native, constitutive, inducible and/or tissue-specific, are known in the art that may be used in the compositions of the invention. "Operably linked" should be construed to include RNA expression and control sequences in addition to DNA expression and control sequences.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence, which is required for expression of a gene product operably linked to the promoter/ regulatory sequence. In some instances, this sequence may be the core promoter sequence and in other instances, this sequence may also include an enhancer sequence and other regulatory elements, which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

As used herein, the term "pharmaceutical composition" refers to a mixture of at least one compound useful within the invention with other chemical components, such as carriers, stabilizers, diluents, adjuvants, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, the term "effective amount" or "therapeutically effective amount" means that amount of a composition (e.g., vaccine composition) or active ingredient (e.g., virus like particles (VLPs), virions, viral vectors, antigen, nucleic acid molecule) necessary to achieve an intended result e.g., to produce an intended immunological, pharmacological, therapeutic and/or protective result (e.g., that amount of VLPs, virions, or viral vectors sufficient to induce a measurable immune response, to prevent a particular disease condition, to reduce the severity of and/or ameliorate the disease condition or at least one symptom and/or condition associated therewith).

A "subject" or "patient," as used therein, may be a human or non-human mammal. Non-human mammals include, for example, livestock and pets, such as ovine, bovine, porcine, canine, feline and murine mammals. Preferably, the subject is human. In some embodiments, the subject is a domestic pet or livestock. In some embodiments, the subject is a cat. In some embodiments, the subject is a dog. In some other embodiments, the subject is a ferret.

"Titers" are numerical measures of the concentration of a virus or viral vector compared to a reference sample, where the concentration is determined either by the activity of the virus, or by measuring the number of viruses in a unit volume of buffer. The titer of viral stocks are determined, e.g., by measuring the infectivity of a solution or solutions (typically serial dilutions) of the viruses, e.g., on HeLa cells using the soft agar method (see, Graham & Van Der eb (1973) Virology 52:456-467) or by monitoring resistance conferred to cells, e.g., G418 resistance encoded by the virus or vector, or by quantitating the viruses by UV spectrophotometry (see, Chardonnet & Dales (1970) Virology 40:462-477).

"Vaccination" refers to the process of inoculating a subject with an antigen to elicit an immune response in the subject, that helps to prevent or treat the disease or disorder the antigen is connected with. The term "immunization" is used interchangeably herein with vaccination.

A "vector" is a composition of matter which comprises a nucleic acid and which can be used to deliver the nucleic acid to the interior of a cell. Numerous vectors are known in the art including, but not limited to, linear polynucleotides, polynucleotides associated with ionic or amphiphilic compounds, plasmids, and viruses. In the present disclosure, the term "vector" includes an autonomously replicating virus.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to compositions and methods for generating vaccines against a SARS-CoV-2 virus. The SARS-CoV-2 virus is also referred to herein as 2019-nCoV or 2019 Novel Coronavirus.

Described herein is a vaccine against the SARS-CoV-2 virus that uses a rabies virus-based vector that has proven to be an efficient vector against emerging and re-emerging infectious diseases. It was previously demonstrated that inactivated rabies virus particles containing MERS-CoV spike S1 protein induce potent immune responses against MERS-CoV and RABV and provide protection in animal systems.

The 2019-nCoV vaccine described herein has the following advantages:

- The construct is based on a currently available rabies vaccine product, and therefore will facilitate entry of a vaccine into a clinical phase one study to be prepared within a short time period. Bharat Biotech Ltd (BBIL) produce currently 20 million doses of the RABV vaccine a year.
- The construct can be rapidly scaled, as needed, for additional clinical trials and commercial manufacture.
- The construct can be manufactured at low cost-of-goods. Rabies vaccines have been commercially produced for decades, costs are well known and are inexpensive. The present vaccine uses the same manufacturing process as the current human rabies vaccine. When vaccinating millions of people in resource-limited areas, a low-cost vaccine is a significant advantage
- The vaccine should be safe for all population groups. In some embodiments, the vaccine is based on the killed rabies vaccine backbone since the rabies vaccine has decades of safe use across diverse populations.
- Proof of concept has been demonstrated by protecting in animal models based on challenge studies with the related MERS-CoV in two mouse models and alpacas (camelid).
- Long-term protection is expected since the RABV vaccine often provides life-long protection.
- The vaccine can be produced by an experienced commercial-scale manufacturing partner, Bharat Biotech, who has successfully met WHO pre-qualification standards for other vaccines, and can move quickly into clinical trials and commercial production. Bharat Biotech meets the FDA, EMA, and WHO PQ standards for cGMP.
- Utilises a unique polysaccharide adjuvant, Advax-SM, that has already been extensively tested in human clinical trials, being shown to enhance both humoral and cellular immunity. Most notably, addition of Advax-SM to prototype cGMP whole cell and recombinant spike protein SARS vaccines, not only enhanced neutralising antibody responses and prevented lung viral replication but also completely prevented vaccine-enhanced eosinophilic lung pathology in response to SARS virus exposure.
- Both the RABV vector and the utilized adjuvant can be stabilized and stored at room temperature.

Constructs

In one aspect, the present invention includes an isolated nucleic acid encoding a recombinant virus comprising a SARS-CoV-2 spike protein (S) or a portion thereof. In some embodiments, the virus is a rhabdovirus. In some embodiments, the virus is a rabies virus, a vesicular stomatitis virus (VSV), or a measles virus. In a particular embodiment, the virus is a rabies virus. The nucleic acid can comprises sequences that are codon-optimized for expression in a cell (e.g., a mammalian cell, a human cell).

In one embodiment, the SARS-CoV-2 spike protein (S) or the portion thereof comprises the amino acid sequence as set forth in SEQ ID NO: 28:

```
MFVFLVLLPLVSSQCVNLTTRTQLPPAYTNSFTRGVYYPDKVFRSSVLHSTQDLFLPF

FSNVTWFHAIHVSGTNGTKRFDNPVLPFNDGVYFASTEKSNIIRGWIFGTTLDSKTQS

LLIVNNATNVVIKVCEFQFCNDPFLGVYYHKNNKSWMESEFRVYSSANNCTFEYVS

QPFLMDLEGKQGNFKNLREFVFKNIDGYFKIYSKHTPINLVRDLPQGFSALEPLVDLP

IGINITRFQTLLALHRSYLTPGDSSSGWTAGAAAYYVGYLQPRTFLLKYNENGTITDA

VDCALDPLSETKCTLKSFTVEKGIYQTSNFRVQPTESIVRFPNITNLCPFGEVFNATRF

ASVYAWNRKRISNCVADYSVLYNSASFSTFKCYGVSPTKLNDLCFTNVYADSFVIRG

DEVRQIAPGQTGKIADYNYKLPDDFTGCVIAWNSNNLDSKVGGNYNYLYRLFRKSN

LKPFERDISTEIYQAGSTPCNGVEGFNCYFPLQSYGFQPTNGVGYQPYRVVVLSFELL

HAPATVCGPKKSTNLVKNKCVNFNFNGLTGTGVLTESNKKFLPFQQFGRDIADTTD

AVRDPQTLEILDITPCSFGGVSVITPGTNTSNQVAVLYQDVNCTEVPVAIHADQLTPT

WRVYSTGSNVFQTRAGCLIGAEHVNNSYECDIPIGAGICASYQTQTNSPR.
```

In another embodiment, the SARS-CoV-2 spike protein (S) or the portion thereof comprises the amino acid sequence as set forth in SEQ ID NO: 29:

```
MFVFLVLLPLVSSQCVNLTTRTQLPPAYTNSFTRGVYYPDKVFRSSVLHSTQDLFLPF

FSNVTWFHAIHVSGTNGTKRFDNPVLPFNDGVYFASTEKSNIIRGWIFGTTLDSKTQS

LLIVNNATNVVIKVCEFQFCNDPFLGVYYHKNNKSWMESEFRVYSSANNCTFEYVS

QPFLMDLEGKQGNFKNLREFVFKNIDGYFKIYSKHTPINLVRDLPQGFSALEPLVDLP
```

-continued

IGINITRFQTLLALHRSYLTPGDSSSGWTAGAAAYYVGYLQPRTFLLKYNENGTITDA

VDCALDPLSETKCTLKSFTVEKGIYQTSNFRVQPTESIVRFPNITNLCPFGEVFNATRF

ASVYAWNRKRISNCVADYSVLYNSASFSTFKCYGVSPTKLNDLCFTNVYADSFVIRG

DEVRQIAPGQTGKIADYNYKLPDDFTGCVIAWNSNNLDSKVGGNYNYLYRLFRKSN

LKPFERDISTEIYQAGSTPCNGVEGFNCYFPLQSYGFQPTNGVGYQPYRVVVLSFELL

HAPATVCGPKKSTNLVKNKCVNFNFNGLTGTGVLTESNKKFLPFQQFGRDIADTTD

AVRDPQTLEILDITPCSFGGVSVITPGTNTSNQVAVLYQDVNCTEVPVAIHADQLTPT

WRVYSTGSNVFQTRAGCLIGAEHVNNSYECDIPIGAGICASYQTQTNSPRRARSVAS

QSIIAYTMSLGAENSVAYSNNSIAIPTNFTISVTTEILPVSMTKTSVDCTMYICGDSTEC

SNLLLQYGSFCTQLNRALTGIAVEQDKNTQEVFAQVKQIYKTPPIKDFGGFNFSQILP

DPSKPSKRSFIEDLLFNKVTLADAGFIKQYGDCLGDIAARDLICAQKFNGLTVLPPLL

TDEMIAQYTSALLAGTITSGWTFGAGAALQIPFAMQMAYRFNGIGVTQNVLYENQK

LIANQFNSAIGKIQDSLSSTASALGKLQDVVNQNAQALNTLVKQLSSNFGAISSVLND

ILSRLDKVEAEVQIDRLITGRLQSLQTYVTQQLIRAAEIRASANLAATKMSECVLGQS

KRVDFCGKGYHLMSFPQSAPHGVVFLHVTYVPAQEKNFTTAPAICHDGKAHF'PREG

VFVSNGTHWFVTQRNFYEPQIITTDNTFVSGNCDVVIGIVNNTVYDPLQPELDSFKEE

LDKYFKNHTSPDVDLGDISGINASVVNIQKEIDRLNEVAKNLNESLIDLQELGKYEQY

IKWPWYIWLGFIAGLIAIVMVTIMLCCMTSCCSCLKGCCSCGSCCKFDEDDSEPVLK

GVKLHYT.

In one embodiment, the SARS-CoV-2 spike protein (S) or the portion thereof comprises the amino acid sequence as set forth in SEQ ID NO: 30:

MFVFLVLLPLVSSQCVNLTTRTQLPPAYTNSFTRGVYYPDKVFRSSVLHSTQDLFLPF

FSNVTWFHAIHVSGTNGTKRFDNPVLPFNDGVYFASTEKSNIIRGWIFGTTLDSKTQS

LLIVNNATNVVIKVCEFQFCNDPFLGVYYHKNNKSWMESEFRVYSSANNCTFEYVS

QPFLMDLEGKQGNFKNLREFVFKNIDGYFKIYSKHTPINLVRDLPQGFSALEPLVDLP

IGINITRFQTLLALHRSYLTPGDSSSGWTAGAAAYYVGYLQPRTFLLKYNENGTITDA

VDCALDPLSETKCTLKSFTVEKGIYQTSNFRVQPTESIVRFPNITNLCPFGEVFNATRF

ASVYAWNRKRISNCVADYSVLYNSASFSTFKCYGVSPTKLNDLCFTNVYADSFVIRG

DEVRQIAPGQTGKIADYNYKLPDDFTGCVIAWNSNNLDSKVGGNYNYLYRLFRKSN

LKPFERDISTEIYQAGSTPCNGVEGFNCYFPLQSYGFQPTNGVGYQPYRVVVLSFELL

HAPATVCGPKKSTNLVKNKCVNFNFNGLTGTGVLTESNKKFLPFQQFGRDIADTTD

AVRDPQTLEILDITPCSFGGVSVITPGTNTSNQVAVLYQDVNCTEVPVAIHADQLTPT

WRVYSTGSNVFQTRAGCLIGAEHVNNSYECDIPIGAGICASYQTQTNSPRSVGDEAE

DFVEVHLPDVHNQVSGVDLGLPNWGKYVLLSAGALTALMLIIFLMTCCRRVNRSEP

TQHNLRGTGREVSVTPQSGKIISSWESHKSGGETRL.

In another embodiment, the SARS-CoV-2 spike protein (S) or the portion thereof comprises the amino acid sequence as set forth in SEQ ID NO: 31:

MFVFLVLLPLVSSQCVNLTTRTQLPPAYTNSFTRGVYYPDKVFRSSVLHSTQDLFLPF

FSNVTWFHAIHVSGTNGTKRFDNPVLPFNDGVYFASTEKSNIIRGWIFGTTLDSKTQS

LLIVNNATNVVIKVCEFQFCNDPFLGVYYHKNNKSWMESEFRVYSSANNCTFEYVS

QPFLMDLEGKQGNFKNLREFVFKNIDGYFKIYSKHTPINLVRDLPQGFSALEPLVDLP

IGINITRFQTLLALHRSYLTPGDSSSGWTAGAAAYYVGYLQPRTFLLKYNENGTITDA

VDCALDPLSETKCTLKSFTVEKGIYQTSNFRVQPTESIVRFPNITNLCPFGEVFNATRF

ASVYAWNRKRISNCVADYSVLYNSASFSTFKCYGVSPTKLNDLCFTNVYADSFVIRG

DEVRQIAPGQTGKIADYNYKLPDDFTGCVIAWNSNNLDSKVGGNYNYLYRLFRKSN

LKPFERDISTEIYQAGSTPCNGVEGFNCYFPLQSYGFQPTNGVGYQPYRVVVLSFELL

HAPATVCGPKKSTNLVKNKCVNFNFNGLTGTGVLTESNKKFLPFQQFGRDIADTTD

AVRDPQTLEILDITPCSFGGVSVITPGTNTSNQVAVLYQDVNCTEVPVAIHADQLTPT

WRVYSTGSNVFQTRAGCLIGAEHVNNSYECDIPIGAGICASYQTQTNSPR.

In another embodiment, an N protein (N) or the portion thereof is provided, comprising the amino acid sequence as set forth in SEQ ID NO: 32:

MATLLRSLALFKRNKDKPPITSGSGGAIRGIKHIIIVPIPGDSSITTRSRLLDRLVRLIGN

PDVSGPKLTGALIGILSLFVESPGQLIQRITDDPDVSIRLLEVVQSDQSQSGLTFASRGT

NMEDEADQYFSHDDPISSDQSRFGWFGNKEISDIEVQDPEGFNMILGTILAQIWVLLA

KAVTAPDTAADSELRRWIKYTQQRRVVGEFRLERKWLDVVRNRIAEDLSLRRFMV

ALILDIKRTPGNKPRIAEMICDIDTYIVEAGLASFILTIKFGIETMYPALGLHEFAGELST

LESLMNLYQQMGETAPYMVILENSIQNKFSAGSYPLLWSYAMGVGVELENSMGGL

NFGRSYFDPAYFRLGQEMVRRSAGKVSSTLASELGITAEDARLVSEIAMHTTEDKISR

AVGPRQAQVSFLHGDQSENELPRLGGKEDRRVKQSRGEARESYRETGPSRASDARAAH

LPTGTPLDIDTATESSQDPQDSRRSADALLRLQAMAGISEEQGSDTDTPIVYNDRNLLD.

In another embodiment, the SARS-CoV-2 spike protein (S) or the portion thereof is a variant spike polypeptide comprising one or more alterations (e.g., substitution(s), insertion(s), deletion(s), addition(s), modification(s)) in its amino acid sequence relative to the amino acid sequence set forth as SEQ ID NO: 28, 29, 30, or 31.

In other embodiments, the SARS-CoV-2 spike protein (S) or the portion thereof is a variant spike polypeptide comprising, relative to the amino acid sequence set forth as SEQ ID NO: 28, 29, 30, or 31, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more alterations.

In one embodiment, the SARS-CoV-2 spike protein (S) or the portion thereof is a variant spike polypeptide comprising at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but not 100%, sequence identity to the amino acid sequence set forth as SEQ ID NO: 28, 29, 30, or 31.

In another embodiment, the N protein (N) or the portion thereof is a variant N polypeptide comprising one or more alterations (e.g., substitution(s), insertion(s), deletion(s), addition(s), modification(s)) in its amino acid sequence relative to the amino acid sequence set forth as SEQ ID NO: 32.

In other embodiments, the N protein (N) or the portion thereof is a variant N polypeptide comprising, relative to the amino acid sequence set forth as SEQ ID NO: 32, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more alterations.

In one embodiment, the N protein (N) or the portion thereof is a variant N polypeptide comprising at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but not 100%, sequence identity to the amino acid sequence set forth as SEQ ID NO: 32.

In some embodiments, the recombinant virus expresses a full-length SARS-CoV-2 spike protein (S). In some other embodiments, the recombinant virus expresses a portion of the SARS-CoV-2 spike protein (S). In one embodiment, the portion of the SARS-CoV-2 spike protein (S) is a receptor binding site of the SARS-CoV-2 spike protein (S). In another embodiment, the portion of the SARS-CoV-2 spike protein (S) is the S1 domain. In another embodiment, the portion of the SARS-CoV-2 spike protein (S) is the N-terminal 750 amino acids of the SARS-CoV-2 spike protein (S).

In some embodiments, the SARS-CoV-2 spike protein (S) or portion thereof is fused to a glycoprotein (G) or a portion thereof. In some embodiments, the glycoprotein (G) comprises a mutation substituting arginine with glutamic acid at position 333. In some embodiments, the portion of glycoprotein (G) comprises an ectodomain, a cytoplasmic domain, and a transmembrane domain. In other embodiments, the portion of the glycoprotein (G) comprises 1 to about 100 amino acids of the ectodomain or a trimerization domain. In some embodiments, the portion of the glycoprotein (G) comprises 31 amino acids of the ectodomain. In some embodiments, the glycoprotein (G) comprises 31 amino acids of the ectodomain and the full-length cytoplasmic domain.

In some embodiments, the sequence encoding the SARS-CoV-2 spike protein (S) or portion thereof is codon-optimized for expression in a cell. In some embodiments, the sequence encoding the the SARS-CoV-2 spike protein (S) or portion thereof fused to a glycoprotein (G) or portion thereof is codon-optimized for expression in a cell.

In some embodiments, the nucleic acid comprises a sequence encoding at least a portion of the genome of the virus. In some embodiments, the isolated nucleic acid comprises the full-length genome.

In one embodiment, the nucleic acid comprises (a) a sequence encoding at least a portion of the genome of a vesicular stomatitis virus (VSV), and (b) a sequence encoding a protein comprising a SARS-CoV-2 spike protein (S) or a portion thereof. In some embodiments, the protein comprising a SARS-CoV-2 spike protein (S) or a portion thereof is a fusion protein comprising a glycoprotein (G) or a portion thereof and a SARS-CoV-2 spike protein (S) or a portion thereof. In some embodiments, the fusion protein comprises a glycoprotein (G) or portion thereof fused to the S1 domain of a SARS-CoV-2 spike protein (S).

In another embodiment, the nucleic acid comprises the sequence of SEQ ID NO: 1, shown below:

```
CTGACGCGCCCTGTAGCGGCGCATTAAGCGCGGCGGGTGTGGTGGTTACGCGCA

GCGTGACCGCTACACTTGCCAGCGCCCTAGCGCCCGCTCCTTTCGCTTTCTTCCCT

TCCTTTCTCGCCACGTTCGCCGGCTTTCCCCGTCAAGCTCTAAATCGGGGCTCC

CTTTAGGGTTCCGATTTAGTGCTTTACGGCACCTCGACCCCAAAAAACTTGATTA

GGGTGATGGTTCACGTAGTGGGCCATCGCCCTGATAGACGGTTTTTCGCCCTTTG

ACGTTGGAGTCCACGTTCTTTAATAGTGGACTCTTGTTCCAAACTGGAACAACAC

TCAACCCTATCTCGGTCTATTCTTTTGATTTATAAGGGATTTTGCCGATTTCGGCC

TATTGGTTAAAAAATGAGCTGATTTAACAAAAATTTAACGCGAATTTTAACAAA

ATATTAACGCTTACAATTTCCATTCGCCATTCAGGCTGCGCAACTGTTGGGAAGG

GCGATCGGTGCGGGCCTCTTCGCTATTACGCCAGCTGGCGAAAGGGGATGTGC

TGCAAGGCGATTAAGTTGGGTAACGCCAGGGTTTTCCCAGTCACGACGTTGTAA

AACGACGGCCAGTGAGcgcgccCTAGTTATTAATAGTAATCAATTACGGGGTCATT

AGTTCATAGCCCATATATGGAGTTCCGCGTTACATAACTTACGGTAAATGGCCCG

CCTGGCTGACCGCCCAACGACCCCCGCCCATTGACGTCAATAATGACGTATGTTC

CCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCT

ATTGACGTCAATGACGGTAAATGGCCCGCCTGGCATTATGCCCAGTACATGACCT

TATGGGACTTTCCTACTTGGCAGTACATCTACGTATTAGTCATCGCTATTACCATG

GTGATGCGGTTTTGGCAGTACATCAATGGGCGTGGATAGCGGTTTGACTCACGG

GGATTTCCAAGTCTCCACCCCATTGACGTCAATGGGAGTTTGTTTTGGCACCAAA

ATCAACGGGACTTTCCAAAATGTCGTAACAACTCCGCCCCATTGACGCAAATGG

GCGGTAGGCGTGTACGGTGGGAGGTCTATATAAGCAGAGCTCTCTGGCTAACTA

GAGAACCCACTGCTTACTGGCTTATCGAAATTAATACGACTCACTATAGGGAGA

CCCAAGCTGGCTAGGGTCTTCGTCTGATGAGTCCGTGAGGACGAAACCCGGCGT

ACCGGGTCACGAAGACAAACAAACCATTATTATCATTAAAAGGCTCAGGAGAAA

CTTTAACAGTAATCAAAATGTCTGTTACAGTCAAGAGAATCATTGACAACACAGT

CATAGTTCCAAAACTTCCTGCAAATGAGGATCCAGTGGAATACCCGGCAGATTA

CTTCAGAAAATCAAAGGAGATTCCTCTTTACATCAATACTACAAAAAGTTTGTCA

GATCTAAGAGGATATGTCTACCAAGGCCTCAAATCCGGAAATGTATCAATCATA
```

-continued

```
CATGTCAACAGCTACTTGTATGGAGCATTAAAGGACATCCGGGGTAAGTTGGAT
AAAGATTGGTCAAGTTTCGGAATAAACATCGGGAAAGCAGGGGATACAATCGGA
ATATTTGACCTTGTATCCTTGAAAGCCCTGGACGGCGTACTTCCAGATGGAGTAT
CGGATGCTTCCAGAACCAGCGCAGATGACAAATGGTTGCCTTTGTATCTACTTGG
CTTATACAGAGTGGGCAGAACACAAATGCCTGAATACAGAAAAAAGCTCATGGA
TGGGCTGACAAATCAATGCAAAATGATCAATGAACAGTTTGAACCTCTTGTGCC
AGAAGGTCGTGACATTTTTGATGTGTGGGGAAATGACAGTAATTACACAAAAAT
TGTCGCTGCAGTGGACATGTTCTTCCACATGTTCAAAAAACATGAATGTGCCTCG
TTCAGATACGGAACTATTGTTTCCAGATTCAAAGATTGTGCTGCATTGGCAACAT
TTGGACACCTCTGCAAAATAACCGGAATGTCTACAGAAGATGTAACGACCTGGA
TCTTGAACCGAGAAGTTGCAGATGAAATGGTCCAAATGATGCTTCCAGGCCAAG
AAATTGACAAGGCCGATTCATACATGCCTTATTTGATCGACTTTGGATTGTCTTCT
AAGTCTCCATATTCTTCCGTCAAAAACCCTGCCTTCCACTTCTGGGGCAATTGA
CAGCTCTTCTGCTCAGATCCACCAGAGCAAGGAATGCCCGACAGCCTGATGACA
TTGAGTATACATCTCTTACTACAGCAGGTTTGTTGTACGCTTATGCAGTAGGATC
CTCTGCCGACTTGGCACAACAGTTTTGTGTTGGAGATAACAAATACACTCCAGAT
GATAGTACCGGAGGATTGACGACTAATGCACCGCCACAAGGCAGAGATGTGGTC
GAATGGCTCGGATGGTTTGAAGATCAAAACAGAAAACCGACTCCTGATATGATG
CAGTATGCGAAAAGAGCAGTCATGTCACTGCAAGGCCTAAGAGAGAAGACAATT
GGCAAGTATGCTAAGTCAGAATTTGACAAATGACCCTATAATTCTCAGATCACCT
ATTATATATTATGCTACATATGAAAAAAACTAACAGATATCATGGATAATCTCAC
AAAAGTTCGTGAGTATCTCAAGTCCTATTCTCGTCTGGATCAGGCGGTAGGAGAG
ATAGATGAGATCGAAGCACAACGAGCTGAAAAGTCCAATTATGAGTTGTTCCAA
GAGGATGGAGTGGAAGAGCATACTAAGCCCTCTTATTTTCAGGCAGCAGATGAT
TCTGACACAGAATCTGAACCAGAAATTGAAGACAATCAAGGTTTGTATGCACCA
GATCCAGAAGCTGAGCAAGTTGAAGGCTTTATACAGGGGCCTTTAGATGACTAT
GCAGATGAGGAAGTGGATGTTGTATTTACTTCGGACTGGAAACAGCCTGAGCTT
GAATCTGACGAGCATGGAAAGACCTTACGGTTGACATCGCCAGAGGGTTTAAGT
GGGAGAGCAGAAATCCCAGTGGCTTTCGACGATTAAAGCAGTCGTGCAAAGTGCC
AAATACTGGAATCTGGCAGAGTGCACATTTGAAGCATCGGGAGAAGGGGTCATT
ATGAAGGAGCGCCAGATAACTCCGGATGTATATAAGGTCACTCCAGTGATGAAC
ACACATCCGTCCCAATCAGAAGCAGTATCAGATGTTTGGTCTCTCTCAAAGACAT
CCATGACTTTCCAACCCAAGAAAGCAAGTCTTCAGCCTCTCACCATATCCTTGGA
TGAATTGTTCTCATCTAGAGGAGAGTTCATCTCTGTCGGAGGTGACGGACGAATG
TCTCATAAAGAGGCCATCCTGCTCGGCCTGAGATACAAAAAGTTGTACAATCAG
GCGAGAGTCAAATATTCTCTGTAGACTATGAAAAAAAGTAACAGATATCACGAT
CTAAGTGTTATCCCAATCCATTCATCATGAGTTCCTTAAAGAAGATTCTCGGTCT
GAAGGGGAAAGGTAAGAAATCTAAGAAATTAGGGATCGCACCACCCCCTTATGA
AGAGGACACTAGCATGGAGTATGCTCCGAGCGCTCCAATTGACAAATCCTATTTT
GGAGTTGACGAGATGGACACCTATGATCCGAATCAATTAAGATATGAGAAATTC
```

-continued

```
TTCTTTACAGTGAAAATGACGGTTAGATCTAATCGTCCGTTCAGAACATACTCAG
ATGTGGCAGCCGCTGTATCCCATTGGGATCACATGTACATCGGAATGGCAGGGA
AACGTCCCTTCTACAAAATCTTGGCTTTTTTGGGTTCTTCTAATCTAAAGGCCACT
CCAGCGGTATTGGCAGATCAAGGTCAACCAGAGTATCACACTCACTGCGAAGGC
AGGGCTTATTTGCCACATAGGATGGGAAGACCCCTCCCATGCTCAATGTACCA
GAGCACTTCAGAAGACCATTCAATATAGGTCTTTACAAGGGAACGATTGAGCTC
ACAATGACCATCTACGATGATGAGTCACTGGAAGCAGCTCCTATGATCTGGGAT
CATTTCAATTCTTCCAAATTTTCTGATTTCAGAGAGAAGGCCTTAATGTTTGGCCT
GATTGTCGAGAAAAAGGCATCTGGAGCGTGGGTCCTGGATTCTATCAGCCACTTC
AAATGAGCTAGTCTAACTTCTAGCTTCTGAACAATCCCCGGTTTACTCAGTCTCT
CCTAATTCCAGCCTCTCGAACAACTAATATCCTGTCTTTTCTATCCCTATGAAAAA
AACTAACAGAGATCGATCTGTTTACGCGTCACTATGAAGTGCCTTTTGTACTTAG
CCTTTTTATTCATTGGGGTGAATTGCAAGTTCACCATAGTTTTTCCACACAACCAA
AAAGGAAACTGGAAAAATGTTCCTTCTAATTACCATTATTGCCCGTCAAGCTCAG
ATTTAAATTGGCATAATGACTTAATAGGCACAGCCATACAAGTCAAAATGCCCA
AGAGTCACAAGGCTATTCAAGCAGACGGTTGGATGTGTCATGCTTCCAAATGGG
TCACTACTTGTGATTTCCGCTGGTATGGACCGAAGTATATAACACAGTCCATCCG
ATCCTTCACTCCATCTGTAGAACAATGCAAGGAAAGCATTGAACAAACGAAACA
AGGAACTTGGCTGAATCCAGGCTTCCCTCCTCAAAGTTGTGGATATGCAACTGTG
ACGGATGCCGAAGCAGTGATTGTCCAGGTGACTCCTCACCATGTGCTGGTTGATG
AATACACAGGAGAATGGGTTGATTCACAGTTCATCAACGGAAAATGCAGCAATT
ACATATGCCCCACTGTCCATAACTCTACAACCTGGCATTCTGACTATAAGGTCAA
AGGGCTATGTGATTCTAACCTCATTTCCATGGACATCACCTTCTTCTCAGAGGAC
GGAGAGCTATCATCCCTGGGAAAGGAGGGCACAGGGTTCAGAAGTAACTACTTT
GCTTATGAAACTGGAGGCAAGGCCTGCAAAATGCAATACTGCAAGCATTGGGGA
GTCAGACTCCCATCAGGTGTCTGGTTCGAGATGGCTGATAAGGATCTCTTTGCTG
CAGCCAGATTCCCTGAATGCCCAGAAGGGTCAAGTATCTCTGCTCCATCTCAGAC
CTCAGTGGATGTAAGTCTAATTCAGGACGTTGAGAGGATCTTGGATTATTCCCTC
TGCCAAGAAACCTGGAGCAAAATCAGAGCGGGTCTTCCAATCTCTCCAGTGGAT
CTCAGCTATCTTGCTCCTAAAAACCCAGGAACCGGTCCTGCTTTCACCATAATCA
ATGGTACCCTAAAATACTTTGAGACCAGATACATCAGAGTCGATATTGCTGCTCC
AATCCTCTCAAGAATGGTCGGAATGATCAGTGGAACTACCACAGAAAGGGAACT
GTGGGATGACTGGGCACCATATGAAGACGTGGAAATTGGACCCAATGGAGTTCT
GAGGACCAGTTCAGGATATAAGTTTCCTTTATACATGATTGGACATGGTATGTTG
GACTCCGATCTTCATCTTAGCTCAAAGGCTCAGGTGTTCGAACATCCTCACATTC
AAGACGCTGCTTCGCAACTTCCTGATGATGAGAGTTTATTTTTTGGTGATACTGG
GCTATCCAAAAATCCAATCGAGCTTGTAGAAGGTTGGTTCAGTAGTTGGAAAAG
CTCTATTGCCTCTTTTTTCTTTATCATAGGGTTAATCATTGGACTATTCTTGGTTCT
CCGAGTTGGTATCCATCTTTGCATTAAATTAAAGCACACCAAGAAAAGACAGAT
TTATACAGACATAGAGATGAACCGACTTGGAAAGTAACTCAAATCCTGCTAGGT
ATGAAAAAAACTAACaGATATCACGCTCGAGCGTACGCCACCATGTTCGTGTTTC
```

-continued

```
TGGTGCTGCTGCCTCTGGTGAGCTCCCAGTGCGTGAACCTGACCACAAGGACCC

AGCTGCCCCTGCCTATACCAATTCCTTCACACGGGGCGTGTACTATCCCGACAA

GGTGTTCCGGAGCAGCGTGCTGCACTCCACACAGGATCTGTTTCTGCCTTTCTTTT

CTAACGTGACCTGGTTCCACGCCATCCACGTGAGCGGCACCAATGGCACAAAGC

GGTTCGACAATCCAGTGCTGCCCTTTAACGATGGCGTGTACTTCGCCTCCACCGA

GAAGTCTAACATCATCAGAGGCTGGATCTTTGGCACCACACTGGACAGCAAGAC

ACAGTCCCTGCTGATCGTGAACAATGCCACCAACGTGGTCATCAAGGTGTGCGA

GTTCCAGTTTTGTAATGATCCATTCCTGGGCGTGTACTATCACAAGAACAATAAG

TCTTGGATGGAGAGCGAGTTTCGCGTGTATTCCTCTGCCAACAATTGCACATTTG

AGTACGTGTCCCAGCCCTTCCTGATGGACCTGGAGGGCAAGCAGGGCAATTTCA

AGAACCTGAGGGAGTTCGTGTTTAAGAATATCGATGGCTACTTCAAAATCTACTC

CAAGCACACCCCAATCAACCTGGTGCGCGACCTGCCACAGGGCTTCTCTGCCCTG

GAGCCACTGGTGGATCTGCCCATCGGCATCAACATCACCCGGTTTCAGACACTGC

TGGCCCTGCACAGAAGCTACCTGACACCAGGCGACAGCTCCTCTGGATGGACCG

CAGGAGCAGCAGCCTACTATGTGGGCTATCTGCAGCCCAGGACCTTCCTGCTGA

AGTACAACGAGAATGGCACCATCACAGACGCCGTGGATTGCGCCCTGGATCCCC

TGTCTGAGACCAAGTGTACACTGAAGAGCTTTACCGTGGAGAAGGGCATCTATC

AGACAAGCAATTTCAGGGTGCAGCCTACCGAGTCCATCGTGCGCTTTCCCAATAT

CACAAACCTGTGCCCTTTTGGCGAGGTGTTCAACGCAACCCGCTTCGCCAGCGTG

TACGCCTGGAATAGGAAGCGCATCTCCAACTGCGTGGCCGACTATTCTGTGCTGT

ACAACAGCGCCTCCTTCTCTACCTTTAAGTGCTATGGCGTGAGCCCCACAAAGCT

GAATGACCTGTGCTTTACCAACGTGTACGCCGATTCCTTCGTGATCAGGGGCGAC

GAGGTGCGCCAGATCGCACCAGGACAGACAGGCAAGATCGCAGACTACAATTAT

AAGCTGCCTGACGATTTCACCGGCTGCGTGATCGCCTGGAACTCTAACAATCTGG

ATAGCAAAGTGGGCGGCAACTACAATTATCTGTACCGGCTGTTTAGAAAGTCTA

ATCTGAAGCCATTCGAGAGGGACATCTCCACAGAAATCTACCAGGCCGGCTCTA

CCCCCTGCAATGGCGTGGAGGGCTTTAACTGTTATTTCCCTCTGCAGAGCTACGG

CTTCCAGCCAACAAACGGCGTGGGCTATCAGCCCTACCGCGTGGTGGTGCTGTCT

TTTGAGCTGCTGCACGCACCTGCAACAGTGTGCGGACCAAAGAAGAGCACCAAT

CTGGTGAAGAACAAGTGCGTGAACTTCAACTTCAACGGACTGACCGGAACAGGC

GTGCTGACCGAGTCCAACAAGAAGTTCCTGCCTTTTCAGCAGTTCGGCAGGGAC

ATCGCAGATACCACAGACGCCGTGCGCGACCCTCAGACCCTGGAGATCCTGGAC

ATCACACCATGCTCCTTCGGCGGCGTGTCTGTGATCACACCAGGCACCAATACAA

GCAACCAGGTGGCCGTGCTGTATCAGGACGTGAATTGTACCGAGGTGCCAGTGG

CAATCCACGCAGATCAGCTGACCCCTACATGGCGGGTGTACTCTACCGGCAGCA

ACGTGTTCCAGACAAGAGCCGGATGCCTGATCGGAGCAGAGCACGTGAACAATA

GCTATGAGTGCGACATCCCTATCGGCGCCGGCATCTGTGCCTCCTACCAGACCCA

GACAAACTCCCCAAGGTCTGTGGGCGATACAGGCCTGTCCAAGAATCCAATCGA

GCTGGTAGAGGGCTGGTTCAGCAGTTGGAAAAGCTCCATCGCCTCCTTTTTCTTT

ATCATCGGCCTGATCATCGGACTGTTCCTGGTGCTCCGCGTGGGTATCCACCTGT
```

-continued

```
GCATCAAGCTGAAGCACACCAAGAAAAGACAGATTTATACAGACATCGAGATGA
ACCGCCTGGGAAAGTGAGCTAGCCAGATTCTTCATGTTTGGACCAAATCAACTTG
TGATACCATGCTCAAAGAGGCCTCAATTATATTTGAGTTTTTAATTTTTATGAAA
AAAACTAACAGCAATCATGGAAGTCCACGATTTTGAGACCGACGAGTTCAATGA
TTTCAATGAAGATGACTATGCCACAAGAGAATTCCTGAATCCCGATGAGCGCAT
GACGTACTTGAATCATGCTGATTACAATTTGAATTCTCCTCTAATTAGTGATGAT
ATTGACAATTTGATCAGGAAATTCAATTCTCTTCCGATTCCCTCGATGTGGGATA
GTAAGAACTGGGATGGAGTTCTTGAGATGTTAACATCATGTCAAGCCAATCCCAT
CTCAACATCTCAGATGCATAAATGGATGGGAAGTTGGTTAATGTCTGATAATCAT
GATGCCAGTCAAGGGTATAGTTTTTTACATGAAGTGGACAAAGAGGCAGAAATA
ACATTTGACGTGGTGGAGACCTTCATCCGCGGCTGGGGCAACAAACCAATTGAA
TACATCAAAAAGGAAAGATGGACTGACTCATTCAAAATTCTCGCTTATTTGTGTC
AAAAGTTTTTGGACTTACACAAGTTGACATTAATCTTAAATGCTGTCTCTGAGGT
GGAATTGCTCAACTTGGCGAGGACTTTCAAAGGCAAAGTCAGAAGAAGTTCTCA
TGGAACGAACATATGCAGGATTAGGGTTCCCAGCTTGGGTCCTACTTTTATTTCA
GAAGGATGGGCTTACTTCAAGAAACTTGATATTCTAATGGACCGAAACTTTCTGT
TAATGGTCAAAGATGTGATTATAGGGAGGATGCAAACGGTGCTATCCATGGTAT
GTAGAATAGACAACCTGTTCTCAGAGCAAGACATCTTCTCCCTTCTAAATATCTA
CAGAATTGGAGATAAAATTGTGGAGAGGCAGGGAAATTTTTCTTATGACTTGATT
AAAATGGTGGAACCGATATGCAACTTGAAGCTGATGAAATTAGCAAGAGAATCA
AGGCCTTTAGTCCCACAATTCCCTCATTTTGAAAATCATATCAAGACTTCTGTTG
ATGAAGGGGCAAAAATTGACCGAGGTATAAGATTCCTCCATGATCAGATAATGA
GTGTGAAAACAGTGGATCTCACACTGGTGATTTATGGATCGTTCAGACATTGGGG
TCATCCTTTTATAGATTATTACACTGGACTAGAAAAATTACATTCCCAAGTAACC
ATGAAGAAAGATATTGATGTGTCATATGCAAAAGCACTTGCAAGTGATTTAGCT
CGGATTGTTCTATTTCAACAGTTCAATGATCATAAAAAGTGGTTCGTGAATGGAG
ACTTGCTCCCTCATGATCATCCCTTTAAAAGTCATGTTAAAGAAAATACATGGCC
CACAGCTGCTCAAGTTCAAGATTTTGGAGATAAATGGCATGAACTTCCGCTGATT
AAATGTTTTGAAATACCCGACTTACTAGACCCATCGATAATATACTCTGACAAAA
GTCATTCAATGAATAGGTCAGAGGTGTTGAAACATGTCCGAATGAATCCGAACA
CTCCTATCCCTAGTAAAAAGGTGTTGCAGACTATGTTGGACACAAAGGCTACCA
ATTGGAAAGAATTTCTTAAAGAGATTGATGAGAAGGGCTTAGATGATGATGATC
TAATTATTGGTCTTAAAGGAAAGGAGAGGGAACTGAAGTTGGCAGGTAGATTTT
TCTCCCTAATGTCTTGGAAATTGCGAGAATACTTTGTAATTACCGAATATTTGAT
AAAGACTCATTTCGTCCCTATGTTTAAAGGCCTGACAATGGCGGACGATCTAACT
GCAGTCATTAAAAAGATGTTAGATTCCTCATCCGGCCAAGGATTGAAGTCATATG
AGGCAATTTGCATAGCCAATCACATTGATTACGAAAAATGGAATAACCACCAAA
GGAAGTTATCAAACGGCCCAGTGTTCCGAGTTATGGGCCAGTTCTTAGGTTATCC
ATCCTTAATCGAGAGAACTCATGAATTTTTTGAGAAAAGTCTTATATACTACAAT
GGAAGACCAGACTTGATGCGTGTTCACAACAACACACTGATCAATTCAACCTCC
CAACGAGTTTGTTGGCAAGGACAAGAGGGTGGACTGGAAGGTCTACGGCAAAA
```

-continued

```
AGGATGGACTATCCTCAATCTACTGGTTATTCAAAGAGAGGCTAAAATCAGAAA

CACTGCTGTCAAAGTCTTGGCACAAGGTGATAATCAAGTTATTTGCACACAGTAT

AAAACGAAGAAATCGAGAAACGTTGTAGAATTACAGGGTGCTCTCAATCAAATG

GTTTCTAATAATGAGAAAATTATGACTGCAATCAAAATAGGGACAGGGAAGTTA

GGACTTTTGATAAATGACGATGAGACTATGCAATCTGCAGATTACTTGAATTATG

GAAAAATACCGATTTTCCGTGGAGTGATTAGAGGGTTAGAGACCAAGAGATGGT

CACGAGTGACTTGTGTCACCAATGACCAAATACCCACTTGTGCTAATATAATGAG

CTCAGTTTCCACAAATGCTCTCACCGTAGCTCATTTTGCTGAGAACCCAATCAAT

GCCATGATACAGTACAATTATTTTGGGACATTTGCTAGACTCTTGTTGATGATGC

ATGATCCTGCTCTTCGTCAATCATTGTATGAAGTTCAAGATAAGATACCGGGCTT

GCACAGTTCTACTTTCAAATACGCCATGTTGTATTTGGACCCTTCCATTGGAGGA

GTGTCGGGCATGTCTTTGTCCAGGTTTTTGATTAGAGCCTTCCCAGATCCCGTAA

CAGAAAGTCTCTCATTCTGGAGATTCATCCATGTACATGCTCGAAGTGAGCATCT

GAAGGAGATGAGTGCAGTATTTGGAAACCCCGAGATAGCCAAGTTTCGAATAAC

TCACATAGACAAGCTAGTAGAAGATCCAACCTCTCTGAACATCGCTATGGGAAT

GAGTCCAGCGAACTTGTTAAAGACTGAGGTTAAAAAATGCTTAATCGAATCAAG

ACAAACCATCAGGAACCAGGTGATTAAGGATGCAACCATATATTTGTATCATGA

AGAGGATCGGCTCAGAAGTTTCTTATGGTCAATAAATCCTCTGTTCCCTAGATTT

TTAAGTGAATTCAAATCAGGCACTTTTTTGGGAGTCGCAGACGGGCTCATCAGTC

TATTTCAAAATTCTCGTACTATTCGGAACTCCTTTAAGAAAAAGTATCATAGGGA

ATTGGATGATTTGATTGTGAGGAGTGAGGTATCCTCTTTGACACATTTAGGGAAA

CTTCATTTGAGAAGGGGATCATGTAAAATGTGGACATGTTCAGCTACTCATGCTG

ACACATTAAGATACAAATCCTGGGGCCGTACAGTTATTGGGACAACTGTACCCC

ATCCATTAGAAATGTTGGGTCCACAACATCGAAAAGAGACTCCTTGTGCACCAT

GTAACACATCAGGGTTCAATTATGTTTCTGTGCATTGTCCAGACGGGATCCATGA

CGTCTTTAGTTCACGGGGACCATTGCCTGCTTATCTAGGGTCTAAAACATCTGAA

TCTACATCTATTTTGCAGCCTTGGGAAAGGGAAAGCAAAGTCCCACTGATTAAA

AGAGCTACACGTCTTAGAGATGCTATCTCTTGGTTTGTTGAACCCGACTCTAAAC

TAGCAATGACTATACTTTCTAACATCCACTCTTTAACAGGCGAAGAATGGACCAA

AAGGCAGCATGGGTTCAAAAGAACAGGGTCTGCCCTTCATAGGTTTTCGACATCT

CGGATGAGCCATGGTGGGTTCGCATCTCAGAGCACTGCAGCATTGACCAGGTTG

ATGGCAACTACAGACACCATGAGGGATCTGGGAGATCAGAATTTCGACTTTTTAT

TCCAAGCAACGTTGCTCTATGCTCAAATTACCACCACTGTTGCAAGAGACGGATG

GATCACCAGTTGTACAGATCATTATCATATTGCCTGTAAGTCCTGTTTGAGACCC

ATAGAAGAGATCACCCTGGACTCAAGTATGGACTACACGCCCCCAGATGTATCC

CATGTGCTGAAGACATGGAGGAATGGGAAGGTTCGTGGGACAAGAGATAAA

ACAGATCTATCCTTTAGAAGGGAATTGGAAGAATTTAGCACCTGCTGAGCAATC

CTATCAAGTCGGCAGATGTATAGGTTTTCTATATGGAGACTTGGCGTATAGAAAA

TCTACTCATGCCGAGGACAGTTCTCTATTTCCTCTATCTATACAAGGTCGTATTAG

AGGTCGAGGTTTCTTAAAAGGGTTGCTAGACGGATTAATGAGAGCAAGTTGCTG
```

-continued

```
CCAAGTAATACACCGGAGAAGTCTGGCTCATTTGAAGAGGCCGGCCAACGCAGT

GTACGGAGGTTTGATTTACTTGATTGATAAATTGAGTGTATCACCTCCATTCCTTT

CTCTTACTAGATCAGGACCTATTAGAGACGAATTAGAAACGATTCCCCACAAGA

TCCCAACCTCCTATCCGACAAGCAACCGTGATATGGGGGTGATTGTCAGAAATTA

CTTCAAATACCAATGCCGTCTAATTGAAAAGGGAAAATACAGATCACATTATTC

ACAATTATGGTTATTCTCAGATGTCTTATCCATAGACTTCATTGGACCATTCTCTA

TTTCCACCACCCTCTTGCAAATCCTATACAAGCCATTTTTATCTGGGAAAGATAA

GAATGAGTTGAGAGAGCTGGCAAATCTTTCTTCATTGCTAAGATCAGGAGAGGG

GTGGGAAGACATACATGTGAAATTCTTCACCAAGGACATATTATTGTGTCCAGA

GGAAATCAGACATGCTTGCAAGTTCGGGATTGCTAAGGATAATAATAAAGACAT

GAGCTATCCCCCTTGGGGAAGGGAATCCAGAGGGACAATTACAACAATCCCTGT

TTATTATACGACCACCCCTTACCCAAAGATGCTAGAGATGCCTCCAAGAATCCAA

AATCCCCTGCTGTCCGGAATCAGGTTGGGCCAATTACCAACTGGCGCTCATTATA

AAATTCGGAGTATATTACATGGAATGGGAATCCATTACAGGGACTTCTTGAGTTG

TGGAGACGGCTCCGGAGGGATGACTGCTGCATTACTACGAGAAAATGTGCATAG

CAGAGGAATATTCAATAGTCTGTTAGAATTATCAGGGTCAGTCATGCGAGGCGC

CTCTCCTGAGCCCCCAGTGCCCTAGAAACTTTAGGAGGAGATAAATCGAGATG

TGTAAATGGTGAAACATGTTGGAATATCCATCTGACTTATGTGACCCAAGGACT

TGGGACTATTTCCTCCGACTCAAAGCAGGCTTGGGGCTTCAAATTGATTTAATTG

TAATGGATATGGAAGTTCGGGATTCTTCTACTAGCCTGAAAATTGAGACGAATGT

TAGAAATTATGTGCACCGGATTTTGGATGAGCAAGGAGTTTTAATCTACAAGACT

TATGAACATATATTTGTGAGAGCGAAAAGAATGCAGTAACAATCCTTGGTCCC

ATGTTCAAGACGGTCGACTTAGTTCAAACAGAATTTAGTAGTTCTCAAACGTCTG

AAGTATATATGGTATGTAAAGGTTTGAAGAAATTAATCGATGAACCCAATCCCG

ATTGGTCTTCCATCAATGAATCCTGGAAAAACCTGTACGCATTCCAGTCATCAGA

ACAGGAATTTGCCAGAGCAAAGAAGGTTAGTACATACTTTACCTTGACAGGTAT

TCCCTCCCAATTCATTCCTGATCCTTTTGTAAACATTGAGACTATGCTACAAATAT

TCGGAGTACCCACGGGTGTGTCTCATGCGGCTGCCTTAAAATCATCTGATAGACC

TGCAGATTTATTGACCATTAGCCTTTTTTATATGGCGATTATATCGTATTATAACA

TCAATCATATCAGAGTAGGACCGATACCTCCGAACCCCCCATCAGATGGAATTG

CACAAAATGTGGGGATCGCTATAACTGGTATAAGCTTTTGGCTGAGTTTGATGGA

GAAAGACATTCCACTATATCAACAGTGTTTAGCAGTTATCCAGCAATCATTCCCG

ATTAGGTGGGAGGCTGTTTCAGTAAAAGGAGGATACAAGCAGAAGTGGAGTACT

AGAGGTGATGGCTCCCAAAAGATACCCGAACTTCAGACTCCTTGGCCCCAATC

GGGAACTGGATCAGATCTCTGGAATTGGTCCGAAACCAAGTTCGTCTAAATCCAT

TCAATGAGATCTTGTTCAATCAGCTATGTCGTACAGTGGATAATCATTTGAAATG

GTCAAATTTGCGAAGAAACACAGGAATGATTGAATGGATCAATAGACGAATTTC

AAAAGAAGACCGGTCTATACTGATGTTGAAGAGTGACCTACACGAGGAAAACTC

TTGGAGAGATTAAAAAATCATGAGGAGACTCCAAACTTTAAGTATGAAAAAAAC

TTTGATCCTTAAGACCCTCTTGTGGTTTTATTTTTTATCTGGTTTTGTGGTCTTCG

TGGGTCGGCATGGCATCTCCACCTCCTCGCGGTCCGACCTGGGCATCCGAAGGA
```

```
GGACGCACGTCCACTCGGATGGCTAAGGGAGAGCCAGAAAATAACTAGTGGATC

CGGCTGCTAACAAAGCCCGAAAGGAAGCTGAGTTGGCTGCTGCCACCGCTGAGC

AATAACTAGCATAACCCCTTGGGGCCTCTAAACGGGTCTTGAGGGGTTTTTGCT

GAAAGtCGCGCTTGGCGTAATCATGGTCATAGCTGTTTCCTGTGTGAAATTGTTAT

CCGCTCACAATTCCACACAACATACGAGCCGGAAGCATAAAGTGTAAAGCCTGG

GGTGCCTAATGAGTGAGCTAACTCACATTAATTGCGTTGCGCTCACTGCCCGCTT

TCCAGTCGGGAAACCTGTCGTGCCAGCTGCATTAATGAATCGGCCAACGCGCGG

GGAGAGGCGGTTTGCGTATTGGGCGCTCTTCCGCTTCCTCGCTCACTGACTCGCT

GCGCTCGGTCGTTCGGCTGCGGCGAGCGGTATCAGCTCACTCAAAGGCGGTAAT

ACGGTTATCCACAGAATCAGGGGATAACGCAGGAAAGAACATGTGAGCAAAAG

GCCAGCAAAAGGCCAGGAACCGTAAAAAGGCCGCGTTGCTGGCGTTTTTCCATA

GGCTCCGCCCCCTGACGAGCATCACAAAAATCGACGCTCAAGTCAGAGGTGGC

GAAACCCGACAGGACTATAAAGATACCAGGCGTTTCCCCCTGGAAGCTCCCTCG

TGCGCTCTCCTGTTCCGACCCTGCCGCTTACCGGATACCTGTCCGCCTTTCTCCCT

TCGGGAAGCGTGGCGCTTTCTCATAGCTCACGCTGTAGGTATCTCAGTTCGGTGT

AGGTCGTTCGCTCCAAGCTGGGCTGTGTGCACGAACCCCCCGTTCAGCCCGACCG

CTGCGCCTTATCCGGTAACTATCGTCTTGAGTCCAACCCGGTAAGACACGACTTA

TCGCCACTGGCAGCAGCCACTGGTAACAGGATTAGCAGAGCGAGGTATGTAGGC

GGTGCTACAGAGTTCTTGAAGTGGTGGCCTAACTACGGCTACACTAGAAGGACA

GTATTTGGTATCTGCGCTCTGCTGAAGCCAGTTACCTTCGGAAAAAGAGTTGGTA

GCTCTTGATCCGGCAAACAAACCACCGCTGGTAGCGGTGGTTTTTTTGTTTGCAA

GCAGCAGATTACGCGCAGAAAAAAAGGATCTCAAGAAGATCCTTTGATCTTTTC

TACGGGGTCTGACGCTCAGTGGAACGAAAACTCACGTTAAGGGATTTTGGTCAT

GAGATTATCAAAAAGGATCTTCACCTAGATCCTTTTAAATTAAAAATGAAGTTTT

AAATCAATCTAAAGTATATATGAGTAAACTTGGTCTGACAGTTACCAATGCTTAA

TCAGTGAGGCACCTATCTCAGCGATCTGTCTATTTCGTTCATCCATAGTTGCCTGA

CTCCCCGTCGTGTAGATAACTACGATACGGGAGGGCTTACCATCTGGCCCCAGTG

CTGCAATGATACCGCGAGACCCACGCTCACCGGCTCCAGATTTATCAGCAATAA

ACCAGCCAGCCGGAAGGGCCGAGCGCAGAAGTGGTCCTGCAACTTTATCCGCCT

CCATCCAGTCTATTAATTGTTGCCGGGAAGCTAGAGTAAGTAGTTCGCCAGTTAA

TAGTTTGCGCAACGTTGTTGCCATTGCTACAGGCATCGTGGTGTCACGCTCGTCG

TTTGGTATGGCTTCATTCAGCTCCGGTTCCCAACGATCAAGGCGAGTTACATGAT

CCCCCATGTTGTGCAAAAAAGCGGTTAGCTCCTTCGGTCCTCCGATCGTTGTCAG

AAGTAAGTTGGCCGCAGTGTTATCACTCATGGTTATGGCAGCACTGCATAATTCT

CTTACTGTCATGCCATCCGTAAGATGCTTTTCTGTGACTGGTGAGTACTCAACCA

AGTCATTCTGAGAATAGTGTATGCGGCGACCGAGTTGCTCTTGCCCGGCGTCAAT

ACGGGATAATACCGCGCCACATAGCAGAACTTTAAAAGTGCTCATCATTGGAAA

ACGTTCTTCGGGGCGAAAACTCTCAAGGATCTTACCGCTGTTGAGATCCAGTTCG

ATGTAACCCACTCGTGCACCCAACTGATCTTCAGCATCTTTTACTTTCACCAGCG

TTTCTGGGTGAGCAAAAACAGGAAGGCAAAATGCCGCAAAAAAGGGAATAAGG
```

-continued

```
GCGACACGGAAATGTTGAATACTCATACTCTTCCTTTTTCAATATTATTGAAGCA

TTTATCAGGGTTATTGTCTCATGAGCGGATACATATTTGAATGTATTTAGAAAAA

TAAACAAATAGGGGTTCCGCGCACATTTCCCCGAAAAGTGCCAC.
```

In one embodiment, the nucleic acid comprises (a) a sequence encoding at least a portion of the genome of a rabies virus and (b) a sequence encoding a protein comprising a SARS-CoV-2 spike protein (S) or a portion thereof. In some embodiments, the at least a portion of the genome of the rabies virus comprises an N gene and a P gene, and the sequence encoding the protein comprising the SARS-CoV-2 spike protein (S) or portion thereof is inserted into a position between the N gene and P gene. In some embodiments, the protein comprising a SARS-CoV-2 spike protein (S) or a portion thereof is a fusion protein comprising a glycoprotein (G) or a portion thereof and a SARS-CoV-2 spike protein (S) or a portion thereof. In some embodiments, the fusion protein comprises a glycoprotein (G) or portion thereof fused to the S1 domain of a SARS-CoV-2 spike protein (S).

In another embodiment, the nucleic acid comprises the sequence of SEQ ID NO: 2, shown below:

```
CTGACGCGCCCTGTAGCGGCGCATTAAGCGCGGCGGGTGTGGTGGTTACGCGCA

GCGTGACCGCTACACTTGCCAGCGCCCTAGCGCCCGCTCCTTTCGCTTTCTTCCCT

TCCTTTCTCGCCACGTTCGCCGGCTTTCCCCGTCAAGCTCTAAATCGGGGCTCC

CTTTAGGGTTCCGATTTAGTGCTTTACGGCACCTCGACCCCAAAAAACTTGATTA

GGGTGATGGTTCACGTAGTGGGCCATCGCCCTGATAGACGGTTTTTCGCCCTTTG

ACGTTGGAGTCCACGTTCTTTAATAGTGGACTCTTGTTCCAAACTGGAACAACAC

TCAACCCTATCTCGGTCTATTCTTTTGATTTATAAGGGATTTTGCCGATTTCGGCC

TATTGGTTAAAAAATGAGCTGATTTAACAAAAATTTAACGCGAATTTTAACAAA

ATATTAACGCTTACAATTTCCATTCGCCATTCAGGCTGCGCAACTGTTGGGAAGG

GCGATCGGTGCGGGCCTCTTCGCTATTACGCCAGCTGGCGAAAGGGGGATGTGC

TGCAAGGCGATTAAGTTGGGTAACGCCAGGGTTTTCCCAGTCACGACGTTGTAA

AACGACGGCCAGTGAGcgcgccCTAGTTATTAATAGTAATCAATTACGGGGTCATT

AGTTCATAGCCCATATATGGAGTTCCGCGTTACATAACTTACGGTAAATGGCCCG

CCTGGCTGACCGCCCAACGACCCCCGCCCATTGACGTCAATAATGACGTATGTTC

CCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCT

ATTGACGTCAATGACGGTAAATGGCCCGCCTGGCATTATGCCCAGTACATGACCT

TATGGGACTTTCCTACTTGGCAGTACATCTACGTATTAGTCATCGCTATTACCATG

GTGATGCGGTTTTGGCAGTACATCAATGGGCGTGGATAGCGGTTTGACTCACGG

GGATTTCCAAGTCTCCACCCCATTGACGTCAATGGGAGTTTGTTTTGGCACCAAA

ATCAACGGGACTTTCCAAAATGTCGTAACAACTCCGCCCCATTGACGCAAATGG

GCGGTAGGCGTGTACGGTGGGAGGTCTATATAAGCAGAGCTCTCTGGCTAACTA

GAGAACCCACTGCTTACTGGCTTATCGAAATTAATACGACTCACTATAGGGAGA

CCCAAGCTGGCTAGATTAAGCGTCTGATGAGTCCGTGAGGACGAAACCCGGCGT

ACCGGGTCACGCTTAACAACCAGATCAAAGAAAAAACAGACATTGTCAATTGCA

AAGCAAAAATGTAACACCCCTACAATGGATGCCGACAAGATTGTATTCAAAGTC

AATAATCAGGTGGTCTCTTTGAAGCCTGAGATTATCGTGGATCAATATGAGTACA

AGTACCCTGCCATCAAAGATTTGAAAAAGCCCTGTATAACCCTAGGAAAGGCTC

CCGATTTAAATAAAGCATACAAGTCAGTTTTGTCAGGCATGAGCGCCGCCAAAC

TTAATCCTGACGATGTATGTTCCTATTTGGCAGCGGCAATGCAGTTTTTTGAGGG

GACATGTCCGGAAGACTGGACCAGCTATGGAATTGTGATTGCACGAAAAGGAGA
```

-continued

```
TAAGATCACCCCAGGTTCTCTGGTGGAGATAAAACGTACTGATGTAGAAGGGAA

TTGGGCTCTGACAGGAGGCATGGAACTGACAAGAGACCCCACTGTCCCTGAGCA

TGCGTCCTTAGTCGGTCTTCTCTTGAGTCTGTATAGGTTGAGCAAAATATCCGGG

CAAAACACTGGTAACTATAAGACAAACATTGCAGACAGGATAGAGCAGATTTTT

GAGACAGCCCCTTTTGTTAAAATCGTGGAACACCATACTCTAATGACAACTCACA

AaATGTGTGCTAATTGGAGTACTATACCAAACTTCAGATTTTTGGCCGGAACCTA

TGACATGTTTTTCTCCCGGATTGAGCATCTATATTCAGCAATCAGAGTGGGCACA

GTTGTCACTGCTTATGAAGACTGTTCAGGACTGGTATCATTTACTGGGTTCATAA

AACAAATCAATCTCACCGCTAGAGAGGCAATACTATATTTCTTCCACAAGAACTT

TGAGGAAGAGATAAGAAGAATGTTTGAGCCAGGGCAGGAGACAGCTGTTCCTCA

CTCTTATTTCATCCACTTCCGTTCACTAGGCTTGAGTGGGAAATCTCCTTATTCAT

CAAATGCTGTTGGTCACGTGTTCAATCTCATTCACTTTGTAGGATGCTATATGGG

TCAAGTCAGATCCCTAAATGCAACGGTTATTGCTGCATGTGCTCCTCATGAAATG

TCTGTTCTAGGGGGCTATCTGGGAGAGGAATTCTTCGGGAAAGGGACATTTGAA

AGAAGATTCTTCAGAGATGAGAAAGAACTTCAAGAATACGAGGCGGCTGAACTG

ACAAAGACTGACGTAGCACTGGCAGATGATGGAACTGTCAACTCTGACGACGAG

GACTACTTTTCAGGTGAAACCAGAAGTCCGGAGGCTGTTTATACTCGAATCATGA

TGAATGGAGGTCGACTAAAGAGATCTCACATACGGAGATATGTCTCAGTCAGTT

CCAATCATCAAGCCCGTCCAAACTCATTCGCCGAGTTTCTAAACAAGACATATTC

GAGTGACTCATAAcatgaaaaaaactaacacccctcccGTACGCCACCATGTTCGTGTTTCTGG

TGCTGCTGCCTCTGGTGAGCTCCCAGTGCGTGAACCTGACCACAAGGACCCAGCT

GCCCCCTGCCTATACCAATTCCTTCACACGGGGCGTGTACTATCCCGACAAGGTG

TTCCGGAGCAGCGTGCTGCACTCCACACAGGATCTGTTTCTGCCTTTCTTTTCTAA

CGTGACCTGGTTCCACGCCATCCACGTGAGCGGCACCAATGGCACAAAGCGGTT

CGACAATCCAGTGCTGCCCTTTAACGATGGCGTGTACTTCGCCTCCACCGAGAAG

TCTAACATCATCAGAGGCTGGATCTTTGGCACCACACTGGACAGCAAGACACAG

TCCCTGCTGATCGTGAACAATGCCACCAACGTGGTCATCAAGGTGTGCGAGTTCC

AGTTTTGTAATGATCCATTCCTGGGCGTGTACTATCACAAGAACAATAAGTCTTG

GATGGAGAGCGAGTTTCGCGTGTATTCCTCTGCCAACAATTGCACATTTGAGTAC

GTGTCCCAGCCCTTCCTGATGGACCTGGAGGGCAAGCAGGGCAATTTCAAGAAC

CTGAGGGAGTTCGTGTTTAAGAATATCGATGGCTACTTCAAAATCTACTCCAAGC

ACACCCCAATCAACCTGGTGCGCGACCTGCCACAGGGCTTCTCTGCCCTGGAGCC

ACTGGTGGATCTGCCCATCGGCATCAACATCACCCGGTTTCAGACACTGCTGGCC

CTGCACAGAAGCTACCTGACACCAGGCGACAGCTCCTCTGGATGGACCGCAGGA

GCAGCAGCCTACTATGTGGGCTATCTGCAGCCCAGGACCTTCCTGCTGAAGTACA

ACGAGAATGGCACCATCACAGACGCCGTGGATTGCGCCCTGGATCCCCTGTCTG

AGACCAAGTGTACACTGAAGAGCTTTACCGTGGAGAAGGGCATCTATCAGACAA

GCAATTTCAGGGTGCAGCCTACCGAGTCCATCGTGCGCTTTCCCAATATCACAAA

CCTGTGCCCTTTTGGCGAGGTGTTCAACGCAACCCGCTTCGCCAGCGTGTACGCC

TGGAATAGGAAGCGCATCTCCAACTGCGTGGCCGACTATTCTGTGCTGTACAACA
```

-continued

```
GCGCCTCCTTCTCTACCTTTAAGTGCTATGGCGTGAGCCCCACAAAGCTGAATGA
CCTGTGCTTTACCAACGTGTACGCCGATTCCTTCGTGATCAGGGGCGACGAGGTG
CGCCAGATCGCACCAGGACAGACAGGCAAGATCGCAGACTACAATTATAAGCTG
CCTGACGATTTCACCGGCTGCGTGATCGCCTGGAACTCTAACAATCTGGATAGCA
AAGTGGGCGGCAACTACAATTATCTGTACCGGCTGTTTAGAAAGTCTAATCTGAA
GCCATTCGAGAGGGACATCTCCACAGAAATCTACCAGGCCGGCTCTACCCCCTG
CAATGGCGTGGAgGGCTTTAACTGTTATTTCCCTCTGCAGAgCTACgGCTTCCAGC
CAACAAACGGCGTGGGCTATCAGCCCTACCGCGTGGTGGTGCTGTCTTTTGAGCT
GCTGCACGCACcTGCAACAGTGTGCGGACCAAAGAAGAGCACCAATCTGGTGAA
GAACAAGTGCGTGAACTTCAACTTCAACGGACTGACCGGAACAGGCGTGCTGAC
CGAGTCCAACAAGAAGTTCCTGCCTTTTCAGCAGTTCGGCAGGGACATCGCAGA
TACCACAGACGCCGTGCGCGACCCTCAGACCCTGGAGATCCTGGACATCACACC
ATGCTCCTTCGGCGGCGTGTCTGTGATCACACCAGGCACCAATACAAGCAACCA
GGTGGCCGTGCTGTATCAGGACGTGAATTGTACCGAGGTGCCAGTGGCAATCCA
CGCAGATCAGCTGACCCCTACATGGCGGGTGTACTCTACCGGCAGCAACGTGTT
CCAGACAAGAGCCGGATGCCTGATCGGAGCAGAGCACGTGAACAATAGCTATG
AGTGCGACATCCCTATCGGCGCCGGCATCTGTGCCTCCTACCAGACCCAGACAA
ACTCCCCAAGGTCTGTGGGAGATGAGGCCGAAGACTTTGTGGAAGTCCACCTGC
CTGATGTGCATAACCAGGTGTCTGGCGTCGACCTGGGACTGCCAAATTGGGGCA
AGTACGTGCTGCTGAGTGCTGGAGCACTGACTGCCCTGATGCTGATCATTTTCCT
GATGACCTGCTGTCGGCGCGTGAACAGAAGTGAGCCCACTCAGCACAATCTGCG
AGGAACCGGGAGAGAAGTGTCAGTCACACCTCAGAGCGGGAAAATCATTAGTA
GTTGGGAATCACATAAAAGCGGGGGCGAGACCAGGCTGTGAGCTAGCCATGAA
AAAAACTAACACCCCTCCTTTCGAACCATCCCAAACATGAGCAAGATCTTTGTCA
ATCCTAGTGCTATTAGAGCCGGTCTGGCCGATCTTGAGATGGCTGAAGAAACTGT
TGATCTGATCAATAGAAATATCGAAGACAATCAGGCTCATCTCCAAGGGGAACC
CATAGAGGTGGACAATCTCCCTGAGGATATGGGGCGACTTCACCTGGATGATGG
AAAATCGCCCAACCATGGTGAGATAGCCAAGGTGGGAGAAGGCAAGTATCGAG
AGGACTTTCAGATGGATGAAGGAGAGGATCCTAGCTTCCTGTTCCAGTCATACCT
GGAAAATGTTGGAGTCCAAATAGTCAGACAAATGAGGTCAGGAGAGAGATTTCT
CAAGATATGGTCACAGACCGTAGAAGAGATTATATCCTATGTCGCGGTCAACTTT
CCCAACCCTCCAGGAAAGTCTTCAGAGGATAAATCAACCCAGACTACTGGCCGA
GAGCTCAAGAAGGAGACAACACCCACTCCTTCTCAGAGAGAAAGCCAATCATCG
AAAGCCAGGATGGCGGCTCAAATTGCTTCTGGCCCTCCAGCCCTTGAATGGTCG
GCTACCAATGAAGAGGATGATCTATCAGTGGAGGCTGAGATCGCTCACCAGATT
GCAGAAAGTTTCTCCAAAAAATATAAGTTTCCCTCTCGATCCTCAGGGATACTCT
TGTATAATTTTGAGCAATTGAAAATGAACCTTGATGATATAGTTAAAGAGGCAA
AAAATGTACCAGGTGTGACCCGTTTAGCCCATGACGGGTCCAAACTCCCCCTAA
GATGTGTACTGGGATGGGTCGCTTTGGCCAACTCTAAGAAATTCCAGTTGTTAGT
CGAATCCGACAAGCTGAGTAAAATCATGCAAGATGACTTGAATCGCTATACATC
TTGCTAACCGAACCTCTCCCCTCAGTCCCTCTAGACAATAAAATCCGAGATGTCC
```

```
CAAAGTCAACATGAAAAAAACAGGCAACACCACTGATAAAATGAACCTCCTACG

TAAGATAGTGAAAAACCGCAGGGACGAGGACACTCAAAAATCCTCTCCCGCGTC

AGCCCCTCTGGATGACGATGACTTGTGGCTTCCACCCCCTGAATACGTCCCGCTG

AAAGAACTTACAGGCAAGAAGAACATGAGGAACTTTTGTATCAACGGAAGGGTT

AAAGTGTGTAGCCCGAATGGTTACTCGTTCAGGATCCTGCGGCACATTCTGAAAT

CATTCGACGAGATATATTCTGGGAATCATAGGATGATCGGGTTAGTCAAAGTGG

TTATTGGACTGGCTTTGTCAGGATCTCCAGTCCCTGAGGGCCTGAACTGGGTATA

CAAATTGAGGAGAACCTTTATCTTCCAGTGGGCTGATTCCAGGGGCCCTCTTGAA

GGGGAGGAGTTGGAATACTCTCAGGAGATCACTTGGGATGATGATACTGAGTTC

GTCGGATTGCAAATAAGAGTGATTGCAAAACAGTGTCATATCCAGGGCAGAGTC

TGGTGTATCAACATGAACCCGAGAGCATGTCAACTATGGTCTGACATGTCTCTTC

AGACACAAAGGTCCGAAGAGGACAAAGATTCCTCTCTGCTTCTAGAATAATCAG

ATTATATCCCGCAAATTTATCACTTGTTTACCTCTGGAGGAGAGAACATATGGGC

TCAACTCCAACCCTTGGGAGCAATATAACAAAAAACATGTTATGGTGCCATTAA

ACCGCTGCATTTCATCAAAGTCAAGTTGATTACCTTTACATTTTGATCCTCTTGGA

TGTGAAAAAAACTATTAACATCCCTCAAAAGACcccgggAAAGATGGTTCCTCAGG

CTCTCCTGTTTGTACCCCTTCTGGTTTTTCCATTGTGTTTTGGGAAATTCCCTATTT

ACACGATACCAGACAAGCTTGGTCCCTGGAGTCCGATTGACATACATCACCTCA

GCTGCCCAAACAATTTGGTAGTGGAGGACGAAGGATGCACCAACCTGTCAGGGT

TCTCCTACATGGAACTTAAAGTTGGATACATCTTAGCCATAAAAGTGAACGGGTT

CACTTGCACAGGCGTTGTGACGGAGGCTGAAACCTACACTAACTTCGTTGGTTAT

GTCACAACCACGTTCAAAAGAAAGCATTTCCGCCCAACACCAGATGCATGTAGA

GCCGCGTACAACTGGAAGATGGCCGGTGACCCCAGATATGAAGAGTCTCTACAC

AATCCGTACCCTGACTACCGCTGGCTTCGAACTGTAAAAACCACCAAGGAGTCT

CTCGTTATCATATCTCCAAGTGTGGCAGATTTGGACCCATATGACAGATCCCTTC

ACTCGAGGGTCTTCCCTAGCGGGAAGTGCTCAGGAGTAGCGGTGTCTTCTACCTA

CTGCTCCACTAACCACGATTACACCATTTGGATGCCCGAGAATCCGAGACTAGG

GATGTCTTGTGACATTTTTACCAATAGTAGAGGGAAGAGAGCATCCAAAGGGAG

TGAGACTTGCGGCTTTGTAGATGAAAGAGGCCTATATAAGTCTTTAAAAGGAGC

ATGCAAACTCAAGTTATGTGGAGTTCTAGGACTTAGACTTATGGATGGAACATG

GGTCTCGATGCAAACATCAAATGAAACCAAATGGTGCCCTCCCGATAAGTTGGT

GAACCTGCACGACTTTCGCTCAGACGAAATTGAGCACCTTGTTGTAGAGGAGTTG

GTCAGGAAGAGAGAGGAGTGTCTGGATGCACTAGAGTCCATCATGACAACCAAG

TCAGTGAGTTTCAGACGTCTCAGTCATTTAAGAAAACTTGTCCCTGGGTTTGGAA

AAGCATATACCATATTCAACAAGACCTTGATGGAAGCCGATGCTCACTACAAGT

CAGTCgagACTTGGAATGAGATCCTCCCTTCAAAAGGGTGTTTAAGAGTTGGGGG

GAGGTGTCATCCTCATGTGAACGGGGTGTTTTTCAATGGTATAATATTAGGACCT

GACGGCAATGTCTTAATCCCAGAGATGCAATCATCCCTCCTCCAGCAACATATGG

AGTTGTTGGAATCCTCGGTTATCCCCCTTGTGCACCCCCTGGCAGACCCGTCTAC

CGTTTTCAAGGACGGTGACGAGGCTGAGGATTTTGTTGAAGTTCACCTTCCCGAT
```

```
GTGCACAATCAGGTCTCAGGAGTTGACTTGGGTCTCCCGAACTGGGGGAAGTAT

GTATTACTGAGTGCAGGGGCCCTGACTGCCTTGATGTTGATAATTTTCCTGATGA

CATGTTGTAGAAGAGTCAATCGATCAGAACCTACGCAACACAATCTCAGAGGGA

CAGGGAGGGAGGTGTCAGTCACTCCCCAAAGCGGGAAGATCATATCTTCATGGG

AATCACACAAGAGTGGGGGTGAGACCAGACTGTAAttaattaaCGTCCTTTCAACGAT

CCAAGTCcatgaaaaaaactaacaccccctcccgtacctagcTTATAAAGTGCTGGGTCATCTAAGCTT

TTCAGTCGAGAAAAAAACATTAGATCAGAAGAACAACTGGCAACACTTCTCAAC

CTGAGACTTACTTCAAGATGCTCGATCCTGGAGAGGTCTATGATGACCCTATTGA

CCCAATCGAGTTAGAGGCTGAACCCAGAGGAACCCCCATTGTCCCCAACATCTT

GAGGAACTCTGACTACAATCTCAACTCTCCTTTGATAGAAGATCCTGCTAGACTA

ATGTTAGAATGGTTAAAAACAGGGAATAGACCTTATCGGATGACTCTAACAGAC

AATTGCTCCAGGTCTTTCAGAGTTTTGAAAGATTATTTCAAGAAGGTAGATTTGG

GTTCTCTCAAGGTGGGCGGAATGGCTGCACAGTCAATGATTTCTCTCTGGTTATA

TGGTGCCCACTCTGAATCCAACAGGAGCCGGAGATGTATAACAGACTTGGCCCA

TTTCTATTCCAAGTCGTCCCCCATAGAGAAGCTGTTGAATCTCACGCTAGGAAAT

AGAGGGCTGAGAATCCCCCAGAGGGAGTGTTAAGTTGCCTTGAGAGGGTTGAT

TATGATAATGCATTTGGAAGGTATCTTGCCAACACGTATTCCTCTTACTTGTTCTT

CCATGTAATCACCTTATACATGAACGCCCTAGACTGGGATGAAGAAAAGACCAT

CCTAGCATTATGGAAAGATTTAACCTCAGTGGACATCGGGAAGGACTTGGTAAA

GTTCAAAGACCAAATATGGGGACTGCTGATCGTGACAAAGGACTTTGTTTACTCC

CAAAGTTCCAATTGTCTTTTTGACAGAAACTACACACTTATGCTAAAAGATCTTT

TCTTGTCTCGCTTCAACTCCTTAATGGTCTTGCTCTCTCCCCCAGAGCCCCGATAC

TCAGATGACTTGATATCTCAACTATGCCAGCTGTACATTGCTGGGGATCAAGTCT

TGTCTATGTGTGGAAACTCCGGCTATGAAGTCATCAAAATATTGGAGCCATATGT

CGTGAATAGTTTAGTCCAGAGAGCAGAAAAGTTTAGGCCTCTCATTCATTCCTTG

GGAGACTTTCCTGTATTTATAAAAGACAAGGTAAGTCAACTTGAAGAGACGTTC

GGTCCCTGTGCAAGAAGGTTCTTTAGGGCTCTGGATCAATTCGACAACATACATG

ACTTGGTTTTTGTGTTTGGCTGTTACAGGCATTGGGGGCACCCATATATAGATTA

TCGAAAGGGTCTGTCAAAACTATATGATCAGGTTCACCTTAAAAAAATGATAGA

TAAGTCCTACCAGGAGTGCTTAGCAAGCGACCTAGCCAGGAGGATCCTTAGATG

GGGTTTTGATAAGTACTCCAAGTGGTATCTGGATTCAAGATTCCTAGCCCGAGAC

CACCCCTTGACTCCTTATATCAAAACCCAAACATGGCCACCCAAACATATTGTAG

ACTTGGTGGGGATACATGGCACAAGCTCCCGATCACGCAGATCTTTGAGATTCC

TGAATCAATGGATCCGTCAGAAATATTGGATGACAAATCACATTCTTTCACCAGA

ACGAGACTAGCTTCTTGGCTGTCAGAAAACCGAGGGGGGCCTGTTCCTAGCGAA

AAAGTTATTATCACGGCCCTGTCTAAGCCGCCTGTCAATCCCCGAGAGTTTCTGA

GGTCTATAGACCTCGGAGGATTGCCAGATGAAGACTTGATAATTGGCCTCAAGC

CAAAGGAACGGGAATTGAAGATTGAAGGTCGATTCTTTGCTCTAATGTCATGGA

ATCTAAGATTGTATTTTGTCATCACTGAAAAACTCTTGGCCAACTACATCTTGCC

ACTTTTTGACGCGCTGACTATGACAGACAACCTGAACAAGGTGTTTAAAAAGCT

GATCGACAGGGTCACCGGGCAAGGGCTTTTGGACTATTCAAGGGTCACATATGC
```

-continued

```
ATTTCACCTGGACTATGAAAAGTGGAACAACCATCAAAGATTAGAGTCAACAGA

GGATGTATTTTCTGTCCTAGATCAAGTGTTTGGATTGAAGAGAGTGTTTTCTAGA

ACACACGAGTTTTTTCAAAAGGCCTGGATCTATTATTCAGACAGATCAGACCTCA

TCGGGTTACGGGAGGATCAAATATACTGCTTAGATGCGTCCAACGGCCCAACCT

GTTGGAATGGCCAGGATGGCGGGCTAGAAGGCTTACGGCAGAAGGGCTGGAGTC

TAGTCAGCTTATTGATGATAGATAGAGAATCTCAAATCAGGAACACAAGAACCA

AAATACTAGCTCAAGGAGACAACCAGGTTTTATGTCCGACATACATGTTGTCGCC

AGGGCTATCTCAAGAGGGGCTCCTCTATGAATTGGAGAGAATATCAAGGAATGC

ACTTTCGATATACAGAGCCGTCGAGGAAGGGGCATCTAAGCTAGGGCTGATCAT

CAAGAAAGAAGAGACCATGTGTAGTTATGACTTCCTCATCTATGGAAAAACCCC

TTTGTTTAGAGGTAACATATTGGTGCCTGAGTCCAAAAGATGGGCCAGAGTCTCT

TGCGTCTCTAATGACCAAATAGTCAACCTCGCCAATATAATGTCGACAGTGTCCA

CCAATGCGCTAACAGTGGCACAACACTCTCAATCTTTGATCAAACCGATGAGGG

ATTTTCTGCTCATGTCAGTACAGGCAGTCTTTCACTACCTGCTATTTAGCCCAATC

TTAAAGGGAAGAGTTTACAAGATTCTGAGCGCTGAAGGGGAGAGCTTTCTCCTA

GCCATGTCAAGGATAATCTATCTAGATCCTTCTTTGGGAGGGATATCTGGAATGT

CCCTCGGAAGATTCCATATACGACAGTTCTCAGACCCTGTCTCTGAAGGGTTATC

CTTCTGGAGAGATCTGGTTAAGCTCCCAAGAGTCCTGGATTCACGCGTTGTGT

CAAGAGGCTGGAAACCCAGATCTTGGAGAGAGAACACTCGAGAGCTTCACTCGC

CTTCTAGAAGATCCGACCACCTTAAATATCAGAGGAGGGGCCAGTCCTACCATT

CTACTCAAGGATGCAATCAGAAAGGCTTTATATGACGAGGTGGACAAGGTGGAA

AATTCAGAGTTTCGAGAGGCAATCCTGTTGTCCAAGACCCATAGAGATAATTTTA

TACTCTTCTTAATATCTGTTGAGCCTCTGTTTCCTCGATTTCTCAGTGAGCTATTC

AGTTCGTCTTTTTTGGGAATCCCCGAGTCAATCATTGGATTGATACAAAACTCCC

GAACGATAAGAAGGCAGTTTAGAAAGAGTCTCTCAAAAACTTTAGAAGAATCCT

TCTACAACTCAGAGATCCACGGGATTAGTCGGATGACCCAGACACCTCAGAGGG

TTGGGGGGTGTGGCCTTGCTCTTCAGAGAGGGCAGATCTACTTAGGGAGATCTC

TTGGGGAAGAAAAGTGGTAGGCACGACAGTTCCTCACCCTTCTGAGATGTTGGG

ATTACTTCCCAAGTCCTCTATTTCTTGCACTTGTGGAGCAACAGGAGGAGGCAAT

CCTAGAGTTTCTGTATCAGTACTCCCGTCCTTTGATCAGTCATTTTTTTCACGAGG

CCCCCTAAAGGGATACTTGGGCTCGTCCACCTCTATGTCGACCCAGCTATTCCAT

GCATGGGAAAAAGTCACTAATGTTCATGTGGTGAAGAGAGCTCTATCGTTAAAA

GAATCTATAAACTGGTTCATTACTAGAGATTCCAACTTGGCTCAAGCTCTAATTA

GGAACATTATGTCTCTGACAGGCCCTGATTTCCCTCTAGAGGAGGCCCCTGTCTT

CAAAAGGACGGGGTCAGCCTTGCATAGGTTCAAGTCTGCCAGATACAGCGAAGG

AGGGTATTCTTCTGTCTGCCCGAACCTCCTCTCTCATATTTCTGTTAGTACAGACA

CCATGTCTGATTTGACCCAAGACGGGAAGAACTACGATTTCATGTTCCAGCCATT

GATGCTTTATGCACAGACATGGACATCAGAGCTGGTACAGAGAGACACAAGGCT

AAGAGACTCTACGTTTCATTGGCACCTCCGATGCAACAGGTGTGTGAGACCCATT

GACGACGTGACCCTGGAGACCTCTCAGATCTTCGAGTTTCCGGATGTGTCGAAAA
```

-continued

```
GAATATCCAGAATGGTTTCTGGGGCTGTGCCTCACTTCCAGAGGCTTCCCGATAT
CCGTCTGAGACCAGGAGATTTTGAATCTCTAAGCGGTAGAGAAAAGTCTCACCA
TATCGGATCAGCTCAGGGGCTCTTATACTCAATCTTAGTGGCAATTCACGACTCA
GGATACAATGATGGAACCATCTTCCCTGTCAACATATACGGCAAGGTTTCCCCTA
GAGACTATTTGAGAGGGCTCGCAAGGGGAGTATTGATAGGATCCTCGATTTGCTT
CTTGACAAGAATGACAAATATCAATATTAATAGACCTCTTGAATTGGTCTCAGGG
GTAATCTCATATATTCTCCTGAGGCTAGATAACCATCCCTCCTTGTACATAATGCT
CAGAGAACCGTCTCTTAGAGGAGAGATATTTTCTATCCCTCAGAAAATCCCCGCC
GCTTATCCAACCACTATGAAAGAAGGCAACAGATCAATCTTGTGTTATCTCCAAC
ATGTGCTACGCTATGAGCGAGAGATAATCACGGCGTCTCCAGAGAATGACTGGC
TATGGATCTTTTCAGACTTTAGAAGTGCCAAAATGACGTACCTATCCCTCATTAC
TTACCAGTCTCATCTTCTACTCCAGAGGGTTGAGAGAAACCTATCTAAGAGTATG
AGAGATAACCTGCGACAATTGAGTTCTTTGATGAGGCAGGTGCTGGGCGGGCAC
GGAGAAGATACCTTAGAGTCAGACGACAACATTCAACGACTGCTAAAAGACTCT
TTACGAAGGACAAGATGGGTGGATCAAGAGGTGCGCCATGCAGCTAGAACCATG
ACTGGAGATTACAGCCCCAACAAGAAGGTGTCCCGTAAGGTAGGATGTTCAGAA
TGGGTCTGCTCTGCTCAACAGGTTGCAGTCTCTACCTCAGCAAACCCGGCCCCTG
TCTCGGAGCTTGACATAAGGGCCCTCTCTAAGAGGTTCCAGAACCCTTTGATCTC
GGGCTTGAGAGTGGTTCAGTGGGCAACCGGTGCTCATTATAAGCTTAAGCCTATT
CTAGATGATCTCAATGTTTTCCCATCTCTCTGCCTTGTAGTTGGGGACGGGTCAG
GGGGGATATCAAGGGCAGTCCTCAACATGTTTCCAGATGCCAAGCTTGTGTTCAA
CAGTCTTTTAGAGGTGAATGACCTGATGGCTTCCGGAACACATCCACTGCCTCCT
TCAGCAATCATGAGGGGAGGAAATGATATCGTCTCCAGAGTGATAGATCTTGAC
TCAATCTGGGAAAAACCGTCCGACTTGAGAAACTTGGCAACCTGGAAATACTTC
CAGTCAGTCCAAAAGCAGGTCAACATGTCCTATGACCTCATTATTTGCGATGCAG
AAGTTACTGACATTGCATCTATCAACCGGATCACCCTGTTAATGTCCGATTTTGC
ATTGTCTATAGATGGACCACTCTATTTGGTCTTCAAAACTTATGGGACTATGCTA
GTAAATCCAAACTACAAGGCTATTCAACACCTGTCAAGAGCGTTCCCCTCGGTCA
CAGGGTTTATCACCCAAGTAACTTCGTCTTTTTCATCTGAGCTCTACCTCCGATTC
TCCAAACGAGGGAAGTTTTTCAGAGATGCTGAGTACTTGACCTCTTCCACCCTTC
GAGAAATGAGCCTTGTGTTATTCAATTGTAGCAGCCCCAAGAGTGAGATGCAGA
GAGCTCGTTCCTTGAACTATCAGGATCTTGTGAGAGGATTTCCTGAAGAAATCAT
ATCAAATCCTTACAATGAGATGATCATAACTCTGATTGACAGTGATGTAGAATCT
TTTCTAGTCCACAAGATGGTTGATGATCTTGAGTTACAGAGGGGAACTCTGTCTA
AAGTGGCTATCATTATAGCCATCATGATAGTTTTCTCCAACAGAGTCTTCAACGT
TTCCAAACCCCTAACTGACCCCTCGTTCTATCCACCGTCTGATCCCAAAATCCTG
AGGCACTTCAACATATGTTGCAGTACTATGATGTATCTATCTACTGCTTTAGGTG
ACGTCCCTAGCTTCGCAAGACTTCACGACCTGTATAACAGACCTATAACTTATTA
CTTCAGAAAGCAAGTCATTCGAGGGAACGTTTATCTATCTTGGAGTTGGTCCAAC
GACACCTCAGTGTTCAAAAGGGTAGCCTGTAATTCTAGCCTGAGTCTGTCATCTC
ACTGGATCAGGTTGATTTACAAGATAGTGAAGACTACCAGACTCGTTGGCAGCA
```

```
TCAAGGATCTATCCAGAGAAGTGGAAAGACACCTTCATAGGTACAACAGGTGGA

TCACCCTAGAGGATATCAGATCTAGATCATCCCTACTAGACTACAGTTGCCTGTG

AACCGGATACTCCTGGAAGCCTGCCCATGCTAAGACTCTTGTGTGATGTATCTTG

AAAAAAACAAGATCCTAAATCTGAACCTTTGGTTGTTTGATTGTTTTTCTCAttifigtt gtttatttgttaagcgtGGGTCGGCATGGCATCTCCACCTCCTCGCGGTCCGACCTGGGCAT CCGAAGGAGGACGCACGTCCACTCGGATGGCTAAGGGAGagccagaaGGATCCGGC

TGCTAACAAAGCCCGAAAGGAAGCTGAGTTGGCTGCTGCCACCGCTGAGCAATA

ACTAGCATAACCCCTTGGGGCCTCTAAACGGGTCTTGAGGGGTTTTTTGCTGAAA

GtCGCGCTTGGCGTAATCATGGTCATAGCTGTTTCCTGTGTGAAATTGTTATCCGC

TCACAATTCCACACAACATACGAGCCGGAAGCATAAAGTGTAAAGCCTGGGGTG

CCTAATGAGTGAGCTAACTCACATTAATTGCGTTGCGCTCACTGCCCGCTTTCCA

GTCGGGAAACCTGTCGTGCCAGCTGCATTAATGAATCGGCCAACGCGCGGGGAG

AGGCGGTTTGCGTATTGGGCGCTCTTaCGCTTCCTCGCTCACTGACTCGCTGCGCT

CGGTCGTTCGGCTGCGGCGAGCGGTATCAGCTCACTCAAAGGCGGTAATACGGT

TATCCACAGAATCAGGGGATAACGCAGGAAAGAACATGTGAGCAAAAGGCCAG

CAAAAGGCCAGGAACCGTAAAAAGGCCGCGTTGCTGGCGTTTTTCCATAGGCTC

CGCCCCCCTGACGAGCATCACAAAAATCGACGCTCAAGTCAGAGGTGGCGAAAC

CCGACAGGACTATAAAGATACCAGGCGTTTCCCCCTGGAAGCTCCCTCGTGCGCT

CTCCTGTTCCGACCCTGCCGCTTACCGGATACCTGTCCGCCTTTCTCCCTTCGGGA

AGCGTGGCGCTTTCTCATAGCTCACGCTGTAGGTATCTCAGTTCGGTGTAGGTCG

TTCGCTCCAAGCTGGGCTGTGTGCACGAACCCCCCGTTCAGCCCGACCGCTGCGC

CTTATCCGGTAACTATCGTCTTGAGTCCAACCCGGTAAGACACGACTTATCGCCA

CTGGCAGCAGCCACTGGTAACAGGATTAGCAGAGCGAGGTATGTAGGCGGTGCT

ACAGAGTTCTTGAAGTGGTGGCCTAACTACGGCTACACTAGAAGGACAGTATTT

GGTATCTGCGCTCTGCTGAAGCCAGTTACCTTCGGAAAAAGAGTTGGTAGCTCTT

GATCCGGCAAACAAACCACCGCTGGTAGCGGTGGTTTTTTTGTTTGCAAGCAGCA

GATTACGCGCAGAAAAAAAGGATCTCAAGAAGATCCTTTGATCTTTTCTACGGG

GTCTGACGCTCAGTGGAACGAAAACTCACGTTAAGGGATTTTGGTCATGAGATT

ATCAAAAAGGATCTTCACCTAGATCCTTTTAAATTAAAAATGAAGTTTTAAATCA

ATCTAAAGTATATATGAGTAAACTTGGTCTGACAGTTACCAATGCTTAATCAGTG

AGGCACCTATCTCAGCGATCTGTCTATTTCGTTCATCCATAGTTGCCTGACTCCCC

GTCGTGTAGATAACTACGATACGGGAGGGCTTACCATCTGGCCCCAGTGCTGCA

ATGATACCGCGAGACCCACGCTCACCGGCTCCAGATTTATCAGCAATAAACCAG

CCAGCCGGAAGGGCCGAGCGCAGAAGTGGTCCTGCAACTTTATCCGCCTCCATC

CAGTCTATTAATTGTTGCCGGGAAGCTAGAGTAAGTAGTTCGCCAGTTAATAGTT

TGCGCAACGTTGTTGCCATTGCTACAGGCATCGTGGTGTCACGCTCGTCGTTTGG

TATGGCTTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCAGAAGTA

AGTTGGCCGCAGTGTTATCACTCATGGTTATGGCAGCACTGCATAATTCTCTTAC

TGTCATGCCATCCGTAAGATGCTTTTCTGTGACTGGTGAGTACTCAACCAAGTCA
```

-continued
```
TTCTGAGAATAGTGTATGCGGCGACCGAGTTGCTCTTGCCCGGCGTCAATACGGG

ATAATACCGCGCCACATAGCAGAACTTTAAAAGTGCTCATCATTGGAAAACGTT

CTTCGGGGCGAAAACTCTCAAGGATCTTACCGCTGTTGAGATCCAGTTCGATGTA

ACCCACTCGTGCACCCAACTGATCTTCAGCATCTTTTACTTTCACCAGCGTTTCTG

GGTGAGCAAAAACAGGAAGGCAAAATGCCGCAAAAAAGGGAATAAGGGCGACA

CGGAAATGTTGAATACTCATACTCTTCCTTTTTCAATATTATTGAAGCATTTATCA

GGGTTATTGTCTCATGAGCGGATACATATTTGAATGTATTTAGAAAAATAAACAA

ATAGGGGTTCCGCGCACATTTCCCCGAAAAGTGCCAC.
```

In one embodiment, the nucleic acid comprises a sequence encoding at least a portion of the genome of a measles virus and (b) a sequence encoding a SARS-CoV-2 spike protein (S) or a portion thereof. In some embodiments, the sequence encoding the SARS-CoV-2 spike protein (S) or portion thereof is inserted into position 2, 3, or 6 of the genome of the measles virus.

In one embodiment, the nucleic acid comprises the sequence of SEQ ID NO: 3, shown below:

```
GGACGCGCCCTGTAGCGGCGCATTAAGCGCGGCGGGTGTGGTGGTTACGCGCAG

CGTGACCGCTACACTTGCCAGCGCCCTAGCGCCCGCTCCTTTCGCTTTCTTCCCTT

CCTTTCTCGCCACGTTCGCCGGCTTTCCCCGTCAAGCTCTAAATCGGGGGCTCCC

TTTAGGGTTCCGATTTAGTGCTTTACGGCACCTCGACCCCAAAAAACTTGATTAG

GGTGATGGTTCACGTAGTGGGCCATCGCCCTGATAGACGGTTTTTCGCCCTTTGA

CGTTGGAGTCCACGTTCTTTAATAGTGGACTCTTGTTCCAAACTGGAACAACACT

CAACCCTATCTCGGTCTATTCTTTTGATTTATAAGGGATTTTGCCGATTTCGGCCT

ATTGGTTAAAAAATGAGCTGATTTAACAAAAATTTAACGCGAATTTTAACAAAA

TATTAACGTTTACAATTTCGCGCCATTCGCCATTCAGGCTGCGCAACTGTTGGGA

AGGGCGATCGGTGCGGGCCTCTTCGCTATTACGCCAGCTGGCGAAAGGGGGATG

TGCTGCAAGGCGATTAAGTTGGGTAACGCCAGGGTTTTCCCAGTCACGACGTTGT

AAAACGACGGCCAGTGCGCGCCGTTAATACGACTCACTATAGGGAGACCCAAGC

TGGCTAGCTTTGTTTGGTCTGATGAGTCCCGTGAGGACGAAACCCGGCGTACCGG

GTCACCAAACAAAGTTGGGTAAGGATAGTTCAATCAATGATCATCTTCTAGTGCA

CTTAGGATTCAAGATCCTATTATCAGGGACAAGAGCAGGATTAGGGATATCCGA

GATGGCCACACTTTTAAGGAGCTTAGCATTGTTCAAAAGAAACAAGGACAAACC

ACCCATTACATCAGGATCCGGTGGAGCCATCAGAGGAATCAAACACATTATTAT

AGTACCAATCCCTGGAGATTCCTCAATTACCACTCGATCCAGACTTCTGGACCGG

TTGGTGAGGTTAATTGGAAACCCGGATGTGAGCGGGCCCAAACTAACAGGGCA

CTAATAGGTATATTATCCTTATTTGTGGAGTCTCCAGGTCAATTGATTCAGAGGA

TCACCGATGACCCTGACGTTAGCATAAGGCTGTTAGAGGTTGTCCAGAGTGACC

AGTCACAATCTGGCCTTACCTTCGCATCAAGAGGTACCAACATGGAGGATGAGG

CGGACCAATACTTTTCACATGATGATCCAATTAGTAGTGATCAATCCAGGTTCGG

ATGGTTCGGGAACAAGGAAATCTCAGATATTGAAGTGCAAGACCCTGAGGGATT

CAACATGATTCTGGGTACCATCCTAGCCCAAATTTGGGTCTTGCTCGCAAAGGCG

GTTACGGCCCCAGACACGGCAGCTGATTCGGAGCTAAGAAGGTGGATAAAGTAC

ACCCAACAAAGAAGGGTAGTTGGTGAATTTAGATTGGAGAGAAAATGGTTGGAT
```

-continued

```
GTGGTGAGGAACAGGATTGCCGAGGACCTCTCCTTACGCCGATTCATGGTCGCTC

TAATCCTGGATATCAAGAGAACACCCGGAAACAAACCCAGGATTGCTGAAATGA

TATGTGACATTGATACATATCGTAGAGGCAGGATTAGCCAGTTTTATCCTGAC

TATTAAGTTTGGGATAGAAACTATGTATCCTGCTCTTGGACTGCATGAATTTGCT

GGTGAGTTATCCACACTTGAGTCCTTGATGAACCTTTACCAGCAAATGGGGGAA

ACTGCACCCTACATGGTAATCCTGGAGAACTCAATTCAGAACAAGTTCAGTGCA

GGATCATACCCTCTGCTCTGGAGCTATGCCATGGGAGTAGGAGTGGAACTTGAA

AACTCCATGGGAGGTTTGAACTTTGGCCGATCTTACTTTGATCCAGCATATTTTA

GATTAGGGCAAGAGATGGTAAGGAGGTCAGCTGGAAAGGTCAGTTCCACATTGG

CATCTGAACTCGGTATCACTGCCGAGGATGCAAGGCTTGTTTCAGAGATTGCAAT

GCATACTACTGAGGACAAGATCAGTAGAGCGGTTGGACCCAGACAAGCCCAAGT

ATCATTTCTACACGGTGATCAAAGTGAGAATGAGCTACCGAGATTGGGGGGCAA

GGAAGATAGGAGGGTCAAACAGAGTCGAGGAGAAGCCAGGGAGAGCTACAGAG

AAACCGGGCCCAGCAGAGCAAGTGATGCGAGAGCTGCCCATCTTCCAACCGGCA

CACCCCTAGACATTGACACTGCAACGGAGTCCAGCCAAGATCCGCAGGACAGTC

GAAGGTCAGCTGACGCCCTGCTTAGGCTGCAAGCCATGGCAGGAATCTCGGAAG

AACAAGGCTCAGACACGGACACCCCTATAGTGTACAATGACAGAAATCTTCTAG

ACTAGGTGCGAGAGGCCGAGGGCCAGAACAACATCCGCCTACCATCCATCATTG

TTATAAAAAACTTAGGAACCAggtccacacaGagtgatACGCGTACGCCACCATGTTCGT

GTTTCTGGTGCTGCTGCCTCTGGTGAGCTCCCAGTGCGTGAACCTGACCACAAGG

ACCCAGCTGCCCCCTGCCTATACCAATTCCTTCACACGGGGCGTGTACTATCCCG

ACAAGGTGTTCCGGAGCAGCGTGCTGCACTCCACACAGGATCTGTTTCTGCCTTT

CTTTTCTAACGTGACCTGGTTCCACGCCATCCACGTGAGCGGCACCAATGGCACA

AAGCGGTTCGACAATCCAGTGCTGCCCTTTAACGATGGCGTGTACTTCGCCTCCA

CCGAGAAGTCTAACATCATCAGAGGCTGGATCTTTGGCACCACACTGGACAGCA

AGACACAGTCCCTGCTGATCGTGAACAATGCCACCAACGTGGTCATCAAGGTGT

GCGAGTTCCAGTTTTGTAATGATCCATTCCTGGGCGTGTACTATCACAAGAACAA

TAAGTCTTGGATGGAGAGCGAGTTTCGCGTGTATTCCTCTGCCAACAATTGCACA

TTTGAGTACGTGTCCCAGCCCTTCCTGATGGACCTGGAGGGCAAGCAGGGCAATT

TCAAGAACCTGAGGGAGTTCGTGTTTAAGAATATCGATGGCTACTTCAAAATCTA

CTCCAAGCACACCCCAATCAACCTGGTGCGCGACCTGCCACAGGGCTTCTCTGCC

CTGGAGCCACTGGTGGATCTGCCCATCGGCATCAACATCACCCGGTTTCAGACAC

TGCTGGCCCTGCACAGAAGCTACCTGACACCAGGCGACAGCTCCTCTGGATGGA

CCGCAGGAGCAGCAGCCTACTATGTGGGCTATCTGCAGCCCAGGACCTTCCTGCT

GAAGTACAACGAGAATGGCACCATCACAGACGCCGTGGATTGCGCCCTGGATCC

CCTGTCTGAGACCAAGTGTACACTGAAGAGCTTTACCGTGGAGAAGGGCATCTA

TCAGACAAGCAATTTCAGGGTGCAGCCTACCGAGTCCATCGTGCGCTTTCCCAAT

ATCACAAACCTGTGCCCTTTTGGCGAGGTGTTCAACGCAACCCGCTTCGCCAGCG

TGTACGCCTGGAATAGGAAGCGCATCTCCAACTGCGTGGCCGACTATTCTGTGCT

GTACAACAGCGCCTCCTTCTCTACCTTTAAGTGCTATGGCGTGAGCCCCACAAAG
```

-continued

```
CTGAATGACCTGTGCTTTACCAACGTGTACGCCGATTCCTTCGTGATCAGGGGCG

ACGAGGTGCGCCAGATCGCACCAGGACAGACAGGCAAGATCGCAGACTACAAT

TATAAGCTGCCTGACGATTTCACCGGCTGCGTGATCGCCTGGAACTCTAACAATC

TGGATAGCAAAGTGGGCGGCAACTACAATTATCTGTACCGGCTGTTTAGAAAGT

CTAATCTGAAGCCATTCGAGAGGGACATCTCCACAGAAATCTACCAGGCCGGCT

CTACCCCCTGCAATGGCGTGGAGGGCTTTAACTGTTATTTCCCTCTGCAGAGCTA

CGGCTTCCAGCCAACAAACGGCGTGGGCTATCAGCCCTACCGCGTGGTGGTGCT

GTCTTTTGAGCTGCTGCACGCACCTGCAACAGTGTGCGGACCAAAGAAGAGCAC

CAATCTGGTGAAGAACAAGTGCGTGAACTTCAACTTCAACGGACTGACCGGAAC

AGGCGTGCTGACCGAGTCCAACAAGAAGTTCCTGCCTTTTCAGCAGTTCGGCAG

GGACATCGCAGATACCACAGACGCCGTGCGCGACCCTCAGACCCTGGAGATCCT

GGACATCACACCATGCTCCTTCGGCGGCGTGTCTGTGATCACACCAGGCACCAAT

ACAAGCAACCAGGTGGCCGTGCTGTATCAGGACGTGAATTGTACCGAGGTGCCA

GTGGCAATCCACGCAGATCAGCTGACCCCTACATGGCGGGTGTACTCTACCGGC

AGCAACGTGTTCCAGACAAGAGCCGGATGCCTGATCGGAGCAGAGCACGTGAAC

AATAGCTATGAGTGCGACATCCCTATCGGCGCCGGCATCTGTGCCTCCTACCAGA

CCCAGACAAACTCCCCAAGGAGAGCACGGTCTGTGGCCAGCCAGTCCATCATCG

CCTATACCATGAGCCTGGGCGCCGAGAATTCCGTGGCCTACTCCAACAATTCTAT

CGCCATCCCTACCAACTTCACAATCTCCGTGACCACAGAGATCCTGCCAGTGAGC

ATGACCAAGACATCCGTGGACTGCACAATGTATATCTGTGGCGATTCCACCGAGT

GCTCTAACCTGCTGCTGCAGTACGGCTCTTTTTGTACCCAGCTGAATAGAGCCCT

GACAGGCATCGCCGTGGAGCAGGACAAGAACACACAGGAGGTGTTCGCCCAGG

TGAAGCAAATCTACAAGACCCCACCCATCAAGGACTTTGGCGGCTTCAACTTCA

GCCAGATCCTGCCCGATCCTAGCAAGCCATCCAAGCGGTCTTTTATCGAGGACCT

GCTGTTCAACAAGGTGACCCTGGCCGATGCCGGCTTCATCAAGCAGTATGGCGA

TTGCCTGGGCGACATCGCCGCCAGAGACCTGATCTGTGCCCAGAAGTTTAATGG

CCTGACCGTGCTGCCTCCACTGCTGACAGATGAGATGATCGCCCAGTACACATCT

GCCCTGCTGGCCGGAACCATCACAAGCGGATGGACCTTCGGCGCAGGAGCCGCC

CTGCAGATCCCCTTTGCCATGCAGATGGCCTATCGGTTCAACGGCATCGGCGTGA

CCCAGAATGTGCTGTACGAGAACCAGAAGCTGATCGCCAATCAGTTTAACTCCG

CCATCGGCAAGATCCAGGACTCTCTGAGCTCCACAGCCAGCGCCCTGGGCAAGC

TGCAGGATGTGGTGAATCAGAACGCCCAGGCCCTGAATACCCTGGTGAAGCAGC

TGTCTAGCAACTTCGGCGCCATCTCCTCTGTGCTGAATGACATCCTGAGCCGGCT

GGACAAGGTGGAGGCAGAGGTGCAGATCGACCGGCTGATCACAGGCAGACTGC

AGTCCCTGCAGACCTACGTGACACAGCAGCTGATCAGGGCAGCAGAGATCAGGG

CCTCTGCCAATCTGGCCGCCACCAAGATGAGCGAGTGCGTGCTGGGCCAGTCCA

AGAGAGTGGACTTTTGTGGCAAGGGCTATCACCTGATGAGCTTCCCACAGTCCGC

CCCTCACGGAGTGGTGTTTCTGCACGTGACCTACGTGCCAGCCCAGGAGAAGAA

CTTCACCACAGCACCAGCAATCTGCCACGATGGCAAGGCACACTTTCCTAGGGA

GGGCGTGTTCGTGAGCAACGGCACCCACTGGTTTGTGACACAGCGCAATTTCTAC

GAGCCACAGATCATCACCACAGACAATACATTCGTGTCCGGCAACTGTGACGTG
```

-continued

```
GTCATCGGCATCGTGAACAATACCGTGTATGATCCTCTGCAGCCAGAGCTGGACT

CTTTTAAGGAGGAGCTGGATAAGTACTTCAAGAATCACACCAGCCCCGACGTGG

ATCTGGGCGACATCTCTGGCATCAATGCCAGCGTGGTGAACATCCAGAAGGAGA

TCGACAGGCTGAACGAGGTGGCCAAGAATCTGAACGAGTCCCTGATCGATCTGC

AGGAGCTGGGCAAGTATGAGCAGTACATCAAGTGGCCCTGGTATATCTGGCTGG

GCTTCATCGCCGGCCTGATCGCCATCGTGATGGTGACCATCATGCTGTGCTGTAT

GACAAGCTGCTGTTCCTGCCTGAAGGGCTGCTGTTCTTGTGGCAGCTGCTGTAAG

TTTGATGAGGACGATAGCGAGCCTGTGCTGAAGGGCGTGAAGCTGCACTACACC

TGATAGCTAGCGATCGCGTGCGAGAGGCCAGAACAACATCCGCCTACCATCCAT

CATTGTTATAAAAAACTTAGGAACCAGGTCCACACAGCCGCCAGCCCATCAACC

ATCCACTCCCACGATTGGAGCCAATGGCAGAAGAGCAGGCACGCCATGTCAAAA

ACGGACTGGAATGCATCCGGGCTCTCAAGGCCGAGCCCATCGGCTCACTGGCCA

TCGAGGAAGCTATGGCAGCATGGTCAGAAATATCAGACAACCCAGGACAGGAG

CGAGCCACCTGCAGGGAAGAGAAGGCAGGCAGTTCGGGTCTCAGCAAACCATG

CCTCTCAGCAATTGGATCAACTGAAGGCGGTGCACCTCGCATCCGCGGTCAGGG

ACCTGGAGAGAGCGATGACGACGCTGAAACTTTGGGAATCCCCCCAAGAAATCT

CCAGGCATCAAGCACTGGGTTACAGTGTTATTACGTTTATGATCACAGCGGTGAA

GCGGTTAAGGGAATCCAAGATGCTGACTCTATCATGGTTCAATCAGGCCTTGATG

GTGATAGCACCCTCTCAGGAGGAGACAATGAATCTGAAAACAGCGATGTGGATA

TTGGCGAACCTGATACCGAGGGATATGCTATCACTGACCGGGGATCTGCTCCCAT

CTCTATGGGGTTCAGGGCTTCTGATGTTGAAACTGCAGAAGGAGGGGAGATCCA

CGAGCTCCTGAGACTCCAATCCAGAGGCAACAACTTTCCGAAGCTTGGGAAAAC

TCTCAATGTTCCTCCGCCCCCGGACCCCGGTAGGGCCAGCACTTCCGGGACACCC

ATTAAAAAGGGCACAGACGCGAGATTAGCCTCATTTGGAACGGAGATCGCGTCT

TTATTGACAGGTGGTGCAACCCAATGTGCTCGAAAGTCACCCTCGGAACCATCA

GGGCCAGGTGCACCTGCGGGGAATGTCCCCGAGTGTGTGAGCAATGCCGCACTG

ATACAGGAGTGGACACCCGAATCTGGTACCACAATCTCCCCGAGATCCCAGAAT

AATGAAGAAGGGGGAGACTATTATGATGATGAGCTGTTCTCTGATGTCCAAGAT

ATTAAAACAGCCTTGGCCAAAATACACGAGGATAATCAGAAGATAATCTCCAAG

CTAGAATCACTGCTGTTATTGAAGGGAGAAGTTGAGTCAATTAAGAAGCAGATC

AACAGGCAAAATATCAGCATATCCACCCTGGAAGGACACCTCTCAAGCATCATG

ATCGCCATTCCTGGACTTGGGAAGGATCCCAACGACCCCACTGCAGATGTCGAA

ATCAATCCCGACTTGAAACCCATCATAGGCAGAGATTCAGGCCGAGCACTGGCC

GAAGTTCTCAAGAAACCCGTTGCCAGCCGACAACTCCAAGGAATGACAAATGGA

CGGACCAGTTCCAGAGGACAGCTGCTGAAGGAATTTCAGCTAAAGCCGATCGGG

AAAAAGATGAGCTCAGCCGTCGGGTTTGTTCCTGACACCGGCCCTGCATCACGC

AGTGTAATCCGCTCCATTATAAAATCCAGCCGGCTAGAGGAGGATCGGAAGCGT

TACCTGATGACTCTCCTTGATGATATCAAAGGAGCCAATGATCTTGCCAAGTTCC

ACCAGATGCTGATGAAGATAATAATGAAGTAGCTACAGCTCAACTTACCTGCCA

ACCCCATGCCAGTCGACCCACCTAGTACAACCTAAATCCATTATAAAAAACTTA
```

-continued

```
GGAGCAAAGTGATTGCCTCCCAAGGTCCACAATGACAGAGACCTACGACTTCGA
CAAGTCGGCATGGGACATCAAAGGGTCGATCGCTCCGATACAACCCACCACCTA
CAGTGATGGCAGGCTGGTGCCCCAGGTCAGAGTCATAGATCCTGGTCTAGGCGA
CAGGAAGGATGAATGCTTTATGTACATGTTTCTGCTGGGGGTTGTTGAGGACAGC
GATTCCCTAGGGCCTCCAATCGGGCGAGCATTTGGGTTCCTGCCCTTAGGTGTTG
GCAGATCCACAGCAAAGCCCGAAAAACTCCTCAAAGAGGCCACTGAGCTTGACA
TAGTTGTTAGACGTACAGCAGGGCTCAATGAAAAACTGGTGTTCTACAACAACA
CCCCACTAACTCTCCTCACACCTTGGAGAAAGGTCCTAACAACAGGGAGTGTCTT
CAACGCAAACCAAGTGTGCAATGCGGTTAATCTGATACCGCTCGATACCCCGCA
GAGGTTCCGTGTTGTTTATATGAGCATCACCCGTCTTTCGGATAACGGGTATTAC
ACCGTTCCTAGAAGAATGCTGGAATTCAGATCGGTCAATGCAGTGGCCTTCAACC
TGCTGGTGACCCTTAGGATTGACAAGGCGATAGGCCCTGGGAAGATCATCGACA
ATACAGAGCAACTTCCTGAGGCAACATTTATGGTCCACATCGGGAACTTCAGGA
GAAAGAAGAGTGAAGTCTACTCTGCCGATTATTGCAAAATGAAAATCGAAAAGA
TGGGCCTGGTTTTTGCACTTGGTGGGATAGGGGGCACCAGTCTTCACATTAGAAG
CACAGGCAAAATGAGCAAGACTCTCCATGCACAACTCGGGTTCAAGAAGACCTT
ATGTTACCCGCTGATGGATATCAATGAAGACCTTAATCGATTACTCTGGAGGAGC
AGATGCAAGATAGTAAGAATCCAGGCAGTTTTGCAGCCATCAGTTCCTCAAGAA
TTCCGCATTTACGACGACGTGATCATAAATGATGACCAAGGACTATTCAAAGTTC
TGTAGACCGTAGTGCCCAGCAATGCCCGAAAACGACCCCCCTCACAATGACAGC
CAGAAGGCCCGGACAAAAAAGCCCCCTCCGAAAGACTCCACGGACCAAGCGAG
AGGCCAGCCAGCAGCCGACGGCAAGCGCGAACACCAGGCGGCCCCAGCACAGA
ACAGCCCTGACACAAGGCCACCACCAGCCACCCCAATCTGCATCCTCCTCGTGG
GACCCCCGAGGACCAACCCCCAAGGCTGCCCCCGATCCAAACCACCAACCGCAT
CCCCACCACCCCCGGGAAAGAAACCCCCAGCAATTGGAAGGCCCCTCCCCCTCT
TCCTCAACACAAGAACTCCACAACCGAACCGCACAAGCGACCGAGGTGACCCAA
CCGCAGGCATCCGACTCCCTAGACAGATCCTCTCTCCCCGGCAAACTAAACAAA
ACTTAGGGCCAAGGAACATACACACCCAACAGAACCCAGACCCCGGCCCACGGC
GCCGCGCCCCAACCCCCGACAACCAGAGGGAGCCCCCAACCAATCCCGCCGGC
TCCCCCGGTGCCCACAGGCAGGGACACCAACCCCCGAACAGACCCAGCACCCAA
CCATCGACAATCCAAGACGGGGGGCCCCCCAAAAAAAGGCCCCCAGGGGCC
GACAGCCAGCACCGCGAGGAAGCCCACCCACCCCACACACGACCACGGCAACC
AAACCAGAACCCAGACCACCCTGGGCCACCAGCTCCCAGACTCGGCCATCACCC
CGCAGAAAGGAAAGGCCACAACCCGCGCACCCCAGCCCCGATCCGGCGGGGAG
CCACCCAACCCGAACCAGCACCCAAGAGCGATCCCCGAAGGACCCCCGAACCGC
AAAGGACATCAGTATCCCACAGCCTCTCCAAGTCCCCCGGTCTCCTCCTCTTCTC
GAAGGGACCAAAAGATCAATCCACCACACCCGACGACACTCAACTCCCCACCCC
TAAAGGAGACACCGGGAATCCCAGAATCAAGACTCATCCAATGTCCATCATGGG
TCTCAAGGTGAACGTCTCTGCCATATTCATGGCAGTACTGTTAACTCTCCAAACA
CCCACCGGTCAAATCCATTGGGGCAATCTCTCTAAGATAGGGGTGGTAGGAATA
GGAAGTGCAAGCTACAAAGTTATGACTCGTTCCAGCCATCAATCATTAGTCATAA
```

-continued

AATTAATGCCCAATATAACTCTCCTCAATAACTGCACGAGGGTAGAGATTGCAG

AATACAGGAGACTACTGAGAACAGTTTTGGAACCAATTAGAGATGCACTTAATG

CAATGACCCAGAATATAAGACCGGTTCAGAGTGTAGCTTCAAGTAGGAGACACA

AGAGATTTGCGGGAGTAGTCCTGGCAGGTGCGGCCCTAGGCGTTGCCACAGCTG

CTCAGATAACAGCCGGCATTGCACTTCACCAGTCCATGCTGAACTCTCAAGCCAT

CGACAATCTGAGAGCGAGCCTGGAAACTACTAATCAGGCAATTGAGACAATCAG

ACAAGCAGGGCAGGAGATGATATTGGCTGTTCAGGGTGTCCAAGACTACATCAA

TAATGAGCTGATACCGTCTATGAACCAACTATCTTGTGATTTAATCGGCCAGAAG

CTCGGGCTCAAATTGCTCAGATACTATACAGAAATCCTGTCATTATTTGGCCCCA

GTTTACGGGACCCCATATCTGCGGAGATATCTATCCAGGCTTTGAGCTATGCGCT

TGGAGGAGACATCAATAAGGTGTTAGAAAAGCTCGGATACAGTGGAGGTGATTT

ACTGGGCATCTTAGAGAGCGGAGGAATAAAGGCCCGGATAACTCACGTCGACAC

AGAGTCCTACTTCATTGTCCTCAGTATAGCCTATCCGACGCTGTCCGAGATTAAG

GGGGTGATTGTCCACCGGCTAGAGGGGGTCTCGTACAACATAGGCTCTCAAGAG

TGGTATACCACTGTGCCCAAGTATGTTGCAACCCAAGGGTACCTTATCTCGAATT

TTGATGAGTCATCGTGTACTTTCATGCCAGAGGGGACTGTGTGCAGCCAAAATGC

CTTGTACCCGATGAGTCCTCTGCTCCAAGAATGCCTCCGGGGTACACCAAGTCC

TGTGCTCGTACACTCGTATCCGGGTCTTTTGGGAACCGGTTCATTTTATCACAAG

GGAACCTAATAGCCAATTGTGCATCAATCCTTTGCAAGTGTTACACAACAGGAA

CGATCATTAATCAAGACCCTGACAAGATCCTAACATACATTGCTGCCGATCACTG

CCCGGTAGTCGAGGTGAACGGCGTGACCATCCAAGTCGGGAGCAGGAGGTATCC

AGACGCTGTGTACTTGCACAGAATTGACCTCGGTCCTCCCATATCATTGGAGAGG

TTGGACGTAGGGACAAATCTGGGGAATGCAATTGCTAAGTTGGAGGATGCCAAG

GAATTGTTGGAGTCATCGGACCAGATATTGAGGAGTATGAAAGGTTTATCGAGC

ACTAGCATAGTCTACATCCTGATTGCAGTGTGTCTTGGAGGGTTGATAGGGATCC

CCGCTTTAATATGTTGCTGCAGGGGGCGTTGTAACAAAAAGGGAGAACAAGTTG

GTATGTCAAGACCAGGCCTAAAGCCTGATCTTACGGGAACATCAAAATCCTATG

TAAGGTCGCTCTGATCCTCTACAACTCTTGAAACACAAATGTCCCACAAGTCTCC

TCTTCGTCATCAAGCAACCACCGCACCCAGCATCAAGCCCACCTGAAATTATCTC

CGGCTTCCCTCTGGCCGAACAATATCGGTAGTTAATTAAAACTTAGGGTGCAAGA

TCATCGATAATGTCACCACAACGAGACCGGATAAATGCCTTCTACAAAGATAAC

CCCCATCCCAAGGGAAGTAGGATAGTCATTAACAGAGAACATCTTATGATTGAT

AGACCTTATGTTTTGCTGGCTGTTCTGTTTGTCATGTTTCTGAGCTTGATCGGGTT

GCTAGCCATTGCAGGAATTCGACTTCATCGGGCAGCCATCTACACCGCAGAGAT

CCATAAAAGCCTCAGCACCAATCTAGATGTAACTAACTCAATCGAGCATCAGGT

CAAGGACGTGCTGACACCACTCTTCAAAATCATCGGTGATGAAGTGGGCCTGAG

GACACCTCAGAGATTCACTGACCTAGTGAAATTAATCTCTGACAAGATTAAATTC

CTTAATCCGGATAGGGAGTACGACTTCAGAGATCTCACTTGGTGTATCAACCCGC

CAGAGAGAATCAAATTGGATTATGATCAATACTGTGCAGATGTGGCTGCTGAAG

AGCTCATGAATGCATTGGTGAACTCAACTCTACTGGAGACCAGAACAACCAATC

-continued

```
AGTTCCTAGCTGTCTCAAAGGGAAACTGCTCAGGGCCCACTACAATCAGAGGTC
AATTCTCAAACATGTCGCTGTCCCTGTTAGACTTGTATTTAGGTCGAGGTTACAA
TGTGTCATCTATAGTCACTATGACATCCCAGGGAATGTATGGGGGAACTTACCTA
GTGGAAAAGCCTAATCTGAGCAGCAAAAGGTCAGAGTTGTCACAACTGAGCATG
TACCGAGTGTTTGAAGTAGGTGTTATCAGAAATCCGGGTTTGGGGGCTCCGGTGT
TCCATATGACAAACTATCTTGAGCAACCAGTCAGTAATGATCTCAGCAACTGTAT
GGTGGCTTTGGGGGAGCTCAAACTCGCAGCCCTTTGTCACGGGGAAGATTCTATC
ACAATTCCCTATCAGGGATCAGGGAAAGGTGTCAGCTTCCAGCTCGTCAAGCTA
GGTGTCTGGAAATCCCCAACCGACATGCAATCCTGGGTCCCCTTATCAACGGATG
ATCCAGTGATAGACAGGCTTTACCTCTCATCTCACAGAGGTGTTATCGCTGACAA
CCAAGCAAAATGGGCTGTCCCGACAACACGAACAGATGACAAGTTGCGAATGG
AGACATGCTTCCAACAGGCGTGTAAGGGTAAAATCCAAGCACTCTGCGAGAATC
CCGAGTGGGCACCATTGAAGGATAACAGGATTCCTTCATACGGGGTCTTGTCTGT
TGATCTGAGTCTGACAGTTGAGCTTAAAATCAAAATTGCTTCGGGATTCGGGCCA
TTGATCACACACGGTTCAGGGATGGACCTATACAAATCCAACCACAACAATGTG
TATTGGCTGACTATCCCGCCAATGAAGAACCTAGCCTTAGGTGTAATCAACACAT
TGGAGTGGATACCGAGATTCAAGGTTAGTCCCTACCTCTTCACTGTCCCAATTAA
GGAAGCAGGCGAAGACTGCCATGCCCCAACATACCTACCTGCGGAGGTGGATGG
TGATGTCAAACTCAGTTCCAATCTGGTGATTCTACCTGGTCAAGATCTCCAATAT
GTTTTGGCAACCTACGATACTTCCAGGGTTGAACATGCTGTGGTTTATTACGTTT
ACAGCCCAAGCCGCTCATTTTCTTACTTTTATCCTTTTAGGTTGCCTATAAAGGGG
GTCCCCATCGAATTACAAGTGGAATGCTTCACATGGGACCAAAAACTCTGGTGC
CGTCACTTCTGTGTGCTTGCGGACTCAGAATCTGGTGGACATATCACTCACTCTG
GGATGGTGGGCATGGGAGTCAGCTGCACAGTCACCCGGGAAGATGGAACCAATC
GCAGATAGGGCTGCTAGTGAACCAATCACATGATGTCACCCAGACATCAGGCAT
ACCCACTAGTGTGAAATAGACATCAGAATTAAGAAAAACGTAGGGTCCAAGTGG
TTCCCCGTTATGGACTCGCTATCTGTCAACCAGATCTTATACCCTGAAGTTCACCT
AGATAGCCCGATAGTTACCAATAAGATAGTAGCCATCCTGGAGTATGCTCGAGT
CCCTCACGCTTACAGCCTGGAGGACCCTACACTGTGTCAGAACATCAAGCACCG
CCTAAAAAACGGATTTTCCAACCAAATGATTATAAACAATGTGGAAGTTGGGAA
TGTCATCAAGTCCAAGCTTAGGAGTTATCCGGCCCACTCTCATATTCCATATCCA
AATTGTAATCAGGATTTATTTAACATAGAAGACAAAGAGTCAACGAGGAAGATC
CGTGAACTCCTCAAAAAGGGGAATTCGCTGTACTCCAAAGTCAGTGATAAGGTT
TTCCAATGCTTAAGGGACACTAACTCACGGCTTGGCCTAGGCTCCGAATTGAGGG
AGGACATCAAGGAGAAAGTTATTAACTTGGGAGTTTACATGCACAGCTCCCAGT
GGTTTGAGCCCTTTCTGTTTTGGTTTACAGTCAAGACTGAGATGAGGTCAGTGAT
TAAATCACAAACCCATACTTGCCATAGGAGGAGACACACACCTGTATTCTTCACT
GGTAGTTCAGTTGAGTTGCTAATCTCTCGTGACCTTGTTGCTATAATCAGTAAAG
AGTCTCAACATGTATATTACCTGACATTTGAACTGGTTTTGATGTATTGTGATGTC
ATAGAGGGGAGGTTAATGACAGAGACCGCTATGACTATTGATGCTAGGTATACA
GAGCTTCTAGGAAGAGTCAGATACATGTGGAAACTGATAGATGGTTTCTTCCCTG
```

```
CACTCGGGAATCCAACTTATCAAATTGTAGCCATGCTGGAGCCTCTTTCACTTGC

TTACCTGCAGCTGAGGGATATAACAGTAGAACTCAGAGGTGCTTTCCTTAACCAC

TGCTTTACTGAAATACATGATGTTCTTGACCAAAACGGGTTTTCTGATGAAGGTA

CTTATCATGAGTTAACTGAAGCTCTAGATTACATTTTCATAACTGATGACATACA

TCTGACAGGGGAGATTTTCTCATTTTTCAGAAGTTTCGGCCACCCCAGACTTGAA

GCAGTAACGGCTGCTGAAAATGTTAGGAAATACATGAATCAGCCTAAAGTCATT

GTGTATGAGACTCTGATGAAAGGTCATGCCATATTTTGTGGAATCATAATCAACG

GCTATCGTGACAGGCACGGAGGCAGTTGGCCACCGCTGACCCTCCCCCTGCATG

CTGCAGACACAATCCGGAATGCTCAAGCTTCAGGTGAAGGGTTAACACATGAGC

AGTGCGTTGATAACTGGAAATCTTTTGCTGGAGTGAAATTTGGCTGCTTTATGCC

TCTTAGCCTGGATAGTGATCTGACAATGTACCTAAAGGACAAGGCACTTGCTGCT

CTCCAAAGGGAATGGGATTCAGTTTACCCGAAAGAGTTCCTGCGTTACGACCCTC

CCAAGGGAACCGGGTCACGGAGGCTTGTAGATGTTTTCCTTAATGATTCGAGCTT

TGACCCATATGATGTGATAATGTATGTTGTAAGTGGAGCTTACCTCCATGACCCT

GAGTTCAACCTGTCTTACAGCCTGAAAGAAAAGGAGATCAAGGAAACAGGTAGA

CTTTTTGCTAAAATGACTTACAAAATGAGGGCATGCCAAGTGATTGCTGAAAATC

TAATCTCAAACGGGATTGGCAAATATTTTAAGGACAATGGGATGGCCAAGGATG

AGCACGATTTGACTAAGGCACTCCACACTCTAGCTGTCTCAGGAGTCCCCAAAG

ATCTCAAAGAAAGTCACAGGGGGGGCCAGTCTTAAAAACCTACTCCCGAAGCC

CAGTCCACACAAGTACCAGGAACGTGAGAGCAGCAAAAGGGTTTATAGGGTTCC

CTCAAGTAATTCGGCAGGACCAAGACACTGATCATCCGGAGAATATGGAAGCTT

ACGAGACAGTCAGTGCATTTATCACGACTGATCTCAAGAAGTACTGCCTTAATTG

GAGATATGAGACCATCAGCTTGTTTGCACAGAGGCTAAATGAGATTTACGGATT

GCCCTCATTTTTCCAGTGGCTGCATAAGAGGCTTGAGACCTCTGTCCTGTATGTA

AGTGACCCTCATTGCCCCCCCGACCTTGACGCCCATATCCCGTTATATAAAGTCC

CCAATGATCAAATCTTCATTAAGTACCCTATGGGAGGTATAGAAGGGTATTGTCA

GAAGCTGTGGACCATCAGCACCATTCCCTATCTATACCTGGCTGCTTATGAGAGC

GGAGTAAGGATTGCTTCGTTAGTGCAAGGGGACAATCAGACCATAGCCGTAACA

AAAAGGGTACCCAGCACATGGCCCTACAACCTTAAGAAACGGGAAGCTGCTAGA

GTAACTAGAGATTACTTTGTAATTCTTAGGCAAAGGCTACATGATATTGGCCATC

ACCTCAAGGCAAATGAGACAATTGTTTCATCACATTTTTTGTCTATTCAAAAGG

AATATATTATGATGGGCTACTTGTGTCCCAATCACTCAAGAGCATCGCAAGATGT

GTATTCTGGTCAGAGACTATAGTTGATGAAACAAGGGCAGCATGCAGTAATATT

GCTACAACAATGGCTAAAAGCATCGAGAGAGGTTATGACCGTTACCTTGCATAT

TCCCTGAACGTCCTAAAAGTGATACAGCAAATTCTGATCTCTCTTGGCTTCACAA

TCAATTCAACCATGACCCGGGATGTAGTCATACCCCTCCTCACAAACAACGACCT

CTTAATAAGGATGGCACTGTTGCCCGCTCCTATTGGGGGATGAATTATCTGAAT

ATGAGCAGGCTGTTTGTCAGAAACATCGGTGATCCAGTAACATCATCAATTGCTG

ATCTCAAGAGAATGATTCTCGCCTCACTAATGCCTGAAGAGACCCTCCATCAGGT

AATGACACAACAACCGGGGGACTCTTCATTCCTAGACTGGGCTAGCGACCCTTA
```

-continued

```
CTCAGCAAATCTTGTATGTGTCCAGAGCATCACTAGACTCCTCAAGAACATAACT

GCAAGGTTTGTCCTGATCCATAGTCCAAACCCAATGTTAAAAGGATTATTCCATG

ATGACAGTAAAGAAGAGGACGAGGGACTGGCGGCATTCCTCATGGACAGGCAT

ATTATAGTACCTAGGGCAGCTCATGAAATCCTGGATCATAGTGTCACAGGGGCA

AGAGAGTCTATTGCAGGCATGCTGGATACCACAAAAGGCTTGATTCGAGCCAGC

ATGAGGAAGGGGGGTTTAACCTCTCGAGTGATAACCAGATTGTCCAATTATGAC

TATGAACAATTCAGAGCAGGGATGGTGCTATTGACAGGAAGAAAGAGAAATGTC

CTCATTGACAAAGAGTCATGTTCAGTGCAGCTGGCGAGAGCTCTAAGAAGCCAT

ATGTGGGCGAGGCTAGCTCGAGGACGGCCTATTTACGGCCTTGAGGTCCCTGAT

GTACTAGAATCTATGCGAGGCCACCTTATTCGGCGTCATGAGACATGTGTCATCT

GCGAGTGTGGATCAGTCAACTACGGATGGTTTTTGTCCCCTCGGGTTGCCAACT

GGATGATATTGACAAGGAAACATCATCCTTGAGAGTCCCATATATTGGTTCTACC

ACTGATGAGAGAACAGACATGAAGCTTGCCTTCGTAAGAGCCCCAAGTCGATCC

TTGCGATCTGCTGTTAGAATAGCAACAGTGTACTCATGGGCTTACGGTGATGATG

ATAGCTCTTGGAACGAAGCCTGGTTGTTGGCTAGGCAAAGGGCCAATGTGAGCC

TGGAGGAGCTAAGGGTGATCACTCCCATCTCAACTTCGACTAATTTAGCGCATAG

GTTGAGGGATCGTAGCACTCAAGTGAAATACTCAGGTACATCCCTTGTCCGAGTG

GCGAGGTATACCACAATCTCCAACGACAATCTCTCATTTGTCATATCAGATAAGA

AGGTTGATACTAACTTTATATACCAACAAGGAATGCTTCTAGGGTTGGGTGTTTT

AGAAACATTGTTTCGACTCGAGAAAGATACCGGATCATCTAACACGGTATTACA

TCTTCACGTCGAAACAGATTGTTGCGTGATCCCGATGATAGATCATCCCAGGATA

CCCAGCTCCCGCAAGCTAGAGCTGAGGGCAGAGCTATGTACCAACCCATTGATA

TATGATAATGCACCTTTAATTGACAGAGATGCAACAAGGCTATACACCCAGAGC

CATAGGAGGCACCTTGTGGAATTTGTTACATGGTCCACACCCCAACTATATCACA

TTTTAGCTAAGTCCACAGCACTATCTATGATTGACCTGGTAACAAAATTTGAGAA

GGACCATATGAATGAAATTTCAGCTCTCATAGGGGATGACGATATCAATAGTTTC

ATAACTGAGTTTCTGCTCATAGAGCCAAGATTATTCACTATCTACTTGGGCCAGT

GTGCGGCCATCAATTGGGCATTTGATGTACATTATCATAGACCATCAGGGAAATA

TCAGATGGGTGAGCTGTTGTCATCGTTCCTTTCTAGAATGAGCAAAGGAGTGTTT

AAGGTGCTTGTCAATGCTCTAAGCCACCCAAAGATCTACAAGAAATTCTGGCATT

GTGGTATTATAGAGCCTATCCATGGTCCTTCACTTGATGCTCAAAACTTGCACAC

AACTGTGTGCAACATGGTTTACACATGCTATATGACCTACCTCGACCTGTTGTTG

AATGAAGAGTTAGAAGAGTTCACATTTCTCTTGTGTGAAAGCGACGAGGATGTA

GTACCGGACAGATTCGACAACATCCAGGCAAAACACTTATGTGTTCTGGCAGAT

TTGTACTGTCAACCAGGGACCTGCCCACCAATTCGAGGTCTAAGACCGGTAGAG

AAATGTGCAGTTCTAACCGACCATATCAAGGCAGAGGCTATGTTATCTCCAGCA

GGATCTTCGTGGAACATAAATCCAATTATTGTAGACCATTACTCATGCTCCCTGA

CTTATCTCCGGCGAGGATCGATCAAACAGATAAGATTGAGAGTTGATCCAGGAT

TCATTTTCGACGCCCTCGCTGAGGTAAATGTCAGTCAGCCAAAGATCGGCAGCA

ACAACATCTCAAATATGAGCATCAAGGCTTTCAGACCCCCACACGATGATGTTG

CAAAATTGCTCAAAGATATCAACACAAGCAAGCACAATCTTCCCATTTCAGGGG
```

-continued

```
GCAATCTCGCCAATTATGAAATCCATGCTTTCCGCAGAATCGGGTTGAACTCATC
TGCTTGCTACAAAGCTGTTGAGATATCAACATTAATTAGGAGATGCCTTGAGCCA
GGGGAGGACGGCTTGTTCTTGGGTGAGGGATCGGGTTCTATGTTGATCACTTATA
AGGAGATACTTAAACTAAACAAGTGCTTCTATAATAGTGGGGTTTCCGCCAATTC
TAGATCTGGTCAAAGGGAATTAGCACCCTATCCCTCCGAAGTTGGCCTTGTCGAA
CACAGAATGGGAGTAGGTAATATTGTCAAAGTGCTCTTTAACGGGAGGCCCGAA
GTCACGTGGGTAGGCAGTGTAGATTGCTTCAATTTCATAGTTAGTAATATCCCTA
CCTCTAGTGTGGGGTTTATCCATTCAGATATAGAGACCTTGCCTGACAAAGATAC
TATAGAGAAGCTAGAGGAATTGGCAGCCATCTTATCGATGGCTCTGCTCCTGGGC
AAAATAGGATCAATACTGGTGATTAAGCTTATGCCTTTCAGCGGGGATTTTGTTC
AGGGATTTATAAGTTATGTAGGGTCTCATTATAGAGAAGTGAACCTTGTATACCC
TAGATACAGCAACTTCATATCTACTGAATCTTATTTGGTTATGACAGATCTCAAG
GCTAACCGGCTAATGAATCCTGAAAAGATTAAGCAGCAGATAATTGAATCATCT
GTGAGGACTTCACCTGGACTTATAGGTCACATCCTATCCATTAAGCAACTAAGCT
GCATACAAGCAATTGTGGGAGACGCAGTTAGTAGAGGTGATATCAATCCTACTC
TGAAAAAACTTACACCTATAGAGCAGGTGCTGATCAATTGCGGGTTGGCAATTA
ACGGACCTAAGCTGTGCAAAGAATTGATCCACCATGATGTTGCCTCAGGGCAAG
ATGGATTGCTTAATTCTATACTCATCCTCTACAGGGAGTTGGCAAGATTCAAAGA
CAACCAAAGAAGTCAACAAGGGATGTTCCACGCCTACCCCGTATTGGTAAGTAG
CAGGCAACGAGAACTTATATCTAGGATCACCCGCAAATTTTGGGGGCACATTCTT
CTTTACTCCGGGAACAAAAAGTTGATAAATAAGTTTATCCAGAATCTCAAGTCCG
GCTATCTGATACTAGACTTACACCAGAATATCTTCGTTAAGAATCTATCCAAGTC
AGAGAAACAGATTATTATGACGGGGGGTTTGAAACGTGAGTGGGTTTTTAAGGT
AACAGTCAAGGAGACCAAAGAATGGTATAAGTTAGTCGGATACAGTGCCCTGAT
TAAGGACTAATTGGTTGAACTCCGGAACCCTAATCCTGCCCTAGGTGGTTAGGCA
TTATTTGCAATATATTAAAGAAAACTTTGAAAATACGAAGTTTCTATTCCCAGCT
TTGTCTGGTggccggcatAgtcccagcctcctcgctggcgctggctgggcaacattccgagggggaccgtccccAcggtaa
tggcgaatgggacgcggccgatccggctgctaacaaagcccgaaaggaagctgagttggctgctgGcGcTGgctgGgcaata
actagcataaccccttggggcctctaaacgggtcttgagggtttttttgctgaaaggaggaactatatccggatgcGGCCGC
GCGCTTGGCGTAATCATGGTCATAGCTGTTTCCTGTGTGAAATTGTTATCCGCTCAC
AATTCCACACAACATACGAGCCGGAAGCATAAAGTGTAAAGCCTGGGGTGCCTA
ATGAGTGAGCTAACTCACATTAATTGCGTTGCGCTCACTGCCCGCTTTCCAGTCG
GGAAACCTGTCGTGCCAGCTGCATTAATGAATCGGCCAACGCGCGGGGAGAGGC
GGTTTGCGTATTGGGCGCTCTTCCGCTTCCTCGCTCACTGACTCGCTGCGCTCGGT
CGTTCGGCTGCGGCGAGCGGTATCAGCTCACTCAAAGGCGGTAATACGGTTATC
CACAGAATCAGGGGATAACGCAGGAAAGAACATGTGAGCAAAAGGCCAGCAAA
AGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGA
CAGGACTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGGGAAGC
```

```
GTGGCGCTTTCTCATAGCTCACGCTGTAGGTATCTCAGTTCGGTGTAGGTCGTTC

GCTCCAAGCTGGGCTGTGTGCACGAACCCCCCGTTCAGCCCGACCGCTGCGCCTT

ATCCGGTAACTATCGTCTTGAGTCCAACCCGGTAAGACACGACTTATCGCCACTG

GCAGCAGCCACTGGTAACAGGATTAGCAGAGCGAGGTATGTAGGCGGTGCTACA

GAGTTCTTGAAGTGGTGGCCTAACTACGGCTACACTAGAAGGACAGTATTTGGT

ATCTGCGCTCTGCTGAAGCCAGTTACCTTCGGAAAAAGAGTTGGTAGCTCTTGAT

CCGGCAAACAAACCACCGCTGGTAGCGGTGGTTTTTTTGTTTGCAAGCAGCAGAT

TACGCGCAGAAAAAAAGGATCTCAAGAAGATCCTTTGATCTTTTCTACGGGGTCT

GACGCTCAGTGGAACGAAAACTCACGTTAAGGGATTTTGGTCATGAGATTATCA

AAAAGGATCTTCACCTAGATCCTTTTAAATTAAAAATGAAGTTTTAAATCAATCT

AAAGTATATATGAGTAAACTTGGTCTGACAGTTACCAATGCTTAATCAGTGAGGC

ACCTATCTCAGCGATCTGTCTATTTCGTTCATCCATAGTTGCCTGACTCCCCGTCG

TGTAGATAACTACGATACGGGAGGGCTTACCATCTGGCCCCAGTGCTGCAATGA

TACCGCGAGACCCACGCTCACCGGCTCCAGATTTATCAGCAATAAACCAGCCAG

CCGGAAGGGCCGAGCGCAGAAGTGGTCCTGCAACTTTATCCGCCTCCATCCAGT

CTATTAATTGTTGCCGGGAAGCTAGAGTAAGTAGTTCGCCAGTTAATAGTTTGCG

CAACGTTGTTGCCATTGCTACAGGCATCGTGGTGTCACGCTCGTCGTTTGGTATG

GCTTCATTCAGCTCCGGTTCCCAACGATCAAGGCGAGTTACATGATCCCCCATGT

TGTGCAAAAAAGCGGTTAGCTCCTTCGGTCCTCCGATCGTTGTCAGAAGTAAGTT

GGCCGCAGTGTTATCACTCATGGTTATGGCAGCACTGCATAATTCTCTTACTGTC

ATGCCATCCGTAAGATGCTTTTCTGTGACTGGTGAGTACTCAACCAAGTCATTCT

GAGAATAGTGTATGCGGCGACCGAGTTGCTCTTGCCCGGCGTCAATACGGGATA

ATACCGCGCCACATAGCAGAACTTTAAAAGTGCTCATCATTGGAAAACGTTCTTC

GGGGCGAAAACTCTCAAGGATCTTACCGCTGTTGAGATCCAGTTCGATGTAACCC

ACTCGTGCACCCAACTGATCTTCAGCATCTTTTACTTTCACCAGCGTTTCTGGGTG

AGCAAAAACAGGAAGGCAAAATGCCGCAAAAAAGGGAATAAGGGCGACACGG

AAATGTTGAATACTCATACTCTTCCTTTTTCAATATTATTGAAGCATTTATCAGGG

TTATTGTCTCATGAGCGGATACATATTTGAATGTATTTAGAAAAATAAACAAATA

GGGGTTCCGCGCACATTTCCCCGAAAAGTGCCACCTG.
```

In another embodiment, the nucleic acid comprises the sequence of SEQ ID NO: 4, shown below:

```
GGACGCGCCCTGTAGCGGCGCATTAAGCGCGGCGGGTGTGGTGGTTACGCGCAG

CGTGACCGCTACACTTGCCAGCGCCCTAGCGCCCGCTCCTTTCGCTTTCTTCCCTT

CCTTTCTCGCCACGTTCGCCGGCTTTCCCCGTCAAGCTCTAAATCGGGGGCTCCC

TTTAGGGTTCCGATTTAGTGCTTTACGGCACCTCGACCCCAAAAAACTTGATTAG

GGTGATGGTTCACGTAGTGGGCCATCGCCCTGATAGACGGTTTTTCGCCCTTTGA

CGTTGGAGTCCACGTTCTTTAATAGTGGACTCTTGTTCCAAACTGGAACAACACT

CAACCCTATCTCGGTCTATTCTTTTGATTTATAAGGGATTTTGCCGATTTCGGCCT

ATTGGTTAAAAAATGAGCTGATTTAACAAAAATTTAACGCGAATTTTAACAAAA

TATTAACGTTTACAATTTCGCGCCATTCGCCATTCAGGCTGCGCAACTGTTGGGA
```

-continued

```
AGGGCGATCGGTGCGGGCCTCTTCGCTATTACGCCAGCTGGCGAAAGGGGGATG

TGCTGCAAGGCGATTAAGTTGGGTAACGCCAGGGTTTTCCCAGTCACGACGTTGT

AAAACGACGGCCAGTGCGCGCCGTTAATACGACTCACTATAGGGAGACCCAAGC

TGGCTAGCTTTGTTTGGTCTGATGAGTCCCGTGAGGACGAAACCCGGCGTACCGG

GTCACCAAACAAAGTTGGGTAAGGATAGTTCAATCAATGATCATCTTCTAGTGCA

CTTAGGATTCAAGATCCTATTATCAGGGACAAGAGCAGGATTAGGGATATCCGA

GATGGCCACACTTTTAAGGAGCTTAGCATTGTTCAAAAGAAACAAGGACAAACC

ACCCATTACATCAGGATCCGGTGGAGCCATCAGAGGAATCAAACACATTATTAT

AGTACCAATCCCTGGAGATTCCTCAATTACCACTCGATCCAGACTTCTGGACCGG

TTGGTGAGGTTAATTGGAAACCCGGATGTGAGCGGGCCCAAACTAACAGGGGCA

CTAATAGGTATATTATCCTTATTTGTGGAGTCTCCAGGTCAATTGATTCAGAGGA

TCACCGATGACCCTGACGTTAGCATAAGGCTGTTAGAGGTTGTCCAGAGTGACC

AGTCACAATCTGGCCTTACCTTCGCATCAAGAGGTACCAACATGGAGGATGAGG

CGGACCAATACTTTTCACATGATGATCCAATTAGTAGTGATCAATCCAGGTTCGG

ATGGTTCGGGAACAAGGAAATCTCAGATATTGAAGTGCAAGACCCTGAGGGATT

CAACATGATTCTGGGTACCATCCTAGCCCAAATTTGGGTCTTGCTCGCAAAGGCG

GTTACGGCCCCAGACACGGCAGCTGATTCGGAGCTAAGAAGGTGGATAAAGTAC

ACCCAACAAAGAAGGGTAGTTGGTGAATTTAGATTGGAGAGAAAATGGTTGGAT

GTGGTGAGGAACAGGATTGCCGAGGACCTCTCCTTACGCCGATTCATGGTCGCTC

TAATCCTGGATATCAAGAGAACACCCGGAAACAAACCCAGGATTGCTGAAATGA

TATGTGACATTGATACATATATCGTAGAGGCAGGATTAGCCAGTTTTATCCTGAC

TATTAAGTTTGGGATAGAAACTATGTATCCTGCTCTTGGACTGCATGAATTTGCT

GGTGAGTTATCCACACTTGAGTCCTTGATGAACCTTTACCAGCAAATGGGGGAA

ACTGCACCCTACATGGTAATCCTGGAGAACTCAATTCAGAACAAGTTCAGTGCA

GGATCATACCCTCTGCTCTGGAGCTATGCCATGGGAGTAGGAGTGGAACTTGAA

AACTCCATGGGAGGTTTGAACTTTGGCCGATCTTACTTTGATCCAGCATATTTTA

GATTAGGGCAAGAGATGGTAAGGAGGTCAGCTGGAAAGGTCAGTTCCACATTGG

CATCTGAACTCGGTATCACTGCCGAGGATGCAAGGCTTGTTTCAGAGATTGCAAT

GCATACTACTGAGGACAAGATCAGTAGAGCGGTTGGACCCAGACAAGCCCAAGT

ATCATTTCTACACGGTGATCAAAGTGAGAATGAGCTACCGAGATTGGGGGGCAA

GGAAGATAGGAGGGTCAAACAGAGTCGAGGAGAAGCCAGGGAGAGCTACAGAG

AAACCGGGCCCAGCAGAGCAAGTGATGCGAGAGCTGCCCATCTTCCAACCGGCA

CACCCCTAGACATTGACACTGCAACGGAGTCCAGCCAAGATCCGCAGGACAGTC

GAAGGTCAGCTGACGCCCTGCTTAGGCTGCAAGCCATGGCAGGAATCTCGGAAG

AACAAGGCTCAGACACGGACACCCCTATAGTGTACAATGACAGAAATCTTCTAG

ACTAGGTGCGAGAGGCCGAGGGCCAGAACAACATCCGCCTACCATCCATCATTG

TTATAAAAAACTTAGGAACCAGGTCCACACAGCCGCCAGCCCATCAACCATCCA

CTCCCACGATTGGAGCCAATGGCAGAAGAGCAGGCACGCCATGTCAAAAACGG

ACTGGAATGCATCCGGGCTCTCAAGGCCGAGCCCATCGGCTCACTGGCCATCGA

GGAAGCTATGGCAGCATGGTCAGAAATATCAGACAACCCAGGACAGGAGCGAG
```

-continued

```
CCACCTGCAGGGAAGAGAAGGCAGGCAGTTCGGGTCTCAGCAAACCATGCCTCT
CAGCAATTGGATCAACTGAAGGCGGTGCACCTCGCATCCGCGGTCAGGGACCTG
GAGAGAGCGATGACGACGCTGAAACTTTGGGAATCCCCCCAAGAAATCTCCAGG
CATCAAGCACTGGGTTACAGTGTTATTACGTTTATGATCACAGCGGTGAAGCGGT
TAAGGGAATCCAAGATGCTGACTCTATCATGGTTCAATCAGGCCTTGATGGTGAT
AGCACCCTCTCAGGAGGAGACAATGAATCTGAAAACAGCGATGTGGATATTGGC
GAACCTGATACCGAGGGATATGCTATCACTGACCGGGGATCTGCTCCCATCTCTA
TGGGGTTCAGGGCTTCTGATGTTGAAACTGCAGAAGGAGGGGAGATCCACGAGC
TCCTGAGACTCCAATCCAGAGGCAACAACTTTCCGAAGCTTGGGAAAACTCTCA
ATGTTCCTCCGCCCCCGGACCCCGGTAGGGCCAGCACTTCCGGGACACCCATTAA
AAAGGGCACAGACGCGAGATTAGCCTCATTTGGAACGGAGATCGCGTCTTTATT
GACAGGTGGTGCAACCCAATGTGCTCGAAAGTCACCCTCGGAACCATCAGGGCC
AGGTGCACCTGCGGGGAATGTCCCCGAGTGTGTGAGCAATGCCGCACTGATACA
GGAGTGGACACCCGAATCTGGTACCACAATCTCCCCGAGATCCCAGAATAATGA
AGAAGGGGGAGACTATTATGATGATGAGCTGTTCTCTGATGTCCAAGATATTAA
AACAGCCTTGGCCAAAATACACGAGGATAATCAGAAGATAATCTCCAAGCTAGA
ATCACTGCTGTTATTGAAGGGAGAAGTTGAGTCAATTAAGAAGCAGATCAACAG
GCAAAATATCAGCATATCCACCCTGGAAGGACACCTCTCAAGCATCATGATCGC
CATTCCTGGACTTGGGAAGGATCCCAACGACCCCACTGCAGATGTCGAAATCAA
TCCCGACTTGAAACCCATCATAGGCAGAGATTCAGGCCGAGCACTGGCCGAAGT
TCTCAAGAAACCCGTTGCCAGCCGACAACTCCAAGGAATGACAAATGGACGGAC
CAGTTCCAGAGGACAGCTGCTGAAGGAATTTCAGCTAAAGCCGATCGGGAAAAA
GATGAGCTCAGCCGTCGGGTTTGTTCCTGACACCGGCCCTGCATCACGCAGTGTA
ATCCGCTCCATTATAAAATCCAGCCGGCTAGAGGAGGATCGGAAGCGTTACCTG
ATGACTCTCCTTGATGATATCAAAGGAGCCAATGATCTTGCCAAGTTCCACCAGA
TGCTGATGAAGATAATAATGAAGTAGCTACAGCTCAACTTACCTGCCAACCCCAT
GCCAGTCGATCATCCATCATTGTTATAAAAAACTTAGGAACCAggtccacacaGagtgat
ACGCGTACGCCACCATGTTCGTGTTTCTGGTGCTGCTGCCTCTGGTGAGCTCCCA
GTGCGTGAACCTGACCACAAGGACCCAGCTGCCCCCTGCCTATACCAATTCCTTC
ACACGGGCGTGTACTATCCCGACAAGGTGTTCCGGAGCAGCGTGCTGCACTCC
ACACAGGATCTGTTTCTGCCTTTCTTTTCTAACGTGACCTGGTTCCACGCCATCCA
CGTGAGCGGCACCAATGGCACAAAGCGGTTCGACAATCCAGTGCTGCCCTTTAA
CGATGGCGTGTACTTCGCCTCCACCGAGAAGTCTAACATCATCAGAGGCTGGAT
CTTTGGCACCACACTGGACAGCAAGACACAGTCCCTGCTGATCGTGAACAATGC
CACCAACGTGGTCATCAAGGTGTGCGAGTTCCAGTTTTGTAATGATCCATTCCTG
GGCGTGTACTATCACAAGAACAATAAGTCTTGGATGGAGAGCGAGTTTCGCGTG
TATTCCTCTGCCAACAATTGCACATTTGAGTACGTGTCCCAGCCCTTCCTGATGG
ACCTGGAGGGCAAGCAGGGCAATTTCAAGAACCTGAGGGAGTTCGTGTTTAAGA
ATATCGATGGCTACTTCAAAATCTACTCCAAGCACACCCCAATCAACCTGGTGCG
CGACCTGCCACAGGGCTTCTCTGCCCTGGAGCCACTGGTGGATCTGCCCATCGGC
ATCAACATCACCCGGTTTCAGACACTGCTGGCCCTGCACAGAAGCTACCTGACA
```

-continued

```
CCAGGCGACAGCTCCTCTGGATGGACCGCAGGAGCAGCAGCCTACTATGTGGGC
TATCTGCAGCCCAGGACCTTCCTGCTGAAGTACAACGAGAATGGCACCATCACA
GACGCCGTGGATTGCGCCCTGGATCCCCTGTCTGAGACCAAGTGTACACTGAAG
AGCTTTACCGTGGAGAAGGGCATCTATCAGACAAGCAATTTCAGGGTGCAGCCT
ACCGAGTCCATCGTGCGCTTTCCCAATATCACAAACCTGTGCCCTTTTGGCGAGG
TGTTCAACGCAACCCGCTTCGCCAGCGTGTACGCCTGGAATAGGAAGCGCATCT
CCAACTGCGTGGCCGACTATTCTGTGCTGTACAACAGCGCCTCCTTCTCTACCTTT
AAGTGCTATGGCGTGAGCCCCACAAAGCTGAATGACCTGTGCTTTACCAACGTGT
ACGCCGATTCCTTCGTGATCAGGGGCGACGAGGTGCGCCAGATCGCACCAGGAC
AGACAGGCAAGATCGCAGACTACAATTATAAGCTGCCTGACGATTTCACCGGCT
GCGTGATCGCCTGGAACTCTAACAATCTGGATAGCAAAGTGGGCGGCAACTACA
ATTATCTGTACCGGCTGTTTAGAAAGTCTAATCTGAAGCCATTCGAGAGGGACAT
CTCCACAGAAATCTACCAGGCCGGCTCTACCCCCTGCAATGGCGTGGAGGGCTTT
AACTGTTATTTCCCTCTGCAGAGCTACGGCTTCCAGCCAACAAACGGCGTGGGCT
ATCAGCCCTACCGCGTGGTGGTGCTGTCTTTTGAGCTGCTGCACGCACCTGCAAC
AGTGTGCGGACCAAAGAAGAGCACCAATCTGGTGAAGAACAAGTGCGTGAACTT
CAACTTCAACGGACTGACCGGAACAGGCGTGCTGACCGAGTCCAACAAGAAGTT
CCTGCCTTTTCAGCAGTTCGGCAGGGACATCGCAGATACCACAGACGCCGTGCG
CGACCCTCAGACCCTGGAGATCCTGGACATCACACCATGCTCCTTCGGCGGCGTG
TCTGTGATCACACCAGGCACCAATACAAGCAACCAGGTGGCCGTGCTGTATCAG
GACGTGAATTGTACCGAGGTGCCAGTGGCAATCCACGCAGATCAGCTGACCCCT
ACATGGCGGGTGTACTCTACCGGCAGCAACGTGTTCCAGACAAGAGCCGGATGC
CTGATCGGAGCAGAGCACGTGAACAATAGCTATGAGTGCGACATCCCTATCGGC
GCCGGCATCTGTGCCTCCTACCAGACCCAGACAAACTCCCCAAGGAGAGCACGG
TCTGTGGCCAGCCAGTCCATCATCGCCTATACCATGAGCCTGGGCGCCGAGAATT
CCGTGGCCTACTCCAACAATTCTATCGCCATCCCTACCAACTTCACAATCTCCGT
GACCACAGAGATCCTGCCAGTGAGCATGACCAAGACATCCGTGGACTGCACAAT
GTATATCTGTGGCGATTCCACCGAGTGCTCTAACCTGCTGCTGCAGTACGGCTCT
TTTTGTACCCAGCTGAATAGAGCCCTGACAGGCATCGCCGTGGAGCAGGACAAG
AACACACAGGAGGTGTTCGCCCAGGTGAAGCAAATCTACAAGACCCCACCCATC
AAGGACTTTGGCGGCTTCAACTTCAGCCAGATCCTGCCCGATCCTAGCAAGCCAT
CCAAGCGGTCTTTTATCGAGGACCTGCTGTTCAACAAGGTGACCCTGGCCGATGC
CGGCTTCATCAAGCAGTATGGCGATTGCCTGGGCGACATCGCCGCCAGAGACCT
GATCTGTGCCCAGAAGTTTAATGGCCTGACCGTGCTGCCTCCACTGCTGACAGAT
GAGATGATCGCCCAGTACACATCTGCCCTGCTGGCCGGAACCATCACAAGCGGA
TGGACCTTCGGCGCAGGAGCCGCCCTGCAGATCCCCTTTGCCATGCAGATGGCCT
ATCGGTTCAACGGCATCGGCGTGACCCAGAATGTGCTGTACGAGAACCAGAAGC
TGATCGCCAATCAGTTTAACTCCGCCATCGGCAAGATCCAGGACTCTCTGAGCTC
CACAGCCAGCGCCCTGGGCAAGCTGCAGGATGTGGTGAATCAGAACGCCCAGGC
CCTGAATACCCTGGTGAAGCAGCTGTCTAGCAACTTCGGCGCCATCTCCTCTGTG
```

-continued

```
CTGAATGACATCCTGAGCCGGCTGGACAAGGTGGAGGCAGAGGTGCAGATCGAC

CGGCTGATCACAGGCAGACTGCAGTCCCTGCAGACCTACGTGACACAGCAGCTG

ATCAGGGCAGCAGAGATCAGGGCCTCTGCCAATCTGGCCGCCACCAAGATGAGC

GAGTGCGTGCTGGGCCAGTCCAAGAGAGTGGACTTTTGTGGCAAGGGCTATCAC

CTGATGAGCTTCCCACAGTCCGCCCCTCACGGAGTGGTGTTTCTGCACGTGACCT

ACGTGCCAGCCCAGGAGAAGAACTTCACCACAGCACCAGCAATCTGCCACGATG

GCAAGGCACACTTTCCTAGGGAGGGCGTGTTCGTGAGCAACGGCACCCACTGGT

TTGTGACACAGCGCAATTTCTACGAGCCACAGATCATCACCACAGACAATACAT

TCGTGTCCGGCAACTGTGACGTGGTCATCGGCATCGTGAACAATACCGTGTATGA

TCCTCTGCAGCCAGAGCTGGACTCTTTTAAGGAGGAGCTGGATAAGTACTTCAAG

AATCACACCAGCCCCGACGTGGATCTGGGCGACATCTCTGGCATCAATGCCAGC

GTGGTGAACATCCAGAAGGAGATCGACAGGCTGAACGAGGTGGCCAAGAATCT

GAACGAGTCCCTGATCGATCTGCAGGAGCTGGGCAAGTATGAGCAGTACATCAA

GTGGCCCTGGTATATCTGGCTGGGCTTCATCGCCGGCCTGATCGCCATCGTGATG

GTGACCATCATGCTGTGCTGTATGACAAGCTGCTGTTCCTGCCTGAAGGGCTGCT

GTTCTTGTGGCAGCTGCTGTAAGTTTGATGAGGACGATAGCGAGCCTGTGCTGAA

GGGCGTGAAGCTGCACTACACCTGATAGCTAGCGATCGCCCACCTAGTACAACC

TAAATCCATTATAAAAAACTTAGGAGCAAAGTGATTGCCTCCCAAGGTCCACAA

TGACAGAGACCTACGACTTCGACAAGTCGGCATGGGACATCAAAGGGTCGATCG

CTCCGATACAACCCACCACCTACAGTGATGGCAGGCTGGTGCCCCAGGTCAGAG

TCATAGATCCTGGTCTAGGCGACAGGAAGGATGAATGCTTTATGTACATGTTTCT

GCTGGGGGTTGTTGAGGACAGCGATTCCCTAGGGCCTCCAATCGGGCGAGCATT

TGGGTTCCTGCCCTTAGGTGTTGGCAGATCCACAGCAAAGCCCGAAAAACTCCTC

AAAGAGGCCACTGAGCTTGACATAGTTGTTAGACGTACAGCAGGGCTCAATGAA

AAACTGGTGTTCTACAACAACACCCCACTAACTCTCCTCACACCTTGGAGAAAG

GTCCTAACAACAGGGAGTGTCTTCAACGCAAACCAAGTGTGCAATGCGGTTAAT

CTGATACCGCTCGATACCCCGCAGAGGTTCCGTGTTGTTTATATGAGCATCACCC

GTCTTTCGGATAACGGGTATTACACCGTTCCTAGAAGAATGCTGGAATTCAGATC

GGTCAATGCAGTGGCCTTCAACCTGCTGGTGACCCTTAGGATTGACAAGGCGAT

AGGCCCTGGGAAGATCATCGACAATACAGAGCAACTTCCTGAGGCAACATTTAT

GGTCCACATCGGGAACTTCAGGAGAAAGAAGAGTGAAGTCTACTCTGCCGATTA

TTGCAAAATGAAAATCGAAAAGATGGGCCTGGTTTTTGCACTTGGTGGGATAGG

GGGCACCAGTCTTCACATTAGAAGCACAGGCAAAATGAGCAAGACTCTCCATGC

ACAACTCGGGTTCAAGAAGACCTTATGTTACCCGCTGATGGATATCAATGAAGA

CCTTAATCGATTACTCTGGAGGAGCAGATGCAAGATAGTAAGAATCCAGGCAGT

TTTGCAGCCATCAGTTCCTCAAGAATTCCGCATTTACGACGACGTGATCATAAAT

GATGACCAAGGACTATTCAAAGTTCTGTAGACCGTAGTGCCCAGCAATGCCCGA

AAACGACCCCCCTCACAATGACAGCCAGAAGGCCCGGACAAAAAAGCCCCCTCC

GAAAGACTCCACGGACCAAGCGAGAGGCCAGCCAGCAGCCGACGGCAAGCGCG

AACACCAGGCGGCCCCAGCACAGAACAGCCCTGACACAAGGCCACCACCAGCC

ACCCCAATCTGCATCCTCCTCGTGGGACCCCCGAGGACCAACCCCCAAGGCTGC
```

-continued

```
CCCCGATCCAAACCACCAACCGCATCCCCACCACCCCCGGGAAAGAAACCCCCA
GCAATTGGAAGGCCCCTCCCCCTCTTCCTCAACACAAGAACTCCACAACCGAAC
CGCACAAGCGACCGAGGTGACCCAACCGCAGGCATCCGACTCCCTAGACAGATC
CTCTCTCCCCGGCAAACTAAACAAAACTTAGGGCCAAGGAACATACACACCCAA
CAGAACCCAGACCCCGGCCCACGGCGCCGCGCCCCCAACCCCCGACAACCAGAG
GGAGCCCCCAACCAATCCCGCCGGCTCCCCGGTGCCCACAGGCAGGGACACCA
ACCCCCGAACAGACCCAGCACCCAACCATCGACAATCCAAGACGGGGGGCCCC
CCCAAAAAAAGGCCCCCAGGGGCCGACAGCCAGCACCGCGAGGAAGCCCACCC
ACCCCACACACGACCACGGCAACCAAACCAGAACCCAGACCACCCTGGGCCACC
AGCTCCCAGACTCGGCCATCACCCCGCAGAAAGGAAAGGCCACAACCCGCGCAC
CCCAGCCCCGATCCGGCGGGGAGCCACCCAACCCGAACCAGCACCCAAGAGCG
ATCCCCGAAGGACCCCCGAACCGCAAAGGACATCAGTATCCCACAGCCTCTCCA
AGTCCCCCGGTCTCCTCCTCTTCTCGAAGGGACCAAAAGATCAATCCACCACACC
CGACGACACTCAACTCCCCACCCCTAAAGGAGACACCGGGAATCCCAGAATCAA
GACTCATCCAATGTCCATCATGGGTCTCAAGGTGAACGTCTCTGCCATATTCATG
GCAGTACTGTTAACTCTCCAAACACCCACCGGTCAAATCCATTGGGGCAATCTCT
CTAAGATAGGGGTGGTAGGAATAGGAAGTGCAAGCTACAAAGTTATGACTCGTT
CCAGCCATCAATCATTAGTCATAAAATTAATGCCCAATATAACTCTCCTCAATAA
CTGCACGAGGGTAGAGATTGCAGAATACAGGAGACTACTGAGAACAGTTTTGGA
ACCAATTAGAGATGCACTTAATGCAATGACCCAGAATATAAGACCGGTTCAGAG
TGTAGCTTCAAGTAGGAGACACAAGAGATTTGCGGGAGTAGTCCTGGCAGGTGC
GGCCCTAGGCGTTGCCACAGCTGCTCAGATAACAGCCGGCATTGCACTTCACCA
GTCCATGCTGAACTCTCAAGCCATCGACAATCTGAGAGCGAGCCTGGAAACTAC
TAATCAGGCAATTGAGACAATCAGACAAGCAGGGCAGGAGATGATATTGGCTGT
TCAGGGTGTCCAAGACTACATCAATAATGAGCTGATACCGTCTATGAACCAACT
ATCTTGTGATTTAATCGGCCAGAAGCTCGGGCTCAAATTGCTCAGATACTATACA
GAAATCCTGTCATTATTTGGCCCCAGTTTACGGGACCCCATATCTGCGGAGATAT
CTATCCAGGCTTTGAGCTATGCGCTTGGAGGAGACATCAATAAGGTGTTAGAAA
AGCTCGGATACAGTGGAGGTGATTTACTGGGCATCTTAGAGAGCGGAGGAATAA
AGGCCCGGATAACTCACGTCGACACAGAGTCCTACTTCATTGTCCTCAGTATAGC
CTATCCGACGCTGTCCGAGATTAAGGGGGTGATTGTCCACCGGCTAGAGGGGT
CTCGTACAACATAGGCTCTCAAGAGTGGTATACCACTGTGCCCAAGTATGTTGCA
ACCCAAGGGTACCTTATCTCGAATTTTGATGAGTCATCGTGTACTTTCATGCCAG
AGGGGACTGTGTGCAGCCAAAATGCCTTGTACCCGATGAGTCCTCTGCTCCAAG
AATGCCTCCGGGGTACACCAAGTCCTGTGCTCGTACACTCGTATCCGGGTCTTT
TGGGAACCGGTTCATTTTATCACAAGGGAACCTAATAGCCAATTGTGCATCAATC
CTTTGCAAGTGTTACACAACAGGAACGATCATTAATCAAGACCCTGACAAGATC
CTAACATACATTGCTGCCGATCACTGCCCGGTAGTCGAGGTGAACGGCGTGACC
ATCCAAGTCGGGAGCAGGAGGTATCCAGACGCTGTGTACTTGCACAGAATTGAC
CTCGGTCCTCCCATATCATTGGAGAGGTTGGACGTAGGGACAAATCTGGGGAAT
```

-continued

```
GCAATTGCTAAGTTGGAGGATGCCAAGGAATTGTTGGAGTCATCGGACCAGATA

TTGAGGAGTATGAAAGGTTTATCGAGCACTAGCATAGTCTACATCCTGATTGCAG

TGTGTCTTGGAGGGTTGATAGGGATCCCCGCTTTAATATGTTGCTGCAGGGGCG

TTGTAACAAAAAGGGAGAACAAGTTGGTATGTCAAGACCAGGCCTAAAGCCTGA

TCTTACGGGAACATCAAAATCCTATGTAAGGTCGCTCTGATCCTCTACAACTCTT

GAAACACAAATGTCCCACAAGTCTCCTCTTCGTCATCAAGCAACCACCGCACCC

AGCATCAAGCCCACCTGAAATTATCTCCGGCTTCCCTCTGGCCGAACAATATCGG

TAGTTAATTAAAACTTAGGGTGCAAGATCATCGATAATGTCACCACAACGAGAC

CGGATAAATGCCTTCTACAAAGATAACCCCCATCCCAAGGGAAGTAGGATAGTC

ATTAACAGAGAACATCTTATGATTGATAGACCTTATGTTTTGCTGGCTGTTCTGTT

TGTCATGTTTCTGAGCTTGATCGGGTTGCTAGCCATTGCAGGAATTCGACTTCAT

CGGGCAGCCATCTACACCGCAGAGATCCATAAAAGCCTCAGCACCAATCTAGAT

GTAACTAACTCAATCGAGCATCAGGTCAAGGACGTGCTGACACCACTCTTCAAA

ATCATCGGTGATGAAGTGGGCCTGAGGACACCTCAGAGATTCACTGACCTAGTG

AAATTAATCTCTGACAAGATTAAATTCCTTAATCCGGATAGGGAGTACGACTTCA

GAGATCTCACTTGGTGTATCAACCCGCCAGAGAGAATCAAATTGGATTATGATC

AATACTGTGCAGATGTGGCTGCTGAAGAGCTCATGAATGCATTGGTGAACTCAA

CTCTACTGGAGACCAGAACAACCAATCAGTTCCTAGCTGTCTCAAAGGGAAACT

GCTCAGGGCCCACTACAATCAGAGGTCAATTCTCAAACATGTCGCTGTCCCTGTT

AGACTTGTATTTAGGTCGAGGTTACAATGTGTCATCTATAGTCACTATGACATCC

CAGGGAATGTATGGGGGAACTTACCTAGTGGAAAAGCCTAATCTGAGCAGCAAA

AGGTCAGAGTTGTCACAACTGAGCATGTACCGAGTGTTTGAAGTAGGTGTTATCA

GAAATCCGGGTTTGGGGGCTCCGGTGTTCCATATGACAAACTATCTTGAGCAACC

AGTCAGTAATGATCTCAGCAACTGTATGGTGGCTTTGGGGGAGCTCAAACTCGC

AGCCCTTTGTCACGGGGAAGATTCTATCACAATTCCCTATCAGGGATCAGGGAA

AGGTGTCAGCTTCCAGCTCGTCAAGCTAGGTGTCTGGAAATCCCCAACCGACAT

GCAATCCTGGGTCCCCTTATCAACGGATGATCCAGTGATAGACAGGCTTTACCTC

TCATCTCACAGAGGTGTTATCGCTGACAACCAAGCAAAATGGGCTGTCCCGACA

ACACGAACAGATGACAAGTTGCGAATGGAGACATGCTTCCAACAGGCGTGTAAG

GGTAAAATCCAAGCACTCTGCGAGAATCCCGAGTGGGCACCATTGAAGGATAAC

AGGATTCCTTCATACGGGGTCTTGTCTGTTGATCTGAGTCTGACAGTTGAGCTTA

AAATCAAAATTGCTTCGGGATTCGGGCCATTGATCACACACGGTTCAGGGATGG

ACCTATACAAATCCAACCACAACAATGTGTATTGGCTGACTATCCCGCCAATGA

AGAACCTAGCCTTAGGTGTAATCAACACATTGGAGTGGATACCGAGATTCAAGG

TTAGTCCCTACCTCTTCACTGTCCCAATTAAGGAAGCAGGCGAAGACTGCCATGC

CCCAACATACCTACCTGCGGAGGTGGATGGTGATGTCAAACTCAGTTCCAATCTG

GTGATTCTACCTGGTCAAGATCTCCAATATGTTTTGGCAACCTACGATACTTCCA

GGGTTGAACATGCTGTGGTTTATTACGTTTACAGCCCAAGCCGCTCATTTTCTTAC

TTTTATCCTTTTAGGTTGCCTATAAAGGGGGTCCCCATCGAATTACAAGTGGAAT

GCTTCACATGGGACCAAAAACTCTGGTGCCGTCACTTCTGTGTGCTTGCGGACTC

AGAATCTGGTGGACATATCACTCACTCTGGGATGGTGGGCATGGGAGTCAGCTG
```

-continued

```
CACAGTCACCCGGGAAGATGGAACCAATCGCAGATAGGGCTGCTAGTGAACCAA

TCACATGATGTCACCCAGACATCAGGCATACCCACTAGTGTGAAATAGACATCA

GAATTAAGAAAAACGTAGGGTCCAAGTGGTTCCCCGTTATGGACTCGCTATCTGT

CAACCAGATCTTATACCCTGAAGTTCACCTAGATAGCCCGATAGTTACCAATAAG

ATAGTAGCCATCCTGGAGTATGCTCGAGTCCCTCACGCTTACAGCCTGGAGGACC

CTACACTGTGTCAGAACATCAAGCACCGCCTAAAAAACGGATTTTCCAACCAAA

TGATTATAAACAATGTGGAAGTTGGGAATGTCATCAAGTCCAAGCTTAGGAGTT

ATCCGGCCCACTCTCATATTCCATATCCAAATTGTAATCAGGATTTATTTAACAT

AGAAGACAAAGAGTCAACGAGGAAGATCCGTGAACTCCTCAAAAAGGGGAATT

CGCTGTACTCCAAAGTCAGTGATAAGGTTTTCCAATGCTTAAGGGACACTAACTC

ACGGCTTGGCCTAGGCTCCGAATTGAGGGAGGACATCAAGGAGAAAGTTATTAA

CTTGGGAGTTTACATGCACAGCTCCCAGTGGTTTGAGCCCTTTCTGTTTTGGTTTA

CAGTCAAGACTGAGATGAGGTCAGTGATTAAATCACAAACCCATACTTGCCATA

GGAGGAGACACACACCTGTATTCTTCACTGGTAGTTCAGTTGAGTTGCTAATCTC

TCGTGACCTTGTTGCTATAATCAGTAAAGAGTCTCAACATGTATATTACCTGACA

TTTGAACTGGTTTTGATGTATTGTGATGTCATAGAGGGGAGGTTAATGACAGAGA

CCGCTATGACTATTGATGCTAGGTATACAGAGCTTCTAGGAAGAGTCAGATACAT

GTGGAAACTGATAGATGGTTTCTTCCCTGCACTCGGGAATCCAACTTATCAAATT

GTAGCCATGCTGGAGCCTCTTTCACTTGCTTACCTGCAGCTGAGGGATATAACAG

TAGAACTCAGAGGTGCTTTCCTTAACCACTGCTTTACTGAAATACATGATGTTCT

TGACCAAAACGGGTTTTCTGATGAAGGTACTTATCATGAGTTAACTGAAGCTCTA

GATTACATTTTCATAACTGATGACATACATCTGACAGGGGAGATTTTCTCATTTTT

CAGAAGTTTCGGCCACCCCAGACTTGAAGCAGTAACGGCTGCTGAAAATGTTAG

GAAATACATGAATCAGCCTAAAGTCATTGTGTATGAGACTCTGATGAAAGGTCA

TGCCATATTTTGTGGAATCATAATCAACGGCTATCGTGACAGGCACGGAGGCAG

TTGGCCACCGCTGACCCTCCCCCTGCATGCTGCAGACACAATCCGGAATGCTCAA

GCTTCAGGTGAAGGGTTAACACATGAGCAGTGCGTTGATAACTGGAAATCTTTTG

CTGGAGTGAAATTTGGCTGCTTTATGCCTCTTAGCCTGGATAGTGATCTGACAAT

GTACCTAAAGGACAAGGCACTTGCTGCTCTCCAAAGGGAATGGGATTCAGTTTA

CCCGAAAGAGTTCCTGCGTTACGACCCTCCCAAGGGAACCGGGTCACGGAGGCT

TGTAGATGTTTTCCTTAATGATTCGAGCTTTGACCCATATGATGTGATAATGTATG

TTGTAAGTGGAGCTTACCTCCATGACCCTGAGTTCAACCTGTCTTACAGCCTGAA

AGAAAAGGAGATCAAGGAAACAGGTAGACTTTTTGCTAAAATGACTTACAAAAT

GAGGGCATGCCAAGTGATTGCTGAAAATCTAATCTCAAACGGGATTGGCAAATA

TTTTAAGGACAATGGGATGGCCAAGGATGAGCACGATTTGACTAAGGCACTCCA

CACTCTAGCTGTCTCAGGAGTCCCCAAAGATCTCAAAGAAAGTCACAGGGGGGG

GCCAGTCTTAAAAACCTACTCCCGAAGCCCAGTCCACACAAGTACCAGGAACGT

GAGAGCAGCAAAAGGGTTTATAGGGTTCCCTCAAGTAATTCGGCAGGACCAAGA

CACTGATCATCCGGAGAATATGGAAGCTTACGAGACAGTCAGTGCATTTATCAC

GACTGATCTCAAGAAGTACTGCCTTAATTGGAGATATGAGACCATCAGCTTGTTT
```

-continued

```
GCACAGAGGCTAAATGAGATTTACGGATTGCCCTCATTTTTCCAGTGGCTGCATA
AGAGGCTTGAGACCTCTGTCCTGTATGTAAGTGACCCTCATTGCCCCCCCGACCT
TGACGCCCATATCCCGTTATATAAAGTCCCCAATGATCAAATCTTCATTAAGTAC
CCTATGGGAGGTATAGAAGGGTATTGTCAGAAGCTGTGGACCATCAGCACCATT
CCCTATCTATACCTGGCTGCTTATGAGAGCGGAGTAAGGATTGCTTCGTTAGTGC
AAGGGGACAATCAGACCATAGCCGTAACAAAAAGGGTACCCAGCACATGGCCC
TACAACCTTAAGAAACGGGAAGCTGCTAGAGTAACTAGAGATTACTTTGTAATT
CTTAGGCAAAGGCTACATGATATTGGCCATCACCTCAAGGCAAATGAGACAATT
GTTTCATCACATTTTTTTGTCTATTCAAAAGGAATATATTATGATGGGCTACTTGT
GTCCCAATCACTCAAGAGCATCGCAAGATGTGTATTCTGGTCAGAGACTATAGTT
GATGAAACAAGGGCAGCATGCAGTAATATTGCTACAACAATGGCTAAAAGCATC
GAGAGAGGTTATGACCGTTACCTTGCATATTCCCTGAACGTCCTAAAAGTGATAC
AGCAAATTCTGATCTCTCTTGGCTTCACAATCAATTCAACCATGACCCGGGATGT
AGTCATACCCCTCCTCACAAACAACGACCTCTTAATAAGGATGGCACTGTTGCCC
GCTCCTATTGGGGGATGAATTATCTGAATATGAGCAGGCTGTTTGTCAGAAACA
TCGGTGATCCAGTAACATCATCAATTGCTGATCTCAAGAGAATGATTCTCGCCTC
ACTAATGCCTGAAGAGACCCTCCATCAGGTAATGACACAACAACCGGGGGACTC
TTCATTCCTAGACTGGGCTAGCGACCCTTACTCAGCAAATCTTGTATGTGTCCAG
AGCATCACTAGACTCCTCAAGAACATAACTGCAAGGTTTGTCCTGATCCATAGTC
CAAACCCAATGTTAAAAGGATTATTCCATGATGACAGTAAAGAAGAGGACGAGG
GACTGGCGGCATTCCTCATGGACAGGCATATTATAGTACCTAGGGCAGCTCATG
AAATCCTGGATCATAGTGTCACAGGGGCAAGAGAGTCTATTGCAGGCATGCTGG
ATACCACAAAAGGCTTGATTCGAGCCAGCATGAGGAAGGGGGGTTTAACCTCTC
GAGTGATAACCAGATTGTCCAATTATGACTATGAACAATTCAGAGCAGGGATGG
TGCTATTGACAGGAAGAAAGAGAAATGTCCTCATTGACAAAGAGTCATGTTCAG
TGCAGCTGGCGAGAGCTCTAAGAAGCCATATGTGGGCGAGGCTAGCTCGAGGAC
GGCCTATTTACGGCCTTGAGGTCCCTGATGTACTAGAATCTATGCGAGGCCACCT
TATTCGGCGTCATGAGACATGTGTCATCTGCGAGTGTGGATCAGTCAACTACGGA
TGGTTTTTTGTCCCCTCGGGTTGCCAACTGGATGATATTGACAAGGAAACATCAT
CCTTGAGAGTCCCATATATTGGTTCTACCACTGATGAGAGAACAGACATGAAGCT
TGCCTTCGTAAGAGCCCCAAGTCGATCCTTGCGATCTGCTGTTAGAATAGCAACA
GTGTACTCATGGGCTTACGGTGATGATGATAGCTCTTGGAACGAAGCCTGGTTGT
TGGCTAGGCAAAGGGCCAATGTGAGCCTGGAGGAGCTAAGGGTGATCACTCCCA
TCTCAACTTCGACTAATTTAGCGCATAGGTTGAGGGATCGTAGCACTCAAGTGAA
ATACTCAGGTACATCCCTTGTCCGAGTGGCGAGGTATACCACAATCTCCAACGAC
AATCTCTCATTTGTCATATCAGATAAGAAGGTTGATACTAACTTTATATACCAAC
AAGGAATGCTTCTAGGGTTGGGTGTTTTAGAAACATTGTTTCGACTCGAGAAAGA
TACCGGATCATCTAACACGGTATTACATCTTCACGTCGAAACAGATTGTTGCGTG
ATCCCGATGATAGATCATCCCAGGATACCCAGCTCCCGCAAGCTAGAGCTGAGG
GCAGAGCTATGTACCAACCCATTGATATATGATAATGCACCTTTAATTGACAGAG
ATGCAACAAGGCTATACACCCAGAGCCATAGGAGGCACCTTGTGGAATTTGTTA
```

-continued

```
CATGGTCCACACCCCAACTATATCACATTTTAGCTAAGTCCACAGCACTATCTAT
GATTGACCTGGTAACAAAATTTGAGAAGGACCATATGAATGAAATTTCAGCTCT
CATAGGGGATGACGATATCAATAGTTTCATAACTGAGTTTCTGCTCATAGAGCCA
AGATTATTCACTATCTACTTGGGCCAGTGTGCGGCCATCAATTGGGCATTTGATG
TACATTATCATAGACCATCAGGGAAATATCAGATGGGTGAGCTGTTGTCATCGTT
CCTTTCTAGAATGAGCAAAGGAGTGTTTAAGGTGCTTGTCAATGCTCTAAGCCAC
CCAAAGATCTACAAGAAATTCTGGCATTGTGGTATTATAGAGCCTATCCATGGTC
CTTCACTTGATGCTCAAAACTTGCACACAACTGTGTGCAACATGGTTTACACATG
CTATATGACCTACCTCGACCTGTTGTTGAATGAAGAGTTAGAAGAGTTCACATTT
CTCTTGTGTGAAAGCGACGAGGATGTAGTACCGGACAGATTCGACAACATCCAG
GCAAAACACTTATGTGTTCTGGCAGATTTGTACTGTCAACCAGGGACCTGCCCAC
CAATTCGAGGTCTAAGACCGGTAGAGAAATGTGCAGTTCTAACCGACCATATCA
AGGCAGAGGCTATGTTATCTCCAGCAGGATCTTCGTGGAACATAAATCCAATTAT
TGTAGACCATTACTCATGCTCCCTGACTTATCTCCGGCGAGGATCGATCAAACAG
ATAAGATTGAGAGTTGATCCAGGATTCATTTTCGACGCCCTCGCTGAGGTAAATG
TCAGTCAGCCAAAGATCGGCAGCAACAACATCTCAAATATGAGCATCAAGGCTT
TCAGACCCCCACACGATGATGTTGCAAAATTGCTCAAAGATATCAACACAAGCA
AGCACAATCTTCCCATTTCAGGGGGCAATCTCGCCAATTATGAAATCCATGCTTT
CCGCAGAATCGGGTTGAACTCATCTGCTTGCTACAAAGCTGTTGAGATATCAACA
TTAATTAGGAGATGCCTTGAGCCAGGGGAGGACGGCTTGTTCTTGGGTGAGGGA
TCGGGTTCTATGTTGATCACTTATAAGGAGATACTTAAACTAAACAAGTGCTTCT
ATAATAGTGGGGTTTCCGCCAATTCTAGATCTGGTCAAAGGGAATTAGCACCCTA
TCCCTCCGAAGTTGGCCTTGTCGAACACAGAATGGGAGTAGGTAATATTGTCAA
AGTGCTCTTTAACGGGAGGCCCGAAGTCACGTGGGTAGGCAGTGTAGATTGCTT
CAATTTCATAGTTAGTAATATCCCTACCTCTAGTGTGGGGTTTATCCATTCAGATA
TAGAGACCTTGCCTGACAAAGATACTATAGAGAAGCTAGAGGAATTGGCAGCCA
TCTTATCGATGGCTCTGCTCCTGGGCAAAATAGGATCAATACTGGTGATTAAGCT
TATGCCTTTCAGCGGGGATTTTGTTCAGGGATTTATAAGTTATGTAGGGTCTCATT
ATAGAGAAGTGAACCTTGTATACCCTAGATACAGCAACTTCATATCTACTGAATC
TTATTTGGTTATGACAGATCTCAAGGCTAACCGGCTAATGAATCCTGAAAAGATT
AAGCAGCAGATAATTGAATCATCTGTGAGGACTTCACCTGGACTTATAGGTCAC
ATCCTATCCATTAAGCAACTAAGCTGCATACAAGCAATTGTGGGAGACGCAGTT
AGTAGAGGTGATATCAATCCTACTCTGAAAAAACTTACACCTATAGAGCAGGTG
CTGATCAATTGCGGGTTGGCAATTAACGGACCTAAGCTGTGCAAAGAATTGATC
CACCATGATGTTGCCTCAGGGCAAGATGGATTGCTTAATTCTATACTCATCCTCT
ACAGGGAGTTGGCAAGATTCAAAGACAACCAAAGAAGTCAACAAGGGATGTTC
CACGCCTACCCCGTATTGGTAAGTAGCAGGCAACGAGAACTTATATCTAGGATC
ACCCGCAAATTTTGGGGGCACATTCTTCTTTACTCCGGGAACAAAAAGTTGATAA
ATAAGTTTATCCAGAATCTCAAGTCCGGCTATCTGATACTAGACTTACACCAGAA
TATCTTCGTTAAGAATCTATCCAAGTCAGAGAAACAGATTATTATGACGGGGGGT
```

-continued

```
TTGAAACGTGAGTGGGTTTTTAAGGTAACAGTCAAGGAGACCAAAGAATGGTAT
AAGTTAGTCGGATACAGTGCCCTGATTAAGGACTAATTGGTTGAACTCCGGAAC
CCTAATCCTGCCCTAGGTGGTTAGGCATTATTTGCAATATATTAAAGAAAACTTT
GAAAATACGAAGTTTCTATTCCCAGCTTTGTCTGGTggccggcatAgtcccagcctcctcgctggc
gctggctgggcaacattccgaggggaccgtccccAcggtaatggcgaatgggacgcggccgatccggctgctaacaaagcccga
aaggaagctgagttggctgctgGcGcTGgctgGgcaataactagcataacccctttgggcctctaaacgggtcttgaggggttt
tttgctgaaaggaggaactatatccggatgcGGCCGCGCGCTTGGCGTAATCATGGTCATAGCTGTTT
CCTGTGTGAAATTGTTATCCGCTCACAATTCCACACAACATACGAGCCGGAAGC
ATAAAGTGTAAAGCCTGGGGTGCCTAATGAGTGAGCTAACTCACATTAATTGCG
TTGCGCTCACTGCCCGCTTTCCAGTCGGGAAACCTGTCGTGCCAGCTGCATTAAT
GAATCGGCCAACGCGCGGGAGAGGCGGTTTGCGTATTGGGCGCTCTTCCGCTT
CCTCGCTCACTGACTCGCTGCGCTCGGTCGTTCGGCTGCGGCGAGCGGTATCAGC
TCACTCAAAGGCGGTAATACGGTTATCCACAGAATCAGGGGATAACGCAGGAAA
GAACATGTGAGCAAAAGGCCAGCAAAAGGCCAGGAACCGTAAAAAGGCCGCGT
TGCTGGCGTTTTTCCATAGGCTCCGCCCCCTGACGAGCATCACAAAAATCGACG
CTCAAGTCAGAGGTGGCGAAACCCGACAGGACTATAAAGATACCAGGCGTTTCC
CCCTGGAAGCTCCCTCGTGCGCTCTCCTGTTCCGACCCTGCCGCTTACCGGATAC
CTGTCCGCCTTTCTCCCTTCGGGAAGCGTGGCGCTTTCTCATAGCTCACGCTGTA
GGTATCTCAGTTCGGTGTAGGTCGTTCGCTCCAAGCTGGGCTGTGTGCACGAACC
CCCCGTTCAGCCCGACCGCTGCGCCTTATCCGGTAACTATCGTCTTGAGTCCAAC
CCGGTAAGACACGACTTATCGCCACTGGCAGCAGCCACTGGTAACAGGATTAGC
AGAGCGAGGTATGTAGGCGGTGCTACAGAGTTCTTGAAGTGGTGGCCTAACTAC
GGCTACACTAGAAGGACAGTATTTGGTATCTGCGCTCTGCTGAAGCCAGTTACCT
TCGGAAAAAGAGTTGGTAGCTCTTGATCCGGCAAACAAACCACCGCTGGTAGCG
GTGGTTTTTTGTTTGCAAGCAGCAGATTACGCGCAGAAAAAAAGGATCTCAAG
AAGATCCTTTGATCTTTTCTACGGGGTCTGACGCTCAGTGGAACGAAAACTCACG
TTAAGGGATTTTGGTCATGAGATTATCAAAAAGGATCTTCACCTAGATCCTTTTA
AATTAAAAATGAAGTTTTAAATCAATCTAAAGTATATATGAGTAAACTTGGTCTG
ACAGTTACCAATGCTTAATCAGTGAGGCACCTATCTCAGCGATCTGTCTATTTCG
TTCATCCATAGTTGCCTGACTCCCCGTCGTGTAGATAACTACGATACGGGAGGGC
TTACCATCTGGCCCCAGTGCTGCAATGATACCGCGAGACCCACGCTCACCGGCTC
CAGATTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCTAGAGT
AAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGAT
CAAGGCGAGTTACATGATCCCCCATGTTGTGCAAAAAAGCGGTTAGCTCCTTCGG
TCCTCCGATCGTTGTCAGAAGTAAGTTGGCCGCAGTGTTATCACTCATGGTTATG
GCAGCACTGCATAATTCTCTTACTGTCATGCCATCCGTAAGATGCTTTTCTGTGAC
TGGTGAGTACTCAACCAAGTCATTCTGAGAATAGTGTATGCGGCGACCGAGTTG
CTCTTGCCCGGCGTCAATACGGGATAATACCGCGCCACATAGCAGAACTTTAAA
AGTGCTCATCATTGGAAAACGTTCTTCGGGGCGAAAACTCTCAAGGATCTTACCG
```

-continued

CTGTTGAGATCCAGTTCGATGTAACCCACTCGTGCACCCAACTGATCTTCAGCAT

CTTTTACTTTCACCAGCGTTTCTGGGTGAGCAAAAACAGGAAGGCAAATGCCG

CAAAAAAGGGAATAAGGGCGACACGGAAATGTTGAATACTCATACTCTTCCTTT

TTCAATATTATTGAAGCATTTATCAGGGTTATTGTCTCATGAGCGGATACATATTT

GAATGTATTTAGAAAAATAAACAAATAGGGGTTCCGCGCACATTTCCCCGAAAA

GTGCCACCTG.

In still another embodiment, the nucleic acid comprises the sequence of SEQ ID NO: 5, shown below:

GGACGCGCCCTGTAGCGGCGCATTAAGCGCGGCGGGTGTGGTGGTTACGCGCAG

CGTGACCGCTACACTTGCCAGCGCCCTAGCGCCCGCTCCTTTCGCTTTCTTCCCTT

CCTTTCTCGCCACGTTCGCCGGCTTTCCCCGTCAAGCTCTAAATCGGGGCTCCC

TTTAGGGTTCCGATTTAGTGCTTTACGGCACCTCGACCCCAAAAAACTTGATTAG

GGTGATGGTTCACGTAGTGGGCCATCGCCCTGATAGACGGTTTTTCGCCCTTTGA

CGTTGGAGTCCACGTTCTTTAATAGTGGACTCTTGTTCCAAACTGGAACAACACT

CAACCCTATCTCGGTCTATTCTTTTGATTTATAAGGGATTTTGCCGATTTCGGCCT

ATTGGTTAAAAAATGAGCTGATTTAACAAAAATTTAACGCGAATTTTAACAAAA

TATTAACGTTTACAATTTCGCGCCATTCGCCATTCAGGCTGCGCAACTGTTGGGA

AGGGCGATCGGTGCGGGCCTCTTCGCTATTACGCCAGCTGGCGAAAGGGGGATG

TGCTGCAAGGCGATTAAGTTGGGTAACGCCAGGGTTTTCCCAGTCACGACGTTGT

AAAACGACGGCCAGTGCGCGCCGTTAATACGACTCACTATAGGGAGACCCAAGC

TGGCTAGCTTTGTTTGGTCTGATGAGTCCCGTGAGGACGAAACCCGGCGTACCGG

GTCACCAAACAAAGTTGGGTAAGGATAGTTCAATCAATGATCATCTTCTAGTGCA

CTTAGGATTCAAGATCCTATTATCAGGGACAAGAGCAGGATTAGGGATATCCGA

GATGGCCACACTTTTAAGGAGCTTAGCATTGTTCAAAAGAAACAAGGACAAACC

ACCCATTACATCAGGATCCGGTGGAGCCATCAGAGGAATCAAACACATTATTAT

AGTACCAATCCCTGGAGATTCCTCAATTACCACTCGATCCAGACTTCTGGACCGG

TTGGTGAGGTTAATTGGAAACCCGGATGTGAGCGGGCCCAAACTAACAGGGGCA

CTAATAGGTATATTATCCTTATTTGTGGAGTCTCCAGGTCAATTGATTCAGAGGA

TCACCGATGACCCTGACGTTAGCATAAGGCTGTTAGAGGTTGTCCAGAGTGACC

AGTCACAATCTGGCCTTACCTTCGCATCAAGAGGTACCAACATGGAGGATGAGG

CGGACCAATACTTTTCACATGATGATCCAATTAGTAGTGATCAATCCAGGTTCGG

ATGGTTCGGGAACAAGGAAATCTCAGATATTGAAGTGCAAGACCCTGAGGGATT

CAACATGATTCTGGGTACCATCCTAGCCCAAATTTGGGTCTTGCTCGCAAAGGCG

GTTACGGCCCCAGACACGGCAGCTGATTCGGAGCTAAGAAGGTGGATAAAGTAC

ACCCAACAAAGAAGGGTAGTTGGTGAATTTAGATTGGAGAGAAAATGGTTGGAT

GTGGTGAGGAACAGGATTGCCGAGGACCTCTCCTTACGCCGATTCATGGTCGCTC

TAATCCTGGATATCAAGAGAACACCCGGAAACAAACCCAGGATTGCTGAAATGA

TATGTGACATTGATACATATCGTAGAGGCAGGATTAGCCAGTTTTATCCTGAC

TATTAAGTTTGGGATAGAAACTATGTATCCTGCTCTTGGACTGCATGAATTTGCT

-continued

```
GGTGAGTTATCCACACTTGAGTCCTTGATGAACCTTTACCAGCAAATGGGGAA
ACTGCACCCTACATGGTAATCCTGGAGAACTCAATTCAGAACAAGTTCAGTGCA
GGATCATACCCTCTGCTCTGGAGCTATGCCATGGGAGTAGGAGTGGAACTTGAA
AACTCCATGGGAGGTTTGAACTTTGGCCGATCTTACTTTGATCCAGCATATTTTA
GATTAGGGCAAGAGATGGTAAGGAGGTCAGCTGGAAAGGTCAGTTCCACATTGG
CATCTGAACTCGGTATCACTGCCGAGGATGCAAGGCTTGTTTCAGAGATTGCAAT
GCATACTACTGAGGACAAGATCAGTAGAGCGGTTGGACCCAGACAAGCCCAAGT
ATCATTTCTACACGGTGATCAAAGTGAGAATGAGCTACCGAGATTGGGGGGCAA
GGAAGATAGGAGGGTCAAACAGAGTCGAGGAGAAGCCAGGGAGAGCTACAGAG
AAACCGGGCCCAGCAGAGCAAGTGATGCGAGAGCTGCCCATCTTCCAACCGGCA
CACCCCTAGACATTGACACTGCAACGGAGTCCAGCCAAGATCCGCAGGACAGTC
GAAGGTCAGCTGACGCCCTGCTTAGGCTGCAAGCCATGGCAGGAATCTCGGAAG
AACAAGGCTCAGACACGGACACCCCTATAGTGTACAATGACAGAAATCTTCTAG
ACTAGGTGCGAGAGGCCGAGGGCCAGAACAACATCCGCCTACCATCCATCATTG
TTATAAAAAACTTAGGAACCAGGTCCACACAGCCGCCAGCCCATCAACCATCCA
CTCCCACGATTGGAGCCAATGGCAGAAGAGCAGGCACGCCATGTCAAAAACGG
ACTGGAATGCATCCGGGCTCTCAAGGCCGAGCCCATCGGCTCACTGGCCATCGA
GGAAGCTATGGCAGCATGGTCAGAAATATCAGACAACCCAGGACAGGAGCGAG
CCACCTGCAGGGAAGAGAAGGCAGGCAGTTCGGGTCTCAGCAAACCATGCCTCT
CAGCAATTGGATCAACTGAAGGCGGTGCACCTCGCATCCGCGGTCAGGGACCTG
GAGAGAGCGATGACGACGCTGAAACTTTGGGAATCCCCCCAAGAAATCTCCAGG
CATCAAGCACTGGGTTACAGTGTTATTACGTTTATGATCACAGCGGTGAAGCGGT
TAAGGGAATCCAAGATGCTGACTCTATCATGGTTCAATCAGGCCTTGATGGTGAT
AGCACCCTCTCAGGAGGAGACAATGAATCTGAAAACAGCGATGTGGATATTGGC
GAACCTGATACCGAGGGATATGCTATCACTGACCGGGGATCTGCTCCCATCTCTA
TGGGGTTCAGGGCTTCTGATGTTGAAACTGCAGAAGGAGGGGAGATCCACGAGC
TCCTGAGACTCCAATCCAGAGGCAACAACTTTCCGAAGCTTGGGAAAACTCTCA
ATGTTCCTCCGCCCCGGACCCCGGTAGGGCCAGCACTTCCGGGACACCCATTAA
AAAGGGCACAGACGCGAGATTAGCCTCATTTGGAACGGAGATCGCGTCTTTATT
GACAGGTGGTGCAACCCAATGTGCTCGAAAGTCACCCTCGGAACCATCAGGGCC
AGGTGCACCTGCGGGGAATGTCCCCGAGTGTGTGAGCAATGCCGCACTGATACA
GGAGTGGACACCCGAATCTGGTACCACAATCTCCCCGAGATCCCAGAATAATGA
AGAAGGGGAGACTATTATGATGATGAGCTGTTCTCTGATGTCCAAGATATTAA
AACAGCCTTGGCCAAAATACACGAGGATAATCAGAAGATAATCTCCAAGCTAGA
ATCACTGCTGTTATTGAAGGGAGAAGTTGAGTCAATTAAGAAGCAGATCAACAG
GCAAAATATCAGCATATCCACCCTGGAAGGACACCTCTCAAGCATCATGATCGC
CATTCCTGGACTTGGGAAGGATCCCAACGACCCCACTGCAGATGTCGAAATCAA
TCCCGACTTGAAACCCATCATAGGCAGAGATTCAGGCCGAGCACTGGCCGAAGT
TCTCAAGAAACCCGTTGCCAGCCGACAACTCCAAGGAATGACAAATGGACGGAC
CAGTTCCAGAGGACAGCTGCTGAAGGAATTTCAGCTAAAGCCGATCGGGAAAAA
GATGAGCTCAGCCGTCGGGTTTGTTCCTGACACCGGCCCTGCATCACGCAGTGTA
```

-continued

```
ATCCGCTCCATTATAAAATCCAGCCGGCTAGAGGAGGATCGGAAGCGTTACCTG
ATGACTCTCCTTGATGATATCAAAGGAGCCAATGATCTTGCCAAGTTCCACCAGA
TGCTGATGAAGATAATAATGAAGTAGCTACAGCTCAACTTACCTGCCAACCCCAT
GCCAGTCGACCCACCTAGTACAACCTAAATCCATTATAAAAAACTTAGGAGCAA
AGTGATTGCCTCCCAAGGTCCACAATGACAGAGACCTACGACTTCGACAAGTCG
GCATGGGACATCAAAGGGTCGATCGCTCCGATACAACCCACCACCTACAGTGAT
GGCAGGCTGGTGCCCCAGGTCAGAGTCATAGATCCTGGTCTAGGCGACAGGAAG
GATGAATGCTTTATGTACATGTTTCTGCTGGGGGTTGTTGAGGACAGCGATTCCC
TAGGGCCTCCAATCGGGCGAGCATTTGGGTTCCTGCCCTTAGGTGTTGGCAGATC
CACAGCAAAGCCCGAAAAACTCCTCAAAGAGGCCACTGAGCTTGACATAGTTGT
TAGACGTACAGCAGGGCTCAATGAAAAACTGGTGTTCTACAACAACACCCCACT
AACTCTCCTCACACCTTGGAGAAAGGTCCTAACAACAGGGAGTGTCTTCAACGC
AAACCAAGTGTGCAATGCGGTTAATCTGATACCGCTCGATACCCCGCAGAGGTT
CCGTGTTGTTTATATGAGCATCACCCGTCTTTCGGATAACGGGTATTACACCGTT
CCTAGAAGAATGCTGGAATTCAGATCGGTCAATGCAGTGGCCTTCAACCTGCTG
GTGACCCTTAGGATTGACAAGGCGATAGGCCCTGGGAAGATCATCGACAATACA
GAGCAACTTCCTGAGGCAACATTTATGGTCCACATCGGGAACTTCAGGAGAAAG
AAGAGTGAAGTCTACTCTGCCGATTATTGCAAAATGAAAATCGAAAAGATGGGC
CTGGTTTTTGCACTTGGTGGGATAGGGGGCACCAGTCTTCACATTAGAAGCACAG
GCAAAATGAGCAAGACTCTCCATGCACAACTCGGGTTCAAGAAGACCTTATGTT
ACCCGCTGATGGATATCAATGAAGACCTTAATCGATTACTCTGGAGGAGCAGAT
GCAAGATAGTAAGAATCCAGGCAGTTTTGCAGCCATCAGTTCCTCAAGAATTCC
GCATTTACGACGACGTGATCATAAATGATGACCAAGGACTATTCAAAGTTCTGTA
GACCGTAGTGCCCAGCAATGCCCGAAAACGACCCCCCTCACAATGACAGCCAGA
AGGCCCGGACAAAAAAGCCCCCTCCGAAAGACTCCACGGACCAAGCGAGAGGC
CAGCCAGCAGCCGACGGCAAGCGCGAACACCAGGCGGCCCCAGCACAGAACAG
CCCTGACACAAGGCCACCACCAGCCACCCCAATCTGCATCCTCCTCGTGGGACCC
CCGAGGACCAACCCCCAAGGCTGCCCCCGATCCAAACCACCAACCGCATCCCCA
CCACCCCGGGAAAGAAACCCCCAGCAATTGGAAGGCCCCTCCCCCTCTTCCTC
AACACAAGAACTCCACAACCGAACCGCACAAGCGACCGAGGTGACCCAACCGC
AGGCATCCGACTCCCTAGACAGATCCTCTCTCCCCGGCAAACTAAACAAAACTT
AGGGCCAAGGAACATACACACCCAACAGAACCCAGACCCCGGCCCACGGCGCC
GCGCCCCAACCCCCGACAACCAGAGGGAGCCCCCAACCAATCCCGCCGGCTCC
CCCGGTGCCCACAGGCAGGGACACCAACCCCCGAACAGACCCAGCACCCAACCA
TCGACAATCCAAGACGGGGGGCCCCCCAAAAAAAGGCCCCCAGGGGCCGAC
AGCCAGCACCGCGAGGAAGCCCACCCACCCCACACACGACCACGGCAACCAAA
CCAGAACCCAGACCACCCTGGGCCACCAGCTCCCAGACTCGGCCATCACCCCGC
AGAAAGGAAAGGCCACAACCCGCGCACCCCAGCCCCGATCCGGCGGGGAGCCA
CCCAACCCGAACCAGCACCCAAGAGCGATCCCCGAAGGACCCCCGAACCGCAA
AGGACATCAGTATCCCACAGCCTCTCCAAGTCCCCCGGTCTCCTCCTCTTCTCGA
```

-continued

```
AGGGACCAAAAGATCAATCCACCACACCCGACGACACTCAACTCCCCACCCTA
AAGGAGACACCGGGAATCCCAGAATCAAGACTCATCCAATGTCCATCATGGGTC
TCAAGGTGAACGTCTCTGCCATATTCATGGCAGTACTGTTAACTCTCCAAACACC
CACCGGTCAAATCCATTGGGGCAATCTCTCTAAGATAGGGGTGGTAGGAATAGG
AAGTGCAAGCTACAAAGTTATGACTCGTTCCAGCCATCAATCATTAGTCATAAAA
TTAATGCCCAATATAACTCTCCTCAATAACTGCACGAGGGTAGAGATTGCAGAAT
ACAGGAGACTACTGAGAACAGTTTTGGAACCAATTAGAGATGCACTTAATGCAA
TGACCCAGAATATAAGACCGGTTCAGAGTGTAGCTTCAAGTAGGAGACACAAGA
GATTTGCGGGAGTAGTCCTGGCAGGTGCGGCCCTAGGCGTTGCCACAGCTGCTC
AGATAACAGCCGGCATTGCACTTCACCAGTCCATGCTGAACTCTCAAGCCATCG
ACAATCTGAGAGCGAGCCTGGAAACTACTAATCAGGCAATTGAGACAATCAGAC
AAGCAGGGCAGGAGATGATATTGGCTGTTCAGGGTGTCCAAGACTACATCAATA
ATGAGCTGATACCGTCTATGAACCAACTATCTTGTGATTTAATCGGCCAGAAGCT
CGGGCTCAAATTGCTCAGATACTATACAGAAATCCTGTCATTATTTGGCCCCAGT
TTACGGGACCCCATATCTGCGGAGATATCTATCCAGGCTTTGAGCTATGCGCTTG
GAGGAGACATCAATAAGGTGTTAGAAAAGCTCGGATACAGTGGAGGTGATTTAC
TGGGCATCTTAGAGAGCGGAGGAATAAAGGCCCGGATAACTCACGTCGACACAG
AGTCCTACTTCATTGTCCTCAGTATAGCCTATCCGACGCTGTCCGAGATTAAGGG
GGTGATTGTCCACCGGCTAGAGGGGGTCTCGTACAACATAGGCTCTCAAGAGTG
GTATACCACTGTGCCCAAGTATGTTGCAACCCAAGGGTACCTTATCTCGAATTTT
GATGAGTCATCGTGTACTTTCATGCCAGAGGGGACTGTGTGCAGCCAAAATGCCT
TGTACCCGATGAGTCCTCTGCTCCAAGAATGCCTCCGGGGGTACACCAAGTCCTG
TGCTCGTACACTCGTATCCGGGTCTTTTGGGAACCGGTTCATTTTATCACAAGGG
AACCTAATAGCCAATTGTGCATCAATCCTTTGCAAGTGTTACACAACAGGAACG
ATCATTAATCAAGACCCTGACAAGATCCTAACATACATTGCTGCCGATCACTGCC
CGGTAGTCGAGGTGAACGGCGTGACCATCCAAGTCGGGAGCAGGAGGTATCCAG
ACGCTGTGTACTTGCACAGAATTGACCTCGGTCCTCCCATATCATTGGAGAGGTT
GGACGTAGGGACAAATCTGGGGAATGCAATTGCTAAGTTGGAGGATGCCAAGGA
ATTGTTGGAGTCATCGGACCAGATATTGAGGAGTATGAAAGGTTTATCGAGCAC
TAGCATAGTCTACATCCTGATTGCAGTGTGTCTTGGAGGGTTGATAGGGATCCCC
GCTTTAATATGTTGCTGCAGGGGGCGTTGTAACAAAAAGGGAGAACAAGTTGGT
ATGTCAAGACCAGGCCTAAAGCCTGATCTTACGGGAACATCAAAATCCTATGTA
AGGTCGCTCTGATCCTCTACAACTCTTGAAACACAAATGTCCCACAAGTCTCCTC
TTCGTCATCAAGCAACCACCGCACCCAGCATCAAGCCCACCTGAAATTATCTCCG
GCTTCCCTCTGGCCGAACAATATCGGTAGTTAATTAAAACTTAGGGTGCAAGATC
ATCGATAATGTCACCACAACGAGACCGGATAAATGCCTTCTACAAAGATAACCC
CCATCCCAAGGGAAGTAGGATAGTCATTAACAGAGAACATCTTATGATTGATAG
ACCTTATGTTTTGCTGGCTGTTCTGTTTGTCATGTTTCTGAGCTTGATCGGGTTGC
TAGCCATTGCAGGAATTCGACTTCATCGGGCAGCCATCTACACCGCAGAGATCC
ATAAAAGCCTCAGCACCAATCTAGATGTAACTAACTCAATCGAGCATCAGGTCA
AGGACGTGCTGACACCACTCTTCAAAATCATCGGTGATGAAGTGGGCCTGAGGA
```

-continued

```
CACCTCAGAGATTCACTGACCTAGTGAAATTAATCTCTGACAAGATTAAATTCCT

TAATCCGGATAGGGAGTACGACTTCAGAGATCTCACTTGGTGTATCAACCCGCCA

GAGAGAATCAAATTGGATTATGATCAATACTGTGCAGATGTGGCTGCTGAAGAG

CTCATGAATGCATTGGTGAACTCAACTCTACTGGAGACCAGAACAACCAATCAG

TTCCTAGCTGTCTCAAAGGGAAACTGCTCAGGGCCCACTACAATCAGAGGTCAA

TTCTCAAACATGTCGCTGTCCCTGTTAGACTTGTATTTAGGTCGAGGTTACAATGT

GTCATCTATAGTCACTATGACATCCCAGGGAATGTATGGGGGAACTTACCTAGTG

GAAAAGCCTAATCTGAGCAGCAAAAGGTCAGAGTTGTCACAACTGAGCATGTAC

CGAGTGTTTGAAGTAGGTGTTATCAGAAATCCGGGTTTGGGGGCTCCGGTGTTCC

ATATGACAAACTATCTTGAGCAACCAGTCAGTAATGATCTCAGCAACTGTATGGT

GGCTTTGGGGGAGCTCAAACTCGCAGCCCTTTGTCACGGGGAAGATTCTATCACA

ATTCCCTATCAGGGATCAGGGAAAGGTGTCAGCTTCCAGCTCGTCAAGCTAGGT

GTCTGGAAATCCCCAACCGACATGCAATCCTGGGTCCCCTTATCAACGGATGATC

CAGTGATAGACAGGCTTTACCTCTCATCTCACAGAGGTGTTATCGCTGACAACCA

AGCAAAATGGGCTGTCCCGACAACACGAACAGATGACAAGTTGCGAATGGAGA

CATGCTTCCAACAGGCGTGTAAGGGTAAAATCCAAGCACTCTGCGAGAATCCCG

AGTGGGCACCATTGAAGGATAACAGGATTCCTTCATACGGGGTCTTGTCTGTTGA

TCTGAGTCTGACAGTTGAGCTTAAAATCAAAATTGCTTCGGGATTCGGGCCATTG

ATCACACACGGTTCAGGGATGGACCTATACAAATCCAACCACAACAATGTGTAT

TGGCTGACTATCCCGCCAATGAAGAACCTAGCCTTAGGTGTAATCAACACATTGG

AGTGGATACCGAGATTCAAGGTTAGTCCCTACCTCTTCACTGTCCCAATTAAGGA

AGCAGGCGAAGACTGCCATGCCCCAACATACCTACCTGCGGAGGTGGATGGTGA

TGTCAAACTCAGTTCCAATCTGGTGATTCTACCTGGTCAAGATCTCCAATATGTTT

TGGCAACCTACGATACTTCCAGGGTTGAACATGCTGTGGTTTATTACGTTTACAG

CCCAAGCCGCTCATTTTCTTACTTTTATCCTTTTAGGTTGCCTATAAAGGGGGTCC

CCATCGAATTACAAGTGGAATGCTTCACATGGGACCAAAAACTCTGGTGCCGTC

ACTTCTGTGTGCTTGCGGACTCAGAATCTGGTGGACATATCACTCACTCTGGGAT

GGTGGGCATGGGAGTCAGCTGCACAGTCACCCGGGAAGATGGAACCAATCGCA

GATAGGGCTGCTAGTGAACCAATCACATGATGTCACCCAGACATCAGGCATACC

CACCATCCATCATTGTTATAAAAAACTTAGGAACCAGGTCCACACAGAGTGATA

CGCGTACGCCACCATGTTCGTGTTTCTGGTGCTGCTGCCTCTGGTGAGCTCCCAG

TGCGTGAACCTGACCACAAGGACCCAGCTGCCCCCTGCCTATACCAATTCCTTCA

CACGGGGCGTGTACTATCCCGACAAGGTGTTCCGGAGCAGCGTGCTGCACTCCA

CACAGGATCTGTTTCTGCCTTTCTTTTCTAACGTGACCTGGTTCCACGCCATCCAC

GTGAGCGGCACCAATGGCACAAAGCGGTTCGACAATCCAGTGCTGCCCTTTAAC

GATGGCGTGTACTTCGCCTCCACCGAGAAGTCTAACATCATCAGAGGCTGGATCT

TTGGCACCACACTGGACAGCAAGACACAGTCCCTGCTGATCGTGAACAATGCCA

CCAACGTGGTCATCAAGGTGTGCGAGTTCCAGTTTTGTAATGATCCATTCCTGGG

CGTGTACTATCACAAGAACAATAAGTCTTGGATGGAGAGCGAGTTTCGCGTGTA

TTCCTCTGCCAACAATTGCACATTTGAGTACGTGTCCCAGCCCTTCCTGATGGAC
```

-continued

```
CTGGAGGGCAAGCAGGGCAATTTCAAGAACCTGAGGGAGTTCGTGTTTAAGAAT
ATCGATGGCTACTTCAAAATCTACTCCAAGCACACCCCAATCAACCTGGTGCGCG
ACCTGCCACAGGGCTTCTCTGCCCTGGAGCCACTGGTGGATCTGCCCATCGGCAT
CAACATCACCCGGTTTCAGACACTGCTGGCCCTGCACAGAAGCTACCTGACACC
AGGCGACAGCTCCTCTGGATGGACCGCAGGAGCAGCAGCCTACTATGTGGGCTA
TCTGCAGCCCAGGACCTTCCTGCTGAAGTACAACGAGAATGGCACCATCACAGA
CGCCGTGGATTGCGCCCTGGATCCCCTGTCTGAGACCAAGTGTACACTGAAGAG
CTTTACCGTGGAGAAGGGCATCTATCAGACAAGCAATTTCAGGGTGCAGCCTAC
CGAGTCCATCGTGCGCTTTCCCAATATCACAAACCTGTGCCCTTTTGGCGAGGTG
TTCAACGCAACCCGCTTCGCCAGCGTGTACGCCTGGAATAGGAAGCGCATCTCC
AACTGCGTGGCCGACTATTCTGTGCTGTACAACAGCGCCTCCTTCTCTACCTTTA
AGTGCTATGGCGTGAGCCCCACAAAGCTGAATGACCTGTGCTTTACCAACGTGTA
CGCCGATTCCTTCGTGATCAGGGGCGACGAGGTGCGCCAGATCGCACCAGGACA
GACAGGCAAGATCGCAGACTACAATTATAAGCTGCCTGACGATTTCACCGGCTG
CGTGATCGCCTGGAACTCTAACAATCTGGATAGCAAAGTGGGCGGCAACTACAA
TTATCTGTACCGGCTGTTTAGAAAGTCTAATCTGAAGCCATTCGAGAGGGACATC
TCCACAGAAATCTACCAGGCCGGCTCTACCCCCTGCAATGGCGTGGAGGGCTTT
AACTGTTATTTCCCTCTGCAGAGCTACGGCTTCCAGCCAACAAACGGCGTGGGCT
ATCAGCCCTACCGCGTGGTGGTGCTGTCTTTTGAGCTGCTGCACGCACCTGCAAC
AGTGTGCGGACCAAAGAAGAGCACCAATCTGGTGAAGAACAAGTGCGTGAACTT
CAACTTCAACGGACTGACCGGAACAGGCGTGCTGACCGAGTCCAACAAGAAGTT
CCTGCCTTTTCAGCAGTTCGGCAGGGACATCGCAGATACCACAGACGCCGTGCG
CGACCCTCAGACCCTGGAGATCCTGGACATCACACCATGCTCCTTCGGCGGCGTG
TCTGTGATCACACCAGGCACCAATACAAGCAACCAGGTGGCCGTGCTGTATCAG
GACGTGAATTGTACCGAGGTGCCAGTGGCAATCCACGCAGATCAGCTGACCCCT
ACATGGCGGGTGTACTCTACCGGCAGCAACGTGTTCCAGACAAGAGCCGGATGC
CTGATCGGAGCAGAGCACGTGAACAATAGCTATGAGTGCGACATCCCTATCGGC
GCCGGCATCTGTGCCTCCTACCAGACCCAGACAAACTCCCCAAGGAGAGCACGG
TCTGTGGCCAGCCAGTCCATCATCGCCTATACCATGAGCCTGGGCGCCGAGAATT
CCGTGGCCTACTCCAACAATTCTATCGCCATCCCTACCAACTTCACAATCTCCGT
GACCACAGAGATCCTGCCAGTGAGCATGACCAAGACATCCGTGGACTGCACAAT
GTATATCTGTGGCGATTCCACCGAGTGCTCTAACCTGCTGCTGCAGTACGGCTCT
TTTTGTACCCAGCTGAATAGAGCCCTGACAGGCATCGCCGTGGAGCAGGACAAG
AACACACAGGAGGTGTTCGCCCAGGTGAAGCAAATCTACAAGACCCCACCCATC
AAGGACTTTGGCGGCTTCAACTTCAGCCAGATCCTGCCCGATCCTAGCAAGCCAT
CCAAGCGGTCTTTTATCGAGGACCTGCTGTTCAACAAGGTGACCCTGGCCGATGC
CGGCTTCATCAAGCAGTATGGCGATTGCCTGGGCGACATCGCCGCCAGAGACCT
GATCTGTGCCCAGAAGTTTAATGGCCTGACCGTGCTGCCTCCACTGCTGACAGAT
GAGATGATCGCCCAGTACACATCTGCCCTGCTGGCCGGAACCATCACAAGCGGA
TGGACCTTCGGCGCAGGAGCCGCCCTGCAGATCCCCTTTGCCATGCAGATGGCCT
ATCGGTTCAACGGCATCGGCGTGACCCAGAATGTGCTGTACGAGAACCAGAAGC
```

-continued

```
TGATCGCCAATCAGTTTAACTCCGCCATCGGCAAGATCCAGGACTCTCTGAGCTC
CACAGCCAGCGCCCTGGGCAAGCTGCAGGATGTGGTGAATCAGAACGCCCAGGC
CCTGAATACCCTGGTGAAGCAGCTGTCTAGCAACTTCGGCGCCATCTCCTCTGTG
CTGAATGACATCCTGAGCCGGCTGGACAAGGTGGAGGCAGAGGTGCAGATCGAC
CGGCTGATCACAGGCAGACTGCAGTCCCTGCAGACCTACGTGACACAGCAGCTG
ATCAGGGCAGCAGAGATCAGGGCCTCTGCCAATCTGGCCGCCACCAAGATGAGC
GAGTGCGTGCTGGGCCAGTCCAAGAGAGTGGACTTTTGTGGCAAGGGCTATCAC
CTGATGAGCTTCCCACAGTCCGCCCCTCACGGAGTGGTGTTTCTGCACGTGACCT
ACGTGCCAGCCCAGGAGAAGAACTTCACCACAGCACCAGCAATCTGCCACGATG
GCAAGGCACACTTTCCTAGGGAGGGCGTGTTCGTGAGCAACGGCACCCACTGGT
TTGTGACACAGCGCAATTTCTACGAGCCACAGATCATCACCACAGACAATACAT
TCGTGTCCGGCAACTGTGACGTGGTCATCGGCATCGTGAACAATACCGTGTATGA
TCCTCTGCAGCCAGAGCTGGACTCTTTTAAGGAGGAGCTGGATAAGTACTTCAAG
AATCACACCAGCCCCGACGTGGATCTGGGCGACATCTCTGGCATCAATGCCAGC
GTGGTGAACATCCAGAAGGAGATCGACAGGCTGAACGAGGTGGCCAAGAATCT
GAACGAGTCCCTGATCGATCTGCAGGAGCTGGGCAAGTATGAGCAGTACATCAA
GTGGCCCTGGTATATCTGGCTGGGCTTCATCGCCGGCCTGATCGCCATCGTGATG
GTGACCATCATGCTGTGCTGTATGACAAGCTGCTGTTCCTGCCTGAAGGGCTGCT
GTTCTTGTGGCAGCTGCTGTAAGTTTGATGAGGACGATAGCGAGCCTGTGCTGAA
GGGCGTGAAGCTGCACTACACCTGAGCTAGCGATCGCACTAGTGTGAAATAGAC
ATCAGAATTAAGAAAAACGTAGGGTCCAAGTGGTTCCCCGTTATGGACTCGCTA
TCTGTCAACCAGATCTTATACCCTGAAGTTCACCTAGATAGCCCGATAGTTACCA
ATAAGATAGTAGCCATCCTGGAGTATGCTCGAGTCCCTCACGCTTACAGCCTGGA
GGACCCTACACTGTGTCAGAACATCAAGCACCGCCTAAAAAACGGATTTTCCAA
CCAAATGATTATAAACAATGTGGAAGTTGGGAATGTCATCAAGTCCAAGCTTAG
GAGTTATCCGGCCCACTCTCATATTCCATATCCAAATTGTAATCAGGATTTATTTA
ACATAGAAGACAAAGAGTCAACGAGGAAGATCCGTGAACTCCTCAAAAAGGGG
AATTCGCTGTACTCCAAAGTCAGTGATAAGGTTTTCCAATGCTTAAGGGACACTA
ACTCACGGCTTGGCCTAGGCTCCGAATTGAGGGAGGACATCAAGGAGAAAGTTA
TTAACTTGGGAGTTTACATGCACAGCTCCCAGTGGTTTGAGCCCTTTCTGTTTTGG
TTTACAGTCAAGACTGAGATGAGGTCAGTGATTAAATCACAAACCCATACTTGCC
ATAGGAGGAGACACACACCTGTATTCTTCACTGGTAGTTCAGTTGAGTTGCTAAT
CTCTCGTGACCTTGTTGCTATAATCAGTAAAGAGTCTCAACATGTATATTACCTG
ACATTTGAACTGGTTTTGATGTATTGTGATGTCATAGAGGGGAGGTTAATGACAG
AGACCGCTATGACTATTGATGCTAGGTATACAGAGCTTCTAGGAAGAGTCAGAT
ACATGTGGAAACTGATAGATGGTTTCTTCCCTGCACTCGGGAATCCAACTTATCA
AATTGTAGCCATGCTGGAGCCTCTTTCACTTGCTTACCTGCAGCTGAGGGATATA
ACAGTAGAACTCAGAGGTGCTTTCCTTAACCACTGCTTTACTGAAATACATGATG
TTCTTGACCAAAACGGGTTTTCTGATGAAGGTACTTATCATGAGTTAACTGAAGC
TCTAGATTACATTTTCATAACTGATGACATACATCTGACAGGGGAGATTTTCTCA
```

-continued

```
TTTTTCAGAAGTTTCGGCCACCCCAGACTTGAAGCAGTAACGGCTGCTGAAAATG

TTAGGAAATACATGAATCAGCCTAAAGTCATTGTGTATGAGACTCTGATGAAAG

GTCATGCCATATTTTGTGGAATCATAATCAACGGCTATCGTGACAGGCACGGAG

GCAGTTGGCCACCGCTGACCCTCCCCCTGCATGCTGCAGACACAATCCGGAATG

CTCAAGCTTCAGGTGAAGGGTTAACACATGAGCAGTGCGTTGATAACTGGAAAT

CTTTTGCTGGAGTGAAATTTGGCTGCTTTATGCCTCTTAGCCTGGATAGTGATCTG

ACAATGTACCTAAAGGACAAGGCACTTGCTGCTCTCCAAAGGGAATGGGATTCA

GTTTACCCGAAAGAGTTCCTGCGTTACGACCCTCCCAAGGGAACCGGGTCACGG

AGGCTTGTAGATGTTTTCCTTAATGATTCGAGCTTTGACCCATATGATGTGATAA

TGTATGTTGTAAGTGGAGCTTACCTCCATGACCCTGAGTTCAACCTGTCTTACAG

CCTGAAAGAAAGGAGATCAAGGAAACAGGTAGACTTTTTGCTAAAATGACTTA

CAAAATGAGGGCATGCCAAGTGATTGCTGAAAATCTAATCTCAAACGGGATTGG

CAAATATTTTAAGGACAATGGGATGGCCAAGGATGAGCACGATTTGACTAAGGC

ACTCCACACTCTAGCTGTCTCAGGAGTCCCCAAAGATCTCAAAGAAAGTCACAG

GGGGGGGCCAGTCTTAAAAACCTACTCCCGAAGCCCAGTCCACACAAGTACCAG

GAACGTGAGAGCAGCAAAAGGGTTTATAGGGTTCCCTCAAGTAATTCGGCAGGA

CCAAGACACTGATCATCCGGAGAATATGGAAGCTTACGAGACAGTCAGTGCATT

TATCACGACTGATCTCAAGAAGTACTGCCTTAATTGGAGATATGAGACCATCAGC

TTGTTTGCACAGAGGCTAAATGAGATTTACGGATTGCCCTCATTTTTCCAGTGGC

TGCATAAGAGGCTTGAGACCTCTGTCCTGTATGTAAGTGACCCTCATTGCCCCCC

CGACCTTGACGCCCATATCCCGTTATATAAAGTCCCCAATGATCAAATCTTCATT

AAGTACCCTATGGGAGGTATAGAAGGGTATTGTCAGAAGCTGTGGACCATCAGC

ACCATTCCCTATCTATACCTGGCTGCTTATGAGAGCGGAGTAAGGATTGCTTCGT

TAGTGCAAGGGGACAATCAGACCATAGCCGTAACAAAAAGGGTACCCAGCACA

TGGCCCTACAACCTTAAGAAACGGGAAGCTGCTAGAGTAACTAGAGATTACTTT

GTAATTCTTAGGCAAAGGCTACATGATATTGGCCATCACCTCAAGGCAAATGAG

ACAATTGTTTCATCACATTTTTTTGTCTATTCAAAAGGAATATATTATGATGGGCT

ACTTGTGTCCCAATCACTCAAGAGCATCGCAAGATGTGTATTCTGGTCAGAGACT

ATAGTTGATGAAACAAGGGCAGCATGCAGTAATATTGCTACAACAATGGCTAAA

AGCATCGAGAGAGGTTATGACCGTTACCTTGCATATTCCCTGAACGTCCTAAAAG

TGATACAGCAAATTCTGATCTCTCTTGGCTTCACAATCAATTCAACCATGACCCG

GGATGTAGTCATACCCCTCCTCACAAACAACGACCTCTTAATAAGGATGGCACT

GTTGCCCGCTCCTATTGGGGGATGAATTATCTGAATATGAGCAGGCTGTTTGTC

AGAAACATCGGTGATCCAGTAACATCATCAATTGCTGATCTCAAGAGAATGATT

CTCGCCTCACTAATGCCTGAAGAGACCCTCCATCAGGTAATGACACAACAACCG

GGGGACTCTTCATTCCTAGACTGGGCTAGCGACCCTTACTCAGCAAATCTTGTAT

GTGTCCAGAGCATCACTAGACTCCTCAAGAACATAACTGCAAGGTTTGTCCTGAT

CCATAGTCCAAACCCAATGTTAAAAGGATTATTCCATGATGACAGTAAAGAAGA

GGACGAGGGACTGGCGGCATTCCTCATGGACAGGCATATTATAGTACCTAGGGC

AGCTCATGAAATCCTGGATCATAGTGTCACAGGGGCAAGAGAGTCTATTGCAGG

CATGCTGGATACCACAAAAGGCTTGATTCGAGCCAGCATGAGGAAGGGGGGTTT
```

-continued

```
AACCTCTCGAGTGATAACCAGATTGTCCAATTATGACTATGAACAATTCAGAGCA
GGGATGGTGCTATTGACAGGAAGAAAGAGAAATGTCCTCATTGACAAAGAGTCA
TGTTCAGTGCAGCTGGCGAGAGCTCTAAGAAGCCATATGTGGGCGAGGCTAGCT
CGAGGACGGCCTATTTACGGCCTTGAGGTCCCTGATGTACTAGAATCTATGCGAG
GCCACCTTATTCGGCGTCATGAGACATGTGTCATCTGCGAGTGTGGATCAGTCAA
CTACGGATGGTTTTTTGTCCCCTCGGGTTGCCAACTGGATGATATTGACAAGGAA
ACATCATCCTTGAGAGTCCCATATATTGGTTCTACCACTGATGAGAACAGACA
TGAAGCTTGCCTTCGTAAGAGCCCCAAGTCGATCCTTGCGATCTGCTGTTAGAAT
AGCAACAGTGTACTCATGGGCTTACGGTGATGATGATAGCTCTTGGAACGAAGC
CTGGTTGTTGGCTAGGCAAAGGGCCAATGTGAGCCTGGAGGAGCTAAGGGTGAT
CACTCCCATCTCAACTTCGACTAATTTAGCGCATAGGTTGAGGGATCGTAGCACT
CAAGTGAAATACTCAGGTACATCCCTTGTCCGAGTGGCGAGGTATACCACAATCT
CCAACGACAATCTCTCATTTGTCATATCAGATAAGAAGGTTGATACTAACTTTAT
ATACCAACAAGGAATGCTTCTAGGGTTGGGTGTTTTAGAAACATTGTTTCGACTC
GAGAAAGATACCGGATCATCTAACACGGTATTACATCTTCACGTCGAAACAGAT
TGTTGCGTGATCCCGATGATAGATCATCCCAGGATACCCAGCTCCCGCAAGCTAG
AGCTGAGGGCAGAGCTATGTACCAACCCATTGATATATGATAATGCACCTTTAAT
TGACAGAGATGCAACAAGGCTATACACCCAGAGCCATAGGAGGCACCTTGTGGA
ATTTGTTACATGGTCCACACCCCAACTATATCACATTTTAGCTAAGTCCACAGCA
CTATCTATGATTGACCTGGTAACAAAATTTGAGAAGGACCATATGAATGAAATTT
CAGCTCTCATAGGGGATGACGATATCAATAGTTTCATAACTGAGTTTCTGCTCAT
AGAGCCAAGATTATTCACTATCTACTTGGGCCAGTGTGCGGCCATCAATTGGGCA
TTTGATGTACATTATCATAGACCATCAGGGAAATATCAGATGGGTGAGCTGTTGT
CATCGTTCCTTTCTAGAATGAGCAAAGGAGTGTTTAAGGTGCTTGTCAATGCTCT
AAGCCACCCAAAGATCTACAAGAAATTCTGGCATTGTGGTATTATAGAGCCTATC
CATGGTCCTTCACTTGATGCTCAAAACTTGCACACAACTGTGTGCAACATGGTTT
ACACATGCTATATGACCTACCTCGACCTGTTGTTGAATGAAGAGTTAGAAGAGTT
CACATTTCTCTTGTGTGAAAGCGACGAGGATGTAGTACCGGACAGATTCGACAA
CATCCAGGCAAAACACTTATGTGTTCTGGCAGATTTGTACTGTCAACCAGGGACC
TGCCCACCAATTCGAGGTCTAAGACCGGTAGAGAAATGTGCAGTTCTAACCGAC
CATATCAAGGCAGAGGCTATGTTATCTCCAGCAGGATCTTCGTGGAACATAAATC
CAATTATTGTAGACCATTACTCATGCTCCCTGACTTATCTCCGGCGAGGATCGAT
CAAACAGATAAGATTGAGAGTTGATCCAGGATTCATTTTCGACGCCCTCGCTGAG
GTAAATGTCAGTCAGCCAAAGATCGGCAGCAACAACATCTCAAATATGAGCATC
AAGGCTTTCAGACCCCCACACGATGATGTTGCAAAATTGCTCAAAGATATCAAC
ACAAGCAAGCACAATCTTCCCATTTCAGGGGCAATCTCGCCAATTATGAAATC
CATGCTTTCCGCAGAATCGGGTTGAACTCATCTGCTTGCTACAAAGCTGTTGAGA
TATCAACATTAATTAGGAGATGCCTTGAGCCAGGGGAGGACGGCTTGTTCTTGG
GTGAGGGATCGGGTTCTATGTTGATCACTTATAAGGAGATACTTAAACTAAACA
AGTGCTTCTATAATAGTGGGGTTTCCGCCAATTCTAGATCTGGTCAAAGGGAATT
```

-continued

```
AGCACCCTATCCCTCCGAAGTTGGCCTTGTCGAACACAGAATGGGAGTAGGTAA

TATTGTCAAAGTGCTCTTTAACGGGAGGCCCGAAGTCACGTGGGTAGGCAGTGT

AGATTGCTTCAATTTCATAGTTAGTAATATCCCTACCTCTAGTGTGGGGTTTATCC

ATTCAGATATAGAGACCTTGCCTGACAAAGATACTATAGAGAAGCTAGAGGAAT

TGGCAGCCATCTTATCGATGGCTCTGCTCCTGGGCAAAATAGGATCAATACTGGT

GATTAAGCTTATGCCTTTCAGCGGGGATTTTGTTCAGGGATTTATAAGTTATGTA

GGGTCTCATTATAGAGAAGTGAACCTTGTATACCCTAGATACAGCAACTTCATAT

CTACTGAATCTTATTTGGTTATGACAGATCTCAAGGCTAACCGGCTAATGAATCC

TGAAAAGATTAAGCAGCAGATAATTGAATCATCTGTGAGGACTTCACCTGGACT

TATAGGTCACATCCTATCCATTAAGCAACTAAGCTGCATACAAGCAATTGTGGGA

GACGCAGTTAGTAGAGGTGATATCAATCCTACTCTGAAAAAACTTACACCTATA

GAGCAGGTGCTGATCAATTGCGGGTTGGCAATTAACGGACCTAAGCTGTGCAAA

GAATTGATCCACCATGATGTTGCCTCAGGGCAAGATGGATTGCTTAATTCTATAC

TCATCCTCTACAGGGAGTTGGCAAGATTCAAAGACAACCAAAGAAGTCAACAAG

GGATGTTCCACGCCTACCCCGTATTGGTAAGTAGCAGGCAACGAGAACTTATATC

TAGGATCACCCGCAAATTTTGGGGGCACATTCTTCTTTACTCCGGGAACAAAAAG

TTGATAAATAAGTTTATCCAGAATCTCAAGTCCGGCTATCTGATACTAGACTTAC

ACCAGAATATCTTCGTTAAGAATCTATCCAAGTCAGAGAAACAGATTATTATGAC

GGGGGGTTTGAAACGTGAGTGGGTTTTTAAGGTAACAGTCAAGGAGACCAAAGA

ATGGTATAAGTTAGTCGGATACAGTGCCCTGATTAAGGACTAATTGGTTGAACTC

CGGAACCCTAATCCTGCCCTAGGTGGTTAGGCATTATTTGCAATATATTAAAGAA

AACTTTGAAAATACGAAGTTTCTATTCCCAGCTTTGTCTGGTggccggcatAgtcccagcct cctcgctggcgctggctgggcaacattccgaggggaccgtccccAcggtaatggcgaatgggacgcggccgatccggctgctaa caaagcccgaaaggaagctgagttggctgctgGcGcTGgctgGgcaataactagcataaccccttggggcctctaaacgggtct tgaggggttttttgctgaaaggaggaactatatccggatgcGGCCGCGCGCTTGGCGTAATCATGGTCATA

GCTGTTTCCTGTGTGAAATTGTTATCCGCTCACAATTCCACACAACATACGAGCC

GGAAGCATAAAGTGTAAAGCCTGGGGTGCCTAATGAGTGAGCTAACTCACATTA

ATTGCGTTGCGCTCACTGCCCGCTTTCCAGTCGGGAAACCTGTCGTGCCAGCTGC

ATTAATGAATCGGCCAACGCGCGGGGAGAGGCGGTTTGCGTATTGGGCGCTCTT

CCGCTTCCTCGCTCACTGACTCGCTGCGCTCGGTCGTTCGGCTGCGGCGAGCGGT

ATCAGCTCACTCAAAGGCGGTAATACGGTTATCCACAGAATCAGGGGATAACGC

AGGAAAGAACATGTGAGCAAAAGGCCAGCAAAAGGCCAGGAACCGTAAAAAGG

CCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGC

GTTTCCCCCTGGAAGCTCCCTCGTGCGCTCTCCTGTTCCGACCCTGCCGCTTACCG

GATACCTGTCCGCCTTTCTCCCTTCGGGAAGCGTGGCGCTTTCTCATAGCTCACG

CTGTAGGTATCTCAGTTCGGTGTAGGTCGTTCGCTCCAAGCTGGGCTGTGTGCAC

GAACCCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGA

TTAGCAGAGCGAGGTATGTAGGCGGTGCTACAGAGTTCTTGAAGTGGTGGCCTA

ACTACGGCTACACTAGAAGGACAGTATTTGGTATCTGCGCTCTGCTGAAGCCAGT
```

-continued

```
TACCTTCGGAAAAAGAGTTGGTAGCTCTTGATCCGGCAAACAAACCACCGCTGG

TAGCGGTGGTTTTTTTGTTTGCAAGCAGCAGATTACGCGCAGAAAAAAAGGATCT

CAAGAAGATCCTTTGATCTTTTCTACGGGGTCTGACGCTCAGTGGAACGAAAACT

CACGTTAAGGGATTTTGGTCATGAGATTATCAAAAAGGATCTTCACCTAGATCCT

TTTAAATTAAAAATGAAGTTTTAAATCAATCTAAAGTATATATGAGTAAACTTGG

TCTGACAGTTACCAATGCTTAATCAGTGAGGCACCTATCTCAGCGATCTGTCTAT

TTCGTTCATCCATAGTTGCCTGACTCCCCGTCGTGTAGATAACTACGATACGGGA

GGGCTTACCATCTGGCCCCAGTGCTGCAATGATACCGCGAGACCCACGCTCACC

GGCTCCAGATTTATCAGCAATAAACCAGCCAGCCGGAAGGGCCGAGCGCAGAA

GTGGTCCTGCAACTTTATCCGCCTCCATCCAGTCTATTAATTGTTGCCGGGAAGC

TAGAGTAAGTAGTTCGCCAGTTAATAGTTTGCGCAACGTTGTTGCCATTGCTACA

GGCATCGTGGTGTCACGCTCGTCGTTTGGTATGGCTTCATTCAGCTCCGGTTCCC

AACGATCAAGGCGAGTTACATGATCCCCCATGTTGTGCAAAAAAGCGGTTAGCT

CCTTCGGTCCTCCGATCGTTGTCAGAAGTAAGTTGGCCGCAGTGTTATCACTCAT

GGTTATGGCAGCACTGCATAATTCTCTTACTGTCATGCCATCCGTAAGATGCTTTT

CTGTGACTGGTGAGTACTCAACCAAGTCATTCTGAGAATAGTGTATGCGGCGACC

GAGTTGCTCTTGCCCGGCGTCAATACGGGATAATACCGCGCCACATAGCAGAAC

TTTAAAAGTGCTCATCATTGGAAAACGTTCTTCGGGGCGAAAACTCTCAAGGATC

TTACCGCTGTTGAGATCCAGTTCGATGTAACCCACTCGTGCACCCAACTGATCTT

CAGCATCTTTTACTTTCACCAGCGTTTCTGGGTGAGCAAAAACAGGAAGGCAAA

ATGCCGCAAAAAAGGGAATAAGGGCGACACGGAAATGTTGAATACTCATACTCT

TCCTTTTTCAATATTATTGAAGCATTTATCAGGGTTATTGTCTCATGAGCGGATAC

ATATTTGAATGTATTTAGAAAAATAAACAAATAGGGGTTCCGCGCACATTTCCCC

GAAAAGTGCCACCTG.
```

In one embodiment, the nucleic acid comprises the sequence of SEQ ID NO: 6, shown below (RABV vector: Coravax V1-China (RABVG-E31)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT
```

-continued

```
TTTTCTCCCGGATTGAGCATCTATATTCAGCAATCAGAGTGGGCACAGTTGTCAC
TGCTTATGAAGACTGTTCAGGACTGGTATCATTTACTGGGTTCATAAAACAAATC
AATCTCACCGCTAGAGAGGCAATACTATATTTCTTCCACAAGAACTTTGAGGAAG
AGATAAGAAGAATGTTTGAGCCAGGGCAGGAGACAGCTGTTCCTCACTCTTATTT
CATCCACTTCCGTTCACTAGGCTTGAGTGGGAAATCTCCTTATTCATCAAATGCT
GTTGGTCACGTGTTCAATCTCATTCACTTTGTAGGATGCTATATGGGTCAAGTCA
GATCCCTAAATGCAACGGTTATTGCTGCATGTGCTCCTCATGAAATGTCTGTTCT
AGGGGGCTATCTGGGAGAGGAATTCTTCGGGAAAGGGACATTTGAAAGAAGATT
CTTCAGAGATGAGAAAGAACTTCAAGAATACGAGGCGGCTGAACTGACAAAGA
CTGACGTAGCACTGGCAGATGATGGAACTGTCAACTCTGACGACGAGGACTACT
TTTCAGGTGAAACCAGAAGTCCGGAGGCTGTTTATACTCGAATCATGATGAATG
GAGGTCGACTAAAGAGATCTCACATACGGAGATATGTCTCAGTCAGTTCCAATC
ATCAAGCCCGTCCAAACTCATTCGCCGAGTTTCTAAACAAGACATATTCGAGTGA
CTCATAAcatgaaaaaaactaacacccctcccGTACGCCACCATGTTCGTGTTTCTGGTGCTGCT
GCCTCTGGTGAGCTCCCAGTGCGTGAACCTGACCACAAGGACCCAGCTGCCCCC
TGCCTATACCAATTCCTTCACACGGGGCGTGTACTATCCCGACAAGGTGTTCCGG
AGCAGCGTGCTGCACTCCACACAGGATCTGTTTCTGCCTTTCTTTTCTAACGTGAC
CTGGTTCCACGCCATCCACGTGAGCGGCACCAATGGCACAAAGCGGTTCGACAA
TCCAGTGCTGCCCTTTAACGATGGCGTGTACTTCGCCTCCACCGAGAAGTCTAAC
ATCATCAGAGGCTGGATCTTTGGCACCACACTGGACAGCAAGACACAGTCCCTG
CTGATCGTGAACAATGCCACCAACGTGGTCATCAAGGTGTGCGAGTTCCAGTTTT
GTAATGATCCATTCCTGGGCGTGTACTATCACAAGAACAATAAGTCTTGGATGGA
GAGCGAGTTTCGCGTGTATTCCTCTGCCAACAATTGCACATTTGAGTACGTGTCC
CAGCCCTTCCTGATGGACCTGGAGGGCAAGCAGGGCAATTTCAAGAACCTGAGG
GAGTTCGTGTTTAAGAATATCGATGGCTACTTCAAAATCTACTCCAAGCACACCC
CAATCAACCTGGTGCGCGACCTGCCACAGGGCTTCTCTGCCCTGGAGCCACTGGT
GGATCTGCCCATCGGCATCAACATCACCCGGTTTCAGACACTGCTGGCCCTGCAC
AGAAGCTACCTGACACCAGGCGACAGCTCCTCTGGATGGACCGCAGGAGCAGCA
GCCTACTATGTGGGCTATCTGCAGCCCAGGACCTTCCTGCTGAAGTACAACGAG
AATGGCACCATCACAGACGCCGTGGATTGCGCCCTGGATCCCCTGTCTGAGACC
AAGTGTACACTGAAGAGCTTTACCGTGGAGAAGGGCATCTATCAGACAAGCAAT
TTCAGGGTGCAGCCTACCGAGTCCATCGTGCGCTTTCCCAATATCACAAACCTGT
GCCCTTTTGGCGAGGTGTTCAACGCAACCCGCTTCGCCAGCGTGTACGCCTGGAA
TAGGAAGCGCATCTCCAACTGCGTGGCCGACTATTCTGTGCTGTACAACAGCGCC
TCCTTCTCTACCTTTAAGTGCTATGGCGTGAGCCCCACAAAGCTGAATGACCTGT
GCTTTACCAACGTGTACGCCGATTCCTTCGTGATCAGGGGCGACGAGGTGCGCC
AGATCGCACCAGGACAGACAGGCAAGATCGCAGACTACAATTATAAGCTGCCTG
ACGATTTCACCGGCTGCGTGATCGCCTGGAACTCTAACAATCTGGATAGCAAAGT
GGGCGGCAACTACAATTATCTGTACCGGCTGTTTAGAAAGTCTAATCTGAAGCCA
TTCGAGAGGGACATCTCCACAGAAATCTACCAGGCCGGCTCTACCCCCTGCAAT
```

-continued

```
GGCGTGGAgGGCTTTAACTGTTATTTCCCTCTGCAGAgCTACgGCTTCCAGCCAAC

AAACGGCGTGGGCTATCAGCCCTACCGCGTGGTGGTGCTGTCTTTTGAGCTGCTG

CACGCACcTGCAACAGTGTGCGGACCAAAGAAGAGCACCAATCTGGTGAAGAAC

AAGTGCGTGAACTTCAACTTCAACGGACTGACCGGAACAGGCGTGCTGACCGAG

TCCAACAAGAAGTTCCTGCCTTTTCAGCAGTTCGGCAGGGACATCGCAGATACC

ACAGACGCCGTGCGCGACCCTCAGACCCTGGAGATCCTGGACATCACACCATGC

TCCTTCGGCGGCGTGTCTGTGATCACACCAGGCACCAATACAAGCAACCAGGTG

GCCGTGCTGTATCAGGACGTGAATTGTACCGAGGTGCCAGTGGCAATCCACGCA

GATCAGCTGACCCCTACATGGCGGGTGTACTCTACCGGCAGCAACGTGTTCCAG

ACAAGAGCCGGATGCCTGATCGGAGCAGAGCACGTGAACAATAGCTATGAGTGC

GACATCCCTATCGGCGCCGGCATCTGTGCCTCCTACCAGACCCAGACAAACTCCC

CAAGGTCTGTGGGAGATGAGGCCGAAGACTTTGTGGAAGTCCACCTGCCTGATG

TGCATAACCAGGTGTCTGGCGTCGACCTGGGACTGCCAAATTGGGGCAAGTACG

TGCTGCTGAGTGCTGGAGCACTGACTGCCCTGATGCTGATCATTTTCCTGATGAC

CTGCTGTCGGCGCGTGAACAGAAGTGAGCCCACTCAGCACAATCTGCGAGGAAC

CGGGAGAGAAGTGTCAGTCACACCTCAGAGCGGGAAAATCATTAGTAGTTGGGA

ATCACATAAAAGCGGGGGCGAGACCAGGCTGTGAGCTAGCCATGAAAAAAACT

AACACCCCTCCTTTCGAACCATCCCAAACATGAGCAAGATCTTTGTCAATCCTAG

TGCTATTAGAGCCGGTCTGGCCGATCTTGAGATGGCTGAAGAAACTGTTGATCTG

ATCAATAGAAATATCGAAGACAATCAGGCTCATCTCCAAGGGGAACCCATAGAG

GTGGACAATCTCCCTGAGGATATGGGGCGACTTCACCTGGATGATGGAAAATCG

CCCAACCATGGTGAGATAGCCAAGGTGGGAGAAGGCAAGTATCGAGAGGACTTT

CAGATGGATGAAGGAGAGGATCCTAGCTTCCTGTTCCAGTCATACCTGGAAAAT

GTTGGAGTCCAAATAGTCAGACAAATGAGGTCAGGAGAGAGATTTCTCAAGATA

TGGTCACAGACCGTAGAAGAGATTATATCCTATGTCGCGGTCAACTTTCCCAACC

CTCCAGGAAAGTCTTCAGAGGATAAATCAACCCAGACTACTGGCCGAGAGCTCA

AGAAGGAGACAACACCCACTCCTTCTCAGAGAGAAAGCCAATCATCGAAAGCCA

GGATGGCGGCTCAAATTGCTTCTGGCCCTCCAGCCCTTGAATGGTCGGCTACCAA

TGAAGAGGATGATCTATCAGTGGAGGCTGAGATCGCTCACCAGATTGCAGAAAG

TTTCTCCAAAAAATATAAGTTTCCCTCTCGATCCTCAGGGATACTCTTGTATAATT

TTGAGCAATTGAAAATGAACCTTGATGATATAGTTAAAGAGGCAAAAAATGTAC

CAGGTGTGACCCGTTTAGCCCATGACGGGTCCAAACTCCCCCTAAGATGTGTACT

GGGATGGGTCGCTTTGGCCAACTCTAAGAAATTCCAGTTGTTAGTCGAATCCGAC

AAGCTGAGTAAAATCATGCAAGATGACTTGAATCGCTATACATCTTGCTAACCG

AACCTCTCCCCTCAGTCCCTCTAGACAATAAAATCCGAGATGTCCCAAAGTCAAC

ATGAAAAAAACAGGCAACACCACTGATAAAATGAACCTCCTACGTAAGATAGTG

AAAAACCGCAGGGACGAGGACACTCAAAAATCCTCTCCCGCGTCAGCCCCTCTG

GATGACGATGACTTGTGGCTTCCACCCCCTGAATACGTCCCGCTGAAAGAACTTA

CAGGCAAGAAGAACATGAGGAACTTTTGTATCAACGGAAGGGTTAAAGTGTGTA

GCCCGAATGGTTACTCGTTCAGGATCCTGCGGCACATTCTGAAATCATTCGACGA

GATATATTCTGGGAATCATAGGATGATCGGGTTAGTCAAAGTGGTTATTGGACTG
```

-continued

```
GCTTTGTCAGGATCTCCAGTCCCTGAGGGCCTGAACTGGGTATACAAATTGAGGA

GAACCTTTATCTTCCAGTGGGCTGATTCCAGGGGCCCTCTTGAAGGGGAGGAGTT

GGAATACTCTCAGGAGATCACTTGGGATGATGATACTGAGTTCGTCGGATTGCA

AATAAGAGTGATTGCAAAACAGTGTCATATCCAGGGCAGAGTCTGGTGTATCAA

CATGAACCCGAGAGCATGTCAACTATGGTCTGACATGTCTCTTCAGACACAAAG

GTCCGAAGAGGACAAAGATTCCTCTCTGCTTCTAGAATAATCAGATTATATCCCG

CAAATTTATCACTTGTTTACCTCTGGAGGAGAGAACATATGGGCTCAACTCCAAC

CCTTGGGAGCAATATAACAAAAAACATGTTATGGTGCCATTAAACCGCTGCATTT

CATCAAAGTCAAGTTGATTACCTTTACATTTTGATCCTCTTGGATGTGAAAAAA

CTATTAACATCCCTCAAAAGAcccgggAAAGATGGTTCCTCAGGCTCTCCTGTTTG

TACCCCTTCTGGTTTTTCCATTGTGTTTGGGAAATTCCCTATTTACACGATACCA

GACAAGCTTGGTCCCTGGAGTCCGATTGACATACATCACCTCAGCTGCCCAAAC

AATTTGGTAGTGGAGGACGAAGGATGCACCAACCTGTCAGGGTTCTCCTACATG

GAACTTAAAGTTGGATACATCTTAGCCATAAAAGTGAACGGGTTCACTTGCACA

GGCGTTGTGACGGAGGCTGAAACCTACACTAACTTCGTTGGTTATGTCACAACCA

CGTTCAAAAGAAAGCATTTCCGCCCAACACCAGATGCATGTAGAGCCGCGTACA

ACTGGAAGATGGCCGGTGACCCCAGATATGAAGAGTCTCTACACAATCCGTACC

CTGACTACCGCTGGCTTCGAACTGTAAAAACCACCAAGGAGTCTCTCGTTATCAT

ATCTCCAAGTGTGGCAGATTTGGACCCATATGACAGATCCCTTCACTCGAGGGTC

TTCCCTAGCGGGAAGTGCTCAGGAGTAGCGGTGTCTTCTACCTACTGCTCCACTA

ACCACGATTACACCATTTGGATGCCCGAGAATCCGAGACTAGGGATGTCTTGTG

ACATTTTTACCAATAGTAGAGGGAAGAGAGCATCCAAAGGGAGTGAGACTTGCG

GCTTTGTAGATGAAAGAGGCCTATATAAGTCTTTAAAAGGAGCATGCAAACTCA

AGTTATGTGGAGTTCTAGGACTTAGACTTATGGATGGAACATGGGTCTCGATGCA

AACATCAAATGAAACCAAATGGTGCCCTCCCGATAAGTTGGTGAACCTGCACGA

CTTTCGCTCAGACGAAATTGAGCACCTTGTTGTAGAGGAGTTGGTCAGGAAGAG

AGAGGAGTGTCTGGATGCACTAGAGTCCATCATGACAACCAAGTCAGTGAGTTT

CAGACGTCTCAGTCATTTAAGAAAACTTGTCCCTGGGTTTGGAAAAGCATATACC

ATATTCAACAAGACCTTGATGGAAGCCGATGCTCACTACAAGTCAGTCgagACTT

GGAATGAGATCCTCCCTTCAAAAGGGTGTTTAAGAGTTGGGGGAGGTGTCATC

CTCATGTGAACGGGGTGTTTTTCAATGGTATAATATTAGGACCTGACGGCAATGT

CTTAATCCCAGAGATGCAATCATCCCTCCTCCAGCAACATATGGAGTTGTTGGAA

TCCTCGGTTATCCCCCTTGTGCACCCCCTGGCAGACCCGTCTACCGTTTTCAAGG

ACGGTGACGAGGCTGAGGATTTTGTTGAAGTTCACCTTCCCGATGTGCACAATCA

GGTCTCAGGAGTTGACTTGGGTCTCCCGAACTGGGGGAAGTATGTATTACTGAGT

GCAGGGGCCCTGACTGCCTTGATGTTGATAATTTTCCTGATGACATGTTGTAGAA

GAGTCAATCGATCAGAACCTACGCAACACAATCTCAGAGGGACAGGGAGGGAG

GTGTCAGTCACTCCCCAAAGCGGGAAGATCATATCTTCATGGGAATCACACAAG

AGTGGGGGTGAGACCAGACTGTAAttaattaaCGTCCTTTCAACGATCCAAGTCcatgaaa aaaactaacacccctcccgtacctagcTTATAAAGTGCTGGGTCATCTAAGCTTTTCAGTCGAGA
```

```
-continued
AAAAAACATTAGATCAGAAGAACAACTGGCAACACTTCTCAACCTGAGACTTAC

TTCAAGATGCTCGATCCTGGAGAGGTCTATGATGACCCTATTGACCCAATCGAGT

TAGAGGCTGAACCCAGAGGAACCCCCATTGTCCCCAACATCTTGAGGAACTCTG

ACTACAATCTCAACTCTCCTTTGATAGAAGATCCTGCTAGACTAATGTTAGAATG

GTTAAAAACAGGGAATAGACCTTATCGGATGACTCTAACAGACAATTGCTCCAG

GTCTTTCAGAGTTTTGAAAGATTATTTCAAGAAGGTAGATTTGGGTTCTCTCAAG

GTGGGCGGAATGGCTGCACAGTCAATGATTTCTCTCTGGTTATATGGTGCCCACT

CTGAATCCAACAGGAGCCGGAGATGTATAACAGACTTGGCCCATTTCTATTCCAA

GTCGTCCCCCATAGAGAAGCTGTTGAATCTCACGCTAGGAAATAGAGGGCTGAG

AATCCCCCCAGAGGGAGTGTTAAGTTGCCTTGAGAGGGTTGATTATGATAATGC

ATTTGGAAGGTATCTTGCCAACACGTATTCCTCTTACTTGTTCTTCCATGTAATCA

CCTTATACATGAACGCCCTAGACTGGGATGAAGAAAAGACCATCCTAGCATTAT

GGAAAGATTTAACCTCAGTGGACATCGGGAAGGACTTGGTAAAGTTCAAAGACC

AAATATGGGGACTGCTGATCGTGACAAAGGACTTTGTTTACTCCCAAAGTTCCAA

TTGTCTTTTTGACAGAAACTACACACTTATGCTAAAAGATCTTTTCTTGTCTCGCT

TCAACTCCTTAATGGTCTTGCTCTCTCCCCCAGAGCCCCGATACTCAGATGACTT

GATATCTCAACTATGCCAGCTGTACATTGCTGGGGATCAAGTCTTGTCTATGTGT

GGAAACTCCGGCTATGAAGTCATCAAAATATTGGAGCCATATGTCGTGAATAGT

TTAGTCCAGAGAGCAGAAAAGTTTAGGCCTCTCATTCATTCCTTGGGAGACTTTC

CTGTATTTATAAAAGACAAGGTAAGTCAACTTGAAGAGACGTTCGGTCCCTGTGC

AAGAAGGTTCTTTAGGGCTCTGGATCAATTCGACAACATACATGACTTGGTTTTT

GTGTTTGGCTGTTACAGGCATTGGGGCACCCATATATAGATTATCGAAAGGGTC

TGTCAAAACTATATGATCAGGTTCACCTTAAAAAAATGATAGATAAGTCCTACCA

GGAGTGCTTAGCAAGCGACCTAGCCAGGAGGATCCTTAGATGGGGTTTTGATAA

GTACTCCAAGTGGTATCTGGATTCAAGATTCCTAGCCCGAGACCACCCCTTGACT

CCTTATATCAAAACCCAAACATGGCCACCCAAACATATTGTAGACTTGGTGGGG

GATACATGGCACAAGCTCCCGATCACGCAGATCTTTGAGATTCCTGAATCAATGG

ATCCGTCAGAAATATTGGATGACAAATCACATTCTTTCACCAGAACGAGACTAG

CTTCTTGGCTGTCAGAAAACCGAGGGGGGCCTGTTCCTAGCGAAAAAGTTATTAT

CACGGCCCTGTCTAAGCCGCCTGTCAATCCCCGAGAGTTTCTGAGGTCTATAGAC

CTCGGAGGATTGCCAGATGAAGACTTGATAATTGGCCTCAAGCCAAAGGAACGG

GAATTGAAGATTGAAGGTCGATTCTTTGCTCTAATGTCATGGAATCTAAGATTGT

ATTTTGTCATCACTGAAAAACTCTTGGCCAACTACATCTTGCCACTTTTTGACGCG

CTGACTATGACAGACAACCTGAACAAGGTGTTTAAAAAGCTGATCGACAGGGTC

ACCGGGCAAGGGCTTTTGGACTATTCAAGGGTCACATATGCATTTCACCTGGACT

ATGAAAAGTGGAACAACCATCAAAGATTAGAGTCAACAGAGGATGTATTTTCTG

TCCTAGATCAAGTGTTTGGATTGAAGAGAGTGTTTTCTAGAACACACGAGTTTTT

TCAAAAGGCCTGGATCTATTATTCAGACAGATCAGACCTCATCGGGTTACGGGA

GGATCAAATATACTGCTTAGATGCGTCCAACGGCCCAACCTGTTGGAATGGCCA

GGATGGCGGGCTAGAAGGCTTACGGCAGAAGGGCTGGAGTCTAGTCAGCTTATT

GATGATAGATAGAGAATCTCAAATCAGGAACACAAGAACCAAAATACTAGCTCA
```

-continued

```
AGGAGACAACCAGGTTTTATGTCCGACATACATGTTGTCGCCAGGGCTATCTCAA

GAGGGGCTCCTCTATGAATTGGAGAGAATATCAAGGAATGCACTTTCGATATAC

AGAGCCGTCGAGGAAGGGGCATCTAAGCTAGGGCTGATCATCAAGAAAGAAGA

GACCATGTGTAGTTATGACTTCCTCATCTATGGAAAAACCCCTTTGTTTAGAGGT

AACATATTGGTGCCTGAGTCCAAAAGATGGGCCAGAGTCTCTTGCGTCTCTAATG

ACCAAATAGTCAACCTCGCCAATATAATGTCGACAGTGTCCACCAATGCGCTAA

CAGTGGCACAACACTCTCAATCTTTGATCAAACCGATGAGGGATTTTCTGCTCAT

GTCAGTACAGGCAGTCTTTCACTACCTGCTATTTAGCCCAATCTTAAAGGGAAGA

GTTTACAAGATTCTGAGCGCTGAAGGGGAGAGCTTTCTCCTAGCCATGTCAAGG

ATAATCTATCTAGATCCTTCTTTGGGAGGGATATCTGGAATGTCCCTCGGAAGAT

TCCATATACGACAGTTCTCAGACCCTGTCTCTGAAGGGTTATCCTTCTGGAGAGA

GATCTGGTTAAGCTCCCAAGAGTCCTGGATTCACGCGTTGTGTCAAGAGGCTGGA

AACCCAGATCTTGGAGAGAGAACACTCGAGAGCTTCACTCGCCTTCTAGAAGAT

CCGACCACCTTAAATATCAGAGGAGGGGCCAGTCCTACCATTCTACTCAAGGAT

GCAATCAGAAAGGCTTTATATGACGAGGTGGACAAGGTGGAAAATTCAGAGTTT

CGAGAGGCAATCCTGTTGTCCAAGACCCATAGAGATAATTTTATACTCTTCTTAA

TATCTGTTGAGCCTCTGTTTCCTCGATTTCTCAGTGAGCTATTCAGTTCGTCTTTTT

TGGGAATCCCCGAGTCAATCATTGGATTGATACAAAACTCCCGAACGATAAGAA

GGCAGTTTAGAAAGAGTCTCTCAAAAACTTTAGAAGAATCCTTCTACAACTCAG

AGATCCACGGGATTAGTCGGATGACCCAGACACCTCAGAGGGTTGGGGGGGTGT

GGCCTTGCTCTTCAGAGAGGGCAGATCTACTTAGGGAGATCTCTTGGGGAAGAA

AAGTGGTAGGCACGACAGTTCCTCACCCTTCTGAGATGTTGGGATTACTTCCCAA

GTCCTCTATTTCTTGCACTTGTGGAGCAACAGGAGGAGGCAATCCTAGAGTTTCT

GTATCAGTACTCCCGTCCTTTGATCAGTCATTTTTTTCACGAGGCCCCCTAAAGG

GATACTTGGGCTCGTCCACCTCTATGTCGACCCAGCTATTCCATGCATGGGAAAA

AGTCACTAATGTTCATGTGGTGAAGAGAGCTCTATCGTTAAAAGAATCTATAAAC

TGGTTCATTACTAGAGATTCCAACTTGGCTCAAGCTCTAATTAGGAACATTATGT

CTCTGACAGGCCCTGATTTCCCTCTAGAGGAGGCCCCTGTCTTCAAAAGGACGGG

GTCAGCCTTGCATAGGTTCAAGTCTGCCAGATACAGCGAAGGAGGGTATTCTTCT

GTCTGCCCGAACCTCCTCTCTCATATTTCTGTTAGTACAGACACCATGTCTGATTT

GACCCAAGACGGGAAGAACTACGATTTCATGTTCCAGCCATTGATGCTTTATGCA

CAGACATGGACATCAGAGCTGGTACAGAGAGACACAAGGCTAAGAGACTCTAC

GTTTCATTGGCACCTCCGATGCAACAGGTGTGTGAGACCCATTGACGACGTGACC

CTGGAGACCTCTCAGATCTTCGAGTTTCCGGATGTGTCGAAAAGAATATCCAGAA

TGGTTTCTGGGGCTGTGCCTCACTTCCAGAGGCTTCCCGATATCCGTCTGAGACC

AGGAGATTTTGAATCTCTAAGCGGTAGAGAAAAGTCTCACCATATCGGATCAGC

TCAGGGGCTCTTATACTCAATCTTAGTGGCAATTCACGACTCAGGATACAATGAT

GGAACCATCTTCCCTGTCAACATATACGGCAAGGTTTCCCCTAGAGACTATTTGA

GAGGGCTCGCAAGGGGAGTATTGATAGGATCCTCGATTTGCTTCTTGACAAGAA

TGACAAATATCAATATTAATAGACCTCTTGAATTGGTCTCAGGGGTAATCTCATA
```

-continued

```
TATTCTCCTGAGGCTAGATAACCATCCCTCCTTGTACATAATGCTCAGAGAACCG

TCTCTTAGAGGAGAGATATTTTCTATCCCTCAGAAAATCCCCGCCGCTTATCCAA

CCACTATGAAAGAAGGCAACAGATCAATCTTGTGTTATCTCCAACATGTGCTACG

CTATGAGCGAGAGATAATCACGGCGTCTCCAGAGAATGACTGGCTATGGATCTT

TTCAGACTTTAGAAGTGCCAAAATGACGTACCTATCCCTCATTACTTACCAGTCT

CATCTTCTACTCCAGAGGGTTGAGAGAAACCTATCTAAGAGTATGAGAGATAAC

CTGCGACAATTGAGTTCTTTGATGAGGCAGGTGCTGGGCGGGCACGGAGAAGAT

ACCTTAGAGTCAGACGACAACATTCAACGACTGCTAAAAGACTCTTTACGAAGG

ACAAGATGGGTGGATCAAGAGGTGCGCCATGCAGCTAGAACCATGACTGGAGAT

TACAGCCCCAACAAGAAGGTGTCCCGTAAGGTAGGATGTTCAGAATGGGTCTGC

TCTGCTCAACAGGTTGCAGTCTCTACCTCAGCAAACCCGGCCCCTGTCTCGGAGC

TTGACATAAGGGCCCTCTCTAAGAGGTTCCAGAACCCTTTGATCTCGGGCTTGAG

AGTGGTTCAGTGGGCAACCGGTGCTCATTATAAGCTTAAGCCTATTCTAGATGAT

CTCAATGTTTTCCCATCTCTCTGCCTTGTAGTTGGGGACGGGTCAGGGGGGATAT

CAAGGGCAGTCCTCAACATGTTTCCAGATGCCAAGCTTGTGTTCAACAGTCTTTT

AGAGGTGAATGACCTGATGGCTTCCGGAACACATCCACTGCCTCCTTCAGCAATC

ATGAGGGAGGAAATGATATCGTCTCCAGAGTGATAGATCTTGACTCAATCTGG

GAAAAACCGTCCGACTTGAGAAACTTGGCAACCTGGAAATACTTCCAGTCAGTC

CAAAAGCAGGTCAACATGTCCTATGACCTCATTATTTGCGATGCAGAAGTTACTG

ACATTGCATCTATCAACCGGATCACCCTGTTAATGTCCGATTTTGCATTGTCTATA

GATGGACCACTCTATTTGGTCTTCAAAACTTATGGGACTATGCTAGTAAATCCAA

ACTACAAGGCTATTCAACACCTGTCAAGAGCGTTCCCCTCGGTCACAGGGTTTAT

CACCCAAGTAACTTCGTCTTTTTCATCTGAGCTCTACCTCCGATTCTCCAAACGA

GGGAAGTTTTTCAGAGATGCTGAGTACTTGACCTCTTCCACCCTTCGAGAAATGA

GCCTTGTGTTATTCAATTGTAGCAGCCCCAAGAGTGAGATGCAGAGAGCTCGTTC

CTTGAACTATCAGGATCTTGTGAGAGGATTTCCTGAAGAAATCATATCAAATCCT

TACAATGAGATGATCATAACTCTGATTGACAGTGATGTAGAATCTTTTCTAGTCC

ACAAGATGGTTGATGATCTTGAGTTACAGAGGGGAACTCTGTCTAAAGTGGCTA

TCATTATAGCCATCATGATAGTTTTCTCCAACAGAGTCTTCAACGTTTCCAAACC

CCTAACTGACCCCTCGTTCTATCCACCGTCTGATCCCAAAATCCTGAGGCACTTC

AACATATGTTGCAGTACTATGATGTATCTATCTACTGCTTTAGGTGACGTCCCTA

GCTTCGCAAGACTTCACGACCTGTATAACAGACCTATAACTTATTACTTCAGAAA

GCAAGTCATTCGAGGGAACGTTTATCTATCTTGGAGTTGGTCCAACGACACCTCA

GTGTTCAAAAGGGTAGCCTGTAATTCTAGCCTGAGTCTGTCATCTCACTGGATCA

GGTTGATTTACAAGATAGTGAAGACTACCAGACTCGTTGGCAGCATCAAGGATC

TATCCAGAGAAGTGGAAAGACACCTTCATAGGTACAACAGGTGGATCACCCTAG

AGGATATCAGATCTAGATCATCCCTACTAGACTACAGTTGCCTGTGAACCGGATA

CTCCTGGAAGCCTGCCCATGCTAAGACTCTTGTGTGATGTATCTTGAAAAAAACA

AGATCCTAAATCTGAACCTTTGGTTGTTTGATTGTTTTTCTCAtttttgttgtttatttgttaagcgt.
```

In another embodiment, the nucleic acid comprises the sequence of SEQ ID NO: 7, shown below (RABV vector: Coravax V1-South Africa (RABVG-E31)):

ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAcatgaaaaaaactaacacccctcccGTACGCCACCATGTTCGTGTTTCTGGTGCTGCT

GCCTCTGGTGAGCTCCCAGTGCGTGAACTTCACCACAAGGACCCAGCTGCCCCCT

GCCTATACCAATTCCTTCACACGGGGCGTGTACTATCCCGACAAGGTGTTCCGGA

GCAGCGTGCTGCACTCCACACAGGATCTGTTTCTGCCTTTCTTTTCTAACGTGACC

TGGTTCCACGCCATCCACGTGAGCGGCACCAATGGCACAAAGCGGTTCGCCAAT

CCAGTGCTGCCCTTTAACGATGGCGTGTACTTCGCCTCCACCGAGAAGTCTAACA

TCATCAGAGGCTGGATCTTTGGCACCACACTGGACAGCAAGACACAGTCCCTGC

TGATCGTGAACAATGCCACCAACGTGGTCATCAAGGTGTGCGAGTTCCAGTTTTG

TAATGATCCATTCCTGGGCGTGTACTATCACAAGAACAATAAGTCTTGGATGGAG

AGCGAGTTTCGCGTGTATTCCTCTGCCAACAATTGCACATTTGAGTACGTGTCCC

AGCCCTTCCTGATGGACCTGGAGGGCAAGCAGGGCAATTTCAAGAACCTGAGGG

AGTTCGTGTTTAAGAATATCGATGGCTACTTCAAAATCTACTCCAAGCACACCCC

-continued

```
AATCAACCTGGTGCGCGGCCTGCCACAGGGCTTCTCTGCCCTGGAGCCACTGGTG
GATCTGCCCATCGGCATCAACATCACCCGGTTTCAGACACTGCTGGCCCTGCACA
GAAGCTACCTGACACCAGGCGACAGCTCCTCTGGATGGACCGCAGGAGCAGCAG
CCTACTATGTGGGCTATCTGCAGCCCAGGACCTTCCTGCTGAAGTACAACGAGA
ATGGCACCATCACAGACGCCGTGGATTGCGCCCTGGATCCCCTGTCTGAGACCA
AGTGTACACTGAAGAGCTTTACCGTGGAGAAGGGCATCTATCAGACAAGCAATT
TCAGGGTGCAGCCTACCGAGTCCATCGTGCGCTTTCCCAATATCACAAACCTGTG
CCCTTTTGGCGAGGTGTTCAACGCAACCCGCTTCGCCAGCGTGTACGCCTGGAAT
AGGAAGCGCATCTCCAACTGCGTGGCCGACTATTCTGTGCTGTACAACAGCGCCT
CCTTCTCTACCTTTAAGTGCTATGGCGTGAGCCCCACAAAGCTGAATGACCTGTG
CTTTACCAACGTGTACGCCGATTCCTTCGTGATCAGGGGCGACGAGGTGCGCCA
GATCGCACCAGGACAGACAGGCAATATCGCAGACTACAATTATAAGCTGCCTGA
CGATTTCACCGGCTGCGTGATCGCCTGGAACTCTAACAATCTGGATAGCAAAGTG
GGCGGCAACTACAATTATCTGTACCGGCTGTTTAGAAAGTCTAATCTGAAGCCAT
TCGAGAGGGACATCTCCACAGAAATCTACCAGGCCGGCTCTACCCCCTGCAATG
GCGTGAAGGGCTTTAACTGTTATTTCCCTCTGCAGAGCTACGGCTTCCAGCCAAC
ATATGGCGTGGGCTATCAGCCCTACCGCGTGGTGGTGCTGTCTTTTGAGCTGCTG
CACGCACCTGCAACAGTGTGCGGACCAAAGAAGAGCACCAATCTGGTGAAGAA
CAAGTGCGTGAACTTCAACTTCAACGGACTGACCGGAACAGGCGTGCTGACCGA
GTCCAACAAGAAGTTCCTGCCTTTTCAGCAGTTCGGCAGGGACATCGCAGATAC
CACAGACGCCGTGCGCGACCCTCAGACCCTGGAGATCCTGGACATCACACCATG
CTCCTTCGGCGGCGTGTCTGTGATCACACCAGGCACCAATACAAGCAACCAGGT
GGCCGTGCTGTATCAGGGCGTGAATTGTACCGAGGTGCCAGTGGCAATCCACGC
AGATCAGCTGACCCCTACATGGCGGGTGTACTCTACCGGCAGCAACGTGTTCCA
GACAAGAGCCGGATGCCTGATCGGAGCAGAGCACGTGAACAATAGCTATGAGTG
CGACATCCCTATCGGCGCCGGCATCTGTGCCTCCTACCAGACCCAGACAAACTCC
CCCaagGTCTGTGGGAGATGAGGCCGAAGACTTTGTGGAAGTCCACCTGCCTGATG
TGCATAACCAGGTGTCTGGCGTCGACCTGGGACTGCCAAATTGGGGCAAGTACG
TGCTGCTGAGTGCTGGAGCACTGACTGCCCTGATGCTGATCATTTTCCTGATGAC
CTGCTGTCGGCGCGTGAACAGAAGTGAGCCCACTCAGCACAATCTGCGAGGAAC
CGGGAGAGAAGTGTCAGTCACACCTCAGAGCGGGAAAATCATTAGTAGTTGGGA
ATCACATAAAAGCGGGGCGAGACCAGGCTGTGAGCTAGCCATGAAAAAAACT
AACACCCCTCCTTTCGAACCATCCCAAACATGAGCAAGATCTTTGTCAATCCTAG
TGCTATTAGAGCCGGTCTGGCCGATCTTGAGATGGCTGAAGAAACTGTTGATCTG
ATCAATAGAAATATCGAAGACAATCAGGCTCATCTCCAAGGGGAACCCATAGAG
GTGGACAATCTCCCTGAGGATATGGGGCGACTTCACCTGGATGATGGAAAATCG
CCCAACCATGGTGAGATAGCCAAGGTGGGAGAAGGCAAGTATCGAGAGGACTTT
CAGATGGATGAAGGAGAGGATCCTAGCTTCCTGTTCCAGTCATACCTGGAAAAT
GTTGGAGTCCAAATAGTCAGACAAATGAGGTCAGGAGAGAGATTTCTCAAGATA
TGGTCACAGACCGTAGAAGAGATTATATCCTATGTCGCGGTCAACTTTCCCAACC
CTCCAGGAAAGTCTTCAGAGGATAAATCAACCCAGACTACTGGCCGAGAGCTCA
```

```
AGAAGGAGACAACACCCACTCCTTCTCAGAGAGAAAGCCAATCATCGAAAGCCA
GGATGGCGGCTCAAATTGCTTCTGGCCCTCCAGCCCTTGAATGGTCGGCTACCAA
TGAAGAGGATGATCTATCAGTGGAGGCTGAGATCGCTCACCAGATTGCAGAAAG
TTTCTCCAAAAAATATAAGTTTCCCTCTCGATCCTCAGGGATACTCTTGTATAATT
TTGAGCAATTGAAAATGAACCTTGATGATATAGTTAAAGAGGCAAAAAATGTAC
CAGGTGTGACCCGTTTAGCCCATGACGGGTCCAAACTCCCCCTAAGATGTGTACT
GGGATGGGTCGCTTTGGCCAACTCTAAGAAATTCCAGTTGTTAGTCGAATCCGAC
AAGCTGAGTAAAATCATGCAAGATGACTTGAATCGCTATACATCTTGCTAACCG
AACCTCTCCCCTCAGTCCCTCTAGACAATAAAATCCGAGATGTCCCAAAGTCAAC
ATGAAAAAAACAGGCAACACCACTGATAAAATGAACCTCCTACGTAAGATAGTG
AAAAACCGCAGGGACGAGGACACTCAAAAATCCTCTCCCGCGTCAGCCCCTCTG
GATGACGATGACTTGTGGCTTCCACCCCCTGAATACGTCCCGCTGAAAGAACTTA
CAGGCAAGAAGAACATGAGGAACTTTTGTATCAACGGAAGGGTTAAAGTGTGTA
GCCCGAATGGTTACTCGTTCAGGATCCTGCGGCACATTCTGAAATCATTCGACGA
GATATATTCTGGGAATCATAGGATGATCGGGTTAGTCAAAGTGGTTATTGGACTG
GCTTTGTCAGGATCTCCAGTCCCTGAGGGCCTGAACTGGGTATACAAATTGAGGA
GAACCTTTATCTTCCAGTGGGCTGATTCCAGGGGCCCTCTTGAAGGGGAGGAGTT
GGAATACTCTCAGGAGATCACTTGGGATGATGATACTGAGTTCGTCGGATTGCA
AATAAGAGTGATTGCAAAACAGTGTCATATCCAGGGCAGAGTCTGGTGTATCAA
CATGAACCCGAGAGCATGTCAACTATGGTCTGACATGTCTCTTCAGACACAAAG
GTCCGAAGAGGACAAAGATTCCTCTCTGCTTCTAGAATAATCAGATTATATCCCG
CAAATTTATCACTTGTTTACCTCTGGAGGAGAGAACATATGGGCTCAACTCCAAC
CCTTGGGAGCAATATAACAAAAAACATGTTATGGTGCCATTAAACCGCTGCATTT
CATCAAAGTCAAGTTGATTACCTTTACATTTTGATCCTCTTGGATGTGAAAAAAA
CTATTAACATCCCTCAAAAGACcccgggAAAGATGGTTCCTCAGGCTCTCCTGTTTG
TACCCCTTCTGGTTTTTCCATTGTGTTTTGGGAAATTCCCTATTTACACGATACCA
GACAAGCTTGGTCCCTGGAGTCCGATTGACATACATCACCTCAGCTGCCCAAAC
AATTTGGTAGTGGAGGACGAAGGATGCACCAACCTGTCAGGGTTCTCCTACATG
GAACTTAAAGTTGGATACATCTTAGCCATAAAAGTGAACGGGTTCACTTGCACA
GGCGTTGTGACGGAGGCTGAAACCTACACTAACTTCGTTGGTTATGTCACAACCA
CGTTCAAAAGAAAGCATTTCCGCCCAACACCAGATGCATGTAGAGCCGCGTACA
ACTGGAAGATGGCCGGTGACCCCAGATATGAAGAGTCTCTACACAATCCGTACC
CTGACTACCGCTGGCTTCGAACTGTAAAAACCACCAAGGAGTCTCTCGTTATCAT
ATCTCCAAGTGTGGCAGATTTGGACCCATATGACAGATCCCTTCACTCGAGGGTC
TTCCCTAGCGGGAAGTGCTCAGGAGTAGCGGTGTCTTCTACCTACTGCTCCACTA
ACCACGATTACACCATTTGGATGCCCGAGAATCCGAGACTAGGGATGTCTTGTG
ACATTTTTACCAATAGTAGAGGGAAGAGAGCATCCAAAGGGAGTGAGACTTGCG
GCTTTGTAGATGAAAGAGGCCTATATAAGTCTTTAAAAGGAGCATGCAAACTCA
AGTTATGTGGAGTTCTAGGACTTAGACTTATGGATGGAACATGGGTCTCGATGCA
AACATCAAATGAAACCAAATGGTGCCCTCCCGATAAGTTGGTGAACCTGCACGA
```

-continued

```
CTTTCGCTCAGACGAAATTGAGCACCTTGTTGTAGAGGAGTTGGTCAGGAAGAG

AGAGGAGTGTCTGGATGCACTAGAGTCCATCATGACAACCAAGTCAGTGAGTTT

CAGACGTCTCAGTCATTTAAGAAAACTTGTCCCTGGGTTTGGAAAAGCATATACC

ATATTCAACAAGACCTTGATGGAAGCCGATGCTCACTACAAGTCAGTCgagACTT

GGAATGAGATCCTCCCTTCAAAAGGGTGTTTAAGAGTTGGGGGGAGGTGTCATC

CTCATGTGAACGGGGTGTTTTTCAATGGTATAATATTAGGACCTGACGGCAATGT

CTTAATCCCAGAGATGCAATCATCCCTCCTCCAGCAACATATGGAGTTGTTGGAA

TCCTCGGTTATCCCCCTTGTGCACCCCCTGGCAGACCCGTCTACCGTTTTCAAGG

ACGGTGACGAGGCTGAGGATTTTGTTGAAGTTCACCTTCCCGATGTGCACAATCA

GGTCTCAGGAGTTGACTTGGGTCTCCCGAACTGGGGGAAGTATGTATTACTGAGT

GCAGGGGCCCTGACTGCCTTGATGTTGATAATTTTCCTGATGACATGTTGTAGAA

GAGTCAATCGATCAGAACCTACGCAACACAATCTCAGAGGGACAGGGAGGGAG

GTGTCAGTCACTCCCCAAAGCGGGAAGATCATATCTTCATGGGAATCACACAAG

AGTGGGGGTGAGACCAGACTGTAAttaattaaCGTCCTTTCAACGATCCAAGTCcatgaaa aaaactaacaccccctcccgtacctagcTTATAAAGTGCTGGGTCATCTAAGCTTTTCAGTCGAGA

AAAAAACATTAGATCAGAAGAACAACTGGCAACACTTCTCAACCTGAGACTTAC

TTCAAGATGCTCGATCCTGGAGAGGTCTATGATGACCCTATTGACCCAATCGAGT

TAGAGGCTGAACCCAGAGGAACCCCCATTGTCCCCAACATCTTGAGGAACTCTG

ACTACAATCTCAACTCTCCTTTGATAGAAGATCCTGCTAGACTAATGTTAGAATG

GTTAAAAACAGGGAATAGACCTTATCGGATGACTCTAACAGACAATTGCTCCAG

GTCTTTCAGAGTTTTGAAAGATTATTTCAAGAAGGTAGATTTGGGTTCTCTCAAG

GTGGGCGGAATGGCTGCACAGTCAATGATTTCTCTCTGGTTATATGGTGCCCACT

CTGAATCCAACAGGAGCCGGAGATGTATAACAGACTTGGCCCATTTCTATTCCAA

GTCGTCCCCCATAGAGAAGCTGTTGAATCTCACGCTAGGAAATAGAGGGCTGAG

AATCCCCCCAGAGGGAGTGTTAAGTTGCCTTGAGAGGGTTGATTATGATAATGC

ATTTGGAAGGTATCTTGCCAACACGTATTCCTCTTACTTGTTCTTCCATGTAATCA

CCTTATACATGAACGCCCTAGACTGGGATGAAGAAAAGACCATCCTAGCATTAT

GGAAAGATTTAACCTCAGTGGACATCGGGAAGGACTTGGTAAAGTTCAAAGACC

AAATATGGGACTGCTGATCGTGACAAAGGACTTTGTTTACTCCCAAAGTTCCAA

TTGTCTTTTTGACAGAAACTACACACTTATGCTAAAAGATCTTTTCTTGTCTCGCT

TCAACTCCTTAATGGTCTTGCTCTCTCCCCCAGAGCCCCGATACTCAGATGACTT

GATATCTCAACTATGCCAGCTGTACATTGCTGGGGATCAAGTCTTGTCTATGTGT

GGAAACTCCGGCTATGAAGTCATCAAAATATTGGAGCCATATGTCGTGAATAGT

TTAGTCCAGAGAGCAGAAAAGTTTAGGCCTCTCATTCATTCCTTGGGAGACTTTC

CTGTATTTATAAAAGACAAGGTAAGTCAACTTGAAGAGACGTTCGGTCCCTGTGC

AAGAAGGTTCTTTAGGGCTCTGGATCAATTCGACAACATACATGACTTGGTTTTT

GTGTTTGGCTGTTACAGGCATTGGGGGCACCCATATATAGATTATCGAAAGGGTC

TGTCAAAACTATATGATCAGGTTCACCTTAAAAAAATGATAGATAAGTCCTACCA

GGAGTGCTTAGCAAGCGACCTAGCCAGGAGGATCCTTAGATGGGGTTTTGATAA

GTACTCCAAGTGGTATCTGGATTCAAGATTCCTAGCCCGAGACCACCCCTTGACT

CCTTATATCAAAACCCAAACATGGCCACCCAAACATATTGTAGACTTGGTGGGG
```

-continued

```
GATACATGGCACAAGCTCCCGATCACGCAGATCTTTGAGATTCCTGAATCAATGG

ATCCGTCAGAAATATTGGATGACAAATCACATTCTTTCACCAGAACGAGACTAG

CTTCTTGGCTGTCAGAAACCGAGGGGGGCCTGTTCCTAGCGAAAAAGTTATTAT

CACGGCCCTGTCTAAGCCGCCTGTCAATCCCCGAGAGTTTCTGAGGTCTATAGAC

CTCGGAGGATTGCCAGATGAAGACTTGATAATTGGCCTCAAGCCAAAGGAACGG

GAATTGAAGATTGAAGGTCGATTCTTTGCTCTAATGTCATGGAATCTAAGATTGT

ATTTTGTCATCACTGAAAAACTCTTGGCCAACTACATCTTGCCACTTTTTGACGCG

CTGACTATGACAGACAACCTGAACAAGGTGTTTAAAAAGCTGATCGACAGGGTC

ACCGGGCAAGGGCTTTTGGACTATTCAAGGGTCACATATGCATTTCACCTGGACT

ATGAAAAGTGGAACAACCATCAAAGATTAGAGTCAACAGAGGATGTATTTTCTG

TCCTAGATCAAGTGTTTGGATTGAAGAGAGTGTTTTCTAGAACACACGAGTTTTT

TCAAAAGGCCTGGATCTATTATTCAGACAGATCAGACCTCATCGGGTTACGGGA

GGATCAAATATACTGCTTAGATGCGTCCAACGGCCCAACCTGTTGGAATGGCCA

GGATGGCGGGCTAGAAGGCTTACGGCAGAAGGGCTGGAGTCTAGTCAGCTTATT

GATGATAGATAGAGAATCTCAAATCAGGAACACAAGAACCAAAATACTAGCTCA

AGGAGACAACCAGGTTTTATGTCCGACATACATGTTGTCGCCAGGGCTATCTCAA

GAGGGGCTCCTCTATGAATTGGAGAGAATATCAAGGAATGCACTTTCGATATAC

AGAGCCGTCGAGGAAGGGGCATCTAAGCTAGGGCTGATCATCAAGAAAGAAGA

GACCATGTGTAGTTATGACTTCCTCATCTATGGAAAAACCCCTTTGTTTAGAGGT

AACATATTGGTGCCTGAGTCCAAAAGATGGGCCAGAGTCTCTTGCGTCTCTAATG

ACCAAATAGTCAACCTCGCCAATATAATGTCGACAGTGTCCACCAATGCGCTAA

CAGTGGCACAACACTCTCAATCTTTGATCAAACCGATGAGGGATTTTCTGCTCAT

GTCAGTACAGGCAGTCTTTCACTACCTGCTATTTAGCCCAATCTTAAAGGGAAGA

GTTTACAAGATTCTGAGCGCTGAAGGGGAGAGCTTTCTCCTAGCCATGTCAAGG

ATAATCTATCTAGATCCTTCTTTGGGAGGGATATCTGGAATGTCCCTCGGAAGAT

TCCATATACGACAGTTCTCAGACCCTGTCTCTGAAGGGTTATCCTTCTGGAGAGA

GATCTGGTTAAGCTCCCAAGAGTCCTGGATTCACGCGTTGTGTCAAGAGGCTGGA

AACCCAGATCTTGGAGAGAGAACACTCGAGAGCTTCACTCGCCTTCTAGAAGAT

CCGACCACCTTAAATATCAGAGGAGGGGCCAGTCCTACCATTCTACTCAAGGAT

GCAATCAGAAAGGCTTTATATGACGAGGTGGACAAGGTGGAAAATTCAGAGTTT

CGAGAGGCAATCCTGTTGTCCAAGACCCATAGAGATAATTTTATACTCTTCTTAA

TATCTGTTGAGCCTCTGTTTCCTCGATTTCTCAGTGAGCTATTCAGTTCGTCTTTTT

TGGGAATCCCCGAGTCAATCATTGGATTGATACAAAACTCCCGAACGATAAGAA

GGCAGTTTAGAAAGAGTCTCTCAAAAACTTTAGAAGAATCCTTCTACAACTCAG

AGATCCACGGGATTAGTCGGATGACCCAGACACCTCAGAGGGTTGGGGGGTGT

GGCCTTGCTCTTCAGAGAGGGCAGATCTACTTAGGGAGATCTCTTGGGGAAGAA

AAGTGGTAGGCACGACAGTTCCTCACCCTTCTGAGATGTTGGGATTACTTCCCAA

GTCCTCTATTTCTTGCACTTGTGGAGCAACAGGAGGAGGCAATCCTAGAGTTTCT

GTATCAGTACTCCCGTCCTTTGATCAGTCATTTTTTTCACGAGGCCCCCTAAAGG

GATACTTGGGCTCGTCCACCTCTATGTCGACCCAGCTATTCCATGCATGGGAAAA
```

-continued

```
AGTCACTAATGTTCATGTGGTGAAGAGAGCTCTATCGTTAAAAGAATCTATAAAC
TGGTTCATTACTAGAGATTCCAACTTGGCTCAAGCTCTAATTAGGAACATTATGT
CTCTGACAGGCCCTGATTTCCCTCTAGAGGAGGCCCCTGTCTTCAAAAGGACGGG
GTCAGCCTTGCATAGGTTCAAGTCTGCCAGATACAGCGAAGGAGGGTATTCTTCT
GTCTGCCCGAACCTCCTCTCTCATATTTCTGTTAGTACAGACACCATGTCTGATTT
GACCCAAGACGGGAAGAACTACGATTTCATGTTCCAGCCATTGATGCTTTATGCA
CAGACATGGACATCAGAGCTGGTACAGAGAGACACAAGGCTAAGAGACTCTAC
GTTTCATTGGCACCTCCGATGCAACAGGTGTGTGAGACCCATTGACGACGTGACC
CTGGAGACCTCTCAGATCTTCGAGTTTCCGGATGTGTCGAAAAGAATATCCAGAA
TGGTTTCTGGGGCTGTGCCTCACTTCCAGAGGCTTCCCGATATCCGTCTGAGACC
AGGAGATTTTGAATCTCTAAGCGGTAGAGAAAAGTCTCACCATATCGGATCAGC
TCAGGGGCTCTTATACTCAATCTTAGTGGCAATTCACGACTCAGGATACAATGAT
GGAACCATCTTCCCTGTCAACATATACGGCAAGGTTTCCCCTAGAGACTATTTGA
GAGGGCTCGCAAGGGGAGTATTGATAGGATCCTCGATTTGCTTCTTGACAAGAA
TGACAAATATCAATATTAATAGACCTCTTGAATTGGTCTCAGGGGTAATCTCATA
TATTCTCCTGAGGCTAGATAACCATCCCTCCTTGTACATAATGCTCAGAGAACCG
TCTCTTAGAGGAGAGATATTTTCTATCCCTCAGAAAATCCCCGCCGCTTATCCAA
CCACTATGAAAGAAGGCAACAGATCAATCTTGTGTTATCTCCAACATGTGCTACG
CTATGAGCGAGAGATAATCACGGCGTCTCCAGAGAATGACTGGCTATGGATCTT
TTCAGACTTTAGAAGTGCCAAAATGACGTACCTATCCCTCATTACTTACCAGTCT
CATCTTCTACTCCAGAGGGTTGAGAGAAACCTATCTAAGAGTATGAGAGATAAC
CTGCGACAATTGAGTTCTTTGATGAGGCAGGTGCTGGGCGGGCACGGAGAAGAT
ACCTTAGAGTCAGACGACAACATTCAACGACTGCTAAAAGACTCTTTACGAAGG
ACAAGATGGGTGGATCAAGAGGTGCGCCATGCAGCTAGAACCATGACTGGAGAT
TACAGCCCCAACAAGAAGGTGTCCCGTAAGGTAGGATGTTCAGAATGGGTCTGC
TCTGCTCAACAGGTTGCAGTCTCTACCTCAGCAAACCCGGCCCCTGTCTCGGAGC
TTGACATAAGGGCCCTCTCTAAGAGGTTCCAGAACCCTTTGATCTCGGGCTTGAG
AGTGGTTCAGTGGGCAACCGGTGCTCATTATAAGCTTAAGCCTATTCTAGATGAT
CTCAATGTTTTCCCATCTCTCTGCCTTGTAGTTGGGGACGGGTCAGGGGGATAT
CAAGGGCAGTCCTCAACATGTTTCCAGATGCCAAGCTTGTGTTCAACAGTCTTTT
AGAGGTGAATGACCTGATGGCTTCCGGAACACATCCACTGCCTCCTTCAGCAATC
ATGAGGGAGGAAATGATATCGTCTCCAGAGTGATAGATCTTGACTCAATCTGG
GAAAAACCGTCCGACTTGAGAAACTTGGCAACCTGGAAATACTTCCAGTCAGTC
CAAAAGCAGGTCAACATGTCCTATGACCTCATTATTTGCGATGCAGAAGTTACTG
ACATTGCATCTATCAACCGGATCACCCTGTTAATGTCCGATTTTGCATTGTCTATA
GATGGACCACTCTATTTGGTCTTCAAAACTTATGGGACTATGCTAGTAAATCCAA
ACTACAAGGCTATTCAACACCTGTCAAGAGCGTTCCCCTCGGTCACAGGGTTTAT
CACCCAAGTAACTTCGTCTTTTTCATCTGAGCTCTACCTCCGATTCTCCAAACGA
GGGAAGTTTTTCAGAGATGCTGAGTACTTGACCTCTTCCACCCTTCGAGAAATGA
GCCTTGTGTTATTCAATTGTAGCAGCCCCAAGAGTGAGATGCAGAGAGCTCGTTC
CTTGAACTATCAGGATCTTGTGAGAGGATTTCCTGAAGAAATCATATCAAATCCT
```

-continued

```
TACAATGAGATGATCATAACTCTGATTGACAGTGATGTAGAATCTTTTCTAGTCC

ACAAGATGGTTGATGATCTTGAGTTACAGAGGGGAACTCTGTCTAAAGTGGCTA

TCATTATAGCCATCATGATAGTTTTCTCCAACAGAGTCTTCAACGTTTCCAAACC

CCTAACTGACCCCTCGTTCTATCCACCGTCTGATCCCAAAATCCTGAGGCACTTC

AACATATGTTGCAGTACTATGATGTATCTATCTACTGCTTTAGGTGACGTCCCTA

GCTTCGCAAGACTTCACGACCTGTATAACAGACCTATAACTTATTACTTCAGAAA

GCAAGTCATTCGAGGGAACGTTTATCTATCTTGGAGTTGGTCCAACGACACCTCA

GTGTTCAAAAGGGTAGCCTGTAATTCTAGCCTGAGTCTGTCATCTCACTGGATCA

GGTTGATTTACAAGATAGTGAAGACTACCAGACTCGTTGGCAGCATCAAGGATC

TATCCAGAGAAGTGGAAAGACACCTTCATAGGTACAACAGGTGGATCACCCTAG

AGGATATCAGATCTAGATCATCCCTACTAGACTACAGTTGCCTGTGAACCGGATA

CTCCTGGAAGCCTGCCCATGCTAAGACTCTTGTGTGATGTATCTTGAAAAAAACA

AGATCCTAAATCTGAACCTTTGGTTGTTTGATTGTTTTTCTCAttttttgttgtttat-
ttgttaagcgt.
```

In some embodiments, the nucleic acid comprises the sequence of SEQ ID NO: 8, shown below (RABV vector: Coravax V2-China (RABVG-E51)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT
```

-continued

```
TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAcatgaaaaaaactaacaccccctcccgtacgCCAC-
CATGTTCGTGTTTCTGGTGCTGCTGC

CTCTGGTGAGCTCCCAGTGCGTGAACCTGACCACAAGGACCCAGCTGCCCCCTG

CCTATACCAATTCCTTCACACGGGGCGTGTACTATCCCGACAAGGTGTTCCGGAG

CAGCGTGCTGCACTCCACACAGGATCTGTTTCTGCCTTTCTTTTCTAACGTGACCT

GGTTCCACGCCATCCACGTGAGCGGCACCAATGGCACAAAGCGGTTCGACAATC

CAGTGCTGCCCTTTAACGATGGCGTGTACTTCGCCTCCACCGAGAAGTCTAACAT

CATCAGAGGCTGGATCTTTGGCACCACACTGGACAGCAAGACACAGTCCCTGCT

GATCGTGAACAATGCCACCAACGTGGTCATCAAGGTGTGCGAGTTCCAGTTTTGT

AATGATCCATTCCTGGGCGTGTACTATCACAAGAACAATAAGTCTTGGATGGAG

AGCGAGTTTCGCGTGTATTCCTCTGCCAACAATTGCACATTTGAGTACGTGTCCC

AGCCCTTCCTGATGGACCTGGAGGGCAAGCAGGGCAATTTCAAGAACCTGAGGG

AGTTCGTGTTTAAGAATATCGATGGCTACTTCAAAATCTACTCCAAGCACACCCC

AATCAACCTGGTGCGCGACCTGCCACAGGGCTTCTCTGCCCTGGAGCCACTGGTG

GATCTGCCCATCGGCATCAACATCACCCGGTTTCAGACACTGCTGGCCCTGCACA

GAAGCTACCTGACACCAGGCGACAGCTCCTCTGGATGGACCGCAGGAGCAGCAG

CCTACTATGTGGGCTATCTGCAGCCCAGGACCTTCCTGCTGAAGTACAACGAGA

ATGGCACCATCACAGACGCCGTGGATTGCGCCCTGGATCCCCTGTCTGAGACCA

AGTGTACACTGAAGAGCTTTACCGTGGAGAAGGGCATCTATCAGACAAGCAATT

TCAGGGTGCAGCCTACCGAGTCCATCGTGCGCTTTCCCAATATCACAAACCTGTG

CCCTTTTGGCGAGGTGTTCAACGCAACCCGCTTCGCCAGCGTGTACGCCTGGAAT

AGGAAGCGCATCTCCAACTGCGTGGCCGACTATTCTGTGCTGTACAACAGCGCCT

CCTTCTCTACCTTTAAGTGCTATGGCGTGAGCCCCACAAAGCTGAATGACCTGTG

CTTTACCAACGTGTACGCCGATTCCTTCGTGATCAGGGGCGACGAGGTGCGCCA

GATCGCACCAGGACAGACAGGCAAGATCGCAGACTACAATTATAAGCTGCCTGA

CGATTTCACCGGCTGCGTGATCGCCTGGAACTCTAACAATCTGGATAGCAAAGTG

GGCGGCAACTACAATTATCTGTACCGGCTGTTTAGAAAGTCTAATCTGAAGCCAT

TCGAGAGGGACATCTCCACAGAAATCTACCAGGCCGGCTCTACCCCCTGCAATG

GCGTGGAGGGCTTTAACTGTTATTTCCCTCTGCAGAGCTACGGCTTCCAGCCAAC

AAACGGCGTGGGCTATCAGCCCTACCGCGTGGTGGTGCTGTCTTTTGAGCTGCTG

CACGCACCTGCAACAGTGTGCGGACCAAAGAAGAGCACCAATCTGGTGAAGAA

CAAGTGCGTGAACTTCAACTTCAACGGACTGACCGGAACAGGCGTGCTGACCGA

GTCCAACAAGAAGTTCCTGCCTTTTCAGCAGTTCGGCAGGGACATCGCAGATAC

CACAGACGCCGTGCGCGACCCTCAGACCCTGGAGATCCTGGACATCACACCATG

CTCCTTCGGCGGCGTGTCTGTGATCACACCAGGCACCAATACAAGCAACCAGGT

GGCCGTGCTGTATcAGGACGTGAATTGTACCGAGGTGCCAGTGGCAATCCACGCA

GATCAGCTGACCCCTACATGGCGGGTGTACTCTACCGGCAGCAACGTGTTCCAG

ACAAGAGCCGGATGCCTGATCGGAGCAGAGCACGTGAACAATAGCTATGAGTGC
```

-continued

```
GACATCCCTATCGGCGCCGGCATCTGTGCCTCCTACCAGACCCAGACAAACTCCC

CAGAATCAAGCGTGATTCCTCTGGTCCATCCACTGGCAGATCCCTCCACAGTGTT

CAAAGACGGAGATGAGGCCGAAGACTTTGTGGAAGTCCACCTGCCTGATGTGCA

TAACCAGGTGTCTGGCGTCGACCTGGGACTGCCAAATTGGGGCAAGTACGTGCT

GCTGAGTGCTGGAGCACTGACTGCCCTGATGCTGATCATTTTCCTGATGACCTGC

TGTCGGCGCGTGAACAGAAGTGAGCCCACTCAGCACAATCTGCGAGGAACCGGG

AGAGAAGTGTCAGTCACACCTCAGAGCGGGAAAATCATTAGTAGTTGGGAATCA

CATAAAAGCGGGGGCGAGACCAGGCTGTGAgctagcCATGAAAAAAACTAACACCC

CTCCTTTCGAACCATCCCAAACATGAGCAAGATCTTTGTCAATCCTAGTGCTATT

AGAGCCGGTCTGGCCGATCTTGAGATGGCTGAAGAAACTGTTGATCTGATCAAT

AGAAATATCGAAGACAATCAGGCTCATCTCCAAGGGGAACCCATAGAGGTGGAC

AATCTCCCTGAGGATATGGGGCGACTTCACCTGGATGATGGAAAATCGCCCAAC

CATGGTGAGATAGCCAAGGTGGGAGAAGGCAAGTATCGAGAGGACTTTCAGATG

GATGAAGGAGAGGATCCTAGCTTCCTGTTCCAGTCATACCTGGAAAATGTTGGA

GTCCAAATAGTCAGACAAATGAGGTCAGGAGAGAGATTTCTCAAGATATGGTCA

CAGACCGTAGAAGAGATTATATCCTATGTCGCGGTCAACTTTCCCAACCCTCCAG

GAAAGTCTTCAGAGGATAAATCAACCCAGACTACTGGCCGAGAGCTCAAGAAGG

AGACAACACCCACTCCTTCTCAGAGAGAAAGCCAATCATCGAAAGCCAGGATGG

CGGCTCAAATTGCTTCTGGCCCTCCAGCCCTTGAATGGTCGGCTACCAATGAAGA

GGATGATCTATCAGTGGAGGCTGAGATCGCTCACCAGATTGCAGAAAGTTTCTCC

AAAAAATATAAGTTTCCCTCTCGATCCTCAGGGATACTCTTGTATAATTTTGAGC

AATTGAAAATGAACCTTGATGATATAGTTAAAGAGGCAAAAAATGTACCAGGTG

TGACCCGTTTAGCCCATGACGGGTCCAAACTCCCCCTAAGATGTGTACTGGGATG

GGTCGCTTTGGCCAACTCTAAGAAATTCCAGTTGTTAGTCGAATCCGACAAGCTG

AGTAAAATCATGCAAGATGACTTGAATCGCTATACATCTTGCTAACCGAACCTCT

CCCCTCAGTCCCTCTAGACAATAAAATCCGAGATGTCCCAAAGTCAACATGAAA

AAAACAGGCAACACCACTGATAAAATGAACCTCCTACGTAAGATAGTGAAAAAC

CGCAGGGACGAGGACACTCAAAAATCCTCTCCCGCGTCAGCCCCTCTGGATGAC

GATGACTTGTGGCTTCCACCCCCTGAATACGTCCCGCTGAAAGAACTTACAGGCA

AGAAGAACATGAGGAACTTTTGTATCAACGGAAGGGTTAAAGTGTGTAGCCCGA

ATGGTTACTCGTTCAGGATCCTGCGGCACATTCTGAAATCATTCGACGAGATATA

TTCTGGGAATCATAGGATGATCGGGTTAGTCAAAGTGGTTATTGGACTGGCTTTG

TCAGGATCTCCAGTCCCTGAGGGCCTGAACTGGGTATACAAATTGAGGAGAACC

TTTATCTTCCAGTGGGCTGATTCCAGGGGCCCTCTTGAAGGGGAGGAGTTGGAAT

ACTCTCAGGAGATCACTTGGGATGATGATACTGAGTTCGTCGGATTGCAAATAA

GAGTGATTGCAAAACAGTGTCATATCCAGGGCAGAGTCTGGTGTATCAACATGA

ACCCGAGAGCATGTCAACTATGGTCTGACATGTCTCTTCAGACACAAAGGTCCG

AAGAGGACAAAGATTCCTCTCTGCTTCTAGAATAATCAGATTATATCCCGCAAAT

TTATCACTTGTTTACCTCTGGAGGAGAGAACATATGGGCTCAACTCCAACCCTTG

GGAGCAATATAACAAAAAACATGTTATGGTGCCATTAAACCGCTGCATTTCATC

AAAGTCAAGTTGATTACCTTTACATTTTGATCCTCTTGGATGTGAAAAAAACTAT
```

-continued

```
TAACATCCCTCAAAAGACcccgggAAAGATGGTTCCTCAGGCTCTCCTGTTTGTACC
CCTTCTGGTTTTTCCATTGTGTTTTGGGAAATTCCCTATTTACACGATACCAGACA
AGCTTGGTCCCTGGAGTCCGATTGACATACATCACCTCAGCTGCCCAAACAATTT
GGTAGTGGAGGACGAAGGATGCACCAACCTGTCAGGGTTCTCCTACATGGAACT
TAAAGTTGGATACATCTTAGCCATAAAAGTGAACGGGTTCACTTGCACAGGCGTT
GTGACGGAGGCTGAAACCTACACTAACTTCGTTGGTTATGTCACAACCACGTTCA
AAAGAAAGCATTTCCGCCCAACACCAGATGCATGTAGAGCCGCGTACAACTGGA
AGATGGCCGGTGACCCCAGATATGAAGAGTCTCTACACAATCCGTACCCTGACT
ACCGCTGGCTTCGAACTGTAAAAACCACCAAGGAGTCTCTCGTTATCATATCTCC
AAGTGTGGCAGATTTGGACCCATATGACAGATCCCTTCACTCGAGGGTCTTCCCT
AGCGGGAAGTGCTCAGGAGTAGCGGTGTCTTCTACCTACTGCTCCACTAACCAC
GATTACACCATTTGGATGCCCGAGAATCCGAGACTAGGGATGTCTTGTGACATTT
TTACCAATAGTAGAGGGAAGAGAGCATCCAAAGGGAGTGAGACTTGCGGCTTTG
TAGATGAAAGAGGCCTATATAAGTCTTTAAAAGGAGCATGCAAACTCAAGTTAT
GTGGAGTTCTAGGACTTAGACTTATGGATGGAACATGGGTCTCGATGCAAACAT
CAAATGAAACCAAATGGTGCCCTCCCGATAAGTTGGTGAACCTGCACGACTTTC
GCTCAGACGAAATTGAGCACCTTGTTGTAGAGGAGTTGGTCAGGAAGAGAGAGG
AGTGTCTGGATGCACTAGAGTCCATCATGACAACCAAGTCAGTGAGTTTCAGAC
GTCTCAGTCATTTAAGAAAACTTGTCCCTGGGTTTGGAAAAGCATATACCATATT
CAACAAGACCTTGATGGAAGCCGATGCTCACTACAAGTCAGTCgagACTTGGAAT
GAGATCCTCCCTTCAAAAGGGTGTTTAAGAGTTGGGGGGAGGTGTCATCCTCATG
TGAACGGGGTGTTTTTCAATGGTATAATATTAGGACCTGACGGCAATGTCTTAAT
CCCAGAGATGCAATCATCCCTCCTCCAGCAACATATGGAGTTGTTGGAATCCTCG
GTTATCCCCCTTGTGCACCCCCTGGCAGACCCGTCTACCGTTTTCAAGGACGGTG
ACGAGGCTGAGGATTTTGTTGAAGTTCACCTTCCCGATGTGCACAATCAGGTCTC
AGGAGTTGACTTGGGTCTCCCGAACTGGGGGAAGTATGTATTACTGAGTGCAGG
GGCCCTGACTGCCTTGATGTTGATAATTTTCCTGATGACATGTTGTAGAAGAGTC
AATCGATCAGAACCTACGCAACACAATCTCAGAGGGACAGGGAGGGAGGTGTC
AGTCACTCCCCAAAGCGGGAAGATCATATCTTCATGGGAATCACACAAGAGTGG
GGGTGAGACCAGACTGTAAttaattaaCGTCCTTTCAACGATCCAAGTCcatgaaaaaaactaa
caccccctcccgtacctagcTTATAAAGTGCTGGGTCATCTAAGCTTTTCAGTCGAGAAAAAA
ACATTAGATCAGAAGAACAACTGGCAACACTTCTCAACCTGAGACTTACTTCAA
GATGCTCGATCCTGGAGAGGTCTATGATGACCCTATTGACCCAATCGAGTTAGAG
GCTGAACCCAGAGGAACCCCCATTGTCCCCAACATCTTGAGGAACTCTGACTAC
AATCTCAACTCTCCTTTGATAGAAGATCCTGCTAGACTAATGTTAGAATGGTTAA
AAACAGGGAATAGACCTTATCGGATGACTCTAACAGACAATTGCTCCAGGTCTTT
CAGAGTTTTGAAAGATTATTTCAAGAAGGTAGATTTGGGTTCTCTCAAGGTGGGC
GGAATGGCTGCACAGTCAATGATTTCTCTCTGGTTATATGGTGCCCACTCTGAAT
CCAACAGGAGCCGGAGATGTATAACAGACTTGGCCCATTTCTATTCCAAGTCGTC
CCCCATAGAGAAGCTGTTGAATCTCACGCTAGGAAATAGAGGGCTGAGAATCCC
```

-continued

```
CCCAGAGGGAGTGTTAAGTTGCCTTGAGAGGGTTGATTATGATAATGCATTTGGA

AGGTATCTTGCCAACACGTATTCCTCTTACTTGTTCTTCCATGTAATCACCTTATA

CATGAACGCCCTAGACTGGGATGAAGAAAAGACCATCCTAGCATTATGGAAAGA

TTTAACCTCAGTGGACATCGGGAAGGACTTGGTAAAGTTCAAAGACCAAATATG

GGGACTGCTGATCGTGACAAAGGACTTTGTTTACTCCCAAAGTTCCAATTGTCTT

TTTGACAGAAACTACACACTTATGCTAAAAGATCTTTTCTTGTCTCGCTTCAACTC

CTTAATGGTCTTGCTCTCTCCCCCAGAGCCCCGATACTCAGATGACTTGATATCT

CAACTATGCCAGCTGTACATTGCTGGGGATCAAGTCTTGTCTATGTGTGGAAACT

CCGGCTATGAAGTCATCAAAATATTGGAGCCATATGTCGTGAATAGTTTAGTCCA

GAGAGCAGAAAAGTTTAGGCCTCTCATTCATTCCTTGGGAGACTTTCCTGTATTT

ATAAAAGACAAGGTAAGTCAACTTGAAGAGACGTTCGGTCCCTGTGCAAGAAGG

TTCTTTAGGGCTCTGGATCAATTCGACAACATACATGACTTGGTTTTTGTGTTTGG

CTGTTACAGGCATTGGGGGCACCCATATATAGATTATCGAAAGGGTCTGTCAAA

ACTATATGATCAGGTTCACCTTAAAAAAATGATAGATAAGTCCTACCAGGAGTG

CTTAGCAAGCGACCTAGCCAGGAGGATCCTTAGATGGGGTTTTGATAAGTACTCC

AAGTGGTATCTGGATTCAAGATTCCTAGCCCGAGACCACCCCTTGACTCCTTATA

TCAAAACCCAAACATGGCCACCCAAACATATTGTAGACTTGGTGGGGATACAT

GGCACAAGCTCCCGATCACGCAGATCTTTGAGATTCCTGAATCAATGGATCCGTC

AGAAATATTGGATGACAAATCACATTCTTTCACCAGAACGAGACTAGCTTCTTGG

CTGTCAGAAAACCGAGGGGGGCCTGTTCCTAGCGAAAAAGTTATTATCACGGCC

CTGTCTAAGCCGCCTGTCAATCCCCGAGAGTTTCTGAGGTCTATAGACCTCGGAG

GATTGCCAGATGAAGACTTGATAATTGGCCTCAAGCCAAAGGAACGGGAATTGA

AGATTGAAGGTCGATTCTTTGCTCTAATGTCATGGAATCTAAGATTGTATTTTGTC

ATCACTGAAAAACTCTTGGCCAACTACATCTTGCCACTTTTTGACGCGCTGACTA

TGACAGACAACCTGAACAAGGTGTTTAAAAAGCTGATCGACAGGGTCACCGGGC

AAGGGCTTTTGGACTATTCAAGGGTCACATATGCATTTCACCTGGACTATGAAAA

GTGGAACAACCATCAAAGATTAGAGTCAACAGAGGATGTATTTTCTGTCCTAGA

TCAAGTGTTTGGATTGAAGAGAGTGTTTTCTAGAACACACGAGTTTTTTCAAAAG

GCCTGGATCTATTATTCAGACAGATCAGACCTCATCGGGTTACGGGAGGATCAA

ATATACTGCTTAGATGCGTCCAACGGCCCAACCTGTTGGAATGGCCAGGATGGC

GGGCTAGAAGGCTTACGGCAGAAGGGCTGGAGTCTAGTCAGCTTATTGATGATA

GATAGAGAATCTCAAATCAGGAACACAAGAACCAAAATACTAGCTCAAGGAGA

CAACCAGGTTTTATGTCCGACATACATGTTGTCGCCAGGGCTATCTCAAGAGGGG

CTCCTCTATGAATTGGAGAGAATATCAAGGAATGCACTTTCGATATACAGAGCC

GTCGAGGAAGGGGCATCTAAGCTAGGGCTGATCATCAAGAAAGAAGAGACCAT

GTGTAGTTATGACTTCCTCATCTATGGAAAAACCCCTTTGTTTAGAGGTAACATA

TTGGTGCCTGAGTCCAAAAGATGGGCCAGAGTCTCTTGCGTCTCTAATGACCAAA

TAGTCAACCTCGCCAATATAATGTCGACAGTGTCCACCAATGCGCTAACAGTGG

CACAACACTCTCAATCTTTGATCAAACCGATGAGGGATTTTCTGCTCATGTCAGT

ACAGGCAGTCTTTCACTACCTGCTATTTAGCCCAATCTTAAAGGGAAGAGTTTAC

AAGATTCTGAGCGCTGAAGGGGAGAGCTTTCTCCTAGCCATGTCAAGGATAATC
```

-continued

```
TATCTAGATCCTTCTTTGGGAGGGATATCTGGAATGTCCCTCGGAAGATTCCATA

TACGACAGTTCTCAGACCCTGTCTCTGAAGGGTTATCCTTCTGGAGAGAGATCTG

GTTAAGCTCCCAAGAGTCCTGGATTCACGCGTTGTGTCAAGAGGCTGGAAACCC

AGATCTTGGAGAGAGAACACTCGAGAGCTTCACTCGCCTTCTAGAAGATCCGAC

CACCTTAAATATCAGAGGAGGGGCCAGTCCTACCATTCTACTCAAGGATGCAAT

CAGAAAGGCTTTATATGACGAGGTGGACAAGGTGGAAAATTCAGAGTTTCGAGA

GGCAATCCTGTTGTCCAAGACCCATAGAGATAATTTTATACTCTTCTTAATATCT

GTTGAGCCTCTGTTTCCTCGATTTCTCAGTGAGCTATTCAGTTCGTCTTTTTTGGG

AATCCCCGAGTCAATCATTGGATTGATACAAAACTCCCGAACGATAAGAAGGCA

GTTTAGAAAGAGTCTCTCAAAAACTTTAGAAGAATCCTTCTACAACTCAGAGATC

CACGGGATTAGTCGGATGACCCAGACACCTCAGAGGGTTGGGGGGTGTGGCCT

TGCTCTTCAGAGAGGGCAGATCTACTTAGGGAGATCTCTTGGGGAAGAAAAGTG

GTAGGCACGACAGTTCCTCACCCTTCTGAGATGTTGGGATTACTTCCCAAGTCCT

CTATTTCTTGCACTTGTGGAGCAACAGGAGGAGGCAATCCTAGAGTTTCTGTATC

AGTACTCCCGTCCTTTGATCAGTCATTTTTTTCACGAGGCCCCCTAAAGGGATAC

TTGGGCTCGTCCACCTCTATGTCGACCCAGCTATTCCATGCATGGGAAAAAGTCA

CTAATGTTCATGTGGTGAAGAGAGCTCTATCGTTAAAAGAATCTATAAACTGGTT

CATTACTAGAGATTCCAACTTGGCTCAAGCTCTAATTAGGAACATTATGTCTCTG

ACAGGCCCTGATTTCCCTCTAGAGGAGGCCCCTGTCTTCAAAAGGACGGGGTCA

GCCTTGCATAGGTTCAAGTCTGCCAGATACAGCGAAGGAGGGTATTCTTCTGTCT

GCCCGAACCTCCTCTCTCATATTTCTGTTAGTACAGACACCATGTCTGATTTGACC

CAAGACGGGAAGAACTACGATTTCATGTTCCAGCCATTGATGCTTTATGCACAGA

CATGGACATCAGAGCTGGTACAGAGAGACACAAGGCTAAGAGACTCTACGTTTC

ATTGGCACCTCCGATGCAACAGGTGTGTGAGACCCATTGACGACGTGACCCTGG

AGACCTCTCAGATCTTCGAGTTTCCGGATGTGTCGAAAAGAATATCCAGAATGGT

TTCTGGGGCTGTGCCTCACTTCCAGAGGCTTCCCGATATCCGTCTGAGACCAGGA

GATTTTGAATCTCTAAGCGGTAGAGAAAAGTCTCACCATATCGGATCAGCTCAG

GGGCTCTTATACTCAATCTTAGTGGCAATTCACGACTCAGGATACAATGATGGAA

CCATCTTCCCTGTCAACATATACGGCAAGGTTTCCCCTAGAGACTATTTGAGAGG

GCTCGCAAGGGGAGTATTGATAGGATCCTCGATTTGCTTCTTGACAAGAATGACA

AATATCAATATTAATAGACCTCTTGAATTGGTCTCAGGGGTAATCTCATATATTC

TCCTGAGGCTAGATAACCATCCCTCCTTGTACATAATGCTCAGAGAACCGTCTCT

TAGAGGAGAGATATTTTCTATCCCTCAGAAAATCCCCGCCGCTTATCCAACCACT

ATGAAAGAAGGCAACAGATCAATCTTGTGTTATCTCCAACATGTGCTACGCTATG

AGCGAGAGATAATCACGGCGTCTCCAGAGAATGACTGGCTATGGATCTTTTCAG

ACTTTAGAAGTGCCAAAATGACGTACCTATCCCTCATTACTTACCAGTCTCATCT

TCTACTCCAGAGGGTTGAGAGAAACCTATCTAAGAGTATGAGAGATAACCTGCG

ACAATTGAGTTCTTTGATGAGGCAGGTGCTGGGCGGGCACGGAGAAGATACCTT

AGAGTCAGACGACAACATTCAACGACTGCTAAAAGACTCTTTACGAAGGACAAG

ATGGGTGGATCAAGAGGTGCGCCATGCAGCTAGAACCATGACTGGAGATTACAG
```

-continued

```
CCCCAACAAGAAGGTGTCCCGTAAGGTAGGATGTTCAGAATGGGTCTGCTCTGC

TCAACAGGTTGCAGTCTCTACCTCAGCAAACCCGGCCCCTGTCTCGGAGCTTGAC

ATAAGGGCCCTCTCTAAGAGGTTCCAGAACCCTTTGATCTCGGGCTTGAGAGTGG

TTCAGTGGGCAACCGGTGCTCATTATAAGCTTAAGCCTATTCTAGATGATCTCAA

TGTTTTCCCATCTCTCTGCCTTGTAGTTGGGGACGGGTCAGGGGGATATCAAGG

GCAGTCCTCAACATGTTTCCAGATGCCAAGCTTGTGTTCAACAGTCTTTTAGAGG

TGAATGACCTGATGGCTTCCGGAACACATCCACTGCCTCCTTCAGCAATCATGAG

GGGAGGAAATGATATCGTCTCCAGAGTGATAGATCTTGACTCAATCTGGGAAAA

ACCGTCCGACTTGAGAAACTTGGCAACCTGGAAATACTTCCAGTCAGTCCAAAA

GCAGGTCAACATGTCCTATGACCTCATTATTTGCGATGCAGAAGTTACTGACATT

GCATCTATCAACCGGATCACCCTGTTAATGTCCGATTTTGCATTGTCTATAGATG

GACCACTCTATTTGGTCTTCAAAACTTATGGGACTATGCTAGTAAATCCAAACTA

CAAGGCTATTCAACACCTGTCAAGAGCGTTCCCCTCGGTCACAGGGTTTATCACC

CAAGTAACTTCGTCTTTTTCATCTGAGCTCTACCTCCGATTCTCCAAACGAGGGA

AGTTTTTCAGAGATGCTGAGTACTTGACCTCTTCCACCCTTGAGAAATGAGCCT

TGTGTTATTCAATTGTAGCAGCCCCAAGAGTGAGATGCAGAGAGCTCGTTCCTTG

AACTATCAGGATCTTGTGAGAGGATTTCCTGAAGAAATCATATCAAATCCTTACA

ATGAGATGATCATAACTCTGATTGACAGTGATGTAGAATCTTTTCTAGTCCACAA

GATGGTTGATGATCTTGAGTTACAGAGGGGAACTCTGTCTAAAGTGGCTATCATT

ATAGCCATCATGATAGTTTTCTCCAACAGAGTCTTCAACGTTTCCAAACCCCTAA

CTGACCCCTCGTTCTATCCACCGTCTGATCCCAAAATCCTGAGGCACTTCAACAT

ATGTTGCAGTACTATGATGTATCTATCTACTGCTTTAGGTGACGTCCCTAGCTTCG

CAAGACTTCACGACCTGTATAACAGACCTATAACTTATTACTTCAGAAAGCAAGT

CATTCGAGGGAACGTTTATCTATCTTGGAGTTGGTCCAACGACACCTCAGTGTTC

AAAAGGGTAGCCTGTAATTCTAGCCTGAGTCTGTCATCTCACTGGATCAGGTTGA

TTTACAAGATAGTGAAGACTACCAGACTCGTTGGCAGCATCAAGGATCTATCCA

GAGAAGTGGAAAGACACCTTCATAGGTACAACAGGTGGATCACCCTAGAGGATA

TCAGATCTAGATCATCCCTACTAGACTACAGTTGCCTGTGAACCGGATACTCCTG

GAAGCCTGCCCATGCTAAGACTCTTGTGTGATGTATCTTGAAAAAAACAAGATCC

TAAATCTGAACCTTTGGTTGTTTGATTGTTTTTCTCAtttttgttgtttatttgttaagcgt.
```

In other embodiments, the nucleic acid comprises the sequence of SEQ ID NO: 9, shown below (RABV vector: Coravax V2 South Africa (S1-RABVG-E51)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA
```

-continued

```
CCCCAGGTTCTCTGGTGGAGATAAAACGTACTGATGTAGAAGGGAATTGGGCTC
TGACAGGAGGCATGGAACTGACAAGAGACCCCACTGTCCCTGAGCATGCGTCCT
TAGTCGGTCTTCTCTTGAGTCTGTATAGGTTGAGCAAAATATCCGGGCAAAACAC
TGGTAACTATAAGACAAACATTGCAGACAGGATAGAGCAGATTTTTGAGACAGC
CCCTTTTGTTAAAATCGTGGAACACCATACTCTAATGACAACTCACAAaATGTGT
GCTAATTGGAGTACTATACCAAACTTCAGATTTTTGGCCGGAACCTATGACATGT
TTTTCTCCCGGATTGAGCATCTATATTCAGCAATCAGAGTGGGCACAGTTGTCAC
TGCTTATGAAGACTGTTCAGGACTGGTATCATTTACTGGGTTCATAAAACAAATC
AATCTCACCGCTAGAGAGGCAATACTATATTTCTTCCACAAGAACTTTGAGGAAG
AGATAAGAAGAATGTTTGAGCCAGGGCAGGAGACAGCTGTTCCTCACTCTTATTT
CATCCACTTCCGTTCACTAGGCTTGAGTGGGAAATCTCCTTATTCATCAAATGCT
GTTGGTCACGTGTTCAATCTCATTCACTTTGTAGGATGCTATATGGGTCAAGTCA
GATCCCTAAATGCAACGGTTATTGCTGCATGTGCTCCTCATGAAATGTCTGTTCT
AGGGGGCTATCTGGGAGAGGAATTCTTCGGGAAAGGGACATTTGAAAGAAGATT
CTTCAGAGATGAGAAAGAACTTCAAGAATACGAGGCGGCTGAACTGACAAAGA
CTGACGTAGCACTGGCAGATGATGGAACTGTCAACTCTGACGACGAGGACTACT
TTTCAGGTGAAACCAGAAGTCCGGAGGCTGTTTATACTCGAATCATGATGAATG
GAGGTCGACTAAAGAGATCTCACATACGGAGATATGTCTCAGTCAGTTCCAATC
ATCAAGCCCGTCCAAACTCATTCGCCGAGTTTCTAAACAAGACATATTCGAGTGA
CTCATAAcatgaaaaaaactaacaccccctcccgtacgCCAC-
CATGTTCGTGTTTCTGGTGCTGCTGC
CTCTGGTGAGCTCCCAGTGCGTGAACTTCACCACAAGGACCCAGCTGCCCCTGC
CTATACCAATTCCTTCACACGGGCGTGTACTATCCCGACAAGGTGTTCCGGAGC
AGCGTGCTGCACTCCACACAGGATCTGTTTCTGCCTTTCTTTTCTAACGTGACCTG
GTTCCACGCCATCCACGTGAGCGGCACCAATGGCACAAAGCGGTTCGCCAATCC
AGTGCTGCCCTTTAACGATGGCGTGTACTTCGCCTCCACCGAGAAGTCTAACATC
ATCAGAGGCTGGATCTTTGGCACCACACTGGACAGCAAGACACAGTCCCTGCTG
ATCGTGAACAATGCCACCAACGTGGTCATCAAGGTGTGCGAGTTCCAGTTTTGTA
ATGATCCATTCCTGGGCGTGTACTATCACAAGAACAATAAGTCTTGGATGGAGA
GCGAGTTTCGCGTGTATTCCTCTGCCAACAATTGCACATTTGAGTACGTGTCCCA
GCCCTTCCTGATGGACCTGGAGGGCAAGCAGGGCAATTTCAAGAACCTGAGGGA
GTTCGTGTTTAAGAATATCGATGGCTACTTCAAAATCTACTCCAAGCACACCCCA
ATCAACCTGGTGCGCGGCCTGCCACAGGGCTTCTCTGCCCTGGAGCCACTGGTGG
ATCTGCCCATCGGCATCAACATCACCCGGTTTCAGACACTGCTGGCCCTGCACAG
AAGCTACCTGACACCAGGCGACAGCTCCTCTGGATGGACCGCAGGAGCAGCAGC
CTACTATGTGGGCTATCTGCAGCCCAGGACCTTCCTGCTGAAGTACAACGAGAAT
GGCACCATCACAGACGCCGTGGATTGCGCCCTGGATCCCCTGTCTGAGACCAAG
TGTACACTGAAGAGCTTTACCGTGGAGAAGGGCATCTATCAGACAAGCAATTTC
AGGGTGCAGCCTACCGAGTCCATCGTGCGCTTTCCCAATATCACAAACCTGTGCC
CTTTTGGCGAGGTGTTCAACGCAACCCGCTTCGCCAGCGTGTACGCCTGGAATAG
GAAGCGCATCTCCAACTGCGTGGCCGACTATTCTGTGCTGTACAACAGCGCCTCC
```

-continued

```
TTCTCTACCTTTAAGTGCTATGGCGTGAGCCCCACAAAGCTGAATGACCTGTGCT
TTACCAACGTGTACGCCGATTCCTTCGTGATCAGGGGCGACGAGGTGCGCCAGA
TCGCACCAGGACAGACAGGCAATATCGCAGACTACAATTATAAGCTGCCTGACG
ATTTCACCGGCTGCGTGATCGCCTGGAACTCTAACAATCTGGATAGCAAAGTGG
GCGGCAACTACAATTATCTGTACCGGCTGTTTAGAAAGTCTAATCTGAAGCCATT
CGAGAGGGACATCTCCACAGAAATCTACCAGGCCGGCTCTACCCCCTGCAATGG
CGTGAAGGGCTTTAACTGTTATTTCCCTCTGCAGAGCTACGGCTTCCAGCCAACA
TATGGCGTGGGCTATCAGCCCTACCGCGTGGTGGTGCTGTCTTTTGAGCTGCTGC
ACGCACCTGCAACAGTGTGCGGACCAAAGAAGAGCACCAATCTGGTGAAGAAC
AAGTGCGTGAACTTCAACTTCAACGGACTGACCGGAACAGGCGTGCTGACCGAG
TCCAACAAGAAGTTCCTGCCTTTTCAGCAGTTCGGCAGGGACATCGCAGATACC
ACAGACGCCGTGCGCGACCCTCAGACCCTGGAGATCCTGGACATCACACCATGC
TCCTTCGGCGGCGTGTCTGTGATCACACCAGGCACCAATACAAGCAACCAGGTG
GCCGTGCTGTATCAGGGCGTGAATTGTACCGAGGTGCCAGTGGCAATCCACGCA
GATCAGCTGACCCCTACATGGCGGGTGTACTCTACCGGCAGCAACGTGTTCCAG
ACAAGAGCCGGATGCCTGATCGGAGCAGAGCACGTGAACAATAGCTATGAGTGC
GACATCCCTATCGGCGCCGGCATCTGTGCCTCCTACCAGACCCAGACAAACTCCC
CAGAATCAAGCGTGATTCCTCTGGTCCATCCACTGGCAGATCCCTCCACAGTGTT
CAAAGACGGAGATGAGGCCGAAGACTTTGTGGAAGTCCACCTGCCTGATGTGCA
TAACCAGGTGTCTGGCGTCGACCTGGGACTGCCAAATTGGGGCAAGTACGTGCT
GCTGAGTGCTGGAGCACTGACTGCCCTGATGCTGATCATTTTCCTGATGACCTGC
TGTCGGCGCGTGAACAGAAGTGAGCCCACTCAGCACAATCTGCGAGGAACCGGG
AGAGAAGTGTCAGTCACACCTCAGAGCGGGAAAATCATTAGTAGTTGGGAATCA
CATAAAAGCGGGGGCGAGACCAGGCTGTGAgctagcCATGAAAAAAACTAACACCC
CTCCTTTCGAACCATCCCAAACATGAGCAAGATCTTTGTCAATCCTAGTGCTATT
AGAGCCGGTCTGGCCGATCTTGAGATGGCTGAAGAAACTGTTGATCTGATCAAT
AGAAATATCGAAGACAATCAGGCTCATCTCCAAGGGGAACCCATAGAGGTGGAC
AATCTCCCTGAGGATATGGGGCGACTTCACCTGGATGATGGAAAATCGCCCAAC
CATGGTGAGATAGCCAAGGTGGGAGAAGGCAAGTATCGAGAGGACTTTCAGATG
GATGAAGGAGAGGATCCTAGCTTCCTGTTCCAGTCATACCTGGAAAATGTTGGA
GTCCAAATAGTCAGACAAATGAGGTCAGGAGAGAGATTTCTCAAGATATGGTCA
CAGACCGTAGAAGAGATTATATCCTATGTCGCGGTCAACTTTCCCAACCCTCCAG
GAAAGTCTTCAGAGGATAAATCAACCCAGACTACTGGCCGAGAGCTCAAGAAGG
AGACAACACCCACTCCTTCTCAGAGAGAAAGCCAATCATCGAAAGCCAGGATGG
CGGCTCAAATTGCTTCTGGCCCTCCAGCCCTTGAATGGTCGGCTACCAATGAAGA
GGATGATCTATCAGTGGAGGCTGAGATCGCTCACCAGATTGCAGAAAGTTTCTCC
AAAAAATATAAGTTTCCCTCTCGATCCTCAGGGATACTCTTGTATAATTTTGAGC
AATTGAAAATGAACCTTGATGATATAGTTAAAGAGGCAAAAAATGTACCAGGTG
TGACCCGTTTAGCCCATGACGGGTCCAAACTCCCCCTAAGATGTGTACTGGGATG
GGTCGCTTTGGCCAACTCTAAGAAATTCCAGTTGTTAGTCGAATCCGACAAGCTG
AGTAAAATCATGCAAGATGACTTGAATCGCTATACATCTTGCTAACCGAACCTCT
```

-continued

```
CCCCTCAGTCCCTCTAGACAATAAAATCCGAGATGTCCCAAAGTCAACATGAAA

AAAACAGGCAACACCACTGATAAAATGAACCTCCTACGTAAGATAGTGAAAAAC

CGCAGGGACGAGGACACTCAAAAATCCTCTCCCGCGTCAGCCCCTCTGGATGAC

GATGACTTGTGGCTTCCACCCCCTGAATACGTCCCGCTGAAAGAACTTACAGGCA

AGAAGAACATGAGGAACTTTTGTATCAACGGAAGGGTTAAAGTGTGTAGCCCGA

ATGGTTACTCGTTCAGGATCCTGCGGCACATTCTGAAATCATTCGACGAGATATA

TTCTGGGAATCATAGGATGATCGGGTTAGTCAAAGTGGTTATTGGACTGGCTTTG

TCAGGATCTCCAGTCCCTGAGGGCCTGAACTGGGTATACAAATTGAGGAGAACC

TTTATCTTCCAGTGGGCTGATTCCAGGGGCCCTCTTGAAGGGGAGGAGTTGGAAT

ACTCTCAGGAGATCACTTGGGATGATGATACTGAGTTCGTCGGATTGCAAATAA

GAGTGATTGCAAAACAGTGTCATATCCAGGGCAGAGTCTGGTGTATCAACATGA

ACCCGAGAGCATGTCAACTATGGTCTGACATGTCTCTTCAGACACAAAGGTCCG

AAGAGGACAAAGATTCCTCTCTGCTTCTAGAATAATCAGATTATATCCCGCAAAT

TTATCACTTGTTTACCTCTGGAGGAGAGAACATATGGGCTCAACTCCAACCCTTG

GGAGCAATATAACAAAAAACATGTTATGGTGCCATTAAACCGCTGCATTTCATC

AAAGTCAAGTTGATTACCTTTACATTTTGATCCTCTTGGATGTGAAAAAAACTAT

TAACATCCCTCAAAAGAcccgggAAAGATGGTTCCTCAGGCTCTCCTGTTTGTACC

CCTTCTGGTTTTTCCATTGTGTTTTGGGAAATTCCCTATTTACACGATACCAGACA

AGCTTGGTCCCTGGAGTCCGATTGACATACATCACCTCAGCTGCCCAAACAATTT

GGTAGTGGAGGACGAAGGATGCACCAACCTGTCAGGGTTCTCCTACATGGAACT

TAAAGTTGGATACATCTTAGCCATAAAAGTGAACGGGTTCACTTGCACAGGCGTT

GTGACGGAGGCTGAAACCTACACTAACTTCGTTGGTTATGTCACAACCACGTTCA

AAAGAAAGCATTTCCGCCCAACACCAGATGCATGTAGAGCCGCGTACAACTGGA

AGATGGCCGGTGACCCCAGATATGAAGAGTCTCTACACAATCCGTACCCTGACT

ACCGCTGGCTTCGAACTGTAAAAACCACCAAGGAGTCTCTCGTTATCATATCTCC

AAGTGTGGCAGATTTGGACCCATATGACAGATCCCTTCACTCGAGGGTCTTCCCT

AGCGGGAAGTGCTCAGGAGTAGCGGTGTCTTCTACCTACTGCTCCACTAACCAC

GATTACACCATTTGGATGCCCGAGAATCCGAGACTAGGGATGTCTTGTGACATTT

TTACCAATAGTAGAGGGAAGAGAGCATCCAAAGGGAGTGAGACTTGCGGCTTTG

TAGATGAAAGAGGCCTATATAAGTCTTTAAAAGGAGCATGCAAACTCAAGTTAT

GTGGAGTTCTAGGACTTAGACTTATGGATGGAACATGGGTCTCGATGCAAACAT

CAAATGAAACCAAATGGTGCCCTCCCGATAAGTTGGTGAACCTGCACGACTTTC

GCTCAGACGAAATTGAGCACCTTGTTGTAGAGGAGTTGGTCAGGAAGAGAGAGG

AGTGTCTGGATGCACTAGAGTCCATCATGACAACCAAGTCAGTGAGTTTCAGAC

GTCTCAGTCATTTAAGAAAACTTGTCCCTGGGTTTGGAAAAGCATATACCATATT

CAACAAGACCTTGATGGAAGCCGATGCTCACTACAAGTCAGTCgagACTTGGAAT

GAGATCCTCCCTTCAAAAGGGTGTTTAAGAGTTGGGGGGAGGTGTCATCCTCATG

TGAACGGGGTGTTTTTCAATGGTATAATATTAGGACCTGACGGCAATGTCTTAAT

CCCAGAGATGCAATCATCCCTCCTCCAGCAACATATGGAGTTGTTGGAATCCTCG

GTTATCCCCCTTGTGCACCCCCTGGCAGACCCGTCTACCGTTTTCAAGGACGGTG
```

```
-continued
ACGAGGCTGAGGATTTTGTTGAAGTTCACCTTCCCGATGTGCACAATCAGGTCTC

AGGAGTTGACTTGGGTCTCCCGAACTGGGGGAAGTATGTATTACTGAGTGCAGG

GGCCCTGACTGCCTTGATGTTGATAATTTTCCTGATGACATGTTGTAGAAGAGTC

AATCGATCAGAACCTACGCAACACAATCTCAGAGGGACAGGGAGGGAGGTGTC

AGTCACTCCCCAAAGCGGGAAGATCATATCTTCATGGGAATCACACAAGAGTGG

GGGTGAGACCAGACTGTAAttaattaaCGTCCTTTCAACGATCCAAGTCcatgaaaaaaactaa caccccctcccgtacctagcTTATAAAGTGCTGGGTCATCTAAGCTTTTCAGTCGAGAAAAA

ACATTAGATCAGAAGAACAACTGGCAACACTTCTCAACCTGAGACTTACTTCAA

GATGCTCGATCCTGGAGAGGTCTATGATGACCCTATTGACCCAATCGAGTTAGAG

GCTGAACCCAGAGGAACCCCCATTGTCCCCAACATCTTGAGGAACTCTGACTAC

AATCTCAACTCTCCTTTGATAGAAGATCCTGCTAGACTAATGTTAGAATGGTTAA

AAACAGGGAATAGACCTTATCGGATGACTCTAACAGACAATTGCTCCAGGTCTTT

CAGAGTTTTGAAAGATTATTTCAAGAAGGTAGATTTGGGTTCTCTCAAGGTGGGC

GGAATGGCTGCACAGTCAATGATTTCTCTCTGGTTATATGGTGCCCACTCTGAAT

CCAACAGGAGCCGGAGATGTATAACAGACTTGGCCCATTTCTATTCCAAGTCGTC

CCCCATAGAGAAGCTGTTGAATCTCACGCTAGGAAATAGAGGGCTGAGAATCCC

CCCAGAGGGAGTGTTAAGTTGCCTTGAGAGGGTTGATTATGATAATGCATTTGGA

AGGTATCTTGCCAACACGTATTCCTCTTACTTGTTCTTCCATGTAATCACCTTATA

CATGAACGCCCTAGACTGGGATGAAGAAAAGACCATCCTAGCATTATGGAAAGA

TTTAACCTCAGTGGACATCGGGAAGGACTTGGTAAAGTTCAAAGACCAAATATG

GGGACTGCTGATCGTGACAAAGGACTTTGTTTACTCCCAAAGTTCCAATTGTCTT

TTTGACAGAAACTACACACTTATGCTAAAAGATCTTTTCTTGTCTCGCTTCAACTC

CTTAATGGTCTTGCTCTCTCCCCCAGAGCCCCGATACTCAGATGACTTGATATCT

CAACTATGCCAGCTGTACATTGCTGGGGATCAAGTCTTGTCTATGTGTGGAAACT

CCGGCTATGAAGTCATCAAAATATTGGAGCCATATGTCGTGAATAGTTTAGTCCA

GAGAGCAGAAAAGTTTAGGCCTCTCATTCATTCCTTGGGAGACTTTCCTGTATTT

ATAAAAGACAAGGTAAGTCAACTTGAAGAGACGTTCGGTCCCTGTGCAAGAAGG

TTCTTTAGGGCTCTGGATCAATTCGACAACATACATGACTTGGTTTTTGTGTTTGG

CTGTTACAGGCATTGGGGGCACCCATATATAGATTATCGAAAGGGTCTGTCAAA

ACTATATGATCAGGTTCACCTTAAAAAAATGATAGATAAGTCCTACCAGGAGTG

CTTAGCAAGCGACCTAGCCAGGAGGATCCTTAGATGGGGTTTTGATAAGTACTCC

AAGTGGTATCTGGATTCAAGATTCCTAGCCCGAGACCACCCCTTGACTCCTTATA

TCAAAACCCAAACATGGCCACCCAAACATATTGTAGACTTGGTGGGGATACAT

GGCACAAGCTCCCGATCACGCAGATCTTTGAGATTCCTGAATCAATGGATCCGTC

AGAAATATTGGATGACAAATCACATTCTTTCACCAGAACGAGACTAGCTTCTTGG

CTGTCAGAAACCGAGGGGGGCCTGTTCCTAGCGAAAAAGTTATTATCACGGCC

CTGTCTAAGCCGCCTGTCAATCCCCGAGAGTTTCTGAGGTCTATAGACCTCGGAG

GATTGCCAGATGAAGACTTGATAATTGGCCTCAAGCCAAAGGAACGGGAATTGA

AGATTGAAGGTCGATTCTTTGCTCTAATGTCATGGAATCTAAGATTGTATTTTGTC

ATCACTGAAAAACTCTTGGCCAACTACATCTTGCCACTTTTTGACGCGCTGACTA

TGACAGACAACCTGAACAAGGTGTTTAAAAAGCTGATCGACAGGGTCACCGGGC
```

```
AAGGGCTTTTGGACTATTCAAGGGTCACATATGCATTTCACCTGGACTATGAAAA

GTGGAACAACCATCAAAGATTAGAGTCAACAGAGGATGTATTTTCTGTCCTAGA
```

```
AAGGGCTTTTGGACTATTCAAGGGTCACATATGCATTTCACCTGGACTATGAAAA

GTGGAACAACCATCAAAGATTAGAGTCAACAGAGGATGTATTTTCTGTCCTAGA

TCAAGTGTTTGGATTGAAGAGAGTGTTTTCTAGAACACACGAGTTTTTTCAAAAG

GCCTGGATCTATTATTCAGACAGATCAGACCTCATCGGGTTACGGGAGGATCAA

ATATACTGCTTAGATGCGTCCAACGGCCCAACCTGTTGGAATGGCCAGGATGGC

GGGCTAGAAGGCTTACGGCAGAAGGGCTGGAGTCTAGTCAGCTTATTGATGATA

GATAGAGAATCTCAAATCAGGAACACAAGAACCAAAATACTAGCTCAAGGAGA

CAACCAGGTTTTATGTCCGACATACATGTTGTCGCCAGGGCTATCTCAAGAGGGG

CTCCTCTATGAATTGGAGAGAATATCAAGGAATGCACTTTCGATATACAGAGCC

GTCGAGGAAGGGGCATCTAAGCTAGGGCTGATCATCAAGAAAGAAGAGACCAT

GTGTAGTTATGACTTCCTCATCTATGGAAAAACCCCTTTGTTTAGAGGTAACATA

TTGGTGCCTGAGTCCAAAAGATGGGCCAGAGTCTCTTGCGTCTCTAATGACCAAA

TAGTCAACCTCGCCAATATAATGTCGACAGTGTCCACCAATGCGCTAACAGTGG

CACAACACTCTCAATCTTTGATCAAACCGATGAGGGATTTTCTGCTCATGTCAGT

ACAGGCAGTCTTTCACTACCTGCTATTTAGCCCAATCTTAAAGGGAAGAGTTTAC

AAGATTCTGAGCGCTGAAGGGGAGAGCTTTCTCCTAGCCATGTCAAGGATAATC

TATCTAGATCCTTCTTTGGGAGGGATATCTGGAATGTCCCTCGGAAGATTCCATA

TACGACAGTTCTCAGACCCTGTCTCTGAAGGGTTATCCTTCTGGAGAGAGATCTG

GTTAAGCTCCCAAGAGTCCTGGATTCACGCGTTGTGTCAAGAGGCTGGAAACCC

AGATCTTGGAGAGAGAACACTCGAGAGCTTCACTCGCCTTCTAGAAGATCCGAC

CACCTTAAATATCAGAGGAGGGGCCAGTCCTACCATTCTACTCAAGGATGCAAT

CAGAAAGGCTTTATATGACGAGGTGGACAAGGTGGAAAATTCAGAGTTTCGAGA

GGCAATCCTGTTGTCCAAGACCCATAGAGATAATTTTATACTCTTCTTAATATCT

GTTGAGCCTCTGTTTCCTCGATTTCTCAGTGAGCTATTCAGTTCGTCTTTTTTGGG

AATCCCCGAGTCAATCATTGGATTGATACAAAACTCCCGAACGATAAGAAGGCA

GTTTAGAAAGAGTCTCTCAAAAACTTTAGAAGAATCCTTCTACAACTCAGAGATC

CACGGGATTAGTCGGATGACCCAGACACCTCAGAGGGTTGGGGGGGTGTGGCCT

TGCTCTTCAGAGAGGGCAGATCTACTTAGGGAGATCTCTTGGGGAAGAAAAGTG

GTAGGCACGACAGTTCCTCACCCTTCTGAGATGTTGGGATTACTTCCCAAGTCCT

CTATTTCTTGCACTTGTGGAGCAACAGGAGGAGGCAATCCTAGAGTTTCTGTATC

AGTACTCCCGTCCTTTGATCAGTCATTTTTTTCACGAGGCCCCCTAAAGGGATAC

TTGGGCTCGTCCACCTCTATGTCGACCCAGCTATTCCATGCATGGGAAAAAGTCA

CTAATGTTCATGTGGTGAAGAGAGCTCTATCGTTAAAAGAATCTATAAACTGGTT

CATTACTAGAGATTCCAACTTGGCTCAAGCTCTAATTAGGAACATTATGTCTCTG

ACAGGCCCTGATTTCCCTCTAGAGGAGGCCCCTGTCTTCAAAAGGACGGGGTCA

GCCTTGCATAGGTTCAAGTCTGCCAGATACAGCGAAGGAGGGTATTCTTCTGTCT

GCCCGAACCTCCTCTCTCATATTTCTGTTAGTACAGACACCATGTCTGATTTGACC

CAAGACGGGAAGAACTACGATTTCATGTTCCAGCCATTGATGCTTTATGCACAGA

CATGGACATCAGAGCTGGTACAGAGAGACACAAGGCTAAGAGACTCTACGTTTC

ATTGGCACCTCCGATGCAACAGGTGTGTGAGACCCATTGACGACGTGACCCTGG
```

-continued
```
AGACCTCTCAGATCTTCGAGTTTCCGGATGTGTCGAAAAGAATATCCAGAATGGT

TTCTGGGGCTGTGCCTCACTTCCAGAGGCTTCCCGATATCCGTCTGAGACCAGGA

GATTTTGAATCTCTAAGCGGTAGAGAAAAGTCTCACCATATCGGATCAGCTCAG

GGGCTCTTATACTCAATCTTAGTGGCAATTCACGACTCAGGATACAATGATGGAA

CCATCTTCCCTGTCAACATATACGGCAAGGTTTCCCCTAGAGACTATTTGAGAGG

GCTCGCAAGGGGAGTATTGATAGGATCCTCGATTTGCTTCTTGACAAGAATGACA

AATATCAATATTAATAGACCTCTTGAATTGGTCTCAGGGGTAATCTCATATATTC

TCCTGAGGCTAGATAACCATCCCTCCTTGTACATAATGCTCAGAGAACCGTCTCT

TAGAGGAGAGATATTTTCTATCCCTCAGAAAATCCCCGCCGCTTATCCAACCACT

ATGAAAGAAGGCAACAGATCAATCTTGTGTTATCTCCAACATGTGCTACGCTATG

AGCGAGAGATAATCACGGCGTCTCCAGAGAATGACTGGCTATGGATCTTTTCAG

ACTTTAGAAGTGCCAAAATGACGTACCTATCCCTCATTACTTACCAGTCTCATCT

TCTACTCCAGAGGGTTGAGAGAAACCTATCTAAGAGTATGAGAGATAACCTGCG

ACAATTGAGTTCTTTGATGAGGCAGGTGCTGGGCGGGCACGGAGAAGATACCTT

AGAGTCAGACGACAACATTCAACGACTGCTAAAAGACTCTTTACGAAGGACAAG

ATGGGTGGATCAAGAGGTGCGCCATGCAGCTAGAACCATGACTGGAGATTACAG

CCCCAACAAGAAGGTGTCCCGTAAGGTAGGATGTTCAGAATGGGTCTGCTCTGC

TCAACAGGTTGCAGTCTCTACCTCAGCAAACCCGGCCCCTGTCTCGGAGCTTGAC

ATAAGGGCCCTCTCTAAGAGGTTCCAGAACCCTTTGATCTCGGGCTTGAGAGTGG

TTCAGTGGGCAACCGGTGCTCATTATAAGCTTAAGCCTATTCTAGATGATCTCAA

TGTTTTCCCATCTCTCTGCCTTGTAGTTGGGGACGGGTCAGGGGGGATATCAAGG

GCAGTCCTCAACATGTTTCCAGATGCCAAGCTTGTGTTCAACAGTCTTTTAGAGG

TGAATGACCTGATGGCTTCCGGAACACATCCACTGCCTCCTTCAGCAATCATGAG

GGGAGGAAATGATATCGTCTCCAGAGTGATAGATCTTGACTCAATCTGGGAAAA

ACCGTCCGACTTGAGAAACTTGGCAACCTGGAAATACTTCCAGTCAGTCCAAAA

GCAGGTCAACATGTCCTATGACCTCATTATTTGCGATGCAGAAGTTACTGACATT

GCATCTATCAACCGGATCACCCTGTTAATGTCCGATTTTGCATTGTCTATAGATG

GACCACTCTATTTGGTCTTCAAAACTTATGGGACTATGCTAGTAAATCCAAACTA

CAAGGCTATTCAACACCTGTCAAGAGCGTTCCCCTCGGTCACAGGGTTTATCACC

CAAGTAACTTCGTCTTTTTCATCTGAGCTCTACCTCCGATTCTCCAAACGAGGGA

AGTTTTTCAGAGATGCTGAGTACTTGACCTCTTCCACCCTTCGAGAAATGAGCCT

TGTGTTATTCAATTGTAGCAGCCCCAAGAGTGAGATGCAGAGAGCTCGTTCCTTG

AACTATCAGGATCTTGTGAGAGGATTTCCTGAAGAAATCATATCAAATCCTTACA

ATGAGATGATCATAACTCTGATTGACAGTGATGTAGAATCTTTTCTAGTCCACAA

GATGGTTGATGATCTTGAGTTACAGAGGGGAACTCTGTCTAAAGTGGCTATCATT

ATAGCCATCATGATAGTTTTCTCCAACAGAGTCTTCAACGTTTCCAAACCCCTAA

CTGACCCCTCGTTCTATCCACCGTCTGATCCCAAAATCCTGAGGCACTTCAACAT

ATGTTGCAGTACTATGATGTATCTATCTACTGCTTTAGGTGACGTCCCTAGCTTCG

CAAGACTTCACGACCTGTATAACAGACCTATAACTTATTACTTCAGAAAGCAAGT

CATTCGAGGGAACGTTTATCTATCTTGGAGTTGGTCCAACGACACCTCAGTGTTC

AAAAGGGTAGCCTGTAATTCTAGCCTGAGTCTGTCATCTCACTGGATCAGGTTGA
```

-continued

TTTACAAGATAGTGAAGACTACCAGACTCGTTGGCAGCATCAAGGATCTATCCA

GAGAAGTGGAAAGACACCTTCATAGGTACAACAGGTGGATCACCCTAGAGGATA

TCAGATCTAGATCATCCCTACTAGACTACAGTTGCCTGTGAACCGGATACTCCTG

GAAGCCTGCCCATGCTAAGACTCTTGTGTGATGTATCTTGAAAAAAACAAGATCC

TAAATCTGAACCTTTGGTTGTTTGATTGTTTTTCTCAtttttgttgtttatttgttaagcgt.

In one embodiment, the nucleic acid comprises the sequence of SEQ ID NO: 10, shown below (RABV vector: Coravax V3-China (S1-VSVG-E26)):

ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAcatgaaaaaaactaaccccctcccGTACGCCACCATGTTCGTGTTTCTGGTGCTGCT

GCCTCTGGTGAGCTCCCAGTGCGTGAACCTGACCACAAGGACCCAGCTGCCCCC

TGCCTATACCAATTCCTTCACACGGGGCGTGTACTATCCCGACAAGGTGTTCCGG

AGCAGCGTGCTGCACTCCACACAGGATCTGTTTCTGCCTTTCTTTTCTAACGTGAC

CTGGTTCCACGCCATCCACGTGAGCGGCACCAATGGCACAAAGCGGTTCGACAA

TCCAGTGCTGCCCTTTAACGATGGCGTGTACTTCGCCTCCACCGAGAAGTCTAAC

```
                        -continued
ATCATCAGAGGCTGGATCTTTGGCACCACACTGGACAGCAAGACACAGTCCCTG

CTGATCGTGAACAATGCCACCAACGTGGTCATCAAGGTGTGCGAGTTCCAGTTTT

GTAATGATCCATTCCTGGGCGTGTACTATCACAAGAACAATAAGTCTTGGATGGA

GAGCGAGTTTCGCGTGTATTCCTCTGCCAACAATTGCACATTTGAGTACGTGTCC

CAGCCCTTCCTGATGGACCTGGAGGGCAAGCAGGGCAATTTCAAGAACCTGAGG

GAGTTCGTGTTTAAGAATATCGATGGCTACTTCAAAATCTACTCCAAGCACACCC

CAATCAACCTGGTGCGCGACCTGCCACAGGGCTTCTCTGCCCTGGAGCCACTGGT

GGATCTGCCCATCGGCATCAACATCACCCGGTTTCAGACACTGCTGGCCCTGCAC

AGAAGCTACCTGACACCAGGCGACAGCTCCTCTGGATGGACCGCAGGAGCAGCA

GCCTACTATGTGGGCTATCTGCAGCCCAGGACCTTCCTGCTGAAGTACAACGAG

AATGGCACCATCACAGACGCCGTGGATTGCGCCCTGGATCCCCTGTCTGAGACC

AAGTGTACACTGAAGAGCTTTACCGTGGAGAAGGGCATCTATCAGACAAGCAAT

TTCAGGGTGCAGCCTACCGAGTCCATCGTGCGCTTTCCCAATATCACAAACCTGT

GCCCTTTTGGCGAGGTGTTCAACGCAACCCGCTTCGCCAGCGTGTACGCCTGGAA

TAGGAAGCGCATCTCCAACTGCGTGGCCGACTATTCTGTGCTGTACAACAGCGCC

TCCTTCTCTACCTTTAAGTGCTATGGCGTGAGCCCCACAAAGCTGAATGACCTGT

GCTTTACCAACGTGTACGCCGATTCCTTCGTGATCAGGGGCGACGAGGTGCGCC

AGATCGCACCAGGACAGACAGGCAAGATCGCAGACTACAATTATAAGCTGCCTG

ACGATTTCACCGGCTGCGTGATCGCCTGGAACTCTAACAATCTGGATAGCAAAGT

GGGCGGCAACTACAATTATCTGTACCGGCTGTTTAGAAAGTCTAATCTGAAGCCA

TTCGAGAGGGACATCTCCACAGAAATCTACCAGGCCGGCTCTACCCCCTGCAAT

GGCGTGGAGGGCTTTAACTGTTATTTCCCTCTGCAGAGCTACGGCTTCCAGCCAA

CAAACGGCGTGGGCTATCAGCCCTACCGCGTGGTGGTGCTGTCTTTTGAGCTGCT

GCACGCACCTGCAACAGTGTGCGGACCAAAGAAGAGCACCAATCTGGTGAAGA

ACAAGTGCGTGAACTTCAACTTCAACGGACTGACCGGAACAGGCGTGCTGACCG

AGTCCAACAAGAAGTTCCTGCCTTTTCAGCAGTTCGGCAGGGACATCGCAGATA

CCACAGACGCCGTGCGCGACCCTCAGACCCTGGAGATCCTGGACATCACACCAT

GCTCCTTCGGCGGCGTGTCTGTGATCACACCAGGCACCAATACAAGCAACCAGG

TGGCCGTGCTGTATCAGGACGTGAATTGTACCGAGGTGCCAGTGGCAATCCACG

CAGATCAGCTGACCCCTACATGGCGGGTGTACTCTACCGGCAGCAACGTGTTCC

AGACAAGAGCCGGATGCCTGATCGGAGCAGAGCACGTGAACAATAGCTATGAGT

GCGACATCCCTATCGGCGCCGGCATCTGTGCCTCCTACCAGACCCAGACAAACTC

CCCAAGGTCTGTGGGCGATACAGGCCTGTCCAAGAATCCAATCGAGCTGGTAGA

GGGCTGGTTCAGCAGTTGGAAAAGCTCCATCGCCTCCTTTTTCTTTATCATCGGC

CTGATCATCGGACTGTTCCTGGTGCTCCGCGTGGGTATCCACCTGTGCATCAAGC

TGAAGCACACCAAGAAAAGACAGATTTATACAGACATCGAGATGAACCGCCTGG

GAAAGTGAGCTAGCCATGAAAAAAACTAACACCCCTCCTTTCGAACCATCCCAA

ACATGAGCAAGATCTTTGTCAATCCTAGTGCTATTAGAGCCGGTCTGGCCGATCT

TGAGATGGCTGAAGAAACTGTTGATCTGATCAATAGAAATATCGAAGACAATCA

GGCTCATCTCCAAGGGGAACCCATAGAGGTGGACAATCTCCCTGAGGATATGGG
```

-continued

```
GCGACTTCACCTGGATGATGGAAAATCGCCCAACCATGGTGAGATAGCCAAGGT

GGGAGAAGGCAAGTATCGAGAGGACTTTCAGATGGATGAAGGAGAGGATCCTA

GCTTCCTGTTCCAGTCATACCTGGAAAATGTTGGAGTCCAAATAGTCAGACAAAT

GAGGTCAGGAGAGAGATTTCTCAAGATATGGTCACAGACCGTAGAAGAGATTAT

ATCCTATGTCGCGGTCAACTTTCCCAACCCTCCAGGAAAGTCTTCAGAGGATAAA

TCAACCCAGACTACTGGCCGAGAGCTCAAGAAGGAGACAACACCCACTCCTTCT

CAGAGAGAAAGCCAATCATCGAAAGCCAGGATGGCGGCTCAAATTGCTTCTGGC

CCTCCAGCCCTTGAATGGTCGGCTACCAATGAAGAGGATGATCTATCAGTGGAG

GCTGAGATCGCTCACCAGATTGCAGAAAGTTTCTCCAAAAAATATAAGTTTCCCT

CTCGATCCTCAGGGATACTCTTGTATAATTTTGAGCAATTGAAAATGAACCTTGA

TGATATAGTTAAAGAGGCAAAAAATGTACCAGGTGTGACCCGTTTAGCCCATGA

CGGGTCCAAACTCCCCCTAAGATGTGTACTGGGATGGGTCGCTTTGGCCAACTCT

AAGAAATTCCAGTTGTTAGTCGAATCCGACAAGCTGAGTAAAATCATGCAAGAT

GACTTGAATCGCTATACATCTTGCTAACCGAACCTCTCCCCTCAGTCCCTCTAGA

CAATAAAATCCGAGATGTCCCAAAGTCAACATGAAAAAAACAGGCAACACCACT

GATAAAATGAACCTCCTACGTAAGATAGTGAAAAACCGCAGGGACGAGGACACT

CAAAAATCCTCTCCCGCGTCAGCCCCTCTGGATGACGATGACTTGTGGCTTCCAC

CCCCTGAATACGTCCCGCTGAAAGAACTTACAGGCAAGAAGAACATGAGGAACT

TTTGTATCAACGGAAGGGTTAAAGTGTGTAGCCCGAATGGTTACTCGTTCAGGAT

CCTGCGGCACATTCTGAAATCATTCGACGAGATATATTCTGGGAATCATAGGATG

ATCGGGTTAGTCAAAGTGGTTATTGGACTGGCTTTGTCAGGATCTCCAGTCCCTG

AGGGCCTGAACTGGGTATACAAATTGAGGAGAACCTTTATCTTCCAGTGGGCTG

ATTCCAGGGGCCCTCTTGAAGGGGAGGAGTTGGAATACTCTCAGGAGATCACTT

GGGATGATGATACTGAGTTCGTCGGATTGCAAATAAGAGTGATTGCAAAACAGT

GTCATATCCAGGGCAGAGTCTGGTGTATCAACATGAACCCGAGAGCATGTCAAC

TATGGTCTGACATGTCTCTTCAGACACAAAGGTCCGAAGAGGACAAAGATTCCT

CTCTGCTTCTAGAATAATCAGATTATATCCCGCAAATTTATCACTTGTTTACCTCT

GGAGGAGAGAACATATGGGCTCAACTCCAACCCTTGGGAGCAATATAACAAAAA

ACATGTTATGGTGCCATTAAACCGCTGCATTTCATCAAAGTCAAGTTGATTACCT

TTACATTTTGATCCTCTTGGATGTGAAAAAAACTATTAACATCCCTCAAAAGACcc cgggAAAGATGGTTCCTCAGGCTCTCCTGTTTGTACCCCTTCTGGTTTTTCCATTGT

GTTTTGGGAAATTCCCTATTTACACGATACCAGACAAGCTTGGTCCCTGGAGTCC

GATTGACATACATCACCTCAGCTGCCCAAACAATTTGGTAGTGGAGGACGAAGG

ATGCACCAACCTGTCAGGGTTCTCCTACATGGAACTTAAAGTTGGATACATCTTA

GCCATAAAAGTGAACGGGTTCACTTGCACAGGCGTTGTGACGGAGGCTGAAACC

TACACTAACTTCGTTGGTTATGTCACAACCACGTTCAAAAGAAAGCATTTCCGCC

CAACACCAGATGCATGTAGAGCCGCGTACAACTGGAAGATGGCCGGTGACCCCA

GATATGAAGAGTCTCTACACAATCCGTACCCTGACTACCGCTGGCTTCGAACTGT

AAAAACCACCAAGGAGTCTCTCGTTATCATATCTCCAAGTGTGGCAGATTTGGAC

CCATATGACAGATCCCTTCACTCGAGGGTCTTCCCTAGCGGGAAGTGCTCAGGA

GTAGCGGTGTCTTCTACCTACTGCTCCACTAACCACGATTACACCATTTGGATGC
```

```
CCGAGAATCCGAGACTAGGGATGTCTTGTGACATTTTTACCAATAGTAGAGGGA

AGAGAGCATCCAAAGGGAGTGAGACTTGCGGCTTTGTAGATGAAAGAGGCCTAT

ATAAGTCTTTAAAAGGAGCATGCAAACTCAAGTTATGTGGAGTTCTAGGACTTA

GACTTATGGATGGAACATGGGTCTCGATGCAAACATCAAATGAAACCAAATGGT

GCCCTCCCGATAAGTTGGTGAACCTGCACGACTTTCGCTCAGACGAAATTGAGC

ACCTTGTTGTAGAGGAGTTGGTCAGGAAGAGAGAGGAGTGTCTGGATGCACTAG

AGTCCATCATGACAACCAAGTCAGTGAGTTTCAGACGTCTCAGTCATTTAAGAAA

ACTTGTCCCTGGGTTTGGAAAAGCATATACCATATTCAACAAGACCTTGATGGAA

GCCGATGCTCACTACAAGTCAGTCgagACTTGGAATGAGATCCTCCCTTCAAAAG

GGTGTTTAAGAGTTGGGGGAGGTGTCATCCTCATGTGAACGGGGTGTTTTTCAA

TGGTATAATATTAGGACCTGACGGCAATGTCTTAATCCCAGAGATGCAATCATCC

CTCCTCCAGCAACATATGGAGTTGTTGGAATCCTCGGTTATCCCCCTTGTGCACC

CCCTGGCAGACCCGTCTACCGTTTTCAAGGACGGTGACGAGGCTGAGGATTTTGT

TGAAGTTCACCTTCCCGATGTGCACAATCAGGTCTCAGGAGTTGACTTGGGTCTC

CCGAACTGGGGGAAGTATGTATTACTGAGTGCAGGGGCCCTGACTGCCTTGATG

TTGATAATTTTCCTGATGACATGTTGTAGAAGAGTCAATCGATCAGAACCTACGC

AACACAATCTCAGAGGGACAGGGAGGGAGGTGTCAGTCACTCCCCAAAGCGGG

AAGATCATATCTTCATGGGAATCACACAAGAGTGGGGGTGAGACCAGACTGTAA ttaattaaCGTCCTTTCAACGATCCAAGTCcat-
gaaaaaaactaacaccccctcccgtacctagcTTATAAA

GTGCTGGGTCATCTAAGCTTTTCAGTCGAGAAAAAAACATTAGATCAGAAGAAC

AACTGGCAACACTTCTCAACCTGAGACTTACTTCAAGATGCTCGATCCTGGAGAG

GTCTATGATGACCCTATTGACCCAATCGAGTTAGAGGCTGAACCCAGAGGAACC

CCCATTGTCCCCAACATCTTGAGGAACTCTGACTACAATCTCAACTCTCCTTTGA

TAGAAGATCCTGCTAGACTAATGTTAGAATGGTTAAAAACAGGGAATAGACCTT

ATCGGATGACTCTAACAGACAATTGCTCCAGGTCTTTCAGAGTTTTGAAAGATTA

TTTCAAGAAGGTAGATTTGGGTTCTCTCAAGGTGGGCGGAATGGCTGCACAGTC

AATGATTTCTCTCTGGTTATATGGTGCCCACTCTGAATCCAACAGGAGCCGGAGA

TGTATAACAGACTTGGCCCATTTCTATTCCAAGTCGTCCCCCATAGAGAAGCTGT

TGAATCTCACGCTAGGAAATAGAGGGCTGAGAATCCCCCCAGAGGGAGTGTTAA

GTTGCCTTGAGAGGGTTGATTATGATAATGCATTTGGAAGGTATCTTGCCAACAC

GTATTCCTCTTACTTGTTCTTCCATGTAATCACCTTATACATGAACGCCCTAGACT

GGGATGAAGAAAAGACCATCCTAGCATTATGGAAAGATTTAACCTCAGTGGACA

TCGGGAAGGACTTGGTAAAGTTCAAAGACCAAATATGGGGACTGCTGATCGTGA

CAAAGGACTTTGTTTACTCCCAAAGTTCCAATTGTCTTTTTGACAGAAACTACAC

ACTTATGCTAAAAGATCTTTTCTTGTCTCGCTTCAACTCCTTAATGGTCTTGCTCT

CTCCCCCAGAGCCCCGATACTCAGATGACTTGATATCTCAACTATGCCAGCTGTA

CATTGCTGGGGATCAAGTCTTGTCTATGTGTGGAAACTCCGGCTATGAAGTCATC

AAAATATTGGAGCCATATGTCGTGAATAGTTTAGTCCAGAGAGCAGAAAAGTTT

AGGCCTCTCATTCATTCCTTGGGAGACTTTCCTGTATTTATAAAAGACAAGGTAA

GTCAACTTGAAGAGACGTTCGGTCCCTGTGCAAGAAGGTTCTTTAGGGCTCTGGA
```

-continued

```
TCAATTCGACAACATACATGACTTGGTTTTTGTGTTTGGCTGTTACAGGCATTGG

GGGCACCCATATATAGATTATCGAAAGGGTCTGTCAAAACTATATGATCAGGTTC

ACCTTAAAAAAATGATAGATAAGTCCTACCAGGAGTGCTTAGCAAGCGACCTAG

CCAGGAGGATCCTTAGATGGGGTTTTGATAAGTACTCCAAGTGGTATCTGGATTC

AAGATTCCTAGCCCGAGACCACCCCTTGACTCCTTATATCAAAACCCAAACATGG

CCACCCAAACATATTGTAGACTTGGTGGGGGATACATGGCACAAGCTCCCGATC

ACGCAGATCTTTGAGATTCCTGAATCAATGGATCCGTCAGAAATATTGGATGACA

AATCACATTCTTTCACCAGAACGAGACTAGCTTCTTGGCTGTCAGAAAACCGAGG

GGGGCCTGTTCCTAGCGAAAAAGTTATTATCACGGCCCTGTCTAAGCCGCCTGTC

AATCCCCGAGAGTTTCTGAGGTCTATAGACCTCGGAGGATTGCCAGATGAAGAC

TTGATAATTGGCCTCAAGCCAAAGGAACGGGAATTGAAGATTGAAGGTCGATTC

TTTGCTCTAATGTCATGGAATCTAAGATTGTATTTTGTCATCACTGAAAAACTCTT

GGCCAACTACATCTTGCCACTTTTTGACGCGCTGACTATGACAGACAACCTGAAC

AAGGTGTTTAAAAAGCTGATCGACAGGGTCACCGGGCAAGGGCTTTTGGACTAT

TCAAGGGTCACATATGCATTTCACCTGGACTATGAAAAGTGGAACAACCATCAA

AGATTAGAGTCAACAGAGGATGTATTTTCTGTCCTAGATCAAGTGTTTGGATTGA

AGAGAGTGTTTTCTAGAACACACGAGTTTTTTCAAAAGGCCTGGATCTATTATTC

AGACAGATCAGACCTCATCGGGTTACGGGAGGATCAAATATACTGCTTAGATGC

GTCCAACGGCCCAACCTGTTGGAATGGCCAGGATGGCGGGCTAGAAGGCTTACG

GCAGAAGGGCTGGAGTCTAGTCAGCTTATTGATGATAGATAGAGAATCTCAAAT

CAGGAACACAAGAACCAAAATACTAGCTCAAGGAGACAACCAGGTTTTATGTCC

GACATACATGTTGTCGCCAGGGCTATCTCAAGAGGGGCTCCTCTATGAATTGGAG

AGAATATCAAGGAATGCACTTTCGATATACAGAGCCGTCGAGGAAGGGGCATCT

AAGCTAGGGCTGATCATCAAGAAAGAAGAGACCATGTGTAGTTATGACTTCCTC

ATCTATGGAAAAACCCCTTTGTTTAGAGGTAACATATTGGTGCCTGAGTCCAAAA

GATGGGCCAGAGTCTCTTGCGTCTCTAATGACCAAATAGTCAACCTCGCCAATAT

AATGTCGACAGTGTCCACCAATGCGCTAACAGTGGCACAACACTCTCAATCTTTG

ATCAAACCGATGAGGGATTTTCTGCTCATGTCAGTACAGGCAGTCTTTCACTACC

TGCTATTTAGCCCAATCTTAAAGGGAAGAGTTTACAAGATTCTGAGCGCTGAAG

GGGAGAGCTTTCTCCTAGCCATGTCAAGGATAATCTATCTAGATCCTTCTTTGGG

AGGGATATCTGGAATGTCCCTCGGAAGATTCCATATACGACAGTTCTCAGACCCT

GTCTCTGAAGGGTTATCCTTCTGGAGAGAGATCTGGTTAAGCTCCCAAGAGTCCT

GGATTCACGCGTTGTGTCAAGAGGCTGGAAACCCAGATCTTGGAGAGAGAACAC

TCGAGAGCTTCACTCGCCTTCTAGAAGATCCGACCACCTTAAATATCAGAGGAG

GGGCCAGTCCTACCATTCTACTCAAGGATGCAATCAGAAAGGCTTTATATGACG

AGGTGGACAAGGTGGAAAATTCAGAGTTTCGAGAGGCAATCCTGTTGTCCAAGA

CCCATAGAGATAATTTTATACTCTTCTTAATATCTGTTGAGCCTCTGTTTCCTCGA

TTTCTCAGTGAGCTATTCAGTTCGTCTTTTTTGGGAATCCCCGAGTCAATCATTGG

ATTGATACAAAACTCCCGAACGATAAGAAGGCAGTTTAGAAAGAGTCTCTCAAA

AACTTTAGAAGAATCCTTCTACAACTCAGAGATCCACGGGATTAGTCGGATGAC
```

-continued

```
CCAGACACCTCAGAGGGTTGGGGGGGTGTGGCCTTGCTCTTCAGAGAGGGCAGA

TCTACTTAGGGAGATCTCTTGGGGAAGAAAAGTGGTAGGCACGACAGTTCCTCA

CCCTTCTGAGATGTTGGGATTACTTCCCAAGTCCTCTATTTCTTGCACTTGTGGAG

CAACAGGAGGAGGCAATCCTAGAGTTTCTGTATCAGTACTCCCGTCCTTTGATCA

GTCATTTTTTTCACGAGGCCCCCTAAAGGGATACTTGGGCTCGTCCACCTCTATG

TCGACCCAGCTATTCCATGCATGGGAAAAAGTCACTAATGTTCATGTGGTGAAG

AGAGCTCTATCGTTAAAAGAATCTATAAACTGGTTCATTACTAGAGATTCCAACT

TGGCTCAAGCTCTAATTAGGAACATTATGTCTCTGACAGGCCCTGATTTCCCTCT

AGAGGAGGCCCCTGTCTTCAAAAGGACGGGGTCAGCCTTGCATAGGTTCAAGTC

TGCCAGATACAGCGAAGGAGGGTATTCTTCTGTCTGCCCGAACCTCCTCTCTCAT

ATTTCTGTTAGTACAGACACCATGTCTGATTTGACCCAAGACGGGAAGAACTACG

ATTTCATGTTCCAGCCATTGATGCTTTATGCACAGACATGGACATCAGAGCTGGT

ACAGAGAGACACAAGGCTAAGAGACTCTACGTTTCATTGGCACCTCCGATGCAA

CAGGTGTGTGAGACCCATTGACGACGTGACCCTGGAGACCTCTCAGATCTTCGA

GTTTCCGGATGTGTCGAAAAGAATATCCAGAATGGTTTCTGGGGCTGTGCCTCAC

TTCCAGAGGCTTCCCGATATCCGTCTGAGACCAGGAGATTTTGAATCTCTAAGCG

GTAGAGAAAAGTCTCACCTATCGGATCAGCTCAGGGGCTCTTATACTCAATCTT

AGTGGCAATTCACGACTCAGGATACAATGATGGAACCATCTTCCCTGTCAACATA

TACGGCAAGGTTTCCCCTAGAGACTATTTGAGAGGGCTCGCAAGGGGAGTATTG

ATAGGATCCTCGATTTGCTTCTTGACAAGAATGACAAATATCAATATTAATAGAC

CTCTTGAATTGGTCTCAGGGGTAATCTCATATATTCTCCTGAGGCTAGATAACCA

TCCCTCCTTGTACATAATGCTCAGAGAACCGTCTCTTAGAGGAGAGATATTTTCT

ATCCCTCAGAAAATCCCCGCCGCTTATCCAACCACTATGAAAGAAGGCAACAGA

TCAATCTTGTGTTATCTCCAACATGTGCTACGCTATGAGCGAGAGATAATCACGG

CGTCTCCAGAGAATGACTGGCTATGGATCTTTTCAGACTTTAGAAGTGCCAAAAT

GACGTACCTATCCCTCATTACTTACCAGTCTCATCTTCTACTCCAGAGGGTTGAG

AGAAACCTATCTAAGAGTATGAGAGATAACCTGCGACAATTGAGTTCTTTGATG

AGGCAGGTGCTGGGCGGGCACGGAGAAGATACCTTAGAGTCAGACGACAACATT

CAACGACTGCTAAAAGACTCTTTACGAAGGACAAGATGGGTGGATCAAGAGGTG

CGCCATGCAGCTAGAACCATGACTGGAGATTACAGCCCCAACAAGAAGGTGTCC

CGTAAGGTAGGATGTTCAGAATGGGTCTGCTCTGCTCAACAGGTTGCAGTCTCTA

CCTCAGCAAACCCGGCCCCTGTCTCGGAGCTTGACATAAGGGCCCTCTCTAAGA

GGTTCCAGAACCCTTTGATCTCGGGCTTGAGAGTGGTTCAGTGGGCAACCGGTGC

TCATTATAAGCTTAAGCCTATTCTAGATGATCTCAATGTTTTCCCATCTCTCTGCC

TTGTAGTTGGGGACGGGTCAGGGGGGATATCAAGGGCAGTCCTCAACATGTTTC

CAGATGCCAAGCTTGTGTTCAACAGTCTTTTAGAGGTGAATGACCTGATGGCTTC

CGGAACACATCCACTGCCTCCTTCAGCAATCATGAGGGGAGGAAATGATATCGT

CTCCAGAGTGATAGATCTTGACTCAATCTGGGAAAAACCGTCCGACTTGAGAAA

CTTGGCAACCTGGAAATACTTCCAGTCAGTCCAAAAGCAGGTCAACATGTCCTAT

GACCTCATTATTTGCGATGCAGAAGTTACTGACATTGCATCTATCAACCGGATCA

CCCTGTTAATGTCCGATTTTGCATTGTCTATAGATGGACCACTCTATTTGGTCTTC
```

```
AAAACTTATGGGACTATGCTAGTAAATCCAAACTACAAGGCTATTCAACACCTGT

CAAGAGCGTTCCCCTCGGTCACAGGGTTTATCACCCAAGTAACTTCGTCTTTTTC

ATCTGAGCTCTACCTCCGATTCTCCAAACGAGGGAAGTTTTTCAGAGATGCTGAG

TACTTGACCTCTTCCACCCTTCGAGAAATGAGCCTTGTGTTATTCAATTGTAGCA

GCCCCAAGAGTGAGATGCAGAGAGCTCGTTCCTTGAACTATCAGGATCTTGTGA

GAGGATTTCCTGAAGAAATCATATCAAATCCTTACAATGAGATGATCATAACTCT

GATTGACAGTGATGTAGAATCTTTTCTAGTCCACAAGATGGTTGATGATCTTGAG

TTACAGAGGGGAACTCTGTCTAAAGTGGCTATCATTATAGCCATCATGATAGTTT

TCTCCAACAGAGTCTTCAACGTTTCCAAACCCCTAACTGACCCCTCGTTCTATCC

ACCGTCTGATCCCAAAATCCTGAGGCACTTCAACATATGTTGCAGTACTATGATG

TATCTATCTACTGCTTTAGGTGACGTCCCTAGCTTCGCAAGACTTCACGACCTGT

ATAACAGACCTATAACTTATTACTTCAGAAAGCAAGTCATTCGAGGGAACGTTTA

TCTATCTTGGAGTTGGTCCAACGACACCTCAGTGTTCAAAAGGGTAGCCTGTAAT

TCTAGCCTGAGTCTGTCATCTCACTGGATCAGGTTGATTTACAAGATAGTGAAGA

CTACCAGACTCGTTGGCAGCATCAAGGATCTATCCAGAGAAGTGGAAAGACACC

TTCATAGGTACAACAGGTGGATCACCCTAGAGGATATCAGATCTAGATCATCCCT

ACTAGACTACAGTTGCCTGTGAACCGGATACTCCTGGAAGCCTGCCCATGCTAA

GACTCTTGTGTGATGTATCTTGAAAAAAACAAGATCCTAAATCTGAACCTTTGGT

TGTTTGATTGTTTTTCTCAttttttgttgtttatttgttaagcgt.
```

In one embodiment, the nucleic acid comprises the sequence of SEQ ID NO: 11, shown below (RABV vector: Coravax V3-South Africa (S1-VSVG-E26)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT
```

-continued

```
GTTGGTCACGTGTTCAATCTCATTCACTTTGTAGGATGCTATATGGGTCAAGTCA
GATCCCTAAATGCAACGGTTATTGCTGCATGTGCTCCTCATGAAATGTCTGTTCT
AGGGGGCTATCTGGGAGAGGAATTCTTCGGGAAAGGGACATTTGAAAGAAGATT
CTTCAGAGATGAGAAAGAACTTCAAGAATACGAGGCGGCTGAACTGACAAAGA
CTGACGTAGCACTGGCAGATGATGGAACTGTCAACTCTGACGACGAGGACTACT
TTTCAGGTGAAACCAGAAGTCCGGAGGCTGTTTATACTCGAATCATGATGAATG
GAGGTCGACTAAAGAGATCTCACATACGGAGATATGTCTCAGTCAGTTCCAATC
ATCAAGCCCGTCCAAACTCATTCGCCGAGTTTCTAAACAAGACATATTCGAGTGA
CTCATAAcatgaaaaaaactaaccccctcccGTACGCCACCATGTTCGTGTTTCTGGTGCTGCT
GCCTCTGGTGAGCTCCCAGTGCGTGAACTTCACCACAAGGACCCAGCTGCCCCCT
GCCTATACCAATTCCTTCACACGGGGCGTGTACTATCCCGACAAGGTGTTCCGGA
GCAGCGTGCTGCACTCCACACAGGATCTGTTTCTGCCTTTCTTTTCTAACGTGACC
TGGTTCCACGCCATCCACGTGAGCGGCACCAATGGCACAAAGCGGTTCGCCAAT
CCAGTGCTGCCCTTTAACGATGGCGTGTACTTCGCCTCCACCGAGAAGTCTAACA
TCATCAGAGGCTGGATCTTTGGCACCACACTGGACAGCAAGACACAGTCCCTGC
TGATCGTGAACAATGCCACCAACGTGGTCATCAAGGTGTGCGAGTTCCAGTTTTG
TAATGATCCATTCCTGGGCGTGTACTATCACAAGAACAATAAGTCTTGGATGGAG
AGCGAGTTTCGCGTGTATTCCTCTGCCAACAATTGCACATTTGAGTACGTGTCCC
AGCCCTTCCTGATGGACCTGGAGGGCAAGCAGGGCAATTTCAAGAACCTGAGGG
AGTTCGTGTTTAAGAATATCGATGGCTACTTCAAAATCTACTCCAAGCACACCCC
AATCAACCTGGTGCGCGGCCTGCCACAGGGCTTCTCTGCCCTGGAGCCACTGGTG
GATCTGCCCATCGGCATCAACATCACCCGGTTTCAGACACTGCTGGCCCTGCACA
GAAGCTACCTGACACCAGGCGACAGCTCCTCTGGATGGACCGCAGGAGCAGCAG
CCTACTATGTGGGCTATCTGCAGCCCAGGACCTTCCTGCTGAAGTACAACGAGA
ATGGCACCATCACAGACGCCGTGGATTGCGCCCTGGATCCCCTGTCTGAGACCA
AGTGTACACTGAAGAGCTTTACCGTGGAGAAGGGCATCTATCAGACAAGCAATT
TCAGGGTGCAGCCTACCGAGTCCATCGTGCGCTTTCCCAATATCACAAACCTGTG
CCCTTTTGGCGAGGTGTTCAACGCAACCCGCTTCGCCAGCGTGTACGCCTGGAAT
AGGAAGCGCATCTCCAACTGCGTGGCCGACTATTCTGTGCTGTACAACAGCGCCT
CCTTCTCTACCTTTAAGTGCTATGGCGTGAGCCCCACAAAGCTGAATGACCTGTG
CTTTACCAACGTGTACGCCGATTCCTTCGTGATCAGGGGCGACGAGGTGCGCCA
GATCGCACCAGGACAGACAGGCAATATCGCAGACTACAATTATAAGCTGCCTGA
CGATTTCACCGGCTGCGTGATCGCCTGGAACTCTAACAATCTGGATAGCAAAGTG
GGCGGCAACTACAATTATCTGTACCGGCTGTTTAGAAAGTCTAATCTGAAGCCAT
TCGAGAGGGACATCTCCACAGAAATCTACCAGGCCGGCTCTACCCCCTGCAATG
GCGTGAAGGGCTTTAACTGTTATTTCCCTCTGCAGAGCTACGGCTTCCAGCCAAC
ATATGGCGTGGGCTATCAGCCCTACCGCGTGGTGGTGCTGTCTTTTGAGCTGCTG
CACGCACCTGCAACAGTGTGCGGACCAAAGAAGAGCACCAATCTGGTGAAGAA
CAAGTGCGTGAACTTCAACTTCAACGGACTGACCGGAACAGGCGTGCTGACCGA
GTCCAACAAGAAGTTCCTGCCTTTTCAGCAGTTCGGCAGGGACATCGCAGATAC
```

-continued

```
CACAGACGCCGTGCGCGACCCTCAGACCCTGGAGATCCTGGACATCACACCATG

CTCCTTCGGCGGCGTGTCTGTGATCACACCAGGCACCAATACAAGCAACCAGGT

GGCCGTGCTGTATCAGGGCGTGAATTGTACCGAGGTGCCAGTGGCAATCCACGC

AGATCAGCTGACCCCTACATGGCGGGTGTACTCTACCGGCAGCAACGTGTTCCA

GACAAGAGCCGGATGCCTGATCGGAGCAGAGCACGTGAACAATAGCTATGAGTG

CGACATCCCTATCGGCGCCGGCATCTGTGCCTCCTACCAGACCCAGACAAACTCC

CCAAGGTCTGTGGGCGATACAGGCCTGTCCAAGAATCCAATCGAGCTGGTAGAG

GGCTGGTTCAGCAGTTGGAAAAGCTCCATCGCCTCCTTTTTCTTTATCATCGGCCT

GATCATCGGACTGTTCCTGGTGCTCCGCGTGGGTATCCACCTGTGCATCAAGCTG

AAGCACACCAAGAAAAGACAGATTTATACAGACATCGAGATGAACCGCCTGGG

AAAGTGAGCTAGCCATGAAAAAAACTAACACCCCTCCTTTCGAACCATCCCAAA

CATGAGCAAGATCTTTGTCAATCCTAGTGCTATTAGAGCCGGTCTGGCCGATCTT

GAGATGGCTGAAGAAACTGTTGATCTGATCAATAGAAATATCGAAGACAATCAG

GCTCATCTCCAAGGGGAACCCATAGAGGTGGACAATCTCCCTGAGGATATGGGG

CGACTTCACCTGGATGATGGAAAATCGCCCAACCATGGTGAGATAGCCAAGGTG

GGAGAAGGCAAGTATCGAGAGGACTTTCAGATGGATGAAGGAGAGGATCCTAG

CTTCCTGTTCCAGTCATACCTGGAAAATGTTGGAGTCCAAATAGTCAGACAAATG

AGGTCAGGAGAGAGATTTCTCAAGATATGGTCACAGACCGTAGAAGAGATTATA

TCCTATGTCGCGGTCAACTTTCCCAACCCTCCAGGAAAGTCTTCAGAGGATAAAT

CAACCCAGACTACTGGCCGAGAGCTCAAGAAGGAGACAACACCCACTCCTTCTC

AGAGAGAAAGCCAATCATCGAAAGCCAGGATGGCGGCTCAAATTGCTTCTGGCC

CTCCAGCCCTTGAATGGTCGGCTACCAATGAAGAGGATGATCTATCAGTGGAGG

CTGAGATCGCTCACCAGATTGCAGAAAGTTTCTCCAAAAAATATAAGTTTCCCTC

TCGATCCTCAGGGATACTCTTGTATAATTTTGAGCAATTGAAAATGAACCTTGAT

GATATAGTTAAAGAGGCAAAAAATGTACCAGGTGTGACCCGTTTAGCCCATGAC

GGGTCCAAACTCCCCCTAAGATGTGTACTGGGATGGGTCGCTTTGGCCAACTCTA

AGAAATTCCAGTTGTTAGTCGAATCCGACAAGCTGAGTAAAATCATGCAAGATG

ACTTGAATCGCTATACATCTTGCTAACCGAACCTCTCCCCTCAGTCCCTCTAGAC

AATAAAATCCGAGATGTCCCAAAGTCAACATGAAAAAAACAGGCAACACCACT

GATAAAATGAACCTCCTACGTAAGATAGTGAAAAACCGCAGGGACGAGGACACT

CAAAAATCCTCTCCCGCGTCAGCCCCTCTGGATGACGATGACTTGTGGCTTCCAC

CCCCTGAATACGTCCCGCTGAAAGAACTTACAGGCAAGAAGAACATGAGGAACT

TTTGTATCAACGGAAGGGTTAAAGTGTGTAGCCCGAATGGTTACTCGTTCAGGAT

CCTGCGGCACATTCTGAAATCATTCGACGAGATATATTCTGGGAATCATAGGATG

ATCGGGTTAGTCAAAGTGGTTATTGGACTGGCTTTGTCAGGATCTCCAGTCCCTG

AGGGCCTGAACTGGGTATACAAATTGAGGAGAACCTTTATCTTCCAGTGGGCTG

ATTCCAGGGGCCCTCTTGAAGGGGAGGAGTTGGAATACTCTCAGGAGATCACTT

GGGATGATGATACTGAGTTCGTCGGATTGCAAATAAGAGTGATTGCAAAACAGT

GTCATATCCAGGGCAGAGTCTGGTGTATCAACATGAACCCGAGAGCATGTCAAC

TATGGTCTGACATGTCTCTTCAGACACAAAGGTCCGAAGAGGACAAAGATTCCT

CTCTGCTTCTAGAATAATCAGATTATATCCCGCAAATTTATCACTTGTTTACCTCT
```

-continued

```
GGAGGAGAGAACATATGGGCTCAACTCCAACCCTTGGGAGCAATATAACAAAAA
ACATGTTATGGTGCCATTAAACCGCTGCATTTCATCAAAGTCAAGTTGATTACCT
TTACATTTTGATCCTCTTGGATGTGAAAAAAACTATTAACATCCCTCAAAAGACcc
cgggAAAGATGGTTCCTCAGGCTCTCCTGTTTGTACCCCTTCTGGTTTTTCCATTGT
GTTTTGGGAAATTCCCTATTTACACGATACCAGACAAGCTTGGTCCCTGGAGTCC
GATTGACATACATCACCTCAGCTGCCCAAACAATTTGGTAGTGGAGGACGAAGG
ATGCACCAACCTGTCAGGGTTCTCCTACATGGAACTTAAAGTTGGATACATCTTA
GCCATAAAAGTGAACGGGTTCACTTGCACAGGCGTTGTGACGGAGGCTGAAACC
TACACTAACTTCGTTGGTTATGTCACAACCACGTTCAAAAGAAAGCATTTCCGCC
CAACACCAGATGCATGTAGAGCCGCGTACAACTGGAAGATGGCCGGTGACCCCA
GATATGAAGAGTCTCTACACAATCCGTACCCTGACTACCGCTGGCTTCGAACTGT
AAAAACCACCAAGGAGTCTCTCGTTATCATATCTCCAAGTGTGGCAGATTTGGAC
CCATATGACAGATCCCTTCACTCGAGGGTCTTCCCTAGCGGGAAGTGCTCAGGA
GTAGCGGTGTCTTCTACCTACTGCTCCACTAACCACGATTACACCATTTGGATGC
CCGAGAATCCGAGACTAGGGATGTCTTGTGACATTTTTACCAATAGTAGAGGGA
AGAGAGCATCCAAAGGGAGTGAGACTTGCGGCTTTGTAGATGAAAGAGGCCTAT
ATAAGTCTTTAAAAGGAGCATGCAAACTCAAGTTATGTGGAGTTCTAGGACTTA
GACTTATGGATGGAACATGGGTCTCGATGCAAACATCAAATGAAACCAAATGGT
GCCCTCCCGATAAGTTGGTGAACCTGCACGACTTTCGCTCAGACGAAATTGAGC
ACCTTGTTGTAGAGGAGTTGGTCAGGAAGAGAGAGGAGTGTCTGGATGCACTAG
AGTCCATCATGACAACCAAGTCAGTGAGTTTCAGACGTCTCAGTCATTTAAGAAA
ACTTGTCCCTGGGTTTGGAAAAGCATATACCATATTCAACAAGACCTTGATGGAA
GCCGATGCTCACTACAAGTCAGTCgagACTTGGAATGAGATCCTCCCTTCAAAAG
GGTGTTTAAGAGTTGGGGGGAGGTGTCATCCTCATGTGAACGGGGTGTTTTTCAA
TGGTATAATATTAGGACCTGACGGCAATGTCTTAATCCCAGAGATGCAATCATCC
CTCCTCCAGCAACATATGGAGTTGTTGGAATCCTCGGTTATCCCCCTTGTGCACC
CCCTGGCAGACCCGTCTACCGTTTTCAAGGACGGTGACGAGGCTGAGGATTTTGT
TGAAGTTCACCTTCCCGATGTGCACAATCAGGTCTCAGGAGTTGACTTGGGTCTC
CCGAACTGGGGGAAGTATGTATTACTGAGTGCAGGGGCCCTGACTGCCTTGATG
TTGATAATTTTCCTGATGACATGTTGTAGAAGAGTCAATCGATCAGAACCTACGC
AACACAATCTCAGAGGGACAGGGAGGGAGGTGTCAGTCACTCCCCAAAGCGGG
AAGATCATATCTTCATGGGAATCACACAAGAGTGGGGGTGAGACCAGACTGTAA
ttaattaaCGTCCTTTCAACGATCCAAGTCcat-
gaaaaaaactaacaccccctcccgtacctagcTTATAAA
GTGCTGGGTCATCTAAGCTTTTCAGTCGAGAAAAAAACATTAGATCAGAAGAAC
AACTGGCAACACTTCTCAACCTGAGACTTACTTCAAGATGCTCGATCCTGGAGAG
GTCTATGATGACCCTATTGACCCAATCGAGTTAGAGGCTGAACCCAGAGGAACC
CCCATTGTCCCCAACATCTTGAGGAACTCTGACTACAATCTCAACTCTCCTTTGA
TAGAAGATCCTGCTAGACTAATGTTAGAATGGTTAAAAACAGGGAATAGACCTT
ATCGGATGACTCTAACAGACAATTGCTCCAGGTCTTTCAGAGTTTTGAAAGATTA
TTTCAAGAAGGTAGATTTGGGTTCTCTCAAGGTGGGCGGAATGGCTGCACAGTC
```

-continued

```
AATGATTTCTCTCTGGTTATATGGTGCCCACTCTGAATCCAACAGGAGCCGGAGA

TGTATAACAGACTTGGCCCATTTCTATTCCAAGTCGTCCCCCATAGAGAAGCTGT

TGAATCTCACGCTAGGAAATAGAGGGCTGAGAATCCCCCAGAGGGAGTGTTAA

GTTGCCTTGAGAGGGTTGATTATGATAATGCATTTGGAAGGTATCTTGCCAACAC

GTATTCCTCTTACTTGTTCTTCCATGTAATCACCTTATACATGAACGCCCTAGACT

GGGATGAAGAAAAGACCATCCTAGCATTATGGAAAGATTTAACCTCAGTGGACA

TCGGGAAGGACTTGGTAAAGTTCAAAGACCAAATATGGGGACTGCTGATCGTGA

CAAAGGACTTTGTTTACTCCCAAAGTTCCAATTGTCTTTTTGACAGAAACTACAC

ACTTATGCTAAAAGATCTTTTCTTGTCTCGCTTCAACTCCTTAATGGTCTTGCTCT

CTCCCCCAGAGCCCCGATACTCAGATGACTTGATATCTCAACTATGCCAGCTGTA

CATTGCTGGGGATCAAGTCTTGTCTATGTGTGGAAACTCCGGCTATGAAGTCATC

AAAATATTGGAGCCATATGTCGTGAATAGTTTAGTCCAGAGAGCAGAAAAGTTT

AGGCCTCTCATTCATTCCTTGGGAGACTTTCCTGTATTTATAAAAGACAAGGTAA

GTCAACTTGAAGAGACGTTCGGTCCCTGTGCAAGAAGGTTCTTTAGGGCTCTGGA

TCAATTCGACAACATACATGACTTGGTTTTTGTGTTTGGCTGTTACAGGCATTGG

GGGCACCCATATATAGATTATCGAAAGGGTCTGTCAAAACTATATGATCAGGTTC

ACCTTAAAAAAATGATAGATAAGTCCTACCAGGAGTGCTTAGCAAGCGACCTAG

CCAGGAGGATCCTTAGATGGGGTTTTGATAAGTACTCCAAGTGGTATCTGGATTC

AAGATTCCTAGCCCGAGACCACCCCTTGACTCCTTATATCAAAACCCAAACATGG

CCACCCAAACATATTGTAGACTTGGTGGGGATACATGGCACAAGCTCCCGATC

ACGCAGATCTTTGAGATTCCTGAATCAATGGATCCGTCAGAAATATTGGATGACA

AATCACATTCTTTCACCAGAACGAGACTAGCTTCTTGGCTGTCAGAAAACCGAGG

GGGGCCTGTTCCTAGCGAAAAAGTTATTATCACGGCCCTGTCTAAGCCGCCTGTC

AATCCCCGAGAGTTTCTGAGGTCTATAGACCTCGGAGGATTGCCAGATGAAGAC

TTGATAATTGGCCTCAAGCCAAAGGAACGGGAATTGAAGATTGAAGGTCGATTC

TTTGCTCTAATGTCATGGAATCTAAGATTGTATTTTGTCATCACTGAAAAACTCTT

GGCCAACTACATCTTGCCACTTTTTGACGCGCTGACTATGACAGACAACCTGAAC

AAGGTGTTTAAAAAGCTGATCGACAGGGTCACCGGGCAAGGGCTTTTGGACTAT

TCAAGGGTCACATATGCATTTCACCTGGACTATGAAAAGTGGAACAACCATCAA

AGATTAGAGTCAACAGAGGATGTATTTTCTGTCCTAGATCAAGTGTTTGGATTGA

AGAGAGTGTTTTCTAGAACACACGAGTTTTTTCAAAAGGCCTGGATCTATTATTC

AGACAGATCAGACCTCATCGGGTTACGGGAGGATCAAATATACTGCTTAGATGC

GTCCAACGGCCCAACCTGTTGGAATGGCCAGGATGGCGGGCTAGAAGGCTTACG

GCAGAAGGGCTGGAGTCTAGTCAGCTTATTGATGATAGATAGAGAATCTCAAAT

CAGGAACACAAGAACCAAAATACTAGCTCAAGGAGACAACCAGGTTTTATGTCC

GACATACATGTTGTCGCCAGGGCTATCTCAAGAGGGGCTCCTCTATGAATTGGAG

AGAATATCAAGGAATGCACTTTCGATATACAGAGCCGTCGAGGAAGGGGCATCT

AAGCTAGGGCTGATCATCAAGAAGAAGAGACCATGTGTAGTTATGACTTCCTC

ATCTATGGAAAAACCCCTTTGTTTAGAGGTAACATATTGGTGCCTGAGTCCAAAA

GATGGGCCAGAGTCTCTTGCGTCTCTAATGACCAAATAGTCAACCTCGCCAATAT
```

-continued
```
AATGTCGACAGTGTCCACCAATGCGCTAACAGTGGCACAACACTCTCAATCTTTG

ATCAAACCGATGAGGGATTTTCTGCTCATGTCAGTACAGGCAGTCTTTCACTACC

TGCTATTTAGCCCAATCTTAAAGGGAAGAGTTTACAAGATTCTGAGCGCTGAAG

GGGAGAGCTTTCTCCTAGCCATGTCAAGGATAATCTATCTAGATCCTTCTTTGGG

AGGGATATCTGGAATGTCCCTCGGAAGATTCCATATACGACAGTTCTCAGACCCT

GTCTCTGAAGGGTTATCCTTCTGGAGAGATCTGGTTAAGCTCCCAAGAGTCCT

GGATTCACGCGTTGTGTCAAGAGGCTGGAAACCCAGATCTTGGAGAGAGAACAC

TCGAGAGCTTCACTCGCCTTCTAGAAGATCCGACCACCTTAAATATCAGAGGAG

GGGCCAGTCCTACCATTCTACTCAAGGATGCAATCAGAAAGGCTTTATATGACG

AGGTGGACAAGGTGGAAAATTCAGAGTTTCGAGAGGCAATCCTGTTGTCCAAGA

CCCATAGAGATAATTTTATACTCTTCTTAATATCTGTTGAGCCTCTGTTTCCTCGA

TTTCTCAGTGAGCTATTCAGTTCGTCTTTTTTGGGAATCCCCGAGTCAATCATTGG

ATTGATACAAAACTCCCGAACGATAAGAAGGCAGTTTAGAAAGAGTCTCTCAAA

AACTTTAGAAGAATCCTTCTACAACTCAGAGATCCACGGGATTAGTCGGATGAC

CCAGACACCTCAGAGGGTTGGGGGGGTGTGGCCTTGCTCTTCAGAGAGGGCAGA

TCTACTTAGGGAGATCTCTTGGGGAAGAAAAGTGGTAGGCACGACAGTTCCTCA

CCCTTCTGAGATGTTGGGATTACTTCCCAAGTCCTCTATTTCTTGCACTTGTGGAG

CAACAGGAGGAGGCAATCCTAGAGTTTCTGTATCAGTACTCCCGTCCTTTGATCA

GTCATTTTTTTCACGAGGCCCCCTAAAGGGATACTTGGGCTCGTCCACCTCTATG

TCGACCCAGCTATTCCATGCATGGGAAAAAGTCACTAATGTTCATGTGGTGAAG

AGAGCTCTATCGTTAAAAGAATCTATAAACTGGTTCATTACTAGAGATTCCAACT

TGGCTCAAGCTCTAATTAGGAACATTATGTCTCTGACAGGCCCTGATTTCCCTCT

AGAGGAGGCCCCTGTCTTCAAAAGGACGGGGTCAGCCTTGCATAGGTTCAAGTC

TGCCAGATACAGCGAAGGAGGGTATTCTTCTGTCTGCCCGAACCTCCTCTCTCAT

ATTTCTGTTAGTACAGACACCATGTCTGATTTGACCCAAGACGGGAAGAACTACG

ATTTCATGTTCCAGCCATTGATGCTTTATGCACAGACATGGACATCAGAGCTGGT

ACAGAGAGACACAAGGCTAAGAGACTCTACGTTTCATTGGCACCTCCGATGCAA

CAGGTGTGTGAGACCCATTGACGACGTGACCCTGGAGACCTCTCAGATCTTCGA

GTTTCCGGATGTGTCGAAAAGAATATCCAGAATGGTTTCTGGGGCTGTGCCTCAC

TTCCAGAGGCTTCCCGATATCCGTCTGAGACCAGGAGATTTTGAATCTCTAAGCG

GTAGAGAAAAGTCTCACCATATCGGATCAGCTCAGGGGCTCTTATACTCAATCTT

AGTGGCAATTCACGACTCAGGATACAATGATGGAACCATCTTCCCTGTCAACATA

TACGGCAAGGTTTCCCCTAGAGACTATTTGAGAGGGCTCGCAAGGGGAGTATTG

ATAGGATCCTCGATTTGCTTCTTGACAAGAATGACAAATATCAATATTAATAGAC

CTCTTGAATTGGTCTCAGGGGTAATCTCATATATTCTCCTGAGGCTAGATAACCA

TCCCTCCTTGTACATAATGCTCAGAGAACCGTCTCTTAGAGGAGAGATATTTTCT

ATCCCTCAGAAAATCCCCGCCGCTTATCCAACCACTATGAAAGAAGGCAACAGA

TCAATCTTGTGTTATCTCCAACATGTGCTACGCTATGAGCGAGAGATAATCACGG

CGTCTCCAGAGAATGACTGGCTATGGATCTTTTCAGACTTTAGAAGTGCCAAAAT

GACGTACCTATCCCTCATTACTTACCAGTCTCATCTTCTACTCCAGAGGGTTGAG

AGAAACCTATCTAAGAGTATGAGAGATAACCTGCGACAATTGAGTTCTTTGATG
```

```
AGGCAGGTGCTGGGCGGGCACGGAGAAGATACCTTAGAGTCAGACGACAACATT

CAACGACTGCTAAAAGACTCTTTACGAAGGACAAGATGGGTGGATCAAGAGGTG

CGCCATGCAGCTAGAACCATGACTGGAGATTACAGCCCCAACAAGAAGGTGTCC

CGTAAGGTAGGATGTTCAGAATGGGTCTGCTCTGCTCAACAGGTTGCAGTCTCTA

CCTCAGCAAACCCGGCCCCTGTCTCGGAGCTTGACATAAGGGCCCTCTCTAAGA

GGTTCCAGAACCCTTTGATCTCGGGCTTGAGAGTGGTTCAGTGGGCAACCGGTGC

TCATTATAAGCTTAAGCCTATTCTAGATGATCTCAATGTTTTCCCATCTCTCTGCC

TTGTAGTTGGGGACGGGTCAGGGGGGATATCAAGGGCAGTCCTCAACATGTTTC

CAGATGCCAAGCTTGTGTTCAACAGTCTTTTAGAGGTGAATGACCTGATGGCTTC

CGGAACACATCCACTGCCTCCTTCAGCAATCATGAGGGGAGGAAATGATATCGT

CTCCAGAGTGATAGATCTTGACTCAATCTGGGAAAAACCGTCCGACTTGAGAAA

CTTGGCAACCTGGAAATACTTCCAGTCAGTCCAAAAGCAGGTCAACATGTCCTAT

GACCTCATTATTTGCGATGCAGAAGTTACTGACATTGCATCTATCAACCGGATCA

CCCTGTTAATGTCCGATTTTGCATTGTCTATAGATGGACCACTCTATTTGGTCTTC

AAAACTTATGGGACTATGCTAGTAAATCCAAACTACAAGGCTATTCAACACCTGT

CAAGAGCGTTCCCCTCGGTCACAGGGTTTATCACCCAAGTAACTTCGTCTTTTTC

ATCTGAGCTCTACCTCCGATTCTCCAAACGAGGGAAGTTTTTCAGAGATGCTGAG

TACTTGACCTCTTCCACCCTTCGAGAAATGAGCCTTGTGTTATTCAATTGTAGCA

GCCCCAAGAGTGAGATGCAGAGAGCTCGTTCCTTGAACTATCAGGATCTTGTGA

GAGGATTTCCTGAAGAAATCATATCAAATCCTTACAATGAGATGATCATAACTCT

GATTGACAGTGATGTAGAATCTTTTCTAGTCCACAAGATGGTTGATGATCTTGAG

TTACAGAGGGGAACTCTGTCTAAAGTGGCTATCATTATAGCCATCATGATAGTTT

TCTCCAACAGAGTCTTCAACGTTTCCAAACCCCTAACTGACCCCTCGTTCTATCC

ACCGTCTGATCCCAAAATCCTGAGGCACTTCAACATATGTTGCAGTACTATGATG

TATCTATCTACTGCTTTAGGTGACGTCCCTAGCTTCGCAAGACTTCACGACCTGT

ATAACAGACCTATAACTTATTACTTCAGAAAGCAAGTCATTCGAGGGAACGTTTA

TCTATCTTGGAGTTGGTCCAACGACACCTCAGTGTTCAAAAGGGTAGCCTGTAAT

TCTAGCCTGAGTCTGTCATCTCACTGGATCAGGTTGATTTACAAGATAGTGAAGA

CTACCAGACTCGTTGGCAGCATCAAGGATCTATCCAGAGAAGTGGAAAGACACC

TTCATAGGTACAACAGGTGGATCACCCTAGAGGATATCAGATCTAGATCATCCCT

ACTAGACTACAGTTGCCTGTGAACCGGATACTCCTGGAAGCCTGCCCATGCTAA

GACTCTTGTGTGATGTATCTTGAAAAAAACAAGATCCTAAATCTGAACCTTTGGT

TGTTTGATTGTTTTTCTCAttttttgttgtttatttgttaagcgt.
```
                                                    55

In one embodiment, the nucleic acid comprises the sequence of SEQ ID NO: 12, shown below (RABV vector: Coravax V4-China (S1-RABVG-T2A-P)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA
```

-continued

```
AATAAAGCATACAAGTCAGTTTTGTCAGGCATGAGCGCCGCCAAACTTAATCCT
GACGATGTATGTTCCTATTTGGCAGCGGCAATGCAGTTTTTTGAGGGGACATGTC
CGGAAGACTGGACCAGCTATGGAATTGTGATTGCACGAAAAGGAGATAAGATCA
CCCCAGGTTCTCTGGTGGAGATAAAACGTACTGATGTAGAAGGGAATTGGGCTC
TGACAGGAGGCATGGAACTGACAAGAGACCCCACTGTCCCTGAGCATGCGTCCT
TAGTCGGTCTTCTCTTGAGTCTGTATAGGTTGAGCAAATATCCGGGCAAAACAC
TGGTAACTATAAGACAAACATTGCAGACAGGATAGAGCAGATTTTTGAGACAGC
CCCTTTTGTTAAAATCGTGGAACACCATACTCTAATGACAACTCACAAaATGTGT
GCTAATTGGAGTACTATACCAAACTTCAGATTTTTGGCCGGAACCTATGACATGT
TTTTCTCCCGGATTGAGCATCTATATTCAGCAATCAGAGTGGGCACAGTTGTCAC
TGCTTATGAAGACTGTTCAGGACTGGTATCATTTACTGGGTTCATAAAACAAATC
AATCTCACCGCTAGAGAGGCAATACTATATTTCTTCCACAAGAACTTTGAGGAAG
AGATAAGAAGAATGTTTGAGCCAGGGCAGGAGACAGCTGTTCCTCACTCTTATTT
CATCCACTTCCGTTCACTAGGCTTGAGTGGGAAATCTCCTTATTCATCAAATGCT
GTTGGTCACGTGTTCAATCTCATTCACTTTGTAGGATGCTATATGGGTCAAGTCA
GATCCCTAAATGCAACGGTTATTGCTGCATGTGCTCCTCATGAAATGTCTGTTCT
AGGGGGCTATCTGGGAGAGGAATTCTTCGGGAAAGGGACATTTGAAAGAAGATT
CTTCAGAGATGAGAAAGAACTTCAAGAATACGAGGCGGCTGAACTGACAAAGA
CTGACGTAGCACTGGCAGATGATGGAACTGTCAACTCTGACGACGAGGACTACT
TTTCAGGTGAAACCAGAAGTCCGGAGGCTGTTTATACTCGAATCATGATGAATG
GAGGTCGACTAAAGAGATCTCACATACGGAGATATGTCTCAGTCAGTTCCAATC
ATCAAGCCCGTCCAAACTCATTCGCCGAGTTTCTAAACAAGACATATTCGAGTGA
CTCATAAcatgaaaaaaactaacaccccctcccgtacgGCCACCATGTTCGTGTTTCTGGTGCTGCT
GCCTCTGGTGAGCTCCCAGTGCGTGAACCTGACCACAAGGACCCAGCTGCCCCC
TGCCTATACCAATTCCTTCACACGGGGCGTGTACTATCCCGACAAGGTGTTCCGG
AGCAGCGTGCTGCACTCCACACAGGATCTGTTTCTGCCTTTCTTTTCTAACGTGAC
CTGGTTCCACGCCATCCACGTGAGCGGCACCAATGGCACAAAGCGGTTCGACAA
TCCAGTGCTGCCCTTTAACGATGGCGTGTACTTCGCCTCCACCGAGAAGTCTAAC
ATCATCAGAGGCTGGATCTTTGGCACCACACTGGACAGCAAGACACAGTCCCTG
CTGATCGTGAACAATGCCACCAACGTGGTCATCAAGGTGTGCGAGTTCCAGTTTT
GTAATGATCCATTCCTGGGCGTGTACTATCACAAGAACAATAAGTCTTGGATGGA
GAGCGAGTTTCGCGTGTATTCCTCTGCCAACAATTGCACATTTGAGTACGTGTCC
CAGCCCTTCCTGATGGACCTGGAGGGCAAGCAGGGCAATTTCAAGAACCTGAGG
GAGTTCGTGTTTAAGAATATCGATGGCTACTTCAAAATCTACTCCAAGCACACCC
CAATCAACCTGGTGCGCGACCTGCCACAGGGCTTCTCTGCCCTGGAGCCACTGGT
GGATCTGCCCATCGGCATCAACATCACCCGGTTTCAGACACTGCTGGCCCTGCAC
AGAAGCTACCTGACACCAGGCGACAGCTCCTCTGGATGGACCGCAGGAGCAGCA
GCCTACTATGTGGGCTATCTGCAGCCCAGGACCTTCCTGCTGAAGTACAACGAG
AATGGCACCATCACAGACGCCGTGGATTGCGCCCTGGATCCCCTGTCTGAGACC
AAGTGTACACTGAAGAGCTTTACCGTGGAGAAGGGCATCTATCAGACAAGCAAT
```

-continued

TTCAGGGTGCAGCCTACCGAGTCCATCGTGCGCTTTCCCAATATCACAAACCTGT

GCCCTTTTGGCGAGGTGTTCAACGCAACCCGCTTCGCCAGCGTGTACGCCTGGAA

TAGGAAGCGCATCTCCAACTGCGTGGCCGACTATTCTGTGCTGTACAACAGCGCC

TCCTTCTCTACCTTTAAGTGCTATGGCGTGAGCCCCACAAAGCTGAATGACCTGT

GCTTTACCAACGTGTACGCCGATTCCTTCGTGATCAGGGGCGACGAGGTGCGCC

AGATCGCACCAGGACAGACAGGCAAGATCGCAGACTACAATTATAAGCTGCCTG

ACGATTTCACCGGCTGCGTGATCGCCTGGAACTCTAACAATCTGGATAGCAAAGT

GGGCGGCAACTACAATTATCTGTACCGGCTGTTTAGAAAGTCTAATCTGAAGCCA

TTCGAGAGGGACATCTCCACAGAAATCTACCAGGCCGGCTCTACCCCCTGCAAT

GGCGTGGAGGGCTTTAACTGTTATTTCCCTCTGCAGAGCTACGGCTTCCAGCCAA

CAAACGGCGTGGGCTATCAGCCCTACCGCGTGGTGGTGCTGTCTTTTGAGCTGCT

GCACGCACCTGCAACAGTGTGCGGACCAAAGAAGAGCACCAATCTGGTGAAGA

ACAAGTGCGTGAACTTCAACTTCAACGGACTGACCGGAACAGGCGTGCTGACCG

AGTCCAACAAGAAGTTCCTGCCTTTTCAGCAGTTCGGCAGGGACATCGCAGATA

CCACAGACGCCGTGCGCGACCCTCAGACCCTGGAGATCCTGGACATCACACCAT

GCTCCTTCGGCGGCGTGTCTGTGATCACACCAGGCACCAATACAAGCAACCAGG

TGGCCGTGCTGTATCAGGACGTGAATTGTACCGAGGTGCCAGTGGCAATCCACG

CAGATCAGCTGACCCCTACATGGCGGGTGTACTCTACCGGCAGCAACGTGTTCC

AGACAAGAGCCGGATGCCTGATCGGAGCAGAGCACGTGAACAATAGCTATGAGT

GCGACATCCCTATCGGCGCCGGCATCTGTGCCTCCTACCAGACCCAGACAAACTC

CCCAAGGTCTGTGGGAGATGAGGCCGAAGACTTTGTGGAAGTCCACCTGCCTGA

TGTGCATAACCAGGTGTCTGGCGTCGACCTGGGACTGCCAAATTGGGGCAAGTA

CGTGCTGCTGAGTGCTGGAGCACTGACTGCCCTGATGCTGATCATTTTCCTGATG

ACCTGCTGTCGGCGCGTGAACAGAAGTGAGCCCACTCAGCACAATCTGCGAGGA

ACCGGGAGAGAAGTGTCAGTCACACCTCAGAGCGGGAAAATCATTAGTAGTTGG

GAATCACATAAAAGCGGGGGCGAGACCAGGCTGggatccggctccggcgagggcaggggaagtct actaacatgcggggacgtggaggaaaatcccggccccATGAGCAAGATCTTTGTCAATCCTAGTGCTA

TTAGAGCCGGTCTGGCCGATCTTGAGATGGCTGAAGAAACTGTTGATCTGATCAA

TAGAAATATCGAAGACAATCAGGCTCATCTCCAAGGGGAACCCATAGAGGTGGA

CAATCTCCCTGAGGATATGGGGCGACTTCACCTGGATGATGGAAAATCGCCCAA

CCATGGTGAGATAGCCAAGGTGGGAGAAGGCAAGTATCGAGAGGACTTTCAGAT

GGATGAAGGAGAGGATCCTAGCTTCCTGTTCCAGTCATACCTGGAAAATGTTGG

AGTCCAAATAGTCGACAAATGAGGTCAGGAGAGAGATTTCTCAAGATATGGTC

ACAGACCGTAGAAGAGATTATATCCTATGTCGCGGTCAACTTTCCCAACCCTCCA

GGAAAGTCTTCAGAGGATAAATCAACCCAGACTACTGGCCGAGAGCTCAAGAAG

GAGACAACACCCACTCCTTCTCAGAGAGAAAGCCAATCATCGAAAGCCAGGATG

GCGGCTCAAATTGCTTCTGGCCCTCCAGCCCTTGAATGGTCGGCTACCAATGAAG

AGGATGATCTATCAGTGGAGGCTGAGATCGCTCACCAGATTGCAGAAAGTTTCT

CCAAAAAATATAAGTTTCCCTCTCGATCCTCAGGGATACTCTTGTATAATTTTGA

GCAATTGAAAATGAACCTTGATGATATAGTTAAAGAGGCAAAAAATGTACCAGG

TGTGACCCGTTTAGCCCATGACGGGTCCAAACTCCCCCTAAGATGTGTACTGGGA

-continued

```
TGGGTCGCTTTGGCCAACTCTAAGAAATTCCAGTTGTTAGTCGAATCCGACAAGC
TGAGTAAAATCATGCAAGATGACTTGAATCGCTATACATCTTGCTAACCGAACCT
CTCCCCTCAGTCCCTCTAGACAATAAAATCCGAGATGTCCCAAAGTCAACATGA
AAAAAACAGGCAACACCACTGATAAAATGAACCTCCTACGTAAGATAGTGAAAA
ACCGCAGGGACGAGGACACTCAAAAATCCTCTCCCGCGTCAGCCCCTCTGGATG
ACGATGACTTGTGGCTTCCACCCCCTGAATACGTCCCGCTGAAAGAACTTACAGG
CAAGAAGAACATGAGGAACTTTTGTATCAACGGAAGGGTTAAAGTGTGTAGCCC
GAATGGTTACTCGTTCAGGATCCTGCGGCACATTCTGAAATCATTCGACGAGATA
TATTCTGGGAATCATAGGATGATCGGGTTAGTCAAAGTGGTTATTGGACTGGCTT
TGTCAGGATCTCCAGTCCCTGAGGGCCTGAACTGGGTATACAAATTGAGGAGAA
CCTTTATCTTCCAGTGGGCTGATTCCAGGGGCCCTCTTGAAGGGGAGGAGTTGGA
ATACTCTCAGGAGATCACTTGGGATGATGATACTGAGTTCGTCGGATTGCAAATA
AGAGTGATTGCAAAACAGTGTCATATCCAGGGCAGAGTCTGGTGTATCAACATG
AACCCGAGAGCATGTCAACTATGGTCTGACATGTCTCTTCAGACACAAAGGTCC
GAAGAGGACAAAGATTCCTCTCTGCTTCTAGAATAATCAGATTATATCCCGCAAA
TTTATCACTTGTTTACCTCTGGAGGAGAGAACATATGGGCTCAACTCCAACCCTT
GGGAGCAATATAACAAAAAACATGTTATGGTGCCATTAAACCGCTGCATTTCAT
CAAAGTCAAGTTGATTACCTTTACATTTTGATCCTCTTGGATGTGAAAAAAACTA
TTAACATCCCTCAAAAGACCccgggAAAGATGGTTCCTCAGGCTCTCCTGTTTGTAC
CCCTTCTGGTTTTTCCATTGTGTTTTGGGAAATTCCCTATTTACACGATACCAGAC
AAGCTTGGTCCCTGGAGTCCGATTGACATACATCACCTCAGCTGCCCAAACAATT
TGGTAGTGGAGGACGAAGGATGCACCAACCTGTCAGGGTTCTCCTACATGGAAC
TTAAAGTTGGATACATCTTAGCCATAAAAGTGAACGGGTTCACTTGCACAGGCGT
TGTGACGGAGGCTGAAACCTACACTAACTTCGTTGGTTATGTCACAACCACGTTC
AAAAGAAAGCATTTCCGCCCAACACCAGATGCATGTAGAGCCGCGTACAACTGG
AAGATGGCCGGTGACCCCAGATATGAAGAGTCTCTACACAATCCGTACCCTGAC
TACCGCTGGCTTCGAACTGTAAAAACCACCAAGGAGTCTCTCGTTATCATATCTC
CAAGTGTGGCAGATTTGGACCCATATGACAGATCCCTTCACTCGAGGGTCTTCCC
TAGCGGGAAGTGCTCAGGAGTAGCGGTGTCTTCTACCTACTGCTCCACTAACCAC
GATTACACCATTTGGATGCCCGAGAATCCGAGACTAGGGATGTCTTGTGACATTT
TTACCAATAGTAGAGGGAAGAGAGCATCCAAAGGGAGTGAGACTTGCGGCTTTG
TAGATGAAAGAGGCCTATATAAGTCTTTAAAAGGAGCATGCAAACTCAAGTTAT
GTGGAGTTCTAGGACTTAGACTTATGGATGGAACATGGGTCTCGATGCAAACAT
CAAATGAAACCAAATGGTGCCCTCCCGATAAGTTGGTGAACCTGCACGACTTTC
GCTCAGACGAAATTGAGCACCTTGTTGTAGAGGAGTTGGTCAGGAAGAGAGAGG
AGTGTCTGGATGCACTAGAGTCCATCATGACAACCAAGTCAGTGAGTTTCAGAC
GTCTCAGTCATTTAAGAAAACTTGTCCCTGGGTTTGGAAAAGCATATACCATATT
CAACAAGACCTTGATGGAAGCCGATGCTCACTACAAGTCAGTCgagACTTGGAAT
GAGATCCTCCCTTCAAAAGGGTGTTTAAGAGTTGGGGGGAGGTGTCATCCTCATG
TGAACGGGGTGTTTTTCAATGGTATAATATTAGGACCTGACGGCAATGTCTTAAT
```

```
CCCAGAGATGCAATCATCCCTCCTCCAGCAACATATGGAGTTGTTGGAATCCTCG

GTTATCCCCCTTGTGCACCCCCTGGCAGACCCGTCTACCGTTTTCAAGGACGGTG

ACGAGGCTGAGGATTTTGTTGAAGTTCACCTTCCCGATGTGCACAATCAGGTCTC

AGGAGTTGACTTGGGTCTCCCGAACTGGGGGAAGTATGTATTACTGAGTGCAGG

GGCCCTGACTGCCTTGATGTTGATAATTTTCCTGATGACATGTTGTAGAAGAGTC

AATCGATCAGAACCTACGCAACACAATCTCAGAGGGACAGGGAGGGAGGTGTC

AGTCACTCCCCAAAGCGGGAAGATCATATCTTCATGGGAATCACACAAGAGTGG

GGGTGAGACCAGACTGTAAttaattaaCGTCCTTTCAACGATCCAAGTCcatgaaaaaaactaa caccccctcccgtacctagcTTATAAAGTGCTGGGTCATCTAAGCTTTTCAGTCGAGAAAAA

ACATTAGATCAGAAGAACAACTGGCAACACTTCTCAACCTGAGACTTACTTCAA

GATGCTCGATCCTGGAGAGGTCTATGATGACCCTATTGACCCAATCGAGTTAGAG

GCTGAACCCAGAGGAACCCCCATTGTCCCCAACATCTTGAGGAACTCTGACTAC

AATCTCAACTCTCCTTTGATAGAAGATCCTGCTAGACTAATGTTAGAATGGTTAA

AAACAGGGAATAGACCTTATCGGATGACTCTAACAGACAATTGCTCCAGGTCTTT

CAGAGTTTTGAAAGATTATTTCAAGAAGGTAGATTTGGGTTCTCTCAAGGTGGGC

GGAATGGCTGCACAGTCAATGATTTCTCTCTGGTTATATGGTGCCCACTCTGAAT

CCAACAGGAGCCGGAGATGTATAACAGACTTGGCCCATTTCTATTCCAAGTCGTC

CCCCATAGAGAAGCTGTTGAATCTCACGCTAGGAAATAGAGGGCTGAGAATCCC

CCCAGAGGGAGTGTTAAGTTGCCTTGAGAGGGTTGATTATGATAATGCATTTGGA

AGGTATCTTGCCAACACGTATTCCTCTTACTTGTTCTTCCATGTAATCACCTTATA

CATGAACGCCCTAGACTGGGATGAAGAAAAGACCATCCTAGCATTATGGAAAGA

TTTAACCTCAGTGGACATCGGGAAGGACTTGGTAAAGTTCAAAGACCAAATATG

GGGACTGCTGATCGTGACAAAGGACTTTGTTTACTCCCAAAGTTCCAATTGTCTT

TTTGACAGAAACTACACACTTATGCTAAAAGATCTTTTCTTGTCTCGCTTCAACTC

CTTAATGGTCTTGCTCTCTCCCCCAGAGCCCCGATACTCAGATGACTTGATATCT

CAACTATGCCAGCTGTACATTGCTGGGGATCAAGTCTTGTCTATGTGTGGAAACT

CCGGCTATGAAGTCATCAAAATATTGGAGCCATATGTCGTGAATAGTTTAGTCCA

GAGAGCAGAAAAGTTTAGGCCTCTCATTCATTCCTTGGGAGACTTTCCTGTATTT

ATAAAAGACAAGGTAAGTCAACTTGAAGAGACGTTCGGTCCCTGTGCAAGAAGG

TTCTTTAGGGCTCTGGATCAATTCGACAACATACATGACTTGGTTTTTGTGTTTGG

CTGTTACAGGCATTGGGGGCACCCATATATAGATTATCGAAAGGGTCTGTCAAA

ACTATATGATCAGGTTCACCTTAAAAAAATGATAGATAAGTCCTACCAGGAGTG

CTTAGCAAGCGACCTAGCCAGGAGGATCCTTAGATGGGGTTTTGATAAGTACTCC

AAGTGGTATCTGGATTCAAGATTCCTAGCCCGAGACCACCCCTTGACTCCTTATA

TCAAAACCCAAACATGGCCACCCAAACATATTGTAGACTTGGTGGGGATACAT

GGCACAAGCTCCCGATCACGCAGATCTTTGAGATTCCTGAATCAATGGATCCGTC

AGAAATATTGGATGACAAATCACATTCTTTCACCAGAACGAGACTAGCTTCTTGG

CTGTCAGAAAACCGAGGGGGGCCTGTTCCTAGCGAAAAGTTATTATCACGGCC

CTGTCTAAGCCGCCTGTCAATCCCCGAGAGTTTCTGAGGTCTATAGACCTCGGAG

GATTGCCAGATGAAGACTTGATAATTGGCCTCAAGCCAAAGGAACGGGAATTGA

AGATTGAAGGTCGATTCTTTGCTCTAATGTCATGGAATCTAAGATTGTATTTTGTC
```

-continued

```
ATCACTGAAAAACTCTTGGCCAACTACATCTTGCCACTTTTTGACGCGCTGACTA

TGACAGACAACCTGAACAAGGTGTTTAAAAAGCTGATCGACAGGGTCACCGGGC

AAGGGCTTTTGGACTATTCAAGGGTCACATATGCATTTCACCTGGACTATGAAAA

GTGGAACAACCATCAAAGATTAGAGTCAACAGAGGATGTATTTTCTGTCCTAGA

TCAAGTGTTTGGATTGAAGAGAGTGTTTTCTAGAACACACGAGTTTTTTCAAAAG

GCCTGGATCTATTATTCAGACAGATCAGACCTCATCGGGTTACGGGAGGATCAA

ATATACTGCTTAGATGCGTCCAACGGCCCAACCTGTTGGAATGGCCAGGATGGC

GGGCTAGAAGGCTTACGGCAGAAGGGCTGGAGTCTAGTCAGCTTATTGATGATA

GATAGAGAATCTCAAATCAGGAACACAAGAACCAAAATACTAGCTCAAGGAGA

CAACCAGGTTTTATGTCCGACATACATGTTGTCGCCAGGGCTATCTCAAGAGGGG

CTCCTCTATGAATTGGAGAGAATATCAAGGAATGCACTTTCGATATACAGAGCC

GTCGAGGAAGGGGCATCTAAGCTAGGGCTGATCATCAAGAAAGAAGAGACCAT

GTGTAGTTATGACTTCCTCATCTATGGAAAAACCCCTTTGTTTAGAGGTAACATA

TTGGTGCCTGAGTCCAAAAGATGGGCCAGAGTCTCTTGCGTCTCTAATGACCAAA

TAGTCAACCTCGCCAATATAATGTCGACAGTGTCCACCAATGCGCTAACAGTGG

CACAACACTCTCAATCTTTGATCAAACCGATGAGGGATTTTCTGCTCATGTCAGT

ACAGGCAGTCTTTCACTACCTGCTATTTAGCCCAATCTTAAAGGGAAGAGTTTAC

AAGATTCTGAGCGCTGAAGGGGAGAGCTTTCTCCTAGCCATGTCAAGGATAATC

TATCTAGATCCTTCTTTGGGAGGGATATCTGGAATGTCCCTCGGAAGATTCCATA

TACGACAGTTCTCAGACCCTGTCTCTGAAGGGTTATCCTTCTGGAGAGAGATCTG

GTTAAGCTCCCAAGAGTCCTGGATTCACGCGTTGTGTCAAGAGGCTGGAAACCC

AGATCTTGGAGAGAGAACACTCGAGAGCTTCACTCGCCTTCTAGAAGATCCGAC

CACCTTAAATATCAGAGGAGGGGCCAGTCCTACCATTCTACTCAAGGATGCAAT

CAGAAAGGCTTTATATGACGAGGTGGACAAGGTGGAAAATTCAGAGTTTCGAGA

GGCAATCCTGTTGTCCAAGACCCATAGAGATAATTTTATACTCTTCTTAATATCT

GTTGAGCCTCTGTTTCCTCGATTTCTCAGTGAGCTATTCAGTTCGTCTTTTTTGGG

AATCCCCGAGTCAATCATTGGATTGATACAAAACTCCCGAACGATAAGAAGGCA

GTTTAGAAAGAGTCTCTCAAAAACTTTAGAAGAATCCTTCTACAACTCAGAGATC

CACGGGATTAGTCGGATGACCCAGACACCTCAGAGGGTTGGGGGGGTGTGGCCT

TGCTCTTCAGAGAGGGCAGATCTACTTAGGGAGATCTCTTGGGGAAGAAAAGTG

GTAGGCACGACAGTTCCTCACCCTTCTGAGATGTTGGGATTACTTCCCAAGTCCT

CTATTTCTTGCACTTGTGGAGCAACAGGAGGAGGCAATCCTAGAGTTTCTGTATC

AGTACTCCCGTCCTTTGATCAGTCATTTTTTTCACGAGGCCCCCTAAAGGGATAC

TTGGGCTCGTCCACCTCTATGTCGACCCAGCTATTCCATGCATGGGAAAAAGTCA

CTAATGTTCATGTGGTGAAGAGAGCTCTATCGTTAAAAGAATCTATAAACTGGTT

CATTACTAGAGATTCCAACTTGGCTCAAGCTCTAATTAGGAACATTATGTCTCTG

ACAGGCCCTGATTTCCCTCTAGAGGAGGCCCCTGTCTTCAAAAGGACGGGGTCA

GCCTTGCATAGGTTCAAGTCTGCCAGATACAGCGAAGGAGGGTATTCTTCTGTCT

GCCCGAACCTCCTCTCTCATATTTCTGTTAGTACAGACACCATGTCTGATTTGACC

CAAGACGGGAAGAACTACGATTTCATGTTCCAGCCATTGATGCTTTATGCACAGA
```

-continued

```
CATGGACATCAGAGCTGGTACAGAGAGACACAAGGCTAAGAGACTCTACGTTTC

ATTGGCACCTCCGATGCAACAGGTGTGTGAGACCCATTGACGACGTGACCCTGG

AGACCTCTCAGATCTTCGAGTTTCCGGATGTGTCGAAAAGAATATCCAGAATGGT

TTCTGGGGCTGTGCCTCACTTCCAGAGGCTTCCCGATATCCGTCTGAGACCAGGA

GATTTTGAATCTCTAAGCGGTAGAGAAAAGTCTCACCATATCGGATCAGCTCAG

GGGCTCTTATACTCAATCTTAGTGGCAATTCACGACTCAGGATACAATGATGGAA

CCATCTTCCCTGTCAACATATACGGCAAGGTTTCCCCTAGAGACTATTTGAGAGG

GCTCGCAAGGGGAGTATTGATAGGATCCTCGATTTGCTTCTTGACAAGAATGACA

AATATCAATATTAATAGACCTCTTGAATTGGTCTCAGGGGTAATCTCATATATTC

TCCTGAGGCTAGATAACCATCCCTCCTTGTACATAATGCTCAGAGAACCGTCTCT

TAGAGGAGAGATATTTTCTATCCCTCAGAAAATCCCCGCCGCTTATCCAACCACT

ATGAAAGAAGGCAACAGATCAATCTTGTGTTATCTCCAACATGTGCTACGCTATG

AGCGAGAGATAATCACGGCGTCTCCAGAGAATGACTGGCTATGGATCTTTTCAG

ACTTTAGAAGTGCCAAAATGACGTACCTATCCCTCATTACTTACCAGTCTCATCT

TCTACTCCAGAGGGTTGAGAGAAACCTATCTAAGAGTATGAGAGATAACCTGCG

ACAATTGAGTTCTTTGATGAGGCAGGTGCTGGGCGGGCACGGAGAAGATACCTT

AGAGTCAGACGACAACATTCAACGACTGCTAAAAGACTCTTTACGAAGGACAAG

ATGGGTGGATCAAGAGGTGCGCCATGCAGCTAGAACCATGACTGGAGATTACAG

CCCCAACAAGAAGGTGTCCCGTAAGGTAGGATGTTCAGAATGGGTCTGCTCTGC

TCAACAGGTTGCAGTCTCTACCTCAGCAAACCCGGCCCCTGTCTCGGAGCTTGAC

ATAAGGGCCCTCTCTAAGAGGTTCCAGAACCCTTTGATCTCGGGCTTGAGAGTGG

TTCAGTGGGCAACCGGTGCTCATTATAAGCTTAAGCCTATTCTAGATGATCTCAA

TGTTTTCCCATCTCTCTGCCTTGTAGTTGGGGACGGGTCAGGGGGATATCAAGG

GCAGTCCTCAACATGTTTCCAGATGCCAAGCTTGTGTTCAACAGTCTTTTAGAGG

TGAATGACCTGATGGCTTCCGGAACACATCCACTGCCTCCTTCAGCAATCATGAG

GGGAGGAAATGATATCGTCTCCAGAGTGATAGATCTTGACTCAATCTGGGAAAA

ACCGTCCGACTTGAGAAACTTGGCAACCTGGAAATACTTCCAGTCAGTCCAAAA

GCAGGTCAACATGTCCTATGACCTCATTATTTGCGATGCAGAAGTTACTGACATT

GCATCTATCAACCGGATCACCCTGTTAATGTCCGATTTTGCATTGTCTATAGATG

GACCACTCTATTTGGTCTTCAAAACTTATGGGACTATGCTAGTAAATCCAAACTA

CAAGGCTATTCAACACCTGTCAAGAGCGTTCCCCTCGGTCACAGGGTTTATCACC

CAAGTAACTTCGTCTTTTTCATCTGAGCTCTACCTCCGATTCTCCAAACGAGGGA

AGTTTTTCAGAGATGCTGAGTACTTGACCTCTTCCACCCTTCGAGAAATGAGCCT

TGTGTTATTCAATTGTAGCAGCCCCAAGAGTGAGATGCAGAGAGCTCGTTCCTTG

AACTATCAGGATCTTGTGAGAGGATTTCCTGAAGAAATCATATCAAATCCTTACA

ATGAGATGATCATAACTCTGATTGACAGTGATGTAGAATCTTTTCTAGTCCACAA

GATGGTTGATGATCTTGAGTTACAGAGGGGAACTCTGTCTAAAGTGGCTATCATT

ATAGCCATCATGATAGTTTTCTCCAACAGAGTCTTCAACGTTTCCAAACCCCTAA

CTGACCCCTCGTTCTATCCACCGTCTGATCCCAAAATCCTGAGGCACTTCAACAT

ATGTTGCAGTACTATGATGTATCTATCTACTGCTTTAGGTGACGTCCCTAGCTTCG

CAAGACTTCACGACCTGTATAACAGACCTATAACTTATTACTTCAGAAAGCAAGT
```

-continued

CATTCGAGGGAACGTTTATCTATCTTGGAGTTGGTCCAACGACACCTCAGTGTTC

AAAAGGGTAGCCTGTAATTCTAGCCTGAGTCTGTCATCTCACTGGATCAGGTTGA

TTTACAAGATAGTGAAGACTACCAGACTCGTTGGCAGCATCAAGGATCTATCCA

GAGAAGTGGAAAGACACCTTCATAGGTACAACAGGTGGATCACCCTAGAGGATA

TCAGATCTAGATCATCCCTACTAGACTACAGTTGCCTGTGAACCGGATACTCCTG

GAAGCCTGCCCATGCTAAGACTCTTGTGTGATGTATCTTGAAAAAAACAAGATCC

TAAATCTGAACCTTTGGTTGTTTGATTGTTTTTCTCAttttttgttgtttatttgttaagcgt

In one embodiment, the nucleic acid comprises the sequence of SEQ ID NO: 13, shown below (RABV vector: Coravax V4 South Africa):

ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAcatgaaaaaaactaacacccctcccgtacgGCCACCATGTTCGTGTTTCTGGTGCTGCT

GCCTCTGGTGAGCTCCCAGTGCGTGAACTTCACCACAAGGACCCAGCTGCCCCCT

GCCTATACCAATTCCTTCACACGGGGCGTGTACTATCCCGACAAGGTGTTCCGGA

GCAGCGTGCTGCACTCCACACAGGATCTGTTTCTGCCTTTCTTTTCTAACGTGACC

-continued

```
TGGTTCCACGCCATCCACGTGAGCGGCACCAATGGCACAAAGCGGTTCGCCAAT

CCAGTGCTGCCCTTTAACGATGGCGTGTACTTCGCCTCCACCGAGAAGTCTAACA

TCATCAGAGGCTGGATCTTTGGCACCACACTGGACAGCAAGACACAGTCCCTGC

TGATCGTGAACAATGCCACCAACGTGGTCATCAAGGTGTGCGAGTTCCAGTTTTG

TAATGATCCATTCCTGGGCGTGTACTATCACAAGAACAATAAGTCTTGGATGGAG

AGCGAGTTTCGCGTGTATTCCTCTGCCAACAATTGCACATTTGAGTACGTGTCCC

AGCCCTTCCTGATGGACCTGGAGGGCAAGCAGGGCAATTTCAAGAACCTGAGGG

AGTTCGTGTTTAAGAATATCGATGGCTACTTCAAAATCTACTCCAAGCACACCCC

AATCAACCTGGTGCGCGGCCTGCCACAGGGCTTCTCTGCCCTGGAGCCACTGGTG

GATCTGCCCATCGGCATCAACATCACCCGGTTTCAGACACTGCTGGCCCTGCACA

GAAGCTACCTGACACCAGGCGACAGCTCCTCTGGATGGACCGCAGGAGCAGCAG

CCTACTATGTGGGCTATCTGCAGCCCAGGACCTTCCTGCTGAAGTACAACGAGA

ATGGCACCATCACAGACGCCGTGGATTGCGCCCTGGATCCCTGTCTGAGACCA

AGTGTACACTGAAGAGCTTTACCGTGGAGAAGGGCATCTATCAGACAAGCAATT

TCAGGGTGCAGCCTACCGAGTCCATCGTGCGCTTTCCCAATATCACAAACCTGTG

CCCTTTTGGCGAGGTGTTCAACGCAACCCGCTTCGCCAGCGTGTACGCCTGGAAT

AGGAAGCGCATCTCCAACTGCGTGGCCGACTATTCTGTGCTGTACAACAGCGCCT

CCTTCTCTACCTTTAAGTGCTATGGCGTGAGCCCCACAAAGCTGAATGACCTGTG

CTTTACCAACGTGTACGCCGATTCCTTCGTGATCAGGGGCGACGAGGTGCGCCA

GATCGCACCAGGACAGACAGGCAATATCGCAGACTACAATTATAAGCTGCCTGA

CGATTTCACCGGCTGCGTGATCGCCTGGAACTCTAACAATCTGGATAGCAAAGTG

GGCGGCAACTACAATTATCTGTACCGGCTGTTTAGAAAGTCTAATCTGAAGCCAT

TCGAGAGGGACATCTCCACAGAAATCTACCAGGCCGGCTCTACCCCTGCAATG

GCGTGAAGGGCTTTAACTGTTATTTCCCTCTGCAGAGCTACGGCTTCCAGCCAAC

ATATGGCGTGGGCTATCAGCCCTACCGCGTGGTGGTGCTGTCTTTTGAGCTGCTG

CACGCACCTGCAACAGTGTGCGGACCAAAGAAGAGCACCAATCTGGTGAAGAA

CAAGTGCGTGAACTTCAACTTCAACGGACTGACCGGAACAGGCGTGCTGACCGA

GTCCAACAAGAAGTTCCTGCCTTTTCAGCAGTTCGGCAGGGACATCGCAGATAC

CACAGACGCCGTGCGCGACCCTCAGACCCTGGAGATCCTGGACATCACACCATG

CTCCTTCGGCGGCGTGTCTGTGATCACACCAGGCACCAATACAAGCAACCAGGT

GGCCGTGCTGTATCAGGGCGTGAATTGTACCGAGGTGCCAGTGGCAATCCACGC

AGATCAGCTGACCCCTACATGGCGGGTGTACTCTACCGGCAGCAACGTGTTCCA

GACAAGAGCCGGATGCCTGATCGGAGCAGAGCACGTGAACAATAGCTATGAGTG

CGACATCCCTATCGGCGCCGGCATCTGTGCCTCCTACCAGACCCAGACAAACTCC

CCAGAATCAAGCGTGATTCCTCTGGTCCATCCACTGGCAGATCCCTCCACAGTGT

TCAAAGACGGAGATGAGGCCGAAGACTTTGTGGAAGTCCACCTGCCTGATGTGC

ATAACCAGGTGTCTGGCGTCGACCTGGGACTGCCAAATTGGGGCAAGTACGTGC

TGCTGAGTGCTGGAGCACTGACTGCCCTGATGCTGATCATTTTCCTGATGACCTG

CTGTCGGCGCGTGAACAGAAGTGAGCCCACTCAGCACAATCTGCGAGGAACCGG

GAGAGAAGTGTCAGTCACACCTCAGAGCGGGAAAATCATTAGTAGTTGGGAATC
```

-continued

```
ACATAAAAGCGGGGGCGAGACCAGGCTGggatccggctccggcgagggcaggggaagtctactaacat gcggggacgtggaggaaaatcccggccccATGAGCAAGATCTTTGTCAATCCTAGTGCTATTAG

AGCCGGTCTGGCCGATCTTGAGATGGCTGAAGAAACTGTTGATCTGATCAATAG

AAATATCGAAGACAATCAGGCTCATCTCCAAGGGGAACCCATAGAGGTGGACAA

TCTCCCTGAGGATATGGGGCGACTTCACCTGGATGATGGAAAATCGCCCAACCA

TGGTGAGATAGCCAAGGTGGGAGAAGGCAAGTATCGAGAGGACTTTCAGATGG

ATGAAGGAGAGGATCCTAGCTTCCTGTTCCAGTCATACCTGGAAAATGTTGGAGT

CCAAATAGTCAGACAAATGAGGTCAGGAGAGAGATTTCTCAAGATATGGTCACA

GACCGTAGAAGAGATTATATCCTATGTCGCGGTCAACTTTCCCAACCCTCCAGGA

AAGTCTTCAGAGGATAAATCAACCCAGACTACTGGCCGAGAGCTCAAGAAGGAG

ACAACACCCACTCCTTCTCAGAGAGAAAGCCAATCATCGAAAGCCAGGATGGCG

GCTCAAATTGCTTCTGGCCCTCCAGCCCTTGAATGGTCGGCTACCAATGAAGAGG

ATGATCTATCAGTGGAGGCTGAGATCGCTCACCAGATTGCAGAAAGTTTCTCCAA

AAAATATAAGTTTCCCTCTCGATCCTCAGGGATACTCTTGTATAATTTTGAGCAA

TTGAAAATGAACCTTGATGATATAGTTAAAGAGGCAAAAAATGTACCAGGTGTG

ACCCGTTTAGCCCATGACGGGTCCAAACTCCCCCTAAGATGTGTACTGGGATGG

GTCGCTTTGGCCAACTCTAAGAAATTCCAGTTGTTAGTCGAATCCGACAAGCTGA

GTAAAATCATGCAAGATGACTTGAATCGCTATACATCTTGCTAACCGAACCTCTC

CCCTCAGTCCCTCTAGACAATAAAATCCGAGATGTCCCAAAGTCAACATGAAAA

AAACAGGCAACACCACTGATAAAATGAACCTCCTACGTAAGATAGTGAAAAACC

GCAGGGACGAGGACACTCAAAAATCCTCTCCCGCGTCAGCCCCTCTGGATGACG

ATGACTTGTGGCTTCCACCCCCTGAATACGTCCCGCTGAAAGAACTTACAGGCAA

GAAGAACATGAGGAACTTTTGTATCAACGGAAGGGTTAAAGTGTGTAGCCCGAA

TGGTTACTCGTTCAGGATCCTGCGGCACATTCTGAAATCATTCGACGAGATATAT

TCTGGGAATCATAGGATGATCGGGTTAGTCAAAGTGGTTATTGGACTGGCTTTGT

CAGGATCTCCAGTCCCTGAGGGCCTGAACTGGGTATACAAATTGAGGAGAACCT

TTATCTTCCAGTGGGCTGATTCCAGGGGCCCTCTTGAAGGGGAGGAGTTGGAATA

CTCTCAGGAGATCACTTGGGATGATGATACTGAGTTCGTCGGATTGCAAATAAG

AGTGATTGCAAAACAGTGTCATATCCAGGGCAGAGTCTGGTGTATCAACATGAA

CCCGAGAGCATGTCAACTATGGTCTGACATGTCTCTTCAGACACAAAGGTCCGA

AGAGGACAAAGATTCCTCTCTGCTTCTAGAATAATCAGATTATATCCCGCAAATT

TATCACTTGTTTACCTCTGGAGGAGAGAACATATGGGCTCAACTCCAACCCTTGG

GAGCAATATAACAAAAAACATGTTATGGTGCCATTAAACCGCTGCATTTCATCA

AAGTCAAGTTGATTACCTTTACATTTTGATCCTCTTGGATGTGAAAAAAACTATT

AACATCCCTCAAAAGACCcccgggAAAGATGGTTCCTCAGGCTCTCCTGTTTGTACC

CCTTCTGGTTTTTCCATTGTGTTTTGGGAAATTCCCTATTTACACGATACCAGACA

AGCTTGGTCCCTGGAGTCCGATTGACATACATCACCTCAGCTGCCCAAACAATTT

GGTAGTGGAGGACGAAGGATGCACCAACCTGTCAGGGTTCTCCTACATGGAACT

TAAAGTTGGATACATCTTAGCCATAAAAGTGAACGGGTTCACTTGCACAGGCGTT

GTGACGGAGGCTGAAACCTACACTAACTTCGTTGGTTATGTCACAACCACGTTCA

AAAGAAAGCATTTCCGCCCAACACCAGATGCATGTAGAGCCGCGTACAACTGGA
```

```
AGATGGCCGGTGACCCCAGATATGAAGAGTCTCTACACAATCCGTACCCTGACT

ACCGCTGGCTTCGAACTGTAAAAACCACCAAGGAGTCTCTCGTTATCATATCTCC

AAGTGTGGCAGATTTGGACCCATATGACAGATCCCTTCACTCGAGGGTCTTCCCT

AGCGGGAAGTGCTCAGGAGTAGCGGTGTCTTCTACCTACTGCTCCACTAACCAC

GATTACACCATTTGGATGCCCGAGAATCCGAGACTAGGGATGTCTTGTGACATTT

TTACCAATAGTAGAGGGAAGAGAGCATCCAAAGGGAGTGAGACTTGCGGCTTTG

TAGATGAAAGAGGCCTATATAAGTCTTTAAAAGGAGCATGCAAACTCAAGTTAT

GTGGAGTTCTAGGACTTAGACTTATGGATGGAACATGGGTCTCGATGCAAACAT

CAAATGAAACCAAATGGTGCCCTCCCGATAAGTTGGTGAACCTGCACGACTTTC

GCTCAGACGAAATTGAGCACCTTGTTGTAGAGGAGTTGGTCAGGAAGAGAGAGG

AGTGTCTGGATGCACTAGAGTCCATCATGACAACCAAGTCAGTGAGTTTCAGAC

GTCTCAGTCATTTAAGAAAACTTGTCCCTGGGTTTGGAAAAGCATATACCATATT

CAACAAGACCTTGATGGAAGCCGATGCTCACTACAAGTCAGTCgagACTTGGAAT

GAGATCCTCCCTTCAAAAGGGTGTTTAAGAGTTGGGGGGAGGTGTCATCCTCATG

TGAACGGGGTGTTTTTCAATGGTATAATATTAGGACCTGACGGCAATGTCTTAAT

CCCAGAGATGCAATCATCCCTCCTCCAGCAACATATGGAGTTGTTGGAATCCTCG

GTTATCCCCCTTGTGCACCCCCTGGCAGACCCGTCTACCGTTTTCAAGGACGGTG

ACGAGGCTGAGGATTTTGTTGAAGTTCACCTTCCCGATGTGCACAATCAGGTCTC

AGGAGTTGACTTGGGTCTCCCGAACTGGGGGAAGTATGTATTACTGAGTGCAGG

GGCCCTGACTGCCTTGATGTTGATAATTTTCCTGATGACATGTTGTAGAAGAGTC

AATCGATCAGAACCTACGCAACACAATCTCAGAGGGACAGGGAGGGAGGTGTC

AGTCACTCCCCAAAGCGGGAAGATCATATCTTCATGGGAATCACACAAGAGTGG

GGGTGAGACCAGACTGTAAttaattaaCGTCCTTTCAACGATCCAAGTCcatgaaaaaaactaa caccccctcccgtacctagcTTATAAAGTGCTGGGTCATCTAAGCTTTTCAGTCGAGAAAAAA

ACATTAGATCAGAAGAACAACTGGCAACACTTCTCAACCTGAGACTTACTTCAA

GATGCTCGATCCTGGAGAGGTCTATGATGACCCTATTGACCCAATCGAGTTAGAG

GCTGAACCCAGAGGAACCCCCATTGTCCCCAACATCTTGAGGAACTCTGACTAC

AATCTCAACTCTCCTTTGATAGAAGATCCTGCTAGACTAATGTTAGAATGGTTAA

AAACAGGGAATAGACCTTATCGGATGACTCTAACAGACAATTGCTCCAGGTCTTT

CAGAGTTTTGAAAGATTATTTCAAGAAGGTAGATTTGGGTTCTCTCAAGGTGGGC

GGAATGGCTGCACAGTCAATGATTTCTCTCTGGTTATATGGTGCCCACTCTGAAT

CCAACAGGAGCCGGAGATGTATAACAGACTTGGCCCATTTCTATTCCAAGTCGTC

CCCCATAGAGAAGCTGTTGAATCTCACGCTAGGAAATAGAGGGCTGAGAATCCC

CCCAGAGGGAGTGTTAAGTTGCCTTGAGAGGGTTGATTATGATAATGCATTTGGA

AGGTATCTTGCCAACACGTATTCCTCTTACTTGTTCTTCCATGTAATCACCTTATA

CATGAACGCCCTAGACTGGGATGAAGAAAAGACCATCCTAGCATTATGGAAAGA

TTTAACCTCAGTGGACATCGGGAAGGACTTGGTAAAGTTCAAAGACCAAATATG

GGGACTGCTGATCGTGACAAAGGACTTTGTTTACTCCCAAAGTTCCAATTGTCTT

TTTGACAGAAACTACACACTTATGCTAAAAGATCTTTTCTTGTCTCGCTTCAACTC

CTTAATGGTCTTGCTCTCTCCCCCAGAGCCCCGATACTCAGATGACTTGATATCT
```

-continued

```
CAACTATGCCAGCTGTACATTGCTGGGGATCAAGTCTTGTCTATGTGTGGAAACT

CCGGCTATGAAGTCATCAAAATATTGGAGCCATATGTCGTGAATAGTTTAGTCCA

GAGAGCAGAAAAGTTTAGGCCTCTCATTCATTCCTTGGGAGACTTTCCTGTATTT

ATAAAAGACAAGGTAAGTCAACTTGAAGAGACGTTCGGTCCCTGTGCAAGAAGG

TTCTTTAGGGCTCTGGATCAATTCGACAACATACATGACTTGGTTTTTGTGTTTGG

CTGTTACAGGCATTGGGGGCACCCATATATAGATTATCGAAAGGGTCTGTCAAA

ACTATATGATCAGGTTCACCTTAAAAAAATGATAGATAAGTCCTACCAGGAGTG

CTTAGCAAGCGACCTAGCCAGGAGGATCCTTAGATGGGGTTTTGATAAGTACTCC

AAGTGGTATCTGGATTCAAGATTCCTAGCCCGAGACCACCCCTTGACTCCTTATA

TCAAAACCCAAACATGGCCACCCAAACATATTGTAGACTTGGTGGGGATACAT

GGCACAAGCTCCCGATCACGCAGATCTTTGAGATTCCTGAATCAATGGATCCGTC

AGAAATATTGGATGACAAATCACATTCTTTCACCAGAACGAGACTAGCTTCTTGG

CTGTCAGAAAACCGAGGGGGGCCTGTTCCTAGCGAAAAGTTATTATCACGGCC

CTGTCTAAGCCGCCTGTCAATCCCCGAGAGTTTCTGAGGTCTATAGACCTCGGAG

GATTGCCAGATGAAGACTTGATAATTGGCCTCAAGCCAAAGGAACGGGAATTGA

AGATTGAAGGTCGATTCTTTGCTCTAATGTCATGGAATCTAAGATTGTATTTTGTC

ATCACTGAAAAACTCTTGGCCAACTACATCTTGCCACTTTTTGACGCGCTGACTA

TGACAGACAACCTGAACAAGGTGTTTAAAAAGCTGATCGACAGGGTCACCGGGC

AAGGGCTTTTGGACTATTCAAGGGTCACATATGCATTTCACCTGGACTATGAAAA

GTGGAACAACCATCAAAGATTAGAGTCAACAGAGGATGTATTTTCTGTCCTAGA

TCAAGTGTTTGGATTGAAGAGAGTGTTTTCTAGAACACACGAGTTTTTTCAAAAG

GCCTGGATCTATTATTCAGACAGATCAGACCTCATCGGGTTACGGGAGGATCAA

ATATACTGCTTAGATGCGTCCAACGGCCCAACCTGTTGGAATGGCCAGGATGGC

GGGCTAGAAGGCTTACGGCAGAAGGGCTGGAGTCTAGTCAGCTTATTGATGATA

GATAGAGAATCTCAAATCAGGAACACAAGAACCAAAATACTAGCTCAAGGAGA

CAACCAGGTTTTATGTCCGACATACATGTTGTCGCCAGGGCTATCTCAAGAGGGG

CTCCTCTATGAATTGGAGAGAATATCAAGGAATGCACTTTCGATATACAGAGCC

GTCGAGGAAGGGGCATCTAAGCTAGGGCTGATCATCAAGAAAGAAGAGACCAT

GTGTAGTTATGACTTCCTCATCTATGGAAAAACCCCTTTGTTTAGAGGTAACATA

TTGGTGCCTGAGTCCAAAAGATGGGCCAGAGTCTCTTGCGTCTCTAATGACCAAA

TAGTCAACCTCGCCAATATAATGTCGACAGTGTCCACCAATGCGCTAACAGTGG

CACAACACTCTCAATCTTTGATCAAACCGATGAGGGATTTTCTGCTCATGTCAGT

ACAGGCAGTCTTTCACTACCTGCTATTTAGCCCAATCTTAAAGGGAAGAGTTTAC

AAGATTCTGAGCGCTGAAGGGGAGAGCTTTCTCCTAGCCATGTCAAGGATAATC

TATCTAGATCCTTCTTTGGGAGGGATATCTGGAATGTCCCTCGGAAGATTCCATA

TACGACAGTTCTCAGACCCTGTCTCTGAAGGGTTATCCTTCTGGAGAGAGATCTG

GTTAAGCTCCCAAGAGTCCTGGATTCACGCGTTGTGTCAAGAGGCTGGAAACCC

AGATCTTGGAGAGAGAACACTCGAGAGCTTCACTCGCCTTCTAGAAGATCCGAC

CACCTTAAATATCAGAGGAGGGGCCAGTCCTACCATTCTACTCAAGGATGCAAT

CAGAAAGGCTTTATATGACGAGGTGGACAAGGTGGAAAATTCAGAGTTTCGAGA

GGCAATCCTGTTGTCCAAGACCCATAGAGATAATTTTATACTCTTCTTAATATCT
```

```
GTTGAGCCTCTGTTTCCTCGATTTCTCAGTGAGCTATTCAGTTCGTCTTTTTTGGG

AATCCCCGAGTCAATCATTGGATTGATACAAAACTCCCGAACGATAAGAAGGCA

GTTTAGAAAGAGTCTCTCAAAAACTTTAGAAGAATCCTTCTACAACTCAGAGATC

CACGGGATTAGTCGGATGACCCAGACACCTCAGAGGGTTGGGGGGGTGTGGCCT

TGCTCTTCAGAGAGGGCAGATCTACTTAGGGAGATCTCTTGGGGAAGAAAAGTG

GTAGGCACGACAGTTCCTCACCCTTCTGAGATGTTGGGATTACTTCCCAAGTCCT

CTATTTCTTGCACTTGTGGAGCAACAGGAGGAGGCAATCCTAGAGTTTCTGTATC

AGTACTCCCGTCCTTTGATCAGTCATTTTTTTCACGAGGCCCCCTAAAGGGATAC

TTGGGCTCGTCCACCTCTATGTCGACCCAGCTATTCCATGCATGGGAAAAAGTCA

CTAATGTTCATGTGGTGAAGAGAGCTCTATCGTTAAAAGAATCTATAAACTGGTT

CATTACTAGAGATTCCAACTTGGCTCAAGCTCTAATTAGGAACATTATGTCTCTG

ACAGGCCCTGATTTCCCTCTAGAGGAGGCCCCTGTCTTCAAAAGGACGGGGTCA

GCCTTGCATAGGTTCAAGTCTGCCAGATACAGCGAAGGAGGGTATTCTTCTGTCT

GCCCGAACCTCCTCTCTCATATTTCTGTTAGTACAGACACCATGTCTGATTTGACC

CAAGACGGGAAGAACTACGATTTCATGTTCCAGCCATTGATGCTTTATGCACAGA

CATGGACATCAGAGCTGGTACAGAGAGACACAAGGCTAAGAGACTCTACGTTTC

ATTGGCACCTCCGATGCAACAGGTGTGTGAGACCCATTGACGACGTGACCCTGG

AGACCTCTCAGATCTTCGAGTTTCCGGATGTGTCGAAAAGAATATCCAGAATGGT

TTCTGGGGCTGTGCCTCACTTCCAGAGGCTTCCCGATATCCGTCTGAGACCAGGA

GATTTTGAATCTCTAAGCGGTAGAGAAAAGTCTCACCATATCGGATCAGCTCAG

GGGCTCTTATACTCAATCTTAGTGGCAATTCACGACTCAGGATACAATGATGGAA

CCATCTTCCCTGTCAACATATACGGCAAGGTTTCCCCTAGAGACTATTTGAGAGG

GCTCGCAAGGGGAGTATTGATAGGATCCTCGATTTGCTTCTTGACAAGAATGACA

AATATCAATATTAATAGACCTCTTGAATTGGTCTCAGGGGTAATCTCATATATTC

TCCTGAGGCTAGATAACCATCCCTCCTTGTACATAATGCTCAGAGAACCGTCTCT

TAGAGGAGAGATATTTTCTATCCCTCAGAAAATCCCCGCCGCTTATCCAACCACT

ATGAAAGAAGGCAACAGATCAATCTTGTGTTATCTCCAACATGTGCTACGCTATG

AGCGAGAGATAATCACGGCGTCTCCAGAGAATGACTGGCTATGGATCTTTTCAG

ACTTTAGAAGTGCCAAAATGACGTACCTATCCCTCATTACTTACCAGTCTCATCT

TCTACTCCAGAGGGTTGAGAGAAACCTATCTAAGAGTATGAGAGATAACCTGCG

ACAATTGAGTTCTTTGATGAGGCAGGTGCTGGGCGGGCACGGAGAAGATACCTT

AGAGTCAGACGACAACATTCAACGACTGCTAAAAGACTCTTTACGAAGGACAAG

ATGGGTGGATCAAGAGGTGCGCCATGCAGCTAGAACCATGACTGGAGATTACAG

CCCCAACAAGAAGGTGTCCCGTAAGGTAGGATGTTCAGAATGGGTCTGCTCTGC

TCAACAGGTTGCAGTCTCTACCTCAGCAAACCCGGCCCCTGTCTCGGAGCTTGAC

ATAAGGGCCCTCTCTAAGAGGTTCCAGAACCCTTTGATCTCGGGCTTGAGAGTGG

TTCAGTGGGCAACCGGTGCTCATTATAAGCTTAAGCCTATTCTAGATGATCTCAA

TGTTTTCCCATCTCTCTGCCTTGTAGTTGGGGACGGGTCAGGGGGGATATCAAGG

GCAGTCCTCAACATGTTTCAGATGCCAAGCTTGTGTTCAACAGTCTTTTAGAGG

TGAATGACCTGATGGCTTCCGGAACACATCCACTGCCTCCTTCAGCAATCATGAG
```

-continued

```
GGGAGGAAATGATATCGTCTCCAGAGTGATAGATCTTGACTCAATCTGGGAAAA

ACCGTCCGACTTGAGAAACTTGGCAACCTGGAAATACTTCCAGTCAGTCCAAAA

GCAGGTCAACATGTCCTATGACCTCATTATTTGCGATGCAGAAGTTACTGACATT

GCATCTATCAACCGGATCACCCTGTTAATGTCCGATTTTGCATTGTCTATAGATG

GACCACTCTATTTGGTCTTCAAAACTTATGGGACTATGCTAGTAAATCCAAACTA

CAAGGCTATTCAACACCTGTCAAGAGCGTTCCCCTCGGTCACAGGGTTTATCACC

CAAGTAACTTCGTCTTTTTCATCTGAGCTCTACCTCCGATTCTCCAAACGAGGGA

AGTTTTTCAGAGATGCTGAGTACTTGACCTCTTCCACCCTTCGAGAAATGAGCCT

TGTGTTATTCAATTGTAGCAGCCCCAAGAGTGAGATGCAGAGAGCTCGTTCCTTG

AACTATCAGGATCTTGTGAGAGGATTTCCTGAAGAAATCATATCAAATCCTTACA

ATGAGATGATCATAACTCTGATTGACAGTGATGTAGAATCTTTTCTAGTCCACAA

GATGGTTGATGATCTTGAGTTACAGAGGGGAACTCTGTCTAAAGTGGCTATCATT

ATAGCCATCATGATAGTTTTCTCCAACAGAGTCTTCAACGTTTCCAAACCCCTAA

CTGACCCCTCGTTCTATCCACCGTCTGATCCCAAAATCCTGAGGCACTTCAACAT

ATGTTGCAGTACTATGATGTATCTATCTACTGCTTTAGGTGACGTCCCTAGCTTCG

CAAGACTTCACGACCTGTATAACAGACCTATAACTTATTACTTCAGAAAGCAAGT

CATTCGAGGGAACGTTTATCTATCTTGGAGTTGGTCCAACGACACCTCAGTGTTC

AAAAGGGTAGCCTGTAATTCTAGCCTGAGTCTGTCATCTCACTGGATCAGGTTGA

TTTACAAGATAGTGAAGACTACCAGACTCGTTGGCAGCATCAAGGATCTATCCA

GAGAAGTGGAAAGACACCTTCATAGGTACAACAGGTGGATCACCCTAGAGGATA

TCAGATCTAGATCATCCCTACTAGACTACAGTTGCCTGTGAACCGGATACTCCTG

GAAGCCTGCCCATGCTAAGACTCTTGTGTGATGTATCTTGAAAAAAACAAGATCC

TAAATCTGAACCTTTGGTTGTTTGATTGTTTTTCTCAttfttgttgtttatttgttaagcgt
```

In one embodiment, the nucleic acid comprises the sequence of SEQ ID NO: 14, shown below (RABV vector: Coravax VS China):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAAATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC
```

-continued

```
TGCTTATGAAGACTGTTCAGGACTGGTATCATTTACTGGGTTCATAAAACAAATC
AATCTCACCGCTAGAGAGGCAATACTATATTTCTTCCACAAGAACTTTGAGGAAG
AGATAAGAAGAATGTTTGAGCCAGGGCAGGAGACAGCTGTTCCTCACTCTTATTT
CATCCACTTCCGTTCACTAGGCTTGAGTGGGAAATCTCCTTATTCATCAAATGCT
GTTGGTCACGTGTTCAATCTCATTCACTTTGTAGGATGCTATATGGGTCAAGTCA
GATCCCTAAATGCAACGGTTATTGCTGCATGTGCTCCTCATGAAATGTCTGTTCT
AGGGGGCTATCTGGGAGAGGAATTCTTCGGGAAAGGGACATTTGAAAGAAGATT
CTTCAGAGATGAGAAAGAACTTCAAGAATACGAGGCGGCTGAACTGACAAAGA
CTGACGTAGCACTGGCAGATGATGGAACTGTCAACTCTGACGACGAGGACTACT
TTTCAGGTGAAACCAGAAGTCCGGAGGCTGTTTATACTCGAATCATGATGAATG
GAGGTCGACTAAAGAGATCTCACATACGGAGATATGTCTCAGTCAGTTCCAATC
ATCAAGCCCGTCCAAACTCATTCGCCGAGTTTCTAAACAAGACATATTCGAGTGA
CTCATAAGAAGTTGAATAACAAAATGCCGGAAATCTACGGATTGTGTATATCCA
TCATGAAAAAAACTAACACCCCTCCTTTCGAACCATCCCAAACATGAGCAAGAT
CTTTGTCAATCCTAGTGCTATTAGAGCCGGTCTGGCCGATCTTGAGATGGCTGAA
GAAACTGTTGATCTGATCAATAGAAATATCGAAGACAATCAGGCTCATCTCCAA
GGGGAACCCATAGAGGTGGACAATCTCCCTGAGGATATGGGCGACTTCACCTG
GATGATGGAAAATCGCCCAACCATGGTGAGATAGCCAAGGTGGGAGAAGGCAA
GTATCGAGAGGACTTTCAGATGGATGAAGGAGAGGATCCTAGCTTCCTGTTCCA
GTCATACCTGGAAAATGTTGGAGTCCAAATAGTCAGACAAATGAGGTCAGGAGA
GAGATTTCTCAAGATATGGTCACAGACCGTAGAAGAGATTATATCCTATGTCGCG
GTCAACTTTCCCAACCCTCCAGGAAAGTCTTCAGAGGATAAATCAACCCAGACT
ACTGGCCGAGAGCTCAAGAAGGAGACAACACCCACTCCTTCTCAGAGAGAAAGC
CAATCATCGAAAGCCAGGATGGCGGCTCAAATTGCTTCTGGCCCTCCAGCCCTTG
AATGGTCGGCTACCAATGAAGAGGATGATCTATCAGTGGAGGCTGAGATCGCTC
ACCAGATTGCAGAAAGTTTCTCCAAAAAATATAAGTTTCCCTCTCGATCCTCAGG
GATACTCTTGTATAATTTTGAGCAATTGAAAATGAACCTTGATGATATAGTTAAA
GAGGCAAAAAATGTACCAGGTGTGACCCGTTTAGCCCATGACGGGTCCAAACTC
CCCCTAAGATGTGTACTGGGATGGGTCGCTTTGGCCAACTCTAAGAAATTCCAGT
TGTTAGTCGAATCCGACAAGCTGAGTAAAATCATGCAAGATGACTTGAATCGCT
ATACATCTTGCTAACCGAACCTCTCCCCTCAGTCCCTCTAGACAATAAAATCCGA
GATGTCCCAAAGTCAACATGAAAAAAACAGGCAACACCACTGATAAAATGAAC
CTCCTACGTAAGATAGTGAAAAACCGCAGGGACGAGGACACTCAAAAATCCTCT
CCCGCGTCAGCCCCTCTGGATGACGATGACTTGTGGCTTCCACCCCCTGAATACG
TCCCGCTGAAAGAACTTACAGGCAAGAAGAACATGAGGAACTTTTGTATCAACG
GAAGGGTTAAAGTGTGTAGCCCGAATGGTTACTCGTTCAGGATCCTGCGGCACA
TTCTGAAATCATTCGACGAGATATATTCTGGGAATCATAGGATGATCGGGTTAGT
CAAAGTGGTTATTGGACTGGCTTTGTCAGGATCTCCAGTCCCTGAGGGCCTGAAC
TGGGTATACAAATTGAGGAGAACCTTTATCTTCCAGTGGGCTGATTCCAGGGGCC
CTCTTGAAGGGGAGGAGTTGGAATACTCTCAGGAGATCACTTGGGATGATGATA
CTGAGTTCGTCGGATTGCAAATAAGAGTGATTGCAAAACAGTGTCATATCCAGG
```

-continued

```
GCAGAGTCTGGTGTATCAACATGAACCCGAGAGCATGTCAACTATGGTCTGACA

TGTCTCTTCAGACACAAAGGTCCGAAGAGGACAAAGATTCCTCTCTGCTTCTAGA

ATAATCAGATTATATCCCGCAAATTTATCACTTGTTTACCTCTGGAGGAGAGAAC

ATATGGGCTCAACTCCAACCCTTGGGAGCAATATAACAAAAAACATGTTATGGT

GCCATTAAACCGCTGCATTTCATCAAAGTCAAGTTGATTACCTTTACATTTTGATC

CTCTTGGATGTGAAAAAAACTATTAACATCCCTCAAAAGACCccgggccaccATGTTC

GTGTTTCTGGTGCTGCTGCCTCTGGTGAGCTCCCAGTGCGTGAACCTGACCACAA

GGACCCAGCTGCCCCCTGCCTATACCAATTCCTTCACACGGGGCGTGTACTATCC

CGACAAGGTGTTCCGGAGCAGCGTGCTGCACTCCACACAGGATCTGTTTCTGCCT

TTCTTTTCTAACGTGACCTGGTTCCACGCCATCCACGTGAGCGGCACCAATGGCA

CAAAGCGGTTCGACAATCCAGTGCTGCCCTTTAACGATGGCGTGTACTTCGCCTC

CACCGAGAAGTCTAACATCATCAGAGGCTGGATCTTTGGCACCACACTGGACAG

CAAGACACAGTCCCTGCTGATCGTGAACAATGCCACCAACGTGGTCATCAAGGT

GTGCGAGTTCCAGTTTTGTAATGATCCATTCCTGGGCGTGTACTATCACAAGAAC

AATAAGTCTTGGATGGAGAGCGAGTTTCGCGTGTATTCCTCTGCCAACAATTGCA

CATTTGAGTACGTGTCCCAGCCCTTCCTGATGGACCTGGAGGGCAAGCAGGGCA

ATTTCAAGAACCTGAGGGAGTTCGTGTTTAAGAATATCGATGGCTACTTCAAAAT

CTACTCCAAGCACACCCCAATCAACCTGGTGCGCGACCTGCCACAGGGCTTCTCT

GCCCTGGAGCCACTGGTGGATCTGCCCATCGGCATCAACATCACCCGGTTTCAGA

CACTGCTGGCCCTGCACAGAAGCTACCTGACACCAGGCGACAGCTCCTCTGGAT

GGACCGCAGGAGCAGCAGCCTACTATGTGGGCTATCTGCAGCCCAGGACCTTCC

TGCTGAAGTACAACGAGAATGGCACCATCACAGACGCCGTGGATTGCGCCCTGG

ATCCCCTGTCTGAGACCAAGTGTACACTGAAGAGCTTTACCGTGGAGAAGGGCA

TCTATCAGACAAGCAATTTCAGGGTGCAGCCTACCGAGTCCATCGTGCGCTTTCC

CAATATCACAAACCTGTGCCCTTTTGGCGAGGTGTTCAACGCAACCCGCTTCGCC

AGCGTGTACGCCTGGAATAGGAAGCGCATCTCCAACTGCGTGGCCGACTATTCT

GTGCTGTACAACAGCGCCTCCTTCTCTACCTTTAAGTGCTATGGCGTGAGCCCCA

CAAAGCTGAATGACCTGTGCTTTACCAACGTGTACGCCGATTCCTTCGTGATCAG

GGGCGACGAGGTGCGCCAGATCGCACCAGGACAGACAGGCAAGATCGCAGACT

ACAATTATAAGCTGCCTGACGATTTCACCGGCTGCGTGATCGCCTGGAACTCTAA

CAATCTGGATAGCAAAGTGGGCGGCAACTACAATTATCTGTACCGGCTGTTTAG

AAAGTCTAATCTGAAGCCATTCGAGAGGGACATCTCCACAGAAATCTACCAGGC

CGGCTCTACCCCCTGCAATGGCGTGGAgGGCTTTAACTGTTATTTCCCTCTGCAGA gCTACgGCTTCCAGCCAACAAACGGCGTGGGCTATCAGCCCTACCGCGTGGTGGT

GCTGTCTTTTGAGCTGCTGCACGCACcTGCAACAGTGTGCGGACCAAAGAAGAGC

ACCAATCTGGTGAAGAACAAGTGCGTGAACTTCAACTTCAACGGACTGACCGGA

ACAGGCGTGCTGACCGAGTCCAACAAGAAGTTCCTGCCTTTTCAGCAGTTCGGC

AGGGACATCGCAGATACCACAGACGCCGTGCGCGACCCTCAGACCCTGGAGATC

CTGGACATCACACCATGCTCCTTCGGCGGCGTGTCTGTGATCACACCAGGCACCA

ATACAAGCAACCAGGTGGCCGTGCTGTATCAGGACGTGAATTGTACCGAGGTGC
```

-continued

CAGTGGCAATCCACGCAGATCAGCTGACCCCTACATGGCGGGTGTACTCTACCG

GCAGCAACGTGTTCCAGACAAGAGCCGGATGCCTGATCGGAGCAGAGCACGTGA

ACAATAGCTATGAGTGCGACATCCCTATCGGCGCCGGCATCTGTGCCTCCTACCA

GACCCAGACAAACTCCCCAAGGTCTgtgggaGATGAGGCCGAAGACTTTGTGGAAG

TCCACCTGCCTGATGTGCATAACCAGGTGTCTGGCGTCGACCTGGGACTGCCAAA

TTGGGGCAAGTACGTGCTGCTGAGTGCTGGAGCACTGACTGCCCTGATGCTGATC

ATTTTCCTGATGACCTGCTGTCGGCGCGTGAACAGAAGTGAGCCCACTCAGCAC

AATCTGCGAGGAACCGGGAGAGAAGTGTCAGTCACACCTCAGAGCGGGAAAAT

CATTAGTAGTTGGGAATCACATAAAAGCGGGGGCGAGACCAGGCTGggatccggctcc ggcgagggcaggggaagtctactaacatgcggggacgtggaggaaaatcccggccccATGGTTCCTCAGGCTCT

CCTGTTTGTACCCCTTCTGGTTTTTCCATTGTGTTTGGGAAATTCCCTATTTACAC

GATACCAGACAAGCTTGGTCCCTGGAGTCCGATTGACATACATCACCTCAGCTGC

CCAAACAATTTGGTAGTGGAGGACGAAGGATGCACCAACCTGTCAGGGTTCTCC

TACATGGAACTTAAAGTTGGATACATCTTAGCCATAAAAGTGAACGGGTTCACTT

GCACAGGCGTTGTGACGGAGGCTGAAACCTACACTAACTTCGTTGGTTATGTCAC

AACCACGTTCAAAAGAAAGCATTTCCGCCCAACACCAGATGCATGTAGAGCCGC

GTACAACTGGAAGATGGCCGGTGACCCCAGATATGAAGAGTCTCTACACAATCC

GTACCCTGACTACCGCTGGCTTCGAACTGTAAAAACCACCAAGGAGTCTCTCGTT

ATCATATCTCCAAGTGTGGCAGATTTGGACCCATATGACAGATCCCTTCACTCGA

GGGTCTTCCCTAGCGGGAAGTGCTCAGGAGTAGCGGTGTCTTCTACCTACTGCTC

CACTAACCACGATTACACCATTTGGATGCCCGAGAATCCGAGACTAGGGATGTC

TTGTGACATTTTTACCAATAGTAGAGGGAAGAGAGCATCCAAAGGGAGTGAGAC

TTGCGGCTTTGTAGATGAAAGAGGCCTATATAAGTCTTTAAAAGGAGCATGCAA

ACTCAAGTTATGTGGAGTTCTAGGACTTAGACTTATGGATGGAACATGGGTCTCG

ATGCAAACATCAAATGAAACCAAATGGTGCCCTCCCGATAAGTTGGTGAACCTG

CACGACTTTCGCTCAGACGAAATTGAGCACCTTGTTGTAGAGGAGTTGGTCAGG

AAGAGAGAGGAGTGTCTGGATGCACTAGAGTCCATCATGACAACCAAGTCAGTG

AGTTTCAGACGTCTCAGTCATTTAAGAAAACTTGTCCCTGGGTTTGGAAAAGCAT

ATACCATATTCAACAAGACCTTGATGGAAGCCGATGCTCACTACAAGTCAGTCga gACTTGGAATGAGATCCTCCCTTCAAAAGGGTGTTTAAGAGTTGGGGGGAGGTGT

CATCCTCATGTGAACGGGGTGTTTTTCAATGGTATAATATTAGGACCTGACGGCA

ATGTCTTAATCCCAGAGATGCAATCATCCCTCCTCCAGCAACATATGGAGTTGTT

GGAATCCTCGGTTATCCCCCTTGTGCACCCCCTGGCAGACCCGTCTACCGTTTTC

AAGGACGGTGACGAGGCTGAGGATTTTGTTGAAGTTCACCTTCCCGATGTGCAC

AATCAGGTCTCAGGAGTTGACTTGGGTCTCCCGAACTGGGGGAAGTATGTATTAC

TGAGTGCAGGGGCCCTGACTGCCTTGATGTTGATAATTTTCCTGATGACATGTTG

TAGAAGAGTCAATCGATCAGAACCTACGCAACACAATCTCAGAGGGACAGGGA

GGGAGGTGTCAGTCACTCCCCAAAGCGGGAAGATCATATCTTCATGGGAATCAC

ACAAGAGTGGGGGTGAGACCAGACTGTAAgctagcTTATAAAGTGCTGGGTCATCT

AAGCTTTTCAGTCGAGAAAAAAACATTAGATCAGAAGAACAACTGGCAACACTT

CTCAACCTGAGACTTACTTCAAGATGCTCGATCCTGGAGAGGTCTATGATGACCC

-continued

```
TATTGACCCAATCGAGTTAGAGGCTGAACCCAGAGGAACCCCCATTGTCCCCAA

CATCTTGAGGAACTCTGACTACAATCTCAACTCTCCTTTGATAGAAGATCCTGCT

AGACTAATGTTAGAATGGTTAAAAACAGGGAATAGACCTTATCGGATGACTCTA

ACAGACAATTGCTCCAGGTCTTTCAGAGTTTTGAAAGATTATTTCAAGAAGGTAG

ATTTGGGTTCTCTCAAGGTGGGCGGAATGGCTGCACAGTCAATGATTTCTCTCTG

GTTATATGGTGCCCACTCTGAATCCAACAGGAGCCGGAGATGTATAACAGACTT

GGCCCATTTCTATTCCAAGTCGTCCCCCATAGAGAAGCTGTTGAATCTCACGCTA

GGAAATAGAGGGCTGAGAATCCCCCCAGAGGGAGTGTTAAGTTGCCTTGAGAGG

GTTGATTATGATAATGCATTTGGAAGGTATCTTGCCAACACGTATTCCTCTTACTT

GTTCTTCCATGTAATCACCTTATACATGAACGCCCTAGACTGGGATGAAGAAAAG

ACCATCCTAGCATTATGGAAAGATTTAACCTCAGTGGACATCGGGAAGGACTTG

GTAAAGTTCAAAGACCAAATATGGGGACTGCTGATCGTGACAAAGGACTTTGTT

TACTCCCAAAGTTCCAATTGTCTTTTTGACAGAAACTACACACTTATGCTAAAAG

ATCTTTTCTTGTCTCGCTTCAACTCCTTAATGGTCTTGCTCTCTCCCCCAGAGCCC

CGATACTCAGATGACTTGATATCTCAACTATGCCAGCTGTACATTGCTGGGGATC

AAGTCTTGTCTATGTGTGGAAACTCCGGCTATGAAGTCATCAAAATATTGGAGCC

ATATGTCGTGAATAGTTTAGTCCAGAGAGCAGAAAAGTTTAGGCCTCTCATTCAT

TCCTTGGGAGACTTTCCTGTATTTATAAAAGACAAGGTAAGTCAACTTGAAGAGA

CGTTCGGTCCCTGTGCAAGAAGGTTCTTTAGGGCTCTGGATCAATTCGACAACAT

ACATGACTTGGTTTTTGTGTTTGGCTGTTACAGGCATTGGGGGCACCCATATATA

GATTATCGAAAGGGTCTGTCAAAACTATATGATCAGGTTCACCTTAAAAAAATG

ATAGATAAGTCCTACCAGGAGTGCTTAGCAAGCGACCTAGCCAGGAGGATCCTT

AGATGGGTTTTGATAAGTACTCCAAGTGGTATCTGGATTCAAGATTCCTAGCCC

GAGACCACCCCTTGACTCCTTATATCAAAACCCAAACATGGCCACCCAAACATA

TTGTAGACTTGGTGGGGATACATGGCACAAGCTCCCGATCACGCAGATCTTTGA

GATTCCTGAATCAATGGATCCGTCAGAAATATTGGATGACAAATCACATTCTTTC

ACCAGAACGAGACTAGCTTCTTGGCTGTCAGAAAACCGAGGGGGGCCTGTTCCT

AGCGAAAAAGTTATTATCACGGCCCTGTCTAAGCCGCCTGTCAATCCCCGAGAG

TTTCTGAGGTCTATAGACCTCGGAGGATTGCCAGATGAAGACTTGATAATTGGCC

TCAAGCCAAAGGAACGGGAATTGAAGATTGAAGGTCGATTCTTTGCTCTAATGT

CATGGAATCTAAGATTGTATTTTGTCATCACTGAAAAACTCTTGGCCAACTACAT

CTTGCCACTTTTTGACGCGCTGACTATGACAGACAACCTGAACAAGGTGTTTAAA

AAGCTGATCGACAGGGTCACCGGGCAAGGGCTTTTGGACTATTCAAGGGTCACA

TATGCATTTCACCTGGACTATGAAAAGTGGAACAACCATCAAAGATTAGAGTCA

ACAGAGGATGTATTTTCTGTCCTAGATCAAGTGTTTGGATTGAAGAGAGTGTTTT

CTAGAACACACGAGTTTTTTCAAAAGGCCTGGATCTATTATTCAGACAGATCAGA

CCTCATCGGGTTACGGGAGGATCAAATATACTGCTTAGATGCGTCCAACGGCCC

AACCTGTTGGAATGGCCAGGATGGCGGGCTAGAAGGCTTACGGCAGAAGGGCTG

GAGTCTAGTCAGCTTATTGATGATAGATAGAGAATCTCAAATCAGGAACACAAG

AACCAAAATACTAGCTCAAGGAGACAACCAGGTTTTATGTCCGACATACATGTT
```

-continued

```
GTCGCCAGGGCTATCTCAAGAGGGGCTCCTCTATGAATTGGAGAGAATATCAAG

GAATGCACTTTCGATATACAGAGCCGTCGAGGAAGGGGCATCTAAGCTAGGGCT

GATCATCAAGAAAGAAGAGACCATGTGTAGTTATGACTTCCTCATCTATGGAAA

AACCCCTTTGTTTAGAGGTAACATATTGGTGCCTGAGTCCAAAAGATGGGCCAG

AGTCTCTTGCGTCTCTAATGACCAAATAGTCAACCTCGCCAATATAATGTCGACA

GTGTCCACCAATGCGCTAACAGTGGCACAACACTCTCAATCTTTGATCAAACCGA

TGAGGGATTTTCTGCTCATGTCAGTACAGGCAGTCTTTCACTACCTGCTATTTAGC

CCAATCTTAAAGGGAAGAGTTTACAAGATTCTGAGCGCTGAAGGGGAGAGCTTT

CTCCTAGCCATGTCAAGGATAATCTATCTAGATCCTTCTTTGGGAGGGATATCTG

GAATGTCCCTCGGAAGATTCCATATACGACAGTTCTCAGACCCTGTCTCTGAAGG

GTTATCCTTCTGGAGAGAGATCTGGTTAAGCTCCCAAGAGTCCTGGATTCACGCG

TTGTGTCAAGAGGCTGGAAACCCAGATCTTGGAGAGAGAACACTCGAGAGCTTC

ACTCGCCTTCTAGAAGATCCGACCACCTTAAATATCAGAGGAGGGGCCAGTCCT

ACCATTCTACTCAAGGATGCAATCAGAAAGGCTTTATATGACGAGGTGGACAAG

GTGGAAAATTCAGAGTTTCGAGAGGCAATCCTGTTGTCCAAGACCCATAGAGAT

AATTTTATACTCTTCTTAATATCTGTTGAGCCTCTGTTTCCTCGATTTCTCAGTGA

GCTATTCAGTTCGTCTTTTTTGGGAATCCCCGAGTCAATCATTGGATTGATACAA

AACTCCCGAACGATAAGAAGGCAGTTTAGAAAGAGTCTCTCAAAAACTTTAGAA

GAATCCTTCTACAACTCAGAGATCCACGGGATTAGTCGGATGACCCAGACACCT

CAGAGGGTTGGGGGGTGTGGCCTTGCTCTTCAGAGAGGGCAGATCTACTTAGG

GAGATCTCTTGGGGAAGAAAAGTGGTAGGCACGACAGTTCCTCACCCTTCTGAG

ATGTTGGGATTACTTCCCAAGTCCTCTATTTCTTGCACTTGTGGAGCAACAGGAG

GAGGCAATCCTAGAGTTTCTGTATCAGTACTCCCGTCCTTTGATCAGTCATTTTTT

TCACGAGGCCCCCTAAAGGGATACTTGGGCTCGTCCACCTCTATGTCGACCCAGC

TATTCCATGCATGGGAAAAAGTCACTAATGTTCATGTGGTGAAGAGAGCTCTATC

GTTAAAAGAATCTATAAACTGGTTCATTACTAGAGATTCCAACTTGGCTCAAGCT

CTAATTAGGAACATTATGTCTCTGACAGGCCCTGATTTCCCTCTAGAGGAGGCCC

CTGTCTTCAAAAGGACGGGGTCAGCCTTGCATAGGTTCAAGTCTGCCAGATACA

GCGAAGGAGGGTATTCTTCTGTCTGCCCGAACCTCCTCTCTCATATTTCTGTTAGT

ACAGACACCATGTCTGATTTGACCCAAGACGGGAAGAACTACGATTTCATGTTCC

AGCCATTGATGCTTTATGCACAGACATGGACATCAGAGCTGGTACAGAGAGACA

CAAGGCTAAGAGACTCTACGTTTCATTGGCACCTCCGATGCAACAGGTGTGTGA

GACCCATTGACGACGTGACCCTGGAGACCTCTCAGATCTTCGAGTTTCCGGATGT

GTCGAAAAGAATATCCAGAATGGTTTCTGGGGCTGTGCCTCACTTCCAGAGGCTT

CCCGATATCCGTCTGAGACCAGGAGATTTTGAATCTCTAAGCGGTAGAGAAAAG

TCTCACCATATCGGATCAGCTCAGGGGCTCTTATACTCAATCTTAGTGGCAATTC

ACGACTCAGGATACAATGATGGAACCATCTTCCCTGTCAACATATACGGCAAGG

TTTCCCCTAGAGACTATTTGAGAGGGCTCGCAAGGGGAGTATTGATAGGATCCTC

GATTTGCTTCTTGACAAGAATGACAAATATCAATATTAATAGACCTCTTGAATTG

GTCTCAGGGGTAATCTCATATATTCTCCTGAGGCTAGATAACCATCCCTCCTTGT

ACATAATGCTCAGAGAACCGTCTCTTAGAGGAGAGATATTTTCTATCCCTCAGAA
```

-continued

```
AATCCCCGCCGCTTATCCAACCACTATGAAAGAAGGCAACAGATCAATCTTGTG

TTATCTCCAACATGTGCTACGCTATGAGCGAGAGATAATCACGGCGTCTCCAGAG

AATGACTGGCTATGGATCTTTTCAGACTTTAGAAGTGCCAAAATGACGTACCTAT

CCCTCATTACTTACCAGTCTCATCTTCTACTCCAGAGGGTTGAGAGAAACCTATC

TAAGAGTATGAGAGATAACCTGCGACAATTGAGTTCTTTGATGAGGCAGGTGCT

GGGCGGGCACGGAGAAGATACCTTAGAGTCAGACGACAACATTCAACGACTGCT

AAAAGACTCTTTACGAAGGACAAGATGGGTGGATCAAGAGGTGCGCCATGCAGC

TAGAACCATGACTGGAGATTACAGCCCCAACAAGAAGGTGTCCCGTAAGGTAGG

ATGTTCAGAATGGGTCTGCTCTGCTCAACAGGTTGCAGTCTCTACCTCAGCAAAC

CCGGCCCCTGTCTCGGAGCTTGACATAAGGGCCCTCTCTAAGAGGTTCCAGAACC

CTTTGATCTCGGGCTTGAGAGTGGTTCAGTGGGCAACCGGTGCTCATTATAAGCT

TAAGCCTATTCTAGATGATCTCAATGTTTTCCCATCTCTCTGCCTTGTAGTTGGGG

ACGGGTCAGGGGGGATATCAAGGGCAGTCCTCAACATGTTTCCAGATGCCAAGC

TTGTGTTCAACAGTCTTTTAGAGGTGAATGACCTGATGGCTTCCGGAACACATCC

ACTGCCTCCTTCAGCAATCATGAGGGGAGGAAATGATATCGTCTCCAGAGTGAT

AGATCTTGACTCAATCTGGGAAAAACCGTCCGACTTGAGAAACTTGGCAACCTG

GAAATACTTCCAGTCAGTCCAAAAGCAGGTCAACATGTCCTATGACCTCATTATT

TGCGATGCAGAAGTTACTGACATTGCATCTATCAACCGGATCACCCTGTTAATGT

CCGATTTTGCATTGTCTATAGATGGACCACTCTATTTGGTCTTCAAAACTTATGGG

ACTATGCTAGTAAATCCAAACTACAAGGCTATTCAACACCTGTCAAGAGCGTTCC

CCTCGGTCACAGGGTTTATCACCCAAGTAACTTCGTCTTTTTCATCTGAGCTCTAC

CTCCGATTCTCCAAACGAGGGAAGTTTTTCAGAGATGCTGAGTACTTGACCTCTT

CCACCCTTCGAGAAATGAGCCTTGTGTTATTCAATTGTAGCAGCCCCAAGAGTGA

GATGCAGAGAGCTCGTTCCTTGAACTATCAGGATCTTGTGAGAGGATTTCCTGAA

GAAATCATATCAAATCCTTACAATGAGATGATCATAACTCTGATTGACAGTGATG

TAGAATCTTTTCTAGTCCACAAGATGGTTGATGATCTTGAGTTACAGAGGGGAAC

TCTGTCTAAAGTGGCTATCATTATAGCCATCATGATAGTTTTCTCCAACAGAGTC

TTCAACGTTTCCAAACCCCTAACTGACCCCTCGTTCTATCCACCGTCTGATCCCA

AAATCCTGAGGCACTTCAACATATGTTGCAGTACTATGATGTATCTATCTACTGC

TTTAGGTGACGTCCCTAGCTTCGCAAGACTTCACGACCTGTATAACAGACCTATA

ACTTATTACTTCAGAAAGCAAGTCATTCGAGGGAACGTTTATCTATCTTGGAGTT

GGTCCAACGACACCTCAGTGTTCAAAAGGGTAGCCTGTAATTCTAGCCTGAGTCT

GTCATCTCACTGGATCAGGTTGATTTACAAGATAGTGAAGACTACCAGACTCGTT

GGCAGCATCAAGGATCTATCCAGAGAAGTGGAAAGACACCTTCATAGGTACAAC

AGGTGGATCACCCTAGAGGATATCAGATCTAGATCATCCCTACTAGACTACAGTT

GCCTGTGAACCGGATACTCCTGGAAGCCTGCCCATGCTAAGACTCTTGTGTGATG

TATCTTGAAAAAAACAAGATCCTAAATCTGAACCTTTGGTTGTTTGATTGTTTTTC

TCATTTTGTTGTTTATTTGTTAAGCGT.
```

In one embodiment, the nucleic acid comprises the sequence of SEQ ID NO: 15, shown below (RABV vector: Coravax V5 South Africa):

```
ACGCTTAACAACCAGATCAAAGAAAAAACAGACATTGTCAATTGCAAAGCAAAA
ATGTAACACCCCTACAATGGATGCCGACAAGATTGTATTCAAAGTCAATAATCA
GGTGGTCTCTTTGAAGCCTGAGATTATCGTGGATCAATATGAGTACAAGTACCCT
GCCATCAAAGATTTGAAAAAGCCCTGTATAACCCTAGGAAAGGCTCCCGATTTA
AATAAAGCATACAAGTCAGTTTTGTCAGGCATGAGCGCCGCCAAACTTAATCCT
GACGATGTATGTTCCTATTTGGCAGCGGCAATGCAGTTTTTTGAGGGGACATGTC
CGGAAGACTGGACCAGCTATGGAATTGTGATTGCACGAAAAGGAGATAAGATCA
CCCCAGGTTCTCTGGTGGAGATAAAACGTACTGATGTAGAAGGGAATTGGGCTC
TGACAGGAGGCATGGAACTGACAAGAGACCCCACTGTCCCTGAGCATGCGTCCT
TAGTCGGTCTTCTCTTGAGTCTGTATAGGTTGAGCAAAATATCCGGGCAAAACAC
TGGTAACTATAAGACAAACATTGCAGACAGGATAGAGCAGATTTTTGAGACAGC
CCCTTTTGTTAAAATCGTGGAACACCATACTCTAATGACAACTCACAAATGTGT
GCTAATTGGAGTACTATACCAAACTTCAGATTTTTGGCCGGAACCTATGACATGT
TTTTCTCCCGGATTGAGCATCTATATTCAGCAATCAGAGTGGGCACAGTTGTCAC
TGCTTATGAAGACTGTTCAGGACTGGTATCATTTACTGGGTTCATAAAACAAATC
AATCTCACCGCTAGAGAGGCAATACTATATTTCTTCCACAAGAACTTTGAGGAAG
AGATAAGAAGAATGTTTGAGCCAGGGCAGGAGACAGCTGTTCCTCACTCTTATTT
CATCCACTTCCGTTCACTAGGCTTGAGTGGGAAATCTCCTTATTCATCAAATGCT
GTTGGTCACGTGTTCAATCTCATTCACTTTGTAGGATGCTATATGGGTCAAGTCA
GATCCCTAAATGCAACGGTTATTGCTGCATGTGCTCCTCATGAAATGTCTGTTCT
AGGGGGCTATCTGGGAGAGGAATTCTTCGGGAAAGGGACATTTGAAAGAAGATT
CTTCAGAGATGAGAAAGAACTTCAAGAATACGAGGCGGCTGAACTGACAAAGA
CTGACGTAGCACTGGCAGATGATGGAACTGTCAACTCTGACGACGAGGACTACT
TTTCAGGTGAAACCAGAAGTCCGGAGGCTGTTTATACTCGAATCATGATGAATG
GAGGTCGACTAAAGAGATCTCACATACGGAGATATGTCTCAGTCAGTTCCAATC
ATCAAGCCCGTCCAAACTCATTCGCCGAGTTTCTAAACAAGACATATTCGAGTGA
CTCATAAGAAGTTGAATAACAAAATGCCGGAAATCTACGGATTGTGTATATCCA
TCATGAAAAAAACTAACACCCCTCCTTTCGAACCATCCCAAACATGAGCAAGAT
CTTTGTCAATCCTAGTGCTATTAGAGCCGGTCTGGCCGATCTTGAGATGGCTGAA
GAAACTGTTGATCTGATCAATAGAAATATCGAAGACAATCAGGCTCATCTCCAA
GGGGAACCCATAGAGGTGGACAATCTCCCTGAGGATATGGGGCGACTTCACCTG
GATGATGGAAAATCGCCCAACCATGGTGAGATAGCCAAGGTGGGAGAAGGCAA
GTATCGAGAGGACTTTCAGATGGATGAAGGAGAGGATCCTAGCTTCCTGTTCCA
GTCATACCTGGAAAATGTTGGAGTCCAAATAGTCAGACAAATGAGGTCAGGAGA
GAGATTTCTCAAGATATGGTCACAGACCGTAGAAGAGATTATATCCTATGTCGCG
GTCAACTTTCCCAACCCTCCAGGAAAGTCTTCAGAGGATAAATCAACCCAGACT
ACTGGCCGAGAGCTCAAGAAGGAGACAACACCCCACTCCTTCTCAGAGAGAAAGC
CAATCATCGAAAGCCAGGATGGCGGCTCAAATTGCTTCTGGCCCTCCAGCCCTTG
```

-continued

```
AATGGTCGGCTACCAATGAAGAGGATGATCTATCAGTGGAGGCTGAGATCGCTC
ACCAGATTGCAGAAAGTTTCTCCAAAAAATATAAGTTTCCCTCTCGATCCTCAGG
GATACTCTTGTATAATTTTGAGCAATTGAAAATGAACCTTGATGATATAGTTAAA
GAGGCAAAAAATGTACCAGGTGTGACCCGTTTAGCCCATGACGGGTCCAAACTC
CCCCTAAGATGTGTACTGGGATGGGTCGCTTTGGCCAACTCTAAGAAATTCCAGT
TGTTAGTCGAATCCGACAAGCTGAGTAAAATCATGCAAGATGACTTGAATCGCT
ATACATCTTGCTAACCGAACCTCTCCCCTCAGTCCCTCTAGACAATAAAATCCGA
GATGTCCCAAAGTCAACATGAAAAAAACAGGCAACACCACTGATAAAATGAAC
CTCCTACGTAAGATAGTGAAAAACCGCAGGGACGAGGACACTCAAAAATCCTCT
CCCGCGTCAGCCCCTCTGGATGACGATGACTTGTGGCTTCCACCCCCTGAATACG
TCCCGCTGAAAGAACTTACAGGCAAGAAGAACATGAGGAACTTTTGTATCAACG
GAAGGGTTAAAGTGTGTAGCCCGAATGGTTACTCGTTCAGGATCCTGCGGCACA
TTCTGAAATCATTCGACGAGATATATTCTGGGAATCATAGGATGATCGGGTTAGT
CAAAGTGGTTATTGGACTGGCTTTGTCAGGATCTCCAGTCCCTGAGGGCCTGAAC
TGGGTATACAAATTGAGGAGAACCTTTATCTTCCAGTGGGCTGATTCCAGGGGCC
CTCTTGAAGGGGAGGAGTTGGAATACTCTCAGGAGATCACTTGGGATGATGATA
CTGAGTTCGTCGGATTGCAAATAAGAGTGATTGCAAAACAGTGTCATATCCAGG
GCAGAGTCTGGTGTATCAACATGAACCCGAGAGCATGTCAACTATGGTCTGACA
TGTCTCTTCAGACACAAAGGTCCGAAGAGGACAAAGATTCCTCTCTGCTTCTAGA
ATAATCAGATTATATCCCGCAAATTTATCACTTGTTTACCTCTGGAGGAGAGAAC
ATATGGGCTCAACTCCAACCCTTGGGAGCAATATAACAAAAAACATGTTATGGT
GCCATTAAACCGCTGCATTTCATCAAAGTCAAGTTGATTACCTTTACATTTTGATC
CTCTTGGATGTGAAAAAAACTATTAACATCCCTCAAAAGACCccgggccaccATGTTC
GTGTTTCTGGTGCTGCTGCCTCTGGTGAGCTCCCAGTGCGTGAACTTCACCACAA
GGACCCAGCTGCCCCCTGCCTATACCAATTCCTTCACACGGGGCGTGTACTATCC
CGACAAGGTGTTCCGGAGCAGCGTGCTGCACTCCACACAGGATCTGTTTCTGCCT
TTCTTTTCTAACGTGACCTGGTTCCACGCCATCCACGTGAGCGGCACCAATGGCA
CAAAGCGGTTCGCCAATCCAGTGCTGCCCTTTAACGATGGCGTGTACTTCGCCTC
CACCGAGAAGTCTAACATCATCAGAGGCTGGATCTTTGGCACCACACTGGACAG
CAAGACACAGTCCCTGCTGATCGTGAACAATGCCACCAACGTGGTCATCAAGGT
GTGCGAGTTCCAGTTTTGTAATGATCCATTCCTGGGCGTGTACTATCACAAGAAC
AATAAGTCTTGGATGGAGAGCGAGTTTCGCGTGTATTCCTCTGCCAACAATTGCA
CATTTGAGTACGTGTCCCAGCCCTTCCTGATGGACCTGGAGGGCAAGCAGGGCA
ATTTCAAGAACCTGAGGGAGTTCGTGTTTAAGAATATCGATGGCTACTTCAAAAT
CTACTCCAAGCACACCCCAATCAACCTGGTGCGCGGCCTGCCACAGGGCTTCTCT
GCCCTGGAGCCACTGGTGGATCTGCCCATCGGCATCAACATCACCCGGTTTCAGA
CACTGCTGGCCCTGCACAGAAGCTACCTGACACCAGGCGACAGCTCCTCTGGAT
GGACCGCAGGAGCAGCAGCCTACTATGTGGGCTATCTGCAGCCCAGGACCTTCC
TGCTGAAGTACAACGAGAATGGCACCATCACAGACGCCGTGGATTGCGCCCTGG
ATCCCCTGTCTGAGACCAAGTGTACACTGAAGAGCTTTACCGTGGAGAAGGGCA
TCTATCAGACAAGCAATTTCAGGGTGCAGCCTACCGAGTCCATCGTGCGCTTTCC
```

-continued

```
CAATATCACAAACCTGTGCCCTTTTGGCGAGGTGTTCAACGCAACCCGCTTCGCC

AGCGTGTACGCCTGGAATAGGAAGCGCATCTCCAACTGCGTGGCCGACTATTCT

GTGCTGTACAACAGCGCCTCCTTCTCTACCTTTAAGTGCTATGGCGTGAGCCCCA

CAAAGCTGAATGACCTGTGCTTTACCAACGTGTACGCCGATTCCTTCGTGATCAG

GGGCGACGAGGTGCGCCAGATCGCACCAGGACAGACAGGCAATATCGCAGACT

ACAATTATAAGCTGCCTGACGATTTCACCGGCTGCGTGATCGCCTGGAACTCTAA

CAATCTGGATAGCAAAGTGGGCGGCAACTACAATTATCTGTACCGGCTGTTTAG

AAAGTCTAATCTGAAGCCATTCGAGAGGGACATCTCCACAGAAATCTACCAGGC

CGGCTCTACCCCCTGCAATGGCGTGAAGGGCTTTAACTGTTATTTCCCTCTGCAG

AGCTACGGCTTCCAGCCAACATATGGCGTGGGCTATCAGCCCTACCGCGTGGTG

GTGCTGTCTTTTGAGCTGCTGCACGCACCTGCAACAGTGTGCGGACCAAAGAAG

AGCACCAATCTGGTGAAGAACAAGTGCGTGAACTTCAACTTCAACGGACTGACC

GGAACAGGCGTGCTGACCGAGTCCAACAAGAAGTTCCTGCCTTTTCAGCAGTTC

GGCAGGGACATCGCAGATACCACAGACGCCGTGCGCGACCCTCAGACCCTGGAG

ATCCTGGACATCACACCATGCTCCTTCGGCGGCGTGTCTGTGATCACACCAGGCA

CCAATACAAGCAACCAGGTGGCCGTGCTGTATCAGGGCGTGAATTGTACCGAGG

TGCCAGTGGCAATCCACGCAGATCAGCTGACCCCTACATGGCGGGTGTACTCTA

CCGGCAGCAACGTGTTCCAGACAAGAGCCGGATGCCTGATCGGAGCAGAGCACG

TGAACAATAGCTATGAGTGCGACATCCCTATCGGCGCCGGCATCTGTGCCTCCTA

CCAGACCCAGACAAACTCCCCAGAATCAAGCGTGATTCCTCTGGTCCATCCACTG

GCAGATCCCTCCACAGTGTTCAAAGACGGAGATGAGGCCGAAGACTTTGTGGAA

GTCCACCTGCCTGATGTGCATAACCAGGTGTCTGGCGTCGACCTGGGACTGCCAA

ATTGGGGCAAGTACGTGCTGCTGAGTGCTGGAGCACTGACTGCCCTGATGCTGAT

CATTTTCCTGATGACCTGCTGTCGGCGCGTGAACAGAAGTGAGCCCACTCAGCAC

AATCTGCGAGGAACCGGGAGAGAAGTGTCAGTCACACCTCAGAGCGGGAAAAT

CATTAGTAGTTGGGAATCACATAAAAGCGGGGGCGAGACCAGGCTGggatccggctcc ggcgagggcagggggaagtctactaacatgcggggacgtggaggaaaatcccggccccATGGTTCCTCAGGCTCT

CCTGTTTGTACCCCTTCTGGTTTTTCCATTGTGTTTGGGAAATTCCCTATTTACAC

GATACCAGACAAGCTTGGTCCCTGGAGTCCGATTGACATACATCACCTCAGCTGC

CCAAACAATTTGGTAGTGGAGGACGAAGGATGCACCAACCTGTCAGGGTTCTCC

TACATGGAACTTAAAGTTGGATACATCTTAGCCATAAAAGTGAACGGGTTCACTT

GCACAGGCGTTGTGACGGAGGCTGAAACCTACACTAACTTCGTTGGTTATGTCAC

AACCACGTTCAAAAGAAAGCATTTCCGCCCAACACCAGATGCATGTAGAGCCGC

GTACAACTGGAAGATGGCCGGTGACCCCAGATATGAAGAGTCTCTACACAATCC

GTACCCTGACTACCGCTGGCTTCGAACTGTAAAAACCACCAAGGAGTCTCTCGTT

ATCATATCTCCAAGTGTGGCAGATTTGGACCCATATGACAGATCCCTTCACTCGA

GGGTCTTCCCTAGCGGGAAGTGCTCAGGAGTAGCGGTGTCTTCTACCTACTGCTC

CACTAACCACGATTACACCATTTGGATGCCCGAGAATCCGAGACTAGGGATGTC

TTGTGACATTTTTACCAATAGTAGAGGGAAGAGAGCATCCAAAGGGAGTGAGAC

TTGCGGCTTTGTAGATGAAAGAGGCCTATATAAGTCTTTAAAAGGAGCATGCAA
```

-continued

```
ACTCAAGTTATGTGGAGTTCTAGGACTTAGACTTATGGATGGAACATGGGTCTCG
ATGCAAACATCAAATGAAACCAAATGGTGCCCTCCCGATAAGTTGGTGAACCTG
CACGACTTTCGCTCAGACGAAATTGAGCACCTTGTTGTAGAGGAGTTGGTCAGG
AAGAGAGAGGAGTGTCTGGATGCACTAGAGTCCATCATGACAACCAAGTCAGTG
AGTTTCAGACGTCTCAGTCATTTAAGAAAACTTGTCCCTGGGTTTGGAAAAGCAT
ATACCATATTCAACAAGACCTTGATGGAAGCCGATGCTCACTACAAGTCAGTCga
gACTTGGAATGAGATCCTCCCTTCAAAAGGGTGTTTAAGAGTTGGGGGGAGGTGT
CATCCTCATGTGAACGGGGTGTTTTTCAATGGTATAATATTAGGACCTGACGGCA
ATGTCTTAATCCCAGAGATGCAATCATCCCTCCTCCAGCAACATATGGAGTTGTT
GGAATCCTCGGTTATCCCCCTTGTGCACCCCCTGGCAGACCCGTCTACCGTTTTC
AAGGACGGTGACGAGGCTGAGGATTTTGTTGAAGTTCACCTTCCCGATGTGCAC
AATCAGGTCTCAGGAGTTGACTTGGGTCTCCCGAACTGGGGGAAGTATGTATTAC
TGAGTGCAGGGGCCCTGACTGCCTTGATGTTGATAATTTTCCTGATGACATGTTG
TAGAAGAGTCAATCGATCAGAACCTACGCAACACAATCTCAGAGGGACAGGGA
GGGAGGTGTCAGTCACTCCCCAAAGCGGGAAGATCATATCTTCATGGGAATCAC
ACAAGAGTGGGGGTGAGACCAGACTGTAAgctagcTTATAAAGTGCTGGGTCATCT
AAGCTTTTCAGTCGAGAAAAAAACATTAGATCAGAAGAACAACTGGCAACACTT
CTCAACCTGAGACTTACTTCAAGATGCTCGATCCTGGAGAGGTCTATGATGACCC
TATTGACCCAATCGAGTTAGAGGCTGAACCCAGAGGAACCCCCATTGTCCCCAA
CATCTTGAGGAACTCTGACTACAATCTCAACTCTCCTTTGATAGAAGATCCTGCT
AGACTAATGTTAGAATGGTTAAAAACAGGGAATAGACCTTATCGGATGACTCTA
ACAGACAATTGCTCCAGGTCTTTCAGAGTTTTGAAAGATTATTTCAAGAAGGTAG
ATTTGGGTTCTCTCAAGGTGGGCGGAATGGCTGCACAGTCAATGATTTCTCTCTG
GTTATATGGTGCCCACTCTGAATCCAACAGGAGCCGGAGATGTATAACAGACTT
GGCCCATTTCTATTCCAAGTCGTCCCCCATAGAGAAGCTGTTGAATCTCACGCTA
GGAAATAGAGGGCTGAGAATCCCCCCAGAGGGAGTGTTAAGTTGCCTTGAGAGG
GTTGATTATGATAATGCATTTGGAAGGTATCTTGCCAACACGTATTCCTCTTACTT
GTTCTTCCATGTAATCACCTTATACATGAACGCCCTAGACTGGGATGAAGAAAAG
ACCATCCTAGCATTATGGAAAGATTTAACCTCAGTGGACATCGGGAAGGACTTG
GTAAAGTTCAAAGACCAAATATGGGGACTGCTGATCGTGACAAAGGACTTTGTT
TACTCCCAAAGTTCCAATTGTCTTTTTGACAGAAACTACACACTTATGCTAAAAG
ATCTTTTCTTGTCTCGCTTCAACTCCTTAATGGTCTTGCTCTCTCCCCCAGAGCCC
CGATACTCAGATGACTTGATATCTCAACTATGCCAGCTGTACATTGCTGGGGATC
AAGTCTTGTCTATGTGTGGAAACTCCGGCTATGAAGTCATCAAAATATTGGAGCC
ATATGTCGTGAATAGTTTAGTCCAGAGAGCAGAAAAGTTTAGGCCTCTCATTCAT
TCCTTGGGAGACTTTCCTGTATTTATAAAAGACAAGGTAAGTCAACTTGAAGAGA
CGTTCGGTCCCTGTGCAAGAAGGTTCTTTAGGGCTCTGGATCAATTCGACAACAT
ACATGACTTGGTTTTTGTGTTTGGCTGTTACAGGCATTGGGGGCACCCATATATA
GATTATCGAAAGGGTCTGTCAAAACTATATGATCAGGTTCACCTTAAAAAAATG
ATAGATAAGTCCTACCAGGAGTGCTTAGCAAGCGACCTAGCCAGGAGGATCCTT
AGATGGGGTTTTGATAAGTACTCCAAGTGGTATCTGGATTCAAGATTCCTAGCCC
```

-continued

```
GAGACCACCCCTTGACTCCTTATATCAAAACCCAAACATGGCCACCCAAACATA

TTGTAGACTTGGTGGGGGATACATGGCACAAGCTCCCGATCACGCAGATCTTTGA

GATTCCTGAATCAATGGATCCGTCAGAAATATTGGATGACAAATCACATTCTTTC

ACCAGAACGAGACTAGCTTCTTGGCTGTCAGAAAACCGAGGGGGGCCTGTTCCT

AGCGAAAAAGTTATTATCACGGCCCTGTCTAAGCCGCCTGTCAATCCCCGAGAG

TTTCTGAGGTCTATAGACCTCGGAGGATTGCCAGATGAAGACTTGATAATTGGCC

TCAAGCCAAAGGAACGGGAATTGAAGATTGAAGGTCGATTCTTTGCTCTAATGT

CATGGAATCTAAGATTGTATTTTGTCATCACTGAAAAACTCTTGGCCAACTACAT

CTTGCCACTTTTTGACGCGCTGACTATGACAGACAACCTGAACAAGGTGTTTAAA

AAGCTGATCGACAGGGTCACCGGGCAAGGGCTTTTGGACTATTCAAGGGTCACA

TATGCATTTCACCTGGACTATGAAAAGTGGAACAACCATCAAAGATTAGAGTCA

ACAGAGGATGTATTTTCTGTCCTAGATCAAGTGTTTGGATTGAAGAGAGTGTTTT

CTAGAACACACGAGTTTTTTCAAAAGGCCTGGATCTATTATTCAGACAGATCAGA

CCTCATCGGGTTACGGGAGGATCAAATATACTGCTTAGATGCGTCCAACGGCCC

AACCTGTTGGAATGGCCAGGATGGCGGGCTAGAAGGCTTACGGCAGAAGGGCTG

GAGTCTAGTCAGCTTATTGATGATAGATAGAGAATCTCAAATCAGGAACACAAG

AACCAAAATACTAGCTCAAGGAGACAACCAGGTTTTATGTCCGACATACATGTT

GTCGCCAGGGCTATCTCAAGAGGGGCTCCTCTATGAATTGGAGAGAATATCAAG

GAATGCACTTTCGATATACAGAGCCGTCGAGGAAGGGGCATCTAAGCTAGGGCT

GATCATCAAGAAAGAAGAGACCATGTGTAGTTATGACTTCCTCATCTATGGAAA

AACCCCTTTGTTTAGAGGTAACATATTGGTGCCTGAGTCCAAAAGATGGGCCAG

AGTCTCTTGCGTCTCTAATGACCAAATAGTCAACCTCGCCAATATAATGTCGACA

GTGTCCACCAATGCGCTAACAGTGGCACAACACTCTCAATCTTTGATCAAACCGA

TGAGGGATTTTCTGCTCATGTCAGTACAGGCAGTCTTTCACTACCTGCTATTTAGC

CCAATCTTAAAGGGAAGAGTTTACAAGATTCTGAGCGCTGAAGGGGAGAGCTTT

CTCCTAGCCATGTCAAGGATAATCTATCTAGATCCTTCTTTGGGAGGGATATCTG

GAATGTCCCTCGGAAGATTCCATATACGACAGTTCTCAGACCCTGTCTCTGAAGG

GTTATCCTTCTGGAGAGAGATCTGGTTAAGCTCCCAAGAGTCCTGGATTCACGCG

TTGTGTCAAGAGGCTGGAAACCCAGATCTTGGAGAGAGAACACTCGAGAGCTTC

ACTCGCCTTCTAGAAGATCCGACCACCTTAAATATCAGAGGAGGGGCCAGTCCT

ACCATTCTACTCAAGGATGCAATCAGAAAGGCTTTATATGACGAGGTGGACAAG

GTGGAAAATTCAGAGTTTCGAGAGGCAATCCTGTTGTCCAAGACCCATAGAGAT

AATTTTATACTCTTCTTAATATCTGTTGAGCCTCTGTTTCCTCGATTTCTCAGTGA

GCTATTCAGTTCGTCTTTTTTGGGAATCCCCGAGTCAATCATTGGATTGATACAA

AACTCCCGAACGATAAGAAGGCAGTTTAGAAAGAGTCTCTCAAAAACTTTAGAA

GAATCCTTCTACAACTCAGAGATCCACGGGATTAGTCGGATGACCCAGACACCT

CAGAGGGTTGGGGGGGTGTGGCCTTGCTCTTCAGAGAGGGCAGATCTACTTAGG

GAGATCTCTTGGGGAAGAAAAGTGGTAGGCACGACAGTTCCTCACCCTTCTGAG

ATGTTGGGATTACTTCCCAAGTCCTCTATTTCTTGCACTTGTGGAGCAACAGGAG

GAGGCAATCCTAGAGTTTCTGTATCAGTACTCCCGTCCTTTGATCAGTCATTTTTT
```

-continued

```
TCACGAGGCCCCCTAAAGGGATACTTGGGCTCGTCCACCTCTATGTCGACCCAGC

TATTCCATGCATGGGAAAAAGTCACTAATGTTCATGTGGTGAAGAGAGCTCTATC

GTTAAAAGAATCTATAAACTGGTTCATTACTAGAGATTCCAACTTGGCTCAAGCT

CTAATTAGGAACATTATGTCTCTGACAGGCCCTGATTTCCCTCTAGAGGAGGCCC

CTGTCTTCAAAAGGACGGGGTCAGCCTTGCATAGGTTCAAGTCTGCCAGATACA

GCGAAGGAGGGTATTCTTCTGTCTGCCCGAACCTCCTCTCTCATATTTCTGTTAGT

ACAGACACCATGTCTGATTTGACCCAAGACGGGAAGAACTACGATTTCATGTTCC

AGCCATTGATGCTTTATGCACAGACATGGACATCAGAGCTGGTACAGAGAGACA

CAAGGCTAAGAGACTCTACGTTTCATTGGCACCTCCGATGCAACAGGTGTGTGA

GACCCATTGACGACGTGACCCTGGAGACCTCTCAGATCTTCGAGTTTCCGGATGT

GTCGAAAAGAATATCCAGAATGGTTTCTGGGGCTGTGCCTCACTTCCAGAGGCTT

CCCGATATCCGTCTGAGACCAGGAGATTTTGAATCTCTAAGCGGTAGAGAAAAG

TCTCACCATATCGGATCAGCTCAGGGGCTCTTATACTCAATCTTAGTGGCAATTC

ACGACTCAGGATACAATGATGGAACCATCTTCCCTGTCAACATATACGGCAAGG

TTTCCCCTAGAGACTATTTGAGAGGGCTCGCAAGGGGAGTATTGATAGGATCCTC

GATTTGCTTCTTGACAAGAATGACAAATATCAATATTAATAGACCTCTTGAATTG

GTCTCAGGGGTAATCTCATATATTCTCCTGAGGCTAGATAACCATCCCTCCTTGT

ACATAATGCTCAGAGAACCGTCTCTTAGAGGAGAGATATTTTCTATCCCTCAGAA

AATCCCCGCCGCTTATCCAACCACTATGAAAGAAGGCAACAGATCAATCTTGTG

TTATCTCCAACATGTGCTACGCTATGAGCGAGAGATAATCACGGCGTCTCCAGAG

AATGACTGGCTATGGATCTTTTCAGACTTTAGAAGTGCCAAAATGACGTACCTAT

CCCTCATTACTTACCAGTCTCATCTTCTACTCCAGAGGGTTGAGAGAAACCTATC

TAAGAGTATGAGAGATAACCTGCGACAATTGAGTTCTTTGATGAGGCAGGTGCT

GGGCGGGCACGGAGAAGATACCTTAGAGTCAGACGACAACATTCAACGACTGCT

AAAAGACTCTTTACGAAGGACAAGATGGGTGGATCAAGAGGTGCGCCATGCAGC

TAGAACCATGACTGGAGATTACAGCCCCAACAAGAAGGTGTCCCGTAAGGTAGG

ATGTTCAGAATGGGTCTGCTCTGCTCAACAGGTTGCAGTCTCTACCTCAGCAAAC

CCGGCCCCTGTCTCGGAGCTTGACATAAGGGCCCTCTCTAAGAGGTTCCAGAACC

CTTTGATCTCGGGCTTGAGAGTGGTTCAGTGGGCAACCGGTGCTCATTATAAGCT

TAAGCCTATTCTAGATGATCTCAATGTTTTCCCATCTCTCTGCCTTGTAGTTGGGG

ACGGGTCAGGGGGGATATCAAGGGCAGTCCTCAACATGTTTCCAGATGCCAAGC

TTGTGTTCAACAGTCTTTTAGAGGTGAATGACCTGATGGCTTCCGGAACACATCC

ACTGCCTCCTTCAGCAATCATGAGGGGAGGAAATGATATCGTCTCCAGAGTGAT

AGATCTTGACTCAATCTGGGAAAAACCGTCCGACTTGAGAAACTTGGCAACCTG

GAAATACTTCCAGTCAGTCCAAAAGCAGGTCAACATGTCCTATGACCTCATTATT

TGCGATGCAGAAGTTACTGACATTGCATCTATCAACCGGATCACCCTGTTAATGT

CCGATTTTGCATTGTCTATAGATGGACCACTCTATTTGGTCTTCAAAACTTATGGG

ACTATGCTAGTAAATCCAAACTACAAGGCTATTCAACACCTGTCAAGAGCGTTCC

CCTCGGTCACAGGGTTTATCACCCAAGTAACTTCGTCTTTTTCATCTGAGCTCTAC

CTCCGATTCTCCAAACGAGGGAAGTTTTTCAGAGATGCTGAGTACTTGACCTCTT

CCACCCTTCGAGAAATGAGCCTTGTGTTATTCAATTGTAGCAGCCCCAAGAGTGA
```

-continued

```
GATGCAGAGAGCTCGTTCCTTGAACTATCAGGATCTTGTGAGAGGATTTCCTGAA

GAAATCATATCAAATCCTTACAATGAGATGATCATAACTCTGATTGACAGTGATG

TAGAATCTTTTCTAGTCCACAAGATGGTTGATGATCTTGAGTTACAGAGGGGAAC

TCTGTCTAAAGTGGCTATCATTATAGCCATCATGATAGTTTTCTCCAACAGAGTC

TTCAACGTTTCCAAACCCCTAACTGACCCCTCGTTCTATCCACCGTCTGATCCCA

AAATCCTGAGGCACTTCAACATATGTTGCAGTACTATGATGTATCTATCTACTGC

TTTAGGTGACGTCCCTAGCTTCGCAAGACTTCACGACCTGTATAACAGACCTATA

ACTTATTACTTCAGAAAGCAAGTCATTCGAGGGAACGTTTATCTATCTTGGAGTT

GGTCCAACGACACCTCAGTGTTCAAAAGGGTAGCCTGTAATTCTAGCCTGAGTCT

GTCATCTCACTGGATCAGGTTGATTTACAAGATAGTGAAGACTACCAGACTCGTT

GGCAGCATCAAGGATCTATCCAGAGAAGTGGAAAGACACCTTCATAGGTACAAC

AGGTGGATCACCCTAGAGGATATCAGATCTAGATCATCCCTACTAGACTACAGTT

GCCTGTGAACCGGATACTCCTGGAAGCCTGCCCATGCTAAGACTCTTGTGTGATG

TATCTTGAAAAAAACAAGATCCTAAATCTGAACCTTTGGTTGTTTGATTGTTTTC

TCATTTTTGTTGTTTATTTGTTAAGCGT.
```

In one embodiment, the nucleic acid comprises the sequence of SEQ ID NO: 16, shown below (RABV vector: Coravax V6 China):

ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAAATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

-continued

```
CTGACGTAGCACTGGCAGATGATGGAACTGTCAACTCTGACGACGAGGACTACT
TTTCAGGTGAAACCAGAAGTCCGGAGGCTGTTTATACTCGAATCATGATGAATG
GAGGTCGACTAAAGAGATCTCACATACGGAGATATGTCTCAGTCAGTTCCAATC
ATCAAGCCCGTCCAAACTCATTCGCCGAGTTTCTAAACAAGACATATTCGAGTGA
CTCATAAGAAGTTGAATAACAAAATGCCGGAAATCTACGGATTGTGTATATCCA
TCATGAAAAAAACTAACACCCCTCCTTTCGAACCATCCCAAACATGAGCAAGAT
CTTTGTCAATCCTAGTGCTATTAGAGCCGGTCTGGCCGATCTTGAGATGGCTGAA
GAAACTGTTGATCTGATCAATAGAAATATCGAAGACAATCAGGCTCATCTCCAA
GGGGAACCCATAGAGGTGGACAATCTCCCTGAGGATATGGGGCGACTTCACCTG
GATGATGGAAAATCGCCCAACCATGGTGAGATAGCCAAGGTGGGAGAAGGCAA
GTATCGAGAGGACTTTCAGATGGATGAAGGAGAGGATCCTAGCTTCCTGTTCCA
GTCATACCTGGAAAATGTTGGAGTCCAAATAGTCAGACAAATGAGGTCAGGAGA
GAGATTTCTCAAGATATGGTCACAGACCGTAGAAGAGATTATATCCTATGTCGCG
GTCAACTTTCCCAACCCTCCAGGAAAGTCTTCAGAGGATAAATCAACCCAGACT
ACTGGCCGAGAGCTCAAGAAGGAGACAACACCCACTCCTTCTCAGAGAGAAAGC
CAATCATCGAAAGCCAGGATGGCGGCTCAAATTGCTTCTGGCCCTCCAGCCCTTG
AATGGTCGGCTACCAATGAAGAGGATGATCTATCAGTGGAGGCTGAGATCGCTC
ACCAGATTGCAGAAAGTTTCTCCAAAAAATATAAGTTTCCCTCTCGATCCTCAGG
GATACTCTTGTATAATTTTGAGCAATTGAAAATGAACCTTGATGATATAGTTAAA
GAGGCAAAAAATGTACCAGGTGTGACCCGTTTAGCCCATGACGGGTCCAAACTC
CCCCTAAGATGTGTACTGGGATGGGTCGCTTTGGCCAACTCTAAGAAATTCCAGT
TGTTAGTCGAATCCGACAAGCTGAGTAAAATCATGCAAGATGACTTGAATCGCT
ATACATCTTGCTAACCGAACCTCTCCCCTCAGTCCCTCTAGACAATAAAATCCGA
GATGTCCCAAAGTCAACATGAAAAAAACAGGCAACACCACTGATAAAATGAAC
CTCCTACGTAAGATAGTGAAAAACCGCAGGGACGAGGACACTCAAAAATCCTCT
CCCGCGTCAGCCCCTCTGGATGACGATGACTTGTGGCTTCCACCCCCTGAATACG
TCCCGCTGAAAGAACTTACAGGCAAGAAGAACATGAGGAACTTTTGTATCAACG
GAAGGGTTAAAGTGTGTAGCCCGAATGGTTACTCGTTCAGGATCCTGCGGCACA
TTCTGAAATCATTCGACGAGATATATTCTGGGAATCATAGGATGATCGGGTTAGT
CAAAGTGGTTATTGGACTGGCTTTGTCAGGATCTCCAGTCCCTGAGGGCCTGAAC
TGGGTATACAAATTGAGGAGAACCTTTATCTTCCAGTGGGCTGATTCCAGGGGCC
CTCTTGAAGGGGAGGAGTTGGAATACTCTCAGGAGATCACTTGGGATGATGATA
CTGAGTTCGTCGGATTGCAAATAAGAGTGATTGCAAAACAGTGTCATATCCAGG
GCAGAGTCTGGTGTATCAACATGAACCCGAGAGCATGTCAACTATGGTCTGACA
TGTCTCTTCAGACACAAAGGTCCGAAGAGGACAAAGATTCCTCTCTGCTTCTAGA
ATAATCAGATTATATCCCGCAAATTTATCACTTGTTTACCTCTGGAGGAGAGAAC
ATATGGGCTCAACTCCAACCCTTGGGAGCAATATAACAAAAAACATGTTATGGT
GCCATTAAACCGCTGCATTTCATCAAAGTCAAGTTGATTACCTTTACATTTTGATC
CTCTTGGATGTGAAAAAAACTATTAACATCCCTCAAAAGACCCcgggAAAGATGGT
TCCTCAGGCTCTCCTGTTTGTACCCCTTCTGGTTTTTCCATTGTGTTTTGGGAAATT
```

-continued

```
CCCTATTTACACGATACCAGACAAGCTTGGTCCCTGGAGTCCGATTGACATACAT
CACCTCAGCTGCCCAAACAATTTGGTAGTGGAGGACGAAGGATGCACCAACCTG
TCAGGGTTCTCCTACATGGAACTTAAAGTTGGATACATCTTAGCCATAAAAGTGA
ACGGGTTCACTTGCACAGGCGTTGTGACGGAGGCTGAAACCTACACTAACTTCGT
TGGTTATGTCACAACCACGTTCAAAAGAAAGCATTTCCGCCCAACACCAGATGC
ATGTAGAGCCGCGTACAACTGGAAGATGGCCGGTGACCCCAGATATGAAGAGTC
TCTACACAATCCGTACCCTGACTACCGCTGGCTTCGAACTGTAAAAACCACCAAG
GAGTCTCTCGTTATCATATCTCCAAGTGTGGCAGATTTGGACCCATATGACAGAT
CCCTTCACTCGAGGGTCTTCCCTAGCGGGAAGTGCTCAGGAGTAGCGGTGTCTTC
TACCTACTGCTCCACTAACCACGATTACACCATTTGGATGCCCGAGAATCCGAGA
CTAGGGATGTCTTGTGACATTTTTACCAATAGTAGAGGGAAGAGAGCATCCAAA
GGGAGTGAGACTTGCGGCTTTGTAGATGAAAGAGGCCTATATAAGTCTTTAAAA
GGAGCATGCAAACTCAAGTTATGTGGAGTTCTAGGACTTAGACTTATGGATGGA
ACATGGGTCTCGATGCAAACATCAAATGAAACCAAATGGTGCCCTCCCGATAAG
TTGGTGAACCTGCACGACTTTCGCTCAGACGAAATTGAGCACCTTGTTGTAGAGG
AGTTGGTCAGGAAGAGAGAGGAGTGTCTGGATGCACTAGAGTCCATCATGACAA
CCAAGTCAGTGAGTTTCAGACGTCTCAGTCATTTAAGAAAACTTGTCCCTGGGTT
TGGAAAAGCATATACCATATTCAACAAGACCTTGATGGAAGCCGATGCTCACTA
CAAGTCAGTCgagACTTGGAATGAGATCCTCCCTTCAAAAGGGTGTTTAAGAGTTG
GGGGGAGGTGTCATCCTCATGTGAACGGGGTGTTTTTCAATGGTATAATATTAGG
ACCTGACGGCAATGTCTTAATCCCAGAGATGCAATCATCCCTCCTCCAGCAACAT
ATGGAGTTGTTGGAATCCTCGGTTATCCCCCTTGTGCACCCCCTGGCAGACCCGT
CTACCGTTTTCAAGGACGGTGACGAGGCTGAGGATTTTGTTGAAGTTCACCTTCC
CGATGTGCACAATCAGGTCTCAGGAGTTGACTTGGGTCTCCCGAACTGGGGAA
GTATGTATTACTGAGTGCAGGGGCCCTGACTGCCTTGATGTTGATAATTTTCCTG
ATGACATGTTGTAGAAGAGTCAATCGATCAGAACCTACGCAACACAATCTCAGA
GGGACAGGGAGGGAGGTGTCAGTCACTCCCCAAAGCGGGAAGATCATATCTTCA
TGGGAATCACACAAGAGTGGGGGTGAGACCAGACTGTAAttaattaaCGTCCTTTCAA
CGATCCAAGTCcatgaaaaaaactaacacccctcccgtacgaccATGTTCGTGTTTCTGGTGCTGCT
GCCTCTGGTGAGCTCCCAGTGCGTGAACCTGACCACAAGGACCCAGCTGCCCCC
TGCCTATACCAATTCCTTCACACGGGGCGTGTACTATCCCGACAAGGTGTTCCGG
AGCAGCGTGCTGCACTCCACACAGGATCTGTTTCTGCCTTTCTTTTCTAACGTGAC
CTGGTTCCACGCCATCCACGTGAGCGGCACCAATGGCACAAAGCGGTTCGACAA
TCCAGTGCTGCCCTTTAACGATGGCGTGTACTTCGCCTCCACCGAGAAGTCTAAC
ATCATCAGAGGCTGGATCTTTGGCACCACACTGGACAGCAAGACACAGTCCCTG
CTGATCGTGAACAATGCCACCAACGTGGTCATCAAGGTGTGCGAGTTCCAGTTTT
GTAATGATCCATTCCTGGGCGTGTACTATCACAAGAACAATAAGTCTTGGATGGA
GAGCGAGTTTCGCGTGTATTCCTCTGCCAACAATTGCACATTTGAGTACGTGTCC
CAGCCCTTCCTGATGGACCTGGAGGGCAAGCAGGGCAATTTCAAGAACCTGAGG
GAGTTCGTGTTTAAGAATATCGATGGCTACTTCAAAATCTACTCCAAGCACACCC
CAATCAACCTGGTGCGCGACCTGCCACAGGGCTTCTCTGCCCTGGAGCCACTGGT
```

```
GGATCTGCCCATCGGCATCAACATCACCCGGTTTCAGACACTGCTGGCCCTGCAC
AGAAGCTACCTGACACCAGGCGACAGCTCCTCTGGATGGACCGCAGGAGCAGCA
GCCTACTATGTGGGCTATCTGCAGCCCAGGACCTTCCTGCTGAAGTACAACGAG
AATGGCACCATCACAGACGCCGTGGATTGCGCCCTGGATCCCCTGTCTGAGACC
AAGTGTACACTGAAGAGCTTTACCGTGGAGAAGGGCATCTATCAGACAAGCAAT
TTCAGGGTGCAGCCTACCGAGTCCATCGTGCGCTTTCCCAATATCACAAACCTGT
GCCCTTTTGGCGAGGTGTTCAACGCAACCCGCTTCGCCAGCGTGTACGCCTGGAA
TAGGAAGCGCATCTCCAACTGCGTGGCCGACTATTCTGTGCTGTACAACAGCGCC
TCCTTCTCTACCTTTAAGTGCTATGGCGTGAGCCCCACAAAGCTGAATGACCTGT
GCTTTACCAACGTGTACGCCGATTCCTTCGTGATCAGGGGCGACGAGGTGCGCC
AGATCGCACCAGGACAGACAGGCAAGATCGCAGACTACAATTATAAGCTGCCTG
ACGATTTCACCGGCTGCGTGATCGCCTGGAACTCTAACAATCTGGATAGCAAAGT
GGGCGGCAACTACAATTATCTGTACCGGCTGTTTAGAAAGTCTAATCTGAAGCCA
TTCGAGAGGGACATCTCCACAGAAATCTACCAGGCCGGCTCTACCCCCTGCAAT
GGCGTGGAgGGCTTTAACTGTTATTTCCCTCTGCAGAgCTACgGCTTCCAGCCAAC
AAACGGCGTGGGCTATCAGCCCTACCGCGTGGTGGTGCTGTCTTTTGAGCTGCTG
CACGCACcTGCAACAGTGTGCGGACCAAAGAAGAGCACCAATCTGGTGAAGAAC
AAGTGCGTGAACTTCAACTTCAACGGACTGACCGGAACAGGCGTGCTGACCGAG
TCCAACAAGAAGTTCCTGCCTTTTCAGCAGTTCGGCAGGGACATCGCAGATACC
ACAGACGCCGTGCGCGACCCTCAGACCCTGGAGATCCTGGACATCACACCATGC
TCCTTCGGCGGCGTGTCTGTGATCACACCAGGCACCAATACAAGCAACCAGGTG
GCCGTGCTGTATCAGGACGTGAATTGTACCGAGGTGCCAGTGGCAATCCACGCA
GATCAGCTGACCCCTACATGGCGGGTGTACTCTACCGGCAGCAACGTGTTCCAG
ACAAGAGCCGGATGCCTGATCGGAGCAGAGCACGTGAACAATAGCTATGAGTGC
GACATCCCTATCGGCGCCGGCATCTGTGCCTCCTACCAGACCCAGACAAACTCCC
CAAGGTCTGTGGGAGATGAGGCCGAAGACTTTGTGGAAGTCCACCTGCCTGATG
TGCATAACCAGGTGTCTGGCGTCGACCTGGGACTGCCAAATTGGGGCAAGTACG
TGCTGCTGAGTGCTGGAGCACTGACTGCCCTGATGCTGATCATTTTCCTGATGAC
CTGCTGTCGGCGCGTGAACAGAAGTGAGCCCACTCAGCACAATCTGCGAGGAAC
CGGGAGAGAAGTGTCAGTCACACCTCAGAGCGGGAAAATCATTAGTAGTTGGGA
ATCACATAAAAGCGGGGCGAGACCAGGCTGggatccggctccggcgagggcaggggaagtctact
aacatgcggggacgtggaggaaaatcccggccccATGCTCGATCCTGGAGAGGTCTATGATGACCC
TATTGACCCAATCGAGTTAGAGGCTGAACCCAGAGGAACCCCCATTGTCCCCAA
CATCTTGAGGAACTCTGACTACAATCTCAACTCTCCTTTGATAGAAGATCCTGCT
AGACTAATGTTAGAATGGTTAAAAACAGGGAATAGACCTTATCGGATGACTCTA
ACAGACAATTGCTCCAGGTCTTTCAGAGTTTTGAAAGATTATTTCAAGAAGGTAG
ATTTGGGTTCTCTCAAGGTGGGCGGAATGGCTGCACAGTCAATGATTTCTCTCTG
GTTATATGGTGCCCACTCTGAATCCAACAGGAGCCGGAGATGTATAACAGACTT
GGCCCATTTCTATTCCAAGTCGTCCCCCATAGAGAAGCTGTTGAATCTCACGCTA
GGAAATAGAGGGCTGAGAATCCCCCCAGAGGGAGTGTTAAGTTGCCTTGAGAGG
```

-continued
GTTGATTATGATAATGCATTTGGAAGGTATCTTGCCAACACGTATTCCTCTTACTT

GTTCTTCCATGTAATCACCTTATACATGAACGCCCTAGACTGGGATGAAGAAAAG

ACCATCCTAGCATTATGGAAAGATTTAACCTCAGTGGACATCGGGAAGGACTTG

GTAAAGTTCAAAGACCAAATATGGGGACTGCTGATCGTGACAAAGGACTTTGTT

TACTCCCAAAGTTCCAATTGTCTTTTTGACAGAAACTACACACTTATGCTAAAAG

ATCTTTTCTTGTCTCGCTTCAACTCCTTAATGGTCTTGCTCTCTCCCCCAGAGCCC

CGATACTCAGATGACTTGATATCTCAACTATGCCAGCTGTACATTGCTGGGGATC

AAGTCTTGTCTATGTGTGGAAACTCCGGCTATGAAGTCATCAAAATATTGGAGCC

ATATGTCGTGAATAGTTTAGTCCAGAGAGCAGAAAAGTTTAGGCCTCTCATTCAT

TCCTTGGGAGACTTTCCTGTATTTATAAAAGACAAGGTAAGTCAACTTGAAGAGA

CGTTCGGTCCCTGTGCAAGAAGGTTCTTTAGGGCTCTGGATCAATTCGACAACAT

ACATGACTTGGTTTTTGTGTTTGGCTGTTACAGGCATTGGGGGCACCCATATATA

GATTATCGAAAGGGTCTGTCAAAACTATATGATCAGGTTCACCTTAAAAAAATG

ATAGATAAGTCCTACCAGGAGTGCTTAGCAAGCGACCTAGCCAGGAGGATCCTT

AGATGGGGTTTTGATAAGTACTCCAAGTGGTATCTGGATTCAAGATTCCTAGCCC

GAGACCACCCCTTGACTCCTTATATCAAAACCCAAACATGGCCACCCAAACATA

TTGTAGACTTGGTGGGGATACATGGCACAAGCTCCCGATCACGCAGATCTTTGA

GATTCCTGAATCAATGGATCCGTCAGAAATATTGGATGACAAATCACATTCTTTC

ACCAGAACGAGACTAGCTTCTTGGCTGTCAGAAAACCGAGGGGGGCCTGTTCCT

AGCGAAAAAGTTATTATCACGGCCCTGTCTAAGCCGCCTGTCAATCCCCGAGAG

TTTCTGAGGTCTATAGACCTCGGAGGATTGCCAGATGAAGACTTGATAATTGGCC

TCAAGCCAAAGGAACGGGAATTGAAGATTGAAGGTCGATTCTTTGCTCTAATGT

CATGGAATCTAAGATTGTATTTTGTCATCACTGAAAAACTCTTGGCCAACTACAT

CTTGCCACTTTTTGACGCGCTGACTATGACAGACAACCTGAACAAGGTGTTTAAA

AAGCTGATCGACAGGGTCACCGGGCAAGGGCTTTTGGACTATTCAAGGGTCACA

TATGCATTTCACCTGGACTATGAAAAGTGGAACAACCATCAAAGATTAGAGTCA

ACAGAGGATGTATTTTCTGTCCTAGATCAAGTGTTTGGATTGAAGAGAGTGTTTT

CTAGAACACACGAGTTTTTTCAAAAGGCCTGGATCTATTATTCAGACAGATCAGA

CCTCATCGGGTTACGGGAGGATCAAATATACTGCTTAGATGCGTCCAACGGCCC

AACCTGTTGGAATGGCCAGGATGGCGGGCTAGAAGGCTTACGGCAGAAGGGCTG

GAGTCTAGTCAGCTTATTGATGATAGATAGAGAATCTCAAATCAGGAACACAAG

AACCAAAATACTAGCTCAAGGAGACAACCAGGTTTTATGTCCGACATACATGTT

GTCGCCAGGGCTATCTCAAGAGGGGCTCCTCTATGAATTGGAGAGAATATCAAG

GAATGCACTTTCGATATACAGAGCCGTCGAGGAAGGGGCATCTAAGCTAGGGCT

GATCATCAAGAAAGAAGAGACCATGTGTAGTTATGACTTCCTCATCTATGGAAA

AACCCCTTTGTTTAGAGGTAACATATTGGTGCCTGAGTCCAAAAGATGGGCCAG

AGTCTCTTGCGTCTCTAATGACCAAATAGTCAACCTCGCCAATATAATGTCGACA

GTGTCCACCAATGCGCTAACAGTGGCACAACACTCTCAATCTTTGATCAAACCGA

TGAGGGATTTTCTGCTCATGTCAGTACAGGCAGTCTTTCACTACCTGCTATTTAGC

CCAATCTTAAAGGGAAGAGTTTACAAGATTCTGAGCGCTGAAGGGGAGAGCTTT

CTCCTAGCCATGTCAAGGATAATCTATCTAGATCCTTCTTTGGGAGGGATATCTG

-continued

```
GAATGTCCCTCGGAAGATTCCATATACGACAGTTCTCAGACCCTGTCTCTGAAGG

GTTATCCTTCTGGAGAGAGATCTGGTTAAGCTCCCAAGAGTCCTGGATTCACGCG

TTGTGTCAAGAGGCTGGAAACCCAGATCTTGGAGAGAGAACACTCGAGAGCTTC

ACTCGCCTTCTAGAAGATCCGACCACCTTAAATATCAGAGGAGGGGCCAGTCCT

ACCATTCTACTCAAGGATGCAATCAGAAAGGCTTTATATGACGAGGTGGACAAG

GTGGAAAATTCAGAGTTTCGAGAGGCAATCCTGTTGTCCAAGACCCATAGAGAT

AATTTTATACTCTTCTTAATATCTGTTGAGCCTCTGTTTCCTCGATTTCTCAGTGA

GCTATTCAGTTCGTCTTTTTTGGGAATCCCCGAGTCAATCATTGGATTGATACAA

AACTCCCGAACGATAAGAAGGCAGTTTAGAAAGAGTCTCTCAAAAACTTTAGAA

GAATCCTTCTACAACTCAGAGATCCACGGGATTAGTCGGATGACCCAGACACCT

CAGAGGGTTGGGGGGTGTGGCCTTGCTCTTCAGAGAGGGCAGATCTACTTAGG

GAGATCTCTTGGGGAAGAAAAGTGGTAGGCACGACAGTTCCTCACCCTTCTGAG

ATGTTGGGATTACTTCCCAAGTCCTCTATTTCTTGCACTTGTGGAGCAACAGGAG

GAGGCAATCCTAGAGTTTCTGTATCAGTACTCCCGTCCTTTGATCAGTCATTTTT

TCACGAGGCCCCCTAAAGGGATACTTGGGCTCGTCCACCTCTATGTCGACCCAGC

TATTCCATGCATGGGAAAAAGTCACTAATGTTCATGTGGTGAAGAGAGCTCTATC

GTTAAAAGAATCTATAAACTGGTTCATTACTAGAGATTCCAACTTGGCTCAAGCT

CTAATTAGGAACATTATGTCTCTGACAGGCCCTGATTTCCCTCTAGAGGAGGCCC

CTGTCTTCAAAAGGACGGGGTCAGCCTTGCATAGGTTCAAGTCTGCCAGATACA

GCGAAGGAGGGTATTCTTCTGTCTGCCCGAACCTCCTCTCTCATATTTCTGTTAGT

ACAGACACCATGTCTGATTTGACCCAAGACGGGAAGAACTACGATTTCATGTTCC

AGCCATTGATGCTTTATGCACAGACATGGACATCAGAGCTGGTACAGAGAGACA

CAAGGCTAAGAGACTCTACGTTTCATTGGCACCTCCGATGCAACAGGTGTGTGA

GACCCATTGACGACGTGACCCTGGAGACCTCTCAGATCTTCGAGTTTCCGGATGT

GTCGAAAAGAATATCCAGAATGGTTTCTGGGGCTGTGCCTCACTTCCAGAGGCTT

CCCGATATCCGTCTGAGACCAGGAGATTTTGAATCTCTAAGCGGTAGAGAAAAG

TCTCACCATATCGGATCAGCTCAGGGCTCTTATACTCAATCTTAGTGGCAATTC

ACGACTCAGGATACAATGATGGAACCATCTTCCCTGTCAACATATACGGCAAGG

TTTCCCCTAGAGACTATTTGAGAGGGCTCGCAAGGGGAGTATTGATAGGATCCTC

GATTTGCTTCTTGACAAGAATGACAAATATCAATATTAATAGACCTCTTGAATTG

GTCTCAGGGGTAATCTCATATATTCTCCTGAGGCTAGATAACCATCCCTCCTTGT

ACATAATGCTCAGAGAACCGTCTCTTAGAGGAGAGATATTTTCTATCCCTCAGAA

AATCCCCGCCGCTTATCCAACCACTATGAAAGAAGGCAACAGATCAATCTTGTG

TTATCTCCAACATGTGCTACGCTATGAGCGAGAGATAATCACGGCGTCTCCAGAG

AATGACTGGCTATGGATCTTTTCAGACTTTAGAAGTGCCAAAATGACGTACCTAT

CCCTCATTACTTACCAGTCTCATCTTCTACTCCAGAGGGTTGAGAGAAACCTATC

TAAGAGTATGAGAGATAACCTGCGACAATTGAGTTCTTTGATGAGGCAGGTGCT

GGGCGGGCACGGAGAAGATACCTTAGAGTCAGACGACAACATTCAACGACTGCT

AAAAGACTCTTTACGAAGGACAAGATGGGTGGATCAAGAGGTGCGCCATGCAGC

TAGAACCATGACTGGAGATTACAGCCCCAACAAGAAGGTGTCCCGTAAGGTAGG
```

-continued

```
ATGTTCAGAATGGGTCTGCTCTGCTCAACAGGTTGCAGTCTCTACCTCAGCAAAC

CCGGCCCCTGTCTCGGAGCTTGACATAAGGGCCCTCTCTAAGAGGTTCCAGAACC

CTTTGATCTCGGGCTTGAGAGTGGTTCAGTGGGCAACCGGTGCTCATTATAAGCT

TAAGCCTATTCTAGATGATCTCAATGTTTTCCCATCTCTCTGCCTTGTAGTTGGGG

ACGGGTCAGGGGGGATATCAAGGGCAGTCCTCAACATGTTTCCAGATGCCAAGC

TTGTGTTCAACAGTCTTTTAGAGGTGAATGACCTGATGGCTTCCGGAACACATCC

ACTGCCTCCTTCAGCAATCATGAGGGGAGGAAATGATATCGTCTCCAGAGTGAT

AGATCTTGACTCAATCTGGGAAAAACCGTCCGACTTGAGAAACTTGGCAACCTG

GAAATACTTCCAGTCAGTCCAAAAGCAGGTCAACATGTCCTATGACCTCATTATT

TGCGATGCAGAAGTTACTGACATTGCATCTATCAACCGGATCACCCTGTTAATGT

CCGATTTTGCATTGTCTATAGATGGACCACTCTATTTGGTCTTCAAAACTTATGGG

ACTATGCTAGTAAATCCAAACTACAAGGCTATTCAACACCTGTCAAGAGCGTTCC

CCTCGGTCACAGGGTTTATCACCCAAGTAACTTCGTCTTTTTCATCTGAGCTCTAC

CTCCGATTCTCCAAACGAGGGAAGTTTTTCAGAGATGCTGAGTACTTGACCTCTT

CCACCCTTCGAGAAATGAGCCTTGTGTTATTCAATTGTAGCAGCCCCAAGAGTGA

GATGCAGAGAGCTCGTTCCTTGAACTATCAGGATCTTGTGAGAGGATTTCCTGAA

GAAATCATATCAAATCCTTACAATGAGATGATCATAACTCTGATTGACAGTGATG

TAGAATCTTTTCTAGTCCACAAGATGGTTGATGATCTTGAGTTACAGAGGGGAAC

TCTGTCTAAAGTGGCTATCATTATAGCCATCATGATAGTTTTCTCCAACAGAGTC

TTCAACGTTTCCAAACCCCTAACTGACCCCTCGTTCTATCCACCGTCTGATCCCA

AAATCCTGAGGCACTTCAACATATGTTGCAGTACTATGATGTATCTATCTACTGC

TTTAGGTGACGTCCCTAGCTTCGCAAGACTTCACGACCTGTATAACAGACCTATA

ACTTATTACTTCAGAAAGCAAGTCATTCGAGGGAACGTTTATCTATCTTGGAGTT

GGTCCAACGACACCTCAGTGTTCAAAAGGGTAGCCTGTAATTCTAGCCTGAGTCT

GTCATCTCACTGGATCAGGTTGATTTACAAGATAGTGAAGACTACCAGACTCGTT

GGCAGCATCAAGGATCTATCCAGAGAAGTGGAAAGACACCTTCATAGGTACAAC

AGGTGGATCACCCTAGAGGATATCAGATCTAGATCATCCCTACTAGACTACAGTT

GCCTGTGAACCGGATACTCCTGGAAGCCTGCCCATGCTAAGACTCTTGTGTGATG

TATCTTGAAAAAAACAAGATCCTAAATCTGAACCTTTGGTTGTTTGATTGTTTTC

TCATTTTTGTTGTTTATTTGTTAAGCGT.
```

In one embodiment, the nucleic acid comprises the sequence of SEQ ID NO: 17, shown below (RABV vector: Coravax V6 South Africa):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA
```

-continued

```
CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAAATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAGAAGTTGAATAACAAAATGCCGGAAATCTACGGATTGTGTATATCCA

TCATGAAAAAAACTAACACCCCTCCTTTCGAACCATCCCAAACATGAGCAAGAT

CTTTGTCAATCCTAGTGCTATTAGAGCCGGTCTGGCCGATCTTGAGATGGCTGAA

GAAACTGTTGATCTGATCAATAGAAATATCGAAGACAATCAGGCTCATCTCCAA

GGGGAACCCATAGAGGTGGACAATCTCCCTGAGGATATGGGGCGACTTCACCTG

GATGATGGAAAATCGCCCAACCATGGTGAGATAGCCAAGGTGGGAGAAGGCAA

GTATCGAGAGGACTTTCAGATGGATGAAGGAGAGGATCCTAGCTTCCTGTTCCA

GTCATACCTGGAAAATGTTGGAGTCCAAATAGTCAGACAAATGAGGTCAGGAGA

GAGATTTCTCAAGATATGGTCACAGACCGTAGAAGAGATTATATCCTATGTCGCG

GTCAACTTTCCCAACCCTCCAGGAAAGTCTTCAGAGGATAAATCAACCCAGACT

ACTGGCCGAGAGCTCAAGAAGGAGACAACACCCACTCCTTCTCAGAGAGAAAGC

CAATCATCGAAAGCCAGGATGGCGGCTCAAATTGCTTCTGGCCCTCCAGCCCTTG

AATGGTCGGCTACCAATGAAGAGGATGATCTATCAGTGGAGGCTGAGATCGCTC

ACCAGATTGCAGAAAGTTTCTCCAAAAAATATAAGTTTCCCTCTCGATCCTCAGG

GATACTCTTGTATAATTTTGAGCAATTGAAAATGAACCTTGATGATATAGTTAAA

GAGGCAAAAAATGTACCAGGTGTGACCCGTTTAGCCCATGACGGGTCCAAACTC

CCCCTAAGATGTGTACTGGGATGGGTCGCTTTGGCCAACTCTAAGAAATTCCAGT

TGTTAGTCGAATCCGACAAGCTGAGTAAAATCATGCAAGATGACTTGAATCGCT

ATACATCTTGCTAACCGAACCTCTCCCCTCAGTCCCTCTAGACAATAAAATCCGA

GATGTCCCAAAGTCAACATGAAAAAAACAGGCAACACCACTGATAAAATGAAC

CTCCTACGTAAGATAGTGAAAAACCGCAGGGACGAGGACACTCAAAAATCCTCT

CCCGCGTCAGCCCCTCTGGATGACGATGACTTGTGGCTTCCACCCCCTGAATACG
```

-continued

```
TCCCGCTGAAAGAACTTACAGGCAAGAAGAACATGAGGAACTTTTGTATCAACG

GAAGGGTTAAAGTGTGTAGCCCGAATGGTTACTCGTTCAGGATCCTGCGGCACA

TTCTGAAATCATTCGACGAGATATATTCTGGGAATCATAGGATGATCGGGTTAGT

CAAAGTGGTTATTGGACTGGCTTTGTCAGGATCTCCAGTCCCTGAGGGCCTGAAC

TGGGTATACAAATTGAGGAGAACCTTTATCTTCCAGTGGGCTGATTCCAGGGGCC

CTCTTGAAGGGGAGGAGTTGGAATACTCTCAGGAGATCACTTGGGATGATGATA

CTGAGTTCGTCGGATTGCAAATAAGAGTGATTGCAAAACAGTGTCATATCCAGG

GCAGAGTCTGGTGTATCAACATGAACCCGAGAGCATGTCAACTATGGTCTGACA

TGTCTCTTCAGACACAAAGGTCCGAAGAGGACAAAGATTCCTCTCTGCTTCTAGA

ATAATCAGATTATATCCCGCAAATTTATCACTTGTTTACCTCTGGAGGAGAGAAC

ATATGGGCTCAACTCCAACCCTTGGGAGCAATATAACAAAAAACATGTTATGGT

GCCATTAAACCGCTGCATTTCATCAAAGTCAAGTTGATTACCTTTACATTTTGATC

CTCTTGGATGTGAAAAAAACTATTAACATCCCTCAAAAGACCccgggAAAGATGGT

TCCTCAGGCTCTCCTGTTTGTACCCCTTCTGGTTTTTCCATTGTGTTTTGGGAAATT

CCCTATTTACACGATACCAGACAAGCTTGGTCCCTGGAGTCCGATTGACATACAT

CACCTCAGCTGCCCAAACAATTTGGTAGTGGAGGACGAAGGATGCACCAACCTG

TCAGGGTTCTCCTACATGGAACTTAAAGTTGGATACATCTTAGCCATAAAAGTGA

ACGGGTTCACTTGCACAGGCGTTGTGACGGAGGCTGAAACCTACACTAACTTCGT

TGGTTATGTCACAACCACGTTCAAAAGAAAGCATTTCCGCCCAACACCAGATGC

ATGTAGAGCCGCGTACAACTGGAAGATGGCCGGTGACCCCAGATATGAAGAGTC

TCTACACAATCCGTACCCTGACTACCGCTGGCTTCGAACTGTAAAAACCACCAAG

GAGTCTCTCGTTATCATATCTCCAAGTGTGGCAGATTTGGACCCATATGACAGAT

CCCTTCACTCGAGGGTCTTCCCTAGCGGGAAGTGCTCAGGAGTAGCGGTGTCTTC

TACCTACTGCTCCACTAACCACGATTACACCATTTGGATGCCCGAGAATCCGAGA

CTAGGGATGTCTTGTGACATTTTTACCAATAGTAGAGGGAAGAGAGCATCCAAA

GGGAGTGAGACTTGCGGCTTTGTAGATGAAAGAGGCCTATATAAGTCTTTAAAA

GGAGCATGCAAACTCAAGTTATGTGGAGTTCTAGGACTTAGACTTATGGATGGA

ACATGGGTCTCGATGCAAACATCAAATGAAACCAAATGGTGCCCTCCCGATAAG

TTGGTGAACCTGCACGACTTTCGCTCAGACGAAATTGAGCACCTTGTTGTAGAGG

AGTTGGTCAGGAAGAGAGAGGAGTGTCTGGATGCACTAGAGTCCATCATGACAA

CCAAGTCAGTGAGTTTCAGACGTCTCAGTCATTTAAGAAAACTTGTCCCTGGGTT

TGGAAAAGCATATACCATATTCAACAAGACCTTGATGGAAGCCGATGCTCACTA

CAAGTCAGTCgagACTTGGAATGAGATCCTCCCTTCAAAAGGGTGTTTAAGAGTTG

GGGGGAGGTGTCATCCTCATGTGAACGGGGTGTTTTTCAATGGTATAATATTAGG

ACCTGACGGCAATGTCTTAATCCCAGAGATGCAATCATCCCTCCTCCAGCAACAT

ATGGAGTTGTTGGAATCCTCGGTTATCCCCCTTGTGCACCCCCTGGCAGACCCGT

CTACCGTTTTCAAGGACGGTGACGAGGCTGAGGATTTTGTTGAAGTTCACCTTCC

CGATGTGCACAATCAGGTCTCAGGAGTTGACTTGGGTCTCCCGAACTGGGGGAA

GTATGTATTACTGAGTGCAGGGGCCCTGACTGCCTTGATGTTGATAATTTTCCTG

ATGACATGTTGTAGAAGAGTCAATCGATCAGAACCTACGCAACACAATCTCAGA
```

-continued

```
GGGACAGGGAGGGAGGTGTCAGTCACTCCCCAAAGCGGGAAGATCATATCTTCA

TGGGAATCACACAAGAGTGGGGGTGAGACCAGACTGTAAttaattaaCGTCCTTTCAA

CGATCCAAGTCcatgaaaaaaactaacacccctcccgtacgaccATGTTCGTGTTTCTGGTGCTGCT

GCCTCTGGTGAGCTCCCAGTGCGTGAACTTCACCACAAGGACCCAGCTGCCCCCT

GCCTATACCAATTCCTTCACACGGGGCGTGTACTATCCCGACAAGGTGTTCCGGA

GCAGCGTGCTGCACTCCACACAGGATCTGTTTCTGCCTTTCTTTTCTAACGTGACC

TGGTTCCACGCCATCCACGTGAGCGGCACCAATGGCACAAAGCGGTTCGCCAAT

CCAGTGCTGCCCTTTAACGATGGCGTGTACTTCGCCTCCACCGAGAAGTCTAACA

TCATCAGAGGCTGGATCTTTGGCACCACACTGGACAGCAAGACACAGTCCCTGC

TGATCGTGAACAATGCCACCAACGTGGTCATCAAGGTGTGCGAGTTCCAGTTTTG

TAATGATCCATTCCTGGGCGTGTACTATCACAAGAACAATAAGTCTTGGATGGAG

AGCGAGTTTCGCGTGTATTCCTCTGCCAACAATTGCACATTTGAGTACGTGTCCC

AGCCCTTCCTGATGGACCTGGAGGGCAAGCAGGGCAATTTCAAGAACCTGAGGG

AGTTCGTGTTTAAGAATATCGATGGCTACTTCAAAATCTACTCCAAGCACACCCC

AATCAACCTGGTGCGCGGCCTGCCACAGGGCTTCTCTGCCCTGGAGCCACTGGTG

GATCTGCCCATCGGCATCAACATCACCCGGTTTCAGACACTGCTGGCCCTGCACA

GAAGCTACCTGACACCAGGCGACAGCTCCTCTGGATGGACCGCAGGAGCAGCAG

CCTACTATGTGGGCTATCTGCAGCCCAGGACCTTCCTGCTGAAGTACAACGAGA

ATGGCACCATCACAGACGCCGTGGATTGCGCCCTGGATCCCCTGTCTGAGACCA

AGTGTACACTGAAGAGCTTTACCGTGGAGAAGGGCATCTATCAGACAAGCAATT

TCAGGGTGCAGCCTACCGAGTCCATCGTGCGCTTTCCCAATATCACAAACCTGTG

CCCTTTTGGCGAGGTGTTCAACGCAACCCGCTTCGCCAGCGTGTACGCCTGGAAT

AGGAAGCGCATCTCCAACTGCGTGGCCGACTATTCTGTGCTGTACAACAGCGCCT

CCTTCTCTACCTTTAAGTGCTATGGCGTGAGCCCCACAAAGCTGAATGACCTGTG

CTTTACCAACGTGTACGCCGATTCCTTCGTGATCAGGGGCGACGAGGTGCGCCA

GATCGCACCAGGACAGACAGGCAATATCGCAGACTACAATTATAAGCTGCCTGA

CGATTTCACCGGCTGCGTGATCGCCTGGAACTCTAACAATCTGGATAGCAAAGTG

GGCGGCAACTACAATTATCTGTACCGGCTGTTTAGAAAGTCTAATCTGAAGCCAT

TCGAGAGGGACATCTCCACAGAAATCTACCAGGCCGGCTCTACCCCCTGCAATG

GCGTGAAGGGCTTTAACTGTTATTTCCCTCTGCAGAGCTACGGCTTCCAGCCAAC

ATATGGCGTGGGCTATCAGCCCTACCGCGTGGTGGTGCTGTCTTTTGAGCTGCTG

CACGCACCTGCAACAGTGTGCGGACCAAAGAAGAGCACCAATCTGGTGAAGAA

CAAGTGCGTGAACTTCAACTTCAACGGACTGACCGGAACAGGCGTGCTGACCGA

GTCCAACAAGAAGTTCCTGCCTTTTCAGCAGTTCGGCAGGGACATCGCAGATAC

CACAGACGCCGTGCGCGACCCTCAGACCCTGGAGATCCTGGACATCACACCATG

CTCCTTCGGCGGCGTGTCTGTGATCACACCAGGCACCAATACAAGCAACCAGGT

GGCCGTGCTGTATCAGGGCGTGAATTGTACCGAGGTGCCAGTGGCAATCCACGC

AGATCAGCTGACCCCTACATGGCGGGTGTACTCTACCGGCAGCAACGTGTTCCA

GACAAGAGCCGGATGCCTGATCGGAGCAGAGCACGTGAACAATAGCTATGAGTG

CGACATCCCTATCGGCGCCGGCATCTGTGCCTCCTACCAGACCCAGACAAACTCC

CCAGAATCAAGCGTGATTCCTCTGGTCCATCCACTGGCAGATCCCTCCACAGTGT
```

TCAAAGACGGAGATGAGGCCGAAGACTTTGTGGAAGTCCACCTGCCTGATGTGC

ATAACCAGGTGTCTGGCGTCGACCTGGGACTGCCAAATTGGGGCAAGTACGTGC

TGCTGAGTGCTGGAGCACTGACTGCCCTGATGCTGATCATTTTCCTGATGACCTG

CTGTCGGCGCGTGAACAGAAGTGAGCCCACTCAGCACAATCTGCGAGGAACCGG

GAGAGAAGTGTCAGTCACACCTCAGAGCGGGAAAATCATTAGTAGTTGGGAATC

ACATAAAAGCGGGGGCGAGACCAGGCTGggatccggctccggcgagggcaggggaagtctactaacat gcggggacgtggaggaaaatcccggccccATGCTCGATCCTGGAGAGGTCTATGATGACCCTAT

TGACCCAATCGAGTTAGAGGCTGAACCCAGAGGAACCCCCATTGTCCCCAACAT

CTTGAGGAACTCTGACTACAATCTCAACTCTCCTTTGATAGAAGATCCTGCTAGA

CTAATGTTAGAATGGTTAAAAACAGGGAATAGACCTTATCGGATGACTCTAACA

GACAATTGCTCCAGGTCTTTCAGAGTTTTGAAAGATTATTTCAAGAAGGTAGATT

TGGGTTCTCTCAAGGTGGGCGGAATGGCTGCACAGTCAATGATTTCTCTCTGGTT

ATATGGTGCCCACTCTGAATCCAACAGGAGCCGGAGATGTATAACAGACTTGGC

CCATTTCTATTCCAAGTCGTCCCCCATAGAGAAGCTGTTGAATCTCACGCTAGGA

AATAGAGGGCTGAGAATCCCCCCAGAGGGAGTGTTAAGTTGCCTTGAGAGGGTT

GATTATGATAATGCATTTGGAAGGTATCTTGCCAACACGTATTCCTCTTACTTGTT

CTTCCATGTAATCACCTTATACATGAACGCCCTAGACTGGGATGAAGAAAAGAC

CATCCTAGCATTATGGAAAGATTTAACCTCAGTGGACATCGGGAAGGACTTGGT

AAAGTTCAAAGACCAAATATGGGGACTGCTGATCGTGACAAAGGACTTTGTTTA

CTCCCAAAGTTCCAATTGTCTTTTTGACAGAAACTACACACTTATGCTAAAAGAT

CTTTTCTTGTCTCGCTTCAACTCCTTAATGGTCTTGCTCTCTCCCCCAGAGCCCCG

ATACTCAGATGACTTGATATCTCAACTATGCCAGCTGTACATTGCTGGGGATCAA

GTCTTGTCTATGTGTGGAAACTCCGGCTATGAAGTCATCAAAATATTGGAGCCAT

ATGTCGTGAATAGTTTAGTCCAGAGAGCAGAAAAGTTTAGGCCTCTCATTCATTC

CTTGGGAGACTTTCCTGTATTTATAAAAGACAAGGTAAGTCAACTTGAAGAGAC

GTTCGGTCCCTGTGCAAGAAGGTTCTTTAGGGCTCTGGATCAATTCGACAACATA

CATGACTTGGTTTTTGTGTTTGGCTGTTACAGGCATTGGGGGCACCCATATATAG

ATTATCGAAAGGGTCTGTCAAAACTATATGATCAGGTTCACCTTAAAAAAATGAT

AGATAAGTCCTACCAGGAGTGCTTAGCAAGCGACCTAGCCAGGAGGATCCTTAG

ATGGGGTTTTGATAAGTACTCCAAGTGGTATCTGGATTCAAGATTCCTAGCCCGA

GACCACCCCTTGACTCCTTATATCAAAACCCAAACATGGCCACCCAAACATATTG

TAGACTTGGTGGGGATACATGGCACAAGCTCCCGATCACGCAGATCTTTGAGA

TTCCTGAATCAATGGATCCGTCAGAAATATTGGATGACAAATCACATTCTTTCAC

CAGAACGAGACTAGCTTCTTGGCTGTCAGAAAACCGAGGGGGCCTGTTCCTAG

CGAAAAAGTTATTATCACGGCCCTGTCTAAGCCGCCTGTCAATCCCCGAGAGTTT

CTGAGGTCTATAGACCTCGGAGGATTGCCAGATGAAGACTTGATAATTGGCCTC

AAGCCAAAGGAACGGGAATTGAAGATTGAAGGTCGATTCTTTGCTCTAATGTCA

TGGAATCTAAGATTGTATTTTGTCATCACTGAAAAACTCTTGGCCAACTACATCT

TGCCACTTTTTGACGCGCTGACTATGACAGACAACCTGAACAAGGTGTTTAAAAA

GCTGATCGACAGGGTCACCGGGCAAGGGCTTTTGGACTATTCAAGGGTCACATA

-continued

```
TGCATTTCACCTGGACTATGAAAAGTGGAACAACCATCAAAGATTAGAGTCAAC
AGAGGATGTATTTTCTGTCCTAGATCAAGTGTTTGGATTGAAGAGAGTGTTTTCT
AGAACACACGAGTTTTTTCAAAAGGCCTGGATCTATTATTCAGACAGATCAGACC
TCATCGGGTTACGGGAGGATCAAATATACTGCTTAGATGCGTCCAACGGCCCAA
CCTGTTGGAATGGCCAGGATGGCGGGCTAGAAGGCTTACGGCAGAAGGGCTGGA
GTCTAGTCAGCTTATTGATGATAGATAGAGAATCTCAAATCAGGAACACAAGAA
CCAAAATACTAGCTCAAGGAGACAACCAGGTTTTATGTCCGACATACATGTTGTC
GCCAGGGCTATCTCAAGAGGGGCTCCTCTATGAATTGGAGAGAATATCAAGGAA
TGCACTTTCGATATACAGAGCCGTCGAGGAAGGGGCATCTAAGCTAGGGCTGAT
CATCAAGAAAGAAGAGACCATGTGTAGTTATGACTTCCTCATCTATGGAAAAAC
CCCTTTGTTTAGAGGTAACATATTGGTGCCTGAGTCCAAAAGATGGGCCAGAGTC
TCTTGCGTCTCTAATGACCAAATAGTCAACCTCGCCAATATAATGTCGACAGTGT
CCACCAATGCGCTAACAGTGGCACAACACTCTCAATCTTTGATCAAACCGATGA
GGGATTTTCTGCTCATGTCAGTACAGGCAGTCTTTCACTACCTGCTATTTAGCCCA
ATCTTAAAGGGAAGAGTTTACAAGATTCTGAGCGCTGAAGGGGAGAGCTTTCTC
CTAGCCATGTCAAGGATAATCTATCTAGATCCTTCTTTGGGAGGGATATCTGGAA
TGTCCCTCGGAAGATTCCATATACGACAGTTCTCAGACCCTGTCTCTGAAGGGTT
ATCCTTCTGGAGAGAGATCTGGTTAAGCTCCCAAGAGTCCTGGATTCACGCGTTG
TGTCAAGAGGCTGGAAACCCAGATCTTGGAGAGAGAACACTCGAGAGCTTCACT
CGCCTTCTAGAAGATCCGACCACCTTAAATATCAGAGGAGGGGCCAGTCCTACC
ATTCTACTCAAGGATGCAATCAGAAAGGCTTTATATGACGAGGTGGACAAGGTG
GAAAATTCAGAGTTTCGAGAGGCAATCCTGTTGTCCAAGACCCATAGAGATAAT
TTTATACTCTTCTTAATATCTGTTGAGCCTCTGTTTCCTCGATTTCTCAGTGAGCT
ATTCAGTTCGTCTTTTTTGGGAATCCCCGAGTCAATCATTGGATTGATACAAAAC
TCCCGAACGATAAGAAGGCAGTTTAGAAAGAGTCTCTCAAAAACTTTAGAAGAA
TCCTTCTACAACTCAGAGATCCACGGGATTAGTCGGATGACCCAGACACCTCAG
AGGGTTGGGGGGGTGTGGCCTTGCTCTTCAGAGAGGGCAGATCTACTTAGGGAG
ATCTCTTGGGGAAGAAAAGTGGTAGGCACGACAGTTCCTCACCCTTCTGAGATGT
TGGGATTACTTCCCAAGTCCTCTATTTCTTGCACTTGTGGAGCAACAGGAGGAGG
CAATCCTAGAGTTTCTGTATCAGTACTCCCGTCCTTTGATCAGTCATTTTTTTCAC
GAGGCCCCCTAAAGGGATACTTGGGCTCGTCCACCTCTATGTCGACCCAGCTATT
CCATGCATGGGAAAAGTCACTAATGTTCATGTGGTGAAGAGAGCTCTATCGTT
AAAAGAATCTATAAACTGGTTCATTACTAGAGATTCCAACTTGGCTCAAGCTCTA
ATTAGGAACATTATGTCTCTGACAGGCCCTGATTTCCCTCTAGAGGAGGCCCCTG
TCTTCAAAAGGACGGGGTCAGCCTTGCATAGGTTCAAGTCTGCCAGATACAGCG
AAGGAGGGTATTCTTCTGTCTGCCCGAACCTCCTCTCTCATATTTCTGTTAGTACA
GACACCATGTCTGATTTGACCCAAGACGGGAAGAACTACGATTTCATGTTCCAGC
CATTGATGCTTTATGCACAGACATGGACATCAGAGCTGGTACAGAGAGACACAA
GGCTAAGAGACTCTACGTTTCATTGGCACCTCCGATGCAACAGGTGTGTGAGACC
CATTGACGACGTGACCCTGGAGACCTCTCAGATCTTCGAGTTTCCGGATGTGTCG
AAAAGAATATCCAGAATGGTTTCTGGGGCTGTGCCTCACTTCCAGAGGCTTCCCG
```

-continued

```
ATATCCGTCTGAGACCAGGAGATTTTGAATCTCTAAGCGGTAGAGAAAAGTCTC
ACCATATCGGATCAGCTCAGGGGCTCTTATACTCAATCTTAGTGGCAATTCACGA
CTCAGGATACAATGATGGAACCATCTTCCCTGTCAACATATACGGCAAGGTTTCC
CCTAGAGACTATTTGAGAGGGCTCGCAAGGGGAGTATTGATAGGATCCTCGATT
TGCTTCTTGACAAGAATGACAAATATCAATATTAATAGACCTCTTGAATTGGTCT
CAGGGGTAATCTCATATATTCTCCTGAGGCTAGATAACCATCCCTCCTTGTACAT
AATGCTCAGAGAACCGTCTCTTAGAGGAGAGATATTTTCTATCCCTCAGAAAATC
CCCGCCGCTTATCCAACCACTATGAAAGAAGGCAACAGATCAATCTTGTGTTATC
TCCAACATGTGCTACGCTATGAGCGAGAGATAATCACGGCGTCTCCAGAGAATG
ACTGGCTATGGATCTTTTCAGACTTTAGAAGTGCCAAAATGACGTACCTATCCCT
CATTACTTACCAGTCTCATCTTCTACTCCAGAGGGTTGAGAGAAACCTATCTAAG
AGTATGAGAGATAACCTGCGACAATTGAGTTCTTTGATGAGGCAGGTGCTGGGC
GGGCACGGAGAAGATACCTTAGAGTCAGACGACAACATTCAACGACTGCTAAAA
GACTCTTTACGAAGGACAAGATGGGTGGATCAAGAGGTGCGCCATGCAGCTAGA
ACCATGACTGGAGATTACAGCCCCAACAAGAAGGTGTCCCGTAAGGTAGGATGT
TCAGAATGGGTCTGCTCTGCTCAACAGGTTGCAGTCTCTACCTCAGCAAACCCGG
CCCCTGTCTCGGAGCTTGACATAAGGGCCCTCTCTAAGAGGTTCCAGAACCCTTT
GATCTCGGGCTTGAGAGTGGTTCAGTGGGCAACCGGTGCTCATTATAAGCTTAAG
CCTATTCTAGATGATCTCAATGTTTTCCCATCTCTCTGCCTTGTAGTTGGGGACGG
GTCAGGGGGATATCAAGGGCAGTCCTCAACATGTTTCCAGATGCCAAGCTTGT
GTTCAACAGTCTTTTAGAGGTGAATGACCTGATGGCTTCCGGAACACATCCACTG
CCTCCTTCAGCAATCATGAGGGGAGGAAATGATATCGTCTCCAGAGTGATAGAT
CTTGACTCAATCTGGGAAAAACCGTCCGACTTGAGAAACTTGGCAACCTGGAAA
TACTTCCAGTCAGTCCAAAAGCAGGTCAACATGTCCTATGACCTCATTATTTGCG
ATGCAGAAGTTACTGACATTGCATCTATCAACCGGATCACCCTGTTAATGTCCGA
TTTTGCATTGTCTATAGATGGACCACTCTATTTGGTCTTCAAAACTTATGGGACTA
TGCTAGTAAATCCAAACTACAAGGCTATTCAACACCTGTCAAGAGCGTTCCCCTC
GGTCACAGGGTTTATCACCCAAGTAACTTCGTCTTTTTCATCTGAGCTCTACCTCC
GATTCTCCAAACGAGGGAAGTTTTTCAGAGATGCTGAGTACTTGACCTCTTCCAC
CCTTCGAGAAATGAGCCTTGTGTTATTCAATTGTAGCAGCCCCAAGAGTGAGATG
CAGAGAGCTCGTTCCTTGAACTATCAGGATCTTGTGAGAGGATTTCCTGAAGAAA
TCATATCAAATCCTTACAATGAGATGATCATAACTCTGATTGACAGTGATGTAGA
ATCTTTTCTAGTCCACAAGATGGTTGATGATCTTGAGTTACAGAGGGGAACTCTG
TCTAAAGTGGCTATCATTATAGCCATCATGATAGTTTTCTCCAACAGAGTCTTCA
ACGTTTCCAAACCCCTAACTGACCCCTCGTTCTATCCACCGTCTGATCCCAAAAT
CCTGAGGCACTTCAACATATGTTGCAGTACTATGATGTATCTATCTACTGCTTTA
GGTGACGTCCCTAGCTTCGCAAGACTTCACGACCTGTATAACAGACCTATAACTT
ATTACTTCAGAAAGCAAGTCATTCGAGGGAACGTTTATCTATCTTGGAGTTGGTC
CAACGACACCTCAGTGTTCAAAAGGGTAGCCTGTAATTCTAGCCTGAGTCTGTCA
TCTCACTGGATCAGGTTGATTTACAAGATAGTGAAGACTACCAGACTCGTTGGCA
```

-continued

GCATCAAGGATCTATCCAGAGAAGTGGAAAGACACCTTCATAGGTACAACAGGT

GGATCACCCTAGAGGATATCAGATCTAGATCATCCCTACTAGACTACAGTTGCCT

GTGAACCGGATACTCCTGGAAGCCTGCCCATGCTAAGACTCTTGTGTGATGTATC

TTGAAAAAAACAAGATCCTAAATCTGAACCTTTGGTTGTTTGATTGTTTTTCTCAT

TTTTGTTGTTTATTTGTTAAGCGT.

In one embodiment, the nucleic acid comprises the sequence of SEQ ID NO: 18, shown below (VSV vector: Convac V1 China):

ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT

GAGGAAGTGGATGTTGTATTTACTTCGGACTGGAAACAGCCTGAGCTTGAATCTG

-continued

```
ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCTCAAAGACATCCATGAC

TTTCCAACCCAAGAAAGCAAGTCTTCAGCCTCTCACCATATCCTTGGATGAATTG

TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCCTAATTCC

AGCCTCTCGAACAACTAATATCCTGTCTTTTCTATCCCTATGAAAAAAACTAACA

GAGATCGATCTGTTTACGCGTCACTATGAAGTGCCTTTTGTACTTAGCCTTTTTAT

TCATTGGGGTGAATTGCAAGTTCACCATAGTTTTTCCACACAACCAAAAAGGAA

ACTGGAAAAATGTTCCTTCTAATTACCATTATTGCCCGTCAAGCTCAGATTTAAA

TTGGCATAATGACTTAATAGGCACAGCCATACAAGTCAAAATGCCCAAGAGTCA

CAAGGCTATTCAAGCAGACGGTTGGATGTGTCATGCTTCCAAATGGGTCACTACT

TGTGATTTCCGCTGGTATGGACCGAAGTATATAACACAGTCCATCCGATCCTTCA

CTCCATCTGTAGAACAATGCAAGGAAAGCATTGAACAAACGAAACAAGGAACTT

GGCTGAATCCAGGCTTCCCTCCTCAAAGTTGTGGATATGCAACTGTGACGGATGC

CGAAGCAGTGATTGTCCAGGTGACTCCTCACCATGTGCTGGTTGATGAATACACA

GGAGAATGGGTTGATTCACAGTTCATCAACGGAAAATGCAGCAATTACATATGC

CCCACTGTCCATAACTCTACAACCTGGCATTCTGACTATAAGGTCAAAGGGCTAT

GTGATTCTAACCTCATTTCCATGGACATCACCTTCTTCTCAGAGGACGGAGAGCT

ATCATCCCTGGGAAAGGAGGGCACAGGGTTCAGAAGTAACTACTTTGCTTATGA

AACTGGAGGCAAGGCCTGCAAAATGCAATACTGCAAGCATTGGGGAGTCAGACT

CCCATCAGGTGTCTGGTTCGAGATGGCTGATAAGGATCTCTTTGCTGCAGCCAGA

TTCCCTGAATGCCCAGAAGGGTCAAGTATCTGCTCCATCTCAGACCTCAGTGG

ATGTAAGTCTAATTCAGGACGTTGAGAGGATCTTGGATTATTCCCTCTGCCAAGA
```

-continued

```
AACCTGGAGCAAAATCAGAGCGGGTCTTCCAATCTCTCCAGTGGATCTCAGCTAT
CTTGCTCCTAAAAACCCAGGAACCGGTCCTGCTTTCACCATAATCAATGGTACCC
TAAAATACTTTGAGACCAGATACATCAGAGTCGATATTGCTGCTCCAATCCTCTC
AAGAATGGTCGGAATGATCAGTGGAACTACCACAGAAAGGGAACTGTGGGATG
ACTGGGCACCATATGAAGACGTGGAAATTGGACCCAATGGAGTTCTGAGGACCA
GTTCAGGATATAAGTTTCCTTTATACATGATTGGACATGGTATGTTGGACTCCGA
TCTTCATCTTAGCTCAAAGGCTCAGGTGTTCGAACATCCTCACATTCAAGACGCT
GCTTCGCAACTTCCTGATGATGAGAGTTTATTTTTTGGTGATACTGGGCTATCCA
AAAATCCAATCGAGCTTGTAGAAGGTTGGTTCAGTAGTTGGAAAAGCTCTATTGC
CTCTTTTTTCTTTATCATAGGGTTAATCATTGGACTATTCTTGGTTCTCCGAGTTG
GTATCCATCTTTGCATTAAATTAAAGCACACCAAGAAAAGACAGATTTATACAG
ACATAGAGATGAACCGACTTGGAAAGTAACTCAAATCCTGCTAGGTATGAAAAA
AACTAACaGATATCACGCTCGAGCGTACGCCACCATGTTCGTGTTTCTGGTGCTG
CTGCCTCTGGTGAGCTCCCAGTGCGTGAACCTGACCACAAGGACCCAGCTGCCC
CCTGCCTATACCAATTCCTTCACACGGGGCGTGTACTATCCCGACAAGGTGTTCC
GGAGCAGCGTGCTGCACTCCACACAGGATCTGTTTCTGCCTTTCTTTTCTAACGT
GACCTGGTTCCACGCCATCCACGTGAGCGGCACCAATGGCACAAAGCGGTTCGA
CAATCCAGTGCTGCCCTTTAACGATGGCGTGTACTTCGCCTCCACCGAGAAGTCT
AACATCATCAGAGGCTGGATCTTTGGCACCACACTGGACAGCAAGACACAGTCC
CTGCTGATCGTGAACAATGCCACCAACGTGGTCATCAAGGTGTGCGAGTTCCAGT
TTTGTAATGATCCATTCCTGGGCGTGTACTATCACAAGAACAATAAGTCTTGGAT
GGAGAGCGAGTTTCGCGTGTATTCCTCTGCCAACAATTGCACATTTGAGTACGTG
TCCCAGCCCTTCCTGATGGACCTGGAGGGCAAGCAGGGCAATTTCAAGAACCTG
AGGGAGTTCGTGTTTAAGAATATCGATGGCTACTTCAAAATCTACTCCAAGCACA
CCCCAATCAACCTGGTGCGCGACCTGCCACAGGGCTTCTCTGCCCTGGAGCCACT
GGTGGATCTGCCCATCGGCATCAACATCACCCGGTTTCAGACACTGCTGGCCCTG
CACAGAAGCTACCTGACACCAGGCGACAGCTCCTCTGGATGGACCGCAGGAGCA
GCAGCCTACTATGTGGGCTATCTGCAGCCCAGGACCTTCCTGCTGAAGTACAACG
AGAATGGCACCATCACAGACGCCGTGGATTGCGCCCTGGATCCCCTGTCTGAGA
CCAAGTGTACACTGAAGAGCTTTACCGTGGAGAAGGGCATCTATCAGACAAGCA
ATTTCAGGGTGCAGCCTACCGAGTCCATCGTGCGCTTTCCCAATATCACAAACCT
GTGCCCTTTTGGCGAGGTGTTCAACGCAACCCGCTTCGCCAGCGTGTACGCCTGG
AATAGGAAGCGCATCTCCAACTGCGTGGCCGACTATTCTGTGCTGTACAACAGC
GCCTCCTTCTCTACCTTTAAGTGCTATGGCGTGAGCCCCACAAAGCTGAATGACC
TGTGCTTTACCAACGTGTACGCCGATTCCTTCGTGATCAGGGGCGACGAGGTGCG
CCAGATCGCACCAGGACAGACAGGCAAGATCGCAGACTACAATTATAAGCTGCC
TGACGATTTCACCGGCTGCGTGATCGCCTGGAACTCTAACAATCTGGATAGCAAA
GTGGGCGGCAACTACAATTATCTGTACCGGCTGTTTAGAAAGTCTAATCTGAAGC
CATTCGAGAGGGACATCTCCACAGAAATCTACCAGGCCGGCTCTACCCCCTGCA
ATGGCGTGGAGGGCTTTAACTGTTATTTCCCTCTGCAGAGCTACGGCTTCCAGCC
```

-continued

```
AACAAACGGCGTGGGCTATCAGCCCTACCGCGTGGTGGTGCTGTCTTTTGAGCTG

CTGCACGCACCTGCAACAGTGTGCGGACCAAAGAAGAGCACCAATCTGGTGAAG

AACAAGTGCGTGAACTTCAACTTCAACGGACTGACCGGAACAGGCGTGCTGACC

GAGTCCAACAAGAAGTTCCTGCCTTTTCAGCAGTTCGGCAGGGACATCGCAGAT

ACCACAGACGCCGTGCGCGACCCTCAGACCCTGGAGATCCTGGACATCACACCA

TGCTCCTTCGGCGGCGTGTCTGTGATCACACCAGGCACCAATACAAGCAACCAG

GTGGCCGTGCTGTATCAGGACGTGAATTGTACCGAGGTGCCAGTGGCAATCCAC

GCAGATCAGCTGACCCCTACATGGCGGGTGTACTCTACCGGCAGCAACGTGTTC

CAGACAAGAGCCGGATGCCTGATCGGAGCAGAGCACGTGAACAATAGCTATGA

GTGCGACATCCCTATCGGCGCCGGCATCTGTGCCTCCTACCAGACCCAGACAAA

CTCCCCAAGGTCTGTGGGCGATACAGGCCTGTCCAAGAATCCAATCGAGCTGGT

AGAGGGCTGGTTCAGCAGTTGGAAAAGCTCCATCGCCTCCTTTTTCTTTATCATC

GGCCTGATCATCGGACTGTTCCTGGTGCTCCGCGTGGGTATCCACCTGTGCATCA

AGCTGAAGCACACCAAGAAAAGACAGATTTATACAGACATCGAGATGAACCGC

CTGGGAAAGTGAGCTAGCCAGATTCTTCATGTTTGGACCAAATCAACTTGTGATA

CCATGCTCAAAGAGGCCTCAATTATATTTGAGTTTTTAATTTTTATGAAAAAAAC

TAACAGCAATCATGGAAGTCCACGATTTTGAGACCGACGAGTTCAATGATTTCA

ATGAAGATGACTATGCCACAAGAGAATTCCTGAATCCCGATGAGCGCATGACGT

ACTTGAATCATGCTGATTACAATTTGAATTCTCCTCTAATTAGTGATGATATTGAC

AATTTGATCAGGAAATTCAATTCTCTTCCGATTCCCTCGATGTGGGATAGTAAGA

ACTGGGATGGAGTTCTTGAGATGTTAACATCATGTCAAGCCAATCCCATCTCAAC

ATCTCAGATGCATAAATGGATGGGAAGTTGGTTAATGTCTGATAATCATGATGCC

AGTCAAGGGTATAGTTTTTTACATGAAGTGGACAAAGAGGCAGAAATAACATTT

GACGTGGTGGAGACCTTCATCCGCGGCTGGGGCAACAAACCAATTGAATACATC

AAAAAGGAAAGATGGACTGACTCATTCAAAATTCTCGCTTATTTGTGTCAAAAGT

TTTTGGACTTACACAAGTTGACATTAATCTTAAATGCTGTCTCTGAGGTGGAATT

GCTCAACTTGGCGAGGACTTTCAAAGGCAAAGTCAGAAGAAGTTCTCATGGAAC

GAACATATGCAGGATTAGGGTTCCCAGCTTGGGTCCTACTTTTATTTCAGAAGGA

TGGGCTTACTTCAAGAAACTTGATATTCTAATGGACCGAAACTTTCTGTTAATGG

TCAAAGATGTGATTATAGGGAGGATGCAAACGGTGCTATCCATGGTATGTAGAA

TAGACAACCTGTTCTCAGAGCAAGACATCTTCTCCCTTCTAAATATCTACAGAAT

TGGAGATAAAATTGTGGAGAGGCAGGGAAATTTTTCTTATGACTTGATTAAAAT

GGTGGAACCGATATGCAACTTGAAGCTGATGAAATTAGCAAGAGAATCAAGGCC

TTTAGTCCCACAATTCCCTCATTTTGAAAATCATATCAAGACTTCTGTTGATGAA

GGGGCAAAAATTGACCGAGGTATAAGATTCCTCCATGATCAGATAATGAGTGTG

AAAACAGTGGATCTCACACTGGTGATTTATGGATCGTTCAGACATTGGGTCATC

CTTTTATAGATTATTACACTGGACTAGAAAAATTACATTCCCAAGTAACCATGAA

GAAAGATATTGATGTGTCATATGCAAAAGCACTTGCAAGTGATTTAGCTCGGATT

GTTCTATTTCAACAGTTCAATGATCATAAAAAGTGGTTCGTGAATGGAGACTTGC

TCCCTCATGATCATCCCTTTAAAAGTCATGTTAAAGAAAATACATGGCCCACAGC

TGCTCAAGTTCAAGATTTTGGAGATAAATGGCATGAACTTCCGCTGATTAAATGT
```

-continued

```
TTTGAAATACCCGACTTACTAGACCCATCGATAATATACTCTGACAAAAGTCATT

CAATGAATAGGTCAGAGGTGTTGAAACATGTCCGAATGAATCCGAACACTCCTA

TCCCTAGTAAAAAGGTGTTGCAGACTATGTTGGACACAAAGGCTACCAATTGGA

AAGAATTTCTTAAAGAGATTGATGAGAAGGGCTTAGATGATGATGATCTAATTA

TTGGTCTTAAAGGAAAGGAGAGGGAACTGAAGTTGGCAGGTAGATTTTTCTCCC

TAATGTCTTGGAAATTGCGAGAATACTTTGTAATTACCGAATATTTGATAAAGAC

TCATTTCGTCCCTATGTTTAAAGGCCTGACAATGGCGGACGATCTAACTGCAGTC

ATTAAAAAGATGTTAGATTCCTCATCCGGCCAAGGATTGAAGTCATATGAGGCA

ATTTGCATAGCCAATCACATTGATTACGAAAAATGGAATAACCACCAAAGGAAG

TTATCAAACGGCCCAGTGTTCCGAGTTATGGGCCAGTTCTTAGGTTATCCATCCT

TAATCGAGAGAACTCATGAATTTTTTGAGAAAAGTCTTATATACTACAATGGAAG

ACCAGACTTGATGCGTGTTCACAACAACACACTGATCAATTCAACCTCCCAACG

AGTTTGTTGGCAAGGACAAGAGGGTGGACTGGAAGGTCTACGGCAAAAAGGAT

GGACTATCCTCAATCTACTGGTTATTCAAAGAGAGGCTAAAATCAGAAACACTG

CTGTCAAAGTCTTGGCACAAGGTGATAATCAAGTTATTTGCACACAGTATAAAAC

GAAGAAATCGAGAAACGTTGTAGAATTACAGGGTGCTCTCAATCAAATGGTTTC

TAATAATGAGAAAATTATGACTGCAATCAAAATAGGGACAGGGAAGTTAGGACT

TTTGATAAATGACGATGAGACTATGCAATCTGCAGATTACTTGAATTATGGAAAA

ATACCGATTTTCCGTGGAGTGATTAGAGGGTTAGAGACCAAGAGATGGTCACGA

GTGACTTGTGTCACCAATGACCAAATACCCACTTGTGCTAATATAATGAGCTCAG

TTTCCACAAATGCTCTCACCGTAGCTCATTTTGCTGAGAACCCAATCAATGCCAT

GATACAGTACAATTATTTTGGGACATTTGCTAGACTCTTGTTGATGATGCATGAT

CCTGCTCTTCGTCAATCATTGTATGAAGTTCAAGATAAGATACCGGGCTTGCACA

GTTCTACTTTCAAATACGCCATGTTGTATTTGGACCCTTCCATTGGAGGAGTGTC

GGGCATGTCTTTGTCCAGGTTTTTGATTAGAGCCTTCCCAGATCCCGTAACAGAA

AGTCTCTCATTCTGGAGATTCATCCATGTACATGCTCGAAGTGAGCATCTGAAGG

AGATGAGTGCAGTATTTGGAAACCCCGAGATAGCCAAGTTTCGAATAACTCACA

TAGACAAGCTAGTAGAAGATCCAACCTCTCTGAACATCGCTATGGGAATGAGTC

CAGCGAACTTGTTAAAGACTGAGGTTAAAAAATGCTTAATCGAATCAAGACAAA

CCATCAGGAACCAGGTGATTAAGGATGCAACCATATATTTGTATCATGAAGAGG

ATCGGCTCAGAAGTTTCTTATGGTCAATAAATCCTCTGTTCCCTAGATTTTTAAGT

GAATTCAAATCAGGCACTTTTTTGGGAGTCGCAGACGGGCTCATCAGTCTATTTC

AAAATTCTCGTACTATTCGGAACTCCTTTAAGAAAAAGTATCATAGGGAATTGGA

TGATTTGATTGTGAGGAGTGAGGTATCCTCTTTGACACATTTAGGGAAACTTCAT

TTGAGAAGGGGATCATGTAAAATGTGGACATGTTCAGCTACTCATGCTGACACA

TTAAGATACAAATCCTGGGGCCGTACAGTTATTGGGACAACTGTACCCCATCCAT

TAGAAATGTTGGGTCCACAACATCGAAAAGAGACTCCTTGTGCACCATGTAACA

CATCAGGGTTCAATTATGTTTCTGTGCATTGTCCAGACGGGATCCATGACGTCTT

TAGTTCACGGGACCATTGCCTGCTTATCTAGGGTCTAAAACATCTGAATCTACA

TCTATTTTGCAGCCTTGGGAAAGGGAAAGCAAAGTCCCACTGATTAAAAGAGCT
```

-continued
```
ACACGTCTTAGAGATGCTATCTCTTGGTTTGTTGAACCCGACTCTAAACTAGCAA

TGACTATACTTTCTAACATCCACTCTTTAACAGGCGAAGAATGGACCAAAAGGC

AGCATGGGTTCAAAAGAACAGGGTCTGCCCTTCATAGGTTTTCGACATCTCGGAT

GAGCCATGGTGGGTTCGCATCTCAGAGCACTGCAGCATTGACCAGGTTGATGGC

AACTACAGACACCATGAGGGATCTGGGAGATCAGAATTTCGACTTTTTATTCCAA

GCAACGTTGCTCTATGCTCAAATTACCACCACTGTTGCAAGAGACGGATGGATCA

CCAGTTGTACAGATCATTATCATATTGCCTGTAAGTCCTGTTTGAGACCCATAGA

AGAGATCACCCTGGACTCAAGTATGGACTACACGCCCCCAGATGTATCCCATGT

GCTGAAGACATGGAGGAATGGGGAAGGTTCGTGGGGACAAGAGATAAAACAGA

TCTATCCTTTAGAAGGGAATTGGAAGAATTTAGCACCTGCTGAGCAATCCTATCA

AGTCGGCAGATGTATAGGTTTTCTATATGGAGACTTGGCGTATAGAAAATCTACT

CATGCCGAGGACAGTTCTCTATTTCCTCTATCTATACAAGGTCGTATTAGAGGTC

GAGGTTTCTTAAAAGGGTTGCTAGACGGATTAATGAGAGCAAGTTGCTGCCAAG

TAATACACCGGAGAAGTCTGGCTCATTTGAAGAGGCCGGCCAACGCAGTGTACG

GAGGTTTGATTTACTTGATTGATAAATTGAGTGTATCACCTCCATTCCTTTCTCTT

ACTAGATCAGGACCTATTAGAGACGAATTAGAAACGATTCCCCACAAGATCCCA

ACCTCCTATCCGACAAGCAACCGTGATATGGGGGTGATTGTCAGAAATTACTTCA

AATACCAATGCCGTCTAATTGAAAAGGGAAAATACAGATCACATTATTCACAAT

TATGGTTATTCTCAGATGTCTTATCCATAGACTTCATTGGACCATTCTCTATTTCC

ACCACCCTCTTGCAAATCCTATACAAGCCATTTTTATCTGGGAAAGATAAGAATG

AGTTGAGAGAGCTGGCAAATCTTTCTTCATTGCTAAGATCAGGAGAGGGGTGGG

AAGACATACATGTGAAATTCTTCACCAAGGACATATTATTGTGTCCAGAGGAAA

TCAGACATGCTTGCAAGTTCGGGATTGCTAAGGATAATAATAAAGACATGAGCT

ATCCCCCTTGGGGAAGGGAATCCAGAGGGACAATTACAACAATCCCTGTTTATT

ATACGACCACCCCTTACCCAAAGATGCTAGAGATGCCTCCAAGAATCCAAAATC

CCCTGCTGTCCGGAATCAGGTTGGGCCAATTACCAACTGGCGCTCATTATAAAT

TCGGAGTATATTACATGGAATGGGAATCCATTACAGGGACTTCTTGAGTTGTGGA

GACGGCTCCGGAGGGATGACTGCTGCATTACTACGAGAAAATGTGCATAGCAGA

GGAATATTCAATAGTCTGTTAGAATTATCAGGGTCAGTCATGCGAGGCGCCTCTC

CTGAGCCCCCAGTGCCCTAGAAACTTTAGGAGGAGATAAATCGAGATGTGTAA

ATGGTGAAACATGTTGGGAATATCCATCTGACTTATGTGACCCAAGGACTTGGG

ACTATTTCCTCCGACTCAAAGCAGGCTTGGGGCTTCAAATTGATTTAATTGTAAT

GGATATGGAAGTTCGGGATTCTTCTACTAGCCTGAAAATTGAGACGAATGTTAG

AAATTATGTGCACCGGATTTTGGATGAGCAAGGAGTTTTAATCTACAAGACTTAT

GGAACATATATTTGTGAGAGCGAAAAGAATGCAGTAACAATCCTTGGTCCCATG

TTCAAGACGGTCGACTTAGTTCAAACAGAATTTAGTAGTTCTCAAACGTCTGAAG

TATATATGGTATGTAAAGGTTTGAAGAAATTAATCGATGAACCCAATCCCGATTG

GTCTTCCATCAATGAATCCTGGAAAAACCTGTACGCATTCCAGTCATCAGAACAG

GAATTTGCCAGAGCAAAGAAGGTTAGTACATACTTTACCTTGACAGGTATTCCCT

CCCAATTCATTCCTGATCCTTTTGTAAACATTGAGACTATGCTACAAATATTCGG

AGTACCCACGGGTGTGTCTCATGCGGCTGCCTTAAAATCATCTGATAGACCTGCA
```

-continued

```
GATTTATTGACCATTAGCCTTTTTTATATGGCGATTATATCGTATTATAACATCAA

TCATATCAGAGTAGGACCGATACCTCCGAACCCCCCATCAGATGGAATTGCACA

AAATGTGGGGATCGCTATAACTGGTATAAGCTTTTGGCTGAGTTTGATGGAGAA

AGACATTCCACTATATCAACAGTGTTTAGCAGTTATCCAGCAATCATTCCCGATT

AGGTGGGAGGCTGTTTCAGTAAAAGGAGGATACAAGCAGAAGTGGAGTACTAG

AGGTGATGGGCTCCCAAAAGATACCCGAACTTCAGACTCCTTGGCCCCAATCGG

GAACTGGATCAGATCTCTGGAATTGGTCCGAAACCAAGTTCGTCTAAATCCATTC

AATGAGATCTTGTTCAATCAGCTATGTCGTACAGTGGATAATCATTTGAAATGGT

CAAATTTGCGAAGAAACACAGGAATGATTGAATGGATCAATAGACGAATTTCAA

AAGAAGACCGGTCTATACTGATGTTGAAGAGTGACCTACACGAGGAAAACTCTT

GGAGAGATTAAAAAATCATGAGGAGACTCCAAACTTTAAGTATGAAAAAAACTT

TGATCCTTAAGACCCTCTTGTGGTTTTTATTTTTTATCTGGTTTTGTGGTCTTCGT.
```

In another embodiment, the nucleic acid comprises the sequence of SEQ ID NO: 19, shown below (VSV vector: Convac V1 South Africa):

```
ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAGAAGACAATTGGCAAGT

ATGCTAAGTCAGAATTTGACAAAATGACCCTATAATTCTCAGATCACCTATTATAT
```

-continued

```
ATTATGCTACATATGAAAAAAACTAACAGATATCATGGATAATCTCACAAAAGT
TCGTGAGTATCTCAAGTCCTATTCTCGTCTGGATCAGGCGGTAGGAGAGATAGAT
GAGATCGAAGCACAACGAGCTGAAAAGTCCAATTATGAGTTGTTCCAAGAGGAT
GGAGTGGAAGAGCATACTAAGCCCTCTTATTTTCAGGCAGCAGATGATTCTGAC
ACAGAATCTGAACCAGAAATTGAAGACAATCAAGGTTTGTATGCACCAGATCCA
GAAGCTGAGCAAGTTGAAGGCTTTATACAGGGGCCTTTAGATGACTATGCAGAT
GAGGAAGTGGATGTTGTATTTACTTCGGACTGGAAACAGCCTGAGCTTGAATCTG
ACGAGCATGGAAAGACCTTACGGTTGACATCGCCAGAGGGTTTAAGTGGAGAGC
AGAAATCCCAGTGGCTTTCGACGATTAAAGCAGTCGTGCAAAGTGCCAAATACT
GGAATCTGGCAGAGTGCACATTTGAAGCATCGGGAGAAGGGGTCATTATGAAGG
AGCGCCAGATAACTCCGGATGTATATAAGGTCACTCCAGTGATGAACACACATC
CGTCCCAATCAGAAGCAGTATCAGATGTTTGGTCTCTCAAAGACATCCATGAC
TTTCCAACCCAAGAAAGCAAGTCTTCAGCCTCTCACCATATCCTTGGATGAATTG
TTCTCATCTAGAGGAGAGTTCATCTCTGTCGGAGGTGACGGACGAATGTCTCATA
AAGAGGCCATCCTGCTCGGCCTGAGATACAAAAAGTTGTACAATCAGGCGAGAG
TCAAATATTCTCTGTAGACTATGAAAAAAAGTAACAGATATCACGATCTAAGTGT
TATCCCAATCCATTCATCATGAGTTCCTTAAAGAAGATTCTCGGTCTGAAGGGGA
AAGGTAAGAAATCTAAGAAATTAGGGATCGCACCACCCCCTTATGAAGAGGACA
CTAGCATGGAGTATGCTCCGAGCGCTCCAATTGACAAATCCTATTTTGGAGTTGA
CGAGATGGACACCTATGATCCGAATCAATTAAGATATGAGAAATTCTTCTTTACA
GTGAAAATGACGGTTAGATCTAATCGTCCGTTCAGAACATACTCAGATGTGGCA
GCCGCTGTATCCCATTGGGATCACATGTACATCGGAATGGCAGGGAAACGTCCC
TTCTACAAAATCTTGGCTTTTTTGGGTTCTTCTAATCTAAAGGCCACTCCAGCGGT
ATTGGCAGATCAAGGTCAACCAGAGTATCACACTCACTGCGAAGGCAGGGCTTA
TTTGCCACATAGGATGGGGAAGACCCCTCCCATGCTCAATGTACCAGAGCACTTC
AGAAGACCATTCAATATAGGTCTTTACAAGGGAACGATTGAGCTCACAATGACC
ATCTACGATGATGAGTCACTGGAAGCAGCTCCTATGATCTGGGATCATTTCAATT
CTTCCAAATTTTCTGATTTCAGAGAGAAGGCCTTAATGTTTGGCCTGATTGTCGA
GAAAAAGGCATCTGGAGCGTGGGTCCTGGATTCTATCAGCCACTTCAAATGAGC
TAGTCTAACTTCTAGCTTCTGAACAATCCCCGGTTTACTCAGTCTCTCCTAATTCC
AGCCTCTCGAACAACTAATATCCTGTCTTTTCTATCCCTATGAAAAAACTAACA
GAGATCGATCTGTTTACGCGTCACTATGAAGTGCCTTTTGTACTTAGCCTTTTTAT
TCATTGGGGTGAATTGCAAGTTCACCATAGTTTTTCCACACAACCAAAAAGGAA
ACTGGAAAAATGTTCCTTCTAATTACCATTATTGCCCGTCAAGCTCAGATTTAAA
TTGGCATAATGACTTAATAGGCACAGCCATACAAGTCAAAATGCCCAAGAGTCA
CAAGGCTATTCAAGCAGACGGTTGGATGTGTCATGCTTCCAAATGGGTCACTACT
TGTGATTTCCGCTGGTATGGACCGAAGTATATAACACAGTCCATCCGATCCTTCA
CTCCATCTGTAGAACAATGCAAGGAAAGCATTGAACAAACGAAACAAGGAACTT
GGCTGAATCCAGGCTTCCCTCCTCAAAGTTGTGGATATGCAACTGTGACGGATGC
CGAAGCAGTGATTGTCCAGGTGACTCCTCACCATGTGCTGGTTGATGAATACACA
```

-continued

```
GGAGAATGGGTTGATTCACAGTTCATCAACGGAAAATGCAGCAATTACATATGC
CCCACTGTCCATAACTCTACAACCTGGCATTCTGACTATAAGGTCAAAGGGCTAT
GTGATTCTAACCTCATTTCCATGGACATCACCTTCTTCTCAGAGGACGGAGAGCT
ATCATCCCTGGGAAAGGAGGGCACAGGGTTCAGAAGTAACTACTTTGCTTATGA
AACTGGAGGCAAGGCCTGCAAAATGCAATACTGCAAGCATTGGGGAGTCAGACT
CCCATCAGGTGTCTGGTTCGAGATGGCTGATAAGGATCTCTTTGCTGCAGCCAGA
TTCCCTGAATGCCCAGAAGGGTCAAGTATCTCTGCTCCATCTCAGACCTCAGTGG
ATGTAAGTCTAATTCAGGACGTTGAGAGGATCTTGGATTATTCCCTCTGCCAAGA
AACCTGGAGCAAAATCAGAGCGGGTCTTCCAATCTCTCCAGTGGATCTCAGCTAT
CTTGCTCCTAAAAACCCAGGAACCGGTCCTGCTTTCACCATAATCAATGGTACCC
TAAAATACTTTGAGACCAGATACATCAGAGTCGATATTGCTGCTCCAATCCTCTC
AAGAATGGTCGGAATGATCAGTGGAACTACCACAGAAAGGGAACTGTGGGATG
ACTGGGCACCATATGAAGACGTGGAAATTGGACCCAATGGAGTTCTGAGGACCA
GTTCAGGATATAAGTTTCCTTTATACATGATTGGACATGGTATGTTGGACTCCGA
TCTTCATCTTAGCTCAAAGGCTCAGGTGTTCGAACATCCTCACATTCAAGACGCT
GCTTCGCAACTTCCTGATGATGAGAGTTTATTTTTTGGTGATACTGGGCTATCCA
AAAATCCAATCGAGCTTGTAGAAGGTTGGTTCAGTAGTTGGAAAAGCTCTATTGC
CTCTTTTTTCTTTATCATAGGGTTAATCATTGGACTATTCTTGGTTCTCCGAGTTG
GTATCCATCTTTGCATTAAATTAAAGCACACCAAGAAAAGACAGATTTATACAG
ACATAGAGATGAACCGACTTGGAAAGTAACTCAAATCCTGCTAGGTATGAAAAA
AACTAACaGATATCACGCTCGAGCCACCATGTTCGTGTTTCTGGTGCTGCTGCCTC
TGGTGAGCTCCCAGTGCGTGAACTTCACCACAAGGACCCAGCTGCCCCCTGCCTA
TACCAATTCCTTCACACGGGGCGTGTACTATCCCGACAAGGTGTTCCGGAGCAGC
GTGCTGCACTCCACACAGGATCTGTTTCTGCCTTTCTTTTCTAACGTGACCTGGTT
CCACGCCATCCACGTGAGCGGCACCAATGGCACAAAGCGGTTCGCCAATCCAGT
GCTGCCCTTTAACGATGGCGTGTACTTCGCCTCCACCGAGAAGTCTAACATCATC
AGAGGCTGGATCTTTGGCACCACACTGGACAGCAAGACACAGTCCCTGCTGATC
GTGAACAATGCCACCAACGTGGTCATCAAGGTGTGCGAGTTCCAGTTTTGTAATG
ATCCATTCCTGGGCGTGTACTATCACAAGAACAATAAGTCTTGGATGGAGAGCG
AGTTTCGCGTGTATTCCTCTGCCAACAATTGCACATTTGAGTACGTGTCCCAGCC
CTTCCTGATGGACCTGGAGGGCAAGCAGGGCAATTTCAAGAACCTGAGGGAGTT
CGTGTTTAAGAATATCGATGGCTACTTCAAAATCTACTCCAAGCACACCCCAATC
AACCTGGTGCGGGCCTGCCACAGGGCTTCTCTGCCCTGGAGCCACTGGTGGATC
TGCCCATCGGCATCAACATCACCCGGTTTCAGACACTGCTGGCCCTGCACAGAA
GCTACCTGACACCAGGCGACAGCTCCTCTGGATGGACCGCAGGAGCAGCAGCCT
ACTATGTGGGCTATCTGCAGCCCAGGACCTTCCTGCTGAAGTACAACGAGAATG
GCACCATCACAGACGCCGTGGATTGCGCCCTGGATCCCCTGTCTGAGACCAAGT
GTACACTGAAGAGCTTTACCGTGGAGAAGGGCATCTATCAGACAAGCAATTTCA
GGGTGCAGCCTACCGAGTCCATCGTGCGCTTTCCCAATATCACAAACCTGTGCCC
TTTTGGCGAGGTGTTCAACGCAACCCGCTTCGCCAGCGTGTACGCCTGGAATAGG
AAGCGCATCTCCAACTGCGTGGCCGACTATTCTGTGCTGTACAACAGCGCCTCCT
```

-continued

```
TCTCTACCTTTAAGTGCTATGGCGTGAGCCCCACAAAGCTGAATGACCTGTGCTT

TACCAACGTGTACGCCGATTCCTTCGTGATCAGGGGCGACGAGGTGCGCCAGAT

CGCACCAGGACAGACAGGCAATATCGCAGACTACAATTATAAGCTGCCTGACGA

TTTCACCGGCTGCGTGATCGCCTGGAACTCTAACAATCTGGATAGCAAAGTGGGC

GGCAACTACAATTATCTGTACCGGCTGTTTAGAAAGTCTAATCTGAAGCCATTCG

AGAGGGACATCTCCACAGAAATCTACCAGGCCGGCTCTACCCCCTGCAATGGCG

TGAAGGGCTTTAACTGTTATTTCCCTCTGCAGAGCTACGGCTTCCAGCCAACATA

TGGCGTGGGCTATCAGCCCTACCGCGTGGTGGTGCTGTCTTTTGAGCTGCTGCAC

GCACCTGCAACAGTGTGCGGACCAAAGAAGAGCACCAATCTGGTGAAGAACAA

GTGCGTGAACTTCAACTTCAACGGACTGACCGGAACAGGCGTGCTGACCGAGTC

CAACAAGAAGTTCCTGCCTTTTCAGCAGTTCGGCAGGGACATCGCAGATACCAC

AGACGCCGTGCGCGACCCTCAGACCCTGGAGATCCTGGACATCACACCATGCTC

CTTCGGCGGCGTGTCTGTGATCACACCAGGCACCAATACAAGCAACCAGGTGGC

CGTGCTGTATCAGGGCGTGAATTGTACCGAGGTGCCAGTGGCAATCCACGCAGA

TCAGCTGACCCCTACATGGCGGGTGTACTCTACCGGCAGCAACGTGTTCCAGAC

AAGAGCCGGATGCCTGATCGGAGCAGAGCACGTGAACAATAGCTATGAGTGCGA

CATCCCTATCGGCGCCGGCATCTGTGCCTCCTACCAGACCCAGACAAACTCCCCA

AGGTCTGTGGGCGATACAGGCCTGTCCAAGAATCCAATCGAGCTGGTAGAGGGC

TGGTTCAGCAGTTGGAAAAGCTCCATCGCCTCCTTTTTCTTTATCATCGGCCTGAT

CATCGGACTGTTCCTGGTGCTCCGCGTGGGTATCCACCTGTGCATCAAGCTGAAG

CACACCAAGAAAAGACAGATTTATACAGACATCGAGATGAACCGCCTGGGAAA

GTGAGCTAGCCAGATTCTTCATGTTTGGACCAAATCAACTTGTGATACCATGCTC

AAAGAGGCCTCAATTATATTTGAGTTTTTAATTTTTATGAAAAAAACTAACAGCA

ATCATGGAAGTCCACGATTTTGAGACCGACGAGTTCAATGATTTCAATGAAGAT

GACTATGCCACAAGAGAATTCCTGAATCCCGATGAGCGCATGACGTACTTGAAT

CATGCTGATTACAATTTGAATTCTCCTCTAATTAGTGATGATATTGACAATTTGAT

CAGGAAATTCAATTCTCTTCCGATTCCCTCGATGTGGGATAGTAAGAACTGGGAT

GGAGTTCTTGAGATGTTAACATCATGTCAAGCCAATCCCATCTCAACATCTCAGA

TGCATAAATGGATGGGAAGTTGGTTAATGTCTGATAATCATGATGCCAGTCAAG

GGTATAGTTTTTTACATGAAGTGGACAAAGAGGCAGAAATAACATTTGACGTGG

TGGAGACCTTCATCCGCGGCTGGGGCAACAAACCAATTGAATACATCAAAAAGG

AAAGATGGACTGACTCATTCAAAATTCTCGCTTATTTGTGTCAAAAGTTTTTGGA

CTTACACAAGTTGACATTAATCTTAAATGCTGTCTCTGAGGTGGAATTGCTCAAC

TTGGCGAGGACTTTCAAAGGCAAAGTCAGAAGAAGTTCTCATGGAACGAACATA

TGCAGGATTAGGGTTCCCAGCTTGGGTCCTACTTTTATTTCAGAAGGATGGGCTT

ACTTCAAGAAACTTGATATTCTAATGGACCGAAACTTTCTGTTAATGGTCAAAGA

TGTGATTATAGGGAGGATGCAAACGGTGCTATCCATGGTATGTAGAATAGACAA

CCTGTTCTCAGAGCAAGACATCTTCTCCCTTCTAAATATCTACAGAATTGGAGAT

AAAATTGTGGAGAGGCAGGGAAATTTTTCTTATGACTTGATTAAAATGGTGGAA

CCGATATGCAACTTGAAGCTGATGAAATTAGCAAGAGAATCAAGGCCTTTAGTC
```

-continued

CCACAATTCCCTCATTTTGAAAATCATATCAAGACTTCTGTTGATGAAGGGGCAA

AAATTGACCGAGGTATAAGATTCCTCCATGATCAGATAATGAGTGTGAAAACAG

TGGATCTCACACTGGTGATTTATGGATCGTTCAGACATTGGGGTCATCCTTTTAT

AGATTATTACACTGGACTAGAAAAATTACATTCCCAAGTAACCATGAAGAAAGA

TATTGATGTGTCATATGCAAAAGCACTTGCAAGTGATTTAGCTCGGATTGTTCTA

TTTCAACAGTTCAATGATCATAAAAAGTGGTTCGTGAATGGAGACTTGCTCCCTC

ATGATCATCCCTTTAAAAGTCATGTTAAAGAAAATACATGGCCCACAGCTGCTCA

AGTTCAAGATTTTGGAGATAAATGGCATGAACTTCCGCTGATTAAATGTTTTGAA

ATACCCGACTTACTAGACCCATCGATAATATACTCTGACAAAAGTCATTCAATGA

ATAGGTCAGAGGTGTTGAAACATGTCCGAATGAATCCGAACACTCCTATCCCTA

GTAAAAAGGTGTTGCAGACTATGTTGGACACAAAGGCTACCAATTGGAAAGAAT

TTCTTAAAGAGATTGATGAGAAGGGCTTAGATGATGATGATCTAATTATTGGTCT

TAAAGGAAAGGAGAGGGAACTGAAGTTGGCAGGTAGATTTTTCTCCCTAATGTC

TTGGAAATTGCGAGAATACTTTGTAATTACCGAATATTTGATAAAGACTCATTTC

GTCCCTATGTTTAAAGGCCTGACAATGGCGGACGATCTAACTGCAGTCATTAAAA

AGATGTTAGATTCCTCATCCGGCCAAGGATTGAAGTCATATGAGGCAATTTGCAT

AGC CAATCACATTGATTACGAAAAATGGAATAACCACCAAAGGAAGTTATCAAA

CGGCCCAGTGTTCCGAGTTATGGGCCAGTTCTTAGGTTATCCATCCTTAATCGAG

AGAACTCATGAATTTTTTGAGAAAAGTCTTATATACTACAATGGAAGACCAGACT

TGATGCGTGTTCACAACAACACACTGATCAATTCAACCTCCCAACGAGTTTGTTG

GCAAGGACAAGAGGGTGGACTGGAAGGTCTACGGCAAAAAGGATGGACTATCC

TCAATCTACTGGTTATTCAAAGAGAGGCTAAAATCAGAAACACTGCTGTCAAAG

TCTTGGCACAAGGTGATAATCAAGTTATTTGCACACAGTATAAAACGAAGAAAT

CGAGAAACGTTGTAGAATTACAGGGTGCTCTCAATCAAATGGTTTCTAATAATGA

GAAAATTATGACTGCAATCAAAATAGGGACAGGGAAGTTAGGACTTTTGATAAA

TGACGATGAGACTATGCAATCTGCAGATTACTTGAATTATGGAAAAATACCGATT

TTCCGTGGAGTGATTAGAGGGTTAGAGACCAAGAGATGGTCACGAGTGACTTGT

GTCACCAATGACCAAATACCCACTTGTGCTAATATAATGAGCTCAGTTTCCACAA

ATGCTCTCACCGTAGCTCATTTTGCTGAGAACCCAATCAATGCCATGATACAGTA

CAATTATTTTGGGACATTTGCTAGACTCTTGTTGATGATGCATGATCCTGCTCTTC

GTCAATCATTGTATGAAGTTCAAGATAAGATACCGGGCTTGCACAGTTCTACTTT

CAAATACGCCATGTTGTATTTGGACCCTTCCATTGGAGGAGTGTCGGGCATGTCT

TTGTCCAGGTTTTTGATTAGAGCCTTCCCAGATCCCGTAACAGAAAGTCTCTCAT

TCTGGAGATTCATCCATGTACATGCTCGAAGTGAGCATCTGAAGGAGATGAGTG

CAGTATTTGGAAACCCCGAGATAGCCAAGTTTCGAATAACTCACATAGACAAGC

TAGTAGAAGATCCAACCTCTCTGAACATCGCTATGGGAATGAGTCCAGCGAACT

TGTTAAAGACTGAGGTTAAAAAATGCTTAATCGAATCAAGACAAACCATCAGGA

ACCAGGTGATTAAGGATGCAACCATATATTTGTATCATGAAGAGGATCGGCTCA

GAAGTTTCTTATGGTCAATAAATCCTCTGTTCCCTAGATTTTTAAGTGAATTCAAA

TCAGGCACTTTTTTGGGAGTCGCGACGGGCTCATCAGTCTATTTCAAAATTCTC

GTACTATTCGGAACTCCTTTAAGAAAAAGTATCATAGGGAATTGGATGATTTGAT

-continued

```
TGTGAGGAGTGAGGTATCCTCTTTGACACATTTAGGGAAACTTCATTTGAGAAGG
GGATCATGTAAAATGTGGACATGTTCAGCTACTCATGCTGACACATTAAGATACA
AATCCTGGGGCCGTACAGTTATTGGGACAACTGTACCCCATCCATTAGAAATGTT
GGGTCCACAACATCGAAAAGAGACTCCTTGTGCACCATGTAACACATCAGGGTT
CAATTATGTTTCTGTGCATTGTCCAGACGGGATCCATGACGTCTTTAGTTCACGG
GGACCATTGCCTGCTTATCTAGGGTCTAAAACATCTGAATCTACATCTATTTTGC
AGCCTTGGGAAAGGGAAAGCAAAGTCCCACTGATTAAAAGAGCTACACGTCTTA
GAGATGCTATCTCTTGGTTTGTTGAACCCGACTCTAAACTAGCAATGACTATACT
TTCTAACATCCACTCTTTAACAGGCGAAGAATGGACCAAAAGGCAGCATGGGTT
CAAAAGAACAGGGTCTGCCCTTCATAGGTTTTCGACATCTCGGATGAGCCATGGT
GGGTTCGCATCTCAGAGCACTGCAGCATTGACCAGGTTGATGGCAACTACAGAC
ACCATGAGGGATCTGGGAGATCAGAATTTCGACTTTTTATTCCAAGCAACGTTGC
TCTATGCTCAAATTACCACCACTGTTGCAAGAGACGGATGGATCACCAGTTGTAC
AGATCATTATCATATTGCCTGTAAGTCCTGTTTGAGACCCATAGAAGAGATCACC
CTGGACTCAAGTATGGACTACACGCCCCCAGATGTATCCCATGTGCTGAAGACA
TGGAGGAATGGGGAAGGTTCGTGGGGACAAGAGATAAAACAGATCTATCCTTTA
GAAGGGAATTGGAAGAATTTAGCACCTGCTGAGCAATCCTATCAAGTCGGCAGA
TGTATAGGTTTTCTATATGGAGACTTGGCGTATAGAAAATCTACTCATGCCGAGG
ACAGTTCTCTATTTCCTCTATCTATACAAGGTCGTATTAGAGGTCGAGGTTTCTTA
AAAGGGTTGCTAGACGGATTAATGAGAGCAAGTTGCTGCCAAGTAATACACCGG
AGAAGTCTGGCTCATTTGAAGAGGCCGGCCAACGCAGTGTACGGAGGTTTGATT
TACTTGATTGATAAATTGAGTGTATCACCTCCATTCCTTTCTCTTACTAGATCAGG
ACCTATTAGAGACGAATTAGAAACGATTCCCCACAAGATCCCAACCTCCTATCC
GACAAGCAACCGTGATATGGGGGTGATTGTCAGAAATTACTTCAAATACCAATG
CCGTCTAATTGAAAAGGGAAAATACAGATCACATTATTCACAATTATGGTTATTC
TCAGATGTCTTATCCATAGACTTCATTGGACCATTCTCTATTTCCACCACCCTCTT
GCAAATCCTATACAAGCCATTTTTATCTGGGAAAGATAAGAATGAGTTGAGAGA
GCTGGCAAATCTTTCTTCATTGCTAAGATCAGGAGAGGGGTGGGAAGACATACA
TGTGAAATTCTTCACCAAGGACATATTATTGTGTCCAGAGGAAATCAGACATGCT
TGCAAGTTCGGGATTGCTAAGGATAATAATAAAGACATGAGCTATCCCCCTTGG
GGAAGGGAATCCAGAGGGACAATTACAACAATCCCTGTTTATTATACGACCACC
CCTTACCCAAAGATGCTAGAGATGCCTCCAAGAATCCAAAATCCCCTGCTGTCCG
GAATCAGGTTGGGCCAATTACCAACTGGCGCTCATTATAAAATTCGGAGTATATT
ACATGGAATGGGAATCCATTACAGGGACTTCTTGAGTTGTGGAGACGGCTCCGG
AGGGATGACTGCTGCATTACTACGAGAAAATGTGCATAGCAGAGGAATATTCAA
TAGTCTGTTAGAATTATCAGGGTCAGTCATGCGAGGCGCCTCTCCTGAGCCCCCC
AGTGCCCTAGAAACTTTAGGAGGAGATAAATCGAGATGTGTAAATGGTGAAACA
TGTTGGGAATATCCATCTGACTTATGTGACCCAAGGACTTGGGACTATTTCCTCC
GACTCAAAGCAGGCTTGGGGCTTCAAATTGATTTAATTGTAATGGATATGGAAGT
TCGGGATTCTTCTACTAGCCTGAAAATTGAGACGAATGTTAGAAATTATGTGCAC
```

-continued

```
CGGATTTTGGATGAGCAAGGAGTTTTAATCTACAAGACTTATGGAACATATATTT

GTGAGAGCGAAAAGAATGCAGTAACAATCCTTGGTCCCATGTTCAAGACGGTCG

ACTTAGTTCAAACAGAATTTAGTAGTTCTCAAACGTCTGAAGTATATATGGTATG

TAAAGGTTTGAAGAAATTAATCGATGAACCCAATCCCGATTGGTCTTCCATCAAT

GAATCCTGGAAAAACCTGTACGCATTCCAGTCATCAGAACAGGAATTTGCCAGA

GCAAAGAAGGTTAGTACATACTTTACCTTGACAGGTATTCCCTCCCAATTCATTC

CTGATCCTTTTGTAAACATTGAGACTATGCTACAAATATTCGGAGTACCCACGGG

TGTGTCTCATGCGGCTGCCTTAAAATCATCTGATAGACCTGCAGATTTATTGACC

ATTAGCCTTTTTTATATGGCGATTATATCGTATTATAACATCAATCATATCAGAGT

AGGACCGATACCTCCGAACCCCCCATCAGATGGAATTGCACAAAATGTGGGGAT

CGCTATAACTGGTATAAGCTTTTGGCTGAGTTTGATGGAGAAAGACATTCCACTA

TATCAACAGTGTTTAGCAGTTATCCAGCAATCATTCCCGATTAGGTGGGAGGCTG

TTTCAGTAAAAGGAGGATACAAGCAGAAGTGGAGTACTAGAGGTGATGGGCTCC

CAAAAGATACCCGAACTTCAGACTCCTTGGCCCCAATCGGGAACTGGATCAGAT

CTCTGGAATTGGTCCGAAACCAAGTTCGTCTAAATCCATTCAATGAGATCTTGTT

CAATCAGCTATGTCGTACAGTGGATAATCATTTGAAATGGTCAAATTTGCGAAGA

AACACAGGAATGATTGAATGGATCAATAGACGAATTTCAAAAGAAGACCGGTCT

ATACTGATGTTGAAGAGTGACCTACACGAGGAAAACTCTTGGAGAGATTAAAAA

ATCATGAGGAGACTCCAAACTTTAAGTATGAAAAAAACTTTGATCCTTAAGACC

CTCTTGTGGTTTTTATTTTTTATCTGGTTTTGTGGTCTTCGT.
```

In some embodiments, the nucleic acid comprises the sequence of SEQ ID NO: 20, shown below (VSV vector: Convac V2 China):

```
ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC
```

-continued

```
ATATTCTTCCGTCAAAAACCCTGCCTTCCACTTCTGGGGGCAATTGACAGCTCTT
CTGCTCAGATCCACCAGAGCAAGGAATGCCCGACAGCCTGATGACATTGAGTAT
ACATCTCTTACTACAGCAGGTTTGTTGTACGCTTATGCAGTAGGATCCTCTGCCG
ACTTGGCACAACAGTTTTGTGTTGGAGATAACAAATACACTCCAGATGATAGTAC
CGGAGGATTGACGACTAATGCACCGCCACAAGGCAGAGATGTGGTCGAATGGCT
CGGATGGTTTGAAGATCAAAACAGAAAACCGACTCCTGATATGATGCAGTATGC
GAAAAGAGCAGTCATGTCACTGCAAGGCCTAAGAGAGAAGACAATTGGCAAGT
ATGCTAAGTCAGAATTTGACAAATGACCCTATAATTCTCAGATCACCTATTATAT
ATTATGCTACATATGAAAAAAACTAACAGATATCATGGATAATCTCACAAAAGT
TCGTGAGTATCTCAAGTCCTATTCTCGTCTGGATCAGGCGGTAGGAGAGATAGAT
GAGATCGAAGCACAACGAGCTGAAAAGTCCAATTATGAGTTGTTCCAAGAGGAT
GGAGTGGAAGAGCATACTAAGCCCTCTTATTTTCAGGCAGCAGATGATTCTGAC
ACAGAATCTGAACCAGAAATTGAAGACAATCAAGGTTTGTATGCACCAGATCCA
GAAGCTGAGCAAGTTGAAGGCTTTATACAGGGGCCTTTAGATGACTATGCAGAT
GAGGAAGTGGATGTTGTATTTACTTCGGACTGGAAACAGCCTGAGCTTGAATCTG
ACGAGCATGGAAAGACCTTACGGTTGACATCGCCAGAGGGTTTAAGTGGAGAGC
AGAAATCCCAGTGGCTTTCGACGATTAAAGCAGTCGTGCAAAGTGCCAAATACT
GGAATCTGGCAGAGTGCACATTTGAAGCATCGGGAGAAGGGGTCATTATGAAGG
AGCGCCAGATAACTCCGGATGTATATAAGGTCACTCCAGTGATGAACACACATC
CGTCCCAATCAGAAGCAGTATCAGATGTTTGGTCTCTCAAAGACATCCATGAC
TTTCCAACCCAAGAAAGCAAGTCTTCAGCCTCTCACCATATCCTTGGATGAATTG
TTCTCATCTAGAGGAGAGTTCATCTCTGTCGGAGGTGACGGACGAATGTCTCATA
AAGAGGCCATCCTGCTCGGCCTGAGATACAAAAAGTTGTACAATCAGGCGAGAG
TCAAATATTCTCTGTAGACTATGAAAAAAAGTAACAGATATCACGATCTAAGTGT
TATCCCAATCCATTCATCATGAGTTCCTTAAAGAAGATTCTCGGTCTGAAGGGGA
AAGGTAAGAAATCTAAGAAATTAGGGATCGCACCACCCCCTTATGAAGAGGACA
CTAGCATGGAGTATGCTCCGAGCGCTCCAATTGACAAATCCTATTTTGGAGTTGA
CGAGATGGACACCTATGATCCGAATCAATTAAGATATGAGAAATTCTTCTTTACA
GTGAAAATGACGGTTAGATCTAATCGTCCGTTCAGAACATACTCAGATGTGGCA
GCCGCTGTATCCCATTGGGATCACATGTACATCGGAATGGCAGGGAAACGTCCC
TTCTACAAAATCTTGGCTTTTTTGGGTTCTTCTAATCTAAAGGCCACTCCAGCGGT
ATTGGCAGATCAAGGTCAACCAGAGTATCACACTCACTGCGAAGGCAGGGCTTA
TTTGCCACATAGGATGGGGAAGACCCCTCCCATGCTCAATGTACCAGAGCACTTC
AGAAGACCATTCAATATAGGTCTTTACAAGGGAACGATTGAGCTCACAATGACC
ATCTACGATGATGAGTCACTGGAAGCAGCTCCTATGATCTGGGATCATTTCAATT
CTTCCAAATTTTCTGATTTCAGAGAGAAGGCCTTAATGTTTGGCCTGATTGTCGA
GAAAAAGGCATCTGGAGCGTGGGTCCTGGATTCTATCAGCCACTTCAAATGAGC
TAGTCTAACTTCTAGCTTCTGAACAATCCCCGGTTTACTCAGTCTCTCCTAATTCC
AGCCTCTCGAACAACTAATATCCTGTCTTTTCTATCCCTATGAAAAAAACTAACA
GAGATCGATCTGTTTACGCGTCACTATGAAGTGCCTTTTGTACTTAGCCTTTTTAT
TCATTGGGGTGAATTGCAAGTTCACCATAGTTTTTCCACACAACCAAAAAGGAA
```

```
ACTGGAAAAATGTTCCTTCTAATTACCATTATTGCCCGTCAAGCTCAGATTTAAA
TTGGCATAATGACTTAATAGGCACAGCCATACAAGTCAAAATGCCCAAGAGTCA
CAAGGCTATTCAAGCAGACGGTTGGATGTGTCATGCTTCCAAATGGGTCACTACT
TGTGATTTCCGCTGGTATGGACCGAAGTATATAACACAGTCCATCCGATCCTTCA
CTCCATCTGTAGAACAATGCAAGGAAAGCATTGAACAAACGAAACAAGGAACTT
GGCTGAATCCAGGCTTCCCTCCTCAAAGTTGTGGATATGCAACTGTGACGGATGC
CGAAGCAGTGATTGTCCAGGTGACTCCTCACCATGTGCTGGTTGATGAATACACA
GGAGAATGGGTTGATTCACAGTTCATCAACGGAAAATGCAGCAATTACATATGC
CCCACTGTCCATAACTCTACAACCTGGCATTCTGACTATAAGGTCAAAGGGCTAT
GTGATTCTAACCTCATTTCCATGGACATCACCTTCTTCTCAGAGGACGGAGAGCT
ATCATCCCTGGGAAAGGAGGGCACAGGGTTCAGAAGTAACTACTTTGCTTATGA
AACTGGAGGCAAGGCCTGCAAAATGCAATACTGCAAGCATTGGGGAGTCAGACT
CCCATCAGGTGTCTGGTTCGAGATGGCTGATAAGGATCTCTTTGCTGCAGCCAGA
TTCCCTGAATGCCCAGAAGGGTCAAGTATCTCTGCTCCATCTCAGACCTCAGTGG
ATGTAAGTCTAATTCAGGACGTTGAGAGGATCTTGGATTATTCCCTCTGCCAAGA
AACCTGGAGCAAAATCAGAGCGGGTCTTCCAATCTCTCCAGTGGATCTCAGCTAT
CTTGCTCCTAAAAACCCAGGAACCGGTCCTGCTTTCACCATAATCAATGGTACCC
TAAAATACTTTGAGACCAGATACATCAGAGTCGATATTGCTGCTCCAATCCTCTC
AAGAATGGTCGGAATGATCAGTGGAACTACCACAGAAAGGGAACTGTGGGATG
ACTGGGCACCATATGAAGACGTGGAAATTGGACCCAATGGAGTTCTGAGGACCA
GTTCAGGATATAAGTTTCCTTTATACATGATTGGACATGGTATGTTGGACTCCGA
TCTTCATCTTAGCTCAAAGGCTCAGGTGTTCGAACATCCTCACATTCAAGACGCT
GCTTCGCAACTTCCTGATGATGAGAGTTTATTTTTTGGTGATACTGGGCTATCCA
AAAATCCAATCGAGCTTGTAGAAGGTTGGTTCAGTAGTTGGAAAAGCTCTATTGC
CTCTTTTTTCTTTATCATAGGGTTAATCATTGGACTATTCTTGGTTCTCCGAGTTG
GTATCCATCTTTGCATTAAATTAAAGCACACCAAGAAAAGACAGATTTATACAG
ACATAGAGATGAACCGACTTGGAAAGTAACTCAAATCCTGCTAGGTATGAAAAA
AACTAACaGATATCACGCTCGAGCGTACGCCACCATGTTCGTGTTTCTGGTGCTG
CTGCCTCTGGTGAGCTCCCAGTGCGTGAACCTGACCACAAGGACCCAGCTGCCC
CCTGCCTATACCAATTCCTTCACACGGGGCGTGTACTATCCCGACAAGGTGTTCC
GGAGCAGCGTGCTGCACTCCACACAGGATCTGTTTCTGCCTTTCTTTTCTAACGT
GACCTGGTTCCACGCCATCCACGTGAGCGGCACCAATGGCACAAAGCGGTTCGA
CAATCCAGTGCTGCCCTTTAACGATGGCGTGTACTTCGCCTCCACCGAGAAGTCT
AACATCATCAGAGGCTGGATCTTTGGCACCACACTGGACAGCAAGACACAGTCC
CTGCTGATCGTGAACAATGCCACCAACGTGGTCATCAAGGTGTGCGAGTTCCAGT
TTTGTAATGATCCATTCCTGGGCGTGTACTATCACAAGAACAATAAGTCTTGGAT
GGAGAGCGAGTTTCGCGTGTATTCCTCTGCCAACAATTGCACATTTGAGTACGTG
TCCCAGCCCTTCCTGATGGACCTGGAGGGCAAGCAGGGCAATTTCAAGAACCTG
AGGGAGTTCGTGTTTAAGAATATCGATGGCTACTTCAAAATCTACTCCAAGCACA
CCCCAATCAACCTGGTGCGCGACCTGCCACAGGGCTTCTCTGCCCTGGAGCCACT
```

-continued

```
GGTGGATCTGCCCATCGGCATCAACATCACCCGGTTTCAGACACTGCTGGCCCTG

CACAGAAGCTACCTGACACCAGGCGACAGCTCCTCTGGATGGACCGCAGGAGCA

GCAGCCTACTATGTGGGCTATCTGCAGCCCAGGACCTTCCTGCTGAAGTACAACG

AGAATGGCACCATCACAGACGCCGTGGATTGCGCCCTGGATCCCCTGTCTGAGA

CCAAGTGTACACTGAAGAGCTTTACCGTGGAGAAGGGCATCTATCAGACAAGCA

ATTTCAGGGTGCAGCCTACCGAGTCCATCGTGCGCTTTCCCAATATCACAAACCT

GTGCCCTTTTGGCGAGGTGTTCAACGCAACCCGCTTCGCCAGCGTGTACGCCTGG

AATAGGAAGCGCATCTCCAACTGCGTGGCCGACTATTCTGTGCTGTACAACAGC

GCCTCCTTCTCTACCTTTAAGTGCTATGGCGTGAGCCCCACAAAGCTGAATGACC

TGTGCTTTACCAACGTGTACGCCGATTCCTTCGTGATCAGGGGCGACGAGGTGCG

CCAGATCGCACCAGGACAGACAGGCAAGATCGCAGACTACAATTATAAGCTGCC

TGACGATTTCACCGGCTGCGTGATCGCCTGGAACTCTAACAATCTGGATAGCAAA

GTGGGCGGCAACTACAATTATCTGTACCGGCTGTTTAGAAAGTCTAATCTGAAGC

CATTCGAGAGGGACATCTCCACAGAAATCTACCAGGCCGGCTCTACCCCCTGCA

ATGGCGTGGAGGGCTTTAACTGTTATTTCCCTCTGCAGAGCTACGGCTTCCAGCC

AACAAACGGCGTGGGCTATCAGCCCTACCGCGTGGTGGTGCTGTCTTTTGAGCTG

CTGCACGCACCTGCAACAGTGTGCGGACCAAAGAAGAGCACCAATCTGGTGAAG

AACAAGTGCGTGAACTTCAACTTCAACGGACTGACCGGAACAGGCGTGCTGACC

GAGTCCAACAAGAAGTTCCTGCCTTTTCAGCAGTTCGGCAGGGACATCGCAGAT

ACCACAGACGCCGTGCGCGACCCTCAGACCCTGGAGATCCTGGACATCACACCA

TGCTCCTTCGGCGGCGTGTCTGTGATCACACCAGGCACCAATACAAGCAACCAG

GTGGCCGTGCTGTATCAGGACGTGAATTGTACCGAGGTGCCAGTGGCAATCCAC

GCAGATCAGCTGACCCCTACATGGCGGGTGTACTCTACCGGCAGCAACGTGTTC

CAGACAAGAGCCGGATGCCTGATCGGAGCAGAGCACGTGAACAATAGCTATGA

GTGCGACATCCCTATCGGCGCCGGCATCTGTGCCTCCTACCAGACCCAGACAAA

CTCCCCAAGGTCTGTGGGAGATGAGGCCGAAGACTTTGTGGAAGTCCACCTGCC

TGATGTGCATAACCAGGTGTCTGGCGTCGACCTGGGACTGCCAAATTGGGGCAA

GTACGTGCTGCTGAGTGCTGGAGCACTGACTGCCCTGATGCTGATCATTTTCCTG

ATGACCTGCTGTCGGCGCGTGAACAGAAGTGAGCCCACTCAGCACAATCTGCGA

GGAACCGGGAGAGAAGTGTCAGTCACACCTCAGAGCGGGAAAATCATTAGTAGT

TGGGAATCACATAAAAGCGGGGGCGAGACCAGGCTGTGAGCTAGCCAGATTCTT

CATGTTTGGACCAAATCAACTTGTGATACCATGCTCAAAGAGGCCTCAATTATAT

TTGAGTTTTTAATTTTTATGAAAAAAACTAACAGCAATCATGGAAGTCCACGATT

TTGAGACCGACGAGTTCAATGATTTCAATGAAGATGACTATGCCACAAGAGAAT

TCCTGAATCCCGATGAGCGCATGACGTACTTGAATCATGCTGATTACAATTTGAA

TTCTCCTCTAATTAGTGATGATATTGACAATTTGATCAGGAAATTCAATTCTCTTC

CGATTCCCTCGATGTGGGATAGTAAGAACTGGGATGGAGTTCTTGAGATGTTAAC

ATCATGTCAAGCCAATCCCATCTCAACATCTCAGATGCATAAATGGATGGGAAG

TTGGTTAATGTCTGATAATCATGATGCCAGTCAAGGGTATAGTTTTTTACATGAA

GTGGACAAAGAGGCAGAAATAACATTTGACGTGGTGGAGACCTTCATCCGCGGC

TGGGGCAACAAACCAATTGAATACATCAAAAAGGAAAGATGGACTGACTCATTC
```

```
AAAATTCTCGCTTATTTGTGTCAAAAGTTTTTGGACTTACACAAGTTGACATTAA

TCTTAAATGCTGTCTCTGAGGTGGAATTGCTCAACTTGGCGAGGACTTTCAAAGG

CAAAGTCAGAAGAAGTTCTCATGGAACGAACATATGCAGGATTAGGGTTCCCAG

CTTGGGTCCTACTTTTATTTCAGAAGGATGGCTTACTTCAAGAAACTTGATATT

CTAATGGACCGAAACTTTCTGTTAATGGTCAAAGATGTGATTATAGGGAGGATG

CAAACGGTGCTATCCATGGTATGTAGAATAGACAACCTGTTCTCAGAGCAAGAC

ATCTTCTCCCTTCTAAATATCTACAGAATTGGAGATAAAATTGTGGAGAGGCAGG

GAAATTTTCTTATGACTTGATTAAAATGGTGGAACCGATATGCAACTTGAAGCT

GATGAAATTAGCAAGAGAATCAAGGCCTTTAGTCCCACAATTCCCTCATTTTGAA

AATCATATCAAGACTTCTGTTGATGAAGGGGCAAAAATTGACCGAGGTATAAGA

TTCCTCCATGATCAGATAATGAGTGTGAAAACAGTGGATCTCACACTGGTGATTT

ATGGATCGTTCAGACATTGGGGTCATCCTTTTATAGATTATTACACTGGACTAGA

AAAATTACATTCCCAAGTAACCATGAAGAAAGATATTGATGTGTCATATGCAAA

AGCACTTGCAAGTGATTTAGCTCGGATTGTTCTATTTCAACAGTTCAATGATCAT

AAAAAGTGGTTCGTGAATGGAGACTTGCTCCCTCATGATCATCCCTTTAAAAGTC

ATGTTAAAGAAAATACATGGCCCACAGCTGCTCAAGTTCAAGATTTTGGAGATA

AATGGCATGAACTTCCGCTGATTAAATGTTTTGAAATACCCGACTTACTAGACCC

ATCGATAATATACTCTGACAAAAGTCATTCAATGAATAGGTCAGAGGTGTTGAA

ACATGTCCGAATGAATCCGAACACTCCTATCCCTAGTAAAAAGGTGTTGCAGACT

ATGTTGGACACAAAGGCTACCAATTGGAAAGAATTTCTTAAAGAGATTGATGAG

AAGGGCTTAGATGATGATGATCTAATTATTGGTCTTAAAGGAAAGGAGAGGGAA

CTGAAGTTGGCAGGTAGATTTTTCTCCCTAATGTCTTGGAAATTGCGAGAATACT

TTGTAATTACCGAATATTTGATAAAGACTCATTTCGTCCCTATGTTTAAAGGCCT

GACAATGGCGGACGATCTAACTGCAGTCATTAAAAAGATGTTAGATTCCTCATCC

GGCCAAGGATTGAAGTCATATGAGGCAATTTGCATAGCCAATCACATTGATTAC

GAAAAATGGAATAACCACCAAAGGAAGTTATCAAACGGCCCAGTGTTCCGAGTT

ATGGGCCAGTTCTTAGGTTATCCATCCTTAATCGAGAGAACTCATGAATTTTTG

AGAAAAGTCTTATATACTACAATGGAAGACCAGACTTGATGCGTGTTCACAACA

ACACACTGATCAATTCAACCTCCCAACGAGTTTGTTGGCAAGGACAAGAGGGTG

GACTGGAAGGTCTACGGCAAAAAGGATGGACTATCCTCAATCTACTGGTTATTC

AAAGAGAGGCTAAAATCAGAAACACTGCTGTCAAAGTCTTGGCACAAGGTGATA

ATCAAGTTATTTGCACACAGTATAAAACGAAGAAATCGAGAAACGTTGTAGAAT

TACAGGGTGCTCTCAATCAAATGGTTTCTAATAATGAGAAAATTATGACTGCAAT

CAAAATAGGGACAGGGAAGTTAGGACTTTTGATAAATGACGATGAGACTATGCA

ATCTGCAGATTACTTGAATTATGGAAAAATACCGATTTTCCGTGGAGTGATTAGA

GGGTTAGAGACCAAGAGATGGTCACGAGTGACTTGTGTCACCAATGACCAAATA

CCCACTTGTGCTAATATAATGAGCTCAGTTTCCACAAATGCTCTCACCGTAGCTC

ATTTTGCTGAGAACCCAATCAATGCCATGATACAGTACAATTATTTGGGACATT

TGCTAGACTCTTGTTGATGATGCATGATCCTGCTCTTCGTCAATCATTGTATGAAG

TTCAAGATAAGATACCGGGCTTGCACAGTTCTACTTTCAAATACGCCATGTTGTA
```

-continued

```
TTTGGACCCTTCCATTGGAGGAGTGTCGGGCATGTCTTTGTCCAGGTTTTTGATTA

GAGCCTTCCCAGATCCCGTAACAGAAAGTCTCTCATTCTGGAGATTCATCCATGT

ACATGCTCGAAGTGAGCATCTGAAGGAGATGAGTGCAGTATTTGGAAACCCCGA

GATAGCCAAGTTTCGAATAACTCACATAGACAAGCTAGTAGAAGATCCAACCTC

TCTGAACATCGCTATGGGAATGAGTCCAGCGAACTTGTTAAAGACTGAGGTTAA

AAAATGCTTAATCGAATCAAGACAAACCATCAGGAACCAGGTGATTAAGGATGC

AACCATATATTTGTATCATGAAGAGGATCGGCTCAGAAGTTTCTTATGGTCAATA

AATCCTCTGTTCCCTAGATTTTTAAGTGAATTCAAATCAGGCACTTTTTGGGAGT

CGCAGACGGGCTCATCAGTCTATTTCAAAATTCTCGTACTATTCGGAACTCCTTT

AAGAAAAAGTATCATAGGGAATTGGATGATTTGATTGTGAGGAGTGAGGTATCC

TCTTTGACACATTTAGGGAAACTTCATTTGAGAAGGGGATCATGTAAAATGTGGA

CATGTTCAGCTACTCATGCTGACACATTAAGATACAAATCCTGGGGCCGTACAGT

TATTGGGACAACTGTACCCCATCCATTAGAAATGTTGGGTCCACAACATCGAAA

AGAGACTCCTTGTGCACCATGTAACACATCAGGGTTCAATTATGTTTCTGTGCAT

TGTCCAGACGGGATCCATGACGTCTTTAGTTCACGGGGACCATTGCCTGCTTATC

TAGGGTCTAAAACATCTGAATCTACATCTATTTTGCAGCCTTGGGAAAGGGAAA

GCAAAGTCCCACTGATTAAAAGAGCTACACGTCTTAGAGATGCTATCTCTTGGTT

TGTTGAACCCGACTCTAAACTAGCAATGACTATACTTTCTAACATCCACTCTTTA

ACAGGCGAAGAATGGACCAAAAGGCAGCATGGGTTCAAAAGAACAGGGTCTGC

CCTTCATAGGTTTTCGACATCTCGGATGAGCCATGGTGGGTTCGCATCTCAGAGC

ACTGCAGCATTGACCAGGTTGATGGCAACTACAGACACCATGAGGGATCTGGGA

GATCAGAATTTCGACTTTTTATTCCAAGCAACGTTGCTCTATGCTCAAATTACCA

CCACTGTTGCAAGAGACGGATGGATCACCAGTTGTACAGATCATTATCATATTGC

CTGTAAGTCCTGTTTGAGACCCATAGAAGAGATCACCCTGGACTCAAGTATGGA

CTACACGCCCCCAGATGTATCCCATGTGCTGAAGACATGGAGGAATGGGGAAGG

TTCGTGGGACAAGAGATAAAACAGATCTATCCTTTAGAAGGGAATTGGAAGAA

TTTAGCACCTGCTGAGCAATCCTATCAAGTCGGCAGATGTATAGGTTTTCTATAT

GGAGACTTGGCGTATAGAAAATCTACTCATGCCGAGGACAGTTCTCTATTTCCTC

TATCTATACAAGGTCGTATTAGAGGTCGAGGTTTCTTAAAAGGGTTGCTAGACGG

ATTAATGAGAGCAAGTTGCTGCCAAGTAATACACCGGAGAAGTCTGGCTCATTT

GAAGAGGCCGGCCAACGCAGTGTACGGAGGTTTGATTTACTTGATTGATAAATT

GAGTGTATCACCTCCATTCCTTTCTCTTACTAGATCAGGACCTATTAGAGACGAA

TTAGAAACGATTCCCCACAAGATCCCAACCTCCTATCCGACAAGCAACCGTGAT

ATGGGGGTGATTGTCAGAAATTACTTCAAATACCAATGCCGTCTAATTGAAAAG

GGAAAATACAGATCACATTATTCACAATTATGGTTATTCTCAGATGTCTTATCCA

TAGACTTCATTGGACCATTCTCTATTTCCACCACCCTCTTGCAAATCCTATACAAG

CCATTTTTATCTGGGAAAGATAAGAATGAGTTGAGAGAGCTGGCAAATCTTTCTT

CATTGCTAAGATCAGGAGAGGGGTGGGAAGACATACATGTGAAATTCTTCACCA

AGGACATATTATTGTGTCCAGAGGAAATCAGACATGCTTGCAAGTTCGGGATTG

CTAAGGATAATAATAAAGACATGAGCTATCCCCCTTGGGGAAGGGAATCCAGAG

GGACAATTACAACAATCCCTGTTTATTATACGACCACCCCTTACCCAAAGATGCT
```

-continued

```
AGAGATGCCTCCAAGAATCCAAAATCCCCTGCTGTCCGGAATCAGGTTGGGCCA

ATTACCAACTGGCGCTCATTATAAAATTCGGAGTATATTACATGGAATGGGAATC

CATTACAGGGACTTCTTGAGTTGTGGAGACGGCTCCGGAGGGATGACTGCTGCA

TTACTACGAGAAAATGTGCATAGCAGAGGAATATTCAATAGTCTGTTAGAATTAT

CAGGGTCAGTCATGCGAGGCGCCTCTCCTGAGCCCCCCAGTGCCCTAGAAACTTT

AGGAGGAGATAAATCGAGATGTGTAAATGGTGAAACATGTTGGGAATATCCATC

TGACTTATGTGACCCAAGGACTTGGGACTATTTCCTCCGACTCAAAGCAGGCTTG

GGGCTTCAAATTGATTTAATTGTAATGGATATGGAAGTTCGGGATTCTTCTACTA

GCCTGAAAATTGAGACGAATGTTAGAAATTATGTGCACCGGATTTTGGATGAGC

AAGGAGTTTTAATCTACAAGACTTATGAACATATATTTGTGAGAGCGAAAAGA

ATGCAGTAACAATCCTTGGTCCCATGTTCAAGACGGTCGACTTAGTTCAAACAGA

ATTTAGTAGTTCTCAAACGTCTGAAGTATATATGGTATGTAAAGGTTTGAAGAAA

TTAATCGATGAACCCAATCCCGATTGGTCTTCCATCAATGAATCCTGGAAAAACC

TGTACGCATTCCAGTCATCAGAACAGGAATTTGCCAGAGCAAAGAAGGTTAGTA

CATACTTTACCTTGACAGGTATTCCCTCCCAATTCATTCCTGATCCTTTTGTAAAC

ATTGAGACTATGCTACAAATATTCGGAGTACCCACGGGTGTGTCTCATGCGGCTG

CCTTAAAATCATCTGATAGACCTGCAGATTTATTGACCATTAGCCTTTTTTATATG

GCGATTATATCGTATTATAACATCAATCATATCAGAGTAGGACCGATACCTCCGA

ACCCCCCATCAGATGGAATTGCACAAAATGTGGGATCGCTATAACTGGTATAA

GCTTTTGGCTGAGTTTGATGGAGAAAGACATTCCACTATATCAACAGTGTTTAGC

AGTTATCCAGCAATCATTCCCGATTAGGTGGGAGGCTGTTTCAGTAAAAGGAGG

ATACAAGCAGAAGTGGAGTACTAGAGGTGATGGGCTCCCAAAAGATACCCGAAC

TTCAGACTCCTTGGCCCCAATCGGGAACTGGATCAGATCTCTGGAATTGGTCCGA

AACCAAGTTCGTCTAAATCCATTCAATGAGATCTTGTTCAATCAGCTATGTCGTA

CAGTGGATAATCATTTGAAATGGTCAAATTTGCGAAGAAACACAGGAATGATTG

AATGGATCAATAGACGAATTTCAAAAGAAGACCGGTCTATACTGATGTTGAAGA

GTGACCTACACGAGGAAAACTCTTGGAGAGATTAAAAAATCATGAGGAGACTCC

AAACTTTAAGTATGAAAAAAACTTTGATCCTTAAGACCCTCTTGTGGTTTTTATTT

TTTATCTGGTTTTGTGGTCTTCGT.
```

In other embodiments, the nucleic acid comprises the sequence of SEQ ID NO: 21, shown below (VSV vector: Convac V2 South Africa):

```
ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT
```

```
TCCAGAACCAGCGCAGATGACAAATGGTTGCCTTTGTATCTACTTGGCTTATACA
GAGTGGGCAGAACACAAATGCCTGAATACAGAAAAAAGCTCATGGATGGGCTG
ACAAATCAATGCAAAATGATCAATGAACAGTTTGAACCTCTTGTGCCAGAAGGT
CGTGACATTTTTGATGTGTGGGGAAATGACAGTAATTACACAAAAATTGTCGCTG
CAGTGGACATGTTCTTCCACATGTTCAAAAAACATGAATGTGCCTCGTTCAGATA
CGGAACTATTGTTTCCAGATTCAAAGATTGTGCTGCATTGGCAACATTTGGACAC
CTCTGCAAAATAACCGGAATGTCTACAGAAGATGTAACGACCTGGATCTTGAAC
CGAGAAGTTGCAGATGAAATGGTCCAAATGATGCTTCCAGGCCAAGAAATTGAC
AAGGCCGATTCATACATGCCTTATTTGATCGACTTTGGATTGTCTTCTAAGTCTCC
ATATTCTTCCGTCAAAAACCCTGCCTTCCACTTCTGGGGCAATTGACAGCTCTT
CTGCTCAGATCCACCAGAGCAAGGAATGCCCGACAGCCTGATGACATTGAGTAT
ACATCTCTTACTACAGCAGGTTTGTTGTACGCTTATGCAGTAGGATCCTCTGCCG
ACTTGGCACAACAGTTTTGTGTTGGAGATAACAAATACACTCCAGATGATAGTAC
CGGAGGATTGACGACTAATGCACCGCCACAAGGCAGAGATGTGGTCGAATGGCT
CGGATGGTTTGAAGATCAAAACAGAAAACCGACTCCTGATATGATGCAGTATGC
GAAAAGAGCAGTCATGTCACTGCAAGGCCTAAGAGAGAAGACAATTGGCAAGT
ATGCTAAGTCAGAATTTGACAAATGACCCTATAATTCTCAGATCACCTATTATAT
ATTATGCTACATATGAAAAAAACTAACAGATATCATGGATAATCTCACAAAAGT
TCGTGAGTATCTCAAGTCCTATTCTCGTCTGGATCAGGCGGTAGGAGAGATAGAT
GAGATCGAAGCACAACGAGCTGAAAAGTCCAATTATGAGTTGTTCCAAGAGGAT
GGAGTGGAAGAGCATACTAAGCCCTCTTATTTTCAGGCAGCAGATGATTCTGAC
ACAGAATCTGAACCAGAAATTGAAGACAATCAAGGTTTGTATGCACCAGATCCA
GAAGCTGAGCAAGTTGAAGGCTTTATACAGGGGCCTTTAGATGACTATGCAGAT
GAGGAAGTGGATGTTGTATTTACTTCGGACTGGAAACAGCCTGAGCTTGAATCTG
ACGAGCATGGAAAGACCTTACGGTTGACATCGCCAGAGGGTTTAAGTGGAGAGC
AGAAATCCCAGTGGCTTTCGACGATTAAAGCAGTCGTGCAAAGTGCCAAATACT
GGAATCTGGCAGAGTGCACATTTGAAGCATCGGGAGAAGGGGTCATTATGAAGG
AGCGCCAGATAACTCCGGATGTATATAAGGTCACTCCAGTGATGAACACACATC
CGTCCCAATCAGAAGCAGTATCAGATGTTTGGTCTCTCTCAAAGACATCCATGAC
TTTCCAACCCAAGAAAGCAAGTCTTCAGCCTCTCACCATATCCTTGGATGAATTG
TTCTCATCTAGAGGAGAGTTCATCTCTGTCGGAGGTGACGGACGAATGTCTCATA
AAGAGGCCATCCTGCTCGGCCTGAGATACAAAAAGTTGTACAATCAGGCGAGAG
TCAAATATTCTCTGTAGACTATGAAAAAAAGTAACAGATATCACGATCTAAGTGT
TATCCCAATCCATTCATCATGAGTTCCTTAAAGAAGATTCTCGGTCTGAAGGGGA
AAGGTAAGAAATCTAAGAAATTAGGGATCGCACCACCCCCTTATGAAGAGGACA
CTAGCATGGAGTATGCTCCGAGCGCTCCAATTGACAAATCCTATTTTGGAGTTGA
CGAGATGGACACCTATGATCCGAATCAATTAAGATATGAGAAATTCTTCTTTACA
GTGAAAATGACGGTTAGATCTAATCGTCCGTTCAGAACATACTCAGATGTGGCA
GCCGCTGTATCCCATTGGGATCACATGTACATCGGAATGGCAGGGAAACGTCCC
TTCTACAAAATCTTGGCTTTTTTGGGTTCTTCTAATCTAAAGGCCACTCCAGCGGT
```

-continued

```
ATTGGCAGATCAAGGTCAACCAGAGTATCACACTCACTGCGAAGGCAGGGCTTA

TTTGCCACATAGGATGGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCTCCTAATTCC

AGCCTCTCGAACAACTAATATCCTGTCTTTTCTATCCCTATGAAAAAAACTAACA

GAGATCGATCTGTTTACGCGTCACTATGAAGTGCCTTTTGTACTTAGCCTTTTTAT

TCATTGGGGTGAATTGCAAGTTCACCATAGTTTTTCCACACAACCAAAAAGGAA

ACTGAAAAATGTTCCTTCTAATTACCATTATTGCCCGTCAAGCTCAGATTTAAA

TTGGCATAATGACTTAATAGGCACAGCCATACAAGTCAAAATGCCCAAGAGTCA

CAAGGCTATTCAAGCAGACGGTTGGATGTGTCATGCTTCCAAATGGGTCACTACT

TGTGATTTCCGCTGGTATGGACCGAAGTATATAACACAGTCCATCCGATCCTTCA

CTCCATCTGTAGAACAATGCAAGGAAAGCATTGAACAAACGAAACAAGGAACTT

GGCTGAATCCAGGCTTCCCTCCTCAAAGTTGTGGATATGCAACTGTGACGGATGC

CGAAGCAGTGATTGTCCAGGTGACTCCTCACCATGTGCTGGTTGATGAATACACA

GGAGAATGGGTTGATTCACAGTTCATCAACGGAAAATGCAGCAATTACATATGC

CCCACTGTCCATAACTCTACAACCTGGCATTCTGACTATAAGGTCAAAGGGCTAT

GTGATTCTAACCTCATTTCCATGGACATCACCTTCTTCTCAGAGGACGGAGAGCT

ATCATCCCTGGGAAAGGAGGGCACAGGGTTCAGAAGTAACTACTTTGCTTATGA

AACTGGAGGCAAGGCCTGCAAAATGCAATACTGCAAGCATTGGGGAGTCAGACT

CCCATCAGGTGTCTGGTTCGAGATGGCTGATAAGGATCTCTTTGCTGCAGCCAGA

TTCCCTGAATGCCCAGAAGGGTCAAGTATCTCTGCTCCATCTCAGACCTCAGTGG

ATGTAAGTCTAATTCAGGACGTTGAGAGGATCTTGGATTATTCCCTCTGCCAAGA

AACCTGGAGCAAAATCAGAGCGGGTCTTCCAATCTCTCCAGTGGATCTCAGCTAT

CTTGCTCCTAAAAACCCAGGAACCGGTCCTGCTTTCACCATAATCAATGGTACCC

TAAAATACTTTGAGACCAGATACATCAGAGTCGATATTGCTGCTCCAATCCTCTC

AAGAATGGTCGGAATGATCAGTGGAACTACCACAGAAAGGGAACTGTGGGATG

ACTGGGCACCATATGAAGACGTGGAAATTGGACCCAATGGAGTTCTGAGGACCA

GTTCAGGATATAAGTTTCCTTTATACATGATTGGACATGGTATGTTGGACTCCGA

TCTTCATCTTAGCTCAAAGGCTCAGGTGTTCGAACATCCTCACATTCAAGACGCT

GCTTCGCAACTTCCTGATGATGAGAGTTTATTTTTTGGTGATACTGGGCTATCCA

AAAATCCAATCGAGCTTGTAGAAGGTTGGTTCAGTAGTTGGAAAAGCTCTATTGC

CTCTTTTTTCTTTATCATAGGGTTAATCATTGGACTATTCTTGGTTCTCCGAGTTG

GTATCCATCTTTGCATTAAATTAAAGCACACCAAGAAAGACAGATTTATACAG

ACATAGAGATGAACCGACTTGGAAAGTAACTCAAATCCTGCTAGGTATGAAAAA

AACTAACaGATATCACGCTCGAGCGTACGCCACCATGTTCGTGTTCTGGTGCTG

CTGCCTCTGGTGAGCTCCCAGTGCGTGAACTTCACCACAAGGACCCAGCTGCCCC

CTGCCTATACCAATTCCTTCACACGGGGCGTGTACTATCCCGACAAGGTGTTCCG

GAGCAGCGTGCTGCACTCCACACAGGATCTGTTTCTGCCTTTCTTTTCTAACGTG
```

-continued

```
ACCTGGTTCCACGCCATCCACGTGAGCGGCACCAATGGCACAAAGCGGTTCGCC

AATCCAGTGCTGCCCTTTAACGATGGCGTGTACTTCGCCTCCACCGAGAAGTCTA

ACATCATCAGAGGCTGGATCTTTGGCACCACACTGGACAGCAAGACACAGTCCC

TGCTGATCGTGAACAATGCCACCAACGTGGTCATCAAGGTGTGCGAGTTCCAGTT

TTGTAATGATCCATTCCTGGGCGTGTACTATCACAAGAACAATAAGTCTTGGATG

GAGAGCGAGTTTCGCGTGTATTCCTCTGCCAACAATTGCACATTTGAGTACGTGT

CCCAGCCCTTCCTGATGGACCTGGAGGGCAAGCAGGGCAATTTCAAGAACCTGA

GGGAGTTCGTGTTTAAGAATATCGATGGCTACTTCAAAATCTACTCCAAGCACAC

CCCAATCAACCTGGTGCGCGGCCTGCCACAGGGCTTCTCTGCCCTGGAGCCACTG

GTGGATCTGCCCATCGGCATCAACATCACCCGGTTTCAGACACTGCTGGCCCTGC

ACAGAAGCTACCTGACACCAGGCGACAGCTCCTCTGGATGGACCGCAGGAGCAG

CAGCCTACTATGTGGGCTATCTGCAGCCCAGGACCTTCCTGCTGAAGTACAACGA

GAATGGCACCATCACAGACGCCGTGGATTGCGCCCTGGATCCCCTGTCTGAGAC

CAAGTGTACACTGAAGAGCTTTACCGTGGAGAAGGGCATCTATCAGACAAGCAA

TTTCAGGGTGCAGCCTACCGAGTCCATCGTGCGCTTTCCCAATATCACAAACCTG

TGCCCTTTTGGCGAGGTGTTCAACGCAACCCGCTTCGCCAGCGTGTACGCCTGGA

ATAGGAAGCGCATCTCCAACTGCGTGGCCGACTATTCTGTGCTGTACAACAGCG

CCTCCTTCTCTACCTTTAAGTGCTATGGCGTGAGCCCCACAAAGCTGAATGACCT

GTGCTTTACCAACGTGTACGCCGATTCCTTCGTGATCAGGGGCGACGAGGTGCGC

CAGATCGCACCAGGACAGACAGGCAATATCGCAGACTACAATTATAAGCTGCCT

GACGATTTCACCGGCTGCGTGATCGCCTGGAACTCTAACAATCTGGATAGCAAA

GTGGGCGGCAACTACAATTATCTGTACCGGCTGTTTAGAAAGTCTAATCTGAAGC

CATTCGAGAGGGACATCTCCACAGAAATCTACCAGGCCGGCTCTACCCCCTGCA

ATGGCGTGAAGGGCTTTAACTGTTATTTCCCTCTGCAGAGCTACGGCTTCCAGCC

AACATATGGCGTGGGCTATCAGCCCTACCGCGTGGTGGTGCTGTCTTTTGAGCTG

CTGCACGCACCTGCAACAGTGTGCGGACCAAAGAAGAGCACCAATCTGGTGAAG

AACAAGTGCGTGAACTTCAACTTCAACGGACTGACCGGAACAGGCGTGCTGACC

GAGTCCAACAAGAAGTTCCTGCCTTTTCAGCAGTTCGGCAGGGACATCGCAGAT

ACCACAGACGCCGTGCGCGACCCTCAGACCCTGGAGATCCTGGACATCACACCA

TGCTCCTTCGGCGGCGTGTCTGTGATCACACCAGGCACCAATACAAGCAACCAG

GTGGCCGTGCTGTATCAGGGCGTGAATTGTACCGAGGTGCCAGTGGCAATCCAC

GCAGATCAGCTGACCCCTACATGGCGGGTGTACTCTACCGGCAGCAACGTGTTC

CAGACAAGAGCCGGATGCCTGATCGGAGCAGAGCACGTGAACAATAGCTATGA

GTGCGACATCCCTATCGGCGCCGGCATCTGTGCCTCCTACCAGACCCAGACAAA

CTCCCCAGAATCAAGCGTGATTCCTCTGGTCCATCCACTGGCAGATCCCTCCACA

GTGTTCAAAGACGGAGATGAGGCCGAAGACTTTGTGGAAGTCCACCTGCCTGAT

GTGCATAACCAGGTGTCTGGCGTCGACCTGGGACTGCCAAATTGGGGCAAGTAC

GTGCTGCTGAGTGCTGGAGCACTGACTGCCCTGATGCTGATCATTTTCCTGATGA

CCTGCTGTCGGCGCGTGAACAGAAGTGAGCCCACTCAGCACAATCTGCGAGGAA

CCGGGAGAGAAGTGTCAGTCACACCTCAGAGCGGGAAAATCATTAGTAGTTGGG
```

-continued

```
AATCACATAAAAGCGGGGGCGAGACCAGGCTGTGAGCTAGCCAGATTCTTCATG
TTTGGACCAAATCAACTTGTGATACCATGCTCAAAGAGGCCTCAATTATATTTGA
GTTTTTAATTTTTATGAAAAAAACTAACAGCAATCATGGAAGTCCACGATTTTGA
GACCGACGAGTTCAATGATTTCAATGAAGATGACTATGCCACAAGAGAATTCCT
GAATCCCGATGAGCGCATGACGTACTTGAATCATGCTGATTACAATTTGAATTCT
CCTCTAATTAGTGATGATATTGACAATTTGATCAGGAAATTCAATTCTCTTCCGA
TTCCCTCGATGTGGGATAGTAAGAACTGGGATGGAGTTCTTGAGATGTTAACATC
ATGTCAAGCCAATCCCATCTCAACATCTCAGATGCATAAATGGATGGGAAGTTG
GTTAATGTCTGATAATCATGATGCCAGTCAAGGGTATAGTTTTTTACATGAAGTG
GACAAAGAGGCAGAAATAACATTTGACGTGGTGGAGACCTTCATCCGCGGCTGG
GGCAACAAACCAATTGAATACATCAAAAAGGAAAGATGGACTGACTCATTCAAA
ATTCTCGCTTATTTGTGTCAAAAGTTTTTGGACTTACACAAGTTGACATTAATCTT
AAATGCTGTCTCTGAGGTGGAATTGCTCAACTTGGCGAGGACTTTCAAAGGCAA
AGTCAGAAGAAGTTCTCATGGAACGAACATATGCAGGATTAGGGTTCCCAGCTT
GGGTCCTACTTTTATTTCAGAAGGATGGGCTTACTTCAAGAAACTTGATATTCTA
ATGGACCGAAACTTTCTGTTAATGGTCAAAGATGTGATTATAGGGAGGATGCAA
ACGGTGCTATCCATGGTATGTAGAATAGACAACCTGTTCTCAGAGCAAGACATCT
TCTCCCTTCTAAATATCTACAGAATTGGAGATAAAATTGTGGAGAGGCAGGGAA
ATTTTTCTTATGACTTGATTAAAATGGTGGAACCGATATGCAACTTGAAGCTGAT
GAAATTAGCAAGAGAATCAAGGCCTTTAGTCCCACAATTCCCTCATTTTGAAAAT
CATATCAAGACTTCTGTTGATGAAGGGGCAAAAATTGACCGAGGTATAAGATTC
CTCCATGATCAGATAATGAGTGTGAAAACAGTGGATCTCACACTGGTGATTTATG
GATCGTTCAGACATTGGGGTCATCCTTTTATAGATTATTACACTGGACTAGAAAA
ATTACATTCCCAAGTAACCATGAAGAAAGATATTGATGTGTCATATGCAAAAGC
ACTTGCAAGTGATTTAGCTCGGATTGTTCTATTTCAACAGTTCAATGATCATAAA
AAGTGGTTCGTGAATGGAGACTTGCTCCCTCATGATCATCCCTTTAAAAGTCATG
TTAAAGAAAATACATGGCCCACAGCTGCTCAAGTTCAAGATTTTGGAGATAAAT
GGCATGAACTTCCGCTGATTAAATGTTTTGAAATACCCGACTTACTAGACCCATC
GATAATATACTCTGACAAAAGTCATTCAATGAATAGGTCAGAGGTGTTGAAACA
TGTCCGAATGAATCCGAACACTCCTATCCCTAGTAAAAAGGTGTTGCAGACTATG
TTGGACACAAAGGCTACCAATTGGAAAGAATTTCTTAAAGAGATTGATGAGAAG
GGCTTAGATGATGATGATCTAATTATTGGTCTTAAAGGAAAGGAGAGGGAACTG
AAGTTGGCAGGTAGATTTTTCTCCCTAATGTCTTGGAAATTGCGAGAATACTTTG
TAATTACCGAATATTTGATAAAGACTCATTTCGTCCCTATGTTTAAAGGCCTGAC
AATGGCGGACGATCTAACTGCAGTCATTAAAAAGATGTTAGATTCCTCATCCGGC
CAAGGATTGAAGTCATATGAGGCAATTTGCATAGCCAATCACATTGATTACGAA
AAATGGAATAACCACCAAAGGAAGTTATCAAACGGCCCAGTGTTCCGAGTTATG
GGCCAGTTCTTAGGTTATCCATCCTTAATCGAGAGAACTCATGAATTTTTTGAGA
AAAGTCTTATATACTACAATGGAAGACCAGACTTGATGCGTGTTCACAACAACA
CACTGATCAATTCAACCTCCCAACGAGTTTGTTGGCAAGGACAAGAGGGTGGAC
TGGAAGGTCTACGGCAAAAAGGATGGACTATCCTCAATCTACTGGTTATTCAAA
```

-continued

```
GAGAGGCTAAAATCAGAAACACTGCTGTCAAAGTCTTGGCACAAGGTGATAATC

AAGTTATTTGCACACAGTATAAAACGAAGAAATCGAGAAACGTTGTAGAATTAC

AGGGTGCTCTCAATCAAATGGTTTCTAATAATGAGAAAATTATGACTGCAATCAA

AATAGGGACAGGGAAGTTAGGACTTTTGATAAATGACGATGAGACTATGCAATC

TGCAGATTACTTGAATTATGGAAAAATACCGATTTTCCGTGGAGTGATTAGAGGG

TTAGAGACCAAGAGATGGTCACGAGTGACTTGTGTCACCAATGACCAAATACCC

ACTTGTGCTAATATAATGAGCTCAGTTTCCACAAATGCTCTCACCGTAGCTCATT

TTGCTGAGAACCCAATCAATGCCATGATACAGTACAATTATTTTGGGACATTTGC

TAGACTCTTGTTGATGATGCATGATCCTGCTCTTCGTCAATCATTGTATGAAGTTC

AAGATAAGATACCGGGCTTGCACAGTTCTACTTTCAAATACGCCATGTTGTATTT

GGACCCTTCCATTGGAGGAGTGTCGGGCATGTCTTTGTCCAGGTTTTTGATTAGA

GCCTTCCCAGATCCCGTAACAGAAAGTCTCTCATTCTGGAGATTCATCCATGTAC

ATGCTCGAAGTGAGCATCTGAAGGAGATGAGTGCAGTATTTGGAAACCCCGAGA

TAGCCAAGTTTCGAATAACTCACATAGACAAGCTAGTAGAAGATCCAACCTCTCT

GAACATCGCTATGGGAATGAGTCCAGCGAACTTGTTAAAGACTGAGGTTAAAAA

ATGCTTAATCGAATCAAGACAAACCATCAGGAACCAGGTGATTAAGGATGCAAC

CATATATTTGTATCATGAAGAGGATCGGCTCAGAAGTTTCTTATGGTCAATAAAT

CCTCTGTTCCCTAGATTTTTAAGTGAATTCAAATCAGGCACTTTTTTGGGAGTCGC

AGACGGGCTCATCAGTCTATTTCAAAATTCTCGTACTATTCGGAACTCCTTTAAG

AAAAAGTATCATAGGGAATTGGATGATTTGATTGTGAGGAGTGAGGTATCCTCTT

TGACACATTTAGGGAAACTTCATTTGAGAAGGGGATCATGTAAAATGTGGACAT

GTTCAGCTACTCATGCTGACACATTAAGATACAAATCCTGGGGCCGTACAGTTAT

TGGGACAACTGTACCCCATCCATTAGAAATGTGGGTCCACAACATCGAAAAGA

GACTCCTTGTGCACCATGTAACACATCAGGGTTCAATTATGTTTCTGTGCATTGTC

CAGACGGGATCCATGACGTCTTTAGTTCACGGGGACCATTGCCTGCTTATCTAGG

GTCTAAAACATCTGAATCTACATCTATTTTGCAGCCTTGGGAAAGGGAAAGCAA

AGTCCCACTGATTAAAAGAGCTACACGTCTTAGAGATGCTATCTCTTGGTTTGTT

GAACCCGACTCTAAACTAGCAATGACTATACTTTCTAACATCCACTCTTTAACAG

GCGAAGAATGGACCAAAAGGCAGCATGGGTTCAAAAGAACAGGGTCTGCCCTTC

ATAGGTTTTCGACATCTCGGATGAGCCATGGTGGGTTCGCATCTCAGAGCACTGC

AGCATTGACCAGGTTGATGGCAACTACAGACACCATGAGGGATCTGGGAGATCA

GAATTTCGACTTTTTATTCCAAGCAACGTTGCTCTATGCTCAAATTACCACCACTG

TTGCAAGAGACGGATGGATCACCAGTTGTACAGATCATTATCATATTGCCTGTAA

GTCCTGTTTGAGACCCATAGAAGAGATCACCCTGGACTCAAGTATGGACTACAC

GCCCCCAGATGTATCCCATGTGCTGAAGACATGGAGGAATGGGGAAGGTTCGTG

GGGACAAGAGATAAAACAGATCTATCCTTTAGAAGGGAATTGGAAGAATTTAGC

ACCTGCTGAGCAATCCTATCAAGTCGGCAGATGTATAGGTTTTCTATATGGAGAC

TTGGCGTATAGAAAATCTACTCATGCCGAGGACAGTTCTCTATTTCCTCTATCTAT

ACAAGGTCGTATTAGAGGTCGAGGTTTCTTAAAAGGGTTGCTAGACGGATTAAT

GAGAGCAAGTTGCTGCCAAGTAATACACCGGAGAAGTCTGGCTCATTTGAAGAG
```

-continued

```
GCCGGCCAACGCAGTGTACGGAGGTTTGATTTACTTGATTGATAAATTGAGTGTA

TCACCTCCATTCCTTTCTCTTACTAGATCAGGACCTATTAGAGACGAATTAGAAA

CGATTCCCCACAAGATCCCAACCTCCTATCCGACAAGCAACCGTGATATGGGGG

TGATTGTCAGAAATTACTTCAAATACCAATGCCGTCTAATTGAAAAGGGAAAAT

ACAGATCACATTATTCACAATTATGGTTATTCTCAGATGTCTTATCCATAGACTTC

ATTGGACCATTCTCTATTTCCACCACCCTCTTGCAAATCCTATACAAGCCATTTTT

ATCTGGGAAAGATAAGAATGAGTTGAGAGAGCTGGCAAATCTTTCTTCATTGCT

AAGATCAGGAGAGGGGTGGGAAGACATACATGTGAAATTCTTCACCAAGGACAT

ATTATTGTGTCCAGAGGAAATCAGACATGCTTGCAAGTTCGGGATTGCTAAGGAT

AATAATAAAGACATGAGCTATCCCCCTTGGGAAGGGAATCCAGAGGGACAATT

ACAACAATCCCTGTTTATTATACGACCACCCCTTACCCAAAGATGCTAGAGATGC

CTCCAAGAATCCAAAATCCCCTGCTGTCCGGAATCAGGTTGGGCCAATTACCAA

CTGGCGCTCATTATAAAATTCGGAGTATATTACATGGAATGGGAATCCATTACAG

GGACTTCTTGAGTTGTGGAGACGGCTCCGGAGGGATGACTGCTGCATTACTACG

AGAAAATGTGCATAGCAGAGGAATATTCAATAGTCTGTTAGAATTATCAGGGTC

AGTCATGCGAGGCGCCTCTCCTGAGCCCCCCAGTGCCCTAGAAACTTTAGGAGG

AGATAAATCGAGATGTGTAAATGGTGAAACATGTTGGGAATATCCATCTGACTT

ATGTGACCCAAGGACTTGGGACTATTTCCTCCGACTCAAAGCAGGCTTGGGGCTT

CAAATTGATTTAATTGTAATGGATATGGAAGTTCGGGATTCTTCTACTAGCCTGA

AAATTGAGACGAATGTTAGAAATTATGTGCACCGGATTTTGGATGAGCAAGGAG

TTTTAATCTACAAGACTTATGGAACATATATTTGTGAGAGCGAAAAGAATGCAGT

AACAATCCTTGGTCCCATGTTCAAGACGGTCGACTTAGTTCAAACAGAATTTAGT

AGTTCTCAAACGTCTGAAGTATATATGGTATGTAAAGGTTTGAAGAAATTAATCG

ATGAACCCAATCCCGATTGGTCTTCCATCAATGAATCCTGGAAAAACCTGTACGC

ATTCCAGTCATCAGAACAGGAATTTGCCAGAGCAAAGAAGGTTAGTACATACTT

TACCTTGACAGGTATTCCCTCCCAATTCATTCCTGATCCTTTTGTAAACATTGAGA

CTATGCTACAAATATTCGGAGTACCCACGGGTGTGTCTCATGCGGCTGCCTTAAA

ATCATCTGATAGACCTGCAGATTTATTGACCATTAGCCTTTTTTATATGGCGATTA

TATCGTATTATAACATCAATCATATCAGAGTAGGACCGATACCTCCGAACCCCCC

ATCAGATGGAATTGCACAAAATGTGGGGATCGCTATAACTGGTATAAGCTTTTG

GCTGAGTTTGATGGAGAAAGACATTCCACTATATCAACAGTGTTTAGCAGTTATC

CAGCAATCATTCCCGATTAGGTGGGAGGCTGTTTCAGTAAAAGGAGGATACAAG

CAGAAGTGGAGTACTAGAGGTGATGGGCTCCCAAAAGATACCCGAACTTCAGAC

TCCTTGGCCCCAATCGGGAACTGGATCAGATCTCTGGAATTGGTCCGAAACCAA

GTTCGTCTAAATCCATTCAATGAGATCTTGTTCAATCAGCTATGTCGTACAGTGG

ATAATCATTTGAAATGGTCAAATTTGCGAAGAAACACAGGAATGATTGAATGGA

TCAATAGACGAATTTCAAAAGAAGACCGGTCTATACTGATGTTGAAGAGTGACC

TACACGAGGAAAACTCTTGGAGAGATTAAAAAATCATGAGGAGACTCCAAACTT

TAAGTATGAAAAAAACTTTGATCCTTAAGACCCTCTTGTGGTTTTTATTTTTATC

TGGTTTTGTGGTCTTCGT.
```

In one embodiment, the nucleic acid comprises the sequence of SEQ ID NO: 22, shown below (VSV vector: Convac V3 China):

```
ACGAAGACAAACAAACCATTATTATCATTAAAAGGCTCAGGAGAAACTT
TAACAGTAATCAAAATGTCTGTTACAGTCAAGAGAATCATTGACAACAC
AGTCATAGTTCCAAAACTTCCTGCAAATGAGGATCCAGTGGAATACCCG
GCAGATTACTTCAGAAAATCAAAGGAGATTCCTCTTTACATCAATACTA
CAAAAAGTTTGTCAGATCTAAGAGGATATGTCTACCAAGGCCTCAAATC
CGGAAATGTATCAATCATACATGTCAACAGCTACTTGTATGGAGCATTA
AAGGACATCCGGGGTAAGTTGGATAAAGATTGGTCAAGTTTCGGAATAA
ACATCGGGAAAGCAGGGGATACAATCGGAATATTTGACCTTGTATCCTT
GAAAGCCCTGGACGGCGTACTTCCAGATGGAGTATCGGATGCTTCCAGA
ACCAGCGCAGATGACAAATGGTTGCCTTTGTATCTACTTGGCTTATACA
GAGTGGGCAGAACACAAATGCCTGAATACAGAAAAAAGCTCATGGATGG
GCTGACAAATCAATGCAAAATGATCAATGAACAGTTTGAACCTCTTGTG
CCAGAAGGTCGTGACATTTTTGATGTGTGGGGAAATGACAGTAATTACA
CAAAAATTGTCGCTGCAGTGGACATGTTCTTCCACATGTTCAAAAAACA
TGAATGTGCCTCGTTCAGATACGGAACTATTGTTTCCAGATTCAAAGAT
TGTGCTGCATTGGCAACATTTGGACACCTCTGCAAAATAACCGGAATGT
CTACAGAAGATGTAACGACCTGGATCTTGAACCGAGAAGTTGCAGATGA
AATGGTCCAAATGATGCTTCCAGGCCAAGAAATTGACAAGGCCGATTCA
TACATGCCTTATTTGATCGACTTTGGATTGTCTTCTAAGTCTCCATATT
CTTCCGTCAAAAACCCTGCCTTCCACTTCTGGGGGCAATTGACAGCTCT
TCTGCTCAGATCCACCAGAGCAAGGAATGCCCGACAGCCTGATGACATT
GAGTATACATCTCTTACTACAGCAGGTTTGTTGTACGCTTATGCAGTAG
GATCCTCTGCCGACTTGGCACAACAGTTTTGTGTTGGAGATAACAAATA
CACTCCAGATGATAGTACCGGAGGATTGACGACTAATGCACCGCCACAA
GGCAGAGATGTGGTCGAATGGCTCGGATGGTTTGAAGATCAAAACAGAA
AACCGACTCCTGATATGATGCAGTATGCGAAAAGAGCAGTCATGTCACT
GCAAGGCCTAAGAGAGAAGACAATTGGCAAGTATGCTAAGTCAGAATTT
GACAAATGACCCTATAATTCTCAGATCACCTATTATATATTATGCTACA
TATGAAAAAAACTAACAGATATCATGGATAATCTCACAAAAGTTCGTGA
GTATCTCAAGTCCTATTCTCGTCTGGATCAGGCGGTAGGAGAGATAGAT
GAGATCGAAGCACAACGAGCTGAAAAGTCCAATTATGAGTTGTTCCAAG
AGGATGGAGTGGAAGAGCATACTAAGCCCTCTTATTTTCAGGCAGCAGA
TGATTCTGACACAGAATCTGAACCAGAAATTGAAGACAATCAAGGTTTG
TATGCACCAGATCCAGAAGCTGAGCAAGTTGAAGGCTTTATACAGGGGC
CTTTAGATGACTATGCAGATGAGGAAGTGGATGTTGTATTTACTTCGGA
CTGGAAACAGCCTGAGCTTGAATCTGACGAGCATGGAAAGACCTTACGG
TTGACATCGCCAGAGGGTTTAAGTGGAGAGCAGAAATCCCAGTGGCTTT
CGACGATTAAAGCAGTCGTGCAAAGTGCCAAATACTGGAATCTGGCAGA
```

-continued

```
GTGCACATTTGAAGCATCGGGAGAAGGGGTCATTATGAAGGAGCGCCAG
ATAACTCCGGATGTATATAAGGTCACTCCAGTGATGAACACACATCCGT
CCCAATCAGAAGCAGTATCAGATGTTTGGTCTCTCTCAAAGACATCCAT
GACTTTCCAACCCAAGAAAGCAAGTCTTCAGCCTCTCACCATATCCTTG
GATGAATTGTTCTCATCTAGAGGAGAGTTCATCTCTGTCGGAGGTGACG
GACGAATGTCTCATAAAGAGGCCATCCTGCTCGGCCTGAGATACAAAAA
GTTGTACAATCAGGCGAGAGTCAAATATTCTCTGTAGACTATGAAAAAA
AGTAACAGATATCACGATCTAAGTGTTATCCCAATCCATTCATCATGAG
TTCCTTAAAGAAGATTCTCGGTCTGAAGGGGAAAGGTAAGAAATCTAAG
AAATTAGGGATCGCACCACCCCCTTATGAAGAGGACACTAGCATGGAGT
ATGCTCCGAGCGCTCCAATTGACAAATCCTATTTTGGAGTTGACGAGAT
GGACACCTATGATCCGAATCAATTAAGATATGAGAAATTCTTCTTTACA
GTGAAAATGACGGTTAGATCTAATCGTCCGTTCAGAACATACTCAGATG
TGGCAGCCGCTGTATCCCATTGGGATCACATGTACATCGGAATGGCAGG
GAAACGTCCCTTCTACAAAATCTTGGCTTTTTTGGGTTCTTCTAATCTA
AAGGCCACTCCAGCGGTATTGGCAGATCAAGGTCAACCAGAGTATCACA
CTCACTGCGAAGGCAGGGCTTATTTGCCACATAGGATGGGGAAGACCCC
TCCCATGCTCAATGTACCAGAGCACTTCAGAAGACCATTCAATATAGGT
CTTTACAAGGGAACGATTGAGCTCACAATGACCATCTACGATGATGAGT
CACTGGAAGCAGCTCCTATGATCTGGGATCATTTCAATTCTTCCAAATT
TTCTGATTTCAGAGAGAAGGCCTTAATGTTTGGCCTGATTGTCGAGAAA
AAGGCATCTGGAGCGTGGGTCCTGGATTCTATCAGCCACTTCAAATGAG
CTAGTCTAACTTCTAGCTTCTGAACAATCCCCGGTTTACTCAGTCTCTC
CTAATTCCAGCCTCTCGAACAACTAATATCCTGTCTTTTCTATCCCTAT
GAAAAAAACTAACAGAGATCGATCTGTTTACGCGTCACTATGAAGTGCC
TTTTGTACTTAGCCTTTTTATTCATTGGGGTGAATTGCAAGTTCACCAT
AGTTTTTCCACACAACCAAAAAGGAAACTGGAAAAATGTTCCTTCTAAT
TACCATTATTGCCCGTCAAGCTCAGATTTAAATTGGCATAATGACTTAA
TAGGCACAGCCATACAAGTCAAAATGCCCAAGAGTCACAAGGCTATTCA
AGCAGACGGTTGGATGTGTCATGCTTCCAAATGGGTCACTACTTGTGAT
TTCCGCTGGTATGGACCGAAGTATATAACACAGTCCATCCGATCCTTCA
CTCCATCTGTAGAACAATGCAAGGAAAGCATTGAACAAACGAAACAAGG
AACTTGGCTGAATCCAGGCTTCCCTCCTCAAAGTTGTGGATATGCAACT
GTGACGGATGCCGAAGCAGTGATTGTCCAGGTGACTCCTCACCATGTGC
TGGTTGATGAATACACAGGAGAATGGGTTGATTCACAGTTCATCAACGG
AAAATGCAGCAATTACATATGCCCCACTGTCCATAACTCTACAACCTGG
CATTCTGACTATAAGGTCAAAGGGCTATGTGATTCTAACCTCATTTCCA
TGGACATCACCTTCTTCTCAGAGGACGGAGAGCTATCATCCCTGGGAAA
GGAGGGCACAGGGTTCAGAAGTAACTACTTTGCTTATGAAACTGGAGGC
AAGGCCTGCAAAATGCAATACTGCAAGCATTGGGGAGTCAGACTCCCAT
CAGGTGTCTGGTTCGAGATGGCTGATAAGGATCTCTTTGCTGCAGCCAG
```

```
ATTCCCTGAATGCCCAGAAGGGTCAAGTATCTCTGCTCCATCTCAGACC
TCAGTGGATGTAAGTCTAATTCAGGACGTTGAGAGGATCTTGGATTATT
CCCTCTGCCAAGAAACCTGGAGCAAAATCAGAGCGGGTCTTCCAATCTC
TCCAGTGGATCTCAGCTATCTTGCTCCTAAAAACCCAGGAACCGGTCCT
GCTTTCACCATAATCAATGGTACCCTAAAATACTTTGAGACCAGATACA
TCAGAGTCGATATTGCTGCTCCAATCCTCTCAAGAATGGTCGGAATGAT
CAGTGGAACTACCACAGAAAGGGAACTGTGGGATGACTGGGCACCATAT
GAAGACGTGGAAATTGGACCCAATGGAGTTCTGAGGACCAGTTCAGGAT
ATAAGTTTCCTTTATACATGATTGGACATGGTATGTTGGACTCCGATCT
TCATCTTAGCTCAAAGGCTCAGGTGTTCGAACATCCTCACATTCAAGAC
GCTGCTTCGCAACTTCCTGATGATGAGAGTTTATTTTTTGGTGATACTG
GGCTATCCAAAAATCCAATCGAGCTTGTAGAAGGTTGGTTCAGTAGTTG
GAAAAGCTCTATTGCCTCTTTTTTCTTTATCATAGGGTTAATCATTGGA
CTATTCTTGGTTCTCCGAGTTGGTATCCATCTTTGCATTAAAATTAAAGC
ACACCAAGAAAAGACAGATTTATACAGACATAGAGATGAACCGACTTGG
AAAGTAACTCAAATCCTGCTAGGTATGAAAAAAACTAACaGATATCACG
CtcgagGCCACCATGTTCGTGTTTCTGGTGCTGCTGCCTCTGGTGAGCT
CCCAGTGCGTGAACCTGACCACAAGGACCCAGCTGCCCCCTGCCTATAC
CAATTCCTTCACACGGGGCGTGTACTATCCCGACAAGGTGTTCCGGAGC
AGCGTGCTGCACTCCACACAGGATCTGTTTCTGCCTTTCTTTTCTAACG
TGACCTGGTTCCACGCCATCCACGTGAGCGGCACCAATGGCACAAAGCG
GTTCGACAATCCAGTGCTGCCCTTTAACGATGGCGTGTACTTCGCCTCC
ACCGAGAAGTCTAACATCATCAGAGGCTGGATCTTTGGCACCACACTGG
ACAGCAAGACACAGTCCCTGCTGATCGTGAACAATGCCACCAACGTGGT
CATCAAGGTGTGCGAGTTCCAGTTTTGTAATGATCCATTCCTGGGCGTG
TACTATCACAAGAACAATAAGTCTTGGATGGAGAGCGAGTTTCGCGTGT
ATTCCTCTGCCAACAATTGCACATTTGAGTACGTGTCCCAGCCCTTCCT
GATGGACCTGGAGGGCAAGCAGGGCAATTTCAAGAACCTGAGGGAGTTC
GTGTTTAAGAATATCGATGGCTACTTCAAAATCTACTCCAAGCACACCC
CAATCAACCTGGTGCGCGACCTGCCACAGGGCTTCTCTGCCCTGGAGCC
ACTGGTGGATCTGCCCATCGGCATCAACATCACCCGGTTTCAGACACTG
CTGGCCCTGCACAGAAGCTACCTGACACCAGGCGACAGCTCCTCTGGAT
GGACCGCAGGAGCAGCAGCCTACTATGTGGGCTATCTGCAGCCCAGGAC
CTTCCTGCTGAAGTACAACGAGAATGGCACCATCACAGACGCCGTGGAT
TGCGCCCTGGATCCCCTGTCTGAGACCAAGTGTACACTGAAGAGCTTTA
CCGTGGAGAAGGGCATCTATCAGACAAGCAATTTCAGGGTGCAGCCTAC
CGAGTCCATCGTGCGCTTTCCCAATATCACAAACCTGTGCCCTTTTGGC
GAGGTGTTCAACGCAACCCGCTTCGCCAGCGTGTACGCCTGGAATAGGA
AGCGCATCTCCAACTGCGTGGCCGACTATTCTGTGCTGTACAACAGCGC
CTCCTTCTCTACCTTTAAGTGCTATGGCGTGAGCCCCACAAAGCTGAAT
```
```
GACCTGTGCTTTACCAACGTGTACGCCGATTCCTTCGTGATCAGGGGCG
ACGAGGTGCGCCAGATCGCACCAGGACAGACAGGCAAGATCGCAGACTA
CAATTATAAGCTGCCTGACGATTTCACCGGCTGCGTGATCGCCTGGAAC
TCTAACAATCTGGATAGCAAAGTGGGCGGCAACTACAATTATCTGTACC
GGCTGTTTAGAAAAGTCTAATCTGAAGCCATTCGAGAGGGACATCTCCAC
AGAAATCTACCAGGCCGGCTCTACCCCCTGCAATGGCGTGGAGGGCTTT
AACTGTTATTTCCCTCTGCAGAGCTACGGCTTCCAGCCAACAAACGGCG
TGGGCTATCAGCCCTACCGCGTGGTGGTGCTGTCTTTTGAGCTGCTGCA
CGCACCTGCAACAGTGTGCGGACCAAAGAAGAGCACCAATCTGGTGAAG
AACAAGTGCGTGAACTTCAACTTCAACGGACTGACCGGAACAGGCGTGC
TGACCGAGTCCAACAAGAAGTTCCTGCCTTTTCAGCAGTTCGGCAGGGA
CATCGCAGATACCACAGACGCCGTGCGCGACCCTCAGACCCTGGAGATC
CTGGACATCACACCATGCTCCTTCGGCGGCGTGTCTGTGATCACACCAG
GCACCAATACAAGCAACCAGGTGGCCGTGCTGTATCAGGACGTGAATTG
TACCGAGGTGCCAGTGGCAATCCACGCAGATCAGCTGACCCCTACATGG
CGGGTGTACTCTACCGGCAGCAACGTGTTCCAGACAAGAGCCGGATGCC
TGATCGGAGCAGAGCACGTGAACAATAGCTATGAGTGCGACATCCCTAT
CGGCGCCGGCATCTGTGCCTCCTACCAGACCCAGACAAACTCCCCAAGG
TCTGGATCCGGCTACATCCCCGAGGCCCCAGAGACGGCCAGGCCTACG
TGCGGAAGGACGGCGAGTGGGTACTGctcagcaccttcctgggcAGCAG
TTGGAAAAGCTCCATCGCCTCCTTTTCTTTATCATCGGCCTGATCATC
GGACTGTTCCTGGTGCTCCGCGTGGGTATCCACCTGTGCATCAAGCTGA
AGCACACCAAGAAAAGACAGATTTATACAGACATCGAGATGAACCGACT
TGGAAAGTAAGCTAGCCAGATTCTTCATGTTTGGACCAAATCAACTTGT
GATACCATGCTCAAAGAGGCCTCAATTATATTTGAGTTTTTAATTTTTA
TGAAAAAAACTAACAGCAATCATGGAAGTCCACGATTTTGAGACCGACG
AGTTCAATGATTTCAATGAAGATGACTATGCCACAAGAGAATTCCTGAA
TCCCGATGAGCGCATGACGTACTTGAATCATGCTGATTACAATTTGAAT
TCTCCTCTAATTAGTGATGATATTGACAATTTGATCAGGAAATTCAATT
CTCTTCCGATTCCCTCGATGTGGGATAGTAAGAACTGGGATGGAGTTCT
TGAGATGTTAACATCATGTCAAGCCAATCCCATCTCAACATCTCAGATG
CATAAATGGATGGGAAGTTGGTTAATGTCTGATAATCATGATGCCAGTC
AAGGGTATAGTTTTTTACATGAAGTGGACAAAGAGGCAGAAATAACATT
TGACGTGGTGGAGACCTTCATCCGCGGCTGGGGCAACAAACCAATTGAA
TACATCAAAAAGGAAAGATGGACTGACTCATTCAAAATTCTCGCTTATT
TGTGTCAAAAGTTTTTGGACTTACACAAGTTGACATTAATCTTAAATGC
TGTCTCTGAGGTGGAATTGCTCAACTTGGCGAGGACTTTCAAAGGCAAA
GTCAGAAGAAGTTCTCATGGAACGAACATATGCAGGATTAGGGTTCCCA
GCTTGGGTCCTACTTTTATTTCAGAAGGATGGGCTTACTTCAAGAAACT
TGATATTCTAATGGACCGAAACTTTCTGTTAATGGTCAAAGATGTGATT
ATAGGGAGGATGCAAACGGTGCTATCCATGGTATGTAGAATAGACAACC
```

```
TGTTCTCAGAGCAAGACATCTTCTCCCTTCTAAATATCTACAGAATTGG
AGATAAAATTGTGGAGAGGCAGGGAAATTTTTCTTATGACTTGATTAAA
ATGGTGGAACCGATATGCAACTTGAAGCTGATGAAATTAGCAAGAGAAT
CAAGGCCTTTAGTCCCACAATTCCCTCATTTTGAAAATCATATCAAGAC
TTCTGTTGATGAAGGGGCAAAAATTGACCGAGGTATAAGATTCCTCCAT
GATCAGATAATGAGTGTGAAAACAGTGGATCTCACACTGGTGATTTATG
GATCGTTCAGACATTGGGGTCATCCTTTTATAGATTATTACACTGGACT
AGAAAAATTACATTCCCAAGTAACCATGAAGAAAGATATTGATGTGTCA
TATGCAAAAGCACTTGCAAGTGATTTAGCTCGGATTGTTCTATTTCAAC
AGTTCAATGATCATAAAAAGTGGTTCGTGAATGGAGACTTGCTCCCTCA
TGATCATCCCTTTAAAAGTCATGTTAAAGAAAATACATGGCCCACAGCT
GCTCAAGTTCAAGATTTTGGAGATAAATGGCATGAACTTCCGCTGATTA
AATGTTTTGAAATACCCGACTTACTAGACCCATCGATAATATACTCTGA
CAAAAGTCATTCAATGAATAGGTCAGAGGTGTTGAAACATGTCCGAATG
AATCCGAACACTCCTATCCCTAGTAAAAAGGTGTTGCAGACTATGTTGG
ACACAAAGGCTACCAATTGGAAAGAATTTCTTAAAGAGATTGATGAGAA
GGGCTTAGATGATGATGATCTAATTATTGGTCTTAAAGGAAAGGAGAGG
GAACTGAAGTTGGCAGGTAGATTTTTCTCCCTAATGTCTTGGAAATTGC
GAGAATACTTTGTAATTACCGAATATTTGATAAAGACTCATTTCGTCCC
TATGTTTAAAGGCCTGACAATGGCGGACGATCTAACTGCAGTCATTAAA
AAGATGTTAGATTCCTCATCCGGCCAAGGATTGAAGTCATATGAGGCAA
TTTGCATAGCCAATCACATTGATTACGAAAAATGGAATAACCACCAAAG
GAAGTTATCAAACGGCCCAGTGTTCCGAGTTATGGGCCAGTTCTTAGGT
TATCCATCCTTAATCGAGAGAACTCATGAATTTTTTGAGAAAAGTCTTA
TATACTACAATGGAAGACCAGACTTGATGCGTGTTCACAACAACACACT
GATCAATTCAACCTCCCAACGAGTTTGTTGGCAAGGACAAGAGGGTGGA
CTGGAAGGTCTACGGCAAAAAGGATGGACTATCCTCAATCTACTGGTTA
TTCAAAGAGAGGCTAAAATCAGAAACACTGCTGTCAAAGTCTTGGCACA
AGGTGATAATCAAGTTATTTGCACACAGTATAAAACGAAGAAATCGAGA
AACGTTGTAGAATTACAGGGTGCTCTCAATCAAATGGTTTCTAATAATG
AGAAAATTATGACTGCAATCAAAATAGGGACAGGGAAGTTAGGACTTTT
GATAAATGACGATGAGACTATGCAATCTGCAGATTACTTGAATTATGGA
AAAATACCGATTTTCCGTGGAGTGATTAGAGGGTTAGAGACCAAGAGAT
GGTCACGAGTGACTTGTGTCACCAATGACCAAATACCCACTTGTGCTAA
TATAATGAGCTCAGTTTCCACAAATGCTCTCACCGTAGCTCATTTTGCT
GAGAACCCAATCAATGCCATGATACAGTACAATTATTTTGGGACATTTG
CTAGACTCTTGTTGATGATGCATGATCCTGCTCTTCGTCAATCATTGTA
TGAAGTTCAAGATAAGATACCGGGCTTGCACAGTTCTACTTTCAAATAC
GCCATGTTGTATTTGGACCCTTCCATTGGAGGAGTGTCGGGCATGTCTT
TGTCCAGGTTTTTGATTAGAGCCTTCCCAGATCCCGTAACAGAAAGTCT
CTCATTCTGGAGATTCATCCATGTACATGCTCGAAGTGAGCATCTGAAG
GAGATGAGTGCAGTATTTGGAAACCCCGAGATAGCCAAGTTTCGAATAA
CTCACATAGACAAGCTAGTAGAAGATCCAACCTCTCTGAACATCGCTAT
GGGAATGAGTCCAGCGAACTTGTTAAAGACTGAGGTTAAAAAATGCTTA
ATCGAATCAAGACAAACCATCAGGAACCAGGTGATTAAGGATGCAACCA
TATATTTGTATCATGAAGAGGATCGGCTCAGAAGTTTCTTATGGTCAAT
AAATCCTCTGTTCCCTAGATTTTTAAGTGAATTCAAATCAGGCACTTTT
TTGGGAGTCGCAGACGGGCTCATCAGTCTATTTCAAAATTCTCGTACTA
TTCGGAACTCCTTTAAGAAAAAGTATCATAGGGAATTGGATGATTTGAT
TGTGAGGAGTGAGGTATCCTCTTTGACACATTTAGGGAAACTTCATTTG
AGAAGGGGATCATGTAAAATGTGGACATGTTCAGCTACTCATGCTGACA
CATTAAGATACAAATCCTGGGGCCGTACAGTTATTGGGACAACTGTACC
CCATCCATTAGAAATGTTGGGTCCACAACATCGAAAAGAGACTCCTTGT
GCACCATGTAACACATCAGGGTTCAATTATGTTTCTGTGCATTGTCCAG
ACGGGATCCATGACGTCTTTAGTTCACGGGGACCATTGCCTGCTTATCT
AGGGTCTAAAACATCTGAATCTACATCTATTTTGCAGCCTTGGGAAAGG
GAAAGCAAAGTCCCACTGATTAAAAGAGCTACACGTCTTAGAGATGCTA
TCTCTTGGTTTGTTGAACCCGACTCTAAACTAGCAATGACTATACTTTC
TAACATCCACTCTTTAACAGGCGAAGAATGGACCAAAAGGCAGCATGGG
TTCAAAAGAACAGGGTCTGCCCTTCATAGGTTTTCGACATCTCGGATGA
GCCATGGTGGGTTCGCATCTCAGAGCACTGCAGCATTGACCAGGTTGAT
GGCAACTACAGACACCATGAGGGATCTGGGAGATCAGAATTTCGACTTT
TTATTCCAAGCAACGTTGCTCTATGCTCAAATTACCACCACTGTTGCAA
GAGACGGATGGATCACCAGTTGTACAGATCATTATCATATTGCCTGTAA
GTCCTGTTTGAGACCCATAGAAGAGATCACCCTGGACTCAAGTATGGAC
TACACGCCCCCAGATGTATCCCATGTGCTGAAGACATGGAGGAATGGGG
AAGGTTCGTGGGACAAGAGATAAAACAGATCTATCCTTTAGAAGGGAA
TTGGAAGAATTTAGCACCTGCTGAGCAATCCTATCAAGTCGGCAGATGT
ATAGGTTTTCTATATGGAGACTTGGCGTATAGAAAATCTACTCATGCCG
AGGACAGTTCTCTATTTCCTCTATCTATACAAGGTCGTATTAGAGGTCG
AGGTTTCTTAAAAGGGTTGCTAGACGGATTAATGAGAGCAAGTTGCTGC
CAAGTAATACACCGGAGAAGTCTGGCTCATTTGAAGAGGCCGGCCAACG
CAGTGTACGGAGGTTTGATTTACTTGATTGATAAATTGAGTGTATCACC
TCCATTCCTTTCTCTTACTAGATCAGGACCTATTAGAGACGAATTAGAA
ACGATTCCCCACAAGATCCCAACCTCCTATCCGACAAGCAACCGTGATA
TGGGGGTGATTGTCAGAAATTACTTCAAATACCAATGCCGTCTAATTGA
AAAGGGAAAATACAGATCACATTATTCACAATTATGGTTATTCTCAGAT
GTCTTATCCATAGACTTCATTGGACCATTCTCTATTTCCACCACCCTCT
TGCAAATCCTATACAAGCCATTTTTATCTGGGAAAGATAAGAATGAGTT
GAGAGAGCTGGCAAATCTTTCTTCATTGCTAAGATCAGGAGAGGGGTGG
GAAGACATACATGTGAAATTCTTCACCAAGGACATATTATTGTGTCCAG
```

```
AGGAAATCAGACATGCTTGCAAGTTCGGGATTGCTAAGGATAATAATAA

AGACATGAGCTATCCCCCTTGGGGAAGGGAATCCAGAGGGACAATTACA

ACAATCCCTGTTTATTATACGACCACCCCTTACCCAAAGATGCTAGAGA

TGCCTCCAAGAATCCAAATCCCCTGCTGTCCGGAATCAGGTTGGGCCA

ATTACCAACTGGCGCTCATTATAAAATTCGGAGTATATTACATGGAATG

GGAATCCATTACAGGGACTTCTTGAGTTGTGGAGACGGCTCCGGAGGGA

TGACTGCTGCATTACTACGAGAAAATGTGCATAGCAGAGGAATATTCAA

TAGTCTGTTAGAATTATCAGGGTCAGTCATGCGAGGCGCCTCTCCTGAG

CCCCCCAGTGCCCTAGAAACTTTAGGAGGAGATAAATCGAGATGTGTAA

ATGGTGAAACATGTTGGGAATATCCATCTGACTTATGTGACCCAAGGAC

TTGGGACTATTTCCTCCGACTCAAAGCAGGCTTGGGGCTTCAAATTGAT

TTAATTGTAATGGATATGGAAGTTCGGGATTCTTCTACTAGCCTGAAAA

TTGAGACGAATGTTAGAAATTATGTGCACCGGATTTTGGATGAGCAAGG

AGTTTTAATCTACAAGACTTATGGAACATATATTTGTGAGAGCGAAAAG

AATGCAGTAACAATCCTTGGTCCCATGTTCAAGACGGTCGACTTAGTTC

AAACAGAATTTAGTAGTTCTCAAACGTCTGAAGTATATATGGTATGTAA

AGGTTTGAAGAAATTAATCGATGAACCCAATCCCGATTGGTCTTCCATC

AATGAATCCTGGAAAAACCTGTACGCATTCCAGTCATCAGAACAGGAAT

TTGCCAGAGCAAAGAAGGTTAGTACATACTTTACCTTGACAGGTATTCC

CTCCCAATTCATTCCTGATCCTTTTGTAAACATTGAGACTATGCTACAA

ATATTCGGAGTACCCACGGGTGTGTCTCATGCGGCTGCCTTAAAATCAT

CTGATAGACCTGCAGATTTATTGACCATTAGCCTTTTTTATATGGCGAT

TATATCGTATTATAACATCAATCATATCAGAGTAGGACCGATACCTCCG

AACCCCCCATCAGATGGAATTGCACAAAATGTGGGGATCGCTATAACTG

GTATAAGCTTTTGGCTGAGTTTGATGGAGAAAGACATTCCACTATATCA

ACAGTGTTTAGCAGTTATCCAGCAATCATTCCCGATTAGGTGGGAGGCT

GTTTCAGTAAAAGGAGGATACAAGCAGAAGTGGAGTACTAGAGGTGATG

GGCTCCCAAAAGATACCCGAACTTCAGACTCCTTGGCCCCAATCGGGAA

CTGGATCAGATCTCTGGAATTGGTCCGAAACCAAGTTCGTCTAAATCCA

TTCAATGAGATCTTGTTCAATCAGCTATGTCGTACAGTGGATAATCATT

TGAAATGGTCAAATTTGCGAAGAAACACAGGAATGATTGAATGGATCAA

TAGACGAATTTCAAAAGAAGACCGGTCTATACTGATGTTGAAGAGTGAC

CTACACGAGGAAAACTCTTGGAGAGATTAAAAAATCATGAGGAGACTCC

AAACTTTAAGTATGAAAAAACTTTGATCCTTAAGACCCTCTTGTGGTT

TTTATTTTTATCTGGTTTTGTGGTCTTCGT.
```

In another embodiment, the nucleic acid comprises the sequence of SEQ ID NO: 23, shown below (VSV vector: Convac V3 South Africa):

```
ACGAAGACAAACAAACCATTATTATCATTAAAAGGCTCAGGAGAAACTT

TAACAGTAATCAAAATGTCTGTTACAGTCAAGAGAATCATTGACAACAC

AGTCATAGTTCCAAAACTTCCTGCAAATGAGGATCCAGTGGAATACCCG

GCAGATTACTTCAGAAAATCAAAGGAGATTCCTCTTTACATCAATACTA

CAAAAGTTTGTCAGATCTAAGAGGATATGTCTACCAAGGCCTCAAATC

CGGAAATGTATCAATCATACATGTCAACAGCTACTTGTATGGAGCATTA

AAGGACATCCGGGGTAAGTTGGATAAAGATTGGTCAAGTTTCGGAATAA

ACATCGGGAAAGCAGGGGATACAATCGGAATATTTGACCTTGTATCCTT

GAAAGCCCTGGACGGCGTACTTCCAGATGGAGTATCGGATGCTTCCAGA

ACCAGCGCAGATGACAAATGGTTGCCTTTGTATCTACTTGGCTTATACA

GAGTGGGCAGAACACAAATGCCTGAATACAGAAAAAAGCTCATGGATGG

GCTGACAAATCAATGCAAAATGATCAATGAACAGTTTGAACCTCTTGTG

CCAGAAGGTCGTGACATTTTTGATGTGTGGGGAAATGACAGTAATTACA

CAAAAATTGTCGCTGCAGTGGACATGTTCTTCCACATGTTCAAAAAACA

TGAATGTGCCTCGTTCAGATACGGAACTATTGTTTCCAGATTCAAAGAT

TGTGCTGCATTGGCAACATTTGGACACCTCTGCAAAATAACCGGAATGT

CTACAGAAGATGTAACGACCTGGATCTTGAACCGAGAAGTTGCAGATGA

AATGGTCCAAATGATGCTTCCAGGCCAAGAAATTGACAAGGCCGATTCA

TACATGCCTTATTTGATCGACTTTGGATTGTCTTCTAAGTCTCCATATT

CTTCCGTCAAAAACCCTGCCTTCCACTTCTGGGGCAATTGACAGCTCT

TCTGCTCAGATCCACCAGAGCAAGGAATGCCCGACAGCCTGATGACATT

GAGTATACATCTCTTACTACAGCAGGTTTGTTGTACGCTTATGCAGTAG

GATCCTCTGCCGACTTGGCACAACAGTTTTGTGTTGGAGATAACAAATA

CACTCCAGATGATAGTACCGGAGGATTGACGACTAATGCACCGCCACAA

GGCAGAGATGGTCGAATGGCTCGGATGGTTTGAAGATCAAAACAGAA

AACCGACTCCTGATATGATGCAGTATGCGAAAAGAGCAGTCATGTCACT

GCAAGGCCTAAGAGAAGACAATTGGCAAGTATGCTAAGTCAGAATTT

GACAAATGACCCTATAATTCTCAGATCACCTATTATATATTATGCTACA

TATGAAAAAACTAACAGATATCATGGATAATCTCACAAAAGTTCGTGA

GTATCTCAAGTCCTATTCTCGTCTGGATCAGGCGGTAGGAGAGATAGAT

GAGATCGAAGCACAACGAGCTGAAAAGTCCAATTATGAGTTGTTCCAAG

AGGATGGAGTGGAAGAGCATACTAAGCCCTCTTATTTTCAGGCAGCAGA

TGATTCTGACACAGAATCTGAACCAGAAATTGAAGACAATCAAGGTTTG

TATGCACCAGATCCAGAAGCTGAGCAAGTTGAAGGCTTTATACAGGGGC

CTTTAGATGACTATGCAGATGAGGAAGTGGATGTTGTATTTACTTCGGA

CTGGAAACAGCCTGAGCTTGAATCTGACGAGCATGGAAAGACCTTACGG

TTGACATCGCCAGAGGGTTTAAGTGGAGAGCAGAAATCCCAGTGGCTTT

CGACGATTAAAGCAGTCGTGCAAAGTGCCAAATACTGGAATCTGGCAGA

GTGCACATTTGAAGCATCGGGAGAAGGGGTCATTATGAAGGAGCGCCAG

ATAACTCCGGATGTATATAAGGTCACTCCAGTGATGAACACACATCCGT

CCCAATCAGAAGCAGTATCAGATGTTTGGTCTCTCTCAAAGACATCCAT

GACTTTCCAACCCAAGAAAGCAAGTCTTCAGCCTCTCACCATATCCTTG

GATGAATTGTTCTCATCTAGAGGAGAGTTCATCTCTGTCGGAGGTGACG
```

-continued

GACGAATGTCTCATAAAGAGGCCATCCTGCTCGGCCTGAGATACAAAAA
GTTGTACAATCAGGCGAGAGTCAAATATTCTCTGTAGACTATGAAAAAA
AGTAACAGATATCACGATCTAAGTGTTATCCCAATCCATTCATCATGAG
TTCCTTAAAGAAGATTCTCGGTCTGAAGGGGAAAGGTAAGAAATCTAAG
AAATTAGGGATCGCACCACCCCCTTATGAAGAGGACACTAGCATGGAGT
ATGCTCCGAGCGCTCCAATTGACAAATCCTATTTTGGAGTTGACGAGAT
GGACACCTATGATCCGAATCAATTAAGATATGAGAAATTCTTCTTTACA
GTGAAAATGACGGTTAGATCTAATCGTCCGTTCAGAACATACTCAGATG
TGGCAGCCGCTGTATCCCATTGGGATCACATGTACATCGGAATGGCAGG
GAAACGTCCCTTCTACAAAATCTTGGCTTTTTTGGGTTCTTCTAATCTA
AAGGCCACTCCAGCGGTATTGGCAGATCAAGGTCAACCAGAGTATCACA
CTCACTGCGAAGGCAGGGCTTATTTGCCACATAGGATGGGGAAGACCCC
TCCCATGCTCAATGTACCAGAGCACTTCAGAAGACCATTCAATATAGGT
CTTTACAAGGGAACGATTGAGCTCACAATGACCATCTACGATGATGAGT
CACTGGAAGCAGCTCCTATGATCTGGGATCATTTCAATTCTTCCAAATT
TTCTGATTTCAGAGAGAAGGCCTTAATGTTTGGCCTGATTGTCGAGAAA
AAGGCATCTGGAGCGTGGGTCCTGGATTCTATCAGCCACTTCAAATGAG
CTAGTCTAACTTCTAGCTTCTGAACAATCCCCGGTTTACTCAGTCTCTC
CTAATTCCAGCCTCTCGAACAACTAATATCCTGTCTTTTCTATCCCTAT
GAAAAAAACTAACAGAGATCGATCTGTTTACGCGTCACTATGAAGTGCC
TTTTGTACTTAGCCTTTTTATTCATTGGGGTGAATTGCAAGTTCACCAT
AGTTTTTCCACACAACCAAAAAGGAAACTGGAAAAATGTTCCTTCTAAT
TACCATTATTGCCCGTCAAGCTCAGATTTAAATTGGCATAATGACTTAA
TAGGCACAGCCATACAAGTCAAAATGCCCAAGAGTCACAAGGCTATTCA
AGCAGACGGTTGGATGTGTCATGCTTCCAAATGGGTCACTACTTGTGAT
TTCCGCTGGTATGGACCGAAGTATATAACACAGTCCATCCGATCCTTCA
CTCCATCTGTAGAACAATGCAAGGAAAGCATTGAACAAACGAAACAAGG
AACTTGGCTGAATCCAGGCTTCCCTCCTCAAAGTTGTGGATATGCAACT
GTGACGGATGCCGAAGCAGTGATTGTCCAGGTGACTCCTCACCATGTGC
TGGTTGATGAATACACAGGAGAATGGGTTGATTCACAGTTCATCAACGG
AAAATGCAGCAATTACATATGCCCCACTGTCCATAACTCTACAACCTGG
CATTCTGACTATAAGGTCAAAGGGCTATGTGATTCTAACCTCATTTCCA
TGGACATCACCTTCTTCTCAGAGGACGGAGAGCTATCATCCCTGGGAAA
GGAGGGCACAGGGTTCAGAAGTAACTACTTTGCTTATGAAACTGGAGGC
AAGGCCTGCAAAATGCAATACTGCAAGCATTGGGGAGTCAGACTCCCAT
CAGGTGTCTGGTTCGAGATGGCTGATAAGGATCTCTTTGCTGCAGCCAG
ATTCCCTGAATGCCCAGAAGGGTCAAGTATCTCTGCTCCATCTCAGACC
TCAGTGGATGTAAGTCTAATTCAGGACGTTGAGAGGATCTTGGATTATT
CCCTCTGCCAAGAAACCTGGAGCAAAATCAGAGCGGGTCTTCCAATCTC
TCCAGTGGATCTCAGCTATCTTGCTCCTAAAAACCCAGGAACCGGTCCT

-continued

GCTTTCACCATAATCAATGGTACCCTAAAATACTTTGAGACCAGATACA
TCAGAGTCGATATTGCTGCTCCAATCCTCTCAAGAATGGTCGGAATGAT
CAGTGGAACTACCACAGAAAGGGAACTGTGGGATGACTGGGCACCATAT
GAAGACGTGGAAATTGGACCCAATGGAGTTCTGAGGACCAGTTCAGGAT
ATAAGTTTCCTTTATACATGATTGGACATGGTATGTTGGACTCCGATCT
TCATCTTAGCTCAAAGGCTCAGGTGTTCGAACATCCTCACATTCAAGAC
GCTGCTTCGCAACTTCCTGATGATGAGAGTTTATTTTTTGGTGATACTG
GGCTATCCAAAAATCCAATCGAGCTTGTAGAAGGTTGGTTCAGTAGTTG
GAAAAGCTCTATTGCCTCTTTTTTCTTTATCATAGGGTTAATCATTGGA
CTATTCTTGGTTCTCCGAGTTGGTATCCATCTTTGCATTAAATTAAAGC
ACACCAAGAAAAGACAGATTTATACAGACATAGAGATGAACCGACTTGG
AAAGTAACTCAAATCCTGCTAGGTATGAAAAAAACTAACaGATATCACG
CtcgagGCCACCATGTTCGTGTTTCTGGTGCTGCTGCCTCTGGTGAGCT
CCCAGTGCGTGAACTTCACCACAAGGACCCAGCTGCCCCCTGCCTATAC
CAATTCCTTCACACGGGGCGTGTACTATCCCGACAAGGTGTTCCGGAGC
AGCGTGCTGCACTCCACACAGGATCTGTTTCTGCCTTTCTTTTCTAACG
TGACCTGGTTCCACGCCATCCACGTGAGCGGCACCAATGGCACAAAGCG
GTTCGCCAATCCAGTGCTGCCCTTTAACGATGGCGTGTACTTCGCCTCC
ACCGAGAAGTCTAACATCATCAGAGGCTGGATCTTTGGCACCACACTGG
ACAGCAAGACACAGTCCCTGCTGATCGTGAACAATGCCACCAACGTGGT
CATCAAGGTGTGCGAGTTCCAGTTTTGTAATGATCCATTCCTGGGCGTG
TACTATCACAAGAACAATAAGTCTTGGATGGAGAGCGAGTTTCGCGTGT
ATTCCTCTGCCAACAATTGCACATTTGAGTACGTGTCCCAGCCCTTCCT
GATGGACCTGGAGGGCAAGCAGGGCAATTTCAAGAACCTGAGGGAGTTC
GTGTTTAAGAATATCGATGGCTACTTCAAAATCTACTCCAAGCACACCC
CAATCAACCTGGTGCGCGGCCTGCCACAGGGCTTCTCTGCCCTGGAGCC
ACTGGTGGATCTGCCCATCGGCATCAACATCACCCGGTTTCAGACACTG
CTGGCCCTGCACAGAAGCTACCTGACACCAGGCGACAGCTCCTCTGGAT
GGACCGCAGGAGCAGCAGCCTACTATGTGGGCTATCTGCAGCCCAGGAC
CTTCCTGCTGAAGTACAACGAGAATGGCACCATCACAGACGCCGTGGAT
TGCGCCCTGGATCCCCTGTCTGAGACCAAGTGTACACTGAAGAGCTTTA
CCGTGGAGAAGGGCATCTATCAGACAAGCAATTTCAGGGTGCAGCCTAC
CGAGTCCATCGTGCGCTTTCCCAATATCACAAACCTGTGCCCTTTTGGC
GAGGTGTTCAACGCAACCCGCTTCGCCAGCGTGTACGCCTGGAATAGGA
AGCGCATCTCCAACTGCGTGGCCGACTATTCTGTGCTGTACAACAGCGC
CTCCTTCTCTACCTTTAAGTGCTATGGCGTGAGCCCCACAAAGCTGAAT
GACCTGTGCTTTACCAACGTGTACGCCGATTCCTTCGTGATCAGGGGCG
ACGAGGTGCGCCAGATCGCACCAGGACAGACAGGCAATATCGCAGACTA
CAATTATAAGCTGCCTGACGATTTCACCGGCTGCGTGATCGCCTGGAAC
TCTAACAATCTGGATAGCAAAGTGGGCGGCAACTACAATTATCTGTACC
GGCTGTTTAGAAAGTCTAATCTGAAGCCATTCGAGAGGGACATCTCCAC

```
AGAAATCTACCAGGCCGGCTCTACCCCCTGCAATGGCGTGAAGGGCTTT
AACTGTTATTTCCCTCTGCAGAGCTACGGCTTCCAGCCAACATATGCG
TGGGCTATCAGCCCTACCGCGTGGTGGTGCTGTCTTTTGAGCTGCTGCA
CGCACCTGCAACAGTGTGCGGACCAAAGAAGAGCACCAATCTGGTGAAG
AACAAGTGCGTGAACTTCAACTTCAACGGACTGACCGGAACAGGCGTGC
TGACCGAGTCCAACAAGAAGTTCCTGCCTTTTCAGCAGTTCGGCAGGGA
CATCGCAGATACCACAGACGCCGTGCGCGACCCTCAGACCCTGGAGATC
CTGGACATCACACCATGCTCCTTCGGCGGCGTGTCTGTGATCACACCAG
GCACCAATACAAGCAACCAGGTGGCCGTGCTGTATCAGGGCGTGAATTG
TACCGAGGTGCCAGTGGCAATCCACGCAGATCAGCTGACCCCTACATGG
CGGGTGTACTCTACCGGCAGCAACGTGTTCCAGACAAGAGCCGGATGCC
TGATCGGAGCAGAGCACGTGAACAATAGCTATGAGTGCGACATCCCTAT
CGGCGCCGGCATCTGTGCCTCCTACCAGACCCAGACAAACTCCCCAAGG
GGATCCGGCTACATCCCCGAGGCCCCCAGAGACGGCCAGGCCTACGTGC
GGAAGGACGGCGAGTGGGTACTGetcagcaccttectgggcAGCAGTTG
GAAAAGCTCCATCGCCTCCTTTTTCTTTATCATCGGCCTGATCATCGGA
CTGTTCCTGGTGCTCCGCGTGGGTATCCACCTGTGCATCAAGCTGAAGC
ACACCAAGAAAAGACAGATTTATACAGACATCGAGATGAACCGACTTGG
AAAGTAAGCTAGCCAGATTCTTCATGTTTGGACCAAATCAACTTGTGAT
ACCATGCTCAAAGAGGCCTCAATTATATTTGAGTTTTTAATTTTTATGA
AAAAAACTAACAGCAATCATGGAAGTCCACGATTTTGAGACCGACGAGT
TCAATGATTTCAATGAAGATGACTATGCCACAAGAGAATTCCTGAATCC
CGATGAGCGCATGACGTACTTGAATCATGCTGATTACAATTTGAATTCT
CCTCTAATTAGTGATGATATTGACAATTTGATCAGGAAATTCAATTCTC
TTCCGATTCCCTCGATGTGGGATAGTAAGAACTGGGATGGAGTTCTTGA
GATGTTAACATCATGTCAAGCCAATCCCATCTCAACATCTCAGATGCAT
AAATGGATGGGAAGTTGGTTAATGTCTGATAATCATGATGCCAGTCAAG
GGTATAGTTTTTTACATGAAGTGGACAAAGAGGCAGAAATAACATTTGA
CGTGGTGGAGACCTTCATCCGCGGCTGGGCAACAAACCAATTGAATAC
ATCAAAAGGAAAGATGGACTGACTCATTCAAAATTCTCGCTTATTTGT
GTCAAAAGTTTTTGGACTTACACAAGTTGACATTAATCTTAAATGCTGT
CTCTGAGGTGGAATTGCTCAACTTGGCGAGGACTTTCAAAGGCAAAGTC
AGAAGAAGTTCTCATGGAACGAACATATGCAGGATTAGGGTTCCCAGCT
TGGGTCCTACTTTTATTTCAGAAGGATGGCTTACTTCAAGAAACTTGA
TATTCTAATGGACCGAAACTTTCTGTTAATGGTCAAAGATGTGATTATA
GGGAGGATGCAAACGGTGCTATCCATGGTATGTAGAATAGACAACCTGT
TCTCAGAGCAAGACATCTTCTCCCTTCTAAATATCTACAGAATTGGAGA
TAAAATTGTGGAGAGGCAGGGAAATTTTCTTATGACTTGATTAAATG
GTGGAACCGATATGCAACTTGAAGCTGATGAAATTAGCAAGAGAATCAA
GGCCTTTAGTCCCACAATTCCCTCATTTTGAAAATCATATCAAGACTTC
```

```
TGTTGATGAAGGGGCAAAAATTGACCGAGGTATAAGATTCCTCCATGAT
CAGATAATGAGTGTGAAAACAGTGGATCTCACACTGGTGATTTATGGAT
CGTTCAGACATTGGGGTCATCCTTTTATAGATTATTACACTGGACTAGA
AAAATTACATTCCCAAGTAACCATGAAGAAAGATATTGATGTGTCATAT
GCAAAAGCACTTGCAAGTGATTTAGCTCGGATTGTTCTATTTCAACAGT
TCAATGATCATAAAAAGTGGTTCGTGAATGGAGACTTGCTCCCTCATGA
TCATCCCTTTAAAAGTCATGTTAAAGAAAATACATGGCCCACAGCTGCT
CAAGTTCAAGATTTTGGAGATAAATGGCATGAACTTCCGCTGATTAAAT
GTTTTGAAATACCCGACTTACTAGACCCATCGATAATATACTCTGACAA
AAGTCATTCAATGAATAGGTCAGAGGTGTTGAAACATGTCCGAATGAAT
CCGAACACTCCTATCCCTAGTAAAAAGGTGTTGCAGACTATGTTGGACA
CAAAGGCTACCAATTGGAAAGAATTTCTTAAAGAGATTGATGAGAAGGG
CTTAGATGATGATGATCTAATTATTGGTCTTAAAGGAAAGGAGAGGGAA
CTGAAGTTGGCAGGTAGATTTTTCTCCCTAATGTCTTGGAAATTGCGAG
AATACTTTGTAATTACCGAATATTTGATAAAGACTCATTTCGTCCCTAT
GTTTAAAGGCCTGACAATGGCGGACGATCTAACTGCAGTCATTAAAAAG
ATGTTAGATTCCTCATCCGGCCAAGGATTGAAGTCATATGAGGCAATTT
GCATAGCCAATCACATTGATTACGAAAAATGGAATAACCACCAAAGGAA
GTTATCAAACGGCCCAGTGTTCCGAGTTATGGGCCAGTTCTTAGGTTAT
CCATCCTTAATCGAGAGAACTCATGAATTTTTTGAGAAAAGTCTTATAT
ACTACAATGGAAGACCAGACTTGATGCGTGTTCACAACAACACACTGAT
CAATTCAACCTCCCAACGAGTTTGTTGGCAAGGACAAGAGGGTGGACTG
GAAGGTCTACGGCAAAAGGATGGACTATCCTCAATCTACTGGTTATTC
AAAGAGAGGCTAAAATCAGAAACACTGCTGTCAAAGTCTTGGCACAAGG
TGATAATCAAGTTATTTGCACACAGTATAAAACGAAGAAATCGAGAAAC
GTTGTAGAATTACAGGGTGCTCTCAATCAAATGGTTTCTAATAATGAGA
AAATTATGACTGCAATCAAAATAGGGACAGGGAAGTTAGGACTTTTGAT
AAATGACGATGAGACTATGCAATCTGCAGATTACTTGAATTATGGAAAA
ATACCGATTTTCCGTGGAGTGATTAGAGGGTTAGAGACCAAGAGATGGT
CACGAGTGACTTGTGTCACCAATGACCAAATACCCACTTGTGCTAATAT
AATGAGCTCAGTTTCCACAAATGCTCTCACCGTAGCTCATTTTGCTGAG
AACCCAATCAATGCCATGATACAGTACAATTATTTTGGGACATTTGCTA
GACTCTTGTTGATGATGCATGATCCTGCTCTTCGTCAATCATTGTATGA
AGTTCAAGATAAGATACCGGGCTTGCACAGTTCTACTTTCAAATACGCC
ATGTTGTATTTGGACCCTTCCATTGGAGGAGTGTCGGGCATGTCTTTGT
CCAGGTTTTTGATTAGAGCCTTCCCAGATCCCGTAACAGAAAGTCTCTC
ATTCTGGAGATTCATCCATGTACATGCTCGAAGTGAGCATCTGAAGGAG
ATGAGTGCAGTATTTGGAAACCCCGAGATAGCCAAGTTTCGAATAACTC
ACATAGACAAGCTAGTAGAAGATCCAACCTCTCTGAACATCGCTATGGG
AATGAGTCCAGCGAACTTGTTAAAGACTGAGGTTAAAAAATGCTTAATC
GAATCAAGACAAACCATCAGGAACCAGGTGATTAAGGATGCAACCATAT
```

-continued

ATTTGTATCATGAAGAGGATCGGCTCAGAAGTTTCTTATGGTCAATAAA

TCCTCTGTTCCCTAGATTTTTAAGTGAATTCAAATCAGGCACTTTTTTG

GGAGTCGCAGACGGGCTCATCAGTCTATTTCAAAATTCTCGTACTATTC

GGAACTCCTTTAAGAAAAAGTATCATAGGGAATTGGATGATTTGATTGT

GAGGAGTGAGGTATCCTCTTTGACACATTTAGGGAAACTTCATTTGAGA

AGGGGATCATGTAAAATGTGGACATGTTCAGCTACTCATGCTGACACAT

TAAGATACAAATCCTGGGGCCGTACAGTTATTGGGACAACTGTACCCCA

TCCATTAGAAATGTTGGGTCCACAACATCGAAAAGAGACTCCTTGTGCA

CCATGTAACACATCAGGGTTCAATTATGTTTCTGTGCATTGTCCAGACG

GGATCCATGACGTCTTTAGTTCACGGGGACCATTGCCTGCTTATCTAGG

GTCTAAAACATCTGAATCTACATCTATTTTGCAGCCTTGGGAAAGGGAA

AGCAAAGTCCCACTGATTAAAAGAGCTACACGTCTTAGAGATGCTATCT

CTTGGTTTGTTGAACCCGACTCTAAACTAGCAATGACTATACTTTCTAA

CATCCACTCTTTAACAGGCGAAGAATGGACCAAAAGGCAGCATGGGTTC

AAAAGAACAGGGTCTGCCCTTCATAGGTTTTCGACATCTCGGATGAGCC

ATGGTGGGTTCGCATCTCAGAGCACTGCAGCATTGACCAGGTTGATGGC

AACTACAGACACCATGAGGGATCTGGGAGATCAGAATTTCGACTTTTTA

TTCCAAGCAACGTTGCTCTATGCTCAAATTACCACCACTGTTGCAAGAG

ACGGATGGATCACCAGTTGTACAGATCATTATCATATTGCCTGTAAGTC

CTGTTTGAGACCCATAGAAGAGATCACCCTGGACTCAAGTATGGACTAC

ACGCCCCCAGATGTATCCCATGTGCTGAAGACATGGAGGAATGGGAAG

GTTCGTGGGACAAGAGATAAAACAGATCTATCCTTTAGAAGGGAATTG

GAAGAATTTAGCACCTGCTGAGCAATCCTATCAAGTCGGCAGATGTATA

GGTTTTCTATATGGAGACTTGGCGTATAGAAAATCTACTCATGCCGAGG

ACAGTTCTCTATTTCCTCTATCTATACAAGGTCGTATTAGAGGTCGAGG

TTTCTTAAAAGGGTTGCTAGACGGATTAATGAGAGCAAGTTGCTGCCAA

GTAATACACCGGAGAAGTCTGGCTCATTTGAAGAGGCCGGCCAACGCAG

TGTACGGAGGTTTGATTTACTTGATTGATAAATTGAGTGTATCACCTCC

ATTCCTTTCTCTTACTAGATCAGGACCTATTAGAGACGAATTAGAAACG

ATTCCCCACAAGATCCCAACCTCCTATCCGACAAGCAACCGTGATATGG

GGGTGATTGTCAGAAATTACTTCAAATACCAATGCCGTCTAATTGAAAA

GGGAAAATACAGATCACATTATTCACAATTATGGTTATTCTCAGATGTC

TTATCCATAGACTTCATTGGACCATTCTCTATTTCCACCACCCTCTTGC

AAATCCTATACAAGCCATTTTTATCTGGGAAAGATAAGAATGAGTTGAG

AGAGCTGGCAAATCTTTCTTCATTGCTAAGATCAGGAGAGGGGTGGGAA

GACATACATGTGAAATTCTTCACCAAGGACATATTATTGTGTCCAGAGG

AAATCAGACATGCTTGCAAGTTCGGGATTGCTAAGGATAATAATAAAGA

CATGAGCTATCCCCCTTGGGGAAGGGAATCCAGAGGGACAATTACAACA

ATCCCTGTTTATTATACGACCACCCCTTACCCAAAGATGCTAGAGATGC

CTCCAAGAATCCAAAATCCCCTGCTGTCCGGAATCAGGTTGGGCCAATT

ACCAACTGGCGCTCATTATAAAATTCGGAGTATATTACATGGAATGGGA

ATCCATTACAGGGACTTCTTGAGTTGTGGAGACGGCTCCGGAGGGATGA

CTGCTGCATTACTACGAGAAAATGTGCATAGCAGAGGAATATTCAATAG

TCTGTTAGAATTATCAGGGTCAGTCATGCGAGGCGCCTCTCCTGAGCCC

CCCAGTGCCCTAGAAACTTTAGGAGGAGATAAATCGAGATGTGTAAATG

GTGAAACATGTTGGGAATATCCATCTGACTTATGTGACCCAAGGACTTG

GGACTATTTCCTCCGACTCAAAGCAGGCTTGGGGCTTCAAATTGATTTA

ATTGTAATGGATATGGAAGTTCGGGATTCTTCTACTAGCCTGAAAATTG

AGACGAATGTTAGAAATTATGTGCACCGGATTTTGGATGAGCAAGGAGT

TTTAATCTACAAGACTTATGGAACATATATTTGTGAGAGCGAAAAGAAT

GCAGTAACAATCCTTGGTCCCATGTTCAAGACGGTCGACTTAGTTCAAA

CAGAATTTAGTAGTTCTCAAACGTCTGAAGTATATATGGTATGTAAAGG

TTTGAAGAAATTAATCGATGAACCCAATCCCGATTGGTCTTCCATCAAT

GAATCCTGGAAAAACCTGTACGCATTCCAGTCATCAGAACAGGAATTTG

CCAGAGCAAAGAAGGTTAGTACATACTTTACCTTGACAGGTATTCCCTC

CCAATTCATTCCTGATCCTTTTGTAAACATTGAGACTATGCTACAAATA

TTCGGAGTACCCACGGGTGTGTCTCATGCGGCTGCCTTAAAATCATCTG

ATAGACCTGCAGATTTATTGACCATTAGCCTTTTTTATATGGCGATTAT

ATCGTATTATAACATCAATCATATCAGAGTAGGACCGATACCTCCGAAC

CCCCCATCAGATGGAATTGCACAAAATGTGGGGATCGCTATAACTGGTA

TAAGCTTTTGGCTGAGTTTGATGGAGAAAGACATTCCACTATATCAACA

GTGTTTAGCAGTTATCCAGCAATCATTCCCGATTAGGTGGGAGGCTGTT

TCAGTAAAAGGAGGATACAAGCAGAAGTGGAGTACTAGAGGTGATGGGC

TCCCAAAAGATACCCGAACTTCAGACTCCTTGGCCCCAATCGGGAACTG

GATCAGATCTCTGGAATTGGTCCGAAACCAAGTTCGTCTAAATCCATTC

AATGAGATCTTGTTCAATCAGCTATGTCGTACAGTGGATAATCATTTGA

AATGGTCAAATTTGCGAAGAAACACAGGAATGATTGAATGGATCAATAG

ACGAATTTCAAAAGAAGACCGGTCTATACTGATGTTGAAGAGTGACCTA

CACGAGGAAAACTCTTGGAGAGATTAAAAAATCATGAGGAGACTCCAAA

CTTTAAGTATGAAAAAACTTTGATCCTTAAGACCCTCTTGTGGTTTTT

ATTTTTTATCTGGTTTTGTGGTCTTCGT.

In some embodiments, the nucleic acid comprises the sequence of SEQ ID NO: 24, shown below (VSV vector: Convac V4 China):

ACGAAGACAAACAAACCATTATTATCATTAAAAGGCTCAGGAG

-continued

```
ACATCGGGAAAGCAGGGGATACAATCGGAATATTTGACCTTGTATCCTT
GAAAGCCCTGGACGGCGTACTTCCAGATGGAGTATCGGATGCTTCCAGA
ACCAGCGCAGATGACAAATGGTTGCCTTTGTATCTACTTGGCTTATACA
GAGTGGGCAGAACACAAATGCCTGAATACAGAAAAAAGCTCATGGATGG
GCTGACAAATCAATGCAAAATGATCAATGAACAGTTTGAACCTCTTGTG
CCAGAAGGTCGTGACATTTTTGATGTGTGGGGAAATGACAGTAATTACA
CAAAAATTGTCGCTGCAGTGGACATGTTCTTCCACATGTTCAAAAAACA
TGAATGTGCCTCGTTCAGATACGGAACTATTGTTTCCAGATTCAAAGAT
TGTGCTGCATTGGCAACATTTGGACACCTCTGCAAAATAACCGGAATGT
CTACAGAAGATGTAACGACCTGGATCTTGAACCGAGAAGTTGCAGATGA
AATGGTCCAAATGATGCTTCCAGGCCAAGAAATTGACAAGGCCGATTCA
TACATGCCTTATTTGATCGACTTTGGATTGTCTTCTAAGTCTCCATATT
CTTCCGTCAAAAACCCTGCCTTCCACTTCTGGGGGCAATTGACAGCTCT
TCTGCTCAGATCCACCAGAGCAAGGAATGCCCGACAGCCTGATGACATT
GAGTATACATCTCTTACTACAGCAGGTTTGTTGTACGCTTATGCAGTAG
GATCCTCTGCCGACTTGGCACAACAGTTTTGTGTTGGAGATAACAAATA
CACTCCAGATGATAGTACCGGAGGATTGACGACTAATGCACCGCCACAA
GGCAGAGATGTGGTCGAATGGCTCGGATGGTTTGAAGATCAAACAGAA
AACCGACTCCTGATATGATGCAGTATGCGAAAAGAGCAGTCATGTCACT
GCAAGGCCTAAGAGAGAAGACAATTGGCAAGTATGCTAAGTCAGAATTT
GACAAATGACCCTATAATTCTCAGATCACCTATTATATATTATGCTACA
TATGAAAAAAACTAACAGATATCATGGATAATCTCACAAAAGTTCGTGA
GTATCTCAAGTCCTATTCTCGTCTGGATCAGGCGGTAGGAGAGATAGAT
GAGATCGAAGCACAACGAGCTGAAAAGTCCAATTATGAGTTGTTCCAAG
AGGATGGAGTGGAAGAGCATACTAAGCCCTCTTATTTTCAGGCAGCAGA
TGATTCTGACACAGAATCTGAACCAGAAATTGAAGACAATCAAGGTTTG
TATGCACCAGATCCAGAAGCTGAGCAAGTTGAAGGCTTTATACAGGGGC
CTTTAGATGACTATGCAGATGAGGAAGTGGATGTTGTATTTACTTCGGA
CTGGAAACAGCCTGAGCTTGAATCTGACGAGCATGGAAAGACCTTACGG
TTGACATCGCCAGAGGGTTTAAGTGGAGAGCAGAAATCCCAGTGGCTTT
CGACGATTAAAGCAGTCGTGCAAAGTGCCAAATACTGGAATCTGGCAGA
GTGCACATTTGAAGCATCGGGAGAAGGGGTCATTATGAAGGAGCGCCAG
ATAACTCCGGATGTATATAAGGTCACTCCAGTGATGAACACACATCCGT
CCCAATCAGAAGCAGTATCAGATGTTTGGTCTCTCTCAAAGACATCCAT
GACTTTCCAACCCAAGAAAGCAAGTCTTCAGCCTCTCACCATATCCTTG
GATGAATTGTTCTCATCTAGAGGAGAGTTCATCTCTGTCGGAGGTGACG
GACGAATGTCTCATAAAGAGGCCATCCTGCTCGGCCTGAGATACAAAAA
GTTGTACAATCAGGCGAGAGTCAAATATTCTCTGTAGACTATGAAAAAA
AGTAACAGATATCACGATCTAAGTGTTATCCCAATCCATTCATCATGAG
TTCCTTAAAGAAGATTCTCGGTCTGAAGGGGAAAGGTAAGAAATCTAAG
AAATTAGGGATCGCACCACCCCCTTATGAAGAGGACACTAGCATGGAGT
ATGCTCCGAGCGCTCCAATTGACAAATCCTATTTTGGAGTTGACGAGAT
GGACACCTATGATCCGAATCAATTAAGATATGAGAAATTCTTCTTTACA
GTGAAAATGACGGTTAGATCTAATCGTCCGTTCAGAACATACTCAGATG
TGGCAGCCGCTGTATCCCATTGGGATCACATGTACATCGGAATGGCAGG
GAAACGTCCCTTCTACAAAATCTTGGCTTTTTTGGGTTCTTCTAATCTA
AAGGCCACTCCAGCGGTATTGGCAGATCAAGGTCAACCAGAGTATCACA
CTCACTGCGAAGGCAGGGCTTATTTGCCACATAGGATGGGGAAGACCCC
TCCCATGCTCAATGTACCAGAGCACTTCAGAAGACCATTCAATATAGGT
CTTTACAAGGGAACGATTGAGCTCACAATGACCATCTACGATGATGAGT
CACTGGAAGCAGCTCCTATGATCTGGGATCATTTCAATTCTTCCAAATT
TTCTGATTTCAGAGAGAAGGCCTTAATGTTTGGCCTGATTGTCGAGAAA
AAGGCATCTGGAGCGTGGGTCCTGGATTCTATCAGCCACTTCAAATGAG
CTAGTCTAACTTCTAGCTTCTGAACAATCCCCGGTTTACTCAGTCTCTC
CTAATTCCAGCCTCTCGAACAACTAATATCCTGTCTTTTCTATCCCTAT
GAAAAAAACTAACAGAGATCGATCTGTTTACGCGTGCCACCATGTTCGT
GTTTCTGGTGCTGCTGCCTCTGGTGAGCTCCCAGTGCGTGAACCTGACC
ACAAGGACCCAGCTGCCCCCTGCCTATACCAATTCCTTCACACGGGGCG
TGTACTATCCCGACAAGGTGTTCCGGAGCAGCGTGCTGCACTCCACACA
GGATCTGTTTCTGCCTTTCTTTTCTAACGTGACCTGGTTCCACGCCATC
CACGTGAGCGGCACCAATGGCACAAAGCGGTTCGACAATCCAGTGCTGC
CCTTTAACGATGGCGTGTACTTCGCCTCCACCGAGAAGTCTAACATCAT
CAGAGGCTGGATCTTTGGCACCACACTGGACAGCAAGACACAGTCCCTG
CTGATCGTGAACAATGCCACCAACGTGGTCATCAAGGTGTGCGAGTTCC
AGTTTTGTAATGATCCATTCCTGGGCGTGTACTATCACAAGAACAATAA
GTCTTGGATGGAGAGCGAGTTTCGCGTGTATTCCTCTGCCAACAATTGC
ACATTTGAGTACGTGTCCCAGCCCTTCCTGATGGACCTGGAGGGCAAGC
AGGGCAATTTCAAGAACCTGAGGGAGTTCGTGTTTAAGAATATCGATGG
CTACTTCAAAATCTACTCCAAGCACACCCCAATCAACCTGGTGCGCGAC
CTGCCACAGGGCTTCTCTGCCCTGGAGCCACTGGTGGATCTGCCCATCG
GCATCAACATCACCCGGTTTCAGACACTGCTGGCCCTGCACAGAAGCTA
CCTGACACCAGGCGACAGCTCCTCTGGATGGACCGCAGGAGCAGCAGCC
TACTATGTGGGCTATCTGCAGCCCAGGACCTTCCTGCTGAAGTACAACG
AGAATGGCACCATCACAGACGCCGTGGATTGCGCCCTGGATCCCCTGTC
TGAGACCAAGTGTACACTGAAGAGCTTTACCGTGGAGAAGGGCATCTAT
CAGACAAGCAATTTCAGGGTGCAGCCTACCGAGTCCATCGTGCGCTTTC
CCAATATCACAAACCTGTGCCCTTTTGGCGAGGTGTTCAACGCAACCCG
CTTCGCCAGCGTGTACGCCTGGAATAGGAAGCGCATCTCCAACTGCGTG
GCCGACTATTCTGTGCTGTACAACAGCGCCTCCTTCTCTACCTTTAAGT
GCTATGGCGTGAGCCCCACAAAGCTGAATGACCTGTGCTTTACCAACGT
GTACGCCGATTCCTTCGTGATCAGGGGCGACGAGGTGCGCCAGATCGCA
```

-continued

CCAGGACAGACAGGCAAGATCGCAGACTACAATTATAAGCTGCCTGACG
ATTTCACCGGCTGCGTGATCGCCTGGAACTCTAACAATCTGGATAGCAA
AGTGGGCGGCAACTACAATTATCTGTACCGGCTGTTTAGAAAGTCTAAT
CTGAAGCCATTCGAGAGGGACATCTCCACAGAAATCTACCAGGCCGGCT
CTACCCCCTGCAATGGCGTGGAGGGCTTTAACTGTTATTTCCCTCTGCA
GAGCTACGGCTTCCAGCCAACAAACGGCGTGGGCTATCAGCCCTACCGC
GTGGTGGTGCTGTCTTTTGAGCTGCTGCACGCACCTGCAACAGTGTGCG
GACCAAAGAAGAGCACCAATCTGGTGAAGAACAAGTGCGTGAACTTCAA
CTTCAACGGACTGACCGGAACAGGCGTGCTGACCGAGTCCAACAAGAAG
TTCCTGCCTTTTCAGCAGTTCGGCAGGGACATCGCAGATACCACAGACG
CCGTGCGCGACCCTCAGACCCTGGAGATCCTGGACATCACACCATGCTC
CTTCGGCGGCGTGTCTGTGATCACACCAGGCACCAATACAAGCAACCAG
GTGGCCGTGCTGTATCAGGACGTGAATTGTACCGAGGTGCCAGTGGCAA
TCCACGCAGATCAGCTGACCCCTACATGGCGGGTGTACTCTACCGGCAG
CAACGTGTTCCAGACAAGAGCCGGATGCCTGATCGGAGCAGAGCACGTG
AACAATAGCTATGAGTGCGACATCCCTATCGGCGCCGGCATCTGTGCCT
CCTACCAGACCCAGACAAACTCCCCAAGGTCTGTGGGCGATACAGGCCT
GTCCAAGAATCCAATCGAGCTGGTAGAGGGCTGGTTCAGCAGTTGGAAA
AGCTCCATCGCCTCCTTTTTCTTTATCATCGGCCTGATCATCGGACTGT
TCCTGGTGCTCCGCGTGGGTATCCACCTGTGCATCAAGCTGAAGCACAC
CAAGAAAAGACAGATTTATACAGACATCGAGATGAACCGCCTGGGAAAG
ggatccggctccggcgagggcaggggaagtctactaacatgcggggacg
tggaggaaaatccggccccATGAAGTGCCTTTTGTACTTAGCCTTTTT
ATTCATTGGGGTGAATTGCAAGTTCACCATAGTTTTTCCACACAACCAA
AAAGGAAACTGGAAAAATGTTCCTTCTAATTACCATTATTGCCCGTCAA
GCTCAGATTTAAATTGGCATAATGACTTAATAGGCACAGCCATACAAGT
CAAAATGCCCAAGAGTCACAAGGCTATTCAAGCAGACGGTTGGATGTGT
CATGCTTCCAAATGGGTCACTACTTGTGATTTCCGCTGGTATGGACCGA
AGTATATAACACAGTCCATCCGATCCTTCACTCCATCTGTAGAACAATG
CAAGGAAAGCATTGAACAAACGAAACAAGGAACTTGGCTGAATCCAGGC
TTCCCTCCTCAAAGTTGTGGATATGCAACTGTGACGGATGCCGAAGCAG
TGATTGTCCAGGTGACTCCTCACCATGTGCTGGTTGATGAATACACAGG
AGAATGGGTTGATTCACAGTTCATCAACGGAAAATGCAGCAATTACATA
TGCCCCACTGTCCATAACTCTACAACCTGGCATTCTGACTATAAGGTCA
AAGGGCTATGTGATTCTAACCTCATTTCCATGGACATCACCTTCTTCTC
AGAGGACGGAGAGCTATCATCCCTGGGAAGGAGGGCACAGGGTTCAGA
AGTAACTACTTTGCTTATGAAACTGGAGGCAAGGCCTGCAAAATGCAAT
ACTGCAAGCATTGGGGAGTCAGACTCCCATCAGGTGTCTGGTTCGAGAT
GGCTGATAAGGATCTCTTTGCTGCAGCCAGATTCCCTGAATGCCCAGAA
GGGTCAAGTATCTCTGCTCCATCTCAGACCTCAGTGGATGTAAGTCTAA -continued TTCAGGACGTTGAGAGGATCTTGGATTATTCCCTCTGCCAAGAAACCTG
GAGCAAAATCAGAGCGGGTCTTCCAATCTCTCCAGTGGATCTCAGCTAT
CTTGCTCCTAAAAACCCAGGAACCGGTCCTGCTTTCACCATAATCAATG
GTACCCTAAAATACTTTGAGACCAGATACATCAGAGTCGATATTGCTGC
TCCAATCCTCTCAAGAATGGTCGGAATGATCAGTGGAACTACCACAGAA
AGGGAACTGTGGGATGACTGGGCACCATATGAAGACGTGGAAATTGGAC
CCAATGGAGTTCTGAGGACCAGTTCAGGATATAAGTTTCCTTTATACAT
GATTGGACATGGTATGTTGGACTCCGATCTTCATCTTAGCTCAAAGGCT
CAGGTGTTCGAACATCCTCACATTCAAGACGCTGCTTCGCAACTTCCTG
ATGATGAGAGTTTATTTTTTGGTGATACTGGGCTATCCAAAAATCCAAT
CGAGCTTGTAGAAGGTTGGTTCAGTAGTTGGAAAAGCTCTATTGCCTCT
TTTTTCTTTATCATAGGGTTAATCATTGGACTATTCTTGGTTCTCCGAG
TTGGTATCCATCTTTGCATTAAATTAAAGCACACCAAGAAAAGACAGAT
TTATACAGACATAGAGATGAACCGACTTGGAAAGTAAgCTAGCCAGATT
CTTCATGTTTGGACCAAATCAACTTGTGATACCATGCTCAAAGAGGCCT
CAATTATATTTGAGTTTTTAATTTTTATGAAAAAAACTAACAGCAATCA
TGGAAGTCCACGATTTTGAGACCGACGAGTTCAATGATTTCAATGAAGA
TGACTATGCCACAAGAGAATTCCTGAATCCCGATGAGCGCATGACGTAC
TTGAATCATGCTGATTACAATTTGAATTCTCCTCTAATTAGTGATGATA
TTGACAATTTGATCAGGAAATTCAATTCTCTTCCGATTCCCTCGATGTG
GGATAGTAAGAACTGGGATGGAGTTCTTGAGATGTTAACATCATGTCAA
GCCAATCCCATCTCAACATCTCAGATGCATAAATGGATGGGAAGTTGGT
TAATGTCTGATAATCATGATGCCAGTCAAGGGTATAGTTTTTACATGA
AGTGGACAAAGAGGCAGAAATAACATTTGACGTGGTGGAGACCTTCATC
CGCGGCTGGGGCAACAAACCAATTGAATACATCAAAAAGGAAAGATGGA
CTGACTCATTCAAAATTCTCGCTTATTTGTGTCAAAAGTTTTTGGACTT
ACACAAGTTGACATTAATCTTAAATGCTGTCTCTGAGGTGGAATTGCTC
AACTTGGCGAGGACTTTCAAAGGCAAAGTCAGAAGAAGTTCTCATGGAA
CGAACATATGCAGGATTAGGGTTCCCAGCTTGGGTCCTACTTTTATTTC
AGAAGGATGGGCTTACTTCAAGAAACTTGATATTCTAATGGACCGAAAC
TTTCTGTTAATGGTCAAAGATGTGATTATAGGGAGGATGCAAACGGTGC
TATCCATGGTATGTAGAATAGACAACCTGTTCTCAGAGCAAGACATCTT
CTCCCTTCTAAATATCTACAGAATTGGAGATAAAATTGTGGAGAGGCAG
GGAAATTTTCTTATGACTTGATTAAAATGGTGGAACCGATATGCAACT
TGAAGCTGATGAAATTAGCAAGAGAATCAAGGCCTTTAGTCCCACAATT
CCCTCATTTTGAAAATCATATCAAGACTTCTGTTGATGAAGGGCAAAA
ATTGACCGAGGTATAAGATTCCTCCATGATCAGATAATGAGTGTGAAAA
CAGTGGATCTCACACTGGTGATTTATGGATCGTTCAGACATTGGGGTCA
TCCTTTTATAGATTATTACACTGGACTAGAAAAATTACATTCCCAAGTA
ACCATGAAGAAAGATATTGATGTGTCATATGCAAAAGCACTTGCAAGTG
ATTTAGCTCGGATTGTTCTATTTCAACAGTTCAATGATCATAAAAAGTG -continued GTTCGTGAATGGAGACTTGCTCCCTCATGATCATCCCTTTAAAAGTCAT
GTTAAAGAAAATACATGGCCCACAGCTGCTCAAGTTCAAGATTTTGGAG
ATAAATGGCATGAACTTCCGCTGATTAAATGTTTTGAAATACCCGACTT
ACTAGACCCATCGATAATATACTCTGACAAAAGTCATTCAATGAATAGG
TCAGAGGTGTTGAAACATGTCCGAATGAATCCGAACACTCCTATCCCTA
GTAAAAGGTGTTGCAGACTATGTTGGACACAAAGGCTACCAATTGGAA
AGAATTTCTTAAAGAGATTGATGAGAAGGGCTTAGATGATGATGATCTA
ATTATTGGTCTTAAAGGAAAGGAGAGGGAACTGAAGTTGGCAGGTAGAT
TTTTCTCCCTAATGTCTTGGAAATTGCGAGAATACTTTGTAATTACCGA
ATATTTGATAAAGACTCATTTCGTCCCTATGTTTAAAGGCCTGACAATG
GCGGACGATCTAACTGCAGTCATTAAAAAGATGTTAGATTCCTCATCCG
GCCAAGGATTGAAGTCATATGAGGCAATTTGCATAGCCAATCACATTGA
TTACGAAAAATGGAATAACCACCAAAGGAAGTTATCAAACGGCCCAGTG
TTCCGAGTTATGGGCCAGTTCTTAGGTTATCCATCCTTAATCGAGAGAA
CTCATGAATTTTTTGAGAAAAGTCTTATATACTACAATGGAAGACCAGA
CTTGATGCGTGTTCACAACAACACACTGATCAATTCAACCTCCCAACGA
GTTTGTTGGCAAGGACAAGAGGGTGGACTGGAAGGTCTACGGCAAAAAG
GATGGACTATCCTCAATCTACTGGTTATTCAAAGAGAGGCTAAAATCAG
AAACACTGCTGTCAAAGTCTTGGCACAAGGTGATAATCAAGTTATTTGC
ACACAGTATAAAACGAAGAAATCGAGAAACGTTGTAGAATTACAGGGTG
CTCTCAATCAAATGGTTTCTAATAATGAGAAAATTATGACTGCAATCAA
AATAGGGACAGGGAAGTTAGGACTTTTGATAAATGACGATGAGACTATG
CAATCTGCAGATTACTTGAATTATGGAAAAATACCGATTTTCCGTGGAG
TGATTAGAGGGTTAGAGACCAAGAGATGGTCACGAGTGACTTGTGTCAC
CAATGACCAAATACCCACTTGTGCTAATATAATGAGCTCAGTTTCCACA
AATGCTCTCACCGTAGCTCATTTTGCTGAGAACCCAATCAATGCCATGA
TACAGTACAATTATTTTGGGACATTTGCTAGACTCTTGTTGATGATGCA
TGATCCTGCTCTTCGTCAATCATTGTATGAAGTTCAAGATAAGATACCG
GGCTTGCACAGTTCTACTTTCAAATACGCCATGTTGTATTTGGACCCTT
CCATTGGAGGAGTGTCGGGCATGTCTTTGTCCAGGTTTTTGATTAGAGC
CTTCCCAGATCCCGTAACAGAAAGTCTCTCATTCTGGAGATTCATCCAT
GTACATGCTCGAAGTGAGCATCTGAAGGAGATGAGTGCAGTATTTGGAA
ACCCCGAGATAGCCAAGTTTCGAATAACTCACATAGACAAGCTAGTAGA
AGATCCAACCTCTCTGAACATCGCTATGGGAATGAGTCCAGCGAACTTG
TTAAAGACTGAGGTTAAAAAATGCTTAATCGAATCAAGACAAACCATCA
GGAACCAGGTGATTAAGGATGCAACCATATATTTGTATCATGAAGAGGA
TCGGCTCAGAAGTTTCTTATGGTCAATAAATCCTCTGTTCCCTAGATTT
TTAAGTGAATTCAAATCAGGCACTTTTTTGGGAGTCGCAGACGGGCTCA
TCAGTCTATTTCAAAATTCTCGTACTATTCGGAACTCCTTTAAGAAAAA
GTATCATAGGGAATTGGATGATTTGATTGTGAGGAGTGAGGTATCCTCT -continued TTGACACATTTAGGGAAACTTCATTTGAGAAGGGGATCATGTAAAATGT
GGACATGTTCAGCTACTCATGCTGACACATTAAGATACAAATCCTGGGG
CCGTACAGTTATTGGGACAACTGTACCCCATCCATTAGAAATGTTGGGT
CCACAACATCGAAAAGAGACTCCTTGTGCACCATGTAACACATCAGGGT
TCAATTATGTTTCTGTGCATTGTCCAGACGGGATCCATGACGTCTTTAG
TTCACGGGACCATTGCCTGCTTATCTAGGGTCTAAAACATCTGAATCT
ACATCTATTTTGCAGCCTTGGGAAAGGGAAAGCAAAGTCCCACTGATTA
AAAGAGCTACACGTCTTAGAGATGCTATCTCTTGGTTTGTTGAACCCGA
CTCTAAACTAGCAATGACTATACTTTCTAACATCCACTCTTTAACAGGC
GAAGAATGGACCAAAAGGCAGCATGGGTTCAAAAGAACAGGGTCTGCCC
TTCATAGGTTTTCGACATCTCGGATGAGCCATGGTGGGTTCGCATCTCA
GAGCACTGCAGCATTGACCAGGTTGATGGCAACTACAGACACCATGAGG
GATCTGGGAGATCAGAATTTCGACTTTTTATTCCAAGCAACGTTGCTCT
ATGCTCAAATTACCACCACTGTTGCAAGAGACGGATGGATCACCAGTTG
TACAGATCATTATCATATTGCCTGTAAGTCCTGTTTGAGACCCATAGAA
GAGATCACCCTGGACTCAAGTATGGACTACACGCCCCCAGATGTATCCC
ATGTGCTGAAGACATGGAGGAATGGGAAGGTTCGTGGGGACAAGAGAT
AAAACAGATCTATCCTTTAGAAGGGAATTGGAAGAATTTAGCACCTGCT
GAGCAATCCTATCAAGTCGGCAGATGTATAGGTTTTCTATATGGAGACT
TGGCGTATAGAAAATCTACTCATGCCGAGGACAGTTCTCTATTTCCTCT
ATCTATACAAGGTCGTATTAGAGGTCGAGGTTTCTTAAAAGGGTTGCTA
GACGGATTAATGAGAGCAAGTTGCTGCCAAGTAATACACCGGAGAAGTC
TGGCTCATTTGAAGAGGCCGGCCAACGCAGTGTACGGAGGTTTGATTTA
CTTGATTGATAAATTGAGTGTATCACCTCCATTCCTTTCTCTTACTAGA
TCAGGACCTATTAGAGACGAATTAGAAACGATTCCCCACAAGATCCCAA
CCTCCTATCCGACAAGCAACCGTGATATGGGGGTGATTGTCAGAAATTA
CTTCAAATACCAATGCCGTCTAATTGAAAAGGGAAAATACAGATCACAT
TATTCACAATTATGGTTATTCTCAGATGTCTTATCCATAGACTTCATTG
GACCATTCTCTATTTCCACCACCCTCTTGCAAATCCTATACAAGCCATT
TTTATCTGGGAAAGATAAGAATGAGTTGAGAGAGCTGGCAAATCTTTCT
TCATTGCTAAGATCAGGAGAGGGGTGGGAAGACATACATGTGAAATTCT
TCACCAAGGACATATTATTGTGTCCAGAGGAAATCAGACATGCTTGCAA
GTTCGGGATTGCTAAGGATAATAATAAAGACATGAGCTATCCCCCTTGG
GGAAGGGAATCCAGAGGGACAATTACAACAATCCCTGTTTATTATACGA
CCACCCCTTACCCAAAGATGCTAGAGATGCCTCCAAGAATCCAAAATCC
CCTGCTGTCCGGAATCAGGTTGGGCCAATTACCAACTGGCGCTCATTAT
AAAATTCGGAGTATATTCATGGAATGGGAATCCATTACAGGGACTTCT
TGAGTTGTGGGACGGCTCCGGAGGGATGACTGCTGCATTACTACGAGA
AAATGTGCATAGCAGAGGAATATTCAATAGTCTGTTAGAATTATCAGGG
TCAGTCATGCGAGGCGCCTCTCCTGAGCCCCCCAGTGCCCTAGAAACTT
TAGGAGGAGATAAATCGAGATGTGTAAATGGTGAAACATGTTGGGAATA

```
TCCATCTGACTTATGTGACCCAAGGACTTGGGACTATTTCCTCCGACTC

AAAGCAGGCTTGGGGCTTCAAATTGATTTAATTGTAATGGATATGGAAG

TTCGGGATTCTTCTACTAGCCTGAAAATTGAGACGAATGTTAGAAATTA

TGTGCACCGGATTTTGGATGAGCAAGGAGTTTTAATCTACAAGACTTAT

GGAACATATATTTGTGAGAGCGAAAAGAATGCAGTAACAATCCTTGGTC

CCATGTTCAAGACGGTCGACTTAGTTCAAACAGAATTTAGTAGTTCTCA

AACGTCTGAAGTATATATGGTATGTAAAGGTTTGAAGAAATTAATCGAT

GAACCCAATCCCGATTGGTCTTCCATCAATGAATCCTGGAAAAACCTGT

ACGCATTCCAGTCATCAGAACAGGAATTTGCCAGAGCAAAGAAGGTTAG

TACATACTTTACCTTGACAGGTATTCCCTCCCAATTCATTCCTGATCCT

TTTGTAAACATTGAGACTATGCTACAAATATTCGGAGTACCCACGGGTG

TGTCTCATGCGGCTGCCTTAAAATCATCTGATAGACCTGCAGATTTATT

GACCATTAGCCTTTTTTATATGGCGATTATATCGTATTATAACATCAAT

CATATCAGAGTAGGACCGATACCTCCGAACCCCCCATCAGATGGAATTG
```

```
CACAAAATGTGGGGATCGCTATAACTGGTATAAGCTTTTGGCTGAGTTT

GATGGAGAAAGACATTCCACTATATCAACAGTGTTTAGCAGTTATCCAG

CAATCATTCCCGATTAGGTGGGAGGCTGTTTCAGTAAAAGGAGGATACA

AGCAGAAGTGGAGTACTAGAGGTGATGGGCTCCCAAAAGATACCCGAAC

TTCAGACTCCTTGGCCCCAATCGGGAACTGGATCAGATCTCTGGAATTG

GTCCGAAACCAAGTTCGTCTAAATCCATTCAATGAGATCTTGTTCAATC

AGCTATGTCGTACAGTGGATAATCATTTGAAATGGTCAAATTTGCGAAG

AAACACAGGAATGATTGAATGGATCAATAGACGAATTTCAAAAGAAGAC

CGGTCTATACTGATGTTGAAGAGTGACCTACACGAGGAAAACTCTTGGA

GAGATTAAAAAATCATGAGGAGACTCCAAACTTTAAGTATGAAAAAAAC

TTTGATCCTTAAGACCCTCTTGTGGTTTTTATTTTTTATCTGGTTTTGT

GGTCTTCGT.
```

In other embodiments, the nucleic acid comprises the sequence of SEQ ID NO: 25, shown below (VSV vector: Convac V4 South Africa):

```
ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAGAAGACAATTGGCAAGT

ATGCTAAGTCAGAATTTGACAAAATGACCCTATAATTCTCAGATCACCTATTATAT
```

-continued

```
ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT

GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCAAAGACATCCATGAC

TTTCCAACCCAAGAAAGCAAGTCTTCAGCCTCTCACCATATCCTTGGATGAATTG

TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCTCCTAATTCC

AGCCTCTCGAACAACTAATATCCTGTCTTTTCTATCCCTATGAAAAAAACTAACA

GAGATCGATCTGTTTACGCGTGCCACCATGTTCGTGTTTCTGGTGCTGCTGCCTCT

GGTGAGCTCCCAGTGCGTGAACTTCACCACAAGGACCCAGCTGCCCCCTGCCTAT

ACCAATTCCTTCACACGGGGCGTGTACTATCCCGACAAGGTGTTCCGGAGCAGC

GTGCTGCACTCCACACAGGATCTGTTTCTGCCTTTCTTTTCTAACGTGACCTGGTT

CCACGCCATCCACGTGAGCGGCACCAATGGCACAAAGCGGTTCGCCAATCCAGT

GCTGCCCTTTAACGATGGCGTGTACTTCGCCTCCACCGAGAAGTCTAACATCATC

AGAGGCTGGATCTTTGGCACCACACTGGACAGCAAGACACAGTCCCTGCTGATC

GTGAACAATGCCACCAACGTGGTCATCAAGGTGTGCGAGTTCCAGTTTTGTAATG

ATCCATTCCTGGGCGTGTACTATCACAAGAACAATAAGTCTTGGATGGAGAGCG
```

-continued

AGTTTCGCGTGTATTCCTCTGCCAACAATTGCACATTTGAGTACGTGTCCCAGCC

CTTCCTGATGGACCTGGAGGGCAAGCAGGGCAATTTCAAGAACCTGAGGGAGTT

CGTGTTTAAGAATATCGATGGCTACTTCAAAATCTACTCCAAGCACACCCCAATC

AACCTGGTGCGCGGCCTGCCACAGGGCTTCTCTGCCCTGGAGCCACTGGTGGATC

TGCCCATCGGCATCAACATCACCCGGTTTCAGACACTGCTGGCCCTGCACAGAA

GCTACCTGACACCAGGCGACAGCTCCTCTGGATGGACCGCAGGAGCAGCAGCCT

ACTATGTGGGCTATCTGCAGCCCAGGACCTTCCTGCTGAAGTACAACGAGAATG

GCACCATCACAGACGCCGTGGATTGCGCCCTGGATCCCCTGTCTGAGACCAAGT

GTACACTGAAGAGCTTTACCGTGGAGAAGGGCATCTATCAGACAAGCAATTTCA

GGGTGCAGCCTACCGAGTCCATCGTGCGCTTTCCCAATATCACAAACCTGTGCCC

TTTTGGCGAGGTGTTCAACGCAACCCGCTTCGCCAGCGTGTACGCCTGGAATAGG

AAGCGCATCTCCAACTGCGTGGCCGACTATTCTGTGCTGTACAACAGCGCCTCCT

TCTCTACCTTTAAGTGCTATGGCGTGAGCCCCACAAAGCTGAATGACCTGTGCTT

TACCAACGTGTACGCCGATTCCTTCGTGATCAGGGGCGACGAGGTGCGCCAGAT

CGCACCAGGACAGACAGGCAATATCGCAGACTACAATTATAAGCTGCCTGACGA

TTTCACCGGCTGCGTGATCGCCTGGAACTCTAACAATCTGGATAGCAAAGTGGGC

GGCAACTACAATTATCTGTACCGGCTGTTTAGAAAGTCTAATCTGAAGCCATTCG

AGAGGGACATCTCCACAGAAATCTACCAGGCCGGCTCTACCCCCTGCAATGGCG

TGAAGGGCTTTAACTGTTATTTCCCTCTGCAGAGCTACGGCTTCCAGCCAACATA

TGGCGTGGGCTATCAGCCCTACCGCGTGGTGGTGCTGTCTTTTGAGCTGCTGCAC

GCACCTGCAACAGTGTGCGGACCAAAGAAGAGCACCAATCTGGTGAAGAACAA

GTGCGTGAACTTCAACTTCAACGGACTGACCGGAACAGGCGTGCTGACCGAGTC

CAACAAGAAGTTCCTGCCTTTTCAGCAGTTCGGCAGGGACATCGCAGATACCAC

AGACGCCGTGCGCGACCCTCAGACCCTGGAGATCCTGGACATCACACCATGCTC

CTTCGGCGGCGTGTCTGTGATCACACCAGGCACCAATACAAGCAACCAGGTGGC

CGTGCTGTATCAGGGCGTGAATTGTACCGAGGTGCCAGTGGCAATCCACGCAGA

TCAGCTGACCCCTACATGGCGGGTGTACTCTACCGGCAGCAACGTGTTCCAGAC

AAGAGCCGGATGCCTGATCGGAGCAGAGCACGTGAACAATAGCTATGAGTGCGA

CATCCCTATCGGCGCCGGCATCTGTGCCTCCTACCAGACCCAGACAAACTCCCCA

AGGTCTGTGGGCGATACAGGCCTGTCCAAGAATCCAATCGAGCTGGTAGAGGGC

TGGTTCAGCAGTTGGAAAAGCTCCATCGCCTCCTTTTTCTTTATCATCGGCCTGAT

CATCGGACTGTTCCTGGTGCTCCGCGTGGGTATCCACCTGTGCATCAAGCTGAAG

CACACCAAGAAAAGACAGATTTATACAGACATCGAGATGAACCGCCTGGGAAA

GggatccggctccggcgagggcaggggaagtctactaacatgcggggacgtggaggaaaatcccggccccATGAAGTG

CCTTTTGTACTTAGCCTTTTTATTCATTGGGGTGAATTGCAAGTTCACCATAGTTT

TTCCACACAACCAAAAAGGAAACTGGAAAAATGTTCCTTCTAATTACCATTATTG

CCCGTCAAGCTCAGATTTAAATTGGCATAATGACTTAATAGGCACAGCCATACA

AGTCAAAATGCCCAAGAGTCACAAGGCTATTCAAGCAGACGGTTGGATGTGTCA

TGCTTCCAAATGGGTCACTACTTGTGATTTCCGCTGGTATGGACCGAAGTATATA

ACACAGTCCATCCGATCCTTCACTCCATCTGTAGAACAATGCAAGGAAAGCATT

GAACAAACGAAACAAGGAACTTGGCTGAATCCAGGCTTCCCTCCTCAAAGTTGT

-continued

```
GGATATGCAACTGTGACGGATGCCGAAGCAGTGATTGTCCAGGTGACTCCTCAC
CATGTGCTGGTTGATGAATACACAGGAGAATGGGTTGATTCACAGTTCATCAAC
GGAAAATGCAGCAATTACATATGCCCCACTGTCCATAACTCTACAACCTGGCATT
CTGACTATAAGGTCAAAGGGCTATGTGATTCTAACCTCATTTCCATGGACATCAC
CTTCTTCTCAGAGGACGGAGAGCTATCATCCCTGGGAAAGGAGGGCACAGGGTT
CAGAAGTAACTACTTTGCTTATGAAACTGGAGGCAAGGCCTGCAAAATGCAATA
CTGCAAGCATTGGGGAGTCAGACTCCCATCAGGTGTCTGGTTCGAGATGGCTGAT
AAGGATCTCTTTGCTGCAGCCAGATTCCCTGAATGCCCAGAAGGGTCAAGTATCT
CTGCTCCATCTCAGACCTCAGTGGATGTAAGTCTAATTCAGGACGTTGAGAGGAT
CTTGGATTATTCCCTCTGCCAAGAAACCTGGAGCAAAATCAGAGCGGGTCTTCCA
ATCTCTCCAGTGGATCTCAGCTATCTTGCTCCTAAAAACCCAGGAACCGGTCCTG
CTTTCACCATAATCAATGGTACCCTAAAATACTTTGAGACCAGATACATCAGAGT
CGATATTGCTGCTCCAATCCTCTCAAGAATGGTCGGAATGATCAGTGGAACTACC
ACAGAAAGGGAACTGTGGGATGACTGGGCACCATATGAAGACGTGGAAATTGG
ACCCAATGGAGTTCTGAGGACCAGTTCAGGATATAAGTTTCCTTTATACATGATT
GGACATGGTATGTTGGACTCCGATCTTCATCTTAGCTCAAAGGCTCAGGTGTTCG
AACATCCTCACATTAAGACGCTGCTTCGCAACTTCCTGATGATGAGAGTTTATT
TTTTGGTGATACTGGGCTATCCAAAAATCCAATCGAGCTTGTAGAAGGTTGGTTC
AGTAGTTGGAAAAGCTCTATTGCCTCTTTTTTCTTTATCATAGGGTTAATCATTGG
ACTATTCTTGGTTCTCCGAGTTGGTATCCATCTTTGCATTAAATTAAAGCACACCA
AGAAAAGACAGATTTATACAGACATAGAGATGAACCGACTTGGAAAGTAAgCTA
GCCAGATTCTTCATGTTTGGACCAAATCAACTTGTGATACCATGCTCAAAGAGGC
CTCAATTATATTTGAGTTTTTAATTTTTATGAAAAAAACTAACAGCAATCATGGA
AGTCCACGATTTTGAGACCGACGAGTTCAATGATTTCAATGAAGATGACTATGCC
ACAAGAGAATTCCTGAATCCCGATGAGCGCATGACGTACTTGAATCATGCTGATT
ACAATTTGAATTCTCCTCTAATTAGTGATGATATTGACAATTTGATCAGGAAATT
CAATTCTCTTCCGATTCCCTCGATGTGGGATAGTAAGAACTGGGATGGAGTTCTT
GAGATGTTAACATCATGTCAAGCCAATCCCATCTCAACATCTCAGATGCATAAAT
GGATGGGAAGTTGGTTAATGTCTGATAATCATGATGCCAGTCAAGGGTATAGTTT
TTTACATGAAGTGGACAAAGAGGCAGAAATAACATTTGACGTGGTGGAGACCTT
CATCCGCGGCTGGGGCAACAAACCAATTGAATACATCAAAAAGGAAAGATGGA
CTGACTCATTCAAAATTCTCGCTTATTTGTGTCAAAAGTTTTTGGACTTACACAAG
TTGACATTAATCTTAAATGCTGTCTCTGAGGTGGAATTGCTCAACTTGGCGAGGA
CTTTCAAAGGCAAAGTCAGAAGAAGTTCTCATGGAACGAACATATGCAGGATTA
GGGTTCCCAGCTTGGGTCCTACTTTTATTTCAGAAGGATGGGCTTACTTCAAGAA
ACTTGATATTCTAATGGACCGAAACTTTCTGTTAATGGTCAAAGATGTGATTATA
GGGAGGATGCAAACGGTGCTATCCATGGTATGTAGAATAGACAACCTGTTCTCA
GAGCAAGACATCTTCTCCCTTCTAAATATCTACAGAATTGGAGATAAAATTGTGG
AGAGGCAGGGAAATTTTTCTTATGACTTGATTAAAATGGTGGAACCGATATGCA
ACTTGAAGCTGATGAAATTAGCAAGAGAATCAAGGCCTTTAGTCCCACAATTCC
```

-continued

```
CTCATTTTGAAAATCATATCAAGACTTCTGTTGATGAAGGGGCAAAAATTGACCG
AGGTATAAGATTCCTCCATGATCAGATAATGAGTGTGAAAACAGTGGATCTCAC
ACTGGTGATTTATGGATCGTTCAGACATTGGGGTCATCCTTTTATAGATTATTAC
ACTGGACTAGAAAAATTACATTCCCAAGTAACCATGAAGAAAGATATTGATGTG
TCATATGCAAAAGCACTTGCAAGTGATTTAGCTCGGATTGTTCTATTTCAACAGT
TCAATGATCATAAAAAGTGGTTCGTGAATGGAGACTTGCTCCCTCATGATCATCC
CTTTAAAAGTCATGTTAAAGAAAATACATGGCCCACAGCTGCTCAAGTTCAAGA
TTTTGGAGATAAATGGCATGAACTTCCGCTGATTAAATGTTTTGAAATACCCGAC
TTACTAGACCCATCGATAATATACTCTGACAAAAGTCATTCAATGAATAGGTCAG
AGGTGTTGAAACATGTCCGAATGAATCCGAACACTCCTATCCCTAGTAAAAAGG
TGTTGCAGACTATGTTGGACACAAAGGCTACCAATTGGAAAGAATTTCTTAAAG
AGATTGATGAGAAGGGCTTAGATGATGATGATCTAATTATTGGTCTTAAAGGAA
AGGAGAGGGAACTGAAGTTGGCAGGTAGATTTTTCTCCCTAATGTCTTGGAAATT
GCGAGAATACTTTGTAATTACCGAATATTTGATAAAGACTCATTTCGTCCCTATG
TTTAAAGGCCTGACAATGGCGGACGATCTAACTGCAGTCATTAAAAAGATGTTA
GATTCCTCATCCGGCCAAGGATTGAAGTCATATGAGGCAATTTGCATAGCCAATC
ACATTGATTACGAAAAATGGAATAACCACCAAAGGAAGTTATCAAACGGCCCAG
TGTTCCGAGTTATGGGCCAGTTCTTAGGTTATCCATCCTTAATCGAGAGAACTCA
TGAATTTTTTGAGAAAAGTCTTATATACTACAATGGAAGACCAGACTTGATGCGT
GTTCACAACAACACACTGATCAATTCAACCTCCCAACGAGTTTGTTGGCAAGGA
CAAGAGGGTGGACTGGAAGGTCTACGGCAAAAAGGATGGACTATCCTCAATCTA
CTGGTTATTCAAAGAGAGGCTAAAATCAGAAACACTGCTGTCAAAGTCTTGGCA
CAAGGTGATAATCAAGTTATTTGCACACAGTATAAAACGAAGAAATCGAGAAAC
GTTGTAGAATTACAGGGTGCTCTCAATCAAATGGTTTCTAATAATGAGAAAATTA
TGACTGCAATCAAAATAGGGACAGGGAAGTTAGGACTTTTGATAAATGACGATG
AGACTATGCAATCTGCAGATTACTTGAATTATGGAAAAATACCGATTTTCCGTGG
AGTGATTAGAGGGTTAGAGACCAAGAGATGGTCACGAGTGACTTGTGTCACCAA
TGACCAAATACCCACTTGTGCTAATATAATGAGCTCAGTTTCCACAAATGCTCTC
ACCGTAGCTCATTTTGCTGAGAACCCAATCAATGCCATGATACAGTACAATTATT
TTGGGACATTTGCTAGACTCTTGTTGATGATGCATGATCCTGCTCTTCGTCAATCA
TTGTATGAAGTTCAAGATAAGATACCGGGCTTGCACAGTTCTACTTTCAAATACG
CCATGTTGTATTTGGACCCTTCCATTGGAGGAGTGTCGGGCATGTCTTTGTCCAG
GTTTTTGATTAGAGCCTTCCCAGATCCCGTAACAGAAAGTCTCTCATTCTGGAGA
TTCATCCATGTACATGCTCGAAGTGAGCATCTGAAGGAGATGAGTGCAGTATTTG
GAAACCCCGAGATAGCCAAGTTTCGAATAACTCACATAGACAAGCTAGTAGAAG
ATCCAACCTCTCTGAACATCGCTATGGGAATGAGTCCAGCGAACTTGTTAAAGAC
TGAGGTTAAAAAATGCTTAATCGAATCAAGACAAACCATCAGGAACCAGGTGAT
TAAGGATGCAACCATATATTTGTATCATGAAGAGGATCGGCTCAGAAGTTTCTTA
TGGTCAATAAATCCTCTGTTCCCTAGATTTTTAAGTGAATTCAAATCAGGCACTTT
TTTGGGAGTCGCAGACGGGCTCATCAGTCTATTTCAAAATTCTCGTACTATTCGG
AACTCCTTTAAGAAAAAGTATCATAGGGAATTGGATGATTTGATTGTGAGGAGT
```

-continued

```
GAGGTATCCTCTTTGACACATTTAGGGAAACTTCATTTGAGAAGGGGATCATGTA

AAATGTGGACATGTTCAGCTACTCATGCTGACACATTAAGATACAAATCCTGGG

GCCGTACAGTTATTGGGACAACTGTACCCCATCCATTAGAAATGTTGGGTCCACA

ACATCGAAAAGAGACTCCTTGTGCACCATGTAACACATCAGGGTTCAATTATGTT

TCTGTGCATTGTCCAGACGGGATCCATGACGTCTTTAGTTCACGGGACCATTGC

CTGCTTATCTAGGGTCTAAAACATCTGAATCTACATCTATTTTGCAGCCTTGGGA

AAGGGAAAGCAAAGTCCCACTGATTAAAGAGCTACACGTCTTAGAGATGCTAT

CTCTTGGTTTGTTGAACCCGACTCTAAACTAGCAATGACTATACTTTCTAACATCC

ACTCTTTAACAGGCGAAGAATGGACCAAAAGGCAGCATGGGTTCAAAAGAACA

GGGTCTGCCCTTCATAGGTTTTCGACATCTCGGATGAGCCATGGTGGGTTCGCAT

CTCAGAGCACTGCAGCATTGACCAGGTTGATGGCAACTACAGACACCATGAGGG

ATCTGGGAGATCAGAATTTCGACTTTTTATTCCAAGCAACGTTGCTCTATGCTCA

AATTACCACCACTGTTGCAAGAGACGGATGGATCACCAGTTGTACAGATCATTAT

CATATTGCCTGTAAGTCCTGTTTGAGACCCATAGAAGAGATCACCCTGGACTCAA

GTATGGACTACACGCCCCCAGATGTATCCCATGTGCTGAAGACATGGAGGAATG

GGGAAGGTTCGTGGGGACAAGAGATAAAACAGATCTATCCTTTAGAAGGGAATT

GGAAGAATTTAGCACCTGCTGAGCAATCCTATCAAGTCGGCAGATGTATAGGTTT

TCTATATGGAGACTGGCGTATAGAAAATCTACTCATGCCGAGGACAGTTCTCTA

TTTCCTCTATCTATACAAGGTCGTATTAGAGGTCGAGGTTTCTTAAAAGGGTTGC

TAGACGGATTAATGAGAGCAAGTTGCTGCCAAGTAATACACCGGAGAAGTCTGG

CTCATTTGAAGAGGCCGGCCAACGCAGTGTACGGAGGTTTGATTTACTTGATTGA

TAAATTGAGTGTATCACCTCCATTCCTTTCTCTTACTAGATCAGGACCTATTAGAG

ACGAATTAGAAACGATTCCCCACAAGATCCCAACCTCCTATCCGACAAGCAACC

GTGATATGGGGTGATTGTCAGAAATTACTTCAAATACCAATGCCGTCTAATTGA

AAAGGGAAAATACAGATCACATTATTCACAATTATGGTTATTCTCAGATGTCTTA

TCCATAGACTTCATTGGACCATTCTCTATTTCCACCACCCTCTTGCAAATCCTATA

CAAGCCATTTTTATCTGGGAAAGATAAGAATGAGTTGAGAGAGCTGGCAAATCT

TTCTTCATTGCTAAGATCAGGAGAGGGGTGGGAAGACATACATGTGAAATTCTTC

ACCAAGGACATATTATTGTGTCCAGAGGAAATCAGACATGCTTGCAAGTTCGGG

ATTGCTAAGGATAATAATAAAGACATGAGCTATCCCCCTTGGGGAAGGGAATCC

AGAGGGACAATTACAACAATCCCTGTTTATTATACGACCACCCCTTACCCAAAG

ATGCTAGAGATGCCTCCAAGAATCCAAAATCCCCTGCTGTCCGGAATCAGGTTG

GGCCAATTACCAACTGGCGCTCATTATAAAATTCGGAGTATATTACATGGAATGG

GAATCCATTACAGGGACTTCTTGAGTTGTGGAGACGGCTCCGGAGGGATGACTG

CTGCATTACTACGAGAAAATGTGCATAGCAGAGGAATATTCAATAGTCTGTTAG

AATTATCAGGGTCAGTCATGCGAGGCGCCTCTCCTGAGCCCCCAGTGCCCTAGA

AACTTTAGGAGGAGATAAATCGAGATGTGTAAATGGTGAAACATGTTGGGAATA

TCCATCTGACTTATGTGACCCAAGGACTTGGGACTATTTCCTCCGACTCAAAGCA

GGCTTGGGGCTTCAAATTGATTTAATTGTAATGGATATGGAAGTTCGGGATTCTT

CTACTAGCCTGAAAATTGAGACGAATGTTAGAAATTATGTGCACCGGATTTTGGA
```

-continued
```
TGAGCAAGGAGTTTTAATCTACAAGACTTATGGAACATATATTTGTGAGAGCGA

AAAGAATGCAGTAACAATCCTTGGTCCCATGTTCAAGACGGTCGACTTAGTTCAA

ACAGAATTTAGTAGTTCTCAAACGTCTGAAGTATATATGGTATGTAAAGGTTTGA

AGAAATTAATCGATGAACCCAATCCCGATTGGTCTTCCATCAATGAATCCTGGAA

AAACCTGTACGCATTCCAGTCATCAGAACAGGAATTTGCCAGAGCAAAGAAGGT

TAGTACATACTTTACCTTGACAGGTATTCCCTCCCAATTCATTCCTGATCCTTTTG

TAAACATTGAGACTATGCTACAAATATTCGGAGTACCCACGGGTGTGTCTCATGC

GGCTGCCTTAAAATCATCTGATAGACCTGCAGATTTATTGACCATTAGCCTTTTTT

ATATGGCGATTATATCGTATTATAACATCAATCATATCAGAGTAGGACCGATACC

TCCGAACCCCCCATCAGATGGAATTGCACAAAATGTGGGGATCGCTATAACTGG

TATAAGCTTTTGGCTGAGTTTGATGGAGAAAGACATTCCACTATATCAACAGTGT

TTAGCAGTTATCCAGCAATCATTCCCGATTAGGTGGGAGGCTGTTTCAGTAAAAG

GAGGATACAAGCAGAAGTGGAGTACTAGAGGTGATGGGCTCCCAAAAGATACC

CGAACTTCAGACTCCTTGGCCCCAATCGGGAACTGGATCAGATCTCTGGAATTGG

TCCGAAACCAAGTTCGTCTAAATCCATTCAATGAGATCTTGTTCAATCAGCTATG

TCGTACAGTGGATAATCATTTGAAATGGTCAAATTTGCGAAGAAACACAGGAAT

GATTGAATGGATCAATAGACGAATTTCAAAAGAAGACCGGTCTATACTGATGTT

GAAGAGTGACCTACACGAGGAAAACTCTTGGAGAGATTAAAAAATCATGAGGA

GACTCCAAACTTTAAGTATGAAAAAAACTTTGATCCTTAAGACCCTCTTGTGGTT

TTTATTTTTTATCTGGTTTTGTGGTCTTCGT.
```

In one embodiment, the nucleic acid comprises the sequence of SEQ ID NO: 26, shown below (VSV vector: Convac VS China):

```
ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC
```

-continued

```
ATATTCTTCCGTCAAAAACCCTGCCTTCCACTTCTGGGGGCAATTGACAGCTCTT
CTGCTCAGATCCACCAGAGCAAGGAATGCCCGACAGCCTGATGACATTGAGTAT
ACATCTCTTACTACAGCAGGTTTGTTGTACGCTTATGCAGTAGGATCCTCTGCCG
ACTTGGCACAACAGTTTTGTGTTGGAGATAACAAATACACTCCAGATGATAGTAC
CGGAGGATTGACGACTAATGCACCGCCACAAGGCAGAGATGTGGTCGAATGGCT
CGGATGGTTTGAAGATCAAAACAGAAAACCGACTCCTGATATGATGCAGTATGC
GAAAAGAGCAGTCATGTCACTGCAAGGCCTAAGAGAGAAGACAATTGGCAAGT
ATGCTAAGTCAGAATTTGACAAATGACCCTATAATTCTCAGATCACCTATTATAT
ATTATGCTACATATGAAAAAAACTAACAGATATCATGGATAATCTCACAAAAGT
TCGTGAGTATCTCAAGTCCTATTCTCGTCTGGATCAGGCGGTAGGAGAGATAGAT
GAGATCGAAGCACAACGAGCTGAAAAGTCCAATTATGAGTTGTTCCAAGAGGAT
GGAGTGGAAGAGCATACTAAGCCCTCTTATTTTCAGGCAGCAGATGATTCTGAC
ACAGAATCTGAACCAGAAATTGAAGACAATCAAGGTTTGTATGCACCAGATCCA
GAAGCTGAGCAAGTTGAAGGCTTTATACAGGGGCCTTTAGATGACTATGCAGAT
GAGGAAGTGGATGTTGTATTTACTTCGGACTGGAAACAGCCTGAGCTTGAATCTG
ACGAGCATGGAAAGACCTTACGGTTGACATCGCCAGAGGGTTTAAGTGGAGAGC
AGAAATCCCAGTGGCTTTCGACGATTAAAGCAGTCGTGCAAAGTGCCAAATACT
GGAATCTGGCAGAGTGCACATTTGAAGCATCGGGAGAAGGGGTCATTATGAAGG
AGCGCCAGATAACTCCGGATGTATATAAGGTCACTCCAGTGATGAACACACATC
CGTCCCAATCAGAAGCAGTATCAGATGTTTGGTCTCTCAAAGACATCCATGAC
TTTCCAACCCAAGAAAGCAAGTCTTCAGCCTCTCACCATATCCTTGGATGAATTG
TTCTCATCTAGAGGAGAGTTCATCTCTGTCGGAGGTGACGGACGAATGTCTCATA
AAGAGGCCATCCTGCTCGGCCTGAGATACAAAAAGTTGTACAATCAGGCGAGAG
TCAAATATTCTCTGTAGACTATGAAAAAAAGTAACAGATATCACGATCTAAGTGT
TATCCCAATCCATTCATCATGAGTTCCTTAAAGAAGATTCTCGGTCTGAAGGGGA
AAGGTAAGAAATCTAAGAAATTAGGGATCGCACCACCCCCTTATGAAGAGGACA
CTAGCATGGAGTATGCTCCGAGCGCTCCAATTGACAAATCCTATTTTGGAGTTGA
CGAGATGGACACCTATGATCCGAATCAATTAAGATATGAGAAATTCTTCTTTACA
GTGAAAATGACGGTTAGATCTAATCGTCCGTTCAGAACATACTCAGATGTGGCA
GCCGCTGTATCCCATTGGGATCACATGTACATCGGAATGGCAGGGAAACGTCCC
TTCTACAAAATCTTGGCTTTTTTGGGTTCTTCTAATCTAAAGGCCACTCCAGCGGT
ATTGGCAGATCAAGGTCAACCAGAGTATCACACTCACTGCGAAGGCAGGGCTTA
TTTGCCACATAGGATGGGAAGACCCCTCCCATGCTCAATGTACCAGAGCACTTC
AGAAGACCATTCAATATAGGTCTTTACAAGGGAACGATTGAGCTCACAATGACC
ATCTACGATGATGAGTCACTGGAAGCAGCTCCTATGATCTGGGATCATTTCAATT
CTTCCAAATTTTCTGATTTCAGAGAGAAGGCCTTAATGTTTGGCCTGATTGTCGA
GAAAAAGGCATCTGGAGCGTGGGTCCTGGATTCTATCAGCCACTTCAAATGAGC
TAGTCTAACTTCTAGCTTCTGAACAATCCCCGGTTTACTCAGTCTCTCCTAATTCC
AGCCTCTCGAACAACTAATATCCTGTCTTTTCTATCCCTATGAAAAAAACTAACA
GAGATCGATCTGTTTACGCGTCACTATGAAGTGCCTTTTGTACTTAGCCTTTTTAT
TCATTGGGGTGAATTGCAAGTTCACCATAGTTTTTCCACACAACCAAAAAGGAA
```

```
ACTGGAAAAATGTTCCTTCTAATTACCATTATTGCCCGTCAAGCTCAGATTTAAA
TTGGCATAATGACTTAATAGGCACAGCCATACAAGTCAAAATGCCCAAGAGTCA
CAAGGCTATTCAAGCAGACGGTTGGATGTGTCATGCTTCCAAATGGGTCACTACT
TGTGATTTCCGCTGGTATGGACCGAAGTATATAACACAGTCCATCCGATCCTTCA
CTCCATCTGTAGAACAATGCAAGGAAAGCATTGAACAAACGAAACAAGGAACTT
GGCTGAATCCAGGCTTCCCTCCTCAAAGTTGTGGATATGCAACTGTGACGGATGC
CGAAGCAGTGATTGTCCAGGTGACTCCTCACCATGTGCTGGTTGATGAATACACA
GGAGAATGGGTTGATTCACAGTTCATCAACGGAAAATGCAGCAATTACATATGC
CCCACTGTCCATAACTCTACAACCTGGCATTCTGACTATAAGGTCAAAGGGCTAT
GTGATTCTAACCTCATTTCCATGGACATCACCTTCTTCTCAGAGGACGGAGAGCT
ATCATCCCTGGGAAGGAGGGCACAGGGTTCAGAAGTAACTACTTTGCTTATGA
AACTGGAGGCAAGGCCTGCAAAATGCAATACTGCAAGCATTGGGGAGTCAGACT
CCCATCAGGTGTCTGGTTCGAGATGGCTGATAAGGATCTCTTTGCTGCAGCCAGA
TTCCCTGAATGCCCAGAAGGGTCAAGTATCTCTGCTCCATCTCAGACCTCAGTGG
ATGTAAGTCTAATTCAGGACGTTGAGAGGATCTTGGATTATTCCCTCTGCCAAGA
AACCTGGAGCAAAATCAGAGCGGGTCTTCCAATCTCTCCAGTGGATCTCAGCTAT
CTTGCTCCTAAAAACCCAGGAACCGGTCCTGCTTTCACCATAATCAATGGTACCC
TAAAATACTTTGAGACCAGATACATCAGAGTCGATATTGCTGCTCCAATCCTCTC
AAGAATGGTCGGAATGATCAGTGGAACTACCACAGAAAGGGAACTGTGGGATG
ACTGGGCACCATATGAAGACGTGGAAATTGGACCCAATGGAGTTCTGAGGACCA
GTTCAGGATATAAGTTTCCTTTATACATGATTGGACATGGTATGTTGGACTCCGA
TCTTCATCTTAGCTCAAAGGCTCAGGTGTTCGAACATCCTCACATTCAAGACGCT
GCTTCGCAACTTCCTGATGATGAGAGTTTATTTTTTGGTGATACTGGGCTATCCA
AAAATCCAATCGAGCTTGTAGAAGGTTGGTTCAGTAGTTGGAAAAGCTCTATTGC
CTCTTTTTTCTTTATCATAGGGTTAATCATTGGACTATTCTTGGTTCTCCGAGTTG
GTATCCATCTTTGCATTAAATTAAAGCACACCAAGAAAAGACAGATTTATACAG
ACATAGAGATGAACCGACTTGGAAAGTAACTCAAATCCTGCTAGGTATGAAAAA
AACTAACaGATATCACGCtcgagGCCACCATGAAGTGCCTGTTGTACTTAGCCTTCC
TGTTCATCGGGGTGAATTGCCGCTTTCCCAATATCACAAACCTGTGCCCTTTTGG
CGAGGTGTTCAACGCAACCCGCTTCGCCAGCGTGTACGCCTGGAATAGGAAGCG
CATCTCCAACTGCGTGGCCGACTATTCTGTGCTGTACAACAGCGCCTCCTTCTCT
ACCTTTAAGTGCTATGGCGTGAGCCCCACAAAGCTGAATGACCTGTGCTTTACCA
ACGTGTACGCCGATTCCTTCGTGATCAGGGGCGACGAGGTGCGCCAGATCGCAC
CAGGACAGACAGGCAAGATCGCAGACTACAATTATAAGCTGCCTGACGATTTCA
CCGGCTGCGTGATCGCCTGGAACTCTAACAATCTGGATAGCAAAGTGGGCGGCA
ACTACAATTATCTGTACCGGCTGTTTAGAAAGTCTAATCTGAAGCCATTCGAGAG
GGACATCTCCACAGAAATCTACCAGGCCGGCTCTACCCCCTGCAATGGCGTGGA
GGGCTTTAACTGTTATTTCCCTCTGCAGAGCTACGGCTTCCAGCCAACAAACGGC
GTGGGCTATCAGCCCTACCGCGTGGTGGTGCTGTCTTTTGAGCTGCTGCACGCAC
CTGCAACAGTGTGCGGACCAAAGAAGAGCACCAATCTGGTGAAGAACAAGTGC
```

-continued

```
GTGAACTTCAAcggCTCTGGATCCGGCTACATCCCCGAGGCCCCCAGAGACGGCC
AGGCCTACGTGCGGAAGGACGGCGAGTGGGTACTGctcagcaccttectgggcAGCAGTTG
GAAAAGCTCCATCGCCTCCTTTTTCTTTATCATCGGCCTGATCATCGGACTGTTCC
TGGTGCTCCGCGTGGGTATCCACCTGTGCATCAAGCTGAAGCACACCAAGAAAA
GACAGATTTATACAGACATCGAGATGAACCGACTTGGAAAGTAAGCTAGCCAGA
TTCTTCATGTTTGGACCAAATCAACTTGTGATACCATGCTCAAAGAGGCCTCAAT
TATATTTGAGTTTTTAATTTTTATGAAAAAAACTAACAGCAATCATGGAAGTCCA
CGATTTTGAGACCGACGAGTTCAATGATTTCAATGAAGATGACTATGCCACAAG
AGAATTCCTGAATCCCGATGAGCGCATGACGTACTTGAATCATGCTGATTACAAT
TTGAATTCTCCTCTAATTAGTGATGATATTGACAATTTGATCAGGAAATTCAATT
CTCTTCCGATTCCCTCGATGTGGGATAGTAAGAACTGGGATGGAGTTCTTGAGAT
GTTAACATCATGTCAAGCCAATCCCATCTCAACATCTCAGATGCATAAATGGATG
GGAAGTTGGTTAATGTCTGATAATCATGATGCCAGTCAAGGGTATAGTTTTTTAC
ATGAAGTGGACAAAGAGGCAGAAATAACATTTGACGTGGTGGAGACCTTCATCC
GCGGCTGGGCAACAAACCAATTGAATACATCAAAAAGGAAAGATGGACTGAC
TCATTCAAAATTCTCGCTTATTTGTGTCAAAAGTTTTTGGACTTACACAAGTTGAC
ATTAATCTTAAATGCTGTCTCTGAGGTGGAATTGCTCAACTTGGCGAGGACTTTC
AAAGGCAAAGTCAGAAGAAGTTCTCATGGAACGAACATATGCAGGATTAGGGTT
CCCAGCTTGGGTCCTACTTTTATTTCAGAAGGATGGGCTTACTTCAAGAAACTTG
ATATTCTAATGGACCGAAACTTTCTGTTAATGGTCAAAGATGTGATTATAGGGAG
GATGCAAACGGTGCTATCCATGGTATGTAGAATAGACAACCTGTTCTCAGAGCA
AGACATCTTCTCCCTTCTAAATATCTACAGAATTGGAGATAAAATTGTGGAGAGG
CAGGGAAATTTTTCTTATGACTTGATTAAAATGGTGGAACCGATATGCAACTTGA
AGCTGATGAAATTAGCAAGAGAATCAAGGCCTTTAGTCCCACAATTCCCTCATTT
TGAAAATCATATCAAGACTTCTGTTGATGAAGGGGCAAAAATTGACCGAGGTAT
AAGATTCCTCCATGATCAGATAATGAGTGTGAAAACAGTGGATCTCACACTGGT
GATTTATGGATCGTTCAGACATTGGGGTCATCCTTTTATAGATTATTACACTGGA
CTAGAAAAATTACATTCCCAAGTAACCATGAAGAAAGATATTGATGTGTCATAT
GCAAAAGCACTTGCAAGTGATTTAGCTCGGATTGTTCTATTTCAACAGTTCAATG
ATCATAAAAAGTGGTTCGTGAATGGAGACTTGCTCCCTCATGATCATCCCTTTAA
AAGTCATGTTAAAGAAAATACATGGCCCACAGCTGCTCAAGTTCAAGATTTTGG
AGATAAATGGCATGAACTTCCGCTGATTAAATGTTTTGAAATACCCGACTTACTA
GACCCATCGATAATATACTCTGACAAAAGTCATTCAATGAATAGGTCAGAGGTG
TTGAAACATGTCCGAATGAATCCGAACACTCCTATCCCTAGTAAAAAGGTGTTGC
AGACTATGTTGGACACAAAGGCTACCAATTGGAAAGAATTTCTTAAAGAGATTG
ATGAGAAGGGCTTAGATGATGATGATCTAATTATTGGTCTTAAAGGAAAGGAGA
GGGAACTGAAGTTGGCAGGTAGATTTTTCTCCCTAATGTCTTGGAAATTGCGAGA
ATACTTTGTAATTACCGAATATTTGATAAAGACTCATTTCGTCCCTATGTTTAAAG
GCCTGACAATGGCGGACGATCTAACTGCAGTCATTAAAAAGATGTTAGATTCCTC
ATCCGGCCAAGGATTGAAGTCATATGAGGCAATTTGCATAGCCAATCACATTGA
TTACGAAAAATGGAATAACCACCAAAGGAAGTTATCAAACGGCCCAGTGTTCCG
```

-continued

```
AGTTATGGGCCAGTTCTTAGGTTATCCATCCTTAATCGAGAGAACTCATGAATTT

TTTGAGAAAAGTCTTATATACTACAATGGAAGACCAGACTTGATGCGTGTTCACA

ACAACACACTGATCAATTCAACCTCCCAACGAGTTTGTTGGCAAGGACAAGAGG

GTGGACTGGAAGGTCTACGGCAAAAAGGATGGACTATCCTCAATCTACTGGTTA

TTCAAAGAGAGGCTAAAATCAGAAACACTGCTGTCAAAGTCTTGGCACAAGGTG

ATAATCAAGTTATTTGCACACAGTATAAAACGAAGAAATCGAGAAACGTTGTAG

AATTACAGGGTGCTCTCAATCAAATGGTTTCTAATAATGAGAAAATTATGACTGC

AATCAAAATAGGGACAGGGAAGTTAGGACTTTTGATAAATGACGATGAGACTAT

GCAATCTGCAGATTACTTGAATTATGGAAAAATACCGATTTTCCGTGGAGTGATT

AGAGGGTTAGAGACCAAGAGATGGTCACGAGTGACTTGTGTCACCAATGACCAA

ATACCCACTTGTGCTAATATAATGAGCTCAGTTTCCACAAATGCTCTCACCGTAG

CTCATTTTGCTGAGAACCCAATCAATGCCATGATACAGTACAATTATTTTGGGAC

ATTTGCTAGACTCTTGTTGATGATGCATGATCCTGCTCTTCGTCAATCATTGTATG

AAGTTCAAGATAAGATACCGGGCTTGCACAGTTCTACTTTCAAATACGCCATGTT

GTATTTGGACCCTTCCATTGGAGGAGTGTCGGGCATGTCTTTGTCCAGGTTTTTG

ATTAGAGCCTTCCCAGATCCCGTAACAGAAAGTCTCTCATTCTGGAGATTCATCC

ATGTACATGCTCGAAGTGAGCATCTGAAGGAGATGAGTGCAGTATTTGGAAACC

CCGAGATAGCCAAGTTTCGAATAACTCACATAGACAAGCTAGTAGAAGATCCAA

CCTCTCTGAACATCGCTATGGGAATGAGTCCAGCGAACTTGTTAAAGACTGAGGT

TAAAAAATGCTTAATCGAATCAAGACAAACCATCAGGAACCAGGTGATTAAGGA

TGCAACCATATATTTGTATCATGAAGAGGATCGGCTCAGAAGTTTCTTATGGTCA

ATAAATCCTCTGTTCCCTAGATTTTTAAGTGAATTCAAATCAGGCACTTTTTTGGG

AGTCGCAGACGGGCTCATCAGTCTATTTCAAAATTCTCGTACTATTCGGAACTCC

TTTAAGAAAAAGTATCATAGGGAATTGGATGATTTGATTGTGAGGAGTGAGGTA

TCCTCTTTGACACATTTAGGGAAACTTCATTTGAGAAGGGGATCATGTAAAATGT

GGACATGTTCAGCTACTCATGCTGACACATTAAGATACAAATCCTGGGGCCGTAC

AGTTATTGGGACAACTGTACCCCATCCATTAGAAATGTTGGGTCCACAACATCGA

AAAGAGACTCCTTGTGCACCATGTAACACATCAGGGTTCAATTATGTTTCTGTGC

ATTGTCCAGACGGGATCCATGACGTCTTTAGTTCACGGGACCATTGCCTGCTTA

TCTAGGGTCTAAAACATCTGAATCTACATCTATTTTGCAGCCTTGGGAAAGGGAA

AGCAAAGTCCCACTGATTAAAAGAGCTACACGTCTTAGAGATGCTATCTCTTGGT

TTGTTGAACCCGACTCTAAACTAGCAATGACTATACTTTCTAACATCCACTCTTTA

ACAGGCAAGAATGGACCAAAAGGCAGCATGGGTTCAAAAGAACAGGGTCTGC

CCTTCATAGGTTTTCGACATCTCGGATGAGCCATGGTGGGTTCGCATCTCAGAGC

ACTGCAGCATTGACCAGGTTGATGGCAACTACAGACACCATGAGGGATCTGGGA

GATCAGAATTTCGACTTTTTATTCCAAGCAACGTTGCTCTATGCTCAAATTACCA

CCACTGTTGCAAGAGACGGATGGATCACCAGTTGTACAGATCATTATCATATTGC

CTGTAAGTCCTGTTTGAGACCCATAGAAGAGATCACCCTGGACTCAAGTATGGA

CTACACGCCCCCAGATGTATCCCATGTGCTGAAGACATGGAGGAATGGGGAAGG

TTCGTGGGGACAAGAGATAAAACAGATCTATCCTTTAGAAGGGAATTGGAAGAA
```

-continued

```
TTTAGCACCTGCTGAGCAATCCTATCAAGTCGGCAGATGTATAGGTTTTCTATAT
GGAGACTTGGCGTATAGAAAATCTACTCATGCCGAGGACAGTTCTCTATTTCCTC
TATCTATACAAGGTCGTATTAGAGGTCGAGGTTTCTTAAAAGGGTTGCTAGACGG
ATTAATGAGAGCAAGTTGCTGCCAAGTAATACACCGGAGAAGTCTGGCTCATTT
GAAGAGGCCGGCCAACGCAGTGTACGGAGGTTTGATTTACTTGATTGATAAATT
GAGTGTATCACCTCCATTCCTTTCTCTTACTAGATCAGGACCTATTAGAGACGAA
TTAGAAACGATTCCCCACAAGATCCCAACCTCCTATCCGACAAGCAACCGTGAT
ATGGGGGTGATTGTCAGAAATTACTTCAAATACCAATGCCGTCTAATTGAAAAG
GGAAAATACAGATCACATTATTCACAATTATGGTTATTCTCAGATGTCTTATCCA
TAGACTTCATTGGACCATTCTCTATTTCCACCACCCTCTTGCAAATCCTATACAAG
CCATTTTTATCTGGGAAAGATAAGAATGAGTTGAGAGAGCTGGCAAATCTTTCTT
CATTGCTAAGATCAGGAGAGGGGTGGGAAGACATACATGTGAAATTCTTCACCA
AGGACATATTATTGTGTCCAGAGGAAATCAGACATGCTTGCAAGTTCGGGATTG
CTAAGGATAATAATAAAGACATGAGCTATCCCCCTTGGGGAAGGGAATCCAGAG
GGACAATTACAACAATCCCTGTTTATTATACGACCACCCCTTACCCAAAGATGCT
AGAGATGCCTCCAAGAATCCAAAATCCCCTGCTGTCCGGAATCAGGTTGGGCCA
ATTACCAACTGGCGCTCATTATAAAATTCGGAGTATATTACATGGAATGGGAATC
CATTACAGGGACTTCTTGAGTTGTGGAGACGGCTCCGGAGGGATGACTGCTGCA
TTACTACGAGAAAATGTGCATAGCAGAGGAATATTCAATAGTCTGTTAGAATTAT
CAGGGTCAGTCATGCGAGGCGCCTCTCCTGAGCCCCCCAGTGCCCTAGAAACTTT
AGGAGGAGATAAATCGAGATGTGTAAATGGTGAAACATGTTGGGAATATCCATC
TGACTTATGTGACCCAAGGACTTGGGACTATTTCCTCCGACTCAAAGCAGGCTTG
GGGCTTCAAATTGATTTAATTGTAATGGATATGGAAGTTCGGGATTCTTCTACTA
GCCTGAAAATTGAGACGAATGTTAGAAATTATGTGCACCGGATTTTGGATGAGC
AAGGAGTTTTAATCTACAAGACTTATGGAACATATATTTGTGAGAGCGAAAAGA
ATGCAGTAACAATCCTTGGTCCCATGTTCAAGACGGTCGACTTAGTTCAAACAGA
ATTTAGTAGTTCTCAAACGTCTGAAGTATATATGGTATGTAAAGGTTTGAAGAAA
TTAATCGATGAACCCAATCCCGATTGGTCTTCCATCAATGAATCCTGGAAAAACC
TGTACGCATTCCAGTCATCAGAACAGGAATTTGCCAGAGCAAAGAAGGTTAGTA
CATACTTTACCTTGACAGGTATTCCCTCCCAATTCATTCCTGATCCTTTTGTAAAC
ATTGAGACTATGCTACAAATATTCGGAGTACCCACGGGTGTGTCTCATGCGGCTG
CCTTAAAATCATCTGATAGACCTGCAGATTTATTGACCATTAGCCTTTTTTATATG
GCGATTATATCGTATTATAACATCAATCATATCAGAGTAGGACCGATACCTCCGA
ACCCCCCATCAGATGGAATTGCACAAAATGTGGGGATCGCTATAACTGGTATAA
GCTTTTGGCTGAGTTTGATGGAGAAAGACATTCCACTATATCAACAGTGTTTAGC
AGTTATCCAGCAATCATTCCCGATTAGGTGGGAGGCTGTTTCAGTAAAAGGAGG
ATACAAGCAGAAGTGGAGTACTAGAGGTGATGGGCTCCCAAAAGATACCCGAAC
TTCAGACTCCTTGGCCCCAATCGGGAACTGGATCAGATCTCTGGAATTGGTCCGA
AACCAAGTTCGTCTAAATCCATTCAATGAGATCTTGTTCAATCAGCTATGTCGTA
CAGTGGATAATCATTTGAAATGGTCAAATTTGCGAAGAAACACAGGAATGATTG
AATGGATCAATAGACGAATTTCAAAAGAAGACCGGTCTATACTGATGTTGAAGA
```

-continued

GTGACCTACACGAGGAAAACTCTTGGAGAGATTAAAAAATCATGAGGAGACTCC

AAACTTTAAGTATGAAAAAAACTTTGATCCTTAAGACCCTCTTGTGGTTTTTATTT

TTTATCTGGTTTTGTGGTCTTCGT.

In other embodiments, the nucleic acid comprises the sequence of SEQ ID NO: 27, shown below (VSV vector: Convac VS South Africa):

ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAATGATCAATGAACAGTTTGAACCTCTTGTGCCAGAAGGT

CGTGACATTTTTGATGTGTGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT

GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

-continued

```
GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCAAAGACATCCATGAC

TTTCCAACCCAAGAAAGCAAGTCTTCAGCCTCTCACCATATCCTTGGATGAATTG

TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCTCCTAATTCC

AGCCTCTCGAACAACTAATATCCTGTCTTTTCTATCCCTATGAAAAAAACTAACA

GAGATCGATCTGTTTACGCGTCACTATGAAGTGCCTTTTGTACTTAGCCTTTTTAT

TCATTGGGGTGAATTGCAAGTTCACCATAGTTTTTCCACACAACCAAAAAGGAA

ACTGGAAAAATGTTCCTTCTAATTACCATTATTGCCCGTCAAGCTCAGATTTAAA

TTGGCATAATGACTTAATAGGCACAGCCATACAAGTCAAAATGCCCAAGAGTCA

CAAGGCTATTCAAGCAGACGGTTGGATGTGTCATGCTTCCAAATGGGTCACTACT

TGTGATTTCCGCTGGTATGGACCGAAGTATATAACACAGTCCATCCGATCCTTCA

CTCCATCTGTAGAACAATGCAAGGAAAGCATTGAACAAACGAAACAAGGAACTT

GGCTGAATCCAGGCTTCCCTCCTCAAAGTTGTGGATATGCAACTGTGACGGATGC

CGAAGCAGTGATTGTCCAGGTGACTCCTCACCATGTGCTGGTTGATGAATACACA

GGAGAATGGGTTGATTCACAGTTCATCAACGGAAAATGCAGCAATTACATATGC

CCCACTGTCCATAACTCTACAACCTGGCATTCTGACTATAAGGTCAAAGGGCTAT

GTGATTCTAACCTCATTTCCATGGACATCACCTTCTTCTCAGAGGACGGAGAGCT

ATCATCCCTGGGAAAGGAGGGCACAGGGTTCAGAAGTAACTACTTTGCTTATGA

AACTGGAGGCAAGGCCTGCAAAATGCAATACTGCAAGCATTGGGGAGTCAGACT

CCCATCAGGTGTCTGGTTCGAGATGGCTGATAAGGATCTCTTTGCTGCAGCCAGA

TTCCCTGAATGCCCAGAAGGGTCAAGTATCTCTGCTCCATCTCAGACCTCAGTGG

ATGTAAGTCTAATTCAGGACGTTGAGAGGATCTTGGATTATTCCCTCTGCCAAGA

AACCTGGAGCAAAATCAGAGCGGGTCTTCCAATCTCTCCAGTGGATCTCAGCTAT
```

-continued

CTTGCTCCTAAAAACCCAGGAACCGGTCCTGCTTTCACCATAATCAATGGTACCC

TAAAATACTTTGAGACCAGATACATCAGAGTCGATATTGCTGCTCCAATCCTCTC

AAGAATGGTCGGAATGATCAGTGGAACTACCACAGAAAGGGAACTGTGGGATG

ACTGGGCACCATATGAAGACGTGGAAATTGGACCCAATGGAGTTCTGAGGACCA

GTTCAGGATATAAGTTTCCTTTATACATGATTGGACATGGTATGTTGGACTCCGA

TCTTCATCTTAGCTCAAAGGCTCAGGTGTTCGAACATCCTCACATTCAAGACGCT

GCTTCGCAACTTCCTGATGATGAGAGTTTATTTTTTGGTGATACTGGGCTATCCA

AAAATCCAATCGAGCTTGTAGAAGGTTGGTTCAGTAGTTGGAAAAGCTCTATTGC

CTCTTTTTTCTTTATCATAGGGTTAATCATTGGACTATTCTTGGTTCTCCGAGTTG

GTATCCATCTTTGCATTAAATTAAAGCACACCAAGAAAAGACAGATTTATACAG

ACATAGAGATGAACCGACTTGGAAAGTAACTCAAATCCTGCTAGGTATGAAAAA

AACTAACaGATATCACGCtcgagGCCACCATGAAGTGCCTGTTGTACTTAGCCTTCC

TGTTCATCGGGGTGAATTGCCGCTTTCCCAATATCACAAACCTGTGCCCTTTTGG

CGAGGTGTTCAACGCAACCCGCTTCGCCAGCGTGTACGCCTGGAATAGGAAGCG

CATCTCCAACTGCGTGGCCGACTATTCTGTGCTGTACAACAGCGCCTCCTTCTCT

ACCTTTAAGTGCTATGGCGTGAGCCCCACAAAGCTGAATGACCTGTGCTTTACCA

ACGTGTACGCCGATTCCTTCGTGATCAGGGGCGACGAGGTGCGCCAGATCGCAC

CAGGACAGACAGGCAATATCGCAGACTACAATTATAAGCTGCCTGACGATTTCA

CCGGCTGCGTGATCGCCTGGAACTCTAACAATCTGGATAGCAAAGTGGGCGGCA

ACTACAATTATCTGTACCGGCTGTTTAGAAAGTCTAATCTGAAGCCATTCGAGAG

GGACATCTCCACAGAAATCTACCAGGCCGGCTCTACCCCCTGCAATGGCGTGAA

GGGCTTTAACTGTTATTTCCCTCTGCAGAGCTACGGCTTCCAGCCAACATATGGC

GTGGGCTATCAGCCCTACCGCGTGGTGGTGCTGTCTTTTGAGCTGCTGCACGCAC

CTGCAACAGTGTGCGGACCAAAGAAGAGCACCAATCTGGTGAAGAACAAGTGC

GTGAACTTCAAcggCTCTGGATCCGGCTACATCCCCGAGGCCCCCAGAGACGGCC

AGGCCTACGTGCGGAAGGACGGCGAGTGGGTACTGctcagcaccttcctgggcAGCAGTTG

GAAAAGCTCCATCGCCTCCTTTTTCTTTATCATCGGCCTGATCATCGGACTGTTCC

TGGTGCTCCGCGTGGGTATCCACCTGTGCATCAAGCTGAAGCACACCAAGAAAA

GACAGATTTATACAGACATCGAGATGAACCGACTTGGAAAGTAAGCTAGCCAGA

TTCTTCATGTTTGGACCAAATCAACTTGTGATACCATGCTCAAAGAGGCCTCAAT

TATATTTGAGTTTTTAATTTTTATGAAAAAAACTAACAGCAATCATGGAAGTCCA

CGATTTTGAGACCGACGAGTTCAATGATTTCAATGAAGATGACTATGCCACAAG

AGAATTCCTGAATCCCGATGAGCGCATGACGTACTTGAATCATGCTGATTACAAT

TTGAATTCTCCTCTAATTAGTGATGATATTGACAATTTGATCAGGAAATTCAATT

CTCTTCCGATTCCCTCGATGTGGGATAGTAAGAACTGGGATGGAGTTCTTGAGAT

GTTAACATCATGTCAAGCCAATCCCATCTCAACATCTCAGATGCATAAATGGATG

GGAAGTTGGTTAATGTCTGATAATCATGATGCCAGTCAAGGGTATAGTTTTTTAC

ATGAAGTGGACAAAGAGGCAGAAATAACATTTGACGTGGTGGAGACCTTCATCC

GCGGCTGGGGCAACAAACCAATTGAATACATCAAAAAGGAAAGATGGACTGAC

TCATTCAAAATTCTCGCTTATTTGTGTCAAAAGTTTTTGGACTTACACAAGTTGAC

ATTAATCTTAAATGCTGTCTCTGAGGTGGAATTGCTCAACTTGGCGAGGACTTTC

```
-continued

AAAGGCAAAGTCAGAAGAAGTTCTCATGGAACGAACATATGCAGGATTAGGGTT

CCCAGCTTGGGTCCTACTTTTATTTCAGAAGGATGGGCTTACTTCAAGAAACTTG

ATATTCTAATGGACCGAAACTTTCTGTTAATGGTCAAAGATGTGATTATAGGGAG

GATGCAAACGGTGCTATCCATGGTATGTAGAATAGACAACCTGTTCTCAGAGCA

AGACATCTTCTCCCTTCTAAATATCTACAGAATTGGAGATAAAATTGTGGAGAGG

CAGGGAAATTTTTCTTATGACTTGATTAAAATGGTGGAACCGATATGCAACTTGA

AGCTGATGAAATTAGCAAGAGAATCAAGGCCTTTAGTCCCACAATTCCCTCATTT

TGAAAATCATATCAAGACTTCTGTTGATGAAGGGGCAAAAATTGACCGAGGTAT

AAGATTCCTCCATGATCAGATAATGAGTGTGAAAACAGTGGATCTCACACTGGT

GATTTATGGATCGTTCAGACATTGGGGTCATCCTTTTATAGATTATTACACTGGA

CTAGAAAAATTACATTCCCAAGTAACCATGAAGAAAGATATTGATGTGTCATAT

GCAAAAGCACTTGCAAGTGATTTAGCTCGGATTGTTCTATTTCAACAGTTCAATG

ATCATAAAAAGTGGTTCGTGAATGGAGACTTGCTCCCTCATGATCATCCCTTTAA

AAGTCATGTTAAAGAAAATACATGGCCCACAGCTGCTCAAGTTCAAGATTTTGG

AGATAAATGGCATGAACTTCCGCTGATTAAATGTTTTGAAATACCCGACTTACTA

GACCCATCGATAATATACTCTGACAAAAGTCATTCAATGAATAGGTCAGAGGTG

TTGAAACATGTCCGAATGAATCCGAACACTCCTATCCCTAGTAAAAAGGTGTTGC

AGACTATGTTGGACACAAAGGCTACCAATTGGAAAGAATTTCTTAAAGAGATTG

ATGAGAAGGGCTTAGATGATGATGATCTAATTATTGGTCTTAAAGGAAAGGAGA

GGGAACTGAAGTTGGCAGGTAGATTTTTCTCCCTAATGTCTTGGAAATTGCGAGA

ATACTTTGTAATTACCGAATATTTGATAAAGACTCATTTCGTCCCTATGTTTAAAG

GCCTGACAATGGCGGACGATCTAACTGCAGTCATTAAAAAGATGTTAGATTCCTC

ATCCGGCCAAGGATTGAAGTCATATGAGGCAATTTGCATAGCCAATCACATTGA

TTACGAAAAATGGAATAACCACCAAAGGAAGTTATCAAACGGCCCAGTGTTCCG

AGTTATGGGCCAGTTCTTAGGTTATCCATCCTTAATCGAGAGAACTCATGAATTT

TTTGAGAAAAGTCTTATATACTACAATGGAAGACCAGACTTGATGCGTGTTCACA

ACAACACACTGATCAATTCAACCTCCCAACGAGTTTGTTGGCAAGGACAAGAGG

GTGGACTGGAAGGTCTACGGCAAAAAGGATGGACTATCCTCAATCTACTGGTTA

TTCAAAGAGAGGCTAAAATCAGAAACACTGCTGTCAAAGTCTTGGCACAAGGTG

ATAATCAAGTTATTTGCACACAGTATAAAACGAAGAAATCGAGAAACGTTGTAG

AATTACAGGGTGCTCTCAATCAAATGGTTTCTAATAATGAGAAAATTATGACTGC

AATCAAAATAGGGACAGGGAAGTTAGGACTTTTGATAAATGACGATGAGACTAT

GCAATCTGCAGATTACTTGAATTATGGAAAAATACCGATTTTCCGTGGAGTGATT

AGAGGGTTAGAGACCAAGAGATGGTCACGAGTGACTTGTGTCACCAATGACCAA

ATACCCACTTGTGCTAATATAATGAGCTCAGTTTCCACAAATGCTCTCACCGTAG

CTCATTTTGCTGAGAACCCAATCAATGCCATGATACAGTACAATTATTTTGGGAC

ATTTGCTAGACTCTTGTTGATGATGCATGATCCTGCTCTTCGTCAATCATTGTATG

AAGTTCAAGATAAGATACCGGGCTTGCACAGTTCTACTTTCAAATACGCCATGTT

GTATTTGGACCCTTCCATTGGAGGAGTGTCGGGCATGTCTTTGTCCAGGTTTTTG

ATTAGAGCCTTCCCAGATCCCGTAACAGAAAGTCTCTCATTCTGGAGATTCATCC
```

-continued

```
ATGTACATGCTCGAAGTGAGCATCTGAAGGAGATGAGTGCAGTATTTGGAAACC
CCGAGATAGCCAAGTTTCGAATAACTCACATAGACAAGCTAGTAGAAGATCCAA
CCTCTCTGAACATCGCTATGGGAATGAGTCCAGCGAACTTGTTAAAGACTGAGGT
TAAAAAATGCTTAATCGAATCAAGACAAACCATCAGGAACCAGGTGATTAAGGA
TGCAACCATATATTTGTATCATGAAGAGGATCGGCTCAGAAGTTTCTTATGGTCA
ATAAATCCTCTGTTCCCTAGATTTTTAAGTGAATTCAAATCAGGCACTTTTTTGGG
AGTCGCAGACGGGCTCATCAGTCTATTTCAAAATTCTCGTACTATTCGGAACTCC
TTTAAGAAAAAGTATCATAGGGAATTGGATGATTTGATTGTGAGGAGTGAGGTA
TCCTCTTTGACACATTTAGGGAAACTTCATTTGAGAAGGGGATCATGTAAAATGT
GGACATGTTCAGCTACTCATGCTGACACATTAAGATACAAATCCTGGGGCCGTAC
AGTTATTGGGACAACTGTACCCCATCCATTAGAAATGTTGGGTCCACAACATCGA
AAAGAGACTCCTTGTGCACCATGTAACACATCAGGGTTCAATTATGTTTCTGTGC
ATTGTCCAGACGGGATCCATGACGTCTTTAGTTCACGGGACCATTGCCTGCTTA
TCTAGGGTCTAAAACATCTGAATCTACATCTATTTTGCAGCCTTGGGAAAGGGAA
AGCAAAGTCCCACTGATTAAAAGAGCTACACGTCTTAGAGATGCTATCTCTTGGT
TTGTTGAACCCGACTCTAAACTAGCAATGACTATACTTTCTAACATCCACTCTTTA
ACAGGCGAAGAATGGACCAAAAGGCAGCATGGGTTCAAAAGAACAGGGTCTGC
CCTTCATAGGTTTTCGACATCTCGGATGAGCCATGGTGGGTTCGCATCTCAGAGC
ACTGCAGCATTGACCAGGTTGATGGCAACTACAGACACCATGAGGGATCTGGGA
GATCAGAATTTCGACTTTTTATTCCAAGCAACGTTGCTCTATGCTCAAATTACCA
CCACTGTTGCAAGAGACGGATGGATCACCAGTTGTACAGATCATTATCATATTGC
CTGTAAGTCCTGTTTGAGACCCATAGAAGAGATCACCCTGGACTCAAGTATGGA
CTACACGCCCCCAGATGTATCCCATGTGCTGAAGACATGGAGGAATGGGGAAGG
TTCGTGGGACAAGAGATAAAACAGATCTATCCTTTAGAAGGGAATTGGAAGAA
TTTAGCACCTGCTGAGCAATCCTATCAAGTCGGCAGATGTATAGGTTTTCTATAT
GGAGACTTGGCGTATAGAAAATCTACTCATGCCGAGGACAGTTCTCTATTTCCTC
TATCTATACAAGGTCGTATTAGAGGTCGAGGTTTCTTAAAAGGGTTGCTAGACGG
ATTAATGAGAGCAAGTTGCTGCCAAGTAATACACCGGAGAAGTCTGGCTCATTT
GAAGAGGCCGGCCAACGCAGTGTACGGAGGTTTGATTTACTTGATTGATAAATT
GAGTGTATCACCTCCATTCCTTTCTCTTACTAGATCAGGACCTATTAGAGACGAA
TTAGAAACGATTCCCCACAAGATCCCAACCTCCTATCCGACAAGCAACCGTGAT
ATGGGGGTGATTGTCAGAAATTACTTCAAATACCAATGCCGTCTAATTGAAAAG
GGAAAATACAGATCACATTATTCACAATTATGGTTATTCTCAGATGTCTTATCCA
TAGACTTCATTGGACCATTCTCTATTTCCACCACCCTCTTGCAAATCCTATACAAG
CCATTTTTATCTGGGAAAGATAAGAATGAGTTGAGAGAGCTGGCAAATCTTTCTT
CATTGCTAAGATCAGGAGAGGGGTGGGAAGACATACATGTGAAATTCTTCACCA
AGGACATATTATTGTGTCCAGAGGAAATCAGACATGCTTGCAAGTTCGGGATTG
CTAAGGATAATAATAAAGACATGAGCTATCCCCCTTGGGGAAGGGAATCCAGAG
GGACAATTACAACAATCCCTGTTTATTATACGACCACCCCTTACCCAAAGATGCT
AGAGATGCCTCCAAGAATCCAAAATCCCCTGCTGTCCGGAATCAGGTTGGGCCA
ATTACCAACTGGCGCTCATTATAAAATTCGGAGTATATTACATGGAATGGGAATC
```

-continued

```
CATTACAGGGACTTCTTGAGTTGTGGAGACGGCTCCGGAGGGATGACTGCTGCA

TTACTACGAGAAAATGTGCATAGCAGAGGAATATTCAATAGTCTGTTAGAATTAT

CAGGGTCAGTCATGCGAGGCGCCTCTCCTGAGCCCCCCAGTGCCCTAGAAACTTT

AGGAGGAGATAAATCGAGATGTGTAAATGGTGAAACATGTTGGGAATATCCATC

TGACTTATGTGACCCAAGGACTTGGGACTATTTCCTCCGACTCAAAGCAGGCTTG

GGGCTTCAAATTGATTTAATTGTAATGGATATGGAAGTTCGGGATTCTTCTACTA

GCCTGAAAATTGAGACGAATGTTAGAAATTATGTGCACCGGATTTTGGATGAGC

AAGGAGTTTTAATCTACAAGACTTATGGAACATATATTTGTGAGAGCGAAAAGA

ATGCAGTAACAATCCTTGGTCCCATGTTCAAGACGGTCGACTTAGTTCAAACAGA

ATTTAGTAGTTCTCAAACGTCTGAAGTATATATGGTATGTAAAGGTTTGAAGAAA

TTAATCGATGAACCCAATCCCGATTGGTCTTCCATCAATGAATCCTGGAAAAACC

TGTACGCATTCCAGTCATCAGAACAGGAATTTGCCAGAGCAAAGAAGGTTAGTA

CATACTTTACCTTGACAGGTATTCCCTCCCAATTCATTCCTGATCCTTTTGTAAAC

ATTGAGACTATGCTACAAATATTCGGAGTACCCACGGGTGTGTCTCATGCGGCTG

CCTTAAAATCATCTGATAGACCTGCAGATTTATTGACCATTAGCCTTTTTTATATG

GCGATTATATCGTATTATAACATCAATCATATCAGAGTAGGACCGATACCTCCGA

ACCCCCCATCAGATGGAATTGCACAAAATGTGGGGATCGCTATAACTGGTATAA

GCTTTTGGCTGAGTTTGATGGAGAAAGACATTCCACTATATCAACAGTGTTTAGC

AGTTATCCAGCAATCATTCCCGATTAGGTGGGAGGCTGTTTCAGTAAAAGGAGG

ATACAAGCAGAAGTGGAGTACTAGAGGTGATGGGCTCCCAAAAGATACCCGAAC

TTCAGACTCCTTGGCCCCAATCGGGAACTGGATCAGATCTCTGGAATTGGTCCGA

AACCAAGTTCGTCTAAATCCATTCAATGAGATCTTGTTCAATCAGCTATGTCGTA

CAGTGGATAATCATTTGAAATGGTCAAATTTGCGAAGAAACACAGGAATGATTG

AATGGATCAATAGACGAATTTCAAAAGAAGACCGGTCTATACTGATGTTGAAGA

GTGACCTACACGAGGAAAACTCTTGGAGAGATTAAAAAATCATGAGGAGACTCC

AAACTTTAAGTATGAAAAAAACTTTGATCCTTAAGACCCTCTTGTGGTTTTATTT

TTTATCTGGTTTTGTGGTCTTCGT.
```

In another aspect, the invention provides an isolated nucleic acid encoding a recombinant fusion protein comprising (a) a glycoprotein (G) of a virus or a portion thereof, and (b) a SARS-CoV-2 spike protein (S) or a portion thereof. In some embodiments, the virus is a rhabdovirus. In some embodiments, the virus is a rabies virus or a vesicular stomatitis virus (VSV). In a particular embodiment, the virus is a rabies virus.

In one embodiment, the portion of the SARS-CoV-2 spike protein (S) is a receptor binding site of the SARS-CoV-2 spike protein (S). In another embodiment, the portion of the SARS-CoV-2 spike protein (S) is the S1 domain. In another embodiment, the portion of the SARS-CoV-2 spike protein (S) is the N-terminal 750 amino acids of the SARS-CoV-2 spike protein (S).

In some embodiments, the glycoprotein (G) comprises a mutation substituting arginine with glutamic acid at position 333. In some embodiments, the portion of glycoprotein (G) comprises an ectodomain, a cytoplasmic domain, and a transmembrane domain. In some embodiments, the portion of the glycoprotein (G) comprises 31 amino acids of the ectodomain. In some embodiments, the glycoprotein (G) comprises 31 amino acids of the ectodomain and the full-length cytoplasmic domain.

In some embodiments, the sequence encoding the SARS-CoV-2 spike protein (S) or portion thereof is codon-optimized for expression in a human cell. In some embodiments, the sequence encoding the the SARS-CoV-2 spike protein (S) or portion thereof fused to a glycoprotein (G) or portion thereof is codon-optimized for expression in a human cell.

In some embodiments, the recombinant fusion protein comprises the sequence of the S1 domain of the SARS-CoV-2 spike protein (S) fused to a rabies glycoprotein (G) or portion thereof, shown as element "WuS1-RABVG" in "BNSP333-COVID19-S1-RVG" in FIG. 18.

In some embodiments, the recombinant fusion protein comprises the sequence of the S1 domain of the SARS-CoV-2 spike protein (S) fused to a VSV glycoprotein (G) or portion thereof, shown as element "WuhanS-coVSV-G-tail" in "VSV-COVID19-S1-VSVG" in FIG. 17.

In other aspects, the present invention provides nucleic acid molecules having double-stranded, single-stranded, and/or combinations of double- and single-stranded regions as well as full or partial complements of any of the sequences of the present disclosure.

In some aspects, the present disclosure provides the following sequences, or complements thereof:

| SEQ ID NO: | Sequence |
|---|---|
| 34 | ATGTGCT...GCGATTAAT...TA |
| 35 | TGTGCTG...ATTAAGTGT...AAG |
| 36 | GTTTTCCCAGTCACGAC |
| 37 | AAAcgacgGcCagtgGaattCCGTTAATACGACTCACTATAGGAAA...GG |
| 38 | ggtTGCGCGCCGTT...GACTCACTATAGGggtT...AGG |
| 39 | gaGagCgcgcatCGaaaTTAATACGACTCACTATAga...TA |
| 40 | GagacGTaCGCGtaaT...ACGACTCACTATAGGGGaga...GGG |
| 41 | TAATAC...ATAGGGTAAT...GGG |
| 42 | gtGtcgtctcgCgcgtgcggCcgcGCTAGCCAGCTTGGGTCTCCCT |
| 43 | gtGtCGTctCt...GGGTAAGGATAgtGtCGTctCtG...GGGTAAGGATA |
| 44 | gtGtgGTctCtG...AGGATAGTTCA<br>gtGtgGTctCtGGTC...GGTAAGGATAGTTCA |
| 45 | gAgaaGGTTTgAgaacgcgTctcGGTACGCCGGGTTT |
| 46 | tgTCaCGGATATCCATCCTGCTCTTGTCCtgTCC |
| 47 | cAgtccaccGgtgTCaCGGATATCCCTAATCCTGCT |
| 48 | GGATTAGGGATATCCGAGATGGCCACACTT |
| 49 | AAGTGTGGCCATCTCGGATATCCCTAATCCTGCTCT |
| 50 | TGGCCACACTTTTAAGGAGCT |
| 51 | CCACCGGATCCTGATGTAAT |
| 52 | CTGGCCTTACCTTCGCATCA |
| 53 | AGGATTAGCCAGTTTTATCCTGACT |
| 54 | AGAAGCCAG...GAGCTACA |
| 55 | gt...AgtgtGcgatcgcgtGCgagaGGCCAGAACAACA |
| 56 | gTGtacGcgtTCc...GCCAGAACAACA<br>gTGtacGcgtTCcTgacG...gagaGGCCAGAACAACA |
| 57 | GTGtGcGgccgctaTaGcgTAAGTTTTTTATAACAATGGTGtGcGgccgctaTaGcg<br>atcTCCTAAGTTTTTTATAACAATG |
| 58 | GtgTGcgGccgTTATAACAATGGtgTGcgGccgctataaCgcgtTTCCTAAGTTTTT<br>TATAACAATG |
| 59 | gtGtgcgGccgctaTaAcGTAAGTTTTTTATAACAATGgtGtgcgGccgc-<br>taTaAcGcG<br>tTTCCTAAGTTTTTTATAACAATG |
| 60 | GACAACCCAGGACAGGAGC |
| 61 | ACTCTCAATGTTCCTCCGCC |
| 62 | GCCATTCCTGGACTTGGGAA |
| 63 | gtgtgcGGccgcAGGTTGTACTAGGTGGGTC |
| 64 | AGTGATTGCCTCCCAAGGTC |
| 65 | TGAG...TTCGTGAGC...TTTCG |
| 66 | tcTCTGTAGACCGTAGTGCCCA |
| 67 | CAACCCCGACAACCAGAG |
| 68 | CACCCCTAAAGGAGACACCG |

| SEQ ID NO: | Sequence |
|---|---|
| 69 | gtgtgAa...TCTCAAgtgtgAagacttcatg...CATCATGGGTCTCAA |
| 70 | GAGCGAGC...AAACTACT |
| 71 | CCCAAGTATGTTGCAACCCA |
| 72 | TCGAGCACTAGCATAGTCTACA |
| 73 | gTGTtctaGATCAGAGCGACCTTACATAGGA |
| 74 | GtgtcgtctctATGTCACCACAACGAGACCGGtg...CG |
| 75 | CTTGATCGGGTTGCTAGCCA |
| 76 | CCAGGGAATGTATGGGGGAA |
| 77 | ATGCTTCCAACAGGCGTGTA |
| 78 | GTTGCCTATAAAGGGGGTCCC |
| 79 | GGGGTCC...AATTACAGG...CA |
| 80 | gtgttCCATCTTgtgttCtagaCTATATTGGTTCCATCTT |
| 81 | gcagAgaCgcgtctTTTTTTATAACAATGgcagAgaCgcgtcTTTTATAACAATG |
| 82 | gcTataaCgcgtatcTTTTTTATAACAATGgcTataaCgcgtaTTTTATAACAATG |
| 83 | TATCACTCTGTGTTTTATAACAATGTATCACTCTGTTTTATAACAATG |
| 84 | GTATGCTCGAGTCCCTCACG |
| 85 | TCTCTCGTGACCTTGTTGCT |
| 86 | ACGGCTGCTGAAAATGTTAGG |
| 87 | AGTTCA...AGCCTAGTTC...GCCT |
| 88 | AGGCTTGAGACCTCTGTCCT |
| 89 | ATGAAACAAGGGCAGCATGC |
| 90 | AGAAGAGGACGAGGGACTGG |
| 91 | CGGGTT...ATGATCGGG...TGAT |
| 92 | TTGTTGCGTGATCCCGATGA |
| 93 | TCAATGCTCTAAGCCACCCA |
| 94 | TCGGCAGCAACAACATCTCA |
| 95 | CCCTACCTCTAGTGTGGGGT |
| 96 | ACGGACCTAAGCTGTGCAAA |
| 97 | CTcgcgAt...ATCCTGCC<br>CTcgcgAtcGcCTAATTG...CGGAACCCTAATCCTGCC |
| 98 | GCCCTAGGTGGTTAGGCATTA |
| 99 | CctTaCCCAaCTTTGTtTGGTGGCCGGCATAGTCCCAGCCT |
| 100 | TCAGCAAAAAACCCCTCA |
| 101 | GgttGcgCGCATCCGGATATAGTTCCTCCTTTGgTT |
| 102 | gaccatgattAcGCcaGCGGCCGCATCCGGATAT |
| 103 | AGCGGATAACAATTTCACACAGGA |
| 104 | TATTACCGCCTTTGAGTGAGCTGA |

| SEQ ID NO: | Sequence |
|---|---|
| 105 | CTTTTTACGGTTCCTGGCCT |
| 106 | ACATTTCCCCGAAAAGTGC |

Pharmaceutical Compositions and Formulations.

The vaccine of the invention may be formulated as a pharmaceutical composition. In some embodiments, the vaccine contains a live virus. In some embodiments, the vaccine contains deactivated viral particles. In some embodiments, the virus is a recombinant virus encoded by any one of the nucleic acid constructs as described herein.

Such a pharmaceutical composition may be in a form suitable for administration to a subject (i.e. mammal), or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In one embodiment, the pharmaceutical compositions useful for practicing the method of the invention may comprise an adjuvant. Non-limiting examples of suitable adjuvants are Freund's complete adjuvant, Freund's incomplete adjuvant, Quil A, Detox, ISCOMs or squalene. In one embodiment, the adjuvant is an ADVAX™ adjuvant. In another embodiment, the adjuvant comprises Sepivac SWE™ adjuvant. In another embodiment, the adjuvant is monophosphoryl Lipid A (MPLA) (PHAD®) in squalene. In one embodiment, the adjuvant is MPLA 3D(6-acyl) PHAD® in 2% squalene. In one embodiment, the adjuvant increases or induces a Th-1 type immune response. The pharmaceutical composition or vaccine composition can comprise any one or more of the adjuvants described herein.

In some embodiments, the adjuvant comprises inulin e.g., delta inulin (e.g., delta inulin manufactured under current Good Manufacturing Practices is referred to in the art as Advax).

In one embodiment, the adjuvant comprises a delta inulin polysaccharide formulated with the TLR9 agonist (e.g., CpG oligodeoxynucleotides (CpG ODN)). In some embodiments, the adjuvant is Advax-SM™ (Vaxine Pty Ltd, Bedford Park, Australia).

In some embodiments, the adjuvant comprises a mixture of an oil component and a surfactant component.

In one embodiment, the composition may be an oil/surfactant dispersion or an oil/surfactant solution.

In other embodiments, the adjuvant comprises an emulsion e.g., an oil in water (o/w) emulsion.

In one embodiment, the composition includes an oil component which is formed from one or more oil(s).

In another embodiment, the oil(s) and the surfactant(s) in the composition are metabolizable (biodegradable) and biocompatible.

In some embodiments, the composition further comprises component(s) in addition to the oil and surfactant components.

In other embodiments, the proportions of the oil component and the surfactant component can vary. In some embodiments, an oil-in-water emulsion comprises oil droplets (e.g., submicron oil droplets as determined by e.g., dynamic light scattering (DLS)) when mixed with a volume of an aqueous material (e.g., water). In other embodiments, the oil droplets have an average diameter of less than about 300 nm when mixed with a volume of an aqueous material (e.g., water), illustratively, about 50 to about 290 nm, about 60 to about 280 nm, about 70 to about 270 nm, about 80 to about 260 nm, about 90 to about 250 nm, about 100 to about 240 nm, about 110 to about 230 nm, about 120 to about 220 nm, about 130 to about 210 nm, and about 140 to about 200 nm. In some embodiments, the oil droplets have an average diameter of about 160 nm (e.g., 160±10 nm), about 155 nm (e.g., 155±10 nm), about 142 nm (e.g., 142±5 nm), about 120 nm (e.g., 120±40 nm), or about 100 nm (e.g., 10±20 nm). In some embodiments, the oil droplets have an average diameter of about 142 nm (e.g., 142±5 nm).

In one embodiment, the total oil component is about 50% to about 90% by volume of the adjuvant composition. In another embodiment, the total oil component is no more than about 50%, no more than about 55%, no more than about 60%, no more than about 65%, no more than about 70%, no more than about 75%, no more than about 80%, no more than about 85%, or no more than about 90% by volume of the adjuvant composition.

In some embodiments, the oil comprises a terpenoid (e.g., a branched, unsaturated terpenoid).

In one embodiment, the oil comprises squalene.

In another embodiment, the oil comprises a saturated analog to squalene. In one embodiment, saturated analog to squalene is squalane.

In one embodiment, the adjuvant comprises a squalene oil in water emulsion. In another embodiment, the squalene in water emulsion comprises one or more non-ionic surfactants and/or other oils and/or stabilizers.

In other embodiments, the adjuvant comprises about 7 mgs to about 13 mgs, about 8 mgs to about 12 mgs, about 8 mgs to about 11 mgs, about 9 mgs to about 10 mgs, about 9.5 mgs to about 9.75 mgs of squalene (e.g., (mgs of squalene per 0.25 ml) or in 0.5 ml vaccine dose)). In one embodiment, the adjuvant comprises about 8.6 mgs, 9.75 mgs, 10.75 mgs, or 12.5 mgs of squalene.

In another embodiment, the adjuvant is a squalene in water emulsion comprising about 7 to about 13 mgs of squalene (e.g., (mgs of squalene per 0.25 ml) or in 0.5 ml vaccine dose)), illustratively, about 7 to about 13 mgs, about 8 to about 12 mgs, about 8 to about 11 mgs, about 9 to about 10 mgs, about 9.5 to about 9.75 mgs of squalene (e.g., (mgs per 0.25 ml) or in 0.5 ml vaccine dose)). In one embodiment, the adjuvant is a squalene in water emulsion comprising about 9.75 mgs of squalene (e.g., (mgs of squalene per 0.25 ml) or in 0.5 ml vaccine dose)).

In other embodiments, the oil component comprises one or more tocopherols (e.g., α, β, γ, δ, ε, ζ tocopherol). In one embodiment, the tocopherol is D-α-tocopherol and/or DL-α-tocopherol. In another embodiment, the α-tocopherol is DL-α-tocopherol. In other embodiments, the oil component of the adjuvant is an oil combination comprising squalene and a tocopherol (e.g. DL-α-tocopherol).

In some embodiments, the surfactant component comprises an ionic, a non-ionic, or a zwitterionic surfactant, and any combination thereof. In one embodiment, the surfactant component comprises only non-ionic surfactant(s).

Examples of surfactants include, but are not limited to, the polyoxyethylene sorbitan esters surfactants (e.g., Tweens, polysorbates, such as, e.g., polysorbate 80 (e.g., Tween™ 80), copolymers of ethylene oxide, propylene oxide, butylene oxide), sorbitan esters (e.g., sorbitan trioleate (e.g., Span™ 85), sorbitan monolaurate), and polyoxyethylene lauryl ether (e.g., Emulgen 104P), octoxynols (e.g., Triton X-100, IGEPAL CA-630/NP-40), phospholipids (e.g., lecithin), and Brij surfactants (e.g., polyoxyl 4 lauryl ether (Brij 30)).

In some embodiments, the surfactant in the composition (% by volume of the oil/surfactant composition) is no more than about: 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, or 10%.

In one embodiment, the surfactant component consists of a mixture of polysorbate 80 (e.g., Tween™ 80) and sorbitan trioleate (e.g., Span™ 85). In another embodiment, the surfactant component consists of a mixture of polysorbate 80 (e.g., Tween™ 80) and sorbitan trioleate (e.g., Span™ 85) in a volume ratio having more sorbitan trioleate (e.g., Span™ 85) than polysorbate 80 (e.g., Tween™ 80). In some embodiments, the surfactant component consists of a mixture of polysorbate 80 (e.g., Tween™ 80) and sorbitan trioleate (e.g., Span™ 85) in a volume ratio that achieves a HLB of about 8. In some embodiments, the surfactant component consists of a mixture (e.g., (mgs of squalene per 0.25 ml) or in 0.5 ml vaccine dose)) of about 1.175 mgs polysorbate 80 (e.g., Tween™ 80) and about 1.175 mgs sorbitan trioleate (e.g., Span™ 85).

In other embodiments, the aqueous component (e.g., water) further comprises one or more components e.g. solutes/salts/buffers. In one embodiment, the salts (e.g., sodium salts) form a pH buffer (e.g. citrate, phosphate). In another embodiments, one or more buffers include, but are not limited to, a citrate buffer, phosphate buffer (e.g., phosphate buffered saline, ammonium phosphate), a Tris buffer, a borate buffer, a succinate buffer, or a histidine buffer. In some embodiment, a buffered aqueous component comprises about 1 to about 20 mM of total buffer.

In other embodiments, the pH of the aqueous component is buffered at about pH 5.5 to about pH 8.0, illustratively, about pH 6.1 to about pH 7.9, about pH 6.2 to about pH 7.8, about pH 6.3 to about pH 7.7, about pH 6.4 to about pH 7.6, about pH 6.5 to about pH 7.5, about pH 6.6 to about pH 7.4, about pH 6.7 to about pH 7.3, about pH 6.8 to about pH 7.2, and about pH 6.9 to about pH 7.1. In one embodiment, the pH of the aqueous component is buffered at about pH: 5.7, 6.0, 6.5, 6.8, or 7.2. In another embodiment, the pH of the aqueous component is buffered at about pH 6.0 to about pH 6.5. In other embodiments, the buffer is 10 mM citrate buffer with a pH of about 6.5.

In other embodiments, the adjuvant is a squalene in water emulsion comprising (e.g., (mgs of squalene per 0.25 ml) or in 0.5 ml vaccine dose)) about 9.75 mgs squalene, 1.175 mgs polysorbate 80 (e.g., Tween™ 80), 1.175 mgs sorbitan trioleate (e.g., Span™ 85), citrate buffer, and a pH of about 6.5.

In some embodiments, an adjuvant of the present disclosure is co-formulated or co-administered with the vaccine.

In other embodiments, an adjuvant of the present disclosure is not co-formulated or co-administered with the vaccine.

Pharmaceutical compositions that are useful in the methods of the invention may be suitably developed for inhalation, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

The composition of the invention may comprise a preservative from about 0.005% to 2.0% by total weight of the composition. The preservative is used to prevent spoilage in the case of exposure to contaminants in the environment.

Administration/Dosing

The regimen of administration of the compositions of the present invention may affect what constitutes an effective amount. For example, the vaccines, polypeptides, and/or the nucleic acids of the invention may be administered to the subject (i.e. mammal) in a single dose, in several divided dosages, as well as staggered dosages may be administered daily or sequentially, or the dose may be continuously infused, or may be a bolus injection. Further, the dosages may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to treat the disease in the subject. An effective amount of the composition necessary to achieve the intended result will vary and will depend on factors such as the disease to be treated or prevented, the age, sex, weight, condition, general health and prior medical history of the subject being treated, and like factors well-known in the medical arts. In particular embodiments, it is especially advantageous to formulate the composition in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the composition and the heterologous protein to be expressed, and the particular therapeutic effect to be achieved.

In some embodiments, the vaccine administered may be in an amount that will depend e.g., on the subject to be treated, the capacity of the subject's immune system to develop the desired immune response, and/or the degree of protection desired.

In other embodiments, the administration of the vaccines of the present invention can be in accordance with any suitable vaccination schedule, e.g., day 0, one month, four months, and twelve months from day 0. In other embodiments, the vaccines described herein may also be given in a single dose schedule, or a multiple dose schedule in which a primary course of vaccination may be with 1-10 separate doses, followed by other doses given at subsequent time intervals required to maintain and/or reinforce the immune response, for example, at 1-4 months for a second dose, and if needed, a subsequent dose(s) after several months. In some embodiment, other examples of suitable immunization schedules include, but are not limited to: (i) 0, 1 month and 6 months, (ii) 0, 7 days and 1 month, (iii) 0 and 1 month, (iv) 0 and 6 months, (v) 0, 1 month and 2 months, or other schedules sufficient to elicit the desired immune responses expected to confer protective immunity, and/or reduce disease symptoms, or reduce severity of disease.

In one embodiment, the administration of the vaccines of the present can be in accordance with any suitable vaccination schedule and/or dosage(s) effective to produce an antigen-specific immune response. In some embodiments, an antigen-specific immune response comprises a B and/or T cell response. In other embodiments, the antigen-specific immune response comprises administration of a single dose (no booster dose). In some embodiments, a second (booster) dose of the vaccine may be administered. In other embodiments, additional doses may be administered.

In some embodiments, the administration of the vaccines of the present can be in accordance with any suitable vaccination schedule and/or dosage(s) effective such that the subjects exhibit a seroconversion rate of at least 60%, at least 70%, at least 80%, at least 85%, at least 90%, or at least 95% following the first dose or the second (booster) dose of the vaccine.

In other embodiments, the administration of the vaccines of the present can be in accordance with any suitable vaccination schedule and/or dosage(s) effective to produce an antigen-specific immune response in the subject, wherein the anti-antigen antibody titer produced in the subject is increased by at least 1 log relative to a control.

In some embodiments, the control is an anti-antigen antibody titer produced in a subject who has not been administered a vaccine of the present disclosure. In other embodiments, the control is a titer produced in a subject that has been administered a live attenuated or inactivated vaccine; a recombinant or purified protein vaccine; or a virus-like particle vaccine.

In one embodiment, the titer produced in the subject is increased by 1-3 log relative to the control. In another embodiment, the titer produced in a subject is increased at least 2 times relative to the control. In other embodiments, the titer produced in the subject is increased at least 3, 4, 5, 10 or more times relative to the control. In one embodiment, the titer produced in the subject is increased at least 10 times relative to a control. In another embodiment, the titer produced in the subject is increased 2-10 times relative to a control.

In some embodiments, the vaccine of the present disclosure is administered to a subject in an effective amount (e.g., an amount effective to induce an immune response). In some embodiments, the effective amount is a dose equivalent to an at least 2-fold, at least 4-fold, at least 10-fold, at least 100-fold, at least 1000-fold reduction in the standard of care dose of a recombinant protein vaccine, wherein the anti-antigen antibody titer produced in the subject is equivalent to an anti-antigen antibody titer produced in a control subject administered the standard of care dose of a recombinant protein vaccine, a purified protein vaccine, a live attenuated vaccine, an inactivated vaccine, or a VLP vaccine. In some embodiments, the effective amount is a dose equivalent to 2-1000-fold reduction in the standard of care dose of a recombinant protein vaccine, a purified protein vaccine, a live attenuated vaccine, an inactivated vaccine, or a VLP vaccine.

In other embodiments, the effective amount of the vaccine administered comprises a total dose of about 0.1 µg to about 1000 µg of the vaccine or active ingredient (e.g., VLP, virion, viral vector, antigen, or nucleic acid molecule), illustratively, about 1 µg to about 900 µg, about 5 µg to about 700 µg, about 10 µg to about 500 µg, about 15 µg to about 300 µg, about 20 µg to about 200 µg, and about 25 µg to about 100 µg, In some embodiments, the effective amount is a total dose of about 25 µg, about 50 µg, or about 100 µg. In other embodiments, the effective amount is a total dose of not less than (NLT) about 1 µg, about 5 µg, about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, or about 100 µg. In other embodiments, the effective amount is a total dose of about 0.1 µg to about 10 µg.

In some embodiments, doses of the vaccine are based on quantification of DNase-resistant particles (DRPs). In one embodiment, DRPs are equivalent to encapsidated vector genomes. In some embodiments, the subject receives at least one dose (e.g., a first dose at time zero) of the vaccine of about $10^5$ to $10^{20}$ about DRPs, illustratively, about $10^6$ to $10^{18}$, about $10^7$ to $10^{17}$, about $10^8$ to $10^{16}$, about $10^9$ to $10^{15}$, about $10^{10}$ to $10^{14}$, and about $10^{11}$ to $10^{13}$ DRPs. In other embodiments, the subject receives at least one dose (e.g., a first does at time zero) of at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, at least about $10^{16}$, at least about $10^{17}$, at least about $10^{18}$, at least about $10^{19}$, or at least about $10^{20}$ DRPs.

In some embodiments, the effective amount is a dose administered to the subject a total of one, two, three, four, five, or more times.

In some embodiments, the efficacy or effectiveness of a vaccine of the present disclosure is equal to or greater than about 60%. Vaccine efficacy or effectiveness may be assessed using e.g., standard analyses and protocols known in the art. In one embodiment, the efficacy or effectiveness of the vaccine is at least about 60%, at least about 65%, at least about 70%, at least about 75%, at least about 80%, at least about 85%, or at least about 90%.

In some embodiments, the vaccine immunizes the subject against a coronavirus (e.g., SARS-CoV-2 virus) for up to 6 months, 1 year or 2 years. In some embodiments, the vaccine immunizes the subject against a coronavirus (e.g., SARS-CoV-2 virus) for at least about 6 months, at least about 1 year, at least about 2 years, at least about 3 years, at least about 4 years, or about 5 years to about 10 years, or more.

Routes of Administration

One skilled in the art will recognize that although more than one route can be used for administration, a particular route can provide a more immediate and more effective reaction than another route. Routes of administration of any of the compositions of the invention include inhalation, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, electroporation and topical administration.

Kits

In some embodiments a kit is provided for treating, preventing, or ameliorating an a given disease, disorder or condition, or a symptom thereof, as described herein wherein the kit comprises: a) a compound or compositions as described herein; and optionally b) an additional agent or therapy as described herein. The kit can further include instructions or a label for using the kit to treat, prevent, or ameliorate the disease, disorder or condition. In yet other embodiments, the invention extends to kits assays for a given disease, disorder or condition, or a symptom thereof, as described herein. Such kits may, for example, contain the reagents from PCR or other nucleic acid hybridization technology (microarrays) or reagents for immunologically based detection techniques (e.g., ELISpot, ELISA).

Methods of Treatment

In one aspect, the invention includes a method of generating an immune response against a SARS-CoV-2 virus in a subject in need thereof. In another aspect, a method of vaccinating a subject against a SARS-CoV-2 virus is provided. In yet another aspect, a method of providing immunity against a SARS-CoV-2 virus in a subject is provided. In still another aspect, a method of treating and/or preventing a disease or disorder associated with SARS-CoV-2 virus in a subject in need thereof. In some embodiments, the method comprises administering to the subject an effective amount of a recombinant virus as described herein. In some embodiments, the method comprises administering to the subject an effective amount of a vaccine described herein.

In some embodiments, the disease or disorder associated with the SARS-CoV-2 virus is a respiratory disease. In some embodiments, the disease or disorder associated with the SARS-CoV-2 virus is coronavirus disease. In some embodiments, the disease or disorder associated with the SARS-CoV-2 virus is COVID-19.

Pharmaceutical compositions comprising the vaccine of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The administration of the vaccine of the invention may be carried out in any convenient manner known to those of skill in the art. The vaccine of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i. v.) injection, or intraperitoneally.

Subjects to which administration of the pharmaceutical compositions of the invention is contemplated include, but are not limited to, humans and other primates, mammals, and birds, including commercially relevant mammals and birds such as cattle, pigs, horses, sheep, chicken, ducks, cats, dogs, and ferrets.

In some embodiments, the subject is a domesticated animal. In some embodiments, the subject is a domestic pet. In some embodiments, the animal is a captive animal, e.g., an animal maintained in an exhibit or in a zoological park. In some embodiments, the animal is livestock. In some embodiments, the subject is an animal susceptible to infection with SARS-CoV-2 and can be a reservoir for the SARS-CoV-2 virus. In some embodiments, the subject is a feline. In some other embodiments, the subject is a canine. In some embodiments, the subject is a member of the Mustelidae family, such as a weasel, polecat, stoat, marten, mink, badger, otter, or ferret. In some embodiments, the subject is a cat. In some other embodiments, the subject is a dog. In some embodiments, the subject is a ferret.

In one aspect, a method of preventing SARS-CoV-2 infection or providing immunity to SARS-CoV-2 in a subject is provided, the method comprising administering to a subject a SARS-CoV-2 vaccine described herein, wherein the subject is a domestic pet selected from a cat, a dog, and a ferret. In particular, felines and ferrets have been identified as a potential host for SARS-CoV-2 (J. Shi et al., *Science* 10.1126/science.abb7015 (2020)). Cats are one of the most favored pets of the USA's citizens. In the United States, one in three households owns a pet cat, with an average of 2.2 cats per cat-owning household. However, pet cats are only a part of the total cat population in the country, which is estimated to be around 76.5 million.

Currently, rabies vaccination is recommended for cats, dogs, and ferrets. CDC guidelines recommend that all dogs, cats, and ferrets should be vaccinated and revaccinated against rabies according to product label directions (www.cdc.gov/rabies/specific_groups/veterinarians/vaccination.html). If a previously vaccinated animal is overdue for a booster, it should be revaccinated. Immediately following the booster, the animal is considered currently vaccinated and should be placed on a vaccination schedule according to the labeled duration of the vaccine used.

The existing RABV vaccine for cats, dogs, or ferrets can be replaced with a rabies virus-based SARS-CoV-2 vaccine to induce protection from both diseases. Thus, in one aspect, a method of providing immunity to rabies and a SARS-CoV-2 associated disease in a subject is provided, wherein the subject is a cat, dog, or ferret. The method includes the step of administering to the subject a vaccine comprising a rabies virus-based SARS-CoV-2 vaccine. In another aspect, a vaccine for cats, dogs, or ferrets is provided, the vaccine comprising a rabies virus-based SARS-CoV-2 vaccine. In some embodiments, the vaccine comprises a recombinant rabies virus comprising a SARS-CoV-2 spike protein (S) or a portion thereof. In some embodiments, the vaccine comprises a recombinant rabies virus comprising a fusion of (a) a glycoprotein (G) of a virus or a portion thereof, and (b) a SARS-CoV-2 spike protein (S) or a portion thereof. In some embodiments, the vaccine comprises an inactivated virus. In particular embodiments, the vaccine comprises an adjuvant. In some embodiments, the vaccine is formulated for administration to a cat. In some other embodiments, the vaccine is formulated for administration to a dog. In still other embodiments, the vaccine is formulated for administration to a ferret.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Green, M. R. & Sambrook, J., Cold Spring Harbor Laboratory Press, 2012); "Oligonucleotide Synthesis, a practical approach" (Paselk R. A., edited by Gait, M. J., IRL Press, Oxford, 1984); "Culture of Animal Cells: A Manual of Basic Technique and Specialized Applications, Sixth Edition" (Freshney, R. I., John Wiley & Sons, Inc., 2010); "Methods in Enzymology" (Vol. 152, Guide to Molecular Cloning Techniques, Berger and Kimmel, Eds., San Diego: Academic Press, Inc., 1987); "Handbook of Experimental Immunology" (Herzenberg L. A., Weir, D. M., Blackwell, C., Wiley, 1997); "Gene Transfer Vectors for Mammalian Cells" (Miller and Calos, eds., Cold Spring Harbor Laboratory, Cold Spring Harbor, 1987); "Short Protocols in Molecular Biology" (Ausubel, F. M., et al., ed., John Wiley & Sons, 2002); "Polymerase Chain Reaction: Principles, Applications and Troubleshooting" (Babar, M. E., publisher VDM Verlag Dr. Müller, 2011); "Current Protocols in Immunology" (Colligan, J. E., et al., ed., Greene Pub. Associates and Wiley-Interscience, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Example 1

RABV, VSV, and MV Expressing Covid S or Covid-S1

The materials and methods employed in Examples 1-5 are now described.
Generation of RABV-, VSV-, and MV-Based Vaccines Against COVID-19
The SARS-CoV-2 spike protein (S) was used in generating the vaccines against COVID-19 described herein. SARS-CoV-2 causes Convid-19. The S1 domain (receptor binding site of the S protein) was incorporated into the Genome of rabies virus (RABV) and vesicular stomatitis virus (VSV). For both constructs part of their native G protein was used to promote the incorporation of the S1 domain. The full-length SARS-CoV-2 S was found to interfere with viral growth (VSV or RABV G) making it almost impossible to produce the vaccine; thus the S1 domain was used instead.

Three measles virus (MV)-based vaccine expressing full-length SARS-CoV-2 spike protein (S) were also prepared. These three viruses express the SARS-CoV-2 spike protein (S) from position 2, 3, or 6 of the genome. Previous research indicates that for measles virus the position a foreign gene is expressed is important for MV replication and immunogenicity of the trans-gene. However this depends on the antigen, so three different viruses were prepared.

Testing of RABV-, VSV-, and MV-Based Vaccines Against COVID-19 in Animals
In the next phase, the vaccines are tested in animals. The receptor for both viruses is believed to be ACE 2. The model that will be used is a hamster or mice (transgenic expressing ACE2 or wildtype infected with an Adenovirus expressing ACE2).
Both live and killed viruses are tested. After immunization mice or hamster are challenged with the SARS-CoV-2 (Convid-19).
Immunological Parameters of the 2019-nCoV Vaccine.
The parameters of the induced humoral and cellular immune responses will be studied after i.m. inoculation of mice (including 2019-nCoV challenge), and non-human primate (NHP) (immunogenicity). ELISA and virus neutralization assays (VNA) will be utilized to analyze the humoral immune response. These assays are developed for mice and NHP and, based on the limited space, only briefly described below. Previous experience will be used in the development of such assays especially in the field of coronaviruses
ELISA Assay for Detection of 2019-nCoV S1 and Vector RABV G-Specific Humoral Responses.
Preparation of highly purified antigens against 2019-nCoV S1 or RABV G. Purification of the HA-tagged soluble protein from the supernatant of transfected 293T cells is carried out as described previously for MERS-CoV (17). Purified proteins can be prepared in the mg range sufficient for large numbers of assay plates. Approximately 10-20 mg of purified RABV G is produced on a regular basis in the Schnell laboratory.

To determine antibody responses to the 2019-nCoV S or RABV G, an indirect ELISA will be developed utilizing purified S1 or G protein (26) and unpublished. Sera from vaccinated mice or NHP will be used at different dilutions to determine the EC50 over time. Serum IgM and IgG antibodies (total IgM, IgG, IgG1, IgG2 for NHP, IgG2c and IgG1 for B6) to each vaccine antigen will be measured by a qualified ELISA that is well established in the Thomas Jefferson University (TJU) laboratories. Prior to performing the ELISA assays, we will qualify the assay for each vaccine antigen. Our ELISA platform will be standardized to measure serum IgG specific for the vaccine antigens by characterizing assay variability, determining the limit of quantitation, defining the positive and negative quality control ranges, and defining assay acceptance criteria. TJU has substantial experience in qualifying and performing ELISA assays using this platform and plan to use it for future clinical studies as well. Assays will be transferred for the human clinical samples to a contractor via IQVIA.

Virus Neutralization assays (VNA) for RABV are well established in the TJU laboratory (12, 27, 28) for mouse, monkey, and human sera. Use of an internal WHO standard, allows determining the international unit (I.U.) achieved by the immunization. The presence of 0.5 I.U or more in the sera is considered a correlate of protection from rabies. VNA for MERS-CoV are established at the University of Maryland in the Frieman lab. Dr. Frieman has a virus sample from CDC from the Washington St patient. He is also recreating multiple strains using his infectious clone and synthesizing full genomes.
Cellular Responses
Most likely, humoral responses are the key for protection based on previous studies of coronaviruses but as a research part, frequencies and cytokine expression profiles of vaccine antigen-specific T cells will be measured in splenocytes or cryopreserved NHP PBMCs using a qualified 13-color ICS assay. In order to assess potential for durable antibody responses, antigen specific IgG+ ELISPOT analysis will be performed to detect antibody-secreting plasma cells in the bone marrow 28 days post-boost immunization.

The results of the experiments are now described.

RABV, VSV, and MV Expressing Covid S or Covid-S1

VSV expressing codon-optimized Covid-S1, RABV expressing codon-optimized Covid-S1, and MV expressing codon-optimized Covid-S from positions 2, 3, and 6 of the genome were generated (FIGS. 1-5; FIGS. 17-21).

Figure 6:
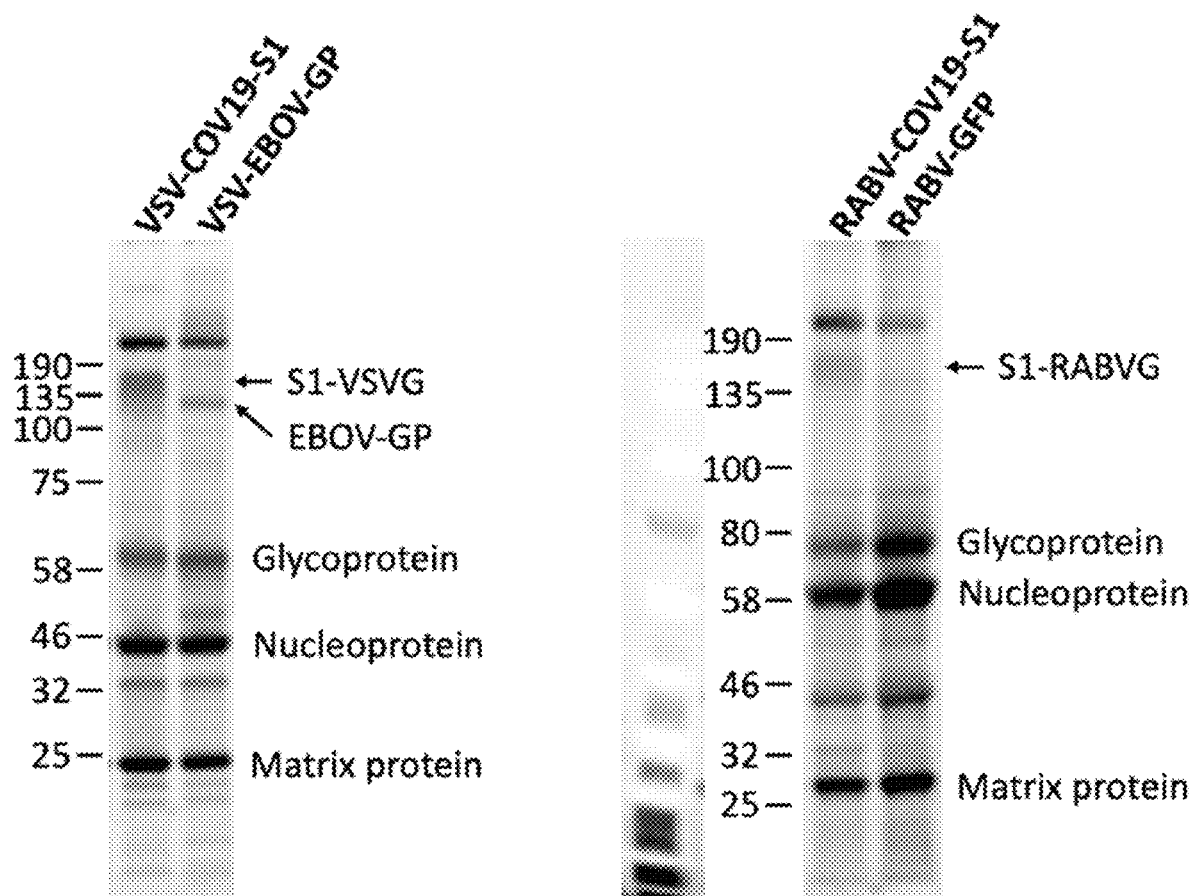
FIG. 6: Characterization of RABV (RABV-COV19-S1) and VSV (VSV-COV19-S1) expressing a chimeric S1-G fusion protein. SDS-PAGE analysis of purified virions after sucrose gradient purification. Letters indicate the positions of the VSV or RABV L, G, N, P, and M proteins. Numbers to the left indicate the sizes of the molecular mass standards. The Covid-19 51 protein is indicated. The controls show VSV and RABV virions.

FIG. 6 shows characterization of RABV (RABV-COV19-S1) and VSV (VSV-COV19-S1) expressing a chimeric S1-G fusion protein. SDS-PAGE analysis of purified virions after sucrose gradient purification. Letters indicate the positions of the VSV or RABV L, G, N, P, and M proteins. Numbers to the left indicate the sizes of the molecular mass standards. The Covid-19 51 protein is indicated. The controls show VSV and RABV virions.

Example 2

A Rabies Vaccine Based Bivalent Vaccine Against 2019-nCoV

Technologies developed for MERS-CoV and SARS-CoV can be transferred to the 2019-nCov. Most vaccine design has focused on the major immunodominant antigen, the Spike (S) protein located on the surface of the virion, which serves as the ligand for the MERS-CoV receptor dipeptidyl peptidase 4 (DPP4, also known as CD26) (1). Similar to MERS-CoV S 2019-nCoV S is a transmembrane glycoprotein that is likely cleaved by the furin protease into S1 and S2 domains as MERS-CoV S (2). Without intending to be bound by theory, it is believed that, as for other coronaviruses such as MERS-CoV, virus neutralizing antibodies (VNA), which are produced in response to infection or vaccination with MERS-CoV S, will neutralize virus infection in vitro and protect lungs from infection in mouse models of disease (3-6).

Described herein is a Rhabdovirus-based vaccine that offers a combination of features that could prove desirable for an effective 2019-nCoV vaccine. Rhabdovirus-vectored vaccine candidates have been developed for several human pathogens (7). More recently both RABV and VSV have been successfully utilized as Ebola virus (EBOV) vaccines and both approaches are either close to clinical trials (RABV) or have already completed phase 2 clinical trials (VSV) (8, 9). Chemically inactivated RABV vaccines are widely used and safe for humans; approximately 100 million doses of inactivated RABV vaccines are administered to humans every year, demonstrating an excellent safety profile (10). Both live and chemically inactivated RABV vaccines are shown to be safe for animals. In a proof of concept study both live-attenuated as well as inactivated RABV-EBOV have been utilized successfully against EBOV and this vaccine enters a phase 1 clinical trial in 2020. (11-14). Construction of an attenuated RABV 2019-CoV based on the well-characterized MERS-CoV vaccine (FIGS. 12 and (15)).

The nucleotide sequence encoding 2019-nCoV S1 protein was inserted into the cBNSP333 vector (FIG. 12; FIG. 18 "BNSP333-COVID19-S1-RVG"). 2019-nCoV S is a glycoprotein anchored in the membrane of the 2019-nCoV virions that projects from the surface of the virus to act as a ligand to susceptible cells, and is therefore a major immunogen. The BNSP333 vaccine vector utilized is derived from the attenuated RABV strain SAD-B19 (16). Several modifications were introduced into the parent strain to increase safety and maximize expression of foreign genes. It was previously shown that foreign genes can be stably introduced into this vector (14, 17-20). Moreover, it was shown that expression of foreign antigens from a position between the RABV N and P gene, as well as codon optimization for human cells of the target gene, results in the highest expression level of the foreign antigen (14). Additionally, replacing the arginine with glutamic acid at position 333 (333R→333E) within the RABV glycoprotein (G) further reduces the pathogenicity of the already highly attenuated vector (19). This improved vector was successfully used to generate candidate vaccines against several emerging zoonotic viral diseases like EBOV and Henipaviruses (14, 21). However, expression of full length CoV S was found to inhibit expression of RABV G protein and reduces viral titers dramatically. However, expression of S1 fused to the C-terminal part of RABV G resulted in strong incorporation of RABV G-MERS-CoV-S1 fusion protein. The RABV G-2019-nCoV-S1 vaccine is similar to the MERS-CoV 331-S1=MERSRAB) expressing the N-terminal 750 aa of 2019-nCoV S fused to a truncated RABV glycoprotein, which comprises 31 aa of the ectodomain (ED) of RABV G and the complete CD and the transmembrane domain of RABV G to allow chimeric glycoprotein incorporation into RABV virions. The chimeric 2019-nCoV S1/RABV G protein utilizes the original 2019-CoV ER translocation sequence (SS) and is generated by PCR of codon optimized cDNA fragments (FIG. 12).

All the following results are presented from previous studies with the MERS construct (MERSRAB). For MERSRAB, infectious virus was recovered. The new virus expressing the S1 fragment grew to similar titers of roughly 108 FFU/mL as the control virus BNSP333 on Vero cells, which are approved for human vaccine production. The BNSP333 RABV expressing the S1 was entitled MERSRAB and the animal efficacy studies listed below resulted from this constructs. The RABV-based MERSRAB vaccine proved efficacious in three different animal models: mice transduced with an Ad5 virus expressing human hDPP4 (the receptor for MERS-CoV), CRISPR-CASc mice expressing human hDPP4 and Alpacas (camelid).

MERSRAB is immunogenic in mice and protects against challenge with MERS-CoV. To analyze the immunogenicity of the MERSRAB (FIG. 12 and FIG. 13), we immunized 4 groups of BALB/c mice (5 mice per group) with 10 μg of the control virus FILORAB1 (Ebola virus vaccine, group1), 10 μg of MERSRAB (groups 2 and 3), or PBS (group 4) at day 0, 7, and 21 post-inoculations. We followed the immune response against RABV G and MERS-CoV S by antigen-specific ELISAs. The antigen-specific IgG responses increased over time and after each immunization; they reached high antibody levels against both RABV G and MERS-CoV S after the third inoculations. MERS-CoV-S specific immune responses were only detected in groups 2 and 3, but RABV G specific IgG was detected in groups 1-3. None of the animals of group 4, which were mock immunized, demonstrated immune responses against RABV G or MERS-CoV S protein, confirming the specificity of the ELISAs assays. Whereas the RABV G-specific ELISA titers are known to predict protection against RABV challenge (22-24), the protective abilities of the MERS-CoV 5-directed antibodies are unknown. Therefore VNA was performed against MERS-CoV of sera on day 35 of the immunized mice of all four groups. Low levels of MERS-CoV neutralizing antibodies were detected in the sera of mice from group 1 (FILORAB1) or mock (PBS) immunized mice (group 4), but the sera of mice immunized with MERSRAB (group 2 and 3) neutralized MERS-CoV at serum dilutions between 1:1280 and 1:5120. This demonstrates a high level of anti-MERS-CoV neutralizing antibody produced in the BNSP333-S1 vaccinated mice.

Figure 13:
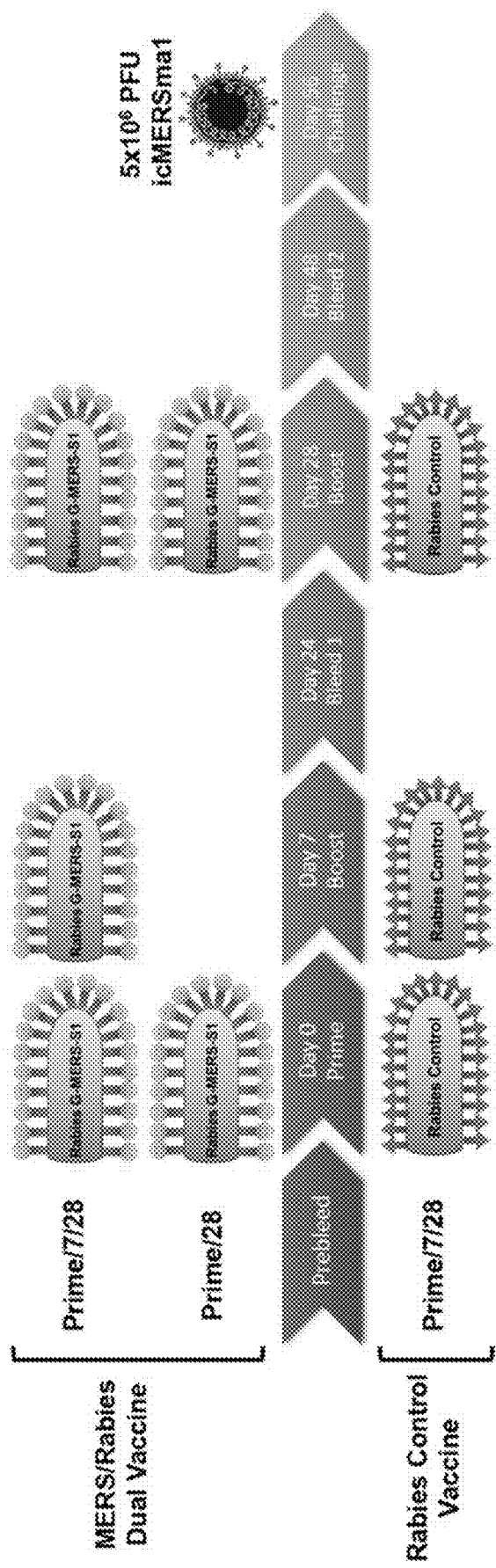
FIG. 13: Schematic illustration of the MERSRAB immunization schedule and challenge with MERS-CoV. Two and three immunization were analyzed with the deactivated vaccine.

Efficacy testing of the RABV-MERS vaccine was performed using the adenovirus-hDPP4 transduced mouse model (25). All four groups of mice were transduced, and after five days, mice in groups 1, 2, and 4 were challenged intranasally (IN) with MERS-CoV at $1\times10^5$ pfu/mouse (strain Jordan-n3/2012). Four days after the challenge, the mice were euthanized, and their lungs were dissected, homogenized, and assayed for viral load by qRT-PCR and a viral plaque assay. For BNSP333-S1 immunized mice, both genomic and mRNA were reduced to background levels similar to those found in mice not transduced by the Ad5-expressing hDPP4. Moreover, the immunization with BNSP333-S1 reduced the viral load in the lungs to a level below detection of the assay. In the next step the RABV based vaccine MERSRAB was tested in the CRISPR-CAS generated transgenic mouse model (mice expressing human hDPP4). Transgenic mice in groups of 10 mice were immunized with 10 µg of the control virus FILORAB (Empty vector, group Rabies control vaccine), 10 µg of MERSRAB (MERS/Rabies dual vaccine), at day 0, 7, and 28 or only at day 0 and 28 (FIG. 13). The immune response against RABV G and MERS-CoV S was followed by antigen-specific ELISAs. The antigen-specific IgG responses increased over time and after each immunization; they reached high antibody levels against both RABV G and MERS-CoV S after the second or third immunization. MERS-CoV-S specific immune responses were only detected in groups 1 and 2 (MERS-Rabies), but RABV G specific IgG was detected in all three groups.

Figures 14A, 14B, 14C:
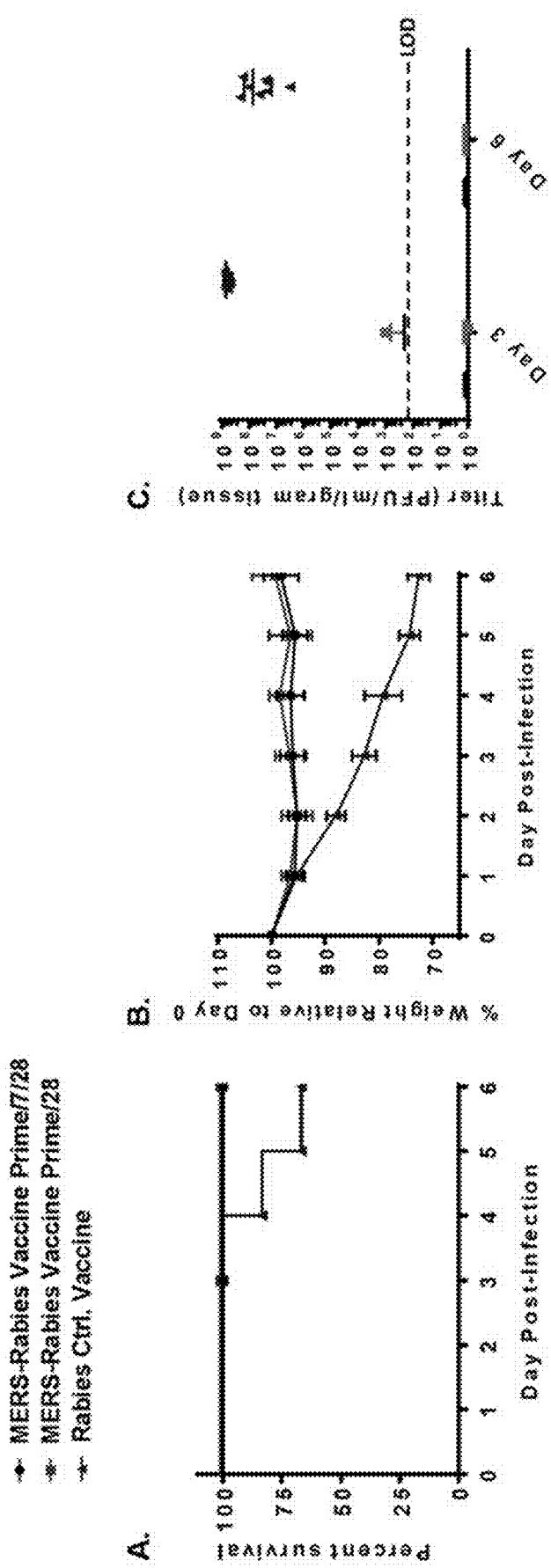
FIGS. 14A-14C: Two or three inoculation with MERSRAB protect animals from weight loss and vaccine induce immune responses control the MERS-CoV challenge viruses to undetectable levels. Animals were immunized and challenge as outlined in FIG. 13.

Whereas the RABV G-specific ELISA titers are known to predict protection against RABV challenge (22-24), the protective abilities of the MERS-CoV S-directed antibodies are not well characterized. The transgenic mice were therefore challenged with pathogenic MERS-CoV at day 56. As shown in FIG. 14A all immunized mice survived the infection whereas 40% of the mock immunized animals succumbed to the infection. As shown all mice, which received one or two inoculation with the MERSRAB were protected from weight-loss completely. Moreover, immunization did reduce viral loads to undetectable levels (FIGS. 14A-14C) whereas the MERS-CoV replicated to very high levels in empty vector immunized animals (FIG. 14C). This can also be seen in FIG. 15. Two or three inoculations with MERSRAB protect animals from viral replication in the lung and MERS-CoV antigen in lungs of immunized mice is detected at day three after challenge, no antigen is detected at day six. In contrast, the lung tissue of animal immunized with the vector only, large amount of tissue damage and viral antigen can be detected at both time points consistent with the viral load shown in FIGS. 14A-14C.

Figure 15:
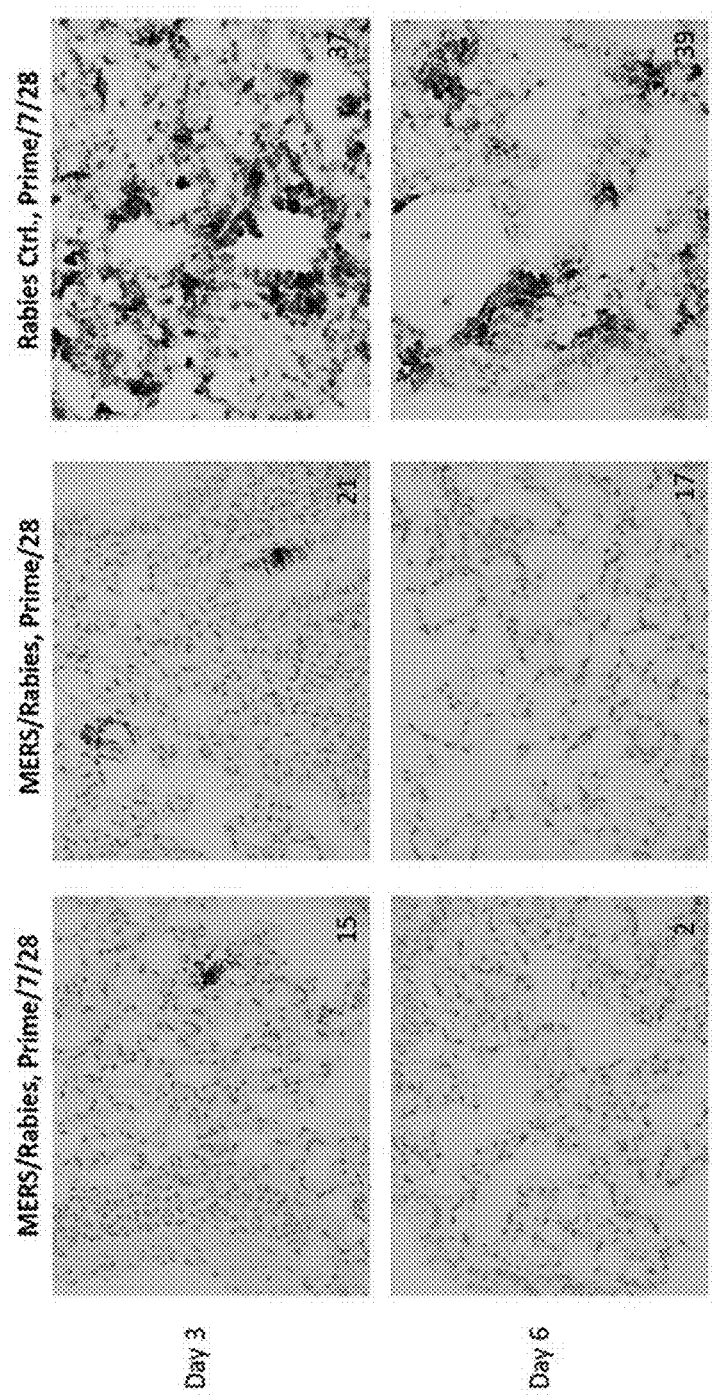
FIG. 15: Two or three inoculation with MERSRAB protect animals from viral replication in the lung. The figure shows that only small amounts of MERS-CoV antigen is detected in lungs of immunized mice at day three after challenge, and no antigen is detected at day six. In contrast, in the lung tissue of animal immunized with the rabies virus vector only large amount of tissue damage and viral antigen can be detected at both time points consistent with the viral load shown in FIG. 14.

Lastly, to determine the potential of preventing transmission from host species to humans, the next study tested if the MERSRAB vaccine was efficacious in Camelids. In brief, a group of five Alpacas were immunized with 107 foci forming units (ffu) of live MERSRAB i.m., or intranasally or immunized i.m. with 100 µg or 300 µg of the inactivated MERSRAB vaccine. After 56 days the animals were challenged with MERS-CoV intranasally and nasal swabs were taken over time to analyse viral shedding. No disease was detected after immunization with either the live or the killed MERSRAB vaccine. As shown in FIG. 15, two inoculations with 100 or 300 µg resulted in almost complete suppression of viral shedding from the infected animals.

Inactivated RABV has a 30-year long history as an efficient and safe vaccine. Taken together, the results presented above clearly indicate that a vaccine based on deactivated RABV particles is a strong candidate against 2019-nCoV infection.

Furthermore, the use of an adjuvant might allow clinical benefit after just one vaccination. Appropriate adjuvant selection is likely be critical to design of a safe and effective nCoV vaccine. Notably, vaccine-enhanced eosinophilic lung disease was seen to be exacerbated when SARS vaccines were formulated with aluminium salt adjuvants whereas it was completely prevented when the same SARS vaccines were formulated with Advax-SM adjuvant, which is a formulation of polysaccharide particles combined with a potent TLR9 agonist. The addition of Advax to a broad range of vaccines results in significant benefits including enhanced protection associated with higher antibody titers, increased B cell receptor affinity maturation, IgG subtype diversification, enhanced memory CD4 and CD8 T cell responses and antigen dose sparing. Advax adjuvant have been shown to provide protective immunity with a single dose in neonatal pups. A particular advantage of Advax adjuvants is that they have already been shown to be safe and well tolerated in human clinical trials in combination with many different antigens thereby facilitating rapid translation of successful vaccines from preclinical studies to human trials.

Adjuvants increase the immunity of vaccines and can also change the antibody isotype. It was previously shown for a rabies virus platform that the addition of MPLA in squalene (PHAD®) increased both the total humoral responses as well as the Th1/TH2 bias. For most viral vaccines, it has been shown that a TH1-bias is beneficial. It has been demonstrated a TH1 bias is necessary for robust protection against EBOV by the FILORAB1 vaccine. For the 2019-nCoV vaccine, the MPLA 3D(6-acyl)PHAD® in 2% Squalene can be used as well as an adjuvant with the potential to increase immunity and induce TH1 responses (e.g., CpG-Oligodeoxynucleotide).

Example 3

Preclinical Studies

The following describes preclinical studies to test the 2019-nCoV vaccine:

1) Most critical is the ability to test efficacy in animal models (small animal and NHP), which will be performed in parallel to the proposed Phase 1 clinical trial to evaluate safety and immunogenicity and potential adverse effects such as enhancement of infection after vaccination. Because 2019-nCoV and the SARS-CoV seem to utilize the same receptor the human ACE2 transgenic mice may be a suitable model for 2019-nCoV, however evaluation of this model has not been characterized and experiments to confirm the model are in the planning stages. NHP animal modelling is expected to start in mid-March 2020. Cynomolgus monkeys, African Green monkeys, common marmosets, and rhesus monkeys will be evaluated for disease development following intratracheal, small-particle aerosol, or large-particle aerosol. The IRF-Frederick has experience with MERS, ebola virus, nipah virus and cowpox aerosol models. The unique positron emission tomography with computed tomography (PET/CT will be incorporated into the animal model to measure disease progression since the nonhuman primate model is expected to be sublethal. CT has been used previously to demonstrate vaccine efficacy and to complement small molecule countermeasure efficacy tests (www.ncbi.nlm.nih.gov/pubmed/26218507 and www.ncbi.nlm.nih.gov/pmc/articles/PMC5640857/).

CT has also been used to evaluated a MERS monoclonal antibody in the rhesus monkey model of MERS and to evaluate disease progression in the common marmoset model of MERS (www.ncbi.nlm.nih.gov/pubmed/26828465 and www.ncbi.nlm.nih.gov/pubmed/26342468)

2) Characterization of the 2019-nCoV vaccine by biochemical and virological assay at TJU 3) Recovery of the vaccine at BBIL under GLP 4) Establish VNA against the 2019-nCoV strain. Establish pseudotype VNA assay for BSL2

5) ELISA for 2019-nCoV S—similar to the previously developed ELISA for MERS-CoV S.

6) Formulation of the vaccine and adjuvant.

Example 4

Clinical Studies

The following describes clinical studies to test the 2019-nCoV vaccine:

Based on the information from preclinical studies, efficacy in animal models will be performed in parallel to the proposed Phase 1 clinical trial to evaluate safety and immunogenicity in human subjects. Of note, our previous discussion (pre-IND) with the FDA for a similar killed rabies-virus based vaccine against EBOV was agreed not to require a toxicity study based on the safety history of deactivated rabies vaccines applied to more than 100 million people. The phase 1 study, if successful, would be followed by a Phase 2 clinical trial to increase the upper end of the age spectrum (since older persons have most severe 2019 nCoV disease) and to expand the cohort size to obtain statistically valid data related to the immune response.

Target populations: Healthy U.S. adults 18 through 55 years of age, inclusive.

Clinical Trial Design: Phase 1 Clinical Trial.

The Phase 1 trial is a randomized, observer-blinded, dose-escalation study to evaluate the safety, reactogenicity, and immunogenicity of the inactivated rabies virus (RABV) based 2019-nCoV vaccine candidates (RABV-nCoV). The clinical trial will be performed at a single site at the University of Maryland, Baltimore, in healthy adults 18 through 55 years of age. Enrolment will proceed in a staged fashion. We will being with 8 subjects in cohort 1. If no pausing rules are met by day 8 following the first dose of vaccine, then cohort 2 can begin immediately after full enrolment of Cohort 1, with no pausing. Cohorts 3 and 4 will proceed simultaneously after review of day 8 data in cohort 2 (assuming no halting rules are met. Importantly, we will include a single dose arm with adjuvant that will commence simultaneously with the 100 ug group (so groups 3 and 4 will be enrolled together after safety data available from all of group 2 through day 8). The study consists of four cohorts totaling 64 subjects (2 rabies vaccine controls and 14 investigational vaccines in each cohort). All study injections will be administered by the intramuscular (IM) route. Treatment assignments are outlined in Table 1.

TABLE 1

Treatment Assignment for the Phase I Ranging Safety Study of the nCoVRAB Vaccine

| Cohort | Sample size | Vaccine | Dose | Timing |
|---|---|---|---|---|
| 1 | 14 | nCoVRAB | 25 µg | Days 0 and 28 |
| 2 | 14 | nCoVRAB | 50 µg | Days 0 and 28 |
| 3 | 14 | nCoVRAB | 100 µg | Days 0 and 28 |
| 4 | 14 | nCoVRA and adjuvant AdVax ® | 50 µg | Days 0 - single dose |
| Control | 8 (2 in each cohort above) | RabAvert © (Rabies Vaccine) | — | Days 0 and 28 (According to label) |

Primary Objective: To assess the safety and tolerability of a 2-dose schedule of the unadjuvanted nCoVRAB and a 1-dose schedule of the adjuvanted vaccine candidates delivered IM at 0 and 28 days.

Secondary Objective: To evaluate the immunogenicity of the nCoVRAB vaccine candidates delivered IM at 0 and 28 days (or day 0 for adjuvanted) at escalating dose levels at Days 0, 28, 56, 120 (with primary measure at day 56 for unadjuvanted and day 28 for adjuvanted).

Primary Endpoints: The number and percentage of study participants who experience any study injection-associated adverse events, solicited systemic events, or serious adverse events at the following time points:

- Solicited events for 7 days after each study injection.
- Unsolicited events through 28 days after the last study injection (Day 56).
- Serious adverse events (SAEs) for 56 days and at Days 56 and 120 and 365 per a scripted interview.
- Number of participants with early discontinuation of study injections and reason for discontinuation.

Secondary Endpoints: Immunogenicity as measured by ELISA to 2019-nCoV and rabies GP.

- nCoV S1- and nCoV S1 and RABV G specific serum IgG ELISA titers per time point through Day 120: geometric mean antibody titers (GMT) and percentage of subjects seroconverting (4-fold rise over baseline).
- nCoV and rabies neutralizing antibody titers through Day 120: GMT and percentage of subjects seroconverting (4-fold rise over baseline); for rabies, percentage of subjects with titers >0.5 IU/ml (correlate of protection).

Exploratory (Future Studies)

- Antigen-specific serum IgM, IgA and IgG subclasses (selected time-points).
- T cell responses (Th1, Th2 and Th17 cytokines and chemokines post vaccination).
- B cell responses (magnitude of antigen-specific plasmablasts and memory B cells post vaccination).
- IgG avidity.

Phase 2 Clinical Trial

This clinical trial is proposed as a Phase 2, randomized, observer-blinded, single antigen level study to evaluate the safety and immunogenicity of a two Dose Rabies-Vectored nCoVRAB Vaccine (or a one dose adjuvanted regimen). Given the demographics of the current NCoV outbreak, we will expand the upper age to 70 years. Volunteers will be assessed before the injection and days 1, 3, 7, 14, and 28 after the vaccine for safety, reactogenicity, and immunogenicity. The clinical trial will be performed in healthy adults meeting all inclusion criteria and no exclusion criteria at 2 sites in the US—Baltimore, Md. and one additional site. total of 200 adults will be consecutively enrolled into groups, stratified by age. All study injections will be administered by the intramuscular (IM) route. Treatment assignments are outlined in Table 2 below.

TABLE 2

Treatment Assignment for the First Dose Ranging Safety Study of the nCoVRAB Vaccine*

| Group | Number of Participants | Study Injections | Antigen Dose* | Dosing Schedule |
|---|---|---|---|---|
| 1 | 180 | nCoVRAB, Liquid | x µg determined in phase 1) | Days 0 and 28 Or one inoculation |
| 2 | 20 | RabAvert | TBD | Days 0 and 28 |

*The overall antigen dose, the relative concentration of the antigen component used for this study will depend upon the outcome of the Phase 1 clinical trial.

Primary Objective: To assess the safety and tolerability of a leading nCoVRAB vaccine candidates delivered IM at 0 and 28 days.

Secondary Objective: To evaluate the immunogenicity of the nCoVRAB vaccine candidates delivered IM at 0 and 28 days at Days 7, 14, 28, 35, 42, 56, 90, 120, 180, and 365.

Primary Endpoints: The number and percentage of study participants who experience any study injection-associated adverse events or serious adverse events at the following time point:
  Solicited events for 7 days after each study injection.
  Unsolicited events through 28 days after the last study injection (Day 56).
  Serious adverse events (SAEs) for 56 days and at Days 56 and 120 and 365 per a scripted interview.
  Number of participants with early discontinuation of study injections and reason for discontinuation.
  Secondary Endpoints/Exploratory endpoints see above (Phase 1 Clinical Trial.)

Example 5

Manufacturing

In the setting of the public health emergency of 2019 Novel Coronavirus (2019-nCoV or SARS-CoV-2), considerations for the development of a 2019-nCoV vaccine must balance manufacturing speed and technical feasibility with clinical safety and immunogenicity considerations. Ultimately, the manufacturing must be scalable, and the delivery simple in order to reach the maximum number of people in the shortest period of time. A collaborator, Bharat Biotech Ltd (BBIL) is a large vaccine manufacturer with the ability to scale production of such a vaccine to millions of doses rapidly. Relying on an existing technology to maximize feasibility and speed of development is the best approach to achieving this goal.

BBIL experience in positioning licensed vaccines for International supplies is summarized in the table below.
Experience in Manufacture and Scale-Up/Infrastructures and Facilities BBIL has several facilities for the manufacturing of Viral, Bacterial and recombinant Drug Substance. BBIL is the largest viral vaccine manufacturer in India. For the manufacturing of viral vaccines, it possesses expertise in the utilization of Vero, MDCK cell lines and platforms like Cell factories, Micro carriers and fermenters. There are 5 viral bulk manufacturing facilities including a pilot plant, these facilities have capabilities ranging from 50 L to 1000 L fermentation and purification by TFF, Gel permeation and Affinity chromatography. These automated facilities can produce up to 500 million doses of vaccines.

BBIL also has capabilities of manufacturing recombinant and bacterial drug substances and these are manufactured in 6 facilities including one pilot plant, BBIL expertise ranges from usage of recombinant E. coli, Yeast, Toxins producing bacteria such as, Diphtheria, tetanus and Whole cell bacteria viz pertussis and Cholera. These organisms are processed from 50 L to 1500 L fermenters and subsequent purifications are carried out using either Ion Exchange, Gel permeation chromatography's.

For Drug Product, all bulk product is either filled in vials, PFS or BFS ranging from 0.5 ML to 25 ml capacities in filling machine having capacity from 50-300 vials per min. Keeping in view, of the various products manufactured and also the products to be manufactured in future, BBIL has a Developmental QC Lab, which in involved in the development and validation of different assays and a Strong QC department for routine batch testing and release of all vaccines and biotherapeutics.

Manufacturing capacity: Approximately, 500 million doses of vaccines and 4 million units of Bio-therapeutics are manufactured per year. About 20-30% of the vaccines are supplied to GAVI countries.

With a strong QC department, BBIL manufacture, test and release following vaccines and biotherapeutics. Apart from the facilities available at BBIL, in case of Emergency situation, higher manufacturing capacities of 5,000 L, at BSL3/Ag+ facility is available at BIOVET, Bengaluru.

Example 6

CORAVAX (rDNA-BBV151)

To evaluate the reactogenicity and safety of BBV151 (inactivated rabies vector platform Corona Virus) vaccine administered via the intramuscular route, a dose escalation study of an intramuscular inactivated rabies vector platform Corona Virus Vaccine (rDNA-BBV151) in healthy volunteers will be performed.

CORAVAX (rDNA-BBV151) is an adjuvanted rabies vectored Corona virus vaccine, that express the S1 domain of the SARSCoV-2 spike (S) protein fused to part of the N terminal domain of the RABV glycoprotein (G) and is incorporated in RABV particles. CORAVAX (rDNA-BBV151) vaccine has two presentations.

TABLE 1

Coronavirus Vaccine (rDNA) - BBVI51 composition

| Dosage form: | | Liquid (Injection for Intramuscular route) | |
|---|---|---|---|
| Composition: | | Each dose of 0.5 ml contains | |
| | I | Active ingredient | Quantity |
| | | Coronavirus Vaccine (rDNA) BBVI51 | NLT 15 (or) 30 mcg |
| | | Inactive ingredients | |
| | | 2-Phenoxyethanol (2-PE) - I.P. | 2.5 mg |
| | | Phosphate Buffered Saline | Qs to 0.25 mL |
| | II | Adjuvant | |
| | | SEPIVAC SWE - Oil in water (O/W) emulsion* | 0.25 ml |

PRESENTATION 1 (BBV151-A)—Ingredients I and II will be provided as two separate vials (each 0.5 mL) and these two vials (A and B) will be mixed at the time of administration. The final reconstituted 1.0 mL volume is equivalent to 2 doses. BBV151-A presentation has two vaccine formulations with a variation in the dosage strength of active ingredient (Figure XA):

BBV151-A1: BBV151-A1 formulation has 15 mcg of the active ingredient.

BBV151-A2: BBV151-A2 formulation has 30 mcg of the active ingredient.

PRESENTATION 2 (BBV151-B): Ingredients I and II will be mixed together, before itself and will be provided as a single vial (0.5 mL dose volume). BBV151-B presentation has only one formulation (Figure XB):

BBV151-B: BBV151-B formulation has 30 mcg of the active ingredient.

The study is designed to evaluate the safety, reactogenicity, and immunogenicity of four groups of healthy volunteers who receive either vaccine or placebo.

Group 1 (BBV151-A1): In this group, 15 participants will be recruited and administered with BBV151-A1 vaccine formulation on day 0 and day 28 via intramuscular route.

Group 2 (BBV151-A2): In this group, 15 participants will be recruited and administered with BBV151-A2 vaccine formulation on day 0 and day 28 via intramuscular route.

Group 3 (BBV151-B): In this group, 15 participants will be recruited and administered with BBV151-B vaccine formulation on day 0 via intramuscular route.

Data will be un-blinded to the third-party bio-statistician and an interim analysis will be performed at day 42 for Immunogenicity and Safety. nAb titer of the COVID-19 virus will be assessed by the MNT/PRNT assay and evaluate the immunogenicity in terms of GMT of vaccine comparison with the placebo group. Serum samples will be assessed for nAb. Binding antibody titer against spike protein of SARS-CoV-2 virus will be assessed for serum samples by using ELISA. Cell Mediated Immunity will be assessed from the subset of the study population.

The GMT will be calculated for neutralization titers in each vaccine group (one dose and two doses) separately. A two-sided 95% confidence interval (CI) for the GMT will be calculated from a 95% CI for the mean of $\log_{10}$-transformed titer, using a normal approximation for the distribution of $\log_{10}$ (titer). The ratio of GMTs in the two vaccine groups (GMT with two doses/GMT with one dose) and the corresponding 95% CI will also be presented. The two-sided 95% CI for the GMT ratio will be calculated from a 95% CI for the difference in means of $\log_{10}$ (titer). The two vaccine groups will be compared using a two-sided two-sample t-test on the means of $\log_{10}$-transformed titers, at the 5% significance level.

To evaluate the humoral immune responses of BBV151, GMT and four-fold seroconversion rate (SCR) of neutralizing antibodies (NAb's) by MNT/PRNT assays across the three groups, from baseline to days 28±2, 42±2, 90±7 and 180±7, will be performed.

To compare the humoral responses between single dose group and double dose group, GMT and four-fold seroconversion rate (SCR) of neutralizing antibodies (NAb's) by MNT/PRNT assays across the three groups, from baseline to days 28+2, 42±2, 90±7 and 180±7.

To evaluate the immune responses against spike protein of SARS-CoV-2 virus and Rabies vector, GMT and four-fold seroconversion rate of binding antibodies (bAb's) IgA and IgG against spike protein across the three groups, from baseline to days 28+2, 42±2, 90±7 and 180±7, will be determined. Immune response (binding/or neutralization) to the vector will be assessed by ELISA from baseline to days 28+2, 42±2, 90±7 and 180±7.

To evaluate the safety of the vaccine in terms of assessing adverse event of special interest (AESI), the occurrence of AESI will be monitored and documented throughout the study duration.

REFERENCES

1. Raj V S, Mou H, Smits S L, Dekkers D H, Muller M A, Dijkman R, Muth D, Demmers J A, Zaki A, Fouchier R A, Thiel V, Drosten C, Rottier P J, Osterhaus A D, Bosch B J, Haagmans B L. Dipeptidyl peptidase 4 is a functional receptor for the emerging human coronavirus-EMC. Nature. 2013; 495(7440):251-4. doi: 10.1038/nature12005. PubMed PMID: 23486063

2. Burkard C, Verheije M H, Wicht O, van Kasteren S I, van Kuppeveld F J, Haagmans B L, Pelkmans L, Rottier P J, Bosch B J, de Haan C A. Coronavirus cell entry occurs through the endo-/lysosomal pathway in a proteolysis-dependent manner. PLoS pathogens. 2014; 10(11): e1004502. doi: 10.1371/journal.ppat.1004502. PubMed PMID: 25375324; PMCID: PMC422306

3. Volz A, Kupke A, Song F, Jany S, Fux R, Shams-Eldin H, Schmidt J, Becker C, Eickmann M, Becker S, Sutter G. Protective Efficacy of Recombinant Modified Vaccinia Virus Ankara Delivering Middle East Respiratory Syndrome Coronavirus Spike Glycoprotein. J Virol. 2015; 89(16):8651-6. doi: 10.1128/JVI.00614-15. PubMed PMID: 26018172; PMCID: PMC4524222

4. Ma C, Wang L, Tao X, Zhang N, Yang Y, Tseng C T, Li F, Zhou Y, Jiang S, Du L. Searching for an ideal vaccine candidate among different MERS coronavirus receptor-binding fragments—the importance of immunofocusing in subunit vaccine design. Vaccine. 2014; 32(46):6170-6. doi: 10.1016/j.vaccine.2014.08.086. PubMed PMID: 25240756; PMCID: PMC4194190

5. Hudacek A W, Al-Saleem F H, Willet M, Eisemann T, Mattis J A, Simpson L L, Schnell M J. Recombinant rabies virus particles presenting botulinum neurotoxin antigens elicit a protective humoral response in vivo. Molecular therapy Methods & clinical development. 2014; 1:14046. doi: 10.1038/mtm.2014.46. PubMed PMID: 26015984; PMCID: 4362357

6. Muthumani K, Falzarano D, Reuschel E L, Tingey C, Flingai S, Villarreal D O, Wise M, Patel A, Izmirly A, Aljuaid A, Seliga A M, Soule G, Morrow M, Kraynyak K A, Khan A S, Scott D P, Feldmann F, LaCasse R, Meade-White K, Okumura A, Ugen K E, Sardesai N Y, Kim J J, Kobinger G, Feldmann H, Weiner D B. A synthetic consensus anti-spike protein DNA vaccine induces protective immunity against Middle East respiratory syndrome coronavirus in nonhuman primates. Sci Transl Med. 2015; 7(301):301ra132. doi: 10.1126/scitranslmed.aac7462. PubMed PMID: 26290414; PMCID: PMC4573558

7. Pfaller C K, Cattaneo R, Schnell M J. Reverse genetics of Mononegavirales: How they work, new vaccines, and new cancer therapeutics. Virology. 2015; 479-480:331-44. doi: 10.1016/j.virol.2015.01.029. PubMed PMID: 25702088; PMCID: 4557643

8. Willet M, Kurup D, Papaneri A, Wirblich C, Hooper J W, Kwilas S A, Keshwara R, Hudacek A, Beilfuss S, Rudolph G, Pommerening E, Vos A, Neubert A, Jahrling P, Blaney J E, Johnson R F, Schnell M J. Preclinical Development of Inactivated Rabies Virus-Based Polyvalent Vaccine Against Rabies and Filoviruses. J Infect Dis. 2015; 212 Suppl 2:S414-24. doi: 10.1093/infdis/jiv251. PubMed PMID: 26063224; PMCID: 4564550

9. Huttner A, Dayer J A, Yerly S, Combescure C, Auderset F, Desmeules J, Eickmann M, Finckh A, Goncalves A R, Hooper J W, Kaya G, Krahling V, Kwilas S, Lemaitre B, Matthey A, Silvera P, Becker S, Fast P E, Moorthy V, Kieny M P, Kaiser L, Siegrist C A, Consortium VS-E. The effect of dose on the safety and immunogenicity of the VSV Ebola candidate vaccine: a randomised double-blind, placebo-controlled phase 1/2 trial. Lancet Infect Dis. 2015; 15(10):1156-66. doi: 10.1016/S1473-3099(15)00154-1. PubMed PMID: 26248510

10. WHO. Rabies, Fact Sheet #99. 2015.

11. Blaney J E, Marzi A, Willet M, Papaneri A B, Wirblich C, Feldmann F, Holbrook M, Jahrling P, Feldmann H, Schnell M J. Antibody quality and protection from lethal Ebola virus challenge in nonhuman primates immunized with rabies virus based bivalent vaccine. PLoS pathogens. 2013; 9(5):e1003389. doi: 10.1371/journal.ppat.1003389. PubMed PMID: 23737747; PMCID: 3667758.

12. Blaney J E, Wirblich C, Papaneri A B, Johnson R F, Myers C J, Juelich T L, Holbrook M R, Freiberg A N, Bernbaum J G, Jahrling P B, Paragas J, Schnell M J. Inactivated or live-attenuated bivalent vaccines that confer protection against rabies and Ebola viruses. J Virol. 2011; 85(20):10605-16. Epub 2011/08/19. doi: 10.1128/JVI.00558-11. PubMed PMID: 21849459; PMCID: 3187516.

13. Blaney J E, Wirblich C, Papaneri A B, Johnson R F, Myers C J, Juelich T L, Holbrook M R, Freiberg A N, Bernbaum J G, Jahrling P B, Paragas J, Schnell M J. Inactivated or live-attenuated bivalent vaccines that confer protection against rabies and Ebola viruses. J Virol. 2011; 85(20):10605-16. Epub 2011/08/19. doi: 10.1128/JVI.00558-11. PubMed PMID: 21849459; PMCID: 3187516.

14. Willet M, Kurup D, Papaneri A, Wirblich C, Hooper J W, Kwilas S A, Keshwara R, Hudacek A, Beilfuss S, Rudolph G, Pommerening E, Vos A, Neubert A, Jahrling P, Blaney J E, Johnson R F, Schnell M J. Preclinical Development of Inactivated Rabies Virus-Based Polyvalent Vaccine Against Rabies and Filoviruses. J Infect Dis. 2015. doi: 10.1093/infdis/jiv251. PubMed PMID: 26063224

15. Wirblich C, Coleman C M, Kurup D, Abraham T S, Bernbaum J G, Jahrling P B, Hensley L E, Johnson R F, Frieman M B, Schnell M J. One-Health: a Safe, Efficient, Dual-Use Vaccine for Humans and Animals against Middle East Respiratory Syndrome Coronavirus and Rabies Virus. Journal of virology. 2017; 91(2). Epub 2016/11/04. doi: 10.1128/JVI.02040-16. PubMed PMID: 27807241; PMCID: PMC5215356

16. Conzelmann K K, Cox J H, Schneider L G, Thiel H J. Molecular cloning and complete nucleotide sequence of the attenuated rabies virus SAD B19. Virology. 1990; 175(2):485-99. PubMed PMID: 2139267

17. Kurup D, Wirblich C, Feldmann H, Marzi A, Schnell M J. Rhabdoviral-Based Vaccine Platforms against Henipaviruses. J Virol. 2014. doi: 10.1128/JVI.02308-14. PubMed PMID: 25320306

18. Hudacek A W, Al-Saleem F H, Willet M, Eisemann T, Mattis J A, Simpson L L, Schnell M J. Recombinant rabies virus particles presenting botulinum neurotoxin antigens elicit a protective humoral response in vivo. Molecular Therapy—Methods & Clinical Development. 2014; 1

19. McGettigan J P, Pomerantz R J, Siler C A, McKenna P M, Foley H D, Dietzschold B, Schnell M J. Second-generation rabies virus-based vaccine vectors expressing human immunodeficiency virus type 1 gag have greatly reduced pathogenicity but are highly immunogenic. J Virol. 2003; 77(1):237-44. Epub 2002/12/13. PubMed PMID: 12477829; PMCID: 140592.

20. McGettigan J P, Naper K, Orenstein J, Koser M, McKenna P M, Schnell M J. Functional human immunodeficiency virus type 1 (HIV-1) Gag-Pol or HIV-1 Gag-Pol and env expressed from a single rhabdovirus-based vaccine vector genome. J Virol. 2003; 77(20):10889-99. Epub 2003/09/27. PubMed PMID: 14512539; PMCID: 224996

21. Kurup D, Wirblich C, Feldmann H, Marzi A, Schnell M J. Rhabdovirus-based vaccine platforms against henipaviruses. J Virol. 2015; 89(1):144-54. doi: 10.1128/JVI.02308-14. PubMed PMID: 25320306; PMCID: 4301098

22. Servat A, Feyssaguet M, Blanchard I, Morize J L, Schereffer J L, Boue F, Cliquet F. A quantitative indirect ELISA to monitor the effectiveness of rabies vaccination in domestic and wild carnivores. J Immunol Methods. 2007; 318(1-2):1-10. doi: 10.1016/j.jim.2006.07.026. PubMed PMID: 17166510

23. Wasniewski M, Cliquet F. Evaluation of ELISA for detection of rabies antibodies in domestic carnivores. J Virol Methods. 2012; 179(1):166-75. doi: 10.1016/j.jviromet.2011.10.019. PubMed PMID: 22080853

24. Wasniewski M, Guiot A L, Schereffer J L, Tribout L, Mahar K, Cliquet F. Evaluation of an ELISA to detect rabies antibodies in orally vaccinated foxes and raccoon dogs sampled in the field. J Virol Methods. 2013; 187(2):264-70. doi: 10.1016/j.jviromet.2012.11.022. PubMed PMID: 23201293

25. Zhao J, Li K, Wohlford-Lenane C, Agnihothram S S, Fett C, Gale M J, Jr., Baric R S, Enjuanes L, Gallagher T, McCray P B, Jr., Perlman S. Rapid generation of a mouse model for Middle East respiratory syndrome. Proc Natl Acad Sci USA. 2014; 111(13):4970-5. Epub 2014/03/07. doi: 10.1073/pnas.1323279111. PubMed PMID: 24599590; PMCID: 3977243

26. Blaney J E, Wirblich C, Papaneri A B, Johnson R F, Myers C J, Juelich T L, Holbrook M R, Freiberg A N, Bernbaum J G, Jahrling P B, Paragas J, Schnell M J. Inactivated or Live-Attenuated Bivalent Vaccines that Confer Protection against Rabies and Ebola Viruses. PLoS Pathog, under review. 2011

27. Johnson R F, Kurup D, Hagen K R, Fisher C, Keshwara R, Papaneri A, Perry D L, Cooper K, Jahrling P B, Wang J T, Ter Meulen J, Wirblich C, Schnell M J. An Inactivated Rabies Virus-Based Ebola Vaccine, FILORAB1, Adjuvanted With Glucopyranosyl Lipid A in Stable Emulsion Confers Complete Protection in Nonhuman Primate Challenge Models. The Journal of infectious diseases. 2016; 214(suppl 3):S342-554. doi: 10.1093/infdis/jiw231. PubMed PMID: 27456709; PMCID: PMC5050469

28. Papaneri A B, Wirblich C, Marissen W E, Schnell M J. Alanine scanning of the rabies virus glycoprotein antigenic site III using recombinant rabies virus: implication for post-exposure treatment. Vaccine. 2013; 31(49):5897-902. Epub 2013/10/15. doi: 10.1016/j.vaccine.2013.09.038. PubMed PMID: 24120673

29. Bhandari N, Rongsen-Chandola T, Bavdekar A, John J, Antony K, Taneja S, Goyal N, Kawade A, Kang G, Rathore S S, Juvekar S, Muliyil J, Arya A, Shaikh H, Abraham V, Vrati S, Proschan M, Kohberger R, Thiry G, Glass R, Greenberg H B, Curlin G, Mohan K, Harshavardhan GVJA, Prasad S, Rao T S, Boslego J, Bhan M K, Group IRV. Efficacy of a monovalent human-bovine (116E) rotavirus vaccine in Indian children in the second year of life. Vaccine. 2014; 32 Suppl 1:A110-6. doi: 10.1016/j.vaccine.2014.04.079. PubMed PMID: 25091663; PMCID: 25091663
30. Bhandari N, Rongsen-Chandola T, Bavdekar A, John J, Antony K, Taneja S, Goyal N, Kawade A, Kang G, Rathore S S, Juvekar S, Muliyil J, Arya A, Shaikh H, Abraham V, Vrati S, Proschan M, Kohberger R, Thiry G, Glass R, Greenberg H B, Curlin G, Mohan K, Harshavardhan G V, Prasad S, Rao T S, Boslego J, Bhan M K. Efficacy of a monovalent human-bovine (116E) rotavirus vaccine in Indian infants: a randomised, double-blind, placebo-controlled trial. Lancet. 2014; 383(9935):2136-43. Epub 2014/03/19. doi: 10.1016/s0140-6736(13) 62630-6. PubMed PMID: 24629994; PMCID: PMC4532697
31. Bhandari N, Sharma P, Taneja S, Kumar T, Rongsen-Chandola T, Appaiahgari M B, Mishra A, Singh S, Vrati S. A dose-escalation safety and immunogenicity study of live attenuated oral rotavirus vaccine 116E in infants: a randomized, double-blind, placebo-controlled trial. J Infect Dis. 2009; 200(3):421-9. Epub 2009/06/24. doi: 10.1086/600104. PubMed PMID: 19545211
32. Bhandari N, Sharma P, Glass R I, Ray P, Greenberg H, Taneja S, Saksena M, Rao C D, Gentsch J R, Parashar U, Maldonado Y, Ward R L, Bhan M K. Safety and immunogenicity of two live attenuated human rotavirus vaccine candidates, 116E and 1321, in infants: results of a randomised controlled trial. Vaccine. 2006; 24(31-32):5817-23. Epub 2006/06/01. doi: 10.1016/j.vaccine.2006.05.001. PubMed PMID: 16735085
33. Mohan V K, Varanasi V, Singh A, Pasetti M F, Levine M M, Venkatesan R, Ella K M. Safety and immunogenicity of a Vi polysaccharide-tetanus toxoid conjugate vaccine (Typbar-TCV) in healthy infants, children, and adults in typhoid endemic areas: a multicenter, 2-cohort, open-label, double-blind, randomized controlled phase 3 study. Clinical infectious diseases: an official publication of the Infectious Diseases Society of America. 2015; 61(3):393-402. Epub 2015/04/15. doi: 10.1093/cid/civ295. PubMed PMID: 25870324
34. Shakya M, Colin-Jones R, Theiss-Nyland K, Voysey M, Pant D, Smith N, Liu X, Tonks S, Mazur O, Farooq Y G, Clarke J, Hill J, Adhikari A, Dongol S, Karkey A, Bajracharya B, Kelly S, Gurung M, Baker S, Neuzil K M, Shrestha S, Basnyat B, Pollard A J. Phase 3 Efficacy Analysis of a Typhoid Conjugate Vaccine Trial in Nepal. New England Journal of Medicine. 2019; 381(23):2209-18. doi: 10.1056/NEJMoa1905047
35. Voysey M, Pollard A J. Seroefficacy of Vi Polysaccharide—Tetanus Toxoid Typhoid Conjugate Vaccine (Typbar TCV). Clinical Infectious Diseases. 2018; 67(1):18-24. doi: 10.1093/cid/cix1145
36. Jin C, Gibani MINI, Moore M, Juel H B, Jones E, Meiring J, Harris V, Gardner J, Nebykova A, Kerridge S A, Hill J, Thomaides-Brears H, Blohmke C J, Yu L-M, Angus B, Pollard A J. Efficacy and immunogenicity of a Vi-tetanus toxoid conjugate vaccine in the prevention of typhoid fever using a controlled human infection model of *Salmonella Typhi*: a randomised controlled, phase 2b trial. The Lancet. 2017; 390(10111):2472-80. doi: doi.org/10.1016/S0140-6736(17)32149-9
37. Vadrevu K M, Potula V, Khalatkar V, Mahantshetty N S, Shah A, Ella R. Persistence of Immune Responses With an Inactivated Japanese Encephalitis Single-Dose Vaccine, JENVAC and Interchangeability With a Live-Attenuated Vaccine. The Journal of Infectious Diseases. 2019. doi: 10.1093/infdis/jiz672
38. Singh A, Mitra M, Sampath G, Venugopal P, Rao J V, Krishnamurthy B, Gupta M K, Sri Krishna S, Sudhakar B, Rao N B, Kaushik Y, Gopinathan K, Hegde N R, Gore M M, Krishna Mohan V, Ella K M. A Japanese Encephalitis Vaccine From India Induces Durable and Cross-protective Immunity Against Temporally and Spatially Wide-ranging Global Field Strains. The Journal of Infectious Diseases. 2015; 212(5):715-25. doi: 10.1093/infdis/jiv023

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A recombinant virus comprising a SARS-CoV-2 spike protein (S) or a portion thereof, wherein the virus is a rabies virus, a vesicular stomatitis virus (VSV), or a measles virus, and wherein the portion of the SARS-CoV-2 spike protein (S) comprises a receptor binding site of the SARS-CoV-2 spike protein (S).

2. The recombinant virus of claim 1, wherein the virus is a rhabdovirus.

3. The recombinant virus of claim 1, wherein the portion of the SARS-CoV-2 spike protein (S) is a S1 domain.

4. The recombinant virus of claim 1, wherein the virus comprises a fusion protein comprising a glycoprotein (G) or portion thereof and the SARS-CoV-2 spike protein (S) or the portion thereof.

5. The recombinant virus of claim 4, wherein the fusion protein comprises the glycoprotein (G) or portion thereof fused to a S1 domain of the SARS-CoV-2 spike protein (S).

6. The recombinant virus of claim 1, wherein the recombinant virus is encoded by a nucleic acid molecule comprising the sequence of any one of SEQ ID NOs: 1-27.

7. A vaccine comprising the recombinant virus claim 1, and a pharmaceutically acceptable carrier.

8. The vaccine of claim 7, further comprising an adjuvant.

9. The vaccine of claim 8, wherein the adjuvant is MPLA 3D(6-acyl) in 2% squalene.

10. The vaccine of claim 7, wherein the virus is deactivated.

11. The recombinant virus of claim 1, wherein the virus comprises the SARS-CoV-2 spike protein (S), wherein the SARS-CoV-2 spike protein (S) comprises the sequence of SEQ ID NO: 28; or a sequence comprising at least 98%, but not 100%, sequence identity to the sequence of SEQ ID NO: 28.

12. The recombinant virus of claim 6, wherein the nucleic acid molecule comprises the sequence of SEQ ID NO: 2.

* * * * *

SEQUENCE LISTING

```
<160> NUMBER OF SEQ ID NOS: 106

<210> SEQ ID NO 1
<211> LENGTH: 17189
<212> TYPE: DNA
<213> ORGANISM: Artificial Sequence
<220> FEATURE:
<223> OTHER INFORMATION: VSV-COVID19-S1-VSVG

<400> SEQUENCE: 1
ctgacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggctttccc cgtcaagctc taaatcgggg gctcccttta gggttccgat     180
ttagtgcttt acggcacctc gaccccaaaa aacttgatta gggtgatggt tcacgtagtg     240
```

-continued

```
ggccatcgcc ctgatagacg gttttttcgcc ctttgacgtt ggagtccacg ttctttaata   300
gtggactctt gttccaaact ggaacaacac tcaaccctat ctcggtctat tcttttgatt   360
tataagggat tttgccgatt tcggcctatt ggttaaaaaa tgagctgatt aacaaaaat    420 ttaacgcgaa ttttaacaaa atattaacgc ttacaatttc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgagc gcgccctagt tattaatagt aatcaattac ggggtcatta   660
gttcatagcc catatatgga gttccgcgtt acataactta cggtaaatgg cccgcctggc   720
tgaccgccca acgaccccg cccattgacg tcaataatga cgtatgttcc catagtaacg   780
ccaataggga ctttccattg acgtcaatgg gtggagtatt tacggtaaac tgcccacttg   840
gcagtacatc aagtgtatca tatgccaagt acgccccta ttgacgtcaa tgacggtaaa    900
tggcccgcct ggcattatgc ccagtacatg accttatggg actttcctac ttggcagtac   960
atctacgtat tagtcatcgc tattaccatg gtgatgcggt tttggcagta catcaatggg  1020
cgtggatagc ggtttgactc acggggattt ccaagtctcc accccattga cgtcaatggg  1080
agtttgtttt ggcaccaaaa tcaacgggac tttccaaaat gtcgtaacaa ctccgcccca  1140
ttgacgcaaa tgggcggtag gcgtgtacgg tgggaggtct atataagcag agctctctgg  1200
ctaactagag aacccactgc ttactggctt atcgaaatta atacgactca ctataggag   1260 acccaagctg gctagggtct tcgtctgatg agtccgtgag gacgaaaccc ggcgtaccgg  1320
gtcacgaaga caaacaaacc attattatca ttaaaaggct caggagaaac tttaacagta  1380
atcaaaatgt ctgttacagt caagagaatc attgacaaca cagtcatagt tccaaaactt  1440
cctgcaaatg aggatccagt ggaatacccg gcagattact tcagaaaatc aaaggagatt  1500
cctctttaca tcaatactac aaaaagtttg tcagatctaa aggatatgt ctaccaaggc   1560 ctcaaatccg gaaatgtatc aatcatacat gtcaacagct acttgtatgg agcattaaag  1620
gacatccggg gtaagttgga taagattgg tcaagtttcg gaataaacat cgggaaagca   1680
ggggatacaa tcggaatatt tgaccttgta tccttgaaag ccctggacgg cgtacttcca  1740
gatggagtat cggatgcttc cagaaccagc gcagatgaca atggttgcc tttgtatcta   1800 cttggcttat acagagtggg cagaacacaa atgcctgaat acagaaaaaa gctcatggat  1860
gggctgacaa tcaatgcaa aatgatcaat gaacagtttg aacctcttgt gccagaaggt  1920
cgtgacattt ttgatgtgtg gggaaatgac agtaattaca caaaaattgt cgctgcagtg  1980
gacatgttct tccacatgtt caaaaaacat gaatgtgcct cgttcagata cggaactatt  2040
gtttccagat tcaaagattg tgctgcattg gcaacatttg gacacctctg caaaataacc  2100
ggaatgtcta cagaagatgt aacgacctgg atcttgaacc gagaagttgc agatgaaatg  2160
gtccaaatga tgcttccagg ccaagaaatt gacaaggccg attcatacat gccttatttg  2220
atcgactttg gattgtcttc taagtctcca tattcttccg tcaaaaaccc tgccttccac  2280 ttctggggc aattgacagc tcttctgctc agatccacca gagcaaggaa tgcccgacag  2340
cctgatgaca ttgagtatac atctcttact acagcaggtt tgttgtacgc ttatgcagta  2400
ggatcctctg ccgacttggc acaacagttt tgtgttggag ataacaaata cactccagat  2460
gatagtaccg gaggattgac gactaatgca ccgccacaag gcagagatgt ggtcgaatgg  2520
ctcggatggt ttgaagatca aaacagaaaa ccgactcctg atatgatgca gtatgcgaaa  2580
```

```
agagcagtca tgtcactgca aggcctaaga gagaagacaa ttggcaagta tgctaagtca    2640
gaatttgaca aatgacccta taattctcag atcacctatt atatattatg ctacatatga    2700
aaaaaactaa cagatatcat ggataatctc acaaaagttc gtgagtatct caagtcctat    2760
tctcgtctgg atcaggcggt aggagagata atgagatcg aagcacaacg agctgaaaag    2820
tccaattatg agttgttcca agaggatgga gtggaagagc atactaagcc ctcttatttt    2880
caggcagcag atgattctga cacagaatct gaaccagaaa ttgaagacaa tcaaggtttg    2940
tatgcaccag atccagaagc tgagcaagtt gaaggcttta cagggggcc tttagatgac    3000 tatgcagatg aggaagtgga tgttgtattt acttcggact ggaaacagcc tgagcttgaa    3060
tctgacgagc atggaaagac cttacggttg acatcgccag agggtttaag tggagagcag    3120
aaatcccagt ggcttttcgac gattaaagca gtcgtgcaaa gtgccaaata ctggaatctg    3180
gcagagtgca catttgaagc atcgggagaa ggggtcatta tgaaggagcg ccagataact    3240
ccggatgtat ataaggtcac tccagtgatg aacacacatc cgtcccaatc agaagcagta    3300
tcagatgttt ggtctctctc aaagacatcc atgactttcc aacccaagaa agcaagtctt    3360
cagcctctca ccatatcctt ggatgaattg ttctcatcta gaggagagtt catctctgtc    3420
ggaggtgacg acgaatgtc tcataaagag gccatcctgc tcggcctgag atacaaaaag    3480
ttgtacaatc aggcgagagt caaatattct ctgtagacta tgaaaaaaag taacagatat    3540
cacgatctaa gtgttatccc aatccattca tcatgagttc cttaaagaag attctcggtc    3600
tgaaggggaa aggtaagaaa tctaagaaat tagggatcgc accaccccct tatgaagagg    3660
acactagcat ggagtatgct ccgagcgctc caattgacaa atcctatttt ggagttgacg    3720
agatggacac ctatgatccg aatcaattaa gatatgagaa attcttcttt acagtgaaaa    3780
tgacggttag atctaatcgt ccgttcagaa catactcaga tgtggcagcc gctgtatccc    3840
attgggatca catgtacatc ggaatggcag ggaaacgtcc cttctacaaa atcttggctt    3900
tttggggttc ttctaatcta aaggccactc cagcggtatt ggcagatcaa ggtcaaccag    3960
agtatcacac tcactgcgaa ggcagggctt atttgccaca taggatgggg aagaccccctc   4020 ccatgctcaa tgtaccagag cacttcagaa gaccattcaa tataggtctt tacaagggaa    4080
cgattgagct cacaatgacc atctacgatg atgagtcact ggaagcagct cctatgatct    4140
gggatcattt caattcttcc aaattttctg atttcagaga gaaggcctta atgtttggcc    4200
tgattgtcga gaaaaaggca tctggagcgt gggtcctgga ttctatcagc cacttcaaat    4260
gagctagtct aacttctagc ttctgaacaa tcccggttt actcagtctc tcctaattcc    4320
agcctctcga caactaata tcctgtcttt tctatcccta tgaaaaaaac taacagagat    4380
cgatctgttt acgcgtcact atgaagtgcc ttttgtactt agccttttta ttcattgggg    4440
tgaattgcaa gttcaccata gttttttccac acaaccaaaa aggaaactgg aaaaatgttc    4500
cttctaatta ccattattgc ccgtcaagct cagatttaaa ttggcataat gacttaatag    4560
gcacagccat acaagtcaaa atgcccaaga gtcacaaggc tattcaagca gacggttgga    4620
tgtgtcatgc ttccaaatgg gtcactactt gtgatttccg ctggtatgga ccgaagtata    4680
taacacagtc catccgatcc ttcactccat ctgtagaaca atgcaaggaa agcattgaac    4740
aaacgaaaca aggaacttgg ctgaatccag cttccctcc tcaaagttgt ggatatgcaa    4800
ctgtgacgga tgccgaagca gtgattgtcc aggtgactcc tcaccatgtg ctggttgatg    4860
aatacacagg agaatgggtt gattcacagt tcatcaacgg aaaatgcagc aattacatat    4920
gccccactgt ccataactct acaacctggc attctgacta taaggtcaaa gggctatgtg    4980
```

```
attctaacct catttccatg gacatcacct tcttctcaga ggacggagag ctatcatccc   5040
tgggaaagga gggcacaggg ttcagaagta actactttgc ttatgaaact ggaggcaagg   5100
cctgcaaaat gcaatactgc aagcattggg gagtcagact cccatcaggt gtctggttcg   5160
agatggctga taaggatctc tttgctgcag ccagattccc tgaatgccca gaagggtcaa   5220
gtatctctgc tccatctcag acctcagtgg atgtaagtct aattcaggac gttgagagga   5280
tcttggatta ttccctctgc caagaaacct ggagcaaaat cagagcgggt cttccaatct   5340
ctccagtgga tctcagctat cttgctccta aaaacccagg aaccggtcct gctttcacca   5400
taatcaatgg taccctaaaa tactttgaga ccagatacat cagagtcgat attgctgctc   5460
caatcctctc aagaatggtc ggaatgatca gtggaactac cacagaaagg gaactgtggg   5520
atgactgggc accatatgaa gacgtggaaa ttggacccaa tggagttctg aggaccagtt   5580
caggatataa gtttccttta tacatgattg gacatggtat gttggactcc gatcttcatc   5640
ttagctcaaa ggctcaggtg ttcgaacatc ctcacattca agacgctgct tcgcaacttc   5700
ctgatgatga gagtttattt tttggtgata ctgggctatc caaaaatcca atcgagcttg   5760
tagaaggttg gttcagtagt tggaaaagct ctattgcctc ttttttcttt atcatagggt   5820
taatcattgg actattcttg gttctccgag ttggtatcca tctttgcatt aaattaaagc   5880
acaccaagaa aagacagatt tatacagaca tagagatgaa ccgacttgga aagtaactca   5940
aatcctgcta ggtatgaaaa aaactaacag atatcacgct cgagcgtacg ccaccatgtt   6000
cgtgtttctg gtgctgctgc ctctggtgag ctcccagtgc gtgaacctga ccacaaggac   6060
ccagctgccc cctgcctata ccaattcctt cacacggggc gtgtactatc ccgacaaggt   6120
gttccggagc agcgtgctgc actccacaca ggatctgttt ctgcctttct tttctaacgt   6180
gacctggttc cacgccatcc acgtgagcgg caccaatggc acaaagcggt tcgacaatcc   6240
agtgctgccc tttaacgatg gcgtgtactt cgcctccacc gagaagtcta acatcatcag   6300
aggctggatc tttggcacca cactggacag caagacacag tccctgctga tcgtgaacaa   6360
tgccaccaac gtggtcatca aggtgtgcga gttccagttt tgtaatgatc cattcctggg   6420
cgtgtactat cacaagaaca ataagtcttg gatggagagc gagtttcgcg tgtattcctc   6480
tgccaacaat tgcacatttg agtacgtgtc ccagcccttc ctgatggacc tggagggcaa   6540
gcagggcaat ttcaagaacc tgagggagtt cgtgtttaag aatatcgatg gctacttcaa   6600
aatctactcc aagcacaccc caatcaacct ggtgcgcgac ctgccacagg gcttctctgc   6660
cctggagcca ctggtggatc tgcccatcgg catcaacatc acccggtttc agacactgct   6720
ggccctgcac agaagctacc tgacaccagg cgacagctcc tctggatgga ccgcaggagc   6780
agcagcctac tatgtgggct atctgcagcc caggaccttc ctgctgaagt acaacgagaa   6840
tggcaccatc acagacgccg tggattgcgc cctggatccc ctgtctgaga ccaagtgtac   6900
actgaagagc tttaccgtgg agaagggcat ctatcagaca agcaatttca gggtgcagcc   6960
taccgagtcc atcgtgcgct ttcccaatat cacaaacctg tgcccttttg gcgaggtgtt   7020
caacgcaacc cgcttcgcca gcgtgtacgc ctggaatagg aagcgcatct ccaactgcgt   7080
ggccgactat tctgtgctgt acaacagcgc ctccttctct acctttaagt gctatggcgt   7140
gagccccaca aagctgaatg acctgtgctt taccaacgtg tacgccgatt ccttcgtgat   7200
caggggcgac gaggtcgcc agatcgcacc aggacagaca ggcaagatcg cagactacaa   7260
ttataagctg cctgacgatt tcaccggctg cgtgatcgcc tggaactcta acaatctgga   7320
```

-continued

```
tagcaaagtg ggcggcaact acaattatct gtaccggctg tttagaaagt ctaatctgaa    7380
gccattcgag agggacatct ccacagaaat ctaccaggcc ggctctaccc cctgcaatgg    7440
cgtggagggc tttaactgtt atttccctct gcagagctac ggcttccagc caacaaacgg    7500
cgtgggctat cagccctacc gcgtggtggt gctgtctttt gagctgctgc acgcacctgc    7560
aacagtgtgc ggaccaaaga agagcaccaa tctggtgaag aacaagtgcg tgaacttcaa    7620
cttcaacgga ctgaccggaa caggcgtgct gaccgagtcc aacaagaagt tcctgccttt    7680
tcagcagttc ggcagggaca tcgcagatac cacagacgcc gtgcgcgacc ctcagaccct    7740
ggagatcctg gacatcacac catgctcctt cggcggcgtg tctgtgatca caccaggcac    7800
caatacaagc aaccaggtgg ccgtgctgta tcaggacgtg aattgtaccg aggtgccagt    7860
ggcaatccac gcagatcagc tgaccccctac atggcgggtg tactctaccg gcagcaacgt    7920
gttccagaca agagccggat gcctgatcgg agcagagcac gtgaacaata gctatgagtg    7980
cgacatccct atcggcgccg gcatctgtgc ctcctaccag acccagacaa actccccaag    8040
gtctgtgggc gatacaggcc tgtccaagaa tccaatcgag ctggtagagg gctggttcag    8100
cagttggaaa agctccatcg cctccttttt ctttatcatc ggcctgatca tcggactgtt    8160
cctggtgctc cgcgtgggta tccacctgtg catcaagctg aagcacacca gaaaagaca    8220
gatttataca gacatcgaga tgaaccgcct gggaaagtga gctagccaga ttcttcatgt    8280
ttggaccaaa tcaacttgtg ataccatgct caaagaggcc tcaattatat ttgagttttt    8340
aatttttatg aaaaaaacta acagcaatca tggaagtcca cgattttgag accgacgagt    8400
tcaatgattt caatgaagat gactatgcca caagagaatt cctgaatccc gatgagcgca    8460
tgacgtactt gaatcatgct gattacaatt tgaattctcc tctaattagt gatgatattg    8520
acaatttgat caggaaattc aattctcttc cgattccctc gatgtgggat agtaagaact    8580
gggatggagt tcttgagatg ttaacatcat gtcaagccaa tcccatctca acatctcaga    8640
tgcataaatg gatgggaagt tggttaatgt ctgataatca tgatgccagt caagggtata    8700
gttttttaca tgaagtggac aaagaggcag aaataacatt tgacgtggtg gagaccttca    8760
tccgcggctg gggcaacaaa ccaattgaat acatcaaaaa ggaaagatgg actgactcat    8820
tcaaaattct cgcttatttg tgtcaaaagt ttttggactt acacaagttg acattaatct    8880
taaatgctgt ctctgaggtg gaattgctca acttggcgag gactttcaaa ggcaaagtca    8940
gaagaagttc tcatggaacg aacatatgca ggattagggt tcccagcttg ggtcctactt    9000
ttatttcaga aggatgggct tacttcaaga aacttgatat tctaatggac cgaaactttc    9060
tgttaatggt caaagatgtg attataggga ggatgcaaac ggtgctatcc atggtatgta    9120
gaatagacaa cctgttctca gagcaagaca tcttctccct tctaaatatc tacagaattg    9180
gagataaaat tgtggagagg caggaaattt ttcttatga cttgattaaa atggtggaac    9240
cgatatgcaa cttgaagctg atgaaattag caagagaatc aaggccttta gtcccacaat    9300
tccctcattt tgaaaatcat atcaagactt ctgttgatga aggggcaaaa attgaccgag    9360
gtataagatt cctccatgat cagataatga gtgtgaaaac agtggatctc acactggtga    9420
tttatggatc gttcagacat tggggtcatc ctttttataga ttattacact ggactagaaa    9480
aattacattc ccaagtaacc atgaagaaag atattgatgt gtcatatgca aaagcacttg    9540
caagtgattt agctcggatt gttctatttc aacagttcaa tgatcataaa agtggttcg    9600
tgaatggaga cttgctccct catgatcatc ccttttaaaag tcatgttaaa gaaaatacat    9660
ggcccacagc tgctcaagtt caagattttg gagataaatg gcatgaactt ccgctgatta    9720
```

```
aatgttttga ataccccgac ttactagacc catcgataat atactctgac aaaagtcatt    9780
caatgaatag gtcagaggtg ttgaaacatg tccgaatgaa tccgaacact cctatcccta    9840
gtaaaaaggt gttgcagact atgttggaca caaaggctac caattggaaa gaatttctta    9900
aagagattga tgagaagggc ttagatgatg atgatctaat tattggtctt aaaggaaagg    9960
agagggaact gaagttggca ggtagatttt tctccctaat gtcttggaaa ttgcgagaat   10020
actttgtaat taccgaatat ttgataaaga ctcatttcgt ccctatgttt aaaggcctga   10080
caatggcgga cgatctaact gcagtcatta aaaagatgtt agattcctca tccggccaag   10140
gattgaagtc atatgaggca atttgcatag ccaatcacat tgattacgaa aaatggaata   10200
accaccaaag gaagttatca aacggcccag tgttccgagt tatgggccag ttcttaggtt   10260
atccatcctt aatcgagaga actcatgaat tttttgagaa aagtcttata tactacaatg   10320
gaagaccaga cttgatgcgt gttcacaaca acacactgat caattcaacc tcccaacgag   10380
tttgttggca aggacaagag ggtggactgg aaggtctacg gcaaaaagga tggactatcc   10440
tcaatctact ggttattcaa agagaggcta aaatcagaaa cactgctgtc aaagtcttgg   10500
cacaaggtga taatcaagtt atttgcacac agtataaaac gaagaaatcg agaaacgttg   10560
tagaattaca gggtgctctc aatcaaatgg tttctaataa tgagaaaatt atgactgcaa   10620
tcaaaatagg gacagggaag ttaggacttt tgataaatga cgatgagact atgcaatctg   10680
cagattactt gaattatgga aaaataccga ttttccgtgg agtgattaga gggttagaga   10740
ccaagagatg gtcacgagtg acttgtgtca ccaatgacca aatacccact tgtgctaata   10800
taatgagctc agtttccaca aatgctctca ccgtagctca ttttgctgag acccaatca    10860
atgccatgat acagtacaat tattttggga catttgctag actcttgttg atgatgcatg   10920
atcctgctct tcgtcaatca ttgtatgaag ttcaagataa gataccgggc ttgcacagtt   10980
ctactttcaa atacgccatg ttgtatttgg acccttccat tggaggagtg tcgggcatgt   11040
ctttgtccag gttttttgatt agagccttcc cagatcccgt aacagaaagt ctctcattct   11100
ggagattcat ccatgtacat gctcgaagtg agcatctgaa ggagatgagt gcagtatttg   11160
gaaaccccga gatagccaag tttcgaataa ctcacataga caagctagta gaagatccaa   11220
cctctctgaa catcgctatg ggaatgagtc cagcgaactt gttaaagact gaggttaaaa   11280
aatgcttaat cgaatcaaga caaaccatca ggaaccaggt gattaaggat gcaaccatat   11340
atttgtatca tgaagaggat cggctcagaa gtttcttatg gtcaataaat cctctgttcc   11400
ctagattttt aagtgaattc aaatcaggca cttttttggg agtcgcagac gggctcatca   11460
gtctatttca aaattctcgt actattcgga actcctttaa gaaaaagtat cataggggaat   11520
tggatgattt gattgtgagg agtgaggtat cctctttgac acatttaggg aaacttcatt   11580
tgagaagggg atcatgtaaa atgtggacat gttcagctac tcatgctgac acattaagat   11640
acaaatcctg gggccgtaca gttattggga caactgtacc ccatccatta gaaatgttgg   11700
gtccacaaca tcgaaaagag actccttgtg caccatgtaa cacatcaggg ttcaattatg   11760
tttctgtgca ttgtccagac gggatccatg acgtctttag ttcacgggga ccattgcctg   11820
cttatcctagg gtctaaaaca tctgaatcta catctatttt gcagccttgg gaaagggaaa   11880
gcaaagtccc actgattaaa agagctacac gtcttagaga tgctatctct tggtttgttg   11940
aacccgactc taaactagca atgactatac tttctaacat ccactcttta acaggcgaag   12000
aatggaccaa aaggcagcat gggttcaaaa gaacagggtc tgcccttcat aggttttcga   12060
```

```
catctcggat gagccatggt gggttcgcat ctcagagcac tgcagcattg accaggttga  12120
tggcaactac agacaccatg agggatctgg gagatcagaa tttcgacttt ttattccaag  12180
caacgttgct ctatgctcaa attaccacca ctgttgcaag agacggatgg atcaccagtt  12240
gtacagatca ttatcatatt gcctgtaagt cctgtttgag acccatagaa gagatcaccc  12300
tggactcaag tatggactac acgccccag atgtatccca tgtgctgaag acatggagga  12360
atggggaagg ttcgtgggga caagagataa aacagatcta tcctttagaa gggaattgga  12420
agaatttagc acctgctgag caatcctatc aagtcggcag atgtataggt tttctatatg  12480
gagacttggc gtatagaaaa tctactcatg ccgaggacag ttctctatttt cctctatcta  12540 tacaaggtcg tattagaggt cgaggtttct taaaagggtt gctagacgga ttaatgagag  12600
caagttgctg ccaagtaata caccggagaa gtctggctca tttgaagagg ccggccaacg  12660
cagtgtacgg aggtttgatt tacttgattg ataaattgag tgtatcacct ccattccttt  12720
ctcttactag atcaggacct attagagacg aattagaaac gattcccac aagatcccaa  12780 cctcctatcc gacaagcaac cgtgtatatgg gggtgattgt cagaaattac ttcaaatacc  12840
aatgccgtct aattgaaaag ggaaaataca gatcacatta ttcacaatta tggttattct  12900
cagatgtctt atccatagac ttcattggac cattctctat ttccaccacc ctcttgcaaa  12960
tcctatacaa gccattttta tctggaaaag ataagaatga gttgagagag ctggcaaatc  13020
tttcttcatt gctaagatca ggagaggggt gggaagacat acatgtgaaa ttcttccaca  13080
aggacatatt attgtgtcca gaggaaatca gacatgcttg caagttcggg attgctaagg  13140
ataataataa agacatgagc tatccccctt ggggaaggga atccagaggg acaattacaa  13200
caatccctgt ttattatacg accacccctt acccaaagat gctagagatg cctccaagaa  13260
tccaaaatcc cctgctgtcc ggaatcaggt tgggccaatt accaactggc gctcattata  13320
aaattcggag tatattacat ggaatgggaa tccattacag ggacttcttg agttgtggag  13380
acggctccgg agggatgact gctgcattac tacgagaaaa tgtgcatagc agaggaatat  13440
tcaatagtct gttagaatta tcagggtcag tcatgcgagg cgcctctcct gagccccca  13500 gtgccctaga aactttagga ggagataaat cgagatgtgt aaatggtgaa acatgttggg  13560
aatatccatc tgacttatgt gacccaagga cttgggacta tttcctccga ctcaaagcag  13620
gctgggggct tcaaattgat ttaattgtaa tggatatgga agttcgggat tcttctacta  13680
gcctgaaaat tgagacgaat gttagaaatt atgtgcaccg gattttggat gagcaaggag  13740
ttttaatcta caagacttat ggaacatata tttgtgagag cgaaaagaat gcagtaacaa  13800
tccttggtcc catgttcaag acggtcgact tagttcaaac agaatttagt agttctcaaa  13860
cgtctgaagt atatatggta tgtaaaggtt tgaagaaatt aatcgatgaa cccaatcccg  13920
attggtcttc catcaatgaa tcctggaaaa acctgtacgc attccagtca tcagaacagg  13980
aatttgccag agcaaagaag gttagtacat actttacctt gacaggtatt ccctcccaat  14040
tcattcctga tccttttgta aacattgaga ctatgctaca aatattcgga gtacccacgg  14100
gtgtgtctca tgcggctgcc ttaaaatcat ctgatagacc tgcagattta ttgaccatta  14160
gcctttttta tatggcgatt atatcgtatt ataacatcaa tcatatcaga gtaggaccga  14220
tacctccgaa cccccatca gatggaattg cacaaaatgt ggggatcgct ataactggta  14280
taagcttttg gctgagtttg atggagaaag acattccact atatcaacag tgtttagcag  14340
ttatccagca atcattcccg attaggtggg aggctgtttc agtaaaagga ggatacaagc  14400
agaagtggag tactagaggt gatgggctcc caaaagatac ccgaacttca gactccttgg  14460
```

```
ccccaatcgg gaactggatc agatctctgg aattggtccg aaaccaagtt cgtctaaatc   14520
cattcaatga gatcttgttc aatcagctat gtcgtacagt ggataatcat ttgaaatggt   14580
caaatttgcg aagaaacaca ggaatgattg aatggatcaa tagacgaatt tcaaaagaag   14640
accggtctat actgatgttg aagagtgacc tacacgagga aaactcttgg agagattaaa   14700
aaatcatgag gagactccaa actttaagta tgaaaaaaac tttgatcctt aagaccctct   14760
tgtggttttt attttttatc tggttttgtg gtcttcgtgg gtcggcatgg catctccacc   14820
tcctcgcggt ccgacctggg catccgaagg aggacgcacg tccactcgga tggctaaggg   14880
agagccagaa ataactagt ggatccggct gctaacaaag cccgaaagga agctgagttg    14940
gctgctgcca ccgctgagca ataactagca taaccccttg gggcctctaa acgggtcttg   15000
agggtttttt tgctgaaagt cgcgcttggc gtaatcatgg tcatagctgt ttcctgtgtg   15060
aaattgttat ccgctcacaa ttccacacaa catacgagcc ggaagcataa agtgtaaagc   15120
ctggggtgcc taatgagtga gctaactcac attaattgcg ttgcgctcac tgcccgcttt   15180
ccagtcggga aacctgtcgt gccagctgca ttaatgaatc ggccaacgcg cggggagagg   15240
cggtttgcgt attgggcgct cttccgcttc ctcgctcact gactcgctgc gctcggtcgt   15300
tcggctgcgg cgagcggtat cagctcactc aaaggcggta atacggttat ccacagaatc   15360
aggggataac gcaggaaaga acatgtgagc aaaaggccag caaaaggcca ggaaccgtaa   15420
aaaggccgcg ttgctggcgt ttttccatag gctccgcccc cctgacgagc atcacaaaaa   15480
tcgacgctca agtcagaggt ggcgaaaccc gacaggacta taaagatacc aggcgtttcc   15540
ccctggaagc tccctcgtgc gctctcctgt tccgaccctg ccgcttaccg gatacctgtc   15600
cgcctttctc ccttcgggaa gcgtggcgct ttctcatagc tcacgctgta ggtatctcag   15660
ttcggtgtag gtcgttcgct ccaagctggg ctgtgtgcac gaaccccccg ttcagcccga   15720
ccgctgcgcc ttatccggta actatcgtct tgagtccaac ccggtaagac acgacttatc   15780
gccactggca gcagccactg gtaacaggat tagcagagcg aggtatgtag gcggtgctac   15840
agagttcttg aagtggtggc ctaactacgg ctacactaga aggacagtat ttggtatctg   15900
cgctctgctg aagccagtta ccttcggaaa aagagttggt agctcttgat ccggcaaaca   15960
aaccaccgct ggtagcggtg gtttttttgt ttgcaagcag cagattacgc gcagaaaaaa   16020
aggatctcaa gaagatcctt tgatcttttc tacggggtct gacgctcagt ggaacgaaaa   16080
ctcacgttaa gggattttgg tcatgagatt atcaaaaagg atcttcacct agatcctttt   16140
aaattaaaaa tgaagtttta aatcaatcta agtatatat gagtaaactt ggtctgacag   16200
ttaccaatgc ttaatcagtg aggcacctat ctcagcgatc tgtctatttc gttcatccat   16260
agttgcctga ctccccgtcg tgtagataac tacgatacgg gagggcttac catctggccc   16320
cagtgctgca atgataccgc gagacccacg ctcaccggct ccagatttat cagcaataaa   16380
ccagccagcc ggaagggccg agcgcagaag tggtcctgca actttatccg cctccatcca   16440
gtctattaat tgttgccggg aagctagagt aagtagttcg ccagttaata gtttgcgcaa   16500
cgttgttgcc attgctacag gcatcgtggt gtcacgctcg tcgtttggta tggcttcatt   16560
cagctccggt tcccaacgat caaggcgagt tacatgatcc cccatgttgt gcaaaaaagc   16620
ggttagctcc ttcggtcctc cgatcgttgt cagaagtaag ttggccgcag tgttatcact   16680
catggttatg gcagcactgc ataattctct tactgtcatg ccatccgtaa gatgcttttc   16740
tgtgactggt gagtactcaa ccaagtcatt ctgagaatag tgtatgcggc gaccgagttg   16800
```

-continued

| | |
|---|---|
| ctcttgcccg gcgtcaatac gggataatac cgcgccacat agcagaactt taaaagtgct | 16860 |
| catcattgga aaacgttctt cggggcgaaa actctcaagg atcttaccgc tgttgagatc | 16920 |
| cagttcgatg taacccactc gtgcacccaa ctgatcttca gcatctttta ctttcaccag | 16980 |
| cgtttctggg tgagcaaaaa caggaaggca aaatgccgca aaaaaggaa taagggcgac | 17040 |
| acggaaatgt tgaatactca tactcttcct ttttcaatat tattgaagca tttatcaggg | 17100 |
| ttattgtctc atgagcggat acatatttga atgtatttag aaaaataaac aaataggggt | 17160 |
| tccgcgcaca tttccccgaa aagtgccac | 17189 |

<210> SEQ ID NO 2
<211> LENGTH: 17611
<212> TYPE: DNA
<213> ORGANISM: Artificial Sequence
<220> FEATURE:
<223> OTHER INFORMATION: BNSP333-COVID19-S1-RVG

<400> SEQUENCE: 2

| | |
|---|---|
| ctgacgcgcc ctgtagcggc gcattaagcg cggcgggtgt ggtggttacg cgcagcgtga | 60 |
| ccgctacact tgccagcgcc ctagcgcccg ctcctttcgc tttcttccct tcctttctcg | 120 |
| ccacgttcgc cggctttccc cgtcaagctc taaatcgggg gctcccttta gggttccgat | 180 |
| ttagtgcttt acggcacctc gaccccaaaa aacttgatta gggtgatggt tcacgtagtg | 240 |
| ggccatcgcc ctgatagacg gttttttcgcc ctttgacgtt ggagtccacg ttctttaata | 300 |
| gtggactctt gttccaaact ggaacaacac tcaaccctat ctcggtctat tcttttgatt | 360 |
| tataagggat tttgccgatt tcggcctatt ggttaaaaaa tgagctgatt taacaaaaat | 420 |
| ttaacgcgaa ttttaacaaa atattaacgc ttacaatttc cattcgccat tcaggctgcg | 480 |
| caactgttgg gaagggcgat cggtgcgggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgagc gcgccctagt tattaatagt aatcaattac ggggtcatta | 660 |
| gttcatagcc catatatgga gttccgcgtt acataactta cggtaaatgg cccgcctggc | 720 |
| tgaccgccca acgaccccg cccattgacg tcaataatga cgtatgttcc catagtaacg | 780 |
| ccaataggga ctttccattg acgtcaatgg gtggagtatt tacggtaaac tgcccacttg | 840 |
| gcagtacatc aagtgtatca tatgccaagt acgccccta ttgacgtcaa tgacggtaaa | 900 |
| tggcccgcct ggcattatgc ccagtacatg accttatggg actttcctac ttggcagtac | 960 |
| atctacgtat tagtcatcgc tattaccatg gtgatgcggt tttggcagta catcaatggg | 1020 |
| cgtggatagc ggtttgactc acggggattt ccaagtctcc accccattga cgtcaatggg | 1080 |
| agtttgtttt ggcaccaaaa tcaacgggac tttccaaaat gtcgtaacaa ctccgcccca | 1140 |
| ttgacgcaaa tgggcggtag gcgtgtacgg tgggaggtct atataagcag agctctctgg | 1200 |
| ctaactagag aacccactgc ttactggctt atcgaaatta atacgactca ctataggag | 1260 |
| acccaagctg gctagattaa gcgtctgatg agtccgtgag gacgaaaccc ggcgtaccgg | 1320 |
| gtcacgctta caaccagat caaagaaaaa acagacattg tcaattgcaa agcaaaaatg | 1380 |
| taacacccct acaatggatg ccgacaagat tgtattcaaa gtcaataatc aggtggtctc | 1440 |
| tttgaagcct gagattatcg tggatcaata tgagtacaag taccctgcca tcaaagattt | 1500 |
| gaaaagccc tgtataaccc taggaaaggc tcccgattta aataaagcat acaagtcagt | 1560 |
| tttgtcaggc atgagcgccg ccaaacttaa tcctgacgat gtatgttcct atttggcagc | 1620 |
| ggcaatgcag ttttttgagg ggacatgtcc ggaagactgg accagctatg gaattgtgat | 1680 |

-continued

```
tgcacgaaaa ggagataaga tcaccccagg ttctctggtg gagataaaac gtactgatgt    1740
agaagggaat tgggctctga caggaggcat ggaactgaca agagacccca ctgtccctga    1800
gcatgcgtcc ttagtcggtc ttctcttgag tctgtatagg ttgagcaaaa tatccgggca    1860
aaacactggt aactataaga caaacattgc agacaggata gagcagattt ttgagacagc    1920
cccttttgtt aaaatcgtgg aacaccatac tctaatgaca actcacaaaa tgtgtgctaa    1980
ttggagtact ataccaaact tcagattttt ggccggaacc tatgacatgt ttttctcccg    2040
gattgagcat ctatattcag caatcagagt gggcacagtt gtcactgctt atgaagactg    2100
ttcaggactg gtatcattta ctgggttcat aaaacaaatc aatctcaccg ctagagaggc    2160
aatactatat ttcttccaca agaactttga ggaagagata agaagaatgt ttgagccagg    2220
gcaggagaca gctgttcctc actcttattt catccacttc cgttcactag gcttgagtgg    2280
gaaatctcct tattcatcaa atgctgttgg tcacgtgttc aatctcattc actttgtagg    2340
atgctatatg ggtcaagtca gatccctaaa tgcaacggtt attgctgcat gtgctcctca    2400
tgaaatgtct gttctagggg gctatctggg agaggaattc ttcgggaaag ggacatttga    2460
aagaagattc ttcagagatg agaaagaact tcaagaatac gaggcggctg aactgacaaa    2520
gactgacgta gcactggcag atgatggaac tgtcaactct gacgacgagg actacttttc    2580
aggtgaaacc agaagtccgg aggctgttta tactcgaatc atgatgaatg gaggtcgact    2640
aaagagatct cacatacgga gatatgtctc agtcagttcc aatcatcaag cccgtccaaa    2700
ctcattcgcc gagtttctaa acaagacata ttcgagtgac tcataacatg aaaaaaacta    2760
acacccctcc cgtacgccac catgttcgtg tttctggtgc tgctgcctct ggtgagctcc    2820
cagtgcgtga acctgaccac aaggaccag ctgcccctg cctataccaa ttccttcaca    2880
cggggcgtgt actatcccga caaggtgttc cggagcagcg tgctgcactc cacacaggat    2940
ctgtttctgc ctttcttttc taacgtgacc tggttccacg ccatccacgt gagcggcacc    3000
aatggcacaa agcggttcga caatccagtg ctgcccttta cgatggcgt gtacttcgcc    3060
tccaccgaga agtctaacat catcagaggc tggatctttg gcaccacact ggacagcaag    3120
acacagtccc tgctgatcgt gaacaatgcc accaacgtgg tcatcaaggt gtgcgagttc    3180
cagttttgta atgatccatt cctgggcgtg tactatcaca agaacaataa gtcttggatg    3240
gagagcgagt tcgcgtgta ttcctctgcc aacaattgca catttgagta cgtgtcccag    3300
cccttcctga tggacctgga gggcaagcag ggcaatttca agaacctgag ggagttcgtg    3360
tttaagaata tcgatggcta cttcaaaatc tactccaagc acaccccaat caacctggtg    3420
cgcgacctgc cacagggctt ctctgccctg gagccactgg tggatctgcc catcggcatc    3480
aacatcaccc ggtttcagac actgctggcc ctgcacagaa gctacctgac accaggcgac    3540
agctcctctg gatggaccgc aggagcagca gcctactatg tgggctatct gcagcccagg    3600
accttcctgc tgaagtacaa cgagaatggc accatcacag acgccgtgga ttgcgccctg    3660
gatcccctgt ctgagaccaa gtgtacactg aagagcttta ccgtggagaa gggcatctat    3720
cagacaagca atttcagggt gcagcctacc gagtccatcg tgcgctttcc caatatcaca    3780
aacctgtgcc ttttggcga ggtgttcaac gcaacccgct cgccagcgt gtacgcctgg    3840
aataggaagc gcatctccaa ctgcgtggcc gactattctg tgctgtacaa cagcgcctcc    3900
ttctctacct ttaagtgcta tggcgtgagc cccacaaagc tgaatgacct gtgctttacc    3960
aacgtgtacg ccgattcctt cgtgatcagg ggcgacgagg tgcgccagat cgcaccagga    4020
```

```
cagacaggca agatcgcaga ctacaattat aagctgcctg acgatttcac cggctgcgtg   4080
atcgcctgga actctaacaa tctggatagc aaagtgggcg gcaactacaa ttatctgtac   4140
cggctgttta gaaagtctaa tctgaagcca ttcgagaggg acatctccac agaaatctac   4200
caggccggct ctaccccctg caatggcgtg gagggcttta actgttattt ccctctgcag   4260
agctacggct tccagccaac aaacggcgtg ggctatcagc cctaccgcgt ggtggtgctg   4320
tcttttgagc tgctgcacgc acctgcaaca gtgtgcggac caagaagag caccaatctg   4380
gtgaagaaca agtgcgtgaa cttcaacttc aacggactga ccggaacagg cgtgctgacc   4440
gagtccaaca gaagttcct gccttttcag cagttcggca gggacatcgc agataccaca   4500
gacgccgtgc gcgaccctca gaccctggag atcctggaca tcacaccatg ctccttcggc   4560
ggcgtgtctg tgatcacacc aggcaccaat acaagcaacc aggtggccgt gctgtatcag   4620
gacgtgaatt gtaccgaggt gccagtggca atccacgcag atcagctgac ccctacatgg   4680
cgggtgtact ctaccggcag caacgtgttc cagacaagag ccggatgcct gatcggagca   4740
gagcacgtga acaatagcta tgagtgcgac atccctatcg gcgccggcat ctgtgcctcc   4800
taccagaccc agacaaactc cccaaggtct gtgggagatg aggccgaaga ctttgtggaa   4860
gtccacctgc ctgatgtgca taccaggtg tctggcgtcg acctgggact gccaaattgg   4920
ggcaagtacg tgctgctgag tgctggagca ctgactgccc tgatgctgat catttccctg   4980
atgacctgct gtcggcgcgt gaacagaagt gagcccactc agcacaatct gcgaggaacc   5040
gggagagaag tgtcagtcac acctcagagc gggaaaatca ttagtagttg gaatcacat   5100
aaaagcgggg gcgagaccag gctgtgagct agccatgaaa aaactaaca cccctccttt   5160
cgaaccatcc caaacatgag caagatcttt gtcaatccta gtgctattag agccggtctg   5220
gccgatcttg agatggctga agaaactgtt gatctgatca atagaaatat cgaagacaat   5280
caggctcatc tccaagggga acccatagag gtggacaatc tccctgagga tatggggcga   5340
cttcacctgg atgatggaaa atcgcccaac catggtgaga tagccaaggt gggagaaggc   5400
aagtatcgag aggactttca gatggatgaa ggagaggatc ctagcttcct gttccagtca   5460
tacctggaaa atgttggagt ccaaatagtc agacaaatga ggtcaggaga gagatttctc   5520
aagatatggt cacagaccgt agaagagatt atatcctatg tcgcggtcaa cttccccaac   5580
cctccaggaa agtcttcaga ggataaatca acccagacta ctggccgaga gctcaagaag   5640
gagacaacac ccactccttc tcagagagaa agccaatcat cgaaagccag gatggcggct   5700
caaattgctt ctggccctcc agcccttgaa tggtcggcta ccaatgaaga ggatgatcta   5760
tcagtggagg ctgagatcgc tcaccagatt gcagaaagtt tctccaaaaa atataagttt   5820
ccctctcgat cctcagggat actcttgtat aattttgagc aattgaaaat gaaccttgat   5880
gatatagtta aagaggcaaa aaatgtacca ggtgtgaccc gtttagccca tgacgggtcc   5940
aaactccccc taagatgtgt actgggatgg gtcgctttgg ccaactctaa gaaattccag   6000
ttgttagtcg aatccgacaa gctgagtaaa atcatgcaag atgacttgaa tcgctataca   6060
tcttgctaac cgaacctctc ccctcagtcc ctctagacaa taaaatccga gatgtcccaa   6120
agtcaacatg aaaaaacag gcaacaccac tgataaaatg aacctcctac gtaagatagt   6180
gaaaaccgc agggacgagg acactcaaaa atcctctccc gcgtcagccc ctctggatga   6240
cgatgacttg tggcttccac cccctgaata cgtcccgctg aaagaactta caggcaagaa   6300
gaacatgagg aactttttgta tcaacggaag ggttaaagtg tgtagcccga atggttactc   6360
gttcaggatc ctgcggcaca ttctgaaatc attcgacgag atatattctg ggaatcatag   6420
```

-continued

```
gatgatcggg ttagtcaaag tggttattgg actggctttg tcaggatctc cagtccctga    6480
gggcctgaac tgggtataca aattgaggag aacctttatc ttccagtggg ctgattccag    6540
gggccctctt gaaggggagg agttggaata ctctcaggag atcacttggg atgatgatac    6600
tgagttcgtc ggattgcaaa taagagtgat tgcaaaacag tgtcatatcc agggcagagt    6660
ctggtgtatc aacatgaacc cgagagcatg tcaactatgg tctgacatgt ctcttcagac    6720 acaaggtcc gaagaggaca aagattcctc tctgcttcta gaataatcag attatatccc     6780
gcaaatttat cacttgttta cctctggagg agagaacata tgggctcaac tccacccctt    6840
gggagcaata taacaaaaaa catgttatgg tgccattaaa ccgctgcatt tcatcaaagt    6900
caagttgatt acctttacat tttgatcctc ttggatgtga aaaaaactat taacatccct    6960
caaaagaccc cgggaaagat ggttcctcag gctctcctgt ttgtacccct tctggttttt    7020
ccattgtgtt ttgggaaatt ccctatttac acgataccag acaagcttgg tccctggagt    7080
ccgattgaca tacatcacct cagctgccca acaatttgg tagtggagga cgaaggatgc     7140
accaacctgt cagggttctc ctacatggaa cttaaagttg gatacatctt agccataaaa    7200
gtgaacgggt tcacttgcac aggcgttgtg acggaggctg aaacctacac taacttcgtt    7260
ggttatgtca caaccacgtt caaaagaaag catttccgcc caacaccaga tgcatgtaga    7320
gccgcgtaca actggaagat ggccggtgac cccagatatg aagagtctct acacaatccg    7380
taccctgact accgctggct tcgaactgta aaaaccacca aggagtctct cgttatcata    7440
tctccaagtg tggcagattt ggacccatat gacagatccc ttcactcgag gtcttccct    7500 agcgggaagt gctcaggagt agcggtgtct tctacctact gctccactaa ccacgattac    7560
accatttgga tgcccgagaa tccgagacta gggatgtctt gtgacatttt taccaatagt    7620
agagggaaga gagcatccaa agggagtgag acttgcggct ttgtagatga aagaggccta    7680
tataagtctt taaaggagc atgcaaactc aagttatgtg gagttctagg acttagactt      7740
atggatggaa catgggtctc gatgcaaaca tcaaatgaaa ccaaatggtg ccctcccgat    7800
aagttggtga acctgcacga ctttcgctca gacgaaattg agcaccttgt tgtagaggag    7860
ttggtcagga agagagagga gtgtctggat gcactagagt ccatcatgac aaccaagtca    7920
gtgagtttca gacgtctcag tcatttaaga aaacttgtcc ctgggtttgg aaaagcatat    7980
accatattca acaagacctt gatggaagcc gatgctcact acaagtcagt cgagacttgg    8040
aatgagatcc tcccttcaaa agggtgttta agagttgggg ggaggtgtca tcctcatgtg    8100 aacgggggtgt ttttcaatgg tataatatta ggacctgacg gcaatgtctt aatcccagag    8160
atgcaatcat ccctcctcca gcaacatatg gagttgttgg aatcctcggt tatccccctt    8220
gtgcaccccc tggcagaccc gtctaccgtt ttcaaggacg tgacgaggc tgaggatttt      8280 gttgaagttc accttcccga tgtgcacaat caggtctcag gagttgactt gggtctcccg    8340
aactggggga agtatgtatt actgagtgca ggggccctga ctgccttgat gttgataatt    8400
ttcctgatga catgttgtag aagagtcaat cgatcagaac ctacgcaaca caatctcaga    8460
gggacaggga gggaggtgtc agtcactccc caaagcggga agatcatatc ttcatgggaa    8520
tcacacaaga gtgggggtga gaccagactg taattaatta acgtcctttc aacgatccaa    8580
gtccatgaaa aaactaaca cccctcccgt acctagctta taaagtgctg ggtcatctaa      8640
gcttttcagt cgagaaaaaa acattagatc agaagaacaa ctggcaacac ttctcaacct    8700
gagacttact tcaagatgct cgatcctgga gaggtctatg atgaccctat tgacccaatc    8760
```

```
gagttagagg ctgaacccag aggaaccccc attgtcccca acatcttgag gaactctgac    8820
tacaatctca actctccttt gatagaagat cctgctagac taatgttaga atggttaaaa    8880
acagggaata gaccttatcg gatgactcta acagacaatt gctccaggtc tttcagagtt    8940
ttgaaagatt atttcaagaa ggtagatttg ggttctctca aggtgggcgg aatggctgca    9000
cagtcaatga tttctctctg gttatatggt gcccactctg aatccaacag gagccggaga    9060
tgtataacag acttggccca tttctattcc aagtcgtccc ccatagagaa gctgttgaat    9120
ctcacgctag gaaatagagg gctgagaatc cccccagagg gagtgttaag ttgccttgag    9180
agggttgatt atgataatgc atttggaagg tatcttgcca acacgtattc ctcttacttg    9240
ttcttccatg taatcacctt atacatgaac gccctagact gggatgaaga aaagaccatc    9300
ctagcattat ggaaagattt aacctcagtg gacatcggga aggacttggt aaagttcaaa    9360
gaccaaatat ggggactgct gatcgtgaca aaggactttg tttactccca aagttccaat    9420 tgtcttttg acagaaacta cacacttatg ctaaaagatc ttttcttgtc tcgcttcaac    9480
tccttaatgg tcttgctctc tccccagag ccccgatact cagatgactt gatatctcaa    9540
ctatgccagc tgtacattgc tggggatcaa gtcttgtcta tgtgtggaaa ctccggctat    9600
gaagtcatca aatattgga gccatatgtc gtgaatagtt tagtccagag agcagaaaag    9660
tttaggcctc tcattcattc cttgggagac tttcctgtat ttataaaaga caaggtaagt    9720
caacttgaag agacgttcgg tccctgtgca agaaggttct ttagggctct ggatcaattc    9780
gacaacatac atgacttggt ttttgtgttt ggctgttaca ggcattgggg gcacccatat    9840
atagattatc gaaagggtct gtcaaaacta tatgatcagg ttcaccttaa aaaaatgata    9900
gataagtcct accaggagtg cttagcaagc gacctagcca ggaggatcct tagatggggt    9960
tttgataagt actccaagtg gtatctggat tcaagattcc tagcccgaga ccaccccttg   10020
actccttata tcaaaaccca aacatggcca cccaaacata ttgtagactt ggtgggggat   10080
acatggcaca agctcccgat cacgcagatc tttgagattc ctgaatcaat ggatccgtca   10140
gaaatattgg atgacaaatc acattctttc accagaacga gactagcttc ttggctgtca   10200
gaaaaccgag gggggcctgt tcctagcgaa aaagttatta tcacggccct gtctaagccg   10260
cctgtcaatc cccgagagtt tctgaggtct atagacctcg gaggattgcc agatgaagac   10320
ttgataattg gcctcaagcc aaaggaacgg gaattgaaga ttgaaggtcg attctttgct   10380
ctaatgtcat ggaatctaag attgtatttt gtcatcactg aaaaactctt ggccaactac   10440
atcttgccac ttttttgacgc gctgactatg acagacaacc tgaacaaggt gtttaaaaag   10500
ctgatcgaca gggtcaccgg gcaagggctt ttggactatt caagggtcac atatgcattt   10560
cacctggact atgaaaagtg gaacaaccat caaagattag agtcaacaga ggatgtattt   10620
tctgtcctag atcaagtgtt tggattgaag agagtgtttt ctagaacaca cgagtttttt   10680
caaaaggcct ggatctatta ttcagacaga tcagacctca tcgggttacg ggaggatcaa   10740
atatactgct tagatgcgtc caacggccca acctgttgga atggccagga tggcgggcta   10800
gaaggcttac ggcagaaggg ctggagtcta gtcagcttat tgatgataga tagagaatct   10860
caaatcagga acacaagaac caaaatacta gctcaaggag acaaccaggt tttatgtccg   10920
acatacatgt tgtcgccagg gctatctcaa gaggggctcc tctatgaatt ggagagaata   10980
tcaaggaatg cactttcgat atacagagcc gtcgaggaag gggcatctaa gctagggctg   11040
atcatcaaga aagaagagac catgtgtagt tatgacttcc tcatctatgg aaaaacccct   11100
ttgtttagag gtaacatatt ggtgcctgag tccaaaagat gggccagagt ctcttgcgtc   11160
```

```
tctaatgacc aaatagtcaa cctcgccaat ataatgtcga cagtgtccac caatgcgcta   11220
acagtggcac aacactctca atctttgatc aaaccgatga gggattttct gctcatgtca   11280
gtacaggcag tctttcacta cctgctattt agcccaatct taaagggaag agtttacaag   11340
attctgagcg ctgaagggga gagctttctc ctagccatgt caaggataat ctatctagat   11400
ccttctttgg gagggatatc tggaatgtcc ctcggaagat tccatatacg acagttctca   11460
gaccctgtct ctgaagggtt atccttctgg agagagatct ggttaagctc caagagtcc    11520 tggattcacg cgttgtgtca agaggctgga aacccagatc ttggagagag aacactcgag   11580
agcttcactc gccttctaga agatccgacc accttaaata tcagaggagg ggccagtcct   11640
accattctac tcaaggatgc aatcagaaag gctttatatg acgaggtgga caaggtggaa   11700
aattcagagt ttcgagaggc aatcctgttg tccaagaccc atagagataa ttttatactc   11760
ttcttaatat ctgttgagcc tctgtttcct cgatttctca gtgagctatt cagttcgtct   11820
tttttgggaa tccccgagtc aatcattgga ttgatacaaa actcccgaac gataagaagg   11880
cagtttagaa agagtctctc aaaaacttta gaagaatcct tctacaactc agagatccac   11940
gggattagtc ggatgaccca gacacctcag agggttgggg gggtgtggcc ttgctcttca   12000
gagagggcag atctacttag ggagatctct tggggaagaa aagtggtagg cacgacagtt   12060
cctcacccct ctgagatgtt gggattactt cccaagtcct ctatttcttg cacttgtgga   12120
gcaacaggag gaggcaatcc tagagtttct gtatcagtac tcccgtcctt tgatcagtca   12180 ttttttcac gaggccccct aaagggatac ttgggctcgt ccacctctat gtcgacccag   12240
ctattccatg catgggaaaa agtcactaat gttcatgtgg tgaagagagc tctatcgtta   12300
aaagaatcta taaactggtt cattactaga gattccaact tggctcaagc tctaattagg   12360
aacattatgt ctctgacagg ccctgatttc cctctagagg aggcccctgt cttcaaaagg   12420
acggggtcag ccttgcatag gttcaagtct gccagataca gcgaaggagg gtattcttct   12480
gtctgcccga acctcctctc tcatatttct gttagtacag acaccatgtc tgatttgacc   12540
caagacggga agaactacga tttcatgttc cagccattga tgctttatgc acagacatgg   12600
acatcagagc tggtacagag agacacaagg ctaagagact ctacgtttca ttggcacctc   12660
cgatgcaaca ggtgtgtgag acccattgac gacgtgaccc tggagacctc tcagatcttc   12720
gagtttccgg atgtgtcgaa aagaatatcc agaatggttt ctggggctgt gcctcacttc   12780
cagaggcttc ccgatatccg tctgagacca ggagattttg aatctctaag cggtagagaa   12840
aagtctcacc atatcggatc agctcagggg ctcttatact caatcttagt ggcaattcac   12900
gactcaggat acaatgatgg aaccatcttc cctgtcaaca tatacggcaa ggtttcccct   12960
agagactatt tgagagggct cgcaaggga gtattgatag gatcctcgat ttgcttcttg   13020
acaagaatga caaatatcaa tattaataga cctcttgaat tggtctcagg ggtaatctca   13080
tatattctcc tgaggctaga taaccatccc tccttgtaca taatgctcag agaaccgtct   13140
cttagaggag agatattttc tatccctcag aaaatccccg ccgcttatcc aaccactatg   13200
aaagaaggca acagatcaat cttgtgttat ctccaacatg tgctacgcta tgagcgagag   13260
ataatcacgg cgtctccaga gaatgactgg ctatggatct tttcagactt tagaagtgcc   13320
aaaatgacgt acctatccct cattacttac cagtctcatc ttctactcca gagggttgag   13380 agaaaccctat ctaagagtat gagagataac ctgcgacaat tgagttcttt gatgaggcag   13440
gtgctgggcg ggcacggaga agataccttta gagtcagacg acaacattca acgactgcta   13500
```

```
aaagactctt tacgaaggac aagatgggtg gatcaagagg tgcgccatgc agctagaacc   13560
atgactggag attacagccc caacaagaag gtgtcccgta aggtaggatg ttcagaatgg   13620
gtctgctctg ctcaacaggt tgcagtctct acctcagcaa acccggcccc tgtctcggag   13680
cttgacataa gggccctctc taagaggttc cagaacccct tgatctcggg cttgagagtg   13740
gttcagtggg caaccggtgc tcattataag cttaagccta ttctagatga tctcaatgtt   13800
ttcccatctc tctgccttgt agttggggac gggtcagggg ggatatcaag ggcagtcctc   13860
aacatgtttc cagatgccaa gcttgtgttc aacagtcttt tagaggtgaa tgacctgatg   13920
gcttccggaa cacatccact gcctccttca gcaatcatga ggggaggaaa tgatatcgtc   13980
tccagagtga tagatcttga ctcaatctgg gaaaaaccgt ccgacttgag aaacttggca   14040
acctggaaat acttccagtc agtccaaaag caggtcaaca tgtcctatga cctcattatt   14100
tgcgatgcag aagttactga cattgcatct atcaaccgga tcaccctgtt aatgtccgat   14160
tttgcattgt ctatagatgg accactctat ttggtcttca aaactatgg gactatgcta    14220 gtaaatccaa actacaaggc tattcaacac ctgtcaagag cgttcccctc ggtcacaggg   14280
tttatcaccc aagtaacttc gtcttttttca tctgagctct acctccgatt ctccaaacga   14340
gggaagtttt tcagagatgc tgagtacttg acctcttcca cccttcgaga aatgagcctt   14400
gtgttattca attgtagcag ccccaagagt gagatgcaga gagctcgttc cttgaactat   14460
caggatcttg tgagaggatt tcctgaagaa atcatatcaa atccttacaa tgagatgatc   14520
ataactctga ttgacagtga tgtagaatct tttctagtcc acaagatggt tgatgatctt   14580
gagttacaga ggggaactct gtctaaagtg gctatcatta tagccatcat gatagttttc   14640
tccaacagag tcttcaacgt ttccaaaccc ctaactgacc cctcgttcta tccaccgtct   14700
gatcccaaaa tcctgaggca cttcaacata tgttgcagta ctatgatgta tctatctact   14760
gctttaggtg acgtccctag cttcgcaaga cttcacgacc tgtataacag acctataact   14820
tattacttca gaaagcaagt cattcgaggg aacgtttatc tatcttggag ttggtccaac   14880
gacacctcag tgttcaaaag ggtagcctgt aattctagcc tgagtctgtc atctcactgg   14940
atcaggttga tttacaagat agtgaagact accagactcg ttggcagcat caaggatcta   15000
tccagagaag tggaaagaca ccttcatagg tacaacaggt ggatcaccct agaggatatc   15060
agatctagat catccctact agactacagt tgcctgtgaa ccggatactc ctggaagcct   15120
gcccatgcta agactcttgt gtgatgtatc ttgaaaaaaa caagatccta aatctgaacc   15180
tttggttgtt tgattgtttt tctcattttt gttgtttatt tgttaagcgt gggtcggcat   15240
ggcatctcca cctcctcgcg gtccgacctg ggcatccgaa ggaggacgca cgtccactcg   15300
gatggctaag ggagagccag aaggatccgg ctgctaacaa agcccgaaag gaagctgagt   15360
tggctgctgc caccgctgag caataactag cataaccccct tggggcctct aaacgggtct   15420
tgagggtttt tttgctgaaa gtcgcgcttg gcgtaatcat ggtcatagct gtttcctgtg   15480
tgaaattgtt atccgctcac aattccacac aacatacgag ccggaagcat aaagtgtaaa   15540
gcctggggtg cctaatgagt gagctaactc acattaattg cgttgcgctc actgcccgct   15600
ttccagtcgg gaaacctgtc gtgccagctg cattaatgaa tcggccaacg cgcgggggaga  15660 ggcggtttgc gtattgggcg ctcttacgct tcctcgctca ctgactcgct gcgctcggtc   15720
gttcggctgc ggcgagcggt atcagctcac tcaaaggcgg taatacggtt atccacagaa   15780
tcaggggata acgcaggaaa gaacatgtga gcaaaaggcc agcaaaaggc caggaaccgt   15840
aaaaaggccg cgttgctggc gttttttccat aggctccgcc ccctgacga gcatcacaaa   15900
```

```
aatcgacgct caagtcagag gtggcgaaac ccgacaggac tataaagata ccaggcgttt    15960
ccccctggaa gctccctcgt gcgctctcct gttccgaccc tgccgcttac cggatacctg    16020
tccgcctttc tcccttcggg aagcgtggcg ctttctcata gctcacgctg taggtatctc    16080
agttcggtgt aggtcgttcg ctccaagctg ggctgtgtgc acgaaccccc cgttcagccc    16140
gaccgctgcg ccttatccgg taactatcgt cttgagtcca acccggtaag acacgactta    16200
tcgccactgg cagcagccac tggtaacagg attagcagag cgaggtatgt aggcggtgct    16260
acagagttct tgaagtggtg cctaactac ggctacacta aaggacagt atttggtatc    16320 tgcgctctgc tgaagccagt taccttcgga aaaagagttg gtagctcttg atccggcaaa    16380
caaaccaccg ctggtagcgg tggttttttt gtttgcaagc agcagattac gcgcagaaaa    16440
aaaggatctc aagaagatcc tttgatcttt tctacggggt ctgacgctca gtggaacgaa    16500
aactcacgtt aagggatttt ggtcatgaga ttatcaaaaa ggatcttcac ctagatcctt    16560
ttaaattaaa aatgaagttt taaatcaatc taaagtatat atgagtaaac ttggtctgac    16620
agttaccaat gcttaatcag tgaggcacct atctcagcga tctgtctatt tcgttcatcc    16680
atagttgcct gactccccgt cgtgtagata actacgatac gggagggctt accatctggc    16740
cccagtgctg caatgatacc gcgagaccca cgctcaccgg ctccagattt atcagcaata    16800
aaccagccag ccggaagggc cgagcgcaga agtggtcctg caactttatc cgcctccatc    16860
cagtctatta attgttgccg ggaagctaga gtaagtagtt cgccagttaa tagtttgcgc    16920
aacgttgttg ccattgctac aggcatcgtg gtgtcacgct cgtcgtttgg tatggcttca    16980
ttcagctccg gttcccaacg atcaaggcga gttacatgat cccccatgtt gtgcaaaaaa    17040
gcggttagct ccttcggtcc tccgatcgtt gtcagaagta agttggccgc agtgttatca    17100
ctcatggtta tggcagcact gcataattct cttactgtca tgccatccgt aagatgcttt    17160
tctgtgactg gtgagtactc aaccaagtca ttctgagaat agtgtatgcg gcgaccgagt    17220
tgctcttgcc cggcgtcaat acgggataat accgcgccac atagcagaac tttaaaagtg    17280
ctcatcattg gaaaacgttc ttcggggcga aaactctcaa ggatcttacc gctgttgaga    17340
tccagttcga tgtaacccac tcgtgcaccc aactgatctt cagcatcttt tactttcacc    17400
agcgtttctg ggtgagcaaa aacaggaagg caaaatgccg caaaaaaggg aataagggcg    17460
acacggaaat gttgaatact catactcttc ctttttcaat attattgaag catttatcag    17520
ggttattgtc tcatgagcgg atacatattt gaatgtattt agaaaaataa acaaataggg    17580
gttccgcgca catttccccg aaaagtgcca c                                  17611
```

<210> SEQ ID NO 3
<211> LENGTH: 22946
<212> TYPE: DNA
<213> ORGANISM: Artificial Sequence
<220> FEATURE:
<223> OTHER INFORMATION: MV-coWuhan-S Position 2

<400> SEQUENCE: 3

```
ggacgcgccc tgtagcggcg cattaagcgc ggcgggtgtg gtggttacgc gcagcgtgac     60
cgctacactt gccagcgccc tagcgcccgc tcctttcgct ttcttccctt cctttctcgc    120
cacgttcgcc ggctttcccc gtcaagctct aaatcggggg ctcccttag ggttccgatt    180 tagtgcttta cggcacctcg accccaaaaa acttgattag ggtgatggtt cacgtagtgg    240
gccatcgccc tgatagacgg ttttcgccc tttgacgttg gagtccacgt tctttaatag    300
```

```
tggactcttg ttccaaactg aacaacact caaccctatc tcggtctatt cttttgattt    360
ataagggatt ttgccgattt cggcctattg gttaaaaaat gagctgattt aacaaaaatt    420
taacgcgaat tttaacaaaa tattaacgtt tacaatttcg cgccattcgc cattcaggct    480
gcgcaactgt tgggaagggc gatcggtgcg ggcctcttcg ctattacgcc agctggcgaa    540 aggggggatgt gctgcaaggc gattaagttg ggtaacgcca gggttttccc agtcacgacg    600
ttgtaaaacg acggccagtg cgcgccgtta atacgactca ctatagggag acccaagctg    660
gctagctttg tttggtctga tgagtcccgt gaggacgaaa cccggcgtac cgggtcacca    720
aacaaagttg ggtaaggata gttcaatcaa tgatcatctt ctagtgcact taggattcaa    780
gatcctatta tcagggacaa gagcaggatt agggatatcc gagatggcca cacttttaag    840
gagcttagca ttgttcaaaa gaaacaagga caaaccaccc attacatcag gatccggtgg    900
agccatcaga ggaatcaaac acattattat agtaccaatc cctggagatt cctcaattac    960
cactcgatcc agacttctgg accggttggt gaggttaatt ggaaacccgg atgtgagcgg   1020
gcccaaacta acagggggcac taataggtat attatcctta tttgtggagt ctccaggtca   1080
attgattcag aggatcaccg atgaccctga cgttagcata aggctgttag aggttgtcca   1140
gagtgaccag tcacaatctg gccttacctt cgcatcaaga ggtaccaaca tggaggatga   1200
ggcggaccaa tacttttcac atgatgatcc aattagtagt gatcaatcca ggttcggatg   1260
gttcgggaac aaggaaatct cagatattga agtgcaagac cctgagggat tcaacatgat   1320
tctgggtacc atcctagccc aaatttgggt cttgctcgca aaggcggtta cggccccaga   1380
cacggcagct gattcggagc taagaaggtg ataaagtac acccaacaaa gaagggtagt   1440
tggtgaattt agattggaga gaaatggtt ggatgtggtg aggaacagga ttgccgagga   1500
cctctcctta cgccgattca tggtcgctct aatcctggat atcaagagaa cacccggaaa   1560
caaacccagg attgctgaaa tgatatgtga cattgataca tatatcgtag aggcaggatt   1620
agccagtttt atcctgacta ttaagtttgg gatagaaact atgtatcctg ctcttggact   1680
gcatgaattt gctggtgagt tatccacact tgagtccttg atgaaccttt accagcaaat   1740
gggggaaact gcaccctaca tggtaatcct ggagaactca attcagaaca gttcagtgc    1800 aggatcatac cctctgctct ggagctatgc catgggagta ggagtggaac ttgaaaactc   1860
catgggaggt ttgaactttg gccgatctta ctttgatcca gcatatttta gattagggca   1920
agagatggta aggaggtcag ctggaaaggt cagttccaca ttggcatctg aactcggtat   1980
cactgccgag gatgcaaggc ttgtttcaga gattgcaatg catactactg aggacaagat   2040
cagtagagcg gttggaccca gacaagccca agtatcattt ctacacggtg atcaaagtga   2100
gaatgagcta ccgagattgg ggggcaagga agataggagg gtcaaacaga gtcgaggaga   2160
agccagggag agctacagag aaaccgggcc cagcagagca agtgatgcga gagctgccca   2220
tcttccaacc ggcacacccc tagacattga cactgcaacg gagtccagcc aagatccgca   2280
ggacagtcga aggtcagctg acgccctgct taggctgcaa gccatggcag gaatctcgga   2340
agaacaaggc tcagacacgg acacccctat agtgtacaat gacagaaatc ttctagacta   2400
ggtgcgagag gccgagggcc agaacaacat ccgcctacca tccatcattg ttataaaaaa   2460
cttaggaacc aggtccacac agagtgatac gcgtacgcca ccatgttcgt gtttctggtg   2520
ctgctgcctc tggtgagctc ccagtgcgtg aacctgacca caaggaccca gctgcccct    2580 gcctatacca attccttcac acggggcgtg tactatcccg acaaggtgtt ccggagcagc   2640
gtgctgcact ccacacagga tctgtttctg cctttcttt ctaacgtgac ctggttccac   2700
```

```
gccatccacg tgagcggcac caatggcaca aagcggttcg acaatccagt gctgcccttt    2760
aacgatggcg tgtacttcgc ctccaccgag aagtctaaca tcatcagagg ctggatcttt    2820
ggcaccacac tggacagcaa gacacagtcc ctgctgatcg tgaacaatgc caccaacgtg    2880
gtcatcaagg tgtgcgagtt ccagttttgt aatgatccat tcctgggcgt gtactatcac    2940
aagaacaata agtcttggat ggagagcgag tttcgcgtgt attcctctgc caacaattgc    3000
acatttgagt acgtgtccca gcccttcctg atggacctgg agggcaagca gggcaatttc    3060
aagaacctga gggagttcgt gtttaagaat atcgatggct acttcaaaat ctactccaag    3120
cacaccccaa tcaacctggt gcgcgacctg ccacagggct tctctgccct ggagccactg    3180
gtggatctgc ccatcggcat caacatcacc cggtttcaga cactgctggc cctgcacaga    3240
agctacctga caccaggcga cagctcctct ggatggaccg caggagcagc agcctactat    3300
gtgggctatc tgcagcccag gaccttcctg ctgaagtaca cgagaatgg caccatcaca    3360 gacgccgtgg attgcgccct ggatcccctg tctgagacca gtgtacact gaagagcttt    3420 accgtggaga agggcatcta tcagacaagc aatttcaggg tgcagcctac cgagtccatc    3480
gtgcgctttc ccaatatcac aaacctgtgc ccttttggcg aggtgttcaa cgcaacccgc    3540
ttcgccagcg tgtacgcctg aataggaag cgcatctcca actgcgtggc cgactattct    3600
gtgctgtaca cagcgcctc cttctctacc tttaagtgct atggcgtgag ccccacaaag    3660
ctgaatgacc tgtgctttac caacgtgtac gccgattcct tcgtgatcag gggcgacgag    3720
gtgcgccaga tcgcaccagg acagacaggc aagatcgcag actacaatta taagctgcct    3780
gacgatttca ccggctgcgt gatcgcctgg aactctaaca tctggatag caaagtgggc    3840 ggcaactaca attatctgta ccggctgttt agaaagtcta atctgaagcc attcgagagg    3900
gacatctcca cagaaatcta ccaggccggc tctaccccct gcaatggcgt ggagggcttt    3960
aactgttatt tccctctgca gagctacggc ttccagccaa caaacggcgt gggctatcag    4020
ccctaccgcg tggtggtgct gtcttttgag ctgctgcacg cacctgcaac agtgtgcgga    4080
ccaaagaaga gcaccaatct ggtgaagaac aagtgcgtga acttcaactt caacggactg    4140
accggaacag gcgtgctgac cgagtccaac aagaagtcc tgcctttca gcagttcggc    4200 agggacatcg cagataccac agacgccgtg cgcgaccctc agaccctgga gatcctggac    4260
atcacaccat gctccttcgg cggcgtgtct gtgatcacac aggcaccaa tacaagcaac    4320 caggtggccg tgctgtatca ggacgtgaat tgtaccgagg tgccagtggc aatccacgca    4380
gatcagctga cccctacatg gcgggtgtac tctaccggca gcaacgtgtt ccagacaaga    4440
gccggatgcc tgatcggagc agagcacgtg aacaatagct atgagtgcga catccctatc    4500
ggcgccggca tctgtgcctc ctaccagacc cagacaaact ccccaaggag agcacggtct    4560
gtggccagcc agtccatcat cgcctatacc atgagcctgg gcgccgagaa ttccgtggcc    4620
tactccaaca attctatcgc catccctacc aacttcacaa tctccgtgac acagagatc    4680 ctgccagtga gcatgaccaa gacatccgtg gactgcacaa tgtatatctg tggcgattcc    4740
accgagtgct ctaacctgct gctgcagtac ggctctttt gtacccagct gaatagagcc    4800
ctgacaggca tcgccgtgga gcaggacaag aacacacagg aggtgttcgc ccaggtgaag    4860
caaatctaca agaccccacc catcaaggac tttggcggct tcaacttcag ccagatcctg    4920
cccgatccta gcaagccatc caagcggtct tttatcgagg acctgctgtt caacaaggtg    4980
accctggccg atgccggctt catcaagcag tatggcgatt gcctgggcga catcgccgcc    5040
```

```
agagacctga tctgtgccca gaagtttaat ggcctgaccg tgctgcctcc actgctgaca    5100
gatgagatga tcgcccagta cacatctgcc ctgctggccg gaaccatcac aagcggatgg    5160
accttcggcg caggagccgc cctgcagatc ccctttgcca tgcagatggc ctatcggttc    5220
aacggcatcg gcgtgaccca gaatgtgctg tacgagaacc agaagctgat cgccaatcag    5280
tttaactccg ccatcggcaa gatccaggac tctctgagct ccacagccag cgccctgggc    5340
aagctgcagg atgtggtgaa tcagaacgcc caggccctga ataccctggt gaagcagctg    5400
tctagcaact tcggcgccat ctcctctgtg ctgaatgaca tcctgagccg gctggacaag    5460
gtggaggcag aggtgcagat cgaccggctg atcacaggca gactgcagtc cctgcagacc    5520
tacgtgacac agcagctgat cagggcagca gagatcaggg cctctgccaa tctggccgcc    5580
accaagatga gcgagtgcgt gctgggccag tccaagagag tggacttttg tggcaagggc    5640
tatcacctga tgagcttccc acagtccgcc cctcacggag tggtgtttct gcacgtgacc    5700
tacgtgccag cccaggagaa gaacttcacc acagcaccag caatctgcca cgatggcaag    5760
gcacactttc ctagggaggg cgtgttcgtg agcaacggca cccactggtt tgtgacacag    5820
cgcaatttct acgagccaca gatcatcacc acagacaata cattcgtgtc cggcaactgt    5880
gacgtggtca tcggcatcgt gaacaatacc gtgtatgatc ctctgcagcc agagctggac    5940
tcttttaagg aggagctgga taagtacttc aagaatcaca ccagccccga cgtggatctg    6000
ggcgacatct ctggcatcaa tgccagcgtg gtgaacatcc agaaggagat cgacaggctg    6060
aacgaggtgg ccaagaatct gaacgagtcc ctgatcgatc tgcaggagct gggcaagtat    6120
gagcagtaca tcaagtggcc ctggtatatc tggctgggct tcatcgccgg cctgatcgcc    6180
atcgtgatgg tgaccatcat gctgtgctgt atgacaagct gctgttcctg cctgaagggc    6240
tgctgttctt gtggcagctg ctgtaagttt gatgaggacg atagcgagcc tgtgctgaag    6300
ggcgtgaagc tgcactacac ctgatagcta gcgatcgcgt gcgagaggcc agaacaacat    6360
ccgcctacca tccatcattg ttataaaaaa cttaggaacc aggtccacac agccgccagc    6420
ccatcaacca tccactccca cgattggagc caatggcaga agagcaggca cgccatgtca    6480
aaaacggact ggaatgcatc cgggctctca aggccgagcc catcggctca ctggccatcg    6540
aggaagctat ggcagcatgg tcagaaatat cagacaaccc aggacaggag cgagccacct    6600
gcagggaaga gaaggcaggc agttcgggtc tcagcaaacc atgcctctca gcaattggat    6660
caactgaagg cggtgcacct cgcatccgcg gtcagggacc tggagagagc gatgacgacg    6720
ctgaaacttt gggaatcccc ccaagaaatc tccaggcatc aagcactggg ttacagtgtt    6780
attacgttta tgatcacagc ggtgaagcgg ttaagggaat ccaagatgct gactctatca    6840
tggttcaatc aggccttgat ggtgatagca ccctctcagg aggagacaat gaatctgaaa    6900
acagcgatgt ggatattggc gaacctgata ccgagggata tgctatcact gaccggggat    6960
ctgctcccat ctctatgggg ttcagggctt ctgatgttga aactgcagaa ggaggggaga    7020
tccacgagct cctgagactc caatccgagg caacaacttt ccgaagcttg ggaaaaactc    7080
tcaatgttcc tccgccccg gacccggta gggccagcac ttccgggaca cccattaaaa    7140
agggcacaga cgcgagatta gcctcatttg aacggagat cgcgtcttta ttgacaggtg    7200
gtgcaaccca atgtgctcga aagtcaccct cggaaccatc agggccaggt gcacctgcgg    7260
ggaatgtccc cgagtgtgtg agcaatgccg cactgataca ggagtggaca cccgaatctg    7320
gtaccacaat ctccccgaga tcccagaata atgaagaagg gggagactat tatgatgatg    7380
agctgttctc tgatgtccaa gatattaaaa cagccttggc caaaatacac gaggataatc    7440
```

```
agaagataat ctccaagcta gaatcactgc tgttattgaa gggagaagtt gagtcaatta    7500
agaagcagat caacaggcaa aatatcagca tatccaccct ggaaggacac ctctcaagca    7560
tcatgatcgc cattcctgga cttgggaagg atcccaacga ccccactgca gatgtcgaaa    7620
tcaatcccga cttgaaaccc atcataggca gagattcagg ccgagcactg ccgaagttc     7680
tcaagaaacc cgttgccagc cgacaactcc aaggaatgac aaatggacgg accagttcca    7740
gaggacagct gctgaaggaa tttcagctaa agccgatcgg gaaaaagatg agctcagccg    7800
tcgggtttgt tcctgacacc ggccctgcat cacgcagtgt aatccgctcc attataaaat    7860
ccagccggct agaggaggat cggaagcgtt acctgatgac tctccttgat gatatcaaag    7920
gagccaatga tcttgccaag ttccaccaga tgctgatgaa gataataatg aagtagctac    7980
agctcaactt acctgccaac ccatgccagt cgacccacc tagtacaacc taaatccatt     8040
ataaaaaact taggagcaaa gtgattgcct cccaaggtcc acaatgacag agacctacga    8100
cttcgacaag tcggcatggg acatcaaagg gtcgatcgct ccgatacaac ccaccaccta    8160
cagtgatggc aggctggtgc cccaggtcag agtcatagat cctggtctag gcgacaggaa    8220
ggatgaatgc tttatgtaca tgtttctgct ggggttgtt gaggacagcg attccctagg     8280
gcctccaatc gggcgagcat ttgggttcct gcccttaggt gttggcagat ccacagcaaa    8340
gcccgaaaaa ctcctcaaag aggccactga gcttgacata gttgttagac gtacagcagg    8400
gctcaatgaa aaactggtgt ctacaacaa caccccacta actctcctca caccttggag     8460
aaaggtccta acaacaggga gtgtcttcaa cgcaaaccaa gtgtgcaatg cggttaatct    8520
gataccgctc gatacccgc agaggttccg tgttgtttat atgagcatca cccgtctttc     8580
ggataacggg tattacaccg ttcctagaag aatgctggaa ttcagatcgg tcaatgcagt    8640
ggccttcaac ctgctggtga cccttaggat tgacaaggcg ataggccctg ggaagatcat    8700
cgacaataca gagcaacttc ctgaggcaac atttatggtc cacatcggga acttcaggag    8760
aaagaagagt gaagtctact ctgccgatta ttgcaaaatg aaaatcgaaa agatgggcct    8820
ggtttttgca cttggtggga taggggcac cagtcttcac attagaagca caggcaaaat    8880
gagcaagact ctccatgcac aactcgggtt caagaagacc ttatgttacc cgctgatgga    8940
tatcaatgaa gaccttaatc gattactctg gaggagcaga tgcaagatag taagaatcca    9000
ggcagttttg cagccatcag ttcctcaaga attccgcatt tacgacgacg tgatcataaa    9060
tgatgaccaa ggactattca aagttctgta gaccgtagtg cccagcaatg cccgaaaacg    9120
acccccctca caatgacagc cagaaggccc ggacaaaaaa gcccctccg aaagactcca     9180
cggaccaagc gagaggccag ccagcagccg acggcaagcg cgaacaccag gcggccccag    9240
cacagaacag ccctgacaca aggccaccac cagccacccc aatctgcatc ctcctcgtgg    9300
gaccccgag gaccaacccc caaggctgcc cccgatccaa accaccaacc gcatccccac    9360
cacccccggg aaagaaaccc ccagcaattg aaggcccct cccctcttc ctcaacacaa     9420
gaactccaca accgaaccgc acaagcgacc gaggtgaccc aaccgcaggc atccgactcc    9480
ctagacagat cctctctccc cggcaaacta aacaaaactt agggccaagg aacatacaca    9540
cccaacagaa cccagacccc ggcccacggc gccgcgcccc caaccccga caaccagagg     9600
gagcccccaa ccaatcccgc cggctccccc ggtgcccaca ggcagggaca ccaaccccg     9660
aacagaccca gcacccaacc atcgacaatc caagacgggg gggcccccc aaaaaaaggc     9720
ccccaggggc cgacagccag caccgcgagg aagcccaccc accccacaca cgaccacggc    9780
```

```
aaccaaacca gaacccagac caccctgggc caccagctcc cagactcggc catcaccccg    9840
cagaaaggaa aggccacaac ccgcgcaccc cagccccgat ccggcgggga gccacccaac    9900
ccgaaccagc acccaagagc gatccccgaa ggaccccga accgcaaagg acatcagtat     9960
cccacagcct ctccaagtcc cccggtctcc tcctcttctc gaagggacca aaagatcaat   10020
ccaccacacc cgacgacact caactcccca ccctaaagg agacaccggg aatcccagaa    10080
tcaagactca tccaatgtcc atcatgggtc tcaaggtgaa cgtctctgcc atattcatgg   10140
cagtactgtt aactctccaa acacccaccg gtcaaatcca ttggggcaat ctctctaaga   10200
taggggtggt aggaatagga agtgcaagct acaaagttat gactcgttcc agccatcaat   10260
cattagtcat aaaattaatg cccaatataa ctctcctcaa taactgcacg agggtagaga   10320
ttgcagaata caggagacta ctgagaacag ttttggaacc aattagagat gcacttaatg   10380
caatgaccca gaatataaga ccggttcaga gtgtagcttc aagtaggaga cacaagagat   10440
ttgcgggagt agtcctggca ggtgcggccc taggcgttgc cacagctgct cagataacag   10500
ccggcattgc acttcaccag tccatgctga actctcaagc catcgacaat ctgagagcga   10560
gcctggaaac tactaatcag gcaattgaga caatcagaca agcagggcag gagatgatat   10620
tggctgttca gggtgtccaa gactacatca ataatgagct gataccgtct atgaaccaac   10680
tatcttgtga tttaatcggc cagaagctcg gctcaaatt gctcagatac tatacagaaa    10740
tcctgtcatt atttggcccc agtttacggg accccatatc tgcggagata tctatccagg   10800
ctttgagcta tgcgcttgga ggagacatca ataaggtgtt agaaaagctc ggatacagtg   10860
gaggtgattt actgggcatc ttagagagcg gaggaataaa ggcccggata actcacgtcg   10920
acacagagtc ctacttcatt gtcctcagta tagcctatcc gacgctgtcc gagattaagg   10980
gggtgattgt ccaccggcta gagggggtct cgtacaacat aggctctcaa gagtggtata   11040
ccactgtgcc caagtatgtt gcaacccaag ggtaccttat ctcgaatttt gatgagtcat   11100
cgtgtacttt catgccagag gggactgtgt gcagccaaaa tgcccttgtac ccgatgagtc   11160
ctctgctcca agaatgcctc cggggtaca ccaagtcctg tgctcgtaca ctcgtatccg    11220
ggtcttttgg gaaccggttc attttatcac aagggaacct aatagccaat tgtgcatcaa   11280
tccttttgcaa gtgttacaca acaggaacga tcattaatca agaccctgac aagatcctaa   11340
catacattgc tgccgatcac tgcccggtag tcgaggtgaa cggcgtgacc atccaagtcg   11400
ggagcaggag gtatccagac gctgtgtact tgcacagaat tgacctcggt cctcccatat   11460
cattggagag gttggacgta gggacaaatc tggggaatgc aattgctaag ttggaggatg   11520
ccaaggaatt gttggagtca tcggaccaga tattgaggag tatgaaaggt ttatcgagca   11580
ctagcatagt ctacatcctg attgcagtgt gtcttggagg gttgataggg atccccgctt   11640
taatatgttg ctgcaggggg cgttgtaaca aaaagggaga acaagttggt atgtcaagac   11700
caggcctaaa gcctgatctt acgggaacat caaaatccta tgtaaggtcg ctctgatcct   11760
ctacaactct tgaaacacaa atgtcccaca agtctcctct tcgtcatcaa gcaaccaccg   11820
cacccagcat caagcccacc tgaaattatc tccggcttcc ctctggccga acaatatcgg   11880
tagttaatta aaacttaggg tgcaagatca tcgataatgt caccacaacg agaccggata   11940
aatgccttct acaaagataa ccccccatccc aagggaagta ggatagtcat taacagagaa   12000
catcttatga ttgatagacc ttatgttttg ctggctgttc tgtttgtcat gtttctgagc   12060
ttgatcgggt tgctagccat tgcaggaatt cgacttcatc gggcagccat ctacaccgca    12120
gagatccata aaagcctcag caccaatcta gatgtaacta actcaatcga gcatcaggtc   12180
```

```
aaggacgtgc tgacaccact cttcaaaatc atcggtgatg aagtgggcct gaggacacct   12240
cagagattca ctgacctagt gaaattaatc tctgacaaga ttaaattcct taatccggat   12300
agggagtacg acttcagaga tctcacttgg tgtatcaacc cgccagagag aatcaaattg   12360
gattatgatc aatactgtgc agatgtggct gctgaagagc tcatgaatgc attggtgaac   12420
tcaactctac tggagaccag aacaaccaat cagttcctag ctgtctcaaa gggaaactgc   12480
tcagggccca ctacaatcag aggtcaattc tcaaacatgt cgctgtccct gttagacttg   12540
tatttaggtc gaggttacaa tgtgtcatct atagtcacta tgacatccca gggaatgtat   12600
gggggaactt acctagtgga aaagcctaat ctgagcagca aaaggtcaga gttgtcacaa   12660
ctgagcatgt accgagtgtt tgaagtaggt gttatcagaa atccgggttt ggggggctccg   12720 gtgttccata tgacaaacta tcttgagcaa ccagtcagta atgatctcag caactgtatg   12780
gtggctttgg gggagctcaa actcgcagcc ctttgtcacg ggaagattc  tatcacaatt   12840 ccctatcagg gatcagggaa aggtgtcagc ttccagctcg tcaagctagg tgtctggaaa   12900
tccccaaccg acatgcaatc ctgggtcccc ttatcaacgg atgatccagt gatagacagg   12960
ctttacctct catctcacag aggtgttatc gctgacaacc aagcaaaatg gctgtcccg    13020 acaacacgaa cagatgacaa gttgcgaatg gagacatgct tccaacaggc gtgtaagggt   13080
aaaatccaag cactctgcga gaatcccgag tgggcaccat tgaaggataa caggattcct   13140
tcatacgggg tcttgtctgt tgatctgagt ctgacagttg agcttaaaat caaaattgct   13200 tcggattcg  ggccattgat cacacacggt tcagggatgg acctatacaa atccaaccac   13260
aacaatgtgt attggctgac tatcccgcca atgaagaacc tagccttagg tgtaatcaac   13320
acattggagt ggataccgag attcaaggtt agtccctacc tcttcactgt cccaattaag   13380
gaagcaggcg aagactgcca tgccccaaca tacctacctg cggaggtgga tggtgatgtc   13440
aaactcagtt ccaatctggt gattctacct ggtcaagatc tccaatatgt tttggcaacc   13500
tacgatactt ccagggttga acatgctgtg gtttattacg tttacagccc aagccgctca   13560
ttttcttact tttatccttt taggttgcct ataaaggggg tccccatcga attcaagtg   13620 gaatgcttca catgggacca aaaactctgg tgccgtcact tctgtgtgct tgcggactca   13680
gaatctggtg gacatatcac tcactctggg atggtgggca tgggagtcag ctgcacagtc   13740
acccgggaag atggaaccaa tcgcagatag ggctgctagt gaaccaatca catgatgtca   13800
cccagacatc aggcataccc actagtgtga aatagacatc agaattaaga aaaacgtagg   13860
gtccaagtgg ttccccgtta tggactcgct atctgtcaac cagatcttat accctgaagt   13920
tcacctagat agcccgatag ttaccaataa gatagtagcc atcctggagt atgctcgagt   13980
ccctcacgct tacagcctgg aggacccttac actgtgtcag aacatcaagc accgcctaaa   14040
aaacggattt tccaaccaaa tgattataaa caatgtggaa gttgggaatg tcatcaagtc   14100
caagcttagg agttatccgg cccactctca tattccatat ccaaattgta atcaggattt   14160
atttaacata aaagacaaag agtcaacgag gaagatccgt gaactcctca aaagggggaa   14220
ttcgctgtac tccaaagtca gtgataaggt tttccaatgc ttaagggaca ctaactcacg   14280
gcttggccta ggctccgaat tgagggagga catcaaggag aaagttatta acttgggagt   14340
ttacatgcac agctcccagt ggttttgagcc cttttctgttt tggtttacag tcaagactga   14400
gatgaggtca gtgattaaat cacaaaccca tacttgccat aggaggagac acacacctgt   14460
attcttcact ggtagttcag ttgagttgct aatctctcgt gaccttgttg ctataatcag   14520
```

```
taaagagtct caacatgtat attacctgac atttgaactg gttttgatgt attgtgatgt    14580
catagagggg aggttaatga cagagaccgc tatgactatt gatgctaggt atacagagct    14640
tctaggaaga gtcagataca tgtggaaact gatagatggt ttcttccctg cactcgggaa    14700
tccaacttat caaattgtag ccatgctgga gcctctttca cttgcttacc tgcagctgag    14760
ggatataaca gtagaactca gaggtgcttt ccttaaccac tgctttactg aaatacatga    14820
tgttcttgac caaacgggt tttctgatga aggtacttat catgagttaa ctgaagctct    14880
agattacatt ttcataactg atgacataca tctgacaggg gagattttct cattttttcag   14940 aagtttcggc cacccagac ttgaagcagt aacggctgct gaaaatgtta ggaaatacat    15000
gaatcagcct aaagtcattg tgtatgagac tctgatgaaa ggtcatgcca tattttgtgg    15060
aatcataatc aacggctatc gtgacaggca cggaggcagt tggccaccgc tgaccctccc    15120
cctgcatgct gcagacacaa tccggaatgc tcaagcttca ggtgaagggt taacacatga    15180
gcagtgcgtt gataactgga atcttttgc tggagtgaaa tttggctgct ttatgcctct    15240
tagcctggat agtgatctga caatgtacct aaaggacaag gcacttgctg ctctccaaag    15300
ggaatgggat tcagtttacc cgaaagagtt cctgcgttac gaccctccca agggaaccgg    15360
gtcacggagg cttgtagatg ttttccttaa tgattcgagc tttgacccat atgatgtgat    15420
aatgtatgtt gtaagtggag cttacctcca tgaccctgag ttcaacctgt cttacagcct    15480
gaaagaaaag gagatcaagg aaacaggtag acttttgct aaaatgactt acaaaatgag    15540
ggcatgccaa gtgattgctg aaaatctaat ctcaaacggg attggcaaat attttaagga    15600
caatgggatg ccaaggatg agcacgattt gactaaggca ctccacactc tagctgtctc    15660
aggagtcccc aaagatctca agaaagtca cagggggggg ccagtcttaa aaacctactc    15720
ccgaagccca gtccacacaa gtaccaggaa cgtgagagca gcaaaagggt ttatagggtt    15780
ccctcaagta attcggcagg accaagacac tgatcatccg gagaatatgg aagcttacga    15840
gacagtcagt gcatttatca cgactgatct caagaagtac tgccttaatt ggagatatga    15900
gaccatcagc ttgtttgcac agaggctaaa tgagatttac ggattgccct cattttttcca    15960 gtggctgcat aagaggcttg agacctctgt cctgtatgta agtgaccctc attgccccc    16020 cgaccttgac gcccatatcc cgttatataa agtccccaat gatcaaatct tcattaagta    16080
ccctatggga ggtatagaag ggtattgtca gaagctgtgg accatcagca ccattcccta    16140 tctataccctg gctgcttatg agagcggagt aaggattgct tcgttagtgc aagggggacaa    16200 tcagaccata gccgtaacaa aaagggtacc cagcacatgg ccctacaacc ttaagaaacg    16260
ggaagctgct agagtaacta gagattactt tgtaattctt aggcaaaggc tacatgatat    16320
tggccatcac ctcaaggcaa atgagacaat tgtttcatca catttttttg tctattcaaa    16380
aggaatatat tatgatgggc tacttgtgtc ccaatcactc aagagcatcg caagatgtgt    16440
attctggtca gagactatag ttgatgaaac aagggcagca tgcagtaata ttgctacaac    16500
aatggctaaa agcatcgaga gaggttatga ccgttacctt gcatattccc tgaacgtcct    16560
aaaagtgata cagcaaattc tgatctctct tggcttcaca atcaattcaa ccatgacccg    16620
ggatgtagtc atacccctcc tcacaaacaa cgacctctta ataaggatgg cactgttgcc    16680
cgctcctatt gggggggatga attatctgaa tatgagcagg ctgtttgtca gaaacatcgg    16740
tgatccagta acatcatcaa ttgctgatcta caagagaatg attctcgcct cactaatgcc    16800
tgaagagacc ctccatcagg taatgacaca acaaccgggg gactcttcat tcctagactg    16860
ggctagcgac ccttactcag caaatcttgt atgtgtccag agcatcacta gactcctcaa    16920
```

```
gaacataact gcaaggtttg tcctgatcca tagtccaaac ccaatgttaa aaggattatt   16980
ccatgatgac agtaaagaag aggacgaggg actggcggca ttcctcatgg acaggcatat   17040
tatagtacct agggcagctc atgaaatcct ggatcatagt gtcacagggg caagagagtc   17100
tattgcaggc atgctggata ccacaaaagg cttgattcga gccagcatga ggaagggggg   17160
tttaacctct cgagtgataa ccagattgtc caattatgac tatgaacaat tcagagcagg   17220
gatggtgcta ttgacaggaa gaaagagaaa tgtcctcatt gacaaagagt catgttcagt   17280
gcagctggcg agagctctaa gaagccatat gtgggcgagg ctagctcgag gacggcctat   17340
ttacggcctt gaggtccctg atgtactaga atctatgcga ggccacctta ttcggcgtca   17400
tgagacatgt gtcatctgcg agtgtggatc agtcaactac ggatggtttt ttgtcccctc   17460
gggttgccaa ctggatgata ttgacaagga aacatcatcc ttgagagtcc catatattgg   17520
ttctaccact gatgagagaa cagacatgaa gcttgccttc gtaagagccc aagtcgatc    17580
cttgcgatct gctgttagaa tagcaacagt gtactcatgg gcttacggtg atgatgatag   17640
ctcttggaac gaagcctggt tgttggctag gcaaagggcc aatgtgagcc tggaggagct   17700
aagggtgatc actcccatct caacttcgac taatttagcg cataggttga gggatcgtag   17760
cactcaagtg aaatactcag gtacatccct tgtccgagtg gcgaggtata ccacaatctc   17820
caacgacaat ctctcatttg tcatatcaga taagaaggtt gatactaact ttatatacca   17880
acaaggaatg cttctagggt tgggtgtttt agaaacattg tttcgactcg agaaagatac   17940
cggatcatct aacacggtat tacatcttca cgtcgaaaca gattgttgcg tgatcccgat   18000
gatagatcat cccaggatac ccagctcccg caagctagag ctgagggcag agctatgtac   18060
caacccattg atatatgata atgcaccttt aattgacaga gatgcaacaa ggctatacac   18120
ccagagccat aggaggcacc ttgtggaatt tgttacatgg tccacacccc aactatatca   18180
cattttagct aagtccacag cactatctat gattgacctg gtaacaaaat ttgagaagga   18240
ccatatgaat gaaatttcag ctctcatagg ggatgacgat atcaatagtt tcataactga   18300
gtttctgctc atagagccaa gattattcac tatctacttg gccagtgtg cggccatcaa   18360
ttgggcattt gatgtacatt atcatagacc atcagggaaa tatcagatgg gtgagctgtt   18420
gtcatcgttc cttttctagaa tgagcaaagg agtgtttaag gtgcttgtca atgctctaag   18480
ccacccaaag atctacaaga aattctggca ttgtggtatt atagagccta tccatggtcc   18540
ttcacttgat gctcaaaact tgcacacaac tgtgtgcaac atggtttaca catgctatat   18600
gacctacctc gacctgttgt tgaatgaaga gttagaagag ttcacatttc tcttgtgtga   18660
aagcgacgag gatgtagtac cggacagatt cgacaacatc caggcaaaac acttatgtgt   18720
tctggcagat ttgtactgtc aaccagggac ctgcccacca attcgaggtc taagaccggt   18780
agagaaatgt gcagttctaa ccgaccatat caaggcagag gctatgttat ctccagcagg   18840
atcttcgtgg aacataaatc caattattgt agaccattac tcatgctccc tgacttatct   18900
ccggcgagga tcgatcaaac agataagatt gagagttgat ccaggattca ttttcgacgc   18960
cctcgctgag gtaaatgtca gtcagccaaa gatcggcagc aacaacatct caaatatgag   19020
catcaaggct ttcagacccc cacacgatga tgttgcaaaa ttgctcaaag atatcaacac   19080
aagcaagcac aatcttccca tttcaggggg caatctcgcc aattatgaaa tccatgcttt   19140
ccgcagaatc gggttgaact catctgcttg ctacaaagct gttgagatat caacattaat   19200
taggagatgc cttgagccag gggaggacgg cttgttcttg ggtgagggat cgggttctat   19260
```

```
gttgatcact tataaggaga tacttaaact aaacaagtgc ttctataata gtggggtttc    19320
cgccaattct agatctggtc aaagggaatt agcaccctat ccctccgaag ttggccttgt    19380
cgaacacaga atgggagtag gtaatattgt caaagtgctc tttaacggga ggcccgaagt    19440
cacgtgggta ggcagtgtag attgcttcaa tttcatagtt agtaatatcc ctacctctag    19500
tgtggggttt atccattcag atatagagac cttgcctgac aaagatacta tagagaagct    19560
agaggaattg gcagccatct tatcgatggc tctgctcctg ggcaaaatag gatcaatact    19620
ggtgattaag cttatgcctt tcagcgggga ttttgttcag ggatttataa gttatgtagg    19680
gtctcattat agagaagtga accttgtata ccctagatac agcaacttca tatctactga    19740
atcttatttg gttatgacag atctcaaggc taaccggcta atgaatcctg aaaagattaa    19800
gcagcagata attgaatcat ctgtgaggac ttcacctgga cttataggtc acatcctatc    19860
cattaagcaa ctaagctgca tacaagcaat tgtgggagac gcagttagta gaggtgatat    19920
caatcctact ctgaaaaaac ttacacctat agagcaggtg ctgatcaatt gcgggttggc    19980
aattaacgga cctaagctgt gcaaagaatt gatccaccat gatgttgcct cagggcaaga    20040
tggattgctt aattctatac tcatcctcta cagggagttg gcaagattca aagacaacca    20100
aagaagtcaa caagggatgt tccacgccta ccccgtattg gtaagtagca ggcaacgaga    20160
acttatatct aggatcaccc gcaaattttg ggggcacatt cttctttact ccgggaacaa    20220
aaagttgata aataagttta tccagaatct caagtccggc tatctgatac tagacttaca    20280
ccagaatatc ttcgttaaga atctatccaa gtcagagaaa cagattatta tgacgggggg    20340
tttgaaacgt gagtgggttt ttaaggtaac agtcaaggag accaaagaat ggtataagtt    20400
agtcggatac agtgccctga ttaaggacta attggttgaa ctccggaacc ctaatcctgc    20460
cctaggtggt taggcattat ttgcaatata ttaaagaaaa ctttgaaaat acgaagtttc    20520
tattcccagc tttgtctggt ggccggcata gtcccagcct cctcgctggc gctggctggg    20580
caacattccg aggggaccgt ccccacggta atggcgaatg ggacgcggcc gatccggctg    20640
ctaacaaagc ccgaaaggaa gctgagttgg ctgctggcgc tggctgggca ataactagca    20700 taacccccttg gggcctctaa acgggtcttg aggggttttt tgctgaaagg aggaactata    20760
tccggatgcg gccgcgcgct tggcgtaatc atggtcatag ctgtttcctg tgtgaaattg    20820
ttatccgctc acaattccac acaacatacg agccggaagc ataaagtgta aagcctgggg    20880
tgcctaatga gtgagctaac tcacattaat tgcgttgcgc tcactgcccg ctttccagtc    20940
gggaaacctg tcgtgccagc tgcattaatg aatcggccaa cgcgcgggga gaggcggttt    21000
gcgtattggg cgctcttccg cttcctcgct cactgactcg ctgcgctcgg tcgttcggct    21060
gcggcgagcg gtatcagctc actcaaaggc ggtaatacgg ttatccacag aatcaggga    21120 taacgcagga aagaacatgt gagcaaaagg ccagcaaaag gccaggaacc gtaaaaaggc    21180
cgcgttgctg gcgttttcc ataggctccg ccccccctgac gagcatcaca aaaatcgacg    21240
ctcaagtcag aggtggcgaa acccgacagg actataaaga taccaggcgt ttccccctgg    21300
aagctccctc gtgcgctctc ctgttccgac cctgccgctt accggatacc tgtccgcctt    21360
tctcccttcg ggaagcgtgg cgctttctca tagctcacgc tgtaggtatc tcagttcggt    21420
gtaggtcgtt cgctccaagc tgggctgtgt gcacgaaccc cccgttcagc ccgaccgctg    21480
cgccttatcc ggtaactatc gtcttgagtc caacccggta agacacgact tatcgccact    21540
ggcagcagcc actggtaaca ggattagcag agcgaggtat gtaggcggtg ctacagagtt    21600
cttgaagtgg tggcctaact acggctacac tagaaggaca gtatttggta tctgcgctct    21660
```

```
gctgaagcca gttaccttcg gaaaaagagt tggtagctct tgatccggca aacaaaccac   21720
cgctggtagc ggtggttttt ttgtttgcaa gcagcagatt acgcgcagaa aaaaggatc    21780 tcaagaagat cctttgatct tttctacggg gtctgacgct cagtggaacg aaaactcacg   21840
ttaagggatt ttggtcatga gattatcaaa aaggatcttc acctagatcc ttttaaatta   21900
aaaatgaagt tttaaatcaa tctaaagtat atatgagtaa acttggtctg acagttacca   21960
atgcttaatc agtgaggcac ctatctcagc gatctgtcta tttcgttcat ccatagttgc   22020
ctgactcccc gtcgtgtaga taactacgat acgggagggc ttaccatctg gccccagtgc   22080
tgcaatgata ccgcgagacc cacgctcacc ggctccagat ttatcagcaa taaaccagcc   22140
agccggaagg gccgagcgca gaagtggtcc tgcaacttta tccgcctcca tccagtctat   22200
taattgttgc cgggaagcta gagtaagtag ttcgccagtt aatagtttgc gcaacgttgt   22260
tgccattgct acaggcatcg tggtgtcacg ctcgtcgttt ggtatggctt cattcagctc   22320
cggttcccaa cgatcaaggc gagttacatg atcccccatg ttgtgcaaaa aagcggttag   22380
ctccttcggt cctccgatcg ttgtcagaag taagttggcc gcagtgttat cactcatggt   22440
tatggcagca ctgcataatt ctcttactgt catgccatcc gtaagatgct tttctgtgac   22500
tggtgagtac tcaaccaagt cattctgaga atagtgtatg cggcgaccga gttgctcttg   22560
cccggcgtca atacgggata taccgcgcc acatagcaga actttaaaag tgctcatcat   22620
tggaaaacgt tcttcggggc gaaaactctc aaggatctta ccgctgttga tccagttc    22680 gatgtaaccc actcgtgcac ccaactgatc ttcagcatct tttactttca ccagcgtttc   22740
tgggtgagca aaaacaggaa ggcaaaatgc cgcaaaaaag ggaataaggg cgacacggaa   22800
atgttgaata ctcatactct tccttttca atattatga agcattatc agggttattg     22860 tctcatgagc ggatacatat ttgaatgtat ttagaaaaat aaacaaatag gggttccgcg   22920
cacatttccc cgaaaagtgc cacctg                                        22946
```

<210> SEQ ID NO 4
<211> LENGTH: 22916
<212> TYPE: DNA
<213> ORGANISM: Artificial Sequence
<220> FEATURE:
<223> OTHER INFORMATION: MV Wu S in position 3

<400> SEQUENCE: 4

```
ggacgcgccc tgtagcggcg cattaagcgc ggcgggtgtg gtggttacgc gcagcgtgac     60
cgctacactt gccagcgccc tagcgcccgc tcctttcgct ttcttccctt cctttctcgc    120
cacgttcgcc ggctttcccc gtcaagctct aaatcggggg ctcccttag ggttccgatt    180 tagtgcttta cggcacctcg accccaaaaa acttgattag ggtgatggtt cacgtagtgg   240
gccatcgccc tgatagacgg ttttcgccc tttgacgttg gagtccacgt tctttaatag    300
tggactcttg ttccaaactg gaacaacact caaccctatc tcggtctatt cttttgattt    360
ataagggatt ttgccgattt cggcctattg gttaaaaaat gagctgattt aacaaaaatt    420
taacgcgaat tttaacaaaa tattaacgtt tacaatttcg cgccattcgc cattcaggct    480
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg cgcgccgtta atacgactca ctatagggag acccaagctg    660
gctagctttg tttggtctga tgagtcccgt gaggacgaaa cccggcgtac cgggtcacca    720
```

```
aacaaagttg ggtaaggata gttcaatcaa tgatcatctt ctagtgcact taggattcaa    780
gatcctatta tcagggacaa gagcaggatt agggatatcc gagatggcca cacttttaag    840
gagcttagca ttgttcaaaa gaaacaagga caaaccaccc attacatcag gatccggtgg    900
agccatcaga ggaatcaaac acattattat agtaccaatc cctggagatt cctcaattac    960
cactcgatcc agacttctgg accggttggt gaggttaatt ggaaacccgg atgtgagcgg   1020
gcccaaacta cagggggcac taataggtat attatcctta tttgtggagt ctccaggtca   1080
attgattcag aggatcaccg atgaccctga cgttagcata aggctgttag aggttgtcca   1140
gagtgaccag tcacaatctg gccttacctt cgcatcaaga ggtaccaaca tggaggatga   1200
ggcggaccaa tacttttcac atgatgatcc aattagtagt gatcaatcca ggttcggatg   1260
gttcgggaac aaggaaatct cagatattga agtgcaagac cctgagggat tcaacatgat   1320
tctgggtacc atcctagccc aaatttgggt cttgctcgca aaggcggtta cggccccaga   1380
cacggcagct gattcggagc taagaaggtg ataaagtac acccaacaaa gaagggtagt    1440
tggtgaattt agattggaga gaaatggtt ggatgtggtg aggaacagga ttgccgagga   1500
cctctcctta cgccgattca tggtcgctct aatcctggat atcaagagaa cacccggaaa   1560
caaacccagg attgctgaaa tgatatgtga cattgataca tatatcgtag aggcaggatt   1620
agccagtttt atcctgacta ttaagtttgg gatagaaact atgtatcctg ctcttggact   1680
gcatgaattt gctggtgagt tatccacact tgagtccttg atgaaccttt accagcaaat   1740
gggggaaact gcaccctaca tggtaatcct ggagaactca attcagaaca agttcagtgc   1800
aggatcatac cctctgctct ggagctatgc catgggagta ggagtggaac ttgaaaactc   1860
catgggaggt ttgaactttg gccgatctta ctttgatcca gcatatttta gattagggca   1920
agagatggta aggaggtcag ctggaaaggt cagttccaca ttggcatctg aactcggtat   1980
cactgccgag gatgcaaggc ttgtttcaga gattgcaatg catactactg aggacaagat   2040
cagtagagcg gttggaccca gacaagccca agtatcattt ctacacggtg atcaaagtga   2100
gaatgagcta ccgagattgg ggggcaagga agataggagg gtcaaacaga gtcgaggaga   2160
agccagggag agctacagag aaaccgggcc cagcagagca agtgatgcga gagctgccca   2220
tcttccaacc ggcacacccc tagacattga cactgcaacg gagtccagcc aagatccgca   2280
ggacagtcga aggtcagctg acgccctgct taggctgcaa gccatggcag gaatctcgga   2340
agaacaaggc tcagacacgg acaccccctat agtgtacaat gacagaaatc ttctagacta   2400
ggtgcgagag gccgagggcc agaacaacat ccgcctacca tccatcattg ttataaaaaa   2460
cttaggaacc aggtccacac agccgccagc ccatcaacca tccactccca cgattggagc   2520
caatggcaga gagcaggca cgccatgtca aaaacggact ggaatgcatc cgggctctca   2580
aggccgagcc catcggctca ctggccatcg aggaagctat ggcagcatgg tcagaaatat   2640
cagacaaccc aggacaggag cgagccacct gcagggaaga gaaggcaggc agttcgggtc   2700
tcagcaaacc atgcctctca gcaattggat caactgaagg cggtgcacct cgcatccgcg   2760
gtcagggacc tggagagagc gatgacgacg ctgaaacttt gggaatcccc ccaagaaatc   2820
tccaggcatc aagcactggg ttacagtgtt attacgttta tgatcacagc ggtgaagcgg   2880
ttaagggaat ccaagatgct gactctatca tggttcaatc aggccttgat ggtgatagca   2940
ccctctcagg aggagacaat gaatctgaaa acagcgatgt ggatattggc gaacctgata   3000
ccgagggata tgctatcact gaccggggat ctgctcccat ctctatgggg ttcagggctt   3060
ctgatgttga aactgcagaa ggaggggaga tccacgagct cctgagactc caatccagag   3120
```

```
gcaacaactt tccgaagctt gggaaaactc tcaatgttcc tccgccccg gaccccggta    3180 gggccagcac ttccgggaca cccattaaaa agggcacaga cgcgagatta gcctcatttg    3240
gaacggagat cgcgtcttta ttgacaggtg gtgcaaccca atgtgctcga aagtcaccct    3300
cggaaccatc agggccaggt gcacctgcgg ggaatgtccc cgagtgtgtg agcaatgccg    3360
cactgataca ggagtggaca cccgaatctg gtaccacaat ctccccgaga tcccagaata    3420
atgaagaagg gggagactat tatgatgatg agctgttctc tgatgtccaa gatattaaaa    3480
cagccttggc caaaatacac gaggataatc agaagataat ctccaagcta gaatcactgc    3540
tgttattgaa gggagaagtt gagtcaatta agaagcagat caacaggcaa aatatcagca    3600
tatccaccct ggaaggacac ctctcaagca tcatgatcgc cattcctgga cttgggaagg    3660
atcccaacga ccccactgca gatgtcgaaa tcaatcccga cttgaaaccc atcataggca    3720
gagattcagg ccgagcactg gccgaagttc tcaagaaacc cgttgccagc cgacaactcc    3780
aaggaatgac aaatggacgg accagttcca gaggacagct gctgaaggaa tttcagctaa    3840
agccgatcgg gaaaaagatg agctcagccg tcgggtttgt tcctgacacc ggccctgcat    3900
cacgcagtgt aatccgctcc attataaaat ccagccggct agaggaggat cggaagcgtt    3960
acctgatgac tctccttgat gatatcaaag gagccaatga tcttgccaag ttccaccaga    4020
tgctgatgaa gataataatg aagtagctac agctcaactt acctgccaac ccatgccag    4080 tcgatcatcc atcattgtta taaaaaactt aggaaccagg tccacacaga gtgatacgcg    4140
tacgccacca tgttcgtgtt tctggtgctg ctgcctctgg tgagctccca gtgcgtgaac    4200
ctgaccacaa ggacccagct gccccctgcc tataccaatt ccttcacacg gggcgtgtac    4260
tatcccgaca aggtgttccg gagcagcgtg ctgcactcca cacaggatct gtttctgcct    4320
ttcttttcta acgtgacctg gttccacgcc atccacgtga gcggcaccaa tggcacaaag    4380
cggttcgaca atccagtgct gcccttaac gatggcgtgt acttcgcctc caccgagaag    4440
tctaacatca tcagaggctg gatctttggc accacactgg acagcaagac acagtccctg    4500
ctgatcgtga acaatgccac caacgtggtc atcaaggtgt gcgagttcca gttttgtaat    4560
gatccattcc tgggcgtgta ctatcacaag aacaataagt cttggatgga gagcgagttt    4620
cgcgtgtatt cctctgccaa caattgcaca tttgagtacg tgtcccagcc cttcctgatg    4680
gacctggagg gcaagcaggg caatttcaag aacctgaggg agttcgtgtt taagaatatc    4740
gatggctact tcaaaatcta ctccaagcac accccaatca acctggtgcg cgacctgcca    4800
cagggcttct ctgccctgga gccactggtg gatctgccca tcggcatcaa catcacccgg    4860
tttcagacac tgctggccct gcacagaagc tacctgacac caggcgacag ctcctctgga    4920
tggaccgcag gagcagcagc ctactatgtg ggctatctgc agcccaggac cttcctgctg    4980
aagtacaacg agaatggcac catcacagac gccgtggatt gcgccctgga tcccctgtct    5040
gagaccaagt gtacactgaa gagctttacc gtggagaagg gcatctatca gacaagcaat    5100
ttcagggtgc agcctaccga gtccatcgtg cgctttccca atatcacaaa cctgtgccct    5160
tttggcgagg tgttcaacgc aacccgcttc gccagcgtgt acgcctggaa taggaagcgc    5220
atctccaact gcgtggccga ctattctgtg ctgtacaaca gcgcctcctt ctctacccttt    5280 aagtgctatg gcgtgagccc cacaaagctg aatgacctgt gctttaccaa cgtgtacgcc    5340
gattccttcg tgatcagggg cgacgaggtg cgccagatcg caccaggaca gacaggcaag    5400
atcgcagact acaattataa gctgcctgac gatttcaccg gctgcgtgat cgcctggaac    5460
```

```
tctaacaatc tggatagcaa agtgggcggc aactacaatt atctgtaccg gctgtttaga    5520
aagtctaatc tgaagccatt cgagagggac atctccacag aaatctacca ggccggctct    5580
accccctgca atggcgtgga gggctttaac tgttatttcc ctctgcagag ctacggcttc    5640
cagccaacaa acggcgtggg ctatcagccc taccgcgtgg tggtgctgtc ttttgagctg    5700
ctgcacgcac ctgcaacagt gtgcggacca agaagagca ccaatctggt gaagaacaag    5760
tgcgtgaact tcaacttcaa cggactgacc ggaacaggcg tgctgaccga gtccaacaag    5820
aagttcctgc cttttcagca gttcggcagg gacatcgcag ataccacaga cgccgtgcgc    5880
gaccctcaga ccctggagat cctggacatc acaccatgct ccttcggcgg cgtgtctgtg    5940
atcacaccag gcaccaatac aagcaaccag gtggccgtgc tgtatcagga cgtgaattgt    6000
accgaggtgc cagtggcaat ccacgcagat cagctgaccc ctacatggcg ggtgtactct    6060
accggcagca acgtgttcca gacaagagcc ggatgcctga tcggagcaga gcacgtgaac    6120
aatagctatg agtgcgacat ccctatcggc gccggcatct gtgcctccta ccagacccag    6180
acaaactccc caaggagagc acggtctgtg gccagccagt ccatcatcgc ctataccatg    6240
agcctgggcg ccgagaattc cgtggcctac tccaacaatt ctatcgccat ccctaccaac    6300
ttcacaatct ccgtgaccac agagatcctg ccagtgagca tgaccaagac atccgtggac    6360
tgcacaatgt atatctgtgg cgattccacc gagtgctcta acctgctgct gcagtacggc    6420 tcttttgta cccagctgaa tagagccctg acaggcatcg ccgtggagca ggacaagaac    6480
acacaggagg tgttcgccca ggtgaagcaa atctacaaga ccccacccat caaggacttt    6540
ggcggcttca acttcagcca gatcctgccc gatcctagca agccatccaa gcggtctttt    6600
atcgaggacc tgctgttcaa caaggtgacc ctggccgatg ccggcttcat caagcagtat    6660
ggcgattgcc tgggcgacat cgccgccaga gacctgatct gtgcccagaa gtttaatggc    6720
ctgaccgtgc tgcctccact gctgacagat gagatgatcg cccagtacac atctgccctg    6780
ctggccggaa ccatcacaag cggatggacc ttcggcgcag gagccgccct gcagatcccc    6840
tttgccatgc agatggccta tcggttcaac ggcatcggcg tgacccagaa tgtgctgtac    6900
gagaaccaga gctgatcgc caatcagttt aactccgcca tcggcaagat ccaggactct    6960
ctgagctcca cagccagcgc cctgggcaag ctgcaggatg tggtgaatca gaacgcccag    7020
gccctgaata ccctggtgaa gcagctgtct agcaacttcg gcgccatctc ctctgtgctg    7080
aatgacatcc tgagccggct ggacaaggtg gaggcagagg tgcagatcga ccggctgatc    7140
acaggcagac tgcagtccct gcagacctac gtgacacagc agctgatcag ggcagcagag    7200
atcagggcct ctgccaatct ggccgccacc aagatgagcg agtgcgtgct gggccagtcc    7260
aagagagtgg acttttgtgg caagggctat acctgatga gcttcccaca gtccgcccct    7320
cacggagtgg tgtttctgca cgtgacctac gtgccagccc aggagaagaa cttcaccaca    7380
gcaccagcaa tctgccacga tggcaaggca cactttccta ggagggcgt gttcgtgagc    7440 aacggcaccc actggtttgt gacacagcgc aatttctacg agccacagat catcaccaca    7500
gacaatacat tcgtgtccgg caactgtgac gtggtcatcg gcatcgtgaa caataccgtg    7560
tatgatcctc tgcagccaga gctggactct tttaaggagg agctggataa gtacttcaag    7620
aatcacacca gccccgacgt ggatctgggc gacatctctg gcatcaatgc cagcgtggtg    7680
aacatccaga aggagatcga caggctgaac gaggtggcca gaatctgaa cgagtccctg    7740 atcgatctgc aggagctggg caagtatgag cagtacatca gtggccctg gtatatctgg    7800 ctgggcttca tcgccggcct gatcgccatc gtgatggtga ccatcatgct gtgctgtatg    7860
```

```
acaagctgct gttcctgcct gaagggctgc tgttcttgtg gcagctgctg taagtttgat    7920
gaggacgata gcgagcctgt gctgaagggc gtgaagctgc actacacctg atagctagcg    7980
atcgcccacc tagtacaacc taaatccatt ataaaaaact taggagcaaa gtgattgcct    8040
cccaaggtcc acaatgacag agacctacga cttcgacaag tcggcatggg acatcaaagg    8100
gtcgatcgct ccgatacaac ccaccaccta cagtgatggc aggctggtgc cccaggtcag    8160
agtcatagat cctggtctag gcgacaggaa ggatgaatgc tttatgtaca tgtttctgct    8220
gggggttgtt gaggacagcg attccctagg gcctccaatc gggcgagcat ttgggttcct    8280
gcccttaggt gttggcagat ccacagcaaa gcccgaaaaa ctcctcaaag aggccactga    8340
gcttgacata gttgttagac gtacagcagg gctcaatgaa aaactggtgt tctacaacaa    8400
caccccacta actctcctca cccttggag aaaggtccta acaacaggga gtgtcttcaa     8460
cgcaaaccaa gtgtgcaatg cggttaatct gataccgctc gataccccgc agaggttccg    8520
tgttgtttat atgagcatca cccgtctttc ggataacggg tattacaccg ttcctagaag    8580
aatgctggaa ttcagatcgg tcaatgcagt ggccttcaac ctgctggtga cccttaggat    8640
tgacaaggcg ataggccctg gaagatcat cgacaataca gagcaacttc ctgaggcaac     8700
atttatggtc cacatcggga acttcaggag aaagaagagt gaagtctact ctgccgatta    8760
ttgcaaaatg aaaatcgaaa agatgggcct ggttttttgca cttggtggga taggggcac    8820
cagtcttcac attagaagca caggcaaaat gagcaagact ctccatgcac aactcgggtt    8880
caagaagacc ttatgttacc cgctgatgga tatcaatgaa gaccttaatc gattactctg    8940
gaggagcaga tgcaagatag taagaatcca ggcagttttg cagccatcag ttcctcaaga    9000
attccgcatt tacgacgacg tgatcataaa tgatgaccaa ggactattca agttctgta     9060
gaccgtagtg cccagcaatg cccgaaaacg acccccctca caatgacagc cagaaggccc    9120
ggacaaaaaa gcccctccg aaagactcca cggaccaagc gagaggccag ccagcagccg     9180
acggcaagcg cgaacaccag gcggccccag cacagaacag ccctgacaca aggccaccac    9240
cagccacccc aatctgcatc ctcctcgtgg gaccccgag gaccaacccc caaggctgcc     9300
cccgatccaa accaccaacc gcatcccac caccccggg aaagaaaccc ccagcaattg      9360
gaaggcccct ccccctcttc ctcaacacaa gaactccaca accgaaccgc acaagcgacc    9420
gaggtgaccc aaccgcaggc atccgactcc ctagacagat cctctctccc cggcaaacta    9480
aacaaaactt agggccaagg aacatacaca cccaacagaa cccagacccc ggcccacggc    9540
gccgcgcccc caaccccga caaccagagg gagcccccaa ccaatcccgc cggctccccc     9600
ggtgcccaca ggcagggaca ccaaccccg aacagaccca gcacccaacc atcgacaatc     9660
caagacgggg gggccccccc aaaaaaaggc cccaggggc cgacagccag caccgcgagg    9720
aagcccaccc accccacaca cgaccacggc aaccaaacca gaacccagac cacccctggc    9780
caccagctcc cagactcggc catcaccccg cagaaaggaa aggccacaac ccgcgcaccc    9840
cagccccgat ccggcgggga gccacccaac ccgaaccagc acccaagagc gatccccgaa    9900
ggaccccga accgcaaagg acatcagtat cccacagcct ctccaagtcc cccggtctcc     9960
tcctcttctc gaagggacca aaagatcaat ccaccacacc cgacgacact caactcccca   10020
cccctaaagg agacaccggg aatcccagaa tcaagactca tccaatgtcc atcatgggtc   10080
tcaaggtgaa cgtctctgcc atattcatgg cagtactgtt aactctccaa acacccaccg   10140
gtcaaatcca ttggggcaat ctctctaaga taggggtggt aggaatagga agtgcaagct   10200
```

```
acaaagttat gactcgttcc agccatcaat cattagtcat aaaattaatg cccaatataa    10260
ctctcctcaa taactgcacg agggtagaga ttgcagaata caggagacta ctgagaacag    10320
ttttggaacc aattagagat gcacttaatg caatgaccca gaatataaga ccggttcaga    10380
gtgtagcttc aagtaggaga cacaagagat ttgcgggagt agtcctggca ggtgcggccc    10440
taggcgttgc cacagctgct cagataacag ccggcattgc acttcaccag tccatgctga    10500
actctcaagc catcgacaat ctgagagcga gcctggaaac tactaatcag caattgaga    10560 caatcagaca agcagggcag gagatgatat tggctgttca gggtgtccaa gactacatca    10620
ataatgagct gataccgtct atgaaccaac tatcttgtga tttaatcggc cagaagctcg    10680
ggctcaaatt gctcagatac tatacagaaa tcctgtcatt atttggcccc agtttacggg    10740
accccatatc tgcggagata tctatccagg ctttgagcta tgcgcttgga ggagacatca    10800
ataaggtgtt agaaaagctc ggatacagtg gaggtgattt actgggcatc ttagagagcg    10860
gaggaataaa ggcccggata actcacgtcg acacagagtc ctacttcatt gtcctcagta    10920
tagcctatcc gacgctgtcc gagattaagg gggtgattgt ccaccggcta gaggggtct    10980 cgtacaacat aggctctcaa gagtggtata ccactgtgcc caagtatgtt gcaacccaag    11040
ggtaccttat ctcgaatttt gatgagtcat cgtgtacttt catgccagag gggactgtgt    11100
gcagccaaaa tgccttgtac ccgatgagtc ctctgctcca agaatgcctc cgggggtaca    11160
ccaagtcctg tgctcgtaca ctcgtatccg ggtcttttgg gaaccggttc attttatcac    11220
aagggaacct aatagccaat tgtgcatcaa tcctttgcaa gtgttacaca acaggaacga    11280
tcattaatca agaccctgac aagatcctaa catacattgc tgccgatcac tgcccggtag    11340
tcgaggtgaa cggcgtgacc atccaagtcg ggagcaggag gtatccagac gctgtgtact    11400
tgcacagaat tgacctcggt cctcccatat cattggagag gttggacgta gggacaaatc    11460
tggggaatgc aattgctaag ttggaggatg ccaaggaatt gttggagtca tcggaccaga    11520
tattgaggag tatgaaaggt ttatcgagca ctagcatagt ctacatcctg attgcagtgt    11580
gtcttggagg gttgatagg atccccgctt taatatgttg ctgcaggggg cgttgtaaca    11640
aaaagggaga acaagttggt atgtcaagac caggcctaaa gcctgatctt acgggaacat    11700
caaaatccta tgtaaggtcg ctctgatcct ctacaactct gaaacacaa atgtcccaca    11760 agtctcctct tcgtcatcaa gcaaccaccg cacccagcat caagcccacc tgaaattatc    11820
tccggcttcc ctctggccga acaatatcgg tagttaatta aaacttaggg tgcaagatca    11880
tcgataatgt caccacaacg agaccggata aatgccttct acaaagataa cccccatccc    11940
aagggaagta ggatagtcat taacagagaa catcttatga ttgatagacc ttatgttttg    12000
ctggctgttc tgtttgtcat gtttctgagc ttgatcgggt tgctagccat tgcaggaatt    12060
cgacttcatc gggcagccat ctacaccgca gagatccata aaagcctcag caccaatcta    12120
gatgtaacta actcaatcga gcatcaggtc aaggacgtgc tgacaccact cttcaaaatc    12180
atcggtgatg aagtgggcct gaggacacct cagagattca ctgacctagt gaaattaatc    12240
tctgacaaga ttaaattcct taatccggat agggagtacg acttcagaga tctcacttgg    12300
tgtatcaacc cgccagagag aatcaaattg gattatgatc aatactgtgc agatgtggct    12360
gctgaagagc tcatgaatgc attggtgaac tcaactctac tggagaccag aacaaccaat    12420
cagttcctag ctgtctcaaa gggaaactgc tcagggccca ctacaatcag aggtcaattc    12480
tcaaacatgt cgctgtccct gttagacttg tatttaggtc gaggttacaa tgtgtcatct    12540
atagtcacta tgacatccca gggaatgtat gggggaactt acctagtgga aaagcctaat    12600
```

-continued

```
ctgagcagca aaaggtcaga gttgtcacaa ctgagcatgt accgagtgtt tgaagtaggt    12660
gttatcagaa atccgggttt gggggctccg gtgttccata tgacaaacta tcttgagcaa    12720
ccagtcagta atgatctcag caactgtatg gtggctttgg gggagctcaa actcgcagcc    12780
ctttgtcacg gggaagattc tatcacaatt ccctatcagg gatcagggaa aggtgtcagc    12840
ttccagctcg tcaagctagg tgtctggaaa tccccaaccg acatgcaatc ctgggtcccc    12900
ttatcaacgg atgatccagt gatagacagg ctttacctct catctcacag aggtgttatc    12960
gctgacaacc aagcaaaatg ggctgtcccg acaacacgaa cagatgacaa gttgcgaatg    13020
gagacatgct tccaacaggc gtgtaagggt aaaatccaag cactctgcga gaatcccgag    13080
tgggcaccat tgaaggataa caggattcct tcatacgggg tcttgtctgt tgatctgagt    13140
ctgacagttg agcttaaaat caaaattgct tcgggattcg ggccattgat cacacacggt    13200
tcagggatgg acctatacaa atccaaccac aacaatgtgt attggctgac tatcccgcca    13260
atgaagaacc tagccttagg tgtaatcaac acattggagt ggataccgag attcaaggtt    13320
agtccctacc tcttcactgt cccaattaag aagcaggcg aagactgcca tgccccaaca    13380
tacctacctg cggaggtgga tggtgatgtc aaactcagtt ccaatctggt gattctacct    13440
ggtcaagatc tccaatatgt tttggcaacc tacgatactt ccagggttga acatgctgtg    13500
gtttattacg tttacagccc aagccgctca ttttcttact tttatccttt taggttgcct    13560
ataaaggggg tccccatcga attacaagtg gaatgcttca catgggacca aaaactctgg    13620
tgccgtcact tctgtgtgct tgcggactca gaatctggtg gacatatcac tcactctggg    13680
atggtgggca tgggagtcag ctgcacagtc acccgggaag atggaaccaa tcgcagatag    13740
ggctgctagt gaaccaatca catgatgtca cccagacatc aggcataccc actagtgtga    13800
aatagacatc agaattaaga aaaacgtagg gtccaagtgg ttccccgtta tggactcgct    13860
atctgtcaac cagatcttat accctgaagt tcacctagat agcccgatag ttaccaataa    13920
gatagtagcc atcctggagt atgctcgagt ccctcacgct tacagcctgg aggaccctac    13980
actgtgtcag aacatcaagc accgcctaaa aaacggattt tccaaccaaa tgattataaa    14040
caatgtggaa gttgggaatg tcatcaagtc caagcttagg agttatccgg cccactctca    14100
tattccatat ccaaattgta atcaggattt atttaacata gaagacaaag agtcaacgag    14160
gaagatccgt gaactcctca aaaaggggaa ttcgctgtac tccaaagtca gtgataaggt    14220
tttccaatgc ttaagggaca ctaactcacg gcttggccta ggctccgaat tgagggagga    14280
catcaaggag aaagttatta acttgggagt ttacatgcac agctcccagt ggtttgagcc    14340
ctttctgttt tggtttacag tcaagactga gatgaggtca gtgattaaat cacaaaccca    14400
tacttgccat aggaggagac acacacctgt attcttcact ggtagttcag ttgagttgct    14460
aatctctcgt gaccttgttg ctataatcag taaagagtct caacatgtat attacctgac    14520
atttgaactg gttttgatgt attgtgatgt catagagggg aggttaatga cagagaccgc    14580
tatgactatt gatgctaggt atacagagct tctaggaaga gtcagataca tgtggaaact    14640
gatagatggt ttcttccctg cactcgggaa tccaacttat caaattgtag ccatgctgga    14700
gcctctttca cttgcttacc tgcagctgag ggatataaca gtagaactca gaggtgcttt    14760
ccttaaccac tgctttactg aaatacatga tgttcttgac caaaacgggt tttctgatga    14820
aggtacttat catgagttaa ctgaagctct agattacatt ttcataactg atgacataca    14880
tctgacaggg gagattttct cattttttcag aagtttcggc cacccccagac ttgaagcagt    14940
```

```
aacggctgct gaaaatgtta ggaaatacat gaatcagcct aaagtcattg tgtatgagac   15000
tctgatgaaa ggtcatgcca tattttgtgg aatcataatc aacggctatc gtgacaggca   15060
cggaggcagt tggccaccgc tgaccctccc cctgcatgct gcagacacaa tccggaatgc   15120
tcaagcttca ggtgaagggt taacacatga gcagtgcgtt gataactgga aatcttttgc   15180
tggagtgaaa tttggctgct ttatgcctct tagcctggat agtgatctga caatgtacct   15240
aaaggacaag gcacttgctg ctctccaaag ggaatgggat tcagtttacc cgaaagagtt   15300
cctgcgttac gaccctccca agggaaccgg gtcacggagg cttgtagatg ttttccttaa   15360
tgattcgagc tttgacccat atgatgtgat aatgtatgtt gtaagtggag cttacctcca   15420
tgaccctgag ttcaacctgt cttacagcct gaaagaaaag gagatcaagg aaacaggtag   15480 acttttgct aaaatgactt acaaaatgag ggcatgccaa gtgattgctg aaaatctaat   15540
ctcaaacggg attggcaaat attttaagga caatgggatg ccaaggatg agcacgattt   15600 gactaaggca ctccacactc tagctgtctc aggagtcccc aaagatctca agaaagtca   15660 caggggggg ccagtcttaa aaacctactc ccgaagccca gtccacacaa gtaccaggaa   15720
cgtgagagca gcaaaagggt ttatagggtt ccctcaagta attcggcagg accaagacac   15780
tgatcatccg gagaatatgg aagcttacga gacagtcagt gcatttatca cgactgatct   15840
caagaagtac tgccttaatt ggagatatga gaccatcagc ttgtttgcac agaggctaaa   15900 tgagattac ggattgccct catttttcca gtggctgcat aagaggcttg agacctctgt   15960
cctgtatgta agtgaccctc attgccccccc cgaccttgac gcccatatcc cgttatataa   16020
agtccccaat gatcaaatct tcattaagta ccctatggga ggtatagaag ggtattgtca   16080
gaagctgtgg accatcagca ccattcccta tctatacctg gctgcttatg agagcggagt   16140
aaggattgct tcgttagtgc aaggggacaa tcagaccata gccgtaacaa aaagggtacc   16200
cagcacatgg ccctacaacc ttaagaaacg ggaagctgct agagtaacta gagattactt   16260
tgtaattctt aggcaaaggc tacatgatat tggccatcac ctcaaggcaa atgagacaat   16320
tgtttcatca catttttttg tctattcaaa aggaatatat tatgatgggc tacttgtgtc   16380
ccaatcactc aagagcatcg caagatgtgt attctggtca gagactatag ttgatgaaac   16440
aagggcagca tgcagtaata ttgctacaac aatggctaaa agcatcgaga gaggttatga   16500
ccgttacctt gcatattccc tgaacgtcct aaaagtgata cagcaaaattc tgatctctct   16560 tggcttcaca atcaattcaa ccatgacccg ggatgtagtc ataccctcc tcacaaacaa   16620 cgacctctta ataaggatgg cactgttgcc cgctcctatt ggggggatga attatctgaa   16680
tatgagcagg ctgtttgtca gaaacatcgg tgatccagta acatcatcaa ttgctgatct   16740
caagagaatg attctcgcct cactaatgcc tgaagagacc ctccatcagg taatgacaca   16800
acaaccgggg gactcttcat tcctagactg ggctagcgac ccttactcag caaatcttgt   16860
atgtgtccag agcatcacta gactcctcaa gaacataact gcaaggtttg tcctgatcca   16920
tagtccaaac ccaatgttaa aaggattatt ccatgatgac agtaaagaag aggacgaggg   16980
actggcggca ttcctcatgg acaggcatat tatagtacct agggcagctc atgaaatcct   17040
ggatcatagt gtcacagggg caagagagtc tattgcaggc atgctggata ccacaaaagg   17100
cttgattcga gccagcatga ggaaggggg tttaacctct cgagtgataa ccagattgtc   17160
caattatgac tatgaacaat tcagagcagg gatggtgcta ttgacaggaa gaaagagaaa   17220
tgtcctcatt gacaaagagt catgttcagt gcagctggcg agagctctaa gaagccatat   17280
gtgggcgagg ctagctcgag gacggcctat ttacggcctt gaggtccctg atgtactaga   17340
```

```
atctatgcga ggccacctta ttcggcgtca tgagacatgt gtcatctgcg agtgtggatc    17400
agtcaactac ggatggtttt ttgtcccctc gggttgccaa ctggatgata ttgacaagga    17460
aacatcatcc ttgagagtcc catatattgg ttctaccact gatgagagaa cagacatgaa    17520
gcttgccttc gtaagagccc caagtcgatc cttgcgatct gctgttagaa tagcaacagt    17580
gtactcatgg gcttacggtg atgatgatag ctcttggaac gaagcctggt tgttggctag    17640
gcaaagggcc aatgtgagcc tggaggagct aagggtgatc actcccatct caacttcgac    17700
taatttagcg cataggttga gggatcgtag cactcaagtg aaatactcag gtacatccct    17760
tgtccgagtg gcgaggtata ccacaatctc aacgacaat ctctcatttg tcatatcaga     17820
taagaaggtt gatactaact ttatatacca acaaggaatg cttctagggt tgggtgtttt    17880
agaaacattg tttcgactcg agaaagatac cggatcatct aacacggtat tacatcttca    17940
cgtcgaaaca gattgttgcg tgatcccgat gatagatcat cccaggatac ccagctcccg    18000
caagctagag ctgagggcag agctatgtac caacccattg atatatgata atgcacctttt   18060 aattgacaga gatgcaacaa ggctatacac ccagagccat aggaggcacc ttgtggaatt    18120
tgttacatgg tccacacccc aactatatca cattttagct aagtccacag cactatctat    18180
gattgacctg gtaacaaaat ttgagaagga ccatatgaat gaaatttcag ctctcatagg    18240
ggatgacgat atcaatagtt tcataactga gtttctgctc atagagccaa gattattcac    18300
tatctacttg ggccagtgtg cggccatcaa ttgggcattt gatgtacatt atcatagacc    18360
atcagggaaa tatcagatgg gtgagctgtt gtcatcgttc ctttctagaa tgagcaaagg    18420
agtgtttaag gtgcttgtca atgctctaag ccacccaaag atctacaaga aattctggca    18480
ttgtggtatt atagagccta tccatggtcc ttcacttgat gctcaaaact tgcacacaac    18540
tgtgtgcaac atggtttaca catgctatat gacctacctc gacctgttgt tgaatgaaga    18600
gttagaagag ttcacatttc tcttgtgtga aagcgacgag gatgtagtac cggacagatt    18660
cgacaacatc caggcaaaac acttatgtgt tctggcagat ttgtactgtc aaccagggac    18720
ctgcccacca attcgaggtc taagaccggt agagaaatgt gcagttctaa ccgaccatat    18780
caaggcagag gctatgttat ctccagcagg atcttcgtgg aacataaatc caattattgt    18840
agaccattac tcatgctccc tgacttatct ccggcgagga tcgatcaaac agataagatt    18900
gagagttgat ccaggattca ttttcgacgc cctcgctgag gtaaatgtca gtcagccaaa    18960
gatcggcagc aacaacatct caaatatgag catcaaggct ttcagacccc cacacgatga    19020
tgttgcaaaa ttgctcaaag atatcaacac aagcaagcac aatcttccca tttcaggggg    19080
caatctcgcc aattatgaaa tccatgcttt ccgcagaatc gggttgaact catctgcttg    19140
ctacaaagct gttgagatat caacattaat taggagatgc cttgagccag gggaggacgg    19200
cttgttcttg ggtgagggat cgggttctat gttgatcact tataaggaga tacttaaact    19260
aaacaagtgc ttctataata gtggggtttc cgccaattct agatctggtc aaagggaatt    19320
agcaccctat ccctccgaag ttggccttgt cgaacacaga atgggagtag gtaatattgt    19380
caaagtgctc tttaacggga ggcccgaagt cacgtgggta ggcagtgtag attgcttcaa    19440
tttcatagtt agtaatatcc ctacctctag tgtgggggttt atccattcag atatagagac    19500
cttgcctgac aaagatacta tagagaagct agaggaattg gcagccatct tatcgatggc    19560
tctgctcctg ggcaaaatag gatcaatact ggtgattaag cttatgcctt tcagcgggga    19620
ttttgttcag ggatttataa gttatgtagg gtctcattat agagaagtga accttgtata    19680
```

```
ccctagatac agcaacttca tatctactga atcttatttg gttatgacag atctcaaggc    19740
taaccggcta atgaatcctg aaaagattaa gcagcagata attgaatcat ctgtgaggac    19800
ttcacctgga cttataggtc acatcctatc cattaagcaa ctaagctgca tacaagcaat    19860
tgtgggagac gcagttagta gaggtgatat caatcctact ctgaaaaaac ttacacctat    19920
agagcaggtg ctgatcaatt gcgggttggc aattaacgga cctaagctgt gcaaagaatt    19980
gatccaccat gatgttgcct cagggcaaga tggattgctt aattctatac tcatcctcta    20040
cagggagttg gcaagattca aagacaacca aagaagtcaa caagggatgt ccacgcctta    20100
ccccgtattg gtaagtagca ggcaacgaga acttatatct aggatcaccc gcaaattttg    20160
ggggcacatt cttctttact ccgggaacaa aaagttgata aataagttta ccagaatctt    20220
caagtccggc tatctgatac tagacttaca ccagaatatc ttcgttaaga atctatccaa    20280
gtcagagaaa cagattatta tgacgggggg tttgaaacgt gagtgggttt ttaaggtaac    20340
agtcaaggag accaaagaat ggtataagtt agtcggatac agtgccctga ttaaggacta    20400
attggttgaa ctccggaacc ctaatcctgc cctaggtggt taggcattat ttgcaatata    20460
ttaaagaaaa ctttgaaaat acgaagtttc tattcccagc tttgtctggt ggccggcata    20520
gtcccagcct cctcgctggc gctggctggg caacattccg aggggaccgt ccccacggta    20580
atggcgaatg ggacgcggcc gatccggctg ctaacaaagc ccgaaaggaa gctgagttgg    20640
ctgctggcgc tggctgggca ataactagca taacccccttg gggcctctaa acgggtcttg    20700
aggggttttt tgctgaaagg aggaactata tccggatgcg gccgcgcgct ggcgtaatc    20760
atggtcatag ctgtttcctg tgtgaaattg ttatccgctc acaattccac acaacatacg    20820
agccggaagc ataaagtgta aagcctgggg tgcctaatga gtgagctaac tcacattaat    20880
tgcgttgcgc tcactgcccg ctttccagtc gggaaacctg tcgtgccagc tgcattaatg    20940
aatcggccaa cgcgcgggga gaggcggttt gcgtattggg cgctcttccg cttcctcgct    21000
cactgactcg ctgcgctcgg tcgttcggct gcggcgagcg gtatcagctc actcaaaggc    21060
ggtaatacgg ttatccacag aatcagggga taacgcagga agaacatgt gagcaaaagg    21120
ccagcaaaag gccaggaacc gtaaaaaggc cgcgttgctg cgttttttcc ataggctccg    21180
ccccccctgac gagcatcaca aaaatcgacg ctcaagtcag aggtggcgaa acccgacagg    21240
actataaaga taccaggcgt ttccccctgg aagctccctc gtgcgctctc ctgttccgac    21300
cctgccgctt accggatacc tgtccgcctt tctcccttcg ggaagcgtgg cgctttctca    21360
tagctcacgc tgtaggtatc tcagttcggt gtaggtcgtt cgctccaagc tgggctgtgt    21420
gcacgaaccc cccgttcagc ccgaccgctg cgccttatcc ggtaactatc gtcttgagtc    21480
caacccggta agacacgact tatcgccact ggcagcagcc actggtaaca ggattagcag    21540
agcgaggtat gtaggcggtg ctacagagtt cttgaagtgg tggcctaact acggctacac    21600
tagaaggaca gtatttggta tctgcgctct gctgaagcca gttaccttcg aaaaagagt    21660
tggtagctct tgatccggca aacaaaccac cgctggtagc ggtggttttt tgtttgcaa    21720
gcagcagatt acgcgcagaa aaaaaggatc tcaagaagat cctttgatct tttctacggg    21780
gtctgacgct cagtggaacg aaaactcacg ttaagggatt ttggtcatga gattatcaaa    21840
aaggatcttc acctagatcc ttttaaatta aaaatgaagt tttaaatcaa tctaaagtat    21900
atatgagtaa acttggtctg acagttacca atgcttaatc agtgaggcac ctatctcagc    21960
gatctgtcta tttcgttcat ccatagttgc ctgactcccc gtcgtgtaga taactacgat    22020
acgggagggc ttaccatctg gccccagtgc tgcaatgata ccgcgagacc cacgctcacc    22080
```

```
ggctccagat ttatcagcaa taaaccagcc agccggaagg gccgagcgca gaagtggtcc   22140
tgcaacttta tccgcctcca tccagtctat taattgttgc cgggaagcta gagtaagtag   22200
ttcgccagtt aatagtttgc gcaacgttgt tgccattgct acaggcatcg tggtgtcacg   22260
ctcgtcgttt ggtatggctt cattcagctc cggttcccaa cgatcaaggc gagttacatg   22320
atcccccatg ttgtgcaaaa aagcggttag ctccttcggt cctccgatcg ttgtcagaag   22380
taagttggcc gcagtgttat cactcatggt tatggcagca ctgcataatt ctcttactgt   22440
catgccatcc gtaagatgct tttctgtgac tggtgagtac tcaaccaagt cattctgaga   22500
atagtgtatg cggcgaccga gttgctcttg cccggcgtca atacgggata ataccgcgcc   22560
acatagcaga actttaaaag tgctcatcat tggaaaacgt tcttcggggc gaaaactctc   22620
aaggatctta ccgctgttga gatccagttc gatgtaaccc actcgtgcac ccaactgatc   22680
ttcagcatct tttactttca ccagcgtttc tgggtgagca aaaacaggaa ggcaaaatgc   22740
cgcaaaaaag gaataagggg cgacacggaa atgttgaata ctcatactct tcctttttca   22800
atattattga agcatttatc agggttattg tctcatgagc ggatacatat ttgaatgtat   22860
ttagaaaaat aaacaaatag gggttccgcg cacatttccc cgaaaagtgc cacctg       22916
```

<210> SEQ ID NO 5
<211> LENGTH: 22916
<212> TYPE: DNA
<213> ORGANISM: Artificial Sequence
<220> FEATURE:
<223> OTHER INFORMATION: MV WuhanCoV S in position 6

<400> SEQUENCE: 5

```
ggacgcgccc tgtagcggcg cattaagcgc ggcgggtgtg gtggttacgc gcagcgtgac     60
cgctacactt gccagcgccc tagcgcccgc tcctttcgct ttcttccctt cctttctcgc    120
cacgttcgcc ggctttcccc gtcaagctct aaatcggggg ctcccttag ggttccgatt    180 tagtgcttta cggcacctcg accccaaaaa acttgattag ggtgatggtt cacgtagtgg    240
gccatcgccc tgatagacgg ttttcgccc tttgacgttg gagtccacgt tctttaatag    300
tggactcttg ttccaaactg gaacaacact caacccatc tcggtctatt cttttgattt    360
ataagggatt tgccgattt cggcctattg gttaaaaaat gagctgattt aacaaaaatt    420
taacgcgaat tttaacaaaa tattaacgtt acaatttcg cgccattcgc cattcaggct    480
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg cgcgccgtta atacgactca ctatagggag acccaagctg    660
gctagctttg tttggtctga tgagtcccgt gaggacgaaa cccggcgtac cgggtcacca    720
aacaaagttg ggtaaggata gttcaatcaa tgatcatctt ctagtgcact taggattcaa    780
gatcctatta tcagggacaa gagcaggatt agggatatcc gagatggcca cacttttaag    840
gagcttagca ttgttcaaaa gaaacaagga caaaccaccc attacatcag gatccggtgg    900
agccatcaga ggaatcaaac acattattat agtaccaatc cctggagatt cctcaattac    960
cactcgatcc agacttctgg accggttggt gaggttaatt ggaaacccgg atgtgagcgg   1020
gcccaaacta acaggggcac taataggtat attatcctta tttgtggagt ctccaggtca   1080
attgattcag aggatcaccg atgacccga cgttagcata aggctgttag aggttgtcca   1140
gagtgaccag tcacaatctg gccttacctt cgcatcaaga ggtaccaaca tggaggatga   1200
```

```
ggcggaccaa tacttttcac atgatgatcc aattagtagt gatcaatcca ggttcggatg    1260
gttcgggaac aaggaaatct cagatattga agtgcaagac cctgaggat tcaacatgat    1320 tctgggtacc atcctagccc aaatttgggt cttgctcgca aaggcggtta cggccccaga    1380
cacggcagct gattcggagc taagaaggtg gataaagtac acccaacaaa gaagggtagt    1440
tggtgaattt agattggaga gaaatggtt ggatgtggtg aggaacagga ttgccgagga    1500
cctctcctta cgccgattca tggtcgctct aatcctggat atcaagaaa cacccggaaa    1560 caaacccagg attgctgaaa tgatatgtga cattgataca tatatcgtag aggcaggatt    1620
agccagtttt atcctgacta ttaagtttgg gatagaaact atgtatcctg ctcttggact    1680
gcatgaattt gctggtgagt tatccacact tgagtccttg atgaaccttt accagcaaat    1740
gggggaaact gcaccctaca tggtaatcct ggagaactca attcagaaca agttcagtgc    1800
aggatcatac cctctgctct ggagctatgc catgggagta ggagtggaac ttgaaaactc    1860
catgggaggt ttgaactttg gccgatctta ctttgatcca gcatatttta gattagggca    1920
agagatggta aggaggtcag ctggaaaggt cagttccaca ttggcatctg aactcggtat    1980
cactgccgag gatgcaaggc ttgtttcaga gattgcaatg catactactg aggacaagat    2040
cagtagagcg gttggaccca gacaagccca agtatcattt ctacacggtg atcaaagtga    2100
gaatgagcta ccgagattgg ggggcaagga agataggagg gtcaaacaga gtcgaggaga    2160
agccagggag agctacagag aaaccgggcc cagcagagca agtgatgcga gagctgccca    2220
tcttccaacc ggcacacccc tagacattga cactgcaacg gagtccagcc aagatccgca    2280
ggacagtcga aggtcagctg acgccctgct taggctgcaa gccatggcag gaatctcgga    2340
agaacaaggc tcagacacgg acacccctat agtgtacaat gacagaaatc ttctagacta    2400
ggtgcgagag gccgagggcc agaacaacat ccgcctacca tccatcattg ttataaaaaa    2460
cttaggaacc aggtccacac agccgccagc ccatcaacca tccactccca cgattggagc    2520
caatggcaga gagcaggca cgccatgtca aaaacggact ggaatgcatc cgggctctca    2580
aggccgagcc catcggctca ctggccatcg aggaagctat ggcagcatgg tcagaaatat    2640
cagacaaccc aggacaggag cgagccacct gcagggaaga gaaggcaggc agttcgggtc    2700
tcagcaaacc atgcctctca gcaattggat caactgaagg cggtgcacct cgcatccgcg    2760
gtcagggacc tggagagagc gatgacgacg ctgaaacttt gggaatcccc caagaaatc    2820 tccaggcatc aagcactggg ttacagtgtt attacgttta tgatcacagc ggtgaagcgg    2880
ttaagggaat ccaagatgct gactctatca tggttcaatc aggccttgat ggtgatagca    2940
ccctctcagg aggagacaat gaatctgaaa acagcgatgt ggatattggc gaacctgata    3000
ccgagggata tgctatcact gaccggggat ctgctcccat ctctatgggg ttcagggctt    3060
ctgatgttga aactgcagaa ggagggggaga tccacgagct cctgagactc caatccagag    3120
gcaacaactt tccgaagctt gggaaaactc tcaatgttcc tccgcccccg gaccccggta    3180
gggccagcac ttccgggaca cccattaaaa agggcacaga cgcgagatta gcctcatttg    3240
gaacggagat cgcgtctttta ttgacaggtg gtgcaaccca atgtgctcga aagtcaccct    3300
cggaaccatc agggccaggt gcacctgcgg ggaatgtccc cgagtgtgtg agcaatgccg    3360
cactgataca ggagtggaca cccgaatctg gtaccacaat ctccccgaga tcccagaata    3420
atgaagaagg gggagactat tatgatgatg agctgttctc tgatgtccaa gatattaaaa    3480
cagccttggc caaatacac gaggataatc agaagataat ctccaagcta gaatcactgc    3540
tgttattgaa gggagaagtt gagtcaatta agaagcagat caacaggcaa aatatcagca    3600
```

```
tatccaccct ggaaggacac ctctcaagca tcatgatcgc cattcctgga cttgggaagg   3660
atcccaacga ccccactgca gatgtcgaaa tcaatcccga cttgaaaccc atcataggca   3720
gagattcagg ccgagcactg gccgaagttc tcaagaaacc cgttgccagc cgacaactcc   3780
aaggaatgac aaatggacgg accagttcca gaggacagct gctgaaggaa tttcagctaa   3840
agccgatcgg gaaaaagatg agctcagccg tcgggtttgt tcctgacacc ggccctgcat   3900
cacgcagtgt aatccgctcc attataaaat ccagccggct agaggaggat cggaagcgtt   3960
acctgatgac tctccttgat gatatcaaag gagccaatga tcttgccaag ttccaccaga   4020
tgctgatgaa gataataatg aagtagctac agctcaactt acctgccaac ccatgccag    4080 tcgacccacc tagtacaacc taaatccatt ataaaaact taggagcaaa gtgattgcct   4140
cccaaggtcc acaatgacag agacctacga cttcgacaag tcggcatggg acatcaaagg   4200
gtcgatcgct ccgatacaac ccaccaccta cagtgatggc aggctggtgc cccaggtcag   4260
agtcatagat cctggtctag gcgacaggaa ggatgaatgc tttatgtaca tgtttctgct   4320
gggggttgtt gaggacagcg attccctagg gcctccaatc gggcgagcat ttgggttcct   4380
gcccttaggt gttggcagat ccacagcaaa gcccgaaaaa ctcctcaaag aggccactga   4440
gcttgacata gttgttagac gtacagcagg gctcaatgaa aaactggtgt tctacaacaa   4500
caccccacta actctcctca cccttggag aaaggtccta acaacaggga gtgtcttcaa    4560
cgcaaaccaa gtgtgcaatg cggttaatct gataccgctc gataccccgc agaggttccg   4620
tgttgtttat atgagcatca cccgtctttc ggataacggg tattacaccg ttcctagaag   4680
aatgctggaa ttcagatcgg tcaatgcagt ggccttcaac ctgctggtga cccttaggat   4740
tgacaaggcg ataggccctg gaagatcat cgacaataca gagcaacttc ctgaggcaac    4800
atttatggtc cacatcggga acttcaggag aaagaagagt gaagtctact ctgccgatta   4860
ttgcaaaatg aaaatcgaaa agatgggcct ggttttgca cttggtggga tagggggcac    4920
cagtcttcac attagaagca caggcaaaat gagcaagact ctccatgcac aactcgggtt   4980
caagaagacc ttatgttacc cgctgatgga tatcaatgaa gaccttaatc gattactctg   5040
gaggagcaga tgcaagatag taagaatcca ggcagttttg cagccatcag ttcctcaaga   5100
attccgcatt tacgacgacg tgatcataaa tgatgaccaa ggactattca agttctgta    5160 gaccgtagtg cccagcaatg cccgaaaacg accccctca caatgacagc cagaaggccc    5220
ggacaaaaaa gccccctccg aaagactcca cggaccaagc gagaggccag ccagcagccg   5280
acggcaagcg cgaacaccag gcggcccag cacagaacag ccctgacaca aggccaccac    5340
cagccacccc aatctgcatc ctcctcgtgg acccccgag gaccaacccc caaggctgcc    5400
cccgatccaa accaccaacc gcatcccac caccccggg aaagaaaccc ccagcaattg     5460
gaaggcccct cccctcttc ctcaacacaa gaactccaca accgaaccgc acaagcgacc    5520
gaggtgaccc aaccgcaggc atccgactcc ctagacagat cctctctccc cggcaaacta   5580
aacaaaactt agggccaagg aacatacaca cccaacagaa cccagacccc ggcccacggc   5640
gccgcgcccc caaccccga caaccagagg gagccccaa ccaatcccgc cggctcccc     5700 ggtgcccaca ggcagggaca ccaacccccg aacagaccca gcacccaacc atcgacaatc   5760
caagacgggg gggccccccc aaaaaaaggc cccaggggc cgacagccag caccgcgagg   5820
aagcccaccc accccacaca cgaccacggc aaccaaacca gaaccagac cacccctgggc   5880 caccagctcc cagactcggc catcaccccg cagaaaggaa aggccacaac ccgcgcaccc   5940
```

```
cagccccgat ccggcgggga gccacccaac ccgaaccagc acccaagagc gatccccgaa    6000 ggaccccga accgcaaagg acatcagtat cccacagcct ctccaagtcc cccggtctcc     6060
tcctcttctc gaagggacca aaagatcaat ccaccacacc cgacgacact caactcccca    6120
cccctaaagg agacaccggg aatcccagaa tcaagactca tccaatgtcc atcatgggtc    6180
tcaaggtgaa cgtctctgcc atattcatgg cagtactgtt aactctccaa acacccaccg    6240
gtcaaatcca ttggggcaat ctctctaaga taggggtggt aggaatagga agtgcaagct    6300
acaaagttat gactcgttcc agccatcaat cattagtcat aaaattaatg cccaatataa    6360
ctctcctcaa taactgcacg agggtagaga ttgcagaata caggagacta ctgagaacag    6420
ttttggaacc aattagagat gcacttaatg caatgaccca gaatataaga ccggttcaga    6480
gtgtagcttc aagtaggaga cacaagagat ttgcgggagt agtcctggca ggtgcggccc    6540
taggcgttgc cacagctgct cagataacag ccggcattgc acttcaccag tccatgctga    6600
actctcaagc catcgacaat ctgagagcga gcctggaaac tactaatcag gcaattgaga    6660
caatcagaca agcagggcag gagatgatat tggctgttca gggtgtccaa gactacatca    6720
ataatgagct gataccgtct atgaaccaac tatcttgtga tttaatcggc cagaagctcg    6780
ggctcaaatt gctcagatac tatacagaaa tcctgtcatt atttggcccc agtttacggg    6840
accccatatc tgcggagata tctatccagg ctttgagcta tgcgcttgga ggagacatca    6900
ataaggtgtt agaaaagctc ggatacagtg gaggtgattt actgggcatc ttagagagcg    6960
gaggaataaa ggcccggata actcacgtcg acacagagtc ctacttcatt gtcctcagta    7020
tagcctatcc gacgctgtcc gagattaagg gggtgattgt ccaccggcta gagggggtct    7080
cgtacaacat aggctctcaa gagtggtata ccactgtgcc caagtatgtt gcaacccaag    7140
ggtaccttat ctcgaatttt gatgagtcat cgtgtacttt catgccagag gggactgtgt    7200
gcagccaaaa tgccttgtac ccgatgagtc ctctgctcca agaatgcctc cggggtaca    7260 ccaagtcctg tgctcgtaca ctcgtatccg ggtcttttgg gaaccggttc attttatcac    7320
aagggaacct aatagccaat tgtgcatcaa tcctttgcaa gtgttacaca acaggaacga    7380
tcattaatca agaccctgac aagatcctaa catacattgc tgccgatcac tgcccggtag    7440
tcgaggtgaa cggcgtgacc atccaagtcg ggagcaggag gtatccagac gctgtgtact    7500
tgcacagaat tgacctcggt cctcccatat cattggagag gttggacgta gggacaaatc    7560
tggggaatgc aattgctaag ttggaggatg ccaaggaatt gttggagtca tcggaccaga    7620
tattgaggag tatgaaaggt ttatcgagca ctagcatagt ctacatcctg attgcagtgt    7680
gtcttggagg gttgataggg atccccgctt taatatgttg ctgcaggggg cgttgtaaca    7740
aaaagggaga acaagttggt atgtcaagac caggcctaaa gcctgatctt acgggaacat    7800
caaaatccta tgtaaggtcg ctctgatcct ctacaactct gaaacacaa atgtcccaca     7860 agtctcctct tcgtcatcaa gcaaccaccg cacccagcat caagcccacc tgaaattatc    7920
tccggcttcc ctctggccga acaatatcgg tagttaatta aaacttaggg tgcaagatca    7980
tcgataatgt caccacaacg agaccggata aatgccttct acaaagataa cccccatccc    8040
aagggaagta ggatagtcat taacagagaa catcttatga ttgatagacc ttatgttttg    8100
ctggctgttc tgtttgtcat gtttctgagc ttgatcgggt tgctagccat tgcaggaatt    8160
cgacttcatc gggcagccat ctacaccgca gagatcccata aaagcctcag caccaatcta    8220
gatgtaacta actcaatcga gcatcaggtc aaggacgtgc tgacaccact cttcaaaatc    8280
atcggtgatg aagtgggcct gaggacacct cagagattca ctgacctagt gaaattaatc    8340
```

```
tctgacaaga ttaaattcct taatccggat agggagtacg acttcagaga tctcacttgg    8400
tgtatcaacc cgccagagag aatcaaattg gattatgatc aatactgtgc agatgtggct    8460
gctgaagagc tcatgaatgc attggtgaac tcaactctac tggagaccag aacaaccaat    8520
cagttcctag ctgtctcaaa gggaaactgc tcagggccca ctacaatcag aggtcaattc    8580
tcaaacatgt cgctgtccct gttagacttg tatttaggtc gaggttacaa tgtgtcatct    8640
atagtcacta tgcatcccca gggaatgtat gggggaactt acctagtgga aaagcctaat    8700
ctgagcagca aaggtcaga gttgtcacaa ctgagcatgt accgagtgtt tgaagtaggt    8760
gttatcagaa atccgggttt gggggctccg gtgttccata tgacaaacta tcttgagcaa    8820
ccagtcagta atgatctcag caactgtatg gtggctttgg gggagctcaa actcgcagcc    8880
ctttgtcacg gggaagattc tatcacaatt ccctatcagg gatcaggaa aggtgtcagc    8940 ttccagctcg tcaagctagg tgtctggaaa tccccaaccg acatgcaatc ctgggtcccc    9000
ttatcaacgg atgatccagt gatagacagg ctttacctct catctcacag aggtgttatc    9060
gctgacaacc aagcaaaatg ggctgtcccg acaacacgaa cagatgacaa gttgcgaatg    9120
gagacatgct tccaacaggc gtgtaagggt aaaatccaag cactctgcga gaatcccgag    9180
tgggcaccat tgaaggataa caggattcct tcatacgggg tcttgtctgt tgatctgagt    9240
ctgacagttg agcttaaaat caaaattgct tcgggattcg ggccattgat cacacacggt    9300
tcagggatgg acctatacaa atccaaccac aacaatgtgt attggctgac tatcccgcca    9360
atgaagaacc tagccttagg tgtaatcaac acattggagt ggataccgag attcaaggtt    9420
agtccctacc tcttcactgt cccaattaag gaagcaggcg aagactgcca tgccccaaca    9480
tacctacctg cggaggtgga tgtgatgtc aaactcagtt ccaatctggt gattctacct    9540
ggtcaagatc tccaatatgt tttggcaacc tacgatactt ccagggttga acatgctgtg    9600
gtttattacg tttacagccc aagccgctca ttttcttact tttatccttt taggttgcct    9660
ataaaggggg tccccatcga attacaagtg gaatgcttca catgggacca aaaactctgg    9720
tgccgtcact tctgtgtgct tgcggactca gaatctggtg gacatatcac tcactctggg    9780
atggtgggca tgggagtcag ctgcacagtc acccgggaag atggaaccaa tcgcagatag    9840
ggctgctagt gaaccaatca catgatgtca cccagacatc aggcatacccc accatccatc    9900 attgttataa aaaacttagg aaccaggtcc acacagagta tacgcgtac gccaccatgt    9960 tcgtgtttct ggtgctgctg cctctggtga gctcccagtg cgtgaacctg accacaagga    10020
cccagctgcc ccctgcctat accaattcct tcacacgggg cgtgtactat cccgacaagg    10080
tgttccggag cagcgtgctg cactccacac aggatctgtt tctgcctttc ttttctaacg    10140
tgacctggtt ccacgccatc cacgtgagcg gcaccaatgg cacaaagcgg ttcgacaatc    10200
cagtgctgcc ctttaacgat ggcgtgtact tcgcctccac cgagaagtct aacatcatca    10260
gaggctggat ctttggcacc acactggaca gcaagacaca gtccctgctg atcgtgaaca    10320
atgccaccaa cgtggtcatc aaggtgtgcg agttccagtt ttgtaatgat ccattcctgg    10380
gcgtgtacta tcacaagaac aataagtctt ggatggagag cgagtttcgc gtgtattcct    10440
ctgccaacaa ttgcacattt gagtacgtgt cccagccctt cctgatggac ctggagggca    10500
agcagggcaa tttcaagaac ctgagggagt tcgtgtttaa gaatatcgat ggctacttca    10560
aaatctactc caagcacacc ccaatcaacc tggtgcgcga cctgccacag gcttctctg    10620 ccctggagcc actggtggat ctgcccatcg gcatcaacat cacccggttt cagacactgc    10680
```

```
tggccctgca cagaagctac ctgacaccag gcgacagctc ctctggatgg accgcaggag   10740
cagcagccta ctatgtgggc tatctgcagc ccaggacctt cctgctgaag tacaacgaga   10800
atggcaccat cacagacgcc gtggattgcg ccctggatcc cctgtctgag accaagtgta   10860
cactgaagag ctttaccgtg gagaagggca tctatcagac aagcaatttc agggtgcagc   10920
ctaccgagtc catcgtgcgc tttcccaata tcacaaacct gtgcccttttt ggcgaggtgt   10980 tcaacgcaac ccgcttcgcc agcgtgtacg cctggaatag gaagcgcatc tccaactgcg   11040
tggccgacta ttctgtgctg tacaacagcg cctccttctc tacctttaag tgctatggcg   11100
tgagccccac aaagctgaat gacctgtgct ttaccaacgt gtacgccgat tccttcgtga   11160
tcaggggcga cgaggtgcgc cagatcgcac caggacagac aggcaagatc gcagactaca   11220
attataagct gcctgacgat ttcaccggct gcgtgatcgc ctggaactct aacaatctgg   11280
atagcaaagt gggcggcaac tacaattatc tgtaccggct gtttagaaag tctaatctga   11340
agccattcga gagggacatc tccacagaaa tctaccaggc cggctctacc ccctgcaatg   11400
gcgtggaggg ctttaactgt tatttccctc tgcagagcta cggcttccag ccaacaaacg   11460
gcgtgggcta tcagccctac cgcgtggtgg tgctgtcttt tgagctgctg cacgcacctg   11520
caacagtgtg cggaccaaag aagagcacca atctggtgaa gaacaagtgc gtgaacttca   11580
acttcaacgg actgaccgga acaggcgtgc tgaccgagtc caacaagaag ttcctgcctt   11640
ttcagcagtt cggcagggac atcgcagata ccacagacgc cgtgcgcgac cctcagaccc   11700
tggagatcct ggacatcaca ccatgctcct tcggcggcgt gtctgtgatc acaccaggca   11760
ccaatacaag caaccaggtg gccgtgctgt atcaggacgt gaattgtacc gaggtgccag   11820
tggcaatcca cgcagatcag ctgacccctg catggcgggt gtactctacc ggcagcaacg   11880
tgttccagac aagagccgga tgcctgatcg gagcagagca cgtgaacaat agctatgagt   11940
gcgacatccc tatcggcgcc ggcatctgtg cctcctacca gacccagaca aactcccaa   12000 ggagagcacg gtctgtggcc agccagtcca tcatcgccta ccatgagc ctgggcgccg   12060 agaattccgt ggcctactcc aacaattcta tcgccatccc taccaacttc acaatctccg   12120
tgaccacaga gatcctgcca gtgagcatga ccaagacatc cgtggactgc acaatgtata   12180
tctgtggcga ttccaccgag tgctctaacc tgctgctgca gtacggctct ttttgtaccc   12240
agctgaatag agccctgaca ggcatcgccg tggagcagga caagaacaca caggaggtgt   12300
tcgcccaggt gaagcaaatc tacaagaccc cacccatcaa ggactttggc ggcttcaact   12360
tcagccagat cctgcccgat cctagcaagc catccaagcg gtcttttatc gaggacctgc   12420
tgttcaacaa ggtgacctg ccgatgccg gcttcatcaa gcagtatggc gattgcctgg   12480
gcgacatcgc cgccagagac ctgatctgtg cccagaagtt taatggcctg accgtgctgc   12540
ctccactgct gacagatgag atgatcgccc agtacacatc tgccctgctg gccggaacca   12600
tcacaagcgg atggaccttc ggcgcaggag ccgccctgca gatccccttt gccatgcaga   12660
tggcctatcg gttcaacggc atcggcgtga cccagaatgt gctgtacgag aaccagaagc   12720
tgatcgccaa tcagtttaac tccgccatcg gcaagatcca ggactctctg agctccacag   12780
ccagcgccct gggcaagctg caggatgtgg tgaatcagaa cgcccaggcc ctgaataccc   12840
tggtgaagca gctgtctagc aacttcggcg ccatctcctc tgtgctgaat gacatcctga   12900
gccggctgga caaggtggag gcagaggtgc agatcgaccg gctgatcaca ggcagactgc   12960
agtccctgca gacctacgtg acacagcagc tgatcagggc agcagagatc agggcctctg   13020
ccaatctggc cgccaccaag atgagcgagt gcgtgctggg ccagtccaag agagtggact   13080
```

```
tttgtggcaa gggctatcac ctgatgagct tcccacagtc cgcccctcac ggagtggtgt   13140
ttctgcacgt gacctacgtg ccagcccagg agaagaactt caccacagca ccagcaatct   13200
gccacgatgg caaggcacac tttcctaggg agggcgtgtt cgtgagcaac ggcacccact   13260
ggtttgtgac acagcgcaat ttctacgagc cacagatcat caccacagac aatacattcg   13320
tgtccggcaa ctgtgacgtg gtcatcggca tcgtgaacaa taccgtgtat gatcctctgc   13380
agccagagct ggactctttt aaggaggagc tggataagta cttcaagaat cacaccagcc   13440
ccgacgtgga tctgggcgac atctctggca tcaatgccag cgtggtgaac atccagaagg   13500
agatcgacag gctgaacgag gtggccaaga atctgaacga gtccctgatc gatctgcagg   13560
agctgggcaa gtatgagcag tacatcaagt ggccctggta tatctggctg ggcttcatcg   13620
ccggcctgat cgccatcgtg atggtgacca tcatgctgtg ctgtatgaca agctgctgtt   13680
cctgcctgaa gggctgctgt tcttgtggca gctgctgtaa gtttgatgag gacgatagcg   13740
agcctgtgct gaagggcgtg aagctgcact acacctgagc tagcgatcgc actagtgtga   13800
aatagacatc agaattaaga aaaacgtagg gtccaagtgg ttccccgtta tggactcgct   13860
atctgtcaac cagatcttat accctgaagt tcacctagat agcccgatag ttaccaataa   13920
gatagtagcc atcctggagt atgctcgagt ccctcacgct tacagcctgg aggaccctac   13980
actgtgtcag aacatcaagc accgcctaaa aaacggattt tccaaccaaa tgattataaa   14040
caatgtggaa gttgggaatg tcatcaagtc caagcttagg agttatccgg cccactctca   14100
tattccatat ccaaattgta atcaggattt atttaacata gaagacaaag agtcaacgag   14160
gaagatccgt gaactcctca aaaagggaa ttcgctgtac tccaaagtca gtgataaggt   14220
tttccaatgc ttaagggaca ctaactcacg gcttggccta ggctccgaat tgagggagga   14280
catcaaggag aaagttatta acttgggagt ttacatgcac agctcccagt ggtttgagcc   14340
ctttctgttt tggtttacag tcaagactga gatgaggtca gtgattaaat cacaaaccca   14400
tacttgccat aggaggagac acacacctgt attcttcact ggtagttcag ttgagttgct   14460
aatctctcgt gaccttgttg ctataatcag taaagagtct caacatgtat attacctgac   14520
atttgaactg gttttgatgt attgtgatgt catagagggg aggttaatga cagagaccgc   14580
tatgactatt gatgctaggt atacagagct tctaggaaga gtcagataca tgtggaaact   14640
gatagatggt ttcttcccctg cactcgggaa tccaacttat caaattgtag ccatgctgga   14700
gcctctttca cttgcttacc tgcagctgag ggatataaca gtagaactca gaggtgcttt   14760
ccttaaccac tgctttactg aaatacatga tgttcttgac caaaacgggt tttctgatga   14820
aggtacttat catgagttaa ctgaagctct agattacatt ttcataactg atgacataca   14880
tctgacaggg gagattttct cattttttcag aagtttcggc cacccagac ttgaagcagt   14940 aacggctgct gaaaatgtta ggaaatacat gaatcagcct aaagtcattg tgtatgagac   15000
tctgatgaaa ggtcatgcca tattttgtgg aatcataatc aacggctatc gtgacaggca   15060
cggaggcagt tggccaccgc tgaccctccc cctgcatgct gcagacacaa tccggaatgc   15120
tcaagcttca ggtgaagggt taacacatga gcagtgcgtt gataactgga atcttttttgc   15180 tggagtgaaa tttggctgct ttatgcctct tagcctggat agtgatctga caatgtacct   15240
aaaggacaag gcacttgctg ctctccaaag ggaatgggat tcagtttacc cgaaagagtt   15300
cctgcgttac gaccctccca agggaaccgg gtcacggagg cttgtagatg ttttccttaa   15360
tgattcgagc tttgacccat atgatgtgat aatgtatgtt gtaagtggag cttacctcca   15420
```

```
tgaccctgag ttcaacctgt cttacagcct gaaagaaaag gagatcaagg aaacaggtag    15480 acttttttgct aaaatgactt acaaaatgag ggcatgccaa gtgattgctg aaaatctaat    15540
ctcaaacggg attggcaaat attttaagga caatgggatg gccaaggatg agcacgattt    15600
gactaaggca ctccacactc tagctgtctc aggagtcccc aaagatctca agaaagtca    15660 caggggggg ccagtcttaa aaacctactc ccgaagccca gtccacacaa gtaccaggaa    15720
cgtgagagca gcaaaagggt ttatagggtt ccctcaagta attcggcagg accaagacac    15780
tgatcatccg gagaatatgg aagcttacga gacagtcagt gcatttatca cgactgatct    15840
caagaagtac tgccttaatt ggagatatga gaccatcagc ttgtttgcac agaggctaaa    15900
tgagatttac ggattgccct cattttttcca gtggctgcat aagaggcttg agacctctgt    15960
cctgtatgta agtgaccctc attgccccc cgaccttgac gcccatatcc cgttatataa    16020
agtccccaat gatcaaatct tcattaagta ccctatggga ggtatagaag ggtattgtca    16080
gaagctgtgg accatcagca ccattcccta tctatacctg gctgcttatg agagcggagt    16140
aaggattgct tcgttagtgc aaggggacaa tcagaccata gccgtaacaa aaagggtacc    16200
cagcacatgg ccctacaacc ttaagaaacg ggaagctgct agagtaacta gagattactt    16260
tgtaattctt aggcaaaggc tacatgatat tggccatcac ctcaaggcaa atgagacaat    16320
tgtttcatca cattttttg tctattcaaa aggaatatat tatgatgggc tacttgtgtc    16380
ccaatcactc aagagcatcg caagatgtgt attctggtca gagactatag ttgatgaaac    16440
aagggcagca tgcagtaata ttgctacaac aatggctaaa agcatcgaga gaggttatga    16500
ccgttacctt gcatattccc tgaacgtcct aaaagtgata cagcaaattc tgatctctct    16560
tggcttcaca atcaattcaa ccatgacccg ggatgtagtc ataccctcc tcacaaacaa    16620 cgacctctta ataaggatgg cactgttgcc cgctcctatt gggggatga attatctgaa    16680 tatgagcagg ctgtttgtca gaaacatcgg tgatccagta acatcatcaa ttgctgatct    16740
caagagaatg attctcgcct cactaatgcc tgaagagacc ctccatcagg taatgacaca    16800
acaaccgggg gactcttcat tcctagactg ggctagcgac ccttactcag caaatcttgt    16860
atgtgtccag agcatcacta gactcctcaa gaacataact gcaaggtttg tcctgatcca    16920
tagtccaaac ccaatgttaa aaggattatt ccatgatgac agtaaagaag aggacgaggg    16980
actggcggca ttcctcatgg acaggcatat tatagtacct agggcagctc atgaaatcct    17040
ggatcatagt gtcacagggg caagagagtc tattgcaggc atgctggata ccacaaaagg    17100
cttgattcga gccagcatga ggaagggggg tttaacctct cgagtgataa ccagattgtc    17160
caattatgac tatgaacaat tcagagcagg gatggtgcta ttgacaggaa gaaagagaaa    17220
tgtcctcatt gacaaagagt catgttcagt gcagctggcg agagctctaa gaagccatat    17280
gtgggcgagg ctagctcgag gacggcctat ttacggcctt gaggtccctg atgtactaga    17340
atctatgcga ggccaccttta ttcggcgtca tgagacatgt gtcatctgcg agtgtggatc    17400
agtcaactac ggatggtttt ttgtccctc gggttgccaa ctggatgata ttgacaagga    17460
aacatcatcc ttgagagtcc catatattgg ttctaccact gatgagagaa cagacatgaa    17520
gcttgccttc gtaagagccc caagtcgatc cttgcgatct gctgttagaa tagcaacagt    17580
gtactcatgg gcttacggtg atgatgatag ctcttggaac gaagcctggt tgttggctag    17640
gcaaagggcc aatgtgagcc tggaggagct aagggtgatc actcccatct caacttcgac    17700 taattttagcg cataggttga gggatcgtag cactcaagtg aaatactcag gtacatccct    17760
tgtccgagtg gcgaggtata ccacaatctc caacgacaat ctctcatttg tcatatcaga    17820
```

```
taagaaggtt gatactaact ttatatacca acaaggaatg cttctagggt tgggtgtttt    17880
agaaacattg tttcgactcg agaaagatac cggatcatct aacacggtat tacatcttca    17940
cgtcgaaaca gattgttgcg tgatcccgat gatagatcat cccaggatac ccagctcccg    18000
caagctagag ctgagggcag agctatgtac caacccattg atatatgata atgcacctt     18060 aattgacaga gatgcaacaa ggctatacac ccagagccat aggaggcacc ttgtggaatt    18120
tgttacatgg tccacacccc aactatatca cattttagct aagtccacag cactatctat    18180
gattgacctg gtaacaaaat ttgagaagga ccatatgaat gaaatttcag ctctcatagg    18240
ggatgacgat atcaatagtt tcataactga gtttctgctc atagagccaa gattattcac    18300
tatctacttg ggccagtgtg cggccatcaa ttgggcattt gatgtacatt atcatagacc    18360
atcagggaaa tatcagatgg gtgagctgtt gtcatcgttc ctttctagaa tgagcaaagg    18420
agtgtttaag gtgcttgtca atgctctaag ccacccaaag atctacaaga aattctggca    18480
ttgtggtatt atagagccta tccatggtcc ttcacttgat gctcaaaact tgcacacaac    18540
tgtgtgcaac atggtttaca catgctatat gacctacctc gacctgttgt tgaatgaaga    18600
gttagaagag ttcacatttc tcttgtgtga aagcgacgag gatgtagtac cggacagatt    18660
cgacaacatc caggcaaaac acttatgtgt tctggcagat ttgtactgtc aaccagggac    18720
ctgcccacca attcgaggtc taagaccggt agagaaatgt gcagttctaa ccgaccatat    18780
caaggcagag gctatgttat ctccagcagg atcttcgtgg aacataaatc caattattgt    18840
agaccattac tcatgctccc tgacttatct ccggcgagga tcgatcaaac agataagatt    18900
gagagttgat ccaggattca ttttcgacgc cctcgctgag gtaaatgtca gtcagccaaa    18960
gatcggcagc aacaacatct caaatatgag catcaaggct ttcagacccc cacacgatga    19020
tgttgcaaaa ttgctcaaag atatcaacac aagcaagcac aatcttccca tttcaggggg    19080
caatctcgcc aattatgaaa tccatgcttt ccgcagaatc gggttgaact catctgcttg    19140
ctacaaagct gttgagatat caacattaat taggagatgc cttgagccag gggaggacgg    19200
cttgttcttg ggtgagggat cgggttctat gttgatcact tataaggaga tacttaaact    19260
aaacaagtgc ttctataata gtggggtttc cgccaattct agatctggtc aaagggaatt    19320
agcaccctat ccctccgaag ttggccttgt cgaacacaga atgggagtag gtaatattgt    19380
caaagtgctc tttaacggga ggcccgaagt cacgtgggta ggcagtgtag attgcttcaa    19440
tttcatagtt agtaatatcc ctacctctag tgtggggttt atccattcag atatagagac    19500
cttgcctgac aaagatacta tagagaagct agaggaattg gcagccatct tatcgatggc    19560
tctgctcctg ggcaaaatag gatcaatact ggtgattaag cttatgcctt tcagcgggga    19620
ttttgttcag ggatttataa gttatgtagg gtctccattat agagaagtga accttgtata    19680
ccctagatac agcaacttca tatctactga atcttatttg gttatgacag atctcaaggc    19740
taaccggcta atgaatcctg aaaagattaa gcagcagata attgaatcat ctgtgaggac    19800
ttcacctgga cttataggtc acatcctatc cattaagcaa ctaagctgca tacaagcaat    19860
tgtgggagac gcagttagta gaggtgatat caatcctact ctgaaaaaac ttacacctat    19920
agagcaggtg ctgatcaatt gcgggttggc aattaacgga cctaagctgt gcaaagaatt    19980
gatccaccat gatgttgcct cagggcaaga tggattgctt aattctatac tcatcctcta    20040
cagggagttg gcaagattca aagacaacca aagaagtcaa caaggdatgt ccacgcctg    20100 ccccgtattg gtaagtagca ggcaacgaga acttatatct aggatcaccc gcaaattttg    20160
```

```
ggggcacatt cttctttact ccgggaacaa aaagttgata aataagtttta tccagaatct   20220 caagtccggc tatctgatac tagacttaca ccagaatatc ttcgttaaga atctatccaa   20280
gtcagagaaa cagattatta tgacgggggg tttgaaacgt gagtgggttt ttaaggtaac   20340
agtcaaggag accaaagaat ggtataagtt agtcggatac agtgccctga ttaaggacta   20400
attggttgaa ctccggaacc ctaatcctgc cctaggtggt taggcattat ttgcaatata   20460
ttaaagaaaa ctttgaaaat acgaagtttc tattcccagc tttgtctggt ggccggcata   20520
gtcccagcct cctcgctggc gctggctggg caacattccg aggggaccgt ccccacggta   20580
atggcgaatg ggacgcggcc gatccggctg ctaacaaagc ccgaaaggaa gctgagttgg   20640
ctgctggcgc tggctgggca ataactagca taaccccttg gggcctctaa acgggtcttg   20700
aggggttttt tgctgaaagg aggaactata tccggatgcg gccgcgcgct tggcgtaatc   20760
atggtcatag ctgtttcctg tgtgaaattg ttatccgctc acaattccac acaacatacg   20820
agccggaagc ataaagtgta aagcctgggg tgcctaatga gtgagctaac tcacattaat   20880
tgcgttgcgc tcactgcccg ctttccagtc gggaaacctg tcgtgccagc tgcattaatg   20940
aatcggccaa cgcgcgggga gaggcggttt gcgtattggg cgctcttccg cttcctcgct   21000
cactgactcg ctgcgctcgg tcgttcggct gcggcgagcg gtatcagctc actcaaaggc   21060
ggtaatacgg ttatccacag aatcagggga taacgcagga agaacatgtg agcaaaagg   21120 ccagcaaaag gccaggaacc gtaaaaaggc cgcgttgctg gcgtttttcc ataggctccg   21180
cccccctgac gagcatcaca aaaatcgacg ctcaagtcag aggtggcgaa acccgacagg   21240
actataaaga taccaggcgt ttccccctgg aagctccctc gtgcgctctc ctgttccgac   21300
cctgccgctt accggatacc tgtccgcctt tctcccttcg ggaagcgtgg cgctttctca   21360
tagctcacgc tgtaggtatc tcagttcggt gtaggtcgtt cgctccaagc tgggctgtgt   21420
gcacgaaccc cccgttcagc ccgaccgctg cgccttatcc ggtaactatc gtcttgagtc   21480
caacccggta agacacgact tatcgccact ggcagcagcc actggtaaca ggattagcag   21540
agcgaggtat gtaggcggtg ctacagagtt cttgaagtgg tggcctaact acggctacac   21600
tagaaggaca gtatttggta tctgcgctct gctgaagcca gttaccttcg gaaaaagagt   21660
tggtagctct tgatccggca aacaaaccac cgctggtagc ggtggttttt tgtttgcaa   21720 gcagcagatt acgcgcagaa aaaaaggatc tcaagaagat cctttgatct tttctacggg   21780
gtctgacgct cagtggaacg aaaactcacg ttaagggatt ttggtcatga gattatcaaa   21840
aaggatcttc acctagatcc ttttaaatta aaaatgaagt tttaaatcaa tctaaagtat   21900
atatgagtaa acttggtctg acagttacca atgcttaatc agtgaggcac ctatctcagc   21960
gatctgtcta tttcgttcat ccatagttgc ctgactcccc gtcgtgtaga taactacgat   22020
acgggagggc ttaccatctg gccccagtgc tgcaatgata ccgcgagacc cacgctcacc   22080
ggctccagat ttatcagcaa taaaccagcc agccggaagg gccgagcgca gaagtggtcc   22140
tgcaacttta tccgcctcca tccagtctat taattgttgc cgggaagcta gagtaagtag   22200
ttcgccagtt aatagtttgc gcaacgttgt tgccattgct acaggcatcg tggtgtcacg   22260
ctcgtcgttt ggtatggctt cattcagctc cggttcccaa cgatcaaggc gagttacatg   22320
atcccccatg ttgtgcaaaa aagcggttag ctccttcggt cctccgatcg ttgtcagaag   22380
taagttggcc gcagtgttat cactcatggt tatggcagca ctgcataatt ctcttactgt   22440
catgccatcc gtaagatgct tttctgtgac tggtgagtac tcaaccaagt cattctgaga   22500
atagtgtatg cggcgaccga gttgctcttg cccggcgtca atacgggata ataccgcgcc   22560
```

```
acatagcaga actttaaaag tgctcatcat tggaaaacgt tcttcggggc gaaaactctc    22620
aaggatctta ccgctgttga gatccagttc gatgtaaccc actcgtgcac ccaactgatc    22680
ttcagcatct tttactttca ccagcgtttc tgggtgagca aaaacaggaa ggcaaaatgc    22740
cgcaaaaaag ggaataaggg cgacacggaa atgttgaata ctcatactct tcctttttca    22800
atattattga agcatttatc agggttattg tctcatgagc ggatacatat ttgaatgtat    22860
ttagaaaaat aaacaaatag gggttccgcg cacatttccc cgaaaagtgc cacctg        22916

<210> SEQ ID NO 6
<211> LENGTH: 13907
<212> TYPE: DNA
<213> ORGANISM: Artificial Sequence
<220> FEATURE:
<223> OTHER INFORMATION: RABV vector: Coravax V1-China (RABVG-E31)

<400> SEQUENCE: 6
acgcttaaca accagatcaa agaaaaaaca gacattgtca attgcaaagc aaaaatgtaa      60 caccccctaca atggatgccg acaagattgt attcaaagtc aataatcagg tggtctcttt    120
gaagcctgag attatcgtgg atcaatatga gtacaagtac cctgccatca agatttgaa     180 aaagccctgt ataaccctag gaaaggctcc cgatttaaat aaagcataca agtcagtttt    240
gtcaggcatg agcgccgcca aacttaatcc tgacgatgta tgttcctatt tggcagcggc    300
aatgcagttt tttgagggga catgtccgga agactggacc agctatggaa ttgtgattgc    360
acgaaaagga gataagatca ccccaggttc tctggtggag ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagattttg agacagcccc     600 ttttgttaaa atcgtggaac accatactct aatgacaact cacaaaatgt gtgctaattg    660
gagtactata ccaaacttca gatttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctaggggct atctgggaga ggaattcttc gggaagggga catttgaaag    1140
aagattcttc agagatgaga agaacttca agaatcgag gcggctgaac tgacaaagac     1200
tgacgtagca ctggcagatg atggaactgt caactctgac gacgaggact acttttcagg   1260
tgaaaccaga agtccggagg ctgtttatac tcgaatcatg atgaatggag tcgactaaa    1320 gagatctcac atacggagat atgtctcagt cagttccaat catcaagccc gtccaaactc   1380
attcgccgag ttttctaaaca agacatattc gagtgactca taacatgaaa aaaactaaca   1440 ccccctcccgt acgccaccat gttcgtgttt ctggtgctgc tgcctctggt gagctcccag   1500
tgcgtgaacc tgaccacaag gacccagctg cccctgcct ataccaattc cttcacacgg    1560
ggcgtgtact atcccgacaa ggtgttccgg agcagcgtgc tgcactccac acaggatctg   1620
tttctgcctt tcttttctaa cgtgacctgg ttccacgcca tccacgtgag cggcaccaat   1680
```

-continued

```
ggcacaaagc ggttcgacaa tccagtgctg ccctttaacg atggcgtgta cttcgcctcc    1740
accgagaagt ctaacatcat cagaggctgg atctttggca ccacactgga cagcaagaca    1800
cagtccctgc tgatcgtgaa caatgccacc aacgtggtca tcaaggtgtg cgagttccag    1860
ttttgtaatg atccattcct gggcgtgtac tatcacaaga acaataagtc ttggatggag    1920
agcgagtttc gcgtgtattc ctctgccaac aattgcacat ttgagtacgt gtcccagccc    1980
ttcctgatgg acctggaggg caagcagggc aatttcaaga acctgaggga gttcgtgttt    2040
aagaatatcg atggctactt caaaatctac tccaagcaca ccccaatcaa cctggtgcgc    2100
gacctgccac agggcttctc tgccctggag ccactggtgg atctgcccat cggcatcaac    2160
atcacccggt tcagacact gctggccctg cacagaagct acctgacacc aggcgacagc    2220
tcctctggat ggaccgcagg agcagcagcc tactatgtgg gctatctgca gcccaggacc    2280
ttcctgctga agtacaacga gaatggcacc atcacagacg ccgtggattg cgccctggat    2340
cccctgtctg agaccaagtg tacactgaag agctttaccg tggagaaggg catctatcag    2400
acaagcaatt tcagggtgca gcctaccgag tccatcgtgc gctttcccaa tatcacaaac    2460
ctgtgccctt ttggcgaggt gttcaacgca cccgcttcg ccagcgtgta cgcctggaat    2520
aggaagcgca ctccaactg cgtggccgac tattctgtgc tgtacaacag cgcctccttc    2580
tctaccttta gtgctatgg cgtgagcccc acaaagctga atgacctgtg ctttaccaac    2640
gtgtacgccg attccttcgt gatcagggc gacgaggtgc gccagatcgc accaggacag    2700
acaggcaaga tcgcagacta caattataag ctgcctgacg atttcaccgg ctgcgtgatc    2760
gcctggaact ctaacaatct ggatagcaaa gtgggcggca actacaatta tctgtaccgg    2820
ctgtttagaa agtctaatct gaagccattc gagagggaca tctccacaga aatctaccag    2880
gccggctcta cccctgcaa tggcgtggag ggctttaact gttatttccc tctgcagagc    2940
tacggcttcc agccaacaaa cggcgtgggc tatcagccct accgcgtggt ggtgctgtct    3000
tttgagctgc tgcacgcacc tgcaacagtg tgcggaccaa agaagagcac caatctggtg    3060
aagaacaagt gcgtgaactt caacttcaac ggactgaccg gaacaggcgt gctgaccgag    3120
tccaacaaga agttcctgcc ttttcagcag ttcggcaggg acatcgcaga taccacagac    3180
gccgtgcgcg accctcagac cctggagatc ctggacatca ccatgctctc cttcggcggc    3240
gtgtctgtga tcacaccagg caccaataca agcaaccagg tggccgtgct gtatcaggac    3300
gtgaattgta ccgaggtgcc agtggcaatc cacgcagatc agctgacccc tacatggcgg    3360
gtgtactcta ccggcagcaa cgtgttccag acaagagccg gatgcctgat cggagcagag    3420
cacgtgaaca atagctatga gtgcgacatc cctatcggcg ccggcatctg tgcctcctac    3480
cagacccaga caaactcccc aaggtctgtg ggagatgagg ccgaagactt tgtggaagtc    3540
cacctgcctg atgtgcataa ccaggtgtct ggcgtcgacc tgggactgcc aaattggggc    3600
aagtacgtgc tgctgagtgc tggagcactg actgccctga tgctgatcat tttcctgatg    3660
acctgctgtc ggcgcgtgaa cagaagtgag cccactcagc acaatctgcg aggaaccggg    3720
agagaagtgt cagtcacacc tcagagcggg aaaatcatta gtagttggga atcacataaa    3780
agcgggggcg agaccaggct gtgagctagc catgaaaaaa actaacaccc ctcctttcga    3840
accatcccaa acatgagcaa gatctttgtc aatcctagtg ctattagagc cggtctggcc    3900
gatcttgaga tggctgaaga aactgttgat ctgatcaata gaaatatcga agacaatcag    3960
gctcatctcc aaggggaacc catagaggtg acaatctccc tgaggatat ggggcgactt    4020
cacctggatg atggaaaatc gcccaaccat ggtgagatag ccaaggtggg agaaggcaag    4080
```

```
tatcgagagg actttcagat ggatgaagga gaggatccta gcttcctgtt ccagtcatac   4140
ctggaaaatg ttggagtcca aatagtcaga caaatgaggt caggagagag atttctcaag   4200
atatggtcac agaccgtaga agagattata tcctatgtcg cggtcaactt tcccaaccct   4260
ccaggaaagt cttcagagga taaatcaacc cagactactg gccgagagct caagaaggag   4320
acaacaccca ctccttctca gagagaaagc caatcatcga aagccaggat ggcggctcaa   4380
attgcttctg gccctccagc ccttgaatgg tcggctacca atgaagagga tgatctatca   4440
gtggaggctg agatcgctca ccagattgca gaaagtttct ccaaaaaata aagtttccc    4500 tctcgatcct cagggatact cttgtataat tttgagcaat tgaaaatgaa ccttgatgat   4560
atagttaaag aggcaaaaaa tgtaccaggt gtgacccgtt tagcccatga cgggtccaaa   4620 ctcccccctaa gatgtgtact gggatgggtc gctttggcca actctaagaa attccagttg   4680
ttagtcgaat ccgacaagct gagtaaaatc atgcaagatg acttgaatcg ctatacatct   4740
tgctaaccga acctctcccc tcagtccctc tagacaataa aatccgagat gtcccaaagt   4800
caacatgaaa aaaacaggca acaccactga taaaatgaac ctcctacgta agatagtgaa   4860
aaaccgcagg gacgaggaca ctcaaaaatc ctctcccgcg tcagcccctc tggatgacga   4920
tgacttgtgg cttccacccc ctgaatacgt cccgctgaaa gaacttacag gcaagaagaa   4980
catgaggaac ttttgtatca acggaagggt taaagtgtgt agcccgaatg gttactcgtt   5040
caggatcctg cggcacattc tgaaatcatt cgacgagata tattctggga atcataggat   5100
gatcgggtta gtcaaagtgg ttattggact ggctttgtca ggatctccag tccctgaggg   5160
cctgaactgg gtatacaaat tgaggagaac ctttatcttc cagtgggctg attccagggg   5220
ccctcttgaa ggggaggagt tggaatactc tcaggagatc acttgggatg atgatactga   5280
gttcgtcgga ttgcaaataa gagtgattgc aaaacagtgt catatccagg gcagagtctg   5340
gtgtatcaac atgaacccga gagcatgtca actatggtct gacatgtctc ttcagacaca   5400
aaggtccgaa gaggacaaag attcctctct gcttctagaa taatcagatt atatcccgca   5460
aatttatcac ttgtttacct ctggaggaga aacatatgg gctcaactcc aacccttggg    5520
agcaatataa caaaaaacat gttatggtgc cattaaaccg ctgcatttca tcaaagtcaa   5580
gttgattacc tttacatttt gatcctcttg gatgtgaaaa aaactattaa catccctcaa   5640
aagaccccgg gaaagatggt tcctcaggct ctcctgtttg tacccccttct ggttttcca   5700 ttgtgttttg ggaaattccc tatttacacg ataccagaca agcttggtcc ctggagtccg   5760
attgacatac atcacctcag ctgcccaaac aatttggtag tggaggacga aggatgcacc   5820
aacctgtcag ggttctccta catggaactt aaagttggat acatcttagc cataaaagtg   5880
aacgggttca cttgcacagg cgttgtgacg gaggctgaaa cctacactaa cttcgttggt   5940
tatgtcacaa ccacgttcaa aagaaagcat ttccgcccaa caccagatgc atgtagagcc   6000
gcgtacaact ggaagatggc cggtgacccc agatatgaag agtctctaca caatccgtac   6060
cctgactacc gctggcttcg aactgtaaaa accaccaagg agtctctcgt tatcatatct   6120
ccaagtgtgg cagatttgga cccatatgac agatcccttc actcgagggt cttccctagc   6180
gggaagtgct caggagtagc ggtgtcttct acctactgct ccactaacca cgattacacc   6240
atttggatgc ccgagaatcc gagactaggg atgtcttgtg acatttttac caatagtaga   6300
gggaagagag catccaaagg gagtgagact tgcggctttg tagatgaaag aggcctatat   6360
aagtctttaa aaggagcatg caaactcaag ttatgtggag ttctaggact tagacttatg   6420
```

```
gatggaacat gggtctcgat gcaaacatca aatgaaacca aatggtgccc tcccgataag    6480
ttggtgaacc tgcacgactt tcgctcagac gaaattgagc accttgttgt agaggagttg    6540
gtcaggaaga gagaggagtg tctggatgca ctagagtcca tcatgacaac caagtcagtg    6600
agtttcagac gtctcagtca tttaagaaaa cttgtccctg ggtttggaaa agcatatacc    6660
atattcaaca agaccttgat ggaagccgat gctcactaca agtcagtcga gacttggaat    6720
gagatcctcc cttcaaaagg gtgtttaaga gttgggggga ggtgtcatcc tcatgtgaac    6780
ggggtgtttt tcaatggtat aatattagga cctgacggca atgtcttaat cccagagatg    6840
caatcatccc tcctccagca acatatgag ttgttggaat cctcggttat ccccttgtg       6900 cacccctgg cagacccgtc taccgttttc aaggacggtg acgaggctga ggattttgtt      6960
gaagttcacc ttcccgatgt gcacaatcag gtctcaggag ttgacttggg tctcccgaac    7020
tgggggaagt atgtattact gagtgcaggg gccctgactg ccttgatgtt gataattttc    7080
ctgatgacat gttgtagaag agtcaatcga tcagaaccta cgcaacacaa tctcagaggg    7140
acagggaggg aggtgtcagt cactccccaa agcgggaaga tcatatcttc atgggaatca    7200
cacaagagtg ggggtgagac cagactgtaa ttaattaacg tcctttcaac gatccaagtc    7260
catgaaaaaa actaacaccc ctcccgtacc tagcttataa agtgctgggt catctaagct    7320
tttcagtcga gaaaaaaaca ttagatcaga agaacaactg gcaacacttc tcaacctgag    7380
acttacttca agatgctcga tcctggagag gtctatgatg accctattga cccaatcgag    7440
ttagaggctg aacccagagg aaccccccatt gtccccaaca tcttgaggaa ctctgactac    7500
aatctcaact ctcctttgat agaagatcct gctagactaa tgttagaatg gttaaaaaca    7560
gggaatagac cttatcggat gactctaaca gacaattgct ccaggtcttt cagagttttg    7620
aaagattatt tcaagaaggt agatttgggt tctctcaagg tgggcggaat ggctgcacag    7680
tcaatgattt ctctctggtt atatggtgcc cactctgaat ccaacaggag ccggagatgt    7740
ataacagact tggcccattt ctattccaag tcgtccccca tagagaagct gttgaatctc    7800
acgctaggaa atagagggct gagaatcccc ccagagggag tgttaagttg ccttgagagg    7860
gttgattatg ataatgcatt tggaaggtat cttgccaaca cgtattcctc ttacttgttc    7920
ttccatgtaa tcaccttata catgaacgcc ctagactggg atgaagaaaa gaccatccta    7980
gcattatgga aagatttaac ctcagtggac atcgggaagg acttggtaaa gttcaaagac    8040
caaatatggg gactgctgat cgtgacaaag gactttgttt actcccaaag ttccaattgt    8100 cttttttgaca gaaactacac acttatgcta aaagatcttt tcttgtctcg cttcaactcc    8160
ttaatggtct tgctctctcc cccagagccc cgatactcag atgacttgat atctcaacta    8220
tgccagctgt acattgctgg ggatcaagtc ttgtctatgt gtggaaactc cggctatgaa    8280
gtcatcaaaa tattggagcc atatgtcgtg aatagtttag tccagagagc agaaaagttt    8340
aggcctctca ttcattcctt gggagacttt cctgtattta taaaagacaa ggtaagtcaa    8400
cttgaagaga cgttcggtcc ctgtgcaaga aggttctttaa gggctctgga tcaattcgac   8460
aacatacatg acttggtttt tgtgtttggc tgttacaggc attgggggca cccatatata    8520
gattatcgaa agggtctgtc aaaactatat gatcaggttc accttaaaaa aatgatagat    8580
aagtcctacc aggagtgctt agcaagcgac ctagccagga ggatccttag atgggttttt    8640
gataagtact ccaagtggta tctggattca agattcctag cccgagacca ccccttgact    8700
ccttatatca aaacccaaac atggccaccc aaacatattg tagacttggt ggggatcaca    8760
tggcacaagc tcccgatcac gcagatcttt gagattcctg aatcaatgga tccgtcagaa    8820
```

```
atattggatg acaaatcaca ttctttcacc agaacgagac tagcttcttg gctgtcagaa    8880
aaccgagggg ggcctgttcc tagcgaaaaa gttattatca cggccctgtc taagccgcct    8940
gtcaatcccc gagagtttct gaggtctata gacctcggag gattgccaga tgaagacttg    9000
ataattggcc tcaagccaaa ggaacgggaa ttgaagattg aaggtcgatt ctttgctcta    9060
atgtcatgga atctaagatt gtattttgtc atcactgaaa aactcttggc caactacatc    9120
ttgccacttt ttgacgcgct gactatgaca gacaacctga acaaggtgtt taaaaagctg    9180
atcgacaggg tcaccgggca agggcttttg gactattcaa gggtcacata tgcatttcac    9240
ctggactatg aaaagtggaa caaccatcaa agattagagt caacagagga tgtattttct    9300
gtcctagatc aagtgtttgg attgaagaga gtgttttcta gaacacacga gttttttcaa    9360
aaggcctgga tctattattc agacagatca gacctcatcg ggttacggga ggatcaaata    9420
tactgcttag atgcgtccaa cggcccaacc tgttggaatg gccaggatgg cgggctagaa    9480
ggcttacggc agaagggctg gagtctagtc agcttattga tgatagatag agaatctcaa    9540
atcaggaaca caagaaccaa aatactagct caaggagaca accaggtttt atgtccgaca    9600
tacatgttgt cgccagggct atctcaagag gggctcctct atgaattgga gagaatatca    9660
aggaatgcac tttcgatata cagagccgtc gaggaagggg catctaagct agggctgatc    9720
atcaagaaag aagagaccat gtgtagttat gacttcctca tctatgggaaa aaccccttg    9780 tttagaggta acatattggt gcctgagtcc aaaagatggg ccagagtctc ttgcgtctct    9840
aatgaccaaa tagtcaacct cgccaatata atgtcgacag tgtccaccaa tgcgctaaca    9900
gtggcacaac actctcaatc tttgatcaaa ccgatgaggg attttctgct catgtcagta    9960
caggcagtct ttcactacct gctatttagc ccaatcttaa agggaagagt ttacaagatt   10020
ctgagcgctg aaggggagag cttctcccta gccatgtcaa ggataatcta tctagatcct   10080
tctttgggag ggatatctgg aatgtccctc ggaagattcc atatacgaca gttctcagac   10140
cctgtctctg aagggttatc cttctggaga gagatctggt taagctccca agagtcctgg   10200
attcacgcgt tgtgtcaaga ggctggaaac ccagatcttg agagagaac actcgagagc   10260 ttcactcgcc ttctagaaga tccgaccacc ttaaatatca gaggagggc cagtcctacc   10320 attctactca aggatgcaat cagaaaggct ttatatgacg aggtggacaa ggtggaaaat   10380
tcagagtttc gagaggcaat cctgttgtcc aagacccata gagataattt tatactcttc   10440
ttaatatctg ttgagcctct gtttcctcga tttctcagtg agctattcag ttcgtctttt   10500
ttgggaatcc ccgagtcaat cattggattg atacaaaact cccgaacgat aagaaggcag   10560
tttagaaaga gtctctcaaa aactttagaa gaatccttct acaactcaga gatccacggg   10620
attagtcgga tgacccagac acctcagagg gttgggggg tgtggccttg ctcttcagag   10680
agggcagatc tacttaggga gatctcttgg ggaagaaaag tggtaggcac gacagttcct   10740 caccccttctg agatgttggg attacttccc aagtcctcta tttcttgcac ttgtggagca   10800
acaggaggag gcaatcctag agttctgta tcagtactcc cgtcctttga tcagtcattt   10860
ttttcacgag gccccctaaa gggatacttg ggctcgtcca cctctatgtc gacccagcta   10920
ttccatgcat gggaaaaagt cactaatgtt catgtggtga agagagctct atcgttaaaa   10980
gaatctataa actggttcat tactagagat tccaacttgg ctcaagctct aattaggaac   11040
attatgtctc tgacaggccc tgatttccct ctagaggagg cccctgtctt caaaaggacg   11100
gggtcagcct tgcataggtt caagtctgcc agatacagcg aaggagggta ttcttctgtc   11160
```

```
tgcccgaacc tcctctctca tatttctgtt agtacagaca ccatgtctga tttgacccaa   11220
gacgggaaga actacgattt catgttccag ccattgatgc tttatgcaca gacatggaca   11280
tcagagctgg tacagagaga cacaaggcta agagactcta cgtttcattg gcacctccga   11340
tgcaacaggt gtgtgagacc cattgacgac gtgaccctgg agacctctca gatcttcgag   11400
tttccggatg tgtcgaaaag aatatccaga atggtttctg gggctgtgcc tcacttccag   11460
aggcttcccg atatccgtct gagaccagga gattttgaat ctctaagcgg tagagaaaag   11520
tctcaccata tcggatcagc tcagggctc ttatactcaa tcttagtggc aattcacgac    11580
tcaggataca atgatggaac catcttccct gtcaacatat acggcaaggt ttcccctaga   11640
gactatttga gagggctcgc aaggggagta ttgataggat cctcgatttg cttcttgaca   11700
agaatgacaa atatcaatat taatagacct cttgaattgg tctcagggt aatctctcatat  11760 attctcctga ggctagataa ccatccctcc ttgtacataa tgctcagaga accgtctctt   11820
agaggagaga tattttctat ccctcagaaa atccccgccg cttatccaac cactatgaaa   11880
gaaggcaaca gatcaatctt gtgttatctc caacatgtgc tacgctatga gcgagagata   11940
atcacggcgt ctccagagaa tgactggcta tggatctttt cagactttag aagtgccaaa   12000
atgacgtacc tatccctcat tacttaccag tctcatcttc tactccagag ggttgagaga   12060
aacctatcta agagtatgag agataacctg cgacaattga gttctttgat gaggcaggtg   12120
ctgggcgggc acgagaaga taccttagag tcagacgaca acattcaacg actgctaaaa    12180
gactctttac gaaggacaag atgggtggat caagaggtgc gccatgcagc tagaaccatg   12240 actgagatt acagccccaa caagaaggtg tcccgtaagg taggatgttc agaatgggtc     12300
tgctctgctc aacaggttgc agtctctacc tcagcaaacc cggcccctgt ctcggagctt   12360
gacataaggg ccctctctaa gaggttccag aacccttga tctcgggctt gagagtggtt     12420
cagtgggcaa ccggtgctca ttataagctt aagcctattc tagatgatct caatgttttc   12480
ccatctctct gccttgtagt tggggacggg tcaggggga tatcaaggc agtcctcaac     12540 atgtttccag atgccaagct tgtgttcaac agtctttag aggtgaatga cctgatggct    12600
tccggaacac atccactgcc tccttcagca atcatgaggg gaggaaatga tatcgtctcc   12660
agagtgatag atcttgactc aatctgggaa aaaccgtccg acttgagaaa cttggcaacc   12720
tggaaatact tccagtcagt ccaaaagcag gtcaacatgt cctatgacct cattatttgc   12780
gatgcagaag ttactgacat tgcatctatc aaccggatca ccctgttaat gtccgatttt   12840
gcattgtcta tagatggacc actctatttg gtcttcaaaa cttatgggac tatgctagta   12900
aatccaaact acaaggctat tcaacacctg tcaagagcgt tcccctcggt cacagggttt   12960
atcacccaag taacttcgtc tttttcatct gagctctacc tccgattctc caaacgaggg   13020 aagttttca gagatgctga gtacttgacc tcttccaccc ttcgagaaat gagccttgtg     13080
ttattcaatt gtagcagccc caagagtgag atgcagagag ctcgttcctt gaactatcag   13140
gatcttgtga gaggatttcc tgaagaaatc atatcaaatc cttacaatga gatgatcata   13200
actctgattg acagtgatgt agaatctttt ctagtccaca agatggttga tgatcttgag   13260
ttacagaggg gaactctgtc taaagtggct atcattatag ccatcatgat agttttctcc   13320
aacagagtct tcaacgtttc caaacccta actgacccct cgttctatcc accgtctgat    13380
cccaaaatcc tgaggcactt caacatatgt tgcagtacta tgatgtatct atctactgct   13440
ttaggtgacg tccctagctt cgcaagactt cacgacctgt ataacagacc tataacttat   13500
tacttcagaa agcaagtcat tcgagggaac gtttatctat cttggagttg gtccaacgac   13560
```

```
acctcagtgt tcaaaagggt agcctgtaat tctagcctga gtctgtcatc tcactggatc    13620
aggttgattt acaagatagt gaagactacc agactcgttg gcagcatcaa ggatctatcc    13680
agagaagtgg aaagacacct tcataggtac aacaggtgga tcaccctaga ggatatcaga    13740
tctagatcat ccctactaga ctacagttgc ctgtgaaccg gatactcctg aagcctgcc     13800 catgctaaga ctcttgtgtg atgtatcttg aaaaaaacaa gatcctaaat ctgaaccttt    13860
ggttgtttga ttgttttcct cattttgtt gtttatttgt taagcgt                   13907
```

<210> SEQ ID NO 7
<211> LENGTH: 13907
<212> TYPE: DNA
<213> ORGANISM: Artificial Sequence
<220> FEATURE:
<223> OTHER INFORMATION: RABV vector: Coravax V1-South Africa
      (RABVG-E31)

<400> SEQUENCE: 7

```
acgcttaaca accagatcaa agaaaaaaca gacattgtca attgcaaagc aaaaatgtaa      60 caccectaca atggatgccg acaagattgt attcaaagtc aataatcagg tggtctcttt     120
gaagcctgag attatcgtgg atcaatatga gtacaagtac cctgccatca aagatttgaa     180
aaagccctgt ataaccctag gaaaggctcc cgatttaaat aaagcataca agtcagtttt     240
gtcaggcatg agcgccgcca aacttaatcc tgacgtagta tgttcctatt tggcagcggc     300
aatgcagttt tttgagggga catgtccgga agactggacc agctatggaa ttgtgattgc     360
acgaaaagga gataagatca ccccaggttc tctggtggag ataaaacgta ctgatgtaga     420
agggaattgg gctctgacag gaggcatgga actgacaaga gaccccactg tccctgagca     480
tgcgtcctta gtcggtcttc tcttgagtct gtataggttg agcaaaatat ccgggcaaaa     540
cactggtaac tataagacaa acattgcaga caggatagag cagatttttg agacagcccc     600
ttttgttaaa atcgtggaac accatactct aatgacaact cacaaaatgt gtgctaattg     660
gagtactata ccaaacttca gattttggc cggaacctat gacatgtttt tctcccggat     720
tgagcatcta tattcagcaa tcagagtggg cacagttgtc actgcttatg aagactgttc     780
aggactggta tcatttactg ggttcataaa acaaatcaat ctcaccgcta gagaggcaat     840
actatatttc ttccacaaga actttgagga agagataaga gaatgtttg agccagggca     900 ggagacagct gttcctcact cttatttcat ccacttccgt tcactaggct tgagtgggaa     960
atctccttat tcatcaaatg ctgttggtca cgtgttcaat ctcattcact ttgtaggatg    1020
ctatatgggt caagtcagat ccctaaatgc aacggttatt gctgcatgtg ctcctcatga    1080
aatgtctgtt ctaggggct atctgggaga ggaattcttc gggaaaggga catttgaaag    1140
aagattcttc agagatgaga aagaacttca agaatacgag gcggctgaac tgacaaagac    1200
tgacgtagca ctggcagatg atggaactgt caactctgac gacgaggact acttttcagg    1260
tgaaaccaga agtccggagg ctgtttatac tcgaatcatg atgaatggag gtcgactaaa    1320
gagatctcac atacggagat atgtctcagt cagttccaat catcaagccc gtccaaactc    1380
attcgccgag tttctaaaca agacatattc gagtgactca taacatgaaa aaaactaaca    1440
cccctcccgt acgccaccat gttcgtgttt ctggtgctgc tgcctctggt gagctcccag    1500
tgcgtgaact tcaccacaag gacccagctg cccctgcct ataccaattc cttcacacgg    1560
ggcgtgtact atcccgacaa ggtgttccgg agcagcgtgc tgcactccac acaggatctg    1620
tttctgcctt tctttctaa cgtgacctgg ttccacgcca tccacgtgag cggcaccaat    1680
```

```
ggcacaaagc ggttcgccaa tccagtgctg ccctttaacg atggcgtgta cttcgcctcc    1740
accgagaagt ctaacatcat cagaggctgg atctttggca ccacactgga cagcaagaca    1800
cagtccctgc tgatcgtgaa caatgccacc aacgtggtca tcaaggtgtg cgagttccag    1860
ttttgtaatg atccattcct gggcgtgtac tatcacaaga acaataagtc ttggatggag    1920
agcgagtttc gcgtgtattc ctctgccaac aattgcacat ttgagtacgt gtcccagccc    1980
ttcctgatgg acctggaggg caagcagggc aatttcaaga acctgaggga gttcgtgttt    2040
aagaatatcg atggctactt caaaatctac tccaagcaca ccccaatcaa cctggtgcgc    2100
ggcctgccac agggcttctc tgccctggag ccactggtgg atctgcccat cggcatcaac    2160
atcacccggt ttcagacact gctggccctg cacagaagct acctgacacc aggcgacagc    2220
tcctctggat ggaccgcagg agcagcagcc tactatgtgg gctatctgca gcccaggacc    2280
ttcctgctga agtacaacga gaatggcacc atcacagacg ccgtggattg cgccctggat    2340
cccctgtctg agaccaagtg tacactgaag agctttaccg tggagaaggg catctatcag    2400
acaagcaatt tcagggtgca gcctaccgag tccatcgtgc gctttcccaa tatcacaaac    2460
ctgtgccctt ttggcgaggt gttcaacgca acccgcttcg ccagcgtgta cgcctggaat    2520
aggaagcgca tctccaactg cgtggccgac tattctgtgc tgtacaacag cgcctccttc    2580
tctacctttta agtgctatgg cgtgagcccc acaaagctga atgacctgtg ctttaccaac    2640
gtgtacgccg attccttcgt gatcagggc gacgaggtgc gccagatcgc accaggacag    2700
acaggcaata tcgcagacta caattataag ctgcctgacg atttcaccgg ctgcgtgatc    2760
gcctggaact ctaacaatct ggatagcaaa gtgggcggca actacaatta tctgtaccgg    2820
ctgtttagaa agtctaatct gaagccattc gagagggaca tctccacaga aatctaccag    2880
gccggctcta ccccctgcaa tggcgtgaag ggctttaact gttatttccc tctgcagagc    2940
tacggcttcc agccaacata tggcgtgggc tatcagccct accgcgtggt ggtgctgtct    3000
tttgagctgc tgcacgcacc tgcaacagtg tgcggaccaa agaagagcac caatctggtg    3060
aagaacaagt gcgtgaactt caacttcaac ggactgaccg gaacaggcgt gctgaccgag    3120
tccaacaaga agttcctgcc ttttcagcag ttcggcaggg acatcgcaga taccacagac    3180
gccgtgcgcg accctcagac cctggagatc ctggacatca ccatgctc cttcggcggc    3240
gtgtctgtga tcacaccagg caccaataca agcaaccagg tggccgtgct gtatcagggc    3300
gtgaattgta ccgaggtgcc agtggcaatc cacgcagatc agctgacccc tacatggcgg    3360
gtgtactcta ccggcagcaa cgtgttccag acaagagccg gatgcctgat cggagcagag    3420
cacgtgaaca atagctatga gtgcgacatc cctatcggcg ccggcatctg tgcctcctac    3480
cagacccaga caaactcccc aaggtctgtg ggagatgagg ccgaagactt tgtggaagtc    3540
cacctgcctg atgtgcataa ccaggtgtct ggcgtcgacc tgggactgcc aaattggggc    3600
aagtacgtgc tgctgagtgc tggagcactg actgccctga tgctgatcat tttcctgatg    3660
acctgctgtc ggcgcgtgaa cagaagtgag cccactcagc acaatctgcg aggaaccggg    3720
agagaagtgt cagtcacacc tcagagcggg aaaatcatta gtagttggga atcacataaa    3780
agcgggggcg agaccaggct gtgagctagc catgaaaaaa actaacaccc ctcctttcga    3840
accatcccaa acatgagcaa gatctttgtc aatcctagtg ctattagagc cggtctggcc    3900
gatcttgaga tggctgaaga aactgttgat ctgatcaata gaaatatcga agacaatcag    3960
gctcatctcc aaggggaacc catagaggtg acaatctcc ctgaggatat ggggcgactt    4020
```

-continued

```
cacctggatg atggaaaatc gcccaaccat ggtgagatag ccaaggtggg agaaggcaag    4080
tatcgagagg actttcagat ggatgaagga gaggatccta gcttcctgtt ccagtcatac    4140
ctggaaaatg ttggagtcca aatagtcaga caaatgaggt caggagagag atttctcaag    4200
atatggtcac agaccgtaga agagattata tcctatgtcg cggtcaactt tcccaaccct    4260
ccaggaaagt cttcagagga taaatcaacc cagactactg gccgagagct caagaaggag    4320
acaacaccca ctccttctca gagagaaagc caatcatcga aagccaggat ggcggctcaa    4380
attgcttctg gccctccagc ccttgaatgg tcggctacca atgaagagga tgatctatca    4440
gtggaggctg agatcgctca ccagattgca gaaagtttct ccaaaaaata aagtttccc     4500 tctcgatcct cagggatact cttgtataat tttgagcaat tgaaaatgaa ccttgatgat    4560
atagttaaag aggcaaaaaa tgtaccaggt gtgacccgtt tagcccatga cgggtccaaa    4620 ctcccctaa gatgtgtact gggatgggtc gctttggcca actctaagaa attccagttg     4680
ttagtcgaat ccgacaagct gagtaaaatc atgcaagatg acttgaatcg ctatacatct    4740
tgctaaccga acctctcccc tcagtccctc tagacaataa aatccgagat gtcccaaagt    4800
caacatgaaa aaaacaggca acaccactga taaaatgaac ctcctacgta agatagtgaa    4860
aaaccgcagg gacgaggaca ctcaaaaatc ctctcccgcg tcagcccctc tggatgacga    4920
tgacttgtgg cttccacccc ctgaatacgt cccgctgaaa gaacttacag gcaagaagaa    4980
catgaggaac ttttgtatca acggaagggt aaagtgtgt agcccgaatg gttactcgtt     5040
caggatcctg cggcacattc tgaaatcatt cgacgagata tattctggga atcataggat    5100
gatcgggtta gtcaaagtgg ttattggact ggctttgtca ggatctccag tccctgaggg    5160
cctgaactgg gtatacaaat tgaggagaac ctttatcttc cagtgggctg attccagggg    5220
ccctcttgaa gggaggagt tggaatactc tcaggagatc acttgggatg atgatactga     5280
gttcgtcgga ttgcaaataa gagtgattgc aaaacagtgt catatccagg gcagagtctg    5340
gtgtatcaac atgaacccga gagcatgtca actatggtct gacatgtctc ttcagacaca    5400
aaggtccgaa gaggacaaag attcctctct gcttctagaa taatcagatt atatcccgca    5460
aatttatcac ttgtttacct ctggaggaga aacatatgg gctcaactcc aacccttggg     5520
agcaatataa caaaaaacat gttatggtgc cattaaaccg ctgcatttca tcaaagtcaa    5580
gttgattacc tttacatttt gatcctcttg gatgtgaaaa aaactattaa catccctcaa    5640
aagaccccgg gaaagatggt tcctcaggct ctcctgtttg tacccttct ggttttttcca    5700 ttgtgttttg ggaaattccc tatttacacg ataccagaca agcttggtcc ctggagtccg    5760
attgacatac atcacctcag ctgcccaaac aatttggtag tggaggacga aggatgcacc    5820
aacctgtcag ggttctccta catggaactt aaagttggat acatcttagc cataaaagtg    5880
aacgggttca cttgcacagg cgttgtgacg gaggctgaaa cctacactaa cttcgttggt    5940
tatgtcacaa ccacgttcaa agaaaagcat ttccgcccaa caccagatgc atgtagagcc    6000
gcgtacaact ggaagatggc cggtgacccc agatatgaag agtctctaca caatccgtac    6060
cctgactacc gctggcttcg aactgtaaaa accaccaagg agtctctcgt tatcatatct    6120
ccaagtgtgg cagatttgga cccatatgac agatcccttc actcgagggt cttccctagc    6180
gggaagtgct caggagtagc ggtgtcttct acctactgct ccactaacca cgattacacc    6240
atttggatgc ccgagaatcc gagactaggg atgtcttgtg acatttttac caatagtaga    6300
gggaagagag catccaaagg gagtgagact tgcggctttg tagatgaaag aggcctatat    6360
aagtctttaa aaggagcatg caaactcaag ttatgtggag ttctaggact tagacttatg    6420
```

```
gatggaacat gggtctcgat gcaaacatca aatgaaacca aatggtgccc tcccgataag    6480
ttggtgaacc tgcacgactt tcgctcagac gaaattgagc accttgttgt agaggagttg    6540
gtcaggaaga gagaggagtg tctggatgca ctagagtcca tcatgacaac caagtcagtg    6600
agtttcagac gtctcagtca tttaagaaaa cttgtccctg ggtttggaaa agcatatacc    6660
atattcaaca agaccttgat ggaagccgat gctcactaca agtcagtcga gacttggaat    6720
gagatcctcc cttcaaaagg gtgtttaaga gttgggggga ggtgtcatcc tcatgtgaac    6780
ggggtgtttt tcaatggtat aatattagga cctgacggca atgtcttaat cccagagatg    6840
caatcatccc tcctccagca acatatggag ttgttggaat cctcggttat ccccttgtg     6900 cacccctgg cagacccgtc taccgttttc aaggacggtg acgaggctga ggattttgtt    6960
gaagttcacc ttcccgatgt gcacaatcag gtctcaggag ttgacttggg tctcccgaac    7020
tgggggaagt atgtattact gagtgcaggg gccctgactg ccttgatgtt gataattttc    7080
ctgatgacat gttgtagaag agtcaatcga tcagaaccta cgcaacacaa tctcagaggg    7140
acagggaggg aggtgtcagt cactccccaa agcgggaaga tcatatcttc atgggaatca    7200
cacaagagtg ggggtgagac cagactgtaa ttaattaacg tcctttcaac gatccaagtc    7260
catgaaaaaa actaacaccc ctcccgtacc tagcttataa agtgctgggt catctaagct    7320
tttcagtcga gaaaaaaaca ttagatcaga agaacaactg gcaacacttc tcaacctgag    7380
acttacttca agatgctcga tcctggagag gtctatgatg accctattga cccaatcgag    7440
ttagaggctg aacccagagg aaccccatt gtccccaaca tcttgaggaa ctctgactac    7500
aatctcaact ctcctttgat agaagatcct gctagactaa tgttagaatg gttaaaaaca    7560
gggaatagac cttatcggat gactctaaca gacaattgct ccaggtcttt cagagttttg    7620
aaagattatt tcaagaaggt agatttgggt tctctcaagg tgggcggaat ggctgcacag    7680
tcaatgattt ctctctggtt atatggtgcc cactctgaat ccaacaggag ccggagatgt    7740
ataacagact tggcccattt ctattccaag tcgtccccca tagagaagct gttgaatctc    7800
acgctaggaa atagagggct gagaatcccc ccagagggag tgttaagttg ccttgagagg    7860
gttgattatg ataatgcatt tggaaggtat cttgccaaca cgtattcctc ttacttgttc    7920
ttccatgtaa tcaccttata catgaacgcc ctagactggg atgaagaaaa gaccatccta    7980
gcattatgga aagatttaac ctcagtggac atcgggaagg acttggtaaa gttcaaagac    8040
caaatatggg gactgctgat cgtgacaaag gactttgttt actcccaaag ttccaattgt    8100
ctttttgaca gaaactacac acttatgcta aaagatcttt tcttgtctcg cttcaactcc    8160
ttaatggtct tgctctctcc cccagagccc cgatactcag atgacttgat atctcaacta    8220
tgccagctgt acattgctgg ggatcaagtc ttgtctatgt gtggaaactc cggctatgaa    8280
gtcatcaaaa tattggagcc atatgtcgtg aatagtttag tccagagagc agaaaagttt    8340
aggcctctca ttcattcctt gggagacttt cctgtattta taaagacaa ggtaagtcaa     8400 cttgaagaga cgttcggtcc ctgtgcaaga aggttcttta gggctctgga tcaattcgac    8460
aacatacatg acttggtttt tgtgtttggc tgttacaggc attgggggca cccatatata    8520
gattatcgaa agggtctgtc aaaactatat gatcaggttc accttaaaaa aatgatagat    8580
aagtcctacc aggagtgctt agcaagcgac ctagccagga ggatccttag atgggggtttt    8640 gataagtact ccaagtggta tctggattca agattcctag cccgagacca ccccttgact    8700
ccttatatca aacccaaac atggccaccc aaacatattg tagacttggt gggggataca    8760
```

```
tggcacaagc tcccgatcac gcagatcttt gagattcctg aatcaatgga tccgtcagaa    8820
atattggatg acaaatcaca ttctttcacc agaacgagac tagcttcttg gctgtcagaa    8880
aaccgagggg ggcctgttcc tagcgaaaaa gttattatca cggccctgtc taagccgcct    8940
gtcaatcccc gagagtttct gaggtctata gacctcggag gattgccaga tgaagacttg    9000
ataattggcc tcaagccaaa ggaacgggaa ttgaagattg aaggtcgatt ctttgctcta    9060
atgtcatgga atctaagatt gtattttgtc atcactgaaa aactcttggc caactacatc    9120
ttgccacttt ttgacgcgct gactatgaca gacaacctga caaggtgtt taaaaagctg     9180
atcgacaggg tcaccgggca agggcttttg gactattcaa gggtcacata tgcatttcac    9240
ctggactatg aaaagtggaa caaccatcaa agattagagt caacagagga tgtatttct    9300
gtcctagatc aagtgtttgg attgaagaga gtgttttcta gaacacacga gtttttcaa     9360
aaggcctgga tctattattc agacagatca gacctcatcg ggttacggga ggatcaaata    9420
tactgcttag atgcgtccaa cggcccaacc tgttggaatg gccaggatgg cgggctagaa    9480
ggcttacggc agaagggctg gagtctagtc agcttattga tgatagatag agaatctcaa    9540
atcaggaaca caagaaccaa atactagct caaggagaca accaggtttt atgtccgaca     9600
tacatgttgt cgccagggct atctcaagag gggctcctct atgaattgga gagaatatca    9660
aggaatgcac tttcgatata cagagccgtc gaggaagggg catctaagct agggctgatc    9720
atcaagaaag aagagaccat gtgtagttat gacttcctca tctatggaaa accccctttg    9780
tttagaggta acatattggt gcctgagtcc aaaagatggg ccagagtctc ttgcgtctct    9840
aatgaccaaa tagtcaacct cgccaatata atgtcgacag tgtccaccaa tgcgctaaca    9900
gtggcacaac actctcaatc tttgatcaaa ccgatgaggg attttctgct catgtcagta    9960
caggcagtct ttcactacct gctatttagc ccaatcttaa agggaagagt ttacaagatt   10020
ctgagcgctg aaggggagag ctttctccta gccatgtcaa ggataatcta tctagatcct   10080
tctttgggag ggatatctgg aatgtccctc ggaagattcc atatacgaca gttctcagac   10140
cctgtctctg aagggttatc cttctggaga gagatctggt taagctccca gagtcctgg   10200
attcacgcgt tgtgtcaaga ggctggaaac ccagatcttg gagagagaac actcgagagc   10260
ttcactcgcc ttctagaaga tccgaccacc ttaaatatca gaggagcggc cagtcctacc   10320
attctactca aggatgcaat cagaaaggct ttatatgacg aggtggacaa ggtggaaaat   10380
tcagagtttc gagaggcaat cctgttgtcc aagacccata gagataattt tatactcttc   10440
ttaatatctg ttgagcctct gtttcctcga tttctcagtg agctattcag ttcgtctttt   10500
ttgggaatcc ccgagtcaat cattggattg atacaaaact cccgaacgat aagaaggcag   10560
tttagaaaga gtctctcaaa aactttagaa gaatccttct acaactcaga gatccacggg   10620
attagtcgga tgacccagac acctcagagg gttgggggg tgtggccttg ctcttcagag   10680
agggcagatc tacttaggga gatctcttgg ggaagaaaag tggtaggcac gacagttcct   10740
caccttctg agatgttggg attacttccc aagtcctcta tttcttgcac ttgtggagca   10800
acaggaggag gcaatcctag agtttctgta tcagtactcc cgtcctttga tcagtcattt   10860
ttttcacgag gccccctaaa gggatacttg ggctcgtcca cctctatgtc gacccagcta   10920
ttccatgcat gggaaaagt cactaatgtt catgtggtga agagagctct atcgttaaaa   10980
gaatctataa actggttcat tactagagat tccaacttgg ctcaagctct aattaggaac   11040
attatgtctc tgacaggccc tgatttccct ctagaggagg cccctgtctt caaaaggacg   11100
gggtcagcct tgcataggtt caagtctgcc agatacagcg aaggagggta ttcttctgtc   11160
```

```
tgcccgaacc tcctctctca tatttctgtt agtacagaca ccatgtctga tttgacccaa   11220
gacgggaaga actacgattt catgttccag ccattgatgc tttatgcaca gacatggaca   11280
tcagagctgg tacagagaga cacaaggcta agagactcta cgtttcattg gcacctccga   11340
tgcaacaggt gtgtgagacc cattgacgac gtgaccctgg agacctctca gatcttcgag   11400
tttccggatg tgtcgaaaag aatatccaga atggtttctg gggctgtgcc tcacttccag   11460
aggcttcccg atatccgtct gagaccagga gattttgaat ctctaagcgg tagagaaaag   11520
tctcaccata tcggatcagc tcaggggctc ttatactcaa tcttagtggc aattcacgac   11580
tcaggataca atgatggaac catcttccct gtcaacatat acggcaaggt ttcccctaga   11640
gactatttga gagggctcgc aaggggagta ttgataggat cctcgatttg cttcttgaca   11700
agaatgacaa atatcaatat taatagacct cttgaattgg tctcaggggt aatctcatat   11760
attctcctga ggctagataa ccatccctcc ttgtacataa tgctcagaga accgtctctt   11820
agaggagaga tattttctat ccctcagaaa atccccgccg cttatccaac cactatgaaa   11880
gaaggcaaca gatcaatctt gtgttatctc caacatgtgc tacgctatga gcgagagata   11940
atcacggcgt ctccagagaa tgactggcta tggatctttt cagactttag aagtgccaaa   12000
atgacgtacc tatccctcat tacttaccag tctcatcttc tactccagag ggttgagaga   12060
aacctatcta agagtatgag agataacctg cgacaattga gttctttgat gaggcaggtg   12120
ctgggcgggc acggagaaga taccttagag tcagacgaca acattcaacg actgctaaaa   12180 gactcttta c gaaggacaag atgggtggat caagaggtgc gccatgcagc tagaaccatg   12240
actggagatt acagccccaa caagaaggtg tcccgtaagg taggatgttc agaatgggtc   12300
tgctctgctc aacaggttgc agtctctacc tcagcaaacc cggcccctgt ctcggagctt   12360
gacataaggg ccctctctaa gaggttccag aacccttga tctcgggctt gagagtggtt   12420
cagtgggcaa ccggtgctca ttataagctt aagcctattc tagatgatct caatgttttc   12480
ccatctctct gccttgtagt tggggacggg tcagggggga tatcaagggc agtcctcaac   12540
atgtttccag atgccaagct tgtgttcaac agtcttttag aggtgaatga cctgatggct   12600
tccggaacac atccactgcc tccttcagca atcatgaggg gaggaaatga tatcgtctcc   12660
agagtgatag atcttgactc aatctgggaa aaaccgtccg acttgagaaa cttggcaacc   12720
tggaaatact tccagtcagt ccaaaagcag gtcaacatgt cctatgacct cattatttgc   12780
gatgcagaag ttactgacat tgcatctatc aaccggatca ccctgttaat gtccgatttt   12840
gcattgtcta tagatggacc actctatttg gtcttcaaaa cttatgggac tatgctagta   12900
aatccaaact acaaggctat tcaacacctg tcaagagcgt tcccctcggt cacagggttt   12960
atcacccaag taacttcgtc ttttcatct gagctctacc tccgattctc caaacgaggg   13020 aagttttca gagatgctga gtacttgacc tcttccaccc ttcgagaaat gagccttgtg   13080
ttattcaatt gtagcagccc caagagtgag atgcagagag ctcgttcctt gaactatcag   13140
gatcttgtga gaggatttcc tgaagaaatc atatcaaatc cttacaatga gatgatcata   13200
actctgattg acagtgatgt agaatctttt ctagtccaca agatggttga tgatcttgag   13260
ttacagaggg gaactctgtc taaagtggct atcattatag ccatcatgat agttttctcc   13320
aacagagtct tcaacgtttc caaaccccta actgacccct cgttctatcc accgtctgat   13380
cccaaaatcc tgaggcactt caacatatgt tgcagtacta tgatgtatct atctactgct   13440
ttaggtgacg tccctagctt cgcaagactt cacgacctgt ataacagacc tataacttat   13500
```

```
tacttcagaa agcaagtcat tcgagggaac gtttatctat cttggagttg gtccaacgac    13560
acctcagtgt tcaaaagggt agcctgtaat tctagcctga gtctgtcatc tcactggatc    13620
aggttgattt acaagatagt gaagactacc agactcgttg gcagcatcaa ggatctatcc    13680
agagaagtgg aaagacacct tcataggtac aacaggtgga tcaccctaga ggatatcaga    13740
tctagatcat ccctactaga ctacagttgc ctgtgaaccg atactcctg gaagcctgcc     13800 catgctaaga ctcttgtgtg atgtatcttg aaaaaaacaa gatcctaaat ctgaaccttt    13860
ggttgtttga ttgttttct cattttttgtt gtttatttgt taagcgt                  13907

<210> SEQ ID NO 8
<211> LENGTH: 13958
<212> TYPE: DNA
<213> ORGANISM: Artificial Sequence
<220> FEATURE:
<223> OTHER INFORMATION: RABV vector: Coravax V2-China (RABVG-E51)

<400> SEQUENCE: 8
acgcttaaca accagatcaa agaaaaaaca gacattgtca attgcaaagc aaaaatgtaa       60 caccctaca atggatgccg acaagattgt attcaaagtc aataatcagg tggtctcttt      120
gaagcctgag attatcgtgg atcaaatatg gtacaagtac cctgccatca agatttgaa      180 aaagccctgt ataaccctag gaaaggctcc cgatttaaat aaagcataca agtcagtttt     240
gtcaggcatg agcgccgcca aacttaatcc tgacgatgta tgttcctatt tggcagcggc     300
aatgcagttt tttgaggga catgtccgga agactggacc agctatggaa ttgtgattgc     360
acgaaaagga gataagatca ccccaggttc tctggtggag ataaaacgta ctgatgtaga     420
agggaattgg gctctgacag gaggcatgga actgacaaga gaccccactg tccctgagca     480
tgcgtcctta gtcggtcttc tcttgagtct gtataggttg agcaaaatat ccgggcaaaa     540
cactggtaac tataagacaa acattgcaga caggatagag cagattttg agacagcccc     600 ttttgttaaa atcgtggaac accatactct aatgacaact cacaaaatgt gtgctaattg     660
gagtactata ccaaacttca gatttttggc cggaacctat gacatgtttt tctcccggat     720
tgagcatcta tattcagcaa tcagagtggg cacagttgtc actgcttatg aagactgttc     780
aggactggta tcatttactg ggttcataaa acaaatcaat ctcaccgcta gagaggcaat     840
actatatttc ttccacaaga actttgagga agagataaga gaatgtttg agccagggca     900 ggagacagct gttcctcact cttatttcat ccacttccgt tcactaggct tgagtgggaa     960
atctccttat tcatcaaatg ctgttggtca cgtgttcaat ctcattcact ttgtaggatg    1020
ctatatgggt caagtcagat ccctaaatgc aacggttatt gctgcatgtg ctcctcatga    1080
aatgtctgtt ctaggggct atctgggaga ggaattcttc gggaaaggga catttgaaag    1140
aagattcttc agagatgaga aagaacttca agaatacgag gcggctgaac tgacaaagac    1200
tgacgtagca ctggcagatg atggaactgt caactctgac gacgaggact acttttcagg    1260
tgaaaccaga agtccggagg ctgtttatac tcgaatcatg atgaatggag gtcgactaaa    1320
gagatctcac atacggagat atgtctcagt cagttccaat catcaagccc gtccaaactc    1380
attcgccgag tttctaaaca agacatattc gagtgactca taacatgaaa aaaactaaca    1440
cccctcccgt acgccaccat gttcgtgttt ctggtgctgc tgcctctggt gagctcccag    1500
tgcgtgaacc tgaccacaag gacccagctg ccccctgcct ataccaattc cttcacacgg    1560
ggcgtgtact atcccgacaa ggtgttccgg agcagcgtgc tgcactccac acaggatctg    1620
tttctgcctt tcttttctaa cgtgacctgg ttccacgcca tccacgtgag cggcaccaat    1680
```

-continued

```
ggcacaaagc ggttcgacaa tccagtgctg ccctttaacg atggcgtgta cttcgcctcc   1740
accgagaagt ctaacatcat cagaggctgg atctttggca ccacactgga cagcaagaca   1800
cagtccctgc tgatcgtgaa caatgccacc aacgtggtca tcaaggtgtg cgagttccag   1860
ttttgtaatg atccattcct gggcgtgtac tatcacaaga acaataagtc ttggatggag   1920
agcgagtttc gcgtgtattc ctctgccaac aattgcacat ttgagtacgt gtcccagccc   1980
ttcctgatgg acctggaggg caagcagggc aatttcaaga acctgaggga gttcgtgttt   2040
aagaatatcg atggctactt caaaatctac tccaagcaca ccccaatcaa cctggtgcgc   2100
gacctgccac agggcttctc tgccctggag ccactggtgg atctgcccat cggcatcaac   2160
atcacccggt tcagacact gctggccctg cacagaagct acctgacacc aggcgacagc   2220
tcctctggat ggaccgcagg agcagcagcc tactatgtgg gctatctgca gcccaggacc   2280
ttcctgctga agtacaacga gaatggcacc atcacagacg ccgtggattg cgccctggat   2340
cccctgtctg agaccaagtg tacactgaag agctttaccg tggagaaggg catctatcag   2400
acaagcaatt tcagggtgca gcctaccgag tccatcgtgc gctttcccaa tatcacaaac   2460
ctgtgccctt tggcgaggt gttcaacgca acccgcttcg ccagcgtgta cgcctggaat   2520
aggaagcgca tctccaactg cgtggccgac tattctgtgc tgtacaacag cgcctccttc   2580
tctaccttta gtgctatgg cgtgagcccc acaaagctga atgacctgtg ctttaccaac   2640
gtgtacgccg attccttcgt gatcagggc gacgaggtgc gccagatcgc accaggacag   2700
acaggcaaga tcgcagacta caattataag ctgcctgacg atttcaccgg ctgcgtgatc   2760
gcctggaact ctaacaatct ggatagcaaa gtgggcggca actacaatta tctgtaccgg   2820
ctgtttagaa agtctaatct gaagccattc gagagggaca tctccacaga aatctaccag   2880
gccggctcta cccctgcaa tggcgtggag ggctttaact gttatttccc tctgcagagc   2940
tacggcttcc agccaacaaa cggcgtgggc tatcagccct accgcgtggt ggtgctgtct   3000
tttgagctgc tgcacgcacc tgcaacagtg tgcggaccaa agaagagcac caatctggtg   3060
aagaacaagt gcgtgaactt caacttcaac ggactgaccg gaacaggcgt gctgaccgag   3120
tccaacaaga agttcctgcc ttttcagcag ttcggcaggg acatcgcaga taccacagac   3180
gccgtgcgcg accctcagac cctggagatc ctggacatca caccatgctc cttcggcggc   3240
gtgtctgtga tcacaccagg caccaataca agcaaccagg tggccgtgct gtatcaggac   3300
gtgaattgta ccgaggtgcc agtggcaatc cacgcagatc agctgacccc tacatggcgg   3360
gtgtactcta ccggcagcaa cgtgttccag acaagagccg gatgcctgat cggagcagag   3420
cacgtgaaca atagctatga gtgcgacatc cctatcggcg ccggcatctg tgcctcctac   3480
cagacccaga caaactcccc agaatcaagc gtgattcctc tggtccatcc actggcagat   3540
ccctccacag tgttcaaaga cggagatgag gccgaagact tgtggaagt ccacctgcct   3600 gatgtgcata accaggtgtc tggcgtcgac ctggactgc caaattgggg caagtacgtg   3660
ctgctgagtg ctggagcact gactgccctg atgctgatca ttttcctgat gacctgctgt   3720
cggcgcgtga acagaagtga gcccactcag cacaatctgc gaggaaccgg agagaagtg   3780 tcagtcacac ctcagagcgg gaaaatcatt agtagttggg aatcacataa agcgggggc    3840 gagaccaggc tgtgagctag ccatgaaaaa aactaacacc cctcctttcg aaccatccca   3900
aacatgagca agatctttgt caatcctagt gctattagag ccggtctggc cgatcttgag   3960
atggctgaag aaactgttga tctgatcaat agaaatatcg aagacaatca ggctcatctc   4020
```

-continued

```
caaggggaac ccatagaggt ggacaatctc cctgaggata tggggcgact tcacctggat    4080
gatggaaaat cgcccaacca tggtgagata gccaaggtgg gagaaggcaa gtatcgagag    4140
gactttcaga tggatgaagg agaggatcct agcttcctgt tccagtcata cctggaaaat    4200
gttggagtcc aaatagtcag acaaatgagg tcaggagaga gatttctcaa gatatggtca    4260
cagaccgtag aagagattat atcctatgtc gcggtcaact ttcccaaccc tccaggaaag    4320
tcttcagagg ataaatcaac ccagactact ggccgagagc tcaagaagga cacaacaccc    4380
actccttctc agagagaaag ccaatcatcg aaagccagga tggcggctca aattgcttct    4440
ggccctccag cccttgaatg gtcggctacc aatgaagagg atgatctatc agtggaggct    4500
gagatcgctc accagattgc agaaagtttc tccaaaaaat ataagtttcc ctctcgatcc    4560
tcagggatac tcttgtataa ttttgagcaa ttgaaaatga accttgatga tatagttaaa    4620
gaggcaaaaa atgtaccagg tgtgacccgt ttagcccatg acgggtccaa actcccccta    4680
agatgtgtac tgggatgggt cgctttggcc aactctaaga aattccagtt gttagtcgaa    4740
tccgacaagc tgagtaaaat catgcaagat gacttgaatc gctatacatc ttgctaaccg    4800
aacctctccc ctcagtccct ctagacaata aaatccgaga tgtcccaaag tcaacatgaa    4860
aaaaacaggc aacaccactg ataaaatgaa cctcctacgt aagatagtga aaaaccgcag    4920
ggacgaggac actcaaaaat cctctcccgc gtcagcccct ctggatgacg atgacttgtg    4980
gcttccaccc cctgaatacg tcccgctgaa agaacttaca gcaagaaga acatgaggaa    5040 cttttgtatc aacggaaggg ttaaagtgtg tagcccgaat ggttactcgt tcaggatcct    5100
gcggcacatt ctgaaatcat cgacgagat atattctggg aatcatagga tgatcgggtt    5160
agtcaaagtg gttattggac tggctttgtc aggatctcca gtccctgagg gcctgaactg    5220
ggtatacaaa ttgaggagaa cctttatctt ccagtgggct gattccaggg gccctcttga    5280
aggggaggag ttggaatact ctcaggagat cacttgggat gatgatactg agttcgtcgg    5340
attgcaaata agagtgattg caaaacagtg tcatatccag ggcagagtct ggtgtatcaa    5400
catgaacccg agagcatgtc aactatggtc tgacatgtct cttcagacac aaaggtccga    5460
agaggacaaa gattcctctc tgcttctaga ataatcagat tatatcccgc aaatttatca    5520
cttgtttacc tctgaggag agaacatatg ggctcaactc caaccctt gg gagcaatata    5580 acaaaaaaca tgttatggtg ccattaaacc gctgcatttc atcaaagtca agttgattac    5640 ctttacatt t tgatcctctt ggatgtgaaa aaaactatta acatccctca aaagaccccg    5700
ggaaagatgg ttcctcaggc tctcctgttt gtaccccttc tggttttttcc attgtgtttt    5760 gggaaattcc ctatttacac gataccagac aagcttggtc cctggagtcc gattgacata    5820
catcacctca gctgcccaaa caatttggta gtggaggacg aaggatgcac caacctgtca    5880
gggttctcct acatggaact taaagttgga tacatcttag ccataaaagt gaacgggttc    5940
acttgcacag cgttgtgac ggaggctgaa acctacacta acttcgttgg ttatgtcaca    6000
accacgttca aaagaaagca tttccgccca acaccagatg catgtagagc cgcgtacaac    6060
tggaagatgg ccggtgaccc cagatatgaa gagtctctac acaatccgta ccctgactac    6120
cgctggcttc gaactgtaaa aaccaccaag gagtctctcg ttatcatatc tccaagtgtg    6180
gcagatttgg acccatatga cagatccctt cactcgaggg tcttccctag cgggaagtgc    6240
tcaggagtag cggtgtcttc tacctactgc tccactaacc acgattacac catttggatg    6300
cccgagaatc cgagactagg gatgtcttgt gacattttta ccaatagtag agggaagaga    6360
gcatccaaag ggagtgagac ttgcggcttt gtagatgaaa gaggcctata taagtcttta    6420
```

```
aaaggagcat gcaaactcaa gttatgtgga gttctaggac ttagacttat ggatggaaca   6480
tgggtctcga tgcaaacatc aaatgaaacc aaatggtgcc ctcccgataa gttggtgaac   6540
ctgcacgact ttcgctcaga cgaaattgag caccttgttg tagaggagtt ggtcaggaag   6600
agagaggagt gtctggatgc actagagtcc atcatgacaa ccaagtcagt gagtttcaga   6660
cgtctcagtc atttaagaaa acttgtccct gggtttggaa aagcatatac catattcaac   6720
aagaccttga tggaagccga tgctcactac aagtcagtcg agacttggaa tgagatcctc   6780
ccttcaaaag ggtgtttaag agttgggggg aggtgtcatc ctcatgtgaa cggggtgttt   6840
ttcaatggta taatattagg acctgacggc aatgtcttaa tcccagagat gcaatcatcc   6900
ctcctccagc aacatatgga gttgttggaa tcctcggtta tccccccttgt gcaccccctg   6960 gcagacccgt ctaccgtttt caaggacggt gacgaggctg aggattttgt tgaagttcac   7020
cttcccgatg tgcacaatca ggtctcagga gttgacttgg gtctcccgaa ctgggggaag   7080
tatgtattac tgagtgcagg ggccctgact gccttgatgt tgataatttt cctgatgaca   7140
tgttgtagaa gagtcaatcg atcagaacct acgcaacaca atctcagagg gacagggagg   7200
gaggtgtcag tcactcccca aagcgggaag atcatatctt catgggaatc acacaagagt   7260
gggggtgaga ccagactgta attaattaac gtcctttcaa cgatccaagt ccatgaaaaa   7320
aactaacacc cctcccgtac ctagcttata aagtgctggg tcatctaagc ttttcagtcg   7380
agaaaaaaac attagatcag aagaacaact ggcaacactt ctcaacctga gacttacttc   7440
aagatgctcg atcctggaga ggtctatgat gaccctattg acccaatcga gttagaggct   7500
gaacccagag gaaccccccat tgtccccaac atcttgagga actctgacta caatctcaac   7560
tctcctttga tagaagatcc tgctagacta atgttagaat ggttaaaaac agggaataga   7620
ccttatcgga tgactctaac agacaattgc tccaggtctt tcagagttttt gaaagattat   7680 ttcaagaagg tagatttggg ttctctcaag gtgggcggaa tggctgcaca gtcaatgatt   7740
tctctctggt tatatggtgc ccactctgaa tccaacagga gccggagatg tataacagac   7800
ttggcccatt tctattccaa gtcgtccccc atagagaagc tgttgaatct cacgctagga   7860
aatagagggc tgagaatccc cccagaggga gtgttaagtt gccttgagag ggttgattat   7920
gataatgcat ttggaaggta tcttgccaac acgtattcct cttacttgtt cttccatgta   7980 atcacctttat acatgaacgc cctagactgg gatgaagaaa agaccatcct agcattatgg   8040
aaagatttaa cctcagtgga catcgggaag gacttggtaa agttcaaaga ccaaatatgg   8100
ggactgctga tcgtgacaaa ggactttgtt tactcccaaa gttccaattg tcttttttgac   8160 agaaactaca cacttatgct aaaagatctt ttcttgtctc gcttcaactc cttaatggtc   8220
ttgctctctc ccccagagcc ccgatactca gatgacttga tatctcaact atgccagctg   8280
tacattgctg gggatcaagt cttgtctatg tgtggaaact ccggctatga agtcatcaaa   8340
atattggagc catatgtcgt gaatagttta gtccagagag cagaaaagtt taggcctctc   8400
attcattcct tgggagactt tcctgtatt taaaaagaca aggtaagtca acttgaagag   8460
acgttcggtc cctgtgcaag aaggttcttt agggctctgg atcaattcga caacatacat   8520
gacttggttt ttgtgttttgg ctgttacagg cattgggggc acccatatat agattatcga   8580
aagggtctgt caaaactata tgatcaggtt caccttaaaa aaatgataga taagtcctac   8640
caggagtgct tagcaagcga cctagccagg aggatcctta tgggggttt tgataagtac   8700 tccaagtggt atctggattc aagattccta gcccgagacc accccttgac tccttatatc   8760
```

```
aaaacccaaa catggccacc caaacatatt gtagacttgg tgggggatac atggcacaag    8820
ctcccgatca cgcagatctt tgagattcct gaatcaatgg atccgtcaga aatattggat    8880
gacaaatcac attctttcac cagaacgaga ctagcttctt ggctgtcaga aaaccgaggg    8940
gggcctgttc ctagcgaaaa agttattatc acggccctgt ctaagccgcc tgtcaatccc    9000
cgagagtttc tgaggtctat agacctcgga ggattgccag atgaagactt gataattggc    9060
ctcaagccaa aggaacggga attgaagatt gaaggtcgat tctttgctct aatgtcatgg    9120
aatctaagat tgtattttgt catcactgaa aaactcttgg ccaactacat cttgccactt    9180
tttgacgcgc tgactatgac agacaacctg aacaaggtgt ttaaaaagct gatcgacagg    9240
gtcaccgggc aagggctttt ggactattca agggtcacat atgcatttca cctggactat    9300
gaaaagtgga acaaccatca aagattagag tcaacagagg atgtattttc tgtcctagat    9360
caagtgtttg gattgaagag agtgttttct agaacacacg agttttttca aaaggcctgg    9420
atctattatt cagacagatc agacctcatc gggttacggg aggatcaaat atactgctta    9480
gatgcgtcca acggcccaac ctgttggaat ggccaggatg cgggctaga aggcttacgg    9540
cagaagggct ggagtctagt cagcttattg atgatagata gagaatctca aatcaggaac    9600
acaagaacca aaatactagc tcaaggagac aaccaggttt tatgtccgac atacatgttg    9660
tcgccagggc tatctcaaga ggggctcctc tatgaattgg agagaatatc aaggaatgca    9720
ctttcgatat acagagccgt cgaggaaggg gcatcaagc tagggctgat catcaagaaa    9780
gaagagacca tgtgtagtta tgacttcctc atctatggaa aaaccccttt gtttagaggt    9840
aacatattgg tgcctgagtc caaaagatgg gccagagtct cttgcgtctc taatgaccaa    9900
atagtcaacc tcgccaatat aatgtcgaca gtgtccacca atgcgctaac agtggcacaa    9960
cactctcaat ctttgatcaa accgatgagg gatttttctgc tcatgtcagt acaggcagtc    10020
tttcactacc tgctatttag cccaatctta aagggaagag tttacaagat tctgagcgct    10080
gaaggggaga gctttctcct agccatgtca aggataatct atctagatcc ttctttggga    10140
gggatatctg gaatgtccct cggaagattc catatacgac agttctcaga ccctgtctct    10200
gaagggttat ccttctggag agagatctgg ttaagctccc aagagtcctg gattcacgcg    10260
ttgtgtcaag aggctggaaa cccagatctt ggagagagaa cactcgagag cttcactcgc    10320
cttctagaag atccgaccac cttaaatatc agaggagggg ccagtcctac cattctactc    10380
aaggatgcaa tcagaaaggc tttatatgac gaggtggaca aggtggaaaa ttcagagttt    10440
cgagaggcaa tcctgttgtc caagacccat agagataatt ttatactctt cttaatatct    10500
gttgagcctc tgtttcctcg atttctcagt gagctattca gttcgtcttt tttgggaatc    10560
cccgagtcaa tcattggatt gatacaaaac tcccgaacga taagaaggca gtttagaaag    10620
agtctctcaa aaactttaga agaatccttc tacaactcag agatccacgg gattagtcgg    10680
atgacccaga cacctcagag ggttgggggg gtgtggcctt gctcttcaga gagggcagat    10740
ctacttaggg agatctcttg gggaagaaaa gtggtaggca cgacagttcc tcacccttct    10800
gagatgttgg gattacttcc caagtcctct atttcttgca cttgtggagc aacaggagga    10860
ggcaatccta gagtttctgt atcagtactc ccgtcctttg atcagtcatt ttttcacga    10920
ggcccctaa agggatactt gggctcgtcc acctctatgt cgacccagct attccatgca    10980
tgggaaaaag tcactaatgt tcatgtggtg aagagagctc tatcgttaaa agaatctata    11040
aactggttca ttactagaga ttccaacttg gctcaagctc taattaggaa cattatgtct    11100
ctgacaggcc ctgatttccc tctagaggag gcccctgtct tcaaaaggac ggggtcagcc    11160
```

-continued

```
ttgcataggt tcaagtctgc cagatacagc gaaggagggt attcttctgt ctgcccgaac  11220
ctcctctctc atatttctgt tagtacagac accatgtctg atttgaccca agacgggaag  11280
aactacgatt tcatgttcca gccattgatg ctttatgcac agacatggac atcagagctg  11340
gtacagagag acacaaggct aagagactct acgtttcatt ggcacctccg atgcaacagg  11400
tgtgtgagac ccattgacga cgtgaccctg gagacctctc agatcttcga gtttccggat  11460
gtgtcgaaaa gaatatccag aatggtttct ggggctgtgc ctcacttcca gaggcttccc  11520
gatatccgtc tgagaccagg agattttgaa tctctaagcg gtagagaaaa gtctcaccat  11580
atcggatcag ctcaggggct cttatactca atcttagtgg caattcacga ctcaggatac  11640
aatgatggaa ccatcttccc tgtcaacata tacggcaagg tttcccctag agactatttg  11700
agagggctcg caaggggagt attgatagga tcctcgattt gcttcttgac aagaatgaca  11760
aatatcaata ttaatagacc tcttgaattg gtctcagggg taatctcata tattctcctg  11820
aggctagata accatccctc cttgtacata atgctcagag aaccgtctct tagaggagag  11880
atattttcta tccctcagaa aatccccgcc gcttatccaa ccactatgaa agaaggcaac  11940
agatcaatct tgtgttatct ccaacatgtg ctacgctatg agcgagagat aatcacggcg  12000
tctccagaga atgactggct atggatcttt tcagacttta gaagtgccaa aatgacgtac  12060
ctatccctca ttacttacca gtctcatctt ctactccaga gggttgagag aaacctatct  12120
aagagtatga gagataacct cgacaattg agttctttga tgaggcaggt gctgggcggg  12180
cacggagaag ataccttaga gtcagacgac aacattcaac gactgctaaa agactcttta  12240
cgaaggacaa gatgggtgga tcaagaggtg cgccatgcag ctagaaccat gactggagat  12300
tacagcccca acaagaaggt gtcccgtaag gtaggatgtt cagaatgggt ctgctctgct  12360
caacaggttg cagtctctac ctcagcaaac ccggcccctg tctcggagct tgacataagg  12420
gccctctcta agaggttcca gaacccttg atctcgggct tgagagtggt tcagtgggca  12480
accggtgctc attataagct taagcctatt ctagatgatc tcaatgtttt cccatctctc  12540
tgccttgtag ttggggacgg gtcaggggga atatcaaggg cagtcctcaa catgtttcca  12600
gatgccaagc ttgtgttcaa cagtctttta gaggtgaatg acctgatggc ttccggaaca  12660
catccactgc ctccttcagc aatcatgagg ggaggaaatg atatcgtctc cagagtgata  12720
gatcttgact caatctggga aaaaccgtcc gacttgagaa acttggcaac ctggaaatac  12780
ttccagtcag tccaaaagca ggtcaacatg tcctatgacc tcattatttg cgatgcagaa  12840
gttactgaca ttgcatctat caaccggatc accctgttaa tgtccgattt tgcattgtct  12900
atagatggac cactctattt ggtcttcaaa acttatggga ctatgctagt aaatccaaac  12960
tacaaggcta ttcaacacct gtcaagagcg ttcccctcgg tcacagggtt tatcacccaa  13020
gtaacttcgt cttttcatc tgagctctac ctccgattct ccaaacgagg gaagtttttc  13080
agagatgctg agtacttgac ctcttccacc cttcgagaaa tgagccttgt gttattcaat  13140
tgtagcagcc ccaagagtga gatgcagaga gctcgttcct tgaactatca ggatcttgtg  13200
agaggatttc ctgaagaaat catatcaaat ccttacaatg agatgatcat aactctgatt  13260
gacagtgatg tagaatcttt tctagtccac aagatggttg atgatcttga gttacagagg  13320
ggaactctgt ctaaagtggc tatcattata gccatcatga gtttttctc caacagagtc  13380 ttcaacgttt ccaaacccct aactgacccc tcgttctatc caccgtctga tcccaaaatc  13440
ctgaggcact tcaacatatg ttgcagtact atgatgtatc tatctactgc tttaggtgac  13500
```

```
gtccctagct tcgcaagact tcacgacctg tataacagac ctataactta ttacttcaga   13560
aagcaagtca ttcgagggaa cgtttatcta tcttggagtt ggtccaacga cacctcagtg   13620
ttcaaaaggg tagcctgtaa ttctagcctg agtctgtcat ctcactggat caggttgatt   13680
tacaagatag tgaagactac cagactcgtt ggcagcatca aggatctatc cagagaagtg   13740
gaaagacacc ttcataggta caacaggtgg atcaccctag aggatatcag atctagatca   13800
tccctactag actacagttg cctgtgaacc ggatactcct ggaagcctgc ccatgctaag   13860
actcttgtgt gatgtatctt gaaaaaaaca agatcctaaa tctgaacctt tggttgtttg   13920
attgtttttc tcattttgtg tgtttatttg ttaagcgt                           13958
```

<210> SEQ ID NO 9
<211> LENGTH: 13958
<212> TYPE: DNA
<213> ORGANISM: Artificial Sequence
<220> FEATURE:
<223> OTHER INFORMATION: RABV vector: Coravax V2 South Africa
      (S1-RABVG-E51)

<400> SEQUENCE: 9

```
acgcttaaca accagatcaa agaaaaaaca gacattgtca attgcaaagc aaaaatgtaa     60 caccccctaca atggatgccg acaagattgt attcaaagtc aataatcagg tggtctcttt    120
gaagcctgag attatcgtgg atcaatatga gtacaagtac cctgccatca agatttgaa    180 aaagccctgt ataaccctag gaaaggctcc cgatttaaat aaagcataca agtcagtttt   240
gtcaggcatg agcgccgcca aacttaatcc tgacgatgta tgttcctatt tggcagcggc   300
aatgcagttt tttgagggga catgtccgga agactggacc agctatggaa ttgtgattgc   360
acgaaaagga gataagatca ccccaggttc tctggtggag ataaaacgta ctgatgtaga   420
agggaattgg gctctgacag gaggcatgga actgacaaga gaccccactg tccctgagca   480
tgcgtcctta gtcggtcttc tcttgagtct gtataggttg agcaaaatat ccgggcaaaa   540
cactggtaac tataagacaa acattgcaga caggatagag cagatttttg agacagcccc   600
ttttgttaaa atcgtggaac accatactct aatgacaact cacaaaatgt gtgctaattg   660
gagtactata ccaaacttca gattttttggc cggaaccctat gacatgtttt tctcccggat   720
tgagcatcta tattcagcaa tcagagtggg cacagttgtc actgcttatg aagactgttc   780
aggactggta tcatttactg ggttcataaa acaaatcaat ctcaccgcta gagaggcaat   840
actatatttc ttccacaaga actttgagga agagataaga gaatgtttg agccagggca   900 ggagacagct gttcctcact cttatttcat ccacttccgt tcactaggct gagtgggaa    960 atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctagggggct atctcgggaga ggaattcttc gggaaaggga catttgaaag   1140
aagattcttc agagatgaga agaacttcca agaatacgag gcggctgaac tgacaaagac   1200
tgacgtagca ctggcagatg atggaactgt caactctgac gacgaggact acttttcagg   1260
tgaaaccaga gtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taacatgaaa aaaactaaca   1440 ccccctcccgt acgccaccat gttcgtgttt ctggtgctgc tgcctctggt gagctcccag   1500
tgcgtgaact tcaccacaag gacccagctg cccccctgcct ataccaattc cttcacacgg   1560
```

```
ggcgtgtact atcccgacaa ggtgttccgg agcagcgtgc tgcactccac acaggatctg   1620
tttctgcctt tcttttctaa cgtgacctgg ttccacgcca tccacgtgag cggcaccaat   1680
ggcacaaagc ggttcgccaa tccagtgctg ccctttaacg atggcgtgta cttcgcctcc   1740
accgagaagt ctaacatcat cagaggctgg atctttggca ccacactgga cagcaagaca   1800
cagtccctgc tgatcgtgaa caatgccacc aacgtggtca tcaaggtgtg cgagttccag   1860
ttttgtaatg atccattcct gggcgtgtac tatcacaaga acaataagtc ttggatggag   1920
agcgagtttc gcgtgtattc ctctgccaac aattgcacat ttgagtacgt gtcccagccc   1980
ttcctgatgg acctggaggg caagcagggc aatttcaaga acctgaggga gttcgtgttt   2040
aagaatatcg atggctactt caaaatctac tccaagcaca ccccaatcaa cctggtgcgc   2100
ggcctgccac agggcttctc tgccctggag ccactggtgg atctgcccat cggcatcaac   2160
atcacccggt tcagacact gctggccctg cacagaagct acctgacacc aggcgacagc   2220
tcctctggat ggaccgcagg agcagcagcc tactatgtgg gctatctgca gcccaggacc   2280
ttcctgctga agtacaacga gaatggcacc atcacagacg ccgtggattg cgccctggat   2340
cccctgtctg agaccaagtg tacactgaag agctttaccg tggagaaggg catctatcag   2400
acaagcaatt tcagggtgca gcctaccgag tccatcgtgc gctttcccaa tatcacaaac   2460
ctgtgccctt ttggcgaggt gttcaacgca acccgcttcg ccagcgtgta cgcctggaat   2520
aggaagcgca ctccaactg cgtggccgac tattctgtgc tgtacaacag cgcctccttc   2580
tctaccttta gtgctatgg cgtgagcccc acaaagctga atgacctgtg ctttaccaac   2640
gtgtacgccg attccttcgt gatcagggc gacgaggtgc gccagatcgc accaggacag   2700
acaggcaata tcgcagacta caattataag ctgcctgacg atttcaccgg ctgcgtgatc   2760
gcctggaact ctaacaatct ggatagcaaa gtgggcggca actacaatta tctgtaccgg   2820
ctgtttagaa agtctaatct gaagccattc gagagggaca tctccacaga aatctaccag   2880
gccggctcta cccctgcaa tggcgtgaag ggctttaact gttatttccc tctgcagagc   2940
tacggcttcc agccaacata tggcgtgggc tatcagccct accgcgtggt ggtgctgtct   3000
tttgagctgt gcacgcacc tgcaacagtg tgcggaccaa agaagagcac caatctggtg   3060
aagaacaagt gcgtgaactt caacttcaac ggactgaccg gaacaggcgt gctgaccgag   3120
tccaacaaga gttcctgcc ttttcagcag ttcggcaggg acatcgcaga taccacagac   3180
gccgtgcgcg accctcagac cctggagatc ctggacatca ccatgctc cttcggcggc   3240 gtgtctgtga tcacaccagg caccaataca agcaaccagg tggccgtgct gtatcagggc   3300
gtgaattgta ccgaggtgcc agtggcaatc cacgcagatc agctgacccc tacatggcgg   3360
gtgtactcta ccggcagcaa cgtgttccag acaagagccg gatgcctgat cggagcagag   3420
cacgtgaaca atagctatga gtcgacatc cctatcggcg ccggcatctg tgcctcctac   3480
cagacccaga caaactcccc agaatcaagc gtgattcctc tggtccatcc actggcagat   3540
ccctccacag tgttcaaaga cggagatgag gccgaagact ttgtggaagt ccacctgcct   3600
gatgtgcata accaggtgtc tggcgtcgac ctgggactgc caaattgggg caagtacgtg   3660
ctgctgagtg ctggagcact gactgccctg atgctgatca tttcctgat gacctgctgt   3720 cggcgcgtga acagaagtga gcccactcag cacaatctgc gaggaaccgg gagagaagtg   3780
tcagtcacac ctcagagcgg gaaaatcatt agtagttggg aatcacataa aagcgggggc   3840
gagaccaggc tgtgagctag ccatgaaaaa aactaacacc cctcctttcg aaccatccca   3900
aacatgagca agatctttgt caatcctagt gctattagag ccggtctggc cgatcttgag   3960
```

```
atggctgaag aaactgttga tctgatcaat agaaatatcg aagacaatca ggctcatctc    4020 caagggaac ccatagaggt ggacaatctc cctgaggata tggggcgact tcacctggat    4080
gatggaaaat cgcccaacca tggtgagata gccaaggtgg agaaggcaa gtatcgagag    4140 gactttcaga tggatgaagg agaggatcct agcttcctgt tccagtcata cctggaaaat    4200
gttggagtcc aaatagtcag acaaatgagg tcaggagaga gatttctcaa gatatggtca    4260
cagaccgtag aagagattat atcctatgtc gcggtcaact ttcccaaccc tccaggaaag    4320
tcttcagagg ataaatcaac ccagactact ggccgagagc tcaagaagga gacaacaccc    4380
actccttctc agagagaaag ccaatcatcg aaagccagga tggcggctca aattgcttct    4440
ggccctccag cccttgaatg gtcggctacc aatgaagagg atgatctatc agtggaggct    4500
gagatcgctc accagattgc agaaagtttc tccaaaaaat ataagtttcc ctctcgatcc    4560
tcagggatac tcttgtataa ttttgagcaa ttgaaaatga accttgatga tatagttaaa    4620
gaggcaaaaa atgtaccagg tgtgacccgt ttagcccatg acgggtccaa actcccccta    4680
agatgtgtac tgggatgggt cgctttggcc aactctaaga aattccagtt gttagtcgaa    4740
tccgacaagc tgagtaaaat catgcaagat gacttgaatc gctatacatc ttgctaaccg    4800
aacctctccc ctcagtccct ctagacaata aaatccgaga tgtcccaaag tcaacatgaa    4860 aaaacaggc aacaccactg ataaaatgaa cctcctacgt aagatagtga aaaaccgcag    4920
ggacgaggac actcaaaaat cctctcccgc gtcagcccct ctggatgacg atgacttgtg    4980
gcttccaccc cctgaatacg tcccgctgaa agaacttaca gcaagaaga acatgaggaa    5040 cttttgtatc aacggaaggg ttaaagtgtg tagcccgaat ggttactcgt tcaggatcct    5100
gcggcacatt ctgaaatcat tcgacgagat atattctggg aatcatagga tgatcgggtt    5160
agtcaaagtg gttattggac tggctttgtc aggatctcca gtccctgagg gcctgaactg    5220
ggtatacaaa ttgaggagaa cctttatctt ccagtgggct gattccaggg gccctcttga    5280
aggggaggag ttggaatact ctcaggagat cacttgggat gatgatactg agttcgtcgg    5340
attgcaaata agagtgattg caaaacagtg tcatatccag ggcagagtct ggtgtatcaa    5400
catgaacccg agagcatgtc aactatggtc tgacatgtct cttcagacac aaaggtccga    5460
agaggacaaa gattcctctc tgcttctaga ataatcagat tatatcccgc aaatttatca    5520
cttgtttacc tctggaggag agaacatatg ggctcaactc caacccttgg gagcaatata    5580
acaaaaaaca tgttatggtg ccattaaacc gctgcatttc atcaaagtca agttgattac    5640
ctttacattt tgatcctctt ggatgtgaaa aaaactatta acatccctca aaagaccccg    5700
ggaaagatgg ttcctcaggc tctcctgttt gtaccccttc tggttttttcc attgtgtttt    5760 gggaaattcc ctatttacac gataccagac aagcttggtc cctggagtcc gattgacata    5820
catcacctca gctgcccaaa caatttggta gtggaggacg aaggatgcac caacctgtca    5880
gggttctcct acatggaact taaagttgga tacatcttag ccataaaagt gaacgggttc    5940
acttgcacag gcgttgtgac ggaggctgaa acctacacta acttcgttgg ttatgtcaca    6000
accacgttca aaagaaagca tttccgccca acaccagatg catgtagagc cgcgtacaac    6060
tggaagatgg ccggtgaccc cagatatgaa gagtctctac acaatccgta ccctgactac    6120
cgctggcttc gaactgtaaa aaccaccaag gagtctctcg ttatcatatc tccaagtgtg    6180
gcagatttgg acccatatga cagatcccct cactcgaggg tcttccctag cgggaagtgc    6240
tcaggagtag cggtgtcttc tacctactgc tccactaacc acgattacac catttggatg    6300
```

```
cccgagaatc cgagactagg gatgtcttgt gacattttta ccaatagtag agggaagaga    6360
gcatccaaag ggagtgagac ttgcggcttt gtagatgaaa gaggcctata taagtcttta    6420
aaaggagcat gcaaactcaa gttatgtgga gttctaggac ttagacttat ggatggaaca    6480
tgggtctcga tgcaaacatc aaatgaaacc aatggtgcc ctcccgataa gttggtgaac    6540
ctgcacgact ttcgctcaga cgaaattgag caccttgttg tagaggagtt ggtcaggaag    6600
agagaggagt gtctggatgc actagagtcc atcatgacaa ccaagtcagt gagtttcaga    6660
cgtctcagtc atttaagaaa acttgtccct gggtttggaa aagcatatac catattcaac    6720
aagaccttga tggaagccga tgctcactac aagtcagtcg agacttggaa tgagatcctc    6780
ccttcaaaag ggtgtttaag agttgggggg aggtgtcatc ctcatgtgaa cggggtgttt    6840
ttcaatggta taatattagg acctgacggc aatgtcttaa tcccagagat gcaatcatcc    6900
ctcctccagc aacatatgga gttgttggaa tcctcggtta tcccccttgt gcaccccctg    6960
gcagacccgt ctaccgtttt caaggacggt gacgaggctg aggattttgt tgaagttcac    7020
cttcccgatg tgcacaatca ggtctcagga gttgacttgg gtctcccgaa ctgggggaag    7080
tatgtattac tgagtgcagg ggccctgact gccttgatgt tgataatttt cctgatgaca    7140
tgttgtagaa gagtcaatcg atcagaacct acgcaacaca atctcagagg gacagggagg    7200
gaggtgtcag tcactcccca aagcgggaag atcatatctt catgggaatc acacaagagt    7260
gggggtgaga ccagactgta attaattaac gtcctttcaa cgatccaagt ccatgaaaaa    7320
aactaacacc cctcccgtac ctagcttata aagtgctggg tcatctaagc ttttcagtcg    7380
agaaaaaaac attagatcag aagaacaact ggcaacactt ctcaacctga gacttacttc    7440
aagatgctcg atcctggaga ggtctatgat gaccctattg acccaatcga gttagaggct    7500
gaacccagag gaaccccat tgtccccaac atcttgagga actctgacta caatctcaac    7560
tctcctttga tagaagatcc tgctagacta atgttagaat ggttaaaaac agggaataga    7620
ccttatcgga tgactctaac agacaattgc tccaggtctt tcagagtttt gaaagattat    7680
ttcaagaagg tagatttggg ttctctcaag gtgggcggaa tggctgcaca gtcaatgatt    7740
tctctctggt tatatggtgc ccactctgaa tccaacagga gccggagatg tataacagac    7800
ttggcccatt tctattccaa gtcgtccccc atagagaagc tgttgaatct cacgctagga    7860
aatagagggc tgagaatccc cccagaggga gtgttaagtt gccttgagag ggttgattat    7920
gataatgcat ttggaaggta tcttgccaac acgtattcct cttacttgtt cttccatgta    7980
atcaccttat acatgaacgc cctagactgg gatgaagaaa agaccatcct agcattatgg    8040
aaagatttaa cctcagtgga catcgggaag gacttggtaa agttcaaaga ccaaatatgg    8100
ggactgctga tcgtgacaaa ggactttgtt tactcccaaa gttccaattg tcttttttgac    8160 agaaactaca cacttatgct aaaagatctt ttcttgtctc gcttcaactc cttaatggtc    8220
ttgctctctc ccccagagcc ccgatactca gatgacttga tatctcaact atgccagctg    8280
tacattgctg gggatcaagt cttgtctatg tgtggaaact ccggctatga agtcatcaaa    8340
atattggagc catatgtcgt gaatagttta gtccagagag cagaaaagtt taggcctctc    8400
attcattcct tgggagactt tcctgtattt ataaaagaca aggtaagtca acttgaagag    8460
acgttcggtc cctgtgcaag aaggttcttt agggctctgg atcaattcga caacatacat    8520
gacttggttt ttgtgtttgg ctgttacagg cattgggggc acccatatat agattatcga    8580
aagggtctgt caaaactata tgatcaggtt caccttaaaa aatgatgatga taagtcctac    8640 caggagtgct tagcaagcga cctagccagg aggatcctta gatgggttt tgataagtac    8700
```

```
tccaagtggt atctggattc aagattccta gcccgagacc accccttgac tccttatatc    8760
aaaacccaaa catggccacc caaacatatt gtagacttgg tgggggatac atggcacaag    8820
ctcccgatca cgcagatctt tgagattcct gaatcaatgg atccgtcaga aatattggat    8880
gacaaatcac attctttcac cagaacgaga ctagcttctt ggctgtcaga aaaccgaggg    8940
gggcctgttc ctagcgaaaa agttattatc acggccctgt ctaagccgcc tgtcaatccc    9000
cgagagtttc tgaggtctat agacctcgga ggattgccag atgaagactt gataattggc    9060
ctcaagccaa aggaacggga attgaagatt gaaggtcgat tctttgctct aatgtcatgg    9120
aatctaagat tgtattttgt catcactgaa aaactcttgg ccaactacat cttgccactt    9180
tttgacgcgc tgactatgac agacaacctg aacaaggtgt taaaaagct gatcgacagg     9240
gtcaccgggc aagggcttt ggactattca agggtcacat atgcatttca cctggactat     9300
gaaaagtgga acaaccatca aagattagag tcaacagagg atgtattttc tgtcctagat    9360
caagtgtttg gattgaagag agtgtttttct agaacacacg agttttttca aaaggcctgg    9420
atctattatt cagacagatc agacctcatc gggttacggg aggatcaaat atactgctta    9480
gatgcgtcca acgcccaac ctgttggaat ggccaggatg gcgggctaga aggcttacgg      9540
cagaagggct ggagtctagt cagcttattg atgatagata gagaatctca aatcaggaac    9600
acaagaacca aaatactagc tcaaggagac aaccaggttt tatgtccgac atacatgttg    9660
tcgccagggc tatctcaaga ggggctcctc tatgaattgg agagaatatc aaggaatgca    9720
ctttcgatat acagagccgt cgaggaaggg gcatctaagc tagggctgat catcaagaaa    9780
gaagagacca tgtgtagtta tgacttcctc atctatggaa aaacccctt gtttagaggt     9840
aacatattgg tgcctgagtc caaaagatgg gccagagtct cttgcgtctc taatgaccaa    9900
atagtcaacc tcgccaatat aatgtcgaca gtgtccacca atgcgctaac agtggcacaa    9960
cactctcaat ctttgatcaa accgatgagg gatttctgc tcatgtcagt acaggcagtc   10020
tttcactacc tgctatttag cccaatctta aagggaagag tttacaagat tctgagcgct   10080
gaagggagaa gctttctcct agccatgtca aggataatct atctagatcc ttctttggga   10140
gggatatctg gaatgtccct cggaagattc catatacgac agttctcaga ccctgtctct   10200
gaagggttat ccttctggag agagatctgt ttaagctccc aagagtcctg gattcacgcg   10260
ttgtgtcaag aggctggaaa cccagatctt ggagagagaa cactcgagag cttcactcgc   10320
cttctagaag atccgaccac cttaaatatc agaggagggg ccagtcctac cattctactc   10380
aaggatgcaa tcaagaaggc tttatatgac gaggtggaca aggtggaaaa ttcagagttt   10440
cgagaggcaa tcctgttgtc caagacccat agagataatt ttatactctt cttaatatct   10500
gttgagcctc tgtttcctcg atttctcagt gagctattca gttcgtcttt tttgggaatc   10560
cccgagtcaa tcattggatt gatacaaaac tcccgaacga taagaaggca gtttagaaag   10620
agtctctcaa aaactttaga agaatccttc tacaactcag atccacgg gattagtcgg     10680
atgacccaga cacctcagag ggttggggg gtgtggcctt gctcttcaga gagggcagat    10740
ctacttaggg agatctcttg gggaagaaaa gtggtaggca cgacagttcc tcacccttct   10800
gagatgttgg gattacttcc caagtcctct atttcttgca cttgtggagc aacaggagga   10860
ggcaatccta gagtttctgt atcagtactc ccgtcctttg atcagtcatt tttttcacga    10920
ggccccctaa agggatactt gggctcgtcc acctctatgt cgacccagct attccatgca   10980
tgggaaaaag tcactaatgt tcatgtggtg aagagagctc tatcgttaaa agaatctata   11040
```

```
aactggttca ttactagaga ttccaacttg gctcaagctc taattaggaa cattatgtct  11100
ctgacaggcc ctgatttccc tctagaggag gcccctgtct tcaaaaggac ggggtcagcc  11160
ttgcataggt tcaagtctgc cagatacagc gaaggagggt attcttctgt ctgcccgaac  11220
ctcctctctc atatttctgt tagtacagac accatgtctg atttgaccca agacgggaag  11280
aactacgatt tcatgttcca gccattgatg ctttatgcac agacatggac atcagagctg  11340
gtacagagag acacaaggct aagagactct acgtttcatt ggcacctccg atgcaacagg  11400
tgtgtgagac ccattgacga cgtgaccctg gagacctctc agatcttcga gtttccggat  11460
gtgtcgaaaa gaatatccag aatggttcct ggggctgtgc ctcacttcca gaggcttccc  11520
gatatccgtc tgagaccagg agattttgaa tctctaagcg gtagagaaaa gtctcaccat  11580
atcggatcag ctcaggggct cttatactca atcttagtgg caattcacga ctcaggatac  11640
aatgatggaa ccatcttccc tgtcaacata tacggcaagg tttcccctag agactatttg  11700
agagggctcg caaggggagt attgatagga tcctcgattt gcttcttgac aagaatgaca  11760
aatatcaata ttaatagacc tcttgaattg gtctcagggg taatctcata tattctcctg  11820
aggctagata accatccctc cttgtacata atgctcagag aaccgtctct tagaggagag  11880
atattttcta tccctcagaa aatccccgcc gcttatccaa ccactatgaa agaaggcaac  11940
agatcaatct tgtgttatct ccaacatgtg ctacgctatg agcgagagat aatcacggcg  12000
tctccagaga atgactggct atggatcttt tcagacttta gaagtgccaa aatgacgtac  12060
ctatccctca ttacttacca gtctcatctt ctactccaga gggttgagag aaacctatct  12120
aagagtatga gagataacct gcgacaattg agttctttga tgaggcaggt gctgggcggg  12180
cacggagaag ataccttaga gtcagacgac aacattcaac gactgctaaa agactcttta  12240
cgaaggacaa gatgggtgga tcaagaggtg cgccatgcag ctagaaccat gactggagat  12300
tacagcccca acaagaaggt gtcccgtaag gtaggatgtt cagaatgggt ctgctctgct  12360
caacaggttg cagtctctac ctcagcaaac ccggcccctg tctcggagct tgacataagg  12420
gccctctcta agaggttcca gaacccttg atctcgggct tgagagtggt tcagtgggca  12480
accggtgctc attataagct taagcctatt ctagatgatc tcaatgtttt cccatctctc  12540
tgccttgtag ttggggacgg gtcagggggg atatcaaggg cagtcctcaa catgtttcca  12600
gatgccaagc ttgtgttcaa cagtctttta gaggtgaatg acctgatggc ttccggaaca  12660
catccactgc ctccttcagc aatcatgagg ggaggaaatg atatcgtctc cagagtgata  12720
gatcttgact caatctggga aaaaccgtcc gacttgagaa acttggcaac ctggaaatac  12780
ttccagtcag tccaaaagca ggtcaacatg tcctatgacc tcattatttg cgatgcagaa  12840
gttactgaca ttgcatctat caaccggatc accctgttaa tgtccgattt tgcattgtct  12900
atagatggac cactctattt ggtcttcaaa acttatggga ctatgctagt aaatccaaac  12960
tacaaggcta ttcaacacct gtcaagagcg ttccctctcgg tcacagggtt tatcacccaa  13020
gtaacttcgt cttttttcatc tgagctctac ctccgattct ccaaacgagg gaagtttttc  13080
agagatgctg agtacttgac ctcttccacc cttcgagaaa tgagccttgt gttattcaat  13140
tgtagcagcc ccaagagtga gatgcagaga gctcgttcct tgaactatca ggatcttgtg  13200
agaggatttc ctgaagaaat catatcaaat ccttacaatg agatgatcat aactctgatt  13260
gacagtgatg tagaatcttt tctagtccac aagatggttg atgatcttga gttacagagg  13320
ggaactctgt ctaaagtggc tatcattata gccatcatga tagttttctc caacagagtc  13380
ttcaacgttt ccaaacccct aactgacccc tcgttctatc caccgtctga tcccaaaatc  13440
```

```
ctgaggcact tcaacatatg ttgcagtact atgatgtatc tatctactgc tttaggtgac    13500
gtccctagct tcgcaagact tcacgacctg tataacagac ctataactta ttacttcaga    13560
aagcaagtca ttcgagggaa cgtttatcta tcttggagtt ggtccaacga cacctcagtg    13620
ttcaaaaggg tagcctgtaa ttctagcctg agtctgtcat ctcactggat caggttgatt    13680
tacaagatag tgaagactac cagactcgtt ggcagcatca aggatctatc cagagaagtg    13740
gaaagacacc ttcataggta caacaggtgg atcaccctag aggatatcag atctagatca    13800
tccctactag actacagttg cctgtgaacc ggatactcct ggaagcctgc ccatgctaag    13860
actcttgtgt gatgtatctt gaaaaaaaca agatcctaaa tctgaacctt tggttgtttg    13920
attgtttttc tcatttttgt tgtttatttg ttaagcgt                            13958

<210> SEQ ID NO 10
<211> LENGTH: 13826
<212> TYPE: DNA
<213> ORGANISM: Artificial Sequence
<220> FEATURE:
<223> OTHER INFORMATION: RABV vector: Coravax V3-China (S1-VSVG-E26)

<400> SEQUENCE: 10
acgcttaaca accagatcaa agaaaaaaca gacattgtca attgcaaagc aaaaatgtaa      60 caccoctaca atggatgccg acaagattgt attcaaagtc aataatcagg tggtctcttt     120
gaagcctgag attatcgtgg atcaatatga gtacaagtac cctgccatca agatttgaa      180 aaagccctgt ataaccctag gaaaggctcc cgatttaaat aaagcataca agtcagtttt     240
gtcaggcatg agcgccgcca aacttaatcc tgacgatgta tgttcctatt tggcagcggc     300
aatgcagttt tttgagggga catgtccgga agactggacc agctatgaa ttgtgattgc      360 acgaaaagga gataagatca ccccaggttc tctggtggag ataaaacgta ctgatgtaga     420
agggaattgg gctctgacag gaggcatgga actgacaaga gaccccactg tccctgagca     480
tgcgtcctta gtcggtcttc tcttgagtct gtataggttg agcaaaatat ccgggcaaaa     540
cactggtaac tataagacaa acattgcaga caggatagag cagattttg agacagcccc     600 ttttgttaaa atcgtggaac accatactct aatgacaact cacaaaatgt gtgctaattg     660
gagtactata ccaaacttca gattttggc cggaacctat gacatgtttt tctcccggat      720
tgagcatcta tattcagcaa tcagagtggg cacagttgtc actgcttatg aagactgttc     780
aggactggta tcatttactg ggttcataaa acaaatcaat ctcaccgcta gagaggcaat     840
actatatttc ttccacaaga actttgagga agagataaga agaatgtttg agccagggca     900
ggagacagct gttcctcact cttatttcat ccacttccgt tcactaggct tgagtgggaa     960
atctccttat tcatcaaatg ctgttggtca cgtgttcaat ctcattcact tgtaggatg     1020 ctatatgggt caagtcagat ccctaaatgc aacggttatt gctgcatgtg ctcctcatga    1080
aatgtctgtt ctagggggct atctgggaga ggaattcttc gggaagggga catttgaaag    1140
aagattcttc agagatgaga aagaacttca agaatacgag gcggctgaac tgacaaagac    1200
tgacgtagca ctggcagatg atggaactgt caactctgac gacgaggact actttctcagg   1260 tgaaaccaga agtccggagg ctgtttatac tcgaatcatg atgaatggag gtcgactaaa    1320
gagatctcac atacggagat atgtctcagt cagttccaat catcaagccc gtccaaactc    1380
attcgccgag tttctaaaca agacatattc gagtgactca taacatgaaa aaaactaaca    1440
cccctcccgt acgccaccat gttcgtgttt ctggtgctgc tgcctctggt gagctcccag    1500
```

```
tgcgtgaacc tgaccacaag gacccagctg cccctgcct ataccaattc cttcacacgg    1560
ggcgtgtact atcccgacaa ggtgttccgg agcagcgtgc tgcactccac acaggatctg    1620
tttctgcctt tcttttctaa cgtgacctgg ttccacgcca tccacgtgag cggcaccaat    1680
ggcacaaagc ggttcgacaa tccagtgctg cccttaacg atggcgtgta cttcgcctcc     1740
accgagaagt ctaacatcat cagaggctgg atctttggca ccacactgga cagcaagaca    1800
cagtccctgc tgatcgtgaa caatgccacc aacgtggtca tcaaggtgtg cgagttccag    1860
ttttgtaatg atccattcct gggcgtgtac tatcacaaga acaataagtc ttggatggag    1920
agcgagtttc gcgtgtattc ctctgccaac aattgcacat ttgagtacgt gtcccagccc    1980
ttcctgatgg acctggaggg caagcagggc aatttcaaga acctgaggga gttcgtgttt    2040
aagaatatcg atggctactt caaaatctac tccaagcaca ccccaatcaa cctggtgcgc    2100
gacctgccac agggcttctc tgccctggag ccactggtgg atctgcccat cggcatcaac    2160
atcacccggt ttcagacact gctggccctg cacagaagct acctgacacc aggcgacagc    2220
tcctctggat ggaccgcagg agcagcagcc tactatgtgg gctatctgca gcccaggacc    2280
ttcctgctga gtacaacga gaatggcacc atcacagacg ccgtggattg cgccctggat    2340
cccctgtctg agaccaagtg tacactgaag agctttaccg tggagaaggg catctatcag    2400
acaagcaatt tcagggtgca gcctaccgag tccatcgtgc gctttcccaa tatcacaaac    2460
ctgtgcccct ttggcgaggt gttcaacgca acccgcttcg ccagcgtgta cgcctggaat    2520
aggaagcgca tctccaactg cgtggccgac tattctgtgc tgtacaacag cgcctccttc    2580
tctacctta agtgctatgg cgtgagcccc acaaagctga atgacctgtg ctttaccaac    2640
gtgtacgccg attccttcgt gatcagggc gacgaggtgc gccagatcgc accaggacag    2700
acaggcaaga tcgcagacta caattataag ctgcctgacg atttcaccgg ctgcgtgatc    2760
gcctggaact ctaacaatct ggatagcaaa gtgggcggca actacaatta tctgtaccgg    2820
ctgtttagaa agtctaatct gaagccattc gagagggaca tctccacaga aatctaccag    2880
gccggctcta ccccctgcaa tggcgtggag ggctttaact gttatttccc tctgcagagc    2940
tacggcttcc agccaacaaa cggcgtgggc tatcagccct accgcgtggt ggtgctgtct    3000
tttgagctgc tgcacgcacc tgcaacagtg tgcggaccaa agaagagcac caatctggtg    3060
aagaacaagt gcgtgaactt caacttcaac ggactgaccg gaacaggcgt gctgaccgag    3120
tccaacaaga agttcctgcc ttttcagcag ttcggcaggg acatcgcaga taccacagac    3180
gccgtgcgcg accctcagac cctggagatc ctggacatca ccatgctc cttcggcggc    3240
gtgtctgtga tcacaccagg caccaataca agcaaccagg tggccgtgct gtatcaggac    3300
gtgaattgta ccgaggtgcc agtggcaatc cacgcagatc agctgacccc tacatggcgg    3360
gtgtactcta ccggcagcaa cgtgttccag acaagagccg gatgcctgat cggagcagag    3420
cacgtgaaca atagctatga gtgcgacatc cctatcggcg ccggcatctg tgcctcctac    3480
cagacccaga caaactcccc aaggtctgtg ggcgatacag gcctgtccaa gaatccaatc    3540
gagctggtag agggctggtt cagcagttgg aaaagctcca tcgcctcctt tttctttatc    3600
atcggcctga tcatcggact gttcctggtg ctccgcgtgg gtatccacct gtgcatcaag    3660
ctgaagcaca ccaagaaaag acagatttat acagacatcg agatgaaccg cctgggaaag    3720
tgagctagcc atgaaaaaaa ctaacacccc tcctttcgaa ccatcccaaa catgagcaag    3780
atctttgtca atcctagtgc tattagagcc ggtctggccg atcttgagat ggctgaagaa    3840
actgttgatc tgatcaatag aaatatcgaa gacaatcagg ctcatctcca aggggaaccc    3900
```

```
atagaggtgg acaatctccc tgaggatatg gggcgacttc acctggatga tggaaaatcg    3960
cccaaccatg gtgagatagc caaggtggga gaaggcaagt atcgagagga ctttcagatg    4020
gatgaaggag aggatcctag cttcctgttc cagtcatacc tggaaaatgt tggagtccaa    4080
atagtcagac aaatgaggtc aggagagaga tttctcaaga tatggtcaca gaccgtagaa    4140
gagattatat cctatgtcgc ggtcaacttt cccaaccctc caggaaagtc ttcagaggat    4200
aaatcaaccc agactactgg ccgagagctc aagaaggaga caacacccac tccttctcag    4260
agagaaagcc aatcatcgaa agccaggatg gcggctcaaa ttgcttctgg ccctccagcc    4320
cttgaatggt cggctaccaa tgaagaggat gatctatcag tggaggctga gatcgctcac    4380
cagattgcag aaagtttctc caaaaaatat aagtttccct ctcgatcctc agggatactc    4440
ttgtataatt tgagcaatt gaaaatgaac cttgatgata tagttaaaga ggcaaaaaat    4500
gtaccaggtg tgacccgttt agcccatgac gggtccaaac tcccctaag atgtgtactg    4560 ggatgggtcg ctttggccaa ctctaagaaa ttccagttgt tagtcgaatc cgacaagctg    4620
agtaaaatca tgcaagatga cttgaatcgc tatacatctt gctaaccgaa cctctcccct    4680
cagtccctct agacaataaa atccgagatg tcccaaagtc aacatgaaaa aaacaggcaa    4740
caccactgat aaaatgaacc tcctacgtaa gatagtgaaa accgcaggg acgaggacac    4800 tcaaaaatcc tctcccgcgt cagcccctct ggatgacgat gacttgtggc ttccaccccc    4860
tgaatacgtc ccgctgaaag aacttacagg caagaagaac atgaggaact tttgtatcaa    4920
cggaagggtt aaagtgtgta gcccgaatgg ttactcgttc aggatcctgc ggcacattct    4980
gaaatcattc gacgagatat attctgggaa tcataggatg atcgggttag tcaaagtggt    5040
tattggactg gctttgtcag gatctccagt ccctgagggc ctgaactggg tatacaaatt    5100
gaggagaacc tttatcttcc agtgggctga ttccaggggc cctcttgaag gggaggagtt    5160
ggaatactct caggagatca cttgggatga tgatactgag ttcgtcggat tgcaaataag    5220
agtgattgca aaacagtgtc atatccaggg cagagtctgg tgtatcaaca tgaacccgag    5280
agcatgtcaa ctatggtctg acatgtctct tcagacacaa aggtccgaag aggacaaaga    5340
ttcctctctg cttctagaat aatcagatta tatcccgcaa atttatcact tgtttacctc    5400
tggaggagag aacatatggg ctcaactcca acccttggga gcaatataac aaaaaacatg    5460
ttatggtgcc attaaaccgc tgcatttcat caaagtcaag ttgattacct ttacattttg    5520
atcctcttgg atgtgaaaaa aactattaac atccctcaaa agaccccggg aaagatggtt    5580
cctcaggctc tcctgtttgt accccttctg gttttccat tgtgttttgg gaaattccct    5640
atttacacga taccagacaa gcttggtccc tggagtccga ttgacataca tcacctcagc    5700
tgcccaaaca atttggtagt ggaggacgaa ggatgcacca acctgtcagg gttctcctac    5760
atggaactta aagttggata catcttagcc ataaaagtga acgggttcac ttgcacaggc    5820
gttgtgacga aggctgaaac ctacactaac ttcgttggtt atgtcacaac cacgttcaaa    5880
agaaagcatt tccgcccaac accagatgca tgtagagccg cgtacaactg gaagatggcc    5940 ggtgaccccca gatatgaaga gtctctacac aatccgtacc ctgactaccg ctggcttcga    6000
actgtaaaaa ccaccaagga gtctctcgtt atcatatctc caagtgtggc agatttggac    6060
ccatatgaca gatcccttca ctcgagggtc ttccctagcg ggaagtgctc aggagtagcg    6120
gtgtcttcta cctactgctc cactaaccac gattacacca tttggatgcc cgagaatccg    6180
agactaggga tgtcttgtga cattttacc aatagtagag ggaagagagc atccaaaggg    6240
```

```
agtgagactt gcggctttgt agatgaaaga ggcctatata agtctttaaa aggagcatgc    6300
aaactcaagt tatgtggagt tctaggactt agacttatgg atggaacatg ggtctcgatg    6360
caaacatcaa atgaaaccaa atggtgccct cccgataagt tggtgaacct gcacgacttt    6420
cgctcagacg aaattgagca ccttgttgta gaggagttgg tcaggaagag agaggagtgt    6480
ctggatgcac tagagtccat catgacaacc aagtcagtga gtttcagacg tctcagtcat    6540
ttaagaaaac ttgtccctgg gtttggaaaa gcatatacca tattcaacaa gaccttgatg    6600
gaagccgatg ctcactacaa gtcagtcgag acttggaatg agatcctccc ttcaaaaggg    6660
tgtttaagag ttgggggggag gtgtcatcct catgtgaacg gggtgttttt caatggtata    6720
atattaggac ctgacggcaa tgtcttaatc ccagagatgc aatcatccct cctccagcaa    6780
catatggagt tgttggaatc ctcggttatc ccccttgtgc accccctggc agacccgtct    6840
accgttttca aggacggtga cgaggctgag gattttgttg aagttcacct tcccgatgtg    6900
cacaatcagg tctcaggagt tgacttgggt ctcccgaact gggggaagta tgtattactg    6960
agtgcagggg ccctgactgc cttgatgttg ataattttcc tgatgacatg ttgtagaaga    7020
gtcaatcgat cagaacctac gcaacacaat ctcagaggga cagggaggga ggtgtcagtc    7080
actcccaaaa gcgggaagat catatcttca tgggaatcac acaagagtgg gggtgagacc    7140
agactgtaat taattaacgt cctttcaacg atccaagtcc atgaaaaaaa ctaacacccc    7200
tcccgtacct agcttataaa gtgctgggtc atctaagctt ttcagtcgag aaaaaaacat    7260
tagatcagaa gaacaactgg caacacttct caacctgaga cttacttcaa gatgctcgat    7320
cctggagagg tctatgatga ccctattgac ccaatcgagt tagaggctga acccagagga    7380 accccattg tccccaacat cttgaggaac tctgactaca atctcaactc tcctttgata    7440
gaagatcctg ctagactaat gttagaatgg ttaaaaacag ggaatagacc ttatcggatg    7500
actctaacag acaattgctc caggtctttc agagttttga agattattt caagaaggta    7560 gatttgggtt ctctcaaggt gggcggaatg gctgcacagt caatgatttc tctctggtta    7620
tatggtgccc actctgaatc caacaggagc cggagatgta taacagactt ggcccatttc    7680
tattccaagt cgtcccccat agagaagctg ttgaatctca cgctaggaaa tagagggctg    7740
agaatccccc cagagggagt gttaagttgc cttgagaggg ttgattatga taatgcattt    7800
ggaaggtatc ttgccaacac gtattcctct tacttgttct tccatgtaat caccttatac    7860
atgaacgccc tagactggga tgaagaaaag accatcctag cattatggaa agatttaacc    7920
tcagtggaca tcgggaagga cttggtaaag ttcaaagacc aaatatgggg actgctgatc    7980
gtgacaaagg actttgttta ctcccaaagt tccaattgtc tttttgacag aaactacaca    8040
cttatgctaa aagatctttt cttgtctcgc ttcaactcct taatggtctt gctctctccc    8100
ccagagcccc gatactcaga tgacttgata tctcaactat gccagctgta cattgctggg    8160
gatcaagtct tgtctatgtg tggaaactcc ggctatgaag tcatcaaaat attggagcca    8220
tatgtcgtga atagtttagt ccagagagca gaaaagttta ggcctctcat tcattccttg    8280
ggagactttc ctgtatttat aaaagacaag gtaagtcaac ttgaagagac gttcggtccc    8340
tgtgcaagaa ggttctttag ggctctggat caattcgaca acatacatga cttggttttt    8400
gtgtttggct gttacaggca ttgggggcac ccatatatag attatcgaaa gggtctgtca    8460
aaactatatg atcaggttca ccttaaaaaa atgatagata agtcctacca ggagtgctta    8520
gcaagcgacc tagccaggag gatccttaga tggggttttg ataagtactc caagtggtat    8580
ctggattcaa gattcctagc ccgagaccac cccttgactc cttatatcaa aacccaaaca    8640
```

-continued

```
tggccaccca aacatattgt agacttggtg ggggatacat ggcacaagct cccgatcacg   8700
cagatctttg agattcctga atcaatggat ccgtcagaaa tattggatga caaatcacat   8760
tctttcacca gaacgagact agcttcttgg ctgtcagaaa accgaggggg gcctgttcct   8820
agcgaaaaag ttattatcac ggccctgtct aagccgcctg tcaatcccg agagtttctg    8880 aggtctatag acctcggagg attgccagat gaagacttga taattggcct caagccaaag   8940
gaacgggaat tgaagattga aggtcgattc tttgctctaa tgtcatggaa tctaagattg   9000
tattttgtca tcactgaaaa actcttggcc aactacatct tgccactttt tgacgcgctg   9060
actatgacag acaacctgaa caaggtgttt aaaaagctga tcgacagggt caccgggcaa   9120
gggcttttgg actattcaag ggtcacatat gcatttcacc tggactatga aaagtggaac   9180
aaccatcaaa gattagagtc aacagaggat gtattttctg tcctagatca agtgtttgga   9240
ttgaagagag tgtttttctag aacacacgag tttttttcaaa aggcctggat ctattattca   9300
gacagatcag acctcatcgg gttacggagg atcaaatat actgcttaga tgcgtccaac     9360
ggcccaacct gttggaatgg ccaggatggc gggctagaag gcttacggca aagggctgg    9420 agtctagtca gctattgat gatagataga gaatctcaaa tcaggaacac aagaaccaaa    9480
atactagctc aaggagacaa ccaggttta tgtccgacat acatgttgtc gccagggcta    9540
tctcaagagg ggctcctcta tgaattggag agaatatcaa ggaatgcact ttcgatatac   9600
agagccgtcg aggaaggggc atctaagcta gggctgatca tcaagaaaga agagaccatg   9660
tgtagttatg acttcctcat ctatggaaaa acccctttgt ttagaggtaa catattggtg   9720
cctgagtcca aaagatgggc cagagtctct tgcgtctcta atgaccaaat agtcaacctc   9780
gccaatataa tgtcgacagt gtccaccaat gcgctaacag tggcacaaca ctctcaatct   9840
ttgatcaaac cgatgaggga ttttctgctc atgtcagtac aggcagtctt tcactacctg   9900
ctatttagcc caatcttaaa gggaagagtt tacaagattc tgagcgctga aggggagagc   9960
tttctcctag ccatgtcaag gataatctat ctagatcctt ctttgggagg gatatctgga   10020
atgtccctcg gaagattcca tacgcacag ttctcagacc ctgtctctga agggttatcc    10080
ttctggagag agatctggtt aagctcccaa gagtcctgga ttcacgcgtt gtgtcaagag   10140
gctggaaacc cagatcttgg agagagaaca ctcgagagct tcactcgcct tctagaagat   10200
ccgaccacct taaatatcag aggaggggcc agtcctacca ttctactcaa ggatgcaatc   10260
agaaaggctt tatatgacga ggtggacaag gtggaaaatt cagagtttcg agaggcaatc   10320
ctgttgtcca agaccatag agataatttt atactcttct taatatctgt tgagcctctg    10380
tttcctcgat ttctcagtga gctattcagt tcgtcttttt tgggaatccc cgagtcaatc   10440
attggattga tacaaaactc ccgaacgata agaaggcagt ttagaaagag tctctcaaaa   10500
actttagaag aatccttcta caactcagag atccacggga ttagtcggat gacccagaca   10560
cctcagaggg ttggggggt gtggccttgc tcttcagaga gggcagatct acttaggag    10620 atctcttggg gaagaaaagt ggtaggcacg acagttcctc ccccttctga tgttgggga    10680 ttacttccca agtcctctat ttcttgcact tgtggagcaa caggaggagg caatcctaga   10740
gtttctgtat cagtactccc gtcctttgat cagtcatttt tttcacgagg cccccctaaag  10800 ggatacttgg gctcgtccac ctctatgtcg acccagctat tccatgcatg ggaaaaagtc   10860
actaatgttc atgtggtgaa gagagctcta tcgttaaaag aatctataaa ctggttcatt   10920
actagagatt ccaacttggc tcaagctcta attaggaaca ttatgtctct gacaggccct   10980
```

```
gatttccctc tagaggaggc ccctgtcttc aaaaggacgg ggtcagcctt gcataggttc   11040
aagtctgcca gatacagcga aggagggtat tcttctgtct gcccgaacct cctctctcat   11100
atttctgtta gtacagacac catgtctgat ttgacccaag acgggaagaa ctacgatttc   11160
atgttccagc cattgatgct ttatgcacag acatggacat cagagctggt acagagagac   11220
acaaggctaa gagactctac gtttcattgg cacctccgat gcaacaggtg tgtgagaccc   11280
attgacgacg tgaccctgga gacctctcag atcttcgagt ttccggatgt gtcgaaaaga   11340
atatccagaa tggtttctgg ggctgtgcct cacttccaga ggcttcccga tatccgtctg   11400
agaccaggag attttgaatc tctaagcggt agagaaaagt ctcaccatat cggatcagct   11460
caggggctct tatactcaat cttagtggca attcacgact caggatacaa tgatggaacc   11520
atcttccctg tcaacatata cggcaaggtt tcccctagag actatttgag agggctcgca   11580
aggggagtat tgataggatc ctcgatttgc ttcttgacaa gaatgacaaa tatcaatatt   11640
aatagacctc ttgaattggt ctcagggta atctcatata ttctcctgag gctagataac   11700
catccctcct tgtacataat gctcagagaa ccgtctctta gaggagagat attttctatc   11760
cctcagaaaa tccccgccgc ttatccaacc actatgaaag aaggcaacag atcaatcttg   11820
tgttatctcc aacatgtgct acgctatgag cgagagataa tcacggcgtc tccagagaat   11880
gactggctat ggatcttttc agactttaga agtgccaaaa tgacgtacct atccctcatt   11940
acttaccagt ctcatcttct actccagagg gttgagagaa acctatctaa gagtatgaga   12000
gataacctgc gacaattgag ttctttgatg aggcaggtgc tgggcgggca cggagaagat   12060
accttagagt cagacgacaa cattcaacga ctgctaaaag actctttacg aaggacaaga   12120
tgggtggatc aagaggtgcg ccatgcagct agaaccatga ctggagatta cagccccaac   12180
aagaaggtgt cccgtaaggt aggatgttca gaatgggtct gctctgctca acaggttgca   12240
gtctctacct cagcaaaccc ggcccctgtc tcggagcttg acataagggc cctctctaag   12300
aggttccaga acccttgat ctcgggcttg agagtggttc agtgggcaac cggtgctcat   12360
tataagctta agcctattct agatgatctc aatgttttcc catctctctg ccttgtagtt   12420
ggggacgggt caggggggat atcaagggca gtcctcaaca tgtttccaga tgccaagctt   12480
gtgttcaaca gtcttttaga ggtgaatgac ctgatggctt ccggaacaca tccactgcct   12540
ccttcagcaa tcatgagggg aggaaatgat atcgtctcca gagtgataga tcttgactca   12600
atctgggaaa accgtccga cttgagaaac ttggcaacct ggaaatactt ccagtcagtc   12660
caaaagcagg tcaacatgtc ctatgacctc attatttgcg atgcagaagt tactgacatt   12720
gcatctatca accggatcac cctgttaatg tccgattttg cattgtctat agatggacca   12780
ctctatttgg tcttcaaaac ttatgggact atgctagtaa atccaaacta caaggctatt   12840
caacacctgt caagagcgtt cccctcggtc acagggttta tcacccaagt aacttcgtct   12900
ttttcatctg agctctacct ccgattctcc aaacgaggga agttttttcag agatgctgag   12960 tacttgacct cttccaccct tcgagaaatg agccttgtgt tattcaattg tagcagcccc   13020
aagagtgaga tgcagagagc tcgttccttg aactatcagg atcttgtgag aggatttcct   13080
gaagaaatca tatcaaatcc ttacaatgag atgatcataa ctctgattga cagtgatgta   13140 gaatctttc tagtccacaa gatggttgat gatcttgagt tacagagggg aactctgtct   13200
aaagtggcta tcattatagc catcatgata gttttctcca acagagtctt caacgttttcc   13260 aaacccctaa ctgaccctc gttctatcca ccgtctgatc ccaaaatcct gaggcacttc   13320
aacatatgtt gcagtactat gatgtatcta tctactgctt taggtgacgt ccctagcttc   13380
```

```
gcaagacttc acgacctgta taacagacct ataacttatt acttcagaaa gcaagtcatt    13440
cgagggaacg tttatctatc ttggagttgg tccaacgaca cctcagtgtt caaaagggta    13500
gcctgtaatt ctagcctgag tctgtcatct cactggatca ggttgattta caagatagtg    13560
aagactacca gactcgttgg cagcatcaag gatctatcca gagaagtgga aagacaccett    13620 cataggtaca acaggtggat caccctagag gatatcagat ctagatcatc cctactagac    13680
tacagttgcc tgtgaaccgg atactcctgg aagcctgccc atgctaagac tcttgtgtga    13740
tgtatcttga aaaaacaag atcctaaatc tgaacctttg gttgtttgat tgttttttctc    13800 atttttgttg tttatttgtt aagcgt                                         13826
```

<210> SEQ ID NO 11
<211> LENGTH: 13826
<212> TYPE: DNA
<213> ORGANISM: Artificial Sequence
<220> FEATURE:
<223> OTHER INFORMATION: RABV vector: Coravax V3-South Africa
      (S1-VSVG-E26)

<400> SEQUENCE: 11

```
acgcttaaca accagatcaa agaaaaaaca gacattgtca attgcaaagc aaaaatgtaa      60 caccectaca atggatgccg acaagattgt attcaaagtc aataatcagg tggtctcttt     120
gaagcctgag attatcgtgg atcaatatga gtacaagtac cctgccatca agatttgaa     180 aaagccctgt ataaccctag gaaaggctcc cgatttaaat aaagcataca agtcagtttt     240
gtcaggcatg agcgccgcca aacttaatcc tgacgatgta tgttcctatt tggcagcggc     300
aatgcagttt tttgagggga catgtccgga agactggacc agctatggaa ttgtgattgc     360
acgaaaagga gataagatca ccccaggttc tctggtggag ataaaacgta ctgatgtaga     420
agggaattgg gctctgacag gaggcatgga actgacaaga gaccccactg tccctgagca     480
tgcgtcctta gtcggtcttc tcttgagtct gtataggttg agcaaatat ccgggcaaaa     540 cactggtaac tataagacaa acattgcaga caggatagag cagatttttg agacagcccc     600
ttttgttaaa atcgtggaac accatactct aatgacaact cacaaaatgt gtgctaattg     660
gagtactata ccaaacttca gatttttggc cggaacctat gacatgtttt tctcccggat     720
tgagcatcta tattcagcaa tcagagtggg cacagttgtc actgcttatg aagactgttc     780
aggactggta tcatttactg ggttcataaa acaaatcaat ctcaccgcta gagaggcaat     840
actatatttc ttccacaaga actttgagga agagataaga agaatgtttg agccagggca     900
ggagacagct gttcctcact cttatttcat ccacttccgt tcactaggct gagtgggaa     960 atctccttat tcatcaaatg ctgttggtca cgtgttcaat ctcattcact ttgtaggatg    1020
ctatatgggt caagtcagat ccctaaatgc aacggttatt gctgcatgtg ctcctcatga    1080
aatgtctgtt ctaggggct atctgggaga ggaattcttc gggaaaggga catttgaaag    1140
aagattcttc agagatgaga aagaacttca agaatacgag gcggctgaac tgacaaagac    1200
tgacgtagca ctggcagatg atggaactgt caactctgac gacgaggact acttttcagg    1260
tgaaaccaga agtccggagg ctgtttatac tcgaatcatg atgaatggag tcgactaaa    1320 gagatctcac atacggagat atgtctcagt cagttccaat catcaagccc gtccaaactc    1380
attcgccgag tttctaaaca agacatattc gagtgactca taacatgaaa aaaactaaca    1440
cccctcccgt acgccaccat gttcgtgttt ctggtgctgc tgcctctggt gagctcccag    1500
tgcgtgaact tcaccacaag gacccagctg cccccctgcct ataccaattc cttcacacgg    1560
```

```
ggcgtgtact atcccgacaa ggtgttccgg agcagcgtgc tgcactccac acaggatctg    1620
tttctgcctt tcttttctaa cgtgacctgg ttccacgcca tccacgtgag cggcaccaat    1680
ggcacaaagc ggttcgccaa tccagtgctg ccctttaacg atggcgtgta cttcgcctcc    1740
accgagaagt ctaacatcat cagaggctgg atctttggcc ccacactgga cagcaagaca    1800
cagtccctgc tgatcgtgaa caatgccacc aacgtggtca tcaaggtgtg cgagttccag    1860
ttttgtaatg atccattcct gggcgtgtac atcacaagaa caataagtc ttggatggag     1920
agcgagtttc gcgtgtattc ctctgccaac aattgcacat tgagtacgt gtcccagccc     1980
ttcctgatgg acctggaggg caagcagggc aatttcaaga acctgaggga gttcgtgttt    2040
aagaatatcg atggctactt caaaatctac tccaagcaca ccccaatcaa cctggtgcgc    2100
ggcctgccac agggcttctc tgccctggag ccactggtgg atctgcccat cggcatcaac    2160
atcacccggt tcagacact gctggccctg cacagaagct acctgacacc aggcgacagc      2220
tcctctggat ggaccgcagg agcagcagcc tactatgtgg gctatctgca gcccaggacc    2280
ttcctgctga agtacaacga gaatggcacc atcacagacg ccgtggattg cgccctggat    2340
cccctgtctg agaccaagtg tacactgaag agctttaccg tggagaaggg catctatcag    2400
acaagcaatt tcagggtgca gcctaccgag tccatcgtgc gctttcccaa tatcacaaac    2460
ctgtgccctt ttggcgaggt gttcaacgca cccgcttcg ccagcgtgta cgcctggaat     2520
aggaagcgca tctccaactg cgtggccgac tattctgtgc tgtacaacag cgcctccttc    2580
tctaccttta gtgctatgg cgtgagcccc acaaagctga atgacctgtg ctttaccaac     2640
gtgtacgccg attccttcgt gatcagggc gacgaggtgc gccagatcgc accaggacag     2700
acaggcaata tcgcagacta caattataag ctgcctgacg atttcaccgg ctgcgtgatc    2760
gcctggaact ctaacaatct ggatagcaaa gtgggcggca actacaatta tctgtaccgg    2820
ctgtttagaa agtctaatct gaagccattc gagagggaca tctccacaga aatctaccag    2880
gccggctcta ccccctgcaa tggcgtgaag ggctttaact gttatttccc tctgcagagc    2940
tacggcttcc agccaacata tggcgtgggc tatcagccct accgcgtggt ggtgctgtct    3000
tttgagctgc tgcacgcacc tgcaacagtg tgcggaccaa agaagagcac caatctggtg    3060
aagaacaagt gcgtgaactt caacttcaac ggactgaccg gaacaggcgt gctgaccgag    3120
tccaacaaga agttcctgcc ttttcagcag ttcggcaggg acatcgcaga taccacagac    3180
gccgtgcgcg accctcagac cctggagatc ctggacatca ccatgctc cttcggcggc     3240
gtgtctgtga tcacccagg caccaataca agcaaccagg tggccgtgct gtatcagggc    3300
gtgaattgta ccgaggtgcc agtggcaatc cacgcagatc agctgacccc tacatggcgg    3360
gtgtactcta ccgcagcaa cgtgttccag acaagagccg gatgcctgat cggagcagag    3420
cacgtgaaca atagctatga gtgcgacatc cctatcggcg ccggcatctg tgcctcctac    3480
cagacccaga caaactcccc aaggtctgtg gcgatacag gcctgtccaa gaatccaatc     3540
gagctggtag agggctggtt cagcagttgg aaaagctcca tcgcctcctt tttctttatc    3600
atcggcctga tcatcggact gttcctggtg ctccgcgtgg gtatccacct gtgcatcaag    3660
ctgaagcaca ccaagaaaag acagatttat acagacatcg agatgaaccg cctgggaaag    3720
tgagctagcc atgaaaaaaa ctaacacccc tccttttcgaa ccatcccaaa catgagcaag    3780
atctttgtca atcctagtgc tattagagcc ggtctggccg atcttgagat ggctgaagaa    3840
actgttgatc tgatcaatag aaatatcgaa gacaatcagg ctcatctcca agggaaccc      3900
```

```
atagaggtgg acaatctccc tgaggatatg gggcgacttc acctggatga tggaaaatcg   3960
cccaaccatg gtgagatagc caaggtggga gaaggcaagt atcgagagga ctttcagatg   4020
gatgaaggag aggatcctag cttcctgttc cagtcatacc tggaaaatgt tggagtccaa   4080
atagtcagac aaatgaggtc aggagagaga tttctcaaga tatggtcaca gaccgtagaa   4140
gagattatat cctatgtcgc ggtcaacttt cccaaccctc aggaaagtc ttcagaggat   4200
aaatcaaccc agactactgg ccgagagctc aagaaggaga caacacccac tccttctcag   4260
agagaaagcc aatcatcgaa agccaggatg gcggctcaaa ttgcttctgg ccctccagcc   4320
cttgaatggt cggctaccaa tgaagaggat gatctatcag tggaggctga gatcgctcac   4380
cagattgcag aaagtttctc caaaaaatat aagtttccct ctcgatcctc agggatactc   4440
ttgtataatt ttgagcaatt gaaaatgaac cttgatgata tagttaaaga ggcaaaaaat   4500
gtaccaggtg tgacccgttt agcccatgac gggtccaaac tcccctaag atgtgtactg    4560
ggatgggtcg ctttggccaa ctctaagaaa ttccagttgt tagtcgaatc cgacaagctg   4620
agtaaaatca tgcaagatga cttgaatcgc tatacatctt gctaaccgaa cctctcccct   4680
cagtccctct agacaataaa atccgagatg tcccaaagtc aacatgaaaa aaacaggcaa   4740
caccactgat aaaatgaacc tcctacgtaa gatagtgaaa accgcaggg acgaggacac    4800
tcaaaaatcc tctcccgcgt cagcccctct ggatgacgat gacttgtggc ttccaccccc   4860
tgaatacgtc ccgctgaaag aacttacagg caagaagaac atgaggaact tttgtatcaa   4920
cggaagggtt aaagtgtgta gcccgaatgg ttactcgttc aggatcctgc ggcacattct   4980
gaaatcattc gacgagatat attctgggaa tcataggatg atcgggttag tcaaagtggt   5040
tattggactg gctttgtcag gatctccagt ccctgagggc ctgaactggg tatacaaatt   5100
gaggagaacc tttatcttcc agtgggctga ttccagggge cctcttgaag gggaggagtt   5160
ggaatactct caggagatca cttgggatga tgatactgag ttcgtcggat tgcaaataag   5220
agtgattgca aaacagtgtc atatccaggg cagagtctgg tgtatcaaca tgaacccgag   5280
agcatgtcaa ctatggtctg acatgtctct tcagacacaa aggtccgaag aggacaaaga   5340
ttcctctctg cttctagaat aatcagatta tatcccgcaa atttatcact tgtttacctc   5400
tggaggagag aacatatggg ctcaactcca acccttggga gcaatataac aaaaaacatg   5460
ttatggtgcc attaaaccgc tgcatttcat caaagtcaag ttgattacct ttacattttg   5520
atcctcttgg atgtgaaaaa aactattaac atccctcaaa agaccccggg aaagatggtt   5580
cctcaggctc tcctgtttgt acccctttctg gttttccat tgtgttttgg gaaattccct   5640
atttacacga taccagacaa gcttggtccc tggagtccga ttgacataca tcacctcagc   5700
tgcccaaaca atttggtagt ggaggacgaa ggatgcacca acctgtcagg gttctcctac   5760
atggaactta agttggata catcttagcc ataaaagtga acgggttcac ttgcacaggc    5820
gttgtgacgg aggctgaaac ctacactaac ttcgttggtt atgtcacaac cacgttcaaa   5880
agaaagcatt tccgcccaac accagatgca tgtagagccg cgtacaactg gaagatggcc   5940
ggtgacccca gatatgaaga gtctctacac aatccgtacc ctgactaccg ctggcttcga   6000
actgtaaaaa ccaccaagga gtctctcgtt atcatatctc caagtgtggc agatttggac   6060
ccatatgaca gatcccttca ctcgagggtc ttccctagcg ggaagtgctc aggagtagcg   6120
gtgtcttcta cctactgctc cactaaccac gattacacca tttggatgcc cgagaatccg   6180
agactaggga tgtcttgtga cattttttacc aatagtagag ggaagagagc atccaaaggg   6240
agtgagactt gcggctttgt agatgaaaga ggcctatata agtctttaaa aggagcatgc   6300
```

```
aaactcaagt tatgtggagt tctaggactt agacttatgg atggaacatg ggtctcgatg   6360
caaacatcaa atgaaaccaa atggtgccct cccgataagt tggtgaacct gcacgacttt   6420
cgctcagacg aaattgagca ccttgttgta gaggagttgg tcaggaagag agaggagtgt   6480
ctggatgcac tagagtccat catgacaacc aagtcagtga gtttcagacg tctcagtcat   6540
ttaagaaaac ttgtccctgg gtttggaaaa gcatatacca tattcaacaa gaccttgatg   6600
gaagccgatg ctcactacaa gtcagtcgag acttggaatg agatcctccc ttcaaaaggg   6660
tgtttaagag ttgggggggag tgtcatcct catgtgaacg gggtgttttt caatggtata    6720
atattaggac ctgacggcaa tgtcttaatc ccagagatgc aatcatccct cctccagcaa   6780
catatggagt tgttggaatc ctcggttatc ccccttgtgc acccctggc agacccgtct    6840
accgttttca aggacggtga cgaggctgag gattttgttg aagttcacct tcccgatgtg   6900
cacaatcagg tctcaggagt tgacttgggt ctcccgaact gggggaagta tgtattactg   6960
agtgcagggg ccctgactgc cttgatgttg ataattttcc tgatgacatg ttgtagaaga   7020
gtcaatcgat cagaacctac gcaacacaat ctcagaggga cagggaggga ggtgtcagtc   7080
actccccaaa gcgggaagat catatcttca tgggaatcac acaagagtgg gggtgagacc   7140
agactgtaat taattaacgt cctttcaacg atccaagtcc atgaaaaaaa ctaacacccc   7200
tcccgtacct agcttataaa gtgctgggtc atctaagctt ttcagtcgag aaaaaaacat   7260
tagatcagaa gaacaactgg caacacttct caacctgaga cttacttcaa gatgctcgat   7320
cctggagagg tctatgatga ccctattgac ccaatcgagt tagaggctga acccagagga   7380
accccattg tccccaacat cttgaggaac tctgactaca atctcaactc tcctttgata   7440
gaagatcctg ctagactaat gttagaatgg ttaaaaacag ggaatagacc ttatcggatg   7500
actctaacag acaattgctc caggtctttc agagttttga aagattattt caagaaggta   7560
gatttgggtt ctctcaaggt gggcggaatg gctgcacagt caatgatttc tctctggtta   7620
tatggtgccc actctgaatc caacaggagc cggagatgta taacagactt ggcccatttc   7680
tattccaagt cgtcccccat agagaagctg ttgaatctca cgctaggaaa tagagggctg   7740
agaatccccc cagagggagt gttaagttgc cttgagaggg ttgattatga taatgcattt   7800
ggaaggtatc ttgccaacac gtattcctct tacttgttct tccatgtaat caccttatac   7860
atgaacgccc tagactggga tgaagaaaag accatcctag cattatgaa agatttaacc     7920
tcagtggaca tcgggaagga cttggtaaag ttcaaagacc aaatatgggg actgctgatc   7980
gtgacaaagg actttgttta ctcccaaagt tccaattgtc ttttgacag aaactacaca    8040
cttatgctaa aagatctttt cttgtctcgc ttcaactcct taatggtctt gctctctccc   8100
ccagagcccc gatactcaga tgacttgata tctcaactat gccagctgta cattgctggg   8160
gatcaagtct tgtctatgtg tggaaactcc ggctatgaag tcatcaaaat attggagcca   8220
tatgtcgtga atagtttagt ccagagagca gaaaagttta ggcctctcat tcattccttg   8280
ggagactttc ctgtatttat aaaagacaag gtaagtcaac ttgaagagac gttcggtccc   8340
tgtgcaagaa ggttctttag ggctctggat caattcgaca acatacatga cttggttttt   8400
gtgtttggct gttacaggca ttgggggcac ccatatatag attatcgaaa gggtctgtca   8460
aaactatatg atcaggttca ccttaaaaaa atgatagata agtcctacca ggagtgctta   8520
gcaagcgacc tagccaggag gatccttaga tgggtttg ataagtactc caagtggtat    8580
ctggattcaa gattcctagc ccgagaccac cccttgactc cttatatcaa aacccaaaca   8640
```

```
tggccaccca aacatattgt agacttggtg ggggatacat ggcacaagct cccgatcacg    8700
cagatctttg agattcctga atcaatggat ccgtcagaaa tattggatga caaatcacat    8760
tctttcacca gaacgagact agcttcttgg ctgtcagaaa accgaggggg gcctgttcct    8820
agcgaaaaag ttattatcac ggccctgtct aagccgcctg tcaatccccg agagtttctg    8880
aggtctatag acctcggagg attgccagat gaagacttga taattggcct caagccaaag    8940
gaacgggaat tgaagattga aggtcgattc tttgctctaa tgtcatggaa tctaagattg    9000
tattttgtca tcactgaaaa actcttggcc aactacatct tgccactttt tgacgcgctg    9060
actatgacag acaacctgaa caaggtgttt aaaaagctga tcgacagggt caccgggcaa    9120
gggcttttgg actattcaag ggtcacatat gcatttcacc tggactatga aaagtggaac    9180
aaccatcaaa gattagagtc aacagaggat gtattttctg tcctagatca agtgtttgga    9240
ttgaagagag tgttttctag aacacacgag ttttttcaaa aggcctggat ctattattca    9300
gacagatcag acctcatcgg gttacgggag gatcaaatat actgcttaga tgcgtccaac    9360
ggcccaacct gttggaatgg ccaggatggc gggctagaag gcttacggca gaagggctgg    9420
agtctagtca gcttattgat gatagataga gaatctcaaa tcaggaacac aagaaccaaa    9480
atactagctc aaggagacaa ccaggtttta tgtccgacat acatgttgtc gccagggcta    9540
tctcaagagg ggctcctcta tgaattggag agaatatcaa ggaatgcact ttcgatatac    9600
agagccgtcg aggaaggggc atctaagcta gggctgatca tcaagaaaga agagaccatg    9660
tgtagttatg acttcctcat ctatggaaaa accccttgt ttagaggtaa catattggtg    9720
cctgagtcca aaagatgggc cagagtctct tgcgtctcta atgaccaaat agtcaacctc    9780
gccaatataa tgtcgacagt gtccaccaat gcgctaacag tggcacaaca ctctcaatct    9840
ttgatcaaac cgatgaggga ttttctgctc atgtcagtac aggcagtctt tcactacctg    9900
ctatttagcc aatcttaaa gggaagagtt tacaagattc tgagcgctga aggggagagc    9960
tttctcctag ccatgtcaag gataatctat ctagatcctt ctttgggagg gatatctgga   10020
atgtccctcg gaagattcca tatacgacag ttctcagacc ctgtctctga agggttatcc   10080
ttctggagag agatctggtt aagctcccaa gagtcctgga ttcacgcgtt gtgtcaagag   10140
gctggaaacc cagatcttgg agagagaaca ctcgagagct tcactcgcct tctagaagat   10200
ccgaccacct aaatatcag aggaggggcc agtcctacca ttctactcaa ggatgcaatc   10260
agaaaggctt tatatgacga ggtggacaag gtggaaaatt cagagtttcg agaggcaatc   10320
ctgttgtcca agaccataq agataatttt atactcttct taatatctgt tgagcctctg   10380
tttcctcgat ttctcagtga gctattcagt tcgtcttttt tgggaatccc cgagtcaatc   10440
attggattga tacaaaactc ccgaacgata agaaggcagt ttagaaagag tctctcaaaa   10500
actttagaag aatccttcta caactcagag atccacggga ttagtcggat gacccagaca   10560
cctcagaggg ttgggggggt gtggccttgc tcttcagaga gggcagatct acttaggagg   10620
atctcttggg gaagaaaagt ggtaggcacg acagttcctc acccttctga gatgttggga   10680
ttacttccca gtcctctat ttcttgcact tgtggagcaa caggaggagg caatcctaga   10740
gtttctgtat cagtactccc gtcctttgat cagtcatttt tttcacgagg ccccctaaag   10800
ggatacttgg gctcgtccac ctctatgtcg acccagctat tccatgcatg ggaaaaagtc   10860
actaatgttc atgtggtgaa gagagctcta tcgttaaaag aatctataaa ctggttcatt   10920
actagagatt ccaacttggc tcaagctcta attaggaaca ttatgtctct gacaggcccc   10980
gatttccctc tagaggaggc ccctgtcttc aaaaggacgg ggtcagcctt gcataggttc   11040
```

```
aagtctgcca gatacagcga aggagggtat tcttctgtct gcccgaacct cctctctcat  11100
atttctgtta gtacagacac catgtctgat ttgacccaag acgggaagaa ctacgatttc  11160
atgttccagc cattgatgct ttatgcacag acatggacat cagagctggt acagagagac  11220
acaaggctaa gagactctac gtttcattgg cacctccgat gcaacaggtg tgtgagaccc  11280
attgacgacg tgaccctgga gacctctcag atcttcgagt ttccggatgt gtcgaaaaga  11340
atatccagaa tggtttctgg ggctgtgcct cacttccaga ggcttcccga tatccgtctg  11400
agaccaggag attttgaatc tctaagcggt agagaaaagt ctcaccatat cggatcagct  11460
caggggctct tatactcaat cttagtggca attcacgact caggatacaa tgatggaacc  11520
atcttccctg tcaacatata cggcaaggtt tcccctagag actatttgag agggctcgca  11580
aggggagtat tgataggatc ctcgatttgc ttcttgacaa gaatgacaaa tatcaatatt  11640
aatagacctc ttgaattggt ctcaggggta atctcatata ttctcctgag gctagataac  11700
catccctcct tgtacataat gctcagagaa ccgtctctta gaggagagat attttctatc  11760
cctcagaaaa tccccgccgc ttatccaacc actatgaaag aaggcaacag atcaatcttg  11820
tgttatctcc aacatgtgct acgctatgag cgagagataa tcacggcgtc tccagagaat  11880
gactggctat ggatcttttc agactttaga agtgccaaaa tgacgtacct atccctcatt  11940
acttaccagt ctcatcttct actccagagg gttgagagaa acctatctaa gagtatgaga  12000
gataacctgc gacaattgag ttctttgatg aggcaggtgc tgggcgggca cggagaagat  12060
accttagagt cagacgacaa cattcaacga ctgctaaaag actctttacg aaggacaaga  12120
tgggtggatc aagaggtgcg ccatgcagct agaaccatga ctggagatta cagccccaac  12180
aagaaggtgt cccgtaaggt aggatgttca gaatgggtct gctctgctca acaggttgca  12240
gtctctacct cagcaaaccc ggcccctgtc tcggagcttg ataagggc cctctctaag  12300
aggttccaga acccttttgat ctcgggcttg agagtggttc agtgggcaac cggtgctcat  12360
tataagctta agcctattct agatgatctc aatgttttcc catctctctg ccttgtagtt  12420
ggggacgggt caggggggat atcaagggca gtcctcaaca tgtttccaga tgccaagctt  12480
gtgttcaaca gtcttttaga ggtgaatgac ctgatggctt ccggaacaca tccactgcct  12540
ccttcagcaa tcatgagggg aggaaatgat atcgtctcca gagtgataga tcttgactca  12600
atctgggaaa aaccgtccga cttgagaaac ttggcaacct ggaaatactt ccagtcagtc  12660
caaaagcagg tcaacatgtc ctatgacctc attatttgcg atgcagaagt tactgacatt  12720
gcatctatca accggatcac cctgttaatg tccgattttg cattgtctat agatggacca  12780
ctctatttgg tcttcaaaac ttatgggact atgctagtaa atccaaacta caaggctatt  12840
caacacctgt caagagcgtt cccctcggtc acagggttta tcacccaagt aacttcgtct  12900
ttttcatctg agctctacct ccgattctcc aaacgaggga gttttttcag agatgctgag  12960
tacttgacct cttccaccct tcgagaaatg agccttgtgt tattcaattg tagcagcccc  13020
aagagtgaga tgcagagagc tcgttccttg aactatcagg atcttgtgag aggatttcct  13080
gaagaaatca tatcaaatcc ttacaatgag atgatcataa ctctgattga cagtgatgta  13140
gaatcttttc tagtccacaa gatggttgat gatcttgagt tacagagggg aactctgtct  13200
aaagtggcta tcattatagc catcatgata gttttctcca acagagtctt caacgtttcc  13260
aaaccccctaa ctgaccccctc gttctatcca ccgtctgatc ccaaaatcct gaggcacttc  13320
aacatatgtt gcagtactat gatgtatcta tctactgctt taggtgacgt ccctagcttc  13380
```

```
gcaagacttc acgacctgta taacagacct ataacttatt acttcagaaa gcaagtcatt    13440
cgagggaacg tttatctatc ttggagttgg tccaacgaca cctcagtgtt caaaagggta    13500
gcctgtaatt ctagcctgag tctgtcatct cactggatca ggttgattta caagatagtg    13560
aagactacca gactcgttgg cagcatcaag gatctatcca gagaagtgga aagacacctt    13620
cataggtaca acaggtggat caccctagag gatatcagat ctagatcatc cctactagac    13680
tacagttgcc tgtgaaccgg atactcctgg aagcctgccc atgctaagac tcttgtgtga    13740
tgtatcttga aaaaacaag atcctaaatc tgaacctttg gttgtttgat tgttttctc     13800 attttgttg tttatttgtt aagcgt                                          13826

<210> SEQ ID NO 12
<211> LENGTH: 13926
<212> TYPE: DNA
<213> ORGANISM: Artificial Sequence
<220> FEATURE:
<223> OTHER INFORMATION: RABV vector: Coravax V4-China (S1-RABVG-T2A-P)

<400> SEQUENCE: 12
acgcttaaca accagatcaa agaaaaaaca gacattgtca attgcaaagc aaaaatgtaa     60 caccccctaca atggatgccg acaagattgt attcaaagtc aataatcagg tggtctcttt    120
gaagcctgag attatcgtgg atcaatatga gtacaagtac cctgccatca agatttgaa     180 aaagcccctgt ataaccctag gaaaggctcc cgatttaaat aaagcataca agtcagtttt    240
gtcaggcatg agcgccgcca aacttaatcc tgacgatgta tgttcctatt tggcagcggc    300
aatgcagttt tttgagggga catgtccgga agactggacc agctatggaa ttgtgattgc    360
acgaaaagga gataagatca ccccaggttc tctggtggag ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagattttttg agacagcccc    600 ttttgttaaa atcgtggaac accatactct aatgacaact cacaaaatgt gtgctaattg    660
gagtactata ccaaacttca gatttttggc cggaacctat gacatgtttt ctcccggat    720 tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga gaatgttttg agccagggca    900
ggagacagct gttcctcact cttatttcat ccacttccgt tcactaggct tgagtgggaa    960
atctccttat tcatcaaatg ctgttggtca cgtgttcaat ctcattcact tgtaggatg    1020 ctatatgggt caagtcagat ccctaaatgc aacggttatt gctgcatgtg ctcctcatga    1080
aatgtctgtt ctaggggggct atctgggaga ggaattcttc gggaaaggga catttgaaag    1140
aagattcttc agagatgaga agaacttca agaatacgag gcggctgaac tgacaaagac    1200
tgacgtagca ctggcagatg atggaactgt caactctgac gacgaggact acttttcagg    1260
tgaaaccaga agtccggagg ctgtttatac tcgaatcatg atgaatggag gtcgactaaa    1320
gagatctcac atacggagat atgtctcagt cagttccaat catcaagccc gtccaaactc    1380
attcgccgag tttctaaaca agacatattc gagtgactca taacatgaaa aaaactaaca    1440
cccctcccgt acggccacca tgttcgtgtt tctggtgctg ctgcctctgg tgagctccca    1500
gtgcgtgaac ctgaccacaa ggaccccagct gcccctgcc tataccaatt ccttcacacg    1560
gggcgtgtac tatcccgaca aggtgttccg gagcagcgtg ctgcactcca cacaggatct    1620
```

```
gtttctgcct ttcttttcta acgtgacctg gttccacgcc atccacgtga gcggcaccaa   1680
tggcacaaag cggttcgaca atccagtgct gcccttaac gatggcgtgt acttcgcctc    1740
caccgagaag tctaacatca tcagaggctg gatctttggc accacactgg acagcaagac   1800
acagtccctg ctgatcgtga acaatgccac caacgtggtc atcaaggtgt gcgagttcca   1860
gttttgtaat gatccattcc tgggcgtgta ctatcacaag aacaataagt cttggatgga   1920
gagcgagttt cgcgtgtatt cctctgccaa caattgcaca tttgagtacg tgtcccagcc   1980
cttcctgatg gacctggagg gcaagcaggg caatttcaag aacctgaggg agttcgtgtt   2040
taagaatatc gatggctact tcaaaatcta ctccaagcac accccaatca acctggtgcg   2100
cgacctgcca cagggcttct ctgccctgga gccactggtg gatctgccca tcggcatcaa   2160
catcacccgg tttcagacac tgctggccct gcacagaagc tacctgacac aggcgacag    2220
ctcctctgga tggaccgcag gagcagcagc ctactatgtg ggctatctgc agcccaggac   2280
cttcctgctg aagtacaacg agaatggcac catcacagac gccgtggatt gcgccctgga   2340
tccctgtct gagaccaagt gtacactgaa gagctttacc gtggagaagg gcatctatca    2400
gacaagcaat ttcagggtgc agcctaccga gtccatcgtg cgctttccca atatcacaaa   2460
cctgtgccct tttggcgagg tgttcaacgc aacccgcttc gccagcgtgt acgcctggaa   2520
taggaagcgc atctccaact gcgtggccga ctattctgtg ctgtacaaca gcgcctcctt   2580
ctctaccttt aagtgctatg gcgtgagccc cacaaagctg aatgacctgt gctttaccaa   2640
cgtgtacgcc gattccttcg tgatcagggg cgacgaggtg cgccagatcg caccaggaca   2700
gacaggcaag atcgcagact acaattataa gctgcctgac gatttcaccg gctgcgtgat   2760
cgcctggaac tctaacaatc tggatagcaa agtgggcggc aactacaatt atctgtaccg   2820
gctgtttaga aagtctaatc tgaagccatt cgagagggac atctccacag aaatctacca   2880
ggccggctct accccctgca atggcgtgga gggctttaac tgttattcc ctctgcagag    2940
ctacggcttc cagccaacaa acggcgtggg ctatcagccc taccgcgtgg tggtgctgtc   3000
ttttgagctg ctgcacgcac ctgcaacagt gtgcggacca aagaagagca ccaatctggt   3060
gaagaacaag tgcgtgaact tcaacttcaa cggactgacc ggaacaggcg tgctgaccga   3120
gtccaacaag aagttcctgc cttttcagca gttcggcagg gacatcgcag ataccacaga   3180
cgccgtgcgc gaccctcaga ccctggagat cctggacatc acaccatgct ccttcggcgg   3240
cgtgtctgtg atcacaccag gcaccaatac aagcaaccag gtggccgtgc tgtatcagga   3300
cgtgaattgt accgaggtgc cagtggcaat ccacgcagat cagctgaccc ctacatggcg   3360
ggtgtactct accggcagca acgtgttcca gacaagagcc ggatgcctga tcggagcaga   3420
gcacgtgaac aatagctatg agtgcgacat ccctatcggc gccggcatct gtgcctccta   3480
ccagacccag acaaactccc caaggtctgt gggagatgag gccgaagact tgtggaagt   3540
ccacctgcct gatgtgcata accaggtgtc tggcgtcgac ctgggactgc aaattgggg    3600
caagtacgtg ctgctgagtg ctggagcact gactgccctg atgctgatca ttttcctgat   3660
gacctgctgt cggcgcgtga acagaagtga gcccactcag cacaatctgc gaggaaccgg   3720
gagagaagtg tcagtcacac ctcagagcgg gaaaatcatt agtagttggg aatcacataa   3780
aagcgggggc gagaccaggc tgggatccgg ctccggcgag ggcagggaa gtctactaac    3840
atgcggggac gtgaggaaa atcccggccc catgagcaag atcttttgtca atcctagtgc    3900
tattagagcc ggtctggccg atcttgagat ggctgaagaa actgttgatc tgatcaatag   3960
```

-continued

```
aaatatcgaa gacaatcagg ctcatctcca aggggaaccc atagaggtgg acaatctccc   4020
tgaggatatg gggcgacttc acctggatga tggaaaatcg cccaaccatg gtgagatagc   4080
caaggtggga gaaggcaagt atcgagagga ctttcagatg gatgaaggag aggatcctag   4140
cttcctgttc cagtcatacc tggaaaatgt tggagtccaa atagtcagac aaatgaggtc   4200
aggagagaga tttctcaaga tatggtcaca gaccgtagaa gagattatat cctatgtcgc   4260
ggtcaacttt cccaaccctc caggaaagtc ttcagaggat aaatcaaccc agactactgg   4320
ccgagagctc aagaaggaga caacacccac tccttctcag agagaaagcc aatcatcgaa   4380
agccaggatg gcggctcaaa ttgcttctgg ccctccagcc cttgaatggt cggctaccaa   4440
tgaagaggat gatctatcag tggaggctga gatcgctcac cagattgcag aaagtttctc   4500
caaaaaatat aagtttccct ctcgatcctc agggatactc ttgtataatt ttgagcaatt   4560
gaaaatgaac cttgatgata tagttaaaga ggcaaaaaat gtaccaggtg tgacccgttt   4620
agcccatgac gggtccaaac tcccctaag atgtgtactg gatgggtcg ctttggccaa    4680 ctctaagaaa ttccagttgt tagtcgaatc cgacaagctg agtaaaatca tgcaagatga   4740
cttgaatcgc tatacatctt gctaaccgaa cctctcccct cagtccctct agacaataaa   4800
atccgagatg tcccaaagtc aacatgaaaa aaacaggcaa caccactgat aaaatgaacc   4860
tcctacgtaa gatagtgaaa aaccgcaggg acgaggacac tcaaaaatcc tctcccgcgt   4920
cagcccctct ggatgacgat gacttgtggc ttccaccccc tgaatacgtc ccgctgaaag   4980
aacttacagg caagaagaac atgaggaact tttgtatcaa cggaagggtt aaagtgtgta   5040
gcccgaatgg ttactcgttc aggatcctgc ggcacattct gaaatcattc gacgagatat   5100
attctgggaa tcataggatg atcgggttag tcaaagtggt tattggactg gctttgtcag   5160
gatctccagt ccctgagggc ctgaactggg tatacaaatt gaggagaacc tttatcttcc   5220
agtgggctga ttccaggggc cctcttgaag gggaggagtt ggaatactct caggagatca   5280
cttgggatga tgatactgag ttcgtcggat tgcaaataag agtgattgca aaacagtgtc   5340
atatccaggg cagagtctgg tgtatcaaca tgaacccgag agcatgtcaa ctatggtctg   5400
acatgtctct tcagacacaa aggtccgaag aggacaaaga ttcctctctg cttctagaat   5460
aatcagatta tatcccgcaa atttatcact tgtttacctc tggaggagag aacatatggg   5520
ctcaactcca accttggga gcaatataac aaaaaacatg ttatggtgcc attaaaccgc    5580
tgcatttcat caaagtcaag ttgattacct ttacattttg atcctcttgg atgtgaaaaa   5640
aactattaac atccctcaaa agaccccggg aaagatggtt cctcaggctc tcctgtttgt   5700 acccccttctg gttttccat tgtgttttgg gaaattccct atttacacga taccagacaa    5760
gcttggtccc tggagtccga ttgacataca tcacctcagc tgcccaaaca atttggtagt   5820
ggaggacgaa ggatgcacca acctgtcagg gttctcctac atggaactta agttggata   5880 catcttagcc ataaaagtga acgggttcac ttgcacaggc gttgtgacgg aggctgaaac   5940
ctacactaac ttcgttggtt atgtcacaac cacgttcaaa agaaagcatt tccgcccaac   6000
accagatgca tgtagagccg cgtacaactg gaagatggcc ggtgaccca gatatgaaga    6060 gtctctacac aatccgtacc ctgactaccg ctggcttcga actgtaaaaa ccaccaagga   6120
gtctctcgtt atcatatctc caagtgtggc agatttggac ccatatgaca gatcccttca   6180
ctcgagggtc ttccctagcg ggaagtgctc aggagtagcg gtgtcttcta cctactgctc   6240
cactaaccac gattacacca tttggatgcc cgagaatccg agactaggga tgtcttgtga   6300 cattttttacc aatagtagag ggaagagagc atccaaaggg agtgagactt gcggctttgt   6360
```

```
agatgaaaga ggcctatata agtctttaaa aggagcatgc aaactcaagt tatgtggagt    6420
tctaggactt agacttatgg atggaacatg ggtctcgatg caaacatcaa atgaaaccaa    6480
atggtgccct cccgataagt tggtgaacct gcacgacttt cgctcagacg aaattgagca    6540
ccttgttgta gaggagttgg tcaggaagag agaggagtgt ctggatgcac tagagtccat    6600
catgacaacc aagtcagtga gtttcagacg tctcagtcat ttaagaaaac ttgtccctgg    6660
gtttggaaaa gcatatacca tattcaacaa gaccttgatg gaagccgatg ctcactacaa    6720
gtcagtcgag acttggaatg agatcctccc ttcaaaaggg tgtttaagag ttgggggggag    6780 gtgtcatcct catgtgaacg gggtgttttt caatggtata atattaggac ctgacggcaa    6840
tgtcttaatc ccagagatgc aatcatccct cctccagcaa catatggagt tgttggaatc    6900
ctcggttatc ccccttgtgc acccctggc agaccgtct accgttttca aggacggtga    6960
cgaggctgag gattttgttg aagttcacct tcccgatgtg cacaatcagg tctcaggagt    7020
tgacttgggt ctcccgaact gggggaagta tgtattactg agtgcagggg ccctgactgc    7080
cttgatgttg ataatttttcc tgatgacatg ttgtagaaga gtcaatcgat cagaacctac    7140
gcaacacaat ctcagaggga cagggaggga ggtgtcagtc actccccaaa gcggaaagat    7200
catatcttca tgggaatcac acaagagtgg gggtgagacc agactgtaat taattaacgt    7260
cctttcaacg atccaagtcc atgaaaaaaa ctaacacccc tcccgtacct agcttataaa    7320
gtgctgggtc atctaagctt ttcagtcgag aaaaaaacat tagatcagaa gaacaactgg    7380
caacacttct caacctgaga cttacttcaa gatgctcgat cctggagagg tctatgatga    7440
ccctattgac ccaatcgagt tagaggctga acccagagga accccattg tccccaacat    7500 cttgaggaac tctgactaca atctcaactc tcctttgata gaagatcctg ctagactaat    7560
gttagaatgg ttaaaaacag ggaatagacc ttatcggatg actctaacag acaattgctc    7620
caggtctttc agagttttga aagattattt caagaaggta gatttgggtt ctctcaaggt    7680
gggcggaatg gctgcacagt caatgatttc tctctggtta tatggtgccc actctgaatc    7740
caacaggagc cggagatgta taacagactt ggcccatttc tattccaagt cgtccccat    7800 agagaagctg ttgaatctca cgctaggaaa tagagggctg agaatccccc cagagggagt    7860
gttaagttgc cttgagaggg ttgattatga taatgcattt ggaaggtatc ttgccaacac    7920
gtattcctct tacttgttct tccatgtaat caccttatac atgaacgccc tagactggga    7980
tgaagaaaag accatcctag cattatggaa agatttaacc tcagtggaca tcgggaagga    8040
cttggtaaag ttcaaagacc aaatatgggg actgctgatc gtgacaaagg actttgttta    8100
ctcccaaagt tccaattgtc tttttgacag aaactacaca cttatgctaa aagatctttt    8160
cttgtctcgc ttcaactcct taatggtctt gctctctccc ccagagcccc gatactcaga    8220
tgacttgata tctcaactat gccagctgta cattgctggg gatcaagtct tgtctatgtg    8280
tggaaactcc ggctatgaag tcatcaaaat attggagcca tatgtcgtga atagtttagt    8340
ccagagagca gaaaagttta ggcctctcat tcattccttg ggagactttc ctgtatttat    8400
aaaagacaag gtaagtcaac ttgaagagac gttcggtccc tgtgcaagaa ggttctttag    8460
ggctctggat caattcgaca acatacatga cttggttttt gtgtttggct gttacaggca    8520
ttgggggcac ccatatatag attatcgaaa gggtctgtca aaactatatg atcaggttca    8580
ccttaaaaaa atgatagata agtcctacca ggagtgctta gcaagcgacc tagccaggag    8640
gatccttaga tggggttttg ataagtactc caagtggtat ctggattcaa gattcctagc    8700
```

```
ccgagaccac cccttgactc cttatatcaa aacccaaaca tggccacccca aacatattgt   8760
agacttggtg ggggatacat ggcacaagct cccgatcacg cagatctttg agattcctga   8820
atcaatggat ccgtcagaaa tattggatga caaatcacat tctttcacca gaacgagact   8880
agcttcttgg ctgtcagaaa accgaggggg gcctgttcct agcgaaaaag ttattatcac   8940
ggccctgtct aagccgcctg tcaatccccg agagtttctg aggtctatag acctcggagg   9000
attgccagat gaagacttga taattggcct caagccaaag gaacgggaat tgaagattga   9060
aggtcgattc tttgctctaa tgtcatggaa tctaagattg tattttgtca tcactgaaaa   9120
actcttggcc aactacatct tgccactttt tgacgcgctg actatgacag acaacctgaa   9180
caaggtgttt aaaaagctga tcgacagggt caccgggcaa gggcttttgg actattcaag   9240
ggtcacatat gcatttcacc tggactatga aaagtggaac aaccatcaaa gattagagtc   9300
aacagaggat gtattttctg tcctagatca agtgtttgga ttgaagagag tgttttctag   9360
aacacacgag ttttttcaaa aggcctggat ctattattca gacagatcag acctcatcgg   9420
gttacgggag gatcaaatat actgcttaga tgcgtccaac ggcccaacct gttggaatgg   9480
ccaggatggc gggctagaag gcttacggca gaagggctgg agtctagtca gcttattgat   9540
gatagataga gaatctcaaa tcaggaacac aagaaccaaa atactagctc aaggagacaa   9600
ccaggtttta tgtccgacat acatgttgtc gccagggcta tctcaagagg ggctcctcta   9660
tgaattggag agaatatcaa ggaatgcact ttcgatatac agagccgtcg aggaaggggc   9720
atctaagcta gggctgatca tcaagaaaga agagaccatg tgtagttatg acttcctcat   9780
ctatggaaaa accccttgt ttagaggtaa catattggtg cctgagtcca aaagatgggc   9840
cagagtctct tgcgtctcta atgaccaaat agtcaacctc gccaatataa tgtcgacagt   9900
gtccaccaat gcgctaacag tggcacaaca ctctcaatct ttgatcaaac cgatgaggga   9960
ttttctgctc atgtcagtac aggcagtctt tcactacctg ctatttagcc caatcttaaa  10020
gggaagagtt tacaagattc tgagcgctga aggggagagc tttctcctag ccatgtcaag  10080
gataatctat ctagatcctt ctttgggagg gatatctgga atgtccctcg aagattccA  10140
tatacgacag ttctcagacc ctgtctctga agggttatcc ttctggagag gatctggtt   10200
aagctcccaa gagtcctgga ttcacgcgtt gtgtcaagag gctggaaacc cagatcttgg  10260
agagagaaca ctcgagagct tcactcgcct tctagaagat ccgaccacct taaatatcag  10320
aggaggggcc agtcctacca ttctactcaa ggatgcaatc agaaaggctt tatatgacga  10380
ggtggacaag gtgaaaatt cagagtttcg agaggcaatc ctgttgtcca gacccatag   10440
agataatttt atactcttct taatatctgt tgagcctctg tttcctcgat ttctcagtga  10500
gctattcagt tcgtctttttt tgggaatccc cgagtcaatc attggattga tacaaaactc  10560
ccgaacgata agaaggcagt ttagaaagag tctctcaaaa actttagaag aatccttcta  10620
caactcagag atccacggga ttagtcggat gacccagaca cctcagaggg ttgggggggt  10680
gtggccttgc tcttcagaga gggcagatct acttagggag atctcttggg gaagaaaagt  10740
ggtaggcacg acagttcctc acccttctga gatgttggga ttacttccca agtcctctat  10800
ttcttgcact tgtggagcaa caggaggagg caatcctaga gttctgtat cagtactccc   10860
gtccttgat cagtcatttt tttcacgagg cccctaaag ggatacttgg gctcgtccac    10920
ctctatgtcg acccagctat tccatgcatg ggaaaagtc actaatgttc atgtggtgaa   10980
gagagctcta tcgttaaaag aatctataaa ctggttcatt actagagatt ccaacttggc  11040
tcaagctcta attaggaaca ttatgtctct gacaggccct gatttccctc tagaggaggc  11100
```

```
ccctgtcttc aaaaggacgg ggtcagcctt gcataggttc aagtctgcca gatacagcga   11160
aggagggtat tcttctgtct gcccgaacct cctctctcat atttctgtta gtacagacac   11220
catgtctgat ttgacccaag acgggaagaa ctacgatttc atgttccagc cattgatgct   11280
ttatgcacag acatggacat cagagctggt acagagagac acaaggctaa gagactctac   11340
gtttcattgg cacctccgat gcaacaggtg tgtgagaccc attgacgacg tgaccctgga   11400
gacctctcag atcttcgagt ttccggatgt gtcgaaaaga atatccagaa tggtttctgg   11460
ggctgtgcct cacttccaga ggcttcccga tatccgtctg agaccaggag attttgaatc   11520
tctaagcggt agagaaaagt ctcaccatat cggatcagct cagggggctct tatactcaat   11580
cttagtggca attcacgact caggatacaa tgatggaacc atcttccctg tcaacatata   11640
cggcaaggtt tcccctagag actatttgag agggctcgca aggggagtat tgataggatc   11700
ctcgatttgc ttcttgacaa gaatgacaaa tatcaatatt aatagacctc ttgaattggt   11760
ctcaggggta atctcatata ttctcctgag gctagataac catccctcct tgtacataat   11820
gctcagagaa ccgtctctta gaggagagat attttctatc cctcagaaaa tccccgccgc   11880
ttatccaacc actatgaaag aaggcaacag atcaatcttg tgttatctcc aacatgtgct   11940
acgctatgag cgagagataa tcacggcgtc tccagagaat gactggctat ggatcttttc   12000
agactttaga agtgccaaaa tgacgtacct atccctcatt acttaccagt ctcatcttct   12060
actccagagg gttgagagaa acctatctaa gagtatgaga gataacctgc gacaattgag   12120
ttctttgatg aggcaggtgc tgggcgggca cggagaagat accttagagt cagacgacaa   12180
cattcaacga ctgctaaaag actctttacg aaggacaaga tgggtggatc aagaggtgcg   12240
ccatgcagct agaaccatga ctggagatta cagccccaac aagaaggtgt cccgtaaggt   12300
aggatgttca gaatgggtct gctctgctca acaggttgca gtctctacct cagcaaaccc   12360
ggcccctgtc tcggagcttg acataagggc cctctctaag aggttccaga acccttttgat   12420
ctcgggcttg agagtggttc agtgggcaac cggtgctcat tataagctta agcctattct   12480
agatgatctc aatgttttcc catctctctg ccttgtagtt ggggacgggt caggggggat   12540
atcaagggca gtcctcaaca tgtttccaga tgccaagctt gtgttcaaca gtcttttaga   12600
ggtgaatgac ctgatggctt ccggaacaca tccactgcct ccttcagcaa tcatgagggg   12660
aggaaatgat atcgtctcca gagtgataga tcttgactca atctgggaaa aaccgtccga   12720
cttgagaaac ttggcaacct ggaaatactt ccagtcagtc caaaagcagg tcaacatgtc   12780
ctatgacctc attatttgcg atgcagaagt tactgacatt gcatctatca accggatcac   12840
cctgttaatg tccgattttg cattgtctat agatggacca ctctatttgg tcttcaaaac   12900
ttatgggact atgctagtaa atccaaacta caaggcatt caacacctgt caagagcgtt   12960
ccctcggtc acagggttta tcacccaagt aacttcgtct ttttcatctg agctctacct   13020
ccgattctcc aaacgaggga agtttttcag agatgctgag tacttgacct cttccacccct   13080
tcgagaaatg agccttgtgt tattcaattg tagcagcccc aagagtgaga tgcagagagc   13140
tcgttccttg aactatcagg atcttgtgag aggatttcct gaagaaatca tatcaaatcc   13200
ttacaatgag atgatcataa ctctgattga cagtgatgta gaatcttttc tagtccacaa   13260
gatggttgat gatcttgagt tacagagggg aactctgtct aaagtggcta tcattatagc   13320
catcatgata gttttctcca acagagtctt caacgttttcc aaacccctaa ctgacccctc   13380
gttctatcca ccgtctgatc ccaaaaatcct gaggcacttc aacatatgtt gcagtactat   13440
```

-continued

```
gatgtatcta tctactgctt taggtgacgt ccctagcttc gcaagacttc acgacctgta    13500
taacagacct ataacttatt acttcagaaa gcaagtcatt cgagggaacg tttatctatc    13560
ttggagttgg tccaacgaca cctcagtgtt caaaagggta gcctgtaatt ctagcctgag    13620
tctgtcatct cactggatca ggttgattta caagatagtg aagactacca gactcgttgg    13680
cagcatcaag gatctatcca gagaagtgga aagacacctt cataggtaca acaggtggat    13740
caccctagag gatatcagat ctagatcatc cctactagac tacagttgcc tgtgaaccgg    13800
atactcctgg aagcctgccc atgctaagac tcttgtgtga tgtatcttga aaaaaacaag    13860
atcctaaatc tgaacctttg gttgtttgat tgttttttctc attttttgttg tttatttgtt    13920 aagcgt                                                                13926
```

<210> SEQ ID NO 13
<211> LENGTH: 13977
<212> TYPE: DNA
<213> ORGANISM: Artificial Sequence
<220> FEATURE:
<223> OTHER INFORMATION: RABV vector: Coravax V4 South Africa

<400> SEQUENCE: 13

```
acgcttaaca accagatcaa agaaaaaaca gacattgtca attgcaaagc aaaaatgtaa      60 caccccctaca atggatgccg acaagattgt attcaaagtc aataatcagg tggtctcttt    120
gaagcctgag attatcgtgg atcaatatga gtacaagtac cctgccatca agatttgaa    180 aaagccctgt ataaccctag gaaaggctcc cgatttaaat aaagcataca agtcagtttt    240
gtcaggcatg agcgccgcca aacttaatcc tgacgatgta tgttcctatt tggcagcggc    300
aatgcagttt tttgagggga catgtccgga agactggacc agctatggaa ttgtgattgc    360
acgaaaagga gataagatca ccccaggttc tctggtggag ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagattttttg agacagcccc    600 ttttgttaaa atcgtggaac accatactct aatgacaact cacaaaatgt gtgctaattg    660
gagtactata ccaaacttca gattttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga gaatgtttg agccagggca    900 ggagacagct gttcctcact cttatttcat ccacttccgt tcactaggct tgagtgggaa    960
atctccttat tcatcaaatg ctgttggtca cgtgttcaat ctcattcact tgtaggatg    1020 ctatatgggt caagtcagat ccctaaatgc aacggttatt gctgcatgtg ctcctcatga    1080
aatgtctgtt ctaggggct atctgggaga ggaattcttc gggaaaggga catttgaaag    1140
aagattcttc agagatgaga aagaacttca agaatacgag gcggctgaac tgacaaagac    1200
tgacgtagca ctggcagatg atggaactgt caactctgac gacgaggact actttttcagg    1260 tgaaaccaga agtccggagg ctgttttatac tcgaatcatg atgaatggag tcgactaaa    1320 gagatctcac atacggagat atgtctcagt cagttccaat catcaagccc gtccaaactc    1380
attcgccgag tttctaaaca agacatattc gagtgactca taacatgaaa aaaactaaca    1440
cccctcccgt acggcacca tgttcgtgtt tctggtgctg ctgcctctgg tgagctccca    1500
gtgcgtgaac ttcaccacaa ggaccagct gccccctgcc tataccaatt ccttcacacg    1560
```

```
gggcgtgtac tatcccgaca aggtgttccg gagcagcgtg ctgcactcca cacaggatct    1620
gtttctgcct ttcttttcta acgtgacctg gttccacgcc atccacgtga gcggcaccaa    1680
tggcacaaag cggttcgcca atccagtgct gcccttaac  gatggcgtgt acttcgcctc    1740
caccgagaag tctaacatca tcagaggctg gatctttggc accacactgg acagcaagac    1800
acagtccctg ctgatcgtga caatgccac  caacgtggtc atcaaggtgt gcgagttcca    1860
gttttgtaat gatccattcc tgggcgtgta ctatcacaag aacaataagt cttggatgga    1920
gagcgagttt cgcgtgtatt cctctgccaa caattgcaca tttgagtacg tgtcccagcc    1980
cttcctgatg gacctggagg caagcaggg  caatttcaag aacctgaggg agttcgtgtt    2040
taagaatatc gatggctact tcaaaatcta ctccaagcac accccaatca acctggtgcg    2100
cggcctgcca cagggcttct ctgccctgga gccactggtg gatctgccca tcggcatcaa    2160
catcacccgg tttcagacac tgctggccct gcacagaagc tacctgacac caggcgacag    2220
ctcctctgga tggaccgcag gagcagcagc ctactatgtg ggctatctgc agcccaggac    2280
cttcctgctg aagtacaacg agaatggcac catcacagac gccgtggatt gcgccctgga    2340
tccctgtct  gagaccaagt gtacactgaa gagctttacc gtggagaagg gcatctatca    2400
gacaagcaat ttcagggtgc agcctaccga gtccatcgtg cgctttccca atatcacaaa    2460
cctgtgccct tttggcgagg tgttcaacgc aacccgcttc gccagcgtgt acgcctggaa    2520
taggaagcgc atctccaact gcgtggccga ctattctgtg ctgtacaaca gcgcctcctt    2580
ctctaccttt aagtgctatg gcgtgagccc cacaaagctg aatgacctgt gctttaccaa    2640
cgtgtacgcc gattccttcg tgatcagggg cgacgaggtg cgccagatcg caccaggaca    2700
gacaggcaat atcgcagact acaattataa gctgcctgac gatttcaccg gctgcgtgat    2760
cgcctggaac tctaacaatc tggatagcaa agtgggcggc aactacaatt atctgtaccg    2820
gctgtttaga aagtctaatc tgaagccatt cgagagggac atctccacag aaatctacca    2880
ggccggctct acccctgca  atggcgtgaa gggctttaac tgttatttcc ctctgcagag    2940
ctacggcttc cagccaacat atggcgtggg ctatcagccc taccgcgtgg tggtgctgtc    3000
ttttgagctg ctgcacgcac ctgcaacagt gtgcggacca aagaagagca ccaatctggt    3060
gaagaacaag tgcgtgaact tcaacttcaa cggactgacc ggaacaggcg tgctgaccga    3120
gtccaacaag aagttcctgc cttttcagca gttcggcagg gacatcgcag ataccacaga    3180
cgccgtgcgc gaccctcaga ccctggagat cctggacatc acaccatgct ccttcggcgg    3240
cgtgtctgtg atcacaccag gcaccaatac aagcaaccag gtggccgtgc tgtatcaggg    3300
cgtgaattgt accgaggtgc cagtggcaat ccacgcagat cagctgaccc ctacatggcg    3360
ggtgtactct accggcagca acgtgttcca gacaagagcc ggatgcctga tcggagcaga    3420
gcacgtgaac aatagctatg agtgcgacat ccctatcggc ccggcatct  gtgcctccta    3480
ccagacccag acaaactccc cagaatcaag cgtgattcct ctggtccatc cactggcaga    3540
tccctccaca gtgttcaaag acggagatga ggccgaagac tttgtggaag tccacctgcc    3600
tgatgtgcat aaccaggtgt ctggcgtcga cctgggactg ccaaattggg gcaagtacgt    3660
gctgctgagt gctggagcac tgactgccct gatgctgatc attttcctga tgacctgctg    3720
tcggcgcgtg aacagaagtg agcccactca gcacaatctg cgaggaaccg ggagagaagt    3780
gtcagtcaca cctcagagcg ggaaaatcat tagtagttgg gaatcacata aaagcggggg    3840
cgagaccagg ctgggatccg gctccggcga gggcagggga agtctactaa catgcgggga    3900
```

```
cgtggaggaa aatcccggcc ccatgagcaa gatctttgtc aatcctagtg ctattagagc   3960
cggtctggcc gatcttgaga tggctgaaga aactgttgat ctgatcaata gaaatatcga   4020
agacaatcag gctcatctcc aaggggaacc catagaggtg gacaatctcc ctgaggatat   4080
ggggcgactt cacctggatg atggaaaatc gcccaaccat ggtgagatag ccaaggtggg   4140
agaaggcaag tatcgagagg actttcagat ggatgaagga gaggatccta gcttcctgtt   4200
ccagtcatac ctggaaaatg ttggagtcca aatagtcaga caaatgaggt caggagagag   4260
atttctcaag atatggtcac agaccgtaga agagattata tcctatgtcg cggtcaactt   4320
tcccaacccct ccaggaaagt cttcaggaga taaatcaacc cagactactg gccgagagct   4380
caagaaggag acaacaccca ctccttctca gagagaaagc caatcatcga aagccaggat   4440
ggcggctcaa attgcttctg gccctccagc ccttgaatgg tcggctacca atgaagagga   4500
tgatctatca gtggaggctg agatcgctca ccagattgca gaaagtttct ccaaaaaata   4560
taagtttccc tctcgatcct cagggatact cttgtataat tttgagcaat tgaaaatgaa   4620
ccttgatgat atagttaaag aggcaaaaaa tgtaccaggt gtgacccgtt tagcccatga   4680
cgggtccaaa ctccccctaa gatgtgtact gggatgggtc gctttggcca actctaagaa   4740
attccagttg ttagtcgaat ccgacaagct gagtaaaatc atgcaagatg acttgaatcg   4800
ctatacatct tgctaaccga acctctcccc tcagtccctc tagacaataa aatccgagat   4860
gtcccaaagt caacatgaaa aaaacaggca acaccactga taaaatgaac ctcctacgta   4920
agatagtgaa aaaccgcagg gacgaggaca ctcaaaaatc ctctcccgcg tcagcccctc   4980
tggatgacga tgacttgtgg cttccacccc ctgaatacgt cccgctgaaa gaacttacag   5040
gcaagaagaa catgaggaac ttttgtatca acggaagggt taaagtgtgt agcccgaatg   5100
gttactcgtt caggatcctg cggcacattc tgaaatcatt cgacgagata tattctggga   5160
atcataggat gatcgggtta gtcaaagtgg ttattggact ggctttgtca ggatctccag   5220
tccctgaggg cctgaactgg gtatacaaat tgaggagaac cttatcttc cagtgggctg   5280
attccagggg ccctcttgaa ggggaggagt tggaatactc tcaggagatc acttgggatg   5340
atgatactga gttcgtcgga ttgcaaataa gagtgattgc aaaacagtgt catatccagg   5400
gcagagtctg gtgtatcaac atgaacccga gagcatgtca actatggtct gacatgtctc   5460
ttcagacaca aaggtccgaa gaggacaaag attcctctct gcttctagaa taatcagatt   5520
atatcccgca aatttatcac ttgtttacct ctggaggaga aacatatgg gctcaactcc   5580
aacccttggg agcaatataa caaaaaacat gttatggtgc cattaaaccg ctgcatttca   5640
tcaaagtcaa gttgattacc tttacatttt gatcctcttg gatgtgaaaa aaactattaa   5700
catccctcaa aagaccccgg gaaagatggt tcctcaggct ctcctgtttg taccccttct   5760
ggttttttcca ttgtgttttg ggaaattccc tatttacacg ataccagaca agcttggtcc   5820
ctggagtccg attgacatac atcacctcag ctgcccaaac aatttggtag tggaggacga   5880
aggatgcacc aacctgtcag ggttctccta catggaactt aaagttggat acatcttagc   5940
cataaaagtg aacgggttca cttgcacagg cgttgtgacg gaggctgaaa cctacactaa   6000
cttcgttggt tatgtcacaa ccacgttcaa aagaaagcat ttccgcccaa caccagatgc   6060
atgtagagcc gcgtacaact ggaagatggc cggtgacccc agatatgaag agtctctaca   6120
caatccgtac cctgactacc gctggcttcg aactgtaaaa accaccaagg agtctctcgt   6180
tatcatatct ccaagtgtgg cagatttgga cccatatgac agatcccttc actcgagggt   6240
cttccctagc gggaagtgct caggagtagc ggtgtcttct acctactgct ccactaacca   6300
```

```
cgattacacc atttggatgc ccgagaatcc gagactaggg atgtcttgtg acatttttac    6360
caatagtaga gggaagagag catccaaagg gagtgagact tgcggctttg tagatgaaag    6420
aggcctatat aagtctttaa aaggagcatg caaactcaag ttatgtggag ttctaggact    6480
tagacttatg gatggaacat gggtctcgat gcaaacatca aatgaaacca aatggtgccc    6540
tcccgataag ttggtgaacc tgcacgactt tcgctcagac gaaattgagc accttgttgt    6600
agaggagttg gtcaggaaga gagaggagtg tctggatgca ctagagtcca tcatgacaac    6660
caagtcagtg agtttcagac gtctcagtca tttaagaaaa cttgtccctg ggtttggaaa    6720
agcatatacc atattcaaca agaccttgat ggaagccgat gctcactaca agtcagtcga    6780
gacttggaat gagatcctcc cttcaaaagg gtgtttaaga gttgggggga ggtgtcatcc    6840
tcatgtgaac gggtgttttt tcaatggtat aatattagga cctgacggca atgtcttaat    6900
cccagagatg caatcatccc tcctccagca acatatggag ttgttggaat cctcggttat    6960
ccccccttgtg cacccctgg cagacccgtc taccgttttc aaggacggtg acgaggctga    7020
ggattttgtt gaagttcacc ttcccgatgt gcacaatcag gtctcaggag ttgacttggg    7080
tctcccgaac tggggggaagt atgtattact gagtgcaggg gccctgactg ccttgatgtt    7140
gataatttc ctgatgacat gttgtagaag agtcaatcga tcagaaccta cgcaacacaa    7200
tctcagaggg acagggaggg aggtgtcagt cactccccaa agcgggaaga tcatatcttc    7260
atgggaatca cacaagagtg ggggtgagac cagactgtaa ttaattaacg tcctttcaac    7320
gatccaagtc catgaaaaaa actaacaccc ctcccgtacc tagcttataa agtgctgggt    7380
catctaagct tttcagtcga gaaaaaaaca ttagatcaga agaacaactg caacacttc    7440
tcaacctgag acttacttca agatgctcga tcctggagag gtctatgatg accctattga    7500
cccaatcgag ttagaggctg aacccagagg aaccccatt gtccccaaca tcttgaggaa    7560
ctctgactac aatctcaact ctcctttgat agaagatcct gctagactaa tgttagaatg    7620
gttaaaaaca gggaatagac cttatcggat gactctaaca gacaattgct ccaggtcttt    7680
cagagttttg aaagattatt tcaagaaggt agatttgggt tctctcaagg tgggcggaat    7740
ggctgcacag tcaatgattt ctctctggtt atatggtgcc cactctgaat ccaacaggag    7800
ccggagatgt ataacagact tggcccattt ctattccaag tcgtccccca tagagaagct    7860
gttgaatctc acgctaggaa atagagggct gagaatcccc ccagagggag tgttaagttg    7920
ccttgagagg gttgattatg ataatgcatt tggaaggtat cttgccaaca cgtattcctc    7980
ttacttgttc ttccatgtaa tcaccttata catgaacgcc ctagactggg atgaagaaaa    8040
gaccatccta gcattatgga aagatttaac ctcagtggac atcgggaagg acttggtaaa    8100
gttcaaagac caaatatggg gactgctgat cgtgacaaag gactttgttt actcccaaag    8160
ttccaattgt cttttgaca gaaactacac acttatgcta aaagatcttt tcttgtctcg    8220
cttcaactcc ttaatggtct tgctctctcc cccagagccc cgatactcag atgacttgat    8280
atctcaacta tgccagctgt acattgctgg ggatcaagtc ttgtctatgt gtggaaactc    8340
cggctatgaa gtcatcaaaa tattggagcc atatgtcgtg aatagtttag tccagagagc    8400
agaaaagttt aggcctctca ttcattcctt gggagacttt cctgtattta taaaagacaa    8460
ggtaagtcaa cttgaagaga cgttcggtcc ctgtgcaaga aggttcttta gggctctgga    8520
tcaattcgac aacatacatg acttggtttt tgtgtttggc tgttacaggc attgggggca    8580
cccatatata gattatcgaa agggtctgtc aaaactatat gatcaggttc accttaaaaa    8640
```

```
aatgatagat aagtcctacc aggagtgctt agcaagcgac ctagccagga ggatccttag    8700
atggggtttt gataagtact ccaagtggta tctggattca agattcctag cccgagacca    8760 cccccttgact ccttatatca aaacccaaac atggccaccc aaacatattg tagacttggt   8820 ggggataca tggcacaagc tcccgatcac gcagatcttt gagattcctg aatcaatgga     8880
tccgtcagaa atattggatg acaaatcaca ttctttcacc agaacgagac tagcttcttg    8940
gctgtcagaa aaccgagggg ggcctgttcc tagcgaaaaa gttattatca cggccctgtc    9000
taagccgcct gtcaatcccc gagagtttct gaggtctata gacctcggag gattgccaga    9060
tgaagacttg ataattggcc tcaagccaaa ggaacgggaa ttgaagattg aaggtcgatt    9120
ctttgctcta atgtcatgga atctaagatt gtattttgtc atcactgaaa aactcttggc    9180
caactacatc ttgccacttt ttgacgcgct gactatgaca gacaacctga acaaggtgtt    9240
taaaaagctg atcgacaggg tcaccgggca agggcttttg gactattcaa gggtcacata    9300
tgcatttcac ctggactatg aaaagtggaa caaccatcaa agattagagt caacagagga    9360
tgtattttct gtcctagatc aagtgtttgg attgaagaga gtgttttcta gaacacacga    9420
gttttttcaa aaggcctgga tctattattc agacagatca gacctcatcg ggttacggga    9480
ggatcaaata tactgcttag atgcgtccaa cggcccaacc tgttggaatg ccaggatgg     9540 cgggctagaa ggcttacggc agaagggctg gagtctagtc agcttattga tgatagatag    9600
agaatctcaa atcaggaaca caagaaccaa aatactagct caaggagaca accaggtttt    9660
atgtccgaca tacatgttgt cgccagggct atctcaagag gggctcctct atgaattgga    9720
gagaatatca aggaatgcac tttcgatata cagagccgtc gaggaagggg catctaagct    9780
agggctgatc atcaagaaag aagagaccat gtgtagttat gacttcctca tctatggaaa    9840 aaccccttg tttagaggta acatattggt gcctgagtcc aaaagatggg ccagagtctc     9900
ttgcgtctct aatgaccaaa tagtcaacct cgccaatata atgtcgacag tgtccaccaa    9960
tgcgctaaca gtggcacaac actctcaatc tttgatcaaa ccgatgaggg attttctgct    10020
catgtcagta caggcagtct ttcactacct gctatttagc ccaatcttaa agggaagagt    10080
ttacaagatt ctgagcgctg aaggggagag ctttctccta gccatgtcaa ggataatcta    10140
tctagatcct tctttgggag ggatatctgg aatgtccctc ggaagattcc atatacgaca    10200
gttctcagac cctgtctctg aagggttatc cttctggaga gagatctggt taagctccca    10260
agagtcctgg attcacgcgt tgtgtcaaga ggctggaaac ccagatcttg gagagagaac    10320
actcgagagc ttcactcgcc ttctagaaga tccgaccacc ttaaatatca gaggagggg     10380 cagtcctacc attctactca aggatgcaat cagaaaggct ttatatgacg aggtggacaa    10440
ggtggaaaat tcagagtttc gagaggcaat cctgttgtcc aagacccata gagataattt    10500
tatactcttc ttaatatctg ttgagcctct gtttcctcga tttctcagtg agctattcag    10560
ttcgtctttt ttgggaatcc ccgagtcaat cattggattg atacaaaaact cccgaacgat   10620 aagaaggcag tttagaaaga gtctctcaaa aactttagaa gaatccttct acaactcaga    10680
gatccacggg attagtcgga tgacccagac acctcagagg gttgggggg tgtggccttg     10740 ctcttcagag agggcagatc tactaggga gatctcttgg ggaagaaaag tggtaggcac     10800
gacagttcct caccttctg agatgttggg attacttccc aagtcctcta tttcttgcac     10860
ttgtggagca acaggaggag gcaatcctag agtttctgta tcagtactcc cgtcctttga    10920
tcagtcattt ttttcacgag gcccctaaa gggatacttg ggctcgtcca cctctatgtc     10980
gacccagcta ttccatgcat gggaaaaagt cactaatgtt catgtggtga agagagctct    11040
```

```
atcgttaaaa gaatctataa actggttcat tactagagat tccaacttgg ctcaagctct    11100
aattaggaac attatgtctc tgacaggccc tgatttccct ctagaggagg ccctgtcttc    11160
caaaaggacg gggtcagcct tgcataggtt caagtctgcc agatacagcg aaggagggta    11220
ttcttctgtc tgcccgaacc tcctctctca tatttctgtt agtacagaca ccatgtctga    11280
tttgacccaa gacgggaaga actacgattt catgttccag ccattgatgc tttatgcaca    11340
gacatggaca tcagagctgg tacagagaga cacaaggcta agagactcta cgtttcattg    11400
gcacctccga tgcaacaggt gtgtgagacc cattgacgac gtgaccctgg agacctctca    11460
gatcttcgag tttccggatg tgtcgaaaag aatatccaga atggtttctg ggctgtgcc     11520 tcacttccag aggcttcccg atatccgtct gagaccagga gattttgaat ctctaagcgg    11580
tagagaaaag tctcaccata tcggatcagc tcaggggctc ttatactcaa tcttagtggc    11640
aattcacgac tcaggataca atgatggaac catcttccct gtcaacatat acggcaaggt    11700
ttcccctaga gactatttga gagggctcgc aaggggagta ttgataggat cctcgatttg    11760
cttcttgaca agaatgacaa atatcaatat taatagacct cttgaattgg tctcagggt     11820 aatctcatat attctcctga ggctagataa ccatccctcc ttgtacataa tgctcagaga    11880
accgtctctt agaggagaga tattttctat ccctcagaaa atccccgccg cttatccaac    11940
cactatgaaa gaaggcaaca gatcaatctt gtgttatctc caacatgtgc tacgctatga    12000
gcgagagata atcacggcgt ctccagagaa tgactggcta tggatctttt cagactttag    12060
aagtgccaaa atgacgtacc tatccctcat tacttaccag tctcatcttc tactccagag    12120
ggttgagaga aacctatcta agagtatgag agataacctg cgacaattga gttctttgat    12180
gaggcaggtg ctgggcgggc acggagaaga taccttagag tcagacgaca acattcaacg    12240
actgctaaaa gactctttac gaaggacaag atgggtggat caagaggtgc gccatgcagc    12300
tagaaccatg actggagatt acagccccaa caagaaggtg tcccgtaagg taggatgttc    12360
agaatgggtc tgctctgctc aacaggttgc agtctctacc tcagcaaacc cggcccctgt    12420
ctcggagctt gacataaggg ccctctctaa gaggttccag aacccttga tctcgggctt     12480 gagagtggtt cagtgggcaa ccggtgctca ttataagctt aagcctattc tagatgatct    12540
caatgttttc ccatctctct gccttgtagt tggggacggg tcaggggga tatcaagggc     12600 agtcctcaac atgtttccag atgccaagct tgtgttcaac agtctttag aggtgaatga     12660 cctgatggct tccggaacac atccactgcc tccttcagca atcatgaggg gaggaaatga    12720
tatcgtctcc agagtgatag atcttgactc aatctgggaa aaaccgtccg acttgagaaa    12780
cttggcaacc tggaaatact tccagtcagt ccaaaagcag gtcaacatgt cctatgacct    12840
cattatttgc gatgcagaag ttactgacat tgcatctatc aaccggatca ccctgttaat    12900
gtccgatttt gcattgtcta tagatggacc actctatttg gtcttcaaaa cttatgggac    12960
tatgctagta aatccaaact acaaggctat tcaacacctg tcaagagcgt tcccctcggt    13020
cacagggttt atcacccaag taacttcgtc tttttcatct gagctctacc tccgattctc    13080
caaacgaggg aagtttttca gagatgctga gtacttgacc tcttccaccc ttcgagaaat    13140
gagccttgtg ttattcaatt gtagcagccc caagagtgag atgcagagag ctcgttcctt    13200
gaactatcag gatcttgtga gaggatttcc tgaagaaatc atatcaaatc cttacaatga    13260
gatgatcata actctgattg acagtgatgt agaatctttt ctagtccaca agatggttga    13320
tgatcttgag ttacagaggg gaactctgtc taaagtggct atcattatag ccatcatgat    13380
```

```
agttttctcc aacagagtct tcaacgtttc caaaccccta actgacccct cgttctatcc  13440
accgtctgat cccaaaatcc tgaggcactt caacatatgt tgcagtacta tgatgtatct  13500
atctactgct ttaggtgacg tccctagctt cgcaagactt cacgacctgt ataacagacc  13560
tataacttat tacttcagaa agcaagtcat tcgagggaac gtttatctat cttggagttg  13620
gtccaacgac acctcagtgt tcaaaagggt agcctgtaat tctagcctga gtctgtcatc  13680
tcactggatc aggttgattt acaagatagt gaagactacc agactcgttg gcagcatcaa  13740
ggatctatcc agagaagtgg aaagacacct tcataggtac aacaggtgga tcaccctaga  13800
ggatatcaga tctagatcat ccctactaga ctacagttgc ctgtgaaccg gatactcctg  13860
gaagcctgcc catgctaaga ctcttgtgtg atgtatcttg aaaaaaacaa gatcctaaat  13920
ctgaaccttt ggttgtttga ttgtttttct catttttgtt gtttatttgt taagcgt     13977
```

<210> SEQ ID NO 14
<211> LENGTH: 13923
<212> TYPE: DNA
<213> ORGANISM: Artificial Sequence
<220> FEATURE:
<223> OTHER INFORMATION: RABV vector: Coravax V5 China

<400> SEQUENCE: 14

```
acgcttaaca accagatcaa agaaaaaaca gacattgtca attgcaaagc aaaaatgtaa     60
cacccctaca atggatgccg acaagattgt attcaaagtc aataatcagg tggtctcttt    120
gaagcctgag attatcgtgg atcaatatga gtacaagtac cctgccatca aagatttgaa    180
aaagccctgt ataaccctag gaaaggctcc cgatttaaat aaagcataca agtcagtttt    240
gtcaggcatg agcgccgcca aacttaatcc tgacgatgta tgttcctatt tggcagcggc    300
aatgcagttt tttgagggga catgtccgga agactggacc agctatggaa ttgtgattgc    360
acgaaaagga gataagatca ccccaggttc tctggtggag ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagatttttg agacagcccc    600
ttttgttaaa atcgtggaac accatactct aatgacaact cacaaaatgt gtgctaattg    660
gagtactata ccaaacttca gatttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctagggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caactctgac gacgaggact acttttcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctcctttcg   1500
```

```
aaccatccca aacatgagca agatctttgt caatcctagt gctattagag ccggtctggc   1560
cgatcttgag atggctgaag aaactgttga tctgatcaat agaaatatcg aagacaatca   1620
ggctcatctc caaggggaac ccatagaggt ggacaatctc cctgaggata tggggcgact   1680
tcacctggat gatggaaaat cgcccaacca tggtgagata gccaaggtgg agaaggcaa    1740 gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggctacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctccc ctcagtccct ctagacaata aaatccgaga tgtcccaaag   2460
tcaacatgaa aaaacaggc aacaccactg ataaaatgaa cctcctacgt aagatagtga    2520
aaaaccgcag ggacgaggac actcaaaaat cctctcccgc gtcagcccct ctggatgacg   2580
atgacttgtg gcttccaccc cctgaatacg tcccgctgaa agaacttaca ggcaagaaga   2640
acatgaggaa cttttgtatc aacggaaggg ttaaagtgtg tagcccgaat ggttactcgt   2700
tcaggatcct gcggcacatt ctgaaatcat tcgacgagat atattctggg aatcatagga   2760
tgatcgggtt agtcaaagtg gttattggac tggctttgtc aggatctcca gtccctgagg   2820
gcctgaactg ggtatacaaa ttgaggagaa cctttatctt ccagtgggct gattccaggg   2880
gccctcttga aggggaggag ttggaatact ctcaggagat cacttgggat gatgatactg   2940
agttcgtcgg attgcaaata agagtgattg caaaacagtg tcatatccag ggcagagtct   3000
ggtgtatcaa catgaacccg agagcatgtc aactatggtc tgacatgtct cttcagacac   3060
aaaggtccga agaggacaaa gattcctctc tgcttctaga ataatcagat tatatcccgc   3120
aaatttatca cttgtttacc tctggaggag agaacatatg ggctcaactc caaccccttgg   3180 gagcaatata acaaaaaaca tgttatggtg ccattaaacc gctgcatttc atcaaagtca   3240
agttgattac ctttacattt tgatcctctt ggatgtgaaa aaactatta acatccctca    3300 aaagaccccg ggccaccatg ttcgtgtttc tggtgctgct gcctctggtg agctcccagt   3360
gcgtgaacct gaccacaagg acccagctgc ccctgcctta taccaattcc ttcacacggg   3420
gcgtgtacta tcccgacaag gtgttccgga gcagcgtgct gcactccaca caggatctgt   3480
ttctgccttt ctttttctaac gtgacctggt tccacgccat ccacgtgagc ggcaccaatg   3540
gcacaaagcg gttcgacaat ccagtgctgc cctttaacga tggcgtgtac ttcgcctcca   3600
ccgagaagtc taacatcatc agaggctgga tctttggcac cactggac agcaagacac    3660 agtccctgct gatcgtgaac aatgccacca cgtggtcat caaggtgtgc gagttccagt    3720
tttgtaatga tccattcctg ggcgtgtact atcacaagaa caataagtct tggatggaga   3780
gcgagtttcg cgtgtattcc tctgccaaca attgcacatt tgagtacgtg tcccagccct   3840
```

```
tcctgatgga cctggagggc aagcagggca atttcaagaa cctgagggag ttcgtgttta   3900
agaatatcga tggctacttc aaaatctact ccaagcacac cccaatcaac ctggtgcgcg   3960
acctgccaca gggcttctct gccctggagc cactggtgga tctgcccatc ggcatcaaca   4020
tcacccggtt tcagacactg ctggccctgc acagaagcta cctgacacca ggcgacagct   4080
cctctggatg gaccgcagga gcagcagcct actatgtggg ctatctgcag cccaggacct   4140
tcctgctgaa gtacaacgag aatggcacca tcacagacgc cgtggattgc gccctggatc   4200
ccctgtctga gaccaagtgt acactgaaga gctttaccgt ggagaagggc atctatcaga   4260
caagcaattt cagggtgcag cctaccgagt ccatcgtgcg ctttcccaat atcacaaacc   4320
tgtgcccttt tggcgaggtg ttcaacgcaa cccgcttcgc cagcgtgtac gcctggaata   4380
ggaagcgcat ctccaactgc gtggccgact attctgtgct gtacaacagc gcctccttct   4440
ctacctttaa gtgctatggc gtgagcccca caaagctgaa tgacctgtgc tttaccaacg   4500
tgtacgccga ttccttcgtg atcagggggcg acgaggtgcg ccagatcgca ccaggacaga   4560
caggcaagat cgcagactac aattataagc tgcctgacga tttcaccggc tgcgtgatcg   4620
cctggaactc taacaatctg gatagcaaag tgggcggcaa ctacaattat ctgtaccggc   4680
tgtttagaaa gtctaatctg aagccattcg agagggacat ctccacagaa atctaccagg   4740
ccggctctac cccctgcaat ggcgtggagg ctttaactg ttatttccct ctgcagagct   4800
acggcttcca gccaacaaac ggcgtgggct atcagcccta ccgcgtggtg gtgctgtctt   4860
ttgagctgct gcacgcacct gcaacagtgt gcggaccaaa gaagagcacc aatctggtga   4920
agaacaagtg cgtgaacttc aacttcaacg gactgaccgg aacaggcgtg ctgaccgagt   4980
ccaacaagaa gttcctgcct tttcagcagt cggcaggga catcgcagat accacagacg   5040
ccgtgcgcga ccctcagacc ctggagatcc tggacatcac accatgctcc ttcggcggcg   5100
tgtctgtgat cacaccaggc accaatacaa gcaaccaggt ggccgtgctg tatcaggacg   5160
tgaattgtac cgaggtgcca gtggcaatcc acgcagatca gctgacccct acatggcggg   5220
tgtactctac cggcagcaac gtgttccaga caagagccgg atgcctgatc ggagcagagc   5280
acgtgaacaa tagctatgag tgcgacatcc ctatcggcgc cggcatctgt gcctcctacc   5340
agacccagac aaaactcccca aggtctgtgg agatgaggc cgaagacttt gtggaagtcc   5400
acctgcctga tgtgcataac caggtgtctg cgtcgacct gggactgcca aattggggca   5460
agtacgtgct gctgagtgct ggagcactga ctgccctgat gctgatcatt ttcctgatga   5520
cctgctgtcg cgcgcgtgaac agaagtgagc ccactcagca caatctgcga ggaaccggga   5580
gagaagtgtc agtcacacct cagagcggga aaatcattag tagttgggaa tcacataaaa   5640
gcggggcga ccaggctg ggatccggct ccggcgaggg caggggaagt ctactaacat   5700
gcggggacgt ggaggaaaat cccggcccca tggttcctca ggctctcctg tttgtacccc   5760
ttctggtttt tccattgtgt tttgggaaat tccctattta cacgatacca gacaagcttg   5820
gtccctggag tccgattgac atacatcacc tcagctgccc aaacaatttg gtagtggagg   5880
acgaaggatg caccaacctg tcagggttct cctacatgga acttaaagtt ggatacatct   5940
tagccataaa agtgaacggg ttcacttgca caggcgttgt gacggaggct gaaacctaca   6000
ctaacttcgt tggttatgtc acaaccacgt tcaaaagaaa gcatttccgc ccaacaccag   6060
atgcatgtag agccgcgtac aactggaaga tggccggtga ccccagatat gaagagtctc   6120
tacacaatcc gtaccctgac taccgctggc ttcgaactgc aaaaaccacc aaggagtctc   6180
tcgttatcat atctccaagt gtggcagatt tggacccata tgacagatcc cttcactcga   6240
```

```
gggtcttccc tagcgggaag tgctcaggag tagcggtgtc ttctacctac tgctccacta    6300
accacgatta caccatttgg atgcccgaga atccgagact agggatgtct tgtgacattt    6360
ttaccaatag tagagggaag agagcatcca aagggagtga gacttgcggc tttgtagatg    6420
aaagaggcct atataagtct ttaaaaggag catgcaaact caagttatgt ggagttctag    6480
gacttagact tatggatgga acatgggtct cgatgcaaac atcaaatgaa accaaatggt    6540
gccctcccga taagttggtg aacctgcacg actttcgctc agacgaaatt gagcaccttg    6600
ttgtagagga gttggtcagg aagagagagg agtgtctgga tgcactagag tccatcatga    6660
caaccaagtc agtgagtttc agacgtctca gtcatttaag aaaacttgtc cctgggtttg    6720
gaaaagcata taccatattc aacaagacct tgatggaagc cgatgctcac tacaagtcag    6780
tcgagacttg gaatgagatc ctcccttcaa aagggtgttt aagagttggg gggaggtgtc    6840
atcctcatgt gaacggggtg ttttttcaatg gtataatatt aggacctgac ggcaatgtct    6900
taatcccaga gatgcaatca tccctcctcc agcaacatat ggagttgttg gaatcctcgg    6960
ttatccccct tgtgcacccc ctggcagacc cgtctaccgt tttcaaggac ggtgacgagg    7020
ctgaggattt tgttgaagtt caccttcccg atgtgcacaa tcaggtctca ggagttgact    7080
tgggtctccc gaactggggg aagtatgtat tactgagtgc aggggccctg actgccttga    7140
tgttgataat tttcctgatg acatgttgta gaagagtcaa tcgatcagaa cctacgcaac    7200
acaatctcag agggacaggg agggaggtgt cagtcactcc ccaaagcggg aagatcatat    7260
cttcatggga atcacacaag agtgggggtg agaccagact gtaagctagc ttataaagtg    7320
ctgggtcatc taagcttttc agtcgagaaa aaaacattag atcagaagaa caactggcaa    7380
cacttctcaa cctgagactt acttcaagat gctcgatcct ggagaggtct atgatgaccc    7440
tattgaccca atcgagttag aggctgaacc cagaggaacc cccattgtcc ccaacatctt    7500
gaggaactct gactacaatc tcaactctcc tttgatagaa gatcctgcta gactaatgtt    7560
agaatggtta aaaacaggga atagaccctta tcggatgact ctaacagaca attgctccag    7620
gtctttcaga gttttgaaag attatttcaa gaaggtagat ttgggttctc tcaaggtggg    7680
cggaatggct gcacagtcaa tgatttctct ctggttatat ggtgcccact ctgaatccaa    7740
caggagccgg agatgtataa cagacttggc ccatttctat tccaagtcgt cccccataga    7800
gaagctgttg aatctcacgc taggaaatag agggctgaga atcccccag agggagtgtt    7860 aagttgcctt gagagggttg attatgataa tgcatttgga aggtatcttg ccaacacgta    7920
ttcctcttac ttgttcttcc atgtaatcac cttatacatg aacgccctag actgggatga    7980
agaaaagacc atcctagcat tatggaaaga tttaacctca gtggacatcg ggaaggactt    8040
ggtaaagttc aaagaccaaa tatggggact gctgatcgtg acaaaggact ttgtttactc    8100
ccaaagttcc aattgtcttt ttgacagaaa ctacacactt atgctaaaag atcttttctt    8160
gtctcgcttc aactccttaa tggtcttgct ctctccccca gagccccgat actcagatga    8220
cttgatatct caactatgcc agctgtacat tgctggggat caagtcttgt ctatgtgtgg    8280
aaactccggc tatgaagtca tcaaaatatt ggagccatat gtcgtgaata gtttagtcca    8340
gagagcagaa aagtttaggc ctctcattca ttccttggga gactttcctg tatttataaa    8400
agacaaggta agtcaacttg aagagacgtt cggtccctgt gcaagaaggt tctttagggc    8460
tctggatcaa ttcgacaaca tacatgactt ggttttttgtg tttggctgtt acaggcattg    8520
ggggcaccca tatatagatt atcgaaaggg tctgtcaaaa ctatatgatc aggttcacct    8580
```

```
taaaaaaatg atagataagt cctaccagga gtgcttagca agcgacctag ccaggaggat      8640
ccttagatgg ggttttgata agtactccaa gtggtatctg gattcaagat tcctagcccg      8700
agaccacccc ttgactcctt atatcaaaac ccaaacatgg ccacccaaac atattgtaga      8760
cttggtgggg gatacatggc acaagctccc gatcacgcag atctttgaga ttcctgaatc      8820
aatggatccg tcagaaatat tggatgacaa atcacattct ttcaccagaa cgagactagc      8880
ttcttggctg tcagaaaacc gagggggggcc tgttcctagc gaaaaagtta ttatcacggc      8940
cctgtctaag ccgcctgtca atccccgaga gtttctgagg tctatagacc tcggaggatt      9000
gccagatgaa gacttgataa ttggcctcaa gccaaaggaa cgggaattga agattgaagg      9060
tcgattcttt gctctaatgt catggaatct aagattgtat tttgtcatca ctgaaaaact      9120
cttggccaac tacatcttgc cacttttga cgcgctgact atgacagaca acctgaacaa      9180 ggtgttaaa aagctgatcg acagggtcac cgggcaaggg cttttggact attcaagggt       9240
cacatatgca tttcacctgg actatgaaaa gtggaacaac catcaaagat tagagtcaac      9300
agaggatgta ttttctgtcc tagatcaagt gtttggattg aagagagtgt tttctagaac      9360
acacgagttt tttcaaaagg cctggatcta ttattcagac agatcagacc tcatcgggtt      9420
acgggaggat caaatatact gcttagatgc gtccaacggc ccaacctgtt ggaatggcca      9480
ggatggcggg ctagaaggct tacggcagaa gggctggagt ctagtcagct tattgatgat      9540
agatagagaa tctcaaatca ggaacacaag aaccaaaata ctagctcaag gagacaacca      9600
ggttttatgt ccgacataca tgttgtcgcc agggctatct caagagggc tcctctatga       9660 attggagaga atatcaagga atgcactttc gatatacaga gccgtcgagg aagggcatc      9720 taagctaggg ctgatcatca agaaagaaga gaccatgtgt agttatgact tcctcatcta      9780
tggaaaaacc cctttgttta gaggtaacat attggtgcct gagtccaaaa gatgggccag      9840
agtctcttgc gtctctaatg accaaatagt caacctcgcc aatataatgt cgacagtgtc      9900
caccaatgcg ctaacagtgg cacaacactc tcaatctttg atcaaaccga tgagggattt      9960
tctgctcatg tcagtacagg cagtctttca ctacctgcta tttagcccaa tcttaaaggg      10020
aagagtttac aagattctga gcgctgaagg ggagagcttt ctcctagcca tgtcaaggat      10080 aatctatctac gatccttctt tgggagggat atctggaatg tccctcggaa gattccatat      10140
acgacagttc tcagaccctg tctctgaagg gttatccttc tggagagaga tctggttaag      10200
ctcccaagag tcctggattc acgcgttgtg tcaagaggct ggaaacccag atcttggaga      10260
gagaacactc gagagcttca ctcgcccttct agaagatccg accaccttaa atatcagagg      10320
aggggccagt cctaccattc tactcaagga tgcaatcaga aaggctttat atgacgaggt      10380
ggacaaggtg gaaaattcag agtttcgaga ggcaatcctg ttgtccaaga cccatagaga      10440
taattttata ctcttcttaa tatctgttga gcctctgttt cctcgatttc tcagtgagct      10500
attcagttcg tctttttttgg gaatccccga gtcaatcatt ggattgatac aaaactcccg      10560
aacgataaga aggcagttta gaaagagtct ctcaaaaact ttagaagaat ccttctacaa      10620
ctcagagatc cacgggatta gtcggatgac ccagacacct cagagggttg gggggtgtg      10680 gccttgctct tcagagaggg cagatctact taggagatc tcttggggaa gaaaagtggt      10740
aggcacgaca gttcctcacc cttctgagat gttgggatta cttcccaagt cctctatttc      10800
ttgcacttgt ggagcaacag gaggaggcaa tcctagagtt tctgtatcag tactcccgtc      10860 cttttgatcag tcatttttt cacgaggccc cctaaaggga tacttgggct cgtccacctc     10920
tatgtcgacc cagctattcc atgcatggga aaaagtcact aatgttcatg tggtgaagag      10980
```

```
agctctatcg ttaaaagaat ctataaactg gttcattact agagattcca acttggctca   11040
agctctaatt aggaacatta tgtctctgac aggccctgat ttccctctag aggaggcccc   11100
tgtcttcaaa aggacggggt cagccttgca taggttcaag tctgccagat acagcgaagg   11160
agggtattct tctgtctgcc cgaacctcct ctctcatatt tctgttagta cagacaccat   11220
gtctgatttg acccaagacg ggaagaacta cgatttcatg ttccagccat tgatgcttta   11280
tgcacagaca tggacatcag agctggtaca gagagacaca aggctaagag actctacgtt   11340
tcattggcac ctccgatgca acaggtgtgt gagacccatt gacgacgtga ccctggagac   11400
ctctcagatc ttcgagtttc cggatgtgtc gaaaagaata tccagaatgg tttctggggc   11460
tgtgcctcac ttccagaggc ttcccgatat ccgtctgaga ccaggagatt ttgaatctct   11520
aagcggtaga gaaaagtctc accatatcgg atcagctcag gggctcttat actcaatctt   11580
agtggcaatt cacgactcag gatacaatga tggaaccatc ttccctgtca acatatacgg   11640
caaggtttcc cctagagact atttgagagg gctcgcaagg ggagtattga taggatcctc   11700
gatttgcttc ttgacaagaa tgacaaatat caatattaat agacctcttg aattggtctc   11760
aggggtaatc tcatatattc tcctgaggct agataaccat ccctccttgt acataatgct   11820
cagagaaccg tctcttagag gagagatatt ttctatccct cagaaaatcc ccgccgctta   11880
tccaaccact atgaaagaag gcaacagatc aatcttgtgt tatctccaac atgtgctacg   11940
ctatgagcga gagataatca cggcgtctcc agagaatgac tggctatgga tcttttcaga   12000
ctttagaagt gccaaaatga cgtacctatc cctcattact taccagtctc atcttctact   12060
ccagagggtt gagagaaacc tatctaagag tatgagagat aacctgcgac aattgagttc   12120
tttgatgagg caggtgctgg gcgggcacgg agaagatacc ttagagtcag acgcaaacat   12180
tcaacgactg ctaaaagact cttttacgaag gacaagatgg gtggatcaag aggtgcgcca   12240
tgcagctaga accatgactg gagattacag ccccaacaag aaggtgtccc gtaaggtagg   12300
atgttcagaa tgggtctgct ctgctcaaca ggttgcagtc tctacctcag caaacccggc   12360
ccctgtctcg gagcttgaca taagggccct ctctaagagg ttccagaacc ctttgatctc   12420
gggcttgaga gtggttcagt gggcaaccgg tgctcattat aagcttaagc ctattctaga   12480
tgatctcaat gttttcccat ctctctgcct tgtagttggg gacgggtcag ggggatatc   12540
aagggcagtc ctcaacatgt ttccagatgc caagcttgtg ttcaacagtc ttttagaggt   12600
gaatgacctg atggcttccg gaacacatcc actgcctcct tcagcaatca tgaggggagg   12660
aaatgatatc gtctccagag tgatagatct tgactcaatc tgggaaaaac cgtccgactt   12720
gagaaacttg gcaacctgga aatacttcca gtcagtccaa aagcaggtca acatgtccta   12780
tgacctcatt atttgcgatg cagaagttac tgacattgca tctatcaacc ggatcaccct   12840
gttaatgtcc gattttgcat tgtctataga tggaccactc tatttggtct tcaaaactta   12900
tgggactatg ctagtaaatc caaactacaa ggctattcaa cacctgtcaa gagcgttccc   12960
ctcggtcaca gggtttatca cccaagtaac ttcgtctttt tcatctgagc tctacctccg   13020
attctccaaa cgagggaagt ttttcagaga tgctgagtac ttgacctctt ccaccccttcg   13080
agaaatgagc cttgtgttat tcaattgtag cagccccaag agtgagatgc agagagctcg   13140
ttccttgaac tatcaggatc ttgtgagagg atttcctgaa gaaatcatat caaatcctta   13200
caatgagatg atcataactc tgattgacag tgatgtagaa tctttctag tccacaagat   13260
ggttgatgat cttgagttac agagggaac tctgtctaaa gtggctatca ttatagccat   13320
```

```
catgatagtt ttctccaaca gagtcttcaa cgtttccaaa ccectaactg accectcgtt    13380 ctatccaccg tctgatccca aaatcctgag gcacttcaac atatgttgca gtactatgat    13440
gtatctatct actgctttag gtgacgtccc tagcttcgca agacttcacg acctgtataa    13500
cagacctata acttattact tcagaaagca agtcattcga gggaacgttt atctatcttg    13560
gagttggtcc aacgacacct cagtgttcaa aagggtagcc tgtaattcta gcctgagtct    13620
gtcatctcac tggatcaggt tgatttacaa gatagtgaag actaccgac tcgttggcag     13680 catcaaggat ctatccagag aagtggaaag acaccttcat aggtacaaca ggtggatcac    13740
cctagaggat atcagatcta gatcatccct actagactac agttgcctgt gaaccggata    13800
ctcctggaag cctgcccatg ctaagactct tgtgtgatgt atcttgaaaa aaacaagatc    13860
ctaaatctga acctttggtt gtttgattgt ttttctcatt tttgttgttt atttgttaag    13920
cgt                                                                 13923

<210> SEQ ID NO 15
<211> LENGTH: 13974
<212> TYPE: DNA
<213> ORGANISM: Artificial Sequence
<220> FEATURE:
<223> OTHER INFORMATION: RABV vector: Coravax V5 South Africa

<400> SEQUENCE: 15
acgcttaaca accagatcaa agaaaaaaca gacattgtca attgcaaagc aaaaatgtaa      60 caccectaca atggatgccg acaagattgt attcaaagtc aataatcagg tggtctcttt     120
gaagcctgag attatcgtgg atcaatatga gtacaagtac cctgccatca agatttgaa      180 aaagccctgt ataaccctag gaaaggctcc cgatttaaat aaagcataca agtcagtttt     240
gtcaggcatg agcgccgcca aacttaatcc tgacgtagta tgttcctatt tggcagcggc     300
aatgcagttt tttgagggga catgtccgga agactggacc agctatggaa ttgtgattgc     360
acgaaaagga gataagatca ccccaggttc tctggtggag ataaaacgta ctgatgtaga     420
agggaattgg gctctgacag gaggcatgga actgacaaga gaccccactg tccctgagca     480
tgcgtcctta gtcggtcttc tcttgagtct gtataggttg agcaaaatat ccgggcaaaa     540
cactggtaac tataagacaa acattgcaga caggatagag cagatttttg agacagcccc     600
ttttgttaaa atcgtggaac accatactct aatgacaact cacaaaatgt gtgctaattg     660
gagtactata ccaaacttca gatttttggc cggaacctat gacatgtttt tctcccggat     720
tgagcatcta tattcagcaa tcagagtggg cacagttgtc actgcttatg aagactgttc     780
aggactggta tcatttactg ggttcataaa acaaatcaat ctcaccgcta gagaggcaat     840
actatatttc ttccacaaga actttgagga agagataaga gaatgtttg agccagggca     900 ggagacagct gttcctcact cttatttcat ccacttccgt tcactaggct tgagtgggaa     960
atctccttat tcatcaaatg ctgttggtca cgtgttcaat ctcattcact ttgtaggatg    1020
ctatatgggt caagtcagat ccctaaatgc aacggttatt gctgcatgtg ctcctcatga    1080
aatgtctgtt ctagggggct atctgggaga ggaattcttc gggaaaggga catttgaaag    1140
aagattcttc agagatgaga agaacttca agaatacgag gcggctgaac tgacaaagac    1200
tgacgtagca ctggcagatg atggaactgt caactctgac gacgaggact acttttcagg    1260
tgaaaccaga agtccggagg ctgttttatac tcgaatcatg atgaatggag gtcgactaaa    1320
gagatctcac atacggagat atgtctcagt cagttccaat catcaagccc gtccaaactc    1380
attcgccgag tttctaaaca agacatattc gagtgactca taagaagttg aataacaaaa    1440
```

```
tgccggaaat ctacggattg tgtatatcca tcatgaaaaa aactaacacc cctcctttcg    1500
aaccatccca aacatgagca agatctttgt caatcctagt gctattagag ccggtctggc    1560
cgatcttgag atggctgaag aaactgttga tctgatcaat agaaatatcg aagacaatca    1620
ggctcatctc caagggaac ccatagaggt ggacaatctc cctgaggata tggggcgact    1680
tcacctggat gatggaaaat cgcccaacca tggtgagata gccaaggtgg gagaaggcaa    1740
gtatcgagag gactttcaga tggatgaagg agaggatcct agcttcctgt tccagtcata    1800
cctggaaaat gttggagtcc aaatagtcag acaaatgagg tcaggagaga gatttctcaa    1860
gatatggtca cagaccgtag aagagattat atcctatgtc gcggtcaact ttcccaaccc    1920
tccaggaaag tcttcagagg ataaatcaac ccagactact ggccgagagc tcaagaagga    1980
gacaacaccc actccttctc agagagaaag ccaatcatcg aaagccagga tggcggctca    2040
aattgcttct ggccctccag cccttgaatg gtcggctacc aatgaagagg atgatctatc    2100
agtggaggct gagatcgctc accagattgc agaaagtttc tccaaaaaat ataagtttcc    2160
ctctcgatcc tcagggatac tcttgtataa ttttgagcaa ttgaaaatga accttgatga    2220
tatagttaaa gaggcaaaaa atgtaccagg tgtgacccgt ttagcccatg acgggtccaa    2280
actcccccta agatgtgtac tgggatgggt cgctttggcc aactctaaga aattccagtt    2340
gttagtcgaa tccgacaagc tgagtaaaat catgcaagat gacttgaatc gctatacatc    2400
ttgctaaccg aacctctccc ctcagtccct ctagacaata aaatccgaga tgtcccaaag    2460
tcaacatgaa aaaacaggc aacaccactg ataaaatgaa cctcctacgt aagatagtga    2520
aaaaccgcag ggacgaggac actcaaaaat cctctcccgc gtcagcccct ctggatgacg    2580
atgacttgtg gcttccaccc cctgaatacg tcccgctgaa agaacttaca ggcaagaaga    2640
acatgaggaa cttttgtatc aacggaaggg ttaaagtgtg tagcccgaat ggttactcgt    2700
tcaggatcct gcggcacatt ctgaaatcat tcgacgagat atattctggg aatcatagga    2760
tgatcgggtt agtcaaagtg gttattggac tggctttgtc aggatctcca gtccctgagg    2820
gcctgaactg ggtatacaaa ttgaggagaa cctttatctt ccagtgggct gattccaggg    2880
gccctcttga aggggaggag ttggaatact ctcaggagat cacttgggat gatgatactg    2940
agttcgtcgg attgcaaata agagtgattg caaaacagtg tcatatccag ggcagagtct    3000
ggtgtatcaa catgaacccg agagcatgtc aactatggtc tgacatgtct cttcagacac    3060
aaaggtccga agaggacaaa gattcctctc tgcttctaga ataatcagat tatatcccgc    3120
aaatttatca cttgtttacc tctggaggag agaacatatg ggctcaactc caaccccttgg   3180 gagcaatata acaaaaaaca tgttatggtg ccattaaacc gctgcatttc atcaaagtca    3240
agttgattac ctttacattt tgatcctctt ggatgtgaaa aaaactatta acatccctca    3300
aaagaccccg ggccaccatg ttcgtgtttc tggtgctgct gcctctggtg agctcccagt    3360
gcgtgaactt caccacaagg acccagctgc ccctgcccta taccaattcc ttcacacggg    3420
gcgtgtacta tcccgacaag gtgttccgga gcagcgtgct gcactccaca caggatctgt    3480
ttctgccttt cttttctaac gtgacctggt tccacgccat ccacgtgagc ggcaccaatg    3540
gcacaaagcg gttcgccaat ccagtgctgc ctttaacga tggcgtgtac ttcgcctcca    3600
ccgagaagtc taacatcatc agaggctgga tctttggcac cacactggac agcaagacac    3660
agtccctgct gatcgtgaac aatgccacca acgtggtcat caaggtgtgc gagttccagt    3720
tttgtaatga tccattcctg ggcgtgtact atcacaagaa caataagtct tggatggaga    3780
```

```
gcgagtttcg cgtgtattcc tctgccaaca attgcacatt tgagtacgtg tcccagccct   3840
tcctgatgga cctggagggc aagcagggca atttcaagaa cctgagggag ttcgtgttta   3900
agaatatcga tggctacttc aaaatctact ccaagcacac cccaatcaac ctggtgcgcg   3960
gcctgccaca gggcttctct gccctggagc cactggtgga tctgcccatc ggcatcaaca   4020
tcacccggtt tcagacactg ctggccctgc acagaagcta cctgacacca ggcgacagct   4080
cctctggatg gaccgcagga gcagcagcct actatgtggg ctatctgcag cccaggacct   4140
tcctgctgaa gtacaacgag aatggcacca tcacagacgc cgtggattgc gccctggatc   4200
ccctgtctga ccaagtgt acactgaaga gctttaccgt ggagaagggc atctatcaga   4260
caagcaattt cagggtgcag cctaccgagt ccatcgtgcg ctttcccaat atcacaaacc   4320
tgtgcccttt tggcgaggtg ttcaacgcaa cccgcttcgc cagcgtgtac gcctggaata   4380
ggaagcgcat ctccaactgc gtggccgact attctgtgct gtacaacagc gcctccttct   4440
ctacctttaa gtgctatggc gtgagcccca caaagctgaa tgacctgtgc tttaccaacg   4500
tgtacgccga ttccttcgtg atcaggggcg acgaggtgcg ccagatcgca ccaggacaga   4560
caggcaatat cgcagactac aattataagc tgcctgacga tttcaccggc tgcgtgatcg   4620
cctggaactc taacaatctg gatagcaaag tgggcggcaa ctacaattat ctgtaccggc   4680
tgtttagaaa gtctaatctg aagccattcg agagggacat ctccacagaa atctaccagg   4740
ccggctctac cccctgcaat ggcgtgaagg ctttaactg ttatttccct ctgcagagct   4800
acggcttcca gccaacatat ggcgtgggct atcagcccta ccgcgtggtg gtgctgtctt   4860
ttgagctgct gcacgcacct gcaacagtgt gcggaccaaa gaagagcacc aatctggtga   4920
agaacaagtg cgtgaacttc aacttcaacg gactgaccgg aacaggcgtg ctgaccgagt   4980
ccaacaagaa gttcctgcct tttcagcagt tcggcaggga catcgcagat accacagacg   5040
ccgtgcgcga ccctcagacc ctggagatcc tggacatcac accatgctcc ttcggcggcg   5100
tgtctgtgat cacaccaggc accaatacaa gcaaccaggt ggccgtgctg tatcagggcg   5160
tgaattgtac cgaggtgcca gtggcaatcc acgcagatca gctgaccccct acatggcggg   5220 tgtactctac cggcagcaac gtgttccaga caagagccgg atgcctgatc ggagcagagc   5280
acgtgaacaa tagctatgag tgcgacatcc ctatcggcgc cggcatctgt gcctcctacc   5340
agacccagac aaaactcccca gaatcaagcg tgattcctct ggtccatcca ctggcagatc   5400
cctccacagt gttcaaagac ggagatgagg ccgaagactt tgtggaagtc cacctgcctg   5460
atgtgcataa ccaggtgtct ggcgtcgacc tgggactgcc aaattggggc aagtacgtgc   5520
tgctgagtgc tggagcactg actgccctga tgctgatcat tttcctgatg acctgctgtc   5580
ggcgcgtgaa cagaagtgag cccactcagc acaatctgcg aggaaccggg agagaagtgt   5640
cagtcacacc tcagagcggg aaaatcatta gtagttggga atcacataaa gcggggggcg   5700
agaccaggct gggatccggc tccggcgagg cagggggaag tctactaaca tgcggggacg   5760
tggaggaaaa tcccggcccc atggttcctc aggctctcct gtttgtaccc cttctggttt   5820
ttccattgtg ttttgggaaa ttccctattt acacgatacc agacaagctt ggtccctgga   5880
gtccgattga catacatcac ctcagctgcc caaacaattt ggtagtggag gacgaaggat   5940
gcaccaacct gtcagggttc tcctacatgg aacttaaagt tggatacatc ttagccataa   6000
aagtgaacgg gttcacttgc acaggcgttg tgacggaggc tgaaacctac actaacttcg   6060
ttggttatgt cacaaccacg ttcaaaagaa agcatttccg cccaacacca gatgcatgta   6120
gagccgcgta caactggaag atggccggtg accccagata tgaagagtct ctacacaatc   6180
```

```
cgtaccctga ctaccgctgg cttcgaactg taaaaaccac caaggagtct ctcgttatca    6240
tatctccaag tgtggcagat ttggacccat atgacagatc ccttcactcg agggtcttcc    6300
ctagcgggaa gtgctcagga gtagcggtgt cttctaccta ctgctccact aaccacgatt    6360
acaccatttg gatgcccgag aatccgagac tagggatgtc ttgtgacatt tttaccaata    6420
gtagagggaa gagagcatcc aaagggagtg agacttgcgg cttTgtagat gaaagaggcc    6480
tatataagtc tttaaaagga gcatgcaaac tcaagttatg tggagttcta ggacttagac    6540
ttatggatgg aacatgggtc tcgatgcaaa catcaaatga aaccaaatgg tgccctcccg    6600
ataagttggt gaacctgcac gactttcgct cagacgaaat tgagcacctt gttgtagagg    6660
agttggtcag gaagagagag gagtgtctgg atgcactaga gtccatcatg acaaccaagt    6720
cagtgagttt cagacgtctc agtcatttaa gaaaacttgt ccctgggttt ggaaaagcat    6780
ataccatatt caacaagacc ttgatggaag ccgatgctca ctacaagtca gtcgagactt    6840
ggaatgagat cctcccttca aaagggtgtt taagagttgg ggggaggtgt catcctcatg    6900
tgaacggggt gttttTcaat ggtataatat taggacctga cggcaatgtc ttaatcccag    6960
agatgcaatc atccctcctc cagcaacata tggagttgtt ggaatcctcg gttatccccc    7020
ttgtgcaccc cctggcagac ccgtctaccg ttttcaagga cggtgacgag gctgaggatt    7080
ttgttgaagt tcaccttccc gatgtgcaca atcaggtctc aggagttgac ttgggtctcc    7140
cgaactgggg gaagtatgta ttactgagtg caggggccct gactgccttg atgttgataa    7200
tttTcctgat gacatgttgt agaagagtca atcgatcaga acctacgcaa cacaatctca    7260
gagggacagg gagggaggtg tcagtcactc cccaaagcgg gaagatcata tcttcatggg    7320
aatcacacaa gagtgggggt gagaccagac tgtaagctag cttataaagt gctgggtcat    7380
ctaagctttt cagtcgagaa aaaaacatta gatcagaaga caactggca acacttctca    7440
acctgagact tacttcaaga tgctcgatcc tggagaggtc tatgatgacc ctattgaccc    7500
aatcgagtta gaggctgaac ccagaggaac ccccattgtc cccaacatct tgaggaactc    7560
tgactacaat ctcaactctc ctttgataga agatcctgct agactaatgt tagaatggtt    7620
aaaaacaggg aatagaccct atcggatgac tctaacagac aattgctcca ggtctttcag    7680
agttttgaaa gattatttca agaaggtaga tttgggttct ctcaaggtgg gcggaatggc    7740
tgcacagtca atgattttctc tctggttata tggtgcccac tctgaatcca acaggagccg    7800
gagatgtata acagacttgg cccatttcta ttccaagtcg tcccccatag agaagctgtt    7860
gaatctcacg ctaggaaata gagggctgag aatcccccca gagggagtgt taagttgcct    7920
tgagagggtt gattatgata atgcatttgg aaggtatctt gccaacacgt attcctctta    7980
cttgttcttc catgtaatca ccttatacat gaacgcccta gactgggatg aagaaaagac    8040
catcctagca ttatggaaag atttaacctc agtggacatc gggaaggact tggtaaagtt    8100
caaagaccaa atatggggac tgctgatcgt gacaaaggac tttgtttact cccaaagttc    8160
caattgtctt tttgacagaa actacacact tatgctaaaa gatcttttct tgtctcgctt    8220
caactcctta atggtcttgc tctctccccc agagcccga tactcagatg acttgatatc    8280
tcaactatgc cagctgtaca ttgctgggga tcaagtcttg tctatgtgtg aaactccgg    8340
ctatgaagtc atcaaaatat tggagccata tgtcgtgaat agtttagtcc agagagcaga    8400
aaagtttagg cctctcattc attccttggg agactttcct gtatttataa aagcaaggt    8460
aagtcaactt gaagagacgt tcggtccctg tgcaagaagg ttctttaggg ctctggatca    8520
```

```
attcgacaac atacatgact tggttttttgt gtttggctgt tacaggcatt gggggcaccc   8580
atatatagat tatcgaaagg gtctgtcaaa actatatgat caggttcacc ttaaaaaaat   8640
gatagataag tcctaccagg agtgcttagc aagcgaccta gccaggagga tccttagatg   8700
gggttttgat aagtactcca agtggtatct ggattcaaga ttcctagccc gagaccaccc   8760
cttgactcct tatatcaaaa cccaaacatg gccacccaaa catattgtag acttggtggg   8820
ggatacatgg cacaagctcc cgatcacgca gatctttgag attcctgaat caatggatcc   8880
gtcagaaata ttggatgaca aatcacattc tttcaccaga acgagactag cttcttggct   8940
gtcagaaaac cgaggggggc ctgttcctag cgaaaaagtt attatcacgg ccctgtctaa   9000
gccgcctgtc aatccccgag agtttctgag gtctatagac ctcggaggat tgccagatga   9060
agacttgata attggcctca agccaaagga acgggaattg aagattgaag gtcgattctt   9120
tgctctaatg tcatggaatc taagattgta ttttgtcatc actgaaaaac tcttggccaa   9180
ctacatcttg ccacttttg acgcgctgac tatgacagac aacctgaaca aggtgtttaa   9240
aaagctgatc gacagggtca ccgggcaagg cttttggac tattcaaggg tcacatatgc   9300
atttcacctg gactatgaaa agtggaacaa ccatcaaaga ttagagtcaa cagaggatgt   9360
attttctgtc ctagatcaag tgtttggatt gaagagagtg ttttctagaa cacacgagtt   9420
ttttcaaaag gcctggatct attattcaga cagatcagac ctcatcgggt tacgggagga   9480
tcaaatatac tgcttagatg cgtccaacgg cccaacctgt tggaatggcc aggatggcgg   9540
gctagaaggc ttacggcaga agggctggag tctagtcagc ttattgatga tagatagaga   9600
atctcaaatc aggaacacaa gaaccaaaat actagctcaa ggagacaacc aggttttatg   9660
tccgacatac atgttgtcgc cagggctatc tcaagagggg ctcctctatg aattggagag   9720
aatatcaagg aatgcacttt cgatatacag agccgtcgag gaaggggcat ctaagctagg   9780
gctgatcatc aagaagaag agaccatgtg tagttatgac ttcctcatct atggaaaaac   9840
cccttttgttt agaggtaaca tattggtgcc tgagtccaaa agatgggcca gagtctcttg   9900
cgtctctaat gaccaaatag tcaacctcgc caatataatg tcgacagtgt ccaccaatgc   9960
gctaacagtg gcacaacact ctcaatcttt gatcaaaccg atgagggatt ttctgctcat  10020
gtcagtacag gcagtctttc actacctgct atttagccca atcttaaagg gaagagttta  10080
caagattctg agcgctgaag gggagagctt tctcctagcc atgtcaagga taatctatct  10140
agatccttct ttgggaggga tatctggaat gtccctcgga agattccata tacgacagtt  10200
ctcagaccct gtctctgaag ggttatcctt ctggagagag atctggttaa gctcccaaga  10260
gtcctggatt cacgcgttgt gtcaagaggc tggaaaccca gatcttggag agagaacact  10320
cgagagcttc actcgccttc tagaagatcc gaccacctta aatatcagag gaggggccag  10380
tcctaccatt ctactcaagg atgcaatcag aaaggcttta tatgacgagg tggacaaggt  10440
ggaaaattca gagtttcgag aggcaatcct gttgtccaag acccatagag ataatttttat  10500
actcttctta atatctgttg agcctctgtt tcctcgattt ctcagtgagc tattcagttc  10560
gtctttttg ggaatccccg agtcaatcat tggattgata caaaactccc gaacgataag  10620
aaggcagttt agaaagagtc tctcaaaaac tttagaagaa tccttctaca actcagagat  10680
ccacgggatt agtcggatga cccagacacc tcagagggtt ggggggtgt ggccttgctc  10740
ttcagagagg gcagatctac ttagggagat tcttgggga agaaaagtgg taggcacgac  10800
agttcctcac ccttctgaga tgttgggatt acttcccaag tcctctattt cttgcacttg  10860
tggagcaaca ggaggaggca atcctagagt ttctgtatca gtactcccgt cctttgatca  10920
```

```
gtcatttttt tcacgaggcc ccctaaaggg atacttgggc tcgtccacct ctatgtcgac   10980
ccagctattc catgcatggg aaaaagtcac taatgttcat gtggtgaaga gagctctatc   11040
gttaaaagaa tctataaact ggttcattac tagagattcc aacttggctc aagctctaat   11100
taggaacatt atgtctctga caggccctga tttccctcta gaggaggccc ctgtcttcaa   11160
aaggacgggg tcagccttgc ataggttcaa gtctgccaga tacagcgaag gagggtattc   11220
ttctgtctgc ccgaacctcc tctctcatat ttctgttagt acagacacca tgtctgattt   11280
gacccaagac gggaagaact acgatttcat gttccagcca ttgatgcttt atgcacagac   11340
atggacatca gagctggtac agagagacac aaggctaaga gactctacgt ttcattggca   11400
cctccgatgc aacaggtgtg tgagacccat tgacgacgtg accctggaga cctctcagat   11460
cttcgagttt ccggatgtgt cgaaaagaat atccagaatg gtttctgggg ctgtgcctca   11520
cttccagagg cttcccgata tccgtctgag accaggagat tttgaatctc taagcggtag   11580
agaaaagtct caccatatcg gatcagctca ggggctctta tactcaatct tagtggcaat   11640
tcacgactca ggatacaatg atggaaccat cttccctgtc aacatatacg gcaaggtttc   11700
ccctagagac tatttgagag ggctcgcaag gggagtattg ataggatcct cgatttgctt   11760
cttgacaaga atgacaaata tcaatattaa tagacctctt gaattggtct caggggtaat   11820
ctcatatatt ctcctgaggc tagataacca tccctccttg tacataatgc tcagagaacc   11880
gtctcttaga ggagagatat tttctatccc tcagaaaatc cccgccgctt atccaaccac   11940
tatgaaagaa gcaacagat caatcttgtg ttatctccaa catgtgctac gctatgagcg   12000
agagataatc acggcgtctc cagagaatga ctggctatgg atcttttcag actttagaag   12060
tgccaaaatg acgtacctat ccctcattac ttaccagtct catcttctac tccagagggt   12120
tgagagaaac ctatctaaga gtatgagaga taacctgcga caattgagtt ctttgatgag   12180
gcaggtgctg ggcgggcacg gagaagatac cttagagtca gacgacaaca ttcaacgact   12240
gctaaaagac tctttacgaa ggacaagatg ggtggatcaa gaggtgcgcc atgcagctag   12300
aaccatgact ggagattaca gccccaacaa gaaggtgtcc cgtaaggtag gatgttcaga   12360
atgggtctgc tctgctcaac aggttgcagt ctctacctca gcaaacccgg cccctgtctc   12420
ggagcttgac ataagggccc tctctaagag gttccagaac cctttgatct cgggcttgag   12480
agtggttcag tgggcaaccg gtgctcatta taagcttaag cctattctag atgatctcaa   12540
tgttttccca tctctctgcc ttgtagttgg ggacgggtca gggggatat caagggcagt   12600 cctcaacatg tttccagatg ccaagcttgt gttcaacagt cttttagagg tgaatgacct   12660
gatggcttcc ggaacacatc cactgcctcc ttcagcaatc atgaggggag gaatgatat   12720 cgtctccaga gtgatagatc ttgactcaat ctgggaaaaa ccgtccgact tgagaaactt   12780
ggcaacctgg aaatacttcc agtcagtcca aaagcaggtc aacatgtcct atgacctcat   12840
tatttgcgat gcagaagtta ctgacattgc atctatcaac cggatcaccc tgttaatgtc   12900
cgattttgca ttgtctatag atggaccact ctatttggtc ttcaaaactt atgggactat   12960
gctagtaaat ccaaactaca aggctattca acacctgtca agagcgttcc cctcggtcac   13020
agggtttatc acccaagtaa cttcgtctttt ttcatctgag ctctacctcc gattctccaa   13080
acgagggaag ttttttcagag atgctgagta cttgacctct tccacccttc gagaaatgag   13140
ccttgtgtta ttcaattgta gcagcccaa gagtgagatg cagagagctc gttccttgaa   13200
ctatcaggat cttgtgagag gatttcctga agaaatcata tcaaatcctt acaatgagat   13260
```

| | | | | | |
|---|---|---|---|---|---|
| gatcataact | ctgattgaca | gtgatgtaga | atctttcta | gtccacaaga | tggttgatga | 13320 |
| tcttgagtta | cagaggggaa | ctctgtctaa | agtggctatc | attatagcca | tcatgatagt | 13380 |
| tttctccaac | agagtcttca | acgtttccaa | acccctaact | gaccctcgt | tctatccacc | 13440 |
| gtctgatccc | aaaatcctga | ggcacttcaa | catatgttgc | agtactatga | tgtatctatc | 13500 |
| tactgcttta | ggtgacgtcc | ctagcttcgc | aagacttcac | gacctgtata | acagacctat | 13560 |
| aacttattac | ttcagaaagc | aagtcattcg | agggaacgtt | tatctatctt | ggagttggtc | 13620 |
| caacgacacc | tcagtgttca | aaagggtagc | ctgtaattct | agcctgagtc | tgtcatctca | 13680 |
| ctggatcagg | ttgatttaca | agatagtgaa | gactaccaga | ctcgttggca | gcatcaagga | 13740 |
| tctatccaga | gaagtggaaa | gacaccttca | taggtacaac | aggtggatca | ccctagagga | 13800 |
| tatcagatct | agatcatccc | tactagacta | cagttgcctg | tgaaccggat | actcctggaa | 13860 |
| gcctgcccat | gctaagactc | ttgtgtgatg | tatcttgaaa | aaaacaagat | cctaaatctg | 13920 |
| aacctttggt | tgtttgattg | tttttctcat | ttttgttgtt | tatttgttaa | gcgt | 13974 |

<210> SEQ ID NO 16
<211> LENGTH: 13881
<212> TYPE: DNA
<213> ORGANISM: Artificial Sequence
<220> FEATURE:
<223> OTHER INFORMATION: RABV vector: Coravax V6 China

<400> SEQUENCE: 16

| | | | | | |
|---|---|---|---|---|---|
| acgcttaaca | accagatcaa | agaaaaaaca | gacattgtca | attgcaaagc | aaaaatgtaa | 60 |
| cacccctaca | atggatgccg | acaagattgt | attcaaagtc | aataatcagg | tggtctcttt | 120 |
| gaagcctgag | attatcgtgg | atcaatatga | gtacaagtac | cctgccatca | agatttgaa | 180 |
| aaagccctgt | ataaccctag | gaaaggctcc | cgatttaaat | aaagcataca | agtcagtttt | 240 |
| gtcaggcatg | agcgccgcca | aacttaatcc | tgacgatgta | tgttcctatt | tggcagcggc | 300 |
| aatgcagttt | tttgaggga | catgtccgga | agactggacc | agctatgaa | ttgtgattgc | 360 |
| acgaaaagga | gataagatca | ccccaggttc | tctggtggag | ataaaacgta | ctgatgtaga | 420 |
| agggaattgg | gctctgacag | gaggcatgga | actgacaaga | gaccccactg | tccctgagca | 480 |
| tgcgtcctta | gtcggtcttc | tcttgagtct | gtataggttg | agcaaaatat | ccgggcaaaa | 540 |
| cactggtaac | tataagacaa | acattgcaga | caggatagag | cagatttttg | agacagcccc | 600 |
| ttttgttaaa | atcgtggaac | accatactct | aatgacaact | cacaaaatgt | gtgctaattg | 660 |
| gagtactata | ccaaacttca | gatttttggc | cggaacctat | gacatgtttt | tctcccggat | 720 |
| tgagcatcta | tattcagcaa | tcagagtggg | cacagttgtc | actgcttatg | aagactgttc | 780 |
| aggactggta | tcatttactg | ggttcataaa | acaaatcaat | ctcaccgcta | gagaggcaat | 840 |
| actatatttc | ttccacaaga | actttgagga | agagataaga | agaatgtttg | agccagggca | 900 |
| ggagacagct | gttcctcact | cttatttcat | ccacttccgt | tcactaggct | tgagtgggaa | 960 |
| atctccttat | tcatcaaatg | ctgttggtca | cgtgttcaat | ctcattcact | tgtaggatg | 1020 |
| ctatatgggt | caagtcagat | ccctaaatgc | aacggttatt | gctgcatgtg | ctcctcatga | 1080 |
| aatgtctgtt | ctaggggct | atctgggaga | ggaattcttc | gggaagggga | catttgaaag | 1140 |
| aagattcttc | agagatgaga | aagaacttca | agaatacgag | gcggctgaac | tgacaaagac | 1200 |
| tgacgtagca | ctggcagatg | atggaactgt | caactctgac | gacgaggact | acttttcagg | 1260 |
| tgaaaccaga | agtccggagg | ctgttttatac | tcgaatcatg | atgaatggag | tcgactaaa | 1320 |
| gagatctcac | atacggagat | atgtctcagt | cagttccaat | catcaagccc | gtccaaactc | 1380 |

-continued

```
attcgccgag tttctaaaca agacatattc gagtgactca taagaagttg aataacaaaa    1440
tgccggaaat ctacggattg tgtatatcca tcatgaaaaa aactaacacc cctcctttcg    1500
aaccatccca aacatgagca agatctttgt caatcctagt gctattagag ccggtctggc    1560
cgatcttgag atggctgaag aaactgttga tctgatcaat agaaatatcg aagacaatca    1620
ggctcatctc caaggggaac ccatagaggt ggacaatctc cctgaggata tggggcgact    1680
tcacctggat gatggaaaat cgcccaacca tggtgagata gccaaggtgg agaaggcaa     1740 gtatcgagag gactttcaga tggatgaagg agaggatcct agcttcctgt tccagtcata    1800 cctgaaaat gttggagtcc aaatagtcag acaaatgagg tcaggagaga gatttctcaa     1860
gatatggtca cagaccgtag aagagattat atcctatgtc gcggtcaact ttcccaaccc    1920
tccaggaaag tcttcagagg ataaatcaac ccagactact ggccgagagc tcaagaagga    1980
gacaacaccc actccttctc agagagaaag ccaatcatcg aaagccagga tggcggctca    2040
aattgcttct ggccctccag cccttgaatg gtcggctacc aatgaagagg atgatctatc    2100
agtggaggct gagatcgctc accagattgc agaaagtttc tccaaaaaat ataagtttcc    2160
ctctcgatcc tcagggatac tcttgtataa ttttgagcaa ttgaaaatga accttgatga    2220
tatagttaaa gaggcaaaaa atgtaccagg tgtgacccgt ttagcccatg acgggtccaa    2280
actcccccta agatgtgtac tgggatgggt cgctttggcc aactctaaga aattccagtt    2340
gttagtcgaa tccgacaagc tgagtaaaat catgcaagat gacttgaatc gctatacatc    2400
ttgctaaccg aacctctccc ctcagtccct ctagacaata aaatccgaga tgtcccaaag    2460
tcaacatgaa aaaacaggc aacaccactg ataaaatgaa cctcctacgt aagatagtga     2520
aaaaccgcag ggacgaggac actcaaaaat cctctcccgc gtcagcccct ctggatgacg    2580
atgacttgtg gcttccaccc cctgaatacg tcccgctgaa agaacttaca ggcaagaaga    2640
acatgaggaa cttttgtatc aacggaaggg ttaaagtgtg tagcccgaat ggttactcgt    2700
tcaggatcct gcggcacatt ctgaaatcat tcgacgagat atattctggg aatcatagga    2760
tgatcgggtt agtcaaagtg gttattggac tggctttgtc aggatctcca gtccctgagg    2820
gcctgaactg ggtatacaaa ttgaggagaa cctttatctt ccagtgggct gattccaggg    2880
gccctcttga aggggaggag ttggaatact ctcaggagat cacttgggat gatgatactg    2940
agttcgtcgg attgcaaata agagtgattg caaaacagtg tcatatccag ggcagagtct    3000
ggtgtatcaa catgaacccg agagcatgtc aactatggtc tgacatgtct cttcagacac    3060
aaaggtccga gaggacaaa gattcctctc tgcttctaga ataatcagat tatatcccgc      3120
aaatttatca cttgtttacc tctggaggag agaacatatg ggctcaactc caacccttgg    3180
gagcaatata acaaaaaaca tgttatggtg ccattaaacc gctgcatttc atcaaagtca    3240
agttgattac ctttacattt tgatcctctt ggatgtgaaa aaaactatta acatccctca    3300
aaagaccccg ggaaagatgg ttcctcaggc tctcctgttt gtaccccttc tggttttcc    3360 attgtgttt gggaaattcc ctatttacac gataccagac aagcttggtc cctggagtcc     3420
gattgacata catcacctca gctgcccaaa caatttggta gtggaggacg aaggatgcac    3480
caacctgtca gggttctcct acatggaact taaagttgga tacatcttag ccataaaagt    3540
gaacgggttc acttgcacag gcgttgtgac ggaggctgaa acctacacta acttcgttgg    3600
ttatgtcaca accacgttca aaagaaagca tttccgccca acaccagatg catgtagagc    3660
cgcgtacaac tggaagatgg ccggtgaccc cagatatgaa gagtctctac acaatccgta    3720
```

```
ccctgactac cgctggcttc gaactgtaaa aaccaccaag gagtctctcg ttatcatatc    3780
tccaagtgtg gcagatttgg acccatatga cagatcccct cactcgaggg tcttccctag    3840
cgggaagtgc tcaggagtag cggtgtcttc tacctactgc tccactaacc acgattacac    3900
catttggatg cccgagaatc cgagactagg gatgtcttgt gacatttta ccaatagtag     3960 agggaagaga gcatccaaag ggagtgagac ttgcggcttt gtagatgaaa gaggcctata    4020
taagtcttta aaaggagcat gcaaactcaa gttatgtgga gttctaggac ttagacttat    4080
ggatggaaca tgggtctcga tgcaaacatc aaatgaaacc aaatggtgcc ctcccgataa    4140
gttggtgaac ctgcacgact ttcgctcaga cgaaattgag caccttgttg tagaggagtt    4200
ggtcaggaag agagaggagt gtctggatgc actagagtcc atcatgacaa ccaagtcagt    4260
gagtttcaga cgtctcagtc atttaagaaa acttgtccct gggtttggaa aagcatatac    4320
catattcaac aagaccttga tggaagccga tgctcactac aagtcagtcg agacttggaa    4380
tgagatcctc ccttcaaaag ggtgtttaag agttgggggg aggtgtcatc ctcatgtgaa    4440
cggggtgttt ttcaatggta taatattagg acctgacggg aatgtcttaa tcccagagat    4500
gcaatcatcc ctcctccagc aacatatgga gttgttggaa tcctcggtta tccccttgt    4560 gcaccccctg gcagacccgt ctaccgtttt caaggacggt gacgaggctg aggatttgt    4620 tgaagttcac cttcccgatg tgcacaatca ggtctcagga gttgacttgg gtctcccgaa    4680
ctgggggaag tatgtattac tgagtgcagg ggccctgact gccttgatgt tgataatttt    4740
cctgatgaca tgttgtagaa gagtcaatcg atcagaacct acgcaacaca atctcagagg    4800
gacagggagg gaggtgtcag tcactcccca aagcgggaag atcatatctt catgggaatc    4860
acacaagagt gggggtgaga ccagactgta attaattaac gtccttcaa cgatccaagt     4920 ccatgaaaaa aactaacacc cctcccgtac gaccatgttc gtgtttctgg tgctgctgcc    4980
tctggtgagc tcccagtgcg tgaacctgac cacaaggacc cagctgcccc ctgcctatac    5040
caattccttc acacggggcg tgtactatcc cgacaaggtg ttccggagca gcgtgctgca    5100
ctccacacag gatctgtttc tgcctttctt ttctaacgtg acctggttcc acgccatcca    5160
cgtgagcgga accaatggca caaagcggtt cgacaatcca gtgctgccct taacgatgg    5220 cgtgtacttc gcctccaccg agaagtctaa catcatcaga ggctggatct ttggcaccac    5280
actgacagca aagacacagt ccctgctgat cgtgaacaat gccaccaacg tggtcatcaa    5340
ggtgtgcgag ttccagtttt gtaatgatcc attcctgggc gtgtactatc acaagaacaa    5400
taagtcttgg atggagagcg agtttcgcgt gtattcctct gccaacaatt gcacatttga    5460
gtacgtgtcc cagcccttcc tgatggacct ggagggcaag cagggcaatt tcaagaacct    5520
gagggagttc gtgtttaaga atatcgatgg ctacttcaaa atctactcca agcacacccc    5580
aatcaacctg gtgcgcgacc tgccacaggg cttctctgcc ctggagccac tggtggatct    5640
gcccatcggc atcaacatca cccggtttca gacactgctg gccctgcaca gaagctacct    5700
gacaccaggc gacagctcct ctggatggac cgcaggagca gcagcctact atgtgggcta    5760
tctgcagccc aggaccttcc tgctgaagta caacgagaat ggcaccatca cagacgccgt    5820
ggattgcgcc ctggatcccc tgtctgagac caagtgtaca ctgaagagct ttaccgtgga    5880
gaagggcatc tatcagacaa gcaatttcag ggtgcagcct accgagtcca tcgtgcgctt    5940
tcccaatatc acaaacctgt gccctttggg cgaggtgttc aacgcaaccc gcttcgccag    6000
cgtgtacgcc tggaataggg agcgcatctc caactgcgtg gccgactatt ctgtgctgta    6060
caacagcgcc tccttctcta cctttaagtg ctatggcgtg agccccacaa agctgaatga    6120
```

-continued

```
cctgtgcttt accaacgtgt acgccgattc cttcgtgatc aggggcgacg aggtgcgcca    6180
gatcgcacca ggacagacag gcaagatcgc agactacaat tataagctgc ctgacgattt    6240
caccggctgc gtgatcgcct ggaactctaa caatctggat agcaaagtgg gcggcaacta    6300
caattatctg taccggctgt ttagaaagtc taatctgaag ccattcgaga gggacatctc    6360
cacagaaatc taccaggccg gctctacccc ctgcaatggc gtggagggct ttaactgtta    6420
tttccctctg cagagctacg gcttccagcc aacaaacggc gtgggctatc agccctaccg    6480
cgtggtggtg ctgtcttttg agctgctgca cgcacctgca acagtgtgcg gaccaaagaa    6540
gagcaccaat ctggtgaaga caagtgcgt gaacttcaac ttcaacggac tgaccggaac    6600
aggcgtgctg accgagtcca caagaagtt cctgcctttt cagcagttcg gcaggcacat    6660
cgcagatacc acagacgccg tgcgcgaccc tcagaccctg gagatcctgg acatcacacc    6720
atgctccttc ggcggcgtgt ctgtgatcac accaggcacc aatacaagca accaggtggc    6780
cgtgctgtat caggacgtga attgtaccga ggtgccagtg gcaatccacg cagatcagct    6840 gaccccctaca tggcgggtgt actctaccgg cagcaacgtg ttccagacaa gagccggatg    6900
cctgatcgga gcagagcacg tgaacaatag ctatgagtgc gacatcccta tcggcgccgg    6960
catctgtgcc tcctaccaga cccagacaaa ctccccaagg tctgtgggag atgaggccga    7020
agactttgtg gaagtccacc tgcctgatgt gcataaccag gtgtctggcg tcgacctggg    7080
actgccaaat tggggcaagt acgtgctgct gagtgctgga gcactgactg ccctgatgct    7140
gatcattttc ctgatgacct gctgtcggcg cgtgaacaga agtgagccca ctcagcacaa    7200
tctgcgagga accgggagag aagtgtcagt cacacctcag agcgggaaaa tcattagtag    7260
ttgggaatca cataaaagcg ggggcgagac caggctggga tccggctccg gcagggcag    7320 gggaagtcta ctaacatgcg gggacgtgga ggaaaatccc ggccccatgc tcgatcctgg    7380
agaggtctat gatgacccta ttgacccaat cgagttagag gctgaaccca gaggaacccc    7440
cattgtcccc aacatcttga ggaactctga ctacaatctc aactctcctt tgatagaaga    7500
tcctgctaga ctaatgttag aatggttaaa aacagggaat agaccttatc ggatgactct    7560
aacagacaat tgctccaggt ctttcagagt tttgaaagat tatttcaaga aggtagattt    7620
gggttctctc aaggtgggcg gaatggctgc acagtcaatg atttctctct ggttatatgg    7680
tgcccactct gaatccaaca ggagccgag atgtataaca gacttggccc atttctattc    7740
caagtcgtcc cccatagaga agctgttgaa tctcacgcta ggaaatagag ggctgagaat    7800
ccccccagag ggagtgttaa gttgccttga gagggttgat tatgataatg catttggaag    7860
gtatcttgcc aacacgtatt cctcttactt gttcttccat gtaatcaccc tatacatgaa    7920
cgccctagac tgggatgaag aaaagaccat cctagcatta tggaaagatt taacctcagt    7980
ggacatcggg aaggacttgg taaagttcaa agaccaaata tggggactgc tgatcgtgac    8040
aaaggacttt gtttactccc aaagttccaa ttgtcttttt gacagaaact acacacttat    8100
gctaaaagat ctttttcttgt ctcgcttcaa ctccttaatg gtcttgctct ctcccccaga    8160
gccccgatac tcagatgact tgatatctca actatgccag ctgtacattg ctggggatca    8220
agtcttgtct atgtgtggaa actccggcta tgaagtcatc aaaatattgg agccatatgt    8280
cgtgaatagt ttagtccaga gagcagaaaa gtttaggcct ctcattcatt ccttgggaga    8340 cttcctgta tttataaaag acaaggtaag tcaacttgaa gagacgttcg gtccctgtgc    8400
aagaaggttc tttagggctc tggatcaatt cgacaacata catgacttgg ttttgtgtt    8460
```

-continued

| | |
|---|---|
| tggctgttac aggcattggg ggcacccata tatagattat cgaaagggtc tgtcaaaact | 8520 |
| atatgatcag gttcacctta aaaaaatgat agataagtcc taccaggagt gcttagcaag | 8580 |
| cgacctagcc aggaggatcc ttagatgggg ttttgataag tactccaagt ggtatctgga | 8640 |
| ttcaagattc ctagcccgag accacccctt gactccttat atcaaaaccc aaacatggcc | 8700 |
| acccaaacat attgtagact tggtggggga tacatggcac aagctcccga tcacgcagat | 8760 |
| ctttgagatt cctgaatcaa tggatccgtc agaaatattg gatgacaaat cacattcttt | 8820 |
| caccagaacg agactagctt cttggctgtc agaaaaccga gggggcctg ttcctagcga | 8880 |
| aaaagttatt atcacggccc tgtctaagcc gcctgtcaat ccccgagagt ttctgaggtc | 8940 |
| tatagacctc ggaggattgc cagatgaaga cttgataatt ggcctcaagc caaggaacg | 9000 |
| ggaattgaag attgaaggtc gattctttgc tctaatgtca tggaatctaa gattgtattt | 9060 |
| tgtcatcact gaaaaactct tggccaacta catcttgcca cttttttgacg cgctgactat | 9120 |
| gacagacaac ctgaacaagg tgtttaaaaa gctgatcgac agggtcaccg ggcaagggct | 9180 |
| tttggactat tcaagggtca catatgcatt tcacctggac tatgaaaagt ggaacaacca | 9240 |
| tcaaagatta gagtcaacag aggatgtatt ttctgtccta gatcaagtgt ttggattgaa | 9300 |
| gagagtgttt tctagaacac acgagttttt tcaaaaggcc tggatctatt attcagacag | 9360 |
| atcagacctc atcgggttac gggaggatca aatatactgc ttagatgcgt ccaacggccc | 9420 |
| aacctgttgg aatggccagg atggcgggct agaaggctta cggcagaagg gctggagtct | 9480 |
| agtcagctta ttgatgatag atagagaatc tcaaatcagg aacacaagaa ccaaaatact | 9540 |
| agctcaagga gacaaccagg ttttatgtcc gacatacatg ttgtcgccag ggctatctca | 9600 |
| agagggctc ctctatgaat tggagagaat atcaaggaat gcactttcga tatacagagc | 9660 |
| cgtcgaggaa ggggcatcta agctagggct gatcatcaag aaagaagaga ccatgtgtag | 9720 |
| ttatgacttc ctcatctatg gaaaaacccc tttgtttaga ggtaacatat tggtgcctga | 9780 |
| gtccaaaaga tgggccagag tctcttgcgt ctctaatgac caaatagtca acctcgccaa | 9840 |
| tataatgtcg acagtgtcca ccaatgcgct aacagtggca caacactctc aatctttgat | 9900 |
| caaaccgatg agggattttc tgctcatgtc agtacaggca gtctttcact acctgctatt | 9960 |
| tagcccaatc ttaaagggaa gagtttacaa gattctgagc gctgaagggg agagctttct | 10020 |
| cctagccatg tcaaggataa tctatctaga tccttctttg ggagggatat ctggaatgtc | 10080 |
| cctcggaaga ttccatatac gacagttctc agaccctgtc tctgaagggt tatccttctg | 10140 |
| gagagagatc tggttaagct cccaagagtc ctggattcac gcgttgtgtc aagaggctgg | 10200 |
| aaacccagat cttggagaga gaacactcga gagcttcact cgccttctag aagatccgac | 10260 |
| caccttaaat atcagaggag gggccagtcc taccattcta ctcaaggatg caatcagaaa | 10320 |
| ggctttatat gacgaggtgg acaaggtgga aaattcagag tttcgagagg caatcctgtt | 10380 |
| gtccaagacc catagagata atttatact cttcttaata tctgttgagc ctctgtttcc | 10440 |
| tcgatttctc agtgagctat tcagttcgtc tttttttggga atccccgagt caatcattgg | 10500 |
| attgatacaa aactcccgaa cgataagaag gcagtttaga aagagtctct caaaaacttt | 10560 |
| agaagaatcc ttctacaact cagagatcca cgggattagt cggatgaccc agacacctca | 10620 |
| gagggttggg ggggtgtggc cttgctcttc agagagggca gatctactta gggagatctc | 10680 |
| ttggggaaga aaagtggtag gcacgacagt cctcaccct tctgagatgt tgggattact | 10740 |
| tcccaagtcc tctatttctt gcacttgtgg agcaacagga ggaggcaatc ctagagtttc | 10800 |
| tgtatcagta ctcccgtcct ttgatcagtc atttttttca cgaggccccc taagggata | 10860 |

```
cttgggctcg tccacctcta tgtcgaccca gctattccat gcatgggaaa aagtcactaa   10920
tgttcatgtg gtgaagagag ctctatcgtt aaaagaatct ataaactggt tcattactag   10980
agattccaac ttggctcaag ctctaattag gaacattatg tctctgacag gccctgattt   11040
ccctctagag gaggcccctg tcttcaaaag gacggggtca gccttgcata ggttcaagtc   11100
tgccagatac agcgaaggag ggtattcttc tgtctgcccg aacctcctct ctcatatttc   11160
tgttagtaca gacaccatgt ctgatttgac ccaagacggg aagaactacg atttcatgtt   11220
ccagccattg atgctttatg cacagacatg gacatcagag ctggtacaga gagacacaag   11280
gctaagagac tctacgtttc attggcacct ccgatgcaac aggtgtgtga gacccattga   11340
cgacgtgacc ctggagacct ctcagatctt cgagtttccg gatgtgtcga aaagaatatc   11400
cagaatggtt tctgggctg tgcctcactt ccagaggctt cccgatatcc gtctgagacc   11460
aggagatttt gaatctctaa gcggtagaga aaagtctcac catatcggat cagctcaggg   11520
gctcttatac tcaatcttag tggcaattca cgactcagga tacaatgatg gaaccatctt   11580
ccctgtcaac atatacggca aggtttcccc tagagactat ttgagagggc tcgcaagggg   11640
agtattgata ggatcctcga tttgcttctt gacaagaatg acaaatatca atattaatag   11700
acctcttgaa ttggtctcag gggtaatctc atatattctc ctgaggctag ataaccatcc   11760
ctccttgtac ataatgctca gagaaccgtc tcttagagga gagatatttt ctatccctca   11820
gaaaatcccc gccgcttatc caaccactat gaaagaaggc aacagatcaa tcttgtgtta   11880
tctccaacat gtgctacgct atgagcgaga gataatcacg gcgtctccag agaatgactg   11940
gctatggatc ttttcagact ttagaagtgc caaaatgacg tacctatccc tcattactta   12000
ccagtctcat cttctactcc agagggttga gagaaaccta tctaagagta tgagagataa   12060
cctgcgacaa ttgagttctt tgatgaggca ggtgctgggc gggcacggag aagataccct   12120
agagtcagac gacaacattc aacgactgct aaaagactct ttacgaagga caagatgggt   12180
ggatcaagag gtgcgccatg cagctagaac catgactgga gattacagcc ccaacaagaa   12240
ggtgtcccgt aaggtaggat gttcagaatg ggtctgctct gctcaacagg ttgcagtctc   12300
tacctcagca aacccggccc ctgtctcgga gcttgacata agggccctct ctaagaggtt   12360
ccagaaccct ttgatctcgg gcttgagagt ggttcagtgg gcaaccggtg ctcattataa   12420
gcttaagcct attctagatg atctcaatgt tttcccatct ctctgccttg tagttgggga   12480
cgggtcaggg gggatatcaa gggcagtcct caacatgttt ccagatgcca agcttgtgtt   12540
caacagtctt ttagaggtga atgacctgat ggcttccgga acacatccac tgcctccttc   12600
agcaatcatg agggggaggaa atgatatcgt ctccagagtg atagatcttg actcaatctg   12660
ggaaaaaccg tccgacttga gaaacttggc aacctggaaa tacttccagt cagtccaaaa   12720
gcaggtcaac atgtcctatg acctcattat ttgcgatgca gaagttactg acattgcatc   12780
tatcaaccgg atcaccctgt taatgtccga ttttgcattg tctatagatg gaccactcta   12840
tttggtcttc aaaacttatg ggactatgct agtaaatcca aactacaagg ctattcaaca   12900
cctgtcaaga gcgttcccct cggtcacagg gtttatcacc caagtaactt cgtcttttc    12960 atctgagctc tacctccgat tctccaaacg agggaagttt ttcagagatg ctgagtactt   13020
gacctcttcc acccttcgag aaatgagcct tgtgttattc aattgtagca gccccaagag   13080
tgagatgcag agagctcgtt ccttgaacta tcaggatctt gtgagaggat ttcctgaaga   13140
aatcatatca aatccttaca atgagatgat cataactctg attgacagtg atgtagaatc   13200
```

```
ttttctagtc cacaagatgg ttgatgatct tgagttacag aggggaactc tgtctaaagt    13260
ggctatcatt atagccatca tgatagtttt ctccaacaga gtcttcaacg tttccaaacc    13320
cctaactgac ccctcgttct atccaccgtc tgatcccaaa atcctgaggc acttcaacat    13380
atgttgcagt actatgatgt atctatctac tgctttaggt gacgtcccta gcttcgcaag    13440
acttcacgac ctgtataaca gacctataac ttattacttc agaaagcaag tcattcgagg    13500
gaacgtttat ctatcttgga gttggtccaa cgacacctca gtgttcaaaa gggtagcctg    13560
taattctagc ctgagtctgt catctcactg gatcaggttg atttacaaga tagtgaagac    13620
taccagactc gttggcagca tcaaggatct atccagagaa gtggaaagac accttcatag    13680
gtacaacagg tggatcaccc tagaggatat cagatctaga tcatccctac tagactacag    13740
ttgcctgtga accggatact cctggaagcc tgcccatgct aagactcttg tgtgatgtat    13800
cttgaaaaaa acaagatcct aaatctgaac ctttggttgt ttgattgttt ttctcattt    13860
tgttgtttat ttgttaagcg t                                              13881
```

<210> SEQ ID NO 17
<211> LENGTH: 13932
<212> TYPE: DNA
<213> ORGANISM: Artificial Sequence
<220> FEATURE:
<223> OTHER INFORMATION: RABV vector: Coravax V6 South Africa

<400> SEQUENCE: 17

```
acgcttaaca accagatcaa agaaaaaaca gacattgtca attgcaaagc aaaaatgtaa      60
caccctaca atggatgccg acaagattgt attcaaagtc aataatcagg tggtctcttt     120
gaagcctgag attatcgtgg atcaatatga gtacaagtac cctgccatca aagatttgaa     180
aaagcccctgt ataaccctag gaaaggctcc cgatttaaat aaagcataca agtcagtttt    240
gtcaggcatg agcgccgcca aacttaatcc tgacgatgta tgttcctatt tggcagcggc    300
aatgcagttt tttgagggga catgtccgga agactggacc agctatggaa ttgtgattgc    360
acgaaaagga gataagatca ccccaggttc tctggtggag ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagattttg agacagcccc    600
ttttgttaaa atcgtggaac accatactct aatgacaact cacaaaatgt gtgctaattg    660
gagtactata ccaaacttca gattttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact tgtaggatg    1020
ctatatgggt caagtcagat ccctaaatgc aacggttatt gctgcatgtg ctcctcatga   1080
aatgtctgtt ctagggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caactctgac gacgaggact acttttcagg   1260
tgaaaccaga agtccggagg ctgttttatac tcgaatcatg atgaatggag tcgactaaa   1320
gagatctcac atacggagat atgtctcagt cagttccaat catcaagccc gtccaaactc   1380
```

```
attcgccgag tttctaaaca agacatattc gagtgactca taagaagttg aataacaaaa    1440
tgccggaaat ctacggattg tgtatatcca tcatgaaaaa aactaacacc cctcctttcg    1500
aaccatccca aacatgagca agatctttgt caatcctagt gctattagag ccggtctggc    1560
cgatcttgag atggctgaag aaactgttga tctgatcaat agaaatatcg aagacaatca    1620
ggctcatctc caagggaac ccatagaggt ggacaatctc cctgaggata tggggcgact     1680
tcacctggat gatggaaaat cgcccaacca tggtgagata gccaaggtgg agaaggcaa     1740 gtatcgagag gactttcaga tggatgaagg agaggatcct agcttcctgt tccagtcata    1800 cctgaaaat gttggagtcc aaatagtcag acaaatgagg tcaggagaga gatttctcaa     1860
gatatggtca cagaccgtag aagagattat atcctatgtc gcggtcaact ttcccaaccc    1920
tccaggaaag tcttcagagg ataaatcaac ccagactact ggccgagagc tcaagaagga    1980
gacaacaccc actccttctc agagagaaag ccaatcatcg aaagccagga tggcggctca    2040
aattgcttct ggccctccag cccttgaatg gtcggctacc aatgaagagg atgatctatc    2100
agtggaggct gagatcgctc accagattgc agaaagtttc tccaaaaaat ataagtttcc    2160
ctctcgatcc tcagggatac tcttgtataa ttttgagcaa ttgaaaatga accttgatga    2220
tatagttaaa gaggcaaaaa atgtaccagg tgtgacccgt ttagcccatg acgggtccaa    2280 actccccta agatgtgtac tgggatgggt cgctttggcc aactctaaga aattccagtt     2340
gttagtcgaa tccgacaagc tgagtaaaat catgcaagat gacttgaatc gctatacatc    2400
ttgctaaccg aacctctccc ctcagtccct ctagacaata aaatccgaga tgtcccaaag    2460
tcaacatgaa aaaacaggc aacaccactg ataaaatgaa cctcctacgt aagatagtga     2520 aaaccgcag ggacgaggac actcaaaaat cctctcccgc gtcagcccct ctggatgacg      2580
atgacttgtg gcttccaccc cctgaatacg tcccgctgaa agaacttaca ggcaagaaga    2640
acatgaggaa cttttgtatc aacggaaggg ttaaagtgtg tagcccgaat ggttactcgt    2700
tcaggatcct gcggcacatt ctgaaatcat tcgacgagat atattctggg aatcatagga    2760
tgatcgggtt agtcaaagtg gttattggac tggctttgtc aggatctcca gtccctgagg    2820
gcctgaactg ggtatacaaa ttgaggagaa cctttatctt ccagtgggct gattccaggg    2880
gccctcttga aggggaggag ttggaatact ctcaggagat cacttgggat gatgatactg    2940
agttcgtcgg attgcaaata agagtgattg caaaacagtg tcatatccag ggcagagtct    3000
ggtgtatcaa catgaacccg agagcatgtc aactatggtc tgacatgtct cttcagacac    3060
aaaggtccga gaggacaaa gattcctctc tgcttctaga ataatcagat tatatcccgc      3120
aaatttatca cttgtttacc tctggaggag agaacatatg ggctcaactc caaccttgg     3180 gagcaatata acaaaaaaca tgttatggtg ccattaaacc gctgcatttc atcaaagtca    3240
agttgattac ctttacattt tgatcctctt ggatgtgaaa aaaactatta acatccctca    3300
aaagaccccg ggaaagatgg ttcctcaggc tctcctgttt gtaccccttc tggtttttcc    3360 attgtgttt gggaaattcc ctatttacac gataccagac aagcttggtc cctggagtcc     3420
gattgacata catcacctca gctgcccaaa caatttggta gtggaggacg aaggatgcac    3480
caacctgtca gggttctcct acatggaact taaagttgga tacatcttag ccataaaagt    3540
gaacgggttc acttgcacag gcgttgtgac ggaggctgaa acctacacta acttcgttgg    3600
ttatgtcaca accacgttca aaagaaagca tttccgccca acaccagatg catgtagagc    3660
cgcgtacaac tggaagatgg ccggtgaccc cagatatgaa gagtctctac acaatccgta    3720
```

```
ccctgactac cgctggcttc gaactgtaaa aaccaccaag gagtctctcg ttatcatatc   3780
tccaagtgtg gcagatttgg acccatatga cagatcccct cactcgaggg tcttccctag   3840
cgggaagtgc tcaggagtag cggtgtcttc tacctactgc tccactaacc acgattacac   3900
catttggatg cccgagaatc cgagactagg gatgtcttgt gacatttta ccaatagtag    3960
agggaagaga gcatccaaag ggagtgagac ttgcggcttt gtagatgaaa gaggcctata   4020
taagtcttta aaaggagcat gcaaactcaa gttatgtgga gttctaggac ttagacttat   4080
ggatggaaca tgggtctcga tgcaaacatc aaatgaaacc aaatggtgcc ctcccgataa   4140
gttggtgaac ctgcacgact ttcgctcaga cgaaattgag caccttgttg tagaggagtt   4200
ggtcaggaag agagaggagt gtctggatgc actagagtcc atcatgacaa ccaagtcagt   4260
gagtttcaga cgtctcagtc atttaagaaa acttgtccct gggtttggaa aagcatatac   4320
catattcaac aagaccttga tggaagccga tgctcactac aagtcagtcg agacttggaa   4380
tgagatcctc ccttcaaaag ggtgtttaag agttggggggg aggtgtcatc ctcatgtgaa   4440
cggggtgttt ttcaatggta taatattagg acctgacggc aatgtcttaa tcccagagat   4500
gcaatcatcc ctcctccagc aacatatgga gttgttggaa tcctcggtta tcccccttgt   4560
gcaccccctg gcagacccgt ctaccgtttt caaggacggt gacgaggctg aggattttgt   4620
tgaagttcac cttcccgatg tgcacaatca ggtctcagga gttgacttgg gtctcccgaa   4680
ctgggggaag tatgtattac tgagtgcagg ggccctgact gccttgatgt tgataaattt   4740
cctgatgaca tgttgtagaa gagtcaatcg atcagaacct acgcaacaca atctcagagg   4800
gacagggagg gaggtgtcag tcactcccca aagcgggaag atcatatctt catgggaatc   4860
acacaagagt gggggtgaga ccagactgta attaattaac gtccttcca cgatccaagt    4920
ccatgaaaaa aactaacacc cctcccgtac gaccatgttc gtgtttctgg tgctgctgcc   4980
tctggtgagc tcccagtgcg tgaacttcac cacaaggacc cagctgcccc ctgcctatac   5040
caattccttc acacggggcg tgtactatcc cgacaaggtg ttccggagca gcgtgctgca   5100
ctccacacag gatctgtttc tgcctttctt ttctaacgtg acctggttcc acgccatcca   5160
cgtgagcgga accaatggca caaagcggtt cgccaatcca gtgctgccct taacgatgg    5220
cgtgtacttc gcctccaccg agaagtctaa catcatcaga ggctggatct ttggcaccac   5280
actgaca cagc aagacacagt ccctgctgat cgtgaacaat gccaccaacg tggtcatcaa   5340
ggtgtgcgag ttccagtttt gtaatgatcc attcctgggc gtgtactatc acaagaacaa   5400
taagtcttgg atggagagcg agtttcgcgt gtattcctct gccaacaatt gcacatttga   5460
gtacgtgtcc cagcccttcc tgatggacct ggagggcaag cagggcaatt tcaagaacct   5520
gagggagttc gtgtttaaga atatcgatgg ctacttcaaa atctactcca agcacacccc   5580
aatcaacctg gtgcgcggcc tgccacaggg cttctctgcc ctggagccac tggtggatct   5640
gcccatcggc atcaacatca cccggtttca gacactgctg gccctgcaca gaagctacct   5700
gacaccaggc gacagctcct ctggatggac cgcaggagca gcagcctact atgtgggcta   5760
tctgcagccc aggaccttcc tgctgaagta caacgagaat ggcaccatca cagacgccgt   5820
ggattgcgcc ctggatcccc tgtctgagac caagtgtaca ctgaagagct taccgtgga    5880
gaagggcatc tatcagacaa gcaatttcag ggtgcagcct accgagtcca tcgtgcgctt   5940
tcccaatatc acaaacctgt gccctttttgg cgaggtgttc aacgcaaccc gcttcgccag   6000
cgtgtacgcc tggaataggaa agcgcatctc caactgcgtg gccgactatt ctgtgctgta   6060
caacagcgcc tccttctcta cctttaagtg ctatggcgtg agccccacaa agctgaatga   6120
```

```
cctgtgcttt accaacgtgt acgccgattc cttcgtgatc aggggcgacg aggtgcgcca   6180
gatcgcacca ggacagacag gcaatatcgc agactacaat tataagctgc ctgacgattt   6240
caccggctgc gtgatcgcct ggaactctaa caatctggat agcaaagtgg gcggcaacta   6300
caattatctg taccggctgt ttagaaagtc taatctgaag ccattcgaga gggacatctc   6360
cacagaaatc taccaggccg gctctacccc ctgcaatggc gtgaagggct ttaactgtta   6420
tttccctctg cagagctacg gcttccagcc aacatatggc gtgggctatc agccctaccg   6480
cgtggtggtg ctgtcttttg agctgctgca cgcacctgca acagtgtgcg gaccaaagaa   6540
gagcaccaat ctggtgaaga caagtgcgt gaacttcaac ttcaacggac tgaccggaac   6600
aggcgtgctg accgagtcca caagaagtt cctgcctttt cagcagttcg gcagggacat   6660
cgcagatacc acagacgccg tgcgcgaccc tcagaccctg gagatcctgg acatcacacc   6720
atgctccttc ggcggcgtgt ctgtgatcac accaggcacc aatacaagca ccaggtggc   6780
cgtgctgtat cagggcgtga attgtaccga ggtgccagtg gcaatccacg cagatcagct   6840
gaccccctaca tggcgggtgt actctaccgg cagcaacgtg ttccagacaa gagccggatg   6900
cctgatcgga gcagagcacg tgaacaatag ctatgagtgc gacatcccta tcggcgccgg   6960
catctgtgcc tcctaccaga cccagacaaa ctccccagaa tcaagcgtga ttcctctggt   7020
ccatccactg gcagatccct ccacagtgtt caaagacgga gatgaggccg aagactttgt   7080
ggaagtccac ctgcctgatg tgcataacca ggtgtctggc gtcgacctgg gactgccaaa   7140
ttggggcaag tacgtgctgc tgagtgctgg agcactgact gccctgatgc tgatcatttt   7200
cctgatgacc tgctgtcggc gcgtgaacag aagtgagccc actcagcaca atctgcgagg   7260
aaccgggaga gaagtgtcag tcacacctca gagcgggaaa atcattagta gttgggaatc   7320
acataaaagc gggggcgaga ccaggctggg atccggctcc ggcgagggca ggggaagtct   7380
actaacatgc ggggacgtgg aggaaaatcc cggccccatg ctcgatcctg gagaggtcta   7440
tgatgaccct attgacccaa tcgagttaga ggctgaaccc agaggaaccc ccattgtccc   7500
caacatcttg aggaactctg actacaatct caactctcct ttgatagaag atcctgctag   7560
actaatgtta gaatggttaa aaacagggaa tagaccttat cggatgactc taacagacaa   7620
ttgctccagg tctttcagag ttttgaaaga ttatttcaag aaggtagatt tgggttctct   7680
caaggtgggc ggaatggctg cacagtcaat gatttctctc tggttatatg gtgcccactc   7740
tgaatccaac aggagccgga gatgtataac agacttggcc catttctatt ccaagtcgtc   7800
ccccatagag aagctgttga atctcacgct aggaaataga gggctgagaa tcccccagc   7860
gggagtgtta agttgccttg agagggttga ttatgataat gcatttggaa ggtatcttgc   7920
caacacgtat tcctcttact tgttcttcca tgtaatcacc ttatcatga acgccctaga   7980
ctgggatgaa gaaaagacca tcctagcatt atggaaagat ttaacctcag tggacatcgg   8040
gaaggacttg gtaaagttca agaccaaat atggggactg ctgatcgtga caaaggactt   8100
tgtttactcc caaagttcca attgtctttt tgacagaaac tacacactta tgctaaaga   8160
tcttttcttg tctcgcttca actccttaat ggtcttgctc ctccccag agccccgata   8220
ctcagatgac ttgatatctc aactatgcca gctgtacatt gctggggatc aagtcttgtc   8280
tatgtgtgga aactccggct atgaagtcat caaaatattg gagccatatg tcgtgaatag   8340
tttagtccag agagcagaaa agtttaggcc tctcattcat tccttgggag actttcctgt   8400
atttataaaa gacaaggtaa gtcaacttga agagacgttc ggtccctgtg caagaaggtt   8460
```

```
ctttagggct ctggatcaat tcgacaacat acatgacttg gtttttgtgt ttggctgtta    8520
caggcattgg gggcacccat atatagatta tcgaaagggt ctgtcaaaac tatatgatca    8580
ggttcacctt aaaaaaatga tagataagtc ctaccaggag tgcttagcaa gcgacctagc    8640
caggaggatc cttagatggg gttttgataa gtactccaag tggtatctgg attcaagatt    8700
cctagcccga gaccacccct tgactcctta tatcaaaacc caaacatggc cacccaaaca    8760
tattgtagac ttggtggggg atacatggca caagctcccg atcacgcaga tctttgagat    8820
tcctgaatca atggatccgt cagaaatatt ggatgacaaa tcacattctt tcaccagaac    8880
gagactagct tcttggctgt cagaaaaccg aggggggcct gttcctagcg aaaaagttat    8940
tatcacggcc ctgtctaagc cgcctgtcaa tccccgagag tttctgaggt ctatagacct    9000
cggaggattg ccagatgaag acttgataat tggcctcaag ccaaaggaac gggaattgaa    9060
gattgaaggt cgattctttg ctctaatgtc atggaatcta agattgtatt ttgtcatcac    9120
tgaaaaactc ttggccaact acatcttgcc acttttttgac gcgctgacta tgacagacaa    9180
cctgaacaag gtgtttaaaa agctgatcga cagggtcacc gggcaaggggc ttttggacta    9240 ttcaagggtc acatatgcat ttcacctgga ctatgaaaag tggaacaacc atcaaagatt    9300
agagtcaaca gaggatgtat tttctgtcct agatcaagtg tttggattga agagagtgtt    9360
ttctagaaca cacgagtttt ttcaaaaggc ctggatctat tattcagaca gatcagacct    9420
catcgggtta cggaggatc aaatatactg cttagatgcg tccaacggcc caacctgttg    9480
gaatggccag gatggcgggc tagaaggctt acggcagaag ggctggagtc tagtcagctt    9540
attgatgata gatagagaat ctcaaatcag gaacacaaga accaaaatac tagctcaagg    9600
agacaaccag gttttatgtc cgacatacat gttgtcgcca gggctatctc aagaggggct    9660
cctctatgaa ttggagagaa tatcaaggaa tgcactttcg atatacagag ccgtcgagga    9720
aggggcatct aagctagggc tgatcatcaa gaaagaagag accatgtgta gttatgactt    9780
cctcatctat ggaaaaaccc cttttgtttag aggtaaacata ttggtgcctg agtccaaaag    9840
atgggccaga gtctcttgcg tctctaatga ccaaatagtc aacctcgcca atataatgtc    9900
gacagtgtcc accaatgcgc taacagtggc acaacactct caatctttga tcaaaccgat    9960
gagggatttt ctgctcatgt cagtacaggc agtctttcac tacctgctat ttagcccaat    10020
cttaaaggga agagtttaca agattctgag cgctgaaggg gagagctttc tcctagccat    10080
gtcaaggata atctatctag atccttcttt gggagggata tctggaatgt ccctcggaag    10140
attccatata cgacagttct cagacccgt ctctgaaggg ttatccttct ggagagagat    10200
ctggttaagc tcccaagagt cctggattca cgcgttgtgt caagaggctg aaacccaga    10260 tcttggagag agaacactcg agagcttcac tcgccttcta aagatccga ccaccttaaa    10320 tatcagagga ggggccagtc ctaccattct actcaaggat gcaatcagaa aggctttata    10380
tgacgaggtg gacaaggtgg aaaattcaga gtttcgagag gcaatcctgt tgtccaagac    10440
ccatagagat aatttttatac tcttcttaat atctgttgag cctctgtttc ctcgatttct    10500
cagtgagcta ttcagttcgt ctttttttggg aatccccgag tcaatcattg gattgataca    10560
aaactcccga acgataagaa ggcagtttag aaagagtctc tcaaaaactt tagaagaatc    10620
cttctacaac tcagagatcc acgggattag tcggatgacc cagacacctc agagggttgg    10680
gggggtgtgg ccttgctctt cagagagggc agatctactt agggagatct cttggggaag    10740
aaaagtggta ggcacgacag ttcctcaccc ttctgagatg ttgggattac ttcccaagtc    10800
ctctatttct tgcacttgtg gagcaacagg aggaggcaat cctagagttt ctgtatcagt    10860
```

```
actcccgtcc tttgatcagt cattttttc acgaggcccc ctaaagggat acttgggctc   10920
gtccacctct atgtcgaccc agctattcca tgcatgggaa aaagtcacta atgttcatgt   10980
ggtgaagaga gctctatcgt taaaagaatc tataaactgg ttcattacta gagattccaa   11040
cttggctcaa gctctaatta ggaacattat gtctctgaca ggccctgatt tccctctaga   11100
ggaggcccct gtcttcaaaa ggacggggtc agccttgcat aggttcaagt ctgccagata   11160
cagcgaagga gggtattctt ctgtctgccc gaacctcctc tctcatattt ctgttagtac   11220
agacaccatg tctgatttga cccaagacgg gaagaactac gatttcatgt tccagccatt   11280
gatgctttat gcacagacat ggacatcaga gctggtacag agagacacaa ggctaagaga   11340
ctctacgttt cattggcacc tccgatgcaa caggtgtgtg agacccattg acgacgtgac   11400
cctggagacc tctcagatct tcgagttttcc ggatgtgtcg aaaagaatat ccagaatggt   11460
ttctggggct gtgcctcact tccagaggct tcccgatatc cgtctgagac caggagattt   11520
tgaatctcta agcggtagag aaaagtctca ccatatcgga tcagctcagg ggctcttata   11580
ctcaatctta gtggcaattc acgactcagg atacaatgat ggaaccatct tccctgtcaa   11640
catatacggc aaggtttccc ctagagacta tttgagaggg ctcgcaaggg gagtattgat   11700
aggatcctcg atttgcttct tgacaagaat gacaaatatc aatattaata gacctcttga   11760
attggtctca ggggtaatct catatattct cctgaggcta gataaccatc cctccttgta   11820
cataatgctc agagaaccgt tcttagagg agagatattt tctatccctc agaaaatccc   11880
cgccgcttat ccaaccacta tgaaagaagg caacagatca atcttgtgtt atctccaaca   11940
tgtgctacgc tatgagcgag agataatcac ggcgtctcca gagaatgact ggctatggat   12000
cttttcagac tttagaagtg ccaaaatgac gtacctatcc ctcattactt accagtctca   12060
tcttctactc cagagggttg agagaaacct atctaagagt atgagagata acctgcgaca   12120
attgagttct ttgatgaggc aggtgctggg cgggcacgga gaagatacct tagagtcaga   12180
cgacaacatt caacgactgc taaaagactc tttacgaagg acaagatggg tggatcaaga   12240
ggtgcgccat gcagctagaa ccatgactgg agattacagc cccaacaaga aggtgtcccg   12300
taaggtagga tgttcagaat gggtctgctc tgctcaacag gttgcagtct ctacctcagc   12360
aaacccggcc cctgtctcgg agcttgacat aagggccctc tctaagaggt tccagaaccc   12420
tttgatctcg ggcttgagag tggttcagtg ggcaaccggt gctcattata agcttaagcc   12480
tattctagat gatctcaatg tttttcccatc tctctgcctt gtagttgggg acgggtcagg   12540
ggggatatca agggcagtcc tcaacatgtt tccagatgcc aagcttgtgt tcaacagtct   12600
tttagaggtg aatgacctga tggcttccgg aacacatcca ctgcctcctt cagcaatcat   12660 gagggggagga aatgatatcg tctccagagt gatagatctt gactcaatct gggaaaaacc   12720
gtccgacttg agaaacttgg caacctggaa atacttccag tcagtccaaa agcaggtcaa   12780
catgtcctat gacctcatta tttgcgatgc agaagttact gacattgcat ctatcaaccg   12840
gatcaccctg ttaatgtccg attttgcatt gtctatagat ggaccactct atttggtctt   12900
caaaacttat gggactatgc tagtaaatcc aaactacaag gctattcaac acctgtcaag   12960
agcgttcccc tcggtcacag ggtttatcac ccaagtaact tcgtcttttt catctgagct   13020
ctacctccga ttctccaaac gagggaagtt tttcagagat gctgagtact tgacctcttc   13080
cacccttcga gaaatgagcc ttgtgttatt caattgtagc agccccaaga gtgagatgca   13140
gagagctcgt tccttgaact atcaggatct tgtgagagga tttcctgaag aaatcatatc   13200
```

```
aaatccttac aatgagatga tcataactct gattgacagt gatgtagaat cttttctagt    13260
ccacaagatg gttgatgatc ttgagttaca gaggggaact ctgtctaaag tggctatcat    13320
tatagccatc atgatagttt tctccaacag agtcttcaac gtttccaaac ccctaactga    13380
cccctcgttc tatccaccgt ctgatcccaa atcctgagg  cacttcaaca tatgttgcag    13440
tactatgatg tatctatcta ctgctttagg tgacgtccct agcttcgcaa gacttcacga    13500
cctgtataac agacctataa cttattactt cagaaagcaa gtcattcgag gaacgtttta    13560
tctatcttgg agttggtcca acgacacctc agtgttcaaa agggtagcct gtaattctag    13620
cctgagtctg tcatctcact ggatcaggtt gatttacaag atagtgaaga ctaccagact    13680
cgttggcagc atcaaggatc tatccagaga agtggaaaga caccttcata ggtacaacag    13740
gtggatcacc ctagaggata tcagatctag atcatcccta ctagactaca gttgcctgtg    13800
aaccggatac tcctggaagc ctgcccatgc taagactctt gtgtgatgta tcttgaaaaa    13860
aacaagatcc taaatctgaa cctttggttg tttgattgtt tttctcattt ttgttgttta    13920
tttgttaagc gt                                                        13932
```

<210> SEQ ID NO 18
<211> LENGTH: 13475
<212> TYPE: DNA
<213> ORGANISM: Artificial Sequence
<220> FEATURE:
<223> OTHER INFORMATION: VSV vector: Convac V1 China

<400> SEQUENCE: 18

```
acgaagacaa acaaaccatt attatcatta aaaggctcag gagaaacttt aacagtaatc      60
aaaatgtctg ttacagtcaa gagaatcatt gacaacacag tcatagttcc aaaacttcct     120
gcaaatgagg atccagtgga atcccggca  gattacttca aaaatcaaa  ggagattcct     180 ctttacatca atactacaaa aagtttgtca gatctaagag gatatgtcta ccaaggcctc     240
aaatccggaa atgtatcaat catacatgtc aacagctact gtatggagc  attaaaggac     300 atccggggta agttggataa agattggtca agtttcggaa taaacatcgg gaaagcaggg     360
gatacaatcg gaatatttga ccttgtatcc ttgaaagccc tggacggcgt acttccagat     420
ggagtatcgg atgcttccag aaccagcgca gatgacaaat ggttgccttt gtatctactt     480
ggcttataca gagtgggcag aacacaaatg cctgaataca gaaaaaagct catggatggg     540
ctgacaaatc aatgcaaaat gatcaatgaa cagtttgaac ctcttgtgcc agaaggtcgt     600 gacattttg  atgtgtgggg aaatgacagt aattacacaa aaattgtcgc tgcagtggac     660
atgttcttcc acatgttcaa aaaacatgaa tgtgcctcgt tcagatacgg aactattgtt     720
tccagattca aagattgtgc tgcattggca acatttggac acctctgcaa ataaccgga     780 atgtctacag aagatgtaac gacctggatc ttgaaccgag aagttgcaga tgaaatggtc     840
caaatgatgc ttccaggcca agaaattgac aaggccgatt catacatgcc ttatttgatc     900
gactttggat tgtcttctaa gtctccatat tcttccgtca aaaaccctgc cttccacttc     960
tgggggcaat tgacagctct tctgctcaga tccaccagag caaggaatgc ccgacagcct    1020
gatgacattg agtatacatc tcttactaca gcaggtttgt tgtacgctta tgcagtagga    1080
tcctctgccg acttggcaca acagttttgt gttggagata caaatacac  tccagatgat    1140 agtaccggag gattgacgac taatgcaccg ccacaaggca gagatgtggt cgaatggctc    1200
ggatggtttg aagatcaaaa cagaaaaccg actcctgata tgatgcagta tgcgaaaaga    1260
gcagtcatgt cactgcaagg cctaagagag aagacaattg gcaagtatgc taagtcagaa    1320
```

-continued

```
tttgacaaat gaccctataa ttctcagatc acctattata tattatgcta catatgaaaa    1380
aaactaacag atatcatgga taatctcaca aaagttcgtg agtatctcaa gtcctattct    1440
cgtctggatc aggcggtagg agagatagat gagatcgaag cacaacgagc tgaaaagtcc    1500
aattatgagt tgttccaaga ggatggagtg gaagagcata ctaagccctc ttattttcag    1560
gcagcagatg attctgacac agaatctgaa ccagaaattg aagacaatca aggtttgtat    1620
gcaccagatc cagaagctga gcaagttgaa ggctttatac aggggccttt agatgactat    1680
gcagatgagg aagtggatgt tgtatttact tcggactgga aacagcctga gcttgaatct    1740
gacgagcatg gaaagacctt acggttgaca tcgccagagg gtttaagtgg agagcagaaa    1800
tcccagtggc tttcgacgat taaagcagtc gtgcaaagtg ccaaatactg gaatctggca    1860
gagtgcacat ttgaagcatc gggagaaggg gtcattatga aggagcgcca gataactccg    1920
gatgtatata aggtcactcc agtgatgaac acacatccgt cccaatcaga agcagtatca    1980
gatgtttggt ctctctcaaa gacatccatg actttccaac caagaaagc aagtcttcag    2040 cctctcacca tatccttgga tgaattgttc tcatctagag gagagttcat ctctgtcgga    2100
ggtgacggac gaatgtctca taaagaggcc atcctgctcg gcctgagata caaaaagttg    2160
tacaatcagg cgagagtcaa atattctctg tagactatga aaaaagtaa cagatatcac    2220 gatctaagtg ttatcccaat ccattcatca tgagttcctt aaagaagatt ctcggtctga    2280
aggggaaagg taagaaatct aagaaattag ggatcgcacc accccttat gaagaggaca    2340 ctagcatgga gtatgctccg agcgctccaa ttgacaaatc ctattttgga gttgacgaga    2400
tggacaccta tgatccgaat caattaagat atgagaaatt cttctttaca gtgaaaatga    2460
cggttagatc taatcgtccg ttcagaacat actcagatgt ggcagccgct gtatcccatt    2520
gggatcacat gtacatcgga atggcaggga acgtcccctt ctacaaaatc ttggcttttt    2580
tgggttcttc taatctaaag gccactccag cggtattggc agatcaaggt caaccagagt    2640
atcacactca ctgcgaaggc agggcttatt tgccacatag gatggggaag acccctccca    2700
tgctcaatgt accagagcac ttcagaagac cattcaatat aggtctttac aagggaacga    2760
ttgagctcac aatgaccatc tacgatgatg agtcactgga agcagctcct atgatctggg    2820
atcatttcaa ttcttccaaa ttttctgatt tcagagagaa ggccttaatg tttggcctga    2880
ttgtcgagaa aaaggcatct ggagcgtggg tcctggattc tatcagccac ttcaaatgag    2940
ctagtctaac ttctagcttc tgaacaatcc ccggtttact cagtctctcc taattccagc    3000
ctctcgaaca actaatatcc tgtcttttct atccctatga aaaaactaa cagagatcga    3060 tctgtttacg cgtcactatg aagtgccttt tgtacttagc cttttattc attggggtga    3120 attgcaagtt caccatagtt tttccacaca accaaaaagg aaactggaaa atgttccttt    3180
ctaattacca ttattgcccg tcaagctcag atttaaattg gcataatgac ttaataggca    3240
cagccataca agtcaaaatg cccaagagtc acaaggctat tcaagcagac ggttggatgt    3300
gtcatgcttc caaatgggtc actacttgtg atttccgctg gtatggaccg aagtatataa    3360
cacagtccat ccgatccttc actccatctg tagaacaatg caaggaaagc attgaacaaa    3420
cgaaacaagg aacttggctg aatccaggct tccctcctca aagttgtgga tatgcaactg    3480
tgacggatgc cgaagcagtg attgtccagg tgactcctca ccatgtgctg gttgatgaat    3540
acacaggaga atgggttgat tcacagttca tcaacgaaaa atgcagcaat tacatatgcc    3600
ccactgtcca taactctaca acctggcatt ctgactataa ggtcaaaggg ctatgtgatt    3660
```

```
ctaacctcat ttccatggac atcaccttct tctcagagga cggagagcta tcatccctgg    3720
gaaaggaggg cacagggttc agaagtaact actttgctta tgaaactgga ggcaaggcct    3780
gcaaaatgca atactgcaag cattggggag tcagactccc atcaggtgtc tggttcgaga    3840
tggctgataa ggatctcttt gctgcagcca gattccctga atgcccagaa gggtcaagta    3900
tctctgctcc atctcagacc tcagtggatg taagtctaat tcaggacgtt gagaggatct    3960
tggattattc cctctgccaa gaaacctgga gcaaaatcag agcgggtctt ccaatctctc    4020
cagtggatct cagctatctt gctcctaaaa acccaggaac cggtcctgct ttcaccataa    4080
tcaatggtac cctaaaatac tttgagacca gatacatcag agtcgatatt gctgctccaa    4140
tcctctcaag aatggtcgga atgatcagtg aactaccac agaaagggaa ctgtgggatg      4200
actgggcacc atatgaagac gtggaaattg acccaatgg agttctgagg accagttcag      4260
gatataagtt tcctttatac atgattggac atggtatgtt ggactccgat cttcatctta    4320
gctcaaaggc tcaggtgttc gaacatcctc acattcaaga cgctgcttcg caacttcctg    4380
atgatgagag tttatttttt ggtgatactg ggctatccaa aaatccaatc gagcttgtag    4440
aaggttggtt cagtagttgg aaaagctcta ttgcctcttt tttctttatc atagggttaa    4500
tcattggact attcttggtt ctccgagttg gtatccatct ttgcattaaa ttaaagcaca    4560
ccaagaaaag acagatttat acagacatag atgaaccg acttggaaag taactcaaat      4620
cctgctaggt atgaaaaaaa ctaacagata tcacgctcga gcgtacgcca ccatgttcgt    4680
gtttctggtg ctgctgcctc tggtgagctc ccagtgcgtg aacctgacca caaggaccca    4740 gctgcccct gcctatacca attccttcac acggggcgtg tactatcccg acaaggtgtt      4800
ccggagcagc gtgctgcact ccacacagga tctgtttctg cctttctttt ctaacgtgac    4860
ctggttccac gccatccacg tgagcggcac caatggcaca aagcggttcg acaatccagt    4920
gctgcccttt aacgatggcg tgtacttcgc ctccaccgag aagtctaaca tcatcagagg    4980 ctggatctt ggcaccacac tggacagcaa gacacagtcc ctgctgatcg tgaacaatgc      5040
caccaacgtg gtcatcaagg tgtgcgagtt ccagtttgt aatgatccat tcctgggcgt      5100
gtactatcac aagaacaata agtcttggat ggagagcgag tttcgcgtgt attcctctgc    5160
caacaattgc acatttgagt acgtgtccca gcccttcctg atggacctgg agggcaagca    5220
gggcaatttc aagaacctga gggagttcgt gtttaagaat atcgatggct acttcaaaat    5280
ctactccaag cacaccccaa tcaacctggt gcgcgacctg ccacagggct ctctgccct      5340 ggagccactg gtggatctgc catcggcat caacatcacc cggtttcaga cactgctggc      5400
cctgcacaga agctacctga caccaggcga cagctcctct ggatggaccg caggagcagc    5460
agcctactat gtgggctatc tgcagcccag gaccttcctg ctgaagtaca cgagaatgg      5520 caccatcaca gacgccgtgg attgcgccct ggatccctg tctgagacca agtgtacact      5580
gaagagcttt accgtggaga agggcatcta tcagacaagc aatttcaggg tgcagcctac    5640
cgagtccatc gtgcgctttc caatatcac aaacctgtgc ccttttggcg aggtgttcaa      5700
cgcaacccgc ttcgccagcg tgtacgcctg gaataggaag cgcatctcca actgcgtggc    5760
cgactattct gtgctgtaca acagcgcctc cttctctacc tttaagtgct atggcgtgag    5820
ccccacaaag ctgaatgacc tgtgctttac caacgtgtac gccgattcct tcgtgatcag    5880
gggcgacgag gtgcgccaga tcgcaccagg acagacaggc aagatcgcag actacaatta    5940
taagctgcct gacgatttca ccggctgcgt gatcgcctgg aactctaaca atctggatag    6000
caaagtgggc ggcaactaca attatctgta ccggctgttt agaaagtcta atctgaagcc    6060
```

```
attcgagagg gacatctcca cagaaatcta ccaggccggc tctaccccct gcaatggcgt    6120
ggagggcttt aactgttatt tccctctgca gagctacggc ttccagccaa caaacggcgt    6180
gggctatcag ccctaccgcg tggtggtgct gtcttttgag ctgctgcacg cacctgcaac    6240
agtgtgcgga ccaaagaaga gcaccaatct ggtgaagaac aagtgcgtga acttcaactt    6300
caacggactg accggaacag gcgtgctgac cgagtccaac aagaagttcc tgccttttca    6360
gcagttcggc agggacatcg cagataccac agacgccgtg cgcgaccctc agaccctgga    6420
gatcctggac atcacaccat gctccttcgg cggcgtgtct gtgatcacac aggcaccaa    6480 tacaagcaac caggtggccg tgctgtatca ggacgtgaat tgtaccgagg tgccagtggc    6540
aatccacgca gatcagctga cccctacatg gcgggtgtac tctaccggca gcaacgtgtt    6600
ccagacaaga gccggatgcc tgatcggagc agagcacgtg aacaatagct atgagtgcga    6660
catccctatc ggcgccggca tctgtgcctc ctaccagacc cagacaaact ccccaaggtc    6720
tgtgggcgat acaggcctgt ccaagaatcc aatcgagctg gtagagggct ggttcagcag    6780
ttggaaaagc tccatcgcct ccttttttctt tatcatcggc ctgatcatcg gactgttcct    6840
ggtgctccgc gtgggtatcc acctgtgcat caagctgaag cacaccaaga aaagacagat    6900
ttatacagac atcgagatga accgcctggg aaagtgagct agccagattc ttcatgtttg    6960
gaccaaatca acttgtgata ccatgctcaa agaggcctca attatatttg agttttttaat    7020 ttttatgaaa aaaactaaca gcaatcatgg aagtccacga ttttgagacc gacgagttca    7080
atgatttcaa tgaagatgac tatgccacaa gagaattcct gaatcccgat gagcgcatga    7140
cgtacttgaa tcatgctgat tacaatttga attctcctct aattagtgat gatattgaca    7200
atttgatcag gaaattcaat tctcttccga ttccctcgat gtgggatagt aagaactggg    7260
atggagttct tgagatgtta acatcatgtc aagccaatcc catctcaaca tctcagatgc    7320
ataaatggat gggaagttgg ttaatgtctg ataatcatga tgccagtcaa gggtatagtt    7380
ttttacatga agtggacaaa gaggcagaaa taacatttga cgtggtggag accttcatcc    7440
gcggctgggg caacaaacca attgaataca tcaaaaagga agatggact gactcattca    7500 aaattctcgc ttatttgtgt caaaagtttt tggacttaca caagttgaca ttaatcttaa    7560
atgctgtctc tgaggtggaa ttgctcaact ggcgaggac tttcaaaggc aaagtcagaa    7620
gaagttctca tggaacgaac atatgcagga ttagggttcc cagcttgggt cctactttta    7680
tttcagaagg atgggcttac ttcaagaaac ttgatattct aatggaccga aactttctgt    7740
taatggtcaa agatgtgatt ataggagga tgcaaacggt gctatccatg gtatgtagaa    7800
tagacaacct gttctcagag caagacatct tctcccttct aaatatctac agaattggag    7860
ataaaattgt ggagaggcag ggaaattttt cttatgactt gattaaaatg gtggaaccga    7920
tatgcaactt gaagctgatg aaattagcaa gagaatcaag gcctttagtc ccacaattcc    7980
ctcattttga aaatcatatc aagacttctg ttgatgaagg ggcaaaaatt gaccgaggta    8040
taagattcct ccatgatcag ataatgagtg tgaaaacagt ggatctcaca ctggtgattt    8100
atggatcgtt cagacattgg ggtcatcctt ttatagatta ttacactgga ctagaaaaat    8160
tacattccca agtaaccatg aagaaagata ttgatgtgtc atatgcaaaa gcacttgcaa    8220
gtgatttagc tcggattgtt ctatttcaac agttcaatga tcataaaaag tggttcgtga    8280
atggagactt gctccctcat gatcatccct ttaaagtca tgttaaagaa aatacatggc    8340
ccacagctgc tcaagttcaa gattttggag ataaatggca tgaacttccg ctgattaaat    8400
```

```
gttttgaaat acccgactta ctagacccat cgataatata ctctgacaaa agtcattcaa   8460
tgaataggtc agaggtgttg aaacatgtcc gaatgaatcc gaacactcct atccctagta   8520
aaaaggtgtt gcagactatg ttggacacaa aggctaccaa ttggaaagaa tttcttaaag   8580
agattgatga aagggctta gatgatgatg atctaattat tggtcttaaa ggaaaggaga    8640
gggaactgaa gttggcaggt agattttcct ccctaatgtc ttggaaattg cgagaatact   8700
ttgtaattac cgaatatttg ataaagactc atttcgtccc tatgtttaaa ggcctgacaa   8760
tggcggacga tctaactgca gtcattaaaa agatgttaga ttcctcatcc ggccaaggat   8820
tgaagtcata tgaggcaatt tgcatagcca atcacattga ttacgaaaaa tggaataacc   8880
accaaaggaa gttatcaaac ggcccagtgt tccgagttat gggccagttc ttaggttatc   8940
catccttaat cgagagaact catgaatttt tgagaaaag tcttatatac tacaatggaa    9000
gaccagactt gatgcgtgtt cacaacaaca cactgatcaa ttcaacctcc caacgagttt   9060
gttggcaagg acaagagggt ggactggaag gtctacggca aaaggatgg actatcctca    9120
atctactggt tattcaaaga gaggctaaaa tcagaaacac tgctgtcaaa gtcttggcac   9180
aaggtgataa tcaagttatt tgcacacagt ataaaacgaa gaaatcgaga acgttgtag    9240
aattacaggg tgctctcaat caaatggttt ctaataatga gaaaattatg actgcaatca   9300
aaatagggac agggaagtta ggacttttga taaatgacga tgagactatg caatctgcag   9360
attacttgaa ttatgaaaaa ataccgattt tccgtggagt gattagaggg ttagagacca   9420
agagatggtc acgagtgact tgtgtcacca atgaccaaat acccacttgt gctaatataa   9480
tgagctcagt ttccacaaat gctctcaccg tagctcattt tgctgagaac ccaatcaatg   9540
ccatgataca gtacaattat tttgggacat tgctagact cttgttgatg atgcatgatc    9600
ctgctcttcg tcaatcattg tatgaagttc aagataagat accgggcttg cacagttcta   9660
ctttcaaata cgccatgttg tatttggacc cttccattgg aggagtgtcg ggcatgtctt   9720
tgtccaggtt tttgattaga gccttcccag atcccgtaac agaaagtctc tcattctgga   9780
gattcatcca tgtacatgct cgaagtgagc atctgaagga gatgagtgca gtatttggaa   9840
acccccgagat agccaagttt cgaataactc acatagacaa gctagtagaa gatccaacct   9900
ctctgaacat cgctatggga atgagtccag cgaacttgtt aaagactgag gttaaaaaat   9960
gcttaatcga atcaagacaa accatcagga accaggtgat taaggatgca accatatatt   10020
tgtatcatga agaggatcgg ctcagaagtt tcttatggtc aataaatcct ctgttcccta   10080
gatttttaag tgaattcaaa tcaggcactt ttttgggagt cgcagacggg ctcatcagtc   10140
tatttcaaaa ttctcgtact attcggaact cctttaagaa aaagtatcat agggaattgg   10200
atgatttgat tgtgaggagt gaggtatcct ctttgacaca tttagggaaa cttcatttga   10260
gaaggggatc atgtaaaatg tggacatgtt cagctactca tgctgacaca ttaagataca   10320
aatcctgggg ccgtacagtt attgggacaa ctgtacccca tccattagaa atgtgggtc    10380
cacaacatcg aaaagagact ccttgtgcac catgtaacac atcagggttc aattatgttt   10440
ctgtgcattg tccagacggg atccatgacg tctttagttc acggggacca ttgcctgctt   10500
atctagggtc taaaacatct gaatctacat ctattttgca gccttgggaa agggaaagca   10560
aagtcccact gattaaaaga gctacacgtc ttagagatgc tatctcttgg tttgttgaac   10620
ccgactctaa actagcaatg actatacttt ctaacatcca ctctttaaca ggcgaagaat   10680
ggaccaaaag gcagcatggg ttcaaaagaa cagggtctgc ccttcatagg ttttcgacat   10740
ctcggatgag ccatggtggg ttcgcatctc agagcactgc agcattgacc aggttgatgg   10800
```

```
caactacaga caccatgagg gatctgggag atcagaattt cgactttta ttccaagcaa    10860 cgttgctcta tgctcaaatt accaccactg ttgcaagaga cggatggatc accagttgta    10920
cagatcatta tcatattgcc tgtaagtcct gtttgagacc catagaagag atcaccctgg    10980
actcaagtat ggactacacg cccccagatg tatcccatgt gctgaagaca tggaggaatg    11040
gggaaggttc gtggggacaa gagataaaac agatctatcc tttagaaggg aattggaaga    11100
atttagcacc tgctgagcaa tcctatcaag tcggcagatg tataggtttt ctatatggag    11160
acttggcgta tagaaaatct actcatgccg aggacagttc tctatttcct ctatctatac    11220
aaggtcgtat tagaggtcga ggtttcttaa aagggttgct agacggatta atgagagcaa    11280
gttgctgcca agtaatacac cggagaagtc tggctcattt gaagaggccg gccaacgcag    11340
tgtacggagg tttgatttac ttgattgata aattgagtgt atcacctcca ttcctttctc    11400
ttactagatc aggacctatt agagacgaat tagaaacgat tccccacaag atcccaacct    11460
cctatccgac aagcaaccgt gatatggggg tgattgtcag aaattacttc aaataccaat    11520
gccgtctaat tgaaaaggga aaatacagat cacattattc acaattatgg ttattctcag    11580
atgtcttatc catagacttc attggaccat tctctatttc caccaccctc ttgcaaatcc    11640
tatacaagcc attttttatct gggaaagata agaatgagtt gagagagctg gcaaatcttt    11700
cttcattgct aagatcagga gaggggtggg aagacataca tgtgaaattc ttcaccaagg    11760
acatattatt gtgtccagag gaaatcagac atgcttgcaa gttcgggatt gctaaggata    11820
ataataaaga catgagctat ccccctgg gaagggaatc cagagggaca attacaacaa    11880
tccctgttta ttatacgacc accccttacc caaagatgct agagatgcct ccaagaatcc    11940
aaaatcccct gctgtccgga atcaggttgg gccaattacc aactggcgct cattataaaa    12000
ttcggagtat attacatgga atgggaatcc attacaggga cttcttgagt tgtggagacg    12060
gctccggagg gatgactgct gcattactac gagaaaatgt gcatagcaga ggaatattca    12120
atagtctgtt agaattatca gggtcagtca tgcgaggcgc ctctcctgag ccccccagtg    12180
ccctagaaac tttaggagga gataaatcga gatgtgtaaa tggtgaaaca tgttgggaat    12240
atccatctga cttatgtgac ccaaggactt gggactattt cctccgactc aaagcaggct    12300
tggggcttca aattgattta attgtaatgg atatggaagt tcgggattct tctactagcc    12360
tgaaaattga gacgaatgtt agaaattatg tgcaccggat tttggatgag caggagttt    12420 taatctacaa gacttatgga acatatattt gtgagagcga aaagaatgca gtaacaatcc    12480
ttggtcccat gttcaagacg gtcgacttag ttcaaacaga atttagtagt tctcaaacgt    12540
ctgaagtata tatggtatgt aaaggtttga agaaattaat cgatgaaccc aatcccgatt    12600
ggtcttccat caatgaatcc tggaaaaacc tgtacgcatt ccagtcatca gaacaggaat    12660
ttgccagagc aaagaaggtt agtacatact ttaccttgac aggtattccc tcccaattca    12720
ttcctgatcc tttttgtaaac attgagacta tgctacaaat attcggagta cccacgggtg    12780
tgtctcatgc ggctgcctta aaatcatctg atagacctgc agatttattg accattagcc    12840
ttttttatat ggcgattata tcgtattata acatcaatca tatcagagta ggaccgatac    12900
ctccgaaccc cccatcagat ggaattgcac aaaatgtggg gatcgctata actggtataa    12960
gcttttggct gagtttgatg gagaaagaca ttccactata tcaacagtgt ttagcagtta    13020
tccagcaatc attcccgatt aggtggggagg ctgtttcagt aaaaggagga tacaagcaga    13080
agtggagtac tagaggtgat gggctcccaa aagatacccg aacttcagac tccttggccc    13140
```

-continued

```
caatcgggaa ctggatcaga tctctggaat tggtccgaaa ccaagttcgt ctaaatccat    13200
tcaatgagat cttgttcaat cagctatgtc gtacagtgga taatcatttg aaatggtcaa    13260
atttgcgaag aaacacagga atgattgaat ggatcaatag acgaatttca aaagaagacc    13320
ggtctatact gatgttgaag agtgacctac acgaggaaaa ctcttggaga gattaaaaaa    13380
tcatgaggag actccaaact ttaagtatga aaaaacttt gatccttaag accctcttgt     13440
ggtttttatt ttttatctgg ttttgtggtc ttcgt                               13475
```

<210> SEQ ID NO 19
<211> LENGTH: 13469
<212> TYPE: DNA
<213> ORGANISM: Artificial Sequence
<220> FEATURE:
<223> OTHER INFORMATION: VSV vector: Convac V1 South Africa

<400> SEQUENCE: 19

```
acgaagacaa acaaaccatt attatcatta aaaggctcag agaaactttt aacagtaatc      60
aaaatgtctg ttacagtcaa gagaatcatt gacaacacag tcatagttcc aaaacttcct    120
gcaaatgagg atccagtgga atacccggca gattacttca gaaaatcaaa ggagattcct    180
ctttacatca atactacaaa aagtttgtca gatctaagag gatatgtcta ccaaggcctc    240
aaatccggaa atgtatcaat catacatgtc aacagctact tgtatggagc attaaaggac    300
atccggggta agttggataa agattggtca agtttcggaa taaacatcgg aaagcaggg    360 gatacaatcg gaatatttga ccttgtatcc ttgaaagccc tggacggcgt acttccagat    420
ggagtatcgg atgcttccag aaccagcgca gatgacaaat ggttgccttt gtatctactt    480
ggcttataca gagtgggcag aacacaaatg cctgaataca gaaaaagct catggatggg    540 ctgacaaatc aatgcaaaat gatcaatgaa cagtttgaac ctcttgtgcc agaaggtcgt    600 gacattttg atgtgtgggg aaatgacagt aattacacaa aaattgtcgc tgcagtggac    660
atgttcttcc acatgttcaa aaaacatgaa tgtgcctcgt tcagatacgg aactattgtt    720
tccagattca agattgtgc tgcattggca acatttggac acctctgcaa ataaccgga     780 atgtctacag aagatgtaac gacctggatc ttgaaccgag aagttgcaga tgaaatggtc    840
caaatgatgc ttccaggcca gaaaattgac aaggccgatt catacatgcc ttatttgatc    900
gactttggat tgtcttctaa gtctccatat tcttccgtca aaaaccctgc cttccacttc    960
tgggggcaat tgacagctct tctgctcaga tccaccagag caaggaatgc ccgacagcct   1020
gatgacattg agtatacatc tcttactaca gcaggtttgt tgtacgctta tgcagtagga   1080
tcctctgccg acttggcaca acagttttgt gttggagata caaatacac tccagatgat   1140 agtaccggag gattgacgac taatgcaccg ccacaaggca gagatgtggt cgaatggctc   1200
ggatggtttg aagatcaaaa cagaaaaccg actcctgata tgatgcagta tgcgaaaaga   1260
gcagtcatgt cactgcaagg cctaagagag aagacaattg gcaagtatgc taagtcagaa   1320
tttgacaaat gacctataa ttctcagatc acctattata tattatgcta catatgaaaa    1380
aaactaacag atatcatgga taatctcaca aaagttcgtg agtatctcaa gtcctattct    1440
cgtctggatc aggcggtagg agagatagat gagatcgaag cacaacgagc tgaaaagtcc    1500
aattatgagt tgttccaaga ggatggagtg gaagagcata ctaagccctc ttatttcag   1560 gcagcagatg attctgacac agaatctgaa ccagaaattg aagacaatca aggttttgtat   1620 gcaccagatc cagaagctga gcaagttgaa ggctttatac agggccttt agatgactat    1680 gcagatgagg aagtggatgt tgtatttact tcggactgga aacagcctga gcttgaatct    1740
```

```
gacgagcatg gaaagacctt acggttgaca tcgccagagg gtttaagtgg agagcagaaa    1800
tcccagtggc tttcgacgat taaagcagtc gtgcaaagtg ccaaatactg gaatctggca    1860
gagtgcacat ttgaagcatc gggagaaggg gtcattatga aggagcgcca gataactccg    1920
gatgtatata aggtcactcc agtgatgaac acacatccgt cccaatcaga agcagtatca    1980
gatgtttggt ctctctcaaa gacatccatg actttccaac ccaagaaagc aagtcttcag    2040
cctctcacca tatccttgga tgaattgttc tcatctagag gagagttcat ctctgtcgga    2100
ggtgacggac gaatgtctca taaagaggcc atcctgctcg gcctgagata caaaaagttg    2160
tacaatcagg cgagagtcaa atattctctg tagactatga aaaaagtaa cagatatcac     2220
gatctaagtg ttatcccaat ccattcatca tgagttcctt aaagaagatt ctcggtctga    2280
agggaaagg taagaaatct aagaaattag ggatcgcacc accccttat gaagaggaca      2340
ctagcatgga gtatgctccg agcgctccaa ttgacaaatc ctattttgga gttgacgaga    2400
tggacaccta tgatccgaat caattaagat atgagaaatt cttctttaca gtgaaaatga    2460
cggttagatc taatcgtccg ttcagaacat actcagatgt ggcagccgct gtatcccatt    2520
gggatcacat gtacatcgga atggcaggga acgtcccctt ctacaaaatc ttggcttttt    2580
tgggttcttc taatctaaag gccactccag cggtattggc agatcaaggt caaccagagt    2640
atcacactca ctgcgaaggc agggcttatt tgccacatag gatggggaag acccctccca    2700
tgctcaatgt accagagcac ttcagaagac cattcaatat aggtctttac aagggaacga    2760
ttgagctcac aatgaccatc tacgatgatg agtcactgga agcagctcct atgatctggg    2820
atcatttcaa ttcttccaaa ttttctgatt tcagagagaa ggccttaatg tttggcctga    2880
ttgtcgagaa aaaggcatct ggagcgtggg tcctggattc tatcagccac ttcaaatgag    2940
ctagtctaac ttctagcttc tgaacaatcc ccggtttact cagtctctcc taattccagc    3000
ctctcgaaca actaatatcc tgtcttttct atccctatga aaaaactaa cagagatcga    3060
tctgtttacg cgtcactatg aagtgccttt tgtacttagc cttttattc attggggtga    3120
attgcaagtt caccatagtt tttccacaca accaaaaagg aaactggaaa atgttccttt    3180
ctaattacca ttattgcccg tcaagctcag atttaaattg gcataatgac ttaataggca    3240
cagccataca agtcaaaatg cccaagagtc acaaggctat tcaagcagac ggttggatgt    3300
gtcatgcttc caaatgggtc actacttgtg atttccgctg gtatggaccg aagtatataa    3360
cacagtccat ccgatccttc actccatctg tagaacaatg caaggaaagc attgaacaaa    3420
cgaaacaagg aacttggctg aatccaggct ccctcctca aagttgtgga tatgcaactg    3480
tgacggatgc cgaagcagtg attgtccagg tgactcctca ccatgtgctg gttgatgaat    3540
acacaggaga atgggttgat tcacagttca tcaacgaaaa atgcagcaat tacatatgcc    3600
ccactgtcca taactctaca acctggcatt ctgactataa ggtcaaaggg ctatgtgatt    3660
ctaacctcat ttccatggac atcaccttct ctcagagga cggagagcta tcatccctgg    3720
gaaaggaggg cacagggttc agaagtaact actttgctta tgaaactgga ggcaaggcct    3780
gcaaaatgca atactgcaag cattgggag tcagactccc atcaggtgtc tggttcgaga     3840
tggctgataa ggatctcttt gctgcagcca gattccctga tgcccagaa gggtcaagta     3900
tctctgctcc atctcagacc tcagtggatg taagtctaat tcaggacgtt gagaggatct    3960
tggattattc cctctgccaa gaaacctgga gcaaaatcag agcgggtctt ccaatctctc    4020
cagtggatct cagctatctt gctcctaaaa acccaggaac cggtcctgct ttcaccataa    4080
```

-continued

```
tcaatggtac cctaaaatac tttgagacca gatacatcag agtcgatatt gctgctccaa    4140
tcctctcaag aatggtcgga atgatcagtg gaactaccac agaaagggaa ctgtgggatg    4200
actgggcacc atatgaagac gtggaaattg acccaatgg agttctgagg accagttcag    4260
gatataagtt tcctttatac atgattggac atggtatgtt ggactccgat cttcatctta    4320
gctcaaaggc tcaggtgttc gaacatcctc acattcaaga cgctgcttcg caacttcctg    4380
atgatgagag tttattttt ggtgatactg ggctatccaa aaatccaatc gagcttgtag    4440
aaggttggtt cagtagttgg aaaagctcta ttgcctcttt tttctttatc atagggttaa    4500
tcattggact attcttggtt ctccgagttg gtatccatct ttgcattaaa ttaaagcaca    4560
ccaagaaaag acagatttat acagacatag agatgaaccg acttggaaag taactcaaat    4620
cctgctaggt atgaaaaaaa ctaacagata tcacgctcga gccaccatgt tcgtgttct    4680 ggtgctgctg cctctggtga gctcccagtg cgtgaacttc accacaagga cccagctgcc    4740
ccctgcctat accaattcct tcacacgggg cgtgtactat cccgacaagg tgttccggag    4800
cagcgtgctg cactccacac aggatctgtt tctgcctttc ttttctaacg tgacctggtt    4860
ccacgccatc cacgtgagcg gcaccaatgg cacaaagcgg ttcgccaatc cagtgctgcc    4920
ctttaacgat ggcgtgtact cgcctccac cgagaagtct aacatcatca gaggctggat    4980
ctttggcacc acactggaca gcaagacaca gtccctgctg atcgtgaaca atgccaccaa    5040
cgtggtcatc aaggtgtgcg agttccagtt ttgtaatgat ccattcctgg gcgtgtacta    5100
tcacaagaac aataagtctt ggatggagag cgagtttcgc gtgtattcct ctgccaacaa    5160
ttgcacattt gagtacgtgt cccagccctt cctgatggac ctggagggca agcagggcaa    5220
tttcaagaac ctgagggagt tcgtgtttaa gaatatcgat ggctacttca aaatctactc    5280
caagcacacc ccaatcaacc tggtgcgcgg cctgccacag gcttctctg ccctggagcc    5340 actggtggat ctgcccatcg gcatcaacat caccgggttt cagacactgc tggccctgca    5400
cagaagctac ctgacaccag cgacagctc tctggatgg accgcaggag cagcagccta    5460
ctatgtgggc tatctgcagc ccaggacctt cctgctgaag tacaacgaga atggcaccat    5520
cacagacgcc gtggattgcg ccctggatcc cctgtctgag accaagtgta cactgaagag    5580
ctttaccgtg gagaagggca tctatcagac aagcaatttc agggtgcagc ctaccgagtc    5640
catcgtgcgc tttcccaata tcacaaacct gtgcccttt ggcgaggtgt tcaacgcaac    5700
ccgcttcgcc agcgtgtacg cctggaatag gaagcgcatc tccaactgcg tggccgacta    5760
ttctgtgctg tacaacagcg cctccttctc tacctttaag tgctatggcg tgagccccac    5820
aaagctgaat gacctgtgct ttaccaacgt gtacgccgat tccttcgtga tcaggggcga    5880 cgaggtcgc cagatcgcac caggacagac aggcaatatc gcagactaca attataagct    5940
gcctgacgat ttcaccggct gcgtgatcgc ctggaactct aacaatctgg atagcaaagt    6000
gggcggcaac tacaattatc tgtaccggct gtttagaaag tctaatctga agccattcga    6060
gagggacatc tccacagaaa tctaccaggc cggctctacc ccctgcaatg gcgtgaaggg    6120
ctttaactgt tatttccctc tgcagagcta cggcttccag ccaacatatg cgtgggcta    6180 tcagccctac cgcgtggtgg tgctgtcttt tgagctgctg cacgcacctg caacagtgtg    6240
cggaccaaag aagagcacca atctggtgaa gaacaagtgc gtgaacttca acttcaacgg    6300
actgaccgga acaggcgtgc tgaccgagtc caacaagaag ttcctgcctt ttcagcagtt    6360
cggcagggac atcgcagata ccacagacgc cgtgcgcgac cctcagaccc tggagatcct    6420
ggacatcaca ccatgctcct cggcggcgt gtctgtgatc acaccaggca ccaatacaag    6480
```

```
caaccaggtg gccgtgctgt atcagggcgt gaattgtacc gaggtgccag tggcaatcca    6540
cgcagatcag ctgaccccta catggcgggt gtactctacc ggcagcaacg tgttccagac    6600
aagagccgga tgcctgatcg gagcagagca cgtgaacaat agctatgagt gcgacatccc    6660
tatcggcgcc ggcatctgtg cctcctacca gacccagaca aactccccaa ggtctgtggg    6720
cgatacaggc ctgtccaaga atccaatcga gctggtagag ggctggttca gcagttggaa    6780
aagctccatc gcctcctttt tctttatcat cggcctgatc atcggactgt tcctggtgct    6840
ccgcgtgggt atccacctgt gcatcaagct gaagcacacc aagaaaagac agatttatac    6900
agacatcgag atgaaccgcc tgggaaagtg agctagccag attcttcatg tttggaccaa    6960
atcaacttgt gataccatgc tcaaagaggc ctcaattata tttgagtttt aattttttat    7020
gaaaaaaact aacagcaatc atggaagtcc acgattttga gaccgacgag ttcaatgatt    7080
tcaatgaaga tgactatgcc acaagagaat cctgaatccc gatgagcgc atgacgtact     7140 tgaatcatgc tgattacaat ttgaattctc ctctaattag tgatgatatt gacaatttga    7200
tcaggaaatt caattctctt ccgattccct cgatgtggga tagtaagaac tgggatggag    7260
ttcttgagat gttaacatca tgtcaagcca atcccatctc aacatctcag atgcataaat    7320
ggatgggaag ttggttaatg tctgataatc atgatgccag tcaagggtat agttttttac    7380
atgaagtgga caaagaggca gaaataacat ttgacgtggt ggagaccttc atccgcggct    7440
ggggcaacaa accaattgaa tacatcaaaa aggaaagatg gactgactca ttcaaaattc    7500
tcgcttattt gtgtcaaaag ttttttggact tacacaagtt gacattaatc ttaaatgctg    7560
tctctgaggt ggaattgctc aacttggcga ggactttcaa aggcaaagtc agaagaagtt    7620
ctcatggaac gaacatatgc aggattaggg ttcccagctt gggtcctact tttatttcag    7680
aaggatgggc ttacttcaag aaacttgata ttctaatgga ccgaaacttt ctgttaatgg    7740
tcaaagatgt gattataggg aggatgcaaa cggtgctatc catggtatgt agaatagaca    7800
acctgttctc agagcaagac atcttctccc ttctaaatat ctacagaatt ggagataaaa    7860
ttgtggagag gcagggaaat ttttcttatg acttgattaa aatggtggaa ccgatatgca    7920
acttgaagct gatgaaatta gcaagagaat caaggccttt agtcccacaa ttccctcatt    7980
ttgaaaatca tatcaagact tctgttgatg aaggggcaaa aattgaccga ggtataagat    8040
tcctccatga tcagataatg agtgtgaaaa cagtggatct cacactggtg atttatggat    8100
cgttcagaca ttggggtcat ccttttatag attattacac tggactagaa aaattacatt    8160
cccaagtaac catgaagaaa gatattgatg tgtcatatgc aaaagcactt gcaagtgatt    8220
tagctcggat tgttctattt caacagttca atgatcataa aaagtggttc gtgaatggag    8280
acttgctccc tcatgatcat ccctttaaaa gtcatgttaa agaaaataca tggcccacag    8340
ctgctcaagt tcaagatttt ggagataaat ggcatgaact tccgctgatt aaatgttttg    8400
aaatacccga cttactagac ccatcgataa tatactctga caaagtcat tcaatgaata      8460 ggtcagaggt gttgaaacat gtccgaatga atccgaacac tcctatccct agtaaaaagg    8520
tgttgcagac tatgttggac acaaaggcta ccaattggaa agaatttctt aaagagattg    8580
atgagaaggg cttagatgat gatgatctaa ttattggtct taaggaaag gagagggaac     8640 tgaagttggc aggtagattt ttctcccta a tgtcttggaa attgcgagaa tactttgtaa    8700
ttaccgaata tttgataaag actcatttcg tccctatgtt taaggcctg acaatggcgg     8760 acgatctaac tgcagtcatt aaaaagatgt tagattcctc atccggccaa ggattgaagt    8820
```

```
catatgaggc aatttgcata gccaatcaca ttgattacga aaaatggaat aaccaccaaa  8880
ggaagttatc aaacgcccca gtgttccgag ttatgggcca gttcttaggt tatccatcct  8940
taatcgagag aactcatgaa ttttttgaga aaagtcttat atactacaat ggaagaccag  9000
acttgatgcg tgttcacaac aacacactga tcaattcaac ctcccaacga gtttgttggc  9060
aaggacaaga gggtggactg gaaggtctac ggcaaaaagg atggactatc ctcaatctac  9120
tggttattca aagagaggct aaaatcagaa acactgctgt caaagtcttg cacaaggtg   9180
ataatcaagt tatttgcaca cagtataaaa cgaagaaatc gagaaacgtt gtagaattac  9240
agggtgctct caatcaaatg gtttctaata atgagaaaat tatgactgca atcaaaatag  9300
ggacagggaa gttaggactt tgataaatg acgatgagac tatgcaatct gcagattact   9360
tgaattatgg aaaaatccg attttccgtg gagtgattag agggttagag accaagagat   9420
ggtcacgagt gacttgtgtc accaatgacc aaatacccac ttgtgctaat ataatgagct  9480
cagtttccac aaatgctctc accgtagctc attttgctga aacccaatc aatgccatga    9540
tacagtacaa ttattttggg acatttgcta gactcttgtt gatgatgcat gatcctgctc  9600
ttcgtcaatc attgtatgaa gttcaagata agataccggg cttgcacagt tctactttca  9660
aatacgccat gttgtatttg gacccttcca ttggaggagt gtcgggcatg tctttgtcca  9720
ggttttgat tagagccttc ccagatcccg taacagaaag tctctcattc tggagattca   9780
tccatgtaca tgctcgaagt gagcatctga aggagatgag tgcagtattt ggaaacccca  9840
agatagccaa gtttcgaata actcacatag acaagctagt agaagatcca acctctctga  9900
acatcgctat gggaatgagt ccagcgaact tgttaaagac tgaggttaaa aaatgcttaa  9960
tcgaatcaag acaaaccatc aggaaccagg tgattaagga tgcaaccata tatttgtatc 10020
atgaagagga tcggctcaga agtttcttat ggtcaataaa tcctctgttc cctagatttt 10080
taagtgaatt caaatcaggc acttttttgg gagtcgcaga cgggctcatc agtctatttc 10140
aaaattctcg tactattcgg aactccttta agaaaaagta tcatagggaa ttggatgatt 10200
tgattgtgag gagtgaggta tcctctttga cacatttagg gaaacttcat ttgagaaggg 10260
gatcatgtaa aatgtggaca tgttcagcta ctcatgctga cacattaaga tacaaatcct 10320
ggggccgtac agttattggg acaactgtac cccatccatt agaaatgttg ggtccacaac 10380
atcgaaaaga gactccttgt gcaccatgta acacatcagg gttcaattat gtttctgtgc 10440
attgtccaga cgggatccat gacgtcttta gttcacgggg accattgcct gcttatctag 10500
ggtctaaaac atctgaatct acatctattt tgcagccttg ggaaagggaa agcaaagtcc 10560
cactgattaa aagagctaca cgtcttagag atgctatctc ttggtttgtt gaacccgact 10620
ctaaactagc aatgactata cttttctaaca tccactcttt aacaggcgaa gaatggacca 10680
aaaggcagca tgggttcaaa agaacagggt ctgcccttca taggttttcg acatctcgga 10740
tgagccatgg tgggttcgca tctcagagca ctgcagcatt gaccaggttg atggcaacta 10800
cagacaccat gagggatctg ggagatcaga atttcgactt tttattccaa gcaacgttgc 10860
tctatgctca aattaccacc actgttgcaa gagacggatg gatcaccagt tgtacagatc 10920
attatcatat tgcctgtaag tcctgtttga gacccataga agagatcacc ctggactcaa 10980
gtatggacta cacgccccca gatgtatccc atgtgctgaa gacatggagg aatggggaag 11040
gttcgtgggg acaagagata aaacagatct atccttgaga agggaattgg aagaattta    11100
cacctgctga gcaatcctat caagtcggca gatgtatagg ttttctatat ggagacttgg 11160
cgtatagaaa atctactcat gccgaggaca gttctctatt tcctctatct atacaaggtc 11220
```

```
gtattagagg tcgaggtttc ttaaaagggt tgctagacgg attaatgaga gcaagttgct    11280
gccaagtaat acaccggaga agtctggctc atttgaagag gccggccaac gcagtgtacg    11340
gaggtttgat ttacttgatt gataaattga gtgtatcacc tccattcctt tctcttacta    11400
gatcaggacc tattagagac gaattagaaa cgattcccca caagatccca acctcctatc    11460
cgacaagcaa ccgtgatatg ggggtgattg tcagaaatta cttcaaatac caatgccgtc    11520
taattgaaaa gggaaaatac agatcacatt attcacaatt atggttattc tcagatgtct    11580
tatccataga cttcattgga ccattctcta tttccaccac cctcttgcaa atcctataca    11640
agccattttt atctgggaaa gataagaatg agttgagaga gctggcaaat ctttcttcat    11700
tgctaagatc aggagagggg tgggaagaca tacatgtgaa attcttcacc aaggacatat    11760
tattgtgtcc agaggaaatc agacatgctt gcaagttcgg gattgctaag gataataata    11820
aagacatgag ctatccccct tggggaaggg aatccagagg gacaattaca acaatccctg    11880
tttattatac gaccaccect tacccaaaga tgctagagat gcctccaaga atccaaaatc    11940
ccctgctgtc cggaatcagg ttgggccaat taccaactgg cgctcattat aaaattcgga    12000
gtatattaca tggaatggga atccattaca gggacttctt gagttgtgga gacggctccg    12060
gagggatgac tgctgcatta ctacgagaaa atgtgcatag cagaggaata ttcaatagtc    12120
tgttagaatt atcagggtca gtcatgcgag gcgcctctcc tgagccccec agtgccctag    12180 aaactttagg aggagataaa tcgagatgtg taaatggtga aacatgttgg gaatatccat    12240
ctgacttatg tgacccaagg acttgggact atttcctccg actcaaagca ggcttggggc    12300
ttcaaattga tttaattgta atggatatgg aagttcggga ttcttctact agcctgaaaa    12360
ttgagacgaa tgttagaaat tatgtgcacc ggattttgga tgagcaagga gttttaatct    12420
acaagactta tggaacatat atttgtgaga gcgaaaagaa tgcagtaaca atccttggtc    12480
ccatgttcaa gacggtcgac ttagttcaaa cagaatttag tagttctcaa acgtctgaag    12540
tatatatggt atgtaaaggt ttgaagaaat taatcgatga acccaatccc gattggtctt    12600
ccatcaatga atcctggaaa aacctgtacg cattccagtc atcagaacag gaatttgcca    12660
gagcaaagaa ggttagtaca tactttacct tgacaggtat tccctcccaa ttcattcctg    12720
atccttttgt aaacattgag actatgctac aaatattcgg agtacccacg ggtgtgtctc    12780
atgcggctgc cttaaaatca tctgatagac ctgcagattt attgaccatt agccttttt    12840 atatggcgat tatatcgtat tataacatca atcatatcag agtaggaccg atacctccga    12900 acccccatc agatggaatt gcacaaaatg tggggatcgc tataactggt ataagctttt    12960
ggctgagttt tgatggagaaa gacattccac tatatcaaca gtgtttagca gttatccagc    13020
aatcattccc gattaggtgg gaggctgttt cagtaaaagg aggatacaag cagaagtgga    13080
gtactagagg tgatgggctc ccaaaagata cccgaacttc agactccttg gccccaatcg    13140
ggaactggat cagatctctg gaattggtcc gaaaccaagt tcgtctaaat ccattcaatg    13200
agatcttgtt caatcagcta tgtcgtacag tggataatca tttgaaatgg tcaaatttgc    13260
gaagaaacac aggaatgatt gaatggatca atagacgaat ttcaaaagaa gaccggtcta    13320
tactgatgtt gaagagtgac ctacacgagg aaaactcttg gagagattaa aaaatcatga    13380
ggagactcca aactttaagt atgaaaaaaa ctttgatcct taagaccctc ttgtggtttt    13440
tattttttat ctggttttgt ggtcttcgt                                      13469
```

<210> SEQ ID NO 20

<211> LENGTH: 13556
<212> TYPE: DNA
<213> ORGANISM: Artificial Sequence
<220> FEATURE:
<223> OTHER INFORMATION: VSV vector: Convac V2 China

<400> SEQUENCE: 20
acgaagacaa acaaaccatt attatcatta aaaggctcag gagaaacttt aacagtaatc 60
aaaatgtctg ttacagtcaa gagaatcatt gacaacacag tcatagttcc aaaacttcct 120
gcaaatgagg atccagtgga atacccggca gattacttca gaaaatcaaa ggagattcct 180
ctttacatca atactacaaa aagtttgtca gatctaagag gatatgtcta ccaaggcctc 240
aaatccggaa atgtatcaat catacatgtc aacagctact tgtatggagc attaaaggac 300
atccggggta agttggataa agattggtca agtttcggaa taaacatcgg gaaagcaggg 360
gatacaatcg gaatatttga ccttgtatcc ttgaaagccc tggacggcgt acttccagat 420
ggagtatcgg atgcttccag aaccagcgca gatgacaaat ggttgccttt gtatctactt 480
ggcttataca gagtgggcag aacacaaatg cctgaataca gaaaaaagct catggatggg 540
ctgacaaatc aatgcaaaat gatcaatgaa cagtttgaac ctcttgtgcc agaaggtcgt 600
gacatttttg atgtgtgggg aaatgacagt aattacacaa aaattgtcgc tgcagtggac 660
atgttcttcc acatgttcaa aaaacatgaa tgtgcctcgt tcagatacgg aactattgtt 720
tccagattca aagattgtgc tgcattggca acatttggac acctctgcaa aataaccgga 780
atgtctacag aagatgtaac gacctggatc ttgaaccgag aagttgcaga tgaaatggtc 840
caaatgatgc ttccaggcca agaaattgac aaggccgatt catacatgcc ttatttgatc 900
gactttggat tgtcttctaa gtctccatat tcttccgtca aaaaccctgc cttccacttc 960
tgggggcaat tgacagctct tctgctcaga tccaccagag caaggaatgc ccgacagcct 1020
gatgacattg agtatacatc tcttactaca gcaggtttgt tgtacgctta tgcagtagga 1080
tcctctgccg acttggcaca acagttttgt gttggagata acaaatacac tccagatgat 1140
agtaccggag gattgacgac taatgcaccg ccacaaggca gagatgtggt cgaatggctc 1200
ggatggtttg aagatcaaaa cagaaaaccg actcctgata tgatgcagta tgcgaaaaga 1260
gcagtcatgt cactgcaagg cctaagagag aagacaattg gcaagtatgc taagtcagaa 1320
tttgacaaat gaccctataa ttctcagatc acctattata tattatgcta catatgaaaa 1380
aaactaacag atatcatgga taatctcaca aaagttcgtg agtatctcaa gtcctattct 1440
cgtctggatc aggcggtagg agagatagat gagatcgaag cacaacgagc tgaaaagtcc 1500
aattatgagt tgttccaaga ggatggagtg gaagagcata ctaagccctc ttattttcag 1560
gcagcagatg attctgacac agaatctgaa ccagaaattg aagacaatca aggtttgtat 1620
gcaccagatc cagaagctga gcaagttgaa ggctttatac aggggccttt agatgactat 1680
gcagatgagg aagtggatgt tgtatttact tcggactgga aacagcctga gcttgaatct 1740
gacgagcatg gaaagacctt acggttgaca tcgccagagg gtttaagtgg agagcagaaa 1800
tcccagtggc tttcgacgat taaagcagtc gtgcaaagtg ccaaatactg gaatctggca 1860
gagtgcacat ttgaagcatc gggagaaggg gtcattatga aggagcgcca gataactccg 1920
gatgtatata aggtcactcc agtgatgaac acacatccgt cccaatcaga agcagtatca 1980
gatgtttggt ctctctcaaa gacatccatg actttccaac ccaagaaagc aagtcttcag 2040
cctctcacca tatccttgga tgaattgttc tcatctagag gagagttcat ctctgtcgga 2100
ggtgacggac gaatgtctca taaagaggcc atcctgctcg gcctgagata caaaaagttg 2160

```
tacaatcagg cgagagtcaa atattctctg tagactatga aaaaaagtaa cagatatcac    2220
gatctaagtg ttatcccaat ccattcatca tgagttcctt aaagaagatt ctcggtctga    2280
aggggaaagg taagaaatct aagaaattag ggatcgcacc accccttat gaagaggaca     2340 ctagcatgga gtatgctccg agcgctccaa ttgacaaatc ctattttgga gttgacgaga    2400
tggacaccta tgatccgaat caattaagat atgagaaatt cttctttaca gtgaaaatga    2460
cggttagatc taatcgtccg ttcagaacat actcagatgt ggcagccgct gtatcccatt    2520
gggatcacat gtacatcgga atggcaggga acgtcccttt ctacaaaatc ttggcttttt    2580
tgggttcttc taatctaaag gccactccag cggtattggc agatcaaggt caaccagagt    2640
atcacactca ctgcgaaggc agggcttatt tgccacatag gatggggaag acccctccca    2700
tgctcaatgt accagagcac ttcagaagac cattcaatat aggtctttac aagggaacga    2760
ttgagctcac aatgaccatc tacgatgatg agtcactgga agcagctcct atgatctggg    2820
atcatttcaa ttcttccaaa ttttctgatt tcagagagaa ggccttaatg tttggcctga    2880
ttgtcgagaa aaaggcatct ggagcgtggg tcctggattc tatcagccac ttcaaatgag    2940
ctagtctaac ttctagcttc tgaacaatcc ccggtttact cagtctctcc taattccagc    3000
ctctcgaaca actaatatcc tgtctttcct atccctatga aaaaaactaa cagagatcga    3060
tctgtttacg cgtcactatg aagtgccttt tgtacttagc ctttttattc attggggtga    3120
attgcaagtt caccatagtt tttccacaca accaaaaagg aaactggaaa atgttccttt    3180
ctaattacca ttattgcccg tcaagctcag atttaaattg gcataatgac ttaataggca    3240
cagccataca agtcaaaatg cccaagagtc acaaggctat tcaagcagac ggttggatgt    3300
gtcatgcttc caaatgggtc actacttgtg atttccgctg gtatggaccg aagtatataa    3360
cacagtccat ccgatccttc actccatctg tagaacaatg caaggaaagc attgaacaaa    3420
cgaaacaagg aacttggctg aatccaggct cccctcctca aagttgtgga tatgcaactg    3480
tgacggatgc cgaagcagtg attgtccagg tgactcctca ccatgtgctg gttgatgaat    3540
acacaggaga atgggttgat tcacagttca tcaacggaaa atgcagcaat tacatatgcc    3600
ccactgtcca taactctaca acctggcatt ctgactataa ggtcaaaggg ctatgtgatt    3660
ctaacctcat ttccatggac atcaccttct ctcagagga cggagagcta tcatccctgg    3720
gaaaggaggg cacagggttc agaagtaact actttgctta tgaaactgga ggcaaggcct    3780
gcaaaatgca atactgcaag cattgggag tcagactccc atcaggtgtc tggttcgaga    3840
tggctgataa ggatctcttt gctgcagcca gattccctga atgcccagaa gggtcaagta    3900
tctctgctcc atctcagacc tcagtggatg taagtctaat tcaggacgtt gagaggatct    3960
tggattattc cctctgccaa gaaacctgga gcaaaatcag agcgggtctt ccaatctctc    4020
cagtggatct cagctatctt gctcctaaaa acccaggaac cggtcctgct ttcaccataa    4080
tcaatggtac cctaaaatac tttgagacca gatacatcag agtcgatatt gctgctccaa    4140
tcctctcaag aatggtcgga atgatcagtg aactaccac agaaagggaa ctgtgggatg    4200
actgggcacc atatgaagac gtggaaattg acccaatgg agttctgagg accagttcag    4260
gatataagtt tccttatac atgattggac atggtatgtt ggactccgat cttcatctta    4320
gctcaaaggc tcaggtgttc gaacatcctc acattcaaga cgctgcttcg caacttcctg    4380
atgatgagag tttatttttt ggtgatactg ggctatccaa aaatccaatc gagcttgtag    4440
aaggttggtt cagtagttgg aaaagctcta ttgcctcttt tttcttttatc atagggttaa    4500
```

```
tcattggact attcttggtt ctccgagttg gtatccatct ttgcattaaa ttaaagcaca    4560
ccaagaaaag acagatttat acagacatag agatgaaccg acttggaaag taactcaaat    4620
cctgctaggt atgaaaaaaa ctaacagata tcacgctcga gcgtacgcca ccatgttcgt    4680
gtttctggtg ctgctgcctc tggtgagctc ccagtgcgtg aacctgacca caaggaccca    4740
gctgccccct gcctatacca attccttcac acggggcgtg tactatcccg acaaggtgtt    4800
ccggagcagc gtgctgcact ccacacagga tctgtttctg cctttctttt ctaacgtgac    4860
ctggttccac gccatccacg tgagcggcac caatggcaca aagcggttcg acaatccagt    4920
gctgccettt aacgatggcg tgtacttcgc ctccaccgag aagtctaaca tcatcagagg    4980
ctggatcttt ggcaccacac tggacagcaa gacacagtcc ctgctgatcg tgaacaatgc    5040
caccaacgtg gtcatcaagg tgtgcgagtt ccagttttgt aatgatccat tcctgggcgt    5100
gtactatcac aagaacaata gtcttggat ggagagcgag tttcgcgtgt attcctctgc    5160
caacaattgc acatttgagt acgtgtccca gcccttcctg atggacctgg agggcaagca    5220
gggcaatttc aagaacctga gggagttcgt gtttaagaat atcgatggct acttcaaaat    5280
ctactccaag cacacccccaa tcaacctggt gcgcgacctg ccacagggct tctctgccct    5340
ggagccactg gtggatctgc ccatcggcat caacatcacc cggtttcaga cactgctggc    5400
cctgcacaga agctacctga caccaggcga cagctcctct ggatggaccg caggagcagc    5460
agcctactat gtgggctatc tgcagcccag gaccttcctg ctgaagtaca cgagaatgg    5520
caccatcaca gacgccgtgg attgcgccct ggatccctg tctgagacca gtgtacact    5580
gaagagcttt accgtggaga agggcatcta tcagacaagc aatttcaggg tgcagcctac    5640
cgagtccatc gtgcgctttc caatatcac aaacctgtgc ccttttggcg aggtgttcaa    5700
cgcaacccgc ttcgccagcg tgtacgcctg gaataggaag cgcatctcca actgcgtggc    5760
cgactattct gtgctgtaca acagcgcctc cttctctacc tttaagtgct atggcgtgag    5820
ccccacaaag ctgaatgacc tgtgctttac caacgtgtac gccgattcct tcgtgatcag    5880
gggcgacgag gtgcgccaga tcgcaccagg acagacaggc aagatcgcag actacaatta    5940
taagctgcct gacgatttca ccggctgcgt gatcgcctgg aactctaaca atctggata    6000
caaagtgggc ggcaactaca attatctgta ccggctgttt agaaagtcta atctgaagcc    6060
attcgagagg gacatctcca cagaaatcta ccaggccggc tctacccct gcaatgcgt    6120
ggagggctttt aactgttatt tccctctgca gagctacggc ttccagccaa caacggcgt    6180
gggctatcag ccctaccgcg tggtggtgct gtctttgag ctgctgcacg cacctgcaac    6240
agtgtgcgga ccaaagaaga gcaccaatct ggtgaagaac aagtgcgtga acttcaactt    6300
caacggactg accggaacag gcgtgctgac cgagtccaac aagaagttcc tgcctttca    6360
gcagttcggc agggacatcg cagataccac agacgccgtg cgcgaccctc agaccctgga    6420
gatcctggac atcacaccat gctccttcgg cggcgtgtct gtgatcacac caggcaccaa    6480
tacaagcaac caggtggccg tgctgtatca ggacgtgaat tgtaccgagg tgccagtggc    6540
aatccacgca gatcagctga cccctacatg gcgggtgtac tctaccggca gcaacgtgtt    6600
ccagacaaga gccggatgcc tgatcggagc agagcacgtg aacaatagct atgagtgcga    6660
catccctatc ggcgccggca tctgtgcctc ctaccagacc cagacaaact ccccaaggtc    6720
tgtgggagat gaggccgaag actttgtgga agtccacctg cctgatgtgc ataaccaggt    6780
gtctggcgtc gacctgggac tgccaaattg gggcaagtac gtgctgctga gtgctggagc    6840
actgactgcc ctgatgctga tcattttcct gatgacctgc tgtcggcgcg tgaacagaag    6900
```

```
tgagcccact cagcacaatc tgcgaggaac cgggagagaa gtgtcagtca cacctcagag   6960
cgggaaaatc attagtagtt gggaatcaca taaaagcggg ggcgagacca ggctgtgagc   7020
tagccagatt cttcatgttt ggaccaaatc aacttgtgat accatgctca aagaggcctc   7080
aattatattt gagtttttaa tttttatgaa aaaaactaac agcaatcatg gaagtccacg   7140
attttgagac cgacgagttc aatgatttca tgaagatga ctatgccaca agagaattcc    7200
tgaatcccga tgagcgcatg acgtacttga atcatgctga ttacaatttg aattctcctc   7260
taattagtga tgatattgac aatttgatca ggaaattcaa ttctcttccg attccctcga   7320
tgtgggatag taagaactgg gatggagttc ttgagatgtt aacatcatgt caagccaatc   7380
ccatctcaac atctcagatg cataaatgga tgggaagttg gttaatgtct gataatcatg   7440
atgccagtca agggtatagt tttttacatg aagtggacaa agaggcagaa ataacatttg   7500
acgtggtgga gaccttcatc cgcggctggg gcaacaaacc aattgaatac atcaaaaagg   7560
aaagatggac tgactcattc aaaattctcg cttatttgtg tcaaaagttt ttggacttac   7620
acaagttgac attaatctta aatgctgtct ctgaggtgga attgctcaac ttggcgagga   7680
ctttcaaagg caaagtcaga agaagttctc atggaacgaa catatgcagg attagggttc   7740
ccagcttggg tcctactttt atttcagaag gatgggctta cttcaagaaa cttgatattc   7800
taatggaccg aaactttctg ttaatggtca aagatgtgat tatagggagg atgcaaacgg   7860
tgctatccat ggtatgtaga atagacaacc tgttctcaga gcaagacatc ttctcccttc   7920
taaatatcta cagaattgga gataaaattg tggagaggca gggaaatttt tcttatgact   7980
tgattaaaat ggtggaaccg atatgcaact tgaagctgat gaaattagca agagaatcaa   8040
ggcctttagt cccacaattc cctcattttg aaaatcatat caagacttct gttgatgaag   8100
gggcaaaaat tgaccgaggt ataagattcc tccatgatca gataatgagt gtgaaaacag   8160
tggatctcac actggtgatt tatgatcgt tcagacattg gggtcatcct tttatagatt    8220
attacactgg actagaaaaa ttacattccc aagtaaccat gaagaaagat attgatgtgt   8280
catatgcaaa agcacttgca agtgatttag ctcggattgt tctatttcaa cagttcaatg   8340
atcataaaaa gtggttcgtg aatggagact tgctccctca tgatcatccc tttaaaagtc   8400
atgttaaaga aaatacatgg cccacagctg ctcaagttca agattttgga gataaatggc   8460
atgaacttcc gctgattaaa tgttttgaaa tacccgactt actagaccca tcgataatat   8520
actctgacaa aagtcattca atgaataggt cagaggtgtt gaaacatgtc cgaatgaatc   8580
cgaacactcc tatccctagt aaaaaggtgt tgcagactat gttggacaca aaggctacca   8640
attggaaaga atttcttaaa gagattgatg agaagggctt agatgatgat gatctaatta   8700
ttggtcttaa aggaaaggag agggaactga agttggcagg tagattttc tccctaatgt     8760
cttggaaatt gcgagaatac tttgtaatta ccgaatattt gataaagact catttcgtcc   8820
ctatgtttaa aggcctgaca atggcggacg atctaactgc agtcattaaa aagatgttag   8880
attcctcatc cggccaagga ttgaagtcat atgaggcaat ttgcatagcc aatcacattg   8940
attacgaaaa atggaataac caccaaagga agttatcaaa cggcccagtg ttccgagtta   9000
tgggccagtt cttaggttat ccatccttaa tcgagagaac tcatgaattt tttgagaaaa   9060
gtcttatata ctacaatgga agaccagact tgatgcgtgt tcacaacaac acactgatca   9120
attcaacctc ccaacgagtt tgttggcaag acaagaggg tggactggaa ggtctacggc    9180
aaaaaggatg gactatcctc aatctactgg ttattcaaag agaggctaaa atcagaaaca   9240
```

```
ctgctgtcaa agtcttggca caaggtgata atcaagttat ttgcacacag tataaaacga   9300
agaaatcgag aaacgttgta gaattacagg gtgctctcaa tcaaatggtt tctaataatg   9360
agaaaattat gactgcaatc aaaatagggg cagggaagtt aggacttttg ataaatgacg   9420
atgagactat gcaatctgca gattacttga attatggaaa aataccgatt ttccgtggag   9480
tgattagagg gttagagacc aagagatggt cacgagtgac ttgtgtcacc aatgaccaaa   9540
tacccacttg tgctaatata atgagctcag tttccacaaa tgctctcacc gtagctcatt   9600
ttgctgagaa cccaatcaat gccatgatac agtacaatta ttttgggaca tttgctagac   9660
tcttgttgat gatgcatgat cctgctcttc gtcaatcatt gtatgaagtt caagataaga   9720
taccgggctt gcacagttct actttcaaat acgccatgtt gtatttggac ccttccattg   9780
gaggagtgtc gggcatgtct ttgtccaggt ttttgattag agccttccca gatcccgtaa   9840
cagaaagtct ctcattctgg agattcatcc atgtacatgc tcgaagtgag catctgaagg   9900
agatgagtgc agtatttgga aaccccgaga tagccaagtt tcgaataact cacatagaca   9960
agctagtaga agatccaacc tctctgaaca tcgctatggg aatgagtcca gcgaacttgt  10020
taaagactga ggttaaaaaa tgcttaatcg aatcaagaca aaccatcagg aaccaggtga  10080
ttaaggatgc aaccatatat ttgtatcatg aagaggatcg gctcagaagt ttcttatggt  10140
caataaatcc tctgttccct agattttta gtgaattcaa atcaggcact ttttgggag   10200
tcgcagacgg gctcatcagt ctatttcaaa attctcgtac tattcggaac tccttaaga   10260
aaaagtatca tagggaattg gatgatttga ttgtgaggag tgaggtatcc tctttgacac  10320
atttaggggaa acttcatttg agaagggggat catgtaaaat gtggacatgt tcagctactc  10380
atgctgacac attaagatac aaatcctggg gccgtacagt tattgggaca actgtacccc  10440
atccattaga aatgttgggt ccacaacatc gaaaagagac tccttgtgca ccatgtaaca  10500
catcagggtt caattatgtt tctgtgcatt gtccagacgg gatccatgac gtctttagtt  10560
cacggggacc attgcctgct tatctagggt ctaaaacatc tgaatctaca tctatttttgc 10620
agccttggga aagggaaagc aaagtcccac tgattaaaag agctacacgt cttagagatg  10680
ctatctcttg gtttgttgaa cccgactcta aactagcaat gactatactt tctaacatcc  10740
actctttaac aggcgaagaa tggaccaaaa ggcagcatgg gttcaaaaga acagggtctg  10800
cccttcatag gttttcgaca tctcggatga gccatggtgg gttcgcatct cagagcactg  10860
cagcattgac caggttgatg gcaactacag acaccatgag ggatctggga gatcagaatt  10920
tcgactttt attccaagca acgttgctct atgctcaaat taccaccact gttgcaagag  10980
acggatggat caccagttgt acagatcatt atcatattgc ctgtaagtcc tgtttgagac  11040
ccatagaaga gatcaccctg gactcaagta tggactacac gccccagat gtatcccatg   11100
tgctgaagac atggaggaat ggggaaggtt cgtggggaca agagataaaa cagatctatc  11160
ctttagaagg gaattggaag aatttagcac ctgctgagca atcctatcaa gtcggcagat  11220
gtataggttt tctatatgga gacttggcgt atagaaaatc tactcatgcc gaggacgttt  11280
ctctatttcc tctatctata caaggtcgta ttagaggtcg aggtttctta aagggttgc  11340
tagacggatt aatgagagca agttgctgcc aagtaataca ccggagaagt ctggctcatt  11400
tgaagaggcc ggccaacgca gtgtacggag gtttgattta cttgattgat aaattgagtg  11460
tatcacctcc attcctttct cttactagat caggacctat tagagacgaa ttagaaacga  11520
ttccccacaa gatcccaacc tcctatccga caagcaaccg tgatatgggg gtgattgtca  11580
gaaattactt caaataccaa tgccgtctaa ttgaaaaggg aaaatacaga tcacattatt  11640
```

-continued

```
cacaattatg gttattctca gatgtcttat ccatagactt cattggacca ttctctattt    11700
ccaccaccct cttgcaaatc ctatacaagc cattttatc tgggaaagat aagaatgagt     11760
tgagagagct ggcaaatctt tcttcattgc taagatcagg agaggggtgg aagacatac     11820
atgtgaaatt cttcaccaag acatattat tgtgtccaga ggaaatcaga catgcttgca     11880
agttcgggat tgctaaggat aataataaag acatgagcta tcccccttgg ggaagggaat    11940
ccagagggac aattacaaca atccctgttt attatacgac caccccttac ccaaagatgc    12000
tagagatgcc tccaagaatc caaaatcccc tgctgtccgg aatcaggttg ggccaattac    12060
caactggcgc tcattataaa attcggagta tattacatgg aatgggaatc cattacaggg    12120
acttcttgag ttgtggagac ggctccggag ggatgactgc tgcattacta cgagaaaatg    12180
tgcatagcag aggaatattc aatagtctgt tagaattatc agggtcagtc atgcgaggcg    12240
cctctcctga gcccccagt gccctagaaa ctttaggagg agataaatcg agatgtgtaa     12300
atggtgaaac atgttgggaa tatccatctg acttatgtga cccaaggact tgggactatt    12360
tcctccgact caaagcaggc ttggggcttc aaattgattt aattgtaatg gatatggaag    12420
ttcgggattc ttctactagc ctgaaaattg agacgaatgt tagaaattat gtgcaccgga    12480
ttttggatga gcaaggagtt ttaatctaca agacttatgg aacatatatt tgtgagagcg    12540
aaaagaatgc agtaacaatc cttggtccca tgttcaagac ggtcgactta gttcaaacag    12600
aatttagtag ttctcaaacg tctgaagtat atatggtatg taaaggtttg aagaaattaa    12660
tcgatgaacc caatcccgat tggtcttcca tcaatgaatc ctggaaaaac ctgtacgcat    12720
tccagtcatc agaacaggaa tttgccagag caaagaaggt tagtacatac tttaccttga    12780
caggtattcc ctcccaattc attcctgatc cttttgtaaa cattgagact atgctacaaa    12840
tattcggagt acccacgggt gtgtctcatg cggctgcctt aaaatcatct gatagacctg    12900
cagatttatt gaccattagc cttttttata tggcgattat atcgtattat aacatcaatc    12960
atatcagagt aggaccgata cctccgaacc ccccatcaga tggaattgca caaaatgtgg    13020
ggatcgctat aactggtata agcttttggc tgagtttgat ggagaaagac attccactat    13080
atcaacagtg tttagcagtt atccagcaat cattcccgat taggtgggag ctgtttcag    13140
taaaaggagg atacaagcag aagtggagta ctagaggtga tgggctccca aaagatccc    13200
gaacttcaga ctccttggcc ccaatcggga actggatcag atctctggaa ttggtccgaa    13260
accaagttcg tctaaatcca ttcaatgaga tcttgttcaa tcagctatgt cgtacagtgg    13320
ataatcattt gaaatggtca aatttgcgaa gaaacacagg aatgattgaa tggatcaata    13380
gacgaatttc aaaagaagac cggtctatac tgatgttgaa gagtgaccta cacgaggaaa    13440
actcttggag agattaaaaa atcatgagga gactccaaac tttaagtatg aaaaaaactt    13500
tgatccttaa gaccctcttg tggttttat tttttatctg gttttgtggt cttcgt         13556
```

<210> SEQ ID NO 21
<211> LENGTH: 13607
<212> TYPE: DNA
<213> ORGANISM: Artificial Sequence
<220> FEATURE:
<223> OTHER INFORMATION: VSV vector: Convac V2 South Africa

<400> SEQUENCE: 21

```
acgaagacaa acaaaccatt attatcatta aaaggctcag gagaaacttt aacagtaatc     60
aaaatgtctg ttacagtcaa gagaatcatt gacaacacag tcatagttcc aaaacttcct    120
```

```
gcaaatgagg atccagtgga atacccggca gattacttca gaaaatcaaa ggagattcct      180
ctttacatca atactacaaa aagtttgtca gatctaagag gatatgtcta ccaaggcctc      240
aaatccggaa atgtatcaat catacatgtc aacagctact tgtatggagc attaaaggac      300
atccggggta agttggataa agattggtca agtttcggaa taaacatcgg gaaagcaggg      360
gatacaatcg gaatatttga ccttgtatcc ttgaaagccc tggacggcgt acttccagat      420
ggagtatcgg atgcttccag aaccagcgca gatgacaaat ggttgccttt gtatctactt      480
ggcttataca gagtgggcag aacacaaatg cctgaataca gaaaaaagct catggatggg      540
ctgacaaatc aatgcaaaat gatcaatgaa cagtttgaac ctcttgtgcc agaaggtcgt      600
gacatttttg atgtgtgggg aaatgacagt aattacacaa aaattgtcgc tgcagtggac      660
atgttcttcc acatgttcaa aaaacatgaa tgtgcctcgt tcagatacgg aactattgtt      720
tccagattca aagattgtgc tgcattggca acatttggac acctctgcaa aataaccgga      780
atgtctacag aagatgtaac gacctggatc ttgaaccgag aagttgcaga tgaaatggtc      840
caaatgatgc ttccaggcca agaaattgac aaggccgatt catacatgcc ttatttgatc      900
gactttggat tgtcttctaa gtctccatat tcttccgtca aaaaccctgc cttccacttc      960
tgggggcaat tgacagctct tctgctcaga tccaccagag caaggaatgc ccgacagcct     1020
gatgacattg agtatacatc tcttactaca gcaggtttgt tgtacgctta tgcagtagga     1080
tcctctgccg acttggcaca acagttttgt gttggagata caaatacac tccagatgat     1140 agtaccggag gattgacgac taatgcaccg ccacaaggca gagatgtggt cgaatggctc     1200
ggatggtttg aagatcaaaa cagaaaaccg actcctgata tgatgcagta tgcgaaaaga     1260
gcagtcatgt cactgcaagg cctaagagag aagacaattg gcaagtatgc taagtcagaa     1320
tttgacaaat gaccctataa ttctcagatc acctattata tattatgcta catatgaaaa     1380
aaactaacag atatcatgga taatctcaca aaagttcgtg agtatctcaa gtcctattct     1440
cgtctggatc aggcggtagg agagatagat gagatcgaag cacaacgagc tgaaaagtcc     1500
aattatgagt tgttccaaga ggatggagtg aagagcata ctaagccctc ttattttcag     1560
gcagcagatg attctgacac agaatctgaa ccagaaattg aagacaatca aggtttgtat     1620
gcaccagatc cagaagctga gcaagttgaa ggctttatac aggggccttt agatgactat     1680
gcagatgagg aagtggatgt tgtatttact tcggactgga acagcctga gcttgaatct     1740 gacgagcatg gaaagacctt acggttgaca tcgccagagg gtttaagtgg agagcagaaa     1800
tcccagtggc tttcgacgat taaagcagtc gtgcaaagtg ccaaatactg gaatctggca     1860
gagtgcacat ttgaagcatc gggagaaggg gtcattatga aggagcgcca gataactccg     1920
gatgtatata aggtcactcc agtgatgaac acacatccgt cccaatcaga agcagtatca     1980
gatgtttggt ctctctcaaa gacatccatg actttccaac ccaagaaagc aagtcttcag     2040
cctctcacca tatccttgga tgaattgttc tcatctagag gagagttcat ctctgtcgga     2100
ggtgacggac gaatgtctca taagaggcc atcctgctcg gcctgagata caaaaagttg     2160
tacaatcagg cgagagtcaa atattctctg tagactatga aaaaagtaa cagatatcac     2220 gatctaagtg ttatcccaat ccattcatca tgagttcctt aaagaagatt ctcggtctga     2280
aggggaaagg taagaaatct aagaaattag ggatcgcacc accccttat gaagaggaca     2340 ctagcatgga gtatgctccg agcgctccaa ttgacaaatc ctattttgga gttgacgaga     2400
tggacaccta tgatccgaat caattaagat atgagaaatt cttctttaca gtgaaaatga     2460
cggttagatc taatcgtccg ttcagaacat actcagatgt ggcagccgct gtatcccatt     2520
```

```
gggatcacat gtacatcgga atggcaggga aacgtccctt ctacaaaatc ttggcttttt    2580
tgggttcttc taatctaaag gccactccag cggtattggc agatcaaggt caaccagagt    2640
atcacactca ctgcgaaggc agggcttatt tgccacatag gatggggaag acccctccca    2700
tgctcaatgt accagagcac ttcagaagac cattcaatat aggtctttac aagggaacga    2760
ttgagctcac aatgaccatc tacgatgatg agtcactgga agcagctcct atgatctggg    2820
atcatttcaa ttcttccaaa ttttctgatt tcagagagaa ggccttaatg tttggcctga    2880
ttgtcgagaa aaaggcatct ggagcgtggg tcctggattc tatcagccac ttcaaatgag    2940
ctagtctaac ttctagcttc tgaacaatcc ccggtttact cagtctctcc taattccagc    3000
ctctcgaaca actaatatcc tgtcttttct atccctatga aaaaaactaa cagagatcga    3060
tctgtttacg cgtcactatg aagtgccttt tgtacttagc cttttttatto attggggtga    3120 attgcaagtt caccatagtt tttccacaca accaaaaagg aaactggaaa aatgttcctt    3180
ctaattacca ttattgcccg tcaagctcag atttaaattg gcataatgac ttaataggca    3240
cagccataca agtcaaaatg cccaagagtc acaaggctat tcaagcagac ggttggatgt    3300
gtcatgcttc caaatgggtc actacttgtg atttccgctg gtatggaccg aagtatataa    3360
cacagtccat ccgatccttc actccatctg tagaacaatg caaggaaagc attgaacaaa    3420
cgaaacaagg aacttggctg aatccaggct tccctcctca aagttgtgga tatgcaactg    3480
tgacggatgc cgaagcagtg attgtccagg tgactcctca ccatgtgctg gttgatgaat    3540
acacaggaga atgggttgat tcacagttca tcaacgaaaa atgcagcaat tacatatgcc    3600
ccactgtcca taactctaca acctggcatt ctgactataa ggtcaaaggg ctatgtgatt    3660
ctaacctcat ttccatggac atcaccttct tctcagagga cggagagcta tcatccctgg    3720
gaaaggaggg cacagggttc agaagtaact actttgctta tgaaactgga ggcaaggcct    3780
gcaaaatgca atactgcaag cattgggag tcagactccc atcaggtgtc tggttcgaga    3840
tggctgataa ggatctcttt gctgcagcca gattccctga atgcccagaa gggtcaagta    3900
tctctgctcc atctcagacc tcagtggatg taagtctaat tcaggacgtt gagaggatct    3960
tggattattc cctctgccaa gaaacctgga gcaaaatcag agcgggtctt ccaatctctc    4020
cagtggatct cagctatctt gctcctaaaa acccaggaac cggtcctgct ttcaccataa    4080
tcaatggtac cctaaaatac tttgagacca gatacatcag agtcgatatt gctgctccaa    4140
tcctctcaag aatggtcgga atgatcagtg gaactaccac agaaagggaa ctgtgggatg    4200
actgggcacc atatgaagac gtggaaattg gacccaatgg agttctgagg accagttcag    4260
gatataagtt tccttatac atgattggac atggtatgtt ggactccgat cttcatctta    4320
gctcaaaggc tcaggtgttc gaacatcctc acattcaaga cgctgcttcg caacttcctg    4380
atgatgagag tttatttttt ggtgatactg gctatccaa aaatccaatc gagcttgtag    4440
aaggttggtt cagtagttgg aaaagctcta ttgcctcttt tttctttatc ataggggttaa    4500 tcattggact attcttggtt ctccgagttg gtatccatct ttgcattaaa ttaaagcaca    4560
ccaagaaaag acagatttat acagacatag agatgaaccg acttggaaag taactcaaat    4620
cctgctaggt atgaaaaaaa ctaacagata tcacgctcga gcgtacgcca ccatgttcgt    4680
gtttctggtg ctgctgcctc tggtgagctc ccagtgcgtg aacttcacca caaggaccca    4740
gctgccccct gcctatacca attccttcac acgggcgtg tactatcccg acaaggtgtt    4800
ccggagcagc gtgctgcact ccacacagga tctgtttctg cctttctttt ctaacgtgac    4860
```

```
ctggttccac gccatccacg tgagcggcac caatggcaca aagcggttcg ccaatccagt    4920 gctgccctttt aacgatggcg tgtacttcgc ctccaccgag aagtctaaca tcatcagagg   4980 ctggatctttt ggcaccacac tggacagcaa gacacagtcc ctgctgatcg tgaacaatgc   5040
caccaacgtg gtcatcaagg tgtgcgagtt ccagttttgt aatgatccat tcctgggcgt    5100
gtactatcac aagaacaata agtcttggat ggagagcgag tttcgcgtgt attcctctgc   5160
caacaattgc acatttgagt acgtgtccca gcccttcctg atggacctgg agggcaagca   5220
gggcaatttc aagaacctga gggagttcgt gtttaagaat atcgatggct acttcaaaat   5280
ctactccaag cacacccaa tcaacctggt gcgcggcctg ccacagggct tctctgccct    5340
ggagccactg gtggatctgc ccatcggcat caacatcacc cggtttcaga cactgctggc   5400
cctgcacaga agctacctga caccaggcga cagctcctct ggatggaccg caggagcagc   5460
agcctactat gtgggctatc tgcagcccag gaccttcctg ctgaagtaca cgagaatgg   5520 caccatcaca gacgccgtgg attgcgccct ggatcccctg tctgagacca agtgtacact   5580
gaagagcttt accgtggaga agggcatcta tcagacaagc aatttcaggg tgcagcctac   5640
cgagtccatc gtgcgctttc ccaatatcac aaacctgtgc cctttggcg aggtgttcaa    5700 cgcaacccgc ttcgccagcg tgtacgcctg gaataggaag cgcatctcca actgcgtggc   5760
cgactattct gtgctgtaca acagcgcctc cttctctacc tttaagtgct atggcgtgag   5820
ccccacaaag ctgaatgacc tgtgctttac caacgtgtac gccgattcct tcgtgatcag   5880
gggcgacgag gtgcgccaga tcgcaccagg acagacaggc aatatcgcag actacaatta   5940
taagctgcct gacgatttca ccggctgcgt gatcgcctgg aactctaaca atctggatag   6000
caaagtgggc ggcaactaca attatctgta ccggctgtttt agaaagtcta atctgaagcc   6060
attcgagagg gacatctcca cagaaatcta ccaggccggc tctacccct gcaatggcgt    6120 gaagggctttt aactgttatt tccctctgca gagctacggc ttccagccaa catatggcgt   6180
gggctatcag ccctaccgcg tggtggtgct gtcttttgag ctgctgcacg cacctgcaac   6240
agtgtgcgga ccaaagaaga gcaccaatct ggtgaagaac aagtgcgtga acttcaactt   6300
caacggactg accggaacag gcgtgctgac cgagtccaac aagaagttcc tgccttttca   6360
gcagttcggc agggacatcg cagataccac agacgccgtg cgcgaccctc agaccctgga   6420
gatcctggac atcaccacat gctccttcgg cggcgtgtct gtgatcacac caggcaccaa   6480
tacaagcaac caggtggccg tgctgtatca gggcgtgaat tgtaccgagg tgccagtggc   6540
aatccacgca gatcagctga cccctacatg gcgggtgtac tctaccggca gcaacgtgtt   6600
ccagacaaga gccggatgcc tgatcggagc agagcacgtg aacaatagct atgagtgcga   6660
catccctatc ggcgccggca tctgtgcctc ctaccagacc cagacaaact ccccagaatc   6720
aagcgtgatt cctctggtcc atccactggc agatccctcc acagtgttca agacggaga    6780 tgaggccgaa gactttgtgg aagtccacct gcctgatgtg cataaccagg tgtctggcgt   6840
cgacctggga ctgccaaatt ggggcaagta cgtgctgctg agtgctggag cactgactgc   6900
cctgatgctg atcatttttcc tgatgacctg ctgtcggcgc gtgaacagaa gtgagcccac   6960
tcagcacaat ctgcgaggaa ccgggagaga agtgtcagtc acacctcaga gcggaaaat    7020 cattagtagt tgggaatcac ataaaagcgg gggcgagacc aggctgtgag ctagccagat   7080
tcttcatgtt tggaccaaat caacttgtga taccatgctc aaagaggcct caattatatt   7140
tgagttttta attttatga aaaaaactaa cagcaatcat ggaagtccac gattttgaga   7200
ccgacgagtt caatgatttc aatgaagatg actatgccac aagagaattc ctgaatcccg   7260
```

```
atgagcgcat gacgtacttg aatcatgctg attacaattt gaattctcct ctaattagtg    7320
atgatattga caatttgatc aggaaattca attctcttcc gattccctcg atgtgggata    7380
gtaagaactg ggatggagtt cttgagatgt taacatcatg tcaagccaat cccatctcaa    7440
catctcagat gcataaatgg atgggaagtt ggttaatgtc tgataatcat gatgccagtc    7500
aagggtatag tttttacat gaagtggaca agaggcaga ataacatttt gacgtggtgg      7560
agaccttcat ccgcggctgg ggcaacaaac caattgaata catcaaaaag gaaagatgga    7620
ctgactcatt caaaattctc gcttatttgt gtcaaaagtt tttggactta cacaagttga    7680
cattaatctt aaatgctgtc tctgaggtgg aattgctcaa cttggcgagg actttcaaag    7740
gcaaagtcag aagaagttct catggaacga acatatgcag gattagggtt cccagcttgg    7800
gtcctacttt tatttcagaa ggatgggctt acttcaagaa acttgatatt ctaatggacc    7860
gaaactttct gttaatggtc aaagatgtga ttatagggag gatgcaaacg gtgctatcca    7920
tggtatgtag aatagacaac ctgttctcag agcaagacat cttctccctt ctaaatatct    7980
acagaattgg agataaaatt gtggagaggc agggaaattt ttcttatgac ttgattaaaa    8040
tggtggaacc gatatgcaac ttgaagctga tgaaattagc aagagaatca aggcctttag    8100
tcccacaatt ccctcatttt gaaaatcata tcaagacttc tgttgatgaa ggggcaaaaa    8160
ttgaccgagg tataagattc ctccatgatc agataatgag tgtgaaaaca gtggatctca    8220
cactggtgat ttatggatcg ttcagacatt ggggtcatcc ttttatagat tattacactg    8280
gactagaaaa attacattcc caagtaacca tgaagaaaga tattgatgtg tcatatgcaa    8340
aagcacttgc aagtgattta gctcggattg ttctatttca acagttcaat gatcataaaa    8400
agtggttcgt gaatggagac ttgctccctc atgatcatcc cttttaaagt catgttaaag    8460
aaaatacatg gcccacagct gctcaagttc aagattttgg agataaatgg catgaacttc    8520
cgctgattaa atgttttgaa atacccgact tactagaccc atcgataata tactctgaca    8580
aaagtcattc aatgaatagg tcagaggtgt tgaaacatgt ccgaatgaat ccgaacactc    8640
ctatccctag taaaaaggtg ttgcagacta tgttggacac aaaggctacc aattggaaag    8700
aatttcttaa agagattgat gagaagggct tagatgatga tgatctaatt attggtctta    8760
aaggaaagga gagggaactg aagttggcag gtagattttt ctccctaatg tcttggaaat    8820
tgcgagaata ctttgtaatt accgaatatt tgataaagac tcatttcgtc cctatgttta    8880
aaggcctgac aatggcggac gatctaactg cagtcattaa aaagatgtta gattcctcat    8940
ccggccaagg attgaagtca tatgaggcaa tttgcatagc caatcacatt gattacgaaa    9000
aatggaataa ccaccaaagg aagttatcaa acggcccagt gttccgagtt atgggccagt    9060
tcttaggtta tccatcctta atcgagagaa ctcatgaatt ttttgagaaa agtcttatat    9120
actacaatgg aagaccagac ttgatgcgtg ttcacaacaa cacactgatc aattcaacct    9180
cccaacgagt tgttggcaa ggacaagagg gtggactgga aggtctacgg caaaaaggat     9240
ggactatcct caatctactg gttattcaaa gagaggctaa aatcagaaac actgctgtca    9300
aagtcttggc acaaggtgat aatcaagtta tttgcacaca gtataaaacg aagaaatcga    9360
gaaacgttgt agaattacag ggtgctctca atcaaatggt ttctaataat gagaaaatta    9420
tgactgcaat caaaataggg acagggaagt taggacttttt gataaatgac gatgagacta    9480
tgcaatctgc agattacttg aattatgaaa aaataccgat tttccgtgga gtgattagag    9540
ggttagagac caagagatgg tcacgagtga cttgtgtcac caatgaccaa atacccactt    9600
```

-continued

```
gtgctaatat aatgagctca gtttccacaa atgctctcac cgtagctcat tttgctgaga    9660
acccaatcaa tgccatgata cagtacaatt attttgggac atttgctaga ctcttgttga    9720
tgatgcatga tcctgctctt cgtcaatcat tgtatgaagt tcaagataag ataccgggct    9780
tgcacagttc tactttcaaa tacgccatgt tgtatttgga cccttccatt ggaggagtgt    9840
cgggcatgtc tttgtccagg tttttgatta gagccttccc agatcccgta acagaaagtc    9900
tctcattctg gagattcatc catgtacatg ctcgaagtga gcatctgaag gagatgagtg    9960
cagtatttgg aaaccccgag atagccaagt ttcgaataac tcacatagac aagctagtag   10020
aagatccaac ctctctgaac atcgctatgg gaatgagtcc agcgaacttg ttaaagactg   10080
aggttaaaaa atgcttaatc gaatcaagac aaaccatcag gaaccaggtg attaaggatg   10140
caaccatata tttgtatcat gaagaggatc ggctcagaag tttcttatgg tcaataaatc   10200
ctctgttccc tagatttta agtgaattca aatcaggcac ttttttggga gtcgcagacg    10260
ggctcatcag tctatttcaa aattctcgta ctattcggaa ctcctttaag aaaaagtatc   10320
ataggaatt ggatgatttg attgtgagga gtgaggtatc ctctttgaca catttaggga   10380
aacttcattt gagaagggga tcatgtaaaa tgtggacatg ttcagctact catgctgaca   10440
cattaagata caaatcctgg ggccgtacag ttattgggac aactgtaccc catccattag   10500
aaatgttggg tccacaacat cgaaaagaga ctccttgtgc accatgtaac acatcagggt   10560
tcaattatgt ttctgtgcat tgtccagacg ggatccatga cgtctttagt tcacgggggac   10620
cattgcctgc ttatctaggg tctaaaacat ctgaatctac atctattttg cagccttggg   10680
aaagggaaag caaagtccca ctgattaaaa gagctcacg tcttagagat gctatctctt   10740
ggtttgttga acccgactct aaactagcaa tgactatact ttctaacatc cactcttta   10800
caggcgaaga atggaccaaa aggcagcatg ggttcaaaag aacagggtct gcccttcata   10860
ggttttcgac atctcggatg agccatggtg ggttcgcatc tcagagcact gcagcattga   10920
ccaggttgat ggcaactaca gacaccatga gggatctggg agatcagaat ttcgactttt   10980
tattccaagc aacgttgctc tatgctcaaa ttaccaccac tgttgcaaga gacggatgga   11040
tcaccagttg tacagatcat tatcatattg cctgtaagtc ctgtttgaga cccatagaag   11100
agatcaccct ggactcaagt atggactaca cgcccccaga tgtatcccat gtgctgaaga   11160
catggaggaa tggggaaggt tcgtggggac aagagataaa acagatctat cctttagaag   11220
ggaattggaa gaatttagca cctgctgagc aatcctatca agtcggcaga tgtataggtt   11280
ttctatatgg agacttggcg tatagaaaat ctactcatgc cgaggacagt tctctatttc   11340
ctctatctat acaaggtcgt attagaggtc gaggtttctt aaaagggttg ctagacggat   11400
taatgagagc aagttgctgc caagtaatac accggagaag tctggctcat ttgaagaggc   11460
cggccaacgc agtgtacgga ggtttgattt acttgattga taaattgagt gtatcacctc   11520
cattcctttc tcttactaga tcaggaccta ttagagacga attagaaacg attccccaca   11580
agatcccaac ctcctatccg acaagcaacc gtgatatggg ggtgattgtc agaaattact   11640
tcaaatacca atgccgtcta attgaaaagg gaaaatacag atcacattat tcacaattat   11700
ggttattctc agatgtctta tccatagact tcattggacc attctctatt tccaccaccc   11760
tcttgcaaat cctatacaag ccatttttat ctgggaaaga taagaatgag ttgagagagc   11820
tggcaaatct ttcttcattg ctaagatcag gagaggggtg ggaagacata catgtgaaat   11880
tcttcaccaa ggacatatta ttgtgtccag aggaaatcag acatgcttgc aagttcggga   11940
ttgctaagga taataataaa gacatgagct atccccttg gggaagggaa tccagaggga   12000
```

```
caattacaac aatccctgtt tattatacga ccaccccttaa cccaaagatg ctagagatgc    12060
ctccaagaat ccaaaatccc ctgctgtccg gaatcaggtt gggccaatta ccaactggcg    12120
ctcattataa aattcggagt atattacatg gaatgggaat ccattacagg gacttcttga    12180
gttgtggaga cggctccgga gggatgactg ctgcattact acgagaaaat gtgcatagca    12240
gaggaatatt caatagtctg ttagaattat cagggtcagt catgcgaggc gcctctcctg    12300 agcccccag tgccctagaa actttaggag gagataaatc gagatgtgta aatggtgaaa    12360
catgttggga atatccatct gacttatgtg acccaaggac ttgggactat ttcctccgac    12420
tcaaagcagg cttggggctt caaattgatt taattgtaat ggatatggaa gttcgggatt    12480
cttctactag cctgaaaatt gagacgaatg ttagaaatta tgtgcaccgg attttggatg    12540
agcaaggagt tttaatctac aagacttatg aacatatat ttgtgagagc gaaaagaatg    12600
cagtaacaat ccttggtccc atgttcaaga cggtcgactt agttcaaaca gaatttagta    12660
gttctcaaac gtctgaagta tatatggtat gtaaaggttt gaagaaatta atcgatgaac    12720
ccaatcccga ttggtcttcc atcaatgaat cctggaaaaa cctgtacgca ttccagtcat    12780
cagaacagga atttgccaga gcaaagaagg ttagtacata ctttaccttg acaggtattc    12840
cctcccaatt cattcctgat cctttttgtaa acattgagac tatgctacaa atattcggag    12900
tacccacggg tgtgtctcat gcggctgcct taaaatcatc tgatagacct gcagatttat    12960
tgaccattag ccttttttat atggcgatta tatcgtatta taacatcaat catatcagag    13020
taggaccgat acctccgaac cccccatcag atggaattgc acaaaatgtg gggatcgcta    13080
taactggtat aagcttttgg ctgagtttga tggagaaaga cattccacta tatcaacagt    13140
gtttagcagt tatccagcaa tcattcccga ttaggtggga ggctgtttca gtaaaaggag    13200
gatacaagca gaagtggagt actagaggtg atgggctccc aaaagatacc cgaacttcag    13260
actccttggc cccaatcggg aactggatca gatctctgga attggtccga aaccaagttc    13320
gtctaaatcc attcaatgag atcttgttca atcagctatg tcgtacagtg ataatcatt    13380 tgaaatggtc aaatttgcga agaaacacag gaatgattga atggatcaat agacgaattt    13440
caaaagaaga ccggtctata ctgatgttga agagtgacct acacgaggaa aactcttgga    13500
gagattaaaa aatcatgagg agactccaaa ctttaagtat gaaaaaact ttgatcctta    13560 agaccctctt gtggttttta ttttttatct ggttttgtgg tcttcgt                  13607
```

<210> SEQ ID NO 22
<211> LENGTH: 13506
<212> TYPE: DNA
<213> ORGANISM: Artificial Sequence
<220> FEATURE:
<223> OTHER INFORMATION: VSV vector: Convac V3 China

<400> SEQUENCE: 22

```
acgaagacaa acaaaccatt attatcatta aaaggctcag gagaaacttt aacagtaatc      60
aaaatgtctg ttacagtcaa gagaatcatt gacaacacag tcatagttcc aaaacttcct     120
gcaaatgagg atccagtgga ataccccggca gattacttca gaaaatcaaa ggagattcct     180
ctttacatca atactacaaa aagtttgtca gatctaagag gatatgtcta ccaaggcctc     240
aaatccggaa atgtatcaat catacatgtc aacagctact gtatggagc attaaaggac     300 atccgggta agttggataa agattggtca agtttcggaa taaacatcgg gaaagcaggg     360
gatacaatcg gaatatttga cctttgtatcc ttgaaagccc tggacggcgt acttccagat     420
```

-continued

```
ggagtatcgg atgcttccag aaccagcgca gatgacaaat ggttgccttt gtatctactt    480
ggcttataca gagtgggcag aacacaaatg cctgaataca gaaaaaagct catggatggg    540
ctgacaaatc aatgcaaaat gatcaatgaa cagtttgaac ctcttgtgcc agaaggtcgt    600 gacattttg atgtgtgggg aaatgacagt aattacacaa aaattgtcgc tgcagtggac    660
atgttcttcc acatgttcaa aaacatgaa tgtgcctcgt tcagatacgg aactattgtt    720
tccagattca aagattgtgc tgcattggca acatttggac acctctgcaa ataaccgga    780 atgtctacag aagatgtaac gacctggatc ttgaaccgag aagttgcaga tgaaatggtc    840
caaatgatgc ttccaggcca agaaattgac aaggccgatt catacatgcc ttatttgatc    900
gactttggat tgtcttctaa gtctccatat tcttccgtca aaaaccctgc cttccacttc    960
tgggggcaat tgacagctct tctgctcaga tccaccagag caaggaatgc ccgacagcct   1020
gatgacattg agtatacatc tcttactaca gcaggtttgt tgtacgctta tgcagtagga   1080
tcctctgccg acttggcaca acagttttgt gttggagata caaatacac tccagatgat   1140 agtaccggag gattgacgac taatgcaccg ccacaaggca gagatgtggt cgaatggctc   1200
ggatggtttg aagatcaaaa cagaaaaccg actcctgata tgatgcagta tgcgaaaaga   1260
gcagtcatgt cactgcaagg cctaagagag aagacaattg caagtatgc taagtcagaa    1320 tttgacaaat gaccctataa ttctcagatc acctattata tattatgcta catatgaaaa   1380
aaactaacag atatcatgga taatctcaca aaagttcgtg agtatctcaa gtcctattct   1440
cgtctggatc aggcggtagg agagatagat gagatcgaag cacaacgagc tgaaaagtcc   1500
aattatgagt tgttccaaga ggatggagtg aagagcata ctaagccctc ttattttcag    1560
gcagcagatg attctgacac agaatctgaa ccagaaattg aagacaatca aggtttgtat   1620
gcaccagatc cagaagctga gcaagttgaa ggctttatac aggggccttt agatgactat   1680
gcagatgagg aagtggatgt tgtatttact tcggactgga aacagcctga gcttgaatct   1740
gacgagcatg aaagacctt acggttgaca tcgccagagg gtttaagtgg agagcagaaa    1800
tcccagtggc tttcgacgat taaagcagtc gtgcaaagtg ccaaatactg gaatctggca   1860
gagtgcacat ttgaagcatc gggagaaggg gtcattatga aggagcgcca gataactccg   1920
gatgtatata aggtcactcc agtgatgaac acacatccgt cccaatcaga agcagtatca   1980
gatgtttggt ctctctcaaa gacatccatg actttccaac ccaagaaagc aagtcttcag   2040
cctctcacca tatccttgga tgaattgttc tcatctagag gagagttcat ctctgtcgga   2100
ggtgacggac gaatgtctca taagaggcc atcctgctcg gcctgagata caaaagttg     2160 tacaatcagg cgagagtcaa atattctctg tagactatga aaaaaagtaa cagatatcac   2220
gatctaagtg ttatcccaat ccattcatca tgagttcctt aaagaagatt ctcggtctga   2280
aggggaaagg taagaaatct aagaaattag ggatcgcacc acccccttat gaagaggaca   2340
ctagcatgga gtatgctccg agcgctccaa ttgacaaatc ctattttgga gttgacgaga   2400
tggacaccta tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga acgtcccctt ctacaaaatc ttggcttttt   2580
tgggttcttc taatctaaag gccactccag cggtattggc agatcaaggt caaccagagt   2640
atcacactca ctgcgaaggc agggcttatt tgccacatag gatggggaag accccctccca  2700 tgctcaatgt accagagcac ttcagaagac cattcaatat aggtctttac aagggaacga   2760
ttgagctcac aatgaccatc tacgatgatg agtcactgga agcagctcct atgatctggg   2820
```

```
atcatttcaa ttcttccaaa ttttctgatt tcagagagaa ggccttaatg tttggcctga    2880
ttgtcgagaa aaaggcatct ggagcgtggg tcctggattc tatcagccac ttcaaatgag    2940
ctagtctaac ttctagcttc tgaacaatcc ccggtttact cagtctctcc taattccagc    3000
ctctcgaaca actaatatcc tgtcttttct atccctatga aaaaaactaa cagagatcga    3060
tctgtttacg cgtcactatg aagtgccttt tgtacttagc cttttttattc attggggtga    3120 attgcaagtt caccatagtt tttccacaca accaaaaagg aaactggaaa aatgttcctt    3180
ctaattacca ttattgcccg tcaagctcag atttaaattg gcataatgac ttaataggca    3240
cagccataca agtcaaaatg cccaagagtc acaaggctat tcaagcagac ggttggatgt    3300
gtcatgcttc caaatgggtc actacttgtg atttccgctg gtatggaccg aagtatataa    3360
cacagtccat ccgatccttc actccatctg tagaacaatg caaggaaagc attgaacaaa    3420
cgaaacaagg aacttggctg aatccaggct cccctcctca aagttgtgga tatgcaactg    3480
tgacggatgc cgaagcagtg attgtccagg tgactcctca ccatgtgctg gttgatgaat    3540
acacaggaga atgggttgat tcacagttca tcaacggaaa atgcagcaat tacatatgcc    3600
ccactgtcca taactctaca acctggcatt ctgactataa ggtcaaaggg ctatgtgatt    3660
ctaacctcat ttccatggac atcaccttct tctcagagga cggagagcta tcatccctgg    3720
gaaaggaggg cacagggttc agaagtaact actttgctta tgaaactgga ggcaaggcct    3780
gcaaaatgca atactgcaag cattggggag tcagactccc atcaggtgtc tggttcgaga    3840
tggctgataa ggatctcttt gctgcagcca gattccctga atgcccagaa gggtcaagta    3900
tctctgctcc atctcagacc tcagtggatg taagtctaat tcaggacgtt gagaggatct    3960
tggattattc cctctgccaa gaaacctgga gcaaaatcag agcgggtctt ccaatctctc    4020
cagtggatct cagctatctt gctcctaaaa acccaggaac cggtcctgct ttcaccataa    4080
tcaatggtac cctaaaatac tttgagacca gatacatcag agtcgatatt gctgctccaa    4140
tcctctcaag aatggtcgga atgatcagtg gaactaccac agaaagggaa ctgtgggatg    4200
actgggcacc atatgaagac gtggaaattg gacccaatgg agttctgagg accagttcag    4260
gatataagtt tccctttatac atgattggac atggtatgtt ggactccgat cttcatctta    4320
gctcaaaggc tcaggtgttc gaacatcctc acattcaaga cgctgcttcg caacttcctg    4380
atgatgagag tttatttttt ggtgatactg ggctatccaa aaatccaatc gagccttgtag    4440 aaggttggtt cagtagttgg aaaagctcta ttgcctcttt tttcttttatc atagggttaa    4500 tcattggact attcttggtt ctccgagttg gtatccatct ttgcattaaa ttaaagcaca    4560
ccaagaaaag acagatttat acagacatag agatgaaccg acttggaaag taactcaaat    4620
cctgctaggt atgaaaaaaa ctaacagata tcacgctcga ggccaccatg ttcgtgtttc    4680
tggtgctgct gcctctggtg agctcccagt gcgtgaacct gaccacaagg acccagctgc    4740
cccctgccta taccaattcc ttcacacggg gcgtgtacta tccgacaag gtgttccgga    4800 gcagcgtgct gcactccaca caggatctgt ttctgccttt cttttctaac gtgacctggt    4860
tccacgccat ccacgtgagc ggcaccaatg gcacaaagcg gttcgacaat ccagtgctgc    4920
cctttaacga tggcgtgtac ttcgcctcca ccgagaagtc taacatcatc agaggctgga    4980
tctttggcac cacactggac agcaagacac agtccctgct gatcgtgaac aatgccacca    5040
acgtggtcat caaggtgtgc gagttccagt tttgtaatga tccattcctg ggcgtgtact    5100
atcacaagaa caataagtct tggatggaga gcgagtttcg cgtgtattcc tctgccaaca    5160
```

```
attgcacatt tgagtacgtg tcccagccct tcctgatgga cctggagggc aagcagggca    5220
atttcaagaa cctgagggag ttcgtgttta agaatatcga tggctacttc aaaatctact    5280
ccaagcacac cccaatcaac ctggtgcgcg acctgccaca gggcttctct gccctggagc    5340
cactggtgga tctgcccatc ggcatcaaca tcacccggtt tcagacactg ctggccctgc    5400
acagaagcta cctgacacca ggcgacagct cctctggatg gaccgcagga gcagcagcct    5460
actatgtggg ctatctgcag cccaggacct tcctgctgaa gtacaacgag aatggcacca    5520
tcacagacgc cgtggattgc gccctggatc ccctgtctga gaccaagtgt acactgaaga    5580
gctttaccgt ggagaagggc atctatcaga caagcaattt cagggtgcag cctaccgagt    5640
ccatcgtgcg ctttcccaat atcacaaacc tgtgcccttt ggcgaggtg ttcaacgcaa    5700 cccgcttcgc cagcgtgtac gcctggaata ggaagcgcat ctccaactgc gtggccgact    5760
attctgtgct gtacaacagc gcctccttct ctacctttaa gtgctatggc gtgagcccca    5820
caaagctgaa tgacctgtgc tttaccaacg tgtacgccga ttccttcgtg atcaggggcg    5880
acgaggtgcg ccagatcgca ccaggacaga caggcaagat cgcagactac aattataagc    5940
tgcctgacga tttcaccggc tgcgtgatcg cctggaactc taacaatctg atagcaaag    6000 tgggcggcaa ctacaattat ctgtaccggc tgtttagaaa gtctaatctg aagccattcg    6060
agagggacat ctccacagaa atctaccagg ccggctctac ccctgcaat ggcgtggagg    6120 gctttaactg ttatttccct ctgcagagct acggcttcca ccaacaaac ggcgtgggct    6180 atcagcccta ccgcgtggtg gtgctgtctt ttgagctgct gcacgcacct gcaacagtgt    6240
gcggaccaaa gaagagcacc aatctggtga agaacaagtg cgtgaacttc aacttcaacg    6300
gactgaccgg aacaggcgtg ctgaccgagt ccaacaagaa gttcctgcct tttcagcagt    6360
tcggcaggga catcgcagat accacagacg ccgtgcgcga ccctcagacc ctggagatcc    6420
tggacatcac accatgctcc ttcggcggcg tgtctgtgat cacaccaggc accaatacaa    6480
gcaaccaggt ggccgtgctg tatcaggacg tgaattgtac cgaggtgcca gtggcaatcc    6540
acgcagatca gctgaccccc acatggcggg tgtactctac cggcagcaac gtgttccaga    6600
caagagccga atgcctgatc ggagcagagc acgtgaacaa tagctatgag tgcgacatcc    6660
ctatcggcgc cggcatctgt gcctcctacc agacccagac aaaactcccca aggtctggat    6720 ccggctacat ccccgaggcc cccagagacg gccaggccta cgtgcggaag gacgcgagt    6780 gggtactgct cagcaccttc ctgggcagca gttggaaaag ctccatcgcc tcctttttct    6840
ttatcatcgg cctgatcatc ggactgttcc tggtgctccg cgtgggtatc cacctgtgca    6900
tcaagctgaa gcacaccaag aaaagacaga tttatacaga catcgagatg aaccgacttg    6960
gaaagtaagc tagccagatt cttcatgttt ggaccaaatc aacttgtgat accatgctca    7020
aagaggcctc aattatattt gagttttaa tttttatgaa aaaactaac agcaatcatg    7080 gaagtccacg attttgagac cgacgagttc aatgatttca atgaagatga ctatgccaca    7140
agagaattcc tgaatcccga tgagcgcatg acgtacttga atcatgctga ttacaatttg    7200
aattctcctc taattagtga tgatattgac aatttgatca ggaaattcaa ttctcttccg    7260
attccctcga tgtgggatag taagaactgg atgagttc ttgagatgtt aacatcatgt    7320
caagccaatc ccatctcaac atctcagatg cataaatgga tgggaagttg gttaatgtct    7380
gataatcatg atgccagtca agggtatagt ttttacatg aagtggacaa agaggcagaa    7440
ataacatttg acgtggtgga gaccttcatc cgcggctggg gcaacaaacc aattgaatac    7500
atcaaaaagg aaagatggac tgactcattc aaaattctcg cttatttgtg tcaaaagttt    7560
```

```
ttggacttac acaagttgac attaatctta aatgctgtct ctgaggtgga attgctcaac    7620
ttggcgagga ctttcaaagg caaagtcaga agaagttctc atggaacgaa catatgcagg    7680
attagggttc ccagcttggg tcctactttt atttcagaag gatgggctta cttcaagaaa    7740
cttgatattc taatggaccg aaactttctg ttaatggtca aagatgtgat tataggggag    7800
atgcaaacgg tgctatccat ggtatgtaga atagacaacc tgttctcaga gcaagacatc    7860 ttctccccttc taaatatcta cagaattgga gataaaattg tggagaggca gggaaatttt    7920
tcttatgact tgattaaaat ggtggaaccg atatgcaact gaagctgat gaaattagca     7980 agagaatcaa ggcctttagt cccacaattc cctcattttg aaaatcatat caagacttct    8040
gttgatgaag gggcaaaaat tgaccgaggt ataagattcc tccatgatca gataatgagt    8100
gtgaaaacag tggatctcac actggtgatt tatggatcgt tcagacattg gggtcatcct    8160
tttatagatt attacactgg actagaaaaa ttacattccc aagtaaccat gaagaaagat    8220
attgatgtgt catatgcaaa agcacttgca agtgatttag ctcggattgt tctatttcaa    8280
cagttcaatg atcataaaaa gtggttcgtg aatggagact gctccctca  tgatcatccc    8340 tttaaaagtc atgttaaaga aaatacatgg cccacagctg ctcaagttca agattttgga    8400
gataaatggc atgaacttcc gctgattaaa tgttttgaaa tacccgactt actagaccca    8460
tcgataatat actctgacaa aagtcattca atgaataggt cagaggtgtt gaaacatgtc    8520
cgaatgaatc cgaacactcc tatccctagt aaaaaggtgt tgcagactat gttggacaca    8580
aaggctacca attggaaaga atttcttaaa gagattgatg agaagggctt agatgatgat    8640
gatctaatta ttggtcttaa aggaaaggag agggaactga agttggcagg tagatttttc    8700
tccctaatgt cttggaaatt gcagagaatac tttgtaatta ccgaatattt gataaagact    8760
catttcgtcc ctatgtttaa aggcctgaca atggcggacg atctaactgc agtcattaaa    8820
aagatgttag attcctcatc cggccaagga ttgaagtcat atgaggcaat ttgcatagcc    8880
aatcacattg attacgaaaa atggaataac caccaaagga agttatcaaa cggcccagtg    8940
ttccgagtta tgggccagtt cttaggttat ccatccttaa tcgagagaac tcatgaattt    9000
tttgagaaaa gtcttatata ctacaatgga agaccagact tgatgcgtgt tcacaacaac    9060
acactgatca attcaacctc ccaacgagtt tgttggcaag gacaagaggg tggactggaa    9120
ggtctacggc aaaaaggatg gactatcctc aatctactgg ttattcaaag agaggctaaa    9180
atcagaaaca ctgctgtcaa agtcttggca caaggtgata tcaagttat ttgcacacag     9240 tataaaacga agaaatcgag aaacgttgta gaattacagg gtgctctcaa tcaaatggtt    9300
tctaataatg agaaaattat gactgcaatc aaaatagga cagggaagtt aggactttg     9360 ataaatgacg atgagactat gcaatctgca gattacttga attatggaaa ataccgatt    9420 ttccgtggag tgattagagg gttagagacc aagagatggt cacgagtgac ttgtgtcacc    9480
aatgaccaaa tacccacttg tgctaatata atgagctcag tttccacaaa tgctctcacc    9540
gtagctcatt ttgctgagaa cccaatcaat gccatgatac agtacaatta ttttgggaca    9600
tttgctagac tcttgttgat gatgcatgat cctgctcttc gtcaatcatt gtatgaagtt    9660
caagataaga taccgggctt gcacagttct actttcaaat acgccatgtt gtatttggac    9720
ccttccattg gaggagtgtc gggcatgtct ttgtccaggt ttttgattag agccttccca    9780
gatcccgtaa cagaaagtct ctcattctgg agattcatcc atgtacatgc tcgaagtgag    9840
catctgaagg agatgagtgc agtatttgga aaccccgaga tagccaagtt tcgaataact    9900
```

```
cacatagaca agctagtaga agatccaacc tctctgaaca tcgctatggg aatgagtcca    9960
gcgaacttgt taaagactga ggttaaaaaa tgcttaatcg aatcaagaca aaccatcagg   10020
aaccaggtga ttaaggatgc aaccatatat ttgtatcatg aagaggatcg gctcagaagt   10080
ttcttatggt caataaatcc tctgttccct agattttaa gtgaattcaa atcaggcact    10140
tttttgggag tcgcagacgg gctcatcagt ctatttcaaa attctcgtac tattcggaac   10200
tcctttaaga aaaagtatca tagggaattg gatgatttga ttgtgaggag tgaggtatcc   10260
tctttgacac atttagggaa acttcatttg agaaggggat catgtaaaat gtggacatgt   10320
tcagctactc atgctgacac attaagatac aaatcctggg gccgtacagt tattgggaca   10380
actgtacccc atccattaga aatgttgggt ccacaacatc gaaaagagac tccttgtgca   10440
ccatgtaaca catcagggtt caattatgtt tctgtgcatt gtccagacgg gatccatgac   10500
gtctttagtt cacggggacc attgcctgct tatctagggt ctaaaacatc tgaatctaca   10560
tctattttgc agccttggga aagggaaagc aaagtcccac tgattaaaag agctacacgt   10620
cttagagatg ctatctcttg gtttgttgaa cccgactcta aactagcaat gactatactt   10680
tctaacatcc actcttttaac aggcgaagaa tggaccaaaa ggcagcatgg gttcaaaaga   10740
acagggtctg cccttcatag gttttcgaca tctcggatga gccatggtgg gttcgcatct   10800
cagagcactg cagcattgac caggttgatg gcaactacag acaccatgag ggatctggga   10860
gatcagaatt tcgactttt attccaagca acgttgctct atgctcaaat taccaccact   10920
gttgcaagag acggatggat caccagttgt acagatcatt atcatattgc ctgtaagtcc   10980
tgtttgagac ccatagaaga gatcaccctg gactcaagta tggactacac gccccccagat  11040
gtatcccatg tgctgaagac atggaggaat ggggaaggtt cgtggggaca agagataaaa   11100
cagatctatc ctttagaagg gaattggaag aatttagcac ctgctgagca atcctatcaa   11160
gtcggcagat gtataggttt tctatatgga gacttggcgt atagaaaatc tactcatgcc   11220
gaggacagtt ctctatttcc tctatctata caaggtcgta ttagaggtcg aggtttctta   11280
aaagggttgc tagacggatt aatgagagca agttgctgcc aagtaataca ccggagaagt   11340
ctggctcatt tgaagaggcc ggccaacgca gtgtacggag gtttgattta cttgattgat   11400
aaattgagtg tatcacctcc attcctttct cttactagat caggacctat tagagacgaa   11460
ttagaaacga ttccccacaa gatcccaacc tcctatccga caagcaaccg tgatatgggg   11520
gtgattgtca gaaattactt caaataccaa tgccgtctaa ttgaaaaggg aaaatacaga   11580
tcacattatt cacaattatg gttattctca gatgtcttat ccatagactt cattggacca   11640
ttctctattt ccaccaccct cttgcaaatc ctatacaagc catttttatc tgggaaagat   11700
aagaatgagt tgagagagct ggcaaatctt tcttcattgc taagatcagg agaggggtgg   11760
gaagacatac atgtgaaatt cttccaccaag gacatattat tgtgtccaga ggaaatcaga   11820
catgcttgca agttcgggat tgctaaggat aataataaag acatgagcta tccccttgg    11880
ggaagggaat ccagagggac aattacaaca atccctgttt attatacgac caccccttac   11940
ccaaagatgc tagagatgcc tccaagaatc caaaatcccc tgctgtccgg aatcaggttg   12000
ggccaattac caactggcgc tcattataaa attcggagta tattcatgg aatgggaatc    12060
cattacaggg acttcttgag ttgtggagac ggctccggag ggatgactgc tgcattacta   12120
cgagaaaatg tgcatagcag aggaatattc aatagtctgt tagaattatc agggtcagtc   12180
atgcgaggcg cctctcctga gccccccagt gccctagaaa ctttaggagg agataaatcg   12240
agatgtgtaa atggtgaaac atgttgggaa tatccatctg acttatgtga cccaaggact   12300
```

```
tgggactatt tcctccgact caaagcaggc ttggggcttc aaattgattt aattgtaatg    12360
gatatggaag ttcgggattc ttctactagc ctgaaaattg agacgaatgt tagaaattat    12420
gtgcaccgga ttttggatga gcaaggagtt ttaatctaca agacttatgg aacatatatt    12480
tgtgagagcg aaaagaatgc agtaacaatc cttggtccca tgttcaagac ggtcgactta    12540
gttcaaacag aatttagtag ttctcaaacg tctgaagtat atatggtatg taaaggtttg    12600
aagaaattaa tcgatgaacc caatcccgat tggtcttcca tcaatgaatc ctggaaaaac    12660
ctgtacgcat tccagtcatc agaacaggaa tttgccagag caagaaggt tagtacatac    12720 tttaccttga caggtattcc ctcccaattc attcctgatc cttttgtaaa cattgagact    12780
atgctacaaa tattcggagt acccacgggt gtgtctcatg cggctgcctt aaaatcatct    12840
gatagacctg cagatttatt gaccattagc ctttttata tggcgattat atcgtattat    12900
aacatcaatc atatcagagt aggaccgata cctccgaacc ccccatcaga tggaattgca    12960
caaaatgtgg ggatcgctat aactggtata agcttttggc tgagtttgat ggagaaagac    13020
attccactat atcaacagtg tttagcagtt atccagcaat cattcccgat taggtgggag    13080
gctgtttcag taaaggagg atacaagcag aagtggagta ctagaggtga tgggctccca    13140
aaagataccc gaacttcaga ctccttggcc ccaatcggga actggatcag atctctggaa    13200
ttggtccgaa accaagttcg tctaaatcca ttcaatgaga tcttgttcaa tcagctatgt    13260
cgtacagtgg ataatcattt gaatggtca aatttgcgaa gaaacacagg aatgattgaa    13320
tggatcaata gacgaatttc aaaagaagac cggtctatac tgatgttgaa gagtgaccta    13380
cacgaggaaa actcttggag agattaaaaa atcatgagga gactccaaac tttaagtatg    13440
aaaaaaactt tgatccttaa gaccctcttg tggttttat ttttatctg gttttgtggt    13500 cttcgt                                                               13506
```

<210> SEQ ID NO 23
<211> LENGTH: 13503
<212> TYPE: DNA
<213> ORGANISM: Artificial Sequence
<220> FEATURE:
<223> OTHER INFORMATION: VSV vector: Convac V3 South Africa

<400> SEQUENCE: 23

```
acgaagacaa acaaaccatt attatcatta aaaggctcag gagaaacttt aacagtaatc      60
aaaatgtctg ttacagtcaa gagaatcatt gacaacacag tcatagttcc aaaacttcct     120
gcaaatgagg atccagtgga ataccggca gattacttca gaaaatcaaa ggagattcct     180
ctttacatca atactacaaa aagtttgtca gatctaagag gatatgtcta ccaaggcctc     240
aaatccggaa atgtatcaat catacatgtc aacagctact gtatggagc attaaaggac     300 atccggggta agttggataa agattggtca agtttcggaa taaacatcgg gaaagcaggg     360
gatacaatcg gaatatttga ccttgtatcc ttgaaagccc tggacggcgt acttccagat     420
ggagtatcgg atgcttccag aaccagcgca gatgacaaat ggttgccttt gtatctactt     480
ggcttataca gagtgggcag aacacaaatg cctgaataca gaaaaaagct catggatggg     540
ctgacaaatc aatgcaaaat gatcaatgaa cagtttgaac tcttgtgcc agaaggtcgt     600 gacatttttg atgtgtgggg aaatgacagt aattacacaa aaattgtcgc tgcagtggac     660
atgttcttcc acatgttcaa aaaacatgaa tgtgcctcgt tcagatacgg aactattgtt     720
tccagattca aagattgtgc tgcattggca acatttggac acctctgcaa aataaccgga     780
```

```
atgtctacag aagatgtaac gacctggatc ttgaaccgag aagttgcaga tgaaatggtc    840
caaatgatgc ttccaggcca agaaattgac aaggccgatt catacatgcc ttatttgatc    900
gactttggat tgtcttctaa gtctccatat tcttccgtca aaaaccctgc cttccacttc    960
tgggggcaat tgacagctct tctgctcaga tccaccagag caaggaatgc ccgacagcct   1020
gatgacattg agtatacatc tcttactaca gcaggtttgt tgtacgctta tgcagtagga   1080
tcctctgccg acttggcaca acagttttgt gttggagata caaatacac tccagatgat   1140
agtaccggag gattgacgac taatgcaccg ccacaaggca gagatgtggt cgaatggctc   1200
ggatggtttg aagatcaaaa cagaaaaccg actcctgata tgatgcagta tgcgaaaaga   1260
gcagtcatgt cactgcaagg cctaagagag aagacaattg gcaagtatgc taagtcagaa   1320
tttgacaaat gacccctataa ttctcagatc acctattata tattatgcta catatgaaaa   1380
aaactaacag atatcatgga taatctcaca aaagttcgtg agtatctcaa gtcctattct   1440
cgtctggatc aggcggtagg agagatagat gagatcgaag cacaacgagc tgaaaagtcc   1500
aattatgagt tgttccaaga ggatggagtg gaagagcata ctaagccctc ttattttcag   1560
gcagcagatg attctgacac agaatctgaa ccagaaattg aagacaatca aggtttgtat   1620
gcaccagatc cagaagctga gcaagttgaa ggctttatac aggggccttt agatgactat   1680
gcagatgagg aagtggatgt tgtatttact tcggactgga acagcctga gcttgaatct   1740
gacgagcatg aaaagacctt acggttgaca tcgccagagg gtttaagtgg agagcagaaa   1800
tcccagtggc tttcgacgat taaagcagtc gtgcaaagtg ccaaatactg gaatctggca   1860
gagtgcacat ttgaagcatc gggagaaggg gtcattatga aggagcgcca gataactccg   1920
gatgtatata aggtcactcc agtgatgaac acacatccgt cccaatcaga agcagtatca   1980
gatgtttggt ctctctcaaa gacatccatg actttccaac ccaagaaagc aagtcttcag   2040
cctctcacca tatccttgga tgaattgttc tcatctagag gagagttcat ctctgtcgga   2100
ggtgacggac gaatgtctca taaagaggcc atcctgctcg gcctgagata caaaaagttg   2160
tacaatcagg cgagagtcaa atattctctg tagactatga aaaaagtaa cagatatcac   2220
gatctaagtg ttatcccaat ccattcatca tgagttcctt aaagaagatt ctcggtctga   2280
aggggaaagg taagaaatct aagaaattag ggatcgcacc accccttat gaagaggaca   2340
ctagcatgga gtatgctccg agcgctccaa ttgacaaatc ctattttgga gttgacgaga   2400
tggacaccta tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga acgtcccctt ctacaaaatc ttggcttttt   2580
tgggttcttc taatctaaag gccactccag cggtattggc agatcaaggt caaccagagt   2640
atcacactca ctgcgaaggc agggcttatt tgccacatag gatggggaag acccctccca   2700
tgctcaatgt accagagcac ttcagaagac cattcaatat aggtctttac aagggaacga   2760
ttgagctcac aatgaccatc tacgatgatg agtcactgga agcagctcct atgatctggg   2820
atcatttcaa ttcttccaaa ttttctgatt tcagagagaa ggccttaatg tttggcctga   2880
ttgtcgagaa aaaggcatct ggagcgtggg tcctggattc tatcagccac ttcaaatgag   2940
ctagtctaac ttctagcttc tgaacaatcc ccggtttact cagtctctcc taattccagc   3000
ctctcgaaca actaatatcc tgtcttttct atccctatga aaaaaactaa cagagatcga   3060
tctgtttacg cgtcactatg aagtgccttt tgtacttagc cttttttattc attggggtga   3120
attgcaagtt caccatagtt tttccacaca accaaaaagg aaactggaaa aatgttccct   3180
```

```
ctaattacca ttattgcccg tcaagctcag atttaaattg cataatgac ttaataggca    3240
cagccataca agtcaaaatg cccaagagtc acaaggctat tcaagcagac ggttggatgt    3300
gtcatgcttc caaatgggtc actacttgtg atttccgctg gtatggaccg aagtatataa    3360
cacagtccat ccgatccttc actccatctg tagaacaatg caaggaaagc attgaacaaa    3420
cgaaacaagg aacttggctg aatccaggct tccctcctca aagttgtgga tatgcaactg    3480
tgacggatgc cgaagcagtg attgtccagg tgactcctca ccatgtgctg ttgatgaat    3540
acacaggaga atgggttgat tcacagttca tcaacggaaa atgcagcaat tacatatgcc    3600
ccactgtcca taactctaca acctggcatt ctgactataa ggtcaaaggg ctatgtgatt    3660
ctaacctcat ttccatggac atcaccttct tctcagagga cggagagcta tcatccctgg    3720
gaaaggaggg cacagggttc agaagtaact actttgctta tgaaactgga ggcaaggcct    3780
gcaaaatgca atactgcaag cattggggag tcagactccc atcaggtgtc tggttcgaga    3840
tggctgataa ggatctcttt gctgcagcca gattccctga atgcccagaa gggtcaagta    3900
tctctgctcc atctcagacc tcagtggatg taagtctaat tcaggacgtt gagaggatct    3960
tggattattc cctctgccaa gaaacctgga gcaaaatcag agcgggtctt ccaatctctc    4020
cagtggatct cagctatctt gctcctaaaa acccaggaac cggtcctgct ttcaccataa    4080
tcaatggtac cctaaaatac tttgagacca gatacatcag agtcgatatt gctgctccaa    4140
tcctctcaag aatggtcgga atgatcagtg aactaccac agaaagggaa ctgtgggatg    4200
actgggcacc atatgaagac gtggaaattg acccaatgg agttctgagg accagttcag    4260
gatataagtt tcctttatac atgattggac atggtatgtt ggactccgat cttcatctta    4320
gctcaaaggc tcaggtgttc gaacatcctc acattcaaga cgctgcttcg caacttcctg    4380
atgatgagag tttatttttt ggtgatactg ggctatccaa aaatccaatc gagcttgtag    4440
aaggttggtt cagtagttgg aaaagctcta ttgcctcttt tttctttatc ataggttaa    4500
tcattggact attcttggtt ctccgagttg gtatccatct ttgcattaaa ttaaagcaca    4560
ccaagaaaag acagatttat acagacatag agatgaaccg acttggaaag taactcaaat    4620
cctgctaggt atgaaaaaaa ctaacagata tcacgctcga ggccaccatg ttcgtgtttc    4680
tggtgctgct gcctctggtg agctcccagt gcgtgaactt caccacaagg acccagctgc    4740
cccctgccta taccaattcc ttcacacggg gcgtgtacta tcccgacaag gtgttccgga    4800
gcagcgtgct gcactccaca caggatctgt ttctgccttt cttttctaac gtgacctggt    4860
tccacgccat ccacgtgagc ggcaccaatg gcacaaagcg gttcgccaat ccagtgctgc    4920
cctttaacga tggcgtgtac ttcgcctcca ccgagaagtc taacatcatc agaggctgga    4980
tctttggcac cacactggac agcaagacac agtccctgct gatcgtgaac aatgccacca    5040
acgtggtcat caaggtgtgc gagttccagt tttgtaatga tccattcctg ggcgtgtact    5100
atcacaagaa caataagtct tggatggaga gcgagtttcg cgtgtattcc tctgccaaca    5160
attgcacatt tgagtacgtg tcccagccct tcctgatgga cctggagggc aagcagggca    5220
atttcaagaa cctgagggag ttcgtgtttta agaatatcga tggctacttc aaaatctact    5280
ccaagcacac cccaatcaac ctggtgcgcg gcctgccaca gggcttctct gccctggagc    5340
cactggtgga tctgcccatc ggcatcaaca tcacccggtt tcagacactg ctggccctgc    5400
acagaagcta cctgacacca ggcgacagct cctctggatg gaccgcagga gcagcagcct    5460
actatgtggg ctatctgcag cccaggacct tcctgctgaa gtacaacgag aatggcacca    5520
```

```
tcacagacgc cgtggattgc gccctggatc ccctgtctga gaccaagtgt acactgaaga  5580
gctttaccgt ggagaagggc atctatcaga caagcaattt cagggtgcag cctaccgagt  5640
ccatcgtgcg ctttcccaat atcacaaacc tgtgcccttt tggcgaggtg ttcaacgcaa  5700
cccgcttcgc cagcgtgtac gcctggaata ggaagcgcat ctccaactgc gtggccgact  5760
attctgtgct gtacaacagc gcctccttct ctacctttaa gtgctatggc gtgagcccca  5820
caaagctgaa tgacctgtgc tttaccaacg tgtacgccga ttccttcgtg atcggggcg   5880
acgaggtgcg ccagatcgca ccaggacaga caggcaatat cgcagactac aattataagc  5940
tgcctgacga tttcaccggc tgcgtgatcg cctggaactc taacaatctg gatagcaaag  6000
tgggcggcaa ctacaattat ctgtaccggc tgtttagaaa gtctaatctg aagccattcg  6060
agagggacat ctccacagaa atctaccagg ccggctctac ccctgcaat ggcgtgaagg   6120
gctttaactg ttatttccct ctgcagagct acggcttcca gccaacatat ggcgtgggct  6180
atcagcccta ccgcgtggtg gtgctgtctt tgagctgct gcacgcacct gcaacagtgt   6240
gcggaccaaa gaagagcacc aatctggtga agaacaagtg cgtgaacttc aacttcaacg  6300
gactgaccgg aacaggcgtg ctgaccgagt ccaacaagaa gttcctgcct tttcagcagt  6360
tcggcaggga catcgcagat accacagacg ccgtgcgcga ccctcagacc ctggagatcc  6420
tggacatcac accatgctcc ttcggcggcg tgtctgtgat cacaccaggc accaatacaa  6480
gcaaccaggt ggccgtgctg tatcaggcg tgaattgtac cgaggtgcca gtggcaatcc   6540
acgcagatca gctgaccccct acatggcggg tgtactctac cggcagcaac gtgttccaga  6600
caagagccgg atgcctgatc ggagcagagc acgtgaacaa tagctatgag tcgacatcc   6660
ctatcggcgc cggcatctgt gcctcctacc agacccagac aaactcccca aggggatccg  6720
gctacatccc cgaggccccc agagacggcc aggcctacgt gcggaaggac ggcgagtggg  6780
tactgctcag caccttcctg ggcagcagtt ggaaaagctc catcgcctcc tttttctta   6840
tcatcggcct gatcatcgga ctgttcctgg tgctccgcgt gggtatccac ctgtgcatca  6900
agctgaagca caccaagaaa agacagattt atacagacat cgagatgaac cgacttggaa  6960
agtaagctag ccagattctt catgtttgga ccaaatcaac ttgtgatacc atgctcaaag  7020
aggcctcaat tatatttgag tttttaattt ttatgaaaaa actaacagc aatcatggaa    7080
gtccacgatt ttgagaccga cgagttcaat gatttcaatg aagatgacta tgccacaaga  7140
gaattcctga atcccgatga gcgcatgacg tacttgaatc atgctgatta caatttgaat  7200
tctcctctaa ttagtgatga tattgacaat ttgatcagga aattcaattc tcttccgatt  7260
ccctcgatgt gggatagtaa gaactgggat ggagttcttg agatgttaac atcatgtcaa  7320
gccaatccca tctcaacatc tcagatgcat aaatggatgg aagttggtt aatgtctgat   7380
aatcatgatg ccagtcaagg gtatagtttt ttacatgaag tggacaaaga ggcagaaata  7440
acatttgacg tggtgggaga cttcatccgc ggctggggca caaaccaat tgaatacatc   7500
aaaaaggaaa gatggactga ctcattcaaa attctcgctt atttgtgtca aaagttttg   7560
gacttacaca agttgacatt aatcttaaat gctgtctctg aggtggaatt gctcaacttg  7620
gcgaggactt caaaggcaa agtcagaaga agttctcatg aacgaacat atgcaggatt    7680
agggttccca gcttgggtcc tactttatt tcagaaggat gggcttactt caagaaactt    7740
gatattctaa tggaccgaaa ctttctgtta atggtcaaag atgtgattat agggaggatg  7800
caaacggtgc tatccatggt atgtagaata gacaacctgt tctcagagca agacatcttc  7860
tcccttctaa atatctacag aattggagat aaaattgtgg agaggcaggg aaattttttct 7920
```

-continued

| | |
|---|---|
| tatgacttga ttaaaatggt ggaaccgata tgcaacttga agctgatgaa attagcaaga | 7980 |
| gaatcaaggc ctttagtccc acaattccct cattttgaaa atcatatcaa gacttctgtt | 8040 |
| gatgaagggg caaaaattga ccgaggtata agattcctcc atgatcagat aatgagtgtg | 8100 |
| aaaacagtgg atctcacact ggtgatttat ggatcgttca gacattgggg tcatcctttt | 8160 |
| atagattatt acactggact agaaaaatta cattcccaag taaccatgaa gaaagatatt | 8220 |
| gatgtgtcat atgcaaaagc acttgcaagt gatttagctc ggattgttct atttcaacag | 8280 |
| ttcaatgatc ataaaaagtg gttcgtgaat ggagacttgc tccctcatga tcatcccttt | 8340 |
| aaaagtcatg ttaaagaaaa tacatggccc acagctgctc aagttcaaga ttttggagat | 8400 |
| aaatggcatg aacttccgct gattaaatgt tttgaaatac ccgacttact agacccatcg | 8460 |
| ataatatact ctgacaaaag tcattcaatg aataggtcag aggtgttgaa acatgtccga | 8520 |
| atgaatccga acactcctat ccctagtaaa aaggtgttgc agactatgtt ggacacaaag | 8580 |
| gctaccaatt ggaaagaatt tcttaaagag attgatgaga agggcttaga tgatgatgat | 8640 |
| ctaattattg gtcttaaagg aaaggagagg gaactgaagt tggcaggtag atttttctcc | 8700 |
| ctaatgtctt ggaaattgcg agaatacttt gtaattaccg aatatttgat aaagactcat | 8760 |
| ttcgtcccta tgtttaaagg cctgacaatg gcggacgatc taactgcagt cattaaaaag | 8820 |
| atgttagatt cctcatccgg ccaaggattg aagtcatatg aggcaatttg catagccaat | 8880 |
| cacattgatt acgaaaaatg gaataaccac caaaggaagt tatcaaacgg cccagtgttc | 8940 |
| cgagttatgg gccagttctt aggttatcca tccttaatcg agagaactca tgaattttt | 9000 |
| gagaaaagtc ttatatacta caatggaaga ccagacttga tgcgtgttca caacaacaca | 9060 |
| ctgatcaatt caacctccca acgagtttgt tggcaaggac aagagggtgg actggaaggt | 9120 |
| ctacggcaaa aaggatggac tatcctcaat ctactggtta ttcaaagaga ggctaaaatc | 9180 |
| agaaacactg ctgtcaaagt cttggcacaa ggtgataatc aagttatttg cacacagtat | 9240 |
| aaaacgaaga atcgagaaa cgttgtagaa ttacagggtg ctctcaatca aatggtttct | 9300 |
| aataatgaga aaattatgac tgcaatcaaa atagggacag ggaagttagg acttttgata | 9360 |
| aatgacgatg agactatgca atctgcagat tacttgaatt atggaaaaat accgatttc | 9420 |
| cgtggagtga ttagagggtt agagaccaag agatggtcac gagtgacttg tgtcaccaat | 9480 |
| gaccaaaatac ccacttgtgc taatataatg agctcagttt ccacaaatgc tctcaccgta | 9540 |
| gctcattttg ctgagaaccc aatcaatgcc atgatacagt acaattattt tgggacattt | 9600 |
| gctagactct tgttgatgat gcatgatcct gctcttcgtc aatcattgta tgaagttcaa | 9660 |
| gataagatac cgggcttgca cagttctact ttcaaatacg ccatgttgta tttggaccct | 9720 |
| tccattggag gagtgtcggg catgtctttg tccaggtttt tgattagagc cttcccagat | 9780 |
| cccgtaacag aaagtctctc attctggaga ttcatccatg tacatgctcg aagtgagcat | 9840 |
| ctgaaggaga tgagtgcagt attttggaaac cccgagatag ccaagtttcg aataactcac | 9900 |
| atagacaagc tagtagaaga tccaacctct ctgaacatcg ctatgggaat gagtccagcg | 9960 |
| aacttgttaa agactgaggt taaaaatgc ttaatcgaat caagacaaac catcaggaac | 10020 |
| caggtgatta aggatgcaac catatatttg tatcatgaag aggatcggct cagaagtttc | 10080 |
| ttatggtcaa taaatcctct gttccctaga ttttaagtg aattcaaatc aggcactttt | 10140 |
| ttgggagtcg cagacgggct catcagtcta tttcaaaatt ctcgtactat tcggaactcc | 10200 |
| tttaagaaaa agtatcatag ggaattggat gatttgattg tgaggagtga ggtatcctct | 10260 |

```
ttgacacatt tagggaaact tcatttgaga aggggatcat gtaaaatgtg gacatgttca   10320
gctactcatg ctgacacatt aagatacaaa tcctggggcc gtacagttat tgggacaact   10380
gtacccatc cattagaaat gttgggtcca caacatcgaa aagagactcc ttgtgcacca   10440
tgtaacacat cagggttcaa ttatgttct gtgcattgtc cagacgggat ccatgacgtc   10500
tttagttcac ggggaccatt gcctgcttat ctagggtcta aacatctga atctacatct   10560
attttgcagc cttgggaaag ggaaagcaaa gtcccactga ttaaaagagc tacacgtctt   10620
agagatgcta tctcttggtt tgttgaaccc gactctaaac tagcaatgac tatactttct   10680
aacatccact ctttaacagg cgaagaatgg accaaaaggc agcatgggtt caaaagaaca   10740
gggtctgccc ttcataggtt ttcgacatct cggatgagcc atggtgggtt cgcatctcag   10800
agcactgcag cattgaccag gttgatggca actacagaca ccatgaggga tctgggagat   10860
cagaatttcg acttttatt ccaagcaacg ttgctctatg ctcaaattac caccactgtt   10920
gcaagagacg gatggatcac cagttgtaca gatcattatc atattgcctg taagtcctgt   10980
ttgagaccca tagaagagat caccctggac tcaagtatgg actacacgcc cccagatgta   11040
tcccatgtgc tgaagacatg gaggaatggg gaaggttcgt ggggacaaga gataaaacag   11100
atctatcctt tagaagggaa ttggaagaat ttagcacctg ctgagcaatc ctatcaagtc   11160
ggcagatgta taggttttct atatggagac ttggcgtata gaaaatctac tcatgccgag   11220
gacagttctc tatttcctct atctatacaa ggtcgtatta gaggtcgagg tttcttaaaa   11280
gggttgctag acggattaat gagagcaagt tgctgccaag taatacaccg gagaagtctg   11340
gctcatttga gaggccggc caacgcagtg tacggaggtt tgatttactt gattgataaa   11400
ttgagtgtat cacctccatt cctttctctt actagatcag gacctattag agacgaatta   11460
gaaacgattc cccacaagat cccaacctcc tatccgacaa gcaaccgtga tatggggtg   11520
attgtcagaa attacttcaa ataccaatgc cgtctaattg aaaagggaaa atacagatca   11580
cattattcac aattatggtt attctcagat gtcttatcca tagacttcat tggaccattc   11640
tctatttcca ccaccctctt gcaaatccta tacaagccat ttttatctgg gaaagataag   11700
aatgagttga gagagctggc aaatctttct tcattgctaa gatcaggaga ggggtgggaa   11760
gacatacatg tgaaattctt caccaaggac atattattgt gtccagagga aatcagacat   11820
gcttgcaagt tcgggattgc taaggataat aataaagaca tgagctatcc cccttgggga   11880
agggaatcca gagggacaat tacaacaatc cctgtttatt atacgaccac cccttaccca   11940
aagatgctag atgcctcc aagaatccaa aatcccctgc tgtccggaat caggttgggc   12000
caattaccaa ctggcgctca ttataaaatt cggagtatat tacatggaat gggaatccat   12060
tacagggact tcttgagttg tggagacggc tccggaggga tgactgctgc attactacga   12120
gaaaatgtgc atagcagagg aatattcaat agtctgttag aattatcagg gtcagtcatg   12180
cgaggcgcct ctcctgagcc ccccagtgcc ctagaaactt taggaggaga taaatcgaga   12240
tgtgtaaatg gtgaaacatg ttgggaatat ccatctgact tatgtgaccc aaggacttgg   12300
gactatttcc tccgactcaa agcaggcttg gggcttcaaa ttgatttaat tgtaatggat   12360
atggaagttc gggattcttc tactagcctg aaaattgaga cgaatgttag aaattatgtg   12420
caccggattt tggatgagca aggagtttta atctacaaga cttatggaac atatatttgt   12480
gagagcgaaa agaatgcagt aacaatcctt ggtccatgt tcaagacggt cgacttagtt   12540
caaacagaat ttagtagttc tcaaacgtct gaagtatata tggtatgtaa aggtttgaag   12600
aaattaatcg atgaacccaa tcccgattgg tcttccatca atgaatcctg gaaaaacctg   12660
```

```
tacgcattcc agtcatcaga acaggaattt gccagagcaa agaaggttag tacatacttt    12720
accttgacag gtattccctc ccaattcatt cctgatcctt ttgtaaacat tgagactatg    12780
ctacaaatat tcggagtacc cacgggtgtg tctcatgcgg ctgccttaaa atcatctgat    12840
agacctgcag atttattgac cattagcctt ttttatatgg cgattatatc gtattataac    12900
atcaatcata tcagagtagg accgatacct ccgaaccccc catcagatgg aattgcacaa    12960
aatgtgggga tcgctataac tggtataagc ttttggctga gtttgatgga gaaagacatt    13020
ccactatatc aacagtgttt agcagttatc cagcaatcat tcccgattag gtgggaggct    13080
gtttcagtaa aaggaggata caagcagaag tggagtacta gaggtgatgg gctcccaaaa    13140
gatacccgaa cttcagactc cttggcccca atcgggaact ggatcagatc tctggaattg    13200
gtccgaaacc aagttcgtct aaatccattc aatgagatct tgttcaatca gctatgtcgt    13260
acagtggata atcatttgaa atggtcaaat ttgcgaagaa acacaggaat gattgaatgg    13320
atcaatagac gaatttcaaa agaagaccgg tctatactga tgttgaagag tgacctacac    13380
gaggaaaact cttggagaga ttaaaaaatc atgaggagac tccaaacttt aagtatgaaa    13440
aaaactttga tccttaagac cctcttgtgg ttttttatttt ttatctggtt ttgtggtctt    13500
cgt                                                                 13503
```

<210> SEQ ID NO 24
<211> LENGTH: 13484
<212> TYPE: DNA
<213> ORGANISM: Artificial Sequence
<220> FEATURE:
<223> OTHER INFORMATION: VSV vector: Convac V4 China

<400> SEQUENCE: 24

```
acgaagacaa acaaaccatt attatcatta aaaggctcag gagaaacttt aacagtaatc      60
aaaatgtctg ttacagtcaa gagaatcatt gacaacacag tcatagttcc aaaacttcct     120
gcaaatgagg atccagtgga atacccggca gattacttca gaaaatcaaa ggagattcct     180
ctttacatca atactacaaa aagtttgtca gatctaagag gatatgtcta ccaaggcctc     240
aaatccggaa atgtatcaat catacatgtc aacagctact tgtatggagc attaaaggac     300
atccggggta agttggataa agattggtca agtttcggaa taaacatcgg gaaagcaggg     360
gatacaatcg gaatatttga ccttgtatcc ttgaaagccc tggacggcgt acttccagat     420
ggagtatcgg atgcttccag aaccagcgca gatgacaaat ggttgccttt gtatctactt     480
ggcttataca gagtgggcag aacacaaatg cctgaataca gaaaaaagct catggatggg     540
ctgacaaatc aatgcaaaat gatcaatgaa cagtttgaac ctcttgtgcc agaaggtcgt     600 gacattttg tgtgtgggg aaatgacagt aattacacaa aaattgtcgc tgcagtggac     660
atgttcttcc acatgttcaa aaaacatgaa tgtgcctcgt tcagatacgg aactattgtt     720
tccagattca aagattgtgc tgcattggca acatttggac acctctgcaa ataaccgga     780 atgtctacag aagatgtaac gacctggatc ttgaaccgag aagttgcaga tgaaatggtc     840
caaatgatgc ttccaggcca agaaattgac aaggccgatt catacatgcc ttatttgatc     900
gactttggat tgtcttctaa gtctccatat tcttccgtca aaaaccctgc cttccacttc     960
tgggggcaat tgacagctct tctgctcaga tccaccagag caaggaatgc ccgacagcct    1020
gatgacattg agtatacatc tcttactaca gcaggtttgt tgtacgctta tgcagtagga    1080
tcctctgccg acttggcaca acagtttttgt gttggagata acaaatacac tccagatgat    1140
```

```
agtaccggag gattgacgac taatgcaccg ccacaaggca gagatgtggt cgaatggctc    1200
ggatggtttg aagatcaaaa cagaaaaccg actcctgata tgatgcagta tgcgaaaaga    1260
gcagtcatgt cactgcaagg cctaagagag aagacaattg gcaagtatgc taagtcagaa    1320
tttgacaaat gaccctataa ttctcagatc acctattata tattatgcta catatgaaaa    1380
aaactaacag atatcatgga taatctcaca aaagttcgtg agtatctcaa gtcctattct    1440
cgtctggatc aggcggtagg agagatagat gagatcgaag cacaacgagc tgaaaagtcc    1500
aattatgagt tgttccaaga ggatggagtg gaagagcata ctaagccctc ttattttcag    1560
gcagcagatg attctgacac agaatctgaa ccagaaattg aagacaatca aggtttgtat    1620
gcaccagatc cagaagctga gcaagttgaa ggctttatac aggggccttt agatgactat    1680
gcagatgagg aagtggatgt tgtatttact tcggactgga aacagcctga gcttgaatct    1740
gacgagcatg gaaagacctt acggttgaca tcgccagagg gtttaagtgg agagcagaaa    1800
tcccagtggc tttcgacgat taaagcagtc gtgcaaagtg ccaaatactg gaatctggca    1860
gagtgcacat ttgaagcatc gggagaaggg gtcattatga aggagcgcca gataactccg    1920
gatgtatata aggtcactcc agtgatgaac acacatccgt cccaatcaga agcagtatca    1980
gatgtttggt ctctctcaaa gacatccatg actttccaac ccaagaaagc aagtcttcag    2040
cctctcacca tatccttgga tgaattgttc tcatctagag gagagttcat ctctgtcgga    2100
ggtgacggac gaatgtctca taaagaggcc atcctgctcg gcctgagata caaaagttg     2160 tacaatcagg cgagagtcaa atattctctg tagactatga aaaaagtaa cagatatcac     2220 gatctaagtg ttatcccaat ccattcatca tgagttcctt aaagaagatt ctcggtctga    2280
aggggaaagg taagaaatct aagaaattag ggatcgcacc acccccttat gaagaggaca    2340
ctagcatgga gtatgctccg agcgctccaa ttgacaaatc ctattttgga gttgacgaga    2400
tggacaccta tgatccgaat caattaagat atgagaaatt cttctttaca gtgaaaatga    2460
cggttagatc taatcgtccg ttcagaacat actcagatgt ggcagccgct gtatcccatt    2520
gggatcacat gtacatcgga atggcaggga aacgtccctt ctacaaaatc ttggcttttt    2580
tgggttcttc taatctaaag gccactccag cggtattggc agatcaaggt caaccagagt    2640
atcacactca ctgcgaaggc agggcttatt tgccacatag gatggggaag acccctccca    2700
tgctcaatgt accagagcac ttcagaagac cattcaatat aggtctttac aagggaacga    2760
ttgagctcac aatgaccatc tacgatgatg agtcactgga agcagctcct atgatctggg    2820
atcatttcaa ttcttccaaa ttttctgatt tcagagagaa ggccttaatg tttggcctga    2880
ttgtcgagaa aaaggcatct ggagcgtggg tcctggattc tatcagccac ttcaaatgag    2940
ctagtctaac ttctagcttc tgaacaatcc ccggtttact cagtctctcc taattccagc    3000
ctctcgaaca actaatatcc tgtctttcct atccctatga aaaaaactaa cagagatcga    3060
tctgtttacg cgtgccacca tgttcgtgtt tctggtgctg ctgcctctgg tgagctccca    3120
gtgcgtgaac ctgaccacaa ggacccagct gccccctgcc tataccaatt ccttcacacg    3180
gggcgtgtac tatcccgaca aggtgttccg gagcagcgtg ctgcactcca cacaggatct    3240
gtttctgcct ttcttttcta acgtgacctg gttccacgcc atccacgtga gcggcaccaa    3300
tggcacaaag cggttcgaca atccagtgct gcccttttaac gatggcgtgt acttcgcctc    3360
caccgagaag tctaacatca tcagaggctg gatctttggc accacactgg acagcaagac    3420
acagtccctg ctgatcgtga acaatgccac caacgtggtc atcaaggtgt gcgagttcca    3480
gttttgtaat gatccattcc tgggcgtgta ctatcacaag aacaataagt cttggatgga    3540
```

```
gagcgagttt cgcgtgtatt cctctgccaa caattgcaca tttgagtacg tgtcccagcc    3600
cttcctgatg gacctggagg gcaagcaggg caatttcaag aacctgaggg agttcgtgtt    3660
taagaatatc gatggctact tcaaaatcta ctccaagcac accccaatca acctggtgcg    3720
cgacctgcca cagggcttct ctgccctgga gccactggtg gatctgccca tcggcatcaa    3780
catcacccgg tttcagacac tgctggccct gcacagaagc tacctgacac caggcgacag    3840
ctcctctgga tggaccgcag gagcagcagc ctactatgtg ggctatctgc agcccaggac    3900
cttcctgctg aagtacaacg agaatggcac catcacagac gccgtggatt gcgccctgga    3960
tccCctgtct gagaccaagt gtacactgaa gagctttacc gtggagaagg gcatctatca    4020
gacaagcaat ttcagggtgc agcctaccga gtccatcgtg cgctttccca atatcacaaa    4080
cctgtgccct tttggcgagg tgttcaacgc aacccgcttc gccagcgtgt acgcctggaa    4140
taggaagcgc atctccaact gcgtggccga ctattctgtg ctgtacaaca gcgcctcctt    4200
ctctaccttt aagtgctatg gcgtgagccc cacaaagctg aatgacctgt gctttaccaa    4260
cgtgtacgcc gattccttcg tgatcagggg cgacgaggtg cgccagatcg caccaggaca    4320
gacaggcaag atcgcagact acaattataa gctgcctgac gatttcaccg gctgcgtgat    4380
cgcctggaac tctaacaatc tggatagcaa agtgggcggc aactacaatt atctgtaccg    4440
gctgtttaga aagtctaatc tgaagccatt cgagagggac atctccacag aaatctacca    4500
ggccggctct acccctgca atggcgtgga gggctttaac tgttatttcc ctctgcagag    4560
ctacggcttc cagccaacaa acggcgtggg ctatcagccc taccgcgtgg tggtgctgtc    4620 tttttgagctg ctgcacgcac ctgcaacagt gtgcggacca aagaagagca ccaatctggt    4680
```
(Note: some lines transcribed to best reading)

```
agaatgggtt gattcacagt tcatcaacgg aaaatgcagc aattacatat gccccactgt   5940
ccataactct acaacctggc attctgacta aaggtcaaa gggctatgtg attctaacct   6000
catttccatg gacatcacct tcttctcaga ggacggagag ctatcatccc tgggaaagga   6060
gggcacaggg ttcagaagta actactttgc ttatgaaact ggaggcaagg cctgcaaaat   6120
gcaatactgc aagcattggg gagtcagact cccatcaggt gtctggttcg agatggctga   6180
taaggatctc tttgctgcag ccagattccc tgaatgccca aagggtcaa gtatctctgc   6240
tccatctcag acctcagtgg atgtaagtct aattcaggac gttgagagga tcttggatta   6300
ttccctctgc caagaaacct ggagcaaaat cagagcgggt cttccaatct ctccagtgga   6360
tctcagctat cttgctccta aaacccagg aaccggtcct gctttcacca taatcaatgg   6420
taccctaaaa tactttgaga ccagatacat cagagtcgat attgctgctc caatcctctc   6480
aagaatggtc ggaatgatca gtggaactac cacagaaagg gaactgtggg atgactgggc   6540
accatatgaa gacgtggaaa ttggacccaa tggagttctg aggaccagtt caggatataa   6600
gtttcccttta tacatgattg gacatggtat gttggactcc gatcttcatc ttagctcaaa   6660
ggctcaggtg ttcgaacatc ctcacattca agacgctgct tcgcaacttc ctgatgatga   6720
gagtttatt tttggtgata ctgggctatc caaaaatcca atcgagcttg tagaaggttg   6780
gttcagtagt tggaaaagct ctattgcctc tttttttctt atcatagggt taatcattgg   6840
actattcttg gttctccgag ttggtatcca tctttgcatt aaattaaagc acaccaagaa   6900
aagacagatt tatacagaca tagagatgaa ccgacttgga aagtaagcta gccagattct   6960
tcatgtttgg accaaatcaa cttgtgatac catgctcaaa gaggcctcaa ttatatttga   7020
gttttaatt tttatgaaaa aaactaacag caatcatgga agtccacgat tttgagaccg   7080
acgagttcaa tgatttcaat gaagatgact atgccacaag agaattcctg aatcccgatg   7140
agcgcatgac gtacttgaat catgctgatt acaatttgaa ttctcctcta attagtgatg   7200
atattgacaa tttgatcagg aaattcaatt ctccttccgat tccctcgatg tgggatagta   7260
agaactggga tggagttctt gagatgttaa catcatgtca agccaatccc atctcaacat   7320
ctcagatgca taaatggatg gaagttggt taatgtctga taatcatgat gccagtcaag   7380
ggtatagttt tttacatgaa gtggacaaag aggcagaaat aacatttgac gtggtggaga   7440
ccttcatccg cggctggggc aacaaaccaa ttgaatacat caaaaaggaa agatggactg   7500
actcattcaa aattctcgct tatttgtgtc aaaagttttt ggacttacac aagttgacat   7560
taatcttaaa tgctgtctct gaggtggaat tgctcaactt ggcgaggact ttcaaaggca   7620
aagtcagaag aagttctcat ggaacgaaca tatgcaggat tagggttccc agcttgggtc   7680
ctactttat ttcagaagga tgggcttact tcaagaaact tgatattcta atggaccgaa   7740
actttctgtt aatggtcaaa gatgtgatta tagggaggat gcaaacggtg ctatccatgg   7800
tatgtagaat agacaacctg ttctcagagc aagacatctt ctcccttcta aatatctaca   7860
gaattggaga taaaattgtg gagaggcagg gaaattttc ttatgacttg attaaaatgg   7920
tggaaccgat atgcaacttg aagctgatga aattagcaag agaatcaagg cctttagtcc   7980
cacaattccc tcattttgaa aatcatatca agacttctgt tgatgaaggg gcaaaaattg   8040
accgaggtat aagattcctc catgatcaga taatgagtgt gaaaacagtg gatctcacac   8100
tggtgattta tggatcgttc agacattggg gtcatccttt tatagattat tacactggac   8160
tagaaaaatt acattcccaa gtaaccatga agaaagatat tgatgtgtca tatgcaaaag   8220
cacttgcaag tgatttagct cggattgttc tatttcaaca gttcaatgat cataaaaagt   8280
```

```
ggttcgtgaa tggagacttg ctccctcatg atcatccctt taaaagtcat gttaaagaaa    8340
atacatggcc cacagctgct caagttcaag attttggaga taaatggcat gaacttccgc    8400
tgattaaatg ttttgaaata cccgacttac tagacccatc gataatatac tctgacaaaa    8460
gtcattcaat gaataggtca gaggtgttga aacatgtccg aatgaatccg aacactccta    8520
tccctagtaa aaaggtgttg cagactatgt tggacacaaa ggctaccaat tggaaagaat    8580
ttcttaaaga gattgatgag aagggcttag atgatgatga tctaattatt ggtcttaaag    8640
gaaaggagag ggaactgaag ttggcaggta gattttttctc cctaatgtct tggaaattgc    8700
gagaatactt tgtaattacc gaatatttga taaagactca tttcgtccct atgtttaaag    8760
gcctgacaat ggcggacgat ctaactgcag tcattaaaaa gatgttagat tcctcatccg    8820
gccaaggatt gaagtcatat gaggcaattt gcatagccaa tcacattgat tacgaaaaat    8880
ggaataacca ccaaaggaag ttatcaaacg gcccagtgtt ccgagttatg ggccagttct    8940
taggttatcc atccttaatc gagagaactc atgaattttt tgagaaaagt cttatatact    9000
acaatggaag accagacttg atgcgtgttc acaacaacac actgatcaat tcaacctccc    9060
aacgagtttg ttggcaagga caagagggtg gactggaagg tctacggcaa aaaggatgga    9120
ctatcctcaa tctactggtt attcaaagag aggctaaaat cagaaacact gctgtcaaag    9180
tcttggcaca aggtgataat caagttattt gcacacagta taaaacgaag aaatcgagaa    9240
acgttgtaga attacagggt gctctcaatc aaatggtttc taataatgag aaaattatga    9300
ctgcaatcaa aatagggaca gggaagttag acttttgat aaatgacgat gagactatgc    9360
aatctgcaga ttacttgaat tatggaaaaa taccgatttt ccgtggagtg attagagggt    9420
tagagaccaa gagatggtca cgagtgactt gtgtcaccaa tgaccaaata cccacttgtg    9480
ctaatataat gagctcagtt tccacaaatg ctctcaccgt agctcatttt gctgagaacc    9540
caatcaatgc catgatacag tacaattatt tgggacatt tgctagactc ttgttgatga    9600
tgcatgatcc tgctcttcgt caatcattgt atgaagttca agataagata ccgggcttgc    9660
acagttctac tttcaaatac gccatgttgt atttggaccc ttccattgga ggagtgtcgg    9720
gcatgtcttt gtccaggttt ttgattagag ccttcccaga tcccgtaaca gaaagtctct    9780
cattctggag attcatccat gtacatgctc gaagtgagca tctgaaggag atgagtgcag    9840
tatttggaaa ccccgagata gccaagtttc gaataactca catagacaag ctagtagaag    9900
atccaacctc tctgaacatc gctatgggaa tgagtccagc gaacttgtta aagactgagg    9960
ttaaaaaatg cttaatcgaa tcaagacaaa ccatcaggaa ccaggtgatt aaggatgcaa    10020
ccatatattt gtatcatgaa gaggatcggc tcagaagttt cttatggtca ataaatcctc    10080
tgttccctag attttttaagt gaattcaaat caggcacttt tttgggagtc gcagacgggc    10140
tcatcagtct atttcaaaat tctcgtacta ttcgaactc ctttaagaaa aagtatcata    10200
gggaattgga tgatttgatt gtgaggagtg aggtatcctc tttgacacat ttagggaaac    10260
ttcatttgag aagggggatca tgtaaaatgt ggacatgttc agctactcat gctgacacat    10320
taagatacaa atcctggggc cgtacagtta ttgggacaac tgtaccccat ccattagaaa    10380
tgttgggtcc acaacatcga aaagagactc cttgtgcacc atgtaacaca tcagggttca    10440
attatgtttc tgtgcattgt ccagacggga tccatgacgt ctttagttca cggggaccat    10500
tgcctgctta tctagggtct aaaacatctg aatctacatc tattttgcag ccttgggaaa    10560
gggaaagcaa agtcccactg attaaaagag ctacacgtct tagagatgct atctcttggt    10620
```

```
ttgttgaacc cgactctaaa ctagcaatga ctatactttc taacatccac tctttaacag    10680
gcgaagaatg gaccaaaagg cagcatgggt tcaaaagaac agggtctgcc cttcataggt    10740
tttcgacatc tcggatgagc catggtgggt tcgcatctca gagcactgca gcattgacca    10800
ggttgatggc aactacagac accatgaggg atctgggaga tcagaatttc gactttttat    10860
tccaagcaac gttgctctat gctcaaatta ccaccactgt tgcaagagac ggatggatca    10920
ccagttgtac agatcattat catattgcct gtaagtcctg tttgagaccc atagaagaga    10980
tcaccctgga ctcaagtatg gactacacgc ccccagatgt atcccatgtg ctgaagacat    11040
ggaggaatgg ggaaggttcg tggggacaag agataaaaca gatctatcct ttagaaggga    11100
attggaagaa tttagcacct gctgagcaat cctatcaagt cggcagatgt ataggttttc    11160
tatatggaga cttggcgtat agaaaatcta ctcatgccga ggacagttct ctatttcctc    11220
tatctataca aggtcgtatt agaggtcgag gtttcttaaa agggttgcta gacggattaa    11280
tgagagcaag ttgctgccaa gtaatacacc ggagaagtct ggctcatttg aagaggccgg    11340
ccaacgcagt gtacggaggt ttgatttact tgattgataa attgagtgta tcacctccat    11400
tcctttctct tactagatca ggacctatta gagacgaatt agaaacgatt ccccacaaga    11460
tcccaacctc ctatccgaca agcaaccgtg atatgggggt gattgtcaga aattacttca    11520
aataccaatg ccgtctaatt gaaaagggaa aatacagatc acattattca caattatggt    11580
tattctcaga tgtcttatcc atagacttca ttggaccatt ctctatttcc accaccctct    11640
tgcaaatcct atacaagcca ttttatctg ggaaagataa gaatgagttg agagagctgg    11700
caaatctttc ttcattgcta agatcaggag aggggtggga agacatacat gtgaaattct    11760
tcaccaagga catattattg tgtccagagg aaatcagaca tgcttgcaag ttcgggattg    11820
ctaaggataa taataaagac atgagctatc ccccttgggg aagggaatcc agagggacaa    11880
ttacaacaat ccctgtttat tatacgacca cccccttaccc aaagatgcta gagatgcctc    11940
caagaatcca aaatccccctg ctgtccggaa tcaggtgggg ccaattacca actggcgctc    12000
attataaaat tcggagtata ttacatggaa tgggaatcca ttacagggac ttcttgagtt    12060
gtggagacgc ctccggaggg atgactgctg cattactacg agaaaatgtg catagcagag    12120
gaatattcaa tagtctgtta gaattatcag ggtcagtcat gcgaggcgcc tctcctgagc    12180
cccccagtgc cctagaaact ttaggaggag ataaatcgag atgtgtaaat ggtgaaacat    12240
gttgggaata tccatctgac ttatgtgacc caaggacttg ggactatttc ctccgactca    12300
aagcaggctt ggggcttcaa attgatttaa ttgtaatgga tatggaagtt cgggattctt    12360
ctactagcct gaaaattgag acgaatgtta gaattatgt gcaccggatt ttggatgagc    12420
aaggagtttt aatctacaag acttatgaa catatatttg tgagagcgaa aagaatgcag    12480
taacaatcct tggtcccatg ttcaagacgg tcgacttagt tcaaacagaa tttagtagtt    12540
ctcaaacgtc tgaagtatat atggtatgta aaggtttgaa gaaattaatc gatgaaccca    12600
atcccgattg gtcttccatc aatgaatcct ggaaaaacct gtacgcattc cagtcatcag    12660
aacaggaatt tgccagagca aagaaggtta gtacatactt taccttgaca ggtattccct    12720
cccaattcat tcctgatcct tttgtaaaca ttgagactat gctacaaata ttcggagtac    12780
ccacgggtgt gtctcatgcg gctgccttaa aatcatctga tagacctgca gatttattga    12840
ccattagcct tttttatatg gcgattatat cgtattataa catcaatcat atcagagtag    12900
gaccgatacc tccgaacccc ccatcagatg gaattgcaca aaatgtgggg atcgctataa    12960
ctggtataag cttttggcctg agtttgatgg agaaagacat tccactatat caacagtgtt    13020
```

-continued

```
tagcagttat ccagcaatca ttcccgatta ggtgggaggc tgtttcagta aaaggaggat    13080
acaagcagaa gtggagtact agaggtgatg ggctcccaaa agatacccga acttcagact    13140
ccttggcccc aatcgggaac tggatcagat ctctggaatt ggtccgaaac caagttcgtc    13200
taaatccatt caatgagatc ttgttcaatc agctatgtcg tacagtggat aatcatttga    13260
aatggtcaaa tttgcgaaga aacacaggaa tgattgaatg gatcaataga cgaatttcaa    13320
aagaagaccg gtctatactg atgttgaaga gtgacctaca cgaggaaaac tcttggagag    13380
attaaaaaat catgaggaga ctccaaactt aagtatgaa aaaaactttg atccttaaga    13440
ccctcttgtg gttttatttt tttatctggt tttgtggtct tcgt                    13484
```

<210> SEQ ID NO 25
<211> LENGTH: 13484
<212> TYPE: DNA
<213> ORGANISM: Artificial Sequence
<220> FEATURE:
<223> OTHER INFORMATION: VSV vector: Convac V4 South Africa

<400> SEQUENCE: 25

```
acgaagacaa acaaaccatt attatcatta aaaggctcag gagaaacttt aacagtaatc      60
aaaatgtctg ttacagtcaa gagaatcatt gacaacacag tcatagttcc aaaacttcct     120
gcaaatgagg atccagtgga ataccccggca gattacttca gaaaatcaaa ggagattcct     180
ctttacatca atactacaaa aagtttgtca gatctaagag gatatgtcta ccaaggcctc     240
aaatccggaa atgtatcaat catacatgtc aacagctact tgtatggagc attaaaggac     300
atccggggta agttggataa agattggtca agtttcggaa taaacatcgg gaaagcaggg     360
gatacaatcg gaatatttga ccttgtatcc ttgaaagccc tggacggcgt acttccagat     420
ggagtatcgg atgcttccag aaccagcgca gatgacaaat ggttgccttt gtatctactt     480
ggcttataca gagtgggcag aacacaaatg cctgaataca gaaaaaagct catggatggg     540
ctgacaaatc aatgcaaaat gatcaatgaa cagtttgaac ctcttgtgcc agaaggtcgt     600
gacatttttg atgtgtgggg aaatgacagt aattacacaa aaattgtcgc tgcagtggac     660
atgttcttcc acatgttcaa aaaacatgaa tgtgcctcgt tcagatacgg aactattgtt     720
tccagattca aagattgtgc tgcattggca catttggac acctctgcaa ataaccgga      780 atgtctacag aagatgtaac gacctggatc ttgaaccgag aagttgcaga tgaaatggtc     840
caaatgatgc ttccaggcca agaaattgac aaggccgatt catacatgcc ttatttgatc     900
gactttggat tgtcttctaa gtctccatat tcttccgtca aaaaccctgc cttccacttc     960
tgggggcaat tgacagctct tctgctcaga tccaccagag caaggaatgc ccgacagcct    1020
gatgacattg agtatacatc tcttactaca gcaggtttgt tgtacgctta tgcagtagga    1080
tcctctgccg acttggcaca acagttttgt gttggagata caaatacac tccagatgat    1140 agtaccggag gattgacgac taatgcaccg ccacaaggca gagatgtggt cgaatggctc    1200
ggatggtttg aagatcaaaa cagaaaaccg actcctgata tgatgcagta tgcgaaaaga    1260
gcagtcatgt cactgcaagg cctaagagag aagacaattg caagtatgc taagtcagaa    1320 tttgacaaat gaccctataa ttctcagatc acctattata tattatgcta catatgaaaa    1380
aaactaacag atatcatgga taatctcaca aaagttcgtg agtatctcaa gtcctattct    1440
cgtctggatc aggcggtagg agagatagat gagatcgaag cacaacgagc tgaaaagtcc    1500
aattatgagt tgttccaaga ggatggagtg gaagagcata ctaagccctc ttattttcag    1560
```

```
gcagcagatg attctgacac agaatctgaa ccagaaattg aagacaatca aggtttgtat    1620
gcaccagatc cagaagctga gcaagttgaa ggctttatac aggggccttt agatgactat    1680
gcagatgagg aagtggatgt tgtatttact tcggactgga aacagcctga gcttgaatct    1740
gacgagcatg gaaagacctt acggttgaca tcgccagagg gtttaagtgg agagcagaaa    1800
tcccagtggc tttcgacgat taaagcagtc gtgcaaagtg ccaaatactg gaatctggca    1860
gagtgcacat ttgaagcatc gggagaaggg gtcattatga aggagcgcca gataactccg    1920
gatgtatata aggtcactcc agtgatgaac acacatccgt cccaatcaga agcagtatca    1980
gatgtttggt ctctctcaaa gacatccatg actttccaac caagaaagc aagtcttcag     2040 cctctcacca tatccttgga tgaattgttc tcatctagag gagagttcat ctctgtcgga    2100
ggtgacggac gaatgtctca taaagaggcc atcctgctcg gcctgagata caaaaagttg    2160
tacaatcagg cgagagtcaa atattctctg tagactatga aaaaagtaa cagatatcac      2220 gatctaagtg ttatcccaat ccattcatca tgagttcctt aaagaagatt ctcggtctga    2280
aggggaaagg taagaaatct aagaaattag ggatcgcacc accccttat gaagaggaca     2340 ctagcatgga gtatgctccg agcgctccaa ttgacaaatc ctattttgga gttgacgaga    2400
tggacaccta tgatccgaat caattaagat atgaaaatt cttctttaca gtgaaaatga    2460
cggttagatc taatcgtccg ttcagaacat actcagatgt ggcagccgct gtatcccatt    2520
gggatcacat gtacatcgga atggcaggga acgtcccctt ctacaaaatc ttggctttt     2580 tgggttcttc taatctaaag gccactccag cggtattggc agatcaaggt caaccagagt    2640
atcacactca ctgcgaaggc agggcttatt tgccacatag gatggggaag acccctccca    2700
tgctcaatgt accagagcac ttcagaagac cattcaatat aggtctttac aagggaacga    2760
ttgagctcac aatgaccatc tacgatgatg agtcactgga agcagctcct atgatctggg    2820
atcatttcaa ttcttccaaa ttttctgatt tcagagagaa ggccttaatg tttggcctga    2880
ttgtcgagaa aaaggcatct ggagcgtggg tcctggattc tatcagccac ttcaaatgag    2940
ctagtctaac ttctagcttc tgaacaatcc ccggtttact cagtctctcc taattccagc    3000
ctctcgaaca actaatatcc tgtcttttct atccctatga aaaaaactaa cagagatcga    3060
tctgtttacg cgtgccacca tgttcgtgtt tctggtgctg ctgcctctgg tgagctccca    3120
gtgcgtgaac ttcaccacaa ggacccagct gccccctgcc tataccaatt ccttcacacg    3180
gggcgtgtac tatcccgaca aggtgttccg gagcagcgtg ctgcactcca cacaggatct    3240
gtttctgcct ttcttttcta acgtgacctg gttccacgcc atccacgtga gcggcaccaa    3300
tggcacaaag cggttcgcca atccagtgct gcccttaaac gatggcgtgt acttcgcctc    3360
caccgagaag tctaacatca tcagaggctg gatctttggc accacactgg acagcaagac    3420
acagtccctg ctgatcgtga acaatgccac caacgtggtc atcaaggtgt gcgagttcca    3480
gttttgtaat gatccattcc tgggcgtgta ctatcacaag aacaataagt cttggatgga    3540
gagcgagttt cgcgtgtatt cctctgccaa caattgcaca tttgagtacg tgtcccagcc    3600
cttcctgatg gacctggagg gcaagcaggg caatttcaag aacctgaggg agttcgtgtt    3660
taagaatatc gatggctact tcaaaatcta ctccaagcac accccaatca acctggtgcg    3720
cggcctgcca cagggcttct ctgccctgga gccactggtg gatctgccca tcggcatcaa    3780
catcacccgg tttcagacac tgctggccct gcacagaagc tacctgacac aggcgacag     3840 ctcctctgga tggaccgcag gagcagcagc ctactatgtg ggctatctgc agcccaggac    3900
cttcctgctg aagtacaacg agaatggcac catcacagac gccgtggatt gcgccctgga    3960
```

```
tcccctgtct gagaccaagt gtacactgaa gagctttacc gtggagaagg gcatctatca    4020
gacaagcaat ttcagggtgc agcctaccga gtccatcgtg cgctttccca atatcacaaa    4080
cctgtgccct tttggcgagg tgttcaacgc aacccgcttc gccagcgtgt acgcctggaa    4140
taggaagcgc atctccaact gcgtggccga ctattctgtg ctgtacaaca cgcctccttt    4200
ctctaccttt aagtgctatg gcgtgagccc cacaaagctg aatgacctgt gctttaccaa    4260
cgtgtacgcc gattccttcg tgatcagggg cgacgaggtg cgccagatcg caccaggaca    4320
gacaggcaat atcgcagact acaattataa gctgcctgac gatttcaccg gctgcgtgat    4380
cgcctggaac tctaacaatc tggatagcaa agtgggcggc aactacaatt atctgtaccg    4440
gctgtttaga aagtctaatc tgaagccatt cgagagggac atctccacag aaatctacca    4500
ggccggctct accccctgca atggcgtgaa gggctttaac tgttatttcc ctctgcagag    4560
ctacggcttc cagccaacat atggcgtggg ctatcagccc taccgcgtgg tggtgctgtc    4620
ttttgagctg ctgcacgcac ctgcaacagt gtgcggacca agaagagca ccaatctggt    4680
gaagaacaag tgcgtgaact tcaacttcaa cggactgacc ggaacaggcg tgctgaccga    4740
gtccaacaag aagttcctgc cttttcagca gttcggcagg gacatcgcag ataccacaga    4800
cgccgtgcgc gaccctcaga ccctggagat cctggacatc acaccatgct ccttcggcgg    4860
cgtgtctgtg atcacaccag gcaccaatac aagcaaccag gtggccgtgc tgtatcaggg    4920
cgtgaattgt accgaggtgc cagtggcaat ccacgcagat cagctgaccc ctacatggcg    4980
ggtgtactct accggcagca acgtgttcca gacaagagcc ggatgcctga tcggagcaga    5040
gcacgtgaac aatagctatg agtgcgacat ccctatcggc gccggcatct gtgcctccta    5100
ccagacccag acaaactccc caaggtctgt gggcgataca ggcctgtcca agaatccaat    5160
cgagctggta gagggctggt tcagcagttg gaaaagctcc atcgcctcct tttctttat    5220
catcggcctg atcatcggac tgttcctggt gctccgcgtg ggtatccacc tgtgcatcaa    5280
gctgaagcac accaagaaaa gacagattta tacagacatc gagatgaacc gcctgggaaa    5340
gggatccggc tccggcgagg caggggaag tctactaaca tgcggggacg tggaggaaaa    5400
tccccggcccc atgaagtgcc ttttgtactt agccttttta ttcattgggg tgaattgcaa    5460
gttcaccata gttttccac acaaccaaaa aggaaactgg aaaaatgttc cttctaatta    5520
ccattattgc ccgtcaagct cagatttaaa ttggcataat gacttaatag gcacagccat    5580
acaagtcaaa atgcccaaga gtcacaaggc tattcaagca gacggttgga tgtgtcatgc    5640
ttccaaatgg gtcactactt gtgatttccg ctggtatgga ccgaagtata taacacagtc    5700
catccgatcc ttcactccat ctgtagaaca atgcaaggaa agcattgaac aaacgaaaca    5760
aggaactttgg ctgaatccag gcttccctcc tcaaagttgt ggatatgcaa ctgtgacgga    5820
tgccgaagca gtgattgtcc aggtgactcc tcaccatgtg ctggttgatg aatacacagg    5880
agaatgggtt gattcacagt tcatcaacgg aaaaatgcagc aattacatat gccccactgt    5940
ccataactct acaacctggc attctgacta taaggtcaaa gggctatgtg attctaacct    6000
catttccatg gacatcacct tcttctcaga ggacggagag ctatcatccc tgggaaagga    6060
gggcacaggg ttcagaagta actactttgc ttatgaaact ggaggcaagg cctgcaaaat    6120
gcaatactgc aagcattggg gagtcagact cccatcaggt gtctggttcg agatggctga    6180
taaggatctc tttgctgcag ccagattccc tgaatgccca aagggtcaa gtatctctgc    6240
tccatctcag acctcagtgg atgtaagtct aattcaggac gttgagagga tcttggatta    6300
```

-continued

```
ttccctctgc caagaaacct ggagcaaaat cagagcgggt cttccaatct ctccagtgga    6360
tctcagctat cttgctccta aaaacccagg aaccggtcct gctttcacca taatcaatgg    6420
taccctaaaa tactttgaga ccagatacat cagagtcgat attgctgctc caatcctctc    6480
aagaatggtc ggaatgatca gtggaactac cacagaaagg gaactgtggg atgactgggc    6540
accatatgaa gacgtggaaa ttggacccaa tggagttctg aggaccagtt caggatataa    6600
gtttccttta tacatgattg gacatggtat gttggactcc gatcttcatc ttagctcaaa    6660
ggctcaggtg ttcgaacatc ctcacattca agacgctgct tcgcaacttc ctgatgatga    6720
gagtttattt tttggtgata ctgggctatc caaaaatcca atcgagcttg tagaaggttg    6780
gttcagtagt tggaaaagct ctattgcctc ttttttcttt atcatagggt taatcattgg    6840
actattcttg gttctccgag ttggtatcca tcttttgcatt aaattaaagc acaccaagaa    6900
aagacagatt tatacagaca tagagatgaa ccgacttgga aagtaagcta gccagattct    6960
tcatgtttgg accaaatcaa cttgtgatac catgctcaaa gaggcctcaa ttatatttga    7020
gttttaatt tttatgaaaa aaactaacag caatcatgga agtccacgat tttgagaccg    7080
acgagttcaa tgatttcaat gaagatgact atgccacaag agaattcctg aatcccgatg    7140
agcgcatgac gtacttgaat catgctgatt acaatttgaa ttctcctcta attagtgatg    7200
atattgacaa tttgatcagg aaattcaatt ctcttccgat tccctcgatg tgggatagta    7260
agaactggga tggagttctt gagatgttaa catcatgtca agccaatccc atctcaacat    7320
ctcagatgca taaatggatg ggaagttggt taatgtctga taatcatgat gccagtcaag    7380
ggtatagttt tttacatgaa gtggacaaag aggcagaaat aacatttgac gtggtggaga    7440
ccttcatccg cggctggggc aacaaaccaa ttgaatacat caaaaaggaa agatggactg    7500
actcattcaa aattctcgct tatttgtgtc aaaagttttt ggacttacac aagttgacat    7560
taatcttaaa tgctgtctct gaggtggaat tgctcaactt ggcgaggact ttcaaaggca    7620
aagtcagaag aagttctcat ggaacgaaca tatgcaggat tagggttccc agcttgggtc    7680
ctactttat ttcagaagga tgggcttact tcaagaaact tgatattcta atggaccgaa    7740
actttctgtt aatggtcaaa gatgtgatta taggaggat gcaaacggtg ctatccatgg    7800
tatgtagaat agacaacctg ttctcagagc aagacatctt ctcccttcta aatatctaca    7860
gaattggaga taaaattgtg gagaggcagg gaaattttc ttatgacttg attaaaatgg    7920
tggaaccgat atgcaacttg aagctgatga aattagcaag agaatcaagg cctttagtcc    7980
cacaattccc tcattttgaa aatcatatca agacttctgt tgatgaaggg gcaaaaattg    8040
accgaggtat aagattcctc catgatcaga taatgagtgt gaaaacagtg gatctcacac    8100
tggtgattta tggatcgttc agacattggg gtcatccttt tatagattat tacactggac    8160
tagaaaaatt acattcccaa gtaaccatga agaaagatat tgatgtgtca tatgcaaaag    8220
cacttgcaag tgatttagct cggattgttc tatttcaaca gttcaatgat cataaaaagt    8280
ggttcgtgaa tggagacttg ctccctcatg atcatcccct taaaagtcat gttaaagaaa    8340
atacatggcc cacagctgct caagttcaag attttggaga taaatggcat gaacttccgc    8400
tgattaaatg ttttgaaata cccgacttac tagacccatc gataatatac tctgacaaaa    8460
gtcattcaat gaataggtca gaggtgttga acatgtccg aatgaatccg aacactccta    8520
tccctagtaa aaaggtgttg cagactatgt tggacacaaa ggctaccaat tggaaagaat    8580
ttcttaaaga gattgatgag aagggcttag atgatgatga tctaattatt ggtcttaaag    8640
gaaaggagag ggaactgaag ttggcaggta gattttctc cctaatgtct tggaaattgc    8700
```

```
gagaatactt tgtaattacc gaatatttga taaagactca tttcgtccct atgtttaaag   8760
gcctgacaat ggcggacgat ctaactgcag tcattaaaaa gatgttagat tcctcatccg   8820
gccaaggatt gaagtcatat gaggcaattt gcatagccaa tcacattgat tacgaaaaat   8880
ggaataacca ccaaaggaag ttatcaaacg gcccagtgtt ccgagttatg gccagttct    8940 taggttatcc atccttaatc gagagaactc atgaattttt tgagaaaagt cttatatact   9000
acaatggaag accagacttg atgcgtgttc acaacaacac actgatcaat tcaacctccc   9060
aacgagtttg ttggcaagga caagagggtg gactggaagg tctacggcaa aaaggatgga   9120
ctatcctcaa tctactggtt attcaaagag aggctaaaat cagaaacact gctgtcaaag   9180
tcttggcaca aggtgataat caagttattt gcacacagta taaaacgaag aaatcgagaa   9240
acgttgtaga attacagggt gctctcaatc aaatggtttc taataatgag aaaattatga   9300
ctgcaatcaa aatagggaca gggaagttag acttttgat aaatgacgat gagactatgc    9360
aatctgcaga ttacttgaat tatgaaaaaa taccgatttt ccgtggagtg attagagggt   9420
tagagaccaa gagatggtca cgagtgactt gtgtcaccaa tgaccaaata cccacttgtg   9480
ctaatataat gagctcagtt tccacaaatg ctctcaccgt agctcatttt gctgagaacc   9540
caatcaatgc catgatacag tacaattatt ttgggacatt tgctagactc ttgttgatga   9600
tgcatgatcc tgctcttcgt caatcattgt atgaagttca agataagata ccgggcttgc   9660
acagttctac tttcaaatac gccatgttgt atttggaccc ttccattgga ggagtgtcgg   9720
gcatgtcttt gtccaggttt ttgattagag ccttcccaga tcccgtaaca gaaagtctct   9780
cattctggag attcatccat gtacatgctc gaagtgagca tctgaaggag atgagtgcag   9840
tatttggaaa ccccgagata gccaagtttc gaataactca catagacaag ctagtagaag   9900
atccaacctc tctgaacatc gctatgggaa tgagtccagc gaacttgtta aagactgagg   9960
ttaaaaaatg cttaatcgaa tcaagacaaa ccatcaggaa ccaggtgatt aaggatgcaa  10020
ccatatattt gtatcatgaa gaggatcggc tcagaagttt cttatggtca ataaatcctc  10080
tgttccctag atttttaagt gaattcaaat caggcacttt tttgggagtc gcagacgggc  10140
tcatcagtct atttcaaaat tctcgtacta ttcggaactc ctttaagaaa aagtatcata  10200
gggaattgga tgatttgatt gtgaggagtg aggtatcctc tttgacacat ttagggaaac  10260
ttcatttgag aagggggatca tgtaaaatgt ggacatgttc agctactcat gctgacacat  10320
taagatacaa atcctggggc cgtacagtta ttgggacaac tgtaccccat ccattagaaa  10380
tgttgggtcc acaacatcga aaagagactc cttgtgcacc atgtaacaca tcagggttca  10440
attatgtttc tgtgcattgt ccagacggga tccatgacgt ctttagttca cggggaccat  10500
tgcctgctta tctagggtct aaaacatctg aatctcatc tattttgcag ccttgggaaa   10560
gggaaagcaa agtcccactg attaaaagag ctacacgtct tagagatgct atctcttggt  10620
ttgttgaacc cgactctaaa ctagcaatga ctatactttc taacatccac tctttaacag  10680
gcgaagaatg gaccaaaagg cagcatgggt tcaaaagaac agggtctgcc cttcataggt  10740
tttcgacatc tcggatgagc catggtgggt tcgcatctca gagcactgca gcattgacca  10800
ggttgatggc aactacagac accatgaggg atctgggaga tcagaatttc gacttttat   10860 tccaagcaac gttgctctat gctcaaatta ccaccactgt tgcaagagac ggatggatca  10920
ccagttgtac agatcattat catattgcct gtaagtcctg tttgagaccc atagaagaga  10980
tcaccctgga ctcaagtatg gactacacgc ccccagatgt atcccatgtg ctgaagacat  11040
```

```
ggaggaatgg ggaaggttcg tggggacaag agataaaaca gatctatcct ttagaaggga   11100
attggaagaa tttagcacct gctgagcaat cctatcaagt cggcagatgt ataggttttc   11160
tatatggaga cttggcgtat agaaaatcta ctcatgccga ggacagttct ctatttcctc   11220
tatctataca aggtcgtatt agaggtcgag gtttcttaaa agggttgcta gacggattaa   11280
tgagagcaag ttgctgccaa gtaatacacc ggagaagtct ggctcatttg aagaggccgg   11340
ccaacgcagt gtacggaggt ttgatttact tgattgataa attgagtgta tcacctccat   11400
tcctttctct tactagatca ggacctatta gagacgaatt agaaacgatt ccccacaaga   11460
tcccaacctc ctatccgaca agcaaccgtg atatggggt gattgtcaga aattacttca   11520
aataccaatg ccgtctaatt gaaaagggaa aatacagatc acattattca caattatggt   11580
tattctcaga tgtcttatcc atagacttca ttggaccatt ctctatttcc accaccctct   11640
tgcaaatcct atacaagcca tttttatctg ggaaagataa gaatgagttg agagagctgg   11700
caaatctttc ttcattgcta agatcaggag aggggtggga agacatacat gtgaaattct   11760
tcaccaagga catattattg tgtccagagg aaatcagaca tgcttgcaag ttcgggattg   11820
ctaaggataa taataaagac atgagctatc cccttgggg aagggaatcc agagggacaa    11880
ttacaacaat ccctgtttat tatacgacca ccccttaccc aaagatgcta gagatgcctc   11940
caagaatcca aaatcccctg ctgtccggaa tcaggttggg ccaattacca actggcgctc   12000
attataaaat tcggagtata ttacatgaaa tgggaatcca ttacagggac ttcttgagtt   12060
gtggagacgg ctccggaggg atgactgctg cattactacg agaaaatgtg catagcagag   12120
gaatattcaa tagtctgtta gaattatcag ggtcagtcat gcgaggcgcc tctcctgagc   12180
cccccagtgc cctagaaact ttaggaggag ataaatcgag atgtgtaaat ggtgaaacat   12240
gttgggaata tccatctgac ttatgtgacc caaggacttg ggactatttc ctccgactca   12300
aagcaggctt ggggcttcaa attgatttaa ttgtaatgga tatggaagtt cgggattctt   12360
ctactagcct gaaaattgag acgaatgtta gaaattatgt gcaccggatt ttggatgagc   12420
aaggagtttt aatctacaag acttatggaa catatatttg tgagagcgaa aagaatgcag   12480
taacaatcct tggtcccatg ttcaagacgg tcgacttagt tcaaacagaa tttagtagtt   12540
ctcaaacgtc tgaagtatat atggtatgta aaggtttgaa gaaattaatc gatgaaccca   12600
atcccgattg gtcttccatc aatgaatcct ggaaaaacct gtacgcattc cagtcatcag   12660
aacaggaatt tgccagagca aagaaggtta gtacatactt taccttgaca ggtattccct   12720
cccaattcat tcctgatcct tttgtaaaca ttgagactat gctacaaata ttcggagtac   12780
ccacgggtgt gtctcatgcg gctgccttaa aatcatctga tagacctgca gatttattga   12840
ccattagcct ttttttatatg gcgattatat cgtattataa catcaatcat atcagagtag   12900
gaccgatacc tccgaacccc ccatcagatg gaattgcaca aatgtgggg atcgctataa    12960 ctggtataag cttttggctg agtttgatgg agaaagacat tccactatat caacagtgtt   13020
tagcagttat ccagcaatca ttcccgatta ggtgggaggc tgtttcagta aaaggaggat   13080
acaagcagaa gtggagtact agaggtgatg ggctcccaaa agatacccga acttcagact   13140
ccttggcccc aatcgggaac tggatcagat ctctggaatt ggtccgaaac caagttcgtc   13200
taaatccatt caatgagatc ttgttcaatc agctatgtcg tacagtggat aatcatttga   13260
aatggtcaaa tttgcgaaga aacacaggaa tgattgaatg gatcaataga cgaatttcaa   13320
aagaagaccg gtctatactg atgttgaaga gtgacctaca cgaggaaaac tcttggagag   13380
attaaaaaat catgaggaga ctccaaactt taagtatgaa aaaactttg atccttaaga    13440
```

-continued cctctcttgtg gtttttattt tttatctggt tttgtggtct tcgt        13484

<210> SEQ ID NO 26
<211> LENGTH: 12156
<212> TYPE: DNA
<213> ORGANISM: Artificial Sequence
<220> FEATURE:
<223> OTHER INFORMATION: VSV vector: Convac V5 China

<400> SEQUENCE: 26
acgaagacaa acaaaccatt attatcatta aaaggctcag gagaaacttt aacagtaatc 60
aaaatgtctg ttacagtcaa gagaatcatt gacaacacag tcatagttcc aaaacttcct 120
gcaaatgagg atccagtgga atacccggca gattacttca gaaaatcaaa ggagattcct 180
ctttacatca atactacaaa aagtttgtca gatctaagag gatatgtcta ccaaggcctc 240
aaatccggaa atgtatcaat catacatgtc aacagctact tgtatggagc attaaaggac 300
atccggggta agttggataa agattggtca agtttcggaa taaacatcgg gaaagcaggg 360
gatacaatcg gaatatttga ccttgtatcc ttgaaagccc tggacggcgt acttccagat 420
ggagtatcgg atgcttccag aaccagcgca gatgacaaat ggttgccttt gtatctactt 480
ggcttataca gagtgggcag aacacaaatg cctgaataca gaaaaaagct catggatggg 540
ctgacaaatc aatgcaaaat gatcaatgaa cagtttgaac ctcttgtgcc agaaggtcgt 600
gacatttttg atgtgtgggg aaatgacagt aattacacaa aaattgtcgc tgcagtggac 660
atgttcttcc acatgttcaa aaaacatgaa tgtgcctcgt tcagatacgg aactattgtt 720
tccagattca aagattgtgc tgcattggca acatttggac acctctgcaa aataaccgga 780
atgtctacag aagatgtaac gacctggatc ttgaaccgag aagttgcaga tgaaatggtc 840
caaatgatgc ttccaggcca agaaattgac aaggccgatt catacatgcc ttatttgatc 900
gactttggat tgtcttctaa gtctccatat tcttccgtca aaaaccctgc cttccacttc 960
tgggggcaat tgacagctct tctgctcaga tccaccagag caaggaatgc ccgacagcct 1020
gatgacattg agtatacatc tcttactaca gcaggtttgt tgtacgctta tgcagtagga 1080
tcctctgccg acttggcaca acagttttgt gttggagata acaaatacac tccagatgat 1140
agtaccggag gattgacgac taatgcaccg ccacaaggca gagatgtggt cgaatggctc 1200
ggatggtttg aagatcaaaa cagaaaaccg actcctgata tgatgcagta tgcgaaaaga 1260
gcagtcatgt cactgcaagg cctaagagag aagacaattg gcaagtatgc taagtcagaa 1320
tttgacaaat gaccctataa ttctcagatc acctattata tattatgcta catatgaaaa 1380
aaactaacag atatcatgga taatctcaca aaagttcgtg agtatctcaa gtcctattct 1440
cgtctggatc aggcggtagg agagatagat gagatcgaag cacaacgagc tgaaaagtcc 1500
aattatgagt tgttccaaga ggatggagtg gaagagcata ctaagccctc ttattttcag 1560
gcagcagatg attctgacac agaatctgaa ccagaaattg aagacaatca aggtttgtat 1620
gcaccagatc cagaagctga gcaagttgaa ggctttatac aggggccttt agatgactat 1680
gcagatgagg aagtggatgt tgtatttact tcggactgga aacagcctga gcttgaatct 1740
gacgagcatg gaaagacctt acggttgaca tcgccagagg gtttaagtgg agagcagaaa 1800
tcccagtggc tttcgacgat taaagcagtc gtgcaaagtg ccaaatactg gaatctggca 1860
gagtgcacat ttgaagcatc gggagaaggg gtcattatga aggagcgcca gataactccg 1920
gatgtatata aggtcactcc agtgatgaac acacatccgt cccaatcaga agcagtatca 1980

```
gatgtttggt ctctctcaaa gacatccatg actttccaac ccaagaaagc aagtcttcag    2040
cctctcacca tatccttgga tgaattgttc tcatctagag gagagttcat ctctgtcgga    2100
ggtgacggac gaatgtctca taaagaggcc atcctgctcg gcctgagata caaaaagttg    2160
tacaatcagg cgagagtcaa atattctctg tagactatga aaaaagtaa cagatatcac    2220 gatctaagtg ttatcccaat ccattcatca tgagttcctt aaagaagatt ctcggtctga    2280
aggggaaagg taagaaatct aagaaattag ggatcgcacc acccccttat gaagaggaca    2340
ctagcatgga gtatgctccg agcgctccaa ttgacaaatc ctattttgga gttgacgaga    2400
tggacaccta tgatccgaat caattaagat atgagaaatt cttctttaca gtgaaaatga    2460
cggttagatc taatcgtccg ttcagaacat actcagatgt ggcagccgct gtatcccatt    2520
gggatcacat gtacatcgga atggcaggga aacgtcccct ctacaaaatc ttggcttttt    2580
tgggttcttc taatctaaag gccactccag cggtattggc agatcaaggt caaccagagt    2640
atcacactca ctgcgaaggc agggcttatt tgccacatag gatggggaag acccctccca    2700
tgctcaatgt accagagcac ttcagaagac cattcaatat aggtctttac aagggaacga    2760
ttgagctcac aatgaccatc tacgatgatg agtcactgga agcagctcct atgatctggg    2820
atcatttcaa ttcttccaaa ttttctgatt tcagagagaa ggccttaatg tttggcctga    2880
ttgtcgagaa aaaggcatct ggagcgtggg tcctggattc tatcagccac ttcaaatgag    2940
ctagtctaac ttctagcttc tgaacaatcc ccggtttact cagtctctcc taattccagc    3000
ctctcgaaca actaatatcc tgtcttttct atccctatga aaaaactaa cagagatcga    3060 tctgtttacg cgtcactatg aagtgccttt tgtacttagc cttttattc attggggtga    3120 attgcaagtt caccatagtt tttccacaca accaaaaagg aaactggaaa atgttccttt    3180
ctaattacca ttattgcccg tcaagctcag atttaaattg gcataatgac ttaataggca    3240
cagccataca agtcaaaatg cccaagagtc acaaggctat tcaagcagac ggttggatgt    3300
gtcatgcttc caaatgggtc actacttgtg atttccgctg gtatgaccg aagtatataa    3360 cacagtccat ccgatccttc actccatctg tagaacaatg caaggaaagc attgaacaaa    3420
cgaaacaagg aacttggctg aatccaggct tccctcctca aagttgtgga tatgcaactg    3480
tgacggatgc cgaagcagtg attgtccagg tgactcctca ccatgtgctg gttgatgaat    3540
acacaggaga atgggttgat tcacagttca tcaacggaaa atgcagcaat tacatatgcc    3600
ccactgtcca taactctaca acctggcatt ctgactataa ggtcaaaggg ctatgtgatt    3660
ctaacctcat ttccatggac atcaccttct tctcagagga cggagagcta tcatccctgg    3720
gaaaggaggg cacagggttc agaagtaact actttgctta tgaaactgga ggcaaggcct    3780
gcaaaatgca atactgcaag cattgggag tcagactccc atcaggtgtc tggttcgaga    3840
tggctgataa ggatctcttt gctgcagcca gattccctga tgcccagaa gggtcaagta    3900 tctctgctcc atctcagacc tcagtggatg taagtctaat tcaggacgtt gagaggatct    3960
tggattattc cctctgccaa gaaacctgga gcaaaatcag agcgggtctt ccaatctctc    4020
cagtggatct cagctatctt gctcctaaaa acccaggaac cggtcctgct ttcaccataa    4080
tcaatggtac cctaaaatac tttgagacca gatacatcag agtcgatatt gctgctccaa    4140
tcctctcaag aatggtcgga atgatcagtg gaactaccac agaaagggaa ctgtgggatg    4200
actgggcacc atatgaagac gtggaaattg gacccaatgg agttctgagg accagttcag    4260
gatataagtt tccttttatac atgattggac atggtatgtt ggactccgat cttcatctta    4320
gctcaaaggc tcaggtgttc gaacatcctc acattcaaga cgctgcttcg caacttcctg    4380
```

```
atgatgagag tttattttt ggtgatactg ggctatccaa aaatccaatc gagcttgtag     4440
aaggttggtt cagtagttgg aaaagctcta ttgcctcttt tttctttatc atagggttaa     4500
tcattggact attcttggtt ctccgagttg gtatccatct ttgcattaaa ttaaagcaca     4560
ccaagaaaag acagatttat acagacatag agatgaaccg acttggaaag taactcaaat     4620
cctgctaggt atgaaaaaaa ctaacagata tcacgctcga ggccaccatg aagtgcctgt     4680
tgtacttagc cttcctgttc atcggggtga attgccgctt tcccaatatc acaaacctgt     4740
gcccttttgg cgaggtgttc aacgcaaccc gcttcgccag cgtgtacgcc tggaatagga     4800
agcgcatctc caactgcgtg gccgactatt ctgtgctgta caacagcgcc tccttctcta     4860
cctttaagtg ctatggcgtg agccccacaa agctgaatga cctgtgcttt accaacgtgt     4920
acgccgattc cttcgtgatc aggggcgacg aggtgcgcca gatcgcacca ggacagacag     4980
gcaagatcgc agactacaat tataagctgc ctgacgattt caccggctgc gtgatcgcct     5040
ggaactctaa caatctggat agcaaagtgg gcggcaacta caattatctg taccggctgt     5100
ttagaaagtc taatctgaag ccattcgaga gggacatctc cacagaaatc taccaggccg     5160
gctctacccc ctgcaatggc gtggagggct ttaactgtta tttccctctg cagagctacg     5220
gcttccagcc aacaaacggc gtgggctatc agccctaccg cgtggtggtg ctgtcttttg     5280
agctgctgca cgcacctgca acagtgtgcg gaccaaagaa gagcaccaat ctggtgaaga     5340
acaagtgcgt gaacttcaac ggctctggat ccggctacat ccccgaggcc cccagagacg     5400
gccaggccta cgtgcggaag gacggcgagt gggtactgct cagcaccttc ctgggcagca     5460
gttggaaaag ctccatcgcc tccttttttct ttatcatcgg cctgatcatc ggactgttcc     5520
tggtgctccg cgtgggtatc cacctgtgca tcaagctgaa gcacaccaag aaaagacaga     5580
tttatacaga catcgagatg aaccgacttg gaaagtaagc tagccagatt cttcatgttt     5640
ggaccaaatc aacttgtgat accatgctca aagaggcctc aattatattt gagttttaa     5700 tttttatgaa aaaactaac agcaatcatg gaagtccacg attttgagac cgacgagttc     5760
aatgatttca tgaagatga ctatgccaca agagaattcc tgaatcccga tgagcgcatg     5820
acgtacttga atcatgctga ttacaatttg aattctcctc taattagtga tgatattgac     5880
aatttgatca ggaaattcaa ttctcttccg attccctcga tgtgggatag taagaactgg     5940
gatggagttc ttgagatgtt aacatcatgt caagccaatc ccatctcaac atctcagatg     6000
cataaatgga tgggaagttg gttaatgtct gataatcatg atgccagtca agggtatagt     6060
tttttacatg aagtggacaa agaggcagaa ataacatttg acgtggtgga gaccttcatc     6120
cgcggctggg gcaacaaacc aattgaatac atcaaaaagg aaagatggac tgactcattc     6180
aaaattctcg cttatttgtg tcaaaagttt ttggacttac acaagttgac attaatctta     6240
aatgctgtct ctgaggtgga attgctcaac ttggcgagga ctttcaaagg caaagtcaga     6300
agaagttctc atgaacgaa catatgcagg attagggttc ccagcttggg tcctactttt     6360
atttcagaag gatgggctta cttcaagaaa cttgatattc taatggaccg aaactttctg     6420
ttaatggtca aagatgtgat tatagggagg atgcaaacgg tgctatccat ggtatgtaga     6480
atagacaacc tgttctcaga gcaagacatc ttctccttc taaatatcta cagaattgga     6540
gataaaattg tggagaggca gggaaatttt tcttatgact tgattaaaat ggtggaaccg     6600
atatgcaact tgaagctgat gaaattagca agagaatcaa ggcctttagt cccacaattc     6660 cctcatttttg aaaatcatat caagacttct gttgatgaag gggcaaaaat tgaccgaggt     6720
```

```
ataagattcc tccatgatca gataatgagt gtgaaaacag tggatctcac actggtgatt    6780
tatggatcgt tcagacattg gggtcatcct tttatagatt attacactgg actagaaaaa    6840
ttacattccc aagtaaccat gaagaaagat attgatgtgt catatgcaaa agcacttgca    6900
agtgatttag ctcggattgt tctatttcaa cagttcaatg atcataaaaa gtggttcgtg    6960
aatggagact tgctccctca tgatcatccc tttaaaagtc atgttaaaga aaatacatgg    7020
cccacagctg ctcaagttca agattttgga gataaatggc atgaacttcc gctgattaaa    7080
tgttttgaaa tacccgactt actagaccca tcgataatat actctgacaa aagtcattca    7140
atgaataggt cagaggtgtt gaaacatgtc cgaatgaatc cgaacactcc tatccctagt    7200
aaaaaggtgt tgcagactat gttggacaca aaggctacca attggaaaga atttcttaaa    7260
gagattgatg agaagggctt agatgatgat gatctaatta ttggtcttaa aggaaaggag    7320
agggaactga agttggcagg tagattttc  tccctaatgt cttggaaatt gcgagaatac    7380
tttgtaatta ccgaatattt gataaagact catttcgtcc ctatgtttaa aggcctgaca    7440
atggcggacg atctaactgc agtcattaaa aagatgttag attcctcatc cggccaagga    7500
ttgaagtcat atgaggcaat ttgcatagcc aatcacattg attacgaaaa atggaataac    7560
caccaaagga agttatcaaa cggcccagtg ttccgagtta tgggccagtt cttaggttat    7620
ccatccttaa tcgagagaac tcatgaattt tttgagaaaa gtcttatata ctacaatgga    7680
agaccagact tgatgcgtgt tcacaacaac acactgatca attcaacctc caacgagtt     7740
tgttggcaag acaagaggg  tggactggaa ggtctacggc aaaaaggatg gactatcctc    7800
aatctactgg ttattcaaag agaggctaaa atcagaaaca ctgctgtcaa agtcttggca    7860
caaggtgata atcaagttat ttgcacacag tataaaacga gaaatcgag  aaacgttgta    7920
gaattacagg gtgctctcaa tcaaatggtt tctaataatg agaaaattat gactgcaatc    7980
aaaatagggg cagggaagtt aggactttg  ataaatgacg atgagactat gcaatctgca    8040
gattacttga attatggaaa ataccgatt  tccgtggag  tgattagagg ttagagacc     8100
aagagatggt cacgagtgac ttgtgtcacc aatgaccaaa tacccacttg tgctaatata    8160
atgagctcag tttccacaaa tgctctcacc gtagctcatt ttgctgagaa cccaatcaat    8220
gccatgatac agtacaatta ttttgggaca tttgctagac tcttgttgat gatgcatgat    8280
cctgctcttc gtcaatcatt gtatgaagtt caagataaga taccgggctt gcacagttct    8340
actttcaaat acgccatgtt gtatttggac ccttccattg gaggagtgtc gggcatgtct    8400
ttgtccaggt ttttgattag agccttccca gatcccgtaa cagaaagtct ctcattctgg    8460
agattcatcc atgtacatgc tcgaagtgag catctgaagg agatgagtgc agtatttgga    8520
aaccccgaga tagccaagtt tcgaataact cacatagaca agctagtaga agatccaacc    8580
tctctgaaca tcgctatggg aatgagtcca gcgaacttgt taaagactga ggttaaaaaa    8640
tgcttaatcg aatcaagaca aaccatcagg aaccaggtga ttaaggatgc aaccatatat    8700
ttgtatcatg aagaggatcg gctcagaagt ttcttatggt caataaatcc tctgttccct    8760
agatttttaa gtgaattcaa atcaggcact ttttttggag tcgcagacgg gctcatcagt    8820
ctatttcaaa attctcgtac tattcggaac tccttttaga aaaagtatca tagggaattg    8880
gatgatttga ttgtgaggag tgaggtatcc tctttgacac atttagggaa acttcatttg    8940
agaagggggat catgtaaaat gtggacatgt tcagctactc atgctgacac attaagatac    9000
aaatcctggg gccgtacagt tattgggaca actgtacccc atccattaga aatgttgggt    9060
ccacaacatc gaaaagagac tccttgtgca ccatgtaaca catcagggtt caattatgtt    9120
```

```
tctgtgcatt gtccagacgg gatccatgac gtctttagtt cacggggacc attgcctgct   9180
tatctagggt ctaaaacatc tgaatctaca tctattttgc agccttggga aagggaaagc   9240
aaagtcccac tgattaaaag agctacacgt cttagagatg ctatctcttg gtttgttgaa   9300
cccgactcta aactagcaat gactatactt tctaacatcc actctttaac aggcgaagaa   9360
tggaccaaaa ggcagcatgg gttcaaaaga acagggtctg cccttcatag gttttcgaca   9420
tctcggatga gccatggtgg gttcgcatct cagagcactg cagcattgac caggttgatg   9480
gcaactacag acaccatgag ggatctggga gatcagaatt tcgactttt attccaagca    9540
acgttgctct atgctcaaat taccaccact gttgcaagag acggatggat caccagttgt   9600
acagatcatt atcatattgc ctgtaagtcc tgtttgagac ccatagaaga gatcaccctg   9660
gactcaagta tggactacac gcccccagat gtatcccatg tgctgaagac atggaggaat   9720
ggggaaggtt cgtggggaca agagataaaa cagatctatc ctttagaagg gaattggaag   9780
aatttagcac ctgctgagca atcctatcaa gtcggcagat gtataggttt tctatatgga   9840
gacttggcgt atagaaaatc tactcatgcc gaggacagtt ctctatttcc tctatctata   9900
caaggtcgta ttagaggtcg aggtttctta aaagggttgc tagacggatt aatgagagca   9960
agttgctgcc aagtaataca ccggagaagt ctggctcatt tgaagaggcc ggccaacgca  10020
gtgtacggag gtttgattta cttgattgat aaattgagtg tatcacctcc attccttttct 10080
cttactagat caggacctat tagagacgaa ttagaaacga ttccccacaa gatcccaacc  10140
tcctatccga caagcaaccg tgatatgggg gtgattgtca gaaattactt caaataccaa  10200
tgccgtctaa ttgaaaaggg aaaatacaga tcacattatt cacaattatg gttattctca  10260
gatgtcttat ccatagactt cattggacca ttctctattt ccaccaccct cttgcaaatc  10320
ctatacaagc cattttatc tgggaaagat aagaatgagt tgagagagct ggcaaatctt   10380
tcttcattgc taagatcagg agaggggtgg gaagacatac atgtgaaatt cttcaccaag  10440
gacatattat tgtgtccaga ggaaatcaga catgcttgca agttcgggat tgctaaggat  10500
aataataaag acatgagcta tcccccttgg ggaagggaat ccagagggac aattacaaca  10560
atccctgttt attatacgac cacccctac ccaaagatgc tagagatgcc tccaagaatc    10620
caaaatcccc tgctgtccgg aatcaggttg ggccaattac caactggcgc tcattataaa  10680
attcggagta tattacatgg aatgggaatc cattacaggg acttcttgag ttgtggagac  10740
ggctccggag ggatgactgc tgcattacta cgagaaaatg tgcatagcag aggaatattc  10800
aatagtctgt tagaattatc agggtcagtc atgcgaggcg cctctcctga gccccccagt  10860
gccctagaaa ctttaggagg agataaatcg agatgtgtaa atggtgaaac atgttgggaa  10920
tatccatctg acttatgtga cccaaggact tgggactatt tcctccgact caaagcaggc  10980
ttggggcttc aaattgattt aattgtaatg gatatggaag ttcgggattc ttctactagc  11040
ctgaaaattg agacgaatgt tagaaattat gtgcaccgga ttttggatga gcaaggagtt  11100
ttaatctaca agacttatgg aacatatatt tgtgagagcg aaaagaatgc agtaacaatc  11160
cttggtccca tgttcaagac ggtcgactta gttcaaacag aatttagtag ttctcaaacg  11220
tctgaagtat atatggtatg taaggtttg aagaaattaa tcgatgaacc caatcccgat    11280
tggtcttcca tcaatgaatc ctggaaaaac ctgtacgcat tccagtcatc agaacaggaa  11340
tttgccagag caaagaaggt tagtacatac tttaccttga caggtattcc ctcccaattc  11400
attcctgatc cttttgtaaa cattgagact atgctacaaa tattcggagt acccacgggt  11460
```

```
gtgtctcatg cggctgcctt aaaatcatct gatagacctg cagatttatt gaccattagc    11520
cttttttata tggcgattat atcgtattat aacatcaatc atatcagagt aggaccgata    11580
cctccgaacc ccccatcaga tggaattgca caaaatgtgg ggatcgctat aactggtata    11640
agcttttggc tgagtttgat ggagaaagac attccactat atcaacagtg tttagcagtt    11700
atccagcaat cattcccgat taggtgggag gctgtttcag taaaaggagg atacaagcag    11760
aagtggagta ctagaggtga tgggctccca aaagataccc gaacttcaga ctccttggcc    11820
ccaatcggga actggatcag atctctggaa ttggtccgaa accaagttcg tctaaatcca    11880
ttcaatgaga tcttgttcaa tcagctatgt cgtacagtgg ataatcattt gaaatggtca    11940
aatttgcgaa gaaacacagg aatgattgaa tggatcaata gacgaatttc aaaagaagac    12000
cggtctatac tgatgttgaa gagtgaccta cacgaggaaa actcttggag agattaaaaa    12060
atcatgagga gactccaaac tttaagtatg aaaaaaactt tgatccttaa gaccctcttg    12120
tggtttttat tttttatctg gttttgtggt cttcgt                              12156
```

<210> SEQ ID NO 27
<211> LENGTH: 12156
<212> TYPE: DNA
<213> ORGANISM: Artificial Sequence
<220> FEATURE:
<223> OTHER INFORMATION: VSV vector: Convac V5 South Africa

<400> SEQUENCE: 27

```
acgaagacaa acaaaccatt attatcatta aaaggctcag gagaaacttt aacagtaatc      60
aaaatgtctg ttacagtcaa gagaatcatt gacaacacag tcatagttcc aaaacttcct     120
gcaaatgagg atccagtgga ataccccggca gattacttca gaaaatcaaa ggagattcct     180
ctttacatca atactacaaa aagtttgtca gatctaagag gatatgtcta ccaaggcctc     240
aaatccggaa atgtatcaat catacatgtc aacagctact tgtatggagc attaaaggac     300
atccggggta gttggataaa agattggtca agtttcggaa taaacatcgg gaaagcaggg     360
gatacaatcg gaatatttga ccttgtatcc ttgaaagccc tggacggcgt acttccagat     420
ggagtatcgg atgcttccag aaccagcgca gatgacaaat ggttgccttt gtatctactt     480
ggcttataca gagtgggcag aacacaaatg cctgaataca gaaaaaagct catggatggg     540
ctgacaaatc aatgcaaaat gatcaatgaa cagtttgaac ctcttgtgcc agaaggtcgt     600
gacatttttg atgtgtgggg aaatgacagt aattacacaa aaattgtcgc tgcagtggac     660
atgttcttcc acatgttcaa aaaacatgaa tgtgcctcgt tcagatacgg aactattgtt     720
tccagattca aagattgtgc tgcattggca acatttggac acctctgcaa aataaccgga     780
atgtctacag aagatgtaac gacctggatc ttgaaccgag aagttgcaga tgaaatggtc     840
caaatgatgc ttccaggcca agaaattgac aaggccgatt catacatgcc ttatttgatc     900
gactttggat tgtcttctaa gtctccatat tcttccgtca aaaaccctgc cttccacttc     960
tgggggcaat tgacagctct tctgctcaga tccaccagag caaggaatgc ccgacagcct    1020
gatgacattg agtatacatc tcttactaca gcaggtttgt tgtacgctta tgcagtagga    1080
tcctctgccg acttggcaca acagtttttgt gttggagata caaatacac tccagatgat    1140 agtaccggag gattgacgac taatgcaccg ccacaaggca gagatgtggt cgaatggctc    1200
ggatggtttg aagatcaaaa cagaaaaccg actcctgata tgatgcagta tgcgaaaaga    1260
gcagtcatgt cactgcaagg cctaagagag aagacaattg gcaagtatgc taagtcagaa    1320 tttgacaaaat gaccctataa ttctcagatc acctattata tattatgcta catatgaaaa    1380
```

```
aaactaacag atatcatgga taatctcaca aaagttcgtg agtatctcaa gtcctattct    1440
cgtctggatc aggcggtagg agagatagat gagatcgaag cacaacgagc tgaaaagtcc    1500
aattatgagt tgttccaaga ggatggagtg gaagagcata ctaagccctc ttattttcag    1560
gcagcagatg attctgacac agaatctgaa ccagaaattg aagacaatca aggtttgtat    1620
gcaccagatc cagaagctga gcaagttgaa ggctttatac aggggccttt agatgactat    1680
gcagatgagg aagtggatgt tgtatttact tcggactgga aacagcctga gcttgaatct    1740
gacgagcatg gaaagacctt acggttgaca tcgccagagg gtttaagtgg agagcagaaa    1800
tcccagtggc tttcgacgat taaagcagtc gtgcaaagtg ccaaatactg gaatctggca    1860
gagtgcacat ttgaagcatc gggagaaggg gtcattatga aggagcgcca gataactccg    1920
gatgtatata aggtcactcc agtgatgaac acacatccgt cccaatcaga agcagtatca    1980
gatgtttggt ctctctcaaa gacatccatg actttccaac ccaagaaagc aagtcttcag    2040
cctctcacca tatccttgga tgaattgttc tcatctagag gagagttcat ctctgtcgga    2100
ggtgacggac gaatgtctca taaagaggcc atcctgctcg gcctgagata caaaaagttg    2160
tacaatcagg cgagagtcaa atattctctg tagactatga aaaaaagtaa cagatatcac    2220
gatctaagtg ttatcccaat ccattcatca tgagttcctt aaagaagatt ctcggtctga    2280
agggaaagg taagaaatct aagaaattag ggatcgcacc accccttat gaagaggaca    2340
ctagcatgga gtatgctccg agcgctccaa ttgacaaatc ctattttgga gttgacgaga    2400
tggacaccta tgatccgaat caattaagat atgagaaatt cttctttaca gtgaaaatga    2460
cggttagatc taatcgtccg ttcagaacat actcagatgt ggcagccgct gtatcccatt    2520
gggatcacat gtacatcgga atggcaggga acgtcccctt ctacaaaatc ttggcttttt    2580
tgggttcttc taatctaaag gccactccag cggtattggc agatcaaggt caaccagagt    2640
atcacactca ctgcgaaggc agggcttatt tgccacatag gatggggaag accccctccca    2700
tgctcaatgt accagagcac ttcagaagac cattcaatat aggtctttac aagggaacga    2760
ttgagctcac aatgaccatc tacgatgatg agtcactgga agcagctcct atgatctggg    2820
atcatttcaa ttcttccaaa ttttctgatt tcagagagaa ggccttaatg tttggcctga    2880
ttgtcgagaa aaaggcatct ggagcgtggg tcctggattc tatcagccac ttcaaatgag    2940
ctagtctaac ttctagcttc tgaacaatcc ccggtttact cagtctctcc taattccagc    3000
ctctcgaaca actaatatcc tgtcttttct atccctatga aaaaactaa cagagatcga    3060
tctgtttacg cgtcactatg aagtgccttt tgtacttagc cttttattc attggggtga    3120
attgcaagtt caccatagtt tttccacaca accaaaaagg aaactggaaa atgttccttt    3180
ctaattacca ttattgcccg tcaagctcag atttaaattg gcataatgac ttaataggca    3240
cagccataca agtcaaaatg cccaagagtc acaaggctat tcaagcagac ggttggatgt    3300
gtcatgcttc caaatgggtc actacttgtg atttccgctg gtatggaccg aagtatataa    3360
cacagtccat ccgatccttc actccatctg tagaacaatg caaggaaagc attgaacaaa    3420
cgaaacaagg aacttggctg aatccaggct tccctcctca agttgtgga tatgcaactg    3480
tgacggatgc cgaagcagtg attgtccagg tgactcctca ccatgtgctg gttgatgaat    3540
acacaggaga atggttgat tcacagttca tcaacggaaa atgcagcaat tacatatgcc    3600
ccactgtcca taactctaca acctggcatt ctgactataa ggtcaaaggg ctatgtgatt    3660
ctaacctcat ttccatggac atcaccttct tctcagagga cggagagcta tcatccctgg    3720
```

```
gaaaggaggg cacagggttc agaagtaact actttgctta tgaaactgga ggcaaggcct   3780
gcaaaatgca atactgcaag cattggggag tcagactccc atcaggtgtc tggttcgaga   3840
tggctgataa ggatctcttt gctgcagcca gattccctga atgcccagaa gggtcaagta   3900
tctctgctcc atctcagacc tcagtggatg taagtctaat tcaggacgtt gagaggatct   3960
tggattattc cctctgccaa gaaacctgga gcaaaatcag agcgggtctt ccaatctctc   4020
cagtggatct cagctatctt gctcctaaaa acccaggaac cggtcctgct ttcaccataa   4080
tcaatggtac cctaaaatac tttgagacca gatacatcag agtcgatatt gctgctccaa   4140
tcctctcaag aatggtcgga atgatcagtg gaactaccac agaaagggaa ctgtgggatg   4200
actgggcacc atatgaagac gtggaaattg acccaatgg agttctgagg accagttcag   4260
gatataagtt tcctttatac atgattggac atggtatgtt ggactccgat cttcatctta   4320
gctcaaaggc tcaggtgttc gaacatcctc acattcaaga cgctgcttcg caacttcctg   4380
atgatgagag tttatttttt ggtgatactg ggctatccaa aaatccaatc gagcttgtag   4440
aaggttggtt cagtagttgg aaaagctcta ttgcctcttt tttctttatc ataggggttaa   4500
tcattggact attcttggtt ctccgagttg gtatccatct ttgcattaaa ttaaagcaca   4560
ccaagaaaag acagatttat acagacatag agatgaaccg acttggaaag taactcaaat   4620
cctgctaggt atgaaaaaaa ctaacagata tcacgctcga ggccaccatg aagtgcctgt   4680
tgtacttagc cttcctgttc atcggggtga attgccgctt tcccaatatc acaaacctgt   4740
gccctttggg cgaggtgttc aacgcaaccc gcttcgccag cgtgtacgcc tggaatagga   4800
agcgcatctc caactgcgtg gccgactatt ctgtgctgta caacagcgcc tccttctcta   4860
cctttaagtg ctatggcgtg agccccacaa agctgaatga cctgtgcttt accaacgtgt   4920
acgccgattc cttcgtgatc aggggcgacg aggtgcgcca gatcgcacca ggacagacag   4980
gcaatatcgc agactacaat tataagctgc ctgacgattt caccggctgc gtgatcgcct   5040
ggaactctaa caatcgggat agcaaagtgg gcggcaacta caattatctg taccggctgt   5100
ttagaaagtc taatctgaag ccattcgaga gggacatctc cacagaaatc taccaggccg   5160
gctctacccc ctgcaatggc gtgaagggct ttaactgtta tttccctctg cagagctacg   5220
gcttccagcc aacatatggc gtgggctatc agccctaccg cgtggtggtg ctgtctttttg   5280
agctgctgca cgcacctgca acagtgtgcg gaccaaagaa gagcaccaat ctggtgaaga   5340
acaagtgcgt gaacttcaac ggctctggat ccggctacat ccccgaggcc cccagagacg   5400
gccaggccta cgtgcggaag gacggcgagt gggtactgct cagcaccttc ctgggcagca   5460
gttggaaaag ctccatcgcc tcctttttct ttatcatcgg cctgatcatc ggactgttcc   5520
tggtgctccg cgtgggtatc cacctgtgca tcaagctgaa gcacaccaag aaaagacaga   5580
tttatacaga catcgagatg aaccgacttg gaaagtaagc tagccagatt cttcatgttt   5640
ggaccaaatc aacttgtgat accatgctca aagaggcctc aattatattt gagtttttaa   5700
tttttatgaa aaaaactaac agcaatcatg gaagtccacg attttgagac cgacgagttc   5760
aatgatttca atgaagatga ctatgccaca agagaattcc tgaatcccga tgagcgcatg   5820
acgtacttga atcatgctga ttacaatttg aattctcctc taattagtga tgatattgac   5880
aatttgatca ggaaattcaa ttctcttccg attccctcga tgtgggatag taagaactgg   5940
gatggagttc ttgagatgtt aacatcatgt caagccaatc ccatctcaac atctcagatg   6000
cataaatgga tgggaagttg gttaatgtct gataatcatg atgccagtca agggtatagt   6060
ttttacatg aagtggacaa agaggcagaa ataacatttg acgtggtgga gaccttcatc   6120
```

```
cgcggctggg gcaacaaacc aattgaatac atcaaaaagg aaagatggac tgactcattc    6180
aaaattctcg cttatttgtg tcaaaagttt ttggacttac acaagttgac attaatctta    6240
aatgctgtct ctgaggtgga attgctcaac ttggcgagga ctttcaaagg caaagtcaga    6300
agaagttctc atgaacgaa catatgcagg attagggttc ccagcttggg tcctactttt     6360
atttcagaag gatgggctta cttcaagaaa cttgatattc taatggaccg aaactttctg    6420
ttaatggtca aagatgtgat tatagggagg atgcaaacgg tgctatccat ggtatgtaga    6480
atagacaacc tgttctcaga gcaagacatc ttctcccttc taaatatcta cagaattgga    6540
gataaaattg tggagaggca gggaaatttt tcttatgact tgattaaaat ggtgaaccg     6600 atatgcaact tgaagctgat gaaattagca agagaatcaa ggcctttagt cccacaattc    6660
cctcattttg aaaatcatat caagacttct gttgatgaag gggcaaaaat tgaccgaggt    6720
ataagattcc tccatgatca gataatgagt gtgaaaacag tggatctcac actggtgatt    6780
tatggatcgt tcagacattg gggtcatcct tttatagatt attacactgg actagaaaaa    6840
ttacattccc aagtaaccat gaagaaagat attgatgtgt catatgcaaa agcacttgca    6900
agtgatttag ctcggattgt tctatttcaa cagttcaatg atcataaaaa gtggttcgtg    6960
aatggagact tgctccctca tgatcatccc tttaaaagtc atgttaaaga aaatacatgg    7020
cccacagctg ctcaagttca agattttgga gataaatggc atgaacttcc gctgattaaa    7080
tgttttgaaa tacccgactt actagaccca tcgataatat actctgacaa aagtcattca    7140
atgaataggt cagaggtgtt gaaacatgtc cgaatgaatc cgaacactcc tatccctagt    7200
aaaaaggtgt tgcagactat gttggacaca aaggctacca attggaaaga atttcttaaa    7260
gagattgatg agaagggctt agatgatgat gatctaatta ttggtcttaa aggaaaggag    7320
agggaactga agttggcagg tagatttttc tccctaatgt cttggaaatt gcgagaatac    7380
tttgtaatta ccgaatattt gataaagact catttcgtcc ctatgtttaa aggcctgaca    7440
atggcggacg atctaactgc agtcattaaa aagatgttag attcctcatc cggccaagga    7500
ttgaagtcat atgaggcaat ttgcatagcc aatcacattg attacgaaaa atggaataac    7560
caccaaagga agttatcaaa cggcccagtg ttccgagtta tgggccagtt cttaggttat    7620
ccatccttaa tcgagagaac tcatgaattt tttgagaaaa gtcttatata ctacaatgga    7680
agaccagact tgatgcgtgt tcacaacaac acactgatca attcaacctc caacgagtt    7740 tgttggcaag gacaagaggg tggactggaa ggtctacggc aaaaaggatg gactatcctc    7800
aatctactgg ttattcaaag agaggctaaa atcagaaaca ctgctgtcaa agtcttggca    7860
caaggtgata atcaagttat ttgcacacag tataaaacga agaaatcgag aaacgttgta    7920
gaattacagg gtgctctcaa tcaaatggtt tctaataatg agaaaattat gactgcaatc    7980
aaaataggga cagggaagtt aggacttttg ataaatgacg atgagactat gcaatctgca    8040
gattacttga attatggaaa aataccgatt tccgtggag tgattagagg gttagagacc      8100
aagagatggt cacgagtgac ttgtgtcacc aatgaccaaa tacccacttg tgctaatata    8160
atgagctcag tttccacaaa tgctctcacc gtagctcatt ttgctgagaa cccaatcaat    8220
gccatgatac agtacaatta ttttgggaca tttgctagac tcttgttgat gatgcatgat    8280
cctgctcttc gtcaatcatt gtatgaagtt caagataaga taccgggctt gcacagttct    8340
actttcaaat acgccatgtt gtatttggac ccttccattg gaggagtgtc gggcatgtct    8400
ttgtccaggt ttttgattag agccttccca gatcccgtaa cagaaagtct ctcattctgg    8460
```

```
agattcatcc atgtacatgc tcgaagtgag catctgaagg agatgagtgc agtatttgga    8520
aaccccgaga tagccaagtt tcgaataact cacatagaca agctagtaga agatccaacc    8580
tctctgaaca tcgctatggg aatgagtcca gcgaacttgt taaagactga ggttaaaaaa    8640
tgcttaatcg aatcaagaca aaccatcagg aaccaggtga ttaaggatgc aaccatatat    8700
ttgtatcatg aagaggatcg gctcagaagt ttcttatggt caataaatcc tctgttccct    8760
agatttttaa gtgaattcaa atcaggcact tttttgggag tcgcagacgg gctcatcagt    8820
ctatttcaaa attctcgtac tattcggaac tcctttaaga aaagtatca tagggaattg    8880
gatgatttga ttgtgaggag tgaggtatcc tctttgacac atttagggaa acttcatttg    8940
agaaggggat catgtaaaat gtggacatgt tcagctactc atgctgacac attaagatac    9000
aaatcctggg gccgtacagt tattgggaca actgtacccc atccattaga aatgttgggt    9060
ccacaacatc gaaaagagac tccttgtgca ccatgtaaca catcagggtt caattatgtt    9120
tctgtgcatt gtccagacgg gatccatgac gtctttagtt cacggggacc attgcctgct    9180
tatctagggt ctaaaacatc tgaatctaca tctattttgc agccttggga aagggaaagc    9240
aaagtcccac tgattaaaag agctacacgt cttagagatg ctatctcttg gtttgttgaa    9300
cccgactcta aactagcaat gactatactt tctaacatcc actctttaac aggcgaagaa    9360
tggaccaaaa ggcagcatgg gttcaaaaga acagggtctg cccttcatag gttttcgaca    9420
tctcggatga gccatggtgg gttcgcatct cagagcactg cagcattgac caggttgatg    9480
gcaactacag acaccatgag ggatctggga gatcagaatt tcgactttt attccaagca    9540
acgttgctct atgctcaaat taccaccact gttgcaagag acggatggat caccagttgt    9600
acagatcatt atcatattgc ctgtaagtcc tgtttgagac ccatagaaga gatcaccctg    9660
gactcaagta tggactacac gcccccagat gtatcccatg tgctgaagac atggaggaat    9720
ggggaaggtt cgtggggaca agagataaaa cagatctatc ctttagaagg gaattggaag    9780
aatttagcac ctgctgagca atcctatcaa gtcggcagat gtataggttt tctatatgga    9840
gacttggcgt atagaaaatc tactcatgcc gaggacagtt ctctatttcc tctatctata    9900
caaggtcgta ttagaggtcg aggtttctta aaagggttgc tagacggatt aatgagagca    9960
agttgctgcc aagtaataca ccggagaagt ctggctcatt tgaagaggcc ggccaacgca   10020
gtgtacggag gtttgattta cttgattgat aaattgagtg tatcacctcc attcctttct   10080
cttactagat caggacctat tagagacgaa ttagaaacga ttccccacaa gatcccaacc   10140
tcctatccga caagcaaccg tgatatgggg gtgattgtca gaaattactt caaataccaa   10200
tgccgtctaa ttgaaaaggg aaaatacaga tcacattatt cacaattatg gttattctca   10260
gatgtcttat ccatagactt cattggacca ttctctattt ccaccaccct cttgcaaatc   10320
ctatacaagc catttttatc tgggaaagat aagaatgagt tgagagagct ggcaaatctt   10380
tcttcattgc taagatcagg agaggggtgg aagacatac atgtgaaatt cttcaccaag   10440
gacatattat tgtgtccaga ggaaatcaga catgcttgca agttcgggat tgctaaggat   10500
aataataaag acatgagcta tccccttgg ggaagggaat ccagagggac aattacaaca   10560
atccctgttt attatacgac caccccttac ccaaagatgc tagagatgcc tccaagaatc   10620
caaaatcccc tgctgtccgg aatcaggttg ggccaattac caactggcgc tcattataaa   10680
attcggagta tattacatgg aatgggaatc cattacaggg acttcttgag ttgtggagac   10740
ggctccggag ggatgactgc tgcattacta cgagaaaatg tgcatagcag aggaatattc   10800
aatagtctgt tagaattatc agggtcagtc atgcgaggcg cctctcctga gcccccagt    10860
```

```
gccctagaaa ctttaggagg agataaatcg agatgtgtaa atggtgaaac atgttgggaa   10920
tatccatctg acttatgtga cccaaggact tgggactatt tcctccgact caaagcaggc   10980
ttggggcttc aaattgattt aattgtaatg gatatggaag ttcgggattc ttctactagc   11040
ctgaaaattg agacgaatgt tagaaattat gtgcaccgga ttttggatga gcaaggagtt   11100
ttaatctaca agacttatgg aacatatatt tgtgagagcg aaaagaatgc agtaacaatc   11160
cttggtccca tgttcaagac ggtcgactta gttcaaacag aatttagtag ttctcaaacg   11220
tctgaagtat atatggtatg taaaggtttg aagaaattaa tcgatgaacc caatcccgat   11280
tggtcttcca tcaatgaatc ctggaaaaac ctgtacgcat tccagtcatc agaacaggaa   11340
tttgccagag caagaaggt tagtacatac tttaccttga caggtattcc ctcccaattc   11400
attcctgatc ctttttgtaaa cattgagact atgctacaaa tattcggagt acccacgggg   11460
gtgtctcatg cggctgcctt aaaatcatct gatagacctg cagatttatt gaccattagc   11520 ctttttata tggcgattat atcgtattat aacatcaatc atatcagagt aggaccgata   11580
cctccgaacc ccccatcaga tggaattgca caaaatgtgg ggatcgctat aactggtata   11640
agcttttggc tgagtttgat ggagaaagac attccactat atcaacagtg tttagcagtt   11700
atccagcaat cattcccgat taggtgggag gctgtttcag taaaaggagg atacaagcag   11760
aagtggagta ctagaggtga tgggctccca aaagatacc gaacttcaga ctccttggcc   11820
ccaatcggga actggatcag atctctggaa ttggtccgaa accaagttcg tctaaatcca   11880
ttcaatgaga tcttgttcaa tcagctatgt cgtacagtgg ataatcattt gaaatggtca   11940
aatttgcgaa gaaacacagg aatgattgaa tggatcaata gacgaatttc aaaagaagac   12000
cggtctatac tgatgttgaa gagtgaccta cacgaggaaa actcttggag agattaaaaa   12060
atcatgagga gactccaaac tttaagtatg aaaaaaactt tgatccttaa gaccctcttg   12120
tggtttttat tttttatctg gttttgtggt cttcgt                               12156
```

<210> SEQ ID NO 28
<211> LENGTH: 682
<212> TYPE: PRT
<213> ORGANISM: Artificial Sequence
<220> FEATURE:
<223> OTHER INFORMATION: SARS-CoV-2 spike protein (S) (682 aa)

<400> SEQUENCE: 28

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125
```

-continued

```
Lys Val Cys Glu Phe Gln Phe Cys Asn Asp Pro Phe Leu Gly Val Tyr
            130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
```

```
                545                 550                 555                 560
Pro Phe Gln Gln Phe Gly Arg Asp Ile Ala Asp Thr Thr Asp Ala Val
                    565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg
            675                 680
```

<210> SEQ ID NO 29
<211> LENGTH: 1273
<212> TYPE: PRT
<213> ORGANISM: Artificial Sequence
<220> FEATURE:
<223> OTHER INFORMATION: SARS-CoV-2 spike protein (S) (1273 aa)

<400> SEQUENCE: 29

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
                20                  25                  30

Thr Arg Gly Val Tyr Tyr Pro Asp Lys Val Phe Arg Ser Ser Val Leu
            35                  40                  45

His Ser Thr Gln Asp Leu Phe Leu Pro Phe Phe Ser Asn Val Thr Trp
        50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
                100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
        130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
                180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
        210                 215                 220

Pro Leu Val Asp Leu Pro Ile Gly Ile Asn Ile Thr Arg Phe Gln Thr
```

-continued

```
            225                 230                 235                 240
        Leu Leu Ala Leu His Arg Ser Tyr Leu Thr Pro Gly Asp Ser Ser Ser
                        245                 250                 255
        Gly Trp Thr Ala Gly Ala Ala Tyr Tyr Val Gly Tyr Leu Gln Pro
                        260                 265                 270
        Arg Thr Phe Leu Leu Lys Tyr Asn Glu Asn Gly Thr Ile Thr Asp Ala
                        275                 280                 285
        Val Asp Cys Ala Leu Asp Pro Leu Ser Glu Thr Lys Cys Thr Leu Lys
                        290                 295                 300
        Ser Phe Thr Val Glu Lys Gly Ile Tyr Gln Thr Ser Asn Phe Arg Val
        305                 310                 315                 320
        Gln Pro Thr Glu Ser Ile Val Arg Phe Pro Asn Ile Thr Asn Leu Cys
                        325                 330                 335
        Pro Phe Gly Glu Val Phe Asn Ala Thr Arg Phe Ala Ser Val Tyr Ala
                        340                 345                 350
        Trp Asn Arg Lys Arg Ile Ser Asn Cys Val Ala Asp Tyr Ser Val Leu
                        355                 360                 365
        Tyr Asn Ser Ala Ser Phe Ser Thr Phe Lys Cys Tyr Gly Val Ser Pro
                        370                 375                 380
        Thr Lys Leu Asn Asp Leu Cys Phe Thr Asn Val Tyr Ala Asp Ser Phe
        385                 390                 395                 400
        Val Ile Arg Gly Asp Glu Val Arg Gln Ile Ala Pro Gly Gln Thr Gly
                        405                 410                 415
        Lys Ile Ala Asp Tyr Asn Tyr Lys Leu Pro Asp Asp Phe Thr Gly Cys
                        420                 425                 430
        Val Ile Ala Trp Asn Ser Asn Asn Leu Asp Ser Lys Val Gly Gly Asn
                        435                 440                 445
        Tyr Asn Tyr Leu Tyr Arg Leu Phe Arg Lys Ser Asn Leu Lys Pro Phe
                        450                 455                 460
        Glu Arg Asp Ile Ser Thr Glu Ile Tyr Gln Ala Gly Ser Thr Pro Cys
        465                 470                 475                 480
        Asn Gly Val Glu Gly Phe Asn Cys Tyr Phe Pro Leu Gln Ser Tyr Gly
                        485                 490                 495
        Phe Gln Pro Thr Asn Gly Val Gly Tyr Gln Pro Tyr Arg Val Val Val
                        500                 505                 510
        Leu Ser Phe Glu Leu Leu His Ala Pro Ala Thr Val Cys Gly Pro Lys
                        515                 520                 525
        Lys Ser Thr Asn Leu Val Lys Asn Lys Cys Val Asn Phe Asn Phe Asn
                        530                 535                 540
        Gly Leu Thr Gly Thr Gly Val Leu Thr Glu Ser Asn Lys Lys Phe Leu
        545                 550                 555                 560
        Pro Phe Gln Gln Phe Gly Arg Asp Ile Ala Asp Thr Thr Asp Ala Val
                        565                 570                 575
        Arg Asp Pro Gln Thr Leu Glu Ile Leu Asp Ile Thr Pro Cys Ser Phe
                        580                 585                 590
        Gly Gly Val Ser Val Ile Thr Pro Gly Thr Asn Thr Ser Asn Gln Val
                        595                 600                 605
        Ala Val Leu Tyr Gln Asp Val Asn Cys Thr Glu Val Pro Val Ala Ile
                        610                 615                 620
        His Ala Asp Gln Leu Thr Pro Thr Trp Arg Val Tyr Ser Thr Gly Ser
        625                 630                 635                 640
        Asn Val Phe Gln Thr Arg Ala Gly Cys Leu Ile Gly Ala Glu His Val
                        645                 650                 655
```

-continued

Asn Asn Ser Tyr Glu Cys Asp Ile Pro Ile Gly Ala Gly Ile Cys Ala
        660             665             670

Ser Tyr Gln Thr Gln Thr Asn Ser Pro Arg Arg Ala Arg Ser Val Ala
    675             680             685

Ser Gln Ser Ile Ile Ala Tyr Thr Met Ser Leu Gly Ala Glu Asn Ser
690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
        740             745             750

Leu Leu Gln Tyr Gly Ser Phe Cys Thr Gln Leu Asn Arg Ala Leu Thr
            755             760             765

Gly Ile Ala Val Glu Gln Asp Lys Asn Thr Gln Glu Val Phe Ala Gln
        770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Phe Ile Glu Asp Leu Leu Phe Asn Lys Val Thr Leu Ala Asp Ala Gly
        820             825             830

Phe Ile Lys Gln Tyr Gly Asp Cys Leu Gly Asp Ile Ala Ala Arg Asp
        835             840             845

Leu Ile Cys Ala Gln Lys Phe Asn Gly Leu Thr Val Leu Pro Pro Leu
    850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
            885             890             895

Pro Phe Ala Met Gln Met Ala Tyr Arg Phe Asn Gly Ile Gly Val Thr
        900             905             910

Gln Asn Val Leu Tyr Glu Asn Gln Lys Leu Ile Ala Asn Gln Phe Asn
    915             920             925

Ser Ala Ile Gly Lys Ile Gln Asp Ser Leu Ser Ser Thr Ala Ser Ala
930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
            965             970             975

Leu Asn Asp Ile Leu Ser Arg Leu Asp Lys Val Glu Ala Glu Val Gln
        980             985             990

Ile Asp Arg Leu Ile Thr Gly Arg Leu Gln Ser Leu Gln Thr Tyr Val
        995             1000            1005

Thr Gln Gln Leu Ile Arg Ala Ala Glu Ile Arg Ala Ser Ala Asn
    1010            1015            1020

Leu Ala Ala Thr Lys Met Ser Glu Cys Val Leu Gly Gln Ser Lys
    1025            1030            1035

Arg Val Asp Phe Cys Gly Lys Gly Tyr His Leu Met Ser Phe Pro
    1040            1045            1050

Gln Ser Ala Pro His Gly Val Val Phe Leu His Val Thr Tyr Val
    1055            1060            1065

```
Pro Ala Gln Glu Lys Asn Phe Thr Thr Ala Pro Ala Ile Cys His
   1070                1075                1080

Asp Gly Lys Ala His Phe Pro Arg Glu Gly Val Phe Val Ser Asn
   1085                1090                1095

Gly Thr His Trp Phe Val Thr Gln Arg Asn Phe Tyr Glu Pro Gln
   1100                1105                1110

Ile Ile Thr Thr Asp Asn Thr Phe Val Ser Gly Asn Cys Asp Val
   1115                1120                1125

Val Ile Gly Ile Val Asn Asn Thr Val Tyr Asp Pro Leu Gln Pro
   1130                1135                1140

Glu Leu Asp Ser Phe Lys Glu Glu Leu Asp Lys Tyr Phe Lys Asn
   1145                1150                1155

His Thr Ser Pro Asp Val Asp Leu Gly Asp Ile Ser Gly Ile Asn
   1160                1165                1170

Ala Ser Val Val Asn Ile Gln Lys Glu Ile Asp Arg Leu Asn Glu
   1175                1180                1185

Val Ala Lys Asn Leu Asn Glu Ser Leu Ile Asp Leu Gln Glu Leu
   1190                1195                1200

Gly Lys Tyr Glu Gln Tyr Ile Lys Trp Pro Trp Tyr Ile Trp Leu
   1205                1210                1215

Gly Phe Ile Ala Gly Leu Ile Ala Ile Val Met Val Thr Ile Met
   1220                1225                1230

Leu Cys Cys Met Thr Ser Cys Cys Ser Cys Leu Lys Gly Cys Cys
   1235                1240                1245

Ser Cys Gly Ser Cys Cys Lys Phe Asp Glu Asp Ser Glu Pro
   1250                1255                1260

Val Leu Lys Gly Val Lys Leu His Tyr Thr
   1265                1270

<210> SEQ ID NO 30
<211> LENGTH: 781
<212> TYPE: PRT
<213> ORGANISM: Artificial Sequence
<220> FEATURE:
<223> OTHER INFORMATION: WuS1-RABVG (781 aa)

<400> SEQUENCE: 30

Met Phe Val Phe Leu Val Leu Leu Pro Leu Val Ser Ser Gln Cys Val
1               5                   10                  15

Asn Leu Th

```
Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
```

```
                        565                 570                 575
Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
                610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Ser Val Gly Asp Glu Ala
                675                 680                 685

Glu Asp Phe Val Glu Val His Leu Pro Asp Val His Asn Gln Val Ser
690                 695                 700

Gly Val Asp Leu Gly Leu Pro Asn Trp Gly Lys Tyr Val Leu Leu Ser
705                 710                 715                 720

Ala Gly Ala Leu Thr Ala Leu Met Leu Ile Ile Phe Leu Met Thr Cys
                725                 730                 735

Cys Arg Arg Val Asn Arg Ser Glu Pro Thr Gln His Asn Leu Arg Gly
                740                 745                 750

Thr Gly Arg Glu Val Ser Val Thr Pro Gln Ser Gly Lys Ile Ile Ser
                755                 760                 765

Ser Trp Glu Ser His Lys Ser Gly Gly Glu Thr Arg Leu
770                 775                 780

<210> SEQ ID NO 31
<211> LENGTH: 682
<212> TYPE: PRT
<213> ORGANISM: Artificial Sequence
<220> FEATURE:
<223> OTHER INFORMATION: WuS1-RABVG (682 aa)

<400> SEQUENCE: 31

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
                20                  25                  30

Thr Arg Gly Val Tyr Tyr Pro Asp Lys Val Phe Arg Ser Ser Val Leu
            35                  40                  45

His Ser Thr Gln Asp Leu Phe Leu Pro Phe Phe Ser Asn Val Thr Trp
        50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
                100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
        130                 135                 140

Tyr His Lys Asn Asn Lys Ser Trp Met Glu Ser Glu Phe Arg Val Tyr
```

-continued

```
           145                 150                 155                 160
   Ser Ser Ala Asn Asn Cys Thr Phe Glu Tyr Val Ser Gln Pro Phe Leu
                       165                 170                 175
   Met Asp Leu Glu Gly Lys Gln Gly Asn Phe Lys Asn Leu Arg Glu Phe
               180                 185                 190
   Val Phe Lys Asn Ile Asp Gly Tyr Phe Lys Ile Tyr Ser Lys His Thr
                   195                 200                 205
   Pro Ile Asn Leu Val Arg Asp Leu Pro Gln Gly Phe Ser Ala Leu Glu
           210                 215                 220
   Pro Leu Val Asp Leu Pro Ile Gly Ile Asn Ile Thr Arg Phe Gln Thr
   225                 230                 235                 240
   Leu Leu Ala Leu His Arg Ser Tyr Leu Thr Pro Gly Asp Ser Ser Ser
                       245                 250                 255
   Gly Trp Thr Ala Gly Ala Ala Ala Tyr Tyr Val Gly Tyr Leu Gln Pro
                   260                 265                 270
   Arg Thr Phe Leu Leu Lys Tyr Asn Glu Asn Gly Thr Ile Thr Asp Ala
               275                 280                 285
   Val Asp Cys Ala Leu Asp Pro Leu Ser Glu Thr Lys Cys Thr Leu Lys
           290                 295                 300
   Ser Phe Thr Val Glu Lys Gly Ile Tyr Gln Thr Ser Asn Phe Arg Val
   305                 310                 315                 320
   Gln Pro Thr Glu Ser Ile Val Arg Phe Pro Asn Ile Thr Asn Leu Cys
                       325                 330                 335
   Pro Phe Gly Glu Val Phe Asn Ala Thr Arg Phe Ala Ser Val Tyr Ala
                   340                 345                 350
   Trp Asn Arg Lys Arg Ile Ser Asn Cys Val Ala Asp Tyr Ser Val Leu
               355                 360                 365
   Tyr Asn Ser Ala Ser Phe Ser Thr Phe Lys Cys Tyr Gly Val Ser Pro
           370                 375                 380
   Thr Lys Leu Asn Asp Leu Cys Phe Thr Asn Val Tyr Ala Asp Ser Phe
   385                 390                 395                 400
   Val Ile Arg Gly Asp Glu Val Arg Gln Ile Ala Pro Gly Gln Thr Gly
                       405                 410                 415
   Lys Ile Ala Asp Tyr Asn Tyr Lys Leu Pro Asp Asp Phe Thr Gly Cys
                   420                 425                 430
   Val Ile Ala Trp Asn Ser Asn Asn Leu Asp Ser Lys Val Gly Gly Asn
               435                 440                 445
   Tyr Asn Tyr Leu Tyr Arg Leu Phe Arg Lys Ser Asn Leu Lys Pro Phe
           450                 455                 460
   Glu Arg Asp Ile Ser Thr Glu Ile Tyr Gln Ala Gly Ser Thr Pro Cys
   465                 470                 475                 480
   Asn Gly Val Glu Gly Phe Asn Cys Tyr Phe Pro Leu Gln Ser Tyr Gly
                       485                 490                 495
   Phe Gln Pro Thr Asn Gly Val Gly Tyr Gln Pro Tyr Arg Val Val Val
                   500                 505                 510
   Leu Ser Phe Glu Leu Leu His Ala Pro Ala Thr Val Cys Gly Pro Lys
               515                 520                 525
   Lys Ser Thr Asn Leu Val Lys Asn Lys Cys Val Asn Phe Asn Phe Asn
           530                 535                 540
   Gly Leu Thr Gly Thr Gly Val Leu Thr Glu Ser Asn Lys Lys Phe Leu
   545                 550                 555                 560
   Pro Phe Gln Gln Phe Gly Arg Asp Ile Ala Asp Thr Thr Asp Ala Val
                       565                 570                 575
```

```
Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg
            675                 680

<210> SEQ ID NO 32
<211> LENGTH: 525
<212> TYPE: PRT
<213> ORGANISM: Artificial Sequence
<220> FEATURE:
<223> OTHER INFORMATION: SARS-CoV-2 nucleocapsid protein (N)

<400> SEQUENCE: 32

Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
            35                  40                  45

Ser Arg Leu Leu Asp Arg Leu Val Arg Leu Ile Gly Asn Pro Asp Val
            50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
            85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
            115                 120                 125

Gln Tyr Phe Ser His Asp Asp Pro Ile Ser Ser Asp Gln Ser Arg Phe
            130                 135                 140

Gly Trp Phe Gly Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
            165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
            195                 200                 205

Phe Arg Leu Glu Arg Lys Trp Leu Asp Val Val Arg Asn Arg Ile Ala
            210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
            245                 250                 255
```

```
Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
    290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
    370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
                405                 410                 415

Val Ser Phe Leu His Gly Asp Gln Ser Glu Asn Glu Leu Pro Arg Leu
            420                 425                 430

Gly Gly Lys Glu Asp Arg Arg Val Lys Gln Ser Arg Gly Glu Ala Arg
        435                 440                 445

Glu Ser Tyr Arg Glu Thr Gly Pro Ser Arg Ala Ser Asp Ala Arg Ala
    450                 455                 460

Ala His Leu Pro Thr Gly Thr Pro Leu Asp Ile Asp Thr Ala Thr Glu
465                 470                 475                 480

Ser Ser Gln Asp Pro Gln Asp Ser Arg Arg Ser Ala Asp Ala Leu Leu
                485                 490                 495

Arg Leu Gln Ala Met Ala Gly Ile Ser Glu Glu Gln Gly Ser Asp Thr
            500                 505                 510

Asp Thr Pro Ile Val Tyr Asn Asp Arg Asn Leu Leu Asp
        515                 520                 525

<210> SEQ ID NO 33
<211> LENGTH: 19
<212> TYPE: DNA
<213> ORGANISM: Artificial Sequence
<220> FEATURE:
<223> OTHER INFORMATION: Synthesized

<400> SEQUENCE: 33
cttaatgcgc cgctacagg                                              19

<210> SEQ ID NO 34
<211> LENGTH: 18
<212> TYPE: DNA
<213> ORGANISM: Artificial Sequence
<220> FEATURE:
<223> OTHER INFORMATION: Synthesized

<400> SEQUENCE: 34
atgtgctgcg attaatta                                               18

<210> SEQ ID NO 35
<211> LENGTH: 19
```

<212> TYPE: DNA
<213> ORGANISM: Artificial Sequence
<220> FEATURE:
<223> OTHER INFORMATION: Synthesized

<400> SEQUENCE: 35
tgtgctgatt aagtgtaag                                                    19

<210> SEQ ID NO 36
<211> LENGTH: 17
<212> TYPE: DNA
<213> ORGANISM: Artificial Sequence
<220> FEATURE:
<223> OTHER INFORMATION: Synthesized

<400> SEQUENCE: 36
gttttcccag tcacgac                                                      17

<210> SEQ ID NO 37
<211> LENGTH: 48
<212> TYPE: DNA
<213> ORGANISM: Artificial Sequence
<220> FEATURE:
<223> OTHER INFORMATION: Synthesized

<400> SEQUENCE: 37
aaacgacggc cagtggaatt ccgttaatac gactcactat aggaaagg                    48

<210> SEQ ID NO 38
<211> LENGTH: 34
<212> TYPE: DNA
<213> ORGANISM: Artificial Sequence
<220> FEATURE:
<223> OTHER INFORMATION: Synthesized

<400> SEQUENCE: 38
ggttgcgcgc cgttgactca ctatagggggt tagg                                  34

<210> SEQ ID NO 39
<211> LENGTH: 39
<212> TYPE: DNA
<213> ORGANISM: Artificial Sequence
<220> FEATURE:
<223> OTHER INFORMATION: Synthesized

<400> SEQUENCE: 39
gagagcgcgc atcgaaatta atacgactca ctatagata                              39

<210> SEQ ID NO 40
<211> LENGTH: 39
<212> TYPE: DNA
<213> ORGANISM: Artificial Sequence
<220> FEATURE:
<223> OTHER INFORMATION: Synthesized

<400> SEQUENCE: 40
gagacgtacg cgtaatacga ctcactatag gggagaggg                              39

<210> SEQ ID NO 41
<211> LENGTH: 19
<212> TYPE: DNA
<213> ORGANISM: Artificial Sequence
<220> FEATURE:
<223> OTHER INFORMATION: Synthesized

<400> SEQUENCE: 41
taatacatag ggtaatggg     19

<210> SEQ ID NO 42
<211> LENGTH: 46
<212> TYPE: DNA
<213> ORGANISM: Artificial Sequence
<220> FEATURE:
<223> OTHER INFORMATION: Synthesized

<400> SEQUENCE: 42
gtgtcgtctc gcgcgtgcgg ccgcgctagc cagcttgggt ctccct     46

<210> SEQ ID NO 43
<211> LENGTH: 45
<212> TYPE: DNA
<213> ORGANISM: Artificial Sequence
<220> FEATURE:
<223> OTHER INFORMATION: Synthesized

<400> SEQUENCE: 43
gtgtcgtctc tgggtaagga tagtgtcgtc tctggggtaa ggata     45

<210> SEQ ID NO 44
<211> LENGTH: 53
<212> TYPE: DNA
<213> ORGANISM: Artificial Sequence
<220> FEATURE:
<223> OTHER INFORMATION: Synthesized

<400> SEQUENCE: 44
gtgtggtctc tgaggatagt tcagtgtggt ctctggtcgg taaggatagt tca     53

<210> SEQ ID NO 45
<211> LENGTH: 37
<212> TYPE: DNA
<213> ORGANISM: Artificial Sequence
<220> FEATURE:
<223> OTHER INFORMATION: Synthesized

<400> SEQUENCE: 45
gagaaggttt gagaacgcgt ctcggtacgc cgggttt     37

<210> SEQ ID NO 46
<211> LENGTH: 34
<212> TYPE: DNA
<213> ORGANISM: Artificial Sequence
<220> FEATURE:
<223> OTHER INFORMATION: Synthesized

<400> SEQUENCE: 46
tgtcacggat atccatcctg ctcttgtcct gtcc     34

<210> SEQ ID NO 47
<211> LENGTH: 36
<212> TYPE: DNA
<213> ORGANISM: Artificial Sequence
<220> FEATURE:
<223> OTHER INFORMATION: Synthesized

<400> SEQUENCE: 47
cagtccaccg gtgtcacgga tatccctaat cctgct     36

<210> SEQ ID NO 48
<211> LENGTH: 30
<212> TYPE: DNA
<213> ORGANISM: Artificial Sequence

```
<220> FEATURE:
<223> OTHER INFORMATION: Synthesized

<400> SEQUENCE: 48
ggattaggga tatccgagat ggccacactt                                          30

<210> SEQ ID NO 49
<211> LENGTH: 36
<212> TYPE: DNA
<213> ORGANISM: Artificial Sequence
<220> FEATURE:
<223> OTHER INFORMATION: Synthesized

<400> SEQUENCE: 49
aagtgtggcc atctcggata tccctaatcc tgctct                                   36

<210> SEQ ID NO 50
<211> LENGTH: 21
<212> TYPE: DNA
<213> ORGANISM: Artificial Sequence
<220> FEATURE:
<223> OTHER INFORMATION: Synthesized

<400> SEQUENCE: 50
tggccacact tttaaggagc t                                                   21

<210> SEQ ID NO 51
<211> LENGTH: 20
<212> TYPE: DNA
<213> ORGANISM: Artificial Sequence
<220> FEATURE:
<223> OTHER INFORMATION: Synthesized

<400> SEQUENCE: 51
ccaccggatc ctgatgtaat                                                     20

<210> SEQ ID NO 52
<211> LENGTH: 20
<212> TYPE: DNA
<213> ORGANISM: Artificial Sequence
<220> FEATURE:
<223> OTHER INFORMATION: Synthesized

<400> SEQUENCE: 52
ctggccttac cttcgcatca                                                     20

<210> SEQ ID NO 53
<211> LENGTH: 25
<212> TYPE: DNA
<213> ORGANISM: Artificial Sequence
<220> FEATURE:
<223> OTHER INFORMATION: Synthesized

<400> SEQUENCE: 53
aggattagcc agttttatcc tgact                                               25

<210> SEQ ID NO 54
<211> LENGTH: 17
<212> TYPE: DNA
<213> ORGANISM: Artificial Sequence
<220> FEATURE:
<223> OTHER INFORMATION: Synthesized

<400> SEQUENCE: 54
agaagccagg agctaca                                                        17
```

<210> SEQ ID NO 55
<211> LENGTH: 36
<212> TYPE: DNA
<213> ORGANISM: Artificial Sequence
<220> FEATURE:
<223> OTHER INFORMATION: Synthesized

<400> SEQUENCE: 55
gtagtgtgcg atcgcgtgcg agaggccaga acaaca    36

<210> SEQ ID NO 56
<211> LENGTH: 60
<212> TYPE: DNA
<213> ORGANISM: Artificial Sequence
<220> FEATURE:
<223> OTHER INFORMATION: Synthesized

<400> SEQUENCE: 56
gtgtacgcgt tccgccagaa caacagtgta cgcgttcctg acggagaggc cagaacaaca    60

<210> SEQ ID NO 57
<211> LENGTH: 82
<212> TYPE: DNA
<213> ORGANISM: Artificial Sequence
<220> FEATURE:
<223> OTHER INFORMATION: Synthesized

<400> SEQUENCE: 57
gtgtgcggcc gctatagcgt aagttttta taacaatggt gtgcggccgc tatagcgatc    60
tcctaagttt tttataacaa tg    82

<210> SEQ ID NO 58
<211> LENGTH: 67
<212> TYPE: DNA
<213> ORGANISM: Artificial Sequence
<220> FEATURE:
<223> OTHER INFORMATION: Synthesized

<400> SEQUENCE: 58
gtgtgcggcc gttataacaa tggtgtgcgg ccgctataac gcgtttccta agttttttat    60
aacaatg    67

<210> SEQ ID NO 59
<211> LENGTH: 83
<212> TYPE: DNA
<213> ORGANISM: Artificial Sequence
<220> FEATURE:
<223> OTHER INFORMATION: Synthesized

<400> SEQUENCE: 59
gtgtgcggcc gctataacgt aagttttta taacaatggt gtgcggccgc tataacgcgt    60
ttcctaagtt ttttataaca atg    83

<210> SEQ ID NO 60
<211> LENGTH: 19
<212> TYPE: DNA
<213> ORGANISM: Artificial Sequence
<220> FEATURE:
<223> OTHER INFORMATION: Synthesized

<400> SEQUENCE: 60
gacaacccag gacaggagc    19

```
<210> SEQ ID NO 61
<211> LENGTH: 20
<212> TYPE: DNA
<213> ORGANISM: Artificial Sequence
<220> FEATURE:
<223> OTHER INFORMATION: Synthesized

<400> SEQUENCE: 61
actctcaatg ttcctccgcc                                              20

<210> SEQ ID NO 62
<211> LENGTH: 20
<212> TYPE: DNA
<213> ORGANISM: Artificial Sequence
<220> FEATURE:
<223> OTHER INFORMATION: Synthesized

<400> SEQUENCE: 62
gccattcctg gacttgggaa                                              20

<210> SEQ ID NO 63
<211> LENGTH: 31
<212> TYPE: DNA
<213> ORGANISM: Artificial Sequence
<220> FEATURE:
<223> OTHER INFORMATION: Synthesized

<400> SEQUENCE: 63
gtgtgcggcc gcaggttgta ctaggtgggt c                                 31

<210> SEQ ID NO 64
<211> LENGTH: 20
<212> TYPE: DNA
<213> ORGANISM: Artificial Sequence
<220> FEATURE:
<223> OTHER INFORMATION: Synthesized

<400> SEQUENCE: 64
agtgattgcc tcccaaggtc                                              20

<210> SEQ ID NO 65
<211> LENGTH: 18
<212> TYPE: DNA
<213> ORGANISM: Artificial Sequence
<220> FEATURE:
<223> OTHER INFORMATION: Synthesized

<400> SEQUENCE: 65
tgagttcgtg agctttcg                                                18

<210> SEQ ID NO 66
<211> LENGTH: 22
<212> TYPE: DNA
<213> ORGANISM: Artificial Sequence
<220> FEATURE:
<223> OTHER INFORMATION: Synthesized

<400> SEQUENCE: 66
tctctgtaga ccgtagtgcc ca                                           22

<210> SEQ ID NO 67
<211> LENGTH: 19
<212> TYPE: DNA
<213> ORGANISM: Artificial Sequence
<220> FEATURE:
<223> OTHER INFORMATION: Synthesized
```

```
<400> SEQUENCE: 67 caaccccga caaccagag                                              19

<210> SEQ ID NO 68
<211> LENGTH: 20
<212> TYPE: DNA
<213> ORGANISM: Artificial Sequence
<220> FEATURE:
<223> OTHER INFORMATION: Synthesized

<400> SEQUENCE: 68 caccctaaa ggagacaccg                                             20

<210> SEQ ID NO 69
<211> LENGTH: 44
<212> TYPE: DNA
<213> ORGANISM: Artificial Sequence
<220> FEATURE:
<223> OTHER INFORMATION: Synthesized

<400> SEQUENCE: 69
gtgtgaatct caagtgtgaa gacttcatgc atcatgggtc tcaa                 44

<210> SEQ ID NO 70
<211> LENGTH: 16
<212> TYPE: DNA
<213> ORGANISM: Artificial Sequence
<220> FEATURE:
<223> OTHER INFORMATION: Synthesized

<400> SEQUENCE: 70
gagcgagcaa actact                                                16

<210> SEQ ID NO 71
<211> LENGTH: 20
<212> TYPE: DNA
<213> ORGANISM: Artificial Sequence
<220> FEATURE:
<223> OTHER INFORMATION: Synthesized

<400> SEQUENCE: 71
cccaagtatg ttgcaaccca                                            20

<210> SEQ ID NO 72
<211> LENGTH: 22
<212> TYPE: DNA
<213> ORGANISM: Artificial Sequence
<220> FEATURE:
<223> OTHER INFORMATION: Synthesized

<400> SEQUENCE: 72
tcgagcacta gcatagtcta ca                                         22

<210> SEQ ID NO 73
<211> LENGTH: 31
<212> TYPE: DNA
<213> ORGANISM: Artificial Sequence
<220> FEATURE:
<223> OTHER INFORMATION: Synthesized

<400> SEQUENCE: 73
gtgttctaga tcagagcgac cttacatagg a                               31

<210> SEQ ID NO 74
<211> LENGTH: 36
```

```
<212> TYPE: DNA
<213> ORGANISM: Artificial Sequence
<220> FEATURE:
<223> OTHER INFORMATION: Synthesized

<400> SEQUENCE: 74
gtgtcgtctc tatgtcacca caacgagacc ggtgcg                              36

<210> SEQ ID NO 75
<211> LENGTH: 20
<212> TYPE: DNA
<213> ORGANISM: Artificial Sequence
<220> FEATURE:
<223> OTHER INFORMATION: Synthesized

<400> SEQUENCE: 75
cttgatcggg ttgctagcca                                                20

<210> SEQ ID NO 76
<211> LENGTH: 20
<212> TYPE: DNA
<213> ORGANISM: Artificial Sequence
<220> FEATURE:
<223> OTHER INFORMATION: Synthesized

<400> SEQUENCE: 76
ccagggaatg tatgggggaa                                                20

<210> SEQ ID NO 77
<211> LENGTH: 20
<212> TYPE: DNA
<213> ORGANISM: Artificial Sequence
<220> FEATURE:
<223> OTHER INFORMATION: Synthesized

<400> SEQUENCE: 77
atgcttccaa caggcgtgta                                                20

<210> SEQ ID NO 78
<211> LENGTH: 21
<212> TYPE: DNA
<213> ORGANISM: Artificial Sequence
<220> FEATURE:
<223> OTHER INFORMATION: Synthesized

<400> SEQUENCE: 78
gttgcctata aaggggtcc c                                               21

<210> SEQ ID NO 79
<211> LENGTH: 18
<212> TYPE: DNA
<213> ORGANISM: Artificial Sequence
<220> FEATURE:
<223> OTHER INFORMATION: Synthesized

<400> SEQUENCE: 79
ggggtccaat tacaggca                                                  18

<210> SEQ ID NO 80
<211> LENGTH: 40
<212> TYPE: DNA
<213> ORGANISM: Artificial Sequence
<220> FEATURE:
<223> OTHER INFORMATION: Synthesized

<400> SEQUENCE: 80
```
gtgttccatc ttgtgttcta gactatattg gttccatctt                         40

<210> SEQ ID NO 81
<211> LENGTH: 55
<212> TYPE: DNA
<213> ORGANISM: Artificial Sequence
<220> FEATURE:
<223> OTHER INFORMATION: Synthesized

<400> SEQUENCE: 81
gcagagacgc gtcttttttt ataacaatgg cagagacgcg tcttttataa caatg         55

<210> SEQ ID NO 82
<211> LENGTH: 56
<212> TYPE: DNA
<213> ORGANISM: Artificial Sequence
<220> FEATURE:
<223> OTHER INFORMATION: Synthesized

<400> SEQUENCE: 82
gctataacgc gtatctttt tataacaatg gctataacgc gtattttata acaatg         56

<210> SEQ ID NO 83
<211> LENGTH: 49
<212> TYPE: DNA
<213> ORGANISM: Artificial Sequence
<220> FEATURE:
<223> OTHER INFORMATION: Synthesized

<400> SEQUENCE: 83
tatcactctg tgtttttata acaatgtatc actctgtttt ataacaatg               49

<210> SEQ ID NO 84
<211> LENGTH: 20
<212> TYPE: DNA
<213> ORGANISM: Artificial Sequence
<220> FEATURE:
<223> OTHER INFORMATION: Synthesized

<400> SEQUENCE: 84
gtatgctcga gtccctcacg                                               20

<210> SEQ ID NO 85
<211> LENGTH: 20
<212> TYPE: DNA
<213> ORGANISM: Artificial Sequence
<220> FEATURE:
<223> OTHER INFORMATION: Synthesized

<400> SEQUENCE: 85
tctctcgtga ccttgttgct                                               20

<210> SEQ ID NO 86
<211> LENGTH: 21
<212> TYPE: DNA
<213> ORGANISM: Artificial Sequence
<220> FEATURE:
<223> OTHER INFORMATION: Synthesized

<400> SEQUENCE: 86
acggctgctg aaaatgttag g                                             21

<210> SEQ ID NO 87
<211> LENGTH: 20
<212> TYPE: DNA
<213> ORGANISM: Artificial Sequence

```
<220> FEATURE:
<223> OTHER INFORMATION: Synthesized

<400> SEQUENCE: 87
agttcaagcc tagttcgcct                                               20

<210> SEQ ID NO 88
<211> LENGTH: 20
<212> TYPE: DNA
<213> ORGANISM: Artificial Sequence
<220> FEATURE:
<223> OTHER INFORMATION: Synthesized

<400> SEQUENCE: 88
aggcttgaga cctctgtcct                                               20

<210> SEQ ID NO 89
<211> LENGTH: 20
<212> TYPE: DNA
<213> ORGANISM: Artificial Sequence
<220> FEATURE:
<223> OTHER INFORMATION: Synthesized

<400> SEQUENCE: 89
atgaaacaag ggcagcatgc                                               20

<210> SEQ ID NO 90
<211> LENGTH: 20
<212> TYPE: DNA
<213> ORGANISM: Artificial Sequence
<220> FEATURE:
<223> OTHER INFORMATION: Synthesized

<400> SEQUENCE: 90
agaagaggac gagggactgg                                               20

<210> SEQ ID NO 91
<211> LENGTH: 19
<212> TYPE: DNA
<213> ORGANISM: Artificial Sequence
<220> FEATURE:
<223> OTHER INFORMATION: Synthesized

<400> SEQUENCE: 91
cgggttatga tcgggtgat                                                19

<210> SEQ ID NO 92
<211> LENGTH: 20
<212> TYPE: DNA
<213> ORGANISM: Artificial Sequence
<220> FEATURE:
<223> OTHER INFORMATION: Synthesized

<400> SEQUENCE: 92
ttgttgcgtg atcccgatga                                               20

<210> SEQ ID NO 93
<211> LENGTH: 20
<212> TYPE: DNA
<213> ORGANISM: Artificial Sequence
<220> FEATURE:
<223> OTHER INFORMATION: Synthesized

<400> SEQUENCE: 93
tcaatgctct aagccaccca                                               20
```

<210> SEQ ID NO 94
<211> LENGTH: 20
<212> TYPE: DNA
<213> ORGANISM: Artificial Sequence
<220> FEATURE:
<223> OTHER INFORMATION: Synthesized

<400> SEQUENCE: 94
tcggcagcaa caacatctca                                                    20

<210> SEQ ID NO 95
<211> LENGTH: 20
<212> TYPE: DNA
<213> ORGANISM: Artificial Sequence
<220> FEATURE:
<223> OTHER INFORMATION: Synthesized

<400> SEQUENCE: 95
ccctacctct agtgtggggt                                                    20

<210> SEQ ID NO 96
<211> LENGTH: 20
<212> TYPE: DNA
<213> ORGANISM: Artificial Sequence
<220> FEATURE:
<223> OTHER INFORMATION: Synthesized

<400> SEQUENCE: 96
acggacctaa gctgtgcaaa                                                    20

<210> SEQ ID NO 97
<211> LENGTH: 52
<212> TYPE: DNA
<213> ORGANISM: Artificial Sequence
<220> FEATURE:
<223> OTHER INFORMATION: Synthesized

<400> SEQUENCE: 97
ctcgcgatat cctgccctcg cgatcgccta attgcggaac cctaatcctg cc               52

<210> SEQ ID NO 98
<211> LENGTH: 21
<212> TYPE: DNA
<213> ORGANISM: Artificial Sequence
<220> FEATURE:
<223> OTHER INFORMATION: Synthesized

<400> SEQUENCE: 98
gccctaggtg gttaggcatt a                                                  21

<210> SEQ ID NO 99
<211> LENGTH: 41
<212> TYPE: DNA
<213> ORGANISM: Artificial Sequence
<220> FEATURE:
<223> OTHER INFORMATION: Synthesized

<400> SEQUENCE: 99
ccttacccaa ctttgtttgg tggccggcat agtcccagcc t                            41

<210> SEQ ID NO 100
<211> LENGTH: 18
<212> TYPE: DNA
<213> ORGANISM: Artificial Sequence
<220> FEATURE:
<223> OTHER INFORMATION: Synthesized

```
<400> SEQUENCE: 100
tcagcaaaaa acccctca                                                    18

<210> SEQ ID NO 101
<211> LENGTH: 36
<212> TYPE: DNA
<213> ORGANISM: Artificial Sequence
<220> FEATURE:
<223> OTHER INFORMATION: Synthesized

<400> SEQUENCE: 101
ggttgcgcgc atccggatat agttcctcct ttggtt                                36

<210> SEQ ID NO 102
<211> LENGTH: 34
<212> TYPE: DNA
<213> ORGANISM: Artificial Sequence
<220> FEATURE:
<223> OTHER INFORMATION: Synthesized

<400> SEQUENCE: 102
gaccatgatt acgccagcgg ccgcatccgg atat                                  34

<210> SEQ ID NO 103
<211> LENGTH: 24
<212> TYPE: DNA
<213> ORGANISM: Artificial Sequence
<220> FEATURE:
<223> OTHER INFORMATION: Synthesized

<400> SEQUENCE: 103
agcggataac aatttcacac agga                                             24

<210> SEQ ID NO 104
<211> LENGTH: 24
<212> TYPE: DNA
<213> ORGANISM: Artificial Sequence
<220> FEATURE:
<223> OTHER INFORMATION: Synthesized

<400> SEQUENCE: 104
tattaccgcc tttgagtgag ctga                                             24

<210> SEQ ID NO 105
<211> LENGTH: 20
<212> TYPE: DNA
<213> ORGANISM: Artificial Sequence
<220> FEATURE:
<223> OTHER INFORMATION: Synthesized

<400> SEQUENCE: 105 cttttttacgg ttcctggcct                                                 20

<210> SEQ ID NO 106
<211> LENGTH: 19
<212> TYPE: DNA
<213> ORGANISM: Artificial Sequence
<220> FEATURE:
<223> OTHER INFORMATION: Synthesized

<400> SEQUENCE: 106
acatttcccc gaaaagtgc                                                   19
```